(12) United States Patent
Ellis et al.

(10) Patent No.: US 10,072,011 B2
(45) Date of Patent: Sep. 11, 2018

(54) SUBSTITUTED BRIDGED UREA ANALOGS AS SIRTUIN MODULATORS

(71) Applicant: GlaxoSmithKline Intellectual Property (No.2) Limited, Middlesex (GB)

(72) Inventors: James Lamond Ellis, Collegeville, PA (US); Karen Anderson Evans, Collegeville, PA (US); Ryan Michael Fox, Collegeville, PA (US); William Henry Miller, Collegeville, PA (US); Mark Andrew Seefeld, Collegeville, PA (US)

(73) Assignee: GlaxoSmithKline Intellectual Property (No. 2) Limited, Brentford, Middlesex (GB)

( * ) Notice: Subject to any disclaimer, the term of this patent is extended or adjusted under 35 U.S.C. 154(b) by 0 days.

(21) Appl. No.: 15/527,581

(22) PCT Filed: Nov. 19, 2015

(86) PCT No.: PCT/IB2015/058978
§ 371 (c)(1),
(2) Date: May 17, 2017

(87) PCT Pub. No.: WO2016/079710
PCT Pub. Date: May 26, 2016

(65) Prior Publication Data
US 2017/0362234 A1    Dec. 21, 2017

Related U.S. Application Data

(60) Provisional application No. 62/081,916, filed on Nov. 19, 2014.

(51) Int. Cl.
*C07D 471/18* (2006.01)
*C07D 519/00* (2006.01)
*A61K 31/5517* (2006.01)

(52) U.S. Cl.
CPC ........ *C07D 471/18* (2013.01); *A61K 31/5517* (2013.01); *C07D 519/00* (2013.01)

(58) Field of Classification Search
CPC ........................... C07D 487/08; C07D 487/18
See application file for complete search history.

(56) References Cited

U.S. PATENT DOCUMENTS 9,834,558 B2 * 12/2017 Blum .................. C07D 471/18

FOREIGN PATENT DOCUMENTS

| WO | WO 2006/094210 A2 | | 9/2006 | |
|---|---|---|---|---|
| WO | WO 2011/059839 | * | 5/2011 | .......... C07D 471/04 |
| WO | WO 2011/059839 A1 | | 5/2011 | |
| WO | WO 2014/186313 A1 | | 11/2014 | |

* cited by examiner

*Primary Examiner* — Erich A Leeser
(74) *Attorney, Agent, or Firm* — Nichole Ginanni; Andrea V. Lockenour

(57) ABSTRACT

The present invention relates to novel substituted bridged urea analog compounds of Formula (I) or pharmaceutically acceptable salts thereof, corresponding pharmaceutical compositions, processes for making and use of such compounds, alone or in combination with other therapeutic agents, as Sirtuin Modulators useful for increasing lifespan of a cell, and in treating and/or preventing a wide variety of diseases and disorders, which include, but are not limited to, for example, diseases or disorders related to aging or stress, diabetes, obesity, neurodegenerative diseases, cardiovascular disease, blood clotting disorders, inflammation, cancer, and/or flushing as well as diseases or disorders that would benefit from increased mitochondrial activity.

14 Claims, No Drawings

SUBSTITUTED BRIDGED UREA ANALOGS AS SIRTUIN MODULATORS

This application is a § 371 of International Application No. PCT/IB2015/058978, filed Nov. 19, 2015, which claims the benefit of U.S. Provisional Application No. 62/081,916, filed Nov. 19, 2014, the disclosures of which are incorporated herein in their entireties.

FIELD OF THE INVENTION

In general, the present invention relates to substituted bridged urea analog compounds of Formulas (I) to (V), corresponding analogs or derivatives thereof, or pharmaceutically acceptable salts thereof, corresponding pharmaceutical compositions, processes for making and use of such compounds, alone or in combination with other therapeutic agents, as Sirtuin Modulators useful for increasing lifespan of a cell, and in treating and/or preventing a wide variety of diseases and disorders, which include, but are not limited to, for example, diseases or disorders related to aging or stress, diabetes, obesity, neurodegenerative diseases, cardiovascular disease, blood clotting disorders, inflammation, cancer, and/or flushing as well as diseases or disorders that would benefit from increased mitochondrial activity.

BACKGROUND

The Silent Information Regulator (SIR) family of genes represents a highly conserved group of genes present in the genomes of organisms ranging from archaebacteria to eukaryotes. The encoded SIR proteins are involved in diverse processes from regulation of gene silencing to DNA repair. A well-characterized gene in this family is *S. cerevisiae* SIR2, which is involved in silencing HM loci that contain information specifying yeast mating type, telomere position effects and cell aging. The yeast Sir2 protein belongs to a family of histone deacetylases. The proteins encoded by members of the SIR gene family show high sequence conservation in a 250 amino acid core domain. The Sir2 homolog, CobB, in *Salmonella typhimurium*, functions as an NAD (nicotinamide adenine dinucleotide)-dependent ADP-ribosyl transferase.

The Sir2 protein is a class III deacetylase which uses NAD as a cosubstrate. Unlike other deacetylases, many of which are involved in gene silencing, Sir2 is insensitive to class I and II histone deacetylase inhibitors like trichostatin A (TSA).

Deacetylation of acetyl-lysine by Sir2 is tightly coupled to NAD hydrolysis, producing nicotinamide and a novel acetyl-ADP ribose compound. The NAD-dependent deacetylase activity of Sir2 is essential for its functions, which can connect its biological role with cellular metabolism in yeast. Mammalian Sir2 homologs have NAD-dependent histone deacetylase activity.

Biochemical studies have shown that Sir2 can readily deacetylate the amino-terminal tails of histones H3 and H4, resulting in the formation of 2'/3'-O-acetyl-ADP-ribose (OAADPR) and nicotinamide. Strains with additional copies of SIR2 display increased rDNA silencing and a 30% longer life span. It has also been shown that additional copies of the *C. elegans* SIR2 homolog, sir-2.1, and the *D. melanogaster* dSir2 gene extend life span in those organisms. This implies that the SIR2-dependent regulatory pathway for aging arose early in evolution and has been well conserved. Today, Sir2 genes are believed to have evolved to enhance an organism's health and stress resistance to increase its chance of surviving adversity.

In humans, there are seven Sir2-like genes (SIRT1-SIRT7) that share the conserved catalytic domain of Sir2. SIRT1 is a nuclear protein with the highest degree of sequence similarity to Sir2. SIRT1 regulates multiple cellular targets by deacetylation including the tumor suppressor p53, the cellular signaling factor NF-κB, and the FOXO transcription factor.

SIRT3 is a homolog of SIRT1 that is conserved in prokaryotes and eukaryotes. The SIRT3 protein is targeted to the mitochondrial cristae by a unique domain located at the N-terminus. SIRT3 has $NAD^+$-dependent protein deacetylase activity and is ubiquitously expressed, particularly in metabolically active tissues. Upon transfer to the mitochondria, SIRT3 is believed to be cleaved into a smaller, active form by a mitochondrial matrix processing peptidase (MPP).

Caloric restriction has been known for over 70 years to improve the health and extend the lifespan of mammals. Yeast life span, like that of metazoans, is also extended by interventions that resemble caloric restriction, such as low glucose. The discovery that both yeast and flies lacking the SIR2 gene do not live longer when calorically restricted provides evidence that SIR2 genes mediate the beneficial health effects of a restricted calorie diet. Moreover, mutations that reduce the activity of the yeast glucose-responsive cAMP (adenosine 3',5'-monophosphate)-dependent (PKA) pathway extend life span in wild type cells but not in mutant sir2 strains, demonstrating that SIR2 is likely to be a key downstream component of the caloric restriction pathway.

In addition to therapeutic potential, structural and biophysical studies of SIRT1 activity and activation by small molecule sirtuin modulators would be useful to advance understanding of the biological function of sirtuins, to further the understanding of the mechanism of action of sirtuin activation and to aid in the development of assays that identify novel sirtuin modulators.

The present invention is directed to overcoming these and other problems encountered in the art.

SUMMARY OF THE INVENTION

In general, the present invention relates to substituted bridged urea analog compounds of Formulas (I) to (V), corresponding analogs or derivatives thereof, or pharmaceutically acceptable salts thereof, corresponding pharmaceutical compositions, processes for making and use of such compounds, alone or in combination with other therapeutic agents, as Sirtuin Modulators useful for increasing lifespan of a cell, and in treating and/or preventing a wide variety of diseases and disorders, which include, but are not limited to, for example, diseases or disorders related to aging or stress, diabetes, obesity, neurodegenerative diseases, cardiovascular disease, blood clotting disorders, inflammation, cancer, and/or flushing as well as diseases or disorders that would benefit from increased mitochondrial activity.

In particular, the present invention relates to novel compounds of Formulas (I) to (V), corresponding analogs (i.e., with hydrogen substitution at the $R^2$ position) and corresponding pharmaceutical compositions comprising compounds of Formulas (I) to (V) respectively.

The present invention also relates to processes for making compounds of Formulas (I) to (V), and corresponding analogs (i.e., with hydrogen substitution at the $R^2$ position), respectively.

The present invention also relates to methods or uses for using Sirtuin Modulator compounds as defined herein in treating and/or preventing a wide variety of diseases and disorders, which include, but are not limited to, for example, diseases or disorders related to aging or stress, diabetes, obesity, neurodegenerative diseases, cardiovascular disease, blood clotting disorders, inflammation, cancer, and/or flushing as well as diseases or disorders that would benefit from increased mitochondrial activity, further which may be selected from or include, but are not limited to psoriasis, atopic dermatitis, acne, rosacea, inflammatory bowel disease, osteoporosis, sepsis, arthritis, COPD, systemic lupus erythematosus and ophthalmic inflammation.

DETAILED DESCRIPTION OF THE INVENTION

In general, the present invention relates to substituted bridged urea analog compounds of Formulas (I) to (V), corresponding analogs or derivatives thereof, or pharmaceutically acceptable salts thereof, corresponding pharmaceutical compositions, processes for making and use of such compounds, alone or in combination with other therapeutic agents, as Sirtuin Modulators useful for increasing lifespan of a cell, and in treating and/or preventing a wide variety of diseases and disorders, which include, but are not limited to, for example, diseases or disorders related to aging or stress, diabetes, obesity, neurodegenerative diseases, cardiovascular disease, blood clotting disorders, inflammation, cancer, and/or flushing as well as diseases or disorders that would benefit from increased mitochondrial activity.

Compounds

In particular, the present invention relates to novel compounds of Formulas (I) to (V), corresponding analogs (i.e., with hydrogen substitution at the $R^2$ position) and corresponding pharmaceutical compositions comprising compounds of Formulas (I) to (V), respectively.

International Patent Application No. WO09/061879, International Filing Date: 13 May 2014 discloses novel sirtuin-modulating substituted bridged urea and related analogs compounds of Formula (I):

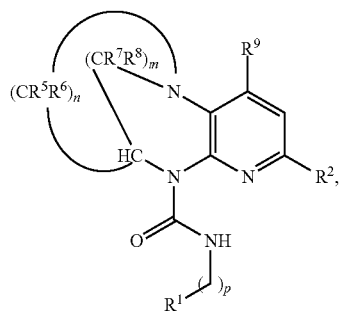

a pharmaceutically acceptable salt thereof, corresponding pharmaceutical compositions, combinations with other therapeutic agents, methods for making and methods or uses for increasing the lifespan of a cell, and treating and/or preventing a wide variety of diseases and disorders including, for example, diseases or disorders related to aging or stress, diabetes, obesity, neurodegenerative diseases, cardiovascular disease, blood clotting disorders, inflammation, cancer, and/or flushing as well as diseases or disorders that would benefit from increased mitochondrial activity.

In one aspect, the present invention provides novel sirtuin-modulating compounds of Structural Formulas (I) to (V), respectively corresponding analogs (i.e., with hydrogen substitution at the $R^2$ position) as are described in detail below.

In one aspect, the present invention relates to a compound of Formula (I):

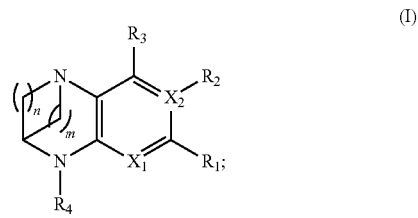

where:
$X_1$ or $X_2$ independently is selected from —N or —C;
$R^1$ is hydrogen, halogen, —CN, carbocyclyl, heterocyclyl, —N-substituted heterocyclyl, aryl, heteroaryl, —C(O)$R_a$ or —C(O)—$NR_bR_c$;
$R^2$ is halogen, -straight or branched $C_1$-$C_6$ alkyl, -straight or branched-$C_1$-$C_6$ haloalkyl, or —C(O)—$NR_bR_c$;
$R^3$ is hydrogen, halogen, -hydroxy, -straight or branched $C_1$-$C_6$ alkyl, or -straight or branched-$C_1$-$C_6$ haloalkyl;
$R^4$ is hydrogen or —C(O)$NR_bR_c$;
where:
when $X_2$ is —N, $R_2$ is non-existent; or
when $X_2$ is —C, $R_2$ is as defined above;
each $R^1$, $R^2$, $R^3$ or $R^4$ as defined above optionally is further substituted with one or more substituents selected from hydrogen, halogen, —OH, —(CH$_2$)$_x$OH, —C≡N, —$NR_dR_e$, -straight or branched $C_1$-$C_6$ alkyl, -straight or branched-$C_1$-$C_6$ haloalkyl, -straight or branched $C_1$-$C_6$ alkoxy, -straight or branched $C_1$-$C_6$ haloalkoxy, —O-straight or branched-$C_1$-$C_6$ haloalkyl, —$C_1$-$C_6$ cycloalkyl, —(CH$_2$)$_x$-cycloalkyl, heterocyclyl, aryl, -heteroaryl, —(CH$_2$)$_x$-heteroaryl, —O—(CH$_2$)$_x$CH(OH)CH$_2$(OH), or —C(O)O$R_f$;
each $R_a$, $R_b$, $R_c$, $R_d$, $R_e$, or $R_f$ as defined above independently is selected from hydrogen, -straight or branched $C_1$-$C_6$ alkyl, -straight or branched-$C_1$-$C_6$ haloalkyl, —$C_1$-$C_6$-cycloalkyl, —(CH$_2$)$_x$$C_1$-$C_6$-cycloalkyl, heterocyclyl, —N— heterocyclyl, aryl, heteroaryl, or —(CH$_2$)$_x$heteroaryl, —(CHR$_g$)$_x$heteroaryl;
where:
$R_g$ is -straight or branched $C_1$-$C_6$ alkyl, -straight or branched-$C_1$-$C_6$ haloalkyl;
each $R_a$, $R_b$, $R_c$ $R_d$, $R_e$, or $R_f$ as defined above optionally is further substituted with one or more substituents selected from hydrogen, halogen, —OH, —C≡N, -straight or branched $C_1$-$C_6$ alkyl, -straight or branched-$C_1$-$C_6$ haloalkyl, -straight or branched $C_1$-$C_6$ alkoxy, —O-straight or branched-$C_1$-$C_6$ haloalkyl, —$C_1$-$C_6$ cycloalkyl, carbocyclyl, —(CH$_2$)$_x$-carbocyclyl, -heterocyclyl, —O-heterocyclyl aryl, -heteroaryl, —(CH$_2$)$_x$-heteroaryl, —O—(CH$_2$)$_x$CH(OH)CH$_2$(OH), —(CH$_2$)$_x$—OH, or —C(O)—OH;
m is an integer from 1 to 3;
n is an integer selected from 1 to 3;
x is 0 or an integer from 1 to 6; or
a pharmaceutically salt thereof.

In another aspect, the present invention relates to a compound of the present invention as defined above (i.e., compounds of Structural Formulas (I) to (V), respectively corresponding analogs (i.e., with hydrogen substitution at the $R^2$ position) and throughout the instant application, where it is provided that:
when n=1, m≠1; and
when n=3, m≠3.

In another aspect, the present invention relates to a compound of the present invention, where $R^2$ is C(O)—$NR_bR_c$; wherein $R_b$ and $R_c$ are as defined above and throughout the present application.

In another aspect, the present invention relates to a compound of Formula (I), where:
m is 1;
n is 2 or 3; and
$R^4$ is hydrogen.

In another aspect, the present invention relates to a compound of Formula (I), where:
m is 1;
n is 2 or 3; and
$R^4$ is —C(O)$NR_bR_c$, where each $R_b$ and $R_c$ is as defined above.

In another aspect, the present invention relates to a compound of Formula (I), where:
m is 1;
n is 2;
$R^1$ is —C(O)$R_a$ or —C(O)—$NR_bR_c$ and $R^4$ is —C(O)$NR_bR_c$; where each $R_b$ and $R_c$ is as defined above.

In one aspect, the present invention relates to a compound of Formula (II):

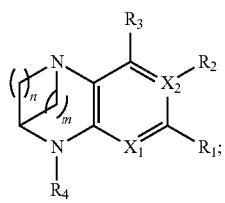

(II)

where:
$X_1$ or $X_2$ independently is selected from —N or —C;
where:
when $X_2$ is —N, $R_2$ is non-existent; or
when $X_2$ is —C, $R_2$ is as defined above;
$R^1$ is hydrogen, halogen, —CN, carbocyclyl, heterocyclyl, —N-substituted heterocyclyl, aryl; heteroaryl, —C(O)$R_a$ or —C(O)—$NR_bR_c$;
$R^2$ is halogen, -straight or branched $C_1$-$C_6$ alkyl, -straight or branched-$C_1$-$C_6$ haloalkyl, or —C(O)—$NR_bR_c$;
$R^3$ is hydrogen, halogen, -hydroxy, -straight or branched $C_1$-$C_6$ alkyl, or -straight or branched-$C_1$-$C_6$ haloalkyl;
$R^4$ is hydrogen or —C(O)$NR_bR_c$;
each $R^1$, $R^2$, $R^3$ or $R^4$ as defined above optionally is further substituted with one or more substituents selected from hydrogen, halogen, —OH, —(CH$_2$)$_x$OH, —C≡N, —$NR_dR_e$, -straight or branched $C_1$-$C_6$ alkyl, -straight or branched-$C_1$-$C_6$ haloalkyl, -straight or branched $C_1$-$C_6$ alkoxy, -straight or branched $C_1$-$C_6$ haloalkoxy, —O-straight or branched-$C_1$-$C_6$ haloalkyl, —$C_1$-$C_6$ cycloalkyl, —(CH$_2$)$_x$-cycloalkyl, heterocyclyl, aryl, -heteroaryl, —(CH$_2$)$_x$-heteroaryl, —O—(CH$_2$)$_x$CH(OH)CH$_2$(OH), or —C(O)O$R_f$;
each $R_a$, $R_b$, $R_c$, $R_d$, $R_e$, or $R_f$ as defined above independently is selected from hydrogen, -straight or branched $C_1$-$C_6$ alkyl, -straight or branched-$C_1$-$C_6$ haloalkyl, —$C_1$-$C_6$-cycloalkyl, —(CH$_2$)$_x$$C_1$-$C_6$-cycloalkyl, heterocyclyl, —N— heterocyclyl, aryl, heteroaryl, or —(CH$_2$)$_x$heteroaryl, —(CHR$_g$)$_x$heteroaryl;
where:
$R_g$ is -straight or branched $C_1$-$C_6$ alkyl, -straight or branched-$C_1$-$C_6$ haloalkyl;
each $R_a$, $R_b$, $R_c$, $R_d$, $R_e$, or $R_f$ as defined above optionally is further substituted with one or more substituents selected from hydrogen, halogen, —OH, —C≡N, -straight or branched $C_1$-$C_6$ alkyl, -straight or branched-$C_1$-$C_6$ haloalkyl, -straight or branched $C_1$-$C_6$ alkoxy, —O-straight or branched-$C_1$-$C_6$ haloalkyl, —$C_1$-$C_6$ cycloalkyl, carbocyclyl, —(CH$_2$)$_x$-carbocyclyl, -heterocyclyl, —O-heterocyclyl aryl, -heteroaryl, —(CH$_2$)$_x$-heteroaryl, —O—(CH$_2$)$_x$CH(OH)CH$_2$(OH), —(CH$_2$)$_x$—OH, or —C(O)—OH;
m is an integer from 1 to 3;
n is an integer selected from 1 to 3;
x is 0 or an integer from 1 to 6; or
a pharmaceutically salt thereof.

The present invention relates to a compound of Formula (III):

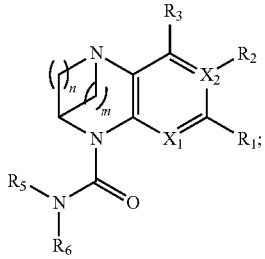

(III)

where:
$X_1$ or $X_2$ independently is selected from —N or —C;
wherein:
when $X_2$ is —N, $R_2$ is non-existent; or
when $X_2$ is —C, $R_2$ is as defined above;
$R^1$ is hydrogen, halogen, —CN, carbocyclyl, heterocyclyl, —N-substituted heterocyclyl, aryl, heteroaryl, —C(O)$R_a$ or —C(O)—$NR_bR_c$;
$R^2$ is halogen, -straight or branched $C_1$-$C_6$ alkyl, -straight or branched-$C_1$-$C_6$ haloalkyl, or —C(O)—$NR_bR_c$;
$R^3$ is hydrogen, halogen, -hydroxy, -straight or branched $C_1$-$C_6$ alkyl, or -straight or branched-$C_1$-$C_6$ haloalkyl;
each $R^5$ and $R^6$ independently is selected from hydrogen, -straight or branched $C_1$-$C_6$ alkyl, -straight or branched-$C_1$-$C_6$ haloalkyl, —$C_1$-$C_6$cycloalkyl, —(CH$_2$)$_x$$C_1$-$C_6$cycloalkyl, heterocyclyl, —N-heterocyclyl, aryl, heteroaryl, or —(CH$_2$)$_x$heteroaryl, —(CHR$_g$)$_x$heteroaryl;
where:
each $R^1$, $R^2$, $R^3$, $R^5$ and $R^6$ as defined above optionally is further substituted with one or more substituents selected from hydrogen, halogen, —OH, —(CH$_2$)$_x$OH, —C≡N, —$NR_dR_e$, -straight or branched $C_1$-$C_6$ alkyl, -straight or branched-$C_1$-$C_6$ haloalkyl, -straight or branched $C_1$-$C_6$ alkoxy, -straight or branched $C_1$-$C_6$ haloalkoxy, —O-straight or branched-$C_1$-$C_6$ haloalkyl, —$C_1$-$C_6$ cycloalkyl, —(CH$_2$)$_x$-cycloalkyl, heterocyclyl, aryl, -heteroaryl, —(CH$_2$)$_x$-heteroaryl, —O—(CH$_2$)$_x$CH(OH)CH$_2$(OH), or —C(O)O$R_f$;
each $R_a$, $R_b$, $R_c$, $R_d$, $R_e$, $R_f$ or $R_g$ as defined above independently is selected from hydrogen, -straight or branched $C_1$-$C_6$ alkyl, -straight or branched-$C_1$-$C_6$ haloalkyl, —$C_1$-$C_6$-cycloalkyl, —$(CH_2)_xC_1$-$C_6$-cycloalkyl, heterocyclyl, —N— heterocyclyl, aryl, heteroaryl, or —$(CH_2)_x$heteroaryl;

where:
each $R_a$, $R_b$, $R_c$, $R_d$, $R_e$, $R_f$ or $R_g$ as defined above optionally is further substituted with one or more substituents selected from hydrogen, halogen, —OH, —$(CH_2)_x$OH, —C≡N, —$NR_hR_i$, -straight or branched $C_1$-$C_6$ alkyl, -straight or branched-$C_1$-$C_6$ haloalkyl, -straight or branched $C_1$-$C_6$ alkoxy, -straight or branched-$C_1$-$C_6$ haloalkoxy, —$C_1$-$C_6$ cycloalkyl, —$(CH_2)_x$-cycloalkyl, heterocyclyl, -heterocyclyl, —O-heterocyclyl, aryl, -heteroaryl, —$(CH_2)_x$-heteroaryl, —O—$(CH_2)_xCH(OH)CH_2$(OH), —$(CH_2)_x$—OH, or —$C(O)OR_j$;
where:
each $R_h$, $R_i$ and $R_j$ independently is selected from hydrogen, -straight or branched $C_1$-$C_6$ alkyl or -straight or branched-$C_1$-$C_6$ haloalkyl;
m is an integer from 1 to 3;
n is an integer selected from 2 to 3;
x is 0 or an integer from 1 to 6; or
a pharmaceutically salt thereof.

The present invention relates to a compound of Formula (IV):

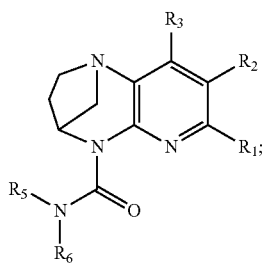

(IV)

where:
$R^1$ is —$C(O)R_a$ or —$C(O)$—$NR_bR_c$;
$R^2$ is halogen, -straight or branched $C_1$-$C_6$ alkyl, -straight or branched-$C_1$-$C_6$ haloalkyl, or —$C(O)$—$NR_bR_c$;
$R^3$ is hydrogen, halogen, -hydroxy, -straight or branched $C_1$-$C_6$ alkyl, or -straight or branched-$C_1$-$C_6$ haloalkyl;
each $R^5$ and $R^6$ independently is selected from hydrogen, -straight or branched $C_1$-$C_6$ alkyl, -straight or branched-$C_1$-$C_6$ haloalkyl, —$C_1$-$C_6$cycloalkyl, —$(CH_2)_xC_1$-$C_6$cycloalkyl, heterocyclyl, —N-heterocyclyl, aryl, heteroaryl, or —$(CH_2)_x$heteroaryl, —$(CHR_g)_x$heteroaryl;
where:
each $R^1$, $R^2$, $R^3$, $R^5$ and $R^6$ as defined above optionally is further substituted with one or more substituents selected from hydrogen, halogen, —OH, —$(CH_2)_x$OH, —C≡N, —$NR_dR_e$, -straight or branched $C_1$-$C_6$ alkyl, -straight or branched-$C_1$-$C_6$ haloalkyl, -straight or branched $C_1$-$C_6$ alkoxy, -straight or branched $C_1$-$C_6$ haloalkoxy, —O-straight or branched-$C_1$-$C_6$ haloalkyl, —$C_1$-$C_6$ cycloalkyl, —$(CH_2)_x$-cycloalkyl, heterocyclyl, aryl, -heteroaryl, —$(CH_2)_x$-heteroaryl, —O—$(CH_2)_xCH(OH)CH_2(OH)$, or —$C(O)OR_j$;
each $R_a$, $R_b$, $R_c$, $R_d$, $R_e$, $R_f$ or $R_g$ as define above independently is selected from hydrogen, -straight or branched $C_1$-$C_6$ alkyl, -straight or branched-$C_1$-$C_6$ haloalkyl, —$C_1$-$C_6$-cycloalkyl, —$(CH_2)_xC_1$-$C_6$-cycloalkyl, heterocyclyl, —N— heterocyclyl, aryl, heteroaryl, or —$(CH_2)_x$heteroaryl;

where:
each $R_a$, $R_b$, $R_c$, $R_d$, $R_e$, $R_f$ or $R_g$ as defined above optionally is further substituted with one or more substituents selected from hydrogen, halogen, —OH, —$(CH_2)_x$OH, —C≡N, —$NR_hR_i$, -straight or branched $C_1$-$C_6$ alkyl, -straight or branched-$C_1$-$C_6$ haloalkyl, -straight or branched $C_1$-$C_6$ alkoxy, -straight or branched-$C_1$-$C_6$ haloalkoxy, —$C_1$-$C_6$ cycloalkyl, —$(CH_2)_x$-cycloalkyl, heterocyclyl, -heterocyclyl, —O-heterocyclyl, aryl, -heteroaryl, —$(CH_2)_x$-heteroaryl, —O—$(CH_2)_xCH(OH)CH_2$(OH), —$(CH_2)_x$—OH, or —$C(O)OR_j$;
where:
each $R_h$, $R_i$ and $R_j$ independently is selected from hydrogen, -straight or branched $C_1$-$C_6$ alkyl or -straight or branched-$C_1$-$C_6$ haloalkyl;
m is an integer from 1 to 3;
n is an integer selected from 2 to 3;
x is 0 or an integer from 1 to 6; or
a pharmaceutically salt thereof.

The present invention relates to a compound of Formula (V):

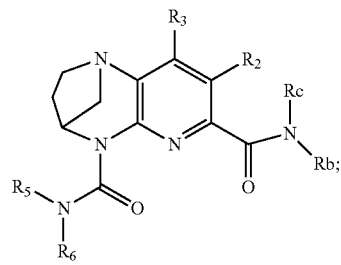

(V)

where:
$R^2$ is halogen, -straight or branched $C_1$-$C_6$ alkyl, -straight or branched-$C_1$-$C_6$ haloalkyl, or —$C(O)$—$NR_bR_c$;
$R^3$ is hydrogen, halogen, -hydroxy, -straight or branched $C_1$-$C_6$ alkyl, or -straight or branched-$C_6$-$C_6$ haloalkyl;
each $R^5$ and $R^6$ independently is selected from hydrogen, -straight or branched $C_1$-$C_6$ alkyl, -straight or branched-$C_1$-$C_6$ haloalkyl, —$C_1$-$C_6$cycloalkyl, —$(CH_2)_xC_1$-$C_6$cycloalkyl, heterocyclyl, —N-heterocyclyl, aryl, heteroaryl, or —$(CH_2)_x$heteroaryl, —$(CHR_g)_x$heteroaryl;
where:
each $R^1$, $R^2$, $R^3$, $R^5$ and $R^6$ as defined above optionally is further substituted with one or more substituents selected from hydrogen, halogen, —OH, —$(CH_2)_x$OH, —C≡N, —$NR_dR_e$, -straight or branched $C_1$-$C_6$ alkyl, -straight or branched-$C_1$-$C_6$ haloalkyl, -straight or branched $C_1$-$C_6$ alkoxy, -straight or branched $C_1$-$C_6$ haloalkoxy, —O-straight or branched-$C_1$-$C_6$ haloalkyl, —$C_1$-$C_6$ cycloalkyl, —$(CH_2)_x$-cycloalkyl, heterocyclyl, aryl, -heteroaryl, —$(CH_2)_x$-heteroaryl, —O—$(CH_2)_xCH(OH)CH_2(OH)$, or —$C(O)OR_j$;
each $R_a$, $R_b$, $R_c$, $R_d$, $R_e$, $R_f$ or $R_g$ as define above independently is selected from hydrogen, -straight or branched $C_1$-$C_6$ alkyl, -straight or branched-$C_1$-$C_6$ haloalkyl, —$C_1$-$C_6$-cycloalkyl, —$(CH_2)_xC_1$-$C_6$-cycloalkyl, heterocyclyl, —N— heterocyclyl, aryl, heteroaryl, or —$(CH_2)_x$heteroaryl;

where:
each $R_a$, $R_b$, $R_c$, $R_d$, $R_e$, $R_f$ or $R_g$ as defined above optionally is further substituted with one or more substituents selected from hydrogen, halogen, —OH, —(CH$_2$)$_x$OH, —C≡N, —NR$_h$R$_i$, -straight or branched C$_1$-C$_6$ alkyl, -straight or branched-C$_1$-C$_6$ haloalkyl, -straight or branched C$_1$-C$_6$ alkoxy, -straight or branched-C$_1$-C$_6$ haloalkoxy, —C$_1$-C$_6$ cycloalkyl, —(CH$_2$)$_x$-cycloalkyl, heterocyclyl, -heterocyclyl, —O-heterocyclyl, aryl, -heteroaryl, —(CH$_2$)$_x$-heteroaryl, —O—(CH$_2$)$_x$CH(OH)CH$_2$(OH), —(CH$_2$)—OH, or —C(O)OR$_j$;

where:
each $R_h$, $R_i$ and $R_j$ independently is selected from hydrogen, -straight or branched C$_1$-C$_6$ alkyl or -straight or branched-C$_1$-C$_6$ haloalkyl;

m is an integer from 1 to 3;
n is an integer selected from 2 to 3;
x is 0 or an integer from 1 to 6; or
a pharmaceutically salt thereof.

In another aspect, the present invention relates to a compound of the present invention as defined above (i.e., compounds of Structural Formulas (I) to (V), respectively, corresponding analogs (i.e., with hydrogen substitution at the R$^2$ position) and throughout the instant application, where it is provided that:
when n=1, m≠1; and
when n=3, m≠3.

In another aspect, the present invention relates to a compound of the present invention, where R$^2$ is C(O)—NR$_b$R$_c$; wherein R$_b$ and R$_c$ are as defined above and throughout the present application.

In another aspect, the present invention relates to a compound of Formula (I), where:
m is 1;
n is 2 or 3; and
R$^4$ is hydrogen.

In another aspect, the present invention relates to a compound of Formula (I), where:
m is 1;
n is 2 or 3; and
R$^4$ is —C(O)NR$_b$R$_c$, wherein each R$_b$ and R$_c$ is as defined above.

In another aspect, the present invention relates to compounds of Formulas (I) to (V), respectively, wherein R$^1$ is selected from:

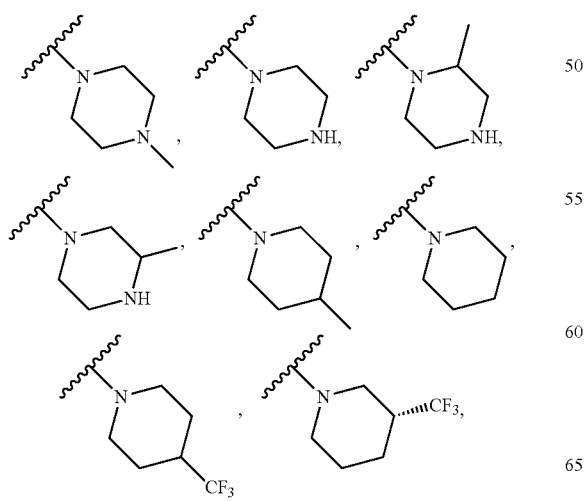

-continued

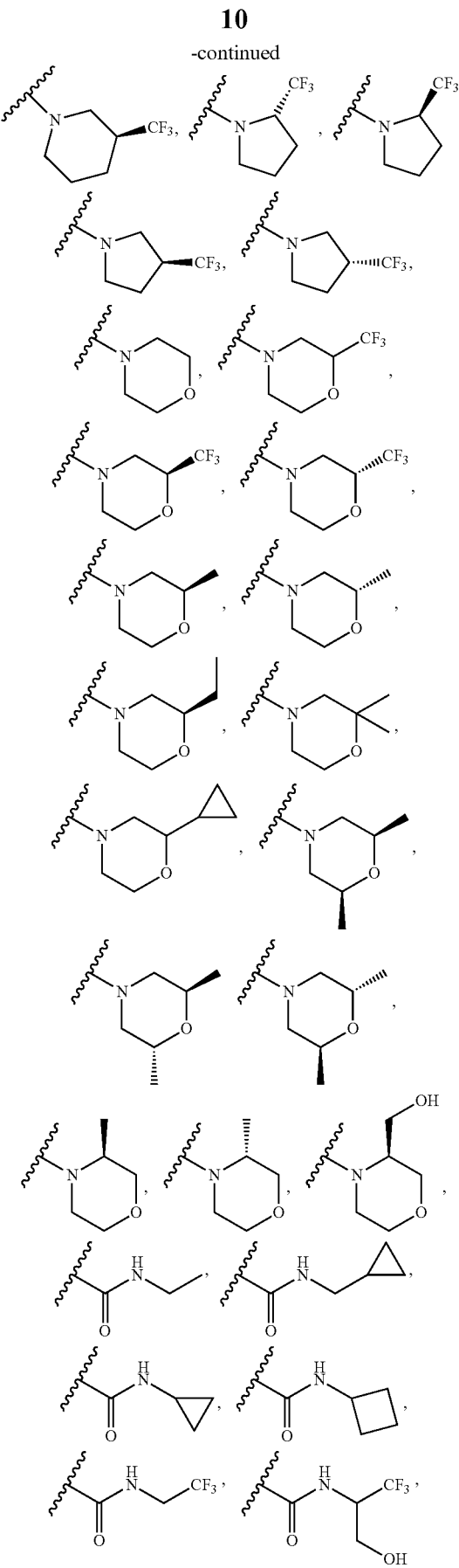

-continued
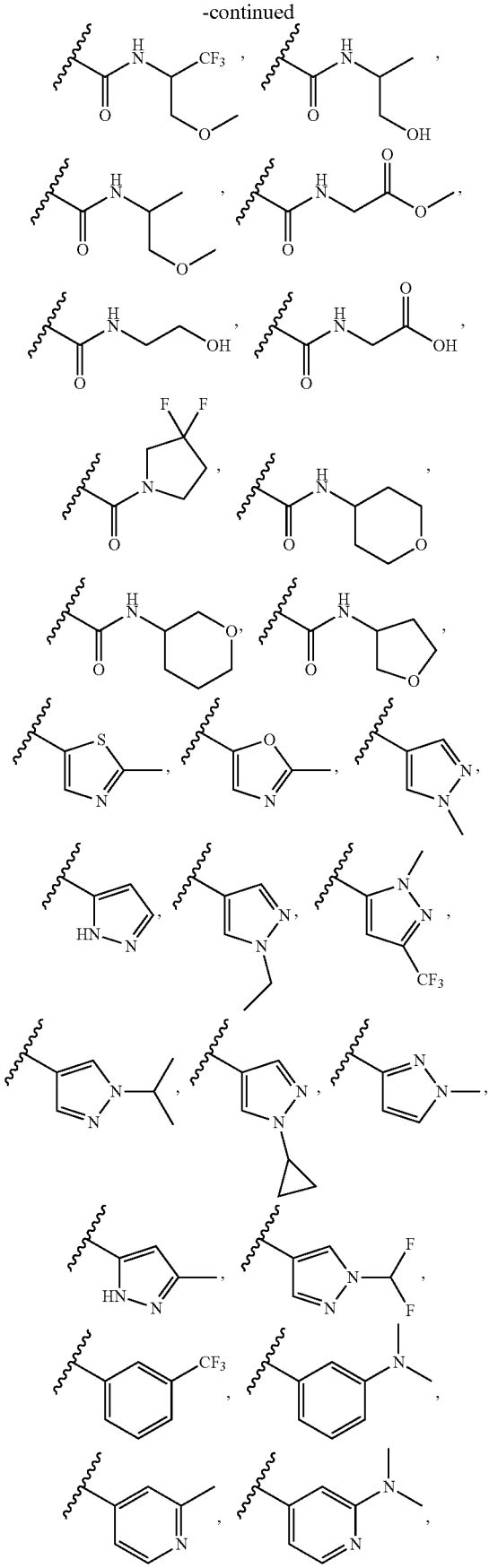
-continued
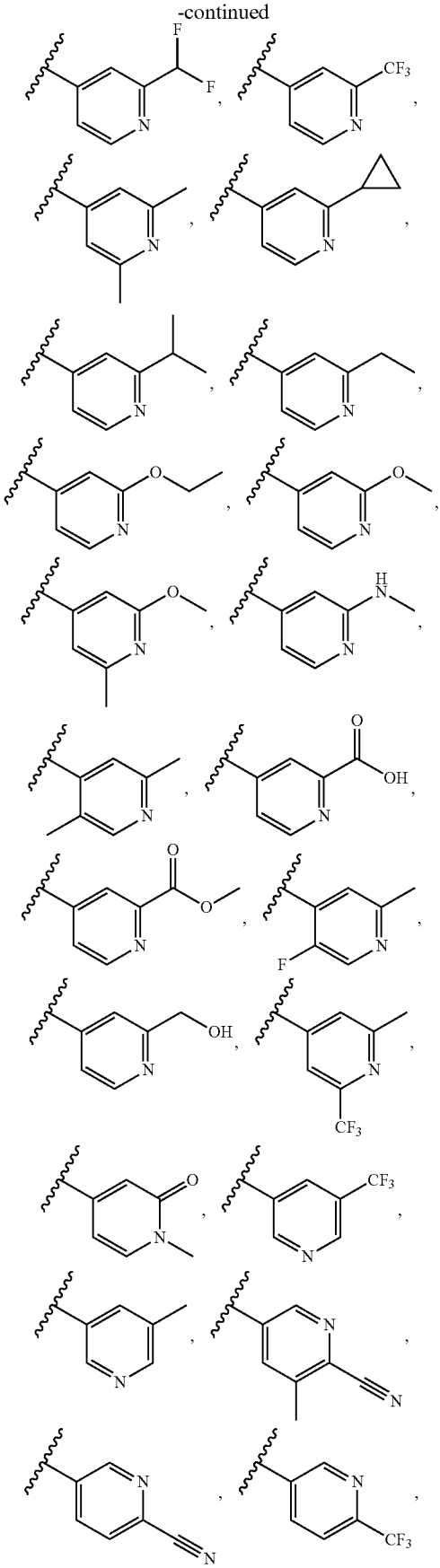

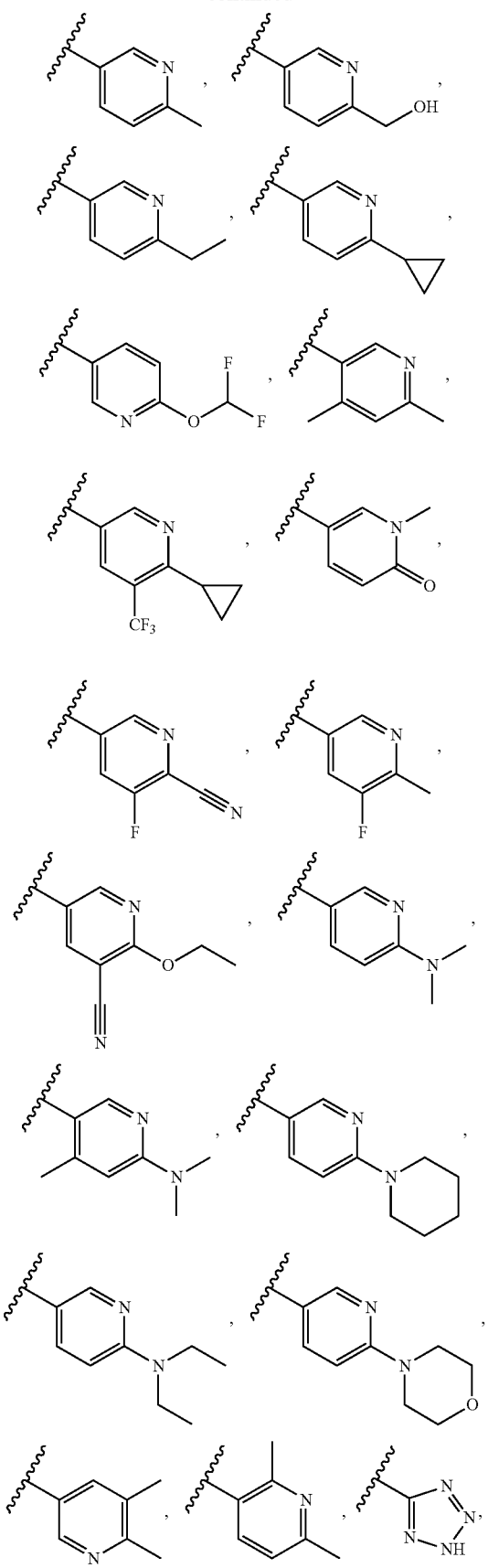
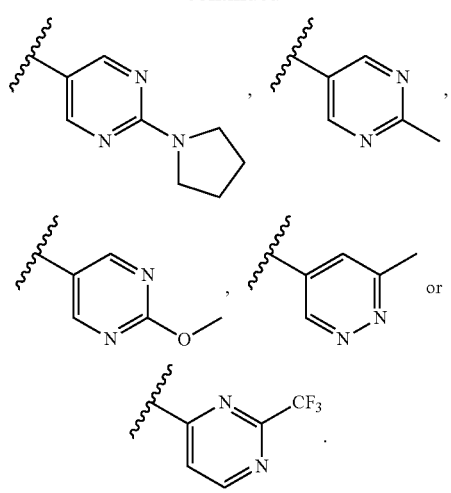
In another aspect, the present invention relates to compounds of Formulas (I) to (V), respectively, wherein $R^1$ is selected from:
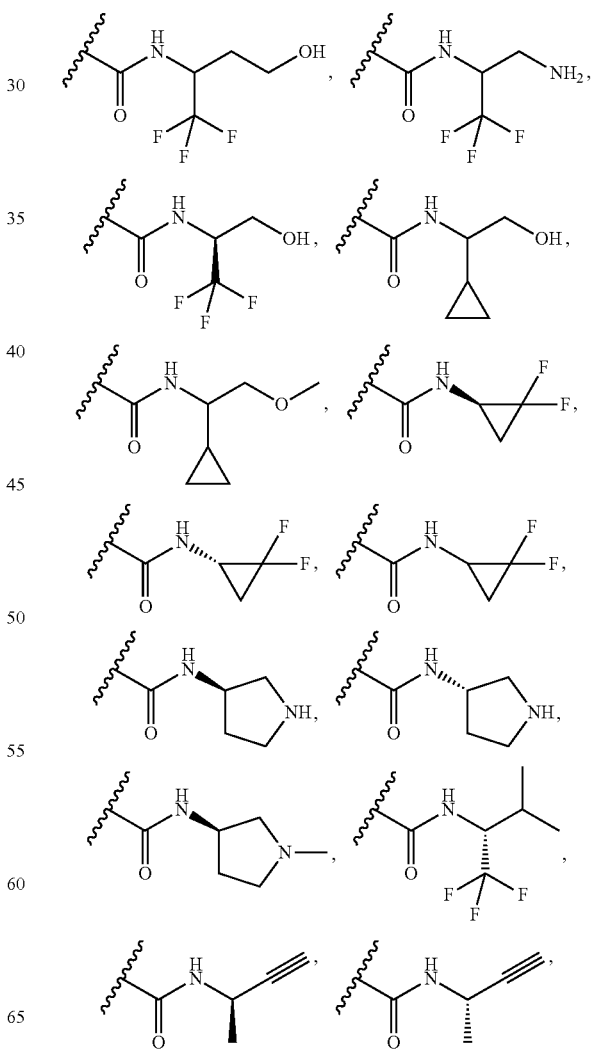

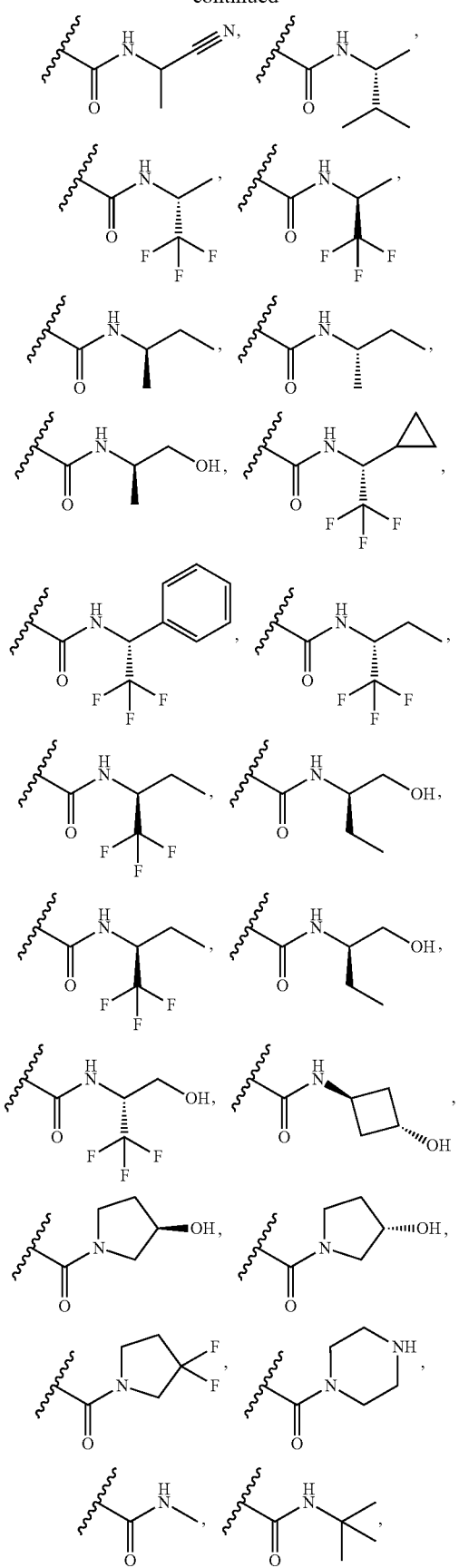
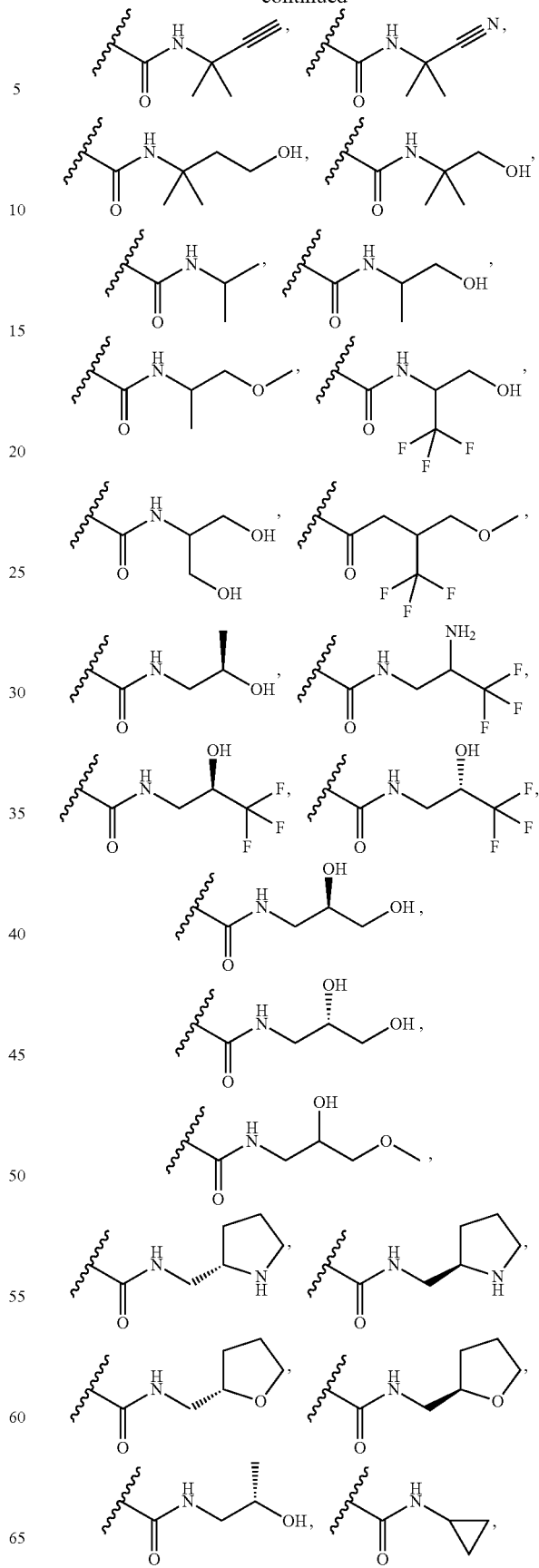

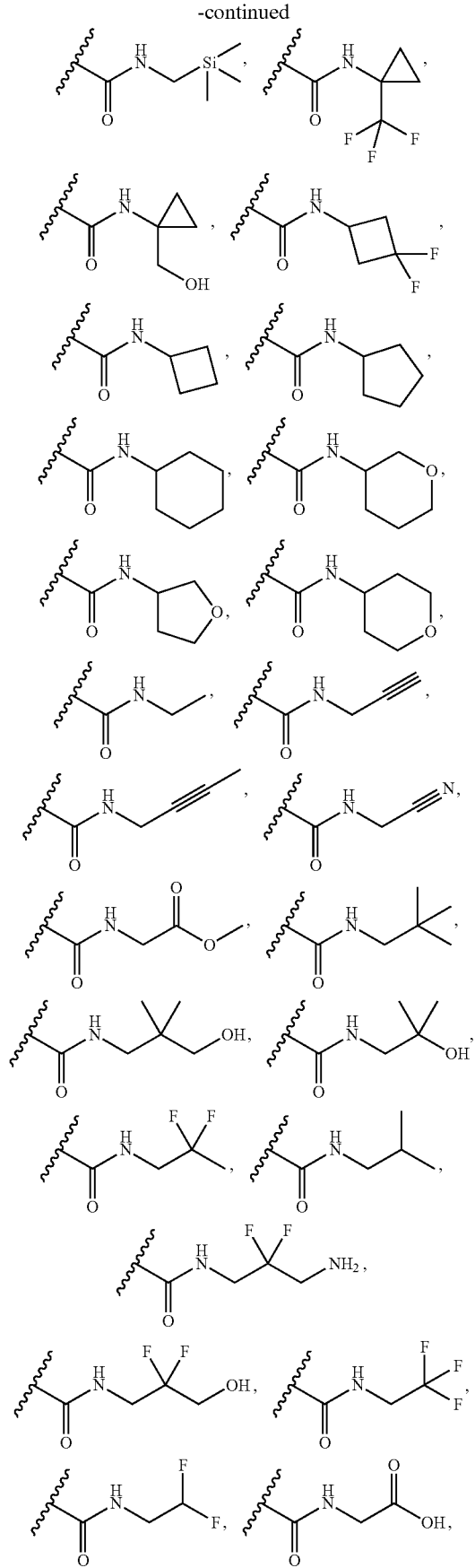
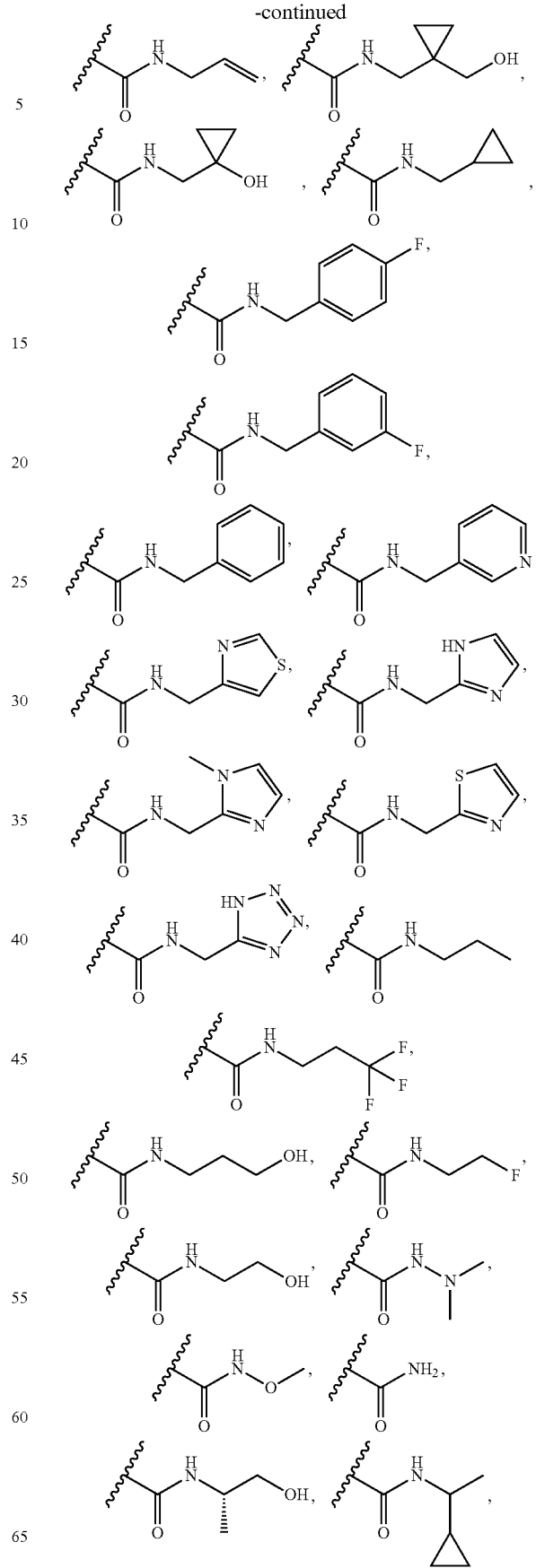

In another aspect, the present invention relates to compound(s) of Formulas (I) to (V), respectively, where $R^4$ is selected from:
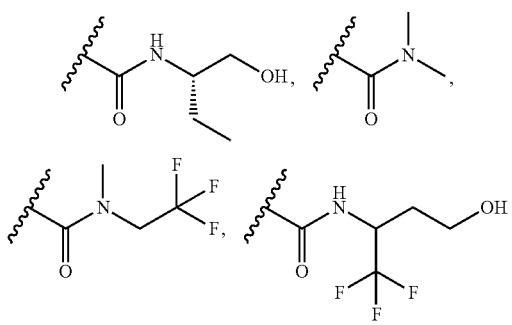

-continued
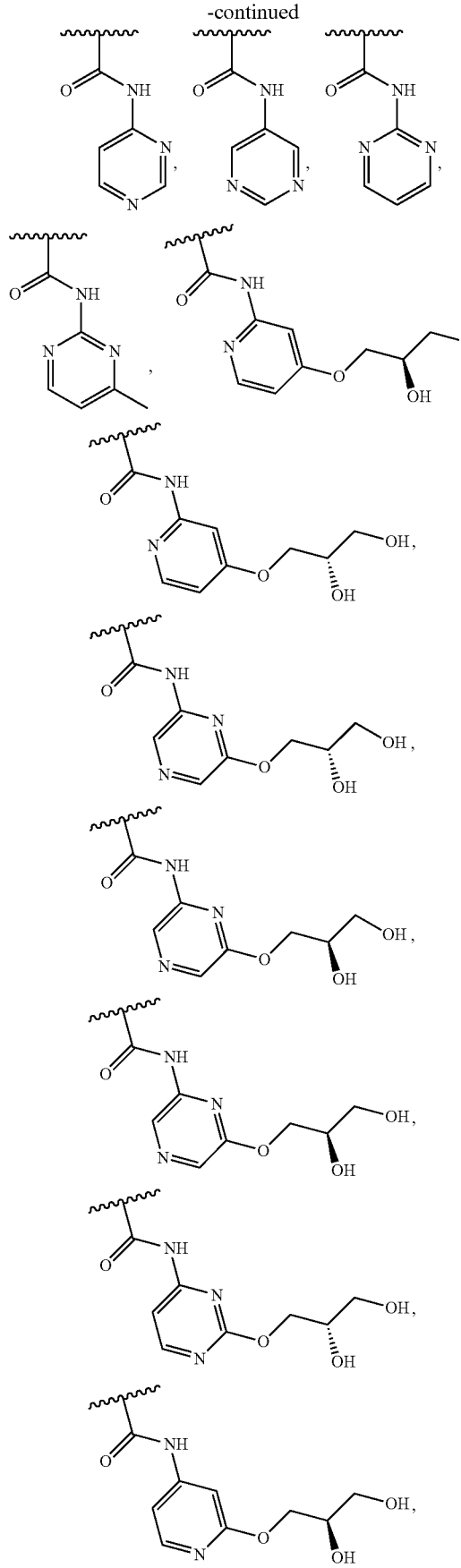
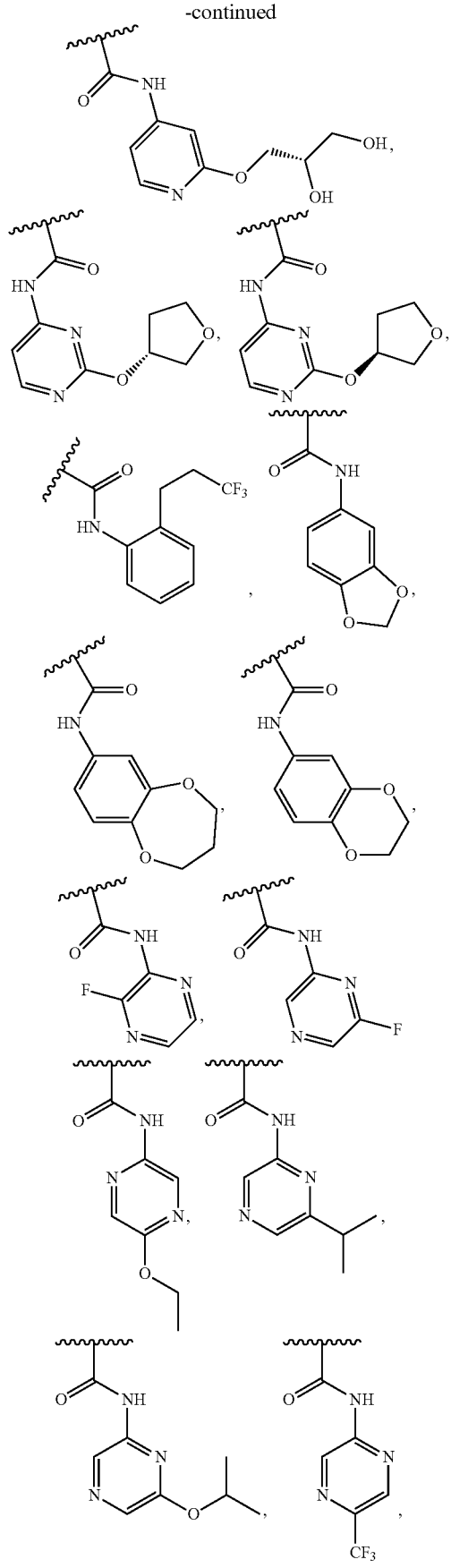

-continued
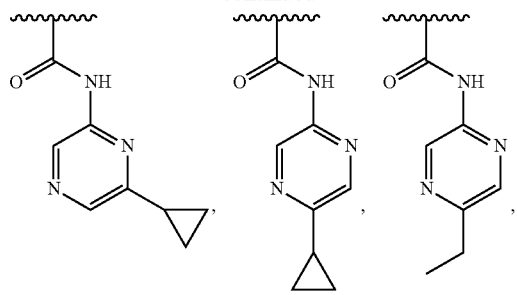
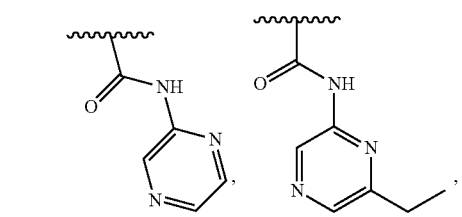
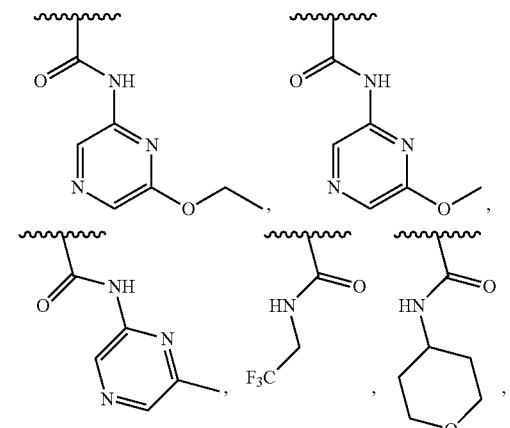
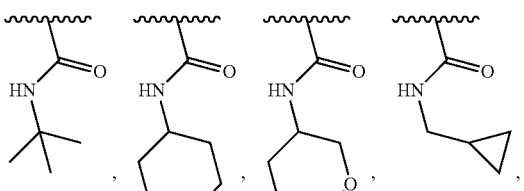
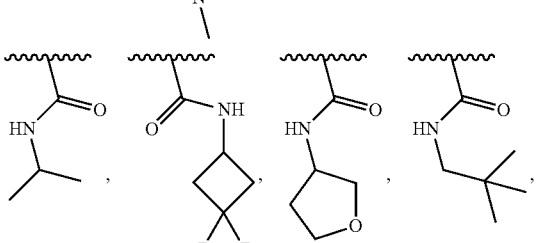
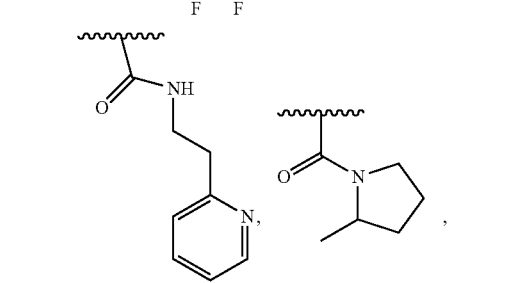
-continued
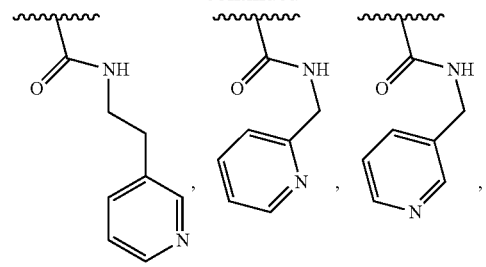
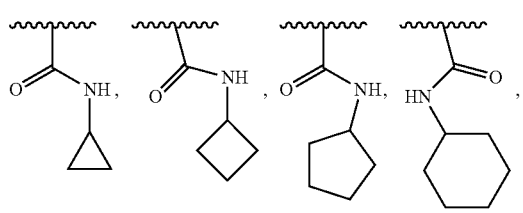
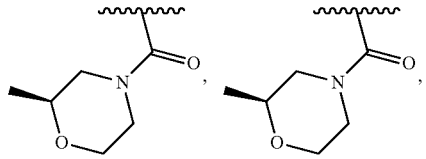
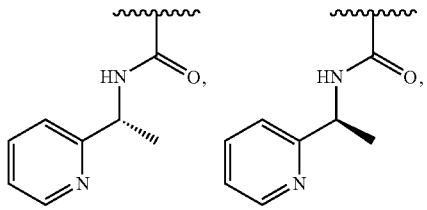
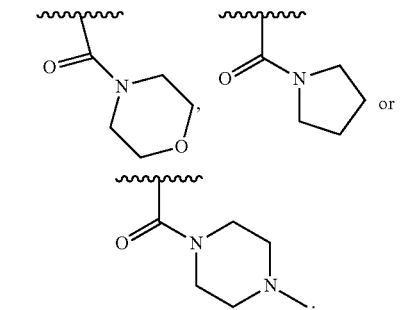
In another aspect, the present invention relates to compound(s) of Formulas (I) to (V), respectively, where $R^4$ is selected from:
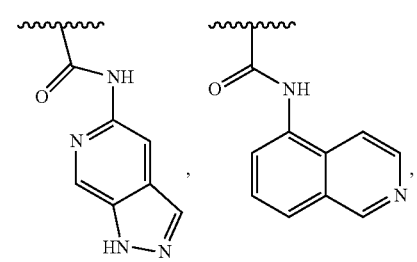

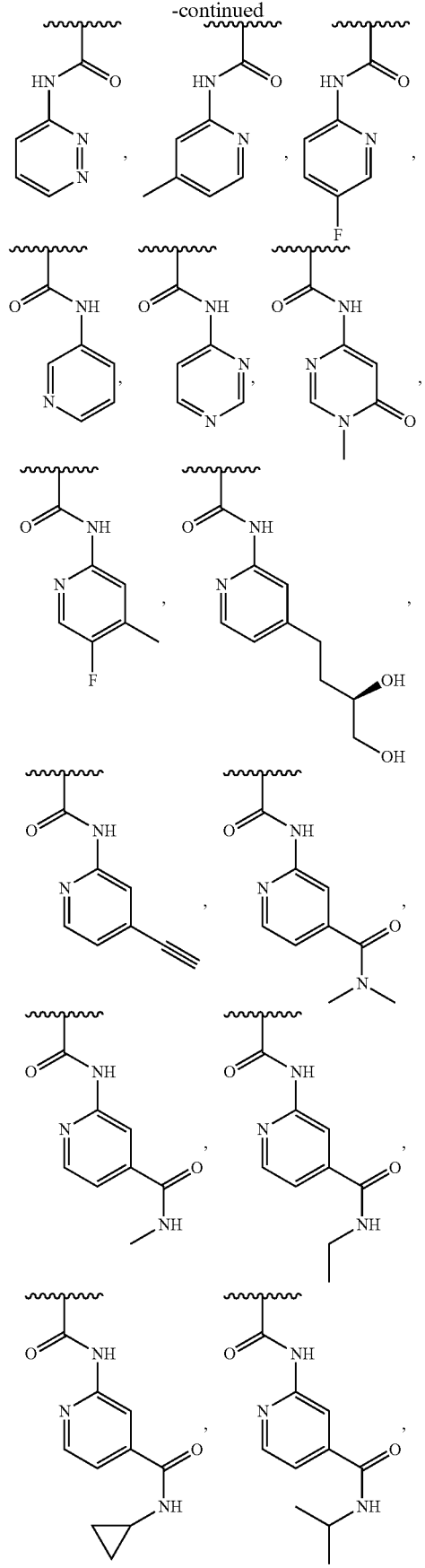
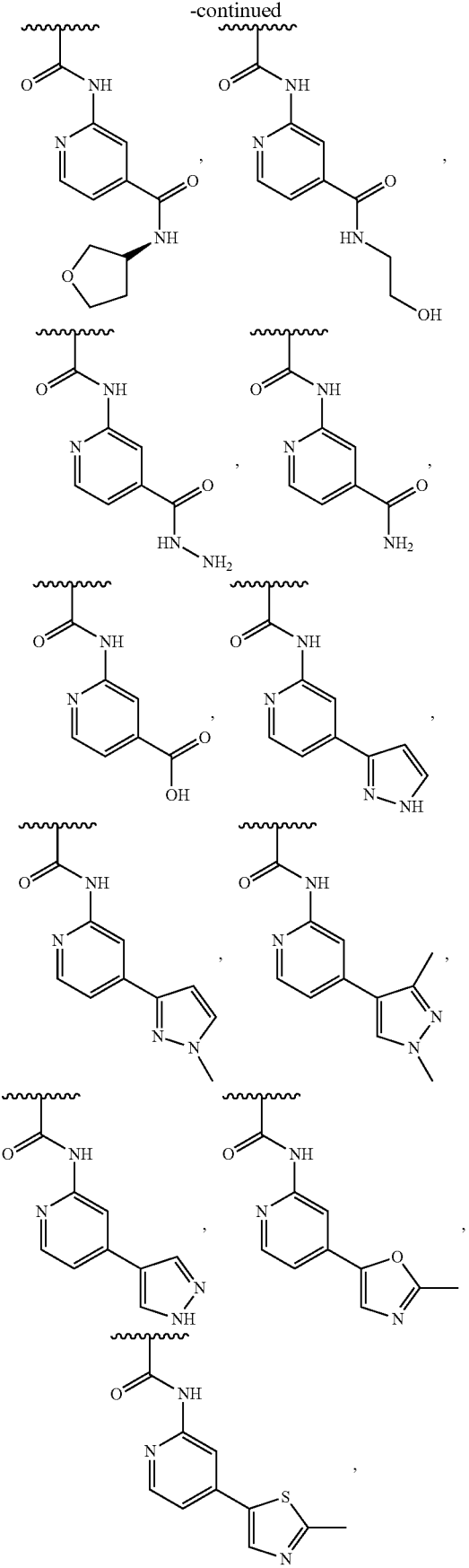

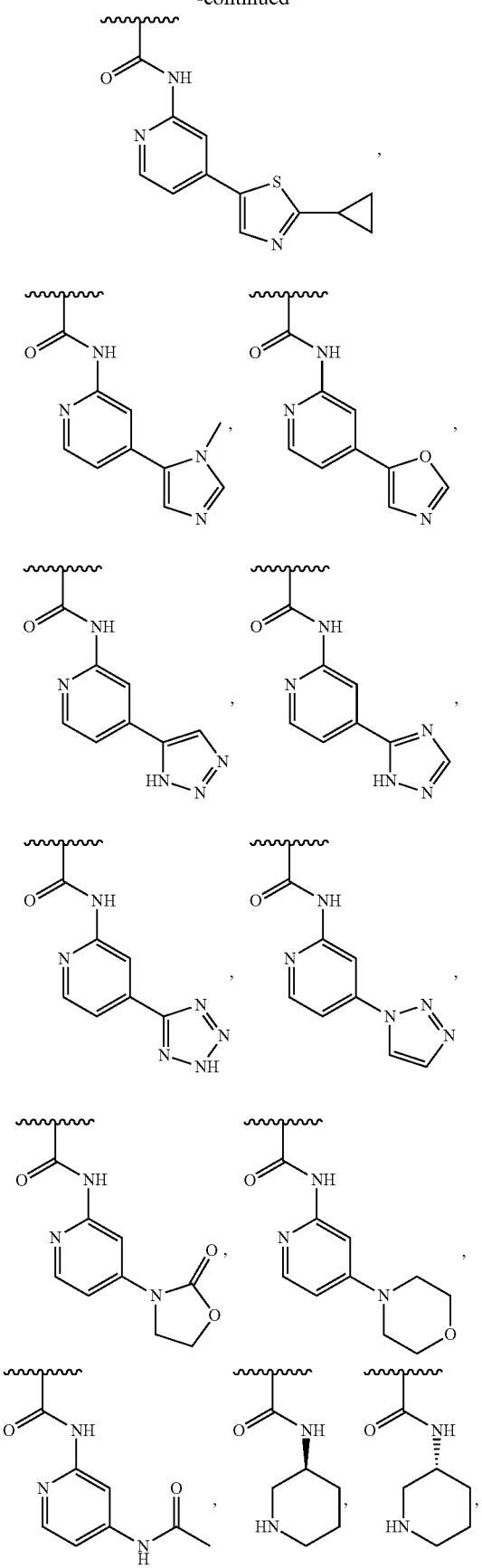
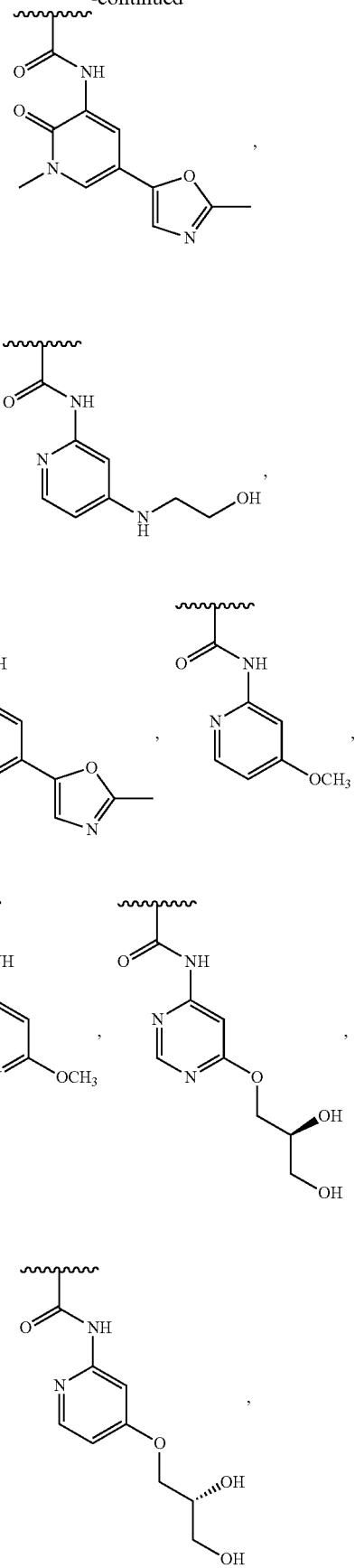

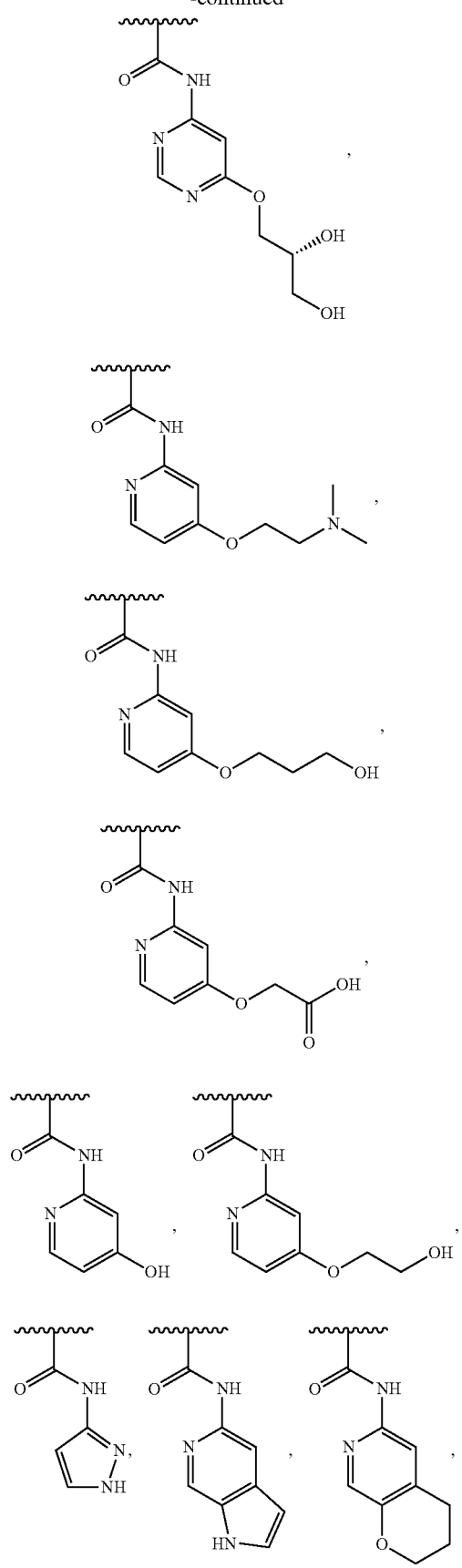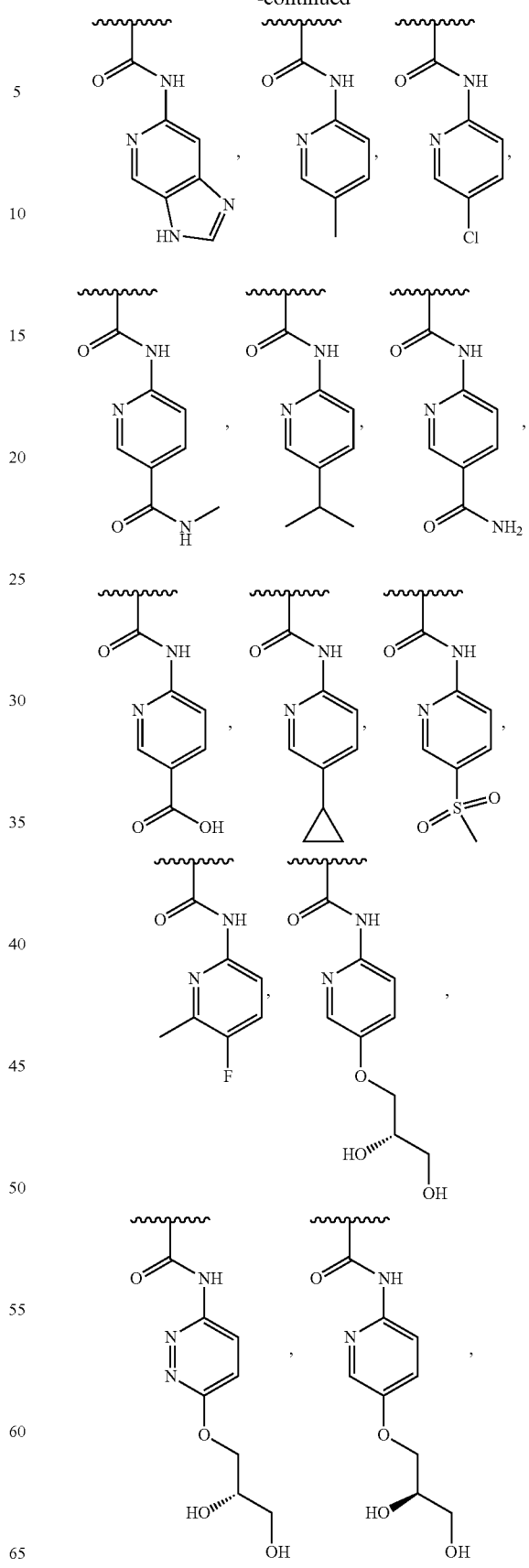

31
-continued
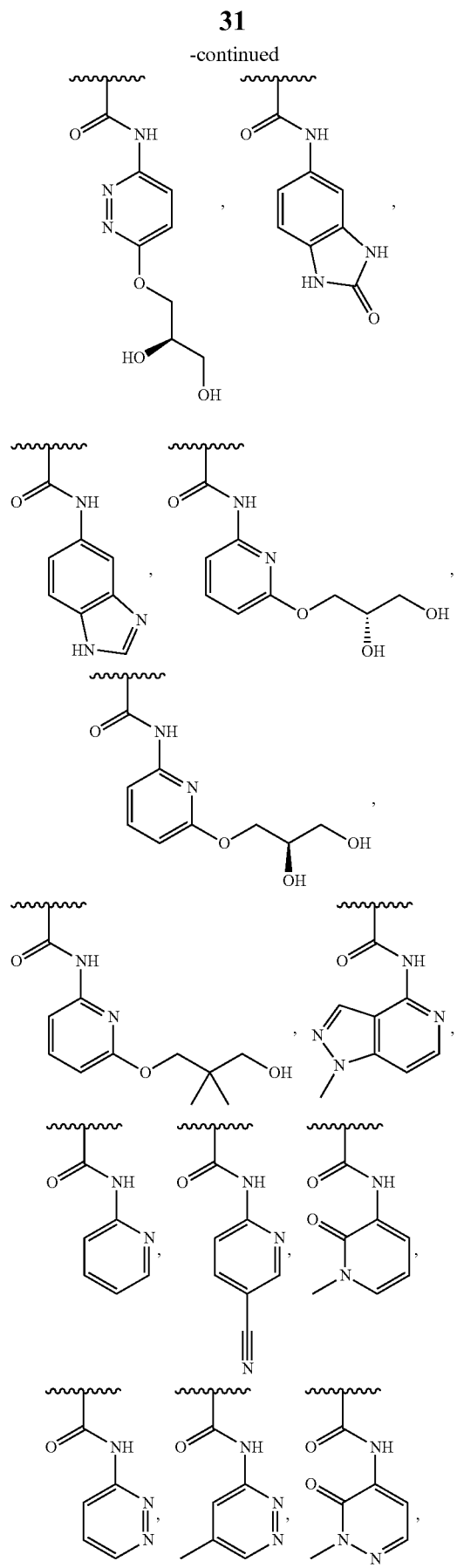
32
-continued
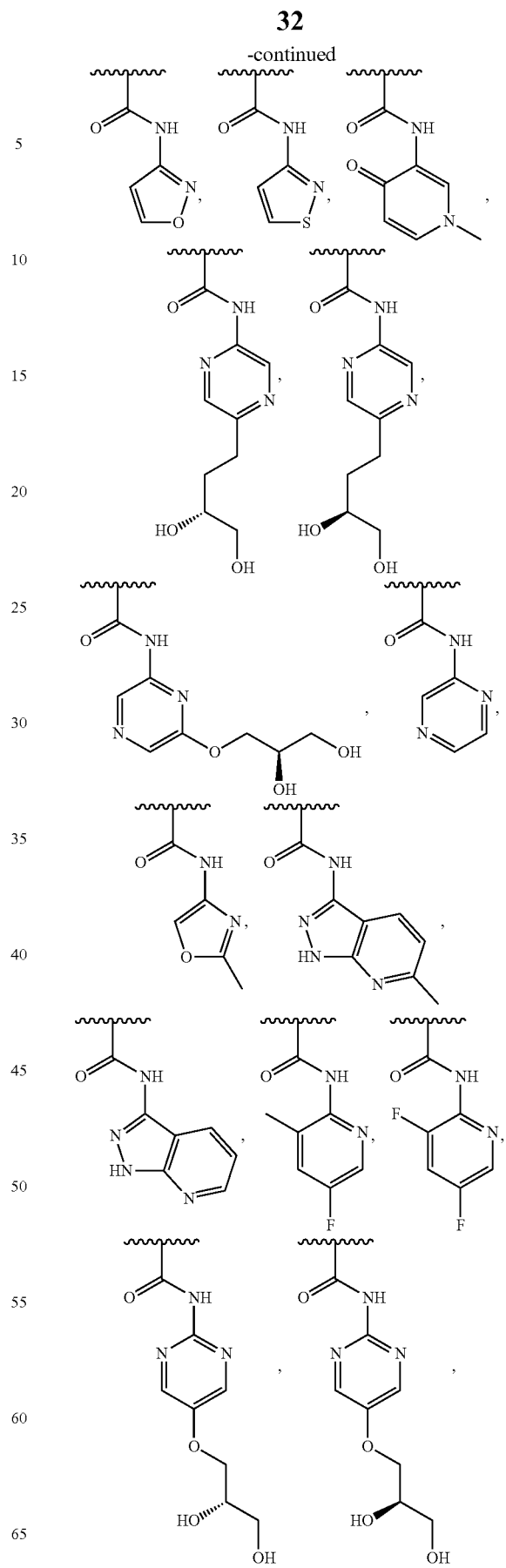

-continued

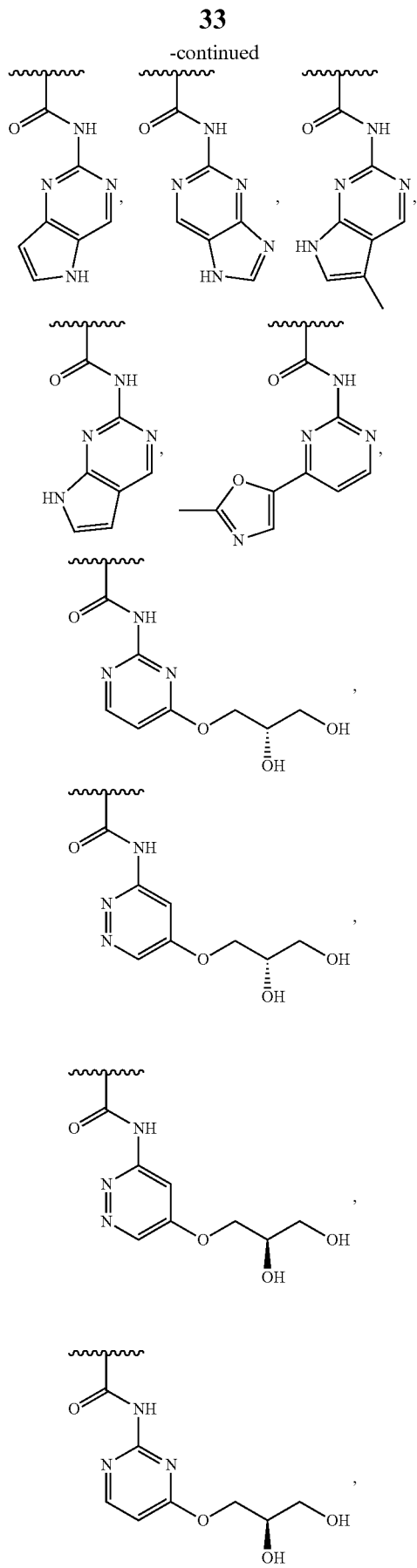

-continued

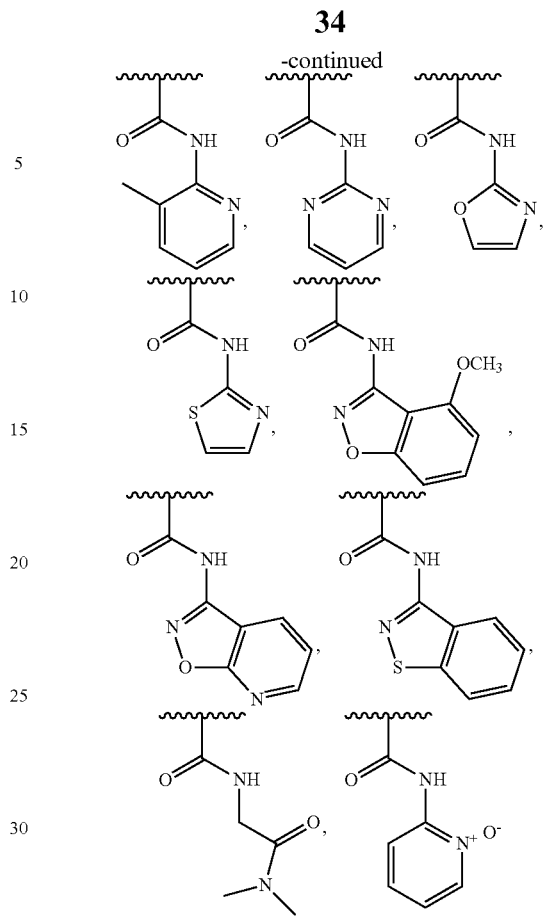

In another aspect, the present invention relates to a compound of Formula (III):

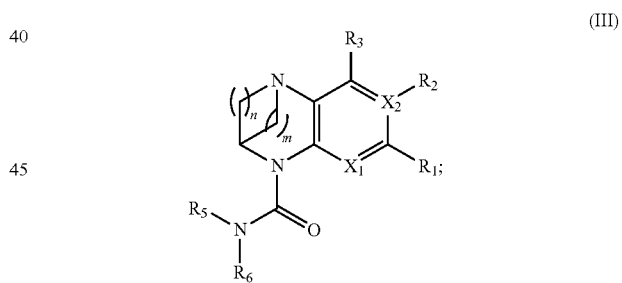

(III)

where:
X₁ or X₂ independently is selected from —N or —C;
where:
when X$_2$ is —N, R$_2$ is non-existent; or
when X$_2$ is —C, R$_2$ is as defined above;
R$^1$ is hydrogen, halogen, —CN, carbocyclyl, heterocyclyl, —N-substituted heterocyclyl, aryl, heteroaryl, —C(O)R$_a$ or —C(O)—NR$_b$R$_c$;
R$^2$ is halogen, -straight or branched C$_1$-C$_6$ alkyl, -straight or branched-C$_1$-C$_6$ haloalkyl, or —C(O)—NR$_b$R$_c$;
R$^3$ is hydrogen, halogen, -hydroxy, -straight or branched C$_1$-C$_6$ alkyl, or -straight or branched-C$_6$-C$_6$ haloalkyl;
each R$^5$ and R$^6$ independently is selected from hydrogen, -straight or branched C$_1$-C$_6$ alkyl, -straight or branched-C$_1$-C$_6$ haloalkyl, —C$_1$-C$_6$cycloalkyl, —(CH$_2$)$_x$C$_1$-C$_6$cycloalkyl, heterocyclyl, —N-heterocyclyl, aryl, heteroaryl, or —(CH$_2$)$_x$heteroaryl, —(CHR$_g$)$_x$heteroaryl;

wherein:
each $R^1$, $R^2$, $R^3$, $R^5$ and $R^6$ as defined above optionally is further substituted with one or more substituents selected from hydrogen, halogen, —OH, —(CH$_2$)$_x$OH, —C≡N, —NR$_d$R$_e$, -straight or branched C$_1$-C$_6$ alkyl, -straight or branched-C$_1$-C$_6$ haloalkyl, -straight or branched C$_1$-C$_6$ alkoxy, -straight or branched C$_1$-C$_6$ haloalkoxy, —O-straight or branched-C$_1$-C$_6$ haloalkyl, —C$_1$-C$_6$ cycloalkyl, —(CH$_2$)$_x$-cycloalkyl, heterocyclyl, aryl, -heteroaryl, —(CH$_2$)$_x$-heteroaryl, —O—(CH$_2$)$_x$CH(OH)CH$_2$(OH), or —C(O)OR$_f$;
each R$_a$, R$_b$, R$_c$, R$_d$, R$_e$, R$_f$ or R$_g$ as defined above independently is selected from hydrogen, -straight or branched C$_1$-C$_6$ alkyl, -straight or branched-C$_1$-C$_6$ haloalkyl, —C$_1$-C$_6$-cycloalkyl, —(CH$_2$)$_x$C$_1$-C$_6$-cycloalkyl, heterocyclyl, —N— heterocyclyl, aryl, heteroaryl, or —(CH$_2$)$_x$heteroaryl;
where:
each R$_a$, R$_b$, R$_c$ R$_d$, R$_e$, R$_f$ or R$_g$ as defined above optionally is further substituted with one or more substituents selected from hydrogen, halogen, —OH, —(CH$_2$)$_x$OH, —C≡N, NR$_h$R$_i$, -straight or branched C$_1$-C$_6$ alkyl, -straight or branched-C$_1$-C$_6$ haloalkyl, -straight or branched C$_1$-C$_6$ alkoxy, -straight or branched-C$_1$-C$_6$ haloalkoxy, —C$_1$-C$_6$ cycloalkyl, —(CH$_2$)$_x$-cycloalkyl, heterocyclyl, -heterocyclyl, —O-heterocyclyl, aryl, -heteroaryl, —(CH$_2$)$_x$-heteroaryl, —O—(CH$_2$)$_x$CH(OH)CH$_2$(OH), —(CH$_2$)$_x$—OH, or —C(O)OR$_j$;
where:
each R$_h$, R$_i$ and R$_j$ independently is selected from hydrogen, -straight or branched C$_1$-C$_6$ alkyl or -straight or branched-C$_1$-C$_6$ haloalkyl;
m is an integer from 1 to 3;
n is an integer selected from 2 to 3;
x is 0 or an integer from 1 to 6; or
a pharmaceutically salt thereof.

In another aspect, the present invention relates to a compound of the present invention, where n is 2 or 3 and m is 1.

In another aspect, the present invention relates to a compound of Formula (IV):

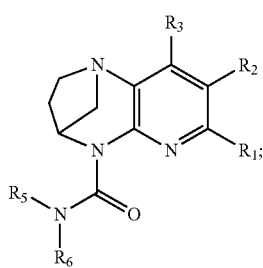

(IV)

where:
$R^1$ is hydrogen, halogen, —CN, carbocyclyl, heterocyclyl, —N-substituted heterocyclyl, aryl, heteroaryl, —C(O)R$_a$ or —C(O)—NR$_b$R$_c$;
$R^2$ is halogen, -straight or branched C$_1$-C$_6$ alkyl, -straight or branched-C$_1$-C$_6$ haloalkyl, or —C(O)—NR$_b$R$_c$;
$R^3$ is hydrogen, halogen, -hydroxy, -straight or branched C$_1$-C$_6$ alkyl, or -straight or branched-C$_1$-C$_6$ haloalkyl;
each $R^5$ and $R^6$ independently is selected from hydrogen, -straight or branched C$_1$-C$_6$ alkyl, -straight or branched-C$_1$-C$_6$ haloalkyl, —C$_1$-C$_6$cycloalkyl, —(CH$_2$)$_x$C$_1$-C$_6$cycloalkyl, heterocyclyl, —N-heterocyclyl, aryl, heteroaryl, or —(CH$_2$)$_x$heteroaryl, —(CHR$_g$)$_x$heteroaryl;
where:
each $R^1$, $R^2$, $R^3$, $R^5$ and $R^6$ as defined above optionally is further substituted with one or more substituents selected from hydrogen, halogen, —OH, —(CH$_2$)$_x$OH, —C≡N, —NR$_d$R$_e$, -straight or branched C$_1$-C$_6$ alkyl, -straight or branched-C$_1$-C$_6$ haloalkyl, -straight or branched C$_1$-C$_6$ alkoxy, -straight or branched C$_1$-C$_6$ haloalkoxy, —O-straight or branched-C$_1$-C$_6$ haloalkyl, —C$_1$-C$_6$ cycloalkyl, —(CH$_2$)$_x$-cycloalkyl, heterocyclyl, aryl, -heteroaryl, —(CH$_2$)$_x$-heteroaryl, —O—(CH$_2$)$_x$CH(OH)CH$_2$(OH), or —C(O)OR$_f$;
each R$_a$, R$_b$, R$_c$, R$_d$, R$_e$, R$_f$ or R$_g$ as defined above independently is selected from hydrogen, -straight or branched C$_1$-C$_6$ alkyl, -straight or branched-C$_1$-C$_6$ haloalkyl, —C$_1$-C$_6$-cycloalkyl, —(CH$_2$)$_x$C$_1$-C$_6$-cycloalkyl, heterocyclyl, —N— heterocyclyl, aryl, heteroaryl, or —(CH$_2$)$_x$heteroaryl;
where:
each R$_a$, R$_b$, R$_c$ R$_d$, R$_e$, R$_f$ or R$_g$ as defined above optionally is further substituted with one or more substituents selected from hydrogen, halogen, —OH, —(CH$_2$)$_x$OH, —C≡N, —NR$_h$R$_i$, -straight or branched C$_1$-C$_6$ alkyl, -straight or branched-C$_1$-C$_6$ haloalkyl, -straight or branched C$_1$-C$_6$ alkoxy, -straight or branched-C$_1$-C$_6$ haloalkoxy, —C$_1$-C$_6$ cycloalkyl, —(CH$_2$)$_x$-cycloalkyl, heterocyclyl, -heterocyclyl, —O-heterocyclyl, aryl, -heteroaryl, —(CH$_2$)$_x$-heteroaryl, —O—(CH$_2$)$_x$CH(OH)CH$_2$(OH), —(CH$_2$)$_x$—OH, or —C(O)OR$_j$;
where:
each R$_h$, R$_i$ and R$_j$ independently is selected from hydrogen, -straight or branched C$_1$-C$_6$ alkyl or -straight or branched-C$_1$-C$_6$ haloalkyl;
m is an integer from 1 to 3;
n is an integer selected from 2 to 3;
x is 0 or an integer from 1 to 6; or
a pharmaceutically salt thereof.

The present invention relates to a compound of Formula (V):

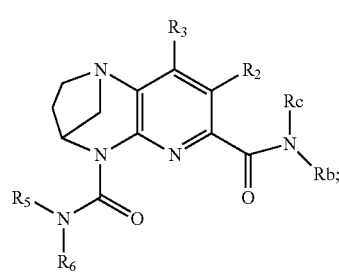

(IV)

wherein:
$R^2$ is halogen, -straight or branched C$_1$-C$_6$ alkyl, -straight or branched-C$_1$-C$_6$ haloalkyl, or —C(O)—NR$_b$R$_c$;
$R^3$ is hydrogen, halogen, -hydroxy, -straight or branched C$_1$-C$_6$ alkyl, or -straight or branched-C$_1$-C$_6$ haloalkyl;
each $R^5$ and $R^6$ independently is selected from hydrogen, -straight or branched C$_1$-C$_6$ alkyl, -straight or branched-C$_1$-C$_6$ haloalkyl, —C$_1$-C$_6$cycloalkyl, —(CH$_2$)$_x$C$_1$-C$_6$cycloalkyl, heterocyclyl, —N-heterocyclyl, aryl, heteroaryl, or —(CH$_2$)$_x$heteroaryl, —(CHR$_g$)$_x$heteroaryl;

wherein:
each $R^1$, $R^2$, $R^3$, $R^5$ and $R^6$ as defined above optionally is further substituted with one or more substituents selected from hydrogen, halogen, —OH, —$(CH_2)_xOH$, —C≡N, —$NR_dR_e$, -straight or branched $C_1$-$C_6$ alkyl, -straight or branched-$C_1$-$C_6$ haloalkyl, -straight or branched $C_1$-$C_6$ alkoxy, -straight or branched $C_1$-$C_6$ haloalkoxy, —O-straight or branched-$C_1$-$C_6$ haloalkyl, —$C_1$-$C_6$ cycloalkyl, —$(CH_2)_x$-cycloalkyl, heterocyclyl, aryl, -heteroaryl, —$(CH_2)_x$-heteroaryl, —O—$(CH_2)_xCH(OH)CH_2(OH)$, or —$C(O)OR_f$;

each $R_a$, $R_b$, $R_c$, $R_d$, $R_e$, $R_f$ or $R_g$ as define above independently is selected from hydrogen, -straight or branched $C_1$-$C_6$ alkyl, -straight or branched-$C_1$-$C_6$ haloalkyl, —$C_1$-$C_6$-cycloalkyl, —$(CH_2)_xC_1$-$C_6$-cycloalkyl, heterocyclyl, —N— heterocyclyl, aryl, heteroaryl, or —$(CH_2)_x$heteroaryl;

wherein:
each $R_a$, $R_b$, $R_c$, $R_d$, $R_e$, $R_f$ or $R_g$ as defined above optionally is further substituted with one or more substituents selected from hydrogen, halogen, —OH, —$(CH_2)_xOH$, —C≡N, —$NR_hR_i$, -straight or branched $C_1$-$C_6$ alkyl, -straight or branched-$C_1$-$C_6$ haloalkyl, -straight or branched $C_1$-$C_6$ alkoxy, -straight or branched-$C_1$-$C_6$ haloalkoxy, —$C_1$-$C_6$ cycloalkyl, —$(CH_2)_x$-cycloalkyl, heterocyclyl, -heterocyclyl, —O-heterocyclyl, aryl, -heteroaryl, —$(CH_2)_x$-heteroaryl, —O—$(CH_2)_xCH(OH)CH_2(OH)$, —$(CH_2)_x$—OH, or —$C(O)OR_j$;

wherein:
each $R_h$, $R_i$ and $R_j$ independently is selected from hydrogen, -straight or branched $C_1$-$C_6$ alkyl or -straight or branched-$C_1$-$C_6$ haloalkyl;

m is an integer from 1 to 3;
n is an integer selected from 2 to 3;
x is 0 or an integer from 1 to 6; or
a pharmaceutically salt thereof.

In another aspect, the present invention relates to a compound which is a corresponding analog or derivative of the present invention s (i.e., with hydrogen substitution at the $R^2$ position):

Terms and Definitions

Section 1

Certain compounds of the present invention may exist in particular geometric or stereoisomeric forms. The present invention contemplates all such compounds, including cis- and trans-isomers, (R)- and (S)-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

The compounds and salts thereof described herein can also be present as the corresponding hydrates (e.g., hemihydrate, monohydrate, dihydrate, trihydrate, tetrahydrate) or solvates. Suitable solvents for preparation of solvates and hydrates can generally be selected by a skilled artisan.

The compounds and salts thereof can be present in amorphous or crystalline (including co-crystalline and polymorph) forms.

Sirtuin-modulating compounds of the invention advantageously modulate the level and/or activity of a sirtuin protein, particularly the deacetylase activity of the sirtuin protein.

Separately or in addition to the above properties, certain sirtuin-modulating compounds of the invention do not substantially have one or more of the following activities: inhibition of PI3-kinase, inhibition of aldoreductase, inhibition of tyrosine kinase, transactivation of EGFR tyrosine kinase, coronary dilation, or spasmolytic activity, at concentrations of the compound that are effective for modulating the deacetylation activity of a sirtuin protein (e.g., such as a SIRT1 and/or a SIRT3 protein).

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_4$ straight chained or branched alkyl group is also referred to as a "lower alkyl" group.

In any of the preceding embodiments, a $C_1$-$C_4$ alkoxy-substituted group may include one or more alkoxy substituents such as one, two or three methoxy groups or a methoxy group and an ethoxy group, for example. Exemplary $C_1$-$C_4$ alkoxy substituents include methoxy, ethoxy, isopropoxy, and tert-butoxy.

In any of the preceding embodiments, a hydroxy-substituted group may include one or more hydroxy substituents, such as two or three hydroxy groups.

A "halogen" refers to F, Cl, Br or I.

A "halogen-substitution" or "halo" substitution designates replacement of one or more hydrogens with F, Cl, Br or I.

In one aspect, the term haloalkyl is defined as any alkyl radical having one or more hydrogen atoms replaced by a halogen atom. In any of the preceding embodiments, a "halo-substituted" group includes from one halo substituent up to perhalo substitution. Exemplary halo-substituted $C_1$-$C_4$ alkyl includes $CFH_2$, $CClH_2$, $CBrH_2$, $CF_2H$, $CCl_2H$, $CBr_2H$, $CF_3$, $CCl_3$, $CBr_3$, $CH_2CH_2F$, $CH_2CH_2Cl$, $CH_2CH_2Br$, $CH_2CHF_2$, $CHFCH_3$, $CHClCH_3$, $CHBrCH_3$, $CF_2CHF_2$, $CF_2CHCl_2$, $CF_2CHBr_2$, $CH(CF_3)_2$, and $C(CF_3)_3$. Perhalo-substituted $C_1$-$C_4$ alkyl, for example, includes $CF_3$, $CCl_3$, $CBr_3$, $CF_2CF_3$, $CCl_2CF_3$ and $CBr_2CF_3$.

The terms "alkenyl" ("alkene") and "alkynyl" ("alkyne") refer to unsaturated aliphatic groups analogous in length and possible substitution to the alkyl groups described above, but that contain at least one double or triple bond respectively.

In any of the preceding embodiments, a "carbocycle" group may refer to a monocyclic carbocycle embodiment and/or a polycyclic carbocycle embodiment, such as a fused, bridged or bicyclic carbocycle embodiment. "Carbocycle" groups of the invention may further refer to an aromatic carbocycle embodiment and/or a non-aromatic carbocycle embodiment, or, in the case of polycyclic embodiments, a carbocycle having both one or more aromatic rings and/or one or more non-aromatic rings. Polycyclic carbocycle embodiments may be a bicyclic ring, a fused ring or a bridged bicycle. Non-limiting exemplary carbocycles include phenyl, cyclohexane, cyclopentane, or cyclohexene, amantadine, cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene, adamantane, decalin, naphthalene, 1,2,3,4-tetrahydronaphthalene, norbornane, decalin, spiropentane, memantine, biperiden, rimantadine, camphor, cholesterol, 4-phenylcyclcohexanol, bicyclo[4.2.0]octane, memantine and 4,5,6,7-tetrahydro-1H-indene and bicyclo[4.1.0]hept-3-ene.

In any of the preceding embodiments, a "heterocycle" group may refer to a monocyclic heterocycle embodiment and/or a polycyclic heterocycle embodiment, such as a fused, bridged or bicyclic heterocycle embodiment. "Heterocycle" groups of the invention may further refer to an aromatic heterocycle embodiment and/or a non-aromatic heterocycle embodiment, or, in the case of polycyclic embodiments, a heterocycle having both one or more aromatic rings and/or one or more non-aromatic rings. Polycyclic heterocycle embodiments may be a bicyclic ring, a fused ring or a bridged bicycle. Non-limiting exemplary heterocycles include pyridyl, pyrrolidine, piperidine, piperazine, pyrrolidine, morpholine, pyrimidine, benzofuran, indole, quinoline, lactones, lactams, benzodiazepine, indole, quinoline, purine, adenine, guanine, 4,5,6,7-tetrahydrobenzo[d]thiazole, hexamine and methenamine.

"Alkenyl" refers to an unsaturated hydrocarbon chain having the specified number of member carbon atoms and having one or more carbon-carbon double bonds within the chain. For example, C2-C6 alkenyl refers to an alkenyl group having from 2 to 6 member carbon atoms. In certain embodiments, alkenyl groups have one carbon-carbon double bond within the chain. In other embodiments, alkenyl groups have more than one carbon-carbon double bond within the chain. Alkenyl groups may be optionally substituted with one or more substituents as defined herein. Alkenyl groups may be straight or branched. Representative branched alkenyl groups have one, two, or three branches. Alkenyl includes ethylenyl, propenyl, butenyl, pentenyl, and hexenyl.

"Alkoxy" refers to an alkyl moiety attached through an oxygen bridge (i.e. a —O—C1-C6 alkyl group wherein C1-C6 is defined herein). Examples of such groups include methoxy, ethoxy, propoxy, butoxy, pentoxy and hexoxy.

"Alkynyl" refers to an unsaturated hydrocarbon chain having the specified number of member carbon atoms and having one or more carbon-carbon triple bonds within the chain. For example, C2-C6 alkynyl refers to an alkynyl group having from 2 to 6 member atoms. In certain embodiments alkynyl groups have one carbon-carbon triple bond within the chain. In other embodiments, alkynyl groups have more than one carbon-carbon triple bond within the chain. For the sake of clarity, unsaturated hydrocarbon chains having one or more carbon-carbon triple bond within the chain and one or more carbon-carbon double bond within the chain are referred to as alkynyl groups. Alkynyl groups may be optionally substituted with one or more substituents as defined herein. Representative branched alkynyl groups have one, two, or three branches. Alkynyl includes ethynyl, propynyl, butynyl, pentynyl, and hexynyl.

The term "aromatic carbocycle" refers to an aromatic hydrocarbon ring system containing at least one aromatic ring. The ring may be fused or otherwise attached to other aromatic carbocyclic rings or non-aromatic carbocyclic rings. Examples of aromatic carbocycle groups include carbocyclic aromatic groups such as phenyl, naphthyl, and anthracyl.

"Azabicyclo" refers to a bicyclic molecule that contains a nitrogen atom in the ring skeleton. The two rings of the bicycle may be fused at two mutually bonded atoms, e.g., indole, across a sequence of atoms, e.g., azabicyclo[2.2.1]heptane, or joined at a single atom, e.g., spirocycle.

"Bicycle" or "bicyclic" refers to a two-ring system in which one, two or three or more atoms are shared between the two rings. Bicycle includes fused bicycles in which two adjacent atoms are shared by each of the two rings, e.g., decalin, indole. Bicycle also includes spiro bicycles in which two rings share a single atom, e.g., spiro[2.2]pentane, 1-oxa-6-azaspiro[3.4]octane. Bicycle further includes bridged bicycles in which at least three atoms are shared between two rings, e.g., norbornane.

"Bridged bicycle" compounds are bicyclic ring systems in which at least three atoms are shared by both rings of the system, i.e., they include at least one bridge of one or more atoms connecting two bridgehead atoms. Bridged azabicyclo refers to a bridged bicyclic molecule that contains a nitrogen atom in at least one of the rings.

The term "Boc" refers to a tert-butyloxycarbonyl group (a common amine protecting group).

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from non-aromatic and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from non-aromatic rings. In an exemplary embodiment, an aromatic ring, e.g., phenyl, may be fused to a non-aromatic or aromatic ring, e.g., cyclohexane, cyclopentane, or cyclohexene. Any combination of non-aromatic and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon ring having the specified number of member carbon atoms which is completely saturated (non-aromatic). Typically, a cycloalkyl group has from 3 to about 10 carbon atoms, more typically 3 to 8 carbon atoms unless otherwise defined. Cycloalkyl groups are monocyclic ring systems. For example, C3-C6 cycloalkyl refers to a cycloalkyl group having from 3 to 6 member atoms. Cycloalkyl groups may be optionally substituted with one or more substituents as defined herein. Cycloalkyl includes cyclopropyl, cyclobutyl, cyclopentyl, and cyclohexyl.

A "cycloalkenyl" group is a cyclic hydrocarbon ring containing one or more double bonds within the ring. For example, C3-C6 cycloalkenyl refers to a cycloalkenyl group having from 3 to 6 member carbon atoms. In certain embodiments, cycloalkenyl groups have one carbon-carbon double bond within the ring. In other embodiments, cycloalkenyl groups have more than one carbon-carbon double bonds within the ring. Cycloalkenyl rings are not aromatic. Cycloalkenyl groups are monocyclic ring systems. Cycloalkenyl groups may be optionally substituted with one or more substituents as defined herein. Cycloalkenyl includes cyclopropenyl, cyclobutenyl, cyclopentenyl, cyclohexenyl, and cyclohexadienyl.

"Aryl" refers to an aromatic hydrocarbon ring system. Aryl groups are monocyclic ring systems or bicyclic ring systems. Monocyclic aryl ring refers to phenyl. Bicyclic aryl rings refer to napthyl and to rings wherein phenyl is fused to a cycloalkyl or cycloalkenyl ring having 5, 6, or 7 member carbon atoms. Aryl groups may be optionally substituted with one or more substituents as defined herein.

The term "heteroaryl" or "aromatic heterocycle" includes substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The term "heteroaryl" also includes ring systems having one or two rings wherein at least one of the rings is heteroaromatic, e.g., the other cyclic rings can be cycloalkyl, cycloalkenyl, cycloalkynyl, aromatic carbocycle, heteroaryl, and/or heterocyclyl. Heteroaryl groups include, for example, pyrrole, furan, thiophene, imidazole, oxazole, thiazole, pyrazole, pyridine, pyrazine, pyridazine, and pyrimidine.

The terms "heterocycle", and "heterocyclic", as used herein, refers to a non-aromatic or aromatic ring comprising one or more heteroatoms selected from, for example, N, O, B and S atoms, preferably N, O, or S. The term "heterocycle" includes both "aromatic heterocycles" and "non-aromatic heterocycles." Heterocycles include 4-7 membered monocyclic and 8-12 membered bicyclic rings. Heterocycle includes bicyclic molecules in which one, two or three or more atoms are shared between the two rings. Each ring of a bicyclic heterocycle may be selected from non-aromatic and aromatic rings. The term "fused heterocycle" refers to a bicyclic heterocycle in which each of the rings shares two adjacent atoms with the other ring. Each ring of a fused heterocycle may be selected from non-aromatic and aromatic rings. In an exemplary embodiment, an aromatic ring, e.g., pyridyl, may be fused to a non-aromatic or aromatic ring, e.g., cyclohexane, cyclopentane, pyrrolidine, 2,3-dihydrofuran or cyclohexene. "Heterocycle" groups include, for example, piperidine, piperazine, pyrrolidine, morpholine, pyrimidine, benzofuran, indole, quinoline, lactones, and lactams. Exemplary "fused heterocycles" include benzodiazepine, indole, quinoline, purine, and 4,5,6,7-tetrahydrobenzo[d]thiazole. "Heterocycles" may be substituted at any one or more positions capable of bearing a hydrogen atom.

"Monocyclic rings" include 5-7 membered aromatic carbocycle or heteroaryl, 3-7 membered cycloalkyl or cycloalkenyl, and 5-7 membered non-aromatic heterocyclyl. Exemplary monocyclic groups include substituted or unsubstituted heterocycles or carbocycles such as thiazolyl, oxazolyl, oxazinyl, thiazinyl, dithianyl, dioxanyl, isoxazolyl, isothiazolyl, triazolyl, furanyl, tetrahydrofuranyl, dihydrofuranyl, pyranyl, tetrazolyl, pyrazolyl, pyrazinyl, pyridazinyl, imidazolyl, pyridinyl, pyrrolyl, dihydropyrrolyl, pyrrolidinyl, piperidinyl, piperazinyl, pyrimidinyl, morpholinyl, tetrahydrothiophenyl, thiophenyl, cyclohexyl, cyclopentyl, cyclopropyl, cyclobutyl, cycloheptanyl, azetidinyl, oxetanyl, thiiranyl, oxiranyl, aziridinyl, and thiomorpholinyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Optionally substituted" indicates that a group, such as alkyl, alkenyl, alkynyl, aryl, cycloalkyl, cycloalkenyl, heterocycloalkyl, or heteroaryl, may be unsubstituted, or the group may be substituted with one or more substituents as defined herein.

As used herein, "substituted" means substituting a hydrogen atom in a structure with an atom or molecule other than hydrogen. "Substituted" in reference to a group indicates that one or more hydrogen atoms attached to a member atom within the group is replaced with a substituent selected from the group of defined substituents. A substitutable atom such as a "substitutable nitrogen" is an atom that bears a hydrogen atom in at least one resonance form. The hydrogen atom may be substituted for another atom or group such as a $CH_3$ or an OH group. For example, the nitrogen in a piperidine molecule is substitutable if the nitrogen is bound to a hydrogen atom. If, for example, the nitrogen of a piperidine is bound to an atom other than hydrogen, the nitrogen is not substitutable. An atom that is not capable of bearing a hydrogen atom in any resonance form is not substitutable. It should be understood that the term "substituted" includes the implicit provision that such substitution be in accordance with the permitted valence of the substituted atom and the substituent, and that the substitution results in a stable compound (i.e. one that does not spontaneously undergo transformation such as by hydrolysis, rearrangement, cyclization, or elimination, and that is sufficiently robust to survive isolation from a reaction mixture). When it is stated that a group may contain one or more substituents, one or more (as appropriate) member atom within the group may be substituted. In addition, a single member atom within the group may be substituted with more than one substituent as long as such substitution is in accordance with the permitted valence of the atom. Suitable substituents are defined herein for each substituted or optionally substituted group.

Combinations of substituents and variables envisioned by this invention are only those that result in the formation of stable compounds. As used herein, the term "stable" refers to compounds that possess stability sufficient to allow manufacture and that maintain the integrity of the compound for a sufficient period of time to be useful for the purposes detailed herein.

Deuterated Compounds

The compounds disclosed herein also include partially and fully deuterated variants. In certain embodiments, deuterated variants may be used for kinetic studies. One of skill in the art can select the sites at which such deuterium atoms are present.

The invention also includes various deuterated forms of the compounds of Formulas (I) to (V) or pharmaceutically acceptable salts thereof. Each available hydrogen atom attached to a carbon atom may be independently replaced with a deuterium atom. A person of ordinary skill in the art will know how to synthesize deuterated forms of the compounds of Formulas (I) to (IV) of the present invention. For example, deuterated materials, such as alkyl groups may be prepared by conventional techniques (see for example: methyl-$d_3$-amine available from Aldrich Chemical Co., Milwaukee, Wis., Cat. No. 489,689-2).

Isotopes

The subject invention also includes isotopically-labeled compounds which are identical to those recited in Formulas (I) and (IV) but for the fact that one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, oxygen, fluorine, iodine and chlorine such as $^{3}H$, $^{11}C$, $^{14}C$, $^{18}F$, $^{123}I$ or $^{125}I$.

Compounds of the present invention and pharmaceutically acceptable salts of said compounds that contain the aforementioned isotopes and/or other isotopes of other atoms are within the scope of the present invention. Isotopically labeled compounds of the present invention, for example those into which radioactive isotopes such as $^{3}H$ or $^{14}C$ have been incorporated, are useful in drug and/or substrate tissue distribution assays. Tritiated, ie. $^{3}H$, and carbon-14, ie. $^{14}C$, isotopes are particularly preferred for their ease of preparation and detectability. $^{11}C$ and $^{18}F$ isotopes are particularly useful in PET (positron emission tomography).

Purity

Because the compounds of the present invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

Salts

In certain embodiments, compounds according to Formula I or a pharmaceutically acceptable salt thereof may contain an acidic functional group. In certain other embodiments, compounds according to Formula I may contain a basic functional group. Thus, the skilled artisan will appreciate that salts of the compounds according to Formula I may be prepared. Indeed, in certain embodiments of the invention, salts of the compounds according to Formula I may be preferred over the respective free base or free acid because, for example, such salts may impart greater stability or solubility to the molecule thereby facilitating formulation into a dosage form.

Because of their potential use in medicine, the salts of the compounds of Formulas (I) to (V) are suitably pharmaceutically acceptable salts. Suitable pharmaceutically acceptable salts include those described by Berge, Bighley and Monkhouse J. Pharm. Sci (1977) 66, pp 1-19.

Also included in the present invention are salts, particularly pharmaceutically acceptable salts, of the compounds described herein. The compounds of the present invention that possess a sufficiently acidic, a sufficiently basic, or both functional groups, can react with any of a number of inorganic bases, and inorganic and organic acids, to form a salt. Alternatively, compounds that are inherently charged, such as those with quaternary nitrogen, can form a salt with an appropriate counterion (e.g., a halide such as bromide, chloride, or fluoride, particularly bromide).

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically enriched" refers to products whose enantiomeric excess is greater than zero. For example, enantiomerically enriched refers to products whose enantiomeric excess is greater than 50% ee, greater than 75% ee, or greater than 90% ee.

"Enantiomerically pure" refers to products whose enantiomeric excess is 99% ee or greater.

"Pharmaceutically acceptable" refers to those compounds, materials, compositions, and dosage forms which are, within the scope of sound medical judgment, suitable for use in contact with the tissues of human beings or animals without excessive toxicity, irritation, or other problem or complication, commensurate with a reasonable benefit/risk ratio.

The compounds according to Formula (I) or a pharmaceutically acceptable salt thereof, may contain one or more asymmetric centers (also referred to as a chiral center) and may, therefore, exist as individual enantiomers, diastereomers, or other stereoisomeric forms, or as mixtures thereof.

Chiral centers, such as chiral carbon atoms, may also be present in a substituent such as an alkyl group. Where the stereochemistry of a chiral center present in Formula I, or in any chemical structure illustrated herein, is not specified, the structure is intended to encompass all individual stereoisomers and all mixtures thereof.

Thus, compounds according to Formula (I) or pharmaceutically acceptable salts thereof, containing one or more chiral centers may be used as racemic mixtures, diastereomeric mixtures, enantiomerically enriched mixtures, diastereomerically enriched mixtures, or as enantiomerically and diastereomerically pure individual stereoisomers.

Individual stereoisomers of a compound according to Formula (I) or a pharmaceutically acceptable salt thereof which contain one or more asymmetric centers may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into a diastereomeric salt, complex or derivative, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

When a disclosed compound or its salt is named or depicted by structure, it is to be understood that the compound or salt, including solvates (particularly, hydrates) thereof, may exist in crystalline forms, non-crystalline forms or a mixture thereof. The compound or salt, or solvates (particularly, hydrates) thereof, may also exhibit polymorphism (i.e. the capacity to occur in different crystalline forms). These different crystalline forms are typically known as "polymorphs."

In light of this, salt forms of the present invention (i.e., which may include different polymorphs, anhydrous forms, solvates, or hydrates thereof) may exhibit characteristic polymorphism. As conventionally understood in the art, polymorphism is defined as an ability of a compound to crystallize as more than one distinct crystalline or "polymorphic" species. A polymorph is defined as a solid crystalline phase of a compound with at least two different arrangements or polymorphic forms of that compound molecule in the solid state.

Polymorphic forms of any given compound, including those of the present invention, are defined by the same chemical formula or composition and are as distinct in chemical structure as crystalline structures of two different chemical compounds. Such compounds may differ in packing, geometrical arrangement of respective crystalline lattices, etc.

It is to be understood that when named or depicted by structure, the disclosed compound, or solvates (particularly, hydrates) thereof, also include all polymorphs thereof. Polymorphs have the same chemical composition but differ in packing, geometrical arrangement, and other descriptive properties of the crystalline solid state.

In light of the foregoing, chemical and/or physical properties or characteristics vary with each distinct polymorphic form, which may include variations in solubility, melting point, density, hardness, crystal shape, optical and electrical properties, vapor pressure, stability, etc.

Solvates and/or hydrates of crystalline salt forms of the present invention also may be formed when solvent molecules are incorporated into the crystalline lattice structure of the compound molecule during the crystallization process. For example, solvate forms of the present invention may incorporate nonaqueous solvents such as methanol and the like as described herein below. Hydrate forms are solvate forms, which incorporate water as a solvent into a crystalline lattice.

Anhydrous with respect to solid state polymorphism refers to a crystalline structure that does not contain a repeating, crystalline solvent in the lattice. However, crystalline materials can be porous and may exhibit reversible surface adsorption of water.

Terms and Definitions

Section 2

1. Definitions

As used herein, the following terms and phrases shall have the meanings set forth below. Unless defined otherwise, all technical and scientific terms used herein have the same meaning as commonly understood to one of ordinary skill in the art.

The term "agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues.

The term "bioavailable", when referring to a compound, is art-recognized and refers to a form of a compound that allows for all or a portion of the amount of compound administered to be absorbed by, incorporated into, or otherwise physiologically available to a subject or patient to whom it is administered.

"Biologically active portion of a sirtuin" refers to a portion of a sirtuin protein having a biological activity, such as the ability to deacetylate ("catalytically active"). Catalytically active portions of a sirtuin may comprise the core domain of sirtuins. Catalytically active portions of SIRT1 having GenBank Accession No. NP_036370 that encompass the $NAD^+$ binding domain and the substrate binding domain, for example, may include without limitation, amino acids 240-664 or 240-505 of GenBank Accession No. NP_036370, which are encoded by the polynucleotide of GenBank Accession No. NM_012238. Therefore, this region is sometimes referred to as the core domain. Other catalytically active portions of SIRT1, also sometimes referred to as core domains, include about amino acids 261 to 447 of GenBank Accession No. NP_036370, which are encoded by nucleotides 834 to 1394 of GenBank Accession No. NM_012238; about amino acids 242 to 493 of GenBank Accession No. NP_036370, which are encoded by nucleotides 777 to 1532 of GenBank Accession No. NM_012238; or about amino acids 254 to 495 of GenBank Accession No. NP_036370, which are encoded by nucleotides 813 to 1538 of GenBank Accession No. NM_012238. Another "biologically active" portion of SIRT1 is amino acids 62-293 or 183-225 of GenBank Accession No. NP_036370, which comprise a domain N-terminal to the core domain that is important to the compound binding site.

The term "companion animals" refers to cats and dogs. As used herein, the term "dog(s)" denotes any member of the species *Canis familiaris*, of which there are a large number of different breeds. The term "cat(s)" refers to a feline animal including domestic cats and other members of the family Felidae, genus *Felis*.

"Diabetes" refers to high blood sugar or ketoacidosis, as well as chronic, general metabolic abnormalities arising from a prolonged high blood sugar status or a decrease in glucose tolerance. "Diabetes" encompasses both the type I and type II (Non Insulin Dependent Diabetes Mellitus or NIDDM) forms of the disease. The risk factors for diabetes include the following factors: waistline of more than 40 inches for men or 35 inches for women, blood pressure of 130/85 mmHg or higher, triglycerides above 150 mg/dl, fasting blood glucose greater than 100 mg/dl or high-density lipoprotein of less than 40 mg/dl in men or 50 mg/dl in women.

The term "$ED_{50}$" refers to the art-recognized measure of effective dose. In certain embodiments, $ED_{50}$ means the dose of a drug which produces 50% of its maximum response or effect, or alternatively, the dose which produces a predetermined response in 50% of test subjects or preparations, such as isolated tissue or cells. The term "$LD_{50}$" refers to the art-recognized measure of lethal dose. In certain embodiments, $LD_{50}$ means the dose of a drug which is lethal in 50% of test subjects. The term "therapeutic index" is an art-recognized term which refers to the therapeutic index of a drug, defined as $LD_{50}/ED_{50}$.

The term "hyperinsulinemia" refers to a state in an individual in which the level of insulin in the blood is higher than normal.

The term "insulin resistance" refers to a state in which a normal amount of insulin produces a subnormal biologic response relative to the biological response in a subject that does not have insulin resistance.

An "insulin resistance disorder," as discussed herein, refers to any disease or condition that is caused by or contributed to by insulin resistance. Examples include: diabetes, obesity, metabolic syndrome, insulin-resistance syndromes, syndrome X, insulin resistance, high blood pressure, hypertension, high blood cholesterol, dyslipidemia, hyperlipidemia, atherosclerotic disease including stroke, coronary artery disease or myocardial infarction, hyperglycemia, hyperinsulinemia and/or hyperproinsulinemia, impaired glucose tolerance, delayed insulin release, diabetic complications, including coronary heart disease, angina pectoris, congestive heart failure, stroke, cognitive functions in dementia, retinopathy, peripheral neuropathy, nephropathy, glomerulonephritis, glomerulosclerosis, nephrotic syndrome, hypertensive nephrosclerosis, some types of cancer (such as endometrial, breast, prostate, and colon), complications of pregnancy, poor female reproductive health (such as menstrual irregularities, infertility, irregular ovulation, polycystic ovarian syndrome (PCOS)), lipodystrophy, cholesterol-related disorders, such as gallstones, cholecystitis and cholelithiasis, gout, obstructive sleep apnea and respiratory problems, osteoarthritis, and bone loss, e.g., osteoporosis in particular.

The term "livestock animals" refers to domesticated quadrupeds, which includes those being raised for meat and various byproducts, e.g., a bovine animal including cattle and other members of the genus Bos, a porcine animal including domestic swine and other members of the genus Sus, an ovine animal including sheep and other members of the genus *Ovis*, domestic goats and other members of the genus *Capra*; domesticated quadrupeds being raised for specialized tasks such as use as a beast of burden, e.g., an equine animal including domestic horses and other members of the family Equidae, genus *Equus*.

The term "mammal" is known in the art, and exemplary mammals include humans, primates, livestock animals (including bovines, porcines, etc.), companion animals (e.g., canines, felines, etc.) and rodents (e.g., mice and rats).

"Obese" individuals or individuals suffering from obesity are generally individuals having a body mass index (BMI) of at least 25 or greater. Obesity may or may not be associated with insulin resistance.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, and intrasternal injection and infusion.

A "patient", "subject", "individual" or "host" refers to either a human or a non-human animal.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prophylactic" or "therapeutic" treatment is art-recognized and refers to administration of a drug to a host. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "pyrogen-free", with reference to a composition, refers to a composition that does not contain a pyrogen in an amount that would lead to an adverse effect (e.g., irritation, fever, inflammation, diarrhea, respiratory distress, endotoxic shock, etc.) in a subject to which the composition has been administered. For example, the term is meant to encompass compositions that are free of, or substantially free of, an endotoxin such as, for example, a lipopolysaccharide (LPS).

"Replicative lifespan" of a cell refers to the number of daughter cells produced by an individual "mother cell." "Chronological aging" or "chronological lifespan," on the other hand, refers to the length of time a population of non-dividing cells remains viable when deprived of nutrients. "Increasing the lifespan of a cell" or "extending the lifespan of a cell," as applied to cells or organisms, refers to increasing the number of daughter cells produced by one cell; increasing the ability of cells or organisms to cope with stresses and combat damage, e.g., to DNA, proteins; and/or increasing the ability of cells or organisms to survive and exist in a living state for longer under a particular condition, e.g., stress (for example, heatshock, osmotic stress, high energy radiation, chemically-induced stress, DNA damage, inadequate salt level, inadequate nitrogen level, or inadequate nutrient level). Lifespan can be increased by at least about 10%, 20%, 30%, 40%, 50%, 60% or between 20% and 70%, 30% and 60%, 40% and 60% or more using methods described herein.

"Sirtuin-modulating compound" refers to a compound that increases the level of a sirtuin protein and/or increases at least one activity of a sirtuin protein. In an exemplary embodiment, a sirtuin-modulating compound may increase at least one biological activity of a sirtuin protein by at least about 10%, 25%, 50%, 75%, 100%, or more. Exemplary biological activities of sirtuin proteins include deacetylation, e.g., of histones and p53; extending lifespan; increasing genomic stability; silencing transcription; and controlling the segregation of oxidized proteins between mother and daughter cells.

proteins include deacetylation, e.g., of an acetylated peptide substrate.

"Sirtuin protein" refers to a member of the sirtuin deacetylase protein family, or preferably to the sir2 family, which include yeast Sir2 (GenBank Accession No. P53685), C. elegans Sir-2.1 (GenBank Accession No. NP_501912), and human SIRT1 (GenBank Accession No. NM_012238 and NP_036370 (or AF083106)) and SIRT2 (GenBank Accession No. NM_012237, NM_030593, NP_036369, NP_085096, and AF083107) proteins. Other family members include the four additional yeast Sir2-like genes termed "HST genes" (homologues of Sir two) HST1, HST2, HST3 and HST4, and the five other human homologues hSIRT3, hSIRT4, hSIRT5, hSIRT6 and hSIRT7 (Brachmann et al. (1995) Genes Dev. 9:2888 and Frye et al. (1999) BBRC 260:273).

"SIRT1 protein" refers to a member of the sir2 family of sirtuin deacetylases. In certain embodiments, a SIRT1 protein includes yeast Sir2 (GenBank Accession No. P53685), C. elegans Sir-2.1 (GenBank Accession No. NP_501912), human SIRT1 (GenBank Accession No. NM_012238 or NP_036370 (or AF083106)), mouse SIRT1 (GenBank Accession No. NM_019812 or NP_062786), and equivalents and fragments thereof. In another embodiment, a SIRT1 protein includes a polypeptide comprising a sequence consisting of, or consisting essentially of, the amino acid sequence set forth in GenBank Accession Nos. NP_036370, NP_501912, NP_085096, NP_036369, or P53685. SIRT1 proteins include polypeptides comprising all or a portion of the amino acid sequence set forth in GenBank Accession Nos. NP_036370, NP_501912, NP_085096, NP_036369, or P53685; the amino acid sequence set forth in GenBank Accession Nos. NP_036370, NP_501912, NP_085096, NP_036369, or P53685 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to GenBank Accession Nos. NP_036370, NP_501912, NP_085096, NP_036369, or P53685, and functional fragments thereof. Polypeptides of the invention also include homologs (e.g., orthologs and paralogs), variants, or fragments, of GenBank Accession Nos. NP_036370, NP_501912, NP_085096, NP_036369, or P53685.

As used herein "SIRT2 protein", "SIRT3 protein", "SIRT4 protein", SIRT5 protein", "SIRT6 protein", and "SIRT7 protein" refer to other mammalian, e.g. human, sirtuin deacetylase proteins that are homologous to SIRT1 protein, particularly in the approximately 275 amino acid conserved catalytic domain. For example, "SIRT3 protein" refers to a member of the sirtuin deacetylase protein family that is homologous to SIRT1 protein. In certain embodiments, a SIRT3 protein includes human SIRT3 (GenBank Accession No. AAH01042, NP_036371, or NP_001017524) and mouse SIRT3 (GenBank Accession No. NP_071878) proteins, and equivalents and fragments thereof. In certain embodiments, a SIRT4 protein includes human SIRT4 (GenBank Accession No. NM_012240 or NP_036372). In certain embodiments, a SIRT5 protein includes human SIRT5 (GenBank Accession No. NM_012241 or NP_036373). In certain embodiments, a SIRT6 protein includes human SIRT6 (GenBank Accession No. NM_016539 or NP_057623). In another embodiment, a SIRT3 protein includes a polypeptide comprising a sequence consisting of, or consisting essentially of, the amino acid sequence set forth in GenBank Accession Nos. AAH01042, NP_036371, NP_001017524, or NP_071878. SIRT3 proteins include polypeptides comprising all or a portion of the amino acid sequence set forth in GenBank Accession AAH01042, NP_036371, NP_001017524, or NP_071878; the amino acid sequence set forth in GenBank Accession Nos. AAH01042, NP_036371, NP_001017524, or NP_071878 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to GenBank Accession Nos. AAH01042, NP_036371, NP_001017524, or NP_071878, and functional fragments thereof. Polypeptides of the invention also include homologs (e.g., orthologs and paralogs), variants, or fragments, of GenBank Accession Nos. AAH01042, NP_036371, NP_001017524, or NP_071878. In certain embodiments, a SIRT3 protein includes a fragment of SIRT3 protein that is produced by cleavage with a mitochondrial matrix processing peptidase (MPP) and/or a mitochondrial intermediate peptidase (MIP).

The term "stereoisomer" as used herein is art-recognized and refers to any of two or more isomers that have the same molecular constitution and differ only in the three-dimensional arrangement of their atomic groupings in space. When used herein to describe a compounds or genus of compounds, stereoisomer includes any portion of the compound or the compound in its entirety. For example, diastereomers and enantiomers are stereoisomers.

The terms "systemic administration" and "administered systemically," are art-recognized and refer to the administration of a subject composition, therapeutic or other material enterally or parenterally.

The term "tautomer" as used herein is art-recognized and refers to any one of the possible alternative structures that may exist as a result of tautomerism, which refers to a form of constitutional isomerism in which a structure may exist in two or more constitutional arrangements, particularly with respect to the position of hydrogens bonded to oxygen. When used herein to describe a compound or genus of compounds, it is further understood that a "tautomer" is readily interconvertible and exists in equilibrium. For example, keto and enol tautomers exist in proportions determined by the equilibrium position for any given condition, or set of conditions:

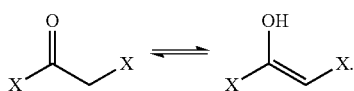

The term "therapeutic agent" is art-recognized and refers to any biologically, physiologically, or pharmacologically active substance that acts locally or systemically in a subject. The term also means any substance intended for use in the diagnosis, cure, mitigation, treatment or prevention of disease or in the enhancement of desirable physical or mental development and/or conditions in an animal or human.

The term "therapeutic effect" is art-recognized and refers to a beneficial local or systemic effect in animals, particularly mammals, and more particularly humans, caused by a pharmacologically active substance. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of skill in the art. For example, certain compositions described herein may be administered in a sufficient amount to produce a desired effect at a reasonable benefit/risk ratio applicable to such treatment.

"Treating" a condition or disease refers to curing as well as ameliorating at least one symptom of the condition or disease.

The term "vision impairment" refers to diminished vision, which is often only partially reversible or irreversible upon treatment (e.g., surgery). Particularly severe vision impairment is termed "blindness" or "vision loss", which refers to a complete loss of vision, vision worse than 20/200 that cannot be improved with corrective lenses, or a visual field of less than 20 degrees diameter (10 degrees radius).

Abbreviations and Symbols

In describing the present invention, chemical elements are identified in accordance with the Periodic Table of the Elements. Abbreviations and symbols utilized herein are in accordance with the common usage of such abbreviations and symbols by those skilled in the chemical and biological arts.

Specifically, the following abbreviations may be used in the examples and throughout the specification:
g (grams); mg (milligrams);
kg (kilograms); µg (micrograms);
L (liters); mL (milliliters);
µL (microliters); psi (pounds per square inch);
M (molar); mM (millimolar);
µM (micromolar); nM (nanomolar);
pM (picomolar); nm (nanometers);
mm (millimeters); wt (weight);
N (Normal); CFU (colony forming units);
I. V. (intravenous); Hz (Hertz);
MHz (megahertz); mol (moles);
mmol (millimoles); RT (room temperature);
min (minutes); h (hours);
b.p. (boiling point); TLC (thin layer chromatography);
$T_r$ (retention time); RP (reverse phase);
MeOH (methanol); i-PrOH (isopropanol);
TEA (triethylamine); TFA (trifluoroacetic acid);
TFAA (trifluoroacetic anhydride); THF (tetrahydrofuran);
DMSO (dimethylsulfoxide); EtOAc (ethyl acetate);
DME (1,2-dimethoxyethane); DCM (dichloromethane);
DCE (dichloroethane); DMF (N,N-dimethylformamide);
DMPU (N,N'-dimethylpropyleneurea); CDI (1,1-carbonyldiimidazole);
IBCF (isobutyl chloroformate); AcOH (acetic acid);
HOAt (1-hydroxy-7-azabenzotriazole);
THP (tetrahydropyran); NMM (N-methylmorpholine);
Pd/C (Palladium on Carbon); MTBE (tert-butyl methyl ether);
HOBT (1-hydroxybenzotriazole); mCPBA (meta-chloroperbenzoic acid;
EDC (1-[3-dimethylamino) propyl]-3-ethylcarbodiimide hydrochloride);
Boc (tert-butyloxycarbonyl); FMOC (9-fluorenylmethoxycarbonyl);
DCC (dicyclohexylcarbodiimide); CBZ (benzyloxycarbonyl);
Ac (acetyl); atm (atmosphere);
TMSE (2-(trimethylsilyl)ethyl); TMS (trimethylsilyl);
TIPS (triisopropylsilyl); TBS (t-butyldimethylsilyl);
DMAP (4-dimethylaminopyridine); BSA (bovine serum albumin)
NAD (nicotinamide adenine dinucleotide);
HPLC (high pressure liquid chromatography);
LC/MS (liquid chromatography/mass spectrometry);
BOP (bis(2-oxo-3-oxazolidinyl)phosphinic chloride);
TBAF (tetra-n-butylammonium fluoride);
HBTU(O-Benzotriazole-1-yl-N,N,N',N'-tetramethyluroniumhexafluoro phosphate).
HEPES (4-(2-hydroxyethyl)-1-piperazine ethane sulfonic acid);
DPPA (diphenylphosphoryl azide); LAH (Lithium aluminum hydride);
$fHNO_3$ (fuming $HNO_3$); NaOMe (sodium methoxide);
EDTA (ethylenediaminetetraacetic acid);
TMEDA (N,N,N',N'-tetramethyl-1,2-ethanediamine);
NBS (N-bromosuccinimide); DIPEA (diisopropylethylamine);
dppf (1,1'-bis(diphenylphosphino)ferrocene); and
NIS (N-iodsuccinimide).

All references to ether are to diethyl ether and brine refers to a saturated aqueous solution of NaCl.

Synthetic Schemes and General Methods of Preparation

The present invention also relates to processes for making compounds of Formulas (I) to (V), corresponding analogs (i.e., with hydrogen substitution at the $R^2$ position), and/or intermediate compounds thereof, respectively.

The compounds of Formulas (I) to (V), corresponding analogs (i.e., with hydrogen substitution at the $R^2$ position) and/or intermediate compounds thereof, or pharmaceutically acceptable salts thereof, may be obtained by using synthetic procedures illustrated in the Schemes below or by drawing on the knowledge of a skilled organic chemist.

The synthesis provided in these Schemes (I) to (VI) are applicable for producing compounds of the invention having a variety of different functional groups employing appropriate precursors, which are suitably protected if needed, to achieve compatibility with the reactions outlined herein. Subsequent deprotection, where needed, affords compounds of the nature generally disclosed. While the Schemes are shown with compounds, they are illustrative of processes that may be used to make the compounds of the invention.

Intermediates (compounds used in the preparation of the compounds of the invention) may also be present as salts. Thus, in reference to intermediates, the phrase "compound(s) of formula (number)" means a compound having that structural formula or a pharmaceutically acceptable salt thereof.

The present invention also relates to processes for making compounds of Formulas (I) to (V), corresponding analogs (i.e., with hydrogen substitution at the $R^2$ position), and/or intermediate compounds thereof, respectively, or pharmaceutically acceptable salts thereof.

The compounds according to Formulas (I) to (V), respectively, The present invention also relates to processes for making compounds of Formulas (I) to (V), corresponding analogs (i.e., with hydrogen substitution at the $R^2$ position), and/or intermediate compounds thereof, respectively, or pharmaceutically acceptable salts thereof are prepared using conventional organic syntheses.

The compounds of the present invention may be obtained by using synthetic procedures illustrated in Schemes below or by drawing on the knowledge of a skilled organic chemist.

Suitable synthetic routes are depicted below in the following general reaction schemes.

Compound Preparation

According to another embodiment, the present invention provides methods of producing the above-defined compounds. The compounds may be synthesized using conventional techniques. Advantageously, these compounds are conveniently synthesized from readily available starting materials.

Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis*, 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

General Procedures

Scheme I

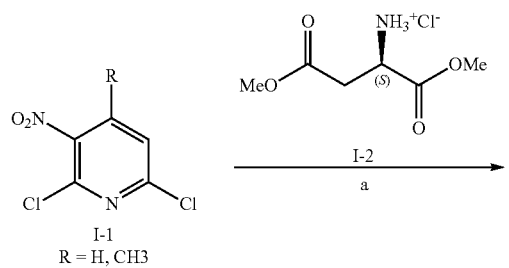

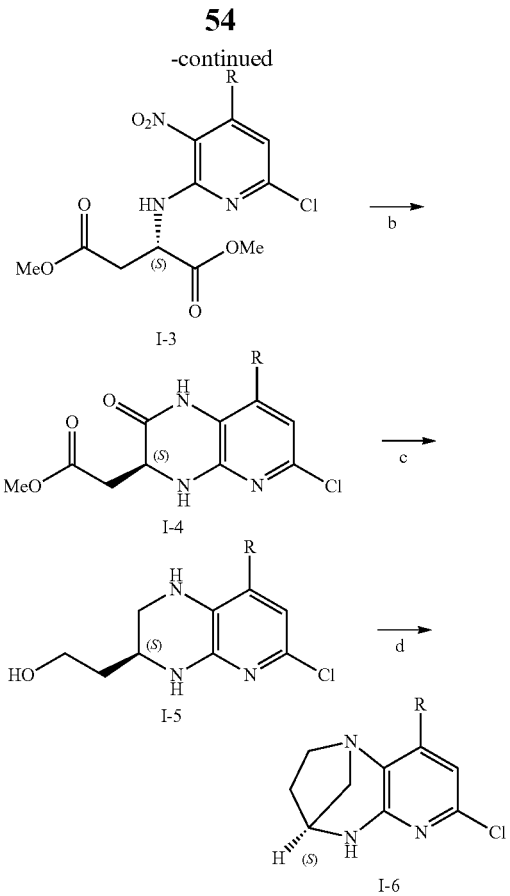

Reagents: (a) THF, NaHCO$_3$, 45° C.; (b) Fe, i-PrOH, HOAc, 70° C.; (c) LiAlH$_4$, THF, 60° C.; (d) POCl$_3$.

The commercial chloropyridine (I-1) was reacted with a nucleophilic amine (I-2) in the presence of a base (to scavenge HCl) in an aprotic solvent (eg., THF, DMF, dioxane) to provide the regioselective addition product (I-3). The nitro functionality of species (I-3) was reduced using Fe(0), (see, Bechamp reduction, Org React. 2, 428, 1944) in the presence of a Bronstead acid (HCl, HOAc) and a protic solvent. Other metals may be used such as Sn to effect this reduction. The resulting intermediate amine species formed in situ reacted with the ester functionality under elevated temperatures to form the cyclic amide I-4. A strong hydride reducing agent, such as LiAlH$_4$, was reacted with compound 1-4 resulting in the reduction of the ester to the corresponding alcohol and simultaneous reduction of the lactam to a cyclic amine. Reductions of this type are well-known to those instructed in the art, see H. C. Brown and S. Krishnamurthy, *Tetrahedron*, 1979, 35, 567. Reaction of the alcohol (I-5) with an activating group (such as POCl$_3$), capable of forming facile leaving group, provided the bicyclic amine compound (I-6).

Scheme II

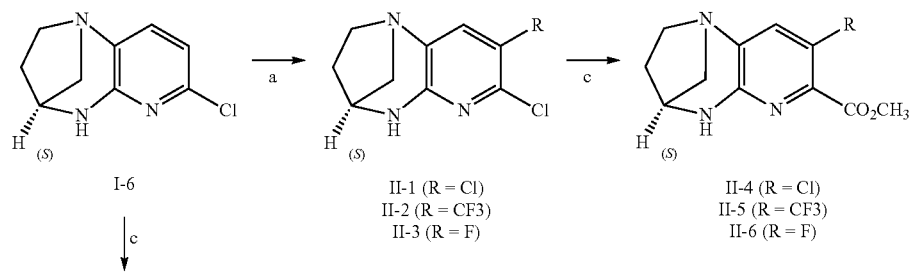

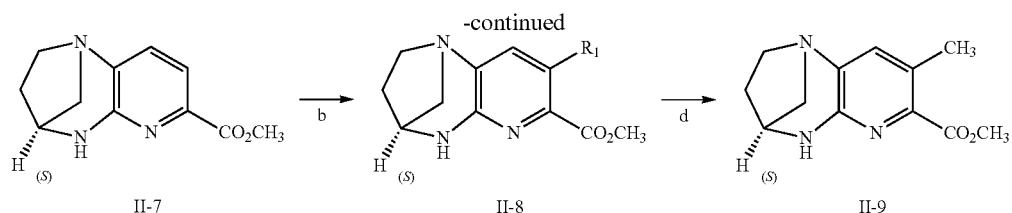
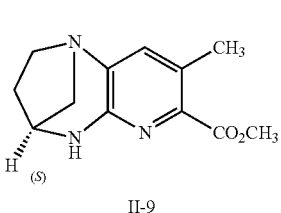

II-7          II-8          II-9

Reagents: (a) NCS, CHCl₃, 70° C. (R═Cl); CuCl, DMPU 1, 10-phenanthroline, trifluoromethyltrimethylsilane, RT, (R═CF₃); N-fluoro-N'-chloromethyltriethylenediamine bis(tetrafluoroborate), Triflic acid, 70° C., (R═F);(b) NBS or NIS, CHCl₃, 70° C.; (c) TEA, CH₃OH, 140° C., 300 psi CO, PdCl₂(dppf); (d) 2, 4, 6-trimethyl-1, 3, 5, 2, 4, 6-trioxatriborinane, PdCl₂(dppf) ─ CH₂Cl₂ adduct, dioxane, 120° C., (R═CH₃).

Compound I-6 was reacted with an electrophilic halogenating reagent, such as NCS, NIS or N-Fluoro-N'-chloromethyltriethylenediamine bis(tetrafluoroborate) in an appropriate solvent to give the corresponding halogenated species II-1-3 in a regioselective manner. Many methods exist to effect the halogenation of an aromatic ring and are well-known to those skilled in the art. Aryl chlorides (I-6) or (II-1-3) were reacted with CO under pressure and elevated temperature in the presence of an alcohol to produce the esters (II-4-7). Carbonylation reactions are described in the literature (see, Principles and Applications of Organotransition Metal Chemistry. Sausalito, Calif.: University Science Books; 1987) and are well known to those skilled in the art. Compound II-7 was reacted with an electrophilic halogenating reagent (NBS or NIS) in an appropriate solvent to give the corresponding halogenated species II-8 in a regioselective manner. The halo functionality of compound II-8 was coupled with a boronic acid using Suzuki coupling chemistry to give II-9. Suzuki-like couplings are typically run using a palladium(0) catalyst such as Pd(PPh₃)₄ with an inorganic base, for example K₂CO₃, Na₂CO₃ or K₃PO₄, in an aqueous mixture containing ethereal solvents such as DME, dioxane, or THF. Methods for palladium-mediated couplings are described in standard reference volumes, such as Schlosser "Organometallics in Synthesis" (published by Wiley and sons).

Scheme III

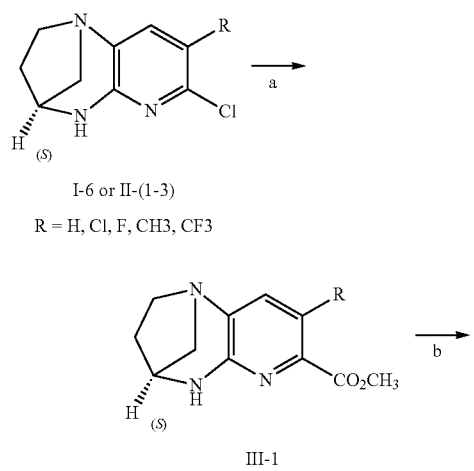

I-6 or II-(1-3)

R = H, Cl, F, CH3, CF3

III-1

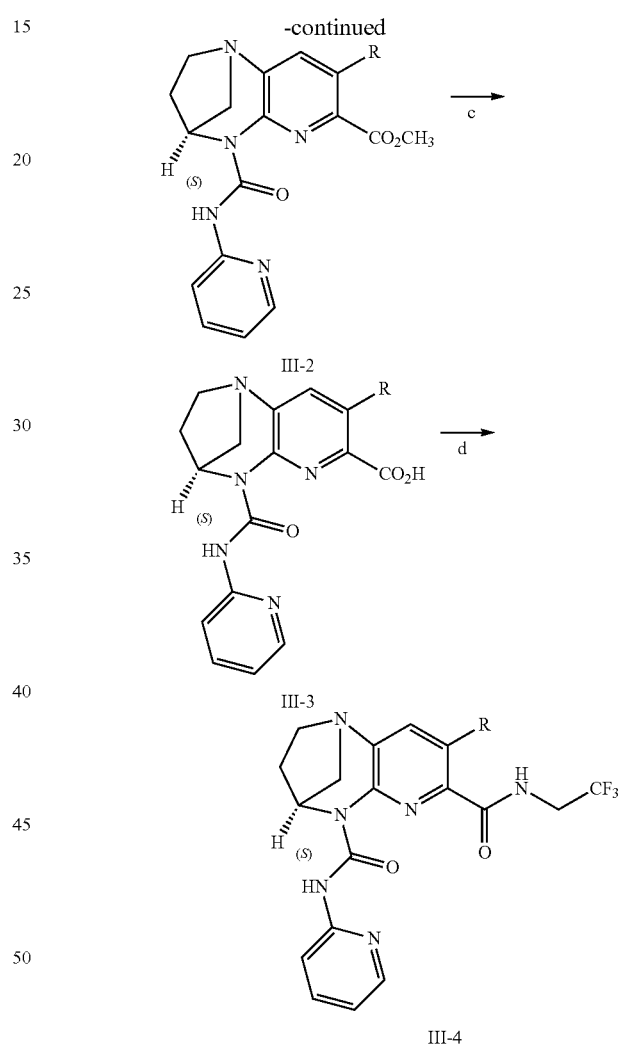

III-2

III-3

III-4

Reagents: (a) TEA, CH₃OH, 140° C., 300 psi CO, PdCl₂(dppf); (b) TEA, THF, triphosgene, aniline, RT; (c) THF, H₂O, LiOH, RT; (d) DIPEA, DMF, HATU, alkyl amine, RT.

Aryl chlorides (I-6) or (II-1-3) were reacted with CO under pressure and elevated temperature in the presence of an alcohol to produce the ester (III-1). Carbonylation reactions are described in the literature (see, Principles and Applications of Organotransition Metal Chemistry. Sausalito, Calif.: University Science Books; 1987) and are well known to those skilled in the art. The amine functionality (III-1) was reacted with an acylating reagent, such as triphosgene or carbonyl diimidazole in an aprotic solvent (DCM, CHCl₃, THF, etc.) followed by treatment in situ with an aniline compound or alkyl amine in the presence of a tertiary alkyl amine base providing ester (III-2). Hydrolysis of the ester functionality in aqueous LiOH formed the acid species (III-3). Carboxylic acid (III-3) was reacted with an alkyl amine in the presence of a coupling reagent (HATU) in a polar aprotic solvent to give the corresponding amide (III-4). A variety of amide coupling reagents such as EDC, PyBrop, etc. are commercially available. Amide coupling reactions are generally run in solvents such as DCM or DMF, utilizing an organic base like $Et_3N$ or $(i-Pr)_2NEt$.

Compound Characteristics and Properties

In an exemplary embodiment, a therapeutic compound may traverse the cytoplasmic membrane of a cell. For example, a compound may have a cell-permeability of at least about 20%, 50%, 75%, 80%, 90% or 95%.

Compounds described herein may also have one or more of the following characteristics: the compound may be essentially non-toxic to a cell or subject; the compound may be an organic molecule or a small molecule of 2000 amu or less, 1000 amu or less; a compound may have a half-life under normal atmospheric conditions of at least about 30 days, 60 days, 120 days, 6 months or 1 year; the compound may have a half-life in solution of at least about 30 days, 60 days, 120 days, 6 months or 1 year; a compound may be more stable in solution than resveratrol by at least a factor of about 50%, 2 fold, 5 fold, 10 fold, 30 fold, 50 fold or 100 fold; a compound may promote deacetylation of the DNA repair factor Ku70; a compound may promote deacetylation of RelA/p65; a compound may increase general turnover rates and enhance the sensitivity of cells to TNF-induced apoptosis.

In certain embodiments, a sirtuin-modulating compound does not have any substantial ability to inhibit a histone deacetylase (HDAC) class I, and/or an HDAC class II at concentrations (e.g., in vivo) effective for modulating the deacetylase activity of the sirtuin. For instance, in preferred embodiments, the sirtuin-modulating compound is a sirtuin-modulating compound and is chosen to have an $EC_{50}$ for activating sirtuin deacetylase activity that is at least 5 fold less than the $EC_{50}$ for inhibition of an HDAC I and/or HDAC II, and even more preferably at least 10 fold, 100 fold or even 1000 fold less. Methods for assaying HDAC I and/or HDAC II activity are well known in the art and kits to perform such assays may be purchased commercially. See e.g., BioVision, Inc. (Mountain View, Calif.; world wide web at biovision.com) and Thomas Scientific (Swedesboro, N.J.; world wide web at tomassci.com).

In certain embodiments, a sirtuin-modulating compound does not have any substantial ability to modulate sirtuin homologs. In certain embodiments, an activator of a human sirtuin protein may not have any substantial ability to activate a sirtuin protein from lower eukaryotes, particularly yeast or human pathogens, at concentrations (e.g., in vivo) effective for activating the deacetylase activity of human sirtuin. For example, a sirtuin-modulating compound may be chosen to have an $EC_{50}$ for activating a human sirtuin, such as SIRT1 and/or SIRT3, deacetylase activity that is at least 5 fold less than the $EC_{50}$ for activating a yeast sirtuin, such as Sir2 (such as Candida, S. cerevisiae, etc.), and even more preferably at least 10 fold, 100 fold or even 1000 fold less. In another embodiment, an inhibitor of a sirtuin protein from lower eukaryotes, particularly yeast or human pathogens, does not have any substantial ability to inhibit a sirtuin protein from humans at concentrations (e.g., in vivo) effective for inhibiting the deacetylase activity of a sirtuin protein from a lower eukaryote. For example, a sirtuin-inhibiting compound may be chosen to have an $IC_{50}$ for inhibiting a human sirtuin, such as SIRT1 and/or SIRT3, deacetylase activity that is at least 5 fold less than the $IC_{50}$ for inhibiting a yeast sirtuin, such as Sir2 (such as Candida, S. cerevisiae, etc.), and even more preferably at least 10 fold, 100 fold or even 1000 fold less.

In certain embodiments, a sirtuin-modulating compound may have the ability to modulate one or more sirtuin protein homologs, such as, for example, one or more of human SIRT1, SIRT2, SIRT3, SIRT4, SIRT5, SIRT6, or SIRT7. In some embodiments, a sirtuin-modulating compound has the ability to modulate both a SIRT1 and a SIRT3 protein.

In other embodiments, a SIRT1 modulator does not have any substantial ability to modulate other sirtuin protein homologs, such as, for example, one or more of human SIRT2, SIRT3, SIRT4, SIRT5, SIRT6, or SIRT7, at concentrations (e.g., in vivo) effective for modulating the deacetylase activity of human SIRT1. For example, a sirtuin-modulating compound may be chosen to have an $ED_{50}$ for modulating human SIRT1 deacetylase activity that is at least 5 fold less than the $ED_{50}$ for modulating one or more of human SIRT2, SIRT3, SIRT4, SIRT5, SIRT6, or SIRT7, and even more preferably at least 10 fold, 100 fold or even 1000 fold less. In some embodiments, a SIRT1 modulator does not have any substantial ability to modulate a SIRT3 protein.

In other embodiments, a SIRT3 modulator does not have any substantial ability to modulate other sirtuin protein homologs, such as, for example, one or more of human SIRT1, SIRT2, SIRT4, SIRT5, SIRT6, or SIRT7, at concentrations (e.g., in vivo) effective for modulating the deacetylase activity of human SIRT3. For example, a sirtuin-modulating compound may be chosen to have an $ED_{50}$ for modulating human SIRT3 deacetylase activity that is at least 5 fold less than the $ED_{50}$ for modulating one or more of human SIRT1, SIRT2, SIRT4, SIRT5, SIRT6, or SIRT7, and even more preferably at least 10 fold, 100 fold or even 1000 fold less. In some embodiments, a SIRT3 modulator does not have any substantial ability to modulate a SIRT1 protein.

In certain embodiments, a sirtuin-modulating compound may have a binding affinity for a sirtuin protein of about $10^{-9}M$, $10^{-10}M$, $10^{-11}M$, $10^{-12}M$ or less. A sirtuin-modulating compound may reduce (activator) or increase (inhibitor) the apparent Km of a sirtuin protein for its substrate or $NAD^+$ (or other cofactor) by a factor of at least about 2, 3, 4, 5, 10, 20, 30, 50 or 100. In certain embodiments, Km values are determined using the mass spectrometry assay described herein. Preferred activating compounds reduce the Km of a sirtuin for its substrate or cofactor to a greater extent than caused by resveratrol at a similar concentration or reduce the Km of a sirtuin for its substrate or cofactor similar to that caused by resveratrol at a lower concentration. A sirtuin-modulating compound may increase the Vmax of a sirtuin protein by a factor of at least about 2, 3, 4, 5, 10, 20, 30, 50 or 100. A sirtuin-modulating compound may have an $ED_{50}$ for modulating the deacetylase activity of a SIRT1 and/or SIRT3 protein of less than about 1 nM, less than about 10 nM, less than about 100 nM, less than about 1 μM, less than about 10 μM, less than about 100 μM, or from about 1-10 nM, from about 10-100 nM, from about 0.1-1 μM, from about 1-10 μM or from about 10-100 μM. A sirtuin-modulating compound may modulate the deacetylase activity of a SIRT1 and/or SIRT3 protein by a factor of at least about 5, 10, 20, 30, 50, or 100, as measured in a cellular assay or in a cell based assay. A sirtuin-modulating compound may cause at least about 10%, 30%, 50%, 80%, 2 fold, 5 fold, 10 fold, 50 fold or 100 fold greater induction of the deacetylase activity of a sirtuin protein relative to the same concentration of resveratrol. A sirtuin-modulating compound may have an $ED_{50}$ for modulating SIRT5 that is at least about 10 fold, 20 fold, 30 fold, 50 fold greater than that for modulating SIRT1 and/or SIRT3.

Exemplary Uses

In certain aspects, the invention provides methods or uses for modulating the level and/or activity of a sirtuin protein and methods or uses thereof.

In certain embodiments, the invention provides methods or uses for using sirtuin-modulating compounds wherein the sirtuin-modulating compounds activate a sirtuin protein, e.g., increase the level and/or activity of a sirtuin protein. Sirtuin-modulating compounds that increase the level and/or activity of a sirtuin protein may be useful for a variety of therapeutic applications including, for example, increasing the lifespan of a cell, and treating and/or preventing a wide variety of diseases and disorders including, for example, diseases or disorders related to aging or stress, diabetes, obesity, neurodegenerative diseases, cardiovascular disease, blood clotting disorders, inflammation, cancer, and/or flushing, etc. The methods or uses of the present invention comprise administering to a subject in need thereof a pharmaceutically effective amount of a sirtuin-modulating compound, e.g., a sirtuin-modulating compound.

Without wishing to be bound by theory, it is believed that activators of the instant invention may interact with a sirtuin at the same location within the sirtuin protein (e.g., active site or site affecting the Km or Vmax of the active site). It is believed that this is the reason why certain classes of sirtuin activators and inhibitors can have substantial structural similarity.

In certain embodiments, the sirtuin-modulating compounds described herein may be taken alone or in combination with other compounds. In certain embodiments, a mixture of two or more sirtuin-modulating compounds may be administered to a subject in need thereof. In another embodiment, a sirtuin-modulating compound that increases the level and/or activity of a sirtuin protein may be administered with one or more of the following compounds: resveratrol, butein, fisetin, piceatannol, or quercetin. In an exemplary embodiment, a sirtuin-modulating compound that increases the level and/or activity of a sirtuin protein may be administered in combination with nicotinic acid or nicotinamide riboside. In another embodiment, a sirtuin-modulating compound that decreases the level and/or activity of a sirtuin protein may be administered with one or more of the following compounds: nicotinamide (NAM); suramin; NF023 (a G-protein antagonist); NF279 (a purinergic receptor antagonist); Trolox (6-hydroxy-2,5,7,8,tetramethylchroman-2-carboxylic acid); (−)-epigallocatechin (hydroxy on sites 3,5,7,3',4',5'); (−)-epigallocatechin gallate (Hydroxy sites 5,7,3',4',5' and gallate ester on 3); cyanidin chloride (3,5,7,3',4'-pentahydroxyflavylium chloride); delphinidin chloride (3,5,7,3',4',5'-hexahydroxyflavylium chloride); myricetin (cannabiscetin; 3,5,7,3',4',5'-hexahydroxyflavone); 3,7,3',4',5'-pentahydroxyflavone; gossypetin (3,5,7,8,3',4'-hexahydroxyflavone), sirtinol; and splitomicin. In yet another embodiment, one or more sirtuin-modulating compounds may be administered with one or more therapeutic agents for the treatment or prevention of various diseases, including, for example, cancer, diabetes, neurodegenerative diseases, cardiovascular disease, blood clotting, inflammation, flushing, obesity, aging, stress, etc. In various embodiments, combination therapies comprising a sirtuin-modulating compound may refer to (1) pharmaceutical compositions that comprise one or more sirtuin-modulating compounds in combination with one or more therapeutic agents (e.g., one or more therapeutic agents described herein); and (2) co-administration of one or more sirtuin-modulating compounds with one or more therapeutic agents wherein the sirtuin-modulating compound and therapeutic agent have not been formulated in the same compositions (but may be present within the same kit or package, such as a blister pack or other multi-chamber package; connected, separately sealed containers (e.g., foil pouches) that can be separated by the user; or a kit where the compound(s) and other therapeutic agent(s) are in separate vessels). When using separate formulations, the sirtuin-modulating compound may be administered simultaneous with, intermittent with, staggered with, prior to, subsequent to, or combinations thereof, the administration of another therapeutic agent.

In certain embodiments, methods or uses for reducing, preventing or treating diseases or disorders using a compound described herein may also comprise increasing the protein level of a sirtuin, such as human SIRT1, SIRT2 and/or SIRT3, or homologs thereof. Increasing protein levels can be achieved by introducing into a cell one or more copies of a nucleic acid that encodes a sirtuin. For example, the level of a sirtuin can be increased in a mammalian cell by introducing into the mammalian cell a nucleic acid encoding the sirtuin, e.g., increasing the level of SIRT1 by introducing a nucleic acid encoding the amino acid sequence set forth in GenBank Accession No. NP_036370 and/or increasing the level of SIRT3 by introducing a nucleic acid encoding the amino acid sequence set forth in GenBank Accession No. AAH01042.

A nucleic acid that is introduced into a cell to increase the protein level of a sirtuin may encode a protein that is at least about 80%, 85%, 90%, 95%, 98%, or 99% identical to the sequence of a sirtuin, e.g., SIRT1 and/or SIRT3 protein. For example, the nucleic acid encoding the protein may be at least about 80%, 85%, 90%, 95%, 98%, or 99% identical to a nucleic acid encoding a SIRT1 (e.g. GenBank Accession No. NM_012238) and/or SIRT3 (e.g., GenBank Accession No. BC001042) protein. The nucleic acid may also be a nucleic acid that hybridizes, preferably under stringent hybridization conditions, to a nucleic acid encoding a wild-type sirtuin, e.g., SIRT1 and/or SIRT3 protein. Stringent hybridization conditions may include hybridization and a wash in 0.2×SSC at 65° C. When using a nucleic acid that encodes a protein that is different from a wild-type sirtuin protein, such as a protein that is a fragment of a wild-type sirtuin, the protein is preferably biologically active, e.g., is capable of deacetylation. It is only necessary to express in a cell a portion of the sirtuin that is biologically active. For example, a protein that differs from wild-type SIRT1 having GenBank Accession No. NP_036370, preferably contains the core structure thereof. The core structure sometimes refers to amino acids 62-293 of GenBank Accession No. NP_036370, which are encoded by nucleotides 237 to 932 of GenBank Accession No. NM_012238, which encompasses the NAD binding as well as the substrate binding domains. The core domain of SIRT1 may also refer to about amino acids 261 to 447 of GenBank Accession No. NP_036370, which are encoded by nucleotides 834 to 1394 of GenBank Accession No. NM_012238; to about amino acids 242 to 493 of GenBank Accession No. NP_036370, which are encoded by nucleotides 777 to 1532 of GenBank Accession No. NM_012238; or to about amino acids 254 to 495 of GenBank Accession No. NP_036370, which are encoded by nucleotides 813 to 1538 of GenBank Accession No. NM_012238. Whether a protein retains a biological function, e.g., deacetylation capabilities, can be determined according to methods known in the art.

In certain embodiments, methods or uses for reducing, preventing or treating diseases or disorders using a sirtuin-modulating compound may also comprise decreasing the protein level of a sirtuin, such as human SIRT1, SIRT2 and/or SIRT3, or homologs thereof. Decreasing a sirtuin protein level can be achieved according to methods or uses known in the art. For example, an siRNA, an antisense nucleic acid, or a ribozyme targeted to the sirtuin can be expressed in the cell. A dominant negative sirtuin mutant, e.g., a mutant that is not capable of deacetylating, may also be used. For example, mutant H363Y of SIRT1, described, e.g., in Luo et al. (2001) Cell 107:137 can be used. Alternatively, agents that inhibit transcription can be used.

Methods or uses for modulating sirtuin protein levels also include methods or uses for modulating the transcription of genes encoding sirtuins, methods or uses for stabilizing/destabilizing the corresponding mRNAs, and other methods known in the art.

Aging/Stress

In one aspect, the invention provides a method extending the lifespan of a cell, extending the proliferative capacity of a cell, slowing aging of a cell, promoting the survival of a cell, delaying cellular senescence in a cell, mimicking the effects of calorie restriction, increasing the resistance of a cell to stress, or preventing apoptosis of a cell, by contacting the cell with a sirtuin-modulating compound of the invention that increases the level and/or activity of a sirtuin protein. In an exemplary embodiment, the methods or uses comprise contacting the cell with a sirtuin-modulating compound.

The methods or uses described herein may be used to increase the amount of time that cells, particularly primary cells (i.e., cells obtained from an organism, e.g., a human), may be kept alive in a cell culture. Embryonic stem (ES) cells and pluripotent cells, and cells differentiated therefrom, may also be treated with a sirtuin-modulating compound that increases the level and/or activity of a sirtuin protein to keep the cells, or progeny thereof, in culture for longer periods of time. Such cells can also be used for transplantation into a subject, e.g., after ex vivo modification.

In one aspect, cells that are intended to be preserved for long periods of time may be treated with a sirtuin-modulating compound that increases the level and/or activity of a sirtuin protein. The cells may be in suspension (e.g., blood cells, serum, biological growth media, etc.) or in tissues or organs. For example, blood collected from an individual for purposes of transfusion may be treated with a sirtuin-modulating compound that increases the level and/or activity of a sirtuin protein to preserve the blood cells for longer periods of time. Additionally, blood to be used for forensic purposes may also be preserved using a sirtuin-modulating compound that increases the level and/or activity of a sirtuin protein. Other cells that may be treated to extend their lifespan or protect against apoptosis include cells for consumption, e.g., cells from non-human mammals (such as meat) or plant cells (such as vegetables).

Sirtuin-modulating compounds that increase the level and/or activity of a sirtuin protein may also be applied during developmental and growth phases in mammals, plants, insects or microorganisms, in order to, e.g., alter, retard or accelerate the developmental and/or growth process.

In another aspect, sirtuin-modulating compounds that increase the level and/or activity of a sirtuin protein may be used to treat cells useful for transplantation or cell therapy, including, for example, solid tissue grafts, organ transplants, cell suspensions, stem cells, bone marrow cells, etc. The cells or tissue may be an autograft, an allograft, a syngraft or a xenograft. The cells or tissue may be treated with the sirtuin-modulating compound prior to administration/implantation, concurrently with administration/implantation, and/or post administration/implantation into a subject. The cells or tissue may be treated prior to removal of the cells from the donor individual, ex vivo after removal of the cells or tissue from the donor individual, or post implantation into the recipient. For example, the donor or recipient individual may be treated systemically with a sirtuin-modulating compound or may have a subset of cells/tissue treated locally with a sirtuin-modulating compound that increases the level and/or activity of a sirtuin protein. In certain embodiments, the cells or tissue (or donor/recipient individuals) may additionally be treated with another therapeutic agent useful for prolonging graft survival, such as, for example, an immunosuppressive agent, a cytokine, an angiogenic factor, etc.

In yet other embodiments, cells may be treated with a sirtuin-modulating compound that increases the level and/or activity of a sirtuin protein in vivo, e.g., to increase their lifespan or prevent apoptosis. For example, skin can be protected from aging (e.g., developing wrinkles, loss of elasticity, etc.) by treating skin or epithelial cells with a sirtuin-modulating compound that increases the level and/or activity of a sirtuin protein. In an exemplary embodiment, skin is contacted with a pharmaceutical or cosmetic composition comprising a sirtuin-modulating compound that increases the level and/or activity of a sirtuin protein. Exemplary skin afflictions or skin conditions that may be treated in accordance with the methods or uses described herein include disorders or diseases associated with or caused by inflammation, sun damage or natural aging. For example, the compositions find utility in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including pemphigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In another embodiment, sirtuin-modulating compounds that increase the level and/or activity of a sirtuin protein may be used for the treatment of wounds and/or burns to promote healing, including, for example, first-, second- or third-degree burns and/or thermal, chemical or electrical burns. The formulations may be administered topically, to the skin or mucosal tissue.

Topical formulations comprising one or more sirtuin-modulating compounds that increase the level and/or activity of a sirtuin protein may also be used as preventive, e.g., chemopreventive, compositions. When used in a chemopreventive method, susceptible skin is treated prior to any visible condition in a particular individual.

Sirtuin-modulating compounds may be delivered locally or systemically to a subject. In certain embodiments, a sirtuin-modulating compound is delivered locally to a tissue or organ of a subject by injection, topical formulation, etc.

In another embodiment, a sirtuin-modulating compound that increases the level and/or activity of a sirtuin protein may be used for treating or preventing a disease or condition induced or exacerbated by cellular senescence in a subject; methods or uses for decreasing the rate of senescence of a subject, e.g., after onset of senescence; methods or uses for extending the lifespan of a subject; methods or uses for treating or preventing a disease or condition relating to lifespan; methods or uses for treating or preventing a disease or condition relating to the proliferative capacity of cells; and methods or uses for treating or preventing a disease or condition resulting from cell damage or death. In certain embodiments, the method does not act by decreasing the rate of occurrence of diseases that shorten the lifespan of a subject. In certain embodiments, a method does not act by reducing the lethality caused by a disease, such as cancer.

In yet another embodiment, a sirtuin-modulating compound that increases the level and/or activity of a sirtuin protein may be administered to a subject in order to generally increase the lifespan of its cells and to protect its cells against stress and/or against apoptosis. It is believed that treating a subject with a compound described herein is similar to subjecting the subject to hormesis, i.e., mild stress that is beneficial to organisms and may extend their lifespan.

Sirtuin-modulating compounds that increase the level and/or activity of a sirtuin protein may be administered to a subject to prevent aging and aging-related consequences or diseases, such as stroke, heart disease, heart failure, arthritis, high blood pressure, and Alzheimer's disease. Other conditions that can be treated include ocular disorders, e.g., associated with the aging of the eye, such as cataracts, glaucoma, and macular degeneration. Sirtuin-modulating compounds that increase the level and/or activity of a sirtuin protein can also be administered to subjects for treatment of diseases, e.g., chronic diseases, associated with cell death, in order to protect the cells from cell death. Exemplary diseases include those associated with neural cell death, neuronal dysfunction, or muscular cell death or dysfunction, such as Parkinson's disease, Alzheimer's disease, multiple sclerosis, amyotrophic lateral sclerosis, and muscular dystrophy; AIDS; fulminant hepatitis; diseases linked to degeneration of the brain, such as Creutzfeld-Jakob disease, retinitis pigmentosa and cerebellar degeneration; myelodysplasia such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; and graft rejections. Cell death can also be caused by surgery, drug therapy, chemical exposure or radiation exposure.

Sirtuin-modulating compounds that increase the level and/or activity of a sirtuin protein can also be administered to a subject suffering from an acute disease, e.g., damage to an organ or tissue, e.g., a subject suffering from stroke or myocardial infarction or a subject suffering from a spinal cord injury. Sirtuin-modulating compounds that increase the level and/or activity of a sirtuin protein may also be used to repair an alcoholic's liver.

Cardiovascular Disease

In another embodiment, the invention provides a method for treating and/or preventing a cardiovascular disease by administering to a subject in need thereof a sirtuin-modulating compound that increases the level and/or activity of a sirtuin protein.

Cardiovascular diseases that can be treated or prevented using the sirtuin-modulating compounds that increase the level and/or activity of a sirtuin protein include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable or preventable using compounds and methods or uses described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated or prevented include those related to platelet aggregation, the retinal arterioles, the glomerular arterioles, the vasa nervorum, cardiac arterioles, and associated capillary beds of the eye, the kidney, the heart, and the central and peripheral nervous systems. The sirtuin-modulating compounds that increase the level and/or activity of a sirtuin protein may also be used for increasing HDL levels in plasma of an individual.

Yet other disorders that may be treated with sirtuin-modulating compounds that increase the level and/or activity of a sirtuin protein include restenosis, e.g., following coronary intervention, and disorders relating to an abnormal level of high density and low density cholesterol.

In certain embodiments, a sirtuin-modulating compound that increases the level and/or activity of a sirtuin protein may be administered as part of a combination therapy with another cardiovascular agent. In certain embodiments, a sirtuin-modulating compound that increases the level and/or activity of a sirtuin protein may be administered as part of a combination therapy with an anti-arrhythmia agent. In another embodiment, a sirtuin-modulating compound that increases the level and/or activity of a sirtuin protein may be administered as part of a combination therapy with another cardiovascular agent.

Cell Death/Cancer

Sirtuin-modulating compounds that increase the level and/or activity of a sirtuin protein may be administered to subjects who have recently received or are likely to receive a dose of radiation or toxin. In certain embodiments, the dose of radiation or toxin is received as part of a work-related or medical procedure, e.g., administered as a prophylactic measure. In another embodiment, the radiation or toxin exposure is received unintentionally. In such a case, the compound is preferably administered as soon as possible after the exposure to inhibit apoptosis and the subsequent development of acute radiation syndrome.

Sirtuin-modulating compounds may also be used for treating and/or preventing cancer. In certain embodiments, sirtuin-modulating compounds that increase the level and/or activity of a sirtuin protein may be used for treating and/or preventing cancer. Calorie restriction has been linked to a reduction in the incidence of age-related disorders including cancer. Accordingly, an increase in the level and/or activity of a sirtuin protein may be useful for treating and/or preventing the incidence of age-related disorders, such as, for example, cancer. Exemplary cancers that may be treated using a sirtuin-modulating compound are those of the brain and kidney; hormone-dependent cancers including breast, prostate, testicular, and ovarian cancers; lymphomas, and leukemias. In cancers associated with solid tumors, a modulating compound may be administered directly into the tumor. Cancer of blood cells, e.g., leukemia, can be treated by administering a modulating compound into the blood stream or into the bone marrow. Benign cell growth, e.g., warts, can also be treated. Other diseases that can be treated include autoimmune diseases, e.g., systemic lupus erythematosus, scleroderma, and arthritis, in which autoimmune cells should be removed. Viral infections such as herpes, HIV, adenovirus, and HTLV-1 associated malignant and benign disorders can also be treated by administration of sirtuin-modulating compound. Alternatively, cells can be obtained from a subject, treated ex vivo to remove certain undesirable cells, e.g., cancer cells, and administered back to the same or a different subject.

Chemotherapeutic agents may be co-administered with modulating compounds described herein as having anti-cancer activity, e.g., compounds that induce apoptosis, compounds that reduce lifespan or compounds that render cells sensitive to stress. Chemotherapeutic agents may be used by themselves with a sirtuin-modulating compound described herein as inducing cell death or reducing lifespan or increasing sensitivity to stress and/or in combination with other chemotherapeutics agents. In addition to conventional chemotherapeutics, the sirtuin-modulating compounds described herein may also be used with antisense RNA, RNAi or other polynucleotides to inhibit the expression of the cellular components that contribute to unwanted cellular proliferation.

Combination therapies comprising sirtuin-modulating compounds and a conventional chemotherapeutic agent may be advantageous over combination therapies known in the art because the combination allows the conventional chemotherapeutic agent to exert greater effect at lower dosage. In a preferred embodiment, the effective dose ($ED_{50}$) for a chemotherapeutic agent, or combination of conventional chemotherapeutic agents, when used in combination with a sirtuin-modulating compound is at least 2 fold less than the $ED_{50}$ for the chemotherapeutic agent alone, and even more preferably at 5 fold, 10 fold or even 25 fold less. Conversely, the therapeutic index (TI) for such chemotherapeutic agent or combination of such chemotherapeutic agent when used in combination with a sirtuin-modulating compound described herein can be at least 2 fold greater than the TI for conventional chemotherapeutic regimen alone, and even more preferably at 5 fold, 10 fold or even 25 fold greater.

Neuronal Diseases/Disorders

In certain aspects, sirtuin-modulating compounds that increase the level and/or activity of a sirtuin protein can be used to treat patients suffering from neurodegenerative diseases, and traumatic or mechanical injury to the central nervous system (CNS), spinal cord or peripheral nervous system (PNS). Neurodegenerative disease typically involves reductions in the mass and volume of the human brain, which may be due to the atrophy and/or death of brain cells, which are far more profound than those in a healthy person that are attributable to aging. Neurodegenerative diseases can evolve gradually, after a long period of normal brain function, due to progressive degeneration (e.g., nerve cell dysfunction and death) of specific brain regions. Alternatively, neurodegenerative diseases can have a quick onset, such as those associated with trauma or toxins. The actual onset of brain degeneration may precede clinical expression by many years. Examples of neurodegenerative diseases include, but are not limited to, Alzheimer's disease (AD), Parkinson's disease (PD), Huntington's disease (HD), amyotrophic lateral sclerosis (ALS; Lou Gehrig's disease), diffuse Lewy body disease, chorea-acanthocytosis, primary lateral sclerosis, ocular diseases (ocular neuritis), chemotherapy-induced neuropathies (e.g., from vincristine, paclitaxel, bortezomib), diabetes-induced neuropathies and Friedreich's ataxia. Sirtuin-modulating compounds that increase the level and/or activity of a sirtuin protein can be used to treat these disorders and others as described below.

AD is a CNS disorder that results in memory loss, unusual behavior, personality changes, and a decline in thinking abilities. These losses are related to the death of specific types of brain cells and the breakdown of connections and their supporting network (e.g. glial cells) between them. The earliest symptoms include loss of recent memory, faulty judgment, and changes in personality. PD is a CNS disorder that results in uncontrolled body movements, rigidity, tremor, and dyskinesia, and is associated with the death of brain cells in an area of the brain that produces dopamine. ALS (motor neuron disease) is a CNS disorder that attacks the motor neurons, components of the CNS that connect the brain to the skeletal muscles.

HD is another neurodegenerative disease that causes uncontrolled movements, loss of intellectual faculties, and emotional disturbance. Tay-Sachs disease and Sandhoff disease are glycolipid storage diseases where GM2 ganglioside and related glycolipids substrates for β-hexosaminidase accumulate in the nervous system and trigger acute neurodegeneration.

It is well-known that apoptosis plays a role in AIDS pathogenesis in the immune system. However, HIV-1 also induces neurological disease, which can be treated with sirtuin-modulating compounds of the invention.

Neuronal loss is also a salient feature of prion diseases, such as Creutzfeldt-Jakob disease in human, BSE in cattle (mad cow disease), Scrapie Disease in sheep and goats, and feline spongiform encephalopathy (FSE) in cats. Sirtuin-modulating compounds that increase the level and/or activity of a sirtuin protein may be useful for treating or preventing neuronal loss due to these prior diseases.

In another embodiment, a sirtuin-modulating compound that increases the level and/or activity of a sirtuin protein may be used to treat or prevent any disease or disorder involving axonopathy. Distal axonopathy is a type of peripheral neuropathy that results from some metabolic or toxic derangement of peripheral nervous system (PNS) neurons.

It is the most common response of nerves to metabolic or toxic disturbances, and as such may be caused by metabolic diseases such as diabetes, renal failure, deficiency syndromes such as malnutrition and alcoholism, or the effects of toxins or drugs. Those with distal axonopathies usually present with symmetrical glove-stocking sensori-motor disturbances. Deep tendon reflexes and autonomic nervous system (ANS) functions are also lost or diminished in affected areas.

Diabetic neuropathies are neuropathic disorders that are associated with diabetes mellitus. Relatively common conditions which may be associated with diabetic neuropathy include third nerve palsy; mononeuropathy; mononeuritis multiplex; diabetic amyotrophy; a painful polyneuropathy; autonomic neuropathy; and thoracoabdominal neuropathy.

Peripheral neuropathy is the medical term for damage to nerves of the peripheral nervous system, which may be caused either by diseases of the nerve or from the side-effects of systemic illness. Major causes of peripheral neuropathy include seizures, nutritional deficiencies, and HIV, though diabetes is the most likely cause.

In an exemplary embodiment, a sirtuin-modulating compound that increases the level and/or activity of a sirtuin protein may be used to treat or prevent multiple sclerosis (MS), including relapsing MS and monosymptomatic MS, and other demyelinating conditions, such as, for example, chronic inflammatory demyelinating polyneuropathy (CIDP), or symptoms associated therewith.

In yet another embodiment, a sirtuin-modulating compound that increases the level and/or activity of a sirtuin protein may be used to treat trauma to the nerves, including, trauma due to disease, injury (including surgical intervention), or environmental trauma (e.g., neurotoxins, alcoholism, etc.).

Sirtuin-modulating compounds that increase the level and/or activity of a sirtuin protein may also be useful to prevent, treat, and alleviate symptoms of various PNS disorders. The term "peripheral neuropathy" encompasses a wide range of disorders in which the nerves outside of the brain and spinal cord—peripheral nerves—have been damaged. Peripheral neuropathy may also be referred to as peripheral neuritis, or if many nerves are involved, the terms polyneuropathy or polyneuritis may be used.

PNS diseases treatable with sirtuin-modulating compounds that increase the level and/or activity of a sirtuin protein include: diabetes, leprosy, Charcot-Marie-Tooth disease, Guillain-Barré syndrome and Brachial Plexus Neuropathies (diseases of the cervical and first thoracic roots, nerve trunks, cords, and peripheral nerve components of the brachial plexus.

In another embodiment, a sirtuin-modulating compound may be used to treat or prevent a polyglutamine disease. Exemplary polyglutamine diseases include Spinobulbar muscular atrophy (Kennedy disease), Huntington's Disease (HD), Dentatorubral-pallidoluysian atrophy (Haw River syndrome), Spinocerebellar ataxia type 1, Spinocerebellar ataxia type 2, Spinocerebellar ataxia type 3 (Machado-Joseph disease), Spinocerebellar ataxia type 6, Spinocerebellar ataxia type 7, and Spinocerebellar ataxia type 17.

In certain embodiments, the invention provides a method to treat a central nervous system cell to prevent damage in response to a decrease in blood flow to the cell. Typically the severity of damage that may be prevented will depend in large part on the degree of reduction in blood flow to the cell and the duration of the reduction. In certain embodiments, apoptotic or necrotic cell death may be prevented. In still a further embodiment, ischemic-mediated damage, such as cytotoxic edema or central nervous system tissue anoxemia, may be prevented. In each embodiment, the central nervous system cell may be a spinal cell or a brain cell.

Another aspect encompasses administrating a sirtuin-modulating compound to a subject to treat a central nervous system ischemic condition. A number of central nervous system ischemic conditions may be treated by the sirtuin-modulating compounds described herein. In certain embodiments, the ischemic condition is a stroke that results in any type of ischemic central nervous system damage, such as apoptotic or necrotic cell death, cytotoxic edema or central nervous system tissue anoxia. The stroke may impact any area of the brain or be caused by any etiology commonly known to result in the occurrence of a stroke. In one alternative of this embodiment, the stroke is a brain stem stroke. In another alternative of this embodiment, the stroke is a cerebellar stroke. In still another embodiment, the stroke is an embolic stroke. In yet another alternative, the stroke may be a hemorrhagic stroke. In a further embodiment, the stroke is a thrombotic stroke.

In yet another aspect, a sirtuin-modulating compound may be administered to reduce infarct size of the ischemic core following a central nervous system ischemic condition. Moreover, a sirtuin-modulating compound may also be beneficially administered to reduce the size of the ischemic penumbra or transitional zone following a central nervous system ischemic condition.

In certain embodiments, a combination drug regimen may include drugs or compounds for the treatment or prevention of neurodegenerative disorders or secondary conditions associated with these conditions. Thus, a combination drug regimen may include one or more sirtuin activators and one or more anti-neurodegeneration agents.

Blood Coagulation Disorders

In other aspects, sirtuin-modulating compounds that increase the level and/or activity of a sirtuin protein can be used to treat or prevent blood coagulation disorders (or hemostatic disorders). As used interchangeably herein, the terms "hemostasis", "blood coagulation," and "blood clotting" refer to the control of bleeding, including the physiological properties of vasoconstriction and coagulation. Blood coagulation assists in maintaining the integrity of mammalian circulation after injury, inflammation, disease, congenital defect, dysfunction or other disruption. Further, the formation of blood clots does not only limit bleeding in case of an injury (hemostasis), but may lead to serious organ damage and death in the context of atherosclerotic diseases by occlusion of an important artery or vein. Thrombosis is thus blood clot formation at the wrong time and place.

Accordingly, the present invention provides anticoagulation and antithrombotic treatments aiming at inhibiting the formation of blood clots in order to prevent or treat blood coagulation disorders, such as myocardial infarction, stroke, loss of a limb by peripheral artery disease or pulmonary embolism.

As used interchangeably herein, "modulating or modulation of hemostasis" and "regulating or regulation of hemostasis" includes the induction (e.g., stimulation or increase) of hemostasis, as well as the inhibition (e.g., reduction or decrease) of hemostasis.

In one aspect, the invention provides a method for reducing or inhibiting hemostasis in a subject by administering a sirtuin-modulating compound that increases the level and/or activity of a sirtuin protein. The compositions, methods or uses disclosed herein are useful for the treatment or prevention of thrombotic disorders. As used herein, the term "thrombotic disorder" includes any disorder or condition characterized by excessive or unwanted coagulation or hemostatic activity, or a hypercoagulable state. Thrombotic disorders include diseases or disorders involving platelet adhesion and thrombus formation, and may manifest as an increased propensity to form thromboses, e.g., an increased number of thromboses, thrombosis at an early age, a familial tendency towards thrombosis, and thrombosis at unusual sites.

In another embodiment, a combination drug regimen may include drugs or compounds for the treatment or prevention of blood coagulation disorders or secondary conditions associated with these conditions. Thus, a combination drug regimen may include one or more sirtuin-modulating compounds that increase the level and/or activity of a sirtuin protein and one or more anti-coagulation or anti-thrombosis agents.

Weight Control

In another aspect, sirtuin-modulating compounds that increase the level and/or activity of a sirtuin protein may be used for treating or preventing weight gain or obesity in a subject. For example, sirtuin-modulating compounds that increase the level and/or activity of a sirtuin protein may be used, for example, to treat or prevent hereditary obesity, dietary obesity, hormone related obesity, obesity related to the administration of medication, to reduce the weight of a subject, or to reduce or prevent weight gain in a subject. A subject in need of such a treatment may be a subject who is obese, likely to become obese, overweight, or likely to become overweight. Subjects who are likely to become obese or overweight can be identified, for example, based on family history, genetics, diet, activity level, medication intake, or various combinations thereof.

In yet other embodiments, sirtuin-modulating compounds that increase the level and/or activity of a sirtuin protein may be administered to subjects suffering from a variety of other diseases and conditions that may be treated or prevented by promoting weight loss in the subject. Such diseases include, for example, high blood pressure, hypertension, high blood cholesterol, dyslipidemia, type 2 diabetes, insulin resistance, glucose intolerance, hyperinsulinemia, coronary heart disease, angina pectoris, congestive heart failure, stroke, gallstones, cholecystitis and cholelithiasis, gout, osteoarthritis, obstructive sleep apnea and respiratory problems, some types of cancer (such as endometrial, breast, prostate, and colon), complications of pregnancy, poor female reproductive health (such as menstrual irregularities, infertility, irregular ovulation), bladder control problems (such as stress incontinence); uric acid nephrolithiasis; psychological disorders (such as depression, eating disorders, distorted body image, and low self-esteem). Finally, patients with AIDS can develop lipodystrophy or insulin resistance in response to combination therapies for AIDS.

In another embodiment, sirtuin-modulating compounds that increase the level and/or activity of a sirtuin protein may be used for inhibiting adipogenesis or fat cell differentiation, whether in vitro or in vivo. Such methods or uses of the present invention may be used for treating or preventing obesity.

In other embodiments, sirtuin-modulating compounds that increase the level and/or activity of a sirtuin protein may be used for reducing appetite and/or increasing satiety, thereby causing weight loss or avoidance of weight gain. A subject in need of such a treatment may be a subject who is overweight, obese or a subject likely to become overweight or obese. The method may comprise administering daily or, every other day, or once a week, a dose, e.g., in the form of a pill, to a subject. The dose may be an "appetite reducing dose."

In an exemplary embodiment, sirtuin-modulating compounds that increase the level and/or activity of a sirtuin protein may be administered as a combination therapy for treating or preventing weight gain or obesity. For example, one or more sirtuin-modulating compounds that increase the level and/or activity of a sirtuin protein may be administered in combination with one or more anti-obesity agents.

In another embodiment, sirtuin-modulating compounds that increase the level and/or activity of a sirtuin protein may be administered to reduce drug-induced weight gain. For example, a sirtuin-modulating compound that increases the level and/or activity of a sirtuin protein may be administered as a combination therapy with medications that may stimulate appetite or cause weight gain, in particular, weight gain due to factors other than water retention.

Metabolic Disorders/Diabetes

In another aspect, sirtuin-modulating compounds that increase the level and/or activity of a sirtuin protein may be used for treating or preventing a metabolic disorder, such as insulin-resistance, a pre-diabetic state, type II diabetes, and/or complications thereof. Administration of a sirtuin-modulating compound that increases the level and/or activity of a sirtuin protein may increase insulin sensitivity and/or decrease insulin levels in a subject. A subject in need of such a treatment may be a subject who has insulin resistance or other precursor symptom of type II diabetes, who has type II diabetes, or who is likely to develop any of these conditions. For example, the subject may be a subject having insulin resistance, e.g., having high circulating levels of insulin and/or associated conditions, such as hyperlipidemia, dyslipogenesis, hypercholesterolemia, impaired glucose tolerance, high blood glucose sugar level, other manifestations of syndrome X, hypertension, atherosclerosis and lipodystrophy.

In an exemplary embodiment, sirtuin-modulating compounds that increase the level and/or activity of a sirtuin protein may be administered as a combination therapy for treating or preventing a metabolic disorder. For example, one or more sirtuin-modulating compounds that increase the level and/or activity of a sirtuin protein may be administered in combination with one or more anti-diabetic agents.

Inflammatory Diseases

In other aspects, sirtuin-modulating compounds that increase the level and/or activity of a sirtuin protein can be used to treat or prevent a disease or disorder associated with inflammation. Sirtuin-modulating compounds that increase the level and/or activity of a sirtuin protein may be administered prior to the onset of, at, or after the initiation of inflammation. When used prophylactically, the compounds are preferably provided in advance of any inflammatory response or symptom. Administration of the compounds may prevent or attenuate inflammatory responses or symptoms.

In another embodiment, sirtuin-modulating compounds that increase the level and/or activity of a sirtuin protein may be used to treat or prevent allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). The compounds may be used to treat chronic hepatitis infection, including hepatitis B and hepatitis C.

Additionally, sirtuin-modulating compounds that increase the level and/or activity of a sirtuin protein may be used to treat autoimmune diseases, and/or inflammation associated with autoimmune diseases, such as arthritis, including rheumatoid arthritis, psoriatic arthritis, and ankylosing spondylitis, as well as organ-tissue autoimmune diseases (e.g., Raynaud's syndrome), ulcerative colitis, Crohn's disease, oral mucositis, scleroderma, myasthenia gravis, transplant rejection, endotoxin shock, sepsis, psoriasis, eczema, dermatitis, multiple sclerosis, autoimmune thyroiditis, uveitis, systemic lupus erythematosus, Addison's disease, autoimmune polyglandular disease (also known as autoimmune polyglandular syndrome), and Grave's disease.

In certain embodiments, one or more sirtuin-modulating compounds that increase the level and/or activity of a sirtuin protein may be taken alone or in combination with other compounds useful for treating or preventing inflammation.

Flushing

In another aspect, sirtuin-modulating compounds that increase the level and/or activity of a sirtuin protein may be used for reducing the incidence or severity of flushing and/or hot flashes which are symptoms of a disorder. For instance, the subject method includes the use of sirtuin-modulating compounds that increase the level and/or activity of a sirtuin protein, alone or in combination with other agents, for reducing incidence or severity of flushing and/or hot flashes in cancer patients. In other embodiments, the method provides for the use of sirtuin-modulating compounds that increase the level and/or activity of a sirtuin protein to reduce the incidence or severity of flushing and/or hot flashes in menopausal and post-menopausal woman.

In another aspect, sirtuin-modulating compounds that increase the level and/or activity of a sirtuin protein may be used as a therapy for reducing the incidence or severity of flushing and/or hot flashes which are side-effects of another drug therapy, e.g., drug-induced flushing. In certain embodiments, a method for treating and/or preventing drug-induced flushing comprises administering to a patient in need thereof a formulation comprising at least one flushing inducing compound and at least one sirtuin-modulating compound that increases the level and/or activity of a sirtuin protein. In other embodiments, a method for treating drug induced flushing comprises separately administering one or more compounds that induce flushing and one or more sirtuin-modulating compounds, e.g., wherein the sirtuin-modulating compound and flushing inducing agent have not been formulated in the same compositions. When using separate formulations, the sirtuin-modulating compound may be administered (1) at the same as administration of the flushing inducing agent, (2) intermittently with the flushing inducing agent, (3) staggered relative to administration of the flushing inducing agent, (4) prior to administration of the flushing inducing agent, (5) subsequent to administration of the flushing inducing agent, and (6) various combination thereof. Exemplary flushing inducing agents include, for example, niacin, raloxifene, antidepressants, anti-psychotics, chemotherapeutics, calcium channel blockers, and antibiotics.

In certain embodiments, sirtuin-modulating compounds that increase the level and/or activity of a sirtuin protein may be used to reduce flushing side effects of a vasodilator or an antilipemic agent (including anticholesteremic agents and lipotropic agents). In an exemplary embodiment, a sirtuin-modulating compound that increases the level and/or activity of a sirtuin protein may be used to reduce flushing associated with the administration of niacin.

In another embodiment, the invention provides a method for treating and/or preventing hyperlipidemia with reduced flushing side effects. In another representative embodiment, the method involves the use of sirtuin-modulating compounds that increase the level and/or activity of a sirtuin protein to reduce flushing side effects of raloxifene. In another representative embodiment, the method involves the use of sirtuin-modulating compounds that increase the level and/or activity of a sirtuin protein to reduce flushing side effects of antidepressants or anti-psychotic agent. For instance, sirtuin-modulating compounds that increase the level and/or activity of a sirtuin protein can be used in conjunction (administered separately or together) with a serotonin reuptake inhibitor, or a 5HT2 receptor antagonist.

In certain embodiments, sirtuin-modulating compounds that increase the level and/or activity of a sirtuin protein may be used as part of a treatment with a serotonin reuptake inhibitor (SRI) to reduce flushing. In still another representative embodiment, sirtuin-modulating compounds that increase the level and/or activity of a sirtuin protein may be used to reduce flushing side effects of chemotherapeutic agents, such as cyclophosphamide and tamoxifen.

In another embodiment, sirtuin-modulating compounds that increase the level and/or activity of a sirtuin protein may be used to reduce flushing side effects of calcium channel blockers, such as amlodipine.

In another embodiment, sirtuin-modulating compounds that increase the level and/or activity of a sirtuin protein may be used to reduce flushing side effects of antibiotics. For example, sirtuin-modulating compounds that increase the level and/or activity of a sirtuin protein can be used in combination with levofloxacin.

Ocular Disorders

One aspect of the present invention is a method for inhibiting, reducing or otherwise treating vision impairment by administering to a patient a therapeutic dosage of sirtuin modulator selected from a compound disclosed herein, or a pharmaceutically acceptable salt, prodrug or a metabolic derivative thereof.

In certain aspects of the invention, the vision impairment is caused by damage to the optic nerve or central nervous system. In particular embodiments, optic nerve damage is caused by high intraocular pressure, such as that created by glaucoma. In other particular embodiments, optic nerve damage is caused by swelling of the nerve, which is often associated with an infection or an immune (e.g., autoimmune) response such as in optic neuritis.

In certain aspects of the invention, the vision impairment is caused by retinal damage. In particular embodiments, retinal damage is caused by disturbances in blood flow to the eye (e.g., arteriosclerosis, vasculitis). In particular embodiments, retinal damage is caused by disruption of the macula (e.g., exudative or non-exudative macular degeneration).

Exemplary retinal diseases include Exudative Age Related Macular Degeneration, Nonexudative Age Related Macular Degeneration, Retinal Electronic Prosthesis and RPE Transplantation Age Related Macular Degeneration, Acute Multifocal Placoid Pigment Epitheliopathy, Acute Retinal Necrosis, Best Disease, Branch Retinal Artery Occlusion, Branch Retinal Vein Occlusion, Cancer Associated and Related Autoimmune Retinopathies, Central Retinal Artery Occlusion, Central Retinal Vein Occlusion, Central Serous Chorioretinopathy, Eales Disease, Epimacular Membrane, Lattice Degeneration, Macroaneurysm, Diabetic Macular Edema, Irvine-Gass Macular Edema, Macular Hole, Subretinal Neovascular Membranes, Diffuse Unilateral Subacute Neuroretinitis, Nonpseudophakic Cystoid Macular Edema, Presumed Ocular Histoplasmosis Syndrome, Exudative Retinal Detachment, Postoperative Retinal Detachment, Proliferative Retinal Detachment, Rhegmatogenous Retinal Detachment, Tractional Retinal Detachment, Retinitis Pigmentosa, CMV Retinitis, Retinoblastoma, Retinopathy of Prematurity, Birdshot Retinopathy, Background Diabetic Retinopathy, Proliferative Diabetic Retinopathy, Hemoglobinopathies Retinopathy, Purtscher Retinopathy, Valsalva Retinopathy, Juvenile Retinoschisis, Senile Retinoschisis, Terson Syndrome and White Dot Syndromes.

Other exemplary diseases include ocular bacterial infections (e.g. conjunctivitis, keratitis, tuberculosis, syphilis, gonorrhea), viral infections (e.g., Ocular Herpes Simplex Virus, Varicella Zoster Virus, Cytomegalovirus retinitis, Human Immunodeficiency Virus (HIV)) as well as progressive outer retinal necrosis secondary to HIV or other HIV-associated and other immunodeficiency-associated ocular diseases. In addition, ocular diseases include fungal infections (e.g., *Candida* choroiditis, histoplasmosis), protozoal infections (e.g., toxoplasmosis) and others such as ocular toxocariasis and sarcoidosis.

One aspect of the invention is a method for inhibiting, reducing or treating vision impairment in a subject undergoing treatment with a chemotherapeutic drug (e.g., a neurotoxic drug, or a drug that raises intraocular pressure, such as a steroid), by administering to the subject in need of such treatment a therapeutic dosage of a sirtuin modulator disclosed herein.

Another aspect of the invention is a method for inhibiting, reducing or treating vision impairment in a subject undergoing surgery, including ocular or other surgeries performed in the prone position such as spinal cord surgery, by administering to the subject in need of such treatment a therapeutic dosage of a sirtuin modulator disclosed herein. Ocular surgeries include cataract, iridotomy and lens replacements.

Another aspect of the invention is the treatment, including inhibition and prophylactic treatment, of age related ocular diseases include cataracts, dry eye, age-related macular degeneration (AMD), retinal damage and the like, by administering to the subject in need of such treatment a therapeutic dosage of a sirtuin modulator disclosed herein.

Another aspect of the invention is the prevention or treatment of damage to the eye caused by stress, chemical insult or radiation, by administering to the subject in need of such treatment a therapeutic dosage of a sirtuin modulator disclosed herein. Radiation or electromagnetic damage to the eye can include that caused by CRT's or exposure to sunlight or UV.

In certain embodiments, a combination drug regimen may include drugs or compounds for the treatment or prevention of ocular disorders or secondary conditions associated with these conditions. Thus, a combination drug regimen may include one or more sirtuin activators and one or more therapeutic agents for the treatment of an ocular disorder.

In certain embodiments, a sirtuin modulator can be administered in conjunction with a therapy for reducing intraocular pressure. In another embodiment, a sirtuin modulator can be administered in conjunction with a therapy for treating and/or preventing glaucoma. In yet another embodiment, a sirtuin modulator can be administered in conjunction with a therapy for treating and/or preventing optic neuritis. In certain embodiments, a sirtuin modulator can be administered in conjunction with a therapy for treating and/or preventing CMV Retinopathy. In another embodiment, a sirtuin modulator can be administered in conjunction with a therapy for treating and/or preventing multiple sclerosis.

Mitochondrial-Associated Diseases and Disorders

In certain embodiments, the invention provides methods or uses for treating diseases or disorders that would benefit from increased mitochondrial activity. The methods or uses of the present invention involve administering to a subject in need thereof a therapeutically effective amount of a sirtuin-modulating compound. Increased mitochondrial activity refers to increasing activity of the mitochondria while maintaining the overall numbers of mitochondria (e.g., mitochondrial mass), increasing the numbers of mitochondria thereby increasing mitochondrial activity (e.g., by stimulating mitochondrial biogenesis), or combinations thereof. In certain embodiments, diseases and disorders that would benefit from increased mitochondrial activity include diseases or disorders associated with mitochondrial dysfunction.

In certain embodiments, methods or uses for treating diseases or disorders that would benefit from increased mitochondrial activity may comprise identifying a subject suffering from a mitochondrial dysfunction. Methods or uses for diagnosing a mitochondrial dysfunction may involve molecular genetics, pathologic and/or biochemical analyses. Diseases and disorders associated with mitochondrial dysfunction include diseases and disorders in which deficits in mitochondrial respiratory chain activity contribute to the development of pathophysiology of such diseases or disorders in a mammal. Diseases or disorders that would benefit from increased mitochondrial activity generally include for example, diseases in which free radical mediated oxidative injury leads to tissue degeneration, diseases in which cells inappropriately undergo apoptosis, and diseases in which cells fail to undergo apoptosis.

In certain embodiments, the invention provides methods or uses for treating a disease or disorder that would benefit from increased mitochondrial activity that involves administering to a subject in need thereof one or more sirtuin-modulating compounds in combination with another therapeutic agent such as, for example, an agent useful for treating mitochondrial dysfunction or an agent useful for reducing a symptom associated with a disease or disorder involving mitochondrial dysfunction.

In exemplary embodiments, the invention provides methods or uses for treating diseases or disorders that would benefit from increased mitochondrial activity by administering to a subject a therapeutically effective amount of a sirtuin-modulating compound. Exemplary diseases or disorders include, for example, neuromuscular disorders (e.g., Friedreich's Ataxia, muscular dystrophy, multiple sclerosis, etc.), disorders of neuronal instability (e.g., seizure disorders, migraine, etc.), developmental delay, neurodegenerative disorders (e.g., Alzheimer's Disease, Parkinson's Disease, amyotrophic lateral sclerosis, etc.), ischemia, renal tubular acidosis, age-related neurodegeneration and cognitive decline, chemotherapy fatigue, age-related or chemotherapy-induced menopause or irregularities of menstrual cycling or ovulation, mitochondrial myopathies, mitochondrial damage (e.g., calcium accumulation, excitotoxicity, nitric oxide exposure, hypoxia, etc.), and mitochondrial deregulation.

Muscular dystrophy refers to a family of diseases involving deterioration of neuromuscular structure and function, often resulting in atrophy of skeletal muscle and myocardial dysfunction, such as Duchenne muscular dystrophy. In certain embodiments, sirtuin-modulating compounds may be used for reducing the rate of decline in muscular functional capacities and for improving muscular functional status in patients with muscular dystrophy.

In certain embodiments, sirtuin-modulating compounds may be useful for treatment mitochondrial myopathies. Mitochondrial myopathies range from mild, slowly progressive weakness of the extraocular muscles to severe, fatal infantile myopathies and multisystem encephalomyopathies. Some syndromes have been defined, with some overlap between them. Established syndromes affecting muscle include progressive external ophthalmoplegia, the Kearns-Sayre syndrome (with ophthalmoplegia, pigmentary retinopathy, cardiac conduction defects, cerebellar ataxia, and sensorineural deafness), the MELAS syndrome (mitochondrial encephalomyopathy, lactic acidosis, and stroke-like episodes), the MERFF syndrome (myoclonic epilepsy and ragged red fibers), limb-girdle distribution weakness, and infantile myopathy (benign or severe and fatal).

In certain embodiments, sirtuin-modulating compounds may be useful for treating patients suffering from toxic damage to mitochondria, such as, toxic damage due to calcium accumulation, excitotoxicity, nitric oxide exposure, drug induced toxic damage, or hypoxia.

In certain embodiments, sirtuin-modulating compounds may be useful for treating diseases or disorders associated with mitochondrial deregulation.

Muscle Performance

In other embodiments, the invention provides methods or uses for enhancing muscle performance by administering a therapeutically effective amount of a sirtuin-modulating compound. For example, sirtuin-modulating compounds may be useful for improving physical endurance (e.g., ability to perform a physical task such as exercise, physical labor, sports activities, etc.), inhibiting or retarding physical fatigues, enhancing blood oxygen levels, enhancing energy in healthy individuals, enhance working capacity and endurance, reducing muscle fatigue, reducing stress, enhancing cardiac and cardiovascular function, improving sexual ability, increasing muscle ATP levels, and/or reducing lactic acid in blood. In certain embodiments, the methods or uses involve administering an amount of a sirtuin-modulating compound that increase mitochondrial activity, increase mitochondrial biogenesis, and/or increase mitochondrial mass.

Sports performance refers to the ability of the athlete's muscles to perform when participating in sports activities.

Enhanced sports performance, strength, speed and endurance are measured by an increase in muscular contraction strength, increase in amplitude of muscle contraction, shortening of muscle reaction time between stimulation and contraction. Athlete refers to an individual who participates in sports at any level and who seeks to achieve an improved level of strength, speed and endurance in their performance, such as, for example, body builders, bicyclists, long distance runners, short distance runners, etc. Enhanced sports performance in manifested by the ability to overcome muscle fatigue, ability to maintain activity for longer periods of time, and have a more effective workout.

In the arena of athlete muscle performance, it is desirable to create conditions that permit competition or training at higher levels of resistance for a prolonged period of time.

It is contemplated that the methods or uses of the present invention will also be effective in the treatment of muscle related pathological conditions, including acute sarcopenia, for example, muscle atrophy and/or cachexia associated with burns, bed rest, limb immobilization, or major thoracic, abdominal, and/or orthopedic surgery.

In certain embodiments, the invention provides novel dietary compositions comprising sirtuin modulators, a method for their preparation, and a method of using the compositions for improvement of sports performance. Accordingly, provided are therapeutic compositions, foods and beverages that have actions of improving physical endurance and/or inhibiting physical fatigues for those people involved in broadly-defined exercises including sports requiring endurance and labors requiring repeated muscle exertions. Such dietary compositions may additional comprise electrolytes, caffeine, vitamins, carbohydrates, etc.

Other Uses

Sirtuin-modulating compounds that increase the level and/or activity of a sirtuin protein may be used for treating or preventing viral infections (such as infections by influenza, herpes or papilloma virus) or as antifungal agents. In certain embodiments, sirtuin-modulating compounds that increase the level and/or activity of a sirtuin protein may be administered as part of a combination drug therapy with another therapeutic agent for the treatment of viral diseases. In another embodiment, sirtuin-modulating compounds that increase the level and/or activity of a sirtuin protein may be administered as part of a combination drug therapy with another anti-fungal agent.

Subjects that may be treated as described herein include eukaryotes, such as mammals, e.g., humans, ovines, bovines, equines, porcines, canines, felines, non-human primate, mice, and rats. Cells that may be treated include eukaryotic cells, e.g., from a subject described above, or plant cells, yeast cells and prokaryotic cells, e.g., bacterial cells. For example, modulating compounds may be administered to farm animals to improve their ability to withstand farming conditions longer.

Sirtuin-modulating compounds that increase the level and/or activity of a sirtuin protein may also be used to increase lifespan, stress resistance, and resistance to apoptosis in plants. In certain embodiments, a compound is applied to plants, e.g., on a periodic basis, or to fungi. In another embodiment, plants are genetically modified to produce a compound. In another embodiment, plants and fruits are treated with a compound prior to picking and shipping to increase resistance to damage during shipping. Plant seeds may also be contacted with compounds described herein, e.g., to preserve them.

In other embodiments, sirtuin-modulating compounds that increase the level and/or activity of a sirtuin protein may be used for modulating lifespan in yeast cells. Situations in which it may be desirable to extend the lifespan of yeast cells include any process in which yeast is used, e.g., the making of beer, yogurt, and bakery items, e.g., bread. Use of yeast having an extended lifespan can result in using less yeast or in having the yeast be active for longer periods of time. Yeast or other mammalian cells used for recombinantly producing proteins may also be treated as described herein.

Sirtuin-modulating compounds that increase the level and/or activity of a sirtuin protein may also be used to increase lifespan, stress resistance and resistance to apoptosis in insects. In this embodiment, compounds would be applied to useful insects, e.g., bees and other insects that are involved in pollination of plants. In a specific embodiment, a compound would be applied to bees involved in the production of honey. Generally, the methods or uses described herein may be applied to any organism, e.g., eukaryote, which may have commercial importance. For example, they can be applied to fish (aquaculture) and birds (e.g., chicken and fowl).

Higher doses of sirtuin-modulating compounds that increase the level and/or activity of a sirtuin protein may also be used as a pesticide by interfering with the regulation of silenced genes and the regulation of apoptosis during development. In this embodiment, a compound may be applied to plants using a method known in the art that ensures the compound is bio-available to insect larvae, and not to plants.

At least in view of the link between reproduction and longevity, sirtuin-modulating compounds that increase the level and/or activity of a sirtuin protein can be applied to affect the reproduction of organisms such as insects, animals and microorganisms.

Additional Embodiments

In one aspect, the present invention relates to a method of increasing sirtuin-1 activity in a cell comprising the step of contacting the cell with a compound of Formula (I) or a pharmaceutically acceptable salt or corresponding pharmaceutical composition, respectively, thereof.

In one aspect, the present invention relates to a method for treating insulin resistance, a metabolic syndrome, diabetes, or complications thereof, or for increasing insulin sensitivity, comprising administering a compound or a pharmaceutically acceptable salt or corresponding pharmaceutical composition, respectively, thereof, to a subject in need thereof.

In one aspect, the present invention relates to a method for treating metabolic dysfunctions comprising administering a compound or a pharmaceutically acceptable salt or corresponding pharmaceutical composition, respectively, thereof, to a subject in need thereof.

In one aspect, the present invention relates to a method for treating diseases or disorders resulting from diminished SIRT1 expression or activity, which comprises administering a compound or a pharmaceutically acceptable salt or corresponding pharmaceutical composition, respectively, thereof, to a subject in need thereof.

In one aspect, the present invention relates to a method where the diseases or disorders resulting from diminished SIRT1 expression or activity are selected from, but not limited to aging or stress, diabetes, metabolic dysfunctions, neurodegenerative diseases, cardiovascular disease, cancer or inflammatory disease.

In one aspect, the present invention relates to a method, where diseases related to aging or stress, diabetes, metabolic dysfunctions, neurodegenerative diseases, cardiovascular disease, cancer or inflammatory disease are selected from psoriasis, atopic dermatitis, acne, rosacea, inflammatory bowel disease, osteoporosis, sepsis, arthritis, COPD, systemic lupus erythematosus and ophthalmic inflammation.

In one aspect, the present invention relates to a method, where diseases related to aging or stress, diabetes, metabolic dysfunctions, neurodegenerative diseases, cardiovascular disease, cancer or inflammatory disease are selected from psoriasis, atopic dermatitis, acne, rosacea, inflammatory bowel disease, osteoporosis, sepsis, arthritis, COPD, systemic lupus erythematosus and ophthalmic inflammation.

In one aspect, the present invention relates to a method for treating psoriasis, which comprises administering a compound or a pharmaceutically acceptable salt or corresponding pharmaceutical composition, respectively, thereof, to a subject in need thereof.

In one aspect, the present invention relates to administering a compound or a pharmaceutically acceptable salt or corresponding pharmaceutical composition, respectively, thereof, for use in therapy in treating a subject suffering from or susceptible to insulin resistance, a metabolic syndrome, diabetes, or complications thereof, or for increasing insulin sensitivity in a subject.

In one aspect, the present invention relates to a use of administering a compound or a pharmaceutically acceptable salt or corresponding pharmaceutical composition, respectively, thereof, in the manufacture of a medicament for use in the treatment of insulin resistance, a metabolic syndrome, diabetes, or complications thereof, or for increasing insulin sensitivity in a subject.

Assays

Yet other methods or uses contemplated herein include screening methods for identifying compounds or agents that modulate sirtuins. An agent may be a nucleic acid, such as an aptamer. Assays may be conducted in a cell based or cell free format. For example, an assay may comprise incubating (or contacting) a sirtuin with a test agent under conditions in which a sirtuin can be modulated by an agent known to modulate the sirtuin, and monitoring or determining the level of modulation of the sirtuin in the presence of the test agent relative to the absence of the test agent. The level of modulation of a sirtuin can be determined by determining its ability to deacetylate a substrate. Exemplary substrates are acetylated peptides which can be obtained from BIOMOL (Plymouth Meeting, Pa.). Preferred substrates include peptides of p53, such as those comprising an acetylated K382. A particularly preferred substrate is the Fluor de Lys-SIRT1 (BIOMOL), i.e., the acetylated peptide Arg-His-Lys-Lys. Other substrates are peptides from human histones H3 and H4 or an acetylated amino acid. Substrates may be fluorogenic. The sirtuin may be SIRT1, Sir2, SIRT3, or a portion thereof. For example, recombinant SIRT1 can be obtained from BIOMOL. The reaction may be conducted for about 30 minutes and stopped, e.g., with nicotinamide. The HDAC fluorescent activity assay/drug discovery kit (AK-500, BIOMOL Research Laboratories) may be used to determine the level of acetylation. Similar assays are described in Bitterman et al. (2002) J. Biol. Chem. 277:45099. The level of modulation of the sirtuin in an assay may be compared to the level of modulation of the sirtuin in the presence of one or more (separately or simultaneously) compounds described herein, which may serve as positive or negative controls. Sirtuins for use in the assays may be full length sirtuin proteins or portions thereof. Since it has been shown herein that activating compounds appear to interact with the N-terminus of SIRT1, proteins for use in the assays include N-terminal portions of sirtuins, e.g., about amino acids 1-176 or 1-255 of SIRT1; about amino acids 1-174 or 1-252 of Sir2.

In certain embodiments, a screening assay comprises (i) contacting a sirtuin with a test agent and an acetylated substrate under conditions appropriate for the sirtuin to deacetylate the substrate in the absence of the test agent; and (ii) determining the level of acetylation of the substrate, wherein a lower level of acetylation of the substrate in the presence of the test agent relative to the absence of the test agent indicates that the test agent stimulates deacetylation by the sirtuin, whereas a higher level of acetylation of the substrate in the presence of the test agent relative to the absence of the test agent indicates that the test agent inhibits deacetylation by the sirtuin.

In another embodiment, the screening assay may detect the formation of a 2'/3'-O-acetyl-ADP-ribose product of sirtuin-mediated NAD-dependent deacetylation. This O-acetyl-ADP-ribose product is formed in equimolar quantities with the deacetylated peptide product of the sirtuin deacetylation reaction. Accordingly, the screening assay may include (i) contacting a sirtuin with a test agent and an acetylated substrate under conditions appropriate for the sirtuin to deacetylate the substrate in the absence of the test agent; and (ii) determining the amount of O-acetyl-ADP-ribose formation, wherein an increase in O-acetyl-ADP-ribose formation in the presence of the test agent relative to the absence of the test agent indicates that the test agent stimulates deacetylation by the sirtuin, while a decrease in O-acetyl-ADP-ribose formation in the presence of the test agent relative to the absence of the test agent indicates that the test agent inhibits deacetylation by the sirtuin.

Methods for identifying an agent that modulates, e.g., stimulates, sirtuins in vivo may comprise (i) contacting a cell with a test agent and a substrate that is capable of entering a cell in the presence of an inhibitor of class I and class II HDACs under conditions appropriate for the sirtuin to deacetylate the substrate in the absence of the test agent; and (ii) determining the level of acetylation of the substrate, wherein a lower level of acetylation of the substrate in the presence of the test agent relative to the absence of the test agent indicates that the test agent stimulates deacetylation by the sirtuin, whereas a higher level of acetylation of the substrate in the presence of the test agent relative to the absence of the test agent indicates that the test agent inhibits deacetylation by the sirtuin. A preferred substrate is an acetylated peptide, which is also preferably fluorogenic, as further described herein. The method may further comprise lysing the cells to determine the level of acetylation of the substrate. Substrates may be added to cells at a concentration ranging from about 1 µM to about 10 mM, preferably from about 10 µM to 1 mM, even more preferably from about 100 µM to 1 mM, such as about 200 µM. A preferred substrate is an acetylated lysine, e.g., ε-acetyl lysine (Fluor de Lys, FdL) or Fluor de Lys-SIRT1. A preferred inhibitor of class I and class II HDACs is trichostatin A (TSA), which may be used at concentrations ranging from about 0.01 to 100 µM, preferably from about 0.1 to 10 µM, such as 1 µM. Incubation of cells with the test compound and the substrate may be conducted for about 10 minutes to 5 hours, preferably for about 1-3 hours. Since TSA inhibits all class I and class II HDACs, and that certain substrates, e.g., Fluor de Lys, is a poor substrate for SIRT2 and even less a substrate for SIRT3-7, such an assay may be used to identify modulators of SIRT1 in vivo.

Methods or Uses in Therapy

The present invention also relates to methods or uses for using Sirtuin Modulator compounds as defined herein in treating and/or preventing a wide variety of diseases and disorders, which include, but are not limited to, for example, diseases or disorders related to aging or stress, diabetes, obesity, neurodegenerative diseases, cardiovascular disease, blood clotting disorders, inflammation, cancer, and/or flushing as well as diseases or disorders that would benefit from increased mitochondrial activity, further which may be selected from or include, but are not limited to psoriasis, atopic dermatitis, acne, rosacea, inflammatory bowel disease, osteoporosis, sepsis, arthritis, COPD, systemic lupus erythematosus and ophthalmic inflammation.

In another aspect, the invention provides methods or uses for using sirtuin-modulating compounds, or compositions comprising sirtuin-modulating compounds. In certain embodiments, sirtuin-modulating compounds that increase the level and/or activity of a sirtuin protein may be used for a variety of therapeutic applications including, for example, increasing the lifespan of a cell, and treating and/or preventing a wide variety of diseases and disorders including, for example, diseases or disorders related to aging or stress, diabetes, obesity, neurodegenerative diseases, chemotherapeutic-induced neuropathy, neuropathy associated with an ischemic event, ocular diseases and/or disorders, cardiovascular disease, blood clotting disorders, inflammation, and/or flushing, etc. Sirtuin-modulating compounds that increase the level and/or activity of a sirtuin protein may also be used for treating a disease or disorder in a subject that would benefit from increased mitochondrial activity, for enhancing muscle performance, for increasing muscle ATP levels, or for treating or preventing muscle tissue damage associated with hypoxia or ischemia. In other embodiments, sirtuin-modulating compounds that decrease the level and/or activity of a sirtuin protein may be used for a variety of therapeutic applications including, for example, increasing cellular sensitivity to stress, increasing apoptosis, treatment of cancer, stimulation of appetite, and/or stimulation of weight gain, etc. As described further below, the methods or uses of the present invention comprise administering to a subject in need thereof a pharmaceutically effective amount of a sirtuin-modulating compound.

In certain aspects, the sirtuin-modulating compounds may be administered alone or in combination with other compounds, including other sirtuin-modulating compounds, or other therapeutic agents.

In another aspect, the present invention relates to a method of increasing sirtuin-1 activity in a cell, which comprises the step of contacting the cell with a compound of Formulas (I) to (V), corresponding analogs or derivatives thereof (i.e., with hydrogen substitution at the $R^2$ position) or a pharmaceutical acceptable salt thereof of the present invention.

In another aspect, the present invention relates to a method of increasing sirtuin-1 activity in a cell comprising the step of contacting the cell with a pharmaceutical composition of the present invention as defined herein In another aspect, the present invention relates to a method for treating insulin resistance, a metabolic syndrome, diabetes, or complications thereof, or for increasing insulin sensitivity, which comprises administering a compound a compound of Formulas (I) to (V), corresponding analogs or derivatives thereof (i.e., with hydrogen substitution at the $R^2$ position) of the present invention to a subject in need thereof.

In another aspect, the present invention relates to a method for treating a subject suffering from or susceptible to insulin resistance, a metabolic syndrome, diabetes, or complications thereof, or for increasing insulin sensitivity in a subject, comprising administering a pharmaceutical composition of the present invention to the subject in need thereof.

In another aspect, the present invention relates to a method for treating insulin resistance, a metabolic syndrome, diabetes, or complications thereof, or for increasing insulin sensitivity, comprising administering a pharmaceutical composition of the present invention to a subject in need thereof.

In another aspect, the present invention relates to a method of increasing sirtuin-1 activity in a cell, which comprises the step of contacting a cell with a compound of Formulas (I) to (V), corresponding analogs or derivatives thereof (i.e., with hydrogen substitution at the $R^2$ position) or a pharmaceutical acceptable salt thereof.

In another aspect, the present invention relates to a method of increasing sirtuin-1 activity in a cell, which comprises the step of contacting a cell with a pharmaceutical composition of the present invention In another aspect, the present invention relates to a method for treating metabolic dysfunctions, which comprises administering a compound of Formulas (I) to (V), corresponding analogs or derivatives thereof (i.e., with hydrogen substitution at the $R^2$ position) or a pharmaceutical acceptable salt thereof to a subject in need thereof.

In another aspect, the present invention relates to a method for treating metabolic dysfunctions comprising administering a pharmaceutical composition of the present invention to a subject in need thereof.

In another aspect, the present invention relates to a method for treating diseases or disorders resulting from diminished SIRT1 expression or activity, which comprises administering a compound of Formulas (I) to (V), corresponding analogs or derivatives thereof (i.e., with hydrogen substitution at the $R^2$ position) or a pharmaceutical acceptable salt thereof to a subject in need thereof.

In another aspect, the present invention relates to method where the diseases or disorders resulting from diminished SIRT1 expression or activity are selected from, but not limited to aging or stress, diabetes, metabolic dysfunctions, neurodegenerative diseases, cardiovascular disease, cancer or inflammatory disease.

In another aspect, the present invention relates to a method where diseases related to aging or stress, diabetes, metabolic dysfunctions, neurodegenerative diseases, cardiovascular disease, cancer or inflammatory disease are selected from psoriasis, atopic dermatitis, acne, rosacea, inflammatory bowel disease, osteoporosis, sepsis, arthritis, COPD, systemic lupus erythematosus and ophthalmic inflammation.

In another aspect, the present invention relates to a method for treating psoriasis, which comprises administering a compound of Formulas (I) to (V), corresponding analogs or derivatives thereof (i.e., with hydrogen substitution at the $R^2$ position) or a pharmaceutical acceptable salt thereof to a subject in need thereof.

In another aspect, the present invention relates to a method for treating psoriasis, which comprises administering a pharmaceutical composition of the present invention to a subject in need thereof Pharmaceutical Compositions and Formulations In general, the present invention relates to substituted bridged urea analog compounds of Formulas (I) to (V), corresponding analogs or derivatives thereof (i.e., with hydrogen substitution at the $R^2$ position), or pharmaceutically acceptable salts thereof, corresponding pharmaceutical compositions, processes for making and use of such compounds, alone or in combination with other therapeutic agents, as Sirtuin Modulators useful for increasing lifespan of a cell, and in treating and/or preventing a wide variety of diseases and disorders, which include, but are not limited to, for example, diseases or disorders related to aging or stress, diabetes, obesity, neurodegenerative diseases, cardiovascular disease, blood clotting disorders, inflammation, cancer, and/or flushing as well as diseases or disorders that would benefit from increased mitochondrial activity.

In particular, the present invention relates to novel compounds of Formulas (I) to (V), corresponding analogs or derivatives thereof (i.e., with hydrogen substitution at the $R^2$ position) or a pharmaceutical acceptable salt thereof and corresponding pharmaceutical compositions comprising compounds of Formulas (I) to (V), respectively.

In another aspect, the present invention relates to a pharmaceutical composition comprising a pharmaceutically acceptable carrier or diluent and a compound of Formulas (I) to (V), corresponding analogs or derivatives thereof (i.e., with hydrogen substitution at the $R^2$ position) or a pharmaceutical acceptable salt thereof.

In another aspect, the present invention relates to a pharmaceutical composition of the present invention, further comprising an additional active agent.

In another aspect, the present invention relates to a pharmaceutical composition comprising a compound of Formulas (I) to (V), corresponding analogs or derivatives thereof (i.e., with hydrogen substitution at the $R^2$ position) or a pharmaceutical acceptable salt thereof and at least one pharmaceutically acceptable carrier.

The compounds described herein may be formulated in a conventional manner using one or more physiologically or pharmaceutically acceptable carriers or excipients. For example, compounds and their pharmaceutically acceptable salts and solvates may be formulated for administration by, for example, injection (e.g. SubQ, IM, IP), inhalation or insufflation (either through the mouth or the nose) or oral, buccal, sublingual, transdermal, nasal, parenteral or rectal administration. In certain embodiments, a compound may be administered locally, at the site where the target cells are present, i.e., in a specific tissue, organ, or fluid (e.g., blood, cerebrospinal fluid, etc.).

The compounds can be formulated for a variety of modes of administration, including systemic and topical or localized administration. Techniques and formulations generally may be found in Remington's Pharmaceutical Sciences, Meade Publishing Co., Easton, Pa. For parenteral administration, injection is preferred, including intramuscular, intravenous, intraperitoneal, and subcutaneous. For injection, the compounds can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets, lozenges, or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For administration by inhalation (e.g., pulmonary delivery), the compounds may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, compounds may also be formulated as a depot preparation. Such long acting formulations may be administered by implantation (for example subcutaneously or intramuscularly) or by intramuscular injection. Thus, for example, compounds may be formulated with suitable polymeric or hydrophobic materials (for example as an emulsion in an acceptable oil) or ion exchange resins, or as sparingly soluble derivatives, for example, as a sparingly soluble salt. Controlled release formula also includes patches.

In certain embodiments, the compounds described herein can be formulated for delivery to the central nervous system (CNS) (reviewed in Begley, Pharmacology & Therapeutics 104: 29-45 (2004)). Conventional approaches for drug delivery to the CNS include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide).

Liposomes are a further drug delivery system which is easily injectable. Accordingly, in the method of invention the active compounds can also be administered in the form of a liposome delivery system. Liposomes are well known by those skilled in the art. Liposomes can be formed from a variety of phospholipids, such as cholesterol, stearylamine of phosphatidylcholines. Liposomes usable for the method of invention encompass all types of liposomes including, but not limited to, small unilamellar vesicles, large unilamellar vesicles and multilamellar vesicles.

Another way to produce a formulation, particularly a solution, of a compound described herein, is through the use of cyclodextrin. By cyclodextrin is meant α-, β-, or γ-cyclodextrin. Cyclodextrins are described in detail in Pitha et al., U.S. Pat. No. 4,727,064. Cyclodextrins are cyclic oligomers of glucose; these compounds form inclusion complexes with any drug whose molecule can fit into the lipophile-seeking cavities of the cyclodextrin molecule.

Rapidly disintegrating or dissolving dosage forms are useful for the rapid absorption, particularly buccal and sublingual absorption, of pharmaceutically active agents. Fast melt dosage forms are beneficial to patients, such as aged and pediatric patients, who have difficulty in swallowing typical solid dosage forms, such as caplets and tablets. Additionally, fast melt dosage forms circumvent drawbacks associated with, for example, chewable dosage forms, wherein the length of time an active agent remains in a patient's mouth plays an important role in determining the amount of taste masking and the extent to which a patient may object to throat grittiness of the active agent.

Pharmaceutical compositions (including cosmetic preparations) may comprise from about 0.00001 to 100% such as from 0.001 to 10% or from 0.1% to 5% by weight of one or more compounds described herein. In other embodiments, the pharmaceutical composition comprises: (i) 0.05 to 1000 mg of the compounds of the invention, or a pharmaceutically acceptable salt thereof, and (ii) 0.1 to 2 grams of one or more pharmaceutically acceptable excipients.

In some embodiments, a compound described herein is incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

Formulations may be colorless, odorless ointments, lotions, creams, microemulsions and gels.

The compounds may be incorporated into ointments, which generally are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing.

The compounds may be incorporated into lotions, which generally are preparations to be applied to the skin surface without friction, and are typically liquid or semiliquid preparations in which solid particles, including the active agent, are present in a water or alcohol base. Lotions are usually suspensions of solids, and may comprise a liquid oily emulsion of the oil-in-water type.

The compounds may be incorporated into creams, which generally are viscous liquid or semisolid emulsions, either oil-in-water or water-in-oil. Cream bases are water-washable, and contain an oil phase, an emulsifier and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington's, supra, is generally a nonionic, anionic, cationic or amphoteric surfactant.

The compounds may be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology (New York: Marcel Dekker, 1992), volume 9).

The compounds may be incorporated into gel formulations, which generally are semisolid systems consisting of either suspensions made up of small inorganic particles (two-phase systems) or large organic molecules distributed substantially uniformly throughout a carrier liquid (single phase gels). Although gels commonly employ aqueous carrier liquid, alcohols and oils can be used as the carrier liquid as well.

Other active agents may also be included in formulations, e.g., other anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate).

In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Conditions of the eye can be treated or prevented by, e.g., systemic, topical, intraocular injection of a compound, or by insertion of a sustained release device that releases a compound. A compound may be delivered in a pharmaceutically acceptable ophthalmic vehicle, such that the compound is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically acceptable ophthalmic vehicle may, for example, be an ointment, vegetable oil or an encapsulating material. Alternatively, the compounds of the invention may be injected directly into the vitreous and aqueous humour. In a further alternative, the compounds may be administered systemically, such as by intravenous infusion or injection, for treatment of the eye.

The compounds described herein may be stored in oxygen free environment. For example, a composition can be prepared in an airtight capsule for oral administration, such as Capsugel from Pfizer, Inc.

Cells, e.g., treated ex vivo with a compound as described herein, can be administered according to methods or uses for administering a graft to a subject, which may be accompanied, e.g., by administration of an immunosuppressant drug, e.g., cyclosporin A. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000.

Toxicity and therapeutic efficacy of compounds can be determined by standard pharmaceutical procedures in cell cultures or experimental animals. The $LD_{50}$ is the dose lethal to 50% of the population. The $ED_{50}$ is the dose therapeutically effective in 50% of the population. The dose ratio between toxic and therapeutic effects ($LD_{50}/ED_{50}$) is the therapeutic index. Compounds that exhibit large therapeutic indexes are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

Kits

Also provided herein are kits, e.g., kits for therapeutic purposes or kits for modulating the lifespan of cells or modulating apoptosis. A kit may comprise one or more compounds as described herein, e.g., in premeasured doses. A kit may optionally comprise devices for contacting cells with the compounds and instructions for use. Devices include syringes, stents and other devices for introducing a compound into a subject (e.g., the blood vessel of a subject) or applying it to the skin of a subject.

In yet another embodiment, the invention provides a composition of matter comprising a compound of this invention and another therapeutic agent (the same ones used in combination therapies and combination compositions) in separate dosage forms, but associated with one another. The term "associated with one another" as used herein means that the separate dosage forms are packaged together or otherwise attached to one another such that it is readily apparent that the separate dosage forms are intended to be sold and administered as part of the same regimen. The compound and the other agent are preferably packaged together in a blister pack or other multi-chamber package, or as connected, separately sealed containers (such as foil pouches or the like) that can be separated by the user (e.g., by tearing on score lines between the two containers).

In still another embodiment, the invention provides a kit comprising in separate vessels, a) a compound of this invention; and b) another therapeutic agent such as those described elsewhere in the specification.

The practice of the present methods will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

The Examples set forth below are illustrative of the present invention and are not intended to limit, in any way, the scope of the present invention.

EXAMPLES

The following examples illustrate the invention. These examples are not intended to limit the scope of the present invention, but rather to provide guidance to the skilled artisan to prepare and use the compounds, compositions, methods and uses of the present invention.

While particular embodiments of the present invention are described, the skilled artisan will appreciate that various changes and modifications can be made without departing from the spirit and scope of the invention.

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification.

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted, and all solvents are highest available purity unless otherwise indicated.

Instrumentation Used
LCMS with PDA:
Waters Alliance2695-2996/Quattromicro
Agilent—1200/SQD
Preparative LC with UV Detector (Prep HPLC):
Waters—2545/2998 PDA and 2487 UV
Shimadzu—LC-20AP/20AV-UV
Gilson—333,334/115-UV
Chiral HPLC:
Waters Alliance—2695/2998 &2996
SFC Purification Systems:
Thar—SFC-80
Waters SFC-200
NMR (400 MHz):
Varian—400 MHz
$^1$H-NMR tabulation was generated with 2014 ACD labs software.
$^1$H NMR (hereinafter also "NMR") spectra were recorded on a Varian-400 MHz spectrometer. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).
LCMS Methods Used
Aca. Method Conditions: RND-ABC-6-MIN
Column: XBridge BEH C18 (50 mm×4.6 mm, 2.5 μm)
Mobile Phase: A: 5 mM Ammonium Bicarbonate in water (PH-10 with Ammonia): ACN
Time (min)/% ACN: 0/5, 0.5/5, 1/15, 3.3/98, 5.2/98, 5.5/5, 6.0/5
Column temp: 35° C., Flow Rate 1.3 ml/min
MS Parameters:
Mass Range: 100-1000
Scan Time: 0.5 Sec
Inter-Scan delay: 0.1 sec
Run Time: 6.0 min
Acq. Method Conditions: RND-FA-4.5-MIN
Column: Acquity BEH C18 (50 mm×2.1 mm, 1.7 um)
Mobile Phase: A: 0.1% FA in water; B: 0.1% FA in ACN
Time (min)/% B: 0/3, 0.4/3, 3.2/98, 3.8/98, 4.2/3, 4.5/3
Column Temp: 35° C., Flow Rate: 0.6 mL/min
MS Parameters:
Mass Range: 100-1000
Scan Time: 0.5 Sec
Inter-Scan delay: 0.1 sec
Run Time: 4.5 min
Acq. Method Conditions: RND-FA-4.5-MIN
Column: Acquity BEH C18 (50 mm×2.1 mm, 1.7 um)
Mobile Phase: A: 0.1% FA in water; B: 0.1% FA in ACN
Time (min)/% B: 0/3, 0.4/3, 3.2/98, 3.8/98, 4.2/3, 4.5/3
Column Temp: 35° C., Flow Rate: 0.6 mL/min
MS Parameters:
Mass Range: 100-1000
Fragmentor: 100
Step Size: 0.1
Run Time: 4.5 min
Aca. Method Conditions: RND-ABC-6.5-MIN
Column: XBridge BEH C18 (50 mm×4.6 mm, 2.5 μm)
Mobile Phase: A: 5 mM Ammonium Bicarbonate in water (PH-10 with Ammonia): ACN
Time (min)/% ACN: 0/5, 0.5/5, 1/15, 3.3/98, 6.0/98, 6.1/5, 6.5/5
Column temp: 35° C., Flow Rate 1.3 ml/min
MS Parameters:
Mass Range: 100-1000
Fragmentor: 100
Step Size: 0.1
Run Time: 6.5 min
Acq. Method Conditions: RND-ABC-10-MIN
Column: XBridge BEH C18 (50 mm×4.6 mm, 2.5 μm)
Mobile Phase: A: 5 mM Ammonium Bicarbonate in water (PH-10 with Ammonia): ACN
Time (min)/% ACN: 0/5, 0.5/5, 1.5/15, 7/98, 9.0/98, 9.5/5, 10/5
Column temp: 35° C., Flow Rate 1.3 ml/min
MS Parameters:
Mass Range: 100-1000
Fragmentor: 100
Step Size: 0.1
Run Time: 10.0 min

INTERMEDIATES

Synthesis of (S)-Dimethyl 2-((6-chloro-3-nitropyridin-2-yl)amino)succinate

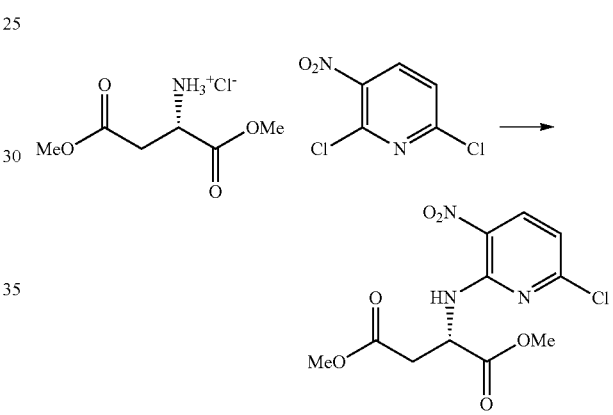

To a 2 L flask equipped with a thermometer, a reflux condenser, and a mechanical stirrer was added 2,6-dichloro-3-nitropyridine (100 g, 0.52 mol), (S)-aspartic acid dimethyl ester hydrochloride (205 g, 1.04 mol), NaHCO$_3$ (174 g, 2.07 mol) and tetrahydrofuran (1 L). The reaction was stirred at 40° C. for 16 h, and was monitored for the disappearance of 2,6-dichloropyridine by HPLC. After the reaction was complete, the solids were filtered away and washed with ethyl acetate (3×300 mL). The combined filtrate and washings were concentrated to dryness, and the residue was taken up in 1 L of ethyl acetate. The solution was stirred with charcoal (200 g) at ambient temperature for 2 h, and the charcoal was filtered away and washed with additional ethyl acetate (3×200 mL). The combined filtrate and washings were concentrated in vacuo to obtain crude (S)-dimethyl 2-((6-chloro-3-nitropyridin-2-yl)amino)succinate (180 g, >100%) as a yellow oil. This was used in the next step without further purification. LRMS (m/z): 318.0 [M+H]$^+$; HRMS (m/z): [M+H]$^+$ calcd for C$_{11}$H$_{13}$N$_3$O$_6$Cl, 318.0493; found, 318.0492; $^1$H-NMR (300 MHz, DMSO-d6): δ 9.00 (d, J=7.9 Hz, 1H, —NH), 8.50 (d, J=8.6 Hz, 1H), 6.92 (d, J=8.6 Hz, 1H), 5.23 (m, J=5.7, 7.9 Hz, 1H, —CHNH), 3.67 (s, 3H), 3.63 (s, 3H), 3.06 (m, J=5.8 Hz, 2H, —CHCH$_2$); $^{13}$C-NMR (APT) (75 MHz, DMSO-d6): δ 170.93 (C), 170.65 (C), 154.65 (C), 150.59 (C), 138.82 (CH), 127.28 (C), 112.81 (CH), 52.23 (CH$_3$), 51.74 (CH$_3$), 50.20 (CH), 35.31 (CH$_2$).

Synthesis of (S)-Methyl 2-(6-chloro-2-oxo-1,2,3,4-tetrahydropyrido[2,3-b]pyrazin-3-yl)acetate

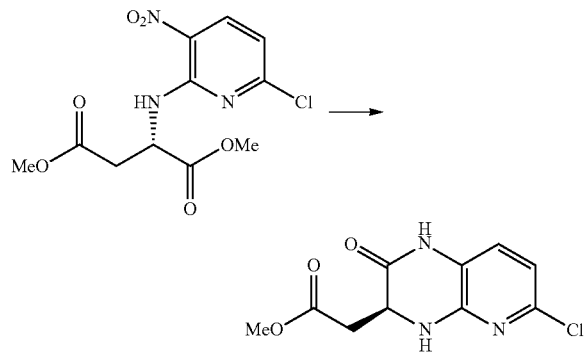

To a 5 L three necked flask equipped with a thermometer, a reflux condenser, and a mechanical stirrer was charged with crude (S)-dimethyl 2-((6-chloro-3-nitropyridin-2-yl)amino)succinate (180 g, 0.52 mol), iron powder (146 g, 2.59 mol), 2-propanol (2 L) and water (700 mL). The mixture was stirred at 40° C., and then acetic acid (15.5 g, 0.259 mmol) was added at a rate sufficient to keep the internal temperature below 70° C. The reaction was stirred at 70° C. for 30 min, HPLC indicated that the reaction was complete. The mixture was cooled to 40° C., then Na$_2$CO$_3$ (165 g, 1.55 mol) was added, and the mixture was stirred for 1 h. The solids were filtered, and the solids were washed with tetrahydrofuran (3×500 mL). The combined filtrate and washings were concentrated in vacuo, and then the residue was stirred in ethanol (1 L) for 12 hrs. The solid was filtered and washed with cold ethanol, and dried in vacuo to obtain (S)-methyl 2-(6-chloro-2-oxo-1,2,3,4-tetrahydropyrido[2,3-b]pyrazin-3-yl)acetate as an off-white solid (91 g, 68%). LRMS (m/z): 256.0 [M+H]$^+$; HRMS (m/z): [M+H]$^+$ calcd for C$_{10}$H$_{11}$N$_3$O$_3$Cl, 256.0489; found, 256.0487; $^1$H-NMR (300 MHz, DMSO-d6): δ 10.55 (br s, 1H, —NHCO), 7.35 (br s, 1H, —NHCH), 6.92 (d, J=7.9 Hz, 1H), 6.57 (d, J=7.8 Hz, 1H), 4.43 (m, J=1.4, 5.1 Hz, 1H, —NHCH), 3.57 (s, 3H, —CO$_2$Me), 2.79 (m, J=5.1, 16.4 Hz, 2H, —CHCH$_2$); $^{13}$C-NMR (APT) (75 MHz, DMSO-d6): δ 170.32 (C), 164.96 (C), 146.13 (C), 140.32 (C), 122.41 (CH), 119.47 (C), 111.31 (CH), 51.81 (CH), 51.39 (CH$_3$), 37.01 (CH$_2$).

Synthesis of (S)-2-(6-Chloro-1,2,3,4-tetrahydro-pyrido[2,3-b]pyrazin-3-yl)ethanol

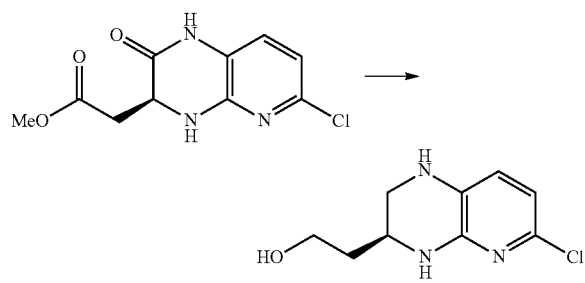

A 5 L 3-necked flask equipped with a mechanical stirrer, a reflux condenser, and a nitrogen inlet was charged with LiAlH$_4$ (60 g, 1.58 mol). The flask was cooled with an ice bath, and tetrahydrofuran (500 mL) was added. The stirred mixture was cooled to 0° C., then a solution of (S)-methyl 2-(6-chloro-2-oxo-1,2,3,4-tetrahydropyrido[2,3-b]pyrazin-3-yl)acetate (81 g, 0.32 mol) in tetrahydrofuran (2 L) was added, while keeping the internal temperature below 5° C. After the addition was complete, the reaction was heated at reflux for 16 h, while monitoring for the appearance of product by HPLC. The ester reduction occurred rapidly, while the lactam reduction required longer for complete reduction. The reaction was cooled to 5° C., and then water (60 mL) was added while keeping the internal temperature below 10° C. After addition was complete, the reaction was stirred for 15 min, then 15% (w/w) NaOH(aq) (60 mL) was added while keeping the internal temperature below 5° C. After addition was complete, the reaction was stirred for 15 min, then water (180 mL) was added and the mixture was stirred at ambient temperature for 1 h. The solids were filtered off and washed with tetrahydrofuran (3×150 mL). The filtrate and washings were concentrated in vacuo, then the solid residue was dried in vacuo to obtain (S)-2-(6-chloro-1,2,3,4-tetrahydropyrido[2,3-b]pyrazin-3-yl)ethanol as a brown solid (55 g, 81%). LRMS (m/z): 214.1 [M+H]$^+$; HRMS (m/z): [M+H]$^+$ calcd for C$_9$H$_{13}$N$_3$OCl, 214.0747; found, 214.0743; $^1$H-NMR (300 MHz, DMSO-d6): δ 6.60 (br s, 1H, —NHCH(CH$_2$)$_2$OH), 6.58 (d, J=7.8 Hz, 1H), 6.32 (d, J=7.8 Hz, 1H), 5.69 (m, 1H, —NHCH$_2$), 4.57 (t, J=5.0 Hz, 1H, —OH), 3.56 (m, J=5.8 Hz, 2H, —CH$_2$OH), 3.47 (m, 1H, —NHCH(CH$_2$)$_2$OH), 3.22 (m, J=2.7, 11.1 Hz, 1H, —NHCHH'), 2.84 (m, J=1.6, 6.7, 11.1 Hz, 1H, —NHCHH'), 1.65 (m, J=6.7 Hz, 1H, —CHH'CH$_2$OH), 1.54 (m, J=6.3 Hz, 1H, —CHH'CH$_2$OH); $^{13}$C-NMR (APT) (75 MHz, DMSO-d6): δ 146.75 (C), 134.44 (C), 128.20 (C), 118.97 (CH), 110.59 (CH), 57.97 (CH$_2$), 47.47 (CH), 43.99 (CH$_2$), 36.60 (CH$_2$).

Synthesis of (4S)-7-Chloro-2,3,4,5-tetrahydro-1,4-methanopyrido[2,3-b][1,4]diazepine

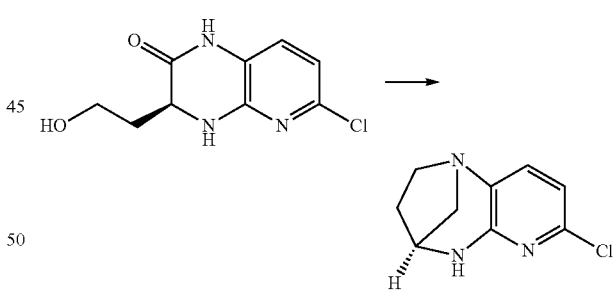

To a solution of (S)-2-(6-chloro-1,2,3,4-tetrahydropyrido[2,3-b]pyrazin-3-yl)ethanol (5; 50 g, 0.234 mol) in CH$_2$Cl$_2$ (500 mL) was added triethylamine (95 g, 0.936 mol). The mixture was stirred at ambient temperature until it was homogeneous, and then cooled to 0° C. To the reaction mixture was added dropwise POCl$_3$ (54 g, 0.351 mol) while maintaining the temperature between 0-5° C. Cooling was removed and the reaction was stirred at ambient temperature for 2 h, while monitoring for the disappearance of the starting alcohol by HPLC.

After the reaction was complete, 1.2M NaHCO$_3$ (aq.) (200 mL) was added. The layers were separated and the aqueous layer was extracted with CH$_2$Cl$_2$. The combined CH$_2$Cl2 layers were extracted with 1M HCl (aq.) (4×300 mL), and the combined HCl layers were adjusted to pH 8 with solid NaHCO₃. The resulting mixture was extracted with CH₂Cl₂ (4×300 mL), and this set of CH₂Cl₂ layers were dried (Na₂SO₄), filtered, and treated with charcoal (50 g). The mixture was stirred at ambient temperature for 3 h, filtered, and the charcoal was washed with CH₂Cl₂ (200 mL). The combined filtrate and wash solution were concentrated to dryness, and the solid residue was dried in vacuo to obtain (4S)-7-chloro-2,3,4,5-tetrahydro-1,4-methanopyrido[2,3-b][1,4]diazepine as an off-white crystalline solid (30 g, 66%). LRMS (m/z): 196.1 [M+H]⁺; HRMS (m/z): [M+H]⁺ calcd for C₉H₁₁N₃Cl, 196.0642; found, 196.0637; ¹H-NMR (300 MHz, DMSO-d6): δ 7.47 (br d, J=4.5 Hz, 1H, —NH), 7.09 (d, J=7.7 Hz, 1H), 6.39 (d, J=7.7 Hz, 1H), 3.89 (m, J=5.0 Hz, 1H, CHNH), 2.95-3.13 (m, 2H, —NCH₂CH₂CHNH), 2.77 (m, 2H, —NCHH'CHNH), 1.98 (m, J=5.0 Hz, 1H, —NHCHCHH'CH₂N), 1.86 (m, J=6.9 Hz, 1H, —NHCHCHH'CH₂N); ¹³C-NMR (APT) (75 MHz, DMSO-d6): δ 153.45 (C), 144.50 (C), 134.32 (CH), 133.19 (C), 109.73 (CH), 59.88 (CH₂), 53.07 (CH₂), 50.08 (CH), 38.38 (CH₂).

Synthesis of (4S)-7-chloro-8-fluoro-2,3,4,5-tetrahydro-1,4-methanopyrido[2,3-b][1,4]diazepine

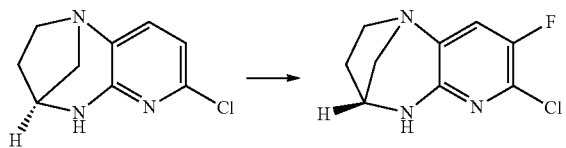 [SMILES: Clc1ccc2c(n1)N[C@H]1CCN2C1 ; Fc1cc2c(nc1Cl)N[C@@H]1CCN2C1]

N-Fluoro-N'-chloromethyltriethylenediamine bis(tetrafluoroborate) (15.20 g, 42.9 mmol) was added to a solution of (4S)-7-chloro-2,3,4,5-tetrahydro-1,4-methanopyrido[2,3-b][1,4]diazepine (7 g, 35.8 mmol) in triflic acid (70 mL) at room temperature and heated to 70° C. for 36 h. Then the reaction mixture neutralized with aq. NaHCO₃ solution and extracted with ethyl acetate (3×500 mL). The combined organic layer was washed with water (2×500 mL) and brine (100 mL), dried over anhydrous Na₂SO₄ and the solvent was removed under reduced pressure to obtain the crude residue. The crude mixture was purified by flash column chromatography (silica-gel: 100-200 mesh, eluent: 1% MeOH in DCM) to afford (4S)-7-chloro-8-fluoro-2,3,4,5-tetrahydro-1,4-methanopyrido[2,3-b][1,4]diazepine (200 mg, 0.805 mmol, yield: 2.25%) as an off white solid. (TLC: Eluent: 5% methanol in DCM, R_f: 0.4), LCMS (m/z) 214.1 [M+H]⁺.

4S)-7-chloro-8-iodo-2, 3, 4, 5-tetrahydro-1,4-methanopyrido [2, 3-b][1, 4]diazepine

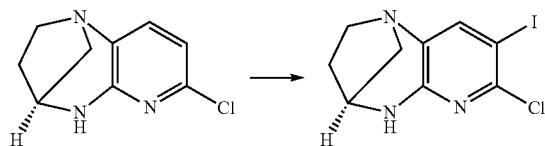 [SMILES: Clc1ccc2c(n1)N[C@H]1CCN2C1 ; Clc1nc2c(cc1I)N1CC[C@@H](C1)N2]

To a stirring solution of (4S)-7-chloro-2,3,4,5-tetrahydro-1,4-methanopyrido[2,3-b][1,4]diazepine (10 g, 51.1 mmol) in chloroform (170 mL) was added NIS (14.95 g, 66.4 mmol). The reaction mixture was stirred at 70° C. for 1 h. The reaction mixture allowed to room temperature, diluted with water (50 ml) and extracted with CHCl₃ (2×100 ml). The combined organic layer was washed with brine solution and dried over anhydrous Na₂SO₄, evaporated under reduced pressure to obtain the crude product. The crude product was purified by flash column chromatography (silica-gel: 100-200 mesh) to afford (4S)-7-chloro-8-iodo-2,3,4,5-tetrahydro-1,4-methanopyrido[2,3-b][1,4]diazepine (7.4 g, 20.53 mmol, 40.2% yield) as a yellow solid (TLC System: Neat EtOAc, (R_f: 0.4). LCMS (m/z) 321.96, [M+H]⁺.

Synthesis (4S)-7-chloro-8-(trifluoromethyl)-2, 3, 4, 5-tetrahydro-1, 4-methanopyrido[2, 3-b][1, 4]diazepine

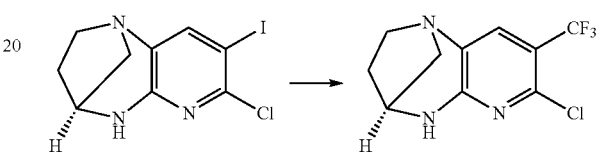

To a stirring solution of copper(I) chloride (1.355 g, 13.68 mmol), potassium tert-butoxide (1.535 g, 13.68 mmol) in DMPU (34 mL) were added trifluoromethyltrimethylsilane (1.983 mL, 13.68 mmol), 1,10-phenanthroline (2.466 g, 13.68 mmol) and (4S)-7-chloro-8-iodo-2,3,4,5-tetrahydro-1,4-methanopyrido[2,3-b][1,4]diazepine (2.2 g, 6.84 mmol) at room temperature. The reaction mixture was stirred at RT for 24 h and poured the reaction mixture in to cold water (210 mL) and extracted with ethyl acetate (2×200 mL). The combined organic layer was dried over anhydrous Na₂SO₄, concentrated under vacuum to obtain the crude compound. The crude product was purified by flash column chromatography (Silica-gel: 100-200 mesh, eluent: 3% CH₂Cl₂ in EtOAc) to afford (4S)-7-chloro-8-(trifluoromethyl)-2, 3, 4, 5-tetrahydro-1,4-methanopyrido [2, 3-b][1, 4]diazepine (650 mg, 2.465 mmol, yield: 36.0%) as an off white solid (TLC System: neat EtOAc, R_f: 0.5). LCMS (m/z): 264.14 [M+H]⁺, Rt=1.78 min.

Synthesis of (R)-dimethyl 2-((6-chloro-3-nitropyridin-2-yl)amino)succinate

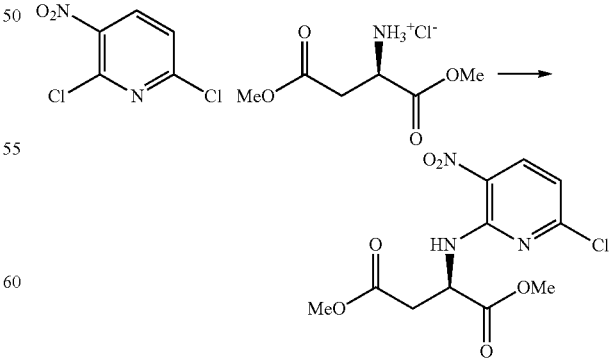

To a suspension of (R)-dimethyl 2-aminosuccinate hydrochloride (25 g, 127 mmol) in Tetrahydrofuran (THF) (130 mL) was added sodium bicarbonate (21.25 g, 253 mmol)

and 2,6-dichloro-3-nitropyridine (12.21 g, 63.3 mmol) under nitrogen. The reaction mixture was stirred at 40° C. for 16 hr. The reaction mixture was filtered and washed with EtOAc (3×25 mL), the filtrate was concentrated to give the crude product which was then added to a silica gel column and was eluted with (9:1) Hex/EtOAc. Collected fractions were evaporated to obtain the desired product (16 g, 49.4 mmol, 39.0%), LCMS (m/z) 318.1 [M+H]+.

Synthesis of (R)-methyl 2-(6-chloro-2-oxo-1,2,3,4-tetrahydropyrido[2,3-b]pyrazin-3-yl)acetate

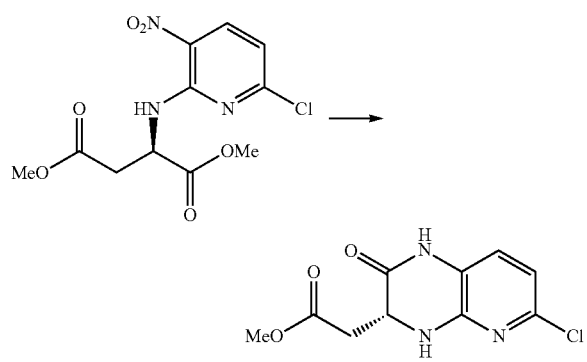

To a solution of (R)-dimethyl 2-((6-chloro-3-nitropyridin-2-yl)amino)succinate (16 g, 50.4 mmol) in isopropanol (200 mL) and Water (60 mL) was added iron (14.06 g, 252 mmol) heated to 40° C. To the above reaction mixture was added acetic acid (1.442 mL, 25.2 mmol) and heated to 70'C for 1 hr. The reaction mixture was cooled to room temperature, filtered through celite and washed with EtOAc (3×20 mL), the filtrate was concentrated and dried. The reaction crude was recrystallized from ethanol to give the desired product (11.5 g, 43.4 mmol, 86%), LCMS (m/z) 256.1 [M+H]+.

Synthesis of (R)-2-(6-chloro-1,2,3,4-tetrahydro-pyrido[2,3-b]pyrazin-3-yl)ethanol

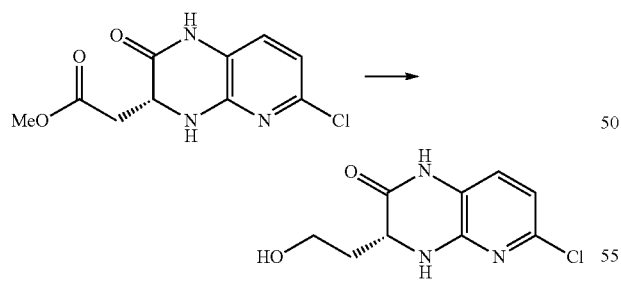

To a suspension of lithium aluminum hydride (8.54 g, 225 mmol) in Tetrahydrofuran (THF) (12 mL) was added a solution of (R)-methyl 2-(6-chloro-2-oxo-1,2,3,4-tetrahydropyrido[2,3-b]pyrazin-3-yl)acetate (11.5 g, 45.0 mmol) in Tetrahydrofuran (THF) (60 mL) dropwise at 0° C. under Nitrogen atmosphere. The reaction mixture was heated to 70° C. for 16 hr. The reaction mixture was cooled to 0° C., quenched with water (8 mL), keeping the internal temperature below 5° C. After addition was complete, the reaction was stirred for 15 min. Next, 10 mL of 15% (W/W) NaOH (aq.) was added, keeping the internal temp below 5° C., After addition was complete, the reaction was stirred for 15 min. To complete the workup, 12 mL of water was added then the mixture was stirred at room temperature for 1 h. The solids were filtered and washed with THF (3×20 mL) The filtrate and washings were concentrated in vacuo. The crude was added to a silica gel column and was eluted with (3:7) Hex/EtOAc. Collected fractions were evaporated to obtain the desired product (6 g, 27.0 mmol, 60.1%), LCMS (m/z) 214.1 [M+H]+.

Synthesis of (4R)-7-chloro-2,3,4,5-tetrahydro-1,4-methanopyrido[2,3-b][1,4]diazepine

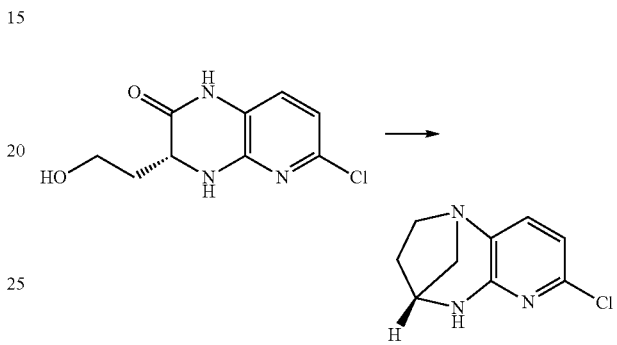

To a solution of (R)-2-(6-chloro-1,2,3,4-tetrahydropyrido [2,3-b]pyrazin-3-yl)ethanol (7 g, 32.8 mmol) in dichloromethane (DCM) (70 mL) was added triethylamine (18.27 mL, 131 mmol) under nitrogen. The mixture was stirred at room temperature until it was homogeneous, Then it was cooled to 0° C. Next POCl3 (4.58 mL, 49.1 mmol) was added dropwise maintaining the temperature 0° C. to 5° C. The reaction mixture was stirred at 25° C. for 2 hr. After the reaction was completed 100 mL 1.2M NaHCO3 (aq.) was added. The layers were separated and the aqueous layer was extracted with DCM (2×200 mL). The combined organic layers were concentrated to dryness. The solid residue was dried in vacuo.

The crude product 8 g was added to a silica gel column and was eluted with 70% EtOAc/Pet ether. Collected fractions was evaporated to obtain the desired product (5.2 g, 26.5 mmol, 81% yield), LCMS (m/z) 195.9 [M+H]+.

Synthesis of 4 Substituted Bicyclic Pyridine Core

Synthesis of 2,6-dichloro-4-methyl-3-nitropyridine

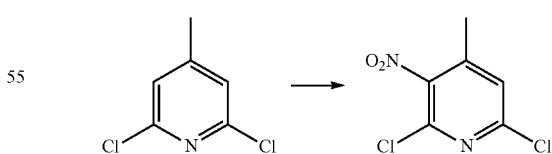

Nitric acid (1.5 mL, 33.6 mmol) was added to a solution of sulfuric acid (2.5 mL, 46.9 mmol) stirred under nitrogen at 0° C. Then 2,6-dichloro-4-methylpyridine (0.500 g, 3.09 mmol) was added at 0° C. Then the reaction mixture was stirred at 100° C. for 16 hr. The reaction was monitored by TLC. After completion, the reaction mixture was quenched with crushed ice and neutralized with NH4OH solution and filtered the solid and dried under vacuum to give the desired product (0.300 g, 1.443 mmol, 46.8% yield) as a pale yellow solid, LCMS (m/z) 206.8 [M+H]⁺.

Synthesis of (S)-dimethyl 2-((6-chloro-4-methyl-3-nitropyridin-2-yl)amino)succinate

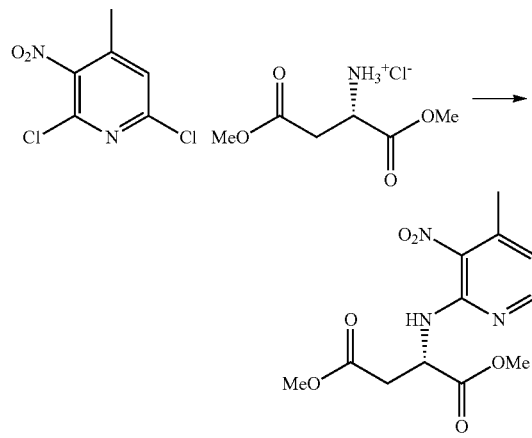

A suspension of 2,6-dichloro-4-methyl-3-nitropyridine (300 mg, 1.449 mmol) and sodium bicarbonate (243 mg, 2.90 mmol) in Tetrahydrofuran (THF) (20 mL)) was added (S)-dimethyl 2-aminosuccinate hydrochloride (430 mg, 2.174 mmol) at 0° C. under nitrogen. Then the reaction mixture was stirred at 65° C. for 24 hr. The reaction was monitored by TLC. The reaction mass filtered and washed with EtOAc (2×30 mL). The filtrate was concentrated under reduced pressure to give the crude material. The crude product was added to a neutral alumina column and was eluted with Hex/EtOAc (9:1). Collected fractions were concentrated under reduced pressure to afford the desired product (250 mg, 0.742 mmol, 51.2% yield) as yellow gummy liquid, LCMS (m/z) 339.1 (M+H)⁺.

Synthesis of (S)-methyl 2-(6-chloro-8-methyl-2-oxo-1,2,3,4-tetrahydropyrido[2,3-b]pyrazin-3-yl)acetate

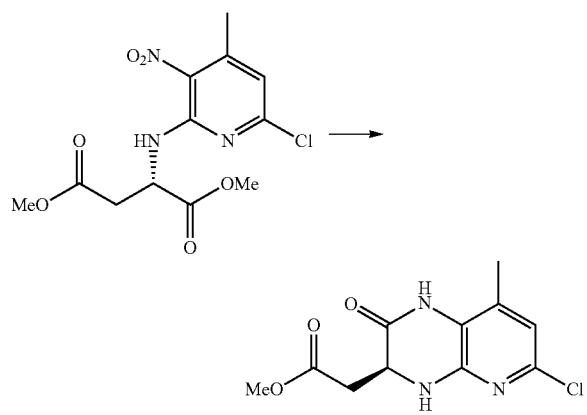

To a suspension of (S)-dimethyl 2-((6-chloro-4-methyl-3-nitropyridin-2-yl)amino)succinate (6.0 g, 18.09 mmol) and iron (5.05 g, 90 mmol) in isopropanol (80 mL) and Water (20 mL) stirred at 40° C. was added acetic acid (1.553 mL, 27.1 mmol). The reaction mixture was stirred at 80° C. for 1 hr. Reaction was monitored by TLC. The reaction mixture was cooled to room temperature, and quenched with saturated sodium bicarbonate solution and extracted with EtOAc. Organic layer washed with brine solution and dried out with sodium sulfate, filtered and evaporated to give the desired product (4.0 g, 14.32 mmol, 79% yield), LCMS (m/z) 269.9 [M+H]⁺.

Synthesis of (S)-2-(6-chloro-8-methyl-1,2,3,4-tetrahydropyrido[2,3-b]pyrazin-3-yl)ethanol

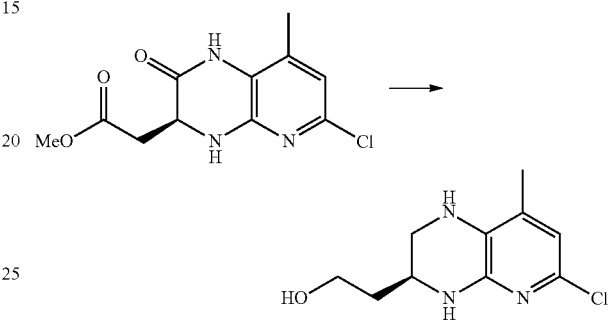

To a solution of aluminum chloride (0.173 g, 1.298 mmol), in Tetrahydrofuran (THF) (2.5 mL) stirred under nitrogen was added 2M solution of lithium aluminum hydride (2.220 mL, 4.44 mmol) in THF dropwise at a rate to control gas evolution. This gave a solution of alane (AlH3) in THF. In a separate flask, a solution of (S)-methyl 2-(6-chloro-8-methyl-2-oxo-1,2,3,4-tetrahydropyrido[2,3-b]pyrazin-3-yl)acetate (0.250 g, 0.927 mmol) in Tetrahydrofuran (THF) (5 mL) was prepared under nitrogen, to this was added the alane solution, dropwise at −78° C. over 15 minutes. When the addition was complete, the cooling bath was removed, and the reaction was allowed to warm to ambient temperature. The reaction was monitored by TLC. The reaction mixture was quenched with 10% NaOH solution at 0° C. and stirred 1 hr and extracted with EtOAc. EtOAc layer washed with water followed by brine solution and dried out with sodium sulfate, filtered and concentrated to give the desired product (150 mg, 0.407 mmol, 43.9% yield) as a pale yellow solid, LCMS (m/z) 228.2 [M+H]⁺.

Synthesis of (4S)-7-chloro-9-methyl-2,3,4,5-tetrahydro-1,4-methanopyrido[2,3-b][1,4]diazepine

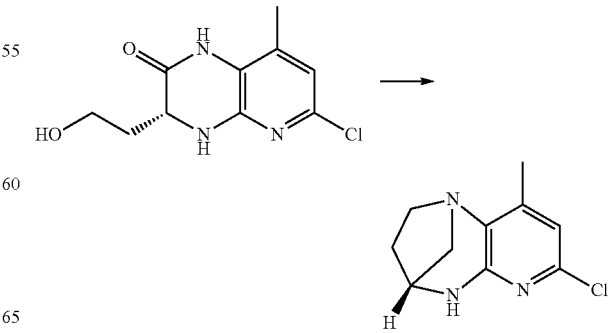

To (S)-2-(6-chloro-8-methyl-1,2,3,4-tetrahydropyrido[2,3-b]pyrazin-3-yl)ethanol (1.8 g, 7.91 mmol), was added HBr (4 mL, 35.4 mmol), the reaction mixture was stirred at 90° C. for 18 hr. The reaction was monitored by TLC. Following completion, the reaction mixture was quenched with saturated sodium bicarbonate solution and extracted with EtOAc. EtOAc layer washed with water followed by brine solution and dried out with sodium sulfate, filtered and concentrated to give crude product. The crude product was added to a neutral alumina and was eluted with 20% EtOAc/Hexane. Collected fractions were evaporated to afford the desired product (0.900 g, 4.27 mmol, 54.0% yield) as a pale yellow solid, LCMS (m/z) 210.2 [M+H]$^+$.

Synthesis of (4S)-methyl 2,3,4,5-tetrahydro-1,4-methanopyrido[2,3-b][1,4]diazepine-7-carboxylate

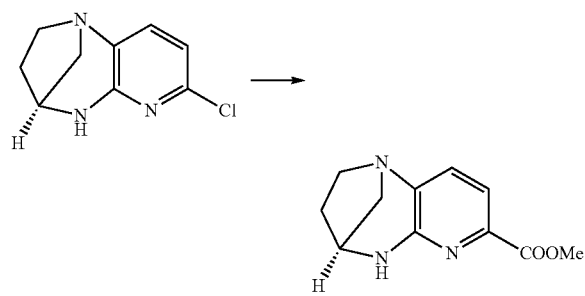

To a degassed solution of (4S)-7-chloro-2,3,4,5-tetrahydro-1,4-methanopyrido[2,3-b][1,4]diazepine (5 g, 25.55 mmol) in anhydrous MeOH (250 ml) were added TEA (17.77 mL, 127.77 mmol) and Pd(dppf)Cl$_2$ (934 mg, 1.2755 mmol) and the reaction mixture was stirred at 110° C. for 20 h under carbon monoxide atmosphere of 300 psi. The suspension was cooled to room temperature and the mixture was concentrated under reduced pressure to afford crude compound. The crude mixture was purified by flash column chromatography (100-200 silica-gel, was eluted with 2% Methanol in DCM) to afford (4S)-methyl-2,3,4,5-tetrahydro-1,4-methanopyrido[2,3-b][1,4]diazepine-7-carboxylate (3 g, 13.68 mmol, 53.5% yield) as a pale brown solid (TLC system: 5% Methanol in DCM, R$_f$ value: 0.2), LCMS (m/z) 220.3 [M+H]$^+$.

Synthesis of (4S)-7-chloro-8-fluoro-2,3,4,5-tetrahydro-1,4-methanopyrido[2,3-b][1,4]diazepine

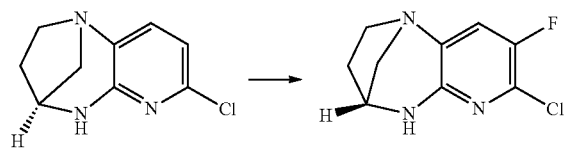 [SMILES: Clc1ccc2c(n1)N[C@H]1CCN2C1 ; Fc1cc2c(nc1Cl)N[C@@H]1CCN2C1]

N-Fluoro-N'-chloromethyltriethylenediamine bis(tetrafluoroborate) (15.20 g, 42.9 mmol) was added to a solution of (4S)-7-chloro-2,3,4,5-tetrahydro-1,4-methanopyrido[2,3-b][1,4]diazepine (7 g, 35.8 mmol) in triflic acid (70 mL) at room temperature and heated to 70° C. for 36 h. Then the reaction mixture neutralized with aq. NaHCO$_3$ solution and extracted with ethyl acetate (3×500 mL). The combined organic layer was washed with water (2×500 mL) and brine (100 mL), dried over anhydrous Na$_2$SO$_4$ and the solvent was removed under reduced pressure to obtain the crude residue. The crude mixture was purified by flash column chromatography (silica-gel: 100-200 mesh, eluent: 1% MeOH in DCM) to afford (4S)-7-chloro-8-fluoro-2,3,4,5-tetrahydro-1,4-methanopyrido[2,3-b][1,4]diazepine (200 mg, 0.805 mmol, yield: 2.25%) as an off white solid. (TLC: Eluent: 5% methanol in DCM, R$_f$: 0.4), LCMS (m/z) 214.1 [M+H]$^+$.

Synthesis of (4S)-5-(pyridin-2-ylcarbamoyl)-2,3,4,5-tetrahydro-1,4-methanopyrido[2,3-b][1,4]diazepine-7-carboxylic acid

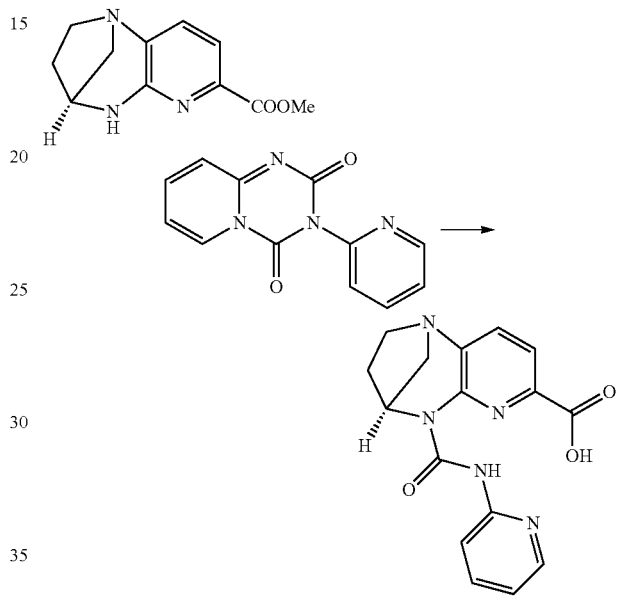

To a stirring solution of (4S)-methyl-2,3,4,5-tetrahydro-1,4-methanopyrido[2,3-b][1,4]diazepine-7-carboxylate (3 g, 13.64 mmol) in THF (60 mL) was added NaH (2.73 g, 68.41 mmol) at 0° C. and stirred for 30 min at same temperature. After 30 min 3-(pyridin-2-yl)-2H-pyrido[1,2-a][1,3,5]triazine-2,4(3H)-dione (4.91 g, 20.46 mmol) was added and the reaction mixture was stirred at 80° C. for 16 h. The reaction mixture was cooled to 0° C. and quenched with 50 ml of ice water and extracted with 2×25 ml of ethyl acetate (to remove non polar impurities). The aqueous solution was neutralized with NaHCO$_3$ solution and extracted with 3×50 ml of 5% methanol in DCM. The combined organic layer was dried over anhydrous sodium sulfate and concentrated under reduced pressure to afford (4S)-5-(pyridin-2-ylcarbamoyl)-2,3,4,5-tetrahydro-1,4-methanopyrido[2,3-b][1,4]diazepine-7-carboxylic acid (1.2 g, 0.254 mmol, 26% yield) as a pale brown solid (TLC system: 10% Methanol in DCM. R$_f$ value: 0.1), LCMS (m/z) 326.3 (M+H)$^+$.

Synthesis of (4S)-methyl 8-fluoro-2,3,4,5-tetrahydro-1,4-methanopyrido[2,3-b][1,4]diazepine-7-carboxylate

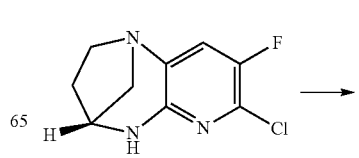

-continued

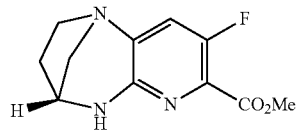

To a solution of (4S)-7-chloro-8-fluoro-2,3,4,5-tetrahydro-1,4-methanopyrido[2,3-b][1,4]diazepine (650 mg, 3.04 mmol) in Methanol (30 mL), was degassed with CO gas for 10 min, then TEA (2.120 mL, 15.21 mmol) and PdCl$_2$ (dppf) (111 mg, 0.152 mmol) were added and filled with 300 psi CO gas. The reaction mixture was stirred at 140° C. for 48 hr in steel bomb. Progress of the reaction was monitored by TLC. TLC indicated formation of a polar multiple sports and SM was consumed. Reaction mass was concentrated and diluted with 50 ml of water and 80 ml of DCM, pass through Hi-flow bed, separated organic layer, extracted with DCM (2×50 ml), combined organic layers, dried over Na$_2$SO$_4$, filtered and concentrated to get crude compound. The crude product was purified by combiflash chromatography using silica gel column (24 g, 60% EtOAc in pet ether). Column was eluted with a gradient of EtOAc in Hexane. Desired compound was eluted with 60% EtOAc in Hexane. Fractions containing pure compound were concentrated under reduced pressure to afford the (4S)-methyl 8-fluoro-2,3,4,5-tetrahydro-1,4-methanopyrido[2,3-b][1,4]diazepine-7-carboxylate (400 mg, 1.358 mmol, 44.6% yield) as an brown color solid, LCMS (m/z): 238.12 [M+H]$^+$.

Synthesis of (4S)-methyl 5-((4-(((S)-2,2-dimethyl-1,3-dioxolan-4-yl)methoxy)pyridin-2-yl)carbamoyl)-8-fluoro-2,3,4,5-tetrahydro-1,4-methanopyrido[2,3-b][1,4]diazepine-7-carboxylate

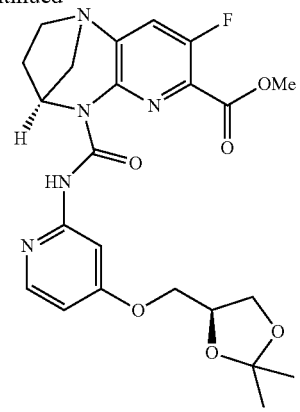

To a stirred solution of (4S)-methyl 8-fluoro-2,3,4,5-tetrahydro-1,4-methanopyrido[2,3-b][1,4]diazepine-7-carboxylate (340 mg, 1.433 mmol) in Tetrahydrofuran (THF) (60 mL), triphosgene (340 mg, 1.147 mmol) and triethylamine (1.199 mL, 8.60 mmol) were added and stirred for 60 min. After 60 min (S)-4-((2,2-dimethyl-1,3-dioxolan-4-yl)methoxy)pyridin-2-amine (643 mg, 2.87 mmol) was added and reaction was maintained at 90° C. for 16 hr under Nitrogen condition. Progress of the reaction was monitored by TLC and LCMS. The reaction mass was cooled to room temperature, diluted with water (100 mL), ethyl acetate (100 mL*2). The combined organic layer was washed with brine (50 mL), dried over Na$_2$SO$_4$, filtered, concentrated under reduced pressure to get the crude brown solid. The crude product was purified by combiflash chromatography using silica gel column (12 g, 60% EtOAc in pet ether). Column was eluted with a gradient of EtOAc in Hexane. Desired compound was eluted with 60% EtOAc in Hexane. Fractions containing pure compound were concentrated under reduced pressure to afford the (4S)-methyl 5-((4-(((S)-2,2-dimethyl-1,3-dioxolan-4-yl)methoxy)pyridin-2-yl)carbamoyl)-8-fluoro-2,3,4,5-tetrahydro-1,4-methanopyrido[2,3-b][1,4]diazepine-7-carboxylate (550 mg, 0.607 mmol, 42.4% yield) as an brown color solid, LCMS (m/z): 488.20 [M+H]$^+$.

Synthesis of (4S)-5-((4-(((S)-2,2-dimethyl-1,3-dioxolan-4-yl)methoxy)pyridin-2-yl)carbamoyl)-8-fluoro-2,3,4,5-tetrahydro-1,4-methanopyrido[2,3-b][1,4]diazepine-7-carboxylic acid

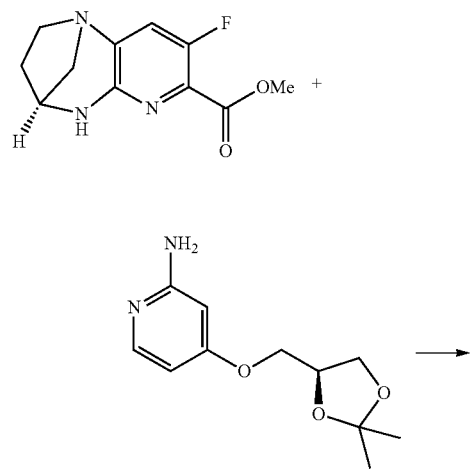

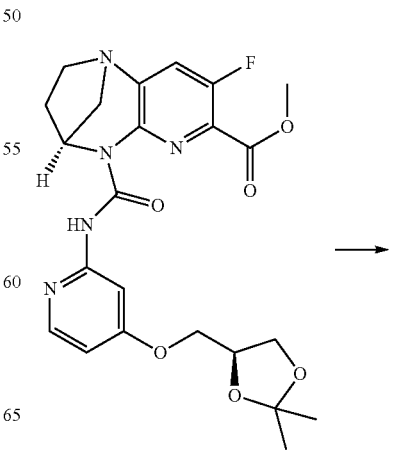

101

-continued

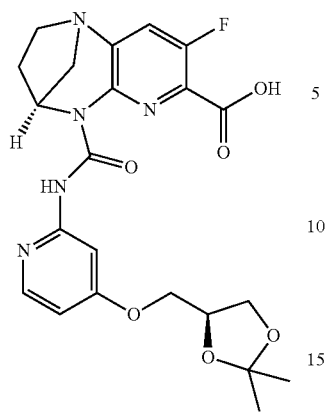

To a stirred solution of (4S)-methyl 5-((4-(((S)-2,2-dimethyl-1,3-dioxolan-4-yl)methoxy)pyridin-2-yl)carbamoyl)-8-fluoro-2,3,4,5-tetrahydro-1,4-methanopyrido[2,3-b][1,4]diazepine-7-carboxylate (500 mg, 1.026 mmol) in Tetrahydrofuran (THF) (20 mL) and Water (6 mL), was added lithium hydroxide (73.7 mg, 3.08 mmol). The reaction mixture was stirred at RT for 12 hr. Progress of the reaction was monitored by TLC; TLC indicated that formation of polar spot and total consumption of starting material. THF was evaporated completely, the reaction mixture was diluted with water (30 ml) and washed with ethyl acetate (30 ml*2). The aqueous layer pH was adjusted to acidic using citric acid, solid was not precipitated. The aqueous layer was extracted with DCM (3×50 ml). The organic layer was dried over anhydrous $Na_2SO_4$, filtered and concentrated under reduced pressure to obtain desired pure product (4S)-5-((4-(((S)-2,2-dimethyl-1,3-dioxolan-4-yl)methoxy)pyridin-2-yl)carbamoyl)-8-fluoro-2,3,4,5-tetrahydro-1,4-methanopyrido[2,3-b][1,4]diazepine-7-carboxylic acid (210 mg, 0.382 mmol, 37.2% yield) as an light brown solid, LCMS (m/z): 473.90 [M+H]⁺.

Synthesis of (4S)—N5-(4-(((S)-2,2-dimethyl-1,3-dioxolan-4-yl)methoxy)pyridin-2-yl)-8-fluoro-N7-((R)-1,1,1-trifluoropropan-2-yl)-3,4-dihydro-1,4-methanopyrido[2,3-b][1,4]diazepine-5,7(2H)-dicarboxamide

102

-continued

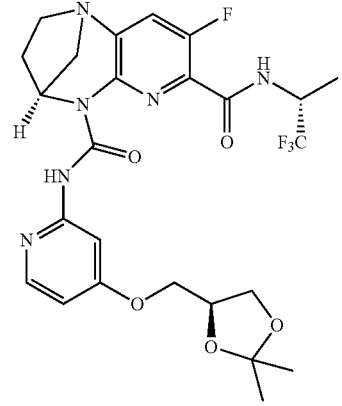

Procedure:

To a stirred solution of (4S)-5-((4-(((S)-2,2-dimethyl-1,3-dioxolan-4-yl)methoxy)pyridin-2-yl)carbamoyl)-8-fluoro-2,3,4,5-tetrahydro-1,4-methanopyrido[2,3-b][1,4]diazepine-7-carboxylic acid (190 mg, 0.401 mmol) in N,N-Dimethylformamide (DMF) (10 mL), stirred under nitrogen at room temperature, was added DIPEA (0.210 mL, 1.204 mmol) followed by HATU (305 mg, 0.803 mmol). After stirring the reaction mixture for 10 min at RT, added (R)-1,1,1-trifluoropropan-2-amine (54.5 mg, 0.482 mmol) under nitrogen. The reaction mixture was stirred at RT for 6 hr. Progress of the reaction was monitored by TLC, TLC indicated formation of a non polar spot and SM was consumed. Cold water (30 mL) was added to the reaction mixture. After stirring for 10 min solid was precipitated out, the obtained solid was filtered and washed with water (20 mL), pet ether (10 mL) and dried under high vacuum to obtain desired pure product (4S)—N5-(4-(((S)-2,2-dimethyl-1,3-dioxolan-4-yl)methoxy)pyridin-2-yl)-8-fluoro-N7-((R)-1,1,1-trifluoropropan-2-yl)-3,4-dihydro-1,4-methanopyrido[2,3-b][1,4]diazepine-5,7(2H)-dicarboxamide (130 mg, 0.223 mmol, 55.6% yield) as an off-white solid. LCMS (m/z): 569.26 (M+H)⁺.

Synthesis of (4S)-methyl 9-methoxy-2,3,4,5-tetrahydro-1,4-methanopyrido[2,3-b][1,4]diazepine-7-carboxylate

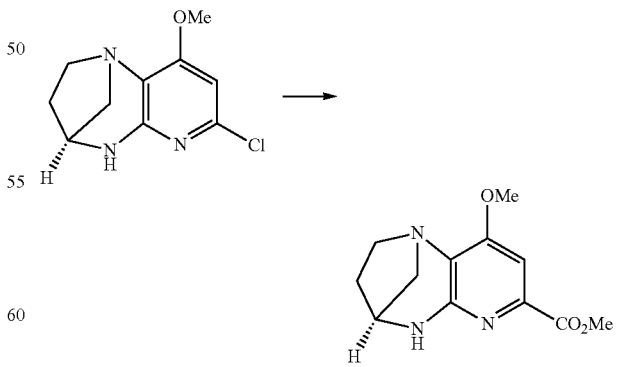

To a solution of (4S)-7-chloro-9-methoxy-2,3,4,5-tetrahydro-1,4-methanopyrido[2,3-b][1,4]diazepine (1.8 g, 7.98 mmol) in Methanol (40 mL) was degassed with argon gas for 30 min, then DIPEA (6.97 mL, 39.9 mmol) and $PdCl_2$ (dppf) (0.584 g, 0.798 mmol) were added and filled with 300 psi CO gas. The reaction mixture was stirred at 110° C. for 24 hr in steel bomb.

Reaction mixture was filtered and concentrated under reduced pressure to afford crude compound The crude compound was purified by 100-200 silica gel column and was eluted with 2% MeOH in DCM to afford pure compound (4S)-methyl 9-methoxy-2,3,4,5-tetrahydro-1,4-methanopyrido[2,3-b][1,4]diazepine-7-carboxylate (1.0 g, 3.11 mmol, 39.0% yield) as brown solid, LCMS (m/z): 250.17 [M+H]+.

Synthesis of (4S)-9-methoxy-5-(pyridin-2-ylcarbamoyl)-2,3,4,5-tetrahydro-1,4-methanopyrido[2,3-b][1,4]diazepine-7-carboxylic acid

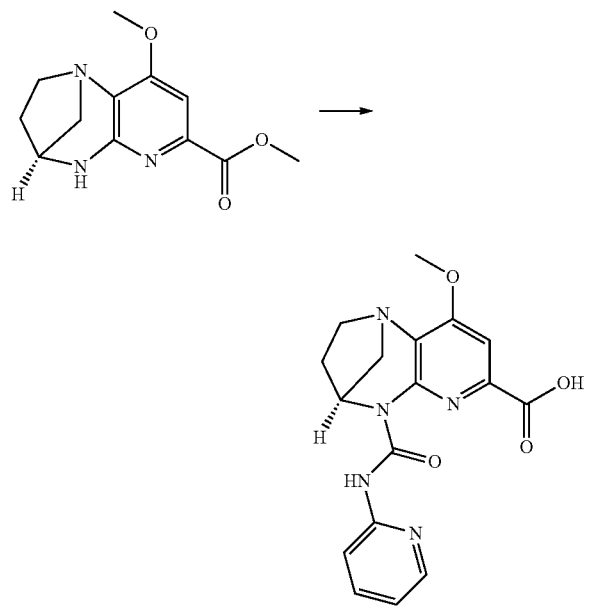 [SMILES: COC(=O)c1cc(OC)c2c(n1)N[C@H]1CCN2C1 ; COc1cc(C(=O)O)nc2c1N1CC[C@@H](C1)N2C(=O)Nc1ccccn1]

To a suspension of NaH (0.481 g, 20.06 mmol), in THF (15 mL) stirred under nitrogen at 0° C. was added (4S)-methyl 9-methoxy-2,3,4,5-tetrahydro-1,4-methanopyrido[2,3-b][1,4]diazepine-7-carboxylate (1.00 g, 4.01 mmol) in THF (15 mL) the reaction mixture was stirred at 28° C. for 30 min. Then added 3-(pyridin-2-yl)-2H-pyrido[1,2-a][1,3,5]triazine-2,4(3H)-dione (1.446 g, 6.02 mmol). The reaction mixture was stirred at 70° C. for 5 hr. Reaction was monitored by TLC. The reaction mixture was cooled to 28° C. poured into ice cold H2O (10 mL) concentrated under reduced pressure dried under high vacuum. The crude mass was extracted with 10% MeOH in DCM (2×50 mL) dried with Na2SO4 filtered and concentrated. The crude product was triturated with ether to obtained (4S)-9-methoxy-5-(pyridin-2-ylcarbamoyl)-2,3,4,5-tetrahydro-1,4-methanopyrido[2,3-b][1,4]diazepine-7-carboxylic acid (1.0 g, 2.363 mmol, 58.9% yield) pale brown solid, LCMS (m/z): 356.18 [M+H]+.

Synthesis of (4S)-methyl 9-methyl-2,3,4,5-tetrahydro-1,4-methanopyrido[2,3-b][1,4]diazepine-7-carboxylate

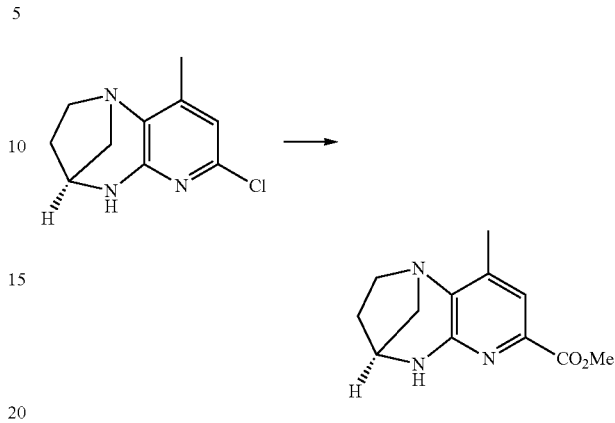

To a solution of (4S)-7-chloro-9-methyl-2,3,4,5-tetrahydro-1,4-methanopyrido[2,3-b][1,4]diazepine (4 g, 19.08 mmol) in Methanol (50 mL) was degassed for 30 min with argon gas, then TEA (13.29 mL, 95 mmol) and PdCl2(dppf) (0.698 g, 0.954 mmol) were added and filled with 300 psi CO gas. The reaction mixture was stirred at 110° C. for 16 hr in steel bomb. Reaction mixture was concentrated under reduced pressure to afford crude compound. The crude product was added to a Neutral alumina column and was eluted with 30% Ethylacetate in Petether Collected fractions are evaporated to afford (4S)-methyl 9-methyl-2,3,4,5-tetrahydro-1,4-methanopyrido[2,3-b][1,4]diazepine-7-carboxylate (2.5 g, 9.78 mmol, 51.3% yield) as a pale Yellow oil, LCMS (m/z): 234.15 [M+H]+.

Synthesis of (4S)-9-methyl-5-(pyridin-2-ylcarbamoyl)-2,3,4,5-tetrahydro-1,4-methanopyrido[2,3-b][1,4]diazepine-7-carboxylic acid

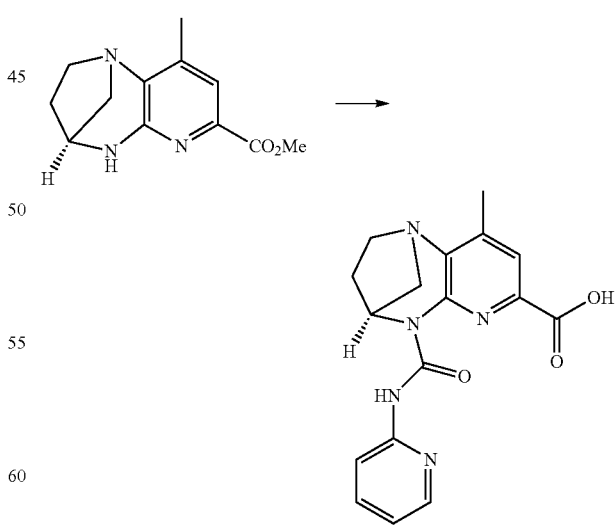

To a solution of (4S)-methyl 9-methyl-2,3,4,5-tetrahydro-1,4-methanopyrido[2,3-b][1,4]diazepine-7-carboxylate (2.5 g, 10.72 mmol) in Tetrahydrofuran (THF) (100 ml) stirred under nitrogen at 0° C. was added NaH (2.143 g, 53.6 mmol)

and stirred for 30 min, then 3-(pyridin-2-yl)-2H-pyrido[1,2-a][1,3,5]triazine-2,4(3H)-dione (3.86 g, 16.08 mmol) was added. The reaction mixture was stirred for 4 h at 80° C. Reaction mixture was quenched with ice water and stirred for 1 h, then washed with 2×100 ml of ethyl acetate. Aqueous layer was neutralized with 1 N HCl solution and extracted with 2×150 ml of 10% methanol in DCM, organic layer was dried over Na$_2$SO$_4$ and concentrated under reduced pressure to afford compound, remaining aqueous layer was concentrated afford residue was triturated with 2×100 ml of 10% methanol and DCM and filtered, filtrate was concentrated under reduced pressure to afford compound was mixed with above extracted compound and washed with diethyl ether to afford pure compound (4S)-9-methyl-5-(pyridin-2-ylcarbamoyl)-2,3,4,5-tetrahydro-1,4-methanopyrido[2,3-b][1,4]diazepine-7-carboxylic acid (1.4 g, 3.54 mmol, 33.1% yield), LCMS (m/z): 340.10 [M+H]$^+$.

Synthesis of (4S)-9-methyl-2,3,4,5-tetrahydro-1,4-methanopyrido[2,3-b][1,4]diazepine-7-carboxylic acid

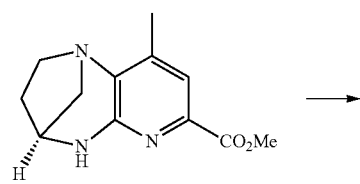

LiOH (1.232 g, 51.4 mmol) was added to a solution of (4S)-methyl 9-methyl-2,3,4,5-tetrahydro-1,4-methanopyrido[2,3-b][1,4]diazepine-7-carboxylate (8 g, 34.3 mmol) in Tetrahydrofuran (THF) (50 mL) and Water (50 mL) at 25° C., stirred for 4 h at same temperature. The reaction mixture was evaporated to get crude was washing with pentane than dried to afford (4S)-9-methyl-2,3,4,5-tetrahydro-1,4-methanopyrido[2,3-b][1,4]diazepine-7-carboxylic acid (6.8 g, 30.8 mmol, 90% yield), as an off White solid, LCMS (m/z): 220.08 [M+H]$^+$.

Synthesis of (4S)-9-methyl-N-(2,2,2-trifluoroethyl)-2,3,4,5-tetrahydro-1,4-methanopyrido[2,3-b][1,4]diazepine-7-carboxamide

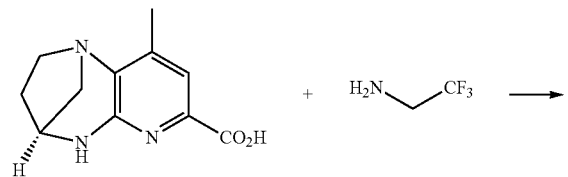

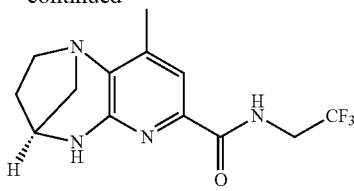

To a solution of (4S)-9-methyl-2,3,4,5-tetrahydro-1,4-methanopyrido[2,3-b][1,4]diazepine-7-carboxylic acid (1 g, 4.56 mmol) in Tetrahydrofuran (THF) (100 mL) stirred under nitrogen at room temp was added HATU (2.60 g, 6.84 mmol) and DIPEA (2.390 mL, 13.68 mmol), To this 2,2,2-trifluoroethanamine Hydrochloride (0.927 g, 6.84 mmol) was added and the reaction mixture was stirred at 27° C. for 16 hr. Reaction mixture was quenched with ice water and extracted with 2×250 ml of ethyl acetate, combined organic layers were washed with 150 ml of brine solution and dried over Na$_2$SO$_4$ and concentrated under reduced pressure to afford the crude product that was added to a Neutral alumina column and was eluted with 30% Ethylacetate in Petether Collected fractions are evaporated to afford (4S)-9-methyl-N-(2,2,2-trifluoroethyl)-2,3,4,5-tetrahydro-1,4-methanopyrido[2,3-b][1,4]diazepine-7-carboxamide (1.1 g, 3.63 mmol, 80% yield) as an pale yellow solid, LCMS (m/z): 301.29 [M+H]$^+$.

Synthesis of (4S)—N5-(4-(((S)-2,2-dimethyl-1,3-dioxolan-4-yl)methoxy)pyridin-2-yl)-9-methyl-N7-(2,2,2-trifluoroethyl)-3,4-dihydro-1,4-methanopyrido[2,3-b][1,4]diazepine-5,7(2H)-dicarboxamide

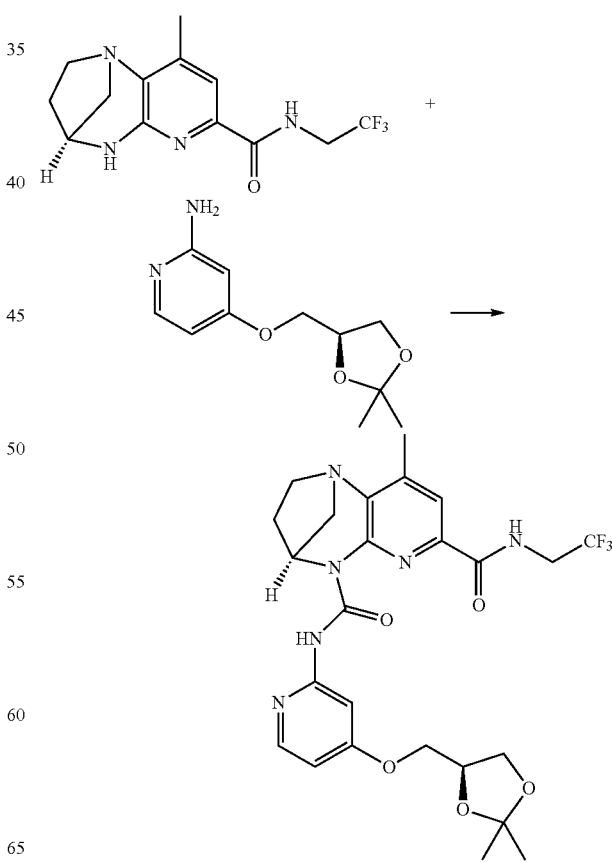

To a solution of (4S)-9-methyl-N-(2,2,2-trifluoroethyl)-2,3,4,5-tetrahydro-1,4-methanopyrido[2,3-b][1,4]diazepine-7-carboxamide (500 mg, 1.665 mmol) in THF (50 ml) and triphosgene (296 mg, 0.999 mmol) at 0° C., Then TEA (1.160 mL, 8.33 mmol) was added and stirred to RT for 1 h. and (S)-4-((2,2-dimethyl-1,3-dioxolan-4-yl)methoxy)pyridin-2-amine (560 mg, 2.498 mmol) was added sub sequentially at 75° C. for 16 h. The reaction was monitored by TLC and LCMS, The reaction mixture was poured in saturated NaHCO$_3$ solution (30 mL) and extracted with ethyl acetate (2×100 mL). The organic layer was dried over anhydrous Na$_2$SO$_4$ and concentrated under reduced pressure to give crude. The crude product was added to a Neutral alumina column and was eluted with 20% Ethylacetate in Petether Collected fractions are evaporated to afford (4S)—N5-(4-(((S)-2,2-dimethyl-1,3-dioxolan-4-yl)methoxy)pyridin-2-yl)-9-methyl-N7-(2,2,2-trifluoroethyl)-3,4-dihydro-1,4-methanopyrido[2,3-b][1,4]diazepine-5,7(2H)-dicarboxamide (250 mg, 0.436 mmol, 26.2% yield) as an White solid, LCMS (m/z): 551.31 [M+H]$^+$.

Synthesis of (4S)-9-methyl-N—((R)-1,1,1-trifluoropropan-2-yl)-2,3,4,5-tetrahydro-1,4-methanopyrido[2,3-b][1,4]diazepine-7-carboxamide

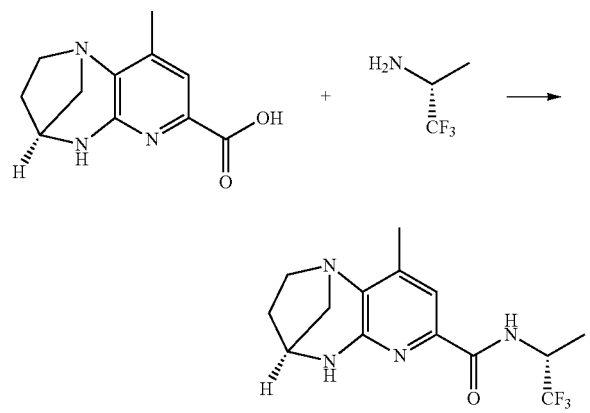

To a solution of (4S)-9-methyl-2,3,4,5-tetrahydro-1,4-methanopyrido[2,3-b][1,4]diazepine-7-carboxylic acid (5 g, 22.81 mmol) in Tetrahydrofuran (THF) (500 mL) stirred under nitrogen at room temp was added DIPEA (11.95 mL, 68.4 mmol) and HATU (13.01 g, 34.2 mmol), To this (R)-1,1,1-trifluoropropan-2-amine, Hydrochloride (5.12 g, 34.2 mmol) was added and the reaction mixture was stirred at 27° C. for 16 hr. Reaction mixture was quenched with ice water and extracted with 2×500 ml of ethyl acetate, combined organic layers were washed with 500 ml of brine solution and dried over Na$_2$SO$_4$ and concentrated under reduced pressure to afford the crude product that was added to a Neutral alumina column and was eluted with 30% Ethylacetate in Petether Collected fractions are evaporated to afford (4S)-9-methyl-N—((R)-1,1,1-trifluoropropan-2-yl)-2,3,4,5-tetrahydro-1,4-methanopyrido[2,3-b][1,4]diazepine-7-carboxamide (6.5 g, 19.01 mmol, 83% yield) as an pale yellow solid, LCMS (m/z): 315.10 [M+H]$^+$.

Synthesis of (4S)—N5-(5-(((R)-2,2-dimethyl-1,3-dioxolan-4-yl)methoxy)pyridin-2-yl)-9-methyl-N7-((R)-1,1,1-trifluoropropan-2-yl)-3,4-dihydro-1,4-methanopyrido[2,3-b][1,4]diazepine-5,7(2H)-dicarboxamide

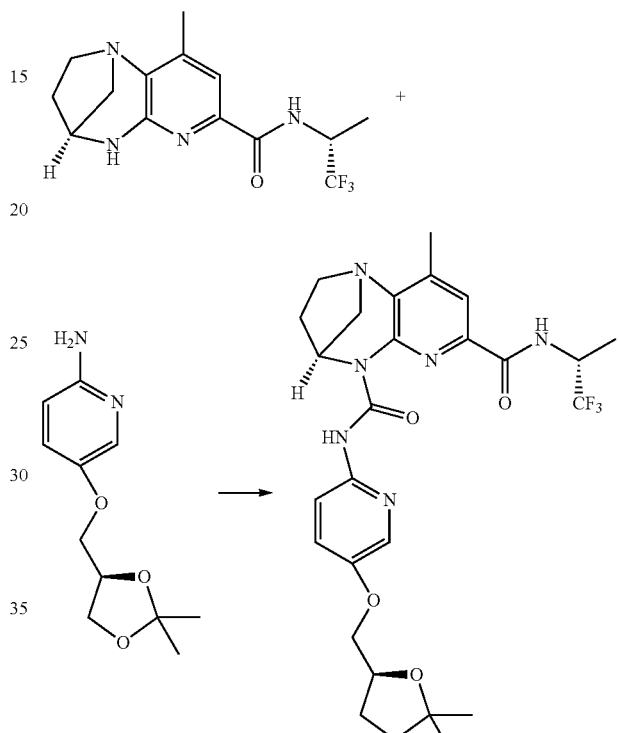

To a solution of (4S)-9-methyl-N—((R)-1,1,1-trifluoropropan-2-yl)-2,3,4,5-tetrahydro-1, -methanopyrido[2,3-b][1,4]diazepine-7-carboxamide (600 mg, 1.909 mmol) in THF (50 ml) and triphosgene (340 mg, 1.145 mmol) at 0° C. Then DIPEA (1.000 mL, 5.73 mmol) was added and stirred to RT for 1 h. and (R)-5-((2,2-dimethyl-1,3-dioxolan-4-yl)methoxy)pyridin-2-amine (642 mg, 2.86 mmol) was added sub sequentially at 75° C. for 16 h. The reaction was monitored by TLC and LCMS, The reaction mixture was poured in saturated NaHCO$_3$ solution (30 mL) and extracted with ethyl acetate (2×100 mL). The organic layer was dried over anhydrous Na$_2$SO$_4$ and concentrated under reduced pressure to give crude. The crude product was added to a Neutral alumina column and was eluted with 20% Ethylacetate in Petether Collected fractions are evaporated to afford (4S)—N5-(5-(((R)-2,2-dimethyl-1,3-dioxolan-4-yl)methoxy)pyridin-2-yl)-9-methyl-N7-((R)-1,1,1-trifluoropropan-2-yl)-3,4-dihydro-1,4-methanopyrido[2,3-b][1,4]diazepine-5,7(2H)-dicarboxamide (550 mg, 0.969 mmol, 50.8% yield) as a White solid, TLC System;—80% EtOAc in Petether, LCMS (m/z): 565.24 [M+H]$^+$.

Synthesis of (4S)—N5-(4-(((S)-2,2-dimethyl-1,3-dioxolan-4-yl)methoxy)pyridin-2-yl)-9-methyl-N7-((R)-1,1,1-trifluoropropan-2-yl)-3,4-dihydro-1,4-methanopyrido[2,3-b][1,4]diazepine-5,7(2H)-dicarboxamide

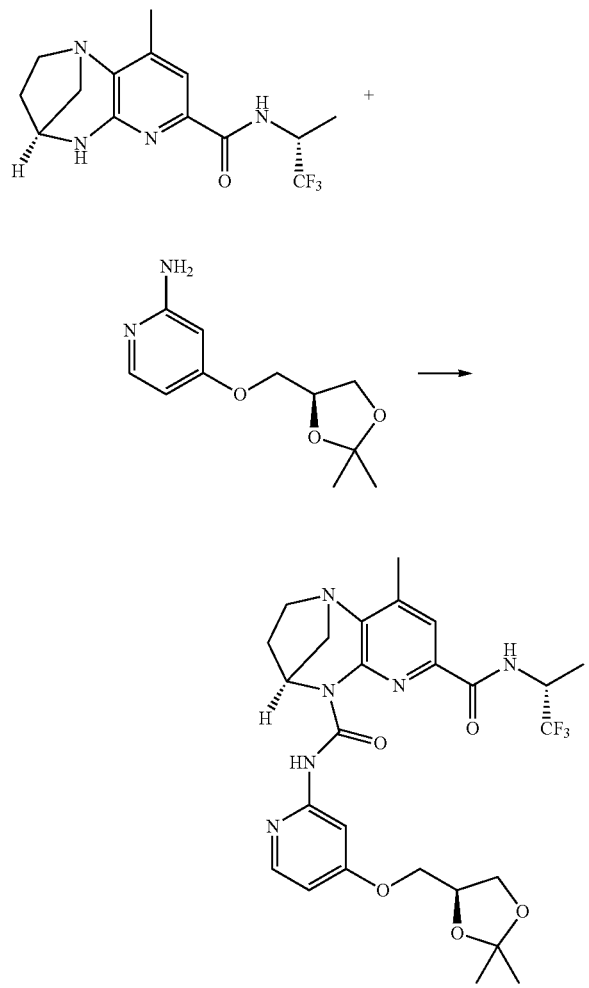 [SMILES: Cc1cc(C(=O)N[C@H](C)C(F)(F)F)nc2c1N1CC[C@@H](C1)N2 ; CC1(C)OC[C@H](COc2ccnc(N)c2)O1 ; Cc1cc(C(=O)N[C@H](C)C(F)(F)F)nc2c1N1CC[C@@H](C1)N2C(=O)Nc1cc(OC[C@H]2COC(C)(C)O2)ccn1]

To a solution of (4S)-9-methyl-N—((R)-1,1,1-trifluoropropan-2-yl)-2,3,4,5-tetrahydro-1,4-methanopyrido[2,3-b][1,4]diazepine-7-carboxamide (600 mg, 1.909 mmol) in THF (50 ml) and triphosgene (340 mg, 1.145 mmol) at 0° C. Then DIPEA (1.000 mL, 5.73 mmol) was added and stirred to RT for 1 h. and (S)-4-((2,2-dimethyl-1,3-dioxolan-4-yl)methoxy)pyridin-2-amine (642 mg, 2.86 mmol) was added sub sequentially at 75° C. for 16 h. The reaction was monitored by TLC and LCMS. The reaction mixture was poured in saturated NaHCO₃ solution (30 mL) and extracted with ethyl acetate (2×100 mL). The organic layer was dried over anhydrous Na₂SO₄ and concentrated under reduced pressure to give crude. The crude product was added to a Neutral alumina column and was eluted with 20% Ethylacetate in Petether Collected fractions are evaporated to afford (4S)—N5-(4-(((S)-2,2-dimethyl-1,3-dioxolan-4-yl)methoxy)pyridin-2-yl)-9-methyl-N7-((R)-1,1,1-trifluoropropan-2-yl)-3,4-dihydro-1,4-methanopyrido[2,3-b][1,4]diazepine-5,7(2H)-dicarboxamide (280 mg, 0.490 mmol, 25.7% yield) as a White solid, LCMS (m/z): 565.55 [M+H]⁺.

Synthesis of (4S)-5-((4-((R)-2,3-dihydroxypropoxy)pyridin-2-yl)carbamoyl)-2,3,4,5-tetrahydro-1,4-methanopyrido[2,3-b][1,4]diazepine-7-carboxylic acid

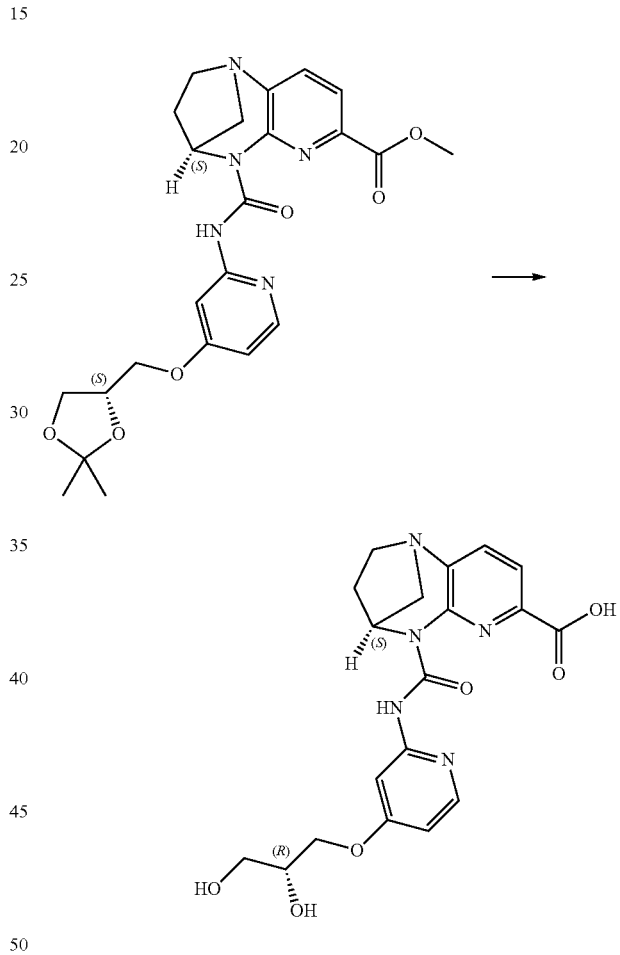

To a solution of (4S)-methyl 5-((4-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylate (2.0 g, 4.26 mmol) in Tetrahydrofuran (THF) (35 mL) and Water (35.0 mL) was added LiOH (0.153 g, 6.39 mmol). The reaction mixture was stirred at RT for 1 hr. Reaction mixture was concentrated under reduced pressure to afford Li salt of the product. Then the salt was diluted with water (100 mL) washed thoroughly with Ethyl acetate (2×100 mL) then the aqueous layer acidified with aq. HCl to afford (4S)-5-((4-((R)-2,3-dihydroxypropoxy)pyridin-2-yl)carbamoyl)-2,3,4,5-tetrahydro-1,4-methanopyrido[2,3-b][1,4]diazepine-7-carboxylic acid (1.5 g, 3.60 mmol, 84% yield) as an Off white solid, LCMS (m/z): 416.07 [M+H]⁺.

111

Synthesis of (4S)-5-((4-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid

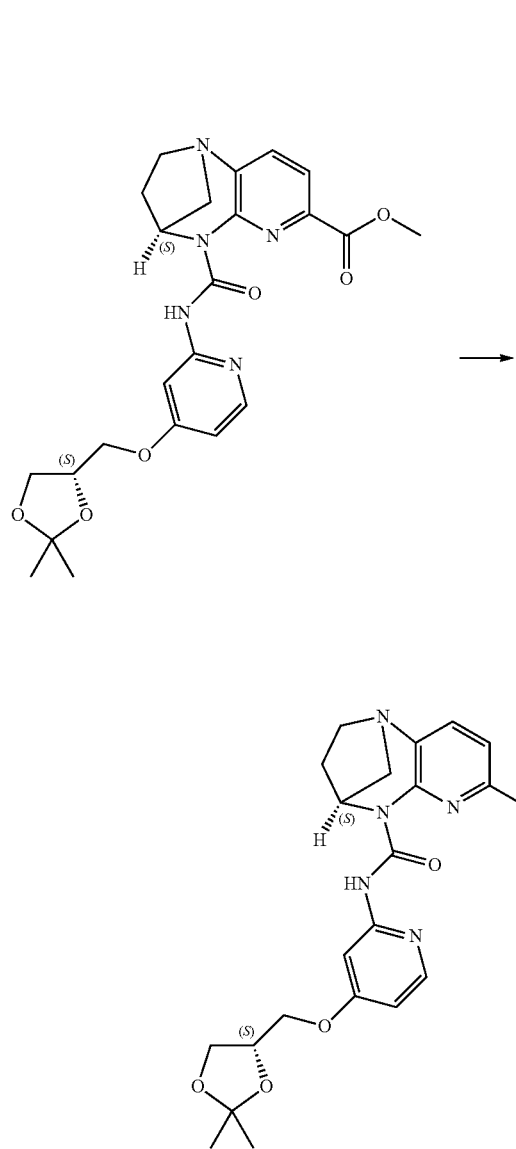

(4S)-methyl 5-((4-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylate (1 g, 2.130 mmol), LiOH (0.204 g, 8.52 mmol) were taken in Tetrahydrofuran (THF) (10 mL), Methanol (10.00 mL) and Water (3 mL) at 0° C., the resulting brown solution was stirred for 3 hr at room temperature. The reaction progress was monitored by TLC 10% MeOH in DCM, TLC indicated formation of multiple spots after 24 h. The reaction mass was concentrated to half volume then neutralized with citric acid, at 0° C., during the process brown solid was precipitated and filtered, dried over vacuum to afford (4S)-5-((4-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid (1 g, 1.936 mmol, 91% yield) as pale brown solid, LCMS (m/z): 456.1 [M+H]$^+$.

112

Synthesis of (4S)-methyl 5-((4-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylate

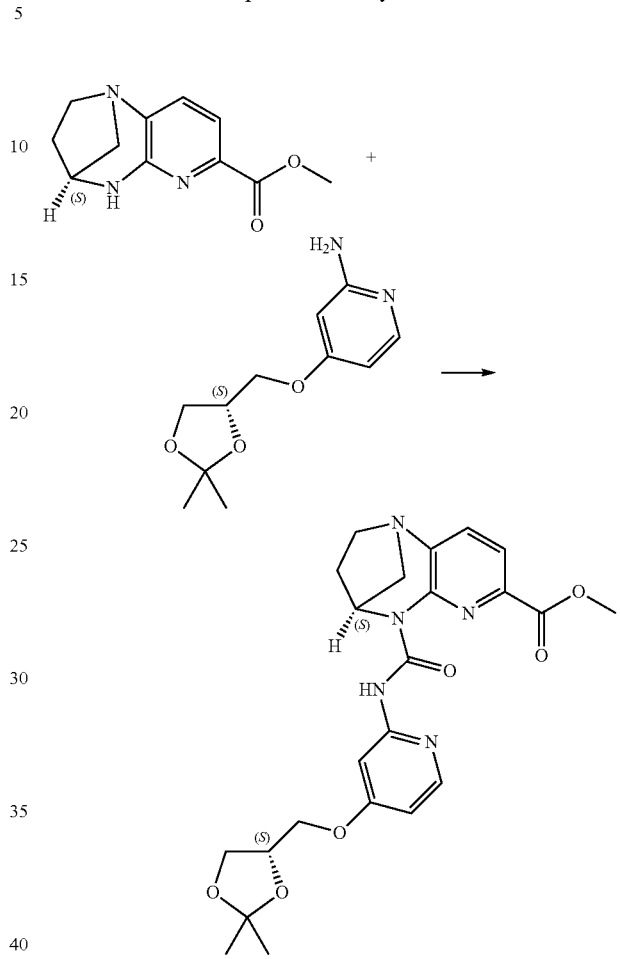

(4S)-methyl 2,3,4,5-tetrahydro-1,4-methanopyrido[2,3-b][1,4]diazepine-7-carboxylate (0.8 g, 3.65 mmol), TEA (2.54 mL, 18.24 mmol) were taken in Tetrahydrofuran (THF) (40 mL) at 0° C., the resulting yellow solution was stirred for 10 min. Then added triphosgene (1.083 g, 3.65 mmol) in one portion at 0° C. The resulting yellow suspension was stirred for 45 min at room temperature. The THF (4 mL) solution of (S)-4-((2,2-dimethyl-1,3-dioxolan-4-yl)methoxy)pyridin-2-amine (0.818 g, 3.65 mmol) was added to the above yellow suspension at 0° C. over a period of 5 min. The resulting yellow suspension was heated to 70° C. for 24 hr. The reaction progress was monitored by TLC 10% MeOH in DCM, TLC indicated formation of multiple spots after 24 h. The reaction mass was cooled to room temperature, diluted with water (20 mL), ethyl acetate (30 mL*2). The combined organic layer was washed with brine (15 mL), dried over Na$_2$SO$_4$ filtered, concentrated under reduced pressure to afford brown solid. The crude product was purified by combiflash chromatography over 230-400 mesh size silica gel. Column was eluted with a gradient of MeOH/DCM. Desired compound was eluted with 10% MeOH in DCM. Fractions containing pure compound were concentrated under reduced pressure to afford (4S)-methyl 5-((4-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]

diazepine-7-carboxylate (1.00 g, 1.495 mmol, 41.0% yield) as off white solid, LCMS 469.9 (m/z): [M+H]⁺.

Synthesis of (4S)—N7-cyclopropyl-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide

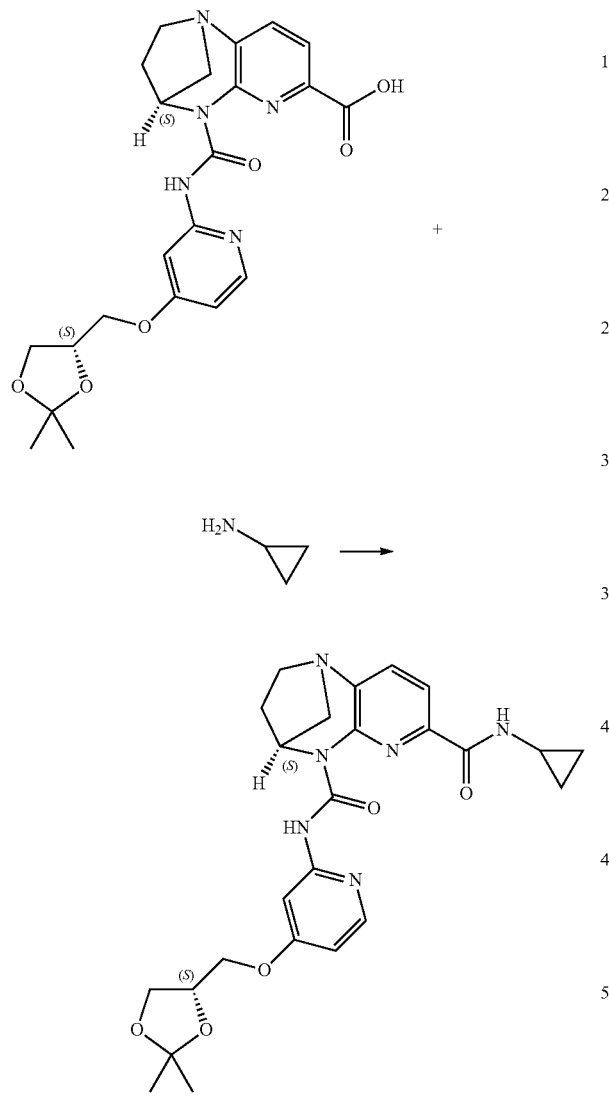

(4S)-5-((4-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid (460 mg, 1.010 mmol) was dissolved in N,N-Dimethylformamide (DMF) (10 mL), TEA (0.141 mL, 1.010 mmol) and added HATU (768 mg, 2.020 mmol), the resulting brown solution was stirred under nitrogen at 0° C. for 30 min. Then, added cyclopropanamine (57.7 mg, 1.010 mmol) in one portion under nitrogen. The resulting reaction mixture was stirred at room temperature for 16 hr. Progress of the reaction was monitored by TLC. TLC indicated formation of a new spot and completed consumption of SM. Reaction mixture was poured in ice cold water (20 ml), brown precipitation formed filtered and dried over vacuum to afford the desired compound (4S)—N7-cyclopropyl-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide (400 mg, 0.777 mmol, 77% yield) as brown solid. LCMS (m/z): 495.13 [M+H]⁺.

Synthesis of (4S)—N5-(4-(((S)-2,2-dimethyl-1,3-dioxolan-4-yl)methoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

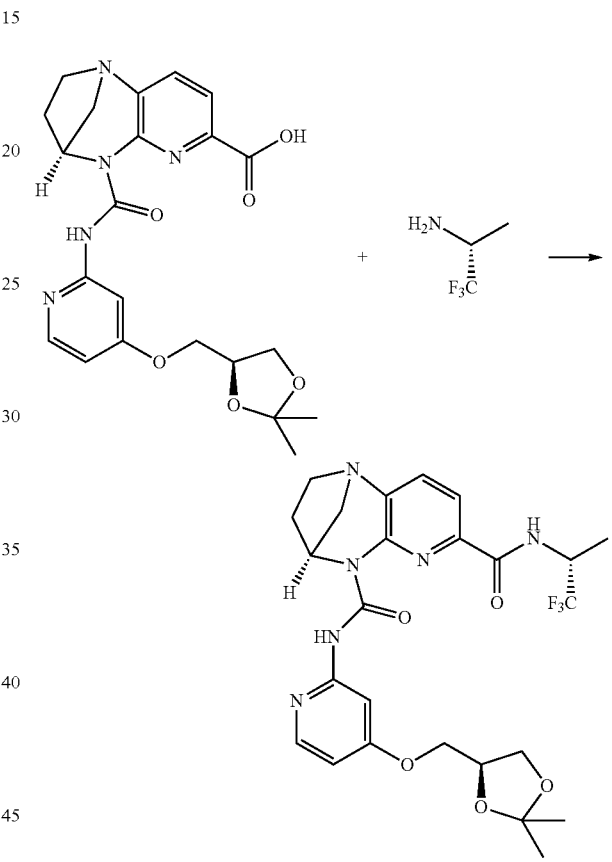

To a stirred solution of (4S)-5-((4-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid (7 g, 15.37 mmol) in N,N-Dimethylformamide (DMF) (100 mL), was added HATU (11.69 g, 30.7 mmol) and TEA (6.43 mL, 46.1 mmol) at 0° C. The reaction mixture was stirred at RT for 16 hr. Progress of the reaction was monitored by TLC, TLC indicated formation of a non polar spot and SM was consumed. Cold water (300 mL) was added to the reaction mixture. After stirring for 10 min, solid was precipitated out, the obtained solid was filtered and washed with water (200 mL), pet ether (200 mL) and dried under high vacuum to obtain desired pure product (4S)—N5-(4-(((S)-2,2-dimethyl-1,3-dioxolan-4-yl)methoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (6 g, 10.68 mmol, 69.5% yield) as a yellow solid. LCMS (m/z): 551.21 [M+H]⁺.

115

Synthesis of (4S)—N7-(cyclopropylmethyl)-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide

116

Synthesis of (4S)—N7-allyl-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide

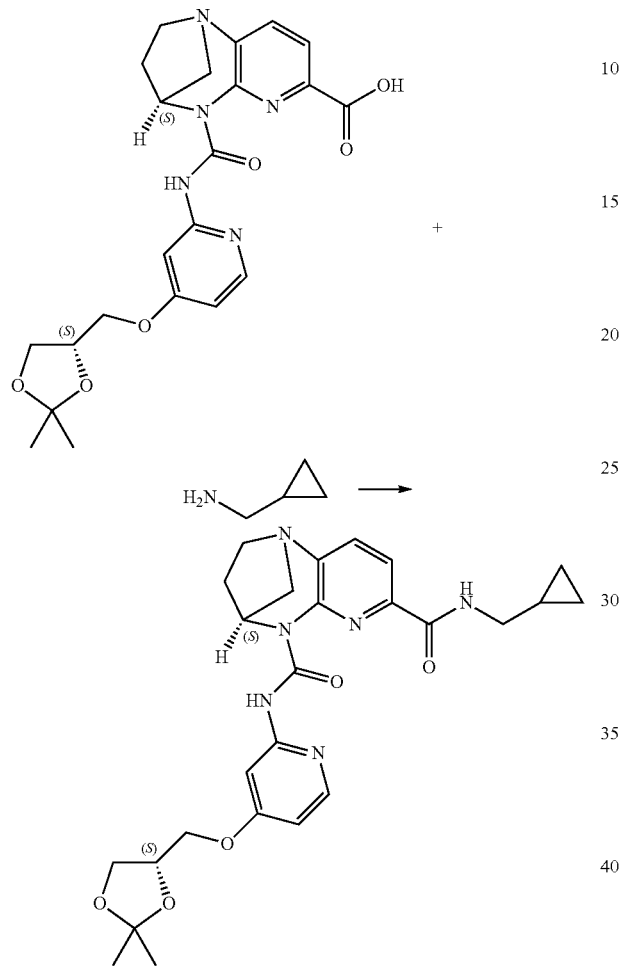

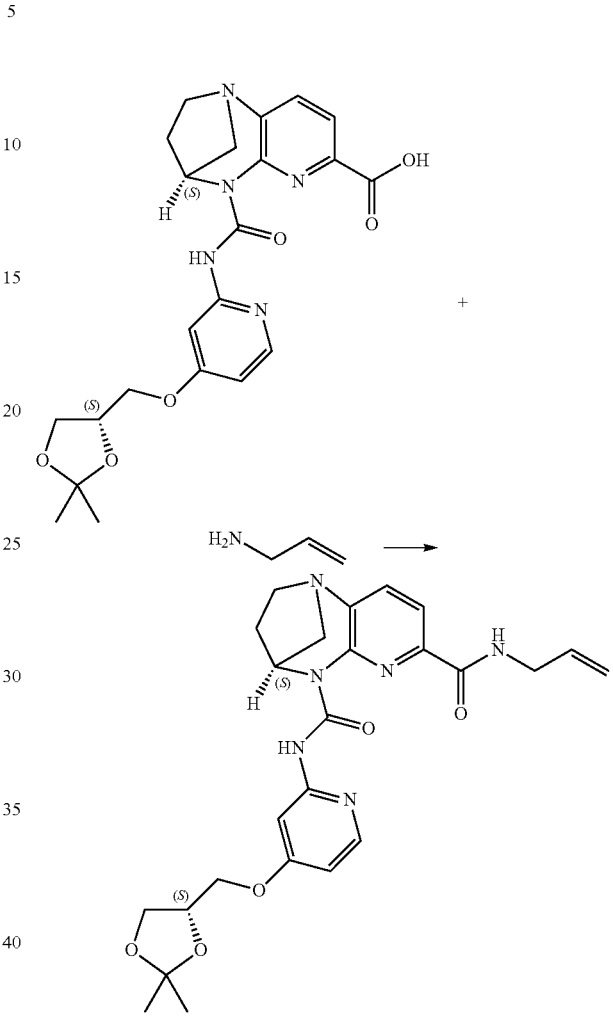

(4S)-methyl 5-((4-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylate (900 mg, 1.917 mmol) and cyclopropylmethanamine (477 mg, 6.71 mmol) were taken in sealed tube and the resulting pale brown solution was heated at 100° C. for 16 hr. Progress of the reaction was monitored by TLC. TLC indicated same rf as SM. Desired mass observed in LCMS. Reaction mixture was concentrated under reduced to pressure to afford pale brown viscous oil. The crude material was purified by combiflash using silica gel column (12 g, 2% MeOH in DCM). Fraction containing pure compound were combined and concentrated under reduced pressure to afford the desired compound (4S)—N7-(cyclopropylmethyl)-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide (650 mg, 1.104 mmol, 57.6% yield) as pale green solid, LCMS (m/z): 510.16 [M+H]$^+$.

To a stirred solution of (4S)-5-((4-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid (600 mg, 1.317 mmol) in N,N-Dimethylformamide (DMF) (7 mL), was added HATU (1002 mg, 2.63 mmol) followed by TEA (0.551 mL, 3.95 mmol) at 0° C. The reaction mixture was stirred at 0° C. for 15 mins, then added prop-2-en-1-amine (75 mg, 1.317 mmol) at 0° C. The reaction mixture was stirred at RT for 16 hr. Progress of the reaction was monitored by TLC, TLC indicated formation of a non polar spot and SM was consumed. Cold water (25 mL) was added to the reaction mixture. After stirring for 10 min solid was precipitated out, the obtained solid was filtered and washed with water (30 mL), pet ether (30 mL) and dried under high vacuum to obtain desired pure product (4S)—N7-allyl-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide (500 mg, 1.001 mmol, 76% yield) as an yellow solid. LCMS (m/z): 495.23 (M+H)$^+$.

Synthesis of (4S)—N7-((R)-1-cyclopropyl-2,2,2-trifluoroethyl)-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide

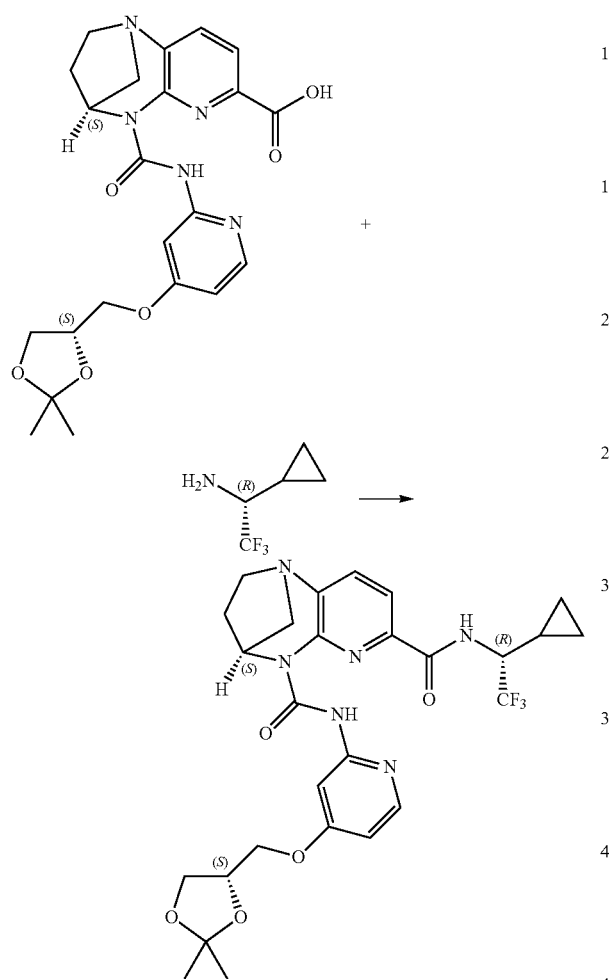

(4S)-5-((4-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid (300 mg, 0.659 mmol) was taken in N,N-Dimethylformamide (DMF) (10 mL), then added DIPEA (0.115 mL, 0.659 mmol) the resulting yellow solution was stirred for 5 min at 0° C. Then, added HATU (250 mg, 0.659 mmol) and stirred for 20 min under nitrogen condition at 0° C. (R)-1-cyclopropyl-2,2,2-trifluoroethanamine hydrochloride (116 mg, 0.659 mmol) was added in one portion to the above stirred yellow color solution, after addition reaction mass turned to brown solution. The resulting reaction mixture was stirred at room temperature for 16 hr. Progress of the reaction was monitored by TLC. TLC indicated consumption of starting material and formation of new multiple non polar spot. Reaction mixture was diluted with ice cold water and stirred for 10 min, then filtered the pale brown solid. The crude material was combined with another batch of the same material (total 680 mg) and was purified by combiflash using silica gel column (12 g, 2% MeOH in DCM). Fraction containing pure compound were combined and concentrated under reduced pressure to afford the desired compound (4S)—N7-((R)-1-cyclopropyl-2,2,2-trifluoroethyl)-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide (500 mg, 0.706 mmol, 107% yield) as pale brown solid, LCMS (m/z): 577.12 [M+H]$^+$.

Synthesis of (4S)—N5-(4-(((S)-2,2-dimethyl-1,3-dioxolan-4-yl)methoxy)pyridin-2-yl)-N7-(2,2,2-trifluoroethyl)-3,4-dihydro-1,4-methanopyrido[2,3-b][1,4]diazepine-5,7(2H)-dicarboxamide

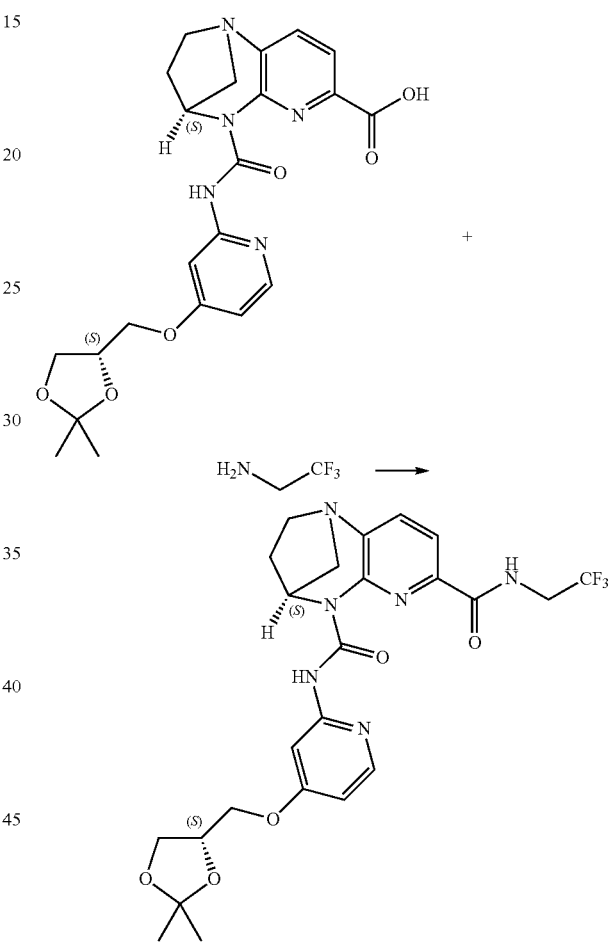

(4S)-5-((4-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid (300 mg, 0.659 mmol), DIPEA (0.115 mL, 0.659 mmol) were stirred in N,N-Dimethylformamide (DMF) (10 mL) at 0° C. for 5 min. Then, added HATU (501 mg, 1.317 mmol) and stirred for 20 min at 0° C. Then added 2,2,2-trifluoroethanamine (65.2 mg, 0.659 mmol) in one portion under nitrogen. The resulting reaction mixture was stirred at room temperature for 16 hr. Progress of the reaction was monitored by TLC. TLC indicated consumption of starting material and formation of non polar spot. The reaction mass was diluted with water, then extracted with ethyl acetate (15 mL). The organic layer was washed with brine (10 mL), dried over Na$_2$SO$_4$, filtered, and concentrated under reduced pressure to afford (4S)—N5-(4-(((S)-2,2-dimethyl-1,3-dioxolan-4- yl)methoxy)pyridin-2-yl)-N7-(2,2,2-trifluoroethyl)-3,4-dihydro-1,4-methanopyrido[2,3-b][1,4]diazepine-5,7(2H)-dicarboxamide (480 mg, 0.870 mmol, 132% yield) as off white solid. This was combined with other batches of the same crude material (580 mg total) and was purified by combiflash using silica gel column (12 g, 2% MeOH in DCM). Fraction containing pure compound were combined and concentrated under reduced pressure to afford the desired compound (4S)—N7-((R)-1-cyclopropyl-2,2,2-trifluoroethyl)-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide (500 mg, 0.706 mmol, 107% yield) as off white solid, LCMS (m/z): 537.23 [M+H]$^+$.

Synthesis of (4S)—N5-(4-(((S)-2,2-dimethyl-1,3-dioxolan-4-yl)methoxy)pyridin-2-yl)-N7-((R)-1,1,1-trifluorobutan-2-yl)-3,4-dihydro-1,4-methanopyrido[2,3-b][1,4]diazepine-5,7(2H)-dicarboxamide

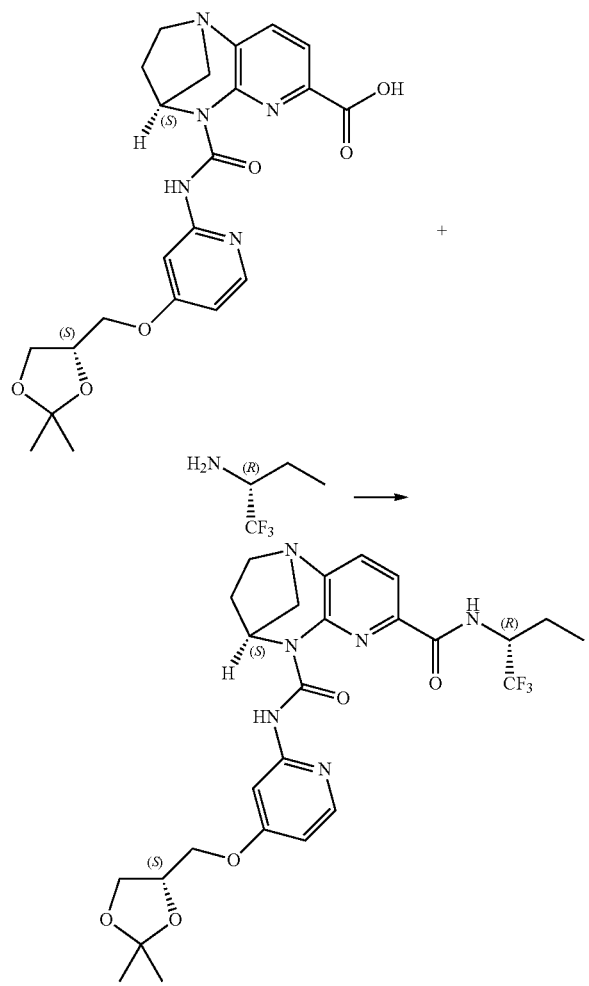

(4S)-5-((4-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid (350 mg, 0.768 mmol), DIPEA (0.134 mL, 0.768 mmol) were stirred in N,N-Dimethylformamide (DMF) (10 mL) at 0° C. for 5 min. Then, added HATU (584 mg, 1.537 mmol) and stirred for 20 min at 0° C. Then added (R)-1,1,1-trifluorobutan-2-amine (98 mg, 0.768 mmol) in one portion under nitrogen. The resulting reaction mixture was stirred at room temperature for 16 hr. Progress of the reaction was monitored by TLC. TLC indicated consumption of starting material and formation of non polar spot. The reaction mass was diluted with water, then extracted with ethyl acetate (15 mL). The organic layer was washed with brine (10 mL), dried over Na$_2$SO$_4$, filtered, and concentrated under reduced pressure to afford to crude brown solid 500 mg. The crude mass was purified by 100-200 mesh silica gel, desired compound was eluted with 4% MeOH in DCM, the compound containing fractions were collected and concentrated under reduced pressure to afford (4S)—N5-(4-(((S)-2,2-dimethyl-1,3-dioxolan-4-yl)methoxy)pyridin-2-yl)-N7-((R)-1,1,1-trifluorobutan-2-yl)-3,4-dihydro-1,4-methanopyrido[2,3-b][1,4]diazepine-5,7(2H)-dicarboxamide (320 mg, 0.549 mmol, 71.4% yield) as off white solid, LCMS (m/z): 565.23 [M+H]$^+$.

Synthesis of (4S)—N5-(4-(((S)-2,2-dimethyl-1,3-dioxolan-4-yl)methoxy)pyridin-2-yl)-N7-((S)-3,3,3-trifluoro-2-hydroxypropyl)-3,4-dihydro-1,4-methanopyrido[2,3-b][1,4]diazepine-5,7(2H)-dicarboxamide

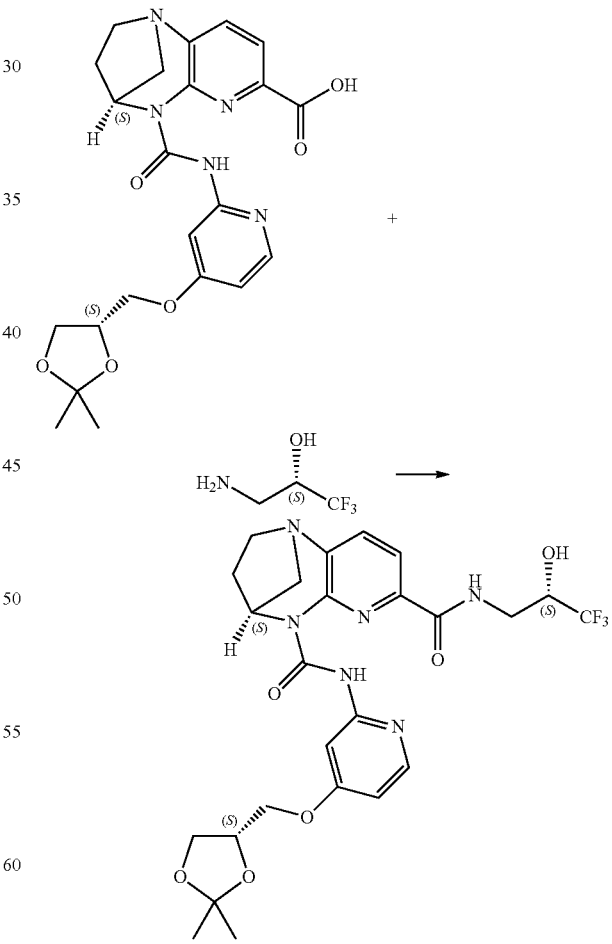

(4S)-5-((4-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid (300 mg, 0.659 mmol), DIPEA (0.115 mL, 0.659 mmol) were stirred in N,N-Dimethylformamide (DMF) (8 mL) at 0° C. for 5 min. Then, added HATU (501 mg, 1.317 mmol) and stirred for 20 min at 0° C. Then added (S)-3-amino-1,1,1-trifluoropropan-2-ol (85 mg, 0.659 mmol) in one portion under nitrogen. The resulting reaction mixture was stirred at room temperature for 16 hr. Progress of the reaction was monitored by TLC. TLC indicated consumption of starting material and formation of non polar spot. The reaction mass was diluted with water, then extracted with ethyl acetate (15 mL). The organic layer was washed with brine (10 mL), dried over Na$_2$SO$_4$, filtered, and concentrated under reduced pressure to afford (4S)—N5-(4-(((S)-2,2-dimethyl-1,3-dioxolan-4-yl)methoxy)pyridin-2-yl)-N7-((S)-3,3,3-trifluoro-2-hydroxypropyl)-3,4-dihydro-1,4-methanopyrido[2,3-b][1,4]diazepine-5,7(2H)-dicarboxamide (180 mg, 0.318 mmol, 48.2% yield) as pale brown solid. LCMS (m/z): 567.25 [M+H]$^+$.

Synthesis of (4S)—N5-(4-(((S)-2,2-dimethyl-1,3-dioxolan-4-yl)methoxy)pyridin-2-yl)-N7-(1,1,1-trifluoro-3-hydroxypropan-2-yl)-3,4-dihydro-1,4-methanopyrido[2,3-b][1,4]diazepine-5,7(2H)-dicarboxamide methanopyrido[2,3-b][1,4]diazepine-7-carboxylic acid (706 mg, 1.549 mmol), DIPEA (271 µl, 1.549 mmol) were stirred in N,N-Dimethylformamide (DMF) (10 mL) at 0° C. for 5 min. Then, added HATU (589 mg, 1.549 mmol) and stirred for 20 min at 0° C. Then added 2-amino-3,3,3-trifluoropropan-1-ol (200 mg, 1.549 mmol) in one portion under nitrogen. The resulting reaction mixture was stirred at room temperature for 16 hr. Progress of the reaction was monitored by TLC. TLC indicated consumption of starting material and formation of non polar spot. The reaction mass was diluted with water, then extracted with ethyl acetate (15 mL). The organic layer was washed with brine (10 mL), dried over Na$_2$SO$_4$, filtered, and concentrated under reduced pressure to afford brown viscous oil. The crude material was purified by using 100-200 silica gel column with 2% MeOH in DCM, the desired eluted compound fractions were concentrated under reduced pressure to afford (4S)—N5-(4-(((S)-2,2-dimethyl-1,3-dioxolan-4-yl)methoxy)pyridin-2-yl)-N7-(1,1,1-trifluoro-3-hydroxypropan-2-yl)-3,4-dihydro-1,4-methanopyrido[2,3-b][1,4]diazepine-5,7(2H)-dicarboxamide (500 mg, 0.715 mmol, 46.1% yield) as pale yellow viscous oil, LCMS (m/z): 567.25 [M+H]$^+$.

Synthesis of (4S)—N7-benzyl-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7 (2H)-dicarboxamide

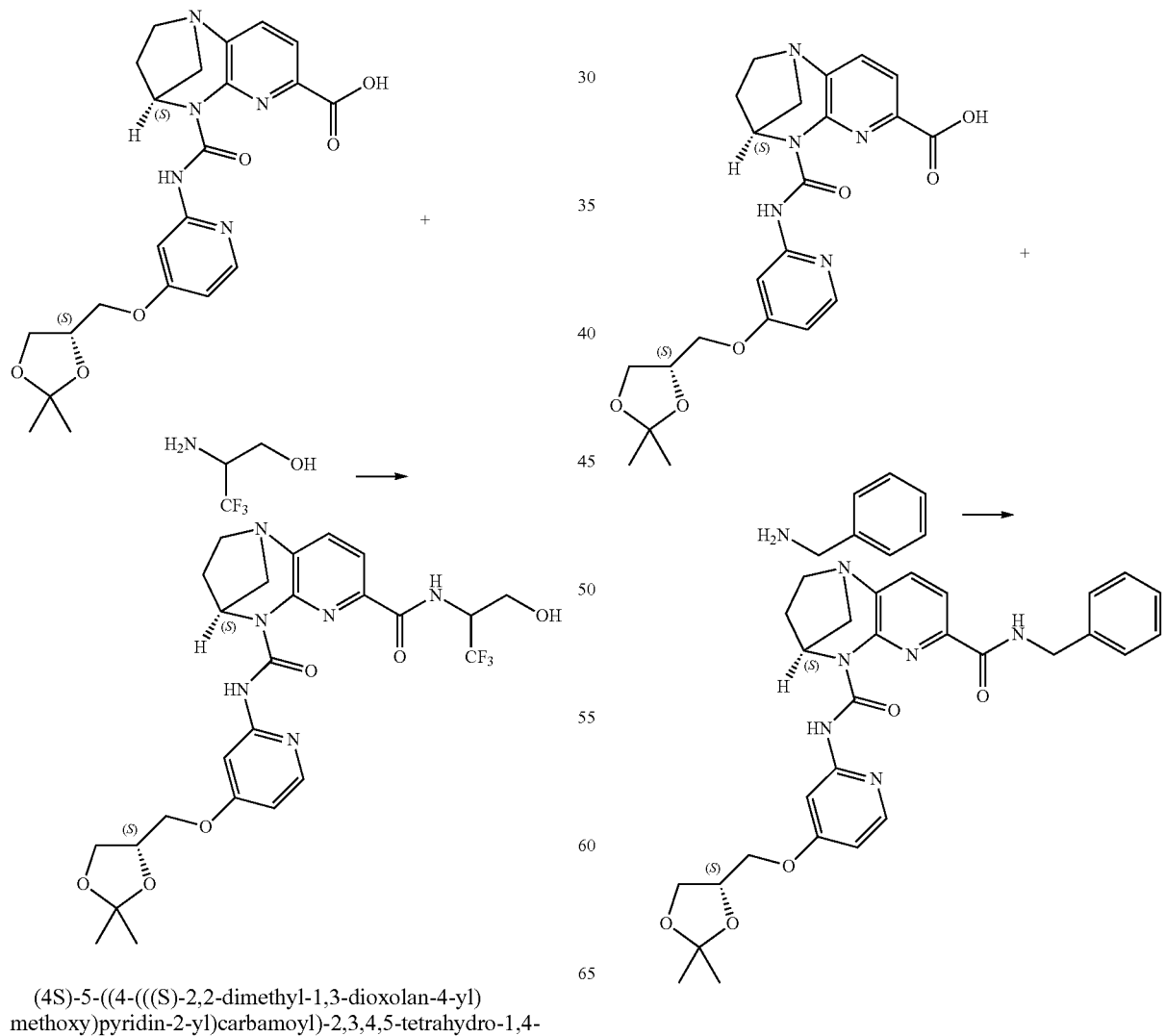

(4S)-5-((4-(((S)-2,2-dimethyl-1,3-dioxolan-4-yl)methoxy)pyridin-2-yl)carbamoyl)-2,3,4,5-tetrahydro-1,4-

To a stirred solution of (4S)-5-((4-(((S)-2,2-dimethyl-1,3-dioxolan-4-yl)methoxy-2-yl)carbamoyl)-2,3,4,5-tetrahydro-1,4-methanopyrido[2,3-b][1,4]diazepine-7-carboxylic acid (700 mg, 1.537 mmol) in Pyridine (8 mL), was added EDC (295 mg, 1.537 mmol) at 0° C. The reaction mixture was stirred at 0° C. for 30 min, then added phenylmethylamine (165 mg, 1.537 mmol) at 0° C. The resulting reaction mixture was stirred at RT for 16 hr. Progress of the reaction was monitored by TLC, TLC indicated formation of a non polar spot and SM was consumed. Cold water (20 mL) was added to the reaction mixture. The aqueous layer was extracted with EtOAc (2×10 mL). The combined organic layer was dried over anhydrous $Na_2SO_4$, filtered and concentrated under reduced pressure to obtain desired crude product. Crude product was purified by column chromatography using 100-200 silica gel (eluent 2% MeOH in DCM). Fraction containing pure compound was evaporated under reduced pressure to obtain desired pure product (4S)—N7-benzyl-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide (100 mg, 0.075 mmol, 34.2% yield) as an brown solid. LCMS (m/z): 545.27 $(M+H)^+$.

Synthesis of (4S)—N5-(4-(((S)-2,2-dimethyl-1,3-dioxolan-4-yl)methoxy)pyridin-2-yl)-N7-((R)-2,2,2-trifluoro-1-phenylethyl)-3,4-dihydro-1,4-methanopyrido[2,3-b][1,4]diazepine-5,7(2H)-dicarboxamide To a stirred solution of (4S)-5-((4-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid (600 mg, 1.317 mmol) in Pyridine (10 mL), was added EDC (379 mg, 1.976 mmol) at 0° C. The reaction mixture was stirred at RT for 30 min, then added (R)-2,2,2-trifluoro-1-phenylethanamine (254 mg, 1.449 mmol) at 0° C. The reaction mixture was stirred at RT for 16 hr. Progress of the reaction was monitored by TLC, TLC indicated formation of a non polar spot and SM was consumed. Pyridine was evaporated and Cold water (20 mL) was added to the reaction mixture. After stirring for 10 min. solid was precipitated out, the obtained solid was filtered and washed with water (30 mL), pet ether (30 mL) and dried under high vacuum to obtain desired pure product (4S)—N5-(4-(((S)-2,2-dimethyl-1,3-dioxolan-4-yl)methoxy)pyridin-2-yl)-N7-((R)-2,2,2-trifluoro-1-phenylethyl)-3,4-dihydro-1,4-methanopyrido[2,3-b][1,4]diazepine-5,7(2H)-dicarboxamide (500 mg, 0.813 mmol, 61.7% yield) as an light brown solid. LCMS (m/z): 613.27 $(M+H)^+$.

Synthesis of (4S)—N5-(4-(((S)-2,2-dimethyl-1,3-dioxolan-4-yl)methoxy)pyridin-2-yl)-N7-(thiazol-2-ylmethyl)-3,4-dihydro-1,4-methanopyrido[2,3-b][1,4]diazepine-5,7(2H)-dicarboxamide

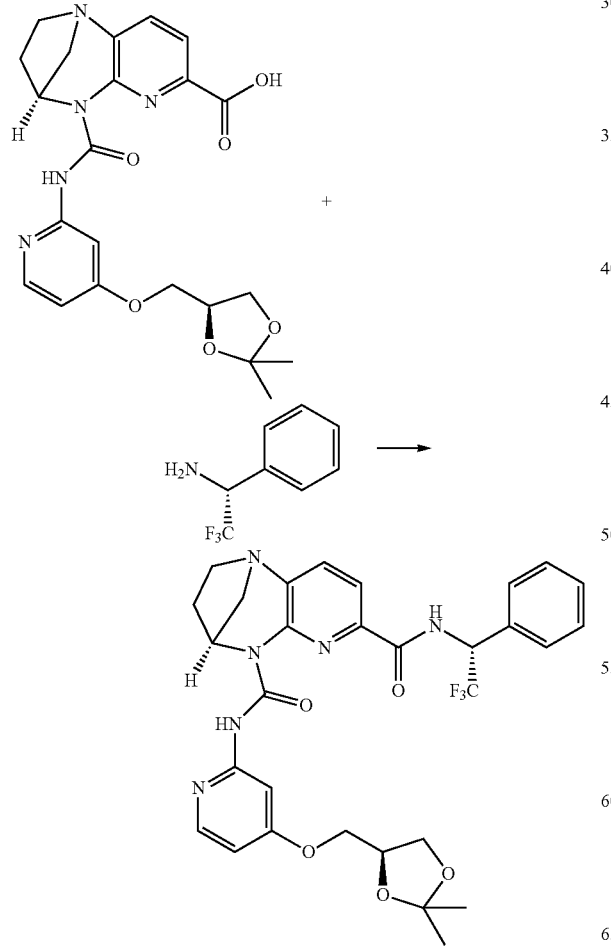

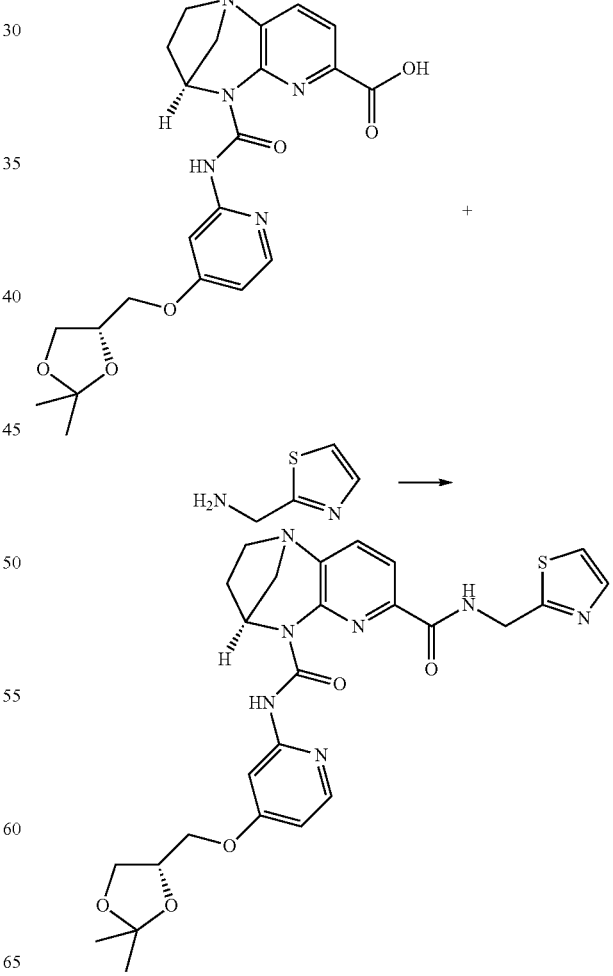

To a stirred solution of (4S)-5-((4-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid (450 mg, 0.988 mmol), thiazol-2-ylmethanamine hydrochloride (223 mg, 1.482 mmol) and HATU (564 mg, 1.482 mmol) in N,N-Dimethylformamide (DMF) (10 mL) under nitrogen atmosphere at 0° C. was added DIPEA (0.863 mL, 4.94 mmol) and stirred at 26° C. for 16 hr. The reaction mixture was diluted with water (10 mL) and extracted into DCM (3×10 mL). Combined organic extracts were dried over anhydrous $Na_2SO_4$, filtered and filtrate was evaporated to afford crude product. The crude compound was purified by Grace using C-18 reserval column, Mobile phase A: 0.1% Formic Acid in water; B: ACN, the product was eluted at 52% ACN in 0.1% Formic Acid in water. The solvent was evaporated and was basified with saturated $NaHCO_3$. The aqueous layer was extracted with DCM. DCM layer was dried over anhydrous $Na_2SO_4$, filtered and evaporated to afford pure (4S)—N5-(4-(((S)-2,2-dimethyl-1,3-dioxolan-4-yl)methoxy)pyridin-2-yl)-N7-(thiazol-2-ylmethyl)-3,4-dihydro-1,4-methanopyrido[2,3-b][1,4]diazepine-5,7(2H)-dicarboxamide (300 mg, 0.510 mmol, 51.6% yield) as an off-white solid, LCMS (m/z): 551.90 $[M+H]^+$.

Synthesis of (4S)—N5-(4-(((S)-2,2-dimethyl-1,3-dioxolan-4-yl)methoxy)pyridin-2-yl)-N7-(thiazol-4-ylmethyl)-3,4-dihydro-1,4-methanopyrido[2,3-b][1,4]diazepine-5,7(2H)-dicarboxamide To solid (4S)-5-((4-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid (450 mg, 0.988 mmol)) in N,N-Dimethylformamide (DMF) (5 mL) stirred under nitrogen at room temp was added solid HATU (564 mg, 1.482 mmol) and DIPEA (0.518 mL, 2.96 mmol) and thiazol-4-ylmethanamine hydrochloride (223 mg, 1.482 mmol) the reaction mixture was stirred at 25° C. for 3 hr. Reaction was monitored by TLC. The organic phase was added water and Extracted ethyl acetate and washed with water 50 mL and saturated brine 100 mL dried over $Na_2SO_4$ and evaporated in vacuum to give the crude products. The sample was absorbed with celite and purified by SPE(GRACE) on reverse phase (C18) 20 g using a 0-50% formic acid, ACN. The appropriate fractions were combined and evaporated in vacuo to give the required product as a off-white solid (4S)—N5-(4-(((S)-2,2-dimethyl-1,3-dioxolan-4-yl)methoxy)pyridin-2-yl)-N7-(thiazol-4-ylmethyl)-3,4-dihydro-1,4-methanopyrido[2,3-b][1,4]diazepine-5,7(2H)-dicarboxamide (250 mg, 0.416 mmol, 42.2% yield), LCMS (m/z): 552.10 $[M+H]^+$.

Synthesis of (4S)—N7-(2-amino-3,3,3-trifluoropropyl)-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide; and (4S)—N7-(2-amino-3,3,3-trifluoropropyl)-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide

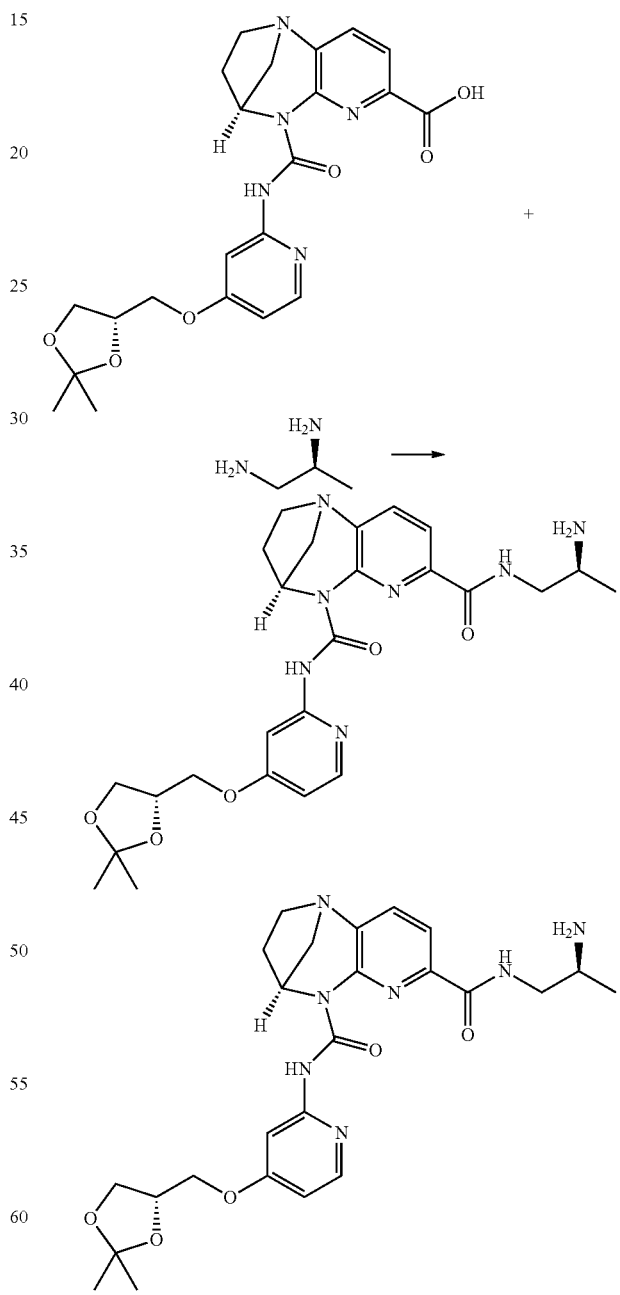

To a stirred solution of (4S)-5-((4-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid (2.0 g, 4.39 mmol) in Tetrahydrofuran (THF) (30 mL) were added HATU (2.004 g, 5.27 mmol), DIPEA (2.301 mL, 13.17 mmol) and 3,3,3-trifluoropropane-1,2-diamine hydrochloride (1.084 g, 6.59 mmol), stirred at 25° C. for 18 hr. Added water (30 mL), extracted with ethyl acetate (3×30 mL). Organic layer was separated and was dried over anhydrous Na$_2$SO$_4$, filtered and filtrate was evaporated to afford crude. Crude compound was purified by flash column chromatography (silicagel, 100-200 mesh Eluent: 60% Ethyl acetate in hexane) to afford 1.6 g with LCMS: 96.69%. Further purified by chiral SFC to afford the two Diastereomers.

Preparative SFC Conditions
Column/dimensions: Chiralpak IC ((250×30) mm, 5μ
% CO2: 55.0%
% Co solvent: 45.0% (0.5% DEA IN ETHANOL)
Total Flow: 90.0 g/min
Back Pressure: 100.0 bar
UV: 214 nm
Stack time: 4.0 min
Load/Inj: 8.0 mg
Solubility: MeOH+DCM
Total No of injections: 200
Instrument details: Make/Model: Thar SFC-200 (NEW-2)

Peak-1

Collected fraction from SFC was concentrated and washed with pentane to afford (4S)—N7-(2-amino-3,3,3-trifluoropropyl)-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide (500 mg, 0.859 mmol, 19.56% yield) as yellow solid, (TLC eluent: 100 ethyl acetate R$_f$ value: 0.3), LCMS: (m/z): 566.25 [M+H]$^+$.

Peak-2

Collected fraction from SFC was concentrated and washed with pentane to afford (4S)—N7-(2-amino-3,3,3-trifluoropropyl)-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide (400 mg, 0.636 mmol, 14.48% yield) as brownish sticky, (TLC eluent: 100 ethyl acetate R$_f$ value: 0.3), LCMS: (m/z): 566.25 [M+H]$^+$.

Synthesis of (4S)—N5-(4-(((S)-2,2-dimethyl-1,3-dioxolan-4-yl)methoxy)pyridin-2-yl)-N7-(3-fluorobenzyl)-3,4-dihydro-1,4-methanopyrido[2,3-b][1,4]diazepine-5,7(2H)-dicarboxamide

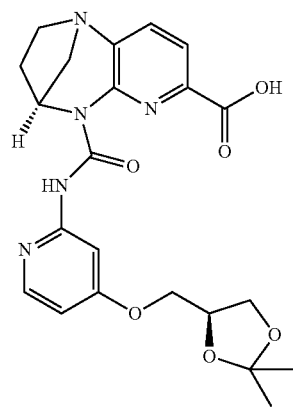

+

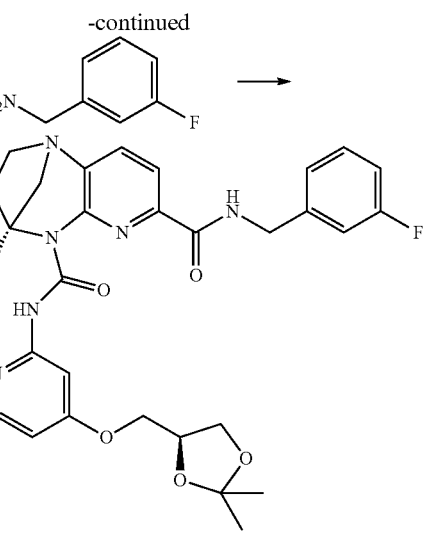

To a stirred solution of (4S)-5-((4-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid (600 mg, 1.317 mmol) in Pyridine (2 mL), was added EDC (505 mg, 2.63 mmol) at 0° C. The reaction mixture was stirred at 0° C. for 30 mins, then added (3-fluorophenyl)methanamine (198 mg, 1.581 mmol) at 0° C. The reaction mixture was stirred at rt for 16 hr. Progress of the reaction was monitored by TLC, TLC indicated formation of a non polar spot and SM was consumed. Pyridine was evaporated completely, cold water (25 mL) was added to the reaction mixture. The aqueous layer was extracted with EtOAc (2×25 mL). The combined organic layer was dried over anhydrous Na$_2$SO$_4$ filtered and concentrated under reduced pressure to obtain desired crude product. Crude product was purified by combi flash column (40 g column, eluent 4% MeOH in DCM), Fraction containing pure compound was evaporated under reduced pressure to obtain desired pure product (4S)—N5-(4-(((S)-2,2-dimethyl-1,3-dioxolan-4-yl)methoxy)pyridin-2-yl)-N7-(3-fluorobenzyl)-3,4-dihydro-1,4-methanopyrido[2,3-b][1,4]diazepine-5,7(2H)-dicarboxamide (500 mg, 0.879 mmol, 66.7% yield) as a brown solid. LCMS (m/z): 563.27 (M+H)$^+$.

Synthesis of (4S)—N5-(4-(((S)-2,2-dimethyl-1,3-dioxolan-4-yl)methoxy)pyridin-2-yl)-N7-(pyridin-3-ylmethyl)-3,4-dihydro-1,4-methanopyrido[2,3-b][1,4]diazepine-5,7(2H)-dicarboxamide

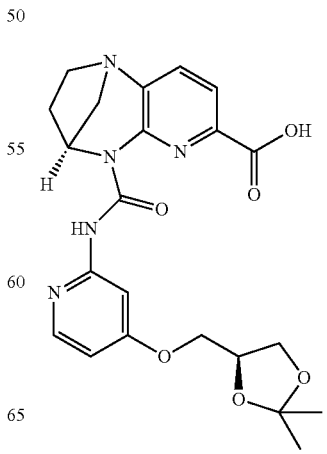

+

-continued

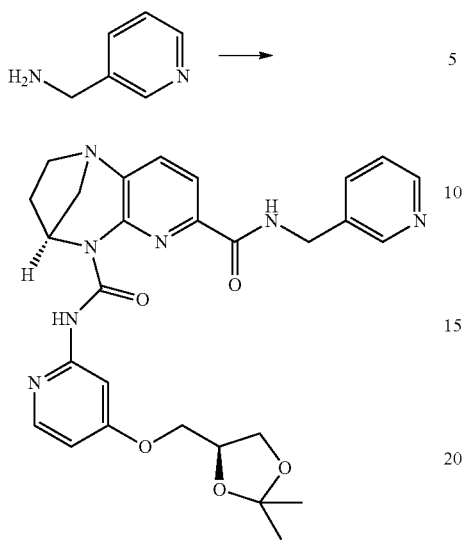

To a stirred solution of (4S)-5-((4-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid (700 mg, 1.537 mmol) in Pyridine (8 mL), was added EDC (442 mg, 2.305 mmol) at 0° C. The reaction mixture was stirred at 0° C. for 30 min, then added pyridin-3-ylmethanamine (199 mg, 1.844 mmol) at 0° C. The resulting reaction mixture was stirred at rt for 16 hr.

Progress of the reaction was monitored by TLC, TLC indicated formation of a non polar spot and SM was consumed. Pyridine was evaporated and Cold water (20 mL) was added to the reaction mixture. After stirring for 10 mins, solid was precipitated out, the obtained solid was filtered and washed with water (30 mL), pet ether (30 mL) and dried under high vacuum to obtain desired pure product (4S)—N5-(4-(((S)-2,2-dimethyl-1,3-dioxolan-4-yl)methoxy)pyridin-2-yl)-N7-(pyridin-3-ylmethyl)-3,4-dihydro-1,4-methanopyrido[2,3-b][1,4]diazepine-5,7(2H)-dicarboxamide (500 mg, 0.857 mmol, 55.7% yield) as an light brown solid, LCMS (m/z): 546.24 (M+H)+.

Synthesis of (4S)-5-(pyrazin-2-ylcarbamoyl)-2,3,4,5-tetrahydro-1,4-methanopyrido[2,3-b][1,4]diazepine-7-carboxylic acid

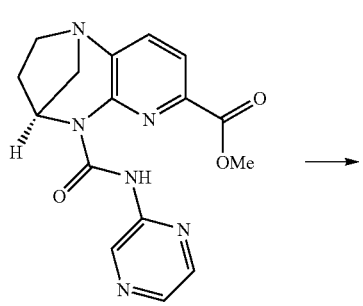

-continued

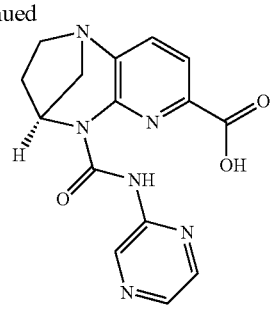

To a stirred solution of (4S)-methyl 5-(pyrazin-2-ylcarbamoyl-2,3,4,5-tetrahydro-1,4-methanopyrido[2,3-b][1,4]diazepine-7-carboxylate (3 g, 8.81 mmol) in Tetrahydrofuran (THF) (15 mL) and Water (10 mL), was added LiOH (0.528 g, 22.04 mmol) and stirred for 12 hr at rt. Reaction progress was monitored by TLC, TLC indicates no starting material and a new polar spot was observed. Reaction mass was concentrated under reduced pressure. Later PH was adjusted to 2 with 2N HCl and obtained solid was filtered and dried under high vacuum to obtain desired pure product (4S)-5-(pyrazin-2-ylcarbamoyl)-2,3,4,5-tetrahydro-1,4-methanopyrido[2,3-b][1,4]diazepine-7-carboxylic acid (2.2 g, 6.59 mmol, 74.7% yield) as off-white solid. LCMS (m/z): 327.09 [M+H]+.

Synthesis of (4S)-methyl 5-(pyrazin-2-ylcarbamoyl)-2,3,4,5-tetrahydro-1,4-methanopyrido[2,3-b][1,4]diazepine-7-carboxylate

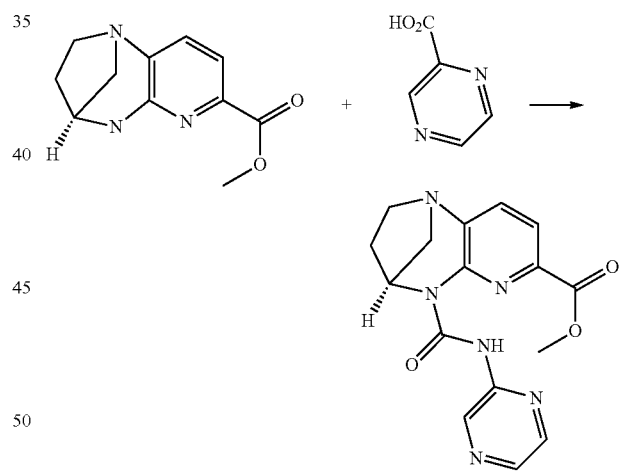

To a stirred solution of pyrazine-2-carboxylic acid (2.264 g, 18.24 mmol) in Toluene (50 mL), was added diphenyl phosphorazidate (5.02 g, 18.24 mmol) and followed by addition of TEA (5.09 mL, 36.5 mmol). The reaction mixture was stirred at 90° C. for 2 h, (4S)-methyl 2,3,4,5-tetrahydro-1,4-methanopyrido[2,3-b][1,4]diazepine-7-carboxylate (4 g, 18.24 mmol) at same temperature and stirred at 90° C. for 16 hr. Progress of the reaction was monitored by TLC, TLC shows along with starting material a non polar spot. Water (50 mL) was added to the reaction mixture and extracted with EtOAC (2×50 mL). The combined organic layer was dried over Na2SO4, filtered and concentrated under reduced pressure to obtain crude product. Crude product was purified by column chromatography using 100-200 silica gel (eluent 0.5-1.5% MeOH in DCM) to obtain the desired pure product (4S)-methyl 5-(pyrazin-2-ylcarbamoyl)-2,3,4,5-tetrahydro-1,4-methanopyrido[2,3-b][1,4]diazepine-7-carboxylate (3.2 g, 9.15 mmol, 50.1% yield) as off-white solid. LCMS (m/z): 341.07 [M+H]+.

Synthesis of (4S)-methyl 5-((5H-pyrrolo[3,2-d]pyrimidin-2-yl)carbamoyl)-2,3,4,5-tetrahydro-1,4-methanopyrido[2,3-b][1,4]diazepine-7-carboxylate

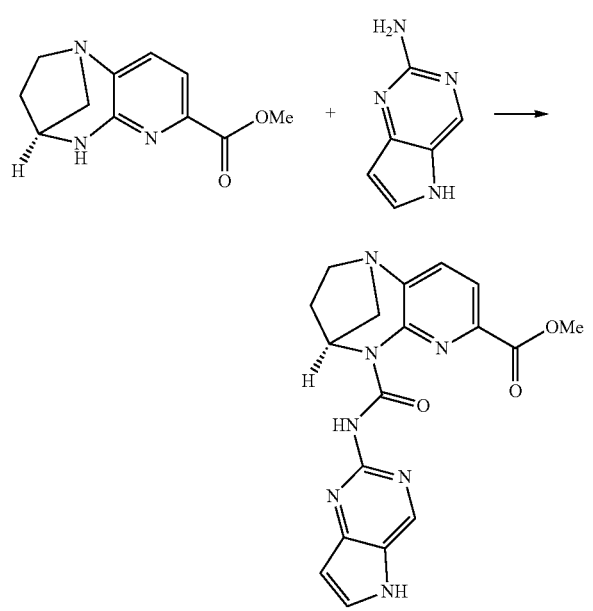 [SMILES: COC(=O)c1ccc2c(n1)N[C@H]1CCN2C1 ; Nc1ncc2[nH]ccc2n1 ; COC(=O)c1ccc2c(n1)N(C(=O)Nc1ncc3[nH]ccc3n1)[C@H]1CCN2C1]

TEA (7.63 mL, 54.7 mmol) & triphosgene (2.71 g, 9.12 mmol) was added to a stirred solution of (4S)-methyl 2,3,4,5-tetrahydro-1,4-methanopyrido[2,3-b][1,4]diazepine-7-carboxylate (2.0 g, 9.12 mmol) in Tetrahydrofuran (THF) (60 mL) under nitrogen at 28° C. The reaction mixture was stirred at rt for 30 min and was added 5H-pyrrolo[3,2-d]pyrimidin-2-amine (3.67 g, 27.4 mmol). The reaction mixture was stirred 16 hr at 65° C. The reaction mixture was cooled to room temp, solvent evaporated under reduced pressure completely and was partitioned between water (30 mL) and DCM (2×50 mL). Organic layer was separated, dried over anhydrous $Na_2SO_4$, filtered and filtrate was evaporated to afford crude product as a brown solid. The crude compound was purified by Grace using C-18 reserval column, Mobile phase A: 0.1% Formic Acid in water; B: ACN, the product was eluted at 18% ACN/0.1% Formic Acid in water. The solvent was evaporated and was basified with saturated $NaHCO_3$. The aqueous layer was extracted with DCM. DCM layer was dried over anhydrous $Na_2SO_4$, filtered and evaporated to afford pure (4S)-methyl 5-((5H-pyrrolo[3,2-d]pyrimidin-2-yl)carbamoyl)-2,3,4,5-tetrahydro-1,4-methanopyrido[2,3-b][1,4]diazepine-7-carboxylate (1.8 g, 3.25 mmol, 35.6% yield) as a pale yellow solid, LCMS (m/z): 380.23 [M+H]+.

Synthesis of (4S)-5-((5H-pyrrolo[3,2-d]pyrimidin-2-yl)carbamoyl)-2,3,4,5-tetrahydro-1,4-methanopyrido[2,3-b][1,4]diazepine-7-carboxylic acid

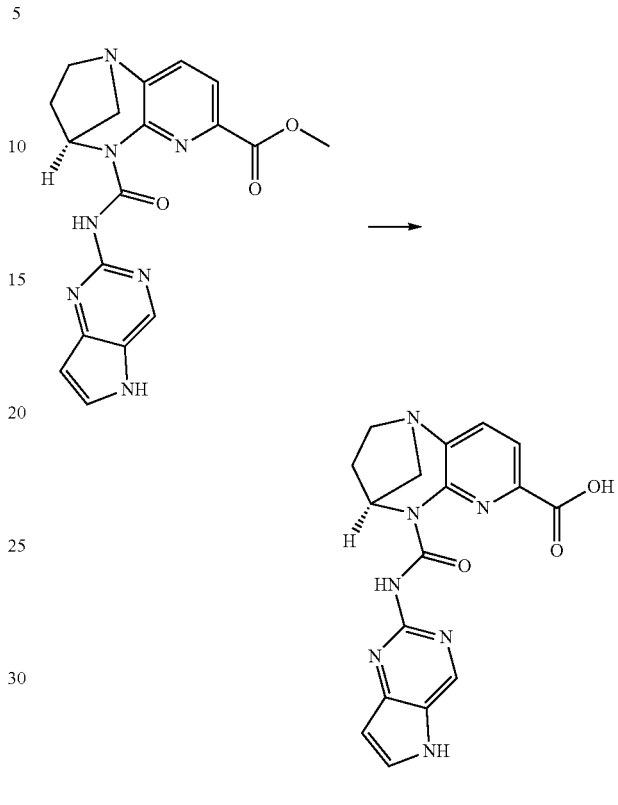

Lithium hydroxide mono hydrate (0.199 g, 4.74 mmol) in Water (4 mL) was added to a stirred solution of (4S)-methyl 5-((5H-pyrrolo[3,2-d]pyrimidin-2-yl)carbamoyl)-2,3,4,5-tetrahydro-1,4-methanopyrido[2,3-b][1,4]diazepine-7-carboxylate (1.8 g, 4.74 mmol) in Tetrahydrofuran (THF) (20 mL) at room temp. The reaction mixture was stirred at 26° C. for 2 hr. The reaction mixture solvent evaporated under reduced pressure completely and was acidified with 1N HCl solution. The reaction mixture was evaporated under reduced pressure completely, added 20% MeOH in DCM (50 ml) and stirred 15 min. Filtered the reaction mass through celite and washed with celite by 20% MeOH in DCM (25 ml). Take filtrate was evaporated to afford crude product (4S)-5-((5H-pyrrolo[3,2-d]pyrimidin-2-yl)carbamoyl)-2,3,4,5-tetrahydro-1,4-methanopyrido[2,3-b][1,4]diazepine-7-carboxylic acid (1.0 g, 2.120 mmol, 44.7% yield) as a brown solid (TLC eluent: 20% MeOH in DCM: $R_f$—0.2.; UV active). LCMS (m/z): 365.9 [M+H]+.

Synthesis of (4S)-methyl 5-((5-fluoropyridin-2-yl)carbamoyl)-2,3,4,5-tetrahydro-1,4-methanopyrido[2,3-b][1,4]diazepine-7-carboxylate

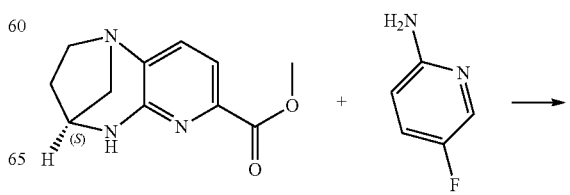

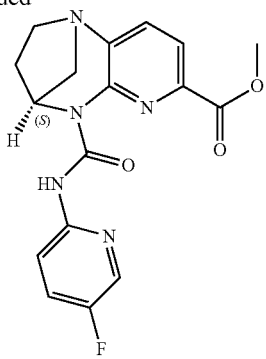

To a stirred solution of (4S)-methyl 2,3,4,5-tetrahydro-1,4-methanopyrido[2,3-b][1,4]diazepine-7-carboxylate (2.5 g, 11.40 mmol) in Tetrahydrofuran (THF) (30 mL), triphosgene (2.71 g, 9.12 mmol) and triethylamine (9.54 mL, 68.4 mmol) were added and stirred for 30 min. After 30 min 5-fluoropyridin-2-amine (2.56 g, 22.81 mmol) was added and reaction was maintained at 75° C. for 6 hr under Nitrogen condition. Reaction progress was monitored by TLC (TLC shows 3 major spots, no SM spot was observed). Water (150 ml) was added to the reaction mixture. Solid was formed and filtered the crude compound. Diethyl ether (2×35 ml) wash was given to the crude compound to get pure (4S)-methyl 5-((5-fluoropyridin-2-yl)carbamoyl)-2,3,4,5-tetrahydro-1,4-methanopyrido[2,3-b][1,4]diazepine-7-carboxylate (2.5 g, 6.63 mmol, 58.2% yield) as a brown color compound, LCMS (m/z): 358.09 [M+H]⁺.

Synthesis of (4S)-5-((5-fluoropyridin-2-yl)carbamoyl)-2,3,4,5-tetrahydro-1,4-methanopyrido[2,3-b][1,4]diazepine-7-carboxylic acid

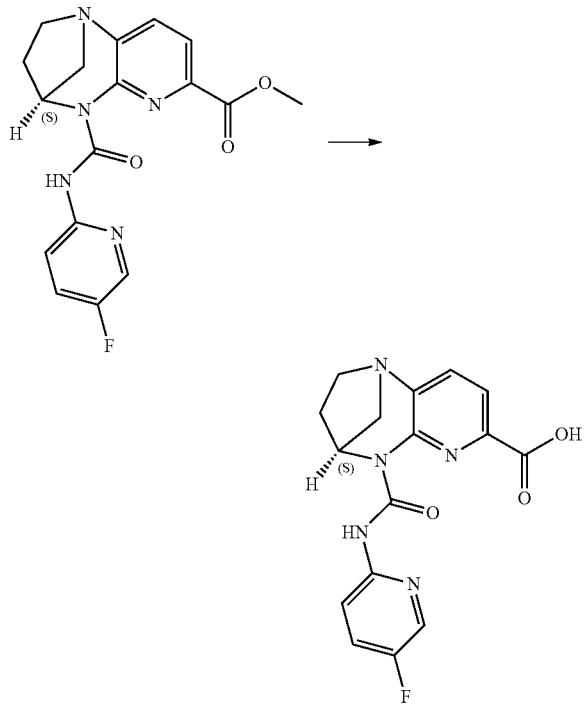

To a stirred solution of (4S)-methyl 5-((5-fluoropyridin-2-yl)carbamoyl)-2,3,4,5-tetrahydro-1,4-methanopyrido[2,3-b][1,4]diazepine-7-carboxylate (2.5 g, 7.00 mmol) in Tetrahydrofuran (THF) (30 mL) and Water (10 mL), was added LiOH (0.503 g, 20.99 mmol) and reaction was maintained at rt for 16 hr. Progress of the reaction was monitored by TLC, TLC shows formation of new polar spot and total consumption of starting material. Evaporated the THF completely and pH of the reaction mixture was adjusted to 5 using 2M HCl. The obtained solid was filtered and washed with water (20 mL) and petether (30 mL) to obtain desired pure product (4S)-5-((5-fluoropyridin-2-yl)carbamoyl)-2,3,4,5-tetrahydro-1,4-methanopyrido[2,3-b][1,4]diazepine-7-carboxylic acid (1.5 g, 4.05 mmol, 57.9% yield) as a light brown solid. LCMS (m/z): 344.02 [M+H]⁺.

Synthesis of (4S)-methyl 5-((7H-pyrrolo[2,3-d]pyrimidin-2-yl)carbamoyl)-2,3,4,5-tetrahydro-1,4-methanopyrido[2,3-b][1,4]diazepine-7-carboxylate

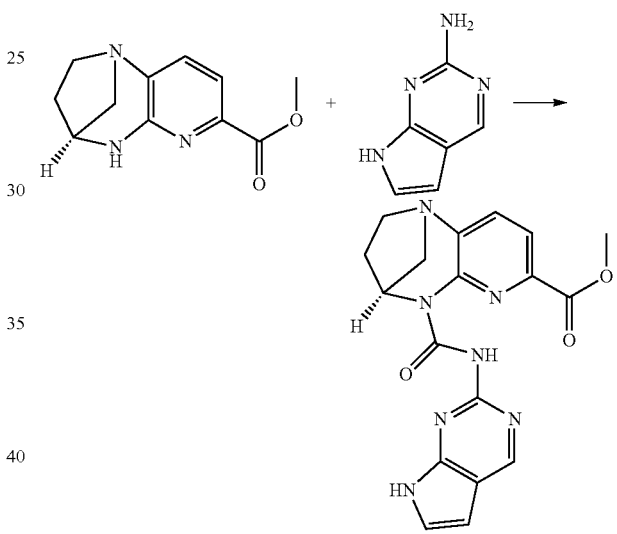

Triphosgene (2.030 g, 6.84 mmol) was added to a stirred solution of (4S)-methyl 2,3,4,5-tetrahydro-1,4-methanopyrido[2,3-b][1,4]diazepine-7-carboxylate (1.5 g, 6.84 mmol), and TEA (5.72 mL, 41.1 mmol) in Tetrahydrofuran (THE) (60 mL) under nitrogen at 28° C. The reaction mixture was stirred at RT for 30 min and, was added 7H-pyrrolo[2,3-d]pyrimidin-2-amine (2.75 g, 20.53 mmol). The reaction mixture was stirred 6 hr at 65° C. The reaction mixture was cooled to room temp, solvent evaporated under reduced pressure completely and was partitioned between water (50 mL) and EtOAc (2×60 mL). Organic layer was separated, dried over anhydrous Na₂SO₄, filtered and filtrate was evaporated to give crude as brown solid. TLC eluent: 100% EtOAc/Hexane, R$_f$: 0.3, UV active. The crude compound was purified by Grace using C-18 reserval column, Mobile phase A: 0.1% Formic Acid in water; B: MeOH, the product was eluted at 28-32% MeOH/0.1% Formic Acid in water. The solvent was evaporated and was basified with saturated NaHCO₃. The aqueous layer was extracted with DCM. DCM layer was dried over anhydrous Na₂SO₄, filtered and evaporated to afford pure (4S)-methyl 5-((7H-pyrrolo[2,3-d]pyrimidin-2-yl)carbamoyl)-2,3,4,5-tetrahydro-1,4-methanopyrido[2,3-b][1,4]diazepine-7-carboxylate (1.4 g, 3.43 mmol, 50.2% yield) as off white solid, LCMS (m/z): 380.0 [M+H]+.

Synthesis of (4S)-5-((7H-pyrrolo[2,3-d]pyrimidin-2-yl)carbamoyl)-2,3,4,5-tetrahydro-1,4-methanopyrido[2,3-b][1,4]diazepine-7-carboxylic acid

N36377-55

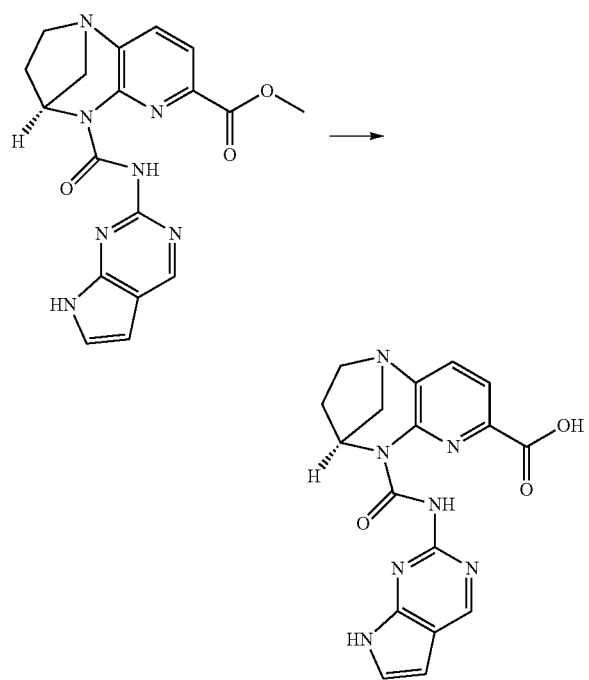

LiOH—H₂O (0.152 g, 6.33 mmol) in Water (10 mL) was added to a stirred solution of (4S)-methyl 5-((7H-pyrrolo[2,3-d]pyrimidin-2-yl)carbamoyl)-2,3,4,5-tetrahydro-1,4-methanopyrido[2,3-b][1,4]diazepine-7-carboxylate (1.2 g, 3.16 mmol) in Tetrahydrofuran (THF) (20 mL) at 0° C. The reaction mixture was stirred at 26° C. for 2 hr. The reaction mixture solvent evaporated under reduced pressure completely and was acidified with 1N HCl solution. The reaction mixture was evaporated under reduced pressure completely, added 20% MeOH in DCM (40 ml) and stirred 15 min. Filtered the reaction mass through celite and washed with celite by 20% MeOH in DCM (15 ml). Take filtrate was evaporated to afford crude (4S)-5-((7H-pyrrolo[2,3-d]pyrimidin-2-yl)carbamoyl)-2,3,4,5-tetrahydro-1,4-methanopyrido[2,3-b][1,4]diazepine-7-carboxylic acid (900 mg, 2.330 mmol, 73.7% yield) as a off white solid, LCMS (m/z): 366.00 [M+H]+.

Synthesis of (4S)-methyl 5-((6-methyl-1H-pyrazolo[3,4-b]pyridin-3-yl)carbamoyl)-2,3,4,5-tetrahydro-4-methanopyrido[2,3-b][1,4]diazepine-7-carboxylate

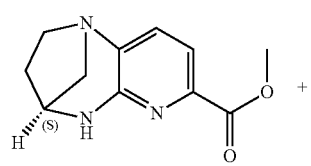

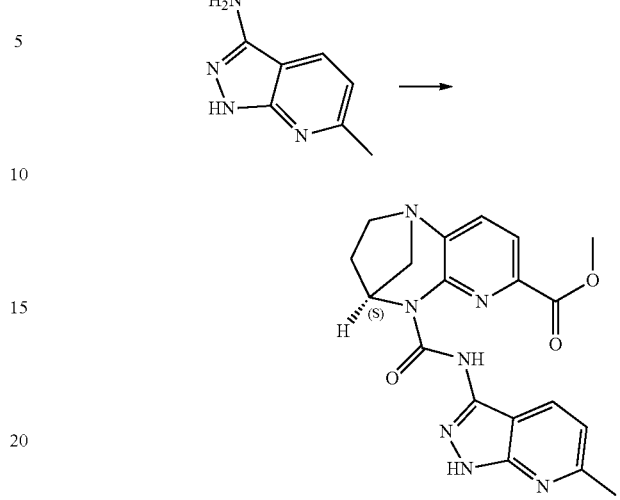

To a solution of (4S)-methyl 2,3,4,5-tetrahydro-1,4-methanopyrido[2,3-b][1,4]diazepine-7-carboxylate (1 g, 4.56 mmol) in stirred under nitrogen at 0° C. triphosgene (1.354 g, 4.56 mmol) and TEA (3.81 mL, 27.4 mmol) was added. Then the reaction mixture was stirred at 30° C. for 30 min and added 6-methyl-1H-pyrazolo[3,4-b]pyridin-3-amine (507 mg, 3.42 mmol), then the reaction mixture was stirred at 90° C. for 16 hr. The reaction was monitored by LCMS and TLC. The reaction mixture was poured in to the cold water (30 mL) and extracted with ethyl acetate (2×50 mL). The organic layer was dried over anhydrous Na₂SO₄ and concentrated under vacuum to obtained crude compound. The crude compound was purified by column chromatography (100-200 silica gel) using gradient mixture of 10% methanol in DCM as eluent to afford the compound (4S)-methyl 5-((6-methyl-1H-pyrazolo[3,4-b]pyridin-3-yl)carbamoyl)-2,3,4,5-tetrahydro-1,4-methanopyrido[2,3-b][1,4]diazepine-7-carboxylate (800 mg, 1.694 mmol, 37.1% yield) as pale brown solid, LCMS (m/z): 394.08 [M+H]+.

Synthesis of (4S)-5-((6-methyl-1H-pyrazolo[3,4-b]pyridin-3-yl)carbamoyl)-2,3,4,5-tetrahydro-1,4-methanopyrido[2,3-b][1,4]diazepine-7-carboxylic acid

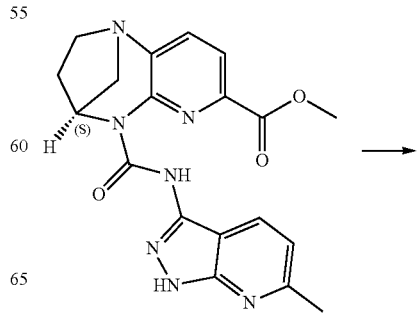

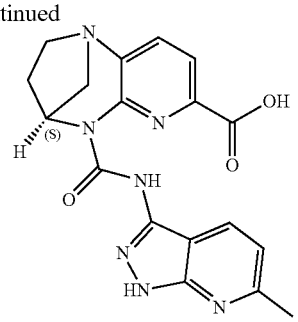

To a solution of (4S)-methyl 5-((6-methyl-1H-pyrazolo[3,4-b]pyridin-3-yl)carbamoyl)-2,3,4,5-tetrahydro-1,4-methanopyrido[2,3-b][1,4]diazepine-7-carboxylate (800 mg, 2.034 mmol) in Tetrahydrofuran (THF) (15 mL) and Water (15.00 mL) was added LiOH (73.1 mg, 3.05 mmol). The reaction mixture was stirred at RT for 2 hr. Reaction mixture was concentrated under reduced pressure to afford compound (4S)-5-((6-methyl-1H-pyrazolo[3,4-b]pyridin-3-yl)carbamoyl)-2,3,4,5-tetrahydro-1,4-methanopyrido[2,3-b][1,4]diazepine-7-carboxylic acid (500 mg, 1.079 mmol, 53.0% yield) as Pale brown solid, LCMS (m/z): 380.09 [M+H]$^+$.

Synthesis of (4S)-methyl 5-((1-methyl-2-oxo-1,2-dihydropyridin-3-yl)carbamoyl)-2,3,4,5-tetrahydro-1,4-methanopyrido[2,3-b][1,4]diazepine-7-carboxylate

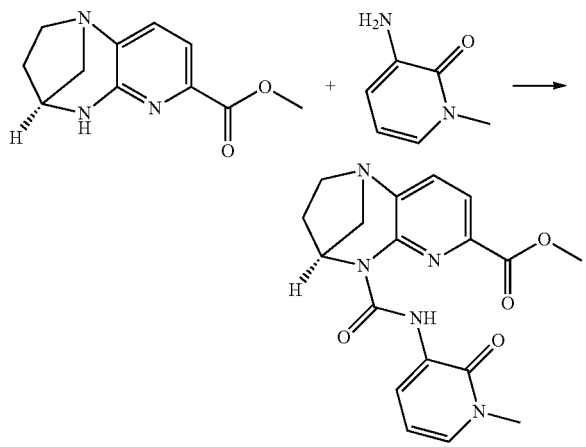

To a solution of (4S)-methyl 2,3,4,5-tetrahydro-1,4-methanopyrido[2,3-b][1,4]diazepine-7-carboxylate (700 mg, 3.19 mmol) in Tetrahydrofuran (THF) (30 mL) was added triphosgene (947 mg, 3.19 mmol) followed by triethylamine (2.67 mL, 19.16 mmol) at rt, the resulting suspension was stirred at rt for 30 min. 3-amino-1-methylpyridin-2(1H)-one (793 mg, 6.39 mmol) was added to the reaction mixture at rt and the resulting suspension was heated to 70° C. for 16 hr. Reaction was monitored by TLC (TLC shows absence of starting material and the new major spot was observed at same Rf to the SM). Reaction mass was diluted with water (30 ml) and aqueous layer was extracted with ethyl acetate (2×30 ml). Organic layer was dried over Na$_2$SO$_4$ filtered and concentrated under reduced pressure to get crude compound as a dark brown liquid. Crude material was purified by column chromatography over silica (100-200 silica gel, 0-15% MeOH in DCM). Fractions containing pure compound were combined and concentrated to afford the desired compound (4S)-methyl 5-((1-methyl-2-oxo-1,2-dihydropyridin-3-yl)carbamoyl)-2,3,4,5-tetrahydro-1,4-methanopyrido[2,3-b][1,4]diazepine-7-carboxylate (550 mg, 1.311 mmol, 41.1% yield) as an off-white solid, LCMS (m/z): 370.15 (M+H)$^+$.

Synthesis of (4S)-5-((1-methyl-2-oxo-1,2-dihydropyridin-3-yl)carbamoyl)-2,3,4,5-tetrahydro-1,4-methanopyrido[2,3-b][1,4]diazepine-7-carboxylic acid

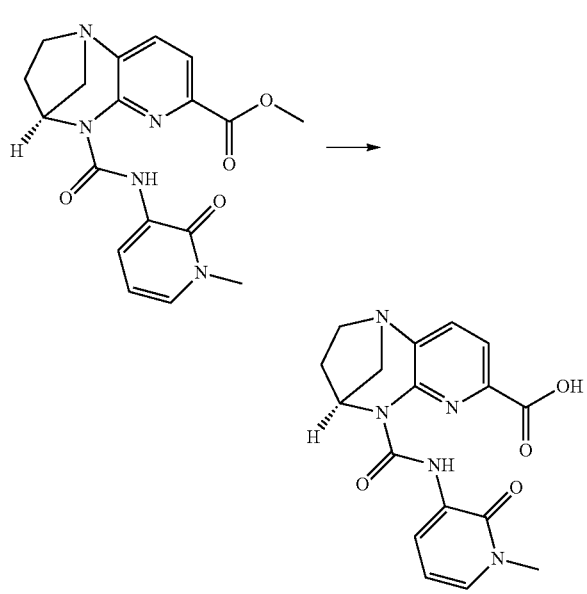

To a solution of (4S)-methyl 5-((1-methyl-2-oxo-1,2-dihydropyridin-3-yl)carbamoyl)-2,3,4,5-tetrahydro-1,4-methanopyrido[2,3-b][1,4]diazepine-7-carboxylate (550 mg, 1.489 mmol) in Tetrahydrofuran (THF) (5 mL), Water (5.00 mL) was added LiOH (107 mg, 4.47 mmol) at rt, the resulting mixture was stirred at rt for 16 hr. After the completion of reaction (monitored by TLC, starting completely consumed and new spot observed), concentrated the reaction mass and dissolved in water. pH of the aqueous layer was adjusted to 4 with 2N HCl to get the solid precipitation, which was filtered and dried to get (4S)-5-((1-methyl-2-oxo-1,2-dihydropyridin-3-yl)carbamoyl)-2,3,4,5-tetrahydro-1,4-methanopyrido[2,3-b][1,4]diazepine-7-carboxylic acid (380 mg, 0.665 mmol, 44.6% yield) as an off-white solid. LCMS (m/z): 356.3 (M+H)$^+$.

Synthesis of (4S)-methyl 5-((1-methyl-6-oxo-1,6-dihydropyrimidin-4-yl)carbamoyl)-2,3,4,5-tetrahydro-1,4-methanopyrido[2,3-b][1,4]diazepine-7-carboxylate

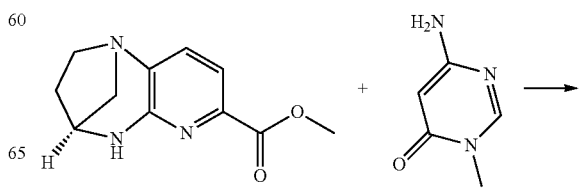

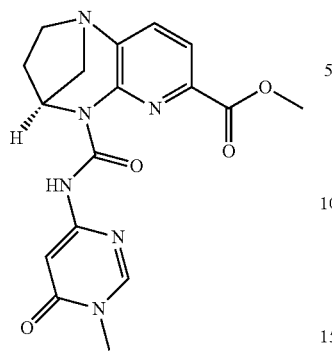

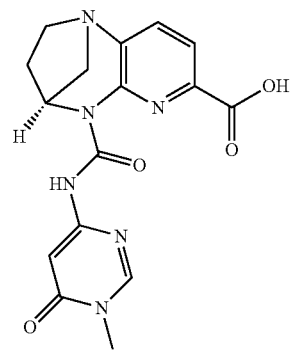

To a solution of (4S)-methyl 2,3,4,5-tetrahydro-1,4-methanopyrido[2,3-b][1,4]diazepine-7-carboxylate (2 g, 9.12 mmol) in Tetrahydrofuran (THF) (80 mL), stirred under Nitrogen at room temperature, was added triphosgene (2.71 g, 9.12 mmol) and DIPEA (4.78 mL, 27.4 mmol). After 30 min at room temperature, was added 6-amino-3-methylpyrimidin-4(3H)-one (1.141 g, 9.12 mmol) in one charge. The reaction mixture was stirred at room temperature for 16 hrs. Progress of the reaction was monitored by TLC. TLC indicated formation of polar spot and some amount of SM. Reaction mass was diluted with 100 ml water, extracted with (2×100 ml) EtOAc. Combined organic layers were washed with 80 ml water, organic layer was dried over $Na_2SO_4$, filtered and concentrated to get crude. Crude material was purified by combiflash using silica gel column (12 g, 5% methanol in DCM). Fractions containing pure compound were combined and concentrated to afford the desired (4S)-methyl 5-((1-methyl-6-oxo-1,6-dihydropyrimidin-4-yl)carbamoyl)-2,3,4,5-tetrahydro-1,4-methanopyrido[2,3-b][1,4]diazepine-7-carboxylate (670 mg, 1.617 mmol, 17.72% yield) as pale brown color solid, LCMS (m/z): 371.05 $(M+H)^+$.

Synthesis of (4S)-5-((1-methyl-6-oxo-1,6-dihydropyrimidin-4-yl)carbamoyl)-2,3,4,5-tetrahydro-1,4-methanopyrido[2,3-b][1,4]diazepine-7-carboxylic acid

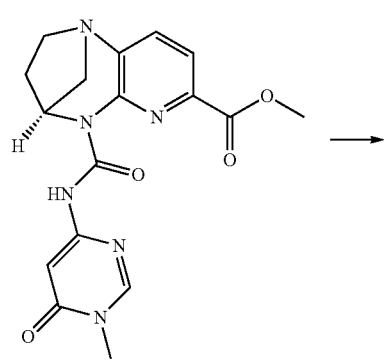

To a suspension of (4S)-methyl 5-((1-methyl-6-oxo-1,6-dihydropyrimidin-4-yl)carbamoyl)-2,3,4,5-tetrahydro-1,4-methanopyrido[2,3-b][1,4]diazepine-7-carboxylate (650 mg, 1.755 mmol), in Tetrahydrofuran (THF) (10 mL) stirred at room temperature, was added a solution of LiOH (105 mg, 4.39 mmol) in Water (5 mL). The resulting reaction mixture was stirred at room temperature for 16 hr. Progress of the reaction was monitored by TLC. TLC indicated formation of polar spot and complete consumption of SM. Reaction mass was concentrated under reduced pressure, added 10 ml of water and washed with 50 ml of EtOAc. Then aqueous was cooled to 0° C. and pH adjusted to 3 with 2N aqueous HCl solution, solid was formed stirred for 15 mins at 0° C. Filtered and dried to get (4S)-5-((1-methyl-6-oxo-1,6-dihydropyrimidin-4-yl)carbamoyl)-2,3,4,5-tetrahydro-1,4-methanopyrido[2,3-b][1,4]diazepine-7-carboxylic acid (400 mg, 1.043 mmol, 59.4% yield) as off white solid, LCMS (m/z): 357.15 $(M+H)^+$.

Synthesis of (4S)-methyl 5-((1-methyl-4-oxo-1,4-dihydropyridin-3-yl)carbamoyl)-2,3,4,5-tetrahydro-1,4-methanopyrido[2,3-b][1,4]diazepine-7-carboxylate

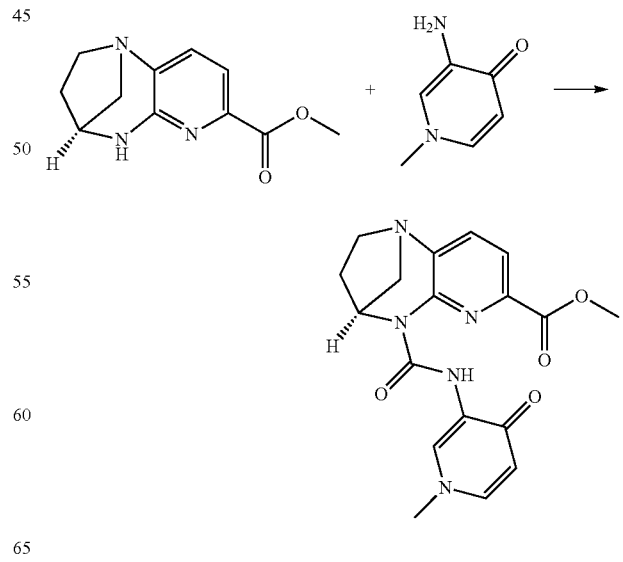

To a stirred solution of (4S)-methyl 2,3,4,5-tetrahydro-1,4-methanopyrido[2,3-b][1,4]diazepine-7-carboxylate (1.5 g, 6.84 mmol) in THF (30 mL) was added TEA (5.72 mL, 41.1 mmol) and triphosgene (2.030 g, 6.84 mmol) under nitrogen at 0° C. Stirred the reaction mixture at 25° C. for 1 hr. After 1 hr added 3-amino-1-methylpyridin-4(1H)-one (1.274 g, 10.26 mmol) to the reaction mass in one charge at 0° C. and heated the RM to 70° C., maintained it at 70° C. for 16 hr. Progress of the reaction was monitored by TLC. Reaction mixture was cooled to room temperature, water (30 mL) was added and extracted with EtOAc (3×40 mL). The combined organic layers were washed with brine solution (100 mL), organic layer was dried over $Na_2SO_4$ and concentrated it to get crude compound. The crude residue was triturated with Diethyl Ether (50 ml) followed by pentane (2×25 ml) to get solid and filter on buchner funnel, dried under vacuum to get compound (4S)-methyl 5-((1-methyl-4-oxo-1,4-dihydro-pyridin-3-yl)carbamoyl)-2,3,4,5-tetrahydro-1,4-methano-pyrido[2,3-b][1,4]diazepine-7-carboxylate (1 g, 2.005 mmol, 29.3% yield) as a pale brown solid, LCMS (m/z): 370.21 $(M+H)^+$.

Synthesis of (4S)-5-((1-methyl-4-oxo-1,4-dihydro-pyridin-3-yl)carbamoyl)-2,3,4,5-tetrahydro-1,4-methanopyrido[2,3-b][1,4]diazepine-7-carboxylic acid

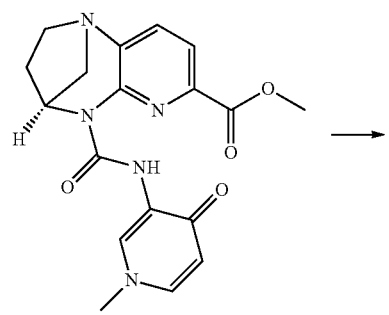

To a stirred solution of (4S)-methyl 5-((1-methyl-4-oxo-1,4-dihydropyridin-3-yl)carbamoyl)-2,3,4,5-tetrahydro-1,4-methanopyrido[2,3-b][1,4]diazepine-7-carboxylate (0.5 g, 1.354 mmol) in THF (30 mL) was added Water (10 mL) and LiOH (0.097 g, 4.06 mmol) at 0° C. and stirred the reaction mixture at 25° C. for 3 hr. THF was concentrated and diluted with water (20 mL) and acidified by adding 2N HCl and resultant solid was filtered to get product, LCMS (m/z): 355.98 $(M+H)^+$.

Synthesis of (4S)-methyl 5-((5-cyanopyridin-2-yl)carbamoyl)-2,3,4,5-tetrahydro-1,4-methanopyrido[2,3-b][1,4]diazepine-7-carboxylate

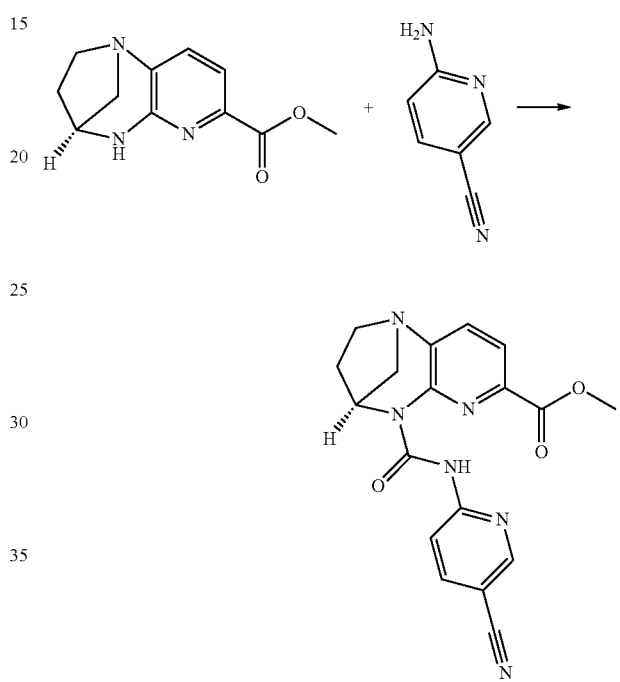

To a stirred solution of (4S)-methyl 2,3,4,5-tetrahydro-1,4-methanopyrido[2,3-b][1,4]diazepine-7-carboxylate (2 g, 9.12 mmol) in Tetrahydrofuran (THF) (20 mL) was added triphosgene (2.71 g, 9.12 mmol) and TEA (3.81 mL, 27.4 mmol) at room temperature under Nitrogen atmosphere. The resulting reaction mixture was stirred at room temperature for 1 hr. To the reaction mixture was added a solution of 6-aminonicotinonitrile (1.630 g, 13.68 mmol) in Tetrahydrofuran (THF) (20.00 mL) at room temperature. The resulting reaction mixture was stirred at 80° C. for 16 hr. Progress of the reaction was monitored by TLC, TLC indicated SM was consumed and non polar spot was formed. Reaction mixture was diluted with water (50 mL), extracted with EtOAc (3×50 mL). Organic layers were combined and washed with brine solution (30 mL), dried over anhydrous $Na_2SO_4$, filtered and concentrated under reduced pressure to get (4S)-methyl 5-((5-cyanopyridin-2-yl)carbamoyl)-2,3,4,5-tetrahydro-1,4-methanopyrido[2,3-b][1,4]diazepine-7-carboxylate (3.0 g, 5.66 mmol, 62.1% yield) as a brown sticky solid, LCMS (m/z): 365.18 $[M+H]^+$.

Synthesis of (4S)-5-((5-cyanopyridin-2-yl)carbamoyl)-2,3,4,5-tetrahydro-1,4-methanopyrido[2,3-b][1,4]diazepine-7-carboxylic acid; and (4S)-5-((5-carbamoylpyridin-2-yl)carbamoyl)-2,3,4,5-tetrahydro-1,4-methanopyrido[2,3-b][1,4]diazepine-7-carboxylic acid

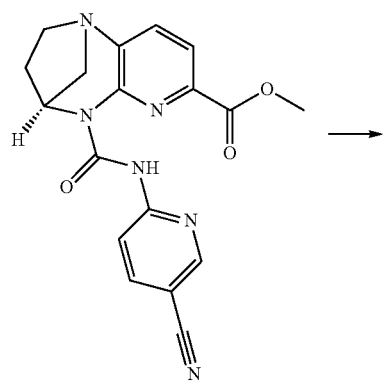

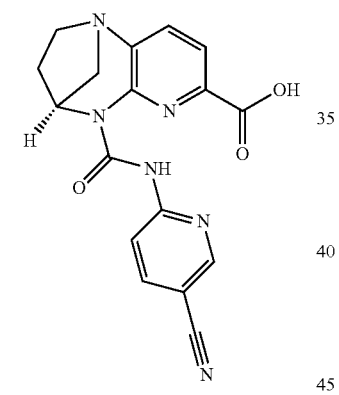

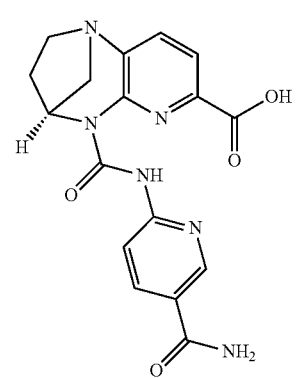

To a stirred solution of (4S)-methyl 5-((5-cyanopyridin-2-yl)carbamoyl-2,3,4,5-tetrahydro-1,4-methanopyrido[2,3-b][1,4]diazepine-7-carboxylate (3.0 g, 8.23 mmol) in Tetrahydrofuran (THF) (30 mL) and Water (10.00 mL) was added lithium hydroxide hydrate (0.691 g, 16.47 mmol). The resulting reaction mixture was stirred at room temperature for 4 hr. Progress of the reaction was monitored by TLC, TLC indicated SM was consumed and polar spots were formed. Reaction mixture was concentrated under vacuum to remove THF and acidified with 2N HCl, solid was precipitate out, solid was filtered and dried well to afford a mixture of (4S)-5-((5-cyanopyridin-2-yl)carbamoyl)-2,3,4,5-tetrahydro-1,4-methanopyrido[2,3-b][1,4]diazepine-7-carboxylic acid (2.5 g, 3.27 mmol, 39.7% yield), LCMS (m/z): 351.17[M+H]$^+$ and (4S)-5-((5-carbamoylpyridin-2-yl)carbamoyl)-2,3,4,5-tetrahydro-1,4-methanopyrido[2,3-b][1,4]diazepine-7-carboxylic acid as a brown solid, LCMS (m/z): 369.20[M+H]$^+$.

Synthesis of (4S)-methyl 5-((6-chloropyrimidin-4-yl)carbamoyl)-2,3,4,5-tetrahydro-1,4-methanopyrido[2,3-b][1,4]diazepine-7-carboxylate

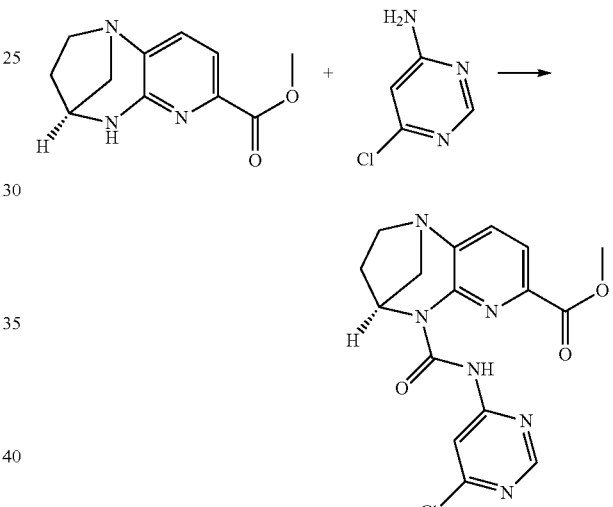

To a suspension of (4S)-methyl 2,3,4,5-tetrahydro-1,4-methanopyrido[2,3-b][1,4]diazepine-7-carboxylate (3 g, 13.68 mmol), triphosgene (2.436 g, 8.21 mmol) and triethylamine (9.54 mL, 68.4 mmol) in Tetrahydrofuran (THF) (30 mL) stirred under nitrogen at room temperature was added solid 6-chloropyrimidin-4-amine (1.950 g, 15.05 mmol). The reaction mixture was stirred at room temperature for 16 hr. Progress of the reaction was monitored by TLC. TLC indicated formation of two no polar spots and complete consumption of SM. Reaction mixture was diluted with cold water (80 ml) and extracted with EtOAc (2×150 ml), separated the organic layer, washed with brine (80 mL), dried over anhydrous Na$_2$SO$_4$, filtered and concentrated under reduced pressure to obtain crude. Crude material was purified by combiflash using silica gel column (40 g, 2% methanol in DCM). Fraction containing pure compound were combined and concentration to afford the desired compound (4S)-methyl 5-((6-chloropyrimidin-4-yl)carbamoyl)-2,3,4,5-tetrahydro-1,4-methanopyrido[2,3-b][1,4]diazepine-7-carboxylate (900 mg, 2.390 mmol, 17.46% yield) as pale yellow solid, LCMS (m/z): 375.05[M+H]$^+$.

145

Synthesis of (4S)-5-((6-chloropyrimidin-4-yl)carbamoyl)-2,3,4,5-tetrahydro-1,4-methanopyrido[2,3-b][1,4]diazepine-7-carboxylic acid

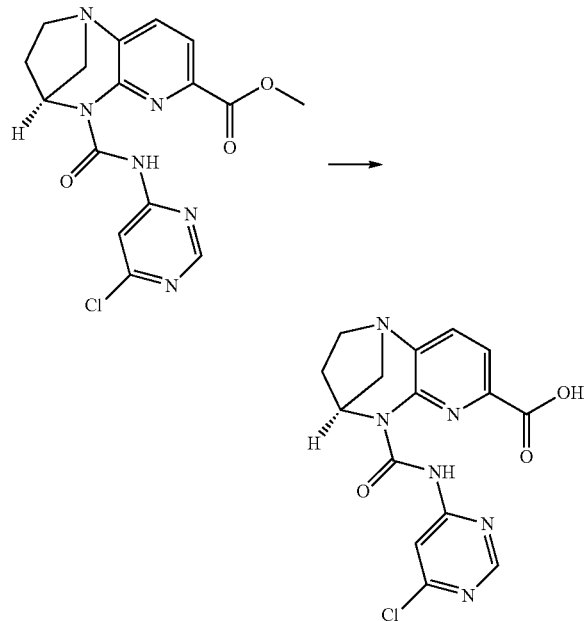

To a stirred solution of (4S)-methyl 5-((6-chloropyrimidin-4-yl)carbamoyl)-2,3,4,5-tetrahydro-1,4-methanopyrido[2,3-b][1,4]diazepine-7-carboxylate (900 mg, 2.401 mmol) in Tetrahydrofuran (THF) (5 mL) was added a solution of lithium hydroxide hydrate (202 mg, 4.80 mmol) in Water (3 mL) at RT, the resulting reaction mass was stirred at room temperature for 16 hr under Nitrogen. Progress of the reaction was monitored by TLC. TLC indicated formation of a polar spot and complete consumption of SM. Reaction mixture was concentrated under reduced pressure, diluted in water (5 mL) and acidified to pH=6 using 1N HCl (4 mL). The resulting solid formed was collected by filtration and dried to give (4S)-5-((6-chloropyrimidin-4-yl)carbamoyl)-2,3,4,5-tetrahydro-1,4-methanopyrido[2,3-b][1,4]diazepine-7-carboxylic acid (600 mg, 1.073 mmol, 44.7% yield) as off white solid, LCMS (m/z): 361.10 [M+H]$^+$.

Synthesis of (4S)—N5-(6-chloropyrimidin-4-yl)-N7-((R)-1,1,1-trifluoropropan-2-yl)-3,4-dihydro-1,4-methanopyrido[2,3-b][1,4]diazepine-5,7(2H)-dicarboxamide

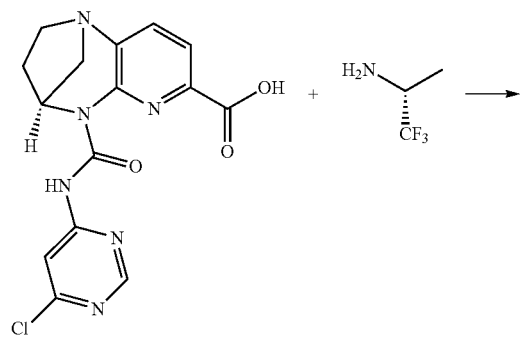

146

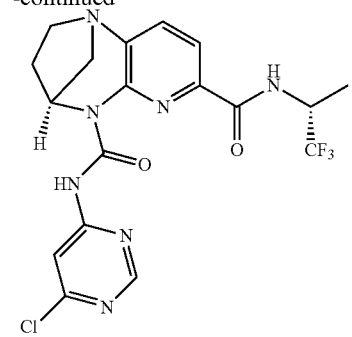

To a stirred suspension of (4S)-5-((6-chloropyrimidin-4-yl)carbamoyl)-2,3,4,5-tetrahydro-1,4-methanopyrido[2,3-b][1,4]diazepine-7-carboxylic acid (1 g, 2.77 mmol) in N,N-Dimethylformamide (DMF) (10 mL) were added HATU (1.581 g, 4.16 mmol) and DIPEA (1.452 mL, 8.32 mmol) at RT, after stirring it for 30 min added (R)-1,1,1-trifluoropropan-2-amine (0.627 g, 5.54 mmol). Stirred the reaction mass at rt for 16 hr. Progress of the reaction was monitored by TLC. TLC indicated starting material was consumed to form new spot with 0.4 R$_f$. Ice cold water (50 mL) added to the reaction mass to get solid. Filtered the solid and dried to get crude compound as Pale yellow solid. The crude compound was triturated with Diethyl ether (20 mL) to afford (4S)—N5-(6-chloropyrimidin-4-yl)-N7-((R)-1,1,1-trifluoropropan-2-yl)-3,4-dihydro-1,4-methanopyrido[2,3-b][1,4]diazepine-5,7(2H)-dicarboxamide (600 mg, 1.183 mmol, 42.7% yield) as Off-white solid, LCMS (m/z): 456.06 (M+H)$^+$.

Synthesis of (4S)—N5-(6-chloropyrimidin-4-yl)-N7-(2,2,2-trifluoroethyl)-3,4-dihydro-1,4-methanopyrido[2,3-b][1,4]diazepine-5,7(2H)-dicarboxamide

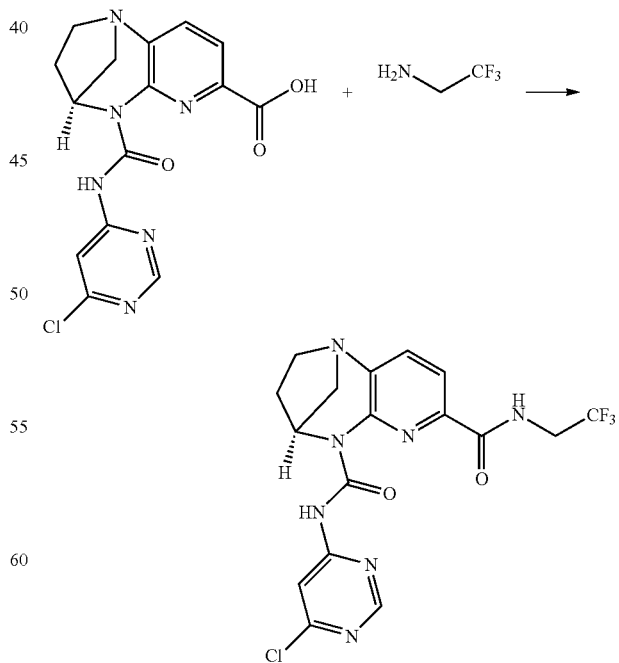

To a stirred suspension of (4S)-5-((6-chloropyrimidin-4-yl)carbamoyl)-2,3,4,5-tetrahydro-1,4-methanopyrido[2,3-b]

[1,4]diazepine-7-carboxylic acid (550 mg, 1.525 mmol) in Dichloromethane (DCM) (5 mL) were added 1-methyl-1H-imidazole (125 mg, 1.525 mmol) and methanesulfonyl chloride (0.119 mL, 1.525 mmol) at rt, after stirring it for 30 min added 2,2,2-trifluoroethanamine hydrochloride (413 mg, 3.05 mmol) and stirred at 50° C. for 3 hr under Nitrogen. Progress of the reaction was monitored by TLC. TLC indicated formation of a non-polar spot and complete consumption of SM. Reaction mixture was poured in cold water (20 ml), excreted with DCM (2×50 ml), separated the organic layer washed with brine (30 mL) dried over anhydrous $Na_2SO_4$, filtered and concentrated under reduced pressure to obtain crude. The crude product was triturated with CAN (5 mL) and dried to give (4S)—N5-(6-chloropyrimidin-4-yl)-N7-(2,2,2-trifluoroethyl)-3,4-dihydro-1,4-methanopyrido[2,3-b][1,4]diazepine-5,7(2H)-dicarboxamide (400 mg, 0.879 mmol, 57.6% yield) as pale yellow solid, LCMS (m/z): 442.15 [M+H]+.

Synthesis of (4S)-methyl 5-((5-bromopyridin-2-yl)carbamoyl)-2,3,4,5-tetrahydro-1,4-methanopyrido[2,3-b][1,4]diazepine-7-carboxylate with cold water (80 ml) and extracted with EtOAc (2×30 ml). Separated the organic layer washed with brine (30 mL) dried over anhydrous $Na_2SO_4$, filtered and concentrated under reduced pressure to obtain crude. Crude material was purified by column chromatography over silica gel (100-200 mesh, 3% MeOH in DCM). Fractions containing pure compound were combined and concentrated to afford the desired compound (4S)-methyl 5-((5-bromopyridin-2-yl) carbamoyl)-2,3,4,5-tetrahydro-1,4-methanopyrido[2,3-b][1,4]diazepine-7-carboxylate (2.650 g, 6.00 mmol, 82% yield) as pale pink solid, LCMS (m/z): 418.02 [M+H]+.

Synthesis of (4S)-5-((5-bromopyridin-2-yl)carbamoyl)-2,3,4,5-tetrahydro-1,4-methanopyrido[2,3-b][1,4]diazepine-7-carboxylic acid

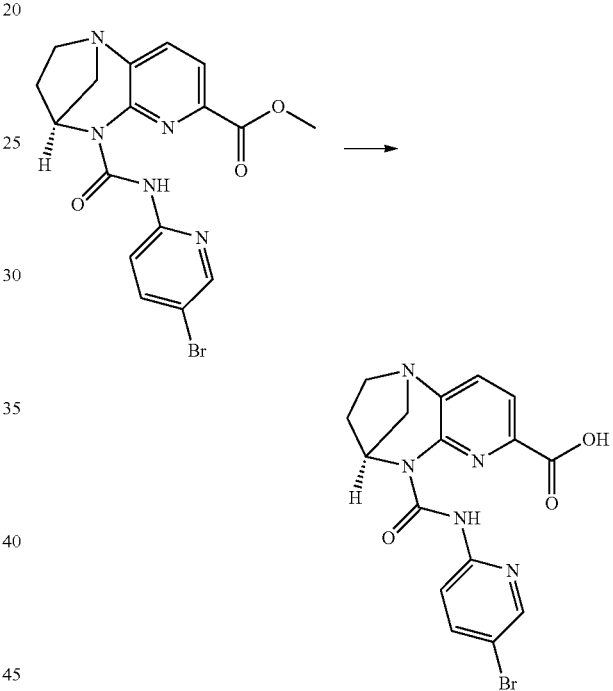

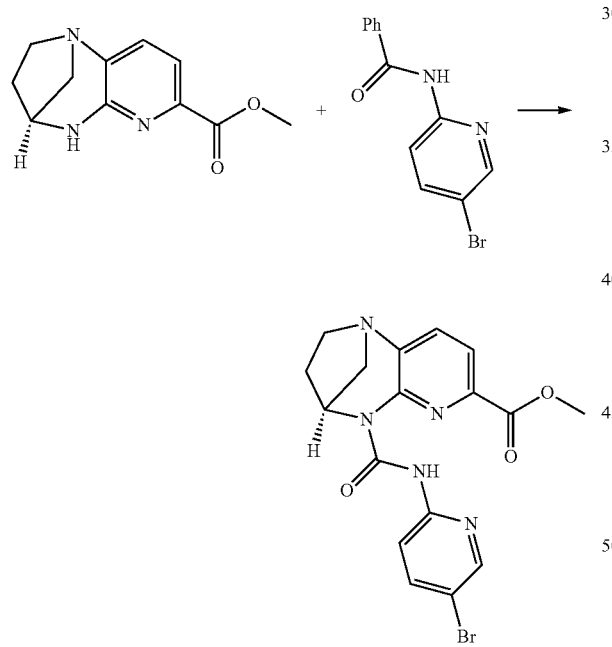

To a solution of (4S)-methyl 2,3,4,5-tetrahydro-1,4-methanopyrido[2,3-b][1,4]diazepine-7-carboxylate (1.6 g, 7.30 mmol) in Tetrahydrofuran (THF) (10 mL) were added phenyl (5-bromopyridin-2-yl)carbamate (3.21 g, 10.95 mmol) and DMAP (2.229 g, 18.24 mmol) at room temperature, the resulting reaction mass was stirred at 70° C. for 16 hr in a seal tube. Progress of the reaction was monitored by TLC. TLC indicated formation of a non polar spot and complete consumption of SM. Reaction mixture was diluted ((4S)-methyl 5-((5-bromopyridin-2-yl)carbamoyl)-2,3,4,5-tetrahydro-1,4-methanopyrido[2,3-b][1,4]diazepine-7-carboxylate (2.60 g, 6.22 mmol) was dissolved in Tetrahydrofuran (THF) (10 mL), Methanol (10.00 mL) and Water (5.00 mL) at 0° C., stirred for 10 min under nitrogen. Then added LiOH (0.595 g, 24.87 mmol) to stirred solution at 0° C. as one lot. The resulting reaction mass was stirred at room temperature for 16 hr. Progress of the reaction was monitored by TLC. TLC indicated formation of polar spot and completed SM. Reaction mixture was concentrated half volume under reduced pressure then diluted with cold water (10 ml) and neutralized with saturated citric acid. during the process pale brown solid was obtained and washed with diethyl ether (30 mL) then dried under vacuum to get desired compound (4S)-5-((5-bromopyridin-2-yl)carbamoyl)-2,3,4,5-tetrahydro-1,4-methanopyrido[2,3-b][1,4]diazepine-7-carboxylic acid (2.0 g, 4.42 mmol, 71.1% yield) as pale brown solid, LCMS (m/z): 404.13 [M+H]+.

Synthesis of (4S)—N5-(5-bromopyridin-2-yl)-N7-(2,2,2-trifluoroethyl)-3,4-dihydro-1,4-methanopyrido[2,3-b][1,4]diazepine-5,7(2H)-dicarboxamide Synthesis of (4S)—N5-(5-(prop-1-en-2-yl)pyridin-2-yl)-N7-(2,2,2-trifluoroethyl)-3,4-dihydro-1,4-methanopyrido[2,3-b][1,4]diazepine-5,7(2H)-dicarboxamide

N37134-28

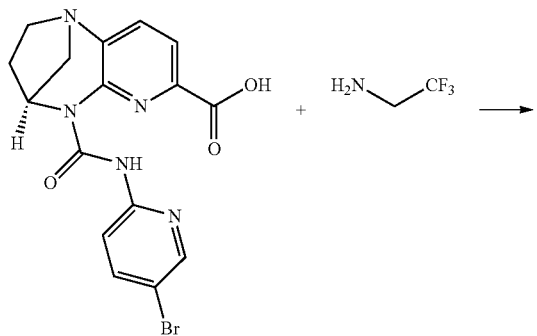

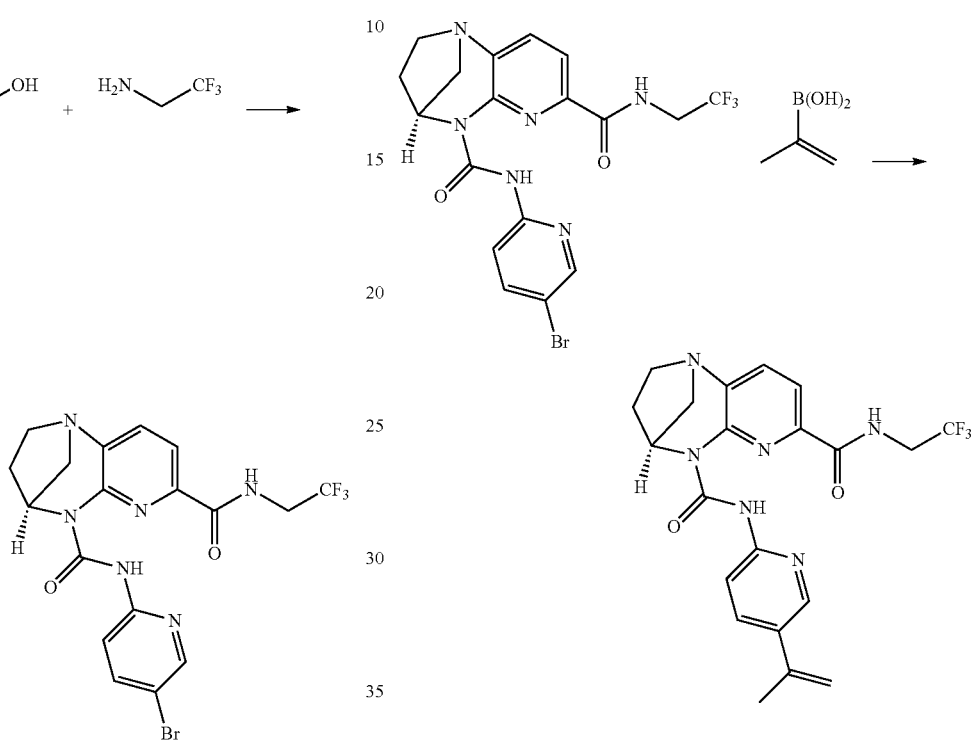

(4S)-5-((5-bromopyridin-2-yl)carbamoyl)-2,3,4,5-tetrahydro-1,4-methanopyrido[2,3-b][1,4]diazepine-7-carboxylic acid (1.94 g, 4.80 mmol), DIPEA (0.838 mL, 4.80 mmol) were stirred in N,N-Dimethylformamide (DMF) (10 mL) at 0° C. for 5 min. Then, added HATU (3.65 g, 9.60 mmol) and stirred for 20 min at 0° C. Then added 2,2,2-trifluoroethanamine (0.475 g, 4.80 mmol) in one portion under nitrogen. The resulting reaction mixture was stirred at room temperature for 16 hr. Progress of the reaction was monitored by TLC. TLC indicated consumption of starting material and formation of non polar spot. The reaction mass was diluted with water, then extracted with ethyl acetate (15 mL). The organic layer was washed with brine (10 mL), dried over Na$_2$SO$_4$, filtered, and concentrated under reduced pressure to afford crude mass (1.5 g). The crude compound was purified by using 100-200 meshed silica gel with eluent (2% MeOH in DCM). The compound containing pure fractions were collected and concentrated under reduced pressure to afford (4S)—N5-(5-bromopyridin-2-yl)-N7-(2,2,2-trifluoroethyl)-3,4-dihydro-1,4-methanopyrido[2,3-b][1,4]diazepine-5,7(2H)-dicarboxamide (900 mg, 1.846 mmol, 38.5% yield) as off white solid, LCMS (m/z): 485.06 [M+H]$^+$.

(4S)—N5-(5-bromopyridin-2-yl)-N7-(2,2,2-trifluoroethyl)-3,4-dihydro-1,4-methanopyrido[2,3-b][1,4]diazepine-5,7(2H)-dicarboxamide (0.7 g, 1.443 mmol) was dissolved in 1,4-Dioxane (5 mL) and Water (1 mL) stirred the solution with degassed under nitrogen for 10 min. Then, added potassium phosphate (0.306 g, 1.443 mmol) and degassed for 5 min and purged with argon. Then, prop-1-en-2-ylboronic acid (0.124 g, 1.443 mmol) at room temperature under argon condition, through out the process degassed the solution. The reaction mass was degassed for 15 min with argon, then added PdCl$_2$(dppf)-CH$_2$Cl$_2$ adduct (1.178 g, 1.443 mmol) and degassed with argon, the resulting reaction mass was stirred for 30 min under degassed with nitrogen. The resulting reaction mixture was stirred at 80° C. for 16 hr. Progress of the reaction was monitored by TLC. TLC indicated formation of a multiple spots along with traces of SM. Reaction mixture was cooled to room temperature, diluted with water (40 ml) and extracted with EtOAc (2×80 ml). The combined organic layer was washed with brine (50 mL), dried over anhydrous Na$_2$SO$_4$, filtered and concentrated under reduced pressure to obtained crude as brown viscous oil (900 mg). Purification: The crude compound was purified by using FCC 100-200 meshed silica gel by eluting with 5% MeOH in DCM. The desired pure fractions were collected and concentrated under reduced pressure to afford (4S)—N5-(5-(prop-1-en-2-yl)pyridin-2-yl)-N7-(2,2,2-trifluoroethyl)-3,4-dihydro-1,4-methanopyrido[2,3-b][1,4]diazepine-5,7(2H)-dicarboxamide (400 mg, 0.822 mmol, 57.0% yield) as off white solid, LCMS (m/z): 447.00 [M+H]$^+$.

151

Synthesis of (4S)-methyl 5-((5-bromo-1-methyl-2-oxo-1,2-dihydropyridin-3-yl)carbamoyl)-2,3,4,5-tetrahydro-1,4-methanopyrido[2,3-b][1,4]diazepine-7-carboxylate

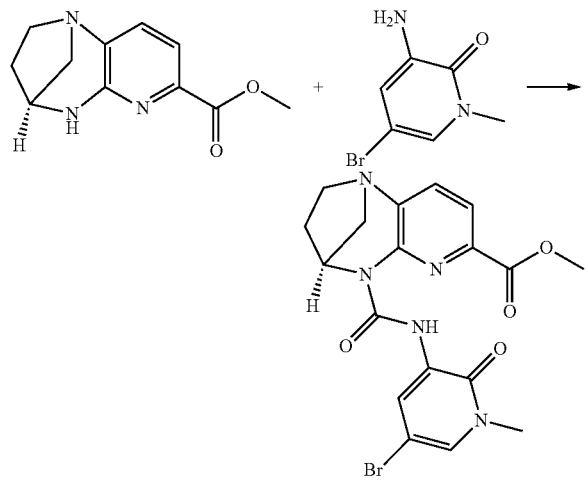

To a stirred solution of (4S)-methyl 2,3,4,5-tetrahydro-1,4-methanopyrido[2,3-b][1,4]diazepine-7-carboxylate (1.5 g, 6.84 mmol) in Tetrahydrofuran (THF) (30 mL) was added TEA (4.77 mL, 34.2 mmol) and triphosgene (2.030 g, 6.84 mmol) at room temperature under Nitrogen atmosphere. The resulting reaction mixture was stirred at room temperature for 1 hr. A solution of 3-amino-5-bromo-1-methylpyridin-2 (1H)-one (1.389 g, 6.84 mmol) in Tetrahydrofuran (THF) (10 mL) was added to the reaction mixture and stirred at 70° C. for 16 hr. Progress of the reaction was monitored by TLC. Reaction mixture was diluted with water (50 mL), extracted with EtOAc (3×50 mL), organic layers were combined and dried over anhydrous Na$_2$SO$_4$, filtered and concentrated under vacuum to afford crude compound. The crude was purified by column chromatography (100-200 mesh silica gel, eluted with 2% MeOH in DCM) to afford (4S)-methyl 5-((5-bromo-1-methyl-2-oxo-1,2-dihydropyridin-3-yl)carbamoyl)-2,3,4,5-tetrahydro-1,4-methanopyrido[2,3-b][1,4]diazepine-7-carboxylate (2.2 g, 2.72 mmol, 39.7% yield) black sticky crude compound, LCMS (m/z): 449.96[M+2H]$^+$ Synthesis of (4S)-5-((5-bromo-1-methyl-2-oxo-1,2-dihydropyridin-3-yl)carbamoyl)-2,3,4,5-tetrahydro-1,4-methanopyrido[2,3-b][1,4]diazepine-7-carboxylic acid

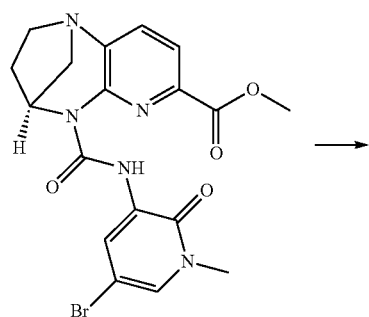

152

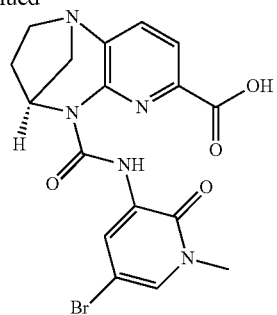

To a stirred solution of (4S)-methyl 5-((5-bromo-1-methyl-2-oxo-1,2-dihydropyridin-3-yl)carbamoyl)-2,3,4,5-tetrahydro-1,4-methanopyrido[2,3-b][1,4]diazepine-7-carboxylate (2.2 g, 4.91 mmol) in Tetrahydrofuran (THF) (30 mL) and Water (10 mL) was added lithium hydroxide hydrate (0.206 g, 4.91 mmol). The resulting reaction mixture was stirred at room temperature for 6 hr. Progress of the reaction was monitored by TLC. Reaction mixture was diluted with water (30 mL), extracted with EtOAc (2×30 mL). Aqueous layer was acidified with 1N HCl, Off-white solid was precipitate out. Solid was filtered and dried well to afford (4S)-5-((5-bromo-1-methyl-2-oxo-1,2-dihydropyridin-3-yl)carbamoyl)-2,3,4,5-tetrahydro-1,4-methanopyrido[2,3-b][1,4]diazepine-7-carboxylic acid (1.0 g, 2.152 mmol, 43.8% yield) as an pale brown solid, LCMS (m/z): 433.9 [M+H]$^+$.

Synthesis of (4S)—N5-(5-bromo-1-methyl-2-oxo-1,2-dihydropyridin-3-yl)-N7-((R)-1,1,1-trifluoropropan-2-yl)-3,4-dihydro-1,4-methanopyrido[2,3-b][1,4]diazepine-5,7(2H)-dicarboxamide

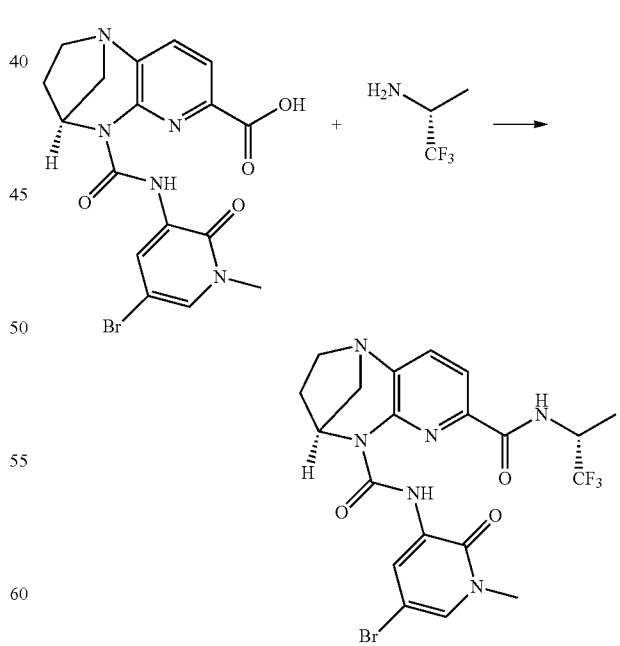

To a stirred solution of (4S)-5-((5-bromo-1-methyl-2-oxo-1,2-dihydropyridin-3-yl)carbamoyl)-2,3,4,5-tetrahydro-1,4-methanopyrido[2,3-b][1,4]diazepine-7-carboxylic acid (950 mg, 2.188 mmol) in Pyridine (20 mL) was added EDC (839 mg, 4.38 mmol) at 0° C. under Nitrogen atmosphere. The resulting reaction mixture was stirred at 0° C. for 30 min. To the reaction mixture was added (R)-1,1,1-trifluoropropan-2-amine hydrochloride (654 mg, 4.38 mmol) and stirred at room temperature for 18 hr. Progress of the reaction was monitored by TLC, TLC indicated SM was consumed and non-polar spot was formed.

Reaction mixture was concentrated under vacuum to get crude compound, crude was diluted with ice cold water (50 mL) and stirred for 10 min, solid was precipitate out. The solid was filtered and dried well to afford (4S)—N5-(5-bromo-1-methyl-2-oxo-1,2-dihydropyridin-3-yl)-N7-((R)-1,1,1-trifluoropropan-2-yl)-3,4-dihydro-1,4-methanopyrido[2,3-b][1,4]diazepine-5,7(2H)-dicarboxamide (900 mg, 1.663 mmol, 76% yield) as a pale brown solid, LCMS (m/z): 528.90 [M+H]⁺.

Synthesis of (4S)-methyl 5-((4-(((R)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylate

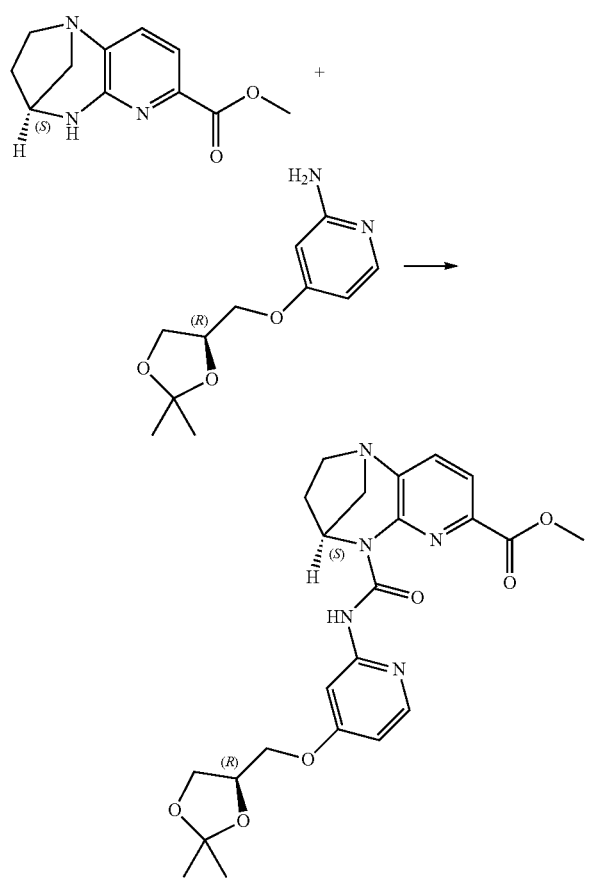

(4S)-methyl 2,3,4,5-tetrahydro-1,4-methanopyrido[2,3-b][1,4]diazepine-7-carboxylate (2.25 g, 10.26 mmol), TEA (7.15 mL, 51.3 mmol) were taken in Tetrahydrofuran (THF) (40 mL) at 0° C., the resulting yellow solution was stirred for 10 min at room temperature. Then added triphosgene (3.05 g, 10.26 mmol) in one portion at 0° C. The resulting yellow suspension was stirred for 45 min at room temperature. The THF (10 mL) solution of (R)-4-((2,2-dimethyl-1,3-dioxolan-4-yl)methoxy)pyridin-2-amine (2.301 g, 10.26 mmol) was added to the above yellow suspension at 0° C. over a period of 2 min. The resulting yellow suspension was heated to 70° C. for 24 hr. The reaction progress was monitored by TLC 5% MeOH in DCM, TLC indicated formation of multiple spots and completion of SM after 24 h. Reaction mixture was cooled to room temperature, then diluted with water (20 mL), extracted with EtOAc (2×40 mL), separated the organic layer washed with brine (20 mL) dried over anhydrous Na₂SO₄, filtered and concentrated under reduced pressure to obtained crude. The crude material was purified by combiflash using silica gel column (12 g, 5% MeOH in DCM). Fraction containing pure compound were combined and concentration to afford the desired compound (4S)-methyl 5-((4-(((R)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylate (3.2 g, 6.09 mmol, 59.4% yield) as yellow solid. LCMS (m/z): 470.19 [M+H]⁺.

Synthesis of (4S)-5-((4-(((R)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid

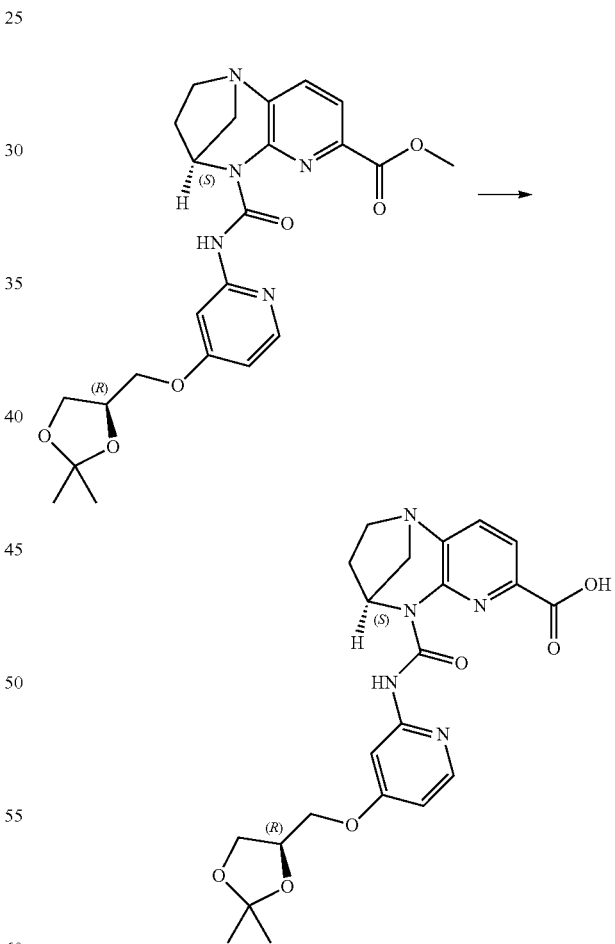

To a stirred suspension of (4S)-methyl 5-((4-(((R)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylate (2.25 g, 4.79 mmol) in Tetrahydrofuran (THF) (10.00 mL), Methanol (10.00 mL) and Water (10 mL) stirred under nitrogen at 0° C. was added LiOH (0.574 g, 23.96 mmol) in water (3 mL) over a period of 2 min. The resulting reaction mixture was stirred at room temperature for 16 hr. Progress of the reaction was monitored by TLC. TLC indicated consumption of starting material and formation of new polar spot. The reaction mass was concentrated under reduced pressure then diluted with 6 mL water, then neutralized with saturated citric acid to brought pH neutral. During the process, off white precipitated, filtered under vacuum and dried afford white solid which was triturated with diethyl ether (20 mL×2) to afford (4S)-5-((4-(((R)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid (1.8 g, 3.93 mmol, 82% yield) as off white solid, LCMS (m/z): 456.18 [M+H]$^+$.

Synthesis of (4S)—N5-(4-(((R)-2,2-dimethyl-1,3-dioxolan-4-yl)methoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide mmol). After stirring the reaction mixture for 10 min at RT, added (R)-1,1,1-trifluoropropan-2-amine (199 mg, 1.756 mmol) under nitrogen. The resulting reaction mixture was stirred at room temperature for 16 hr. Progress of the reaction was monitored by TLC. TLC indicated formation of a non-polar spot and completed consumption of SM and polar spot. Reaction mixture was poured in ice cold water (20 ml), pale brown solid was precipitated, filtered and vacuum to afford the desired compound (4S)—N5-(4-(((R)-2,2-dimethyl-1,3-dioxolan-4-yl)methoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (300 mg, 0.541 mmol, 30.8% yield) as pale brown solid, LCMS (m/z): 551.11 [M+H]$^+$.

Synthesis of (4S)-methyl 5-((6-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylate

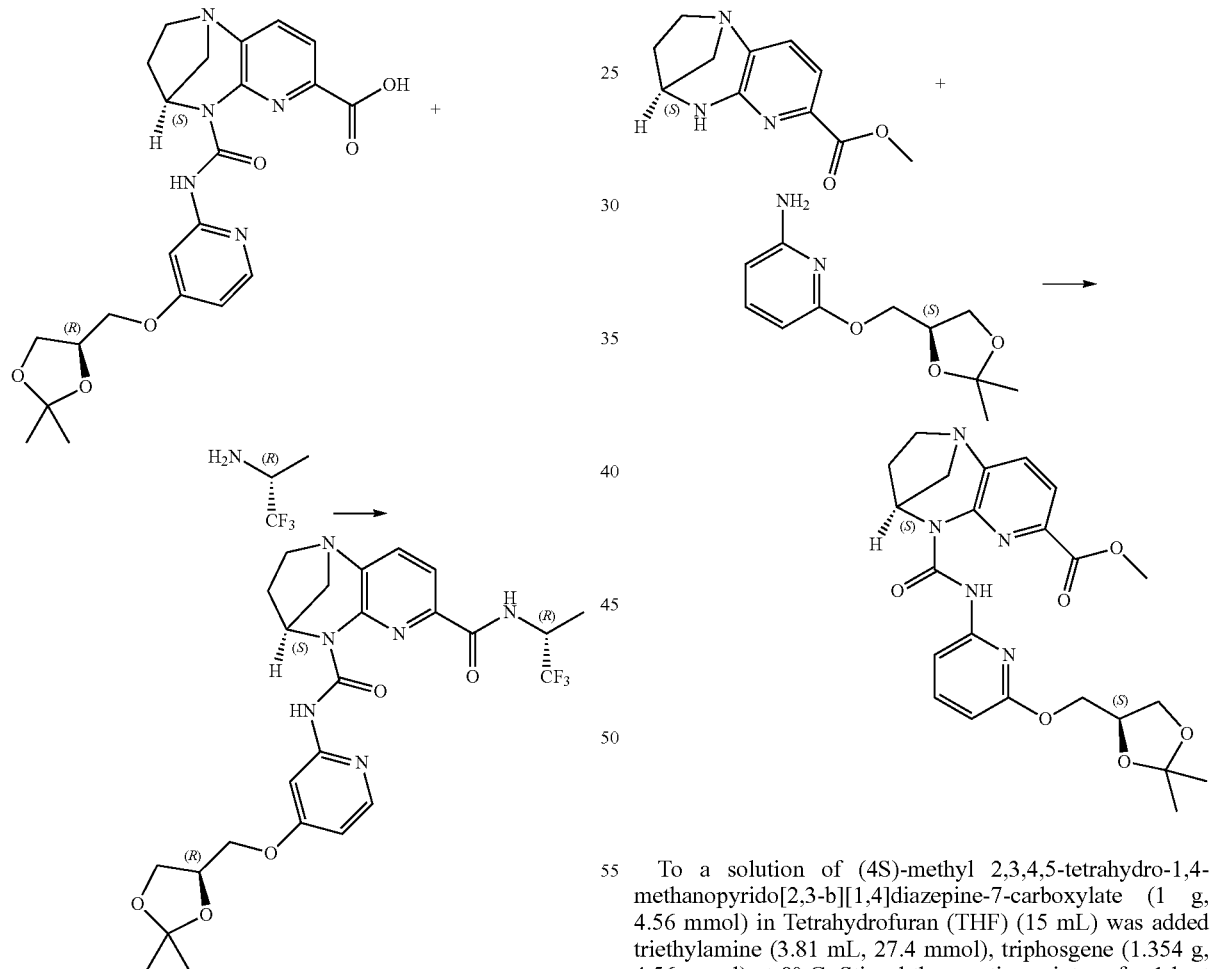

(4S)-5-((4-(((R)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid (800 mg, 1.756 mmol) was dissolved in N,N-Dimethylformamide (DMF) (10 mL), the resulting yellow solution was stirred under nitrogen at 0° C. for 10 min. Then added TEA (0.245 mL, 1.756 mmol) followed by HATU (1336 mg, 3.51

To a solution of (4S)-methyl 2,3,4,5-tetrahydro-1,4-methanopyrido[2,3-b][1,4]diazepine-7-carboxylate (1 g, 4.56 mmol) in Tetrahydrofuran (THF) (15 mL) was added triethylamine (3.81 mL, 27.4 mmol), triphosgene (1.354 g, 4.56 mmol) at 0° C. Stirred the reaction mixture for 1 h at room temp and (S)-6-((2,2-dimethyl-1,3-dioxolan-4-yl)methoxy)pyridin-2-amine (1.227 g, 5.47 mmol) was added, stirred the reaction mixture at 90° C. for 16 hr. The Reaction was monitored by TLC. Reaction mixture was cooled to RT, diluted with water and extracted with ethyl acetate (2×70 mL). Combined organics were washed with brine solution (50 mL), dried over Na$_2$SO$_4$, filtered and concentrated to get the crude compound. The crude product was purified by column chromatography (100-200 silica gel) and product was eluted with 80% EtOAc/PetEther. Collected fractions were evaporated to get product (4S)-methyl 5-((6-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylate (1.2 g, 1.820 mmol, 39.9% yield) as Brown liquid. LCMS (m/z): 469.9 [M+H]+.

Synthesis of (4S)-5-((6-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid

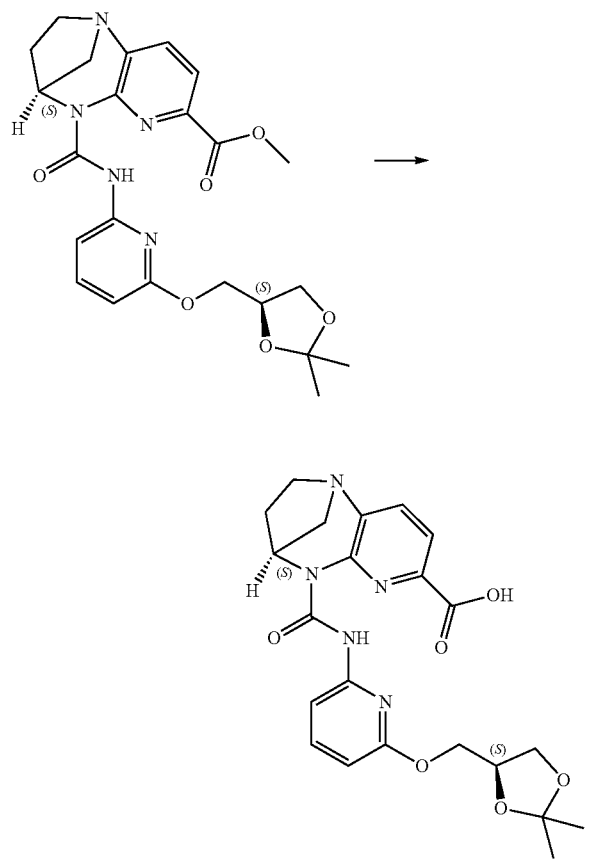

To a solution of (4S)-methyl 5-((6-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylate (1.2 g, 2.56 mmol) in Tetrahydrofuran (THF) (25 mL) and Water (25.00 mL) was added lithium hydroxide monohydrate (0.161 g, 3.83 mmol) the resulting reaction mature was stirred at 25° C. for 5 hr. Reaction mixture was concentrated under reduced pressure to afford crude compound. Crude directly used for next step, LCMS (m/z): 455.9 [M+H]+.

Synthesis of (4S)—N5-(6-(((S)-2,2-dimethyl-1,3-dioxolan-4-yl)methoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

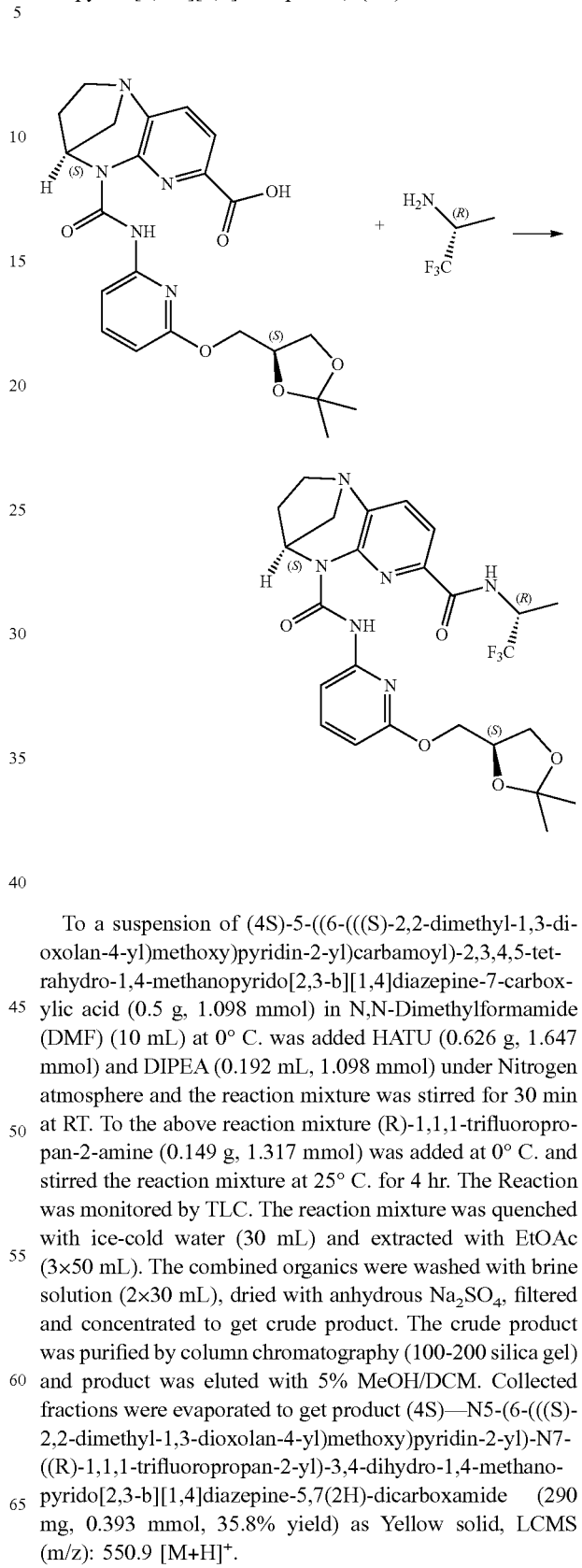

To a suspension of (4S)-5-((6-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid (0.5 g, 1.098 mmol) in N,N-Dimethylformamide (DMF) (10 mL) at 0° C. was added HATU (0.626 g, 1.647 mmol) and DIPEA (0.192 mL, 1.098 mmol) under Nitrogen atmosphere and the reaction mixture was stirred for 30 min at RT. To the above reaction mixture (R)-1,1,1-trifluoropropan-2-amine (0.149 g, 1.317 mmol) was added at 0° C. and stirred the reaction mixture at 25° C. for 4 hr. The Reaction was monitored by TLC. The reaction mixture was quenched with ice-cold water (30 mL) and extracted with EtOAc (3×50 mL). The combined organics were washed with brine solution (2×30 mL), dried with anhydrous Na2SO4, filtered and concentrated to get crude product. The crude product was purified by column chromatography (100-200 silica gel) and product was eluted with 5% MeOH/DCM. Collected fractions were evaporated to get product (4S)—N5-(6-(((S)-2,2-dimethyl-1,3-dioxolan-4-yl)methoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (290 mg, 0.393 mmol, 35.8% yield) as Yellow solid, LCMS (m/z): 550.9 [M+H]+.

159

Synthesis of (4S)-methyl 5-((5-(((R)-2,2-dimethyl-1,3-dioxolan-4-yl)methoxy)pyrazin-2-yl)carbamoyl)-2,3,4,5-tetrahydro-1,4-methanopyrido[2,3-b][1,4]diazepine-7-carboxylate

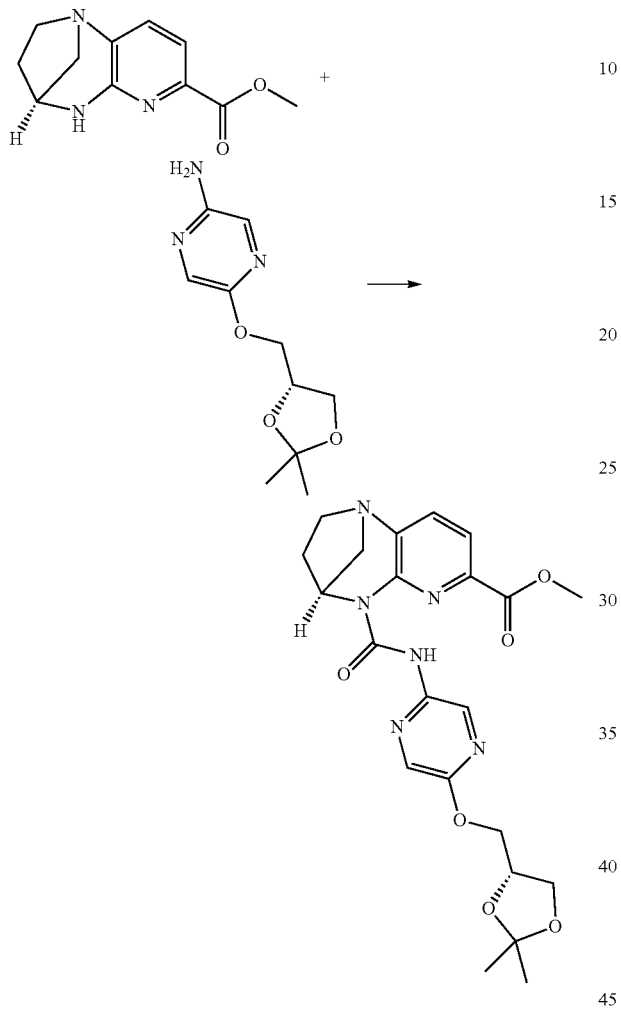

To a stirred solution of (4S)-methyl 2,3,4,5-tetrahydro-1,4-methanopyrido[2,3-b][1,4]diazepine-7-carboxylate (1.0 g, 4.56 mmol) in Tetrahydrofuran (THF) (20 mL) was added triphosgene (1.083 g, 3.65 mmol) and TEA (3.18 mL, 22.81 mmol) under Nitrogen atmosphere. Resulting reaction mixture was stirred at room temperature for 1 hr. To the reaction mixture was added a solution of (R)-5-((2,2-dimethyl-1,3-dioxolan-4-yl)methoxy)pyrazin-2-amine (1.541 g, 6.84 mmol) in Tetrahydrofuran (THF) (10 mL). Resulting reaction mixture was stirred at 70° C. for 18 hr. Progress of the reaction was monitored by TLC. TLC indicated SM was consumed and non polar spot was formed. Reaction mixture was diluted with water (30 mL), extracted with EtOAc (3×30 mL). Organic layers were combined and washed with water (20 mL), brine solution (20 mL), dried over anhydrous $Na_2SO_4$. Organic layer was filtered and concentrated under reduced pressure to get brown sticky crude compound which was purified by column chromatography using 100-200 mesh silica gel and eluted the compound with 3% MeOH in DCM, pure fractions were collected and evaporated under reduced pressure to afford (4S)-methyl 5-((5-(((R)-2,2-dimethyl-1,3-dioxolan-4-yl)methoxy)pyrazin-2-yl)carbamoyl)-2,3,4,5-tetrahydro-1,4-methanopyrido[2,3-b][1,4]diazepine-7-carboxylate (1.65 g, 3.44 mmol, 76% yield) as a yellow solid, LCMS (m/z): 471.14 $[M+H]^+$ Synthesis of (4S)-5-((5-(((R)-2,2-dimethyl-1,3-dioxolan-4-yl)methoxy)pyrazin-2-yl)carbamoyl)-2,3,4,5-tetrahydro-1,4-methanopyrido[2,3-b][1,4]diazepine-7-carboxylic acid

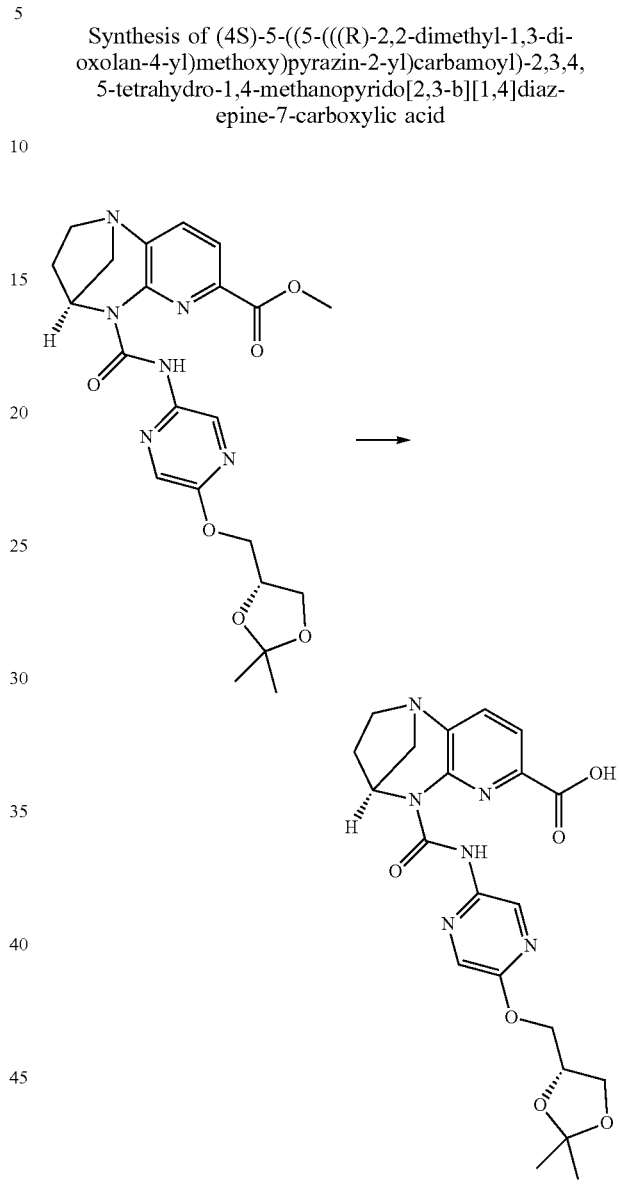

To a stirred solution of (4S)-methyl 5-((5-(((R)-2,2-dimethyl-1,3-dioxolan-4-yl)methoxy)pyrazin-2-yl)carbamoyl)-2,3,4,5-tetrahydro-1,4-methanopyrido[2,3-b][1,4]diazepine-7-carboxylate (1.4 g, 2.98 mmol) in Tetrahydrofuran (THF) (30 mL) and Water (10 mL) was added lithium hydroxide hydrate (0.250 g, 5.95 mmol). The resulting reaction mixture was stirred at room temperature for 4 hr. Progress of the reaction was monitored by TLC, TLC indicates SM was consumed and Polar spot was formed. Reaction mixture was concentrated under reduced pressure to get crude compound which was acidified with saturated citric acid solution, solid was precipitate out which was filtered and dried well to afford (4S)-5-((5-(((R)-2,2-dimethyl-1,3-dioxolan-4-yl)methoxy)pyrazin-2-yl)carbamoyl)-2,3,4,5-tetrahydro-1,4-methanopyrido[2,3-b][1,4]diazepine-7-carboxylic acid (1.2 g, 2.437 mmol, 82% yield) as an Off-white solid, LCMS (m/z): 457.06 $[M+H]^+$.

161

Synthesis of (4S)—N5-(5-(((R)-2,2-dimethyl-1,3-dioxolan-4-yl)methoxy)pyrazin-2-yl)-N7-(2,2,2-trifluoroethyl)-3,4-dihydro-1,4-methanopyrido[2,3-b][1,4]diazepine-5,7(2H)-dicarboxamide

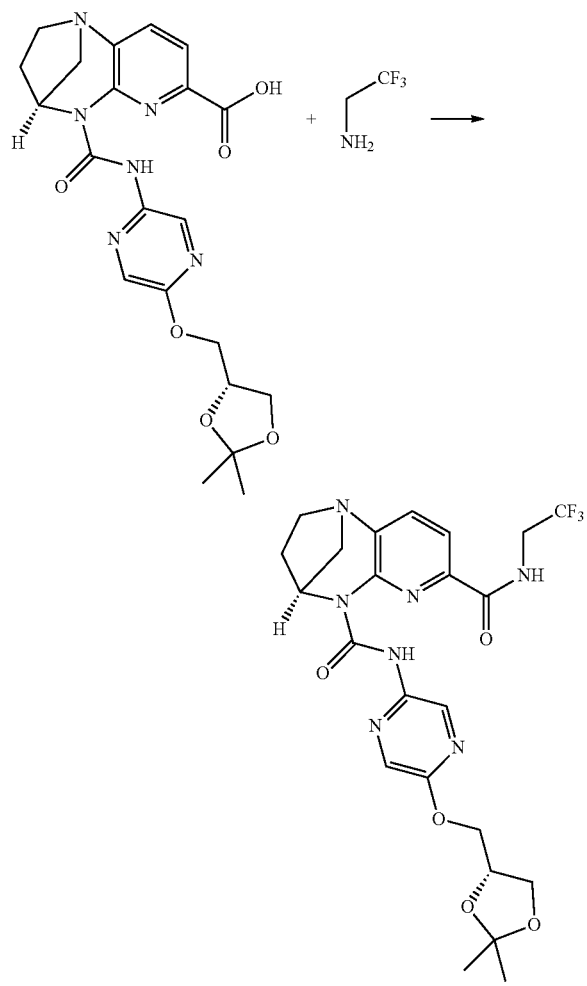

To a stirred solution of (4S)-5-((5-(((R)-2,2-dimethyl-1,3-dioxolan-4-yl)methoxy)pyrazin-2-yl)carbamoyl)-2,3,4,5-tetrahydro-1,4-methanopyrido[2,3-b][1,4]diazepine-7-carboxylic acid (1.2 g, 2.63 mmol) in N,N-Dimethylformamide (DMF) (20 mL) was added HATU (1.499 g, 3.94 mmol) and TEA (1.099 mL, 7.89 mmol) at 0° C., reaction mixture was stirred at 0° C. for 10 min. To the resulting reaction mixture was added 2,2,2-trifluoroethanamine (0.391 g, 3.94 mmol) at 0° C. and stirred at room temperature for 2 hr. Progress of the reaction was monitored by TLC, TLC indicated SM was consumed and non polar spot was formed. Reaction mixture was diluted with water (50 mL), extracted with EtOAc (3×50 mL). Organic layers were combined and washed with water (30 mL), brine solution (30 mL), dried over anhydrous Na$_2$SO$_4$. Organic layer was filtered and concentrated under reduced pressure to get crude compound which was purified by column chromatography using 100-200 mesh silica gel and eluted the desired compound with 3% MeOH in DCM, pure fractions were collected and evaporated under reduced pressure to afford (4S)—N5-(5-(((R)-2,2-dimethyl-1,3-dioxolan-4-yl)methoxy)pyrazin-2-yl)-N7-(2,2,2-trifluoro-

162 ethyl)-3,4-dihydro-1,4-methanopyrido[2,3-b][1,4]diazepine-5,7(2H)-dicarboxamide (520 mg, 0.962 mmol, 36.6% yield) as an Off-white solid, LCMS (m/z): 538.23 [M+H]$^+$.

Synthesis of (4S)-methyl 5-((5-(((S)-2,2-dimethyl-1,3-dioxolan-4-yl)methoxy)pyrazin-2-yl)carbamoyl)-2,3,4,5-tetrahydro-1,4-methanopyrido[2,3-b][1,4]diazepine-7-carboxylate

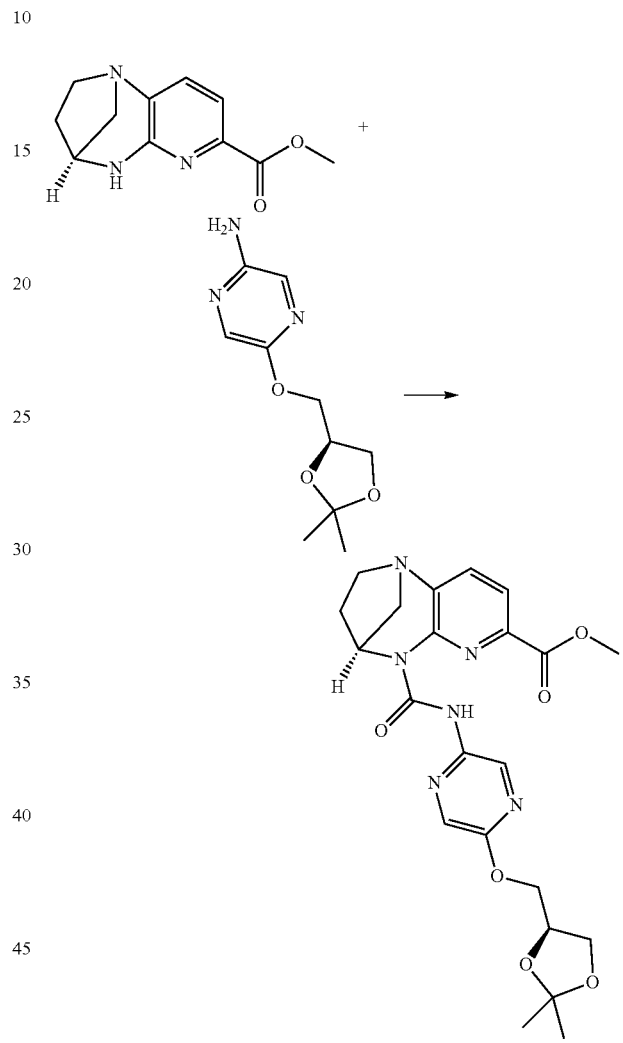

To a stirred solution of (4S)-methyl 2,3,4,5-tetrahydro-1,4-methanopyrido[2,3-b][1,4]diazepine-7-carboxylate (2 g, 9.12 mmol) in Tetrahydrofuran (THF) (20 mL), was added triphosgene (2.71 g, 9.12 mmol) and followed by triethylamine (7.63 mL, 54.7 mmol) at rt. The reaction mixture was stirred for 30 min and added a solution of(S)-5-((2,2-dimethyl-1,3-dioxolan-4-yl)methoxy)pyrazin-2-amine (2.055 g, 9.12 mmol). The reaction mixture was stirred at 65° C. for 16 hr. Progress of the reaction was monitored by TLC. TLC indicated starting material was consumed to form polar spot. Cooled the reaction mass to rt, diluted with water (100 mL) and extracted with EtOAc (100 mL). The organic layer was dried over Na$_2$SO$_4$, filtered and concentrated to get crude compound. The crude product was added to a silica gel (100-200) column and was eluted with Hex/EtOAc. Collected fractions: 70% EtOAc in petether pure product was eluted, concentrated the product fractions to afford (4S)-methyl 5-((5-(((S)-2,2-dimethyl-1,3-dioxolan-4-yl)methoxy)pyrazin-2-yl)carbamoyl)-2,3,4,5-tetrahydro-1,4-methanopyrido[2,3-b][1,4]diazepine-7-carboxylate (2.2 g, 4.57 mmol, 50.1% yield), as light brown solid. LCMS (m/z): 471.23 (M+H)+.

Synthesis of (4S)-5-((5-(((S)-2,2-dimethyl-1,3-dioxolan-4-yl)methoxy)pyrazin-2-yl)carbamoyl)-2,3,4,5-tetrahydro-1,4-methanopyrido[2,3-b][1,4]diazepine-7-carboxylic acid

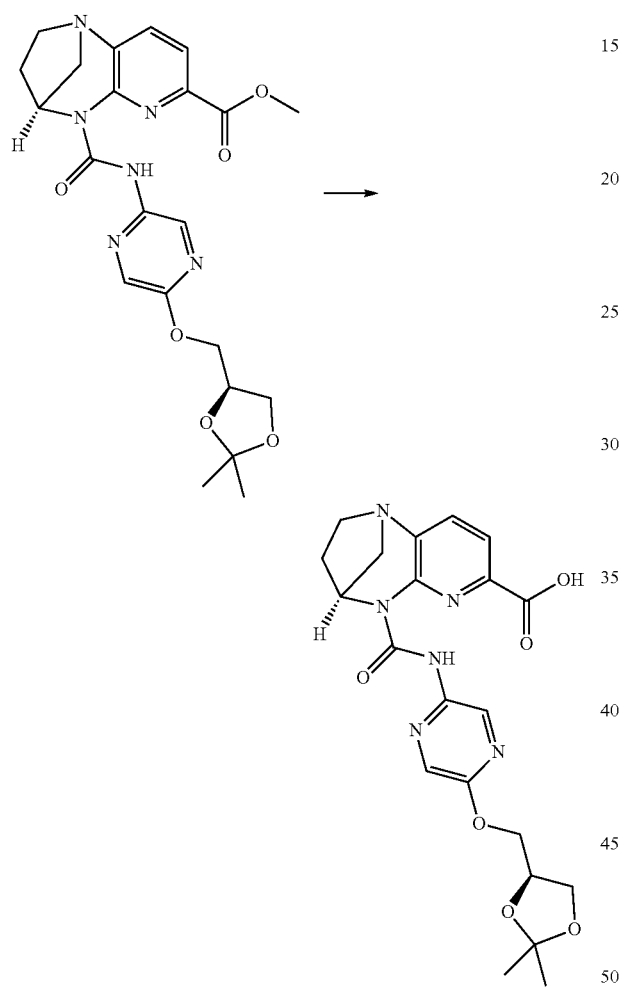

To a solution of (4S)-methyl 5-((5-(((S)-2,2-dimethyl-1,3-dioxolan-4-yl)methoxy)pyrazin-2-yl)carbamoyl)-2,3,4,5-tetrahydro-1,4-methanopyrido[2,3-b][1,4]diazepine-7-carboxylate (2 g, 4.25 mmol), in Tetrahydrofuran (THF) (20 mL), Water (20 mL) stirred at room temp was added LiOH (0.305 g, 12.75 mmol). The reaction mixture was stirred at rt for 4 hr. Progress of the reaction was monitored by TLC. TLC indicated starting material was consumed. Concentrated the THF under vacuum and was cooled to 0° C., acidified with saturated citric acid solution to get solid. The solid was filtered and dried to afford (4S)-5-((5-(((S)-2,2-dimethyl-1,3-dioxolan-4-yl)methoxy)pyrazin-2-yl)carbamoyl)-2,3,4,5-tetrahydro-1,4-methanopyrido[2,3-b][1,4]diazepine-7-carboxylic acid (1.8 g, 2.96 mmol, 69.6% yield) as Light brown solid, LCMS (m/z): 457.0 (M+H)+.

Synthesis of (4S)—N5-(5-(((S)-2,2-dimethyl-1,3-dioxolan-4-yl)methoxy)pyrazin-2-yl)-N7-(2,2,2-trifluoroethyl)-3,4-dihydro-1,4-methanopyrido[2,3-b][1,4]diazepine-5,7(2H)-dicarboxamide

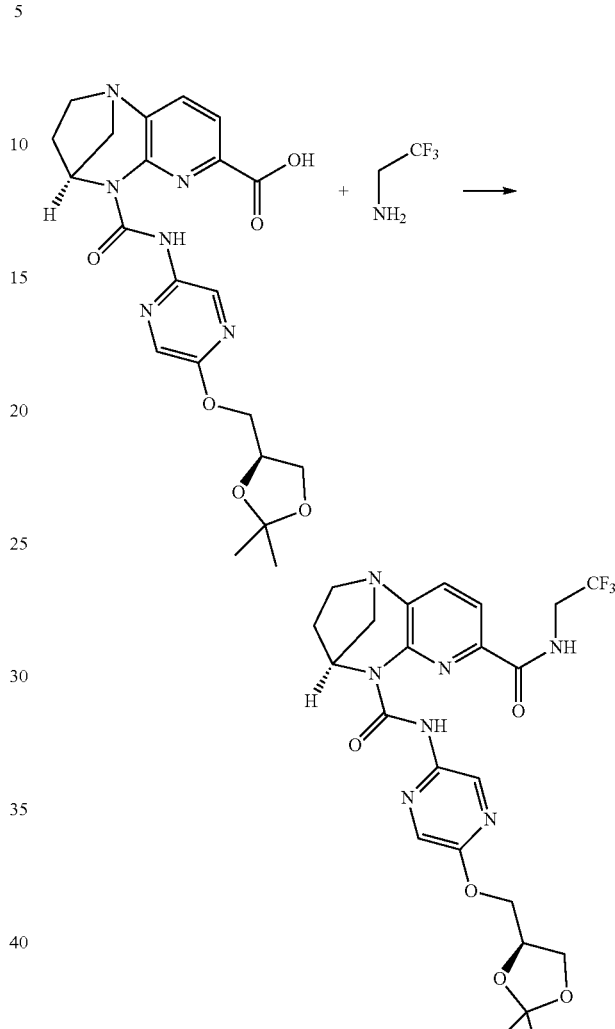

To a suspension of 2,2,2-trifluoroethanamine (260 mg, 2.63 mmol) in N,N-Dimethylformamide (DMF) (5 mL), stirred under nitrogen at room temperature, was added DIPEA (1.531 mL, 8.76 mmol), HATU (1333 mg, 3.51 mmol), reaction mass was stirred for 15 minutes at rt. To this added 2,2,2-trifluoroethanamine (260 mg, 2.63 mmol) at it. The reaction mass was stirred at rt for 4 hr. Progress of the reaction was monitored by TLC. TLC indicated starting material was consumed to form non-polar spot. The reaction mass was poured into ice cold water (50 mL) and extracted with Ethyl acetate (50 mL). The organic layer was dried over Na2SO4, filtered and concentrated to get crude compound as light brown sticky compound. The crude product was added to a combiflash column (24 g) and was eluted with DCM/MeOH. Collected fractions: 3% Methanol in DCM product was eluted. Concentrated the product fractions to afford (4S)—N5-(5-(((S)-2,2-dimethyl-1,3-dioxolan-4-yl)methoxy)pyrazin-2-yl)-N7-(2,2,2-trifluoroethyl)-3,4-dihydro-1,4-methanopyrido[2,3-b][1,4]diazepine-5,7(2H)-dicarboxamide (400 mg, 0.582 mmol, 33.2% yield) as Off-white solid, LCMS (m/z): 538.15 (M+H)+.

165

Synthesis of (4S)-methyl 5-((6-(((R)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylate

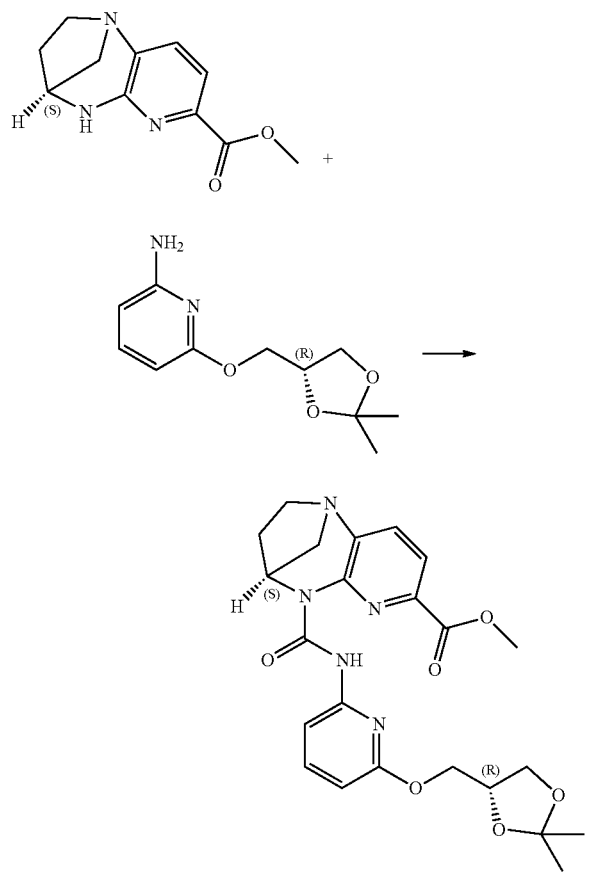

To a solution of (4S)-methyl 2,3,4,5-tetrahydro-1,4-methanopyrido[2,3-b][1,4]diazepine-7-carboxylate (0.7 g, 3.19 mmol) in Tetrahydrofuran (THF) (15 mL) was added triethylamine (2.67 mL, 19.16 mmol), triphosgene (0.947 g, 3.19 mmol) at 0° C. Stirred the reaction mixture for 1 h at room temp and (R)-6-((2,2-dimethyl-1,3-dioxolan-4-yl)methoxy)pyridin-2-amine (1.432 g, 6.39 mmol) was added, stirred the reaction mixture at 90° C. for 16 hr. Reaction mixture was cooled to RT, diluted with water and extracted with ethyl acetate (2×50 mL). Combined organics were washed with brine solution (30 mL), dried over Na$_2$SO$_4$, filtered and concentrated to get the crude compound. The crude product was purified by column chromatography (100-200 silica gel) and product was eluted with 90% EtOAc/PetEther. Collected fractions were evaporated to get pure product (4S)-methyl 5-((6-(((R)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylate (680 mg, 1.304 mmol, 40.8% yield) as Brown liquid. LCMS (m/z): 470.19 (M+H)$^+$.

166

Synthesis of (4S)-5-((6-(((R)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid

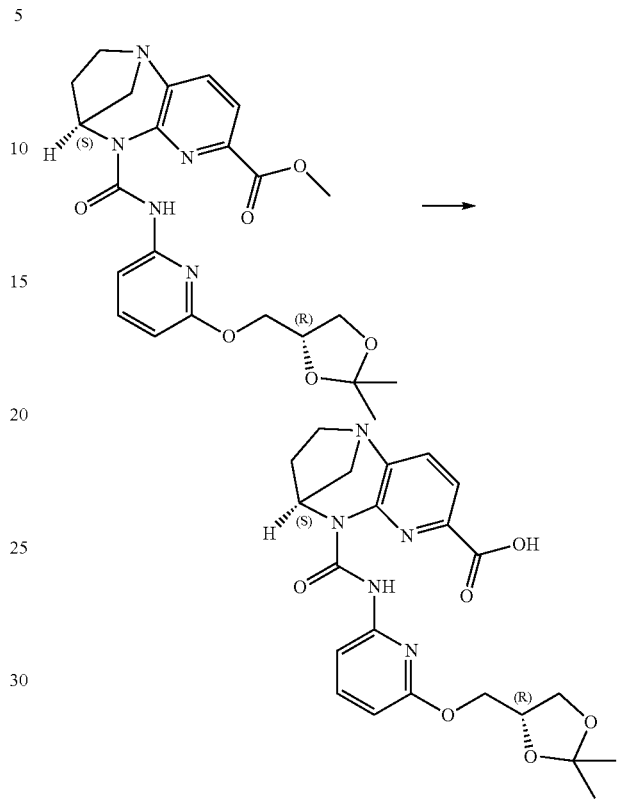

To a solution of (4S)-methyl 5-((6-(((R)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylate (0.65 g, 1.384 mmol) in Tetrahydrofuran (THF) (25 mL) and Water (25.00 mL) was added lithium hydroxide monohydrate (0.087 g, 2.077 mmol) the resulting reaction mixture was stirred at 25° C. for 5 hr. Reaction mixture was concentrated under reduced pressure to afford crude compound. Crude directly used for next step, LCMS (m/z): 456.22 (M+H)$^+$.

Synthesis of (4S)—N5-(6-(((R)-2,2-dimethyl-1,3-dioxolan-4-yl)methoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

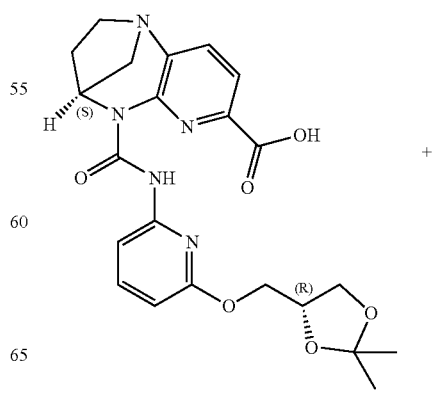

167
-continued

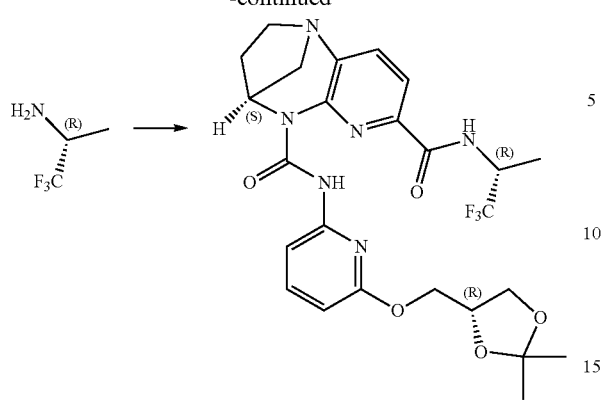

To a suspension of (4S)-5-((6-(((R)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid (0.48 g, 1.054 mmol) in N,N-Dimethylformamide (DMF) (10 mL) at 0° C. was added HATU (0.601 g, 1.581 mmol) and DIPEA (0.184 mL, 1.054 mmol) under Nitrogen atmosphere and the reaction mixture was stirred for 30 min at RT. To the above reaction mixture (R)-1,1,1-trifluoropropan-2-amine (0.143 g, 1.265 mmol) was added at 0° C. and stirred the reaction mixture at 25° C. for 4 hr. The reaction mixture was quenched with ice-cold water (30 mL) and extracted with EtOAc (3×50 mL). The combined organics were washed with brine solution (2×30 mL), dried with anhydrous Na₂SO₄, filtered and concentrated to get crude product. The crude product was purified by column chromatography (100-200 silica gel) and product was eluted with 5% MeOH/DCM. Collected fractions were evaporated to get product (4S)—N5-(6-(((R)-2,2-dimethyl-1,3-dioxolan-4-yl)methoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (430 mg, 0.745 mmol, 70.7% yield) as Brown liquid, LCMS (m/z): 551.39 (M+H)⁺.

Synthesis of (4S)-methyl 5-((4-(((R)-2,2-dimethyl-1,3-dioxolan-4-yl)methoxy)pyrimidin-2-yl)carbamoyl)-2,3,4,5-tetrahydro-1,4-methanopyrido[2,3-b][1,4]diazepine-7-carboxylate

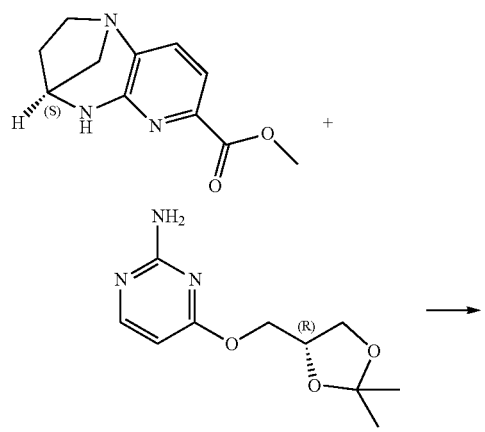

168
-continued

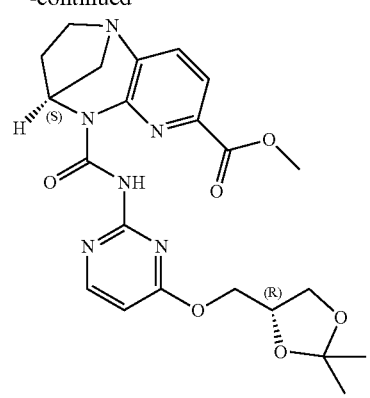

To a solution of (4S)-methyl 2,3,4,5-tetrahydro-1,4-methanopyrido[2,3-b][1,4]diazepine-7-carboxylate (0.5 g, 2.281 mmol) in Tetrahydrofuran (THF) (10 mL) was added triethylamine (1.907 mL, 13.68 mmol), triphosgene (0.677 g, 2.281 mmol) at 0° C. Stirred the reaction mixture for 1 h at room temp and (R)-4-((2,2-dimethyl-1,3-dioxolan-4-yl)methoxy)pyrimidin-2-amine (1.027 g, 4.56 mmol) was added, stirred the reaction mixture at 90° C. for 16 hr. Reaction mixture was cooled to RT, diluted with water and extracted with ethyl acetate (2×50 mL). Combined organics were washed with brine solution (40 mL), dried over Na₂SO₄, filtered and concentrated to get the crude compound. The crude product was purified by column chromatography (100-200 silica gel) and product was eluted with 80% EtOAc/Pet Ether. Collected fractions were evaporated to get pure product (4S)-methyl 5-((4-(((R)-2,2-dimethyl-1,3-dioxolan-4-yl)methoxy)pyrimidin-2-yl)carbamoyl)-2,3,4,5-tetrahydro-1,4-methanopyrido[2,3-b][1,4]diazepine-7-carboxylate (540 mg, 0.797 mmol, 34.9% yield) as Brown liquid, LCMS (m/z): 471.00 (M+H)⁺.

Synthesis of (4S)-5-((4-(((R)-2,2-dimethyl-1,3-dioxolan-4-yl)methoxy)pyrimidin-2-yl)carbamoyl)-2,3,4,5-tetrahydro-1,4-methanopyrido[2,3-b][1,4]diazepine-7-carboxylic

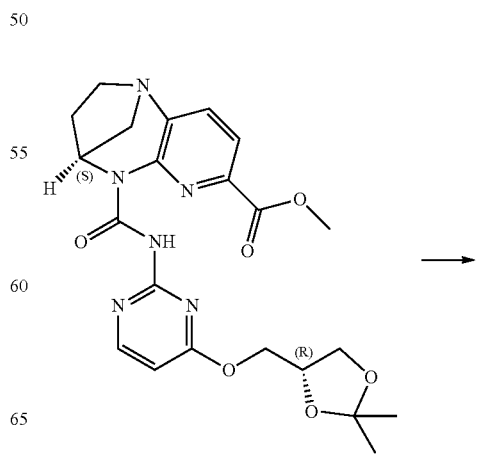

-continued

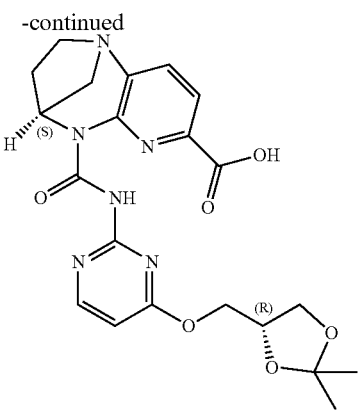

To a solution of (4S)-methyl 5-((4-(((R)-2,2-dimethyl-1,3-dioxolan-4-yl)methoxy)pyrimidin-2-yl)carbamoyl)-2,3,4,5-tetrahydro-1,4-methanopyrido[2,3-b][1,4]diazepine-7-carboxylate (540 mg, 1.148 mmol) in Tetrahydrofuran (THF) (15 mL) and Water (15.00 mL) was added lithium hydroxide (55.0 mg, 2.296 mmol) and the reaction mixture was stirred at 25° C. for 4 hr. Reaction mixture was concentrated under reduced pressure to afford crude compound. Crude directly used for next step, LCMS (m/z): 457.20 (M+H)$^+$.

Synthesis of (4S)—N5-(4-(((R)-2,2-dimethyl-1,3-dioxolan-4-yl)methoxy)pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide

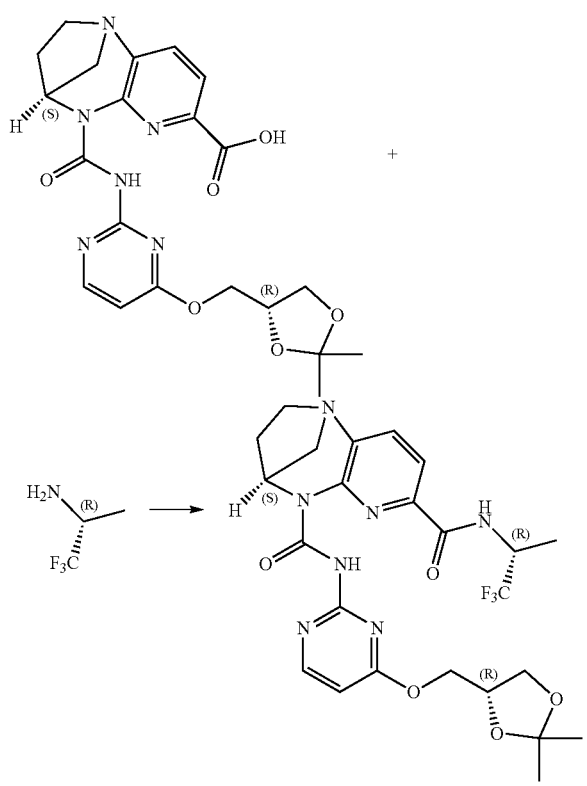

To a solution of (4S)-5-((4-(((R)-2,2-dimethyl-1,3-dioxolan-4-yl)methoxy)pyrimidin-2-yl)carbamoyl)-2,3,4,5-tetrahydro-1,4-methanopyrido[2,3-b][1,4]diazepine-7-carboxylic acid (0.5 g, 1.095 mmol) in N,N-Dimethylformamide (DMF) (10 mL) at 0° C. was added HATU (0.625 g, 1.643 mmol) and DIPEA (0.191 mL, 1.095 mmol) under Nitrogen atmosphere and the reaction mixture was stirred for 30 min at RT. To the above reaction mixture (R)-1,1,1-trifluoropropan-2-amine hydrochloride (0.197 g, 1.314 mmol) was added at 0° C. and stirred the reaction mixture at 25° C. for 4 hr. The reaction mixture was quenched with ice-cold water (30 mL) and extracted with EtOAc (3×50 mL). The combined organics were washed with brine solution (2×30 mL), dried with anhydrous Na$_2$SO$_4$, filtered and concentrated to get crude product. The crude product was purified by column chromatography (100-200 silica gel) and product was eluted with 5% MeOH/CDCM. Collected fractions were evaporated to get product (4S)—N5-(4-(((R)-2,2-dimethyl-1,3-dioxolan-4-yl)methoxy)pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide (320 mg, 0.462 mmol, 42.2% yield) as Brown liquid, LCMS (m/z): 552.30 (M+H)$^+$.

Synthesis of (4S)-methyl 5-((6-(((R)-2,2-dimethyl-1,3-dioxolan-4-yl)methoxy)pyrimidin-4-yl)carbamoyl)-2,3,4,5-tetrahydro-1,4-methanopyrido[2,3-b][1,4]diazepine-7-carboxylate

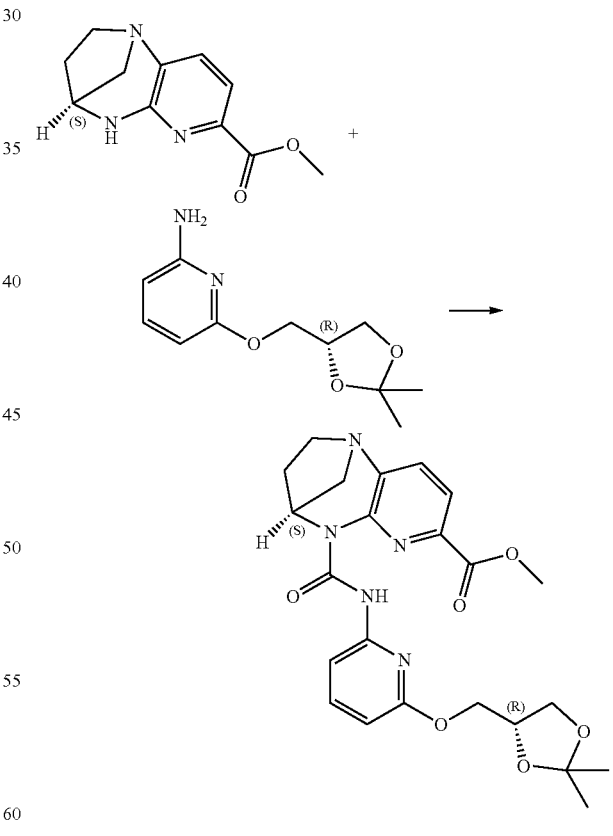

To a solution of (4S)-methyl 2,3,4,5-tetrahydro-1,4-methanopyrido[2,3-b][1,4]diazepine-7-carboxylate (0.7 g, 3.19 mmol) in Tetrahydrofuran (THF) (12 mL) was added triethylamine (2.67 mL, 19.16 mmol), triphosgene (0.947 g, 3.19 mmol) at 0° C. Stirred the reaction mixture for 1 h at room temp and (R)-6-((2,2-dimethyl-1,3-dioxolan-4-yl)

methoxy)pyrimidin-4-amine (1.438 g, 6.39 mmol) was added, stirred the reaction mixture at 90° C. for 16 hr. Reaction mixture was cooled to RT, diluted with water and extracted with ethyl acetate (2×30 mL). Combined organics were washed with brine solution (20 mL), dried over Na$_2$SO$_4$, filtered and concentrated to get the crude compound. The crude product was purified by column chromatography (100-200 silica gel) and product was eluted with 5% MeOH/DCM. Collected fractions were evaporated to get product (4S)-methyl 5-((6-(((R)-2,2-dimethyl-1,3-dioxolan-4-yl)methoxy)pyrimidin-4-yl)carbamoyl)-2,3,4,5-tetrahydro-1,4-methanopyrido[2,3-b][1,4]diazepine-7-carboxylate (680 mg, 0.998 mmol, 31.3% yield) as Brown liquid, LCMS (m/z): 471.2 (M+H)$^+$.

Synthesis of (4S)-5-((6-(((R)-2,2-dimethyl-1,3-dioxolan-4-yl)methoxy)pyrimidin-4-yl)carbamoyl)-2,3,4,5-tetrahydro-1,4-methanopyrido[2,3-b][1,4]diazepine-7-carboxylic acid Synthesis of (4S)—N5-(6-(((R)-2,2-dimethyl-1,3-dioxolan-4-yl)methoxy)pyrimidin-4-yl)-N7-((R)-1,1,1-trifluoropropan-2-yl)-3,4-dihydro-1,4-methanopyrido[2,3-b][1,4]diazepine-5,7(2H)-dicarboxamide

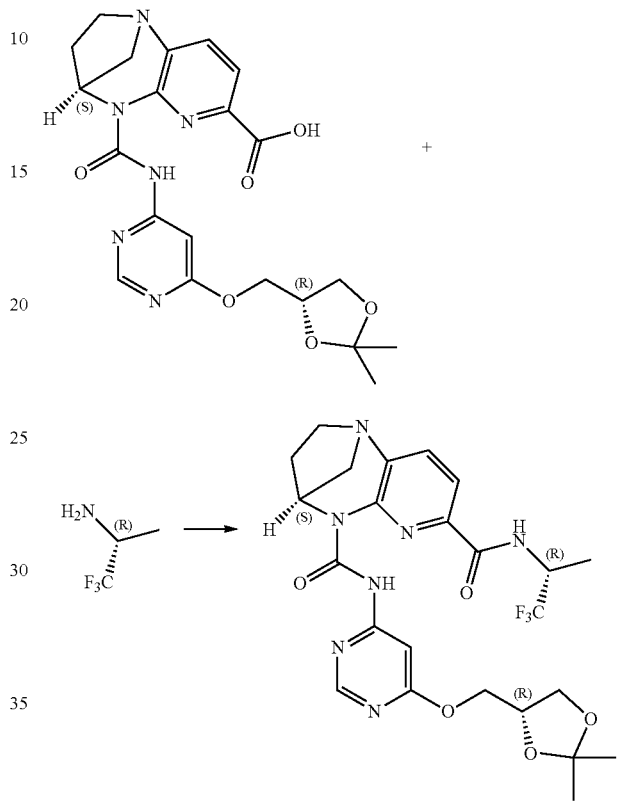

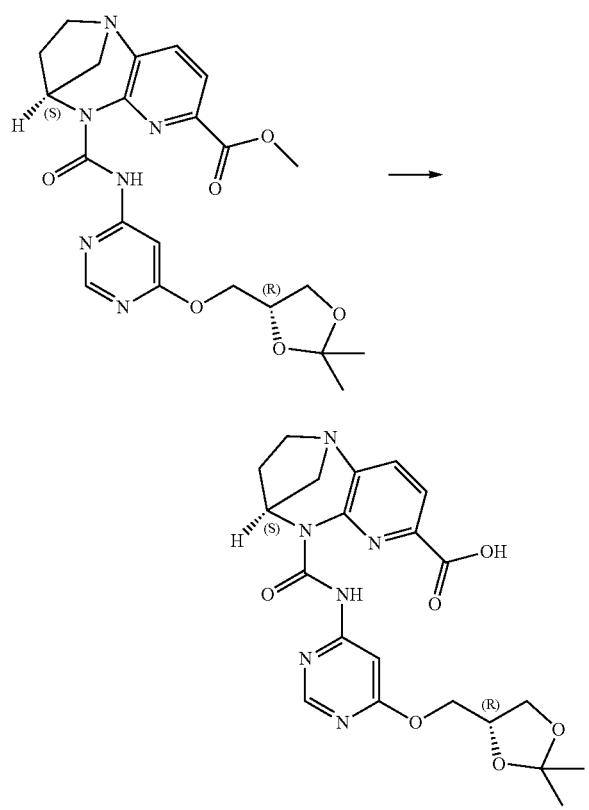

To a solution of (4S)-methyl 5-((6-(((R)-2,2-dimethyl-1,3-dioxolan-4-yl)methoxy)pyrimidin-4-yl)carbamoyl)-2,3,4,5-tetrahydro-1,4-methanopyrido[2,3-b][1,4]diazepine-7-carboxylate (0.65 g, 1.382 mmol) in Tetrahydrofuran (THF) (15 mL) and Water (15.00 mL) was added lithium hydroxide (0.066 g, 2.76 mmol) and the reaction mixture was stirred at 25° C. for 2 hr. Reaction mixture was concentrated under reduced pressure to afford crude compound. Crude directly used for next step, LCMS (m/z): 457.00 (M+H)$^+$.

To a solution of (4S)-5-((6-(((R)-2,2-dimethyl-1,3-dioxolan-4-yl)methoxy)pyrimidin-4-yl)carbamoyl)-2,3,4,5-tetrahydro-1,4-methanopyrido[2,3-b][1,4]diazepine-7-carboxylic acid (0.7 g, 1.534 mmol) in N,N-Dimethylformamide (DMF) (25 mL) at 0° C. was added HATU (0.875 g, 2.300 mmol) and DIPEA (0.804 mL, 4.60 mmol) under Nitrogen atmosphere and the reaction mixture was stirred for 30 min at RT. To the above reaction mixture (R)-1,1,1-trifluoropropan-2-amine hydrochloride (0.275 g, 1.840 mmol) was added at 0° C. and stirred the reaction mixture at 25° C. for 4 hr. The reaction mixture was quenched with ice-cold water (50 mL) and extracted with EtOAc (3×75 mL). The combined organics were washed with brine solution (2×30 mL), dried with anhydrous Na$_2$SO$_4$, filtered and concentrated to get crude product. The crude product was purified by column chromatography (100-200 silica gel) and product was eluted with 5% MeOH/DCM. Collected fractions were evaporated to get product (4S)—N5-(6-(((R)-2,2-dimethyl-1,3-dioxolan-4-yl)methoxy)pyrimidin-4-yl)-N7-((R)-1,1,1-trifluoropropan-2-yl)-3,4-dihydro-1,4-methanopyrido[2,3-b][1,4]diazepine-5,7(2H)-dicarboxamide (580 mg, 0.642 mmol, 41.9% yield) as Brown liquid, LCMS (m/z): 552.36 (M+H)$^+$.

Synthesis of (4S)-methyl 5-((6-(((R)-2,2-dimethyl-1,3-dioxolan-4-yl)methoxy)pyridazin-3-yl)carbamoyl)-2,3,4,5-tetrahydro-1,4-methanopyrido[2,3-b][1,4]diazepine-7-carboxylate

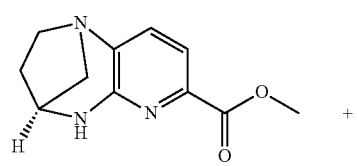

+

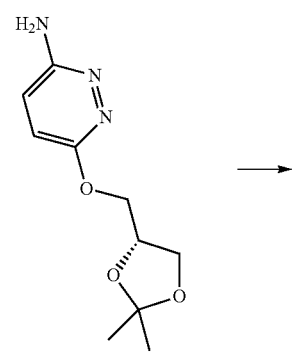

→

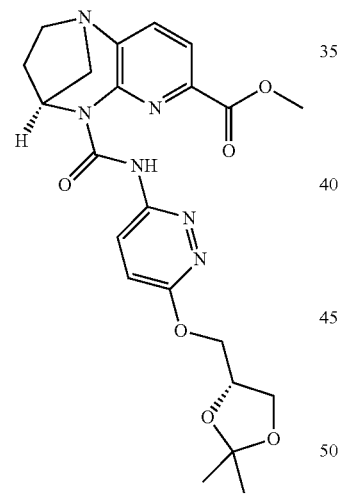

→ fied by column using silica (100-200 mesh); (1-80% ethyl acetate/pet-ether as a eluent). Collected fractions were concentrated under reduced pressure to get (4S)-methyl 5-((6-(((R)-2,2-dimethyl-1,3-dioxolan-4-yl)methoxy)pyridazin-3-yl)carbamoyl)-2,3,4,5-tetrahydro-1,4-methanopyrido[2,3-b][1,4]diazepine-7-carboxylate (1.5 g, 2.91 mmol, 31.9% yield), LCMS (m/z) 471.19 (M+H)+.

Synthesis of (4S)-5-((6-(((R)-2,2-dimethyl-1,3-dioxolan-4-yl)methoxy)pyridazin-3-yl)carbamoyl)-2,3,4,5-tetrahydro-1,4-methanopyrido[2,3-b][1,4]diazepine-7-carboxylic acid

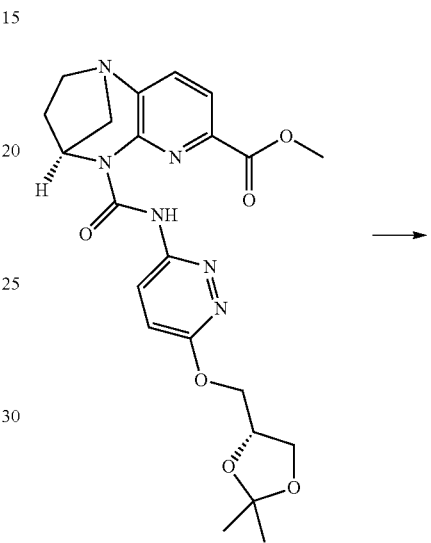

→

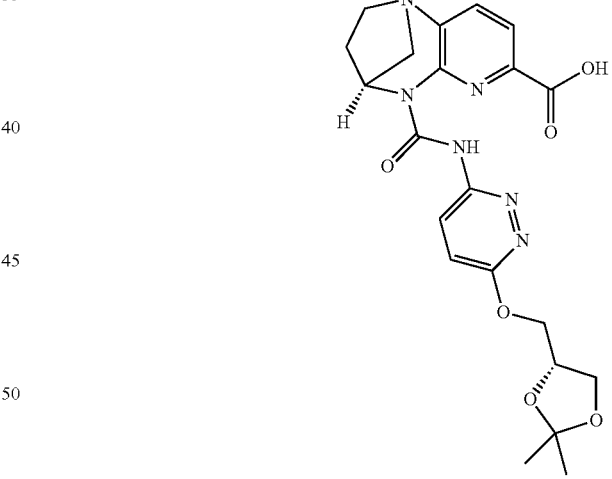

To a stirred solution of (4S)-methyl 2,3,4,5-tetrahydro-1,4-methanopyrido[2,3-b][1,4]diazepine-7-carboxylate (2 g, 9.12 mmol) in Tetrahydrofuran (THF) (10 mL) was added triphosgene (2.71 g, 9.12 mmol) followed by TEA (6.36 mL, 45.6 mmol) at 0° C. The reaction mixture was stirred for 30 min and added a solution of (R)-6-((2,2-dimethyl-1,3-dioxolan-4-yl)methoxy)pyridazin-3-amine (3.08 g, 13.68 mmol). The reaction mixture was stirred at 80° C. for 16 hr. Progress of the reaction was monitored by TLC. Reaction mixture was cooled to RT, water (30 mL) and Ethyl acetate (2×30 mL) was added. Combined organic phases were washed with brine (20 mL), dried over Na2SO4, concentrated under reduced pressure to obtain crude. Obtained crude was puri- In a stirred solution of (4S)-methyl 5-((6-(((R)-2,2-dimethyl-1,3-dioxolan-4-yl)methoxy)pyridazin-3-yl)carbamoyl)-2,3,4,5-tetrahydro-1,4-methanopyrido[2,3-b][1,4]diazepine-7-carboxylate (1.5 g, 3.19 mmol) in Tetrahydrofuran (THF) (15 mL) and Water (8 mL). To this LiOH (0.153 g, 6.38 mmol) was added at RT, reaction mixture was stirred at RT for 4 hr. Progress of the reaction was monitored by TLC. Distilled the solvent from the reaction mixture completely under reduced pressure to obtain solid. The obtained solid was directly used in the next step with out any further purification, LCMS (m/z) 457.1 (M+H)+.

Synthesis of (4S)—N5-(6-(((R)-2,2-dimethyl-1,3-dioxolan-4-yl)methoxy)pyridazin-3-yl)-N7-((R)-1,1,1-trifluoropropan-2-yl)-3,4-dihydro-1,4-methanopyrido[2,3-b][1,4]diazepine-5,7(2H)-dicarboxamide

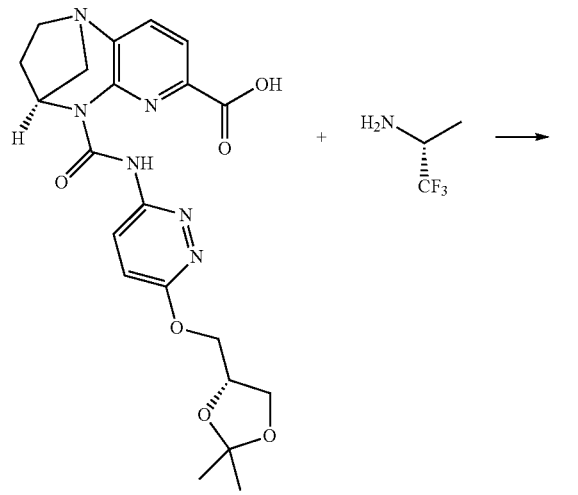

To a solution of (4S)-5-((6-(((R)-2,2-dimethyl-1,3-dioxolan-4-yl)methoxy)pyridazin-3-yl)carbamoyl)-2,3,4,5-tetrahydro-1,4-methanopyrido[2,3-b][1,4]diazepine-7-carboxylic acid (700 mg, 1.534 mmol) in Tetrahydrofuran (THF) (10 mL) stirred under nitrogen at room temp was added HATU (583 mg, 1.534 mmol) and DIPEA (0.402 mL, 2.300 mmol), To this (R)-1,1,1-trifluoropropan-2-amine hydrochloride (229 mg, 1.534 mmol) was added and the reaction mixture was stirred at RT for 3 hr. Progress of the reaction was monitored by TLC. Reaction mixture was quenched with 2×25 ml of water and extracted with 2×50 ml of ethyl acetate, organic layer was washed brine solution (10 ml) and dried over $Na_2SO_4$ and concentrated under reduced pressure to afford crude compound. Obtained crude was purified by column using silica (100-200 mesh; 1-70% Ethyl acetate in pet-ether as a eluting agent). Collected fractions were concentrated under reduced pressure to afford (4S)—N5-(6-(((R)-2,2-dimethyl-1,3-dioxolan-4-yl)methoxy)pyridazin-3-yl)-N7-((R)-1,1,1-trifluoropropan-2-yl)-3,4-dihydro-1,4-methanopyrido[2,3-b][1,4]diazepine-5,7(2H)-dicarboxamide (300 mg, 0.450 mmol, 29.3% yield) as a yellow color liquid, LCMS (m/z) 552.45 (M+H)$^+$.

Synthesis of (4S)-methyl 5-((4-nitropyridin-2-yl)carbamoyl)-2,3,4,5-tetrahydro-1,4-methanopyrido[2,3-b][1,4]diazepine-7-carboxylate

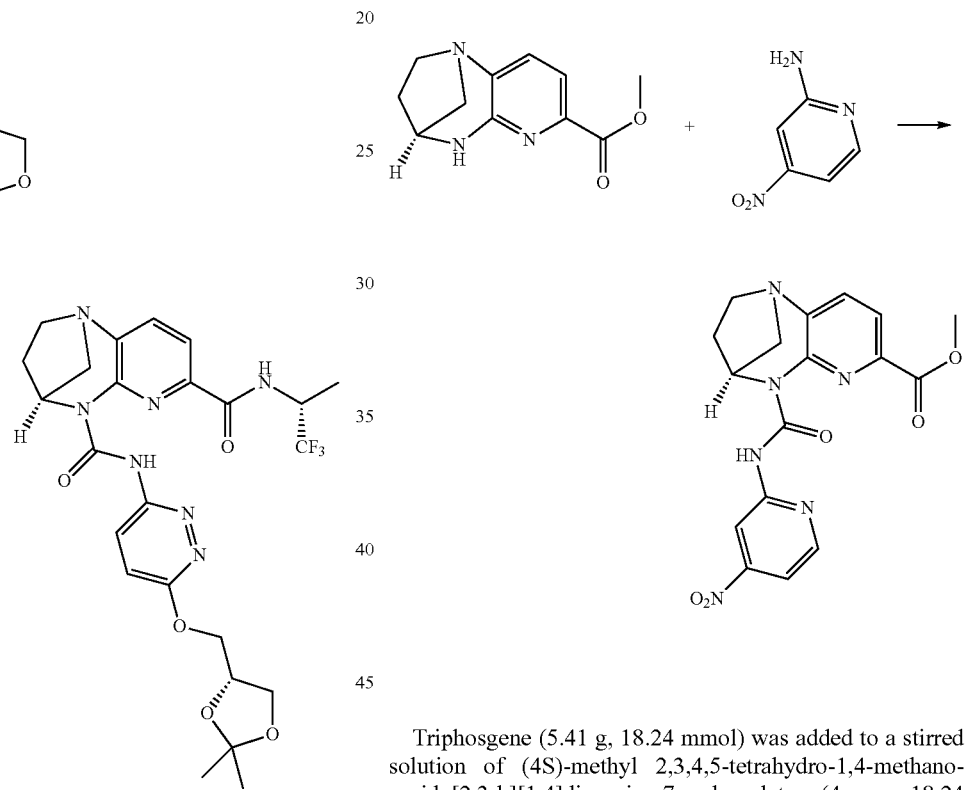

Triphosgene (5.41 g, 18.24 mmol) was added to a stirred solution of (4S)-methyl 2,3,4,5-tetrahydro-1,4-methanopyrido[2,3-b][1,4]diazepine-7-carboxylate (4 g, 18.24 mmol), and TEA (15.26 mL, 109 mmol) in Tetrahydrofuran (THF) (120 mL) under nitrogen at 28° C. The reaction mixture was stirred at rt for 45 min, and was added 4-nitropyridin-2-amine (7.61 g, 54.7 mmol). The reaction mixture was stirred 6 hr at 65° C. The reaction mixture was cooled to room temp, solvent evaporated under reduced pressure completely and was partitioned between water (60 mL) and dichloromethane (2×100 mL). Organic layer was separated, dried over anhydrous $Na_2SO_4$, filtered and filtrate was evaporated to give crude as brown solid. The crude product was dissolved in dichloromethane (50 mL), then to this silica gel (100-200) was added and product was eluted with 90-95% (gradient)ethyl acetate in hexane to afford pure compound (4S)-methyl 5-((4-nitropyridin-2-yl)carbamoyl)-2,3,4,5-tetrahydro-1,4-methanopyrido[2,3-b][1,4]diazepine-7-carboxylate (4.8 g, 10.03 mmol, 55.0% yield) as a yellow solid, LCMS(m/z): 384.90 (M+H)$^+$.

Synthesis of (4S)-5-((4-nitropyridin-2-yl)carbamoyl)-2,3,4,5-tetrahydro-1,4-methanopyrido[2,3-b][1,4]diazepine-7-carboxylic acid

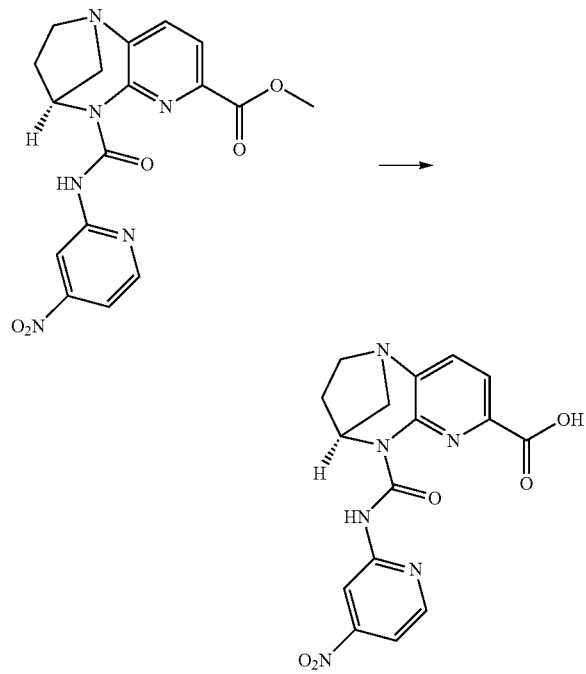

LiOH.H₂O (0.598 g, 24.98 mmol) in Water (10 mL) was added to a stirred solution of (4S)-methyl 5-((4-nitropyridin-2-yl)carbamoyl)-2,3,4,5-tetrahydro-1,4-methanopyrido[2,3-b][1,4]diazepine-7-carboxylate (4.8 g, 12.49 mmol) in Tetrahydrofuran (THF) (60 mL) at 0° C. The reaction mixture was stirred at 26° C. for 2 hr. The solvent (THF) was removed under reduced pressure and diluted with water and acidified with saturated citric acid (pH; 5-6) at 0° C. and stirred for 15 min. The resulting solid was filtered through a Buchner funnel, and dried under vacuum to obtain (4S)-5-((4-nitropyridin-2-yl)carbamoyl)-2,3,4,5-tetrahydro-1,4-methanopyrido[2,3-b][1,4]diazepine-7-carboxylic acid (3.8 mg, 9.34 µmol, 0.075% yield) as a pale yellow solid, LCMS (m/z): 371.21 [M+H]⁺.

Synthesis of (4S)—N5-(4-nitropyridin-2-yl)-N7-(2,2,2-trifluoroethyl)-3,4-dihydro-1,4-methanopyrido[2,3-b][1,4]diazepine-5,7(2H)-dicarboxamide

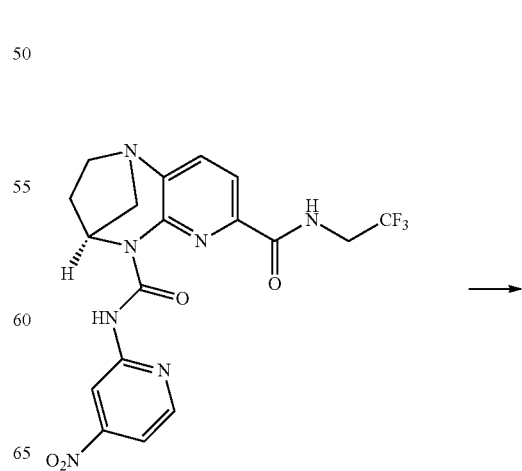

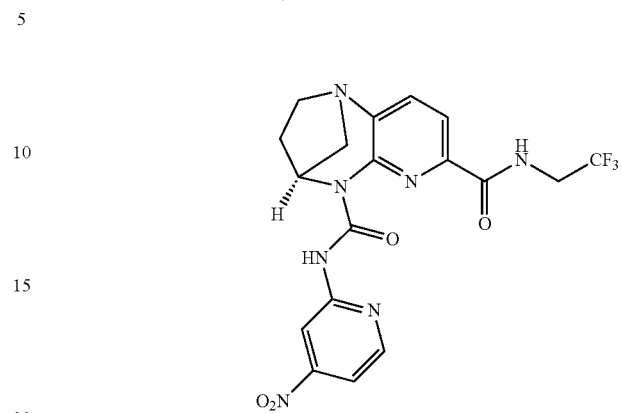

DIPEA (8.96 mL, 51.3 mmol) was added to a stirred solution of (4S)-5-((4-nitropyridin-2-yl)carbamoyl)-2,3,4,5-tetrahydro-1,4-methanopyrido[2,3-b][1,4]diazepine-7-carboxylic acid (3.8 g, 10.26 mmol), 2,2,2-trifluoroethanamine hydrochloride (2.086 g, 15.39 mmol) & HATU (5.85 g, 15.39 mmol) in N,N-Dimethylformamide (DMF) (30 mL) under nitrogen at 0° C. The reaction mixture was stirred at 26° C. for 16 hr. The reaction mixture was partitioned between ice cold water (100 mL) and DCM (2×100 mL). Organic layer was separated, dried over anhydrous Na₂SO₄, filtered and filtrate was evaporated to afford crude. The crude product was dissolved in dichloromethane (50 mL), then to this neutral alumina was added and product was eluted with 50-55% ethyl acetate in hexane to afford pure compound (4S)—N5-(4-nitropyridin-2-yl)-N7-(2,2,2-trifluoroethyl)-3,4-dihydro-1,4-methanopyrido[2,3-b][1,4]diazepine-5,7(2H)-dicarboxamide (3.3 g, 5.80 mmol, 56.5% yield). TLC eluent: 100% ethyl acetate R_f—0.2; UV active). LCMS (m/z): 452.06 [M+H]⁺.

Synthesis of (4S)—N5-(4-aminopyridin-2-yl)-N7-(2,2,2-trifluoroethyl)-3,4-dihydro-1,4-methanopyrido[2,3-b][1,4]diazepine-5,7(2H)-dicarboxamide

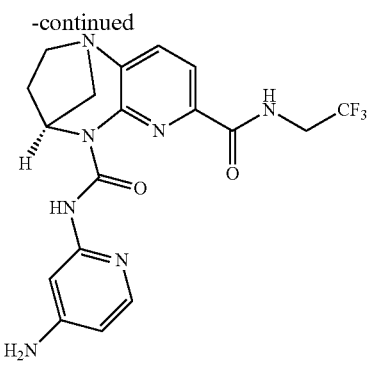

To a solution of (4S)—N5-(4-nitropyridin-2-yl)-N7-(2,2,2-trifluoroethyl)-3,4-dihydro-1,4-methanopyrido[2,3-b][1,4]diazepine-5,7(2H)-dicarboxamide (3.3 g, 7.31 mmol) in Ethanol (40 mL) was added Pd/C (0.156 g, 0.146 mmol). The reaction mixture was stirred under Hydrogen atmosphere at 26° C. for 16 hr. Reaction was monitored by TLC. The reaction mixture was filtered through celite pad and washed with ethanol (100 mL). Filtrate was concentrated under reduced pressure and submitted for analysis. The crude LCMS shows 93% desired mass. It was used for next step, LCMS (m/z): 422.23 [M+H]$^+$.

Synthesis of (4S)-methyl 5-((5-methyl-7H-pyrrolo[2,3-d]pyrimidin-2-yl)carbamoyl)-2,3,4,5-tetrahydro-1,4-methanopyrido[2,3-b][1,4]diazepine-7-carboxylate

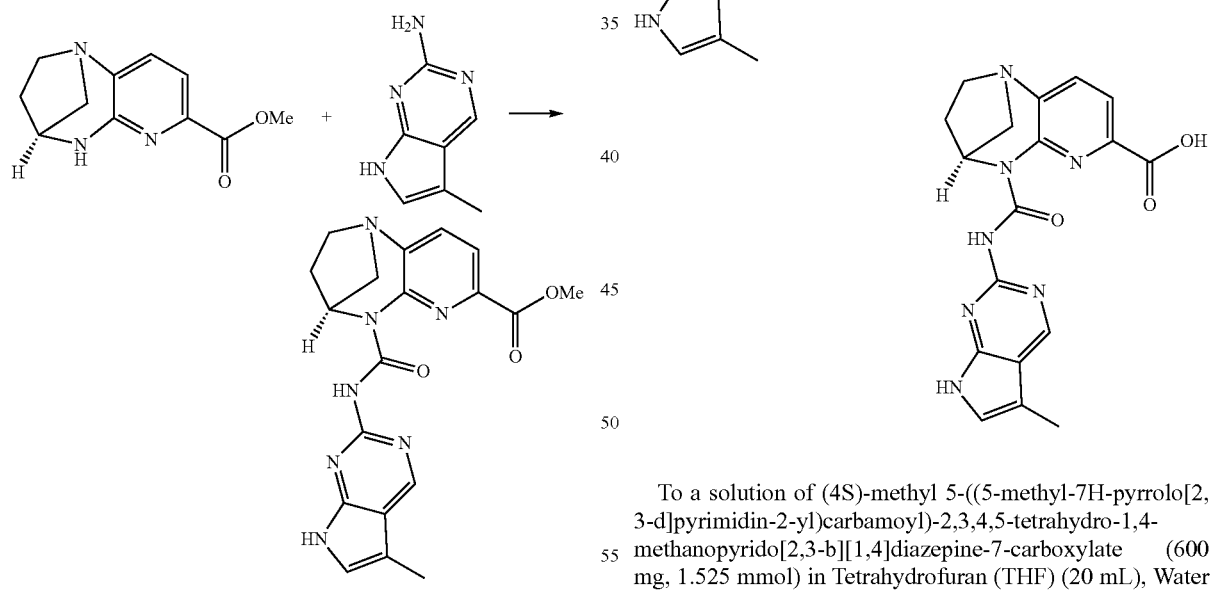

To a stirred solution of (4S)-methyl 2,3,4,5-tetrahydro-1,4-methanopyrido[2,3-b][1,4]diazepine-7-carboxylate (1.0 g, 4.56 mmol), triphosgene (1.354 g, 4.56 mmol) and TEA (3.81 mL, 27.4 mmol) in Tetrahydrofuran (THF) (40 mL) under nitrogen at 28° C. The reaction mixture was stirred at rt for 30 min. 5-methyl-7H-pyrrolo[2,3-d]pyrimidin-2-amine (2.027 g, 13.68 mmol) was added to the reaction mixture. The reaction mixture was stirred for 16 hr at 65° C. and progress of the reaction was monitored by TLC. The reaction mixture was cooled to rt, partitioned between water (20 mL) and EtOAc (3×40 mL). Organic layer was separated and was dried over anhydrous Na$_2$SO$_4$, filtered and filtrate was evaporated to give crude. The crude was purified by GRACE using C-18 reserval column, Mobile phase A: 0.1% Formic Acid in water; B: MeOH, the product was eluted at 50% of MeOH in 0.1% Formic Acid in water. The solvent was evaporated and basified with saturated NaHCO$_3$. The precipitated solid was filtered, and was dried to afford (4S)-methyl 5-((5-methyl-7H-pyrrolo[2,3-d]pyrimidin-2-yl)carbamoyl)-2,3,4,5-tetrahydro-1,4-methanopyrido[2,3-b][1,4]diazepine-7-carboxylate (700 mg, 1.714 mmol, 37.6% yield). TLC eluent: 10% MeOH in DCM: R$_f$—0.3; UV active and LCMS (m/z): 394.0 [M+H]$^+$.

Synthesis of (4S)-5-((5-methyl-7H-pyrrolo[2,3-d]pyrimidin-2-yl)carbamoyl)-2,3,4,5-tetrahydro-1,4-methanopyrido[2,3-b][1,4]diazepine-7-carboxylic acid

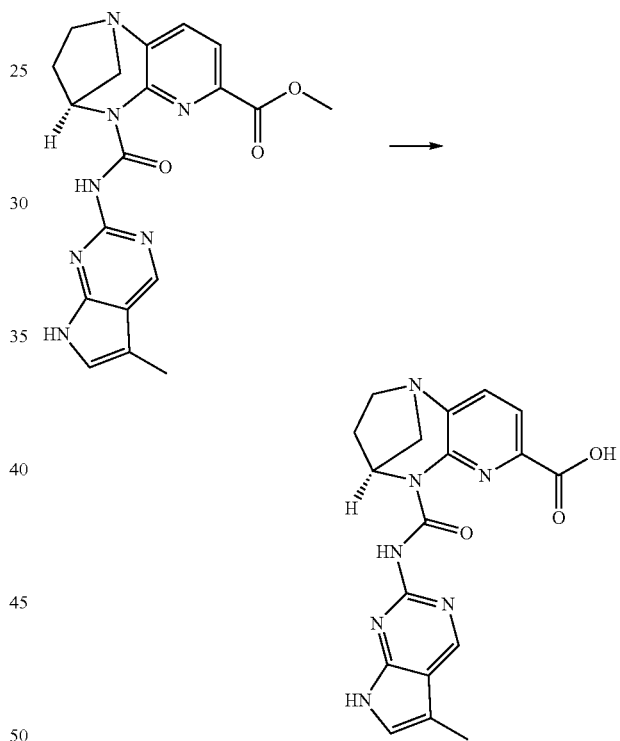

To a solution of (4S)-methyl 5-((5-methyl-7H-pyrrolo[2,3-d]pyrimidin-2-yl)carbamoyl)-2,3,4,5-tetrahydro-1,4-methanopyrido[2,3-b][1,4]diazepine-7-carboxylate (600 mg, 1.525 mmol) in Tetrahydrofuran (THF) (20 mL), Water (6 mL). The reaction mixture cooled to 0° C. and added a solution of lithium hydroxide (73.1 mg, 3.05 mmol) in Water (2 mL). The reaction was stirred at 28° C. for 4 h and progress of the reaction was monitored by TLC. The solvent was evaporated, diluted with water and acidified with 1N HCl (pH; 4-5) at 0° C. The solid was filtered, dried under vacuum to afford (4S)-5-((5-methyl-7H-pyrrolo[2,3-d]pyrimidin-2-yl)carbamoyl)-2,3,4,5-tetrahydro-1,4-methanopyrido[2,3-b][1,4]diazepine-7-carboxylic acid (500 mg, 1.307 mmol, 86% yield) as off white solid, LCMS (m/z): 379.9 [M+H]$^+$.

Synthesis of (4S)-methyl 5-(pyrimidin-2-ylcarbamoyl)-2,3,4,5-tetrahydro-1,4-methanopyrido[2,3-b][1,4]diazepine-7-carboxylate

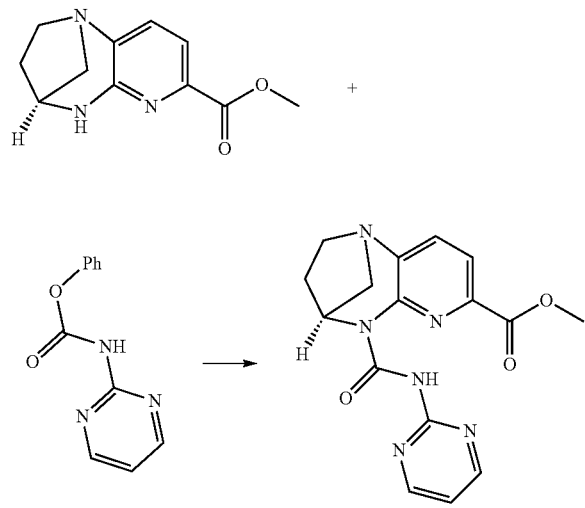 [SMILES: COC(=O)c1ccc2c(n1)N[C@H]1CCN2C1 ; O=C(Nc1ncccn1)Oc1ccccc1 ; COC(=O)c1ccc2c(n1)N(C(=O)Nc1ncccn1)[C@H]1CCN2C1]

A mixture of (4S)-methyl 2,3,4,5-tetrahydro-1,4-methanopyrido[2,3-b][1,4]diazepine-7-carboxylate (4 g, 18.24 mmol), phenyl pyrimidin-2-ylcarbamate (7.85 g, 36.5 mmol) and Tetrahydrofuran (THF) (70 mL) were charged into 250 ml of sealed tube. DMAP (5.57 g, 45.6 mmol) was added to the mixture, resulting reaction mixture was stirred at 70° C. for 16 hr. Progress of the reaction was monitored by TLC. TLC indicated starting material was consumed. Concentrated the reaction mass under vacuum to get crude as brown solid. The crude product was added to a silica gel column and was eluted with DCM/MeOH. Collected fractions: 2% Methanol in DCM product was eluted. Concentrated the product fractions to afford (4S)-methyl 5-(pyrimidin-2-ylcarbamoyl)-2,3,4,5-tetrahydro-1,4-methanopyrido[2,3-b][1,4]diazepine-7-carboxylate (5 g, 10.28 mmol, 56.4% yield) as Off-white solid. LCMS (m/z): 341.0 (M+H)$^+$.

Synthesis of (4S)-5-(pyrimidin-2-ylcarbamoyl)-2,3,4,5-tetrahydro-1,4-methanopyrido[2,3-b][1,4]diazepine-7-carboxylic acid

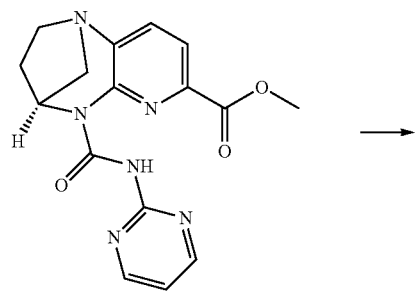

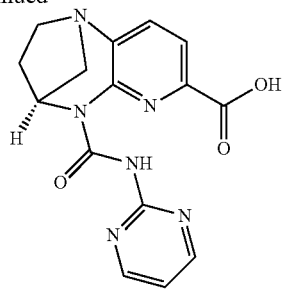

A mixture of (4S)-methyl 5-(pyrimidin-2-ylcarbamoyl)-2,3,4,5-tetrahydro-1,4-methanopyrido[2,3-b][1,4]diazepine-7-carboxylate (5 g, 14.69 mmol) in Tetrahydrofuran (THF) (50 mL) and Water (25 mL), was added LiOH (0.704 g, 29.4 mmol). Resulting reaction mixture was stirred at rt for 16 hr. Progress of the reaction was monitored by TLC. TLC indicated starting material was consumed and new polar spot was formed. Concentrated the reaction mass under vacuum to remove THF, pH of the reaction mixture was adjusted to acidic using 2M HCl. The obtained solid was filtered and washed with pet ether (100 mL) and dried under high vacuum to obtain (4S)-5-(pyrimidin-2-ylcarbamoyl)-2,3,4,5-tetrahydro-1,4-methanopyrido[2,3-b][1,4]diazepine-7-carboxylic acid (4 g, 12.14 mmol, 83% yield) as Off-white solid. LCMS (m/z): 327.16 (M+H)$^+$.

(4S)-methyl 5-((1H-pyrrolo[2,3-c]pyridin-5-yl)carbamoyl)-2,3,4,5-tetrahydro-1,4-methanopyrido[2,3-b][1,4]diazepine-7-carboxylate

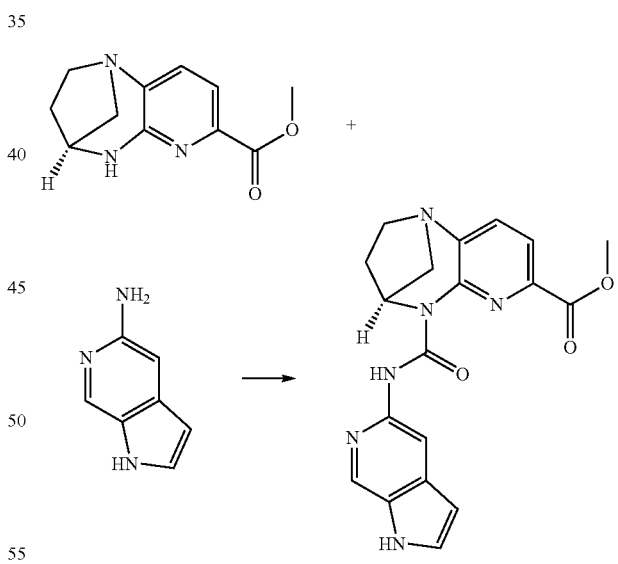

To a solution of (4S)-methyl 2,3,4,5-tetrahydro-1,4-methanopyrido[2,3-b][1,4]diazepine-7-carboxylate (1 g, 4.56 mmol) in Tetrahydrofuran (THF) (45 mL) was added triethylamine (3.81 mL, 27.4 mmol) and triphosgene (1.354 g, 4.56 mmol) at 28° C. The reaction mixture was stirred for 30 min at 28° C. and was added 1H-pyrrolo[2,3-c]pyridin-5-amine (1.518 g, 11.40 mmol). The reaction mixture was stirred for 10 hr at 65° C. Reaction progress was monitored by TLC. The solvent was removed under reduced pressure, diluted with water (40 mL) and extracted with ethyl acetate (2×60 mL). The combined organic layers were washed with water (30 mL), saturated brine solution (20 mL), dried over anhydrous Na$_2$SO$_4$, filtered and concentrated. (TLC eluent: 100% Ethyl acetate: R$_f$—0.2; UV active). The crude compound was dissolved in dichloromethane (10 mL). Neutral alumina was added to the crude compound and purified by column chromatography. Product was eluted with 80-85% ethyl acetate in hexane. Collected fractions were evaporated under reduce pressure to get (4S)-methyl 5-((1H-pyrrolo[2,3-c]pyridin-5-yl)carbamoyl)-2,3,4,5-tetrahydro-1,4-methanopyrido[2,3-b][1,4]diazepine-7-carboxylate (900 mg, 2.297 mmol, 50.4% yield) as an pale yellow solid. LCMS (m/z): 379.08 [M+H]$^+$.

Synthesis of (4S)-5-((1H-pyrrolo[2,3-c]pyridin-5-yl) carbamoyl)-2,3,4,5-tetrahydro-1,4-methanopyrido[2, 3-b][1,4]diazepine-7-carboxylic acid

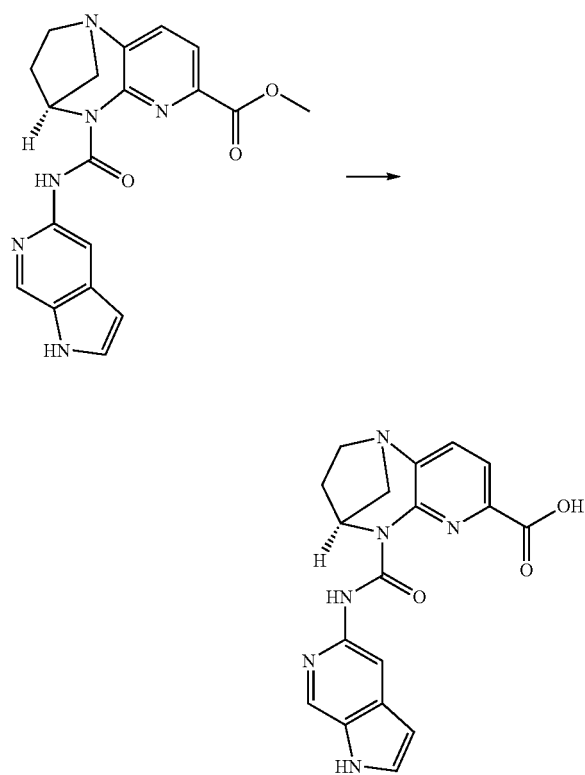

LiOH.H$_2$O (114 mg, 4.76 mmol) in Water (10 mL) was added to a stirred solution of (4S)-methyl 5-((1H-pyrrolo[2,3-c]pyridin-5-yl)carbamoyl)-2,3,4,5-tetrahydro-1,4-methanopyrido[2,3-b][1,4]diazepine-7-carboxylate (900 mg, 2.379 mmol) in Tetrahydrofuran (THF) (25 mL) at 0° C. The reaction mixture was stirred at 28° C. for 4 hr.

The reaction mixture solvent evaporated under reduced pressure completely and was acidified with 1N HCl solution (till pH: 5-6). The reaction mixture was evaporated under reduced pressure completely and co-distilled with toluene (40 mL) to afford product (4S)-5-((1H-pyrrolo[2,3-c]pyridin-5-yl)carbamoyl)-2,3,4,5-tetrahydro-1,4-methanopyrido[2,3-b][1,4]diazepine-7-carboxylic acid (600 mg, 1.379 mmol, 58.0% yield) as a white solid, LCMS (m/z): 364.9 [M+H]$^+$.

Synthesis of (4S)-methyl 5-((7H-purin-2-yl)carbamoyl)-2,3,4,5-tetrahydro-1,4-methanopyrido[2,3-b][1,4]diazepine-7-carboxylate

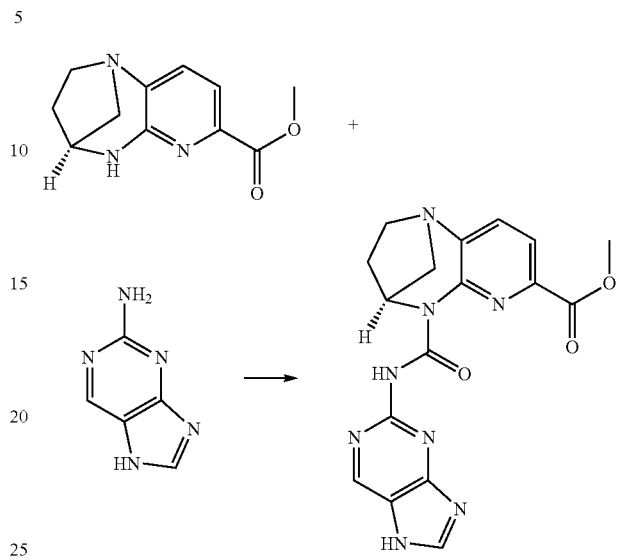

To a stirred solution of (4S)-methyl 2,3,4,5-tetrahydro-1,4-methanopyrido[2,3-b][1,4]diazepine-7-carboxylate (1.0 g, 4.56 mmol), triphosgene (1.354 g, 4.56 mmol) and TEA (3.81 mL, 27.4 mmol) in Tetrahydrofuran (THF) (30 mL) under nitrogen at 28° C. The reaction mixture was stirred at RT for 30 min. 7H-purin-2-amine (1.849 g, 13.68 mmol) was added to the reaction mixture. The reaction mixture was stirred for 16 hr at 65° C. and progress of the reaction was monitored by TLC. The reaction mixture was cooled to rt, partitioned between water (20 mL) and EtOAc (3×40 mL). Organic layer was separated and was dried over anhydrous Na$_2$SO$_4$, filtered and filtrate was evaporated to give crude. The crude was purified by GRACE using C-18 reserval column, Mobile phase A: 0.1% Formic Acid in water; B: ACN, the product was eluted at 35% of MeOH in 0.1% Formic Acid in water. The solvent was evaporated and was basified with saturated NaHCO$_3$. The precipitated solid was filtered, and was dried to afford (4S)-methyl 5-((7H-purin-2-yl)carbamoyl)-2,3,4,5-tetrahydro-1,4-methanopyrido[2,3-b][1,4]diazepine-7-carboxylate (250 mg, 0.632 mmol, 13.86% yield), LCMS (m/z): 381.9 [M+H]$^+$.

Synthesis of (4S)-5-((7H-purin-2-yl)carbamoyl)-2,3,4,5-tetrahydro-1,4-methanopyrido[2,3-b][1,4]diazepine-7-carboxylic acid

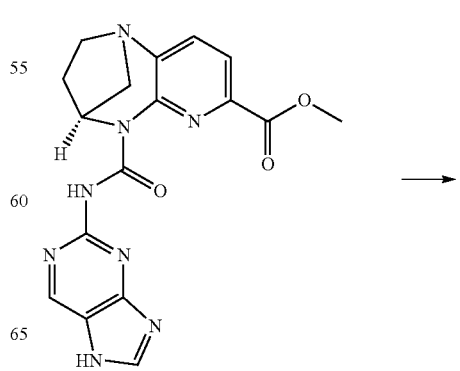

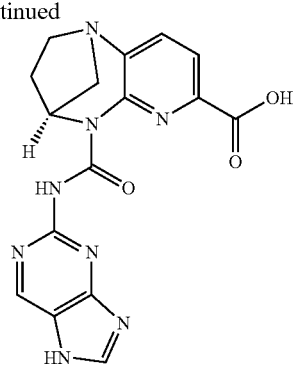

To a solution of (4S)-methyl 5-((7H-purin-2-yl)carbamoyl)-2,3,4,5-tetrahydro-1,4-methanopyrido[2,3-b][1,4]diazepine-7-carboxylate (250 mg, 0.657 mmol) in Tetrahydrofuran (THF) (10 mL), Water (4 mL). The reaction mixture cooled to 0° C. and a solution of lithium hydroxide Monohydrate (55.2 mg, 1.315 mmol) in Water (1 mL) was added. The reaction was stirred at 28° C. for 4 h and progress of the reaction was monitored by TLC. The solvent was evaporated, diluted with water and acidified with 1N HCl (pH; 5-6) at 0° C. The aqueous layer was evaporated under reduced pressure, the crude was purified by GRACE using C-18 reserval column, Mobile phase A: 0.1% Formic Acid in water; B: ACN, the product was eluted at 50% of MeOH in 0.1% Formic Acid in water. The solvent was evaporated to afford (4S)-5-((7H-purin-2-yl)carbamoyl)-2,3,4,5-tetrahydro-1,4-methanopyrido[2,3-b][1,4]diazepine-7-carboxylic acid (200 mg, 0.486 mmol, 74.0% yield) as off white solid, LCMS (m/z): 367.0 [M+H]$^+$.

Synthesis of (4S)-methyl 5-((4-(2-methyloxazol-5-yl)pyrimidin-2-yl)carbamoyl)-2,3,4,5-tetrahydro-1,4-methanopyrido[2,3-b][1,4]diazepine-7-carboxylate To a stirred solution of (4S)-methyl 2,3,4,5-tetrahydro-1,4-methanopyrido[2,3-b][1,4]diazepine-7-carboxylate (1.4 g, 6.39 mmol) in Tetrahydrofuran (THF) (100 mL), triphosgene (1.516 g, 5.11 mmol) and triethylamine (5.34 mL, 38.3 mmol) were added and stirred for 30 min. After 30 min 4-(2-methyloxazol-5-yl)pyrimidin-2-amine (1.125 g, 6.39 mmol) was added and reaction was maintained at 90° C. for 16 hr under Nitrogen condition. Progress of the reaction was monitored by TLC and LCMS. The reaction mass was cooled to room temperature, diluted with water (100 mL), ethyl acetate (100 mL*2). The combined organic layer was washed with brine (50 mL), dried over Na$_2$SO$_4$ filtered, concentrated under reduced pressure to get the crude brown solid. The crude product was purified by combiflash chromatography using silica gel column (24 g, 50% EtOAc in pet ether). Column was eluted with a gradient of EtOAc in Hexane. Desired compound was eluted with 50% EtOAc in Hexane. Fractions containing pure compound were concentrated under reduced pressure to afford the (4S)-methyl 5-((4-(2-methyloxazol-5-yl)pyrimidin-2-yl)carbamoyl)-2,3,4,5-tetrahydro-1,4-methanopyrido[2,3-b][1,4]diazepine-7-carboxylate (1.2 g, 1.906 mmol, 29.9% yield) as an off-white color solid, LCMS (m/z): 422.16 [M+H]$^+$.

Synthesis of (4S)-5-((4-(2-methyloxazol-5-yl)pyrimidin-2-yl)carbamoyl)-2,3,4,5-tetrahydro-1,4-methanopyrido[2,3-b][1,4]diazepine-7-carboxylic acid

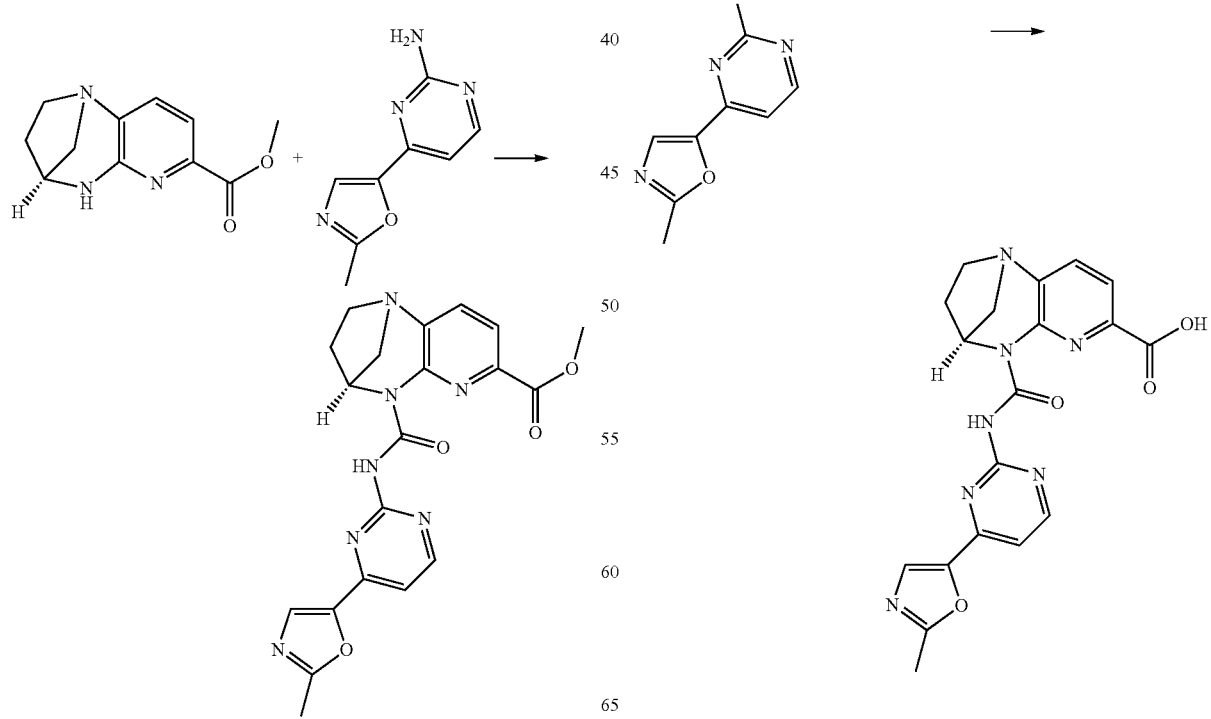

To a stirred solution of (4S)-methyl 5-((4-(2-methyloxazol-5-yl)pyrimidin-2-yl)carbamoyl)-2,3,4,5-tetrahydro-1, 4-methanopyrido[2,3-b][1,4]diazepine-7-carboxylate (1 g, 2.373 mmol) in Tetrahydrofuran (THF) (30 mL) and Water (10 mL), was added lithium hydroxide (0.057 g, 2.373 mmol). The reaction mixture was stirred at RT for 16 hr. Progress of the reaction was monitored by TLC, TLC indicated that formation of polar spot and total consumption of starting material. THF was evaporated completely, the reaction mixture was diluted with water (30 ml) and washed with ethyl acetate (20 ml*2). The aqueous layer pH was adjusted to acidic using citric acid, solid was not precipitated. The aqueous layer was extracted with DCM (2×50 ml). The organic layer was dried over anhydrous $Na_2SO_4$, filtered and concentrated under reduced pressure to obtain desired pure product (4S)-5-((4-(2-methyloxazol-5-yl)pyrimidin-2-yl)carbamoyl)-2,3,4,5-tetrahydro-1,4-methanopyrido[2,3-b][1,4]diazepine-7-carboxylic acid (500 mg, 1.151 mmol, 48.5% yield) as an brown solid, LCMS (m/z): 408.45 $[M+H]^+$.

Synthesis of (4S)-methyl 5-(thiazol-2-ylcarbamoyl)-2,3,4,5-tetrahydro-1,4-methanopyrido[2,3-b][1,4]diazepine-7-carboxylate

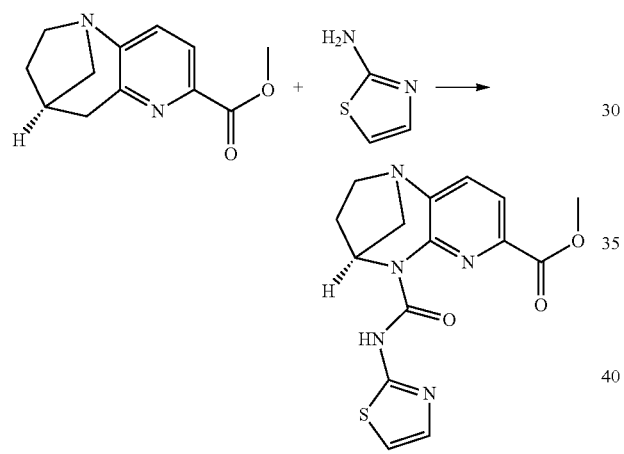

To a stirred solution of (4S)-methyl 2,3,4,5-tetrahydro-1,4-methanopyrido[2,3-b][1,4]diazepine-7-carboxylate (200 mg, 0.912 mmol), and TEA (0.763 mL, 5.47 mmol) in Tetrahydrofuran (THF) (50 mL) was added triphosgene (271 mg, 0.912 mmol) under nitrogen at 28° C. The reaction mixture was stirred at RT for 30 min and was added thiazol-2-amine (137 mg, 1.368 mmol). The reaction mixture was stirred 16 hr at 65° C. The reaction mixture was cooled to 28° C., the reaction mixture was partitioned between water (10 mL) and EtOAc (2×25 mL). Organic layer was separated and was dried over anhydrous $Na_2SO_4$, filtered and filtrate was evaporated to afford crude. The crude was purified by GRACE using C-18 reserval column, Mobile phase A: 0.1% Formic Acid in water; B: ACN, the product was eluted at 25% of ACN in 0.1% Formic Acid in water. The solvent was evaporated and was basified with saturated $NaHCO_3$. The aqueous layer was extracted with DCM, DCM layer was dried over anhydrous $Na_2SO_4$, filtered, and filtrate was evaporated to afford (4S)-methyl 5-(thiazol-2-ylcarbamoyl)-2,3,4,5-tetrahydro-1,4-methanopyrido[2,3-b][1,4]diazepine-7-carboxylate (100 mg, 0.239 mmol, 26.2% yield) as brown solid, LCMS (m/z): 346.01 $[M+H]^+$.

Synthesis of (4S)-5-(thiazol-2-ylcarbamoyl)-2,3,4,5-tetrahydro-1,4-methanopyrido[2,3-b][1,4]diazepine-7-carboxylic acid

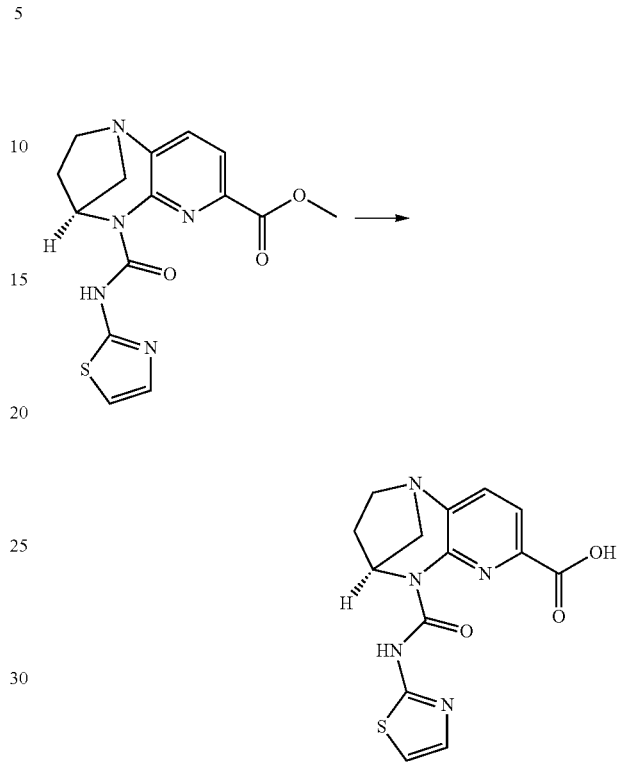

To a stirred solution of (4S)-methyl 5-(thiazol-2-ylcarbamoyl)-2,3,4,5-tetrahydro-1,4-methanopyrido[2,3-b][1,4]diazepine-7-carboxylate (100 mg, 0.290 mmol) in Tetrahydrofuran (THF) (10 mL), and Water (10 mL) was added LiOH (10.40 mg, 0.434 mmol). The Reaction mixture was stirred for 16 hr at 28° C. The reaction mixture was evaporated to afford crude residue, and was acidified with Aq. HCl solution (5 mL). The aqueous solution was extracted with DCM (20 mL). DCM layer was dried over anhydrous $Na_2SO_4$, filtered and filtrate was evaporated to afford crude. The crude was washed with diethyl ether to afford (4S)-5-(thiazol-2-ylcarbamoyl)-2,3,4,5-tetrahydro-1,4-methanopyrido[2,3-b][1,4]diazepine-7-carboxylic acid (50 mg, 0.150 mmol, 51.9% yield) as off white solid, LCMS (m/z): 332.09 $[M+H]^+$.

Synthesis of (4S)-methyl 5-(isothiazol-3-ylcarbamoyl)-2,3,4,5-tetrahydro-1,4-methanopyrido[2,3-b][1,4]diazepine-7-carboxylate

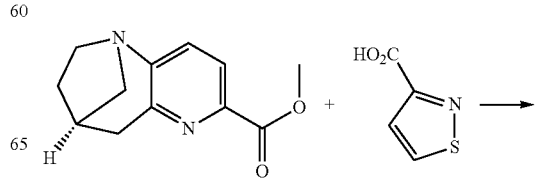

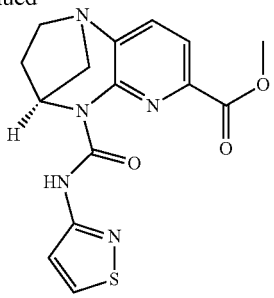

Procedure: To a stirred solution of isothiazole-3-carboxylic acid (700 g, 5.42 mmol) in Tetrahydrofuran (THF) (50 mL) was added TEA (0.756 mL, 5.42 mmol), and DPPA (1.032 mL, 5.42 mmol) at 0° C. The Reaction mixture was stirred for 2 h at 28° C. (4S)-methyl 2,3,4,5-tetrahydro-1,4-methanopyrido[2,3-b][1,4]diazepine-7-carboxylate (832 mg, 3.79 mmol) was added to the reaction mixture and the reaction mixture was stirred for 18 hr at 100° C. The reaction mixture was cooled to 28° C. and was partitioned between water (20 mL) and EtOAc (2×50 mL). EtOAc layer was separated and was dried over anhydrous Na$_2$SO$_4$, filtered and filtrate was evaporated to give crude as brown solid. The crude was purified by chromatography (GRACE using C-18 reserval column, Mobile phase A: 0.1% Formic Acid in water; B: ACN, eluent 45% B in A). Combined fractions were evaporated and basified with saturated NaHCO$_3$ solution. The aqueous layer was extracted with DCM, DCM layer was dried over anhydrous Na$_2$SO$_4$, filtered and filtrate was evaporated to afford pure (4S)-methyl 5-(isothiazol-3-ylcarbamoyl)-2,3,4,5-tetrahydro-1,4-methanopyrido[2,3-b][1,4]diazepine-7-carboxylate (500 mg, 1.374 mmol, 25.4% yield) as yellow solid, LCMS (m/z): 346.01 [M+H]$^+$.

Synthesis of (4S)-5-(isothiazol-3-ylcarbamoyl)-2,3,4,5-tetrahydro-1,4-methanopyrido[2,3-b][1,4]diazepine-7-carboxylic acid

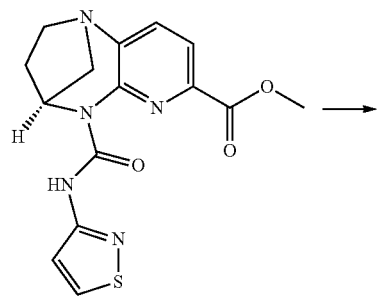

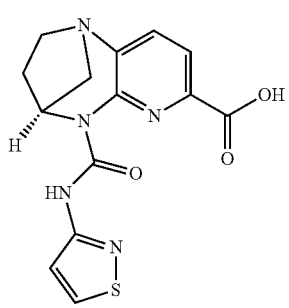

To a stirred solution of (4S)-methyl 5-(isothiazol-3-ylcarbamoyl)-2,3,4,5-tetrahydro-1,4-methanopyrido[2,3-b][1,4]diazepine-7-carboxylate (400 mg, 1.158 mmol) in Tetrahydrofuran (THF) (10 mL), and Water (10 mL) was added LiOH (41.6 mg, 1.737 mmol). The Reaction mixture was stirred for 16 h at 28° C. The reaction mixture was evaporated to afford crude residue, and was acidified with saturated Citric acid solution (10 mL). The aqueous solution was extracted with DCM (20 mL). DCM layer was dried over anhydrous Na$_2$SO$_4$, filtered and filtrate was evaporated to afford crude. The crude was washed with diethyl ether to afford (4S)-5-(isothiazol-3-ylcarbamoyl)-2,3,4,5-tetrahydro-1,4-methanopyrido[2,3-b][1,4]diazepine-7-carboxylic acid (350 mg, 0.462 mmol, 39.9% yield) as off white solid, LCMS (m/z): 332.34 [M+H]$^+$.

Synthesis of (4S)-methyl 5-(pyridin-3-ylcarbamoyl)-2,3,4,5-tetrahydro-1,4-methanopyrido[2,3-b][1,4]diazepine-7-carboxylate

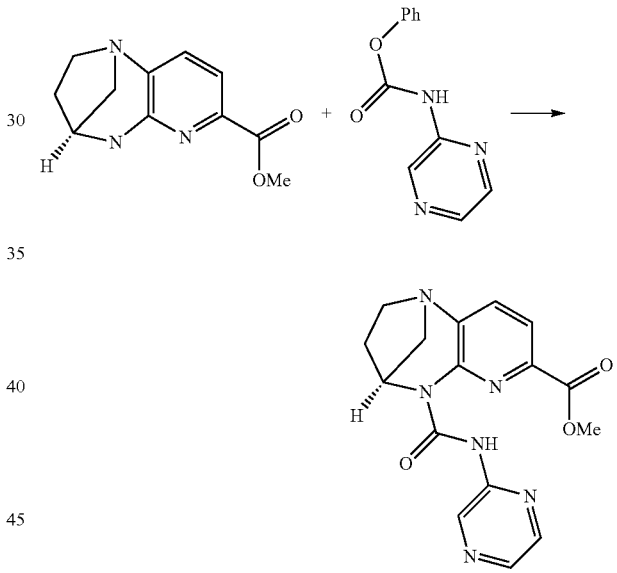

To a solution of (4S)-methyl 2,3,4,5-tetrahydro-1,4-methanopyrido[2,3-b][1,4]diazepine-7-carboxylate (1.7 g, 7.75 mmol), phenyl pyridin-3-ylcarbamate (4.15 g, 19.39 mmol) in Tetrahydrofuran (THF) (50 mL) was added DMAP (2.368 g, 19.39 mmol). The resulting mixture was stirred at 70° C. for 16 hr. After the completion of reaction (monitored by TLC, it shows absence of starting material and formation of new spot), concentrated the reaction mass to get the crude compound as a pale brown liquid. Purification: Crude material was purified by combi flash using silica gel column (24 g, 3% MeOH in DCM). Fractions containing pure compound were combined and concentrated to afford the desired product (4S)-methyl 5-(pyridin-3-ylcarbamoyl)-2,3,4,5-tetrahydro-1,4-methanopyrido[2,3-b][1,4]diazepine-7-carboxylate (2 g, 4.66 mmol, 60.2% yield) as an off-white solid, LCMS (m/z): 340.1 (M+H)$^+$.

Synthesis of (4S)-5-(pyridin-3-ylcarbamoyl)-2,3,4,5-tetrahydro-1,4-methanopyrido[2,3-b][1,4]diazepine-7-carboxylic acid

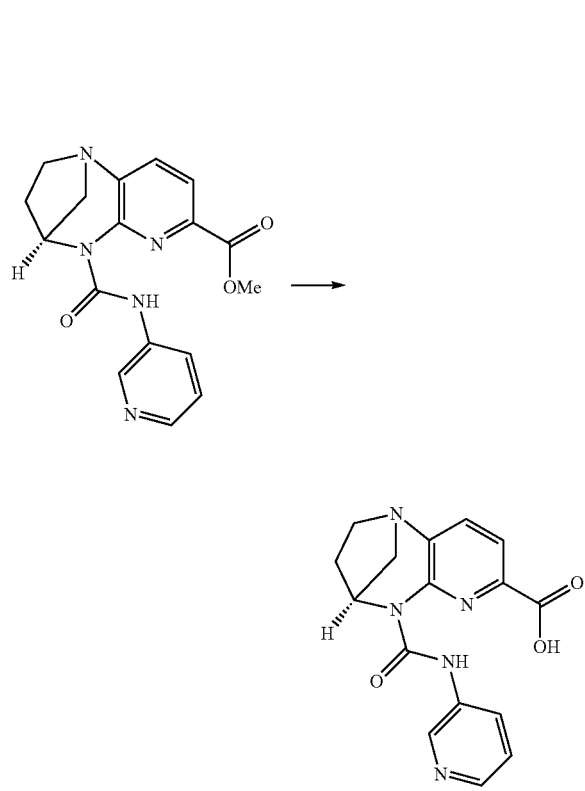

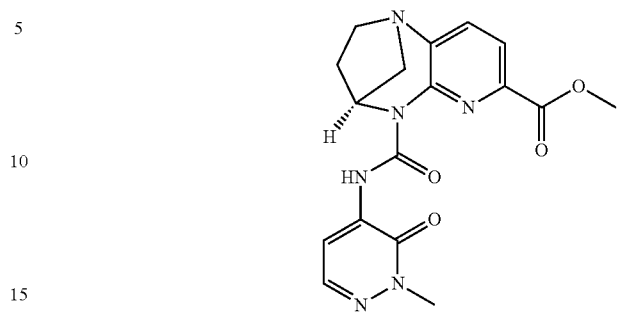

To solution of (4S)-methyl 5-(pyridin-3-ylcarbamoyl)-2,3,4,5-tetrahydro-1,4-methanopyrido[2,3-b][1,4]diazepine-7-carboxylate (2.00 g, 5.89 mmol) in Tetrahydrofuran (THF) (10 mL) was added Water (10 mL) followed by LiOH (0.282 g, 11.79 mmol) at rt. The resulting mixture was stirred at RT for 5 hr. After the completion of reaction (monitored by TLC, it shows absence of starting material and new spot at polar), Reaction mixture was concentrated under reduced pressure, obtained solid was dissolved in water (20 mL) and pH was adjusted to 5 with 1N HCl to get precipitation which was filtered and dried to afford pure compound (4S)-5-(pyridin-3-ylcarbamoyl)-2,3,4,5-tetrahydro-1,4-methanopyrido[2,3-b][1,4]diazepine-7-carboxylic acid (1.8 g, 5.49 mmol, 93% yield) as a white solid, LCMS (m/z): 326.09 (M+H)$^+$.

Synthesis of (4S)-methyl 5-((2-methyl-3-oxo-2,3-dihydropyridazin-4-yl)carbamoyl)-2,3,4,5-tetrahydro-1,4-methanopyrido[2,3-b][1,4]diazepine-7-carboxylate

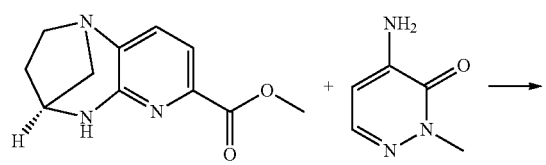

Triphosgene (1.354 g, 4.56 mmol) was added to a stirred solution of (4S)-methyl 2,3,4,5-tetrahydro-1,4-methanopyrido[2,3-b][1,4]diazepine-7-carboxylate (1 g, 4.56 mmol), and TEA (3.81 mL, 27.4 mmol) in Tetrahydrofuran (THF) (75 mL) under nitrogen at 28° C. The reaction mixture was stirred at RT for 30 min. and was added 4-amino-2-methylpyridazin-3(2H)-one (1.712 g, 13.68 mmol). The reaction mixture was stirred 16 hr at 65° C. The reaction mixture was cooled to 28° C., the reaction mixture was partitioned between water (2 mL) and EtOAc (2×25 mL). Organic layer was separated and was dried over anhydrous Na$_2$SO$_4$, filtered and filtrate was evaporated to give crude. The crude was purified by GRACE using C-18 reserval column, Mobile phase A: 0.1% Formic Acid in water; B: ACN, the product was eluted at 35% of ACN in 0.1% Formic Acid in water. The solvent was evaporated and was basified with saturated NaHCO$_3$. The precipitated solid was filtered, and was dried to afford (4S)-methyl 5-((2-methyl-3-oxo-2,3-dihydropyridazin-4-yl)carbamoyl)-2,3,4,5-tetrahydro-1,4-methanopyrido[2,3-b][1,4]diazepine-7-carboxylate (1.2 g, 2.92 mmol, 63.9% yield) as yellow solid, LCMS (m/z): 371.00 (M+H)$^+$.

Synthesis of (4S)-5-((2-methyl-3-oxo-2,3-dihydropyridazin-4-yl)carbamoyl)-2,3,4,5-tetrahydro-1,4-methanopyrido[2,3-b][1,4]diazepine-7-carboxylic acid

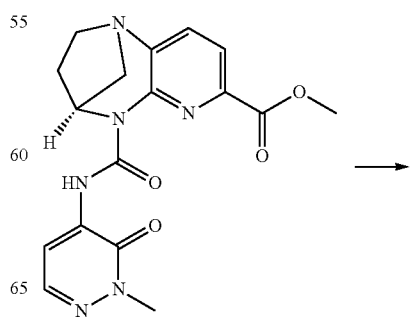

-continued

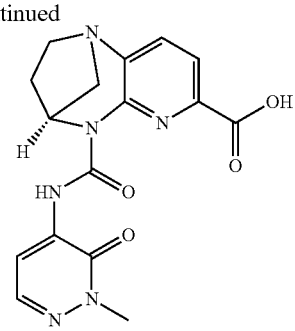

LiOH (0.155 g, 6.48 mmol) was added to a stirred solution of (4S)-methyl 5-((2-methyl-3-oxo-2,3-dihydropyridazin-4-yl)carbamoyl)-2,3,4,5-tetrahydro-1,4-methanopyrido[2,3-b][1,4]diazepine-7-carboxylate (1.2 g, 3.24 mmol) in Tetrahydrofuran (THF) (50 mL), and Water (50 mL). The Reaction mixture was stirred for 16 h at 28° C. The reaction mixture was evaporated to afford crude residue, and was acidified with 1N HCl solution. The precipitated solid was filtered and was dried to afford (4S)-5-((2-methyl-3-oxo-2,3-dihydropyridazin-4-yl)carbamoyl)-2,3,4,5-tetrahydro-1,4-methanopyrido[2,3-b][1,4]diazepine-7-carboxylic acid (770 mg, 1.855 mmol, 57.3% yield) as off white solid, LCMS (m/z): 357.00 (M+H)+.

Synthesis of (4S)-methyl 5-((3,4-dihydro-2H-pyrano[2,3-c]pyridin-6-yl)carbamoyl)-2,3,4,5-tetrahydro-1,4-methanopyrido[2,3-b][1,4]diazepine-7-carboxylate

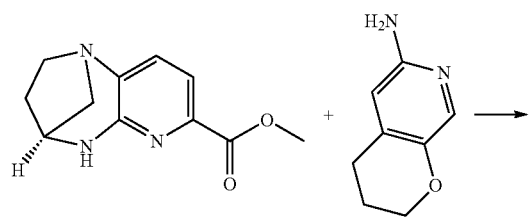

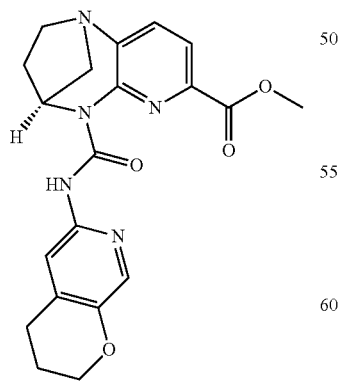

To a suspension of (4S)-methyl 2,3,4,5-tetrahydro-1,4-methanopyrido[2,3-b][1,4]diazepine-7-carboxylate (900 mg, 4.11 mmol) in Tetrahydrofuran (THF) (3 mL) was added 3,4-dihydro-2H-pyrano[2,3-c]pyridin-6-amine followed by triphosgene (1218 mg, 4.11 mmol) at RT. After stirring for 20 min, 3,4-dihydro-2H-pyrano[2,3-c]pyridin-6-amine (925 mg, 6.16 mmol) was added to the reaction mass and then the reaction mixture was stirred at 75° C. for 16 hr. After the completion of reaction (monitored by TLC, starting material consumed and the new spot was observed at just above of starting material as a major spot), water (70 mL) was added to the reaction mass and the aqueous layer was extracted with the ethyl acetate (2×10 ml). The organic layer was dried over $Na_2SO_4$ filtered and concentrated to get brown liquid. Purification: Crude material was purified by combi flash using silica gel column (12 g, 1.8% MeOH in DCM). Fractions containing pure compound were combined and concentrated to get the compound (4S)-methyl 5-((3,4-dihydro-2H-pyrano[2,3-c]pyridin-6-yl)carbamoyl)-2,3,4,5-tetrahydro-1,4-methanopyrido[2,3-b][1,4]diazepine-7-carboxylate (900 mg, 2.083 mmol, 50.7% yield) as a pale yellow solid. LCMS (m/z): 396.00 (M+H)+.

Synthesis of (4S)-5-((3,4-dihydro-2H-pyrano[2,3-c]pyridin-6-yl)carbamoyl)-2,3,4,5-tetrahydro-1,4-methanopyrido[2,3-b][1,4]diazepine-7-carboxylic acid

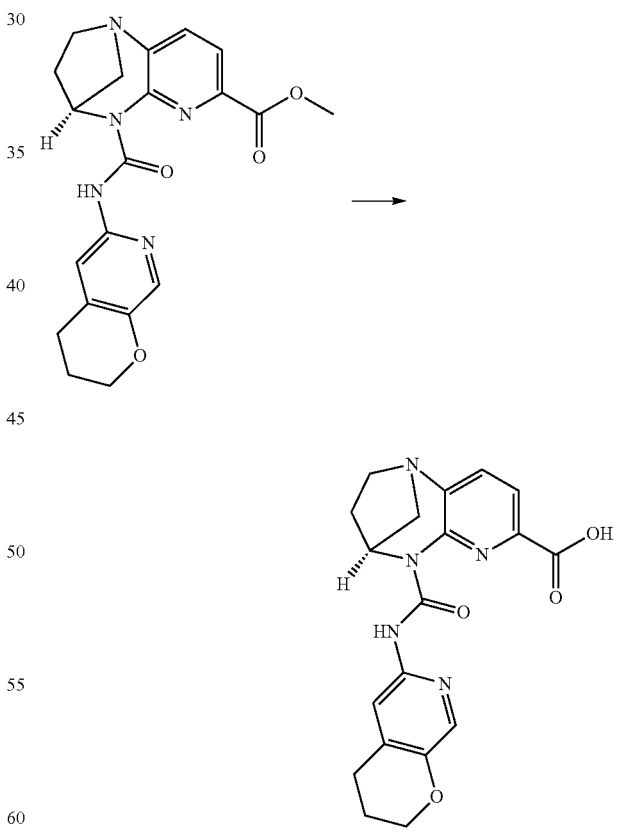

To a solution of (4S)-methyl 5-((3,4-dihydro-2H-pyrano[2,3-c]pyridin-6-yl)carbamoyl)-2,3,4,5-tetrahydro-1,4-methanopyrido[2,3-b][1,4]diazepine-7-carboxylate (900 mg, 2.276 mmol) in Tetrahydrofuran (THF) (5 mL) was added Water (5.00 mL) followed by LiOH (109 mg, 4.55 mmol). The resulting mixture was stirred at rt for 3 hr. After the completion of reaction (monitored by TLC, indicates absence of starting material and new spot was observed at polar), concentrated the reaction mass, the obtained solid was dissolved in water (5 mL) and the aqueous layer was acidified (pH=2) with 2N HCl. The aqueous layer was extracted with 10% MeOH in DCM (4×100 ML). The combined organics were dried over $Na_2SO_4$ filtered and concentrated to get (4S)-5-((3,4-dihydro-2H-pyrano[2,3-c]pyridin-6-yl)carbamoyl)-2,3,4,5-tetrahydro-1,4-methanopyrido[2,3-b][1,4]diazepine-7-carboxylic acid (550 mg, 1.393 mmol, 61.2% yield) as an off-white solid, LCMS (m/z): 382.1 $(M+H)^+$.

Synthesis of (4S)-methyl 5-((5H-pyrrolo[3,2-d]pyrimidin-2-yl)carbamoyl)-2,3,4,5-tetrahydro-1,4-methanopyrido[2,3-b][1,4]diazepine-7-carboxylate

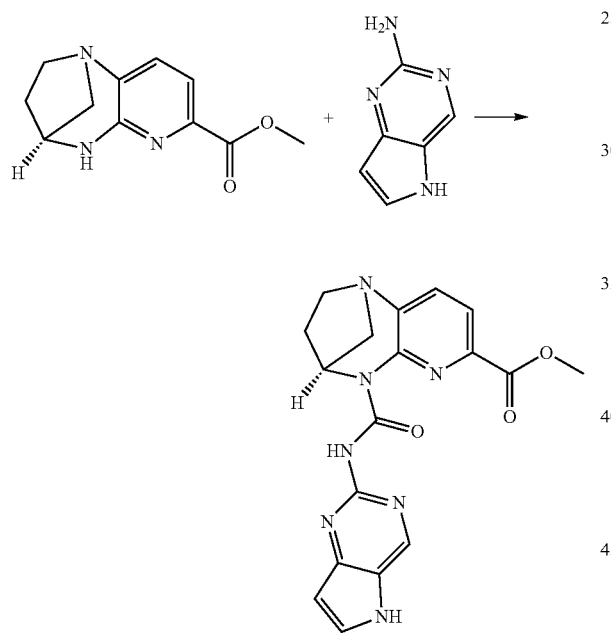

TEA (0.381 mL, 2.74 mmol) & triphosgene (0.135 g, 0.456 mmol) was added to a stirred solution of (4S)-methyl 2,3,4,5-tetrahydro-1,4-methanopyrido[2,3-b][1,4]diazepine-7-carboxylate (0.1 g, 0.456 mmol) in Tetrahydrofuran (THF) (10 mL) under nitrogen at 28° C. The reaction mixture was stirred at rt for 30 min and, was added 5H-pyrrolo[3,2-d]pyrimidin-2-amine (0.184 g, 1.368 mmol). The reaction mixture was stirred 16 hr at 65° C. The reaction mixture was cooled to room temp, solvent evaporated under reduced pressure completely and was partitioned between water (10 mL) and EtOAc (2×20 mL). Organic layer was separated, dried over anhydrous $Na_2SO_4$, filtered and filtrate was evaporated to afford (4S)-methyl 5-((5H-pyrrolo[3,2-d]pyrimidin-2-yl)carbamoyl)-2,3,4,5-tetrahydro-1,4-methanopyrido[2,3-b][1,4]diazepine-7-carboxylate (0.120 g, 0.142 mmol, 31.2% yield) as a brown solid, LCMS (m/z): 381.10 $[M+H]^+$.

Synthesis of (4S)-5-((5H-pyrrolo[3,2-d]pyrimidin-2-yl)carbamoyl)-2,3,4,5-tetrahydro-4-methanopyrido[2,3-b][1,4]diazepine-7-carboxylic acid

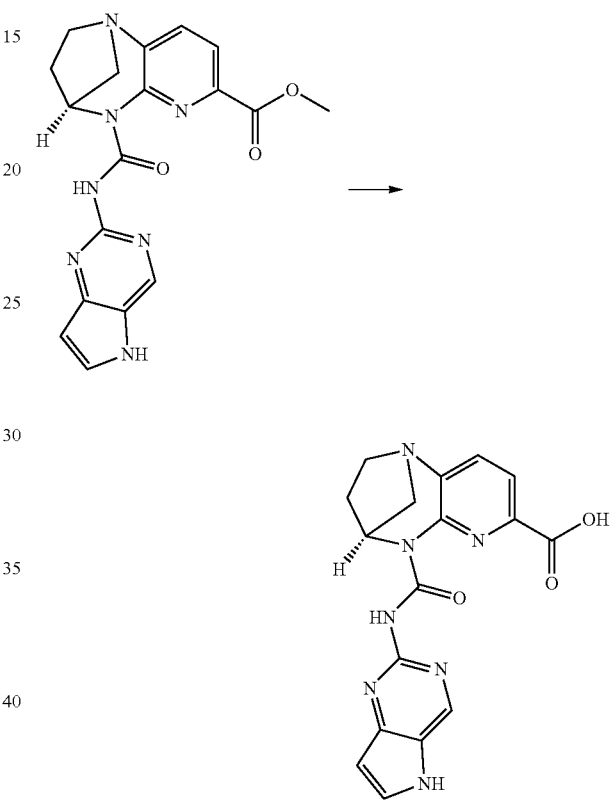

Lithium hydroxide mono hydrate (13.27 mg, 0.316 mmol) in Water (0.5 mL) was added to a stirred solution of (4S)-methyl 5-((5H-pyrrolo[3,2-d]pyrimidin-2-yl)carbamoyl)-2,3,4,5-tetrahydro-1,4-methanopyrido[2,3-b][1,4]diazepine-7-carboxylate (120 mg, 0.316 mmol) in Tetrahydrofuran (THF) (5 mL) at room temp. The reaction mixture was stirred at 26° C. for 2 hr. The reaction mixture solvent evaporated under reduced pressure completely and was acidified with 1N HCl solution. The reaction mixture was evaporated under reduced pressure completely, added 20% MeOH in DCM (10 ml) and stirred 15 min. Filtered the reaction mass through celite and washed with celite by 20% MeOH in DCM (5 ml). Take filtrate was evaporated to afford crude product (4S)-5-((5H-pyrrolo[3,2-d]pyrimidin-2-yl)carbamoyl)-2,3,4,5-tetrahydro-1,4-methanopyrido[2,3-b][1,4]diazepine-7-carboxylic acid (70 mg, 0.144 mmol, 45.4% yield) as a brown color solid, LCMS (m/z): 366.11 $[M+H]^+$.

Synthesis of (4S)—N7-(2,2,2-trifluoroethyl)-N5-(4-((trimethylsilyl)ethynyl)pyridin-2-yl)-3,4-dihydro-1,4-methanopyrido[2,3-b][1,4]diazepine-5,7(2H)-dicarboxamide

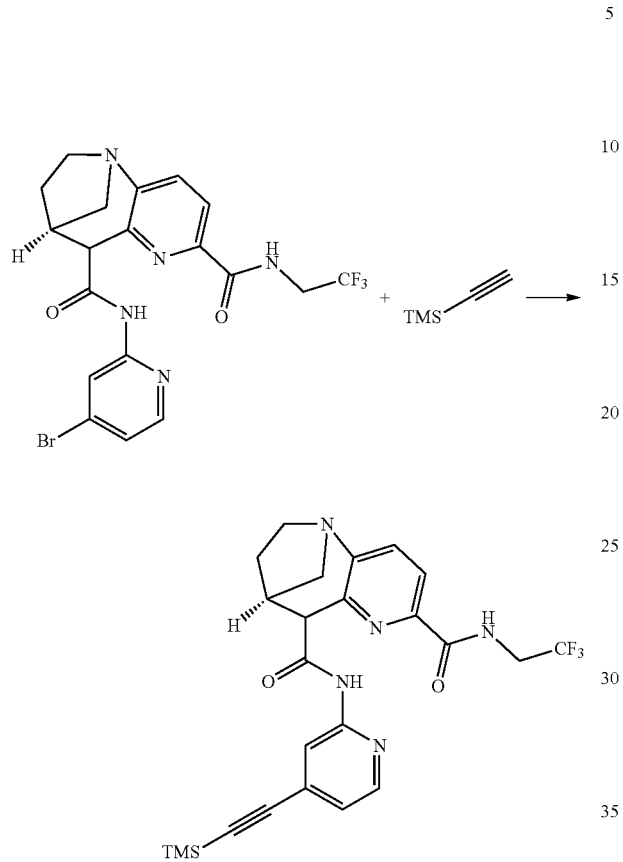

To a stirred solution of (4S)—N5-(4-bromopyridin-2-yl)-N7-(2,2,2-trifluoroethyl)-3,4-dihydro-1,4-methanopyrido[2,3-b][1,4]diazepine-5,7(2H)-dicarboxamide (1 g, 2.061 mmol) in Tetrahydrofuran (THF) (50 mL) was added copper (I) iodide (0.033 g, 0.172 mmol), TEA (2.394 mL, 17.17 mmol), ethynyltrimethylsilane (0.337 g, 3.43 mmol) and bis(triphenylphosphine)palladium(II) chloride (0.121 g, 0.172 mmol) under argon degassed at rt. The resulting reaction mixture was degassed for 20 minutes, after that resulting reaction mixture was stirred at 60° C. for 8 hr. The progress of the reaction was monitored by TLC. Reaction mixture was filtered on celite pad, filtrate was evaporated. The reaction mixture was diluted with ethyl acetate (100 ml) and washed with water. The organic layer was dried over $Na_2SO_4$ filtered, concentrated under reduced pressure to get crude compound. The crude compound was purified by combiflash using silica gel column (24 g, 50% EtOAc in pet ether). Fractions containing pure compound were combined and concentrated to afford the desired compound (4S)—N7-(2,2,2-trifluoroethyl)-N5-(4-((trimethylsilyl)ethynyl)pyridin-2-yl)-3,4-dihydro-1,4-methanopyrido[2,3-b][1,4]diazepine-5,7(2H)-dicarboxamide (700 mg, 0.885 mmol, 51.5% yield) as off-white solid, LCMS (m/z): 503.19 (M+H)+.

Synthesis of (4S)—N5-(4-bromopyridin-2-yl)-N7-(2,2,2-trifluoroethyl)-3,4-dihydro-1,4-methanopyrido[2,3-b][1,4]diazepine-5,7(2H)-dicarboxamide

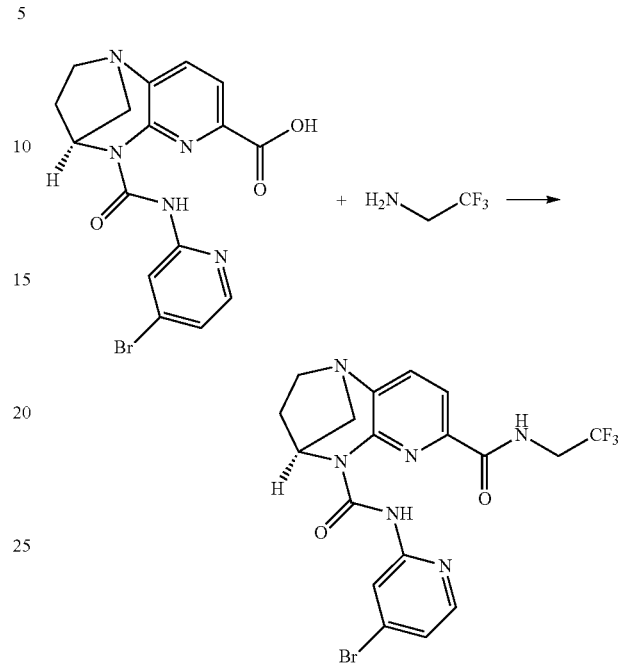

To a solution of (4S)-5-((4-bromopyridin-2-yl)carbamoyl)-2,3,4,5-tetrahydro-1,4-methanopyrido[2,3-b][1,4]diazepine-7-carboxylic acid (600 mg, 1.484 mmol) in N,N-Dimethylformamide (DMF) (15 mL) was added HATU (1129 mg, 2.97 mmol) followed by DIPEA (0.778 mL, 4.45 mmol) at 0° C., the resulting mixture was stirred at same temperature for 10 min. 2,2,2-trifluoroethanamine (294 mg, 2.97 mmol) was added to the reaction mass at 0° C. and the resulting solution was stirred at rt for 16 h. After the completion of reaction (monitored by TLC, indicates absence of starting material and formation of new spot at Rf: 0.5), added water (20 mL) to the reaction mass to get solid precipitation, which was filtered and dried to get (4S)—N5-(4-bromopyridin-2-yl)-N7-(2,2,2-trifluoroethyl)-3,4-dihydro-1,4-methanopyrido[2,3-b][1,4]diazepine-5,7(2H)-dicarboxamide (490 mg, 0.894 mmol, 60.2% yield) as a pale brown solid. LCMS (m/z): 484.9 (M+H)+.

Synthesis of (4S)—N5-(4-bromopyridin-2-yl)-N7-(cyclopropylmethyl)-3,4-dihydro-1,4-methanopyrido[2,3-b][1,4]diazepine-5,7(2H)-dicarboxamide

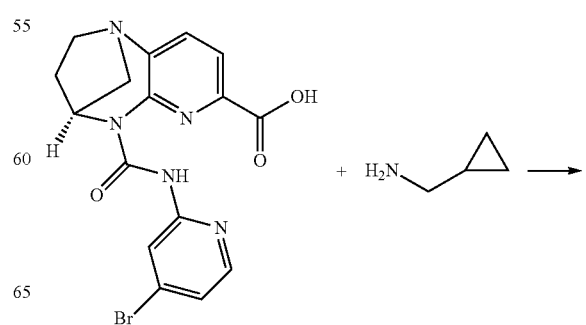

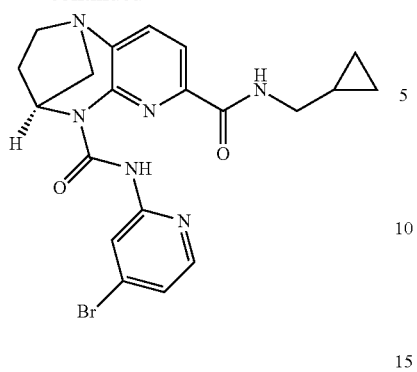

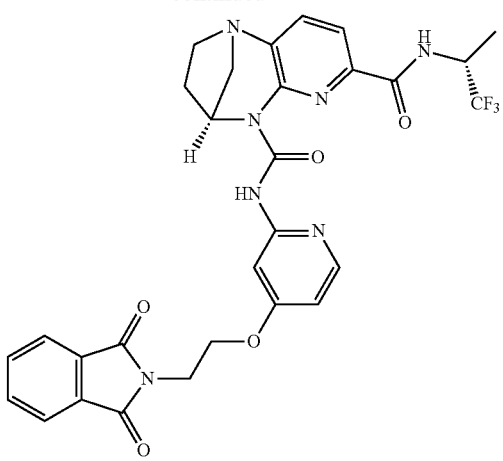

To a stirred solution of (4S)-5-((4-bromopyridin-2-yl)carbamoyl)-2,3,4,5-tetrahydro-1,4-methanopyrido[2,3-b][1,4]diazepine-7-carboxylic acid (500 mg, 1.237 mmol) in N,N-Dimethylformamide (DMF) (3 mL), were added DIPEA (0.648 mL, 3.71 mmol), HATU (941 mg, 2.474 mmol) and cyclopropylmethanamine (97 mg, 1.361 mmol) at 0° C., the reaction mixture was stirred at Room temperature for 4 hr. Reaction progress was monitored by TLC (5% MeOH in DCM). TLC indicated formation of a non-polar spot and complete consumption of SM. The reaction mass was diluted with 50 ml of ice cold water to get solid, which was filtered and dried under high vacuum to get (4S)—N5-(4-bromopyridin-2-yl)-N7-(cyclopropylmethyl)-3,4-dihydro-1,4-methanopyrido[2,3-b][1,4]diazepine-5,7(2H)-dicarboxamide (500 mg, 1.062 mmol, 86% yield) as pale yellow solid, LCMS (m/z): 457.15 [M+H]$^+$.

Synthesis of (4S)—N5-(4-(2-(1,3-dioxoisoindolin-2-yl)ethoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide X-phos (115 mg, 0.240 mmol) followed by K$_3$PO$_4$ (340 mg, 1.602 mmol) were added to a stirred solution of (4S)—N5-(4-bromopyridin-2-yl)-N7-((R)-1,1,1-trifluoropropan-2-yl)-3,4-dihydro-1,4-methanopyrido[2,3-b][1,4]diazepine-5,7(2H)-dicarboxamide (400 mg, 0.801 mmol) and 2-(2-hydroxyethyl)isoindoline-1,3-dione (230 mg, 1.202 mmol) in 1,4-Dioxane (20 mL) then degassed for 10 min by applying argon gas and Pd$_2$(dba)$_3$ (73.4 mg, 0.080 mmol) was added and heated to 100° C. for 16 h in sealed tube. The reaction mixture was cooled to RT then partitioned between water (20 mL) and ethyl acetate (20 mL×2) washed with brine (20 mL) and organic layer was separated and was dried over anhydrous Na$_2$SO$_4$, filtered and filtrate was evaporated to get crude (4S)—N5-(4-(2-(1,3-dioxoisoindolin-2-yl)ethoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (400 mg, 0.302 mmol, 37.7% yield) as a brown gum, LCMS (m/z): 610.88 (M+H)$^+$.

Synthesis of (4S)—N5-(4-bromopyridin-2-yl)-N7-((S)-1,1,1-trifluoropropan-2-yl)-3,4-dihydro-1,4-methanopyrido[2,3-b][1,4]diazepine-5,7(2H)-dicarboxamide

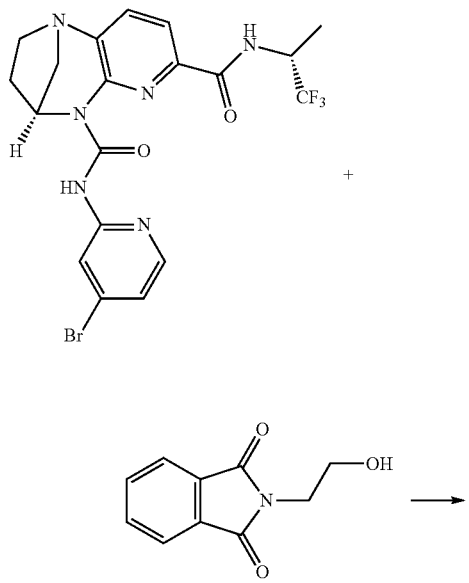

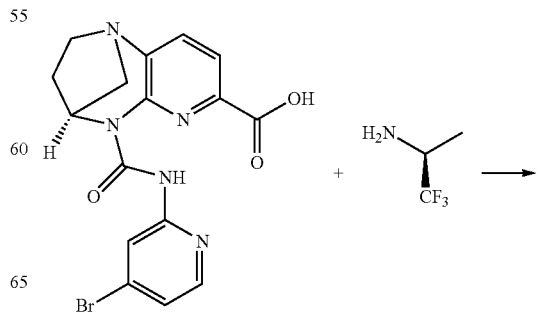

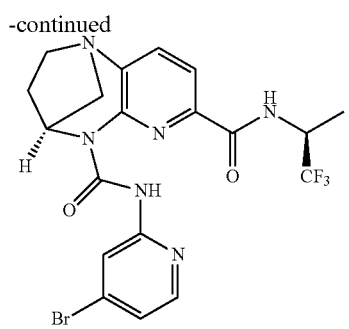

To a stirred solution of (4S)-5-((4-bromopyridin-2-yl)carbamoyl)-2,3,4,5-tetrahydro-1,4-methanopyrido[2,3-b][1,4]diazepine-7-carboxylic acid (1 g, 2.474 mmol) in N,N-Dimethylformamide (DMF) (4 mL), were added DIPEA (1.296 mL, 7.42 mmol), HATU (1.881 g, 4.95 mmol) and (S)-1,1,1-trifluoropropan-2-amine (0.336 g, 2.97 mmol) at Room temperature, the reaction mixture was stirred at Room temperature for 16 hr under Nitrogen. Progress of the reaction was monitored by TLC. TLC indicated formation of a non-polar spot and complete consumption of SM. Reaction mixture was diluted with cold water (20 ml), the resulting solid formed was collected by filtration, washed with water (10 mL) and dried to give (4S)—N5-(4-bromopyridin-2-yl)-N7-((S)-1,1,1-trifluoropropan-2-yl)-3,4-dihydro-1,4-methanopyrido[2,3-b][1,4]diazepine-5,7(2H)-dicarboxamide (1 g, 1.356 mmol, 54.8% yield) as off white solid. LCMS (m/z): 499.0 [M+H]$^+$.

Synthesis of (4S)—N5-(4-bromopyridin-2-yl)-N7-cyclopropyl-3,4-dihydro-1,4-methanopyrido[2,3-b][1,4]diazepine-5,7(2H)-dicarboxamide

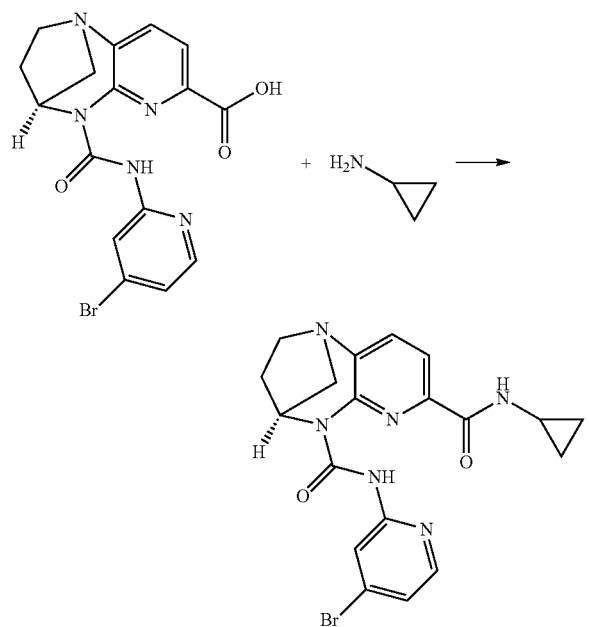

To a solution of (4S)-5-((4-bromopyridin-2-yl)carbamoyl)-2,3,4,5-tetrahydro-1,4-methanopyrido[2,3-b][1,4]diazepine-7-carboxylic acid (600 mg, 1.484 mmol) in N,N-Dimethylformamide (DMF) (15 mL) was added HATU (1129 mg, 2.97 mmol) followed by DIPEA (0.778 mL, 4.45 mmol) at 0° C., the resulting mixture was stirred at same temperature for 10 min. cyclopropanamine (169 mg, 2.97 mmol) was added to the reaction mass at 0° C. and the resulting solution was stirred at rt for 16 h. After the completion of reaction (monitored by TLC, indicates absence of starting material and formation of new spot at Rf: 0.5), added water (20 mL) to the reaction mass to get solid precipitation, which was filtered and dried to get (4S)—N5-(4-bromopyridin-2-yl)-N7-cyclopropyl-3,4-dihydro-1,4-methanopyrido[2,3-b][1,4]diazepine-5,7(2H)-dicarboxamide (500 mg, 0.965 mmol, 65.0% yield) as a light brown solid. LCMS (m/z): 442.9 (M+H)$^+$.

Synthesis of (4S)—N5-(4-bromopyridin-2-yl)-N7-((R)-1,1,1-trifluoropropan-2-yl)-3,4-dihydro-1,4-methanopyrido[2,3-b][1,4]diazepine-5,7(2H)-dicarboxamide

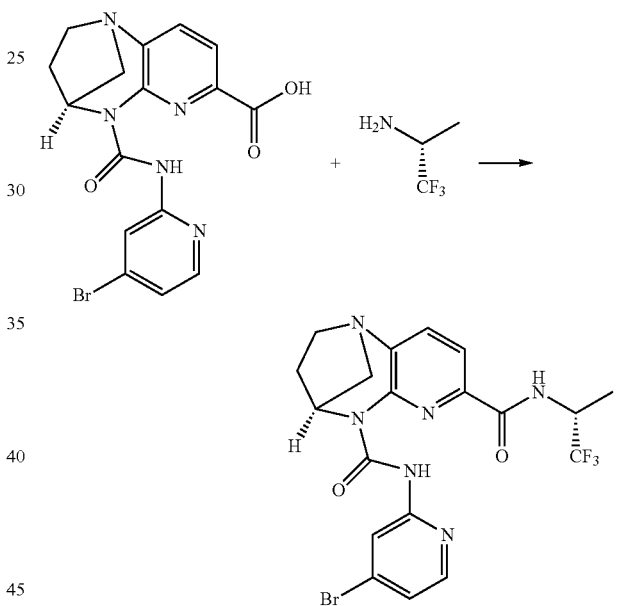

To a solution of (4S)-5-((4-bromopyridin-2-yl)carbamoyl)-2,3,4,5-tetrahydro-1,4-methanopyrido[2,3-b][1,4]diazepine-7-carboxylic acid (6.5 g, 16.08 mmol) in N,N-Dimethylformamide (DMF) (70 mL) was added HATU (12.23 g, 32.2 mmol) followed by DIPEA (8.43 mL, 48.2 mmol) at 0° C., the resulting mixture was stirred at same temperature for 10 min. (R)-1,1,1-trifluoropropan-2-amine (3.64 g, 32.2 mmol) was added to the reaction mass at 0° C. and the resulting solution was stirred at rt for 16 h. After the completion of reaction (monitored by TLC, indicates absence of starting material and formation of new spot at R$_f$: 0.5), added water (100 mL) to the reaction mass to get solid precipitation, which was filtered and dried to get off-white solid. The obtained solid was stirred in diethyl ether (70 mL), filtered and dried to give (4S)—N5-(4-bromopyridin-2-yl)-N7-((R)-1,1,1-trifluoropropan-2-yl)-3,4-dihydro-1,4-methanopyrido[2,3-b][1,4]diazepine-5,7(2H)-dicarboxamide (6 g, 10.95 mmol, 68.1% yield) as an off-white solid, LCMS (m/z): 499.13 (M+H)$^+$.

Synthesis of (4S)-5-((4-bromopyridin-2-yl)carbamoyl)-2,3,4,5-tetrahydro-1,4-methanopyrido[2,3-b][1,4]diazepine-7-carboxylic acid

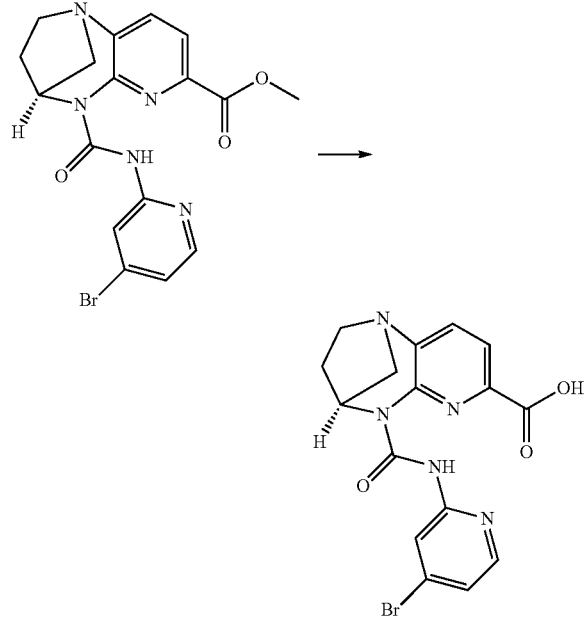

To a solution of (4S)-methyl 5-((4-bromopyridin-2-yl)carbamoyl)-2,3,4,5-tetrahydro-1,4-methanopyrido[2,3-b][1,4]diazepine-7-carboxylate (2.5 g, 5.98 mmol) in Tetrahydrofuran (THF) (20 mL) was added Water (10 mL) and LiOH (0.429 g, 17.93 mmol). Resulting reaction mixture was stirred at rt for 5 hr. After the completion of reaction (monitored by TLC, it shows absence of SM and formation of new spot at polar), concentrated the reaction mass to get off-white solid which was dissolved in water. pH of the aqueous layer was adjusted to 4 to get precipitation which was filtered and dried to get pale brown solid. Obtained solid was triturated with diethyl ether to get pure compound (4S)-5-((4-bromopyridin-2-yl)carbamoyl)-2,3,4,5-tetrahydro-1,4-methanopyrido[2,3-b][1,4]diazepine-7-carboxylic acid (1.7 g, 4.13 mmol, 69.1% yield) as an off-white solid, LCMS (m/z): 404.02 (M+H)$^+$.

Synthesis of (4S)—N5-(4-bromopyridin-2-yl)-N7-(1,1,1-trifluoro-3-hydroxypropan-2-yl)-3,4-dihydro-1,4-methanopyrido[2,3-b][1,4]diazepine-5,7(2H)-dicarboxamide

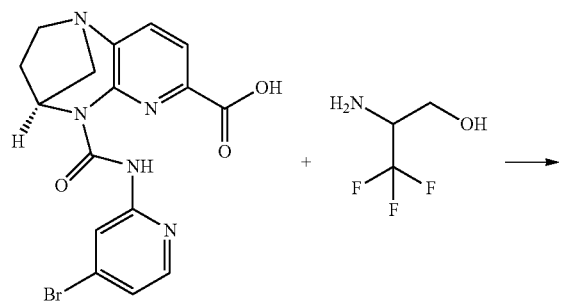

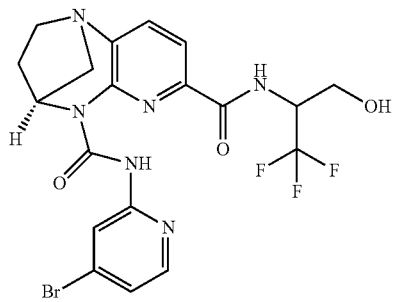

To a stirred solution of 2-amino-3,3,3-trifluoropropan-1-ol hydrochloride (0.491 g, 2.97 mmol) in N,N-Dimethylformamide (DMF) (5 mL), were added DIPEA (1.296 mL, 7.42 mmol), HATU (1.881 g, 4.95 mmol) and (4S)-5-((4-bromopyridin-2-yl)carbamoyl)-2,3,4,5-tetrahydro-1,4-methanopyrido[2,3-b][1,4]diazepine-7-carboxylic acid (1 g, 2.474 mmol) at room temperature, the reaction mixture was stirred at Room temperature for 16 hr under Nitrogen. Progress of the reaction was monitored by TLC. TLC indicated formation of a non-polar spot and complete consumption of SM. Reaction mixture was diluted with cold water (30 ml), extracted with EtOAc (2×50 mL). The combined organic layer was washed with brine (25 mL), dried over Na$_2$SO$_4$, filtered and concentrated under reduced pressure to give crude compound. Crude material was purified by combiflash using silica gel column (24 g, 5% methanol in DCM). Fraction containing pure compound were combined and concentration to afford the desired compound which was triturated with ACN (8 mL) to give (4S)—N5-(4-bromopyridin-2-yl)-N7-(1,1,1-trifluoro-3-hydroxypropan-2-yl)-3,4-dihydro-1,4-methanopyrido[2,3-b][1,4]diazepine-5,7(2H)-dicarboxamide (650 mg, 1.128 mmol, 45.6% yield) as off-white solid, LCMS (m/z): 514.96 [M+H]$^+$.

Synthesis of (4S)-methyl 5-((4-bromopyridin-2-yl)carbamoyl)-2,3,4,5-tetrahydro-1,4-methanopyrido[2,3-b][1,4]diazepine-7-carboxylate

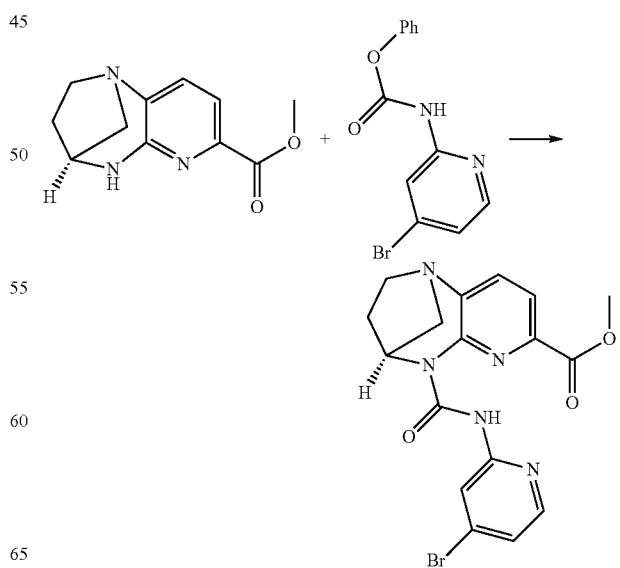

A mixture of (4S)-methyl 2,3,4,5-tetrahydro-1,4-methanopyrido[2,3-b][1,4]diazepine-7-carboxylate (2.5 g, 11.40 mmol), phenyl (4-bromopyridin-2-yl)carbamate (6.68 g, 22.81 mmol) and Tetrahydrofuran (THF) (50 mL) were charged into 100 ml sealed tube. DMAP (2.79 g, 22.81 mmol) was added to the mixture and the resulting mixture was stirred at 70° C. for 16 hr. After the completion of reaction (monitored by TLC, starting completely consumed and new spot observed at $R_f$: 0.5), concentrated the reaction mass and dried to get crude compound as a brown liquid. Crude material was purified by silica gel column (100-200, 3% MeOH in DCM). Fractions containing pure compound were combined and concentrated to afford the desired product (4S)-methyl 5-((4-bromopyridin-2-yl)carbamoyl)-2,3,4,5-tetrahydro-1,4-methanopyrido[2,3-b][1,4]diazepine-7-carboxylate (3.00 g, 6.25 mmol, 54.8% yield). LCMS (m/z): 418.06 (M+H)$^+$.

Synthesis of (4S)—N5-(4-bromopyridin-2-yl)-8-chloro-N7-((R)-1,1,1-trifluoropropan-2-yl)-3,4-dihydro-1,4-methanopyrido[2,3-b][1,4]diazepine-5,7 (2H)-dicarboxamide

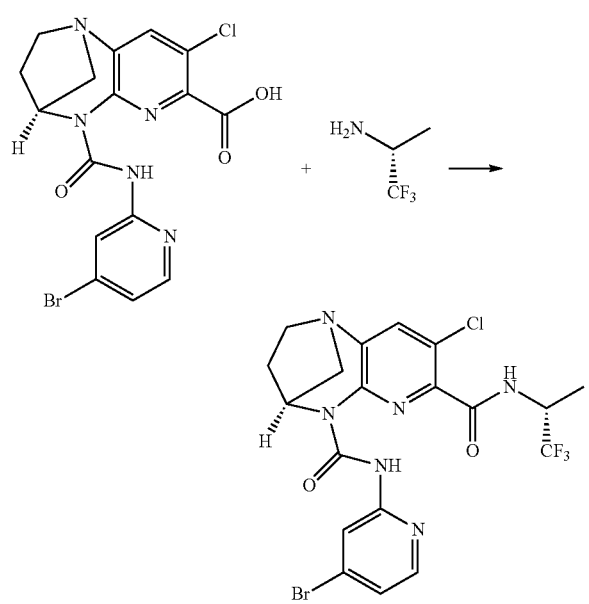

To a solution of (4S)-5-((4-bromopyridin-2-yl)carbamoyl)-8-chloro-2,3,4,5-tetrahydro-1,4-methanopyrido[2,3-b][1,4]diazepine-7-carboxylic acid (2 g, 4.56 mmol) in N,N-Dimethylformamide (DMF) (10 mL) at room temperature, was added HATU (3.47 g, 9.12 mmol) and DIPEA (2.389 mL, 13.68 mmol). The resulting reaction mixture was stirred for 10 min, then added (R)-1,1,1-trifluoropropan-2-amine (0.619 g, 5.47 mmol). The resulting reaction mixture was stirred at room temperature for 16 hr. Progress of the reaction was monitored by TLC. TLC indicated a non polar spot along with small amount of SM. To the reaction mass was diluted 100 ml ice cool water, extracted with EtOAc (2×200 ml), combined organic layer were washed with 100 ml of ice cooled water, dried over Na$_2$SO$_4$, filtered and concentrated to get crude. Crude material was purified by combiflash using silica gel column (24 g, 3% methanol in DCM). Fractions containing pure compound were combined and concentrated to afford the desired (4S)—N5-(4-bromopyridin-2-yl)-8-chloro-N7-((R)-1,1,1-trifluoropropan-2-yl)-3,4-dihydro-1,4-methanopyrido[2,3-b][1,4]diazepine-5,7(2H)-dicarboxamide (1.6 g, 2.95 mmol, 64.8% yield) as an off white solid. LCMS (m/z): 534.96 (M+H)$^+$.

Synthesis of (4S)-5-((4-bromopyridin-2-yl)carbamoyl)-8-chloro-2,3,4,5-tetrahydro-1,4-methanopyrido [2,3-b][1,4]diazepine-7-carboxylic acid

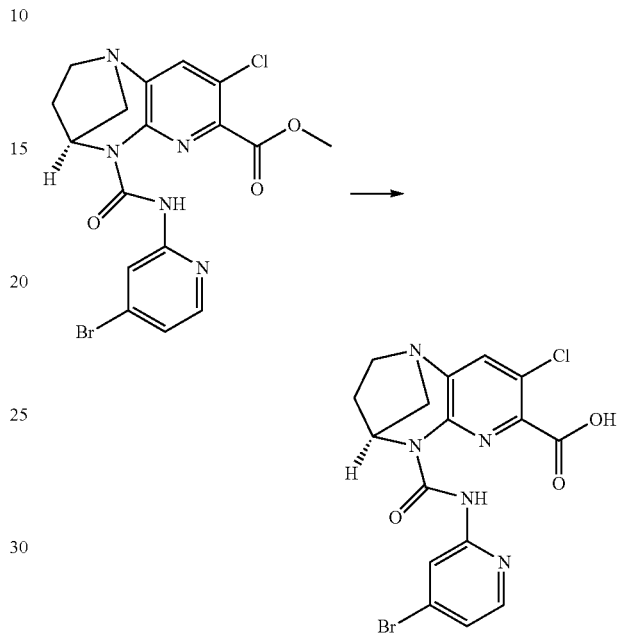

To a suspension of (4S)-methyl 5-((4-bromopyridin-2-yl)carbamoyl)-8-chloro-2,3,4,5-tetrahydro-1,4-methanopyrido[2,3-b][1,4]diazepine-7-carboxylate (4.5 g, 9.94 mmol), in Tetrahydrofuran (THF) (50 mL) stirred at room temperature, was added a solution of LiOH (0.595 g, 24.85 mmol) in Water (20 mL). The reaction mixture was stirred at room temperature for 16 hr. Progress of the reaction was monitored by TLC. TLC indicated formation of polar spot and complete consumption of SM. Reaction mass was concentrated under reduced pressure, added 20 ml of water and washed with 50 ml of EtOAc. pH of aqueous layer was adjusted to 4 with IN HCl at 0° C. Solid was formed, filtered and dried to get (4S)-5-((4-bromopyridin-2-yl)carbamoyl)-8-chloro-2,3,4,5-tetrahydro-1,4-methanopyrido[2,3-b][1,4]diazepine-7-carboxylic acid (4 g, 8.81 mmol, 89% yield) as off white solid, LCMS (m/z): 439.94 (M+H)$^+$.

Synthesis of (4S)-methyl 5-((4-bromopyridin-2-yl) carbamoyl)-8-chloro-2,3,4,5-tetrahydro-1,4-methanopyrido[2,3-b][1,4]diazepine-7-carboxylate

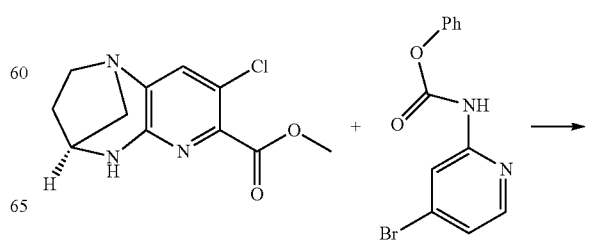

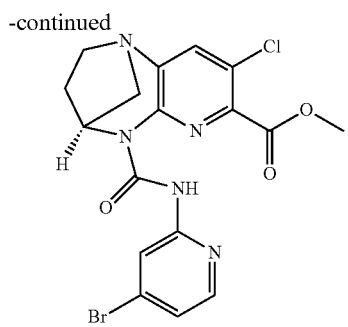

A mixture of (4S)-methyl 8-chloro-2,3,4,5-tetrahydro-1,4-methanopyrido[2,3-b][1,4]diazepine-7-carboxylate (5.5 g, 21.68 mmol), phenyl (4-bromopyridin-2-yl)carbamate (9.53 g, 32.5 mmol) and Tetrahydrofuran (THF) (120 mL) were charged into 250 ml of sealed tube. DMAP (6.62 g, 54.2 mmol) was added to the mixture, resulting reaction mixture was stirred at 70° C. for 16 hr. Progress of the reaction was monitored by TLC. TLC indicated formation of two non polar spots.

Reaction mass was concentrated under reduced pressure to get crude. Crude material was purified by column chromatography over silica gel (100-200 mesh, 1% MeOH in DCM). Fractions containing pure compound were combined and concentrated to afford the desired compound (4S)-methyl 5-((4-bromopyridin-2-yl)carbamoyl)-8-chloro-2,3,4,5-tetrahydro-1,4-methanopyrido[2,3-b][1,4]diazepine-7-carboxylate (4.6 g, 7.83 mmol, 36.1% yield) as pale green solid, LCMS (m/z): 453.99 (M+H)⁺.

Synthesis of (4S)-8-chloro-5-(pyridin-2-ylcarbamoyl)-2,3,4,5-tetrahydro-1,4-methanopyrido[2,3-b][1,4]diazepine-7-carboxylic acid

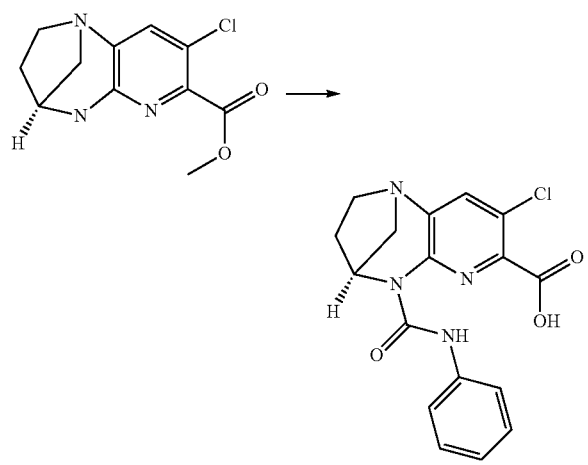

To a solution of (4S)-methyl 8-chloro-2,3,4,5-tetrahydro-1,4-methanopyrido[2,3-b][1,4]diazepine-7-carboxylate (800 mg, 3.15 mmol) in Tetrahydrofuran (THF) (20 mL) stirred under nitrogen at 0° C. was added NaH (378 mg, 15.77 mmol) and stirred for 30 min, then 3-(pyridin-2-yl)-2H-pyrido[1,2-a][1,3,5]triazine-2,4(3H)-dione (909 mg, 3.78 mmol) was added. The reaction mixture was stirred for 16 at 80° C. Reaction mixture was quenched with 2×15 ml of ice water and extracted with ethyl acetate, aqueous layer was neutralized with 1N HCl solution and extracted with 2×25 ml of 5% methanol in DCM, organic layer was dried over Na₂SO₄ and concentrated under reduced pressure to afford compound (4S)-8-chloro-5-(pyridin-2-ylcarbamoyl)-2,3,4,5-tetrahydro-1,4-methanopyrido[2,3-b][1,4]diazepine-7-carboxylic acid (500 mg, 1.390 mmol, 44.1% yield) as pale brown solid, LCMS (m/z): 359.9 (M+H)⁺.

Synthesis of (4S)-methyl 8-chloro-2,3,4,5-tetrahydro-1,4-methanopyrido[2,3-b][1,4]diazepine-7-carboxylate

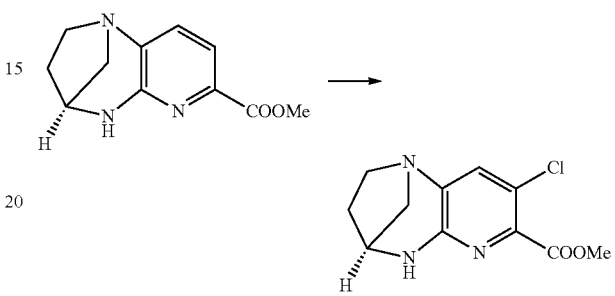

To a solution of (4S)-methyl 2,3,4,5-tetrahydro-1,4-methanopyrido[2,3-b][1,4]diazepine-7-carboxylate (3 g, 13.68 mmol) in Chloroform (50 mL) stirred under nitrogen at room temp was added NCS (1.827 g, 13.68 mmol). The reaction mixture was stirred at 60° C. for 16 hr. Reaction mixture was quenched with water and extracted with 2×50 ml of DCM, organic layer was dried over Na₂SO₄ and concentrated under reduced pressure to afford crude compound. The crude product was purified by flash column chromatography with 100-200 silica gel and was eluted with 70% ethyl acetate in pet ether to afford pure compound (4S)-methyl 8-chloro-2,3,4,5-tetrahydro-1,4-methanopyrido[2,3-b][1,4]diazepine-7-carboxylate (2 g, 7.88 mmol, 57.6% yield) as brown solid, LCMS (m/z): 253.9 (M+H)⁺.

Synthesis of (4S)-methyl 8-chloro-5-((6-methyl-1H-pyrazolo[3,4-b]pyridin-3-yl)carbamoyl)-2,3,4,5-tetrahydro-1,4-methanopyrido[2,3-b][1,4]diazepine-7-carboxylate

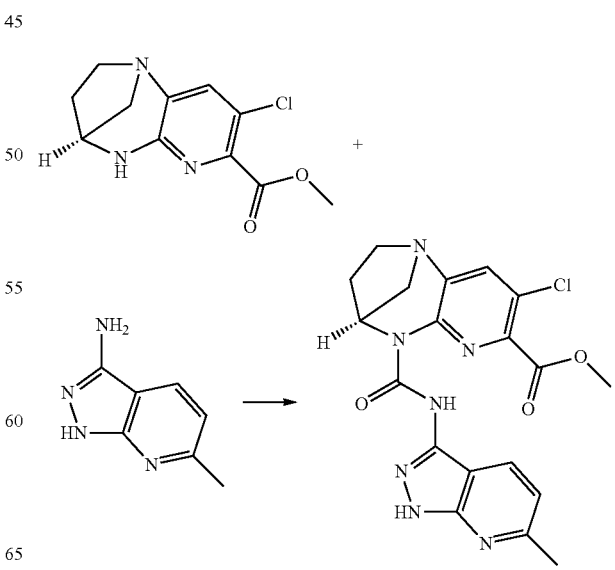

To a stirred solution of (4S)-methyl 8-chloro-2,3,4,5-tetrahydro-1,4-methanopyrido[2,3-b][1,4]diazepine-7-carboxylate (1 g, 3.94 mmol) in Tetrahydrofuran (THF) (30 mL), triphosgene (0.936 g, 3.15 mmol) and triethylamine (3.30 mL, 23.65 mmol) were added and stirred for 30 min. After 30 min 6-methyl-1H-pyrazolo[3,4-b]pyridin-3-amine (1.168 g, 7.88 mmol) was added and reaction was maintained at 75° C. for 6 hr under Nitrogen condition. Reaction progress was monitored by TLC (TLC shows 3 major spots, no SM spot was observed). Water (150 ml) was added to the reaction mixture. Solid was formed and filtered the crude compound. Diethyl ether (2×35 ml) wash was given to the crude compound to get pure (4S)-methyl 8-chloro-5-((6-methyl-1H-pyrazolo[3,4-b]pyridin-3-yl)carbamoyl)-2,3,4,5-tetrahydro-1,4-methanopyrido[2,3-b][1,4]diazepine-7-carboxylate (1.1 g, 2.502 mmol, 63.5% yield) as a brown color compound, LCMS (m/z): 428.33 (M+H)+.

Synthesis of (4S)-8-chloro-5-((6-methyl-1H-pyrazolo[3,4-b]pyridin-3-yl)carbamoyl)-2,3,4,5-tetrahydro-1,4-methanopyrido[2,3-b][1,4]diazepine-7-carboxylic acid

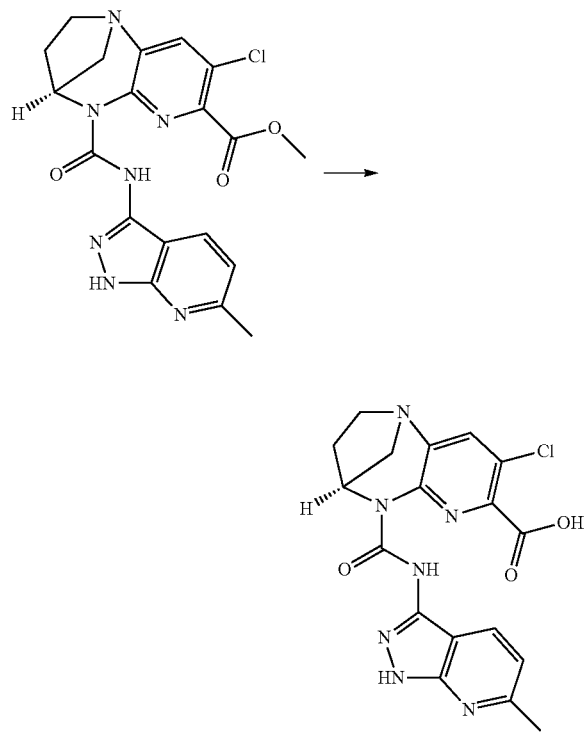

To a solution of (4S)-methyl 8-chloro-5-((6-methyl-1H-pyrazolo[3,4-b]pyridin-3-yl)carbamoyl)-2,3,4,5-tetrahydro-1,4-methanopyrido[2,3-b][1,4]diazepine-7-carboxylate (1 g, 2.337 mmol) in Tetrahydrofuran (THF) (15 mL) and Water (10 mL) was added LiOH (0.168 g, 7.01 mmol) at rt. The resulting suspension was stirred at rt for 3 hr. After the completion of reaction (monitored by TLC, starting material completely consumed and the new spot observed at polar). Concentrated the reaction mass and the obtained material was dissolved in water. The aqueous solution was adjusted pH to 5 with 2N HCl (aqueous) to get pale yellow colored precipitation, which was filtered and dried in vacuum to get pale yellow solid. Obtained solid was triturated with diethyl ether (20 mL) and dried to get (4S)-8-chloro-5-((6-methyl-1H-pyrazolo[3,4-b]pyridin-3-yl)carbamoyl)-2,3,4,5-tetrahydro-1,4-methanopyrido[2,3-b][1,4]diazepine-7-carboxylic acid (900 mg, 1.957 mmol, 84% yield) as light yellow solid, LCMS (m/z): 414.00 (M+H)+.

Synthesis of (2R)-3,3,3-trifluoro-2-((4S)-5-(pyridin-2-ylcarbamoyl)-2,3,4,5-tetrahydro-1,4-methanopyrido[2,3-b][1,4]diazepine-7-carboxamido)propyl methanesulfonate

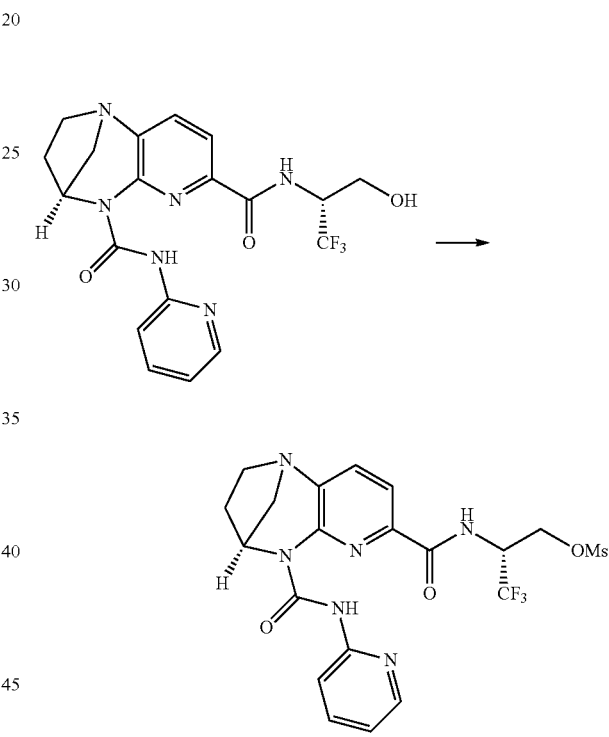

To a solution of (4S)—N5-(pyridin-2-yl)-N7-((R)-1,1,1-trifluoro-3-hydroxypropan-2-yl)-3,4-dihydro-1,4-methanopyrido[2,3-b][1,4]diazepine-5,7(2H)-dicarboxamide (350 mg, 0.802 mmol) and DIPEA (0.140 mL, 0.802 mmol) in Dichloromethane (DCM) (5 mL) stirred under nitrogen at room temp was added neat methanesulfonyl chloride (0.062 mL, 0.802 mmol). The reaction mixture was stirred at room temperature for 1 hr. Progress of the reaction was monitored by TLC. TLC indicated formation of a non-polar spot and complete consumption of SM. Reaction mixture was poured in cold water (30 ml), extracted with DCM (2×30 ml), separated the organic layer, washed with brine (25 mL), dried over anhydrous $Na_2SO_4$, filtered and concentrated under reduced pressure to obtain (2R)-3,3,3-trifluoro-2-((4S)-5-(pyridin-2-ylcarbamoyl)-2,3,4,5-tetrahydro-1,4-methanopyrido[2,3-b][1,4]diazepine-7-carboxamido)propyl methanesulfonate (300 mg, 0.517 mmol, 64.5% yield) as pale brown high viscous liquid, LCMS (m/z): 515.12[M+H]+.

211

Synthesis of tert-butyl (3,3,3-trifluoro-2-((4S)-5-(pyridin-2-ylcarbamoyl)-2,3,4,5-tetrahydro-1,4-methanopyrido[2,3-b][1,4]diazepine-7-carboxamido)propyl)carbamate

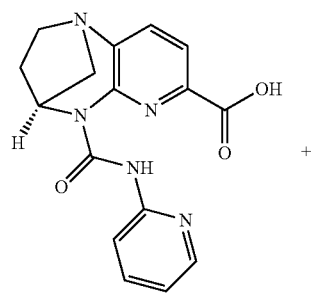

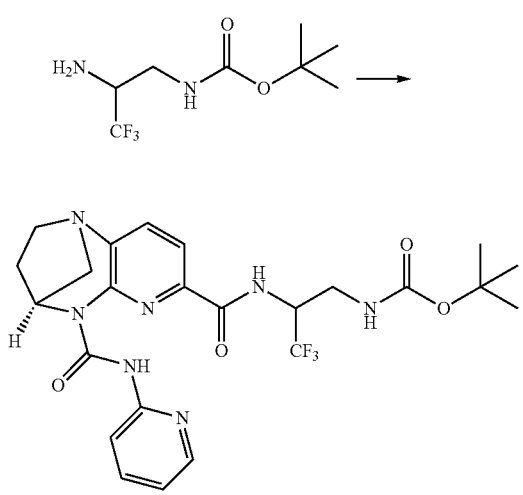

To a solution of (4S)-5-(pyridin-2-ylcarbamoyl)-2,3,4,5-tetrahydro-1,4-methanopyrido[2,3-b][1,4]diazepine-7-carboxylic acid (1.1 g, 3.38 mmol), DIPEA (2.95 mL, 16.91 mmol) and HATU (2.57 g, 6.76 mmol) in N,N-Dimethylformamide (DMF) (8 mL) stirred under nitrogen at room temp was added tert-butyl (2-amino-3,3,3-trifluoropropyl) carbamate (0.772 g, 3.38 mmol) in one charge. The reaction mixture was stirred at room temperature for 16 hr. Progress of the reaction was monitored by TLC. TLC indicated formation of a non-polar spot and complete consumption of SM. Reaction mixture was diluted with cold water (30 ml), extracted with EtOAc (2×40 ml), separated the organic layer, washed with brine (30 mL) dried over anhydrous Na$_2$SO$_4$, filtered and concentrated under reduced pressure to obtain crude. Crude material was purified by combiflash using silica gel column (24 g, 4% methanol in DCM). Fraction containing pure compound were combined and concentration to afford the desired compound tert-butyl (3,3,3-trifluoro-2-((4S)-5-(pyridin-2-ylcarbamoyl)-2,3,4,5-tetrahydro-1,4-methanopyrido[2,3-b][1,4]diazepine-7-car-

212 boxamido)propyl)carbamate (1.1 g, 1.684 mmol, 49.8% yield) as off white solid. LCMS (m/z): 536.23 [M+H]$^+$.

Synthesis of (4S)-phenyl 7-(cyclopropylcarbamoyl)-3,4-dihydro-1,4-methanopyrido[2,3-b][1,4]diazepine-5(2H)-carboxylate

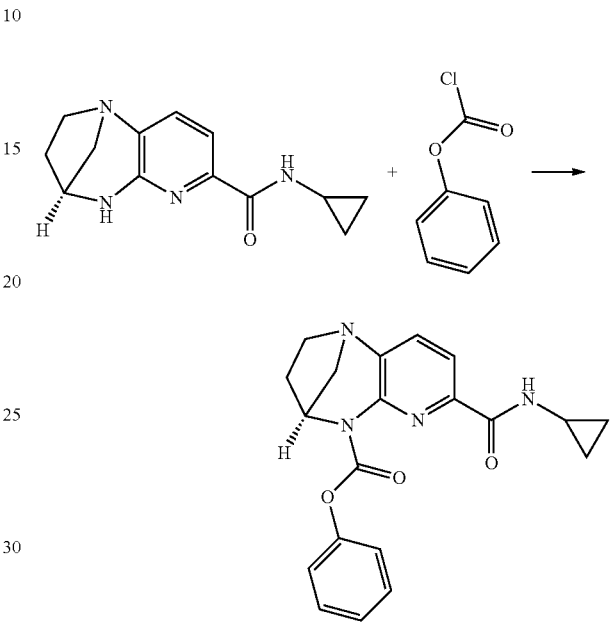

To a solution of (4S)—N-cyclopropyl-2,3,4,5-tetrahydro-1,4-methanopyrido[2,3-b][1,4]diazepine-7-carboxamide (3.5 g, 14.33 mmol), in Dichloromethane (DCM) (30 mL) stirred under nitrogen at 0° C. was added Pyridine (5 mL) and phenyl carbonochloridate (2.243 g, 14.33 mmol). The reaction mixture was stirred at room temperature for 4 hr. Progress of the reaction was monitored by TLC. TLC indicated formation of a non-polar spot and complete consumption of SM. Reaction mixture was poured in cold water (50 ml), extracted with DCM (2×50 ml). Combined organic layer was washed with brine (40 mL) dried over anhydrous Na$_2$SO$_4$, filtered and concentrated under reduced pressure to obtain crude. The crude product was washed with pentane (100 mL) to give (4S)-phenyl 7-(cyclopropylcarbamoyl)-3,4-dihydro-1,4-methanopyrido[2,3-b][1,4]diazepine-5(2H)-carboxylate (3.2 g, 8.09 mmol, 56.5% yield) as pale brown solid, LCMS (m/z): 365.02 [M+H]$^+$.

Synthesis of (4S)-phenyl 7-((cyclopropylmethyl)carbamoyl)-3,4-dihydro-1,4-methanopyrido[2,3-b][1,4]diazepine-5(2H)-carboxylate

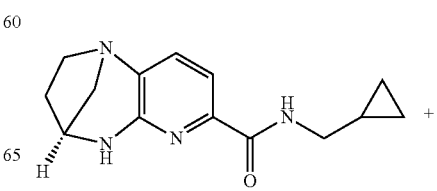

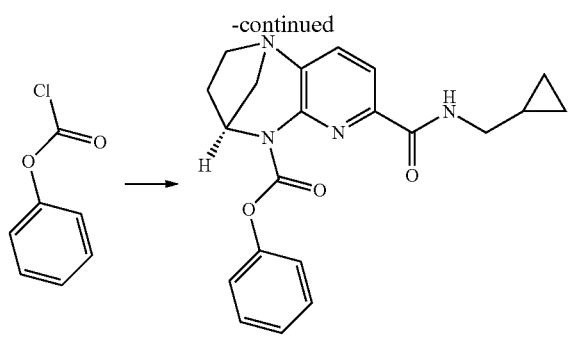

To a stirred solution of (4S)—N-(cyclopropylmethyl)-2,3,4,5-tetrahydro-1,4-methanopyrido[2,3-b][1,4]diazepine-7-carboxamide (5 g, 19.36 mmol) in Dichloromethane (DCM) (50 mL) and Pyridine (6 mL, 74.2 mmol), was added phenyl carbonochloridate (3.64 g, 23.23 mmol) at 0° C. The resulting reaction mixture was stirred at rt for 6 hr. Progress of the reaction was monitored by TLC. TLC indicates total consumption of starting material and formation of new non polar spot. Water (5 mL), was added to the reaction mixture. The aqueous layer was extracted with DCM (2×5 mL), the combined organic layer was dried over anhydrous $Na_2SO_4$, filtered and concentrated under reduced pressure to obtain desired crude product which was purified by column chromatography by using 100-2000 silica gel to afford (4S)-phenyl 7-((cyclopropylmethyl)carbamoyl)-3,4-dihydro-1,4-methanopyrido[2,3-b][1,4]diazepine-5(2H)-carboxylate (3.5 g, 8.42 mmol, 43.5% yield) as white color solid, LCMS (m/z): 379.12 [M+H]$^+$.

Synthesis of (4S)—N-(cyclopropylmethyl)-2,3,4,5-tetrahydro-1,4-methanopyrido[2,3-b][1,4]diazepine-7-carboxamide

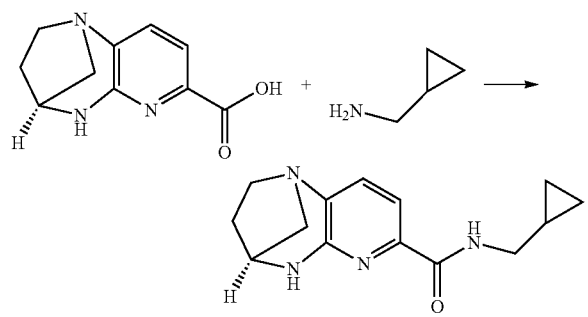

To a suspension of (4S)-2,3,4,5-tetrahydro-1,4-methanopyrido[2,3-b][1,4]diazepine-7-carboxylic acid (1 g, 4.87 mmol) in N,N-Dimethylformamide (DMF) (10 mL), were added DIPEA (4.26 mL, 24.36 mmol), HATU (3.71 g, 9.75 mmol) and cyclopropylmethanamine (0.416 g, 5.85 mmol) at 0° C., the reaction mixture was stirred at RT for 5 hr. Reaction progress was monitored by TLC. (10% MeOH in DCM). $R_f$: 0.2. TLC indicated formation of a non-polar spot and complete consumption of SM. The reaction mixture was concentrated and Residue was taken in EtOAc (100 ml) and organic layer was washed with water, followed by brine solution. Organic layer was dried over $Na_2SO_4$, filtered and concentrated to get crude product. (4S)—N-(cyclopropylmethyl)-2,3,4,5-tetrahydro-1,4-methanopyrido[2,3-b][1,4]diazepine-7-carboxamide (600 mg, 1.649 mmol, 33.8% yield) as white solid. LCMS (m/z): 259.35[M+H]$^+$.

Synthesis of (4S)—N-cyclopropyl-2,3,4,5-tetrahydro-1,4-methanopyrido[2,3-b][1,4]diazepine-7-carboxamide

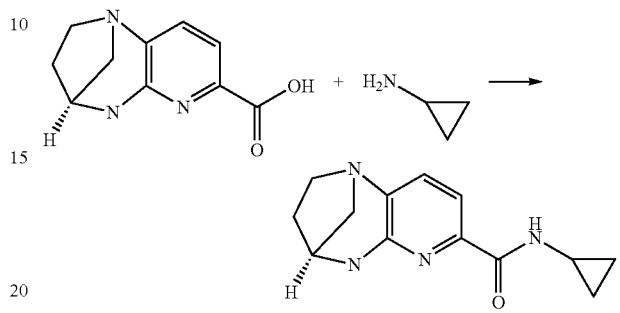

To a stirred solution of (4S)-2,3,4,5-tetrahydro-1,4-methanopyrido[2,3-b][1,4]diazepine-7-carboxylic acid (5.0 g, 24.36 mmol) in N,N-Dimethylformamide (DMF) (50 mL) was added HATU (13.90 g, 36.5 mmol) and TEA (16.98 mL, 122 mmol) at 0° C., reaction mixture was stirred at 0° C. for 15 min under Nitrogen atmosphere, then cyclopropanamine (2.78 g, 48.7 mmol) was added to the reaction mixture and stirred at rt for 4 hr. Progress of the reaction was monitored by TLC, TLC indicates SM was consumed and non-polar spot was formed. Reaction mixture was diluted with ice cold water (100 mL), extracted with EtOAc (3×50 mL), organic layers were combined and washed with water (30 mL), brine solution (30 mL), organic layer dried over anhydrous $Na_2SO_4$, filtered and concentrated under vacuum to get crude compound, crude was purified by column chromatography using 100-200 mesh silica gel and eluted the compound in 5% MeOH in DCM, pure fractions were collected and evaporated under reduced pressure to afford (4S)—N-cyclopropyl-2,3,4,5-tetrahydro-1,4-methanopyrido[2,3-b][1,4]diazepine-7-carboxamide (2.7 g, 10.63 mmol, 43.6% yield) as a brown sticky solid. LCMS (m/z): 245.17 (M+H)$^+$.

Synthesis of (4S)-2,3,4,5-tetrahydro-1,4-methanopyrido[2,3-b][1,4]diazepine-7-carboxylic acid

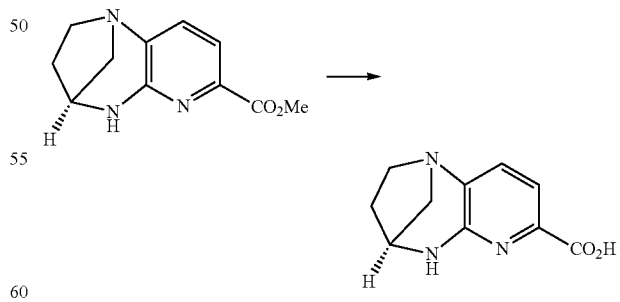

To a solution of (4S)-methyl 2,3,4,5-tetrahydro-1,4-methanopyrido[2,3-b][1,4]diazepine-7-carboxylate (10 g, 45.6 mmol), in Tetrahydrofuran (THF) (100 mL) stirred under nitrogen at room temp, was added a solution of LiOH (3.28 g, 137 mmol) in Water (100 mL) dropwise during 1 min. The reaction mixture was stirred at room temperature for 16 hr. Progress of the reaction was monitored by TLC. TLC indicated formation of a polar spot and complete consumption of SM. Reaction mixture was concentrated under reduced pressure, diluted with cold water (100 ml), washed with DCM (2×200 mL), aq layer was neutralized with 1N HCl (40 mL) to get sticky solid, extracted with 20% MeOH\DCM (2×300), separated the organic layer washed with brine (100 mL) dried over anhydrous $Na_2SO_4$, filtered and concentrated under reduced pressure to get (4S)-2,3,4,5-tetrahydro-1,4-methanopyrido[2,3-b][1,4]diazepine-7-carboxylic acid (8 g, 24.56 mmol, 53.9% yield) as off white solid, LCMS (m/z): 206.1 $[M+H]^+$.

Synthesis of (4S)—N-(2,2,2-trifluoroethyl)-2,3,4,5-tetrahydro-1,4-methanopyrido[2,3-b][1,4]diazepine-7-carboxamide

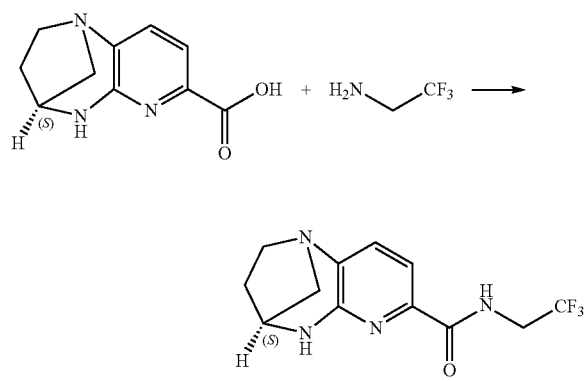

To a stirred solution of (4S)-2,3,4,5-tetrahydro-1,4-methanopyrido[2,3-b][1,4]diazepine-7-carboxylic acid (6 g, 29.2 mmol) in N,N-Dimethylformamide (DMF) (60 mL) was added HATU (16.68 g, 43.9 mmol) and TEA (12.23 mL, 88 mmol) at 0° C. under Nitrogen atmosphere. The resulting reaction mixture was stirred at 0° C. for 15 min, then 2,2,2-trifluoroethanamine (4.34 g, 43.9 mmol) was added to the reaction mixture at 0° C. The resulting reaction mixture was stirred at room temperature for 16 hr. Progress of the reaction was monitored by TLC, TLC indicated SM was consumed and non-polar spot was formed. Reaction mixture was diluted with ice cold water (100 mL), extracted with EtOAc (3×50 mL). Organic layers were combined and washed with water (30 ml), brine solution (30 mL), dried over anhydrous $Na_2SO_4$. Organic layer was filtered and concentrated under vacuum to get crude compound which was purified by column chromatography using 100-200 mesh silica gel and eluted the desired compound with 6% MeOH in DCM, pure fractions were collected and evaporated under reduced pressure to afford (4S)—N-(2,2,2-trifluoroethyl)-2,3,4,5-tetrahydro-1,4-methanopyrido[2,3-b][1,4]diazepine-7-carboxamide (4.5 g, 14.06 mmol, 48.1% yield) as brown sticky compound, LCMS (m/z): 287.04 $[M+H]^+$.

Synthesis of methyl 6-((4S)-7-((2,2,2-trifluoroethyl)carbamoyl)-2,3,4,5-tetrahydro-1,4-methanopyrido[2,3-b][1,4]diazepine-5-carboxamido)nicotinate

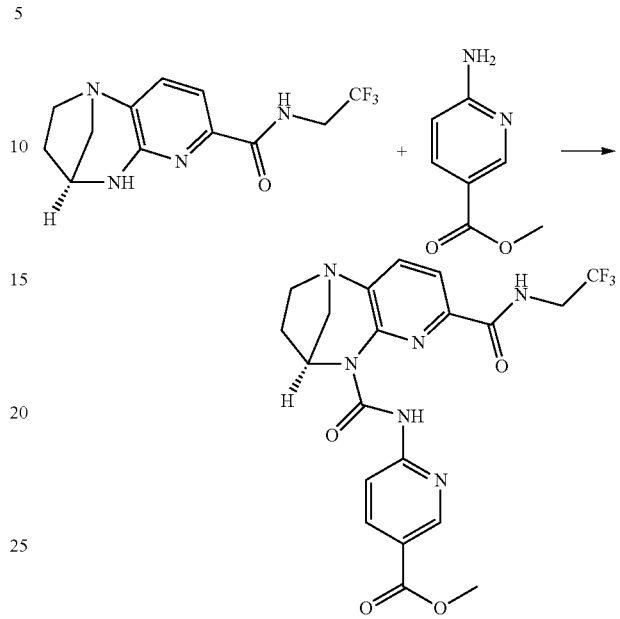

To a stirred solution of (4S)—N-(2,2,2-trifluoroethyl)-2,3,4,5-tetrahydro-1,4-methanopyrido[2,3-b][1,4]diazepine-7-carboxamide (4.5 g, 15.72 mmol) in Tetrahydrofuran (THF) (60 mL) was added triphosgene (4.66 g, 15.72 mmol) and TEA (6.57 mL, 47.2 mmol) at room temperature under Nitrogen atmosphere. The resulting reaction mixture was stirred at room temperature for 1 hr. To the reaction mixture was added a solution of methyl 6-aminonicotinate (4.78 g, 31.4 mmol) in Tetrahydrofuran (THF) (40 mL) at room temperature. The resulting reaction mixture was stirred at 80° C. for 16 hr. Progress of the reaction was monitored by TLC. TLC indicated non polar spot was formed along with SM. Reaction mixture was diluted with water (100 mL), extracted with EtOAc (3×100 mL). Organic layers were combined and washed with brine solution (50 mL), dried over anhydrous $Na_2SO_4$, filtered and concentrated under reduced pressure to get crude compound that was then purified by column chromatography using 100-200-mesh silica gel and eluted the desired compound with 3% MeOH in DCM, pure fractions were collected and evaporated under reduced pressure to afford methyl 6-((4S)-7-((2,2,2-trifluoroethyl)carbamoyl)-2,3,4,5-tetrahydro-1,4-methanopyrido[2,3-b][1,4]diazepine-5-carboxamido)nicotinate (3.5 g, 4.92 mmol, 31.3% yield) as a brown Solid, LCMS (m/z): 465.15 $[M+H]^+$.

Synthesis of (4S)-phenyl 7-((2,2,2-trifluoroethyl)carbamoyl)-3,4-dihydro-1,4-methanopyrido[2,3-b][1,4]diazepine-5(2H)-carboxylate

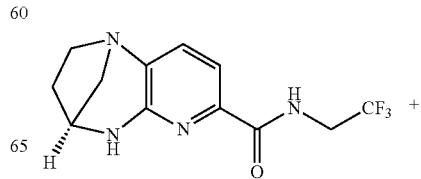

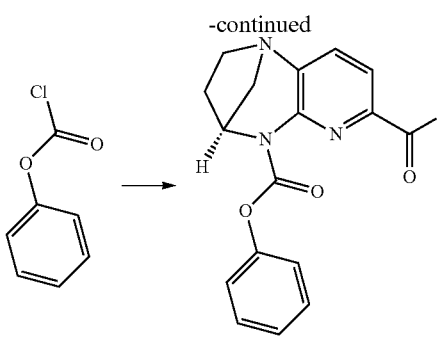

To a stirred solution of (4S)—N-(2,2,2-trifluoroethyl)-2,3,4,5-tetrahydro-1,4-methanopyrido[2,3-b][1,4]diazepine-7-carboxamide (600 mg, 2.096 mmol) in Dichloromethane (DCM) (20 mL) and Pyridine (0.170 mL, 2.096 mmol), was added phenyl carbonochloridate (394 mg, 2.52 mmol) at 0° C. The resulting reaction mixture was stirred at rt for 6 hr. Progress of the reaction was monitored by TLC. TLC indicates total consumption of starting material and formation of new non polar spot. Water (25 mL), was added to the reaction mixture. The aqueous layer was extracted with DCM (2×25 mL), the combined organic layer was dried over anhydrous $Na_2SO_4$, filtered and concentrated under reduced pressure to obtain desired crude product. Crude product was washed with pentane (2×25 mL), filtered the solid and dried under high vacuum to obtain desired pure product (4S)-phenyl 7-((2,2,2-trifluoroethyl)carbamoyl)-3,4-dihydro-1,4-methanopyrido[2,3-b][1,4]diazepine-5(2H)-carboxylate (600 mg, 1.462 mmol, 69.7% yield) as an off-white solid, LCMS (m/z): 407.14 [M+H]+

Synthesis of methyl 2-((4S)-7-((2,2,2-trifluoroethyl)carbamoyl)-2,3,4,5-tetrahydro-1,4-methanopyrido[2,3-b][1,4]diazepine-5-carboxamido)isonicotinate

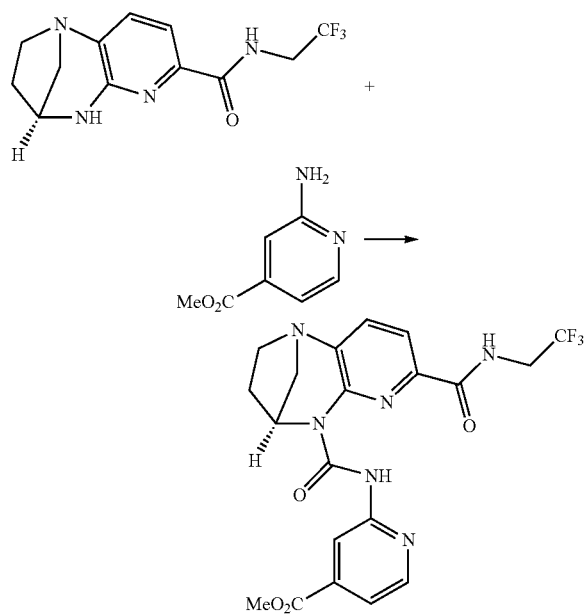

To a stirred solution of (4S)—N-(2,2,2-trifluoroethyl)-2,3,4,5-tetrahydro-1,4-methanopyrido[2,3-b][1,4]diazepine-7-carboxamide (1.5 g, 5.24 mmol) in Tetrahydrofuran (THF) (20 mL), was added Triphosgene (1.555 g, 5.24 mmol) followed by TEA (2.191 mL, 15.72 mmol) at rt. The reaction mixture was allowed to stir at RT for 45 min and added methyl 2-aminoisonicotinate (0.797 g, 5.24 mmol). The reaction mixture was stirred at 75° C. for 16 hr. Progress of the reaction was monitored by TLC, TLC indicated formation of a non polar spot and SM was consumed. Water (20 mL) was added to the reaction mixture, the aqueous layer was extracted with EtOAc (2×25 mL). The combined organic layer was dried over anhydrous $Na_2SO_4$, filtered and concentrated under reduced pressure to obtain desired crude product. Crude material was purified by column chromatography using silica gel (100-200 mesh, 2% MeOH in DCM). Fractions containing pure compound were combined and concentrated to obtain the desired pure product methyl 2-((4S)-7-((2,2,2-trifluoroethyl)carbamoyl)-2,3,4,5-tetrahydro-1,4-methanopyrido[2,3-b][1,4]diazepine-5-carboxamido)isonicotinate (1.5 g, 1.763 mmol, 33.6% yield) as an light yellow solid, LCMS (m/z): 465.13 (M+H)+.

Synthesis of (4S)—N—((R)-1,1,1-trifluoropropan-2-yl)-2,3,4,5-tetrahydro-1,4-methanopyrido[2,3-b][1,4]diazepine-7-carboxamide

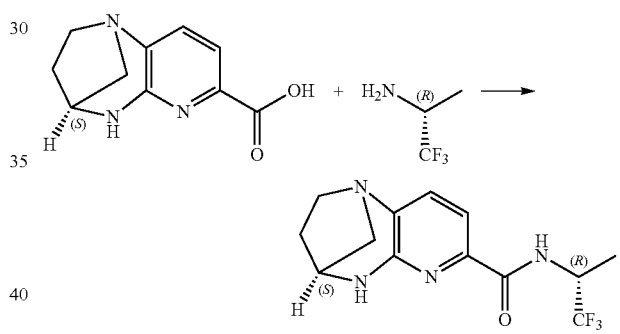

To a stirred solution of (4S)-2,3,4,5-tetrahydro-1,4-methanopyrido[2,3-b][1,4]diazepine-7-carboxylic acid (5 g, 24.36 mmol) in Tetrahydrofuran (THF) (50 mL), was added HATU (18.53 g, 48.7 mmol) followed by TEA (3.40 mL, 24.36 mmol). After stirring the reaction mixture for 10 min at RT, added (R)-1,1,1-trifluoropropan-2-amine (2.76 g, 24.36 mmol) under nitrogen. The resulting reaction mixture was stirred at room temperature for 16 hr. Progress of the reaction was monitored by TLC. TLC indicated total consumption of starting material and formation of a new nonpolar spot. Reaction mixture was poured in ice cold water (500 ml), the aqueous layer was extracted with EtOAc (2×30 ml). The combined organic layers were washed with brine (50 mL). The organic layer was dried over anhydrous $Na_2SO_4$, filtered and concentrated under reduced pressure to obtain crude. The crude material was purified by column chromatography using 100-200 silica gel (eluent as 90% EtOAc in pet ether). Fraction containing pure compound were combined and concentrated to obtain the desired pure product (4S)—N—((R)-1,1,1-trifluoropropan-2-yl)-2,3,4,5-tetrahydro-1,4-methanopyrido[2,3-b][1,4]diazepine-7-carboxamide (6 g, 16.65 mmol, 68.3% yield) as brown solid. LCMS (m/z): 300.99 [M+H]+.

Synthesis of (4S)—N5-(1-benzyl-1H-pyrazol-3-yl)-N7-((R)-1,1,1-trifluoropropan-2-yl)-3,4-dihydro-1,4-methanopyrido[2,3-b][1,4]diazepine-5,7(2H)-dicarboxamide

Synthesis of (4S)—N5-(5-methylpyridin-2-yl)-N7-((R)-1,1,1-trifluoropropan-2-yl)-3,4-dihydro-1,4-methanopyrido[2,3-b][1,4]diazepine-5,7(2H)-dicarboxamide

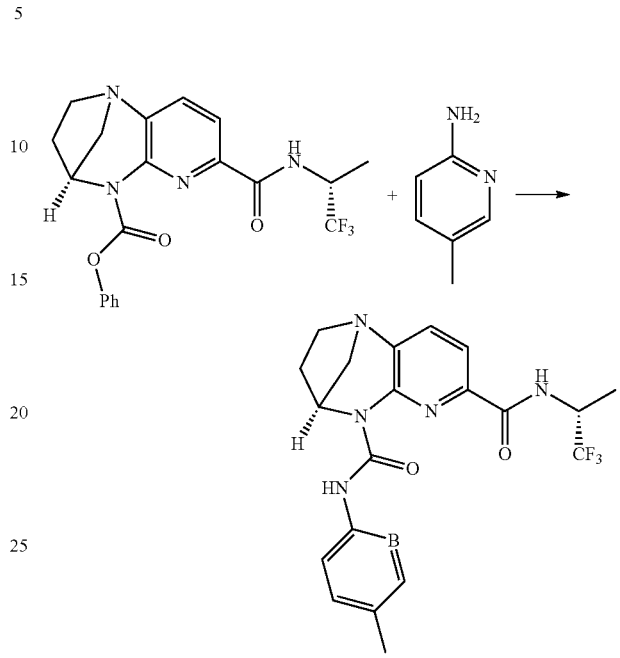

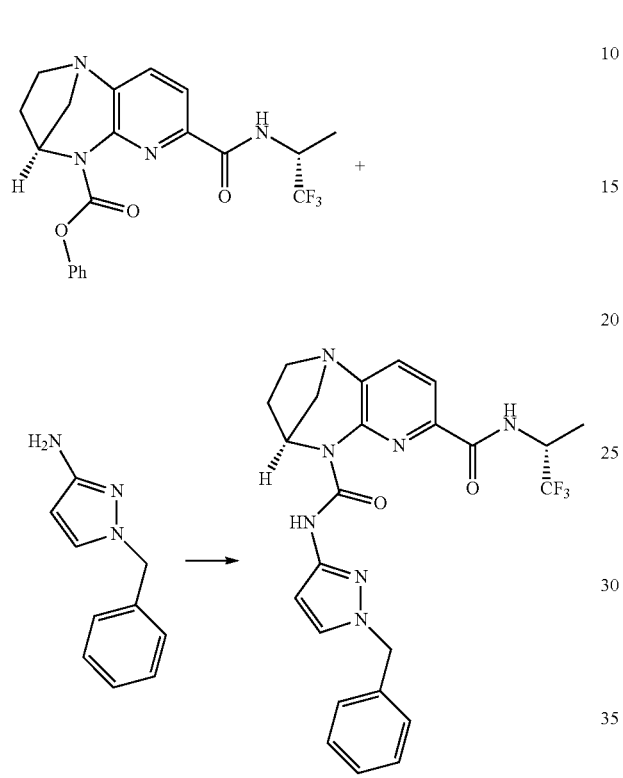

To a stirred solution of 5-methylpyridin-2-amine (309 mg, 2.85 mmol) in Tetrahydrofuran (THF) (80 mL), was added LiHMDS (2.85 mL, 2.85 mmol) dropwise at −78° C. After stirring the reaction mixture at −78° C. for 30 min, added (4S)-phenyl 7-(((R)-1,1,1-trifluoropropan-2-yl)carbamoyl)-3,4-dihydro-1,4-methanopyrido[2,3-b][1,4]diazepine-5(2H)-carboxylate (600 mg, 1.427 mmol) under nitrogen at −78° C. The resulting reaction mixture was stirred at −78° C. for 1 h and at rt for 6 hr. Progress of the reaction was monitored by TLC. TLC indicates formation of new polar spot and consumption of starting material. The reaction mixture was quenched with aqueous NH$_4$Cl (50 mL). The aqueous layer was extracted with EtOAc (2×100 mL), the combined organic layer was dried over anhydrous Na$_2$SO$_4$ filtered and concentrated under reduced pressure to obtain desired crude product. The crude compound was submitted for Prep HPLC, After prep HPLC to afford the (4S)—N5-(5-methylpyridin-2-yl)-N7-((R)-1,1,1-trifluoropropan-2-yl)-3,4-dihydro-1,4-methanopyrido[2,3-b][1,4]diazepine-5,7(2H)-dicarboxamide (228 mg, 0.523 mmol, 36.6% yield) as an pale brown solid, LCMS (m/z): 435.14 [M+H]$^+$.

To a stirred solution of 1-benzyl-1H-pyrazol-3-amine (371 mg, 2.141 mmol) in Tetrahydrofuran (THF) (25 mL), was added a solution of IM LiHMDS (2.85 mL, 2.85 mmol) dropwise at −78° C. After stirring the reaction mixture at −78° C. for 30 min, added a solution of (4S)-phenyl 7-(((R)-1,1,1-trifluoropropan-2-yl)carbamoyl)-3,4-dihydro-1,4-methanopyrido[2,3-b][1,4]diazepine-5(2H)-carboxylate (600 mg, 1.427 mmol) in Tetrahydrofuran (THF) (5 mL) under nitrogen at −78° C. The resulting reaction mixture was stirred at −78° C. for 1 h and at rt for 6 hr. Progress of the reaction was monitored by TLC. TLC indicates formation of new polar spot and consumption of starting material. The reaction mixture was quenched with aqueous NH$_4$Cl (10 mL). The aqueous layer was extracted with EtOAc (2×25 mL), the combined organic layer was dried over anhydrous Na$_2$SO$_4$, filtered and concentrated under reduced pressure to obtain desired crude product. Crude material was purified by combiflash using silica gel column (24 g, 2.0% MeOH in DCM). Fraction containing pure compound were combined and concentrated to obtain desired pure product (4S)—N5-(1-benzyl-1H-pyrazol-3-yl)-N7-((R)-1,1,1-trifluoropropan-2-yl)-3,4-dihydro-1,4-methanopyrido[2,3-b][1,4]diazepine-5,7(2H)-dicarboxamide (400 mg, 0.743 mmol, 52.1% yield) as light yellow solid, LCMS (m/z): 500.37 [M+H]$^+$.

Synthesis of methyl 2-((4S)-7-(((R)-1,1,1-trifluoropropan-2-yl)carbamoyl)-2,3,4,5-tetrahydro-1,4-methanopyrido[2,3-b][1,4]diazepine-5-carboxamido)isonicotinate

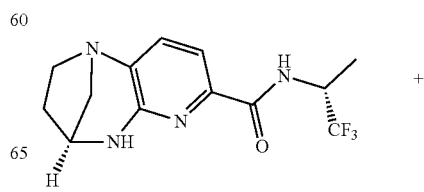

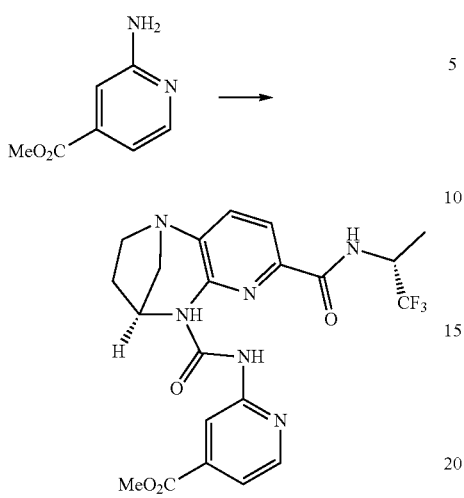

TEA (6.96 mL, 50.0 mmol) followed by triphosgene (2.96 g, 9.99 mmol) were added to a solution of (4S)—N—((R)-1,1,1-trifluoropropan-2-yl)-2,3,4,5-tetrahydro-1,4-methanopyrido[2,3-b][1,4]diazepine-7-carboxamide (3 g, 9.99 mmol) in Tetrahydrofuran (THF) (10 mL) at RT and stirred for 1 h then methyl 2-aminoisonicotinate (1.520 g, 9.99 mmol) was added and heated at 90° C. for 15 h. The reaction mixture was cooled to 28° C. and was partitioned between water (50 mL) and EtOAc (50 mL×2). Organic layers were separated and was dried over anhydrous Na$_2$SO$_4$, filtered and filtrate was evaporated to get crude then it was purified by column chromatography (using 100-200 silica gel, column eluted at 80% ethyl acetate in hexane) to afford the methyl 2-((4S)-7-(((R)-1,1,1-trifluoropropan-2-yl)carbamoyl)-2,3,4,5-tetrahydro-1,4-methanopyrido[2,3-b][1,4]diazepine-5-carboxamido)isonicotinate (2.5 g, 5.23 mmol, 52.3% yield) as an off white solid, LCMS (m/z): 479.26 (M+H)$^+$.

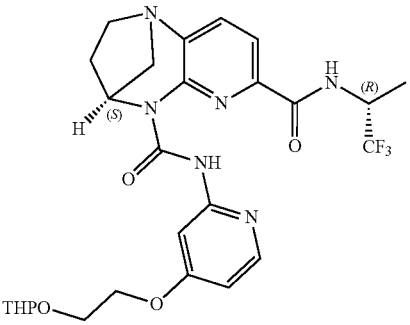

TEA (0.696 mL, 5.00 mmol) followed by triphosgene (296 mg, 0.999 mmol) were added to a solution of (4S)—N—((R)-1,1,1-trifluoropropan-2-yl)-2,3,4,5-tetrahydro-1,4-methanopyrido[2,3-b][1,4]diazepine-7-carboxamide (300 mg, 0.999 mmol) in Tetrahydrofuran (THF) (20 mL) at RT and stirred for 1 h then 4-(2-((tetrahydro-2H-pyran-2-yl)oxy)ethoxy)pyridin-2-amine (286 mg, 1.199 mmol) was added and heated at 80° C. for 15 h. The reaction mixture was cooled to 28° C. and was partitioned between water (25 mL) and EtOAc (30 mL×2). Organic layers were separated and was dried over anhydrous Na$_2$SO$_4$, filtered and filtrate was evaporated to get crude, then purified by column chromatography (using 100-200 silica gel, column eluted at 80% ethyl acetate in n-hexane) to afford the (4S)—N5-(4-(2-((tetrahydro-2H-pyran-2-yl)oxy)ethoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (200 mg, 0.340 mmol, 34.0% yield) as an off white solid, LCMS (m/z): 565.27 [M+H]$^+$.

Synthesis of (4S)—N5-(5-(((S)-2,2-dimethyl-1,3-dioxolan-4-yl)methoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

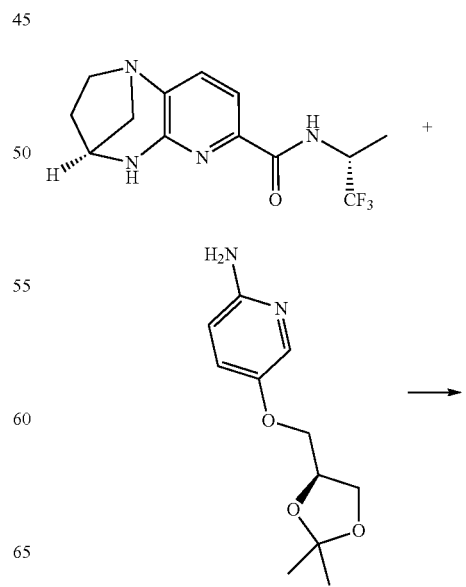

223

-continued

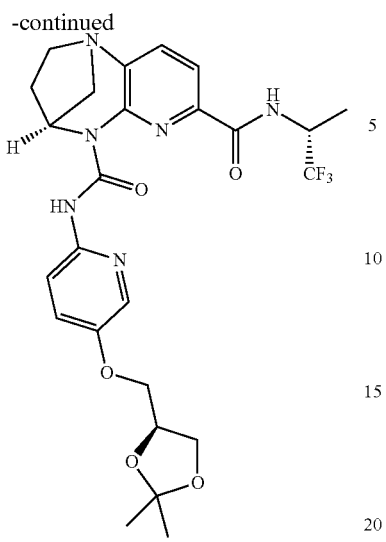

DIPEA (775 mg, 5.99 mmol) followed by triphosgene (593 mg, 1.998 mmol) were added to a solution of (4S)—N—((R)-1,1,1-trifluoropropan-2-yl)-2,3,4,5-tetrahydro-1,4-methanopyrido[2,3-b][1,4]diazepine-7-carboxamide (600 mg, 1.998 mmol) in Tetrahydrofuran (THF) (20 mL) at 25° C., stirred for 1 h and (S)-5-((2,2-dimethyl-1,3-dioxolan-4-yl)methoxy)pyridin-2-amine (896 mg, 4.00 mmol) was added and heated at 70° C. for 18 hr (TLC eluent: 100% ethyl acetate $R_f$: 0.3; UV active). The reaction mixture was cooled to 28° C. and was partitioned between water (20 mL) and EtOAc (50 mL). Organic layer was separated and was dried over anhydrous $Na_2SO_4$, filtered and filtrate was evaporated. Crude compound was purified C-18 column eluted with 60% of ACB in 1% Aq formic acid to afford (4S)—N5-(5-(((S)-2,2-dimethyl-1,3-dioxolan-4-yl)methoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (330 mg, 0.593 mmol, 29.7% yield), as brownish sticky, LCMS (m/z): 550.8 (M+H)⁺.

Synthesis of (4S)—N5-(6-(((S)-2,2-dimethyl-1,3-dioxolan-4-yl)methoxy)pyridazin-3-yl)-N7-((R)-1,1,1-trifluoropropan-2-yl)-3,4-dihydro-1,4-methanopyrido[2,3-b][1,4]diazepine-5,7(2H)-dicarboxamide

224

-continued

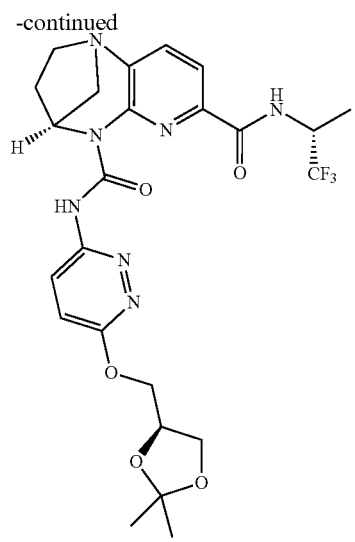

To a stirred solution of (4S)—N—((R)-1,1,1-trifluoropropan-2-yl)-2,3,4,5-tetrahydro-1,4-methanopyrido[2,3-b][1,4]diazepine-7-carboxamide (1.0 g, 3.33 mmol) and TEA (2.79 mL, 19.98 mmol) in Tetrahydrofuran (THF) (30 mL) at RT was added triphosgene (0.988 g, 3.33 mmol). This reaction mixture was stirred for 30 min pyridin-3-amine (387 mg, 4.11 mmol) was added and the reaction mixture stirred at 70° C. for 16 hr. The reaction mixture was cooled to room temperature, concentrated in vacuum and the residue was partitioned between water (100 mL) and EtOAc (2×150 mL). Organic layer was separated and dried over anhydrous $Na_2SO_4$, filtered and filtrate was evaporated to get crude compound. The crude compound was purified by combi flash chromatography 0.1% formic acid in 75% Acetonitrile as a eluent to afford (4S)—N5-(6-(((S)-2,2-dimethyl-1,3-dioxolan-4-yl)methoxy)pyridazin-3-yl)-N7-((R)-1,1,1-trifluoropropan-2-yl)-3,4-dihydro-1,4-methanopyrido[2,3-b][1,4]diazepine-5,7(2H)-dicarboxamide (0.15 g, 0.252 mmol, 7.56% yield) as a white solid, LCMS (m/z) 552.1 (M+H)⁺.

Synthesis of (4S)—N5-(5-(((R)-2,2-dimethyl-1,3-dioxolan-4-yl)methoxy)pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide

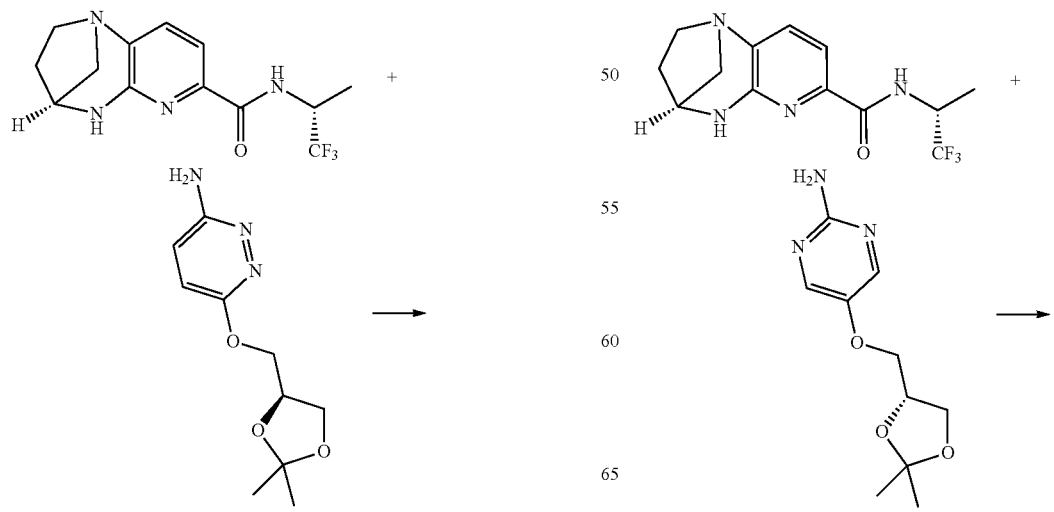

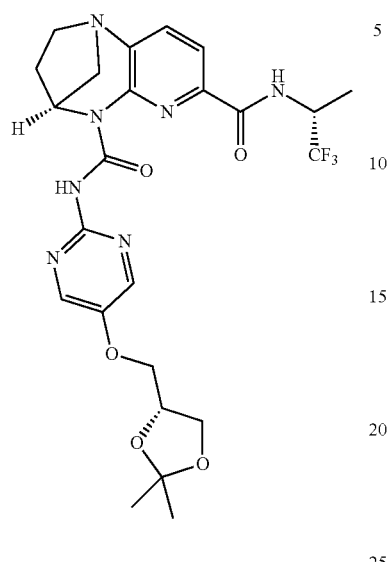

To a solution of (4S)—N—((R)-1,1,1-trifluoropropan-2-yl)-2,3,4,5-tetrahydro-1,4-methanopyrido[2,3-b][1,4]diazepine-7-carboxamide (400 mg, 1.332 mmol), triphosgene (395 mg, 1.332 mmol) in Tetrahydrofuran (THF) (10 mL) stirred under nitrogen at 0° C. and was added triphosgene (395 mg, 1.332 mmol) and TEA (1.114 mL, 7.99 mmol). Then the reaction mixture was stirred at 30° C. for 30 min and added (R)-5-((2,2-dimethyl-1,3-dioxolan-4-yl)methoxy)pyrimidin-2-amine (450 mg, 1.998 mmol), then the reaction mixture was stirred at 80° C. for 16 hr. The reaction was monitored by LCMS and TLC. The reaction mixture was poured in to the cold water (2×20 mL) and extracted with ethyl acetate (2×30 mL). The organic layer was dried over anhydrous $Na_2SO_4$ and concentrated under vacuum to obtained crude compound. The crude product was combined with a previous batch and purified by flash column chromatography (100-200 silica gel) eluting at 80% Ethyl acetate in pet ether to afford pure compound (4S)—N5-(5-(((R)-2,2-dimethyl-1,3-dioxolan-4-yl)methoxy)pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide (250 mg, 0.396 mmol, 29.8% yield) as Off white solid, LCMS (m/z) 552.18 (M+H)$^+$.

Synthesis of (4S)—N5-(5-(((R)-2,2-dimethyl-1,3-dioxolan-4-yl)methoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

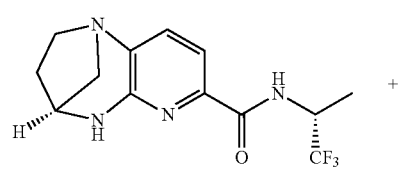 +

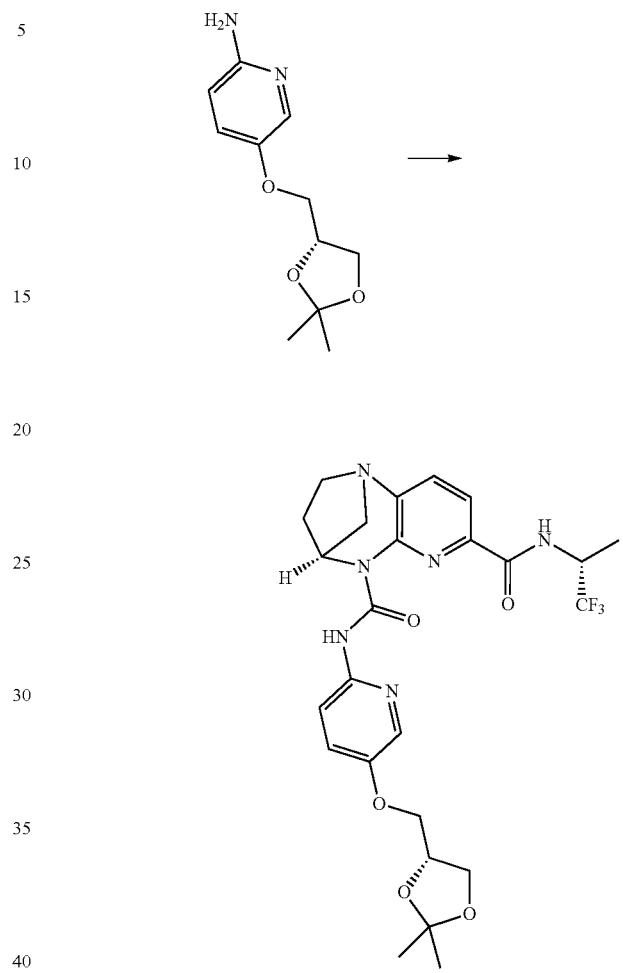

TEA (0.464 mL, 3.33 mmol) followed by triphosgene (494 mg, 1.665 mmol) were added to a solution of (4S)—N—((R)-1,1,1-trifluoropropan-2-yl)-2,3,4,5-tetrahydro-1,4-methanopyrido[2,3-b][1,4]diazepine-7-carboxamide (500 mg, 1.665 mmol) in Tetrahydrofuran (THF) (10 mL) at 0° C. then stirred for 2 h at RT and (R)-5-((2,2-dimethyl-1,3-dioxolan-4-yl)methoxy)pyridin-2-amine (560 mg, 2.498 mmol) was added then heated to 80° C. for 4 h in sealed tube. The reaction mixture was cooled to RT then partitioned between water (40 mL) and ethyl acetate (50 mL), washed with water (40 mL×2) and brine (30 mL). Organic layer was dried over anhydrous $Na_2SO_4$ and solvent removed under reduced pressure to afford the crude, then it was purified by column chromatography (using 100-200 silica gel, column eluted at 80% ethyl acetate in n-hexane) to afford the (4S)—N5-(5-(((R)-2,2-dimethyl-1,3-dioxolan-4-yl)methoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (400 mg, 0.726 mmol, 43.6% yield) as an off white solid, LCMS (m/z): 551.16 (M+H)$^+$.

227

Synthesis of (4S)—N5-(6-(((S)-2,2-dimethyl-1,3-dioxolan-4-yl)methoxy)pyrimidin-4-yl)-N7-((R)-1,1,1-trifluoropropan-2-yl)-3,4-dihydro-1,4-methanopyrido[2,3-b][1,4]diazepine-5,7(2H)-dicarboxamide

228

Synthesis of (4S)—N5-(5-(((S)-2,2-dimethyl-1,3-dioxolan-4-yl)methoxy)pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide

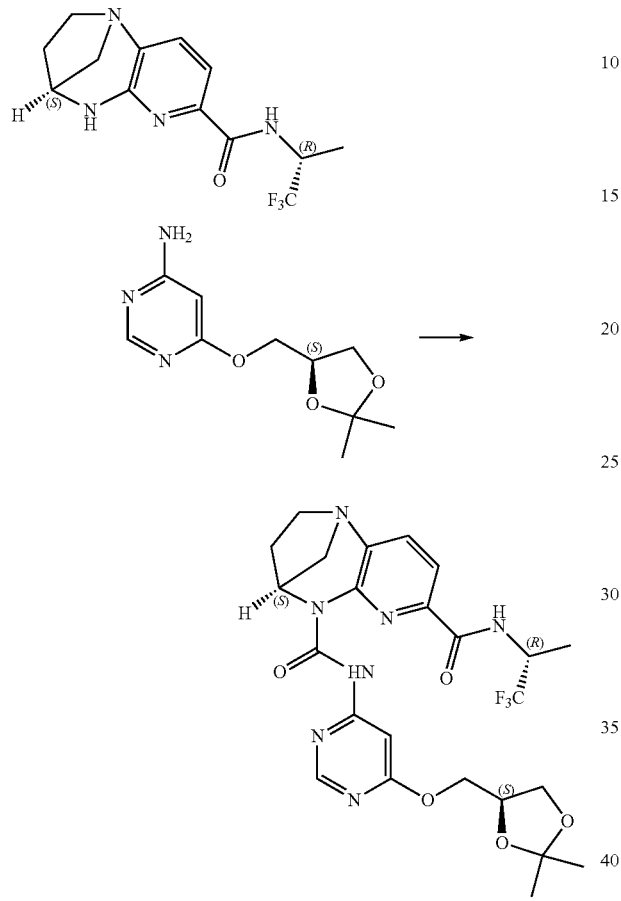

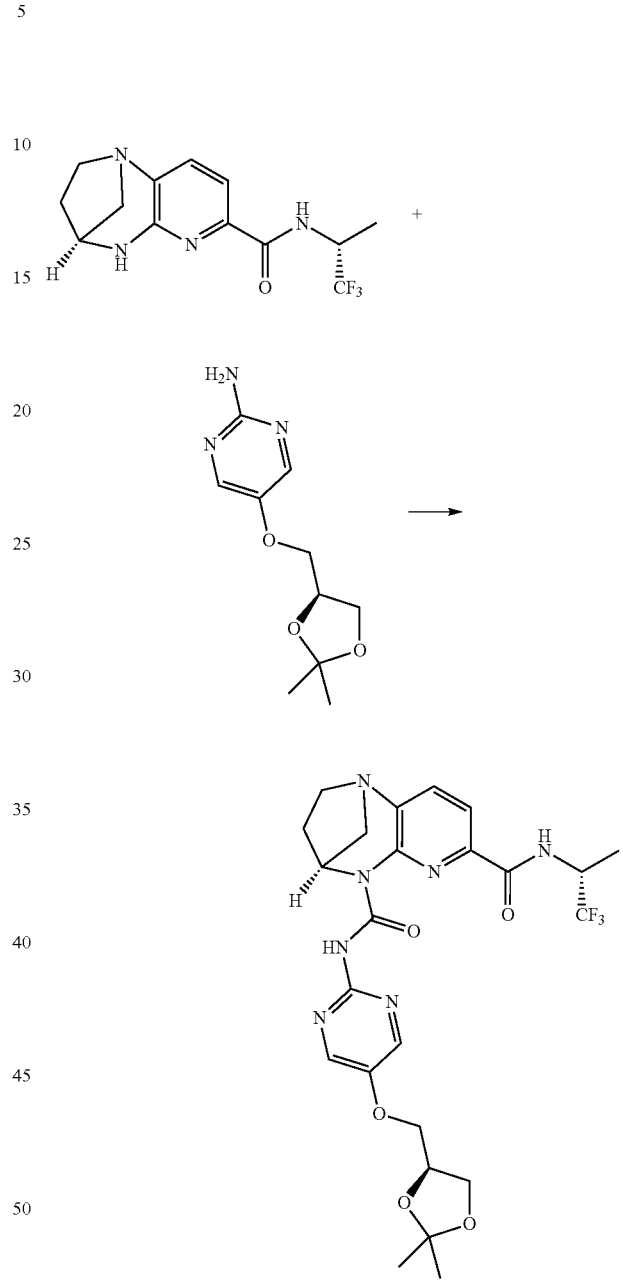

triphosgene (0.494 g, 1.665 mmol) was added to a stirred solution of (4S)—N—((R)-1,1,1-trifluoropropan-2-yl)-2,3,4,5-tetrahydro-1,4-methanopyrido[2,3-b][1,4]diazepine-7-carboxamide (0.5 g, 1.665 mmol) and TEA (1.160 mL, 8.33 mmol) in Tetrahydrofuran (THF) (50 mL) was stirred under nitrogen at room temp for 1 h. To this reaction mixture (S)-6-((2,2-dimethyl-1,3-dioxolan-4-yl)methoxy)pyrimidin-4-amine (0.938 g, 4.16 mmol) was added. The reaction mixture was stirred at 65° C. for 16 h and progress of the reaction was monitored by TLC and LCMS. The reaction mixture was cooled to room temperature, poured in to ice water (250 mL) and extracted with EtOAc (2×200 mL). The combined organic layer was washed with water (250 mL), brine solution (200 mL), dried over $Na_2SO_4$, filtered and evaporated to obtain crude compound. The crude compound was purified by column chromatography using 230-400 silica gel and eluted in 50% ethyl acetate in hexane, the fractions were concentrated to afford (4S)—N5-(6-(((S)-2,2-dimethyl-1,3-dioxolan-4-yl)methoxy)pyrimidin-4-yl)-N7-((R)-1,1,1-trifluoropropan-2-yl)-3,4-dihydro-1,4-methanopyrido[2,3-b][1,4]diazepine-5,7(2H)-dicarboxamide (0.14 g, 0.246 mmol, 14.79% yield) as off white solid, LCMS (m/z): 552.10 $(M+H)^+$.

Triphosgene (494 mg, 1.665 mmol) was added to a stirred solution of (4S)—N—((R)-1,1,1-trifluoropropan-2-yl)-2,3,4,5-tetrahydro-1,4-methanopyrido[2,3-b][1,4]diazepine-7-carboxamide (500 mg, 1.665 mmol), and TEA (1.393 mL, 9.99 mmol) in Tetrahydrofuran (THF) (50 mL) under nitrogen at 28° C. The reaction mixture was stirred at RT for 30 min. and was added (S)-5-((2,2-dimethyl-1,3-dioxolan-4-yl)methoxy)pyrimidin-2-amine (750 mg, 3.33 mmol). The reaction mixture was stirred 16 hr at 65° C. The reaction mixture was cooled to 28° C., the reaction mixture was partitioned between water (2 mL) and EtOAc (2×25 mL). Organic layer was separated and was dried over anhydrous $Na_2SO_4$, filtered and filtrate was evaporated to afford crude.

The crude was purified by GRACE using C-18 reserval column, Mobile phase A: 0.1% Formic Acid in water; B: ACN, the product was eluted at 25% of ACN in 0.1% Formic Acid in water. The solvent was evaporated and was basified with saturated NaHCO$_3$. The aqueous layer was extracted with DCM, DCM layer was dried over anhydrous Na$_2$SO$_4$, filtered, and filtrate was evaporated to afford (4S)—N5-(5-(((S)-2,2-dimethyl-1,3-dioxolan-4-yl)methoxy)pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide (300 mg, 0.250 mmol, 15.04% yield) as brown solid, LCMS (m/z): 552.30 (M+H)$^+$.

Synthesis of (4S)—N5-(4-nitropyridin-2-yl)-N7-((R)-1,1,1-trifluoropropan-2-yl)-3,4-dihydro-1,4-methanopyrido[2,3-b][1,4]diazepine-5,7(2H)-dicarboxamide

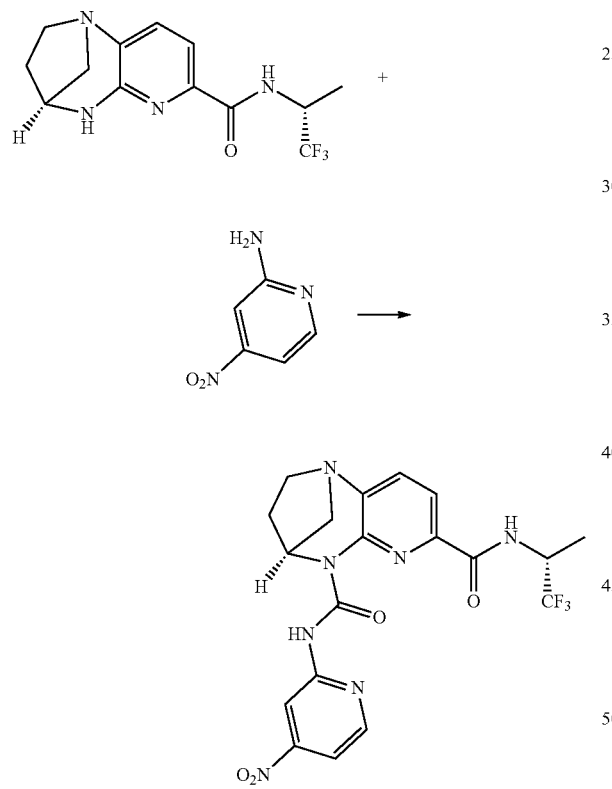

(4S)—N—((R)-1,1,1-trifluoropropan-2-yl)-2,3,4,5-tetrahydro-1,4-methanopyrido[2,3-b][1,4]diazepine-7-carboxamide (2 g, 6.66 mmol) was dissolved in Tetrahydrofuran (THF) (50 mL) stirred under nitrogen at 0° C. were added triphosgene (1.186 g, 4.00 mmol), DIPEA (5.82 mL, 33.3 mmol). The reaction mixture was stirred for 30 min at room temperature. To this 4-nitropyridin-2-amine (1.390 g, 9.99 mmol) was added and stirred for 16 h at 80° C. in a sealed tube. The reaction mixture allowed to room temperature and quenched with 500 ml of water and extracted with 2×800 ml of ethyl acetate, The combined organic layer was dried over Na$_2$SO$_4$ and concentrated under reduced pressure to obtain crude compound. The crude product was purified by flash column chromatography (silica-gel: 100-200 mesh) to afford (4S)—N5-(4-nitropyridin-2-yl)-N7-((R)-1,1,1-trifluoropropan-2-yl)-3,4-dihydro-1,4-methanopyrido[2,3-b][1,4]diazepine-5,7(2H)-dicarboxamide (1.1 g, 2.234 mmol, 33.5% yield) as a brown solid, LCMS (m/z): 466.00 [M+H]$^+$.

Synthesis of (4S)—N5-(4-aminopyridin-2-yl)-N7-((R)-1,1,1-trifluoropropan-2-yl)-3,4-dihydro-1,4-methanopyrido[2,3-b][1,4]diazepine-5,7(2H)-dicarboxamide

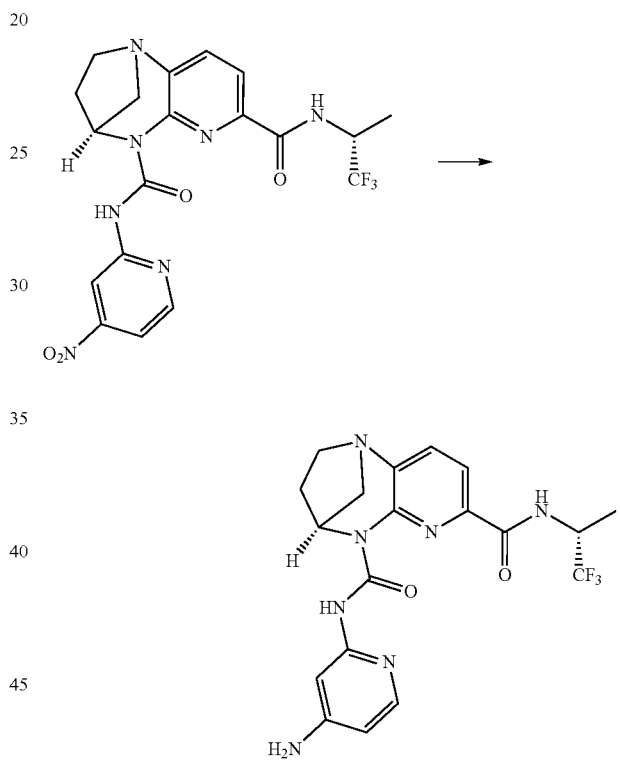

(4S)—N5-(4-nitropyridin-2-yl)-N7-((R)-1,1,1-trifluoropropan-2-yl)-3,4-dihydro-1,4-methanopyrido[2,3-b][1,4]diazepine-5,7(2H)-dicarboxamide (1 g, 2.149 mmol) was dissolved in Ethanol (25 mL) stirred under hydrogen (bladder balloon pressure) at RT were added Pd—C (2.74 g, 2.58 mmol). The reaction mixture was stirred for 16 at RT. After completion of reaction the reaction mixture was filtered through celite pad. The filtrate was evaporated in vacuum to give the crude. The crude product was purified by flash column chromatography (silica-gel: 100-200 mesh) to afford (4S)—N5-(4-aminopyridin-2-yl)-N7-((R)-1,1,1-trifluoropropan-2-yl)-3,4-dihydro-1,4-methanopyrido[2,3-b][1,4]diazepine-5,7(2H)-dicarboxamide (850.2 mg, 1.543 mmol, 71.8% yield), LCMS (m/z): 436.20 [M+H]$^+$.

Synthesis of (4S)—N5-(4-(N-(methylsulfonyl)methylsulfonamido)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

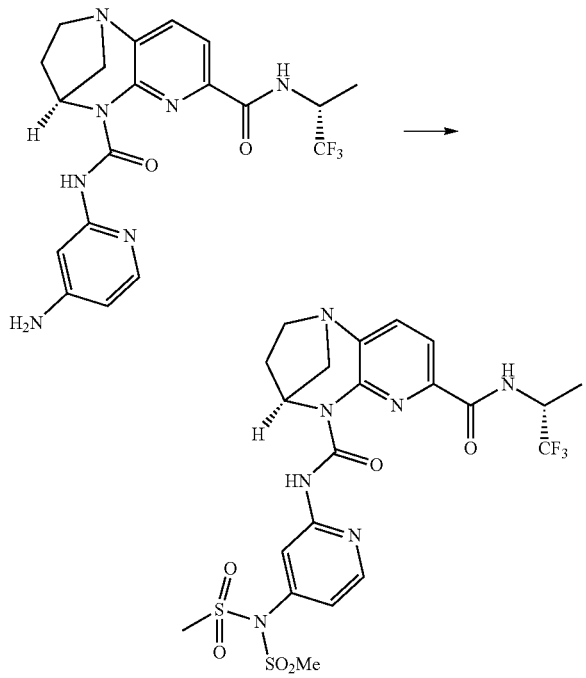

To a solution of (4S)—N5-(4-aminopyridin-2-yl)-N7-((R)-1,1,1-trifluoropropan-2-yl)-3,4-dihydro-1,4-methanopyrido[2,3-b][1,4]diazepine-5,7(2H)-dicarboxamide (250 mg, 0.574 mmol) in Tetrahydrofuran (THF) (15 mL) was added Et₃N (0.400 mL, 2.87 mmol) and mesyl chloride (0.224 mL, 2.87 mmol) under nitrogen at 0° C. The reaction mixture was stirred at 26° C. for 16 hr. The reaction mixture was partitioned between ice cold water (10 mL) and dichloromethane (2×50 mL). Organic layer was separated, dried over anhydrous Na₂SO₄, filtered and filtrate was evaporated to afford crude, LCMS (m/z): 592.2 [M+H]⁺.

Synthesis of (4S)-methyl 8-bromo-2,3,4,5-tetrahydro-1,4-methanopyrido[2,3-b][1,4]diazepine-7-carboxylate

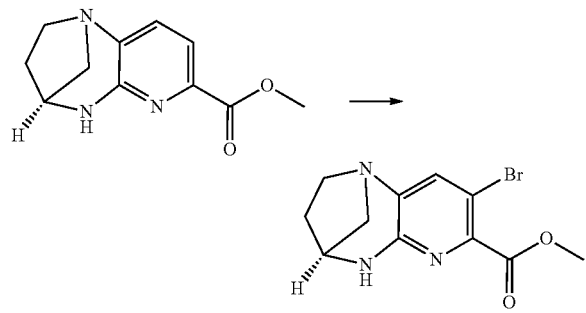

(4S)-methyl 2,3,4,5-tetrahydro-1,4-methanopyrido[2,3-b][1,4]diazepine-7-carboxylate (5 g, 22.81 mmol) was dissolved in Chloroform (50 mL) stirred under nitrogen at 0° C. were added NBS (6.09 g, 34.2 mmol). The reaction mixture was stirred for 5 h at RT. The reaction mixture was quenched with 300 ml of water and extracted with 2×600 mL of DCM, The combined organic layer was dried over Na₂SO₄ and concentrated under reduced pressure to obtain crude. The crude product was purified by flash column chromatography (Neutral alumina) to afford (4S)-methyl 8-bromo-2,3,4,5-tetrahydro-1,4-methanopyrido[2,3-b][1,4]diazepine-7-carboxylate (3.9 g, 12.69 mmol, 55.6% yield) as an Off white solid, LCMS (m/z): 298.01 [M+H]⁺.

Synthesis of (4S)-8-bromo-2,3,4,5-tetrahydro-1,4-methanopyrido[2,3-b][1,4]diazepine-7-carboxylic acid

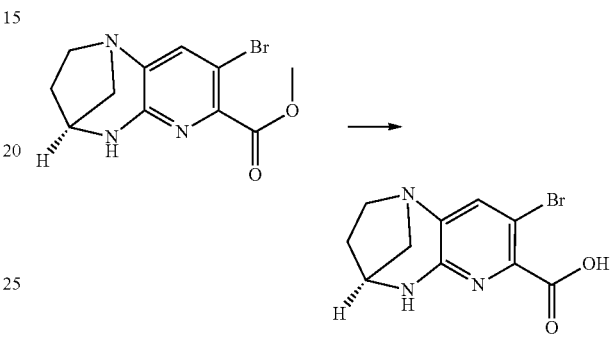

(4S)-methyl 8-bromo-2,3,4,5-tetrahydro-1,4-methanopyrido[2,3-b][1,4]diazepine-7-carboxylate (3 g, 10.06 mmol) was dissolved in Tetrahydrofuran (THF) (20 mL), Water (20 mL) stirred at 0° C. were added LiOH (0.723 g, 30.2 mmol). The reaction mixture was stirred for 3 h at rt. The reaction mixture concentrated under reduced pressure to obtain Residue. The Residue was Neutralized with 1N HCl and again concentrated under reduced pressure, co-distilled with Toluene to give (4S)-8-bromo-2,3,4,5-tetrahydro-1,4-methanopyrido[2,3-b][1,4]diazepine-7-carboxylic acid (2.5 g, 7.74 mmol, 77% yield), LCMS (m/z): 284.0 [M+H]⁺.

Synthesis of (4S)-8-bromo-N-(2,2,2-trifluoroethyl)-2,3,4,5-tetrahydro-1,4-methanopyrido[2,3-b][1,4]diazepine-7-carboxamide

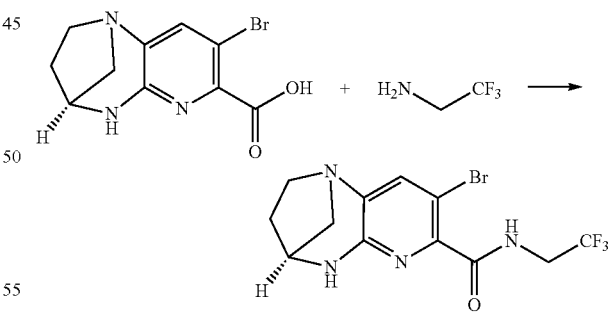

HATU (3.68 g, 9.68 mmol) followed by DIPEA (4.87 mL, 26.4 mmol) were added to a solution of (4S)-8-bromo-2,3,4,5-tetrahydro-1,4-methanopyrido[2,3-b][1,4]diazepine-7-carboxylic acid (2.5 g, 8.80 mmol) in Tetrahydrofuran (THF) (100 mL) at 25° C., stirred for 1 h and 2,2,2-trifluoroethanamine hydrochloride (1.789 g, 13.20 mmol) was added and stirred at RT for 18 h. The reaction mixture was partitioned between water (200 mL) and EtOAc (2×300 mL). Organic layer was separated and was dried over anhydrous Na₂SO₄, filtered and filtrate was evaporated to get crude (TLC eluent: 100% ethyl acetate $R_f$: 0.3; UV active). The crude compound was purified by column chromatography (100-200 mesh) silica gel, eluted at 80% Ethyl acetate in hexane to afford (4S)-8-bromo-N-(2,2,2-trifluoroethyl)-2,3,4,5-tetrahydro-1,4-methanopyrido[2,3-b][1,4]diazepine-7-carboxamide (2.050 g, 5.34 mmol, 60.7% yield) as a pale yellow sticky, LCMS (m/z): 366.95 (M+H)$^+$.

Synthesis of (4S)-8-methoxy-N-(2,2,2-trifluoroethyl)-2,3,4,5-tetrahydro-1,4-methanopyrido[2,3-b][1,4]diazepine-7-carboxamide

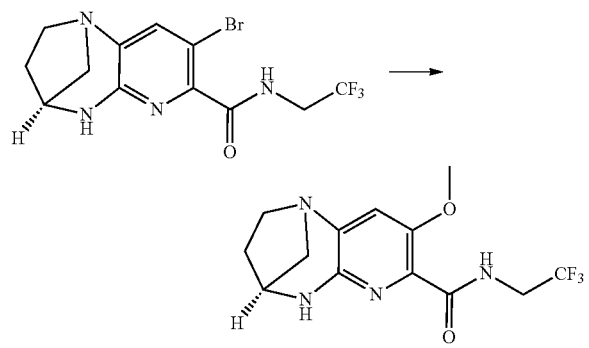

A Solution of sodium methoxide (11.84 g, 110 mmol) in Methanol (50%) were added to a (4S)-8-bromo-N-(2,2,2-trifluoroethyl)-2,3,4,5-tetrahydro-1,4-methanopyrido[2,3-b][1,4]diazepine-7-carboxamide (2 g, 5.48 mmol), stirred the reaction mixture at 80° C. for 4 h. Allowed the reaction mixture to RT, diluted with water (120 mL) extracted with Ethyl acetate (2×250 mL), washed with brine (100 mL). The combined organic layer was dried over Na$_2$SO$_4$ and concentrated under reduced pressure to obtain crude compound. The crude product was purified by flash column chromatography (silica-gel: 100-200 mesh) to obtain (4S)-8-methoxy-N-(2,2,2-trifluoroethyl)-2,3,4,5-tetrahydro-1,4-methanopyrido[2,3-b][1,4]diazepine-7-carboxamide (753 mg, 2.024 mmol, 36.9% yield), LCMS (m/z): 317.34 [M+H]$^+$.

Synthesis of (4S)—N5-(4-(((S)-2,2-dimethyl-1,3-dioxolan-4-yl)methoxy)pyridin-2-yl)-8-methyl-N7-((R)-1,1,1-trifluoropropan-2-yl)-3,4-dihydro-1,4-methanopyrido[2,3-b][1,4]diazepine-5,7(2H)-dicarboxamide

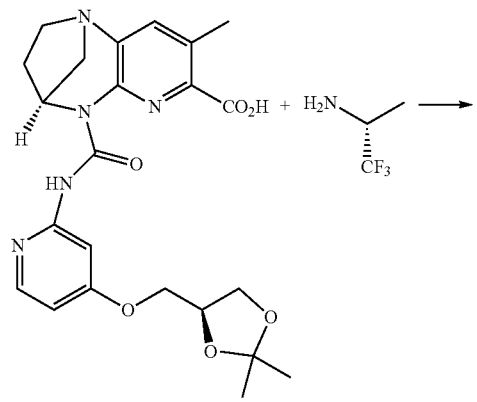

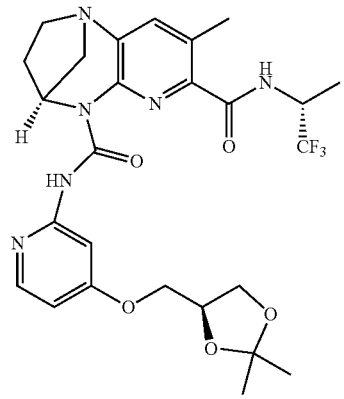

To a stirred solution of (4S)-5-((4-(((S)-2,2-dimethyl-1,3-dioxolan-4-yl)methoxy)pyridin-2-yl)carbamoyl)-8-methyl-2,3,4,5-tetrahydro-1,4-methanopyrido[2,3-b][1,4]diazepine-7-carboxylic acid (270 mg, 0.575 mmol) in N,N-Dimethylformamide (DMF) (7 mL) were added DIPEA (0.502 mL, 2.88 mmol), HATU (328 mg, 0.863 mmol) and (R)-1,1,1-trifluoropropan-2-amine (98 mg, 0.863 mmol) at 0° C. The reaction mixture was stirred at 27° C. for 4 hr. The reaction mixture was diluted with coldwater (60 mL) and stirred for 15 min. The precipitated solid was filtered through Buchner Funnel, washed with water and dried under reduced pressure to get crude compound. It was purified by Grace using C-18 reserval column, Mobile phase A: 0.1% Formic Acid in water; B: ACN, the product was eluted at 60-65% ACN/0.1% Formic Acid in water. The solvent was evaporated and basified with saturated NaHCO$_3$. The precipitated solid was filtered through Buchner Funnel, washed with water and dried under reduced pressure to get desired product (4S)—N5-(4-(((S)-2,2-dimethyl-1,3-dioxolan-4-yl)methoxy)pyridin-2-yl)-8-methyl-N7-((R)-1,1,1-trifluoropropan-2-yl)-3,4-dihydro-1,4-methanopyrido[2,3-b][1,4]diazepine-5,7(2H)-dicarboxamide (250 mg, 0.438 mmol, 76% yield) as a off white solid, LCMS (m/z): 565.37 [M+H]$^+$.

Synthesis of (4S)-5-((4-(((S)-2,2-dimethyl-1,3-dioxolan-4-yl)methoxy)pyridin-2-yl)carbamoyl)-8-methyl-2,3,4,5-tetrahydro-1,4-methanopyrido[2,3-b][1,4]diazepine-7-carboxylic acid

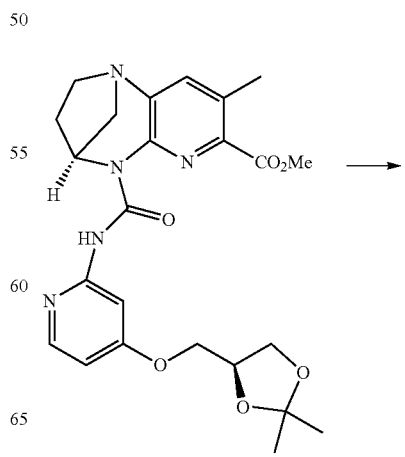

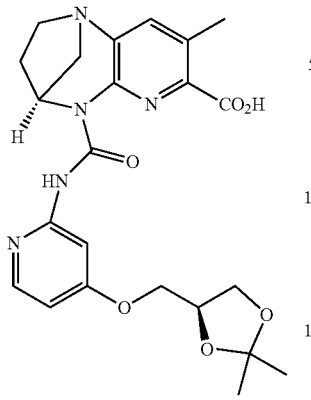

To a stirred solution of (4S)-methyl 5-((4-(((S)-2,2-dimethyl-1,3-dioxolan-4-yl)methoxy)pyridin-2-yl)carbamoyl)-8-methyl-2,3,4,5-tetrahydro-1,4-methanopyrido[2,3-b][1,4]diazepine-7-carboxylate (300 mg, 0.620 mmol) in Tetrahydrofuran (THF) (20 mL) was added LiOH.H$_2$O (29.7 mg, 1.241 mmol) in Water (5 mL) at 0° C. The reaction mixture was stirred at 27° C. for 2 hr. The reaction mixture solvent (THF) was evaporated under reduced pressure and acidified with citric acid solution at 0° C. The aqueous layer was extracted with dichloromethane (2×50 mL). Organic layer was separated, dried over anhydrous Na$_2$SO$_4$, filtered and filtrate was evaporated to give crude. The crude compound was triturated with 50% ethylacetate in hexane and dried to afford (4S)-5-((4-(((S)-2,2-dimethyl-1,3-dioxolan-4-yl)methoxy)pyridin-2-yl)carbamoyl)-8-methyl-2,3,4,5-tetrahydro-1,4-methanopyrido[2,3-b][1,4]diazepine-7-carboxylic acid (270 mg, 0.514 mmol, 83% yield) as an off white solid, LCMS (m/z): 470.28 [M+H]$^+$.

Synthesis of (4S)-methyl 5-((4-(((S)-2,2-dimethyl-1,3-dioxolan-4-yl)methoxy)pyridin-2-yl)carbamoyl)-8-methyl-2,3,4,5-tetrahydro-1,4-methanopyrido[2,3-b][1,4]diazepine-7-carboxylate

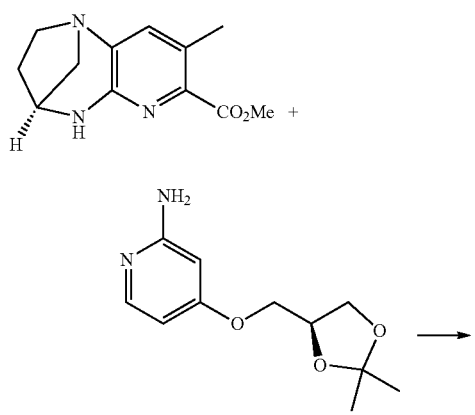

triphosgene (572 mg, 1.929 mmol) was added to a stirred solution of (4S)-methyl 8-methyl-2,3,4,5-tetrahydro-1,4-methanopyrido[2,3-b][1,4]diazepine-7-carboxylate (450 mg, 1.929 mmol), and TEA (1.613 mL, 11.57 mmol) in Tetrahydrofuran (THF) (30 mL) under nitrogen at 28° C. The reaction mixture was stirred at rt for 30 min, and was added (S)-4-((2,2-dimethyl-1,3-dioxolan-4-yl)methoxy)pyridin-2-amine (1082 mg, 4.82 mmol). The reaction mixture was stirred 16 hr at 65° C. The reaction mixture was cooled to room temp, solvent evaporated under reduced pressure completely and was partitioned between water (30 mL) and EtOAc (2×40 mL). Organic layer was separated, dried over anhydrous Na$_2$SO$_4$, filtered and filtrate was evaporated to give crude as brown solid. TLC eluent: 80% EtOAc/Hexane, R$_f$: 0.3, UV active. The crude compound was purified by Grace using C-18 reserval column, Mobile phase A: 0.1% Formic Acid in water; B: MeOH, the product was eluted at 45-50% MeOH/0.1% Formic Acid in water. The solvent was evaporated and was basified with saturated NaHCO$_3$. The aqueous layer was extracted with DCM. DCM layer was dried over anhydrous Na$_2$SO$_4$, filtered and evaporated to afford pure (4S)-methyl 5-((4-(((S)-2,2-dimethyl-1,3-dioxolan-4-yl)methoxy)pyridin-2-yl)carbamoyl)-8-methyl-2,3,4,5-tetrahydro-1,4-methanopyrido[2,3-b][1,4]diazepine-7-carboxylate (300 mg, 0.603 mmol, 31.3% yield) as pale yellow solid, LCMS (m/z): 484.30 [M+H]$^+$.

Synthesis of (4S)-methyl 8-methyl-2,3,4,5-tetrahydro-1,4-methanopyrido[2,3-b][1,4]diazepine-7-carboxylate

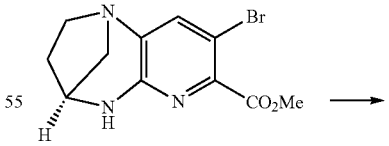

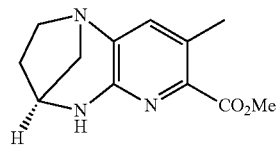

A suspension of (4S)-methyl 8-bromo-2,3,4,5-tetrahydro-1,4-methanopyrido[2,3-b][1,4]diazepine-7-carboxylate (1 g, 3.35 mmol) in 1,4-Dioxane (15 mL) 2,4,6-trimethyl-1,3,5,2,4,6-trioxatriborinane (1.917 mL, 6.71 mmol) and K$_2$CO$_3$ (1.391 g, 10.06 mmol) stirred and degassed with argon at room temp for 15 min, PdCl$_2$(dppf)-CH$_2$Cl2 adduct (0.151 g, 0.184 mmol) was added to the reaction mixture. Then the reaction mixture was stirred 1 hr at 120° C. The reaction mixture was cooled to room temp, and filtered through celite and washed with EtOAc (30 ml). The filtrate was concentrated and purified by column chromatography. The crude product was purified by column chromatography using neutral alumina and was eluted with 35-40% EtOAc in Hexane (gradient system) to afford the desired product (4S)-methyl 8-methyl-2,3,4,5-tetrahydro-1,4-methanopyrido[2,3-b][1,4]diazepine-7-carboxylate (450 mg, 1.754 mmol, 52.3% yield) as a pale yellow solid, LCMS (m/z): 234.01 [M+H]$^+$.

Synthesis of (4S)-5-((5-fluoro-4-methylpyridin-2-yl)carbamoyl)-2,3,4,5-tetrahydro-1,4-methanopyrido[2,3-b][1,4]diazepine-7-carboxylic acid

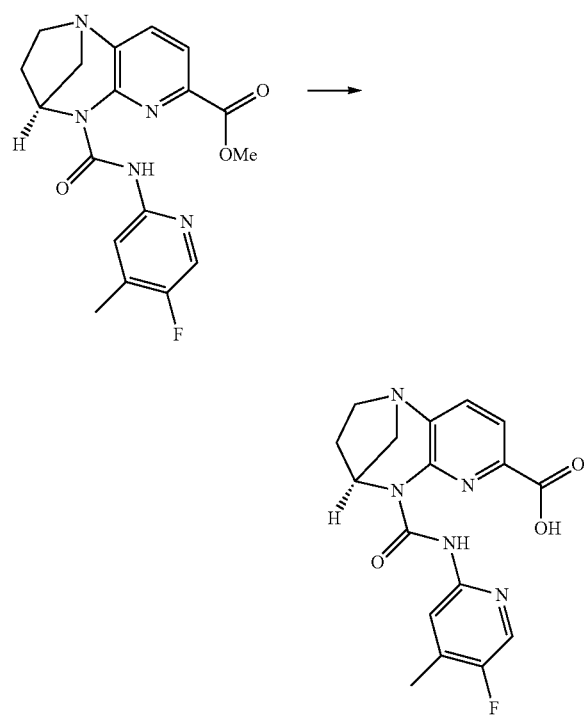 [SMILES: COC(=O)c1ccc2c(n1)N(C(=O)Nc1cc(C)c(F)cn1)[C@H]1CCN2C1 ; Cc1cc(NC(=O)N2c3nc(C(=O)O)ccc3N3CC[C@H]2C3)ncc1F]

To a stirred solution of (4S)-methyl 5-((5-fluoro-4-methylpyridin-2-yl)carbamoyl)-2,3,4,5-tetrahydro-1,4-methanopyrido[2,3-b][1,4]diazepine-7-carboxylate (850 mg, 2.289 mmol) in Tetrahydrofuran (THF) (15 mL) and Water (7.5 mL) was added LiOH (110 mg, 4.58 mmol). Progress of the reaction was monitored by TLC, TLC indicated formation of a polar spot and SM was consumed. THF was evaporated completely and acidified the reaction mixture with 2M HCl. The obtained solid was filtered and washed with petether and dried under high vacuum to obtain desired pure product (4S)-5-((5-fluoro-4-methylpyridin-2-yl)carbamoyl)-2,3,4,5-tetrahydro-1,4-methanopyrido[2,3-b][1,4]diazepine-7-carboxylic acid (700 mg, 1.932 mmol, 84% yield) as an off-white solid. LCMS (m/z): 358.20 (M+H)$^+$.

Synthesis of (4S)-methyl 5-((5-fluoro-4-methylpyridin-2-yl)carbamoyl)-2,3,4,5-tetrahydro-1,4-methanopyrido[2,3-b][1,4]diazepine-7-carboxylate

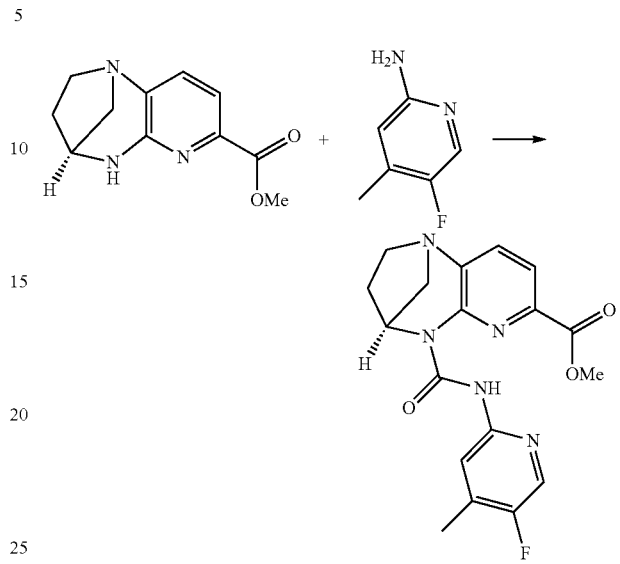

To a stirred solution of (4S)-methyl 2,3,4,5-tetrahydro-1,4-methanopyrido[2,3-b][1,4]diazepine-7-carboxylate (1.2 g, 5.47 mmol) in Tetrahydrofuran (THF) (30 mL), was added triphosgene (1.299 g, 4.38 mmol) followed by TEA (2.289 mL, 16.42 mmol) the reaction mixture was stirred at rt for 15 mins, then added 5-fluoro-4-methylpyridin-2-amine (0.690 g, 5.47 mmol). The reaction mixture was stirred at 80° C. for 16 hr. Progress of the reaction was monitored by TLC. TLC indicated starting material was consumed to form non polar spot. Water (50 mL) was added to the reaction mixture, aqueous layer was extracted with EtOAc (2×40 mL). The combined organic layer was dried over anhydrous Na$_2$SO$_4$, filtered and concentrated to obtain desired crude product. The crude product was purified by column chromatography using 100-200 silica gel (eluent as 60% EtOAc in petether). The fraction containing pure compound was evaporated to obtain desired pure product (4S)-methyl 5-((5-fluoro-4-methylpyridin-2-yl)carbamoyl)-2,3,4,5-tetrahydro-1,4-methanopyrido[2,3-b][1,4]diazepine-7-carboxylate (900 mg, 2.342 mmol, 42.8% yield) as light brown solid, LCMS (m/z): 372.23 (M+H)$^+$.

Synthesis of (4S)-5-((3,5-difluoropyridin-2-yl)carbamoyl)-2,3,4,5-tetrahydro-1,4-methanopyrido[2,3-b][1,4]diazepine-7-carboxylic acid

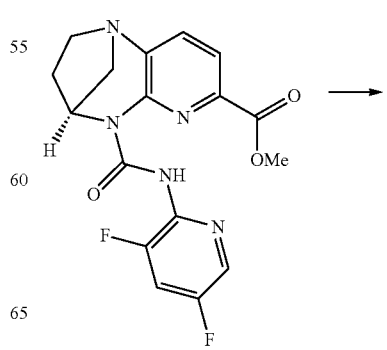

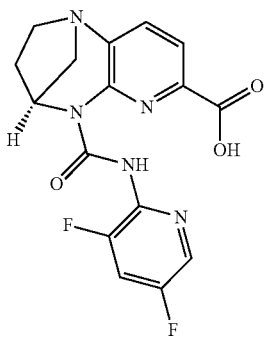

To a stirred solution of (4S)-methyl 5-((3,5-difluoropyridin-2-yl)carbamoyl)-2,3,4,5-tetrahydro-1,4-methanopyrido[2,3-b][1,4]diazepine-7-carboxylate (850 mg, 2.265 mmol) in Tetrahydrofuran (THF) (15 mL) and Water (7.5 mL) was added LiOH (54.2 mg, 2.265 mmol). Progress of the reaction was monitored by TLC, TLC indicated formation of a polar spot and SM was consumed. THF was evaporated completely and acidified the reaction mixture with 2M HCl. The obtained solid was filtered and washed with petether and dried under high vacuum to obtain desired pure product (4S)-5-((3,5-difluoropyridin-2-yl)carbamoyl)-2,3,4,5-tetrahydro-1,4-methanopyrido[2,3-b][1,4]diazepine-7-carboxylic acid (700 mg, 1.918 mmol, 85% yield) as an off-white solid. LCMS (m/z): 362.16 (M+H)+.

Synthesis of (4S)-methyl 5-((3,5-difluoropyridin-2-yl)carbamoyl)-2,3,4,5-tetrahydro-1,4-methanopyrido[2,3-b][1,4]diazepine-7-carboxylate

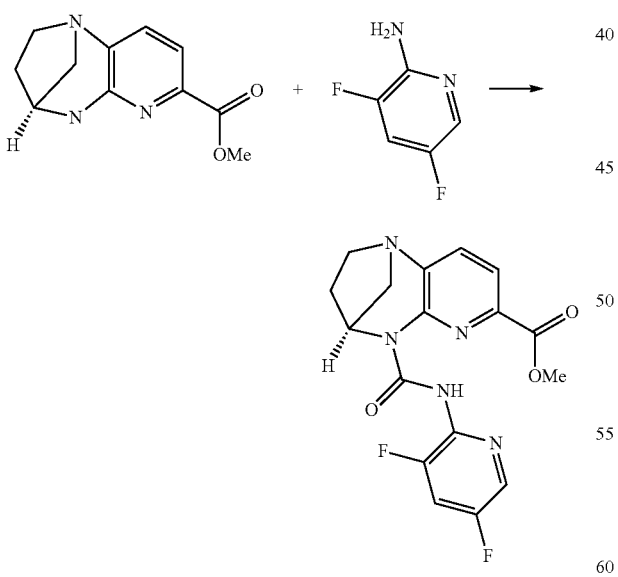

To a stirred solution of (4S)-methyl 2,3,4,3-tetrahydro-1,4-methanopyrido[2,3-b][1,4]diazepine-7-carboxylate (1.2 g, 5.47 mmol) in Tetrahydrofuran (THF) (30 mL), was added triphosgene (1.624 g, 5.47 mmol) followed by TEA (0.763 mL, 5.47 mmol) the reaction mixture was stirred at rt for 15 mins, then added 3,5-difluoropyridin-2-amine (0.712 g, 5.47 mmol). The reaction mixture was stirred at 80° C. for 16 hr. Progress of the reaction was monitored by TLC. TLC indicated starting material was consumed to form non polar spot. Water (50 mL) was added to the reaction mixture, aqueous layer was extracted with EtOAc (2×40 mL). The combined organic layer was dried over anhydrous Na₂SO₄, filtered and concentrated to obtain desired crude product. The crude product was purified by column chromatography using 100-200 silica gel (eluent as 60% EtOAc in petether). The fraction containing pure compound was evaporated to obtain desired pure product (4S)-methyl 5-((3,5-difluoropyridin-2-yl)carbamoyl)-2,3,4,5-tetrahydro-1,4-methanopyrido[2,3-b][1,4]diazepine-7-carboxylate (900 mg, 2.278 mmol, 41.6% yield) as light brown solid, LCMS (m/z): 376.23 (M+H)+.

Synthesis of (4S)-5-((4-((2-hydroxyethyl)amino)pyridin-2-yl)carbamoyl)-2,3,4,5-tetrahydro-1,4-methanopyrido[2,3-b][1,4]diazepine-7-carboxylic acid

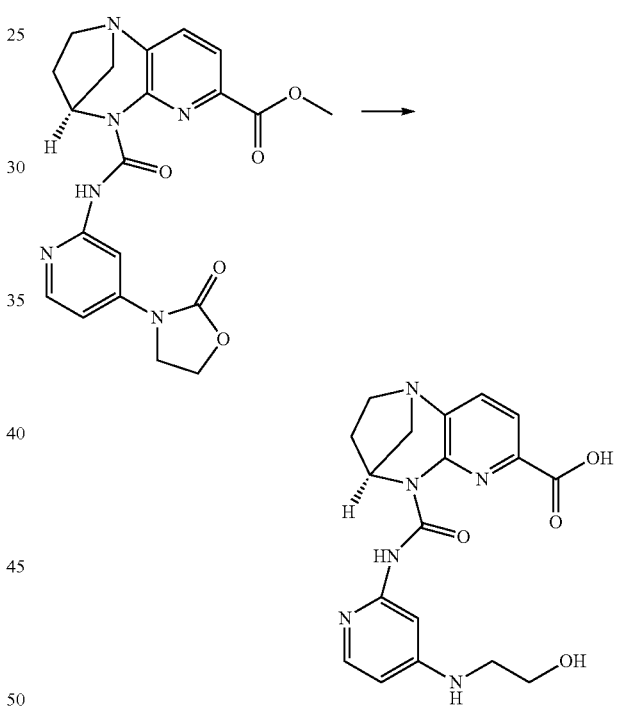

To a stirred solution of (4S)-methyl 5-((4-(2-oxooxazolidin-3-yl)pyridin-2-yl)carbamoyl)-2,3,4,5-tetrahydro-1,4-methanopyrido[2,3-b][1,4]diazepine-7-carboxylate (1.2 g, 2.83 mmol) in Tetrahydrofuran (THF) (50 mL) and Water (15 mL) at 28° C. Then reaction mixture was cooled to 0° C. and add LiOH (0.339 g, 14.14 mmol) at 0° C. and reaction mixture was stirred at 28° C. for 4 hr. Reaction progress was monitored by TLC and LCMS. The reaction mixture solvent was evaporated completely under reduced pressure and obtained crude was taken and adjust pH 2-4 with 1N HCl solution. Then extracted with ethyl acetate (3×100 mL) and washed with brine solution (50 mL). Combined organic layers and dried over Na₂SO₄, filtered and filtrate was concentrated to get crude compound, LCMS (m/z): 385.2 (M+H)+.

Synthesis of (4S)-methyl 5-((4-(2-oxooxazolidin-3-yl)pyridin-2-yl)carbamoyl)-2,3,4,5-tetrahydro-1,4-methanopyrido[2,3-b][1,4]diazepine-7-carboxylate

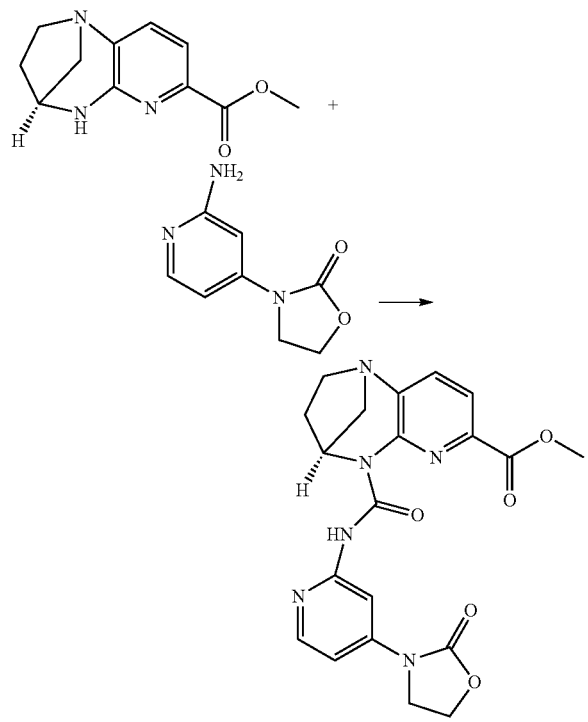

To a stirred solution of (4S)-methyl 2,3,4,5-tetrahydro-1,4-methanopyrido[2,3-b][1,4]diazepine-7-carboxylate (1.25 g, 5.70 mmol) in Tetrahydrofuran (THF) (50 mL) at 28° C. Then add triphosgene (1.015 g, 3.42 mmol) and triethylamine (4.77 mL, 34.2 mmol) at 10° C. Reaction mixture was stirred at 28° C. for 4 hr. Then 3-(2-aminopyridin-4-yl) oxazolidin-2-one (1.532 g, 8.55 mmol) was added to the reaction mixture at 28° C. and stirred at 80° C. for 16 h. The reaction mixture was cooled to RT, diluted with water 100 mL), extracted with ethyl acetate (3×100 mL) and washed with brine solution (50 mL). Organic layer was separated, dried over Na₂SO₄, filtered and concentrated to get crude compound. Crude compound was purified by flash column chromatography using silica gel (100:200 mesh) to afford pure (4S)-methyl 5-((4-(2-oxooxazolidin-3-yl)pyridin-2-yl) carbamoyl)-2,3,4,5-tetrahydro-1,4-methanopyrido[2,3-b][1,4]diazepine-7-carboxylate (1.5 g, 3.36 mmol, 58.9% yield), LCMS (m/z): 425.13 (M+H)⁺.

Synthesis of 3-(2-aminopyridin-4-yl)oxazolidin-2-one

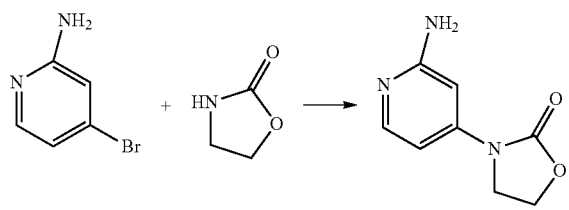 [SMILES: Nc1cc(Br)ccn1 ; O=C1NCCO1 ; Nc1cc(N2CCOC2=O)ccn1]

To a stirred solution of 4-bromopyridin-2-amine (2.0 g, 11.56 mmol) in 1,4-Dioxane (20 ml) was added oxazolidin-2-one (1.510 g, 17.34 mmol), potassium carbonate (3.20 g, 23.12 mmol), copper(I) iodide (0.220 g, 1.156 mmol), N,N'-dimethylethylenediamine (0.204 g, 2.312 mmol) at rt. The resulting reaction mixture was stirred in microwave at 110° C. for 1 hr and progress of the reaction was monitored by TLC. Reaction mixture solvent was evaporated, diluted with water (30 mL) and stirred for 20 minutes solid was filtered and dried under vacuum to obtained 3-(2-aminopyridin-4-yl)oxazolidin-2-one (1.5 g, 8.13 mmol, 70.4% yield) as off white solid, LCMS (m/z): 180.0[M+H]⁺.

Synthesis of (4S)—N5-(4-(((S)-2,2-dimethyl-1,3-dioxolan-4-yl)methoxy)pyridin-2-yl)-N7-(4-fluorobenzyl)-3,4-dihydro-1,4-methanopyrido[2,3-b][1,4]diazepine-5,7(2H)-dicarboxamide

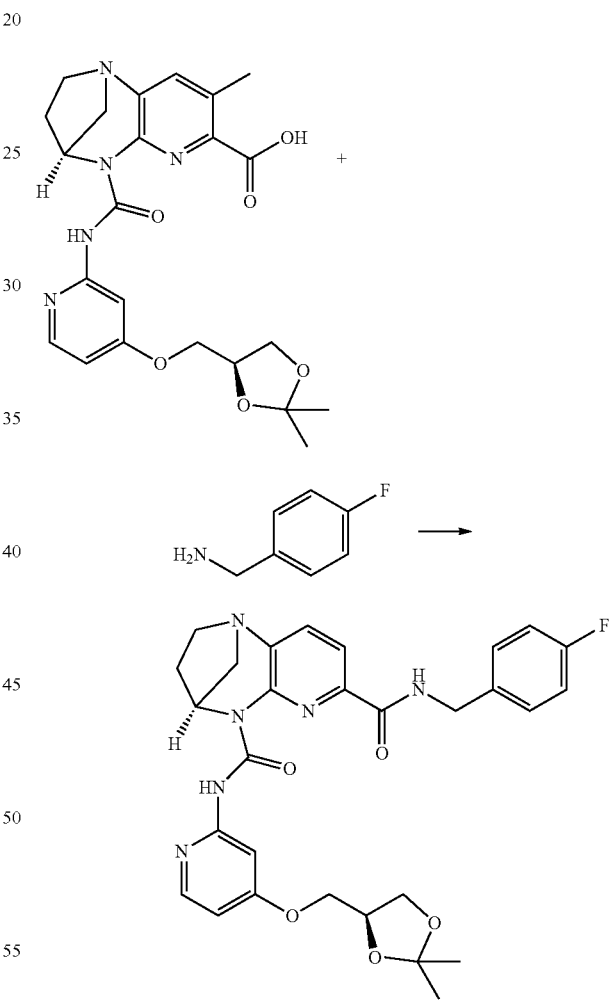

HATU (626 mg, 1.647 mmol) followed by DIPEA (0.192 mL, 1.098 mmol) were added to a solution of (4S)-5-((4-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid (500 mg, 1.098 mmol) in N,N-Dimethylformamide (DMF) (20 mL) at 25° C., stirred for 1 h and (4-fluorophenyl)methanamine (0.206 mL, 1.647 mmol) was added and stirred at RT for 16 h. The reaction mixture was partitioned between water (200 mL) and EtOAc (2×300 mL). Organic layer was separated and was dried over anhydrous Na₂SO₄, filtered and filtrate was evaporated to get Crude. The crude product was purified by flash column chromatography (silica-gel: 100-200 mesh) and was eluted with 2% MeOH-DCM to afford (4S)—N5-(4-(((S)-2,2-dimethyl-1,3-dioxolan-4-yl)methoxy)pyridin-2-yl)-N7-(4-fluorobenzyl)-3,4-dihydro-1,4-methanopyrido[2,3-b][1,4]diazepine-5,7(2H)-dicarboxamide (301.5 mg, 0.530 mmol, 48.3% yield) LCMS (m/z): 563.28 [M+H]⁺.

Synthesis of (4S)—N5-(4-cyanopyridin-2-yl)-N7-((R)-1,1,1-trifluoropropan-2-yl)-3,4-dihydro-1,4-methanopyrido[2,3-b][1,4]diazepine-5,7(2H)-dicarboxamide

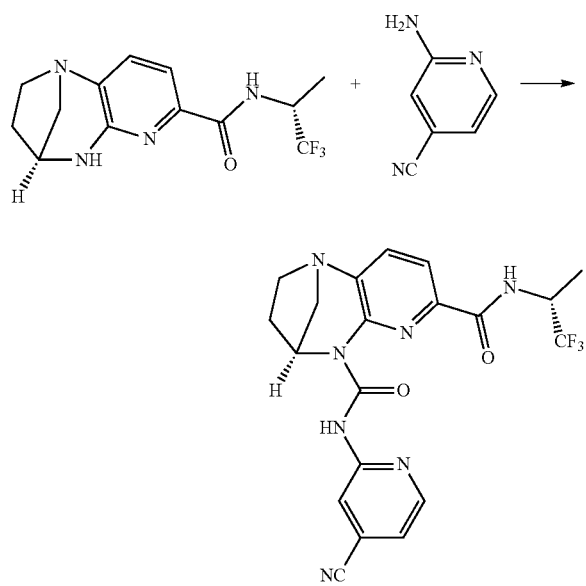

To a stirred solution of (4S)—N—((R)-1,1,1-trifluoropropan-2-yl)-2,3,4,5-tetrahydro-1,4-methanopyrido[2,3-b][1,4]diazepine-7-carboxamide (3.2 g, 10.66 mmol) in THF (50 mL) was added TEA (8.91 mL, 63.9 mmol) and triphosgene (2.214 g, 7.46 mmol) under nitrogen at 0° C. Stirred the reaction mixture at 25° C. for 1 hr. After 1 hr added 2-aminoisonicotinonitrile (2.54 g, 21.31 mmol) to the reaction mass in one charge at 0° C. and heated the RM to 60° C., maintained it at 60° C. for 16 hr. Progress of the reaction was monitored by TLC. Reaction mixture was cooled to room temperature, Reaction mass was filtered to remove salts. The collected filtrate was diluted with water (50 mL) and extracted with EtOAc (3×40 mL). The combined organic layers were washed with brine solution (2×100 mL), organic layer was dried over Na₂SO₄ and concentrated it to get crude compound. The crude product was added to a silica gel (100-200) column and was eluted with 65-70% EtOAc-Pet Ether. Collected fractions were concentrated under vacuo to get compound (4S)—N5-(4-cyanopyridin-2-yl)-N7-((R)-1,1,1-trifluoropropan-2-yl)-3,4-dihydro-1,4-methanopyrido[2,3-b][1,4]diazepine-5,7(2H)-dicarboxamide (1.1 g, 2.430 mmol, 22.80% yield) as a pale yellow solid, LCMS (m/z): 446.12 [M+H]⁺.

Synthesis of 4-morpholinopyridin-2-amine

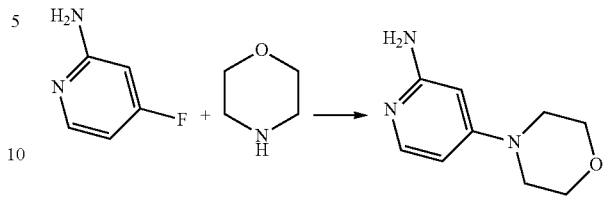

To a suspension of 4-fluoropyridin-2-amine (2.0 g, 17.84 mmol) in morpholine (7.77 g, 89 mmol) was added potassium carbonate (12.33 g, 89 mmol), copper(I) iodide (0.340 g, 1.784 mmol) and N,N'-dimethylethylenediamine (0.315 g, 3.57 mmol) at rt. The resulting reaction mixture was stirred in microwave at 110° C. for 1 h and progress of the reaction was monitored by TLC (TLC eluting system: 10% MeOH in DCM, R_f—: 0.1; UV active). The reaction mixture was quenched with ice water (30 mL) and extracted with EtOAc (3×30 mL). The combined organic layer was washed with brine solution, dried over anhydrous Na₂SO₄ and evaporated to get crude compound. The crude compound was triturated with diethyl ether (3×5 mL) to afford 4-morpholinopyridin-2-amine (1.7 g, 9.15 mmol, 51.3% yield) as Pale yellow solid. LCMS (m/z): 180.26 [M+H]⁺.

Synthesis of (4S)-methyl 5-((4-morpholinopyridin-2-yl)carbamoyl)-2,3,4,5-tetrahydro-1,4-methanopyrido[2,3-b][1,4]diazepine-7-carboxylate

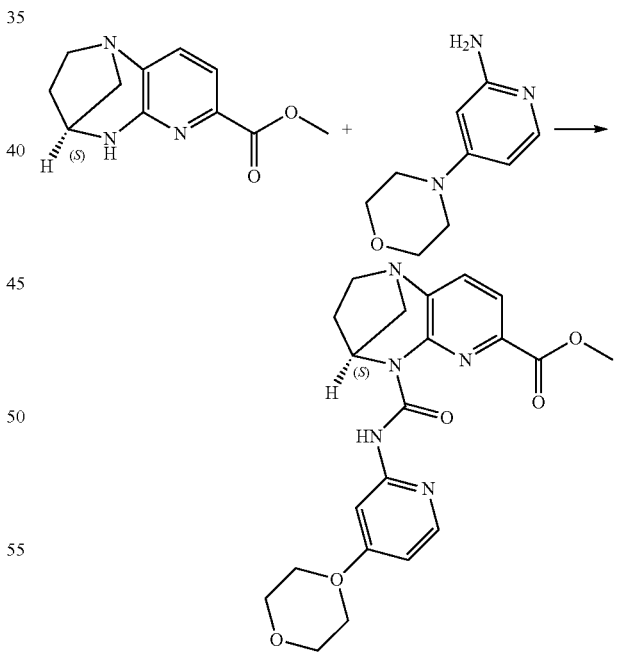

To a stirred solution of (4S)-methyl 2,3,4,5-tetrahydro-1,4-methanopyrido[2,3-b][1,4]diazepine-7-carboxylate (500 mg, 2.281 mmol), triethylamine (1.589 mL, 11.40 mmol) and triphosgene (677 mg, 2.281 mmol) in Tetrahydrofuran (THF) (40 mL) under nitrogen, stirred at rt for 2 h. 4-morpholinopyridin-2-amine (817 mg, 4.56 mmol) was added to the reaction mixture. The reaction mixture was stirred at 70°

C. for 16 h (TLC eluent: 10% MeOH in DCM: $R_f$—0.3; UV active). The reaction mixture was cooled to rt, partitioned between water (30 mL) and EtOAc (3×30 mL). The combined organic layer was washed with brine solution, dried over anhydrous $Na_2SO_4$, filtered and filtrate was evaporated to get crude. The crude compound was purified by column chromatography using neutral alumina and eluted at 20% EtOAc in Pet ether to afford (4S)-methyl 5-((4-morpholinopyridin-2-yl)carbamoyl)-2,3,4,5-tetrahydro-1,4-methanopyrido[2,3-b][1,4]diazepine-7-carboxylate (400 mg, 0.909 mmol, 39.9% yield) as an off white solid, LCMS (m/z): 425.07 [M+H]$^+$.

Synthesis of (4S)—N5-(4-(((S)-2,2-dimethyl-1,3-dioxolan-4-yl)methoxy)pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide N5-(4-(((S)-2,2-dimethyl-1,3-dioxolan-4-yl)methoxy)pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide (550 mg, 0.987 mmol, 56.3% yield) as an white solid, LCMS (m/z): 552.21 [M+H]$^+$.

(4S)—N7-(2,2-difluorocyclopropyl)-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide

&

(4S)—N7-(2,2-difluorocyclopropyl)-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide

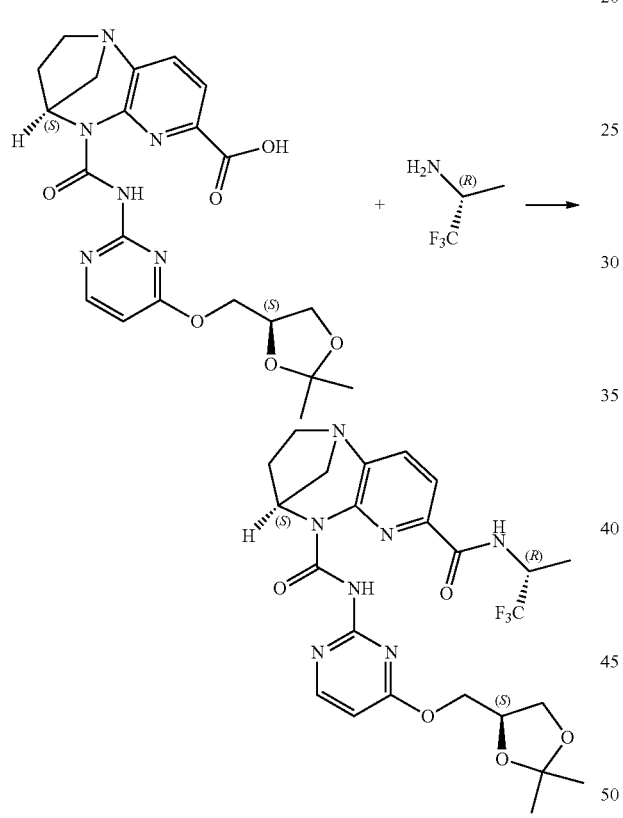

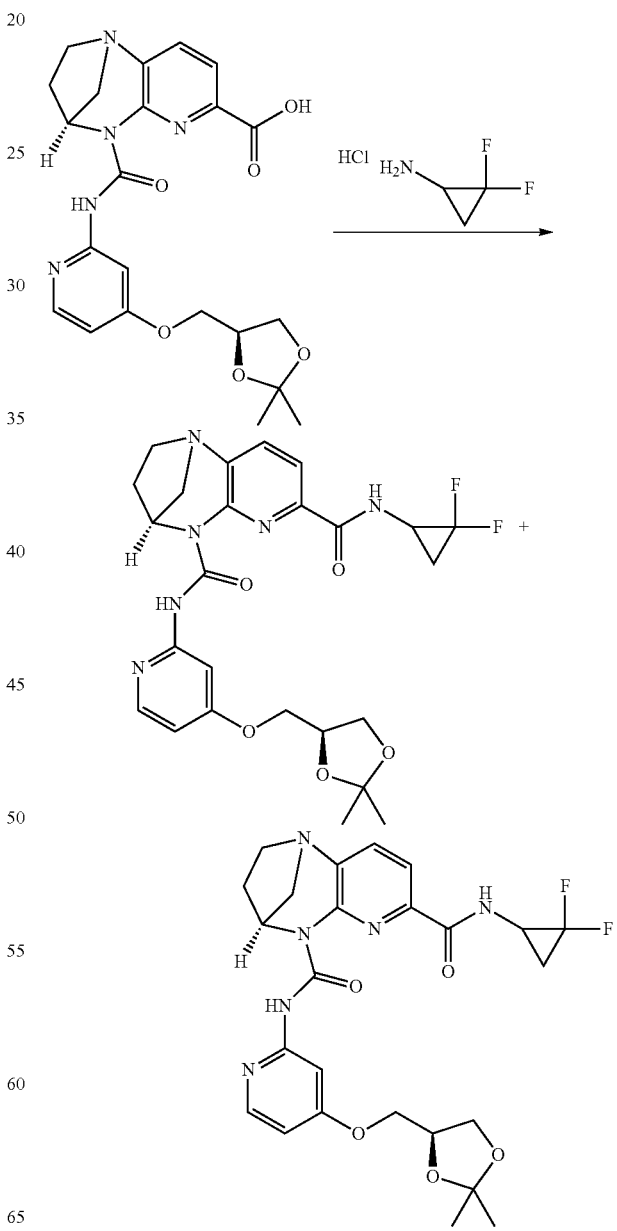

To a stirred solution of (4S)-5-((4-(((S)-2,2-dimethyl-1,3-dioxolan-4-yl)methoxy)pyrimidin-2-yl)carbamoyl)-2,3,4,5-tetrahydro-1,4-methanopyrido[2,3-b][1,4]diazepine-7-carboxylic acid (800 mg, 1.753 mmol) in Tetrahydrofuran (THF) (500 mL) and were added DIPEA (0.918 mL, 5.26 mmol) followed by HATU (1000 mg, 2.63 mmol), The reaction mixture was stirred for 1 h at RT. After 1 h (R)-1,1,1-trifluoropropan-2-amine (297 mg, 2.63 mmol) was added, The resulting reaction mixture was stirred at 27° C. for 16 h. (TLC system: EtOAc, Rf: 0.5). Reaction mixture was poured in ice water (300 mL), excreted with EtOAc (2×500 mL), separated the organic layer dried over anhydrous $Na_2SO_4$, filtered and concentrated under reduced pressure to obtained crude was purified by Neutral alumina column (Eluent: 20% EtOAc in Pet Ether) to afford (4S)—

To a stirred solution of (4S)-5-((4-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid (1.5 g, 3.29 mmol) in Pyridine (10 mL). To this added EDC (1.894 g, 9.88 mmol) at 0° C., reaction mixture was stirred at 0° C. for 30 min, then added 2,2-difluorocyclopropanamine hydrochloride (0.512 g, 3.95 mmol), reaction mixture was stirred at RT for 16 hr. Progress of the reaction was monitored by TLC. Reaction mixture was cooled to RT, Water (50 mL) and extracted with ethyl acetate (2×50 mL), separated organic layer, dried over $Na_2SO_4$, concentrated under reduced pressure to obtain crude. Obtained crude was purified by column using silica (100-200 mesh/3% MeOH/DCM as a eluent), collected fractions were concentrated to get pure compound 500 mg. The obtained pure compound was purified by SFC.

After SFC purification to get (4S)—N7-(2,2-difluorocyclopropyl)-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide (200 mg, 0.374 mmol, 11.36% yield), LCMS (m/z): 531.39 $[M+H]^+$.

(Peak-1) (230 mg, 0.414 mmol, 7.77% yield) and (4S)—N7-(2,2-difluorocyclopropyl)-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide (160 mg, 0.301 mmol, 9.13% yield), LCMS (m/z): 531.07 $[M+H]^+$.

SFC Condition:
Column/dimensions: Chiralpak IC (250×30) mm, 5μ
% CO2:60.0%
% Co solvent: 40.0% (100% IPA)
Total Flow: 100.0 g/min
Back Pressure: 100.0 bar
UV: 212 nm
Stack time: 8.0 min
Load/Inj: 16.0 mg
Instrument details: Make/Model: Thar SFC-200-005

Synthesis of (4S)-5-(isoxazol-3-ylcarbamoyl)-2,3,4,5-tetrahydro-1,4-methanopyrido[2,3-b][1,4]diazepine-7-carboxylic acid

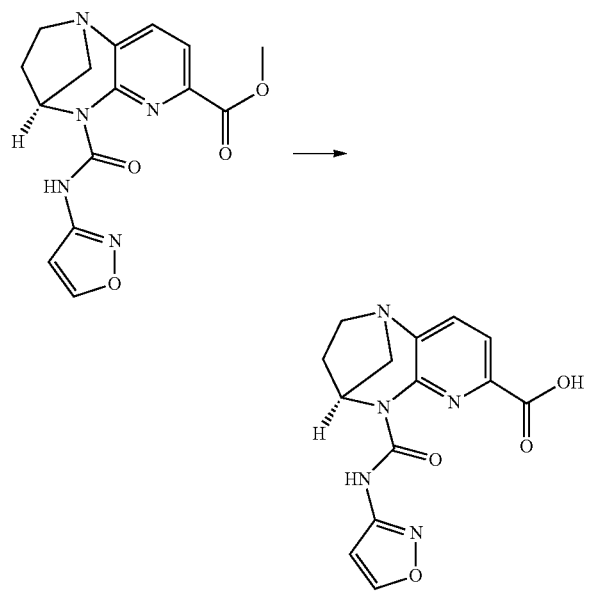

To a solution of (4S)-methyl 5-(isoxazol-3-ylcarbamoyl)-2,3,4,5-tetrahydro-1,4-methanopyrido[2,3-b][1,4]diazepine-7-carboxylate (1.3 g, 3.95 mmol), in Tetrahydrofuran (THF) (50 mL) stirred under nitrogen at room temp, was added a solution of LiOH (0.284 g, 11.84 mmol) in Water (50 mL) dropwise during 1 min. The reaction mixture was stirred at room temperature for 16 hr. Progress of the reaction was monitored by TLC. TLC indicated formation of a polar spot and complete consumption of SM. Reaction mixture was concentrated under reduced pressure, diluted with cold water (20 ml), washed with DCM (2×50 mL), aq layer was neutralized with 1N HCl (40 mL) to get sticky solid, excreted with 20% MeOH\DCM (2×30), separated the organic layer washed with brine (10 mL) dried over anhydrous $Na_2SO_4$, filtered and concentrated under reduced pressure to get desired product. The compound was triturated with Diethyl ether (2×40 ml). The resulting solid was filtered through a Buchner funnel dried under vacuum to get the (4S)-5-(isoxazol-3-ylcarbamoyl)-2,3,4,5-tetrahydro-1,4-methanopyrido[2,3-b][1,4]diazepine-7-carboxylic acid (1 g, 2.95 mmol, 74.8% yield) as an off white solid, LCMS (m/z): 316.10 $[M+H]^+$.

Synthesis of (4S)-methyl 5-(isoxazol-3-ylcarbamoyl)-2,3,4,5-tetrahydro-1,4-methanopyrido[2,3-b][1,4]diazepine-7-carboxylate

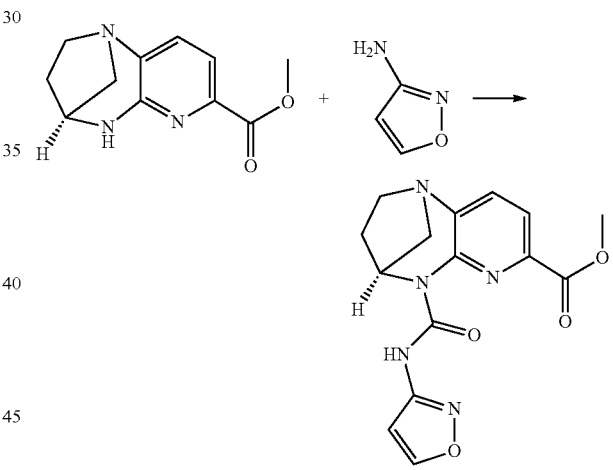

(4S)-methyl 2,3,4,5-tetrahydro-1,4-methanopyrido[2,3-b][1,4]diazepine-7-carboxylate (2 g, 9.12 mmol), triethylamine (3.81 mL, 27.4 mmol) were taken in Tetrahydrofuran (THF) (100 mL) at 0° C., the resulting yellow solution was stirred for 10 min. Then added triphosgene (1.354 g, 4.56 mmol) in one portion at 0° C. The resulting yellow suspension was stirred for 45 min at room temperature. The THF (30 mL) solution of isoxazol-3-amine (1.150 g, 13.68 mmol) was added to the above yellow suspension at 0° C. over a period of 5 min. The resulting yellow suspension was heated to 70° C. for 24 hr. The reaction progress was monitored by TLC 80% EtOAc in pet ether, TLC indicated formation of multiple spots after 24 h. The reaction mass was cooled to room temperature, diluted with water (200 mL), ethyl acetate (300 mL*2). The combined organic layer was washed with brine (150 mL), dried over $Na_2SO_4$ filtered, concentrated under reduced pressure to afford brown solid. The crude product was purified by combiflash chromatography using silica gel column (40 g, 50% EtOAc in pet ether). Column was eluted with a gradient of EtOAc in Hexane. Desired compound was eluted with 50% EtOAc in Hexane. Fractions containing pure compound were concentrated under reduced pressure to afford the (4S)-methyl 5-(isoxazol-3-ylcarbamoyl)-2,3,4,5-tetrahydro-1,4-methanopyrido[2,3-b][1,4]diazepine-7-carboxylate (1.4 g, 3.26 mmol, 35.7% yield) as an off-white solid, LCMS (m/z): 330.10 [M+H]+.

Synthesis of (4S)—N7-cyclopropyl-N5-(4-(((R)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide

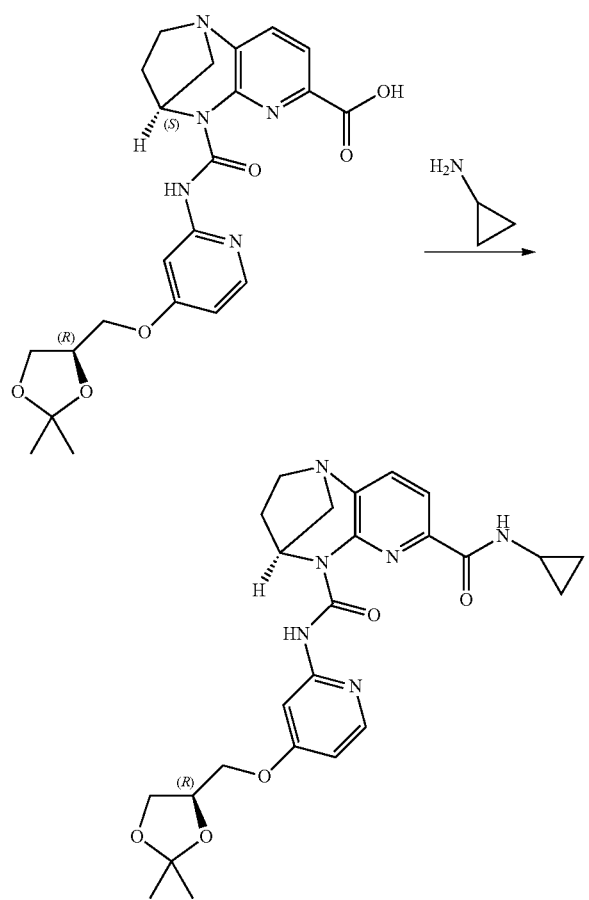

To a solution of (4S)-5-((4-(((R)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid (1 g, 2.196 mmol) in N,N-Dimethylformamide (DMF) (10 mL), stirred under nitrogen at 0° C. and added TEA (0.765 mL, 5.49 mmol) followed by HATU (1.670 g, 4.39 mmol). After stirring the reaction mixture for 10 min at room temperature, added cyclopropanamine (0.439 g, 7.68 mmol) under nitrogen. The resulting reaction mixture was stirred at room temperature for 16 hr. Progress of the reaction was monitored by TLC. TLC indicated formation of a non polar spot, consumption of SM and formation of multiple spots. Reaction mixture was poured in ice cold water (20 ml), extracted with EtOAc (2×30 ml). The combined organic layer was washed with brine (20 mL), dried over anhydrous Na2SO4, filtered and concentrated under reduced pressure to obtain crude as off white solid. The crude material was purified by combiflash using silica gel column (12 g, 10% MeOH in DCM). Fraction containing pure compound were combined and concentrated under reduced pressure to afford the desired compound (4S)—N7-cyclopropyl-N5-(4-(((R)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide (950 mg, 1.865 mmol, 85% yield) as off white solid. LCMS (m/z): 495.28 [M+H]+.

N36375-21-A1

Synthesis of (4S)-5-((4-(((R)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid

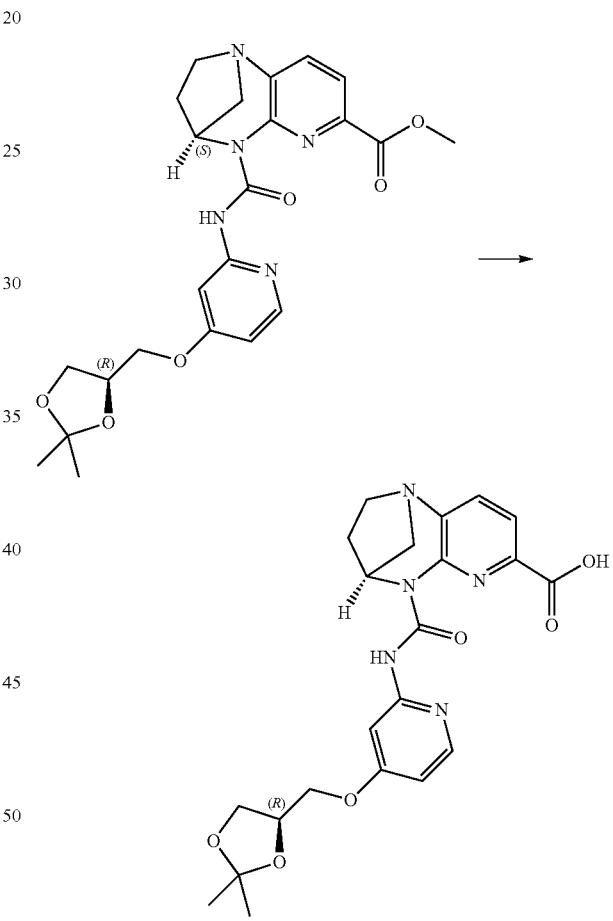

To a stirred suspension of (4S)-methyl 5-((4-(((R)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylate (1.00 g, 2.130 mmol) in Tetrahydrofuran (THF) (10.00 mL), Methanol (10.00 mL) and Water (10 mL) stirred under nitrogen at 0° C. was added LiOH (0.255 g, 10.65 mmol) in water (3 mL) over a period of 2 min. The resulting reaction mixture was stirred at room temperature for 16 hr. Progress of the reaction was monitored by TLC. TLC indicated consumption of starting material and formation of new polar spot. The reaction mass was concentrated under reduced pressure then diluted with 6 mL water, then neutralized with saturated citric acid to brought pH neutral. During the process, off white precipitated, filtered under vacuum and dried afford white solid which was triturated with diethyl ether (20 mL×2) to afford (4S)-5-((4-(((R)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid (1 g, 2.078 mmol, 98% yield) as off white solid. LCMS (m/z): 456.00 [M+H]$^+$.

Synthesis of (4S)-methyl 5-((4-(((R)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylate

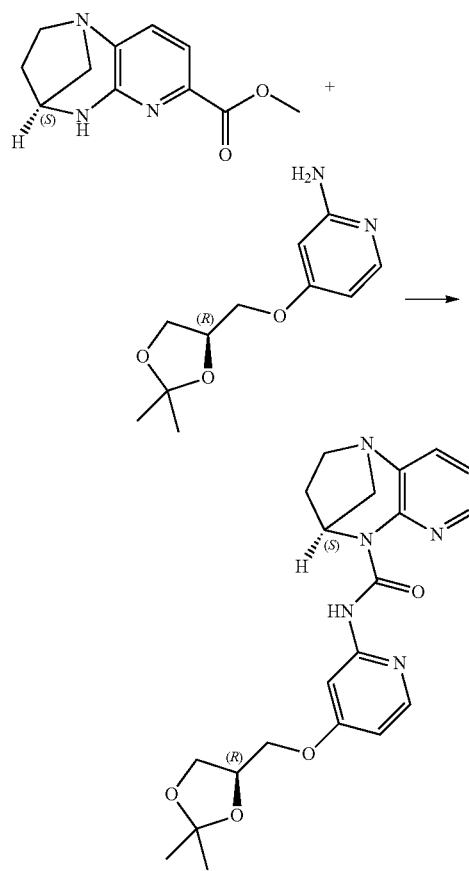

(4S)-methyl 2,3,4,5-tetrahydro-1,4-methanopyrido[2,3-b][1,4]diazepine-7-carboxylate (2.25 g, 10.26 mmol), TEA (7.15 mL, 51.3 mmol) were taken in Tetrahydrofuran (THF) (40 mL) at 0° C., the resulting yellow solution was stirred for 10 min at room temperature. Then added triphosgene (3.05 g, 10.26 mmol) in one portion at 0° C. The resulting yellow suspension was stirred for 45 min at room temperature. The THF (10 mL) solution of (R)-4-((2,2-dimethyl-1,3-dioxolan-4-yl)methoxy)pyridin-2-amine (2.301 g, 10.26 mmol) was added to the above yellow suspension at 0° C. over a period of 2 min. The resulting yellow suspension was heated to 70° C. for 24 hr. The reaction progress was monitored by TLC 5% MeOH in DCM, TLC indicated formation of multiple spots and completion of SM after 24 h. Reaction mixture was cooled to room temperature, then diluted with water (20 mL), excreted with EtOAc (2×40 mL), separated the organic layer washed with brine (20 mL) dried over anhydrous Na$_2$SO$_4$, filtered and concentrated under reduced pressure to obtained crude. The crude material was purified by combiflash using silica gel column (12 g, 5% MeOH in DCM). Fraction containing pure compound were combined and concentration to afford the desired compound (4S)-methyl 5-((4-(((R)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylate (3.2 g, 6.09 mmol, 59.4% yield) as yellow solid. LCMS (m/z): 470.19 [M+H]$^+$.

Synthesis of (4S)-7-(benzylthio)-N-(pyridin-2-yl)-3,4-dihydro-1,4-methanopyrido[2,3-b][1,4]diazepine-5(2H)-carboxamide

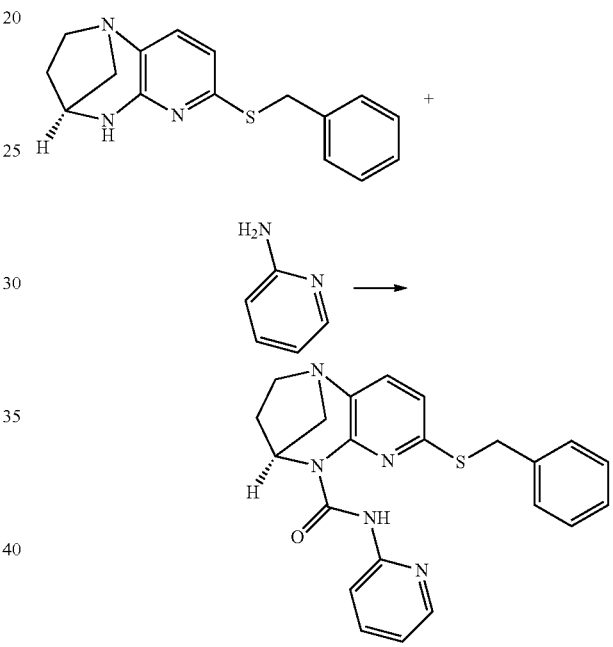

To a suspension of (4S)-7-(benzylthio)-2,3,4,5-tetrahydro-1,4-methanopyrido[2,3-b][1,4]diazepine (3 g, 10.59 mmol) in Tetrahydrofuran (THF) (60 mL) was added DIPEA (9.24 mL, 52.9 mmol) followed by triphosgene (3.14 g, 10.59 mmol) at rt. After stirring for 20 min, pyridin-2-amine (1.993 g, 21.17 mmol) was added to the reaction mass and then the reaction mixture was stirred at 70° C. for 16 hr. After the completion of reaction (monitored by TLC, indicates absence of starting material and the formation of new major spot was observed at Rf: 0.6), water (50 ml) was added to the reaction mass and the aqueous layer was extracted with ethyl acetate (2×50 ml). The organic layer was dried over Na$_2$SO$_4$ filtered and concentrated under reduced pressure to get brown liquid (crude). Crude material was purified by combi flash using silica gel column (24 g, 2% MeOH in DCM). Fractions containing pure compound were combined and concentrated to get the compound (4S)-7-(benzylthio)-N-(pyridin-2-yl)-3,4-dihydro-1,4-methanopyrido[2,3-b][1,4]diazepine-5(2H)-carboxamide (2.3 g, 4.02 mmol, 38.0% yield) as a pale yellow sticky compound. LCMS (m/z): 404.1 (M+H)$^+$.

Synthesis of (4S)-7-(benzylthio)-2,3,4,5-tetrahydro-1,4-methanopyrido[2,3-b][1,4]diazepine

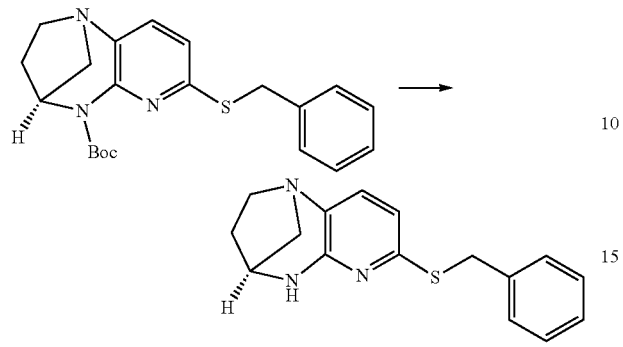

To a stirred solution of (4S)-tert-butyl 7-(benzylthio)-3,4-dihydro-1,4-methanopyrido[2,3-b][1,4]diazepine-5(2H)-carboxylate (4.00 g, 10.43 mmol) in 1,4-Dioxane (20 mL) was added HCl (4M in 1,4-dioxan) (20 mL, 80 mmol), the resulting mixture was stirred at rt for 5 hr. After the completion of reaction (monitored by TLC, indicates absence of starting material and new spot was observed at polar), the reaction mixture was poured into saturated sodium bicarbonate solution (50 ml) and the aqueous layer was extracted with ethyl acetate (2×50 mL). The combined organic layer was dried over $Na_2SO_4$, filtered and concentrated to get (4S)-7-(benzylthio)-2,3,4,5-tetrahydro-1,4-methanopyrido[2,3-b][1,4]diazepine (3.00 g, 9.67 mmol, 93% yield) as a pale yellow solid. LCMS (m/z): 284.1 $(M+H)^+$.

Synthesis of (4S)-tert-butyl 7-(benzylthio)-3,4-dihydro-1,4-methanopyrido[2,3-b][1,4]diazepine-5(2H)-carboxylate

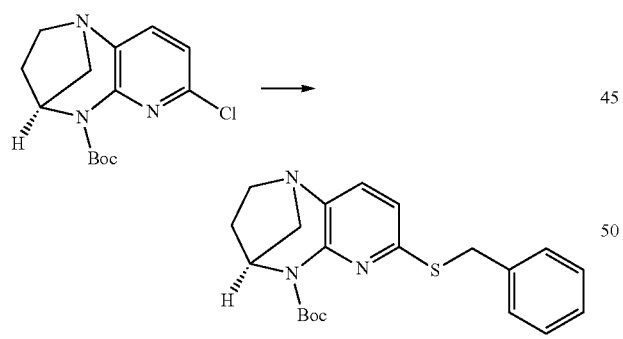

To a stirred solution of phenylmethanethiol (3.78 g, 30.4 mmol) in 1,4-dioxan (40 mL) was added potassium tert-butoxide (3.41 g, 30.4 mmol), the mixture was stirred for 10 min at rt.

A solution of (4S)-tert-butyl 7-chloro-3,4-dihydro-1,4-methanopyrido[2,3-b][1,4]diazepine-5(2H)-carboxylate (6 g, 20.29 mmol) in 1,4-dioxan (40 mL) was added to the reaction mixture, the resulting suspension was stirred at 100° C. for 8 hr. After the completion of reaction (monitored by TLC, starting material was completely consumed and the new spot was observed at just below of SM), reaction mixture was quenched with ice water (100 ml) and the aqueous layer was extracted with ethyl acetate (2×100 mL). The organic layer was dried over $Na_2SO_4$ filtered and concentrated under reduced pressure to get crude compound as a light brown liquid. Crude material was purified by silica gel column (100-200 mesh, 2% MeOH in DCM). Fractions containing pure compound were combined and concentrated to get (4S)-tert-butyl 7-(benzylthio)-3,4-dihydro-1,4-methanopyrido[2,3-b][1,4]diazepine-5(2H)-carboxylate (4 g, 10.38 mmol, 51.2% yield) as a light brown liquid. LCMS (m/z): 384.1 $(M+H)^+$.

Synthesis of (4S)—N7-((1H-imidazol-2-yl)methyl)-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide

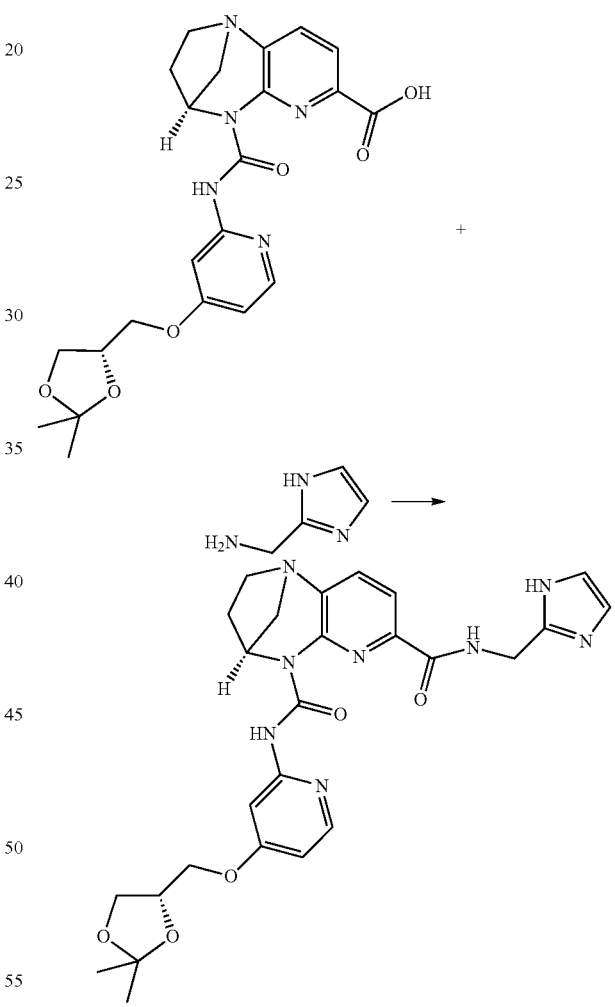

DIPEA (0.805 mL, 4.61 mmol) was added to a stirred solution of (4S)-5-((4-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid (350 mg, 0.768 mmol), (1H-imidazol-2-yl)methanamine (196 mg, 1.153 mmol), and HATU (438 mg, 1.153 mmol) in N,N-Dimethylformamide (DMF) (5 mL) at 28° C. The reaction mixture was stirred for 16 hr at 28° C. Reaction mixture was partitioned between ice cold water (30 mL) and dichloromethane (2×50 mL). Organic layer was separated, dried over anhydrous Na₂SO₄, filtered and filtrate was evaporated to afford crude. TLC eluting system: 100% EtOAc; R_f—0.4; UV active. The crude compound was purified by Grace using C-18 reserval column, Mobile phase A: 0.1% Formic Acid in water; B: MeOH, the product was eluted at 10-15% MeOH/0.1% Formic Acid in water. The solvent was evaporated and was basified with saturated NaHCO₃. The aqueous layer was extracted with DCM. DCM layer was dried over anhydrous Na₂SO₄, filtered and evaporated to afford (4S)—N7-((1H-imidazol-2-yl)methyl)-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide (300 mg, 0.545 mmol, 70.9% yield) as off white solid. LCMS (m/z): 533.04 [M+H]⁻.

Synthesis of (4S)—N7-((1H-tetrazol-5-yl)methyl)-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide

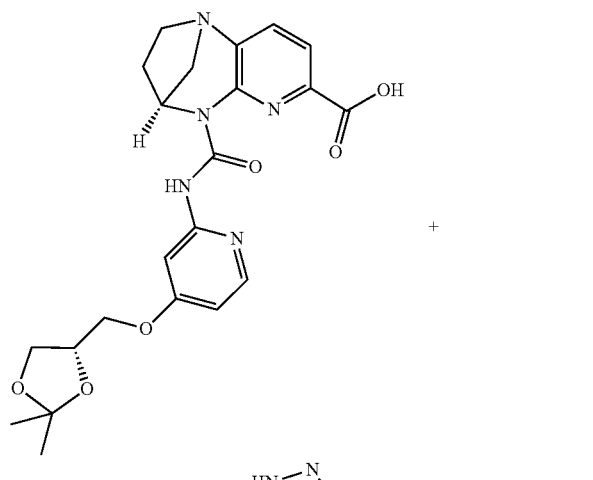

+

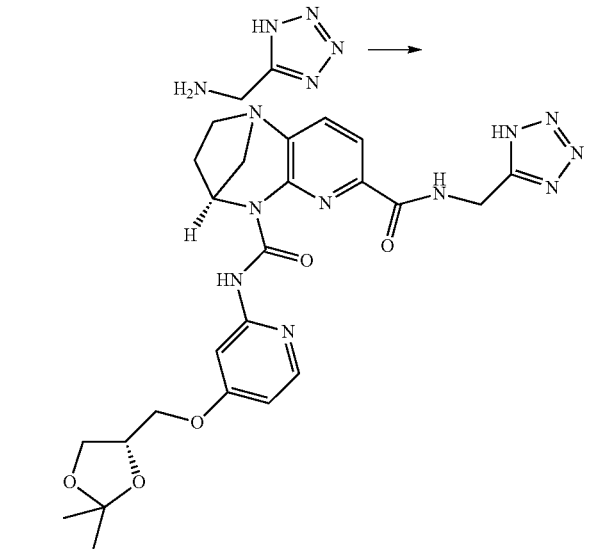

To a stirred solution of (4S)-5-((4-(((S)-2,2-dimethyl-1,3-dioxolan-4-yl)methoxy)pyridin-2-yl)carbamoyl)-2,3,4,5-tetrahydro-1,4-methanopyrido[2,3-b][1,4]diazepine-7-carboxylic acid (500 mg, 1.098 mmol), (1H-tetrazol-5-yl)methanamine hydrochloride (223 mg, 1.647 mmol), and HATU (626 mg, 1.647 mmol) in N,N-Dimethylformamide (DMF) (10 mL) was added DIPEA (1.150 mL, 6.59 mmol) at 28° C. The reaction mixture was stirred for 16 hr at 28° C.

The reaction mixture was partitioned between water (15 mL) and EtOAc (2×15 mL). EtOAc layer was separated and was dried over anhydrous Na₂SO₄, filtered. The filtrate was evaporated to get crude. The crude was purified by chromatography (GRACE using C-18 reserval column, Mobile phase A: 0.1% Formic Acid in water; B: MeOH, eluent 25% B in A). Combined fractions were concentrated basified with saturated NaHCO₃. The aqueous layer was extracted with DCM, DCM layer was dried over anhydrous Na₂SO₄, filtered and filtrate was evaporated to afford (4S)—N7-((1H-tetrazol-5-yl)methyl)-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide (200 mg, 0.332 mmol, 30.3% yield) as off white solid, LCMS (m/z): 537.76 [M+H]⁺.

Synthesis of 2-amino-N-isopropylisonicotinamide

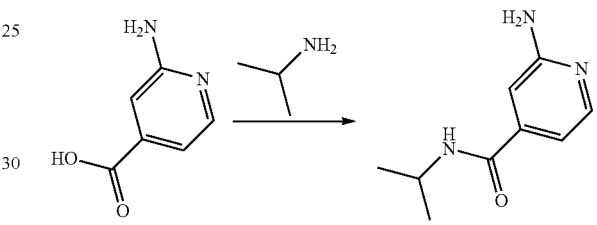

To a stirred solution of 2-aminoisonicotinic acid (2.5 g, 18.10 mmol), HATU (10.32 g, 27.1 mmol) and DIPEA (9.48 mL, 54.3 mmol) in N,N-Dimethylformamide (DMF) (20 mL) at RT was added propan-2-amine (1.605 g, 27.1 mmol) at RT and stirred the reaction mixture at RT for 16 h. The reaction mixture was diluted with water (1000 mL) and extracted with EtOAc (100 mL×2). The combined organic layer was washed with brine solution (50 mL) and dried over anhydrous Na₂SO₄, filtered and filtrate was evaporated to get crude. The crude product was purified by flash column chromatography (using 100-200 silica gel, compound eluted at 80% ethyl acetate in n-hexane to afford the desired product 2-amino-N-isopropylisonicotinamide (1.25 g, 6.56 mmol, 36.2% yield). (TLC: neat ethyl acetate, R_f value: 0.5, UV active). LC-MS: (m/z)=180.1 (M+H)⁺.

Synthesis of 2-amino-N-cyclopropylisonicotinamide

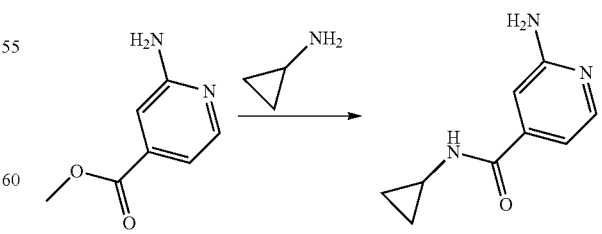

To a stirred solution of methyl 2-aminoisonicotinate (2 g, 13.14 mmol) and cyclopropanamine (7.50 g, 131 mmol) in Dimethyl Sulfoxide (DMSO) (10 mL) at RT and stirred the reaction mixture at 100° C. for 16 h. (TLC system: Ethyl acetate. Rf value: 0.3, UV active). Reaction mixture was cooled to RT and quenched with ice water and extracted with 2×150 ml of ethyl acetate, combined organic layers were washed with 100 ml of water and 50 ml of brine solution, organic layer was dried over Na$_2$SO$_4$, filtered and filtrate was evaporated to get crude compound. The crude product was purified by flash column chromatography (using 100-200 silica gel, compound eluted at 80% ethyl acetate in n-hexane) to afford the desired product 2-amino-N-cyclopropylisonicotinamide (1 g, 5.62 mmol, 42.8% yield). LC-MS: (m/z): 178.0 (M+H)$^+$.

Synthesis of 2-amino-N-ethylisonicotinamide

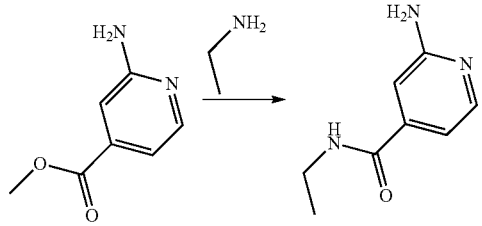

Ethanamine (70% AQ) (0.593 g, 13.14 mmol) was added to methyl 2-aminoisonicotinate (2 g, 13.14 mmol) at RT then heated to 70° C. for 16 h in sealed tube. The reaction mixture solvent was removed by vacuum. It was partitioned between water (10 mL×2) and EtOAc (10 mL×2). Organic layer was separated and was dried over anhydrous Na$_2$SO$_4$, filtered and filtrate was evaporated to get crude 2-amino-N-ethylisonicotinamide (2.1 g, 10.13 mmol, 77% yield) as a brown gum. LCMS (m/z): 166.17 M+H]$^+$.

Synthesis of 4-(pyrrolidin-1-yl)pyridin-2-amine

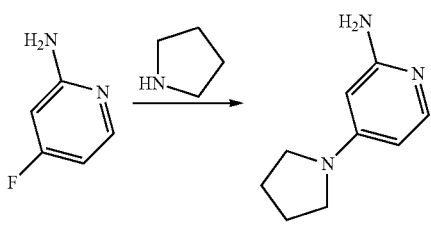

To a solution of 4-fluoropyridin-2-amine (1.5 g, 13.38 mmol), pyrrolidine (2.85 g, 40.1 mmol) in 1,4-Dioxane (5 mL) was added potassium carbonate (7.40 g, 53.5 mmol), copper(I) iodide (0.255 g, 1.338 mmol) and N,N'-dimethylethylenediamine (0.236 g, 2.68 mmol) at rt. The resulting reaction mixture was stirred in microwave at 110° C. for 1 h (TLC System: 10% MeOH in DCM, R$_f$—: 0.1; UV active). The reaction mixture was quenched with ice water (30 mL) and extracted with EtOAc (3×30 mL). The combined organic layer was washed with brine solution, dried over anhydrous Na$_2$SO$_4$, filtered and evaporated to get crude compound. The crude compound was triturated with diethyl ether (3×10 mL) to afford 4-(pyrrolidin-1-yl)pyridin-2-amine (1.0 g, 5.90 mmol, 44.1% yield) as Pale yellow solid. LCMS(m/z): 164.10 [M+H]$^+$.

Synthesis of (S)-4-(2-(1,4-dioxaspiro[4.5]decan-2-yl)ethyl)pyridin-2-amine

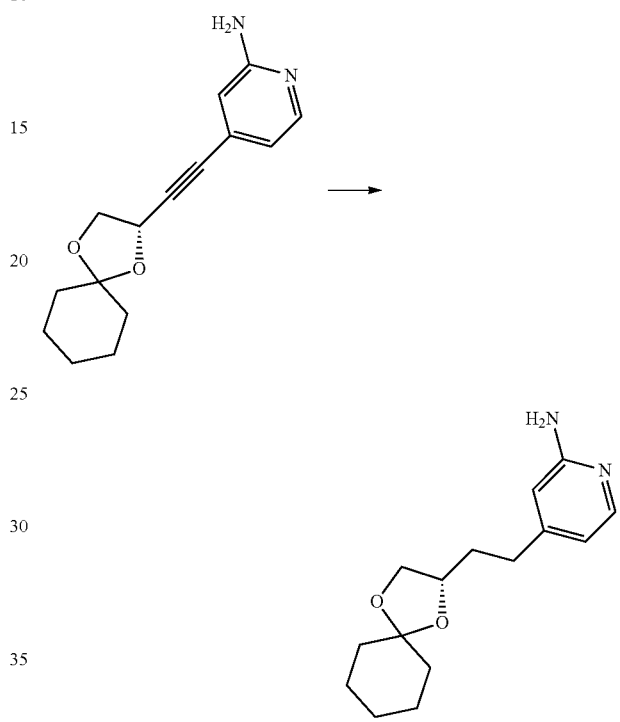

To a stirred solution of (S)-4-(1,4-dioxaspiro[4.5]decan-2-ylethynyl)pyridin-2-amine (4 g, 15.48 mmol) in Methanol (300 mL) was added Pd/C (1.0 g, 0.940 mmol) in 50% water in a hydrogenation flask. The resulting reaction mixture was stirred at room temperature for 6 hr under Hydrogen atmosphere. Progress of the reaction was monitored by TLC. TLC indicated SM was consumed and polar spot was formed. Reaction was filtered through celite, filtrate was concentrated under reduced pressure to afford (S)-4-(2-(1,4-dioxaspiro[4.5]decan-2-yl)ethyl)pyridin-2-amine (3.0 g, 11.44 mmol, 73.8% yield) as a brown sticky solid. LCMS (m/z): 263.63 [M+H]$^+$.

Synthesis of (S)-4-(1,4-dioxaspiro[4.5]decan-2-ylethynyl)pyridin-2-amine

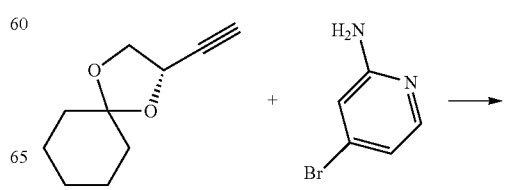

259

-continued

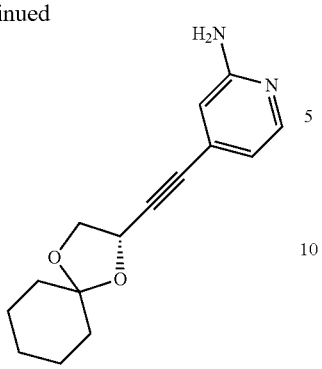

To a stirred solution of 4-bromopyridin-2-amine (4 g, 23.12 mmol) and (S)-2-ethynyl-1,4-dioxaspiro[4.5]decane (5.00 g, 30.1 mmol) in Tetrahydrofuran (THF) (100 mL) was added TEA (9.67 mL, 69.4 mmol). The reaction mixture was degassed for 15 min minutes. To the reaction mixture was added bis(triphenylphosphine)palladium(II) chloride (0.162 g, 0.231 mmol), triphenylphosphine (0.121 g, 0.462 mmol) and copper(I) iodide (0.044 g, 0.231 mmol), again degassed for 5 min's. The resulting reaction mixture was stirred at 70° C. for 16 hr. Progress of the reaction was monitored by TLC. Reaction mixture was diluted with water (100 mL), extracted with EtOAc (3×100 mL), organic layers were combined and washed with brine solution (50 mL), dried over anhydrous $Na_2SO_4$, filtered and concentrated under reduced pressure to obtained crude compound. The crude was purified by column chromatography (100 mesh silica gel, eluent 3% MeOH in DCM) to afford (S)-4-(1,4-dioxaspiro[4.5]decan-2-ylethynyl)pyridin-2-amine (4.0 g, 11.59 mmol, 50.1% yield) as a pale brown solid. LCMS (m/z): 259.22[M+H]$^+$.

Synthesis of (S)-2-ethynyl-1,4-dioxaspiro[4.5]decane

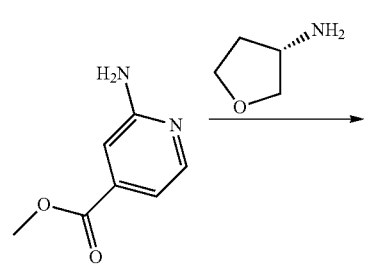

To a stirred solution of (R)-1,4-dioxaspiro[4.5]decane-2-carbaldehyde (12 g, 70.5 mmol) in Methanol (300 mL) was added dimethyl (1-diazo-2-oxopropyl)phosphonate (21.67 g, 113 mmol) and followed by $K_2CO_3$ (21.44 g, 155 mmol) was portion wise added to the reaction mixture over a period of 30 min at 0° C. under Nitrogen atmosphere. The resulting reaction mixture was stirred at room temperature for 12 hr. Progress of the reaction was monitored by TLC, TLC indicated SM was consumed. Reaction mixture was extracted with n-pentane (3×300 mL). Organic layers were combined and washed with water (100 mL), brine solution (100 mL), dried over anhydrous $Na_2SO_4$, filtered and concentrated under reduced pressure to afford (S)-2-ethynyl-1,4-dioxaspiro[4.5]decane (9.0 g, 54.1 mmol, 77% yield) as a pale yellow oily compound.

260

Synthesis of (1S,2S)-1,2-di((R)-1,4-dioxaspiro[4.5]decan-2-yl)ethane-1,2-diol

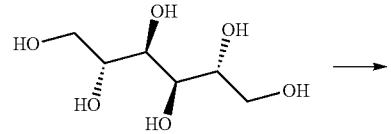

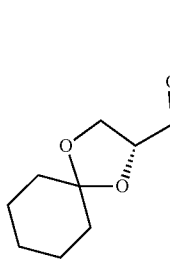

To a stirred solution of (2R,3R,4R,5R)-hexane-1,2,3,4,5,6-hexaol (45 g, 247 mmol) in Dimethyl Sulfoxide (DMSO) (100 mL) was added cyclohexanone (75 mL, 744 mmol), triethyl orthoformate (25 ml, 150 mmol) and $BF_3.OEt_2$ (3 ml, 23.67 mmol). The resulting reaction mixture was stirred at rt for 12 hr. Progress of the reaction was monitored by TLC. Reaction mixture was poured into ice cold $NaHCO_3$ solution, extracted with diethyl ether (3×500 mL). Organic layers were combined and washed with ice cold water (2×500 ml), brine solution (200 mL), dried over anhydrous $Na_2SO_4$. filtered and concentrated under vacuum to get crude compound. The crude was washed with N-pentane and diethyl ether (2:1) and dried well to afford (1S,2S)-1,2-di((R)-1,4-dioxaspiro[4.5]decan-2-yl)ethane-1,2-diol (42 g, 123 mmol, 49.7% yield) as a white solid.

Synthesis of (S)-2-amino-N-(tetrahydrofuran-3-yl)isonicotinamide

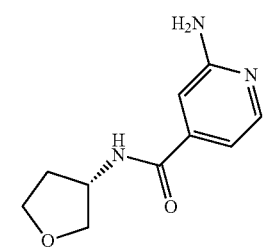

To a stirred solution of methyl 2-aminoisonicotinate (2 g, 13.14 mmol) and (S)-tetrahydrofuran-3-amine (1.145 g, 13.14 mmol) in Tetrahydrofuran (THF) (25 mL) at RT. The reaction mixture was stirred for 16 h at 80° C. The reaction mixture solvent was removed by vacuum. It was partitioned between water (10 mL×2) and EtOAc (10 mL×2). Organic layer was separated and was dried over anhydrous Na₂SO₄, filtered and filtrate was evaporated to get (S)-2-amino-N-(tetrahydrofuran-3-yl)isonicotinamide (1.5 g, 4.35 mmol, 33.1% yield) as an off white solid.

(TLC eluent: Neat ethyl acetate: $R_f$: 0.2; UV active). LCMS (m/z): 208.1 M+H]⁺

Synthesis of 5-chloropyridazin-3-amine

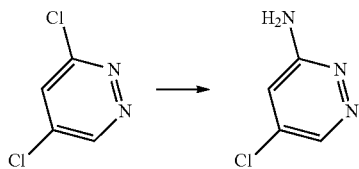 [SMILES: Clc1cnnc(Cl)c1 ; Nc1cc(Cl)cnn1]

To neat 3,5-dichloropyridazine (20 g, 134 mmol), at room temp was added ammonium hydroxide (500 mL, 1.28E+04 mmol). The reaction mixture was stirred at 120° C. for 16 hr. in autoclave. Progress of the reaction was monitored by TLC. TLC indicated starting material was consumed. Cooled the reaction mass to room temperature, concentrated under vacuum to get solid. To this added Diethylether (100 mL), filtered and dried to afford 5-chloropyridazin-3-amine (15 g, 116 mmol, 86% yield) as brown solid. LCMS (m/z): 129.87 (M+H)⁺.

Synthesis of 3-(pyridin-2-yl)-2H-pyrido[1,2-a][1,3,5]triazine-2,4(3H)-dione

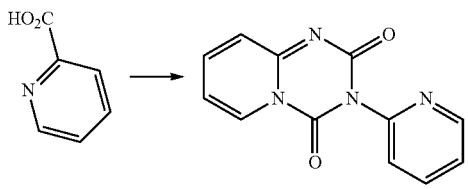 [SMILES: O=C(O)c1ccccn1 ; O=c1nc2ccccn2c(=O)n1-c1ccccn1]

To a solution of picolinic acid (1 g, 8.12 mmol) in Toluene (25 mL) stirred under nitrogen at room temp was added diphenyl phosphorazidate (2.235 g, 8.12 mmol) and TEA (1.132 mL, 8.12 mmol) and stirred for 30 min at room temperature. After that the reaction mixture was stirred at 80° C. for 2 hr. Next, the reaction mixture was cooled to room temperature and filtered, the solid was washed with toluene to afford compound 3-(pyridin-2-yl)-2H-pyrido[1,2-a][1,3,5]triazine-2,4(3H)-dione (600 mg, 2.352 mmol, 29.0% yield), LCMS (m/z) 241.2 [M+H]⁺.

Synthesis of (R)-6-((2,2-dimethyl-1,3-dioxolan-4-yl)methoxy)pyridin-2-amine

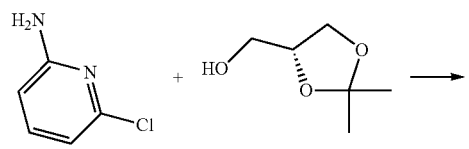

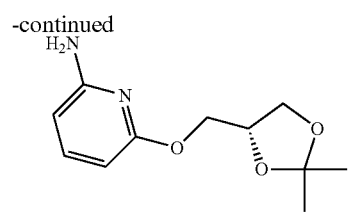

To a stirred suspension of NaH (11.67 g, 292 mmol) in N-Methyl-2-pyrrolidone (NMP) (100 mL) under nitrogen at 0° C. was added a solution of (R)-(2,2-dimethyl-1,3-dioxolan-4-yl)methanol (25.7 g, 194 mmol) in N-Methyl-2-pyrrolidone (NMP) (100 mL) dropwise during 10 min at 0° C. After 10 min added a solution of 6-chloropyridin-2-amine (25 g, 194 mmol) in N-Methyl-2-pyrrolidone (NMP) (100 mL) dropwise during 10 min at 0° C. The reaction mixture was heated at 100° C. for 36 hr. TLC indicates small amount starting material along with product.

Reaction mixture was poured into ice cold water (600 mL), aqueous layer was extracted with EtOAc (2×500 mL). The organic layer was washed with water (3×300 mL) to remove excess NMP. The organic layer was dried over Na₂SO₄, filtered and concentrated under reduced pressure to obtain crude product. Crude product was purified by column chromatography using 100-200 silica gel as a eluent (12-15% EtOAc in petether) to obtain (R)-6-((2,2-dimethyl-1,3-dioxolan-4-yl)methoxy)pyridin-2-amine (10 g, 44.6 mmol, 22.93% yield) as a yellow thick liquid.

Synthesis of (S)-6-((2,2-dimethyl-1,3-dioxolan-4-yl)methoxy)pyridin-2-amine

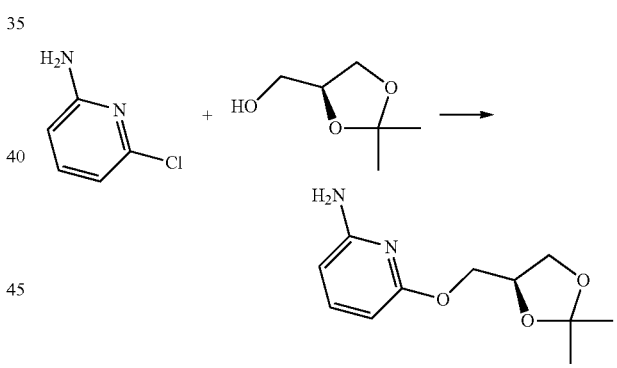

To a stirred suspension of NaH (62.2 g, 1556 mmol) in N-Methyl-2-pyrrolidone (NMP) (800 mL), under nitrogen at 0° C., was added a solution of (S)-(2,2-dimethyl-1,3-dioxolan-4-yl)methanol (206 g, 1556 mmol) in N-Methyl-2-pyrrolidone (NMP) (300 mL) dropwise during 2 h. After stirring for another 10 min added a solution of 6-chloropyridin-2-amine (200 g, 1556 mmol) in N-Methyl-2-pyrrolidone (NMP) (300 mL) dropwise during 30 min at 0° C. The reaction mixture was stirred at 120° C. for 48 hr. TLC indicated that starting material was. Reaction mixture was poured into ice cold water (2000 mL), aqueous layer was extracted with EtOAc (3×1000 mL). The combined organic layer was washed with water (3×1000 mL) to remove excess NMP. The organic layer was dried over Na₂SO₄, filtered and concentrated under reduced pressure to obtain crude product. Crude product was purified by column chromatography using 100-200 silica gel (eluent 12-15% EtOAc in pet ether) to obtain the desired pure product (S)-6-((2,2-dimethyl-1,3- dioxolan-4-yl)methoxy)pyridin-2-amine (75 g, 325 mmol, 20.92% yield) as a yellow viscous liquid. LCMS (m/z): 225 [M+H]$^+$.

Synthesis of (R)-4-((2,2-dimethyl-1,3-dioxolan-4-yl)methoxy)pyridin-2-amine

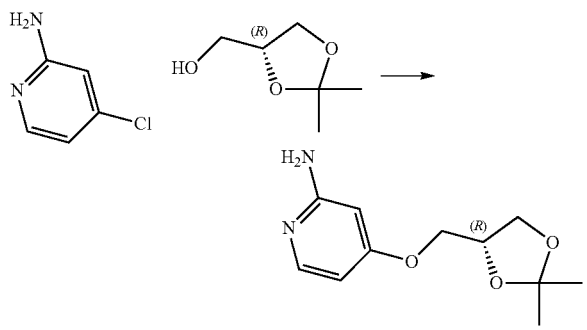

To a suspension of (R)-(2,2-dimethyl-1,3-dioxolan-4-yl)methanol (3.000 g, 22.70 mmol), 4-chloropyridin-2-amine (1.459 g, 11.35 mmol) and sodium (0.522 g, 22.70 mmol) in a sealed tube. The reaction mixture was stirred at 140° C. for 16 h. Next, the reaction mixture was cooled to room temperature, dissolved in MeOH and poured in to ice water and extracted with EtOAc. The organic phase was washed with brine solution and dried over sodium sulfate, filtered and evaporated to get crude compound. The crude compound was purified by column chromatography using silica gel and eluted with 2-3% MeOH/DCM to get pure compound (1.1 g, 21%), LCMS (m/z) 225.2 [M+H]$^+$.

Synthesis of (S)-4-((2,2-dimethyl-1,3-dioxolan-4-yl)methoxy)pyridin-2-amine

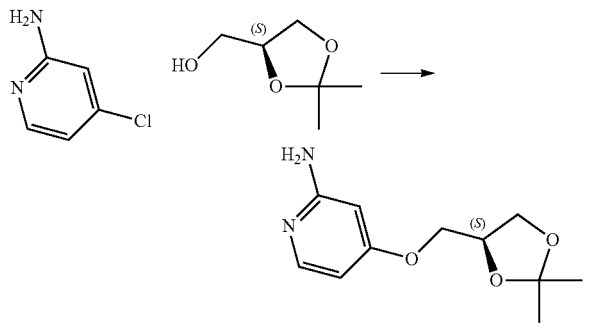

To a suspension of (S)-(2,2-dimethyl-1,3-dioxolan-4-yl)methanol (3.000 g, 22.70 mmol), 4-chloropyridin-2-amine (1.459 g, 11.35 mmol) and sodium (0.522 g, 22.70 mmol) in a sealed tube. The reaction mixture was stirred at 140° C. for 16 h before being cooled to room temperature, dissolved in MeOH and poured in to ice water and extracted with EtOAc. The organic phase was washed with brine solution and dried over sodium sulfate, filtered and evaporated. The crude material was purified by silica gel column chromatography eluting with 2-3% MeOH/DCM to give the desired product (1.2 g, 22%), LCMS (m/z) 225.2 [M+H]$^+$.

Synthesis of (R)-2-(tetrahydrofuran-3-yloxy)pyrimidin-4-amine

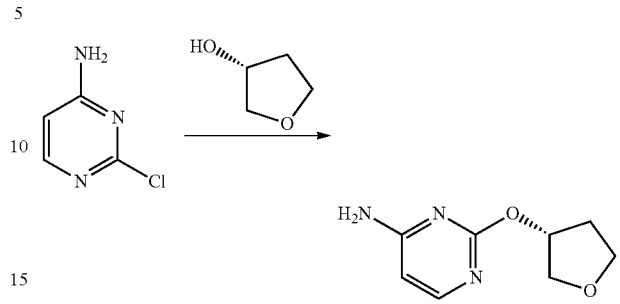

To a stirred solution of (R)-tetrahydrofuran-3-ol (2.72 g, 30.9 mmol) in THF (30 mL) was added NaH (0.926 g, 23.16 mmol) and stirred for 30 min at room temperature. To this 2-chloropyrimidin-4-amine (2.0 g, 15.44 mmol) was added in portions for about 15 min and heated at 70° C. for 16 h. The reaction mixture was allowed to room temperature and subsequently cooled to 0° C., quenched with ice cold water and extracted with ethyl acetate (3×50 mil). The combined organic layer was dried over anhydrous sodium sulfate, filtered and concentrated under reduced pressure to obtain the crude compound. The crude product was purified by flash column chromatography (silica-gel: 100-200 mesh) to afford (R)-2-(tetrahydrofuran-3-yloxy)pyrimidin-4-amine (1.6 g, 8.839 mmol, 51.5% yield) as an off white solid.

Synthesis of (R)-6-((2,2-dimethyl-1,3-dioxolan-4-yl)methoxy)pyrazin-2-amine

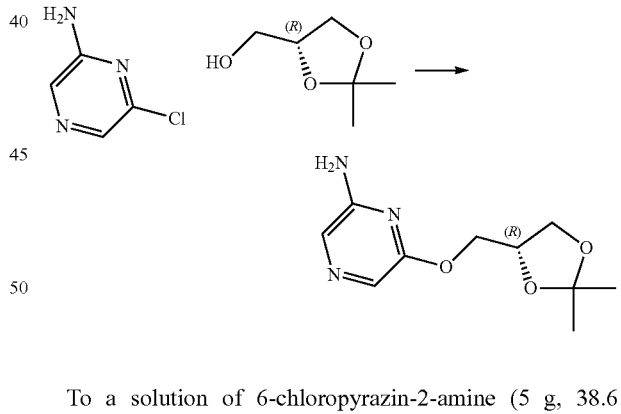

To a solution of 6-chloropyrazin-2-amine (5 g, 38.6 mmol), sodium hydride (2.316 g, 57.9 mmol) and (R)-(2,2-dimethyl-1,3-dioxolan-4-yl)methanol (5.61 g, 42.5 mmol) in Tetrahydrofuran (THF) (50 mL) stirred under nitrogen at 0° C. was added reaction mixture was stirred at 80° C. for 16 h. Reaction mixture was quenched with ice cold water and extracted into ethyl acetate. Organic layer dried over Na$_2$SO$_4$. Solvent evaporated under reduced pressure to afford the crude product. The crude product was added to a silica gel column and was eluted with DCM/MeOH. Fractions with product were combined and evaporated under reduced pressure to give the required product (2.8 g, 11.9 mmol, 31%), LCMS (m/z) 225.9 [M+H]$^+$.

Synthesis of (S)-6-((2,2-dimethyl-1,3-dioxolan-4-yl)methoxy)pyrazin-2-amine

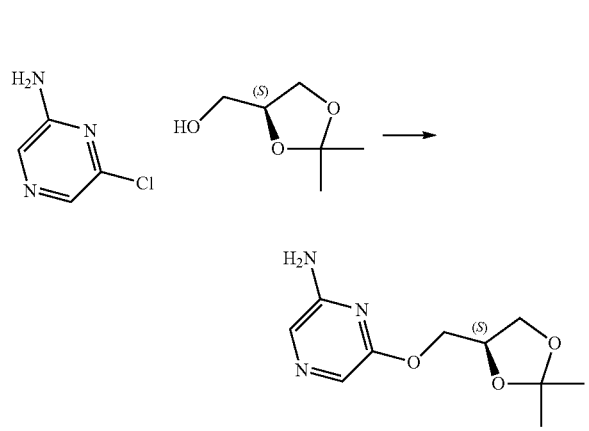

6-chloropyrazin-2-amine (0.980 g, 7.57 mmol), (S)-(2,2-dimethyl-1,3-dioxolan-4-yl)methanol (2 g, 15.13 mmol) and sodium (0.348 g, 15.13 mmol) were taken in a seal tube and heated at 130° C. for 16 hr and then the reaction mixture was quenched with methanol and ice cold water (100 mL) and extracted with ethyl acetate (5×50 mL). The combined organic layers were washed with water, saturated brine solution, dried over anhydrous sodium sulfate, filtered and concentrated to give the product (1 g, 4.26 mmol, 28.2% yield), LCMS (m/z) 265.1 [M+H]$^+$.

Synthesis of (S)-2-((2,2-dimethyl-1,3-dioxolan-4-yl)methoxy)pyrimidin-4-amine

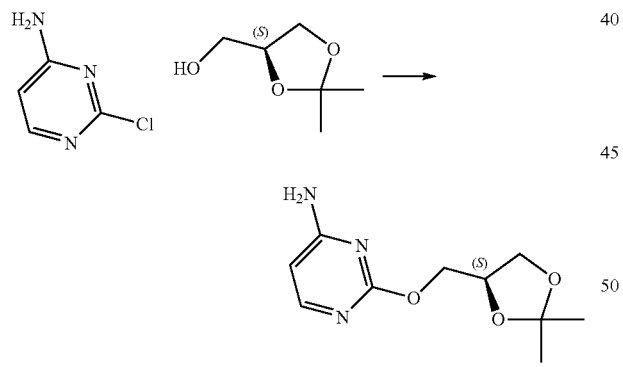

To suspension of (S)-(2,2-dimethyl-1,3-dioxolan-4-yl)methanol (10.20 g, 77 mmol), and NaH (4.63 g, 116 mmol) in tetrahydrofuran (THF) (50 mL) stirred under nitrogen at room temperature was added 2-chloropyrimidin-4-amine (5 g, 38.6 mmol) portion wise over 15 min. The reaction mixture was stirred at 70° C. for 16 hr. Next, the reaction mixture was quenched with solution of aq. NaHCO$_3$ and then extracted with EtOAc, dried Na$_2$SO$_4$ and evaporated. The crude product was added to a silica gel column and was eluted with 50% Hex/EtOAc. Collected fractions were evaporated to give the desired product (3 g, 11.84 mmol, 30.7% yield) as off white solid, LCMS (m/z) 226.2 [M+H]$^+$.

Synthesis of (R)-2-((2,2-dimethyl-1,3-dioxolan-4-yl)methoxy)pyrimidin-4-amine

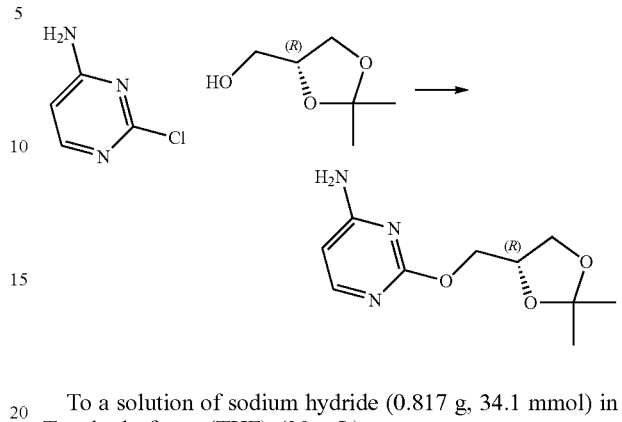

To a solution of sodium hydride (0.817 g, 34.1 mmol) in Tetrahydrofuran (THF) (30 mL) at room temperature was added a solution of (R)-(2,2-dimethyl-1,3-dioxolan-4-yl)methanol (3 g, 22.70 mmol) in THF (5 mL) over 1 min and stirred at room temperature for 15 min then add 2-chloropyrimidin-4-amine (2.059 g, 15.89 mmol) portion wise at room temperature. The reaction mixture was stirred at 65° C. for 16 h. The reaction mixture was poured in to water and extracted with EtOAc (3×100 mL). Then the combined organic layer was washed with water, brine solution, dried over sodium sulfate and evaporated to get 4.0 g of crude compound. The crude compound was purified by column chromatography using 100-200 silica gel mesh and eluted with 2-3% MeOH/DCM to get pure compound (2.5 g, 10.42 mmol, 46%), LCMS (m/z) 226.2 [M+H]$^+$.

Synthesis of (S)-2-((2,2-dimethyl-1,3-dioxolan-4-yl)methoxy)pyridin-4-amine

To a suspension of 2-chloropyridin-4-amine (1.459 g, 11.35 mmol), (S)-(2,2-dimethyl-1,3-dioxolan-4-yl)methanol (3.0 g, 22.70 mmol) was added sodium (0.522 g, 22.70 mmol). The reaction mixture was stirred at 140° C. for 16 hr and progress of the reaction was monitored by The reaction mixture was dissolved in MeOH, poured in to ice water and extracted with EtOAc (3×100 mL). Then the combined organic layer was washed with water, brine solution, dried over sodium sulfate and evaporated to get 4.0 g of crude compound. The crude compound was purified by column chromatography using 100-200 silica gel mesh and eluted with 2-3% MeOH/DCM to get (S)-2-((2,2-dimethyl-1,3-dioxolan-4-yl)methoxy)pyridin-4-amine (2.5 g, 10.73 mmol, 47.3% yield), LCMS (m/z) 225.3 [M+H]$^+$.

Synthesis of (R)-2-((2,2-dimethyl-1,3-dioxolan-4-yl)methoxy)pyridin-4-amine

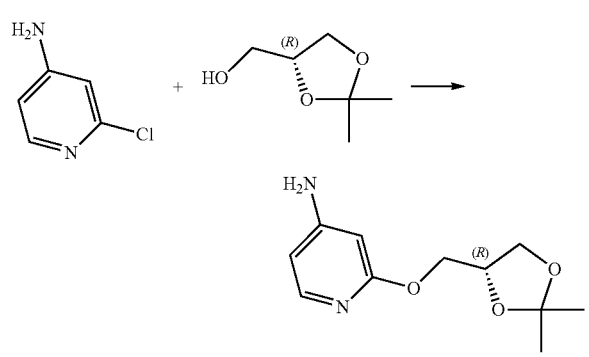

To a solution of 2-chloropyridin-4-amine (4 g, 31.1 mmol), (R)-(2,2-dimethyl-1,3-dioxolan-4-yl)methanol (2.056 g, 15.56 mmol) and sodium (0.715 g, 31.1 mmol) in sealed tube at room temperature. The reaction mixture was stirred at 140° C. for 48 hr. The reaction mixture was cooled to room temp and quenched with MeOH followed by water. Then reaction mass was extracted with the EtOAc. Then organic layer washed with water followed by brine solution and dried out with sodium sulfate and filtered and distill out completely. The crude product was added to a silica gel column and was eluted with Hex/EtOAc (1:1) collected fractions were evaporated to give the desired product (2.250 g, 9.93 mmol, 31.9% yield), LCMS (m/z) 225.0 [M+H]$^+$.

Synthesis of (S)-2-((tetrahydrofuran-3-yl)oxy)pyrimidin-4-amine

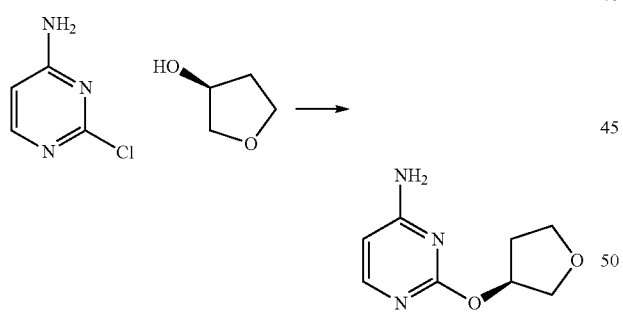

To a stirred solution of 2-chloropyrimidin-4-amine (2 g, 15.44 mmol) in Tetrahydrofuran (THF) (20 mL) was added NaH (0.741 g, 30.9 mmol) portion wise over a period of 5 min at room temperature. Then the reaction was stirred at 30° C. for about 10 min. To the above reaction added (S)-tetrahydrofuran-3-ol (1.088 g, 12.35 mmol) at 30° C. and stirred at 80° C. for 8 hrs. The reaction mixture was quenched with ice cold water at 0° C. and extracted with ethyl acetate. The organic layer was washed thoroughly with water and dried over Na$_2$SO$_4$. The solvent was evaporated under reduced pressure to afford the product. The crude product was triturated with pet ether, LCMS (m/z) 182.2 [M+H]$^+$.

Synthesis of phenyl (1-methyl-1H-pyrazol-4-yl)carbamate

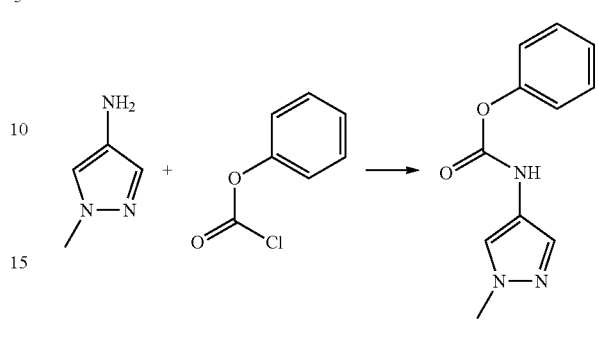

Phenyl carbonochloridate (2.90 g, 18.53 mmol) was added to a stirred solution of pyridine (3.12 mL, 38.6 mmol) in Dichloromethane (DCM) (50 mL) at 0° C. and stirred for 15 min and followed by addition of 1-methyl-1H-pyrazol-4-amine (1.5 g, 15.45 mmol) at same temperature. The reaction mixture was stirred at room temperature for 4 h. After consumption of starting material (monitored by TLC), ice cold water was added, separated organic layer was washed with water and brine. The organic layer was filtered through sodium sulfate and concentrated to get crude compound. The crude compound was purified by column chromatography by using 60-120 (silica gel) and eluted in 50% ethyl acetate in hexane to afford the desired product (1.6 g, 6.41 mmol, 42% yield) as light brown solid, LCMS (m/z) 218.1 (M+H)$^+$.

Synthesis of phenyl pyridin-3-ylcarbamate

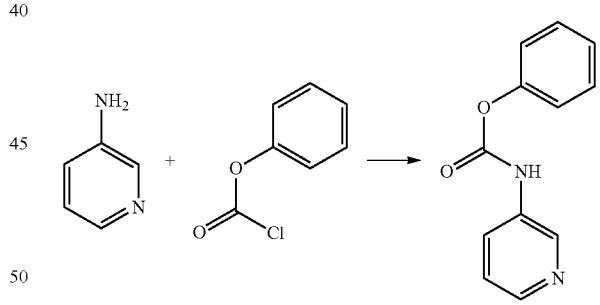

To a solution of phenyl carbonochloridate (2.163 g, 13.81 mmol), and pyridine (1.375 mL, 17.00 mmol) in Dichloromethane (DCM) (30 mL) stirred under nitrogen at room temp was added pyridin-3-amine (1.0 g, 10.63 mmol). The reaction mixture was stirred at RT for 30 min. The reaction mixture was quenched with saturated sodium bicarbonate solution. Separated organic layer and the aqueous layer extracted with DCM (50 ml). Combined DCM layer washed with water and dried out with sodium sulfate, filtered and concentrated under high vacuum to get crude product. The Crude product was added to a silica gel column and was eluted with 20% EtOAc/Hexane. Collected fractions were evaporated to afford the desired product (1.3 g, 6.01 mmol, 57%) as a white solid, LCMS (m/z) 215.1 (M+H)$^+$.

Synthesis of phenyl pyrimidin-2-ylcarbamate

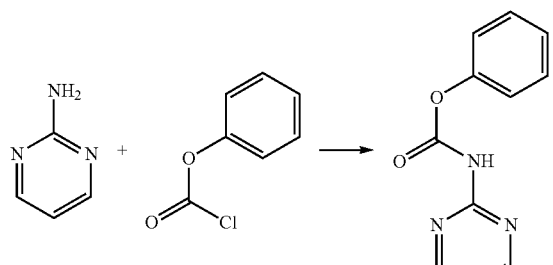

To a solution of phenyl carbonochloridate (2.140 g, 13.67 mmol), and pyridine (1.361 mL, 16.82 mmol) in dichloromethane (DCM) (10 mL) stirred under nitrogen at room temperature was added pyrimidin-2-amine (1.0 g, 10.51 mmol). The reaction mixture was stirred at room temperature for 30 min. The reaction mixture was quenched with saturated sodium bicarbonate solution. Separated organic layer and the aqueous layer extracted with DCM (50 ml). Combined DCM layer washed with water and dried out with sodium sulfate, filtered and concentrated under high vacuum to get crude product. This was added to a silica gel column and was eluted with 20% EtOAc/Hexane. Collected fractions were evaporated to afford the desired product (1.6 g, 6.49 mmol, 61.7%), LCMS (m/z) 216.3 (M+H)+.

Synthesis of phenyl (5-fluoropyridin-2-yl)carbamate

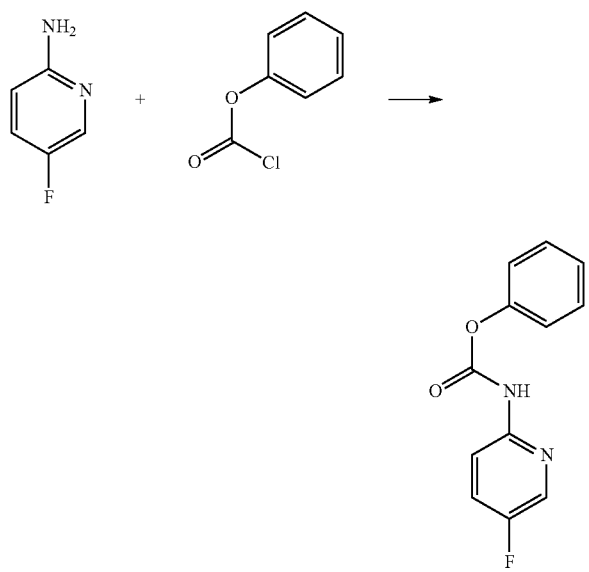

To a solution of phenyl carbonochloridate (1.397 g, 8.92 mmol), and Pyridine (0.721 mL, 8.92 mmol) in dichloromethane (DCM) (40 mL) stirred under nitrogen at room temp was added 5-fluoropyridin-2-amine (1.0 g, 8.92 mmol). The reaction mixture was stirred at RT for 30 min. The reaction mixture was quenched with saturated sodium bicarbonate solution. Separated organic layer and the aque- ous layer extracted with DCM (20 ml). Combined organic layer washed with water followed by brine solution and dried out with sodium sulfate, filtered and concentrated under vacuum to give the desired product (1.4 g, 5.94 mmol, 67%), LCMS (m/z) 233.2 (M+H)+.

Synthesis of phenyl (2-methyl-2H-indazol-5-yl)carbamate

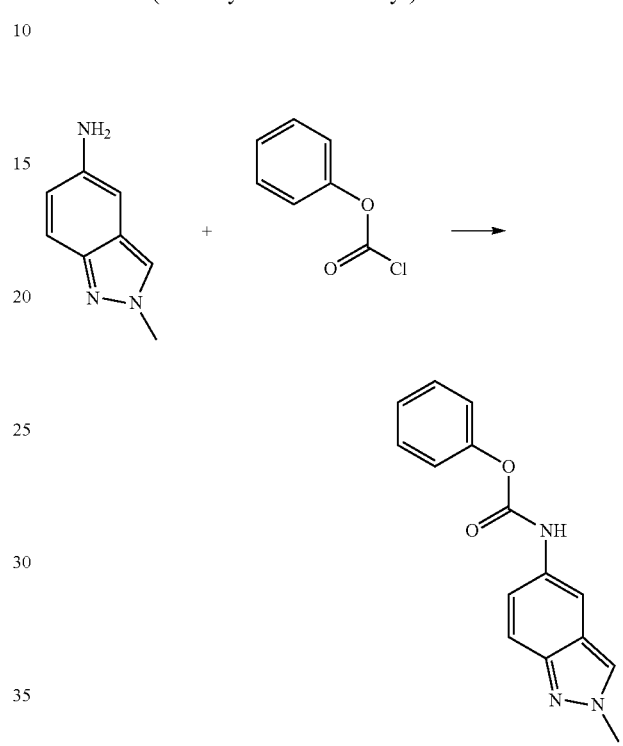

To a solution of phenyl carbonochloridate (0.64 g, 6.79 mmol), and pyridine (0.550 mL, 6.79 mmol) in Dichloromethane (DCM) (40 mL) stirred under nitrogen at room temp was added 2-methyl-2H-indazol-5-amine (1 g, 6.79 mmol). The reaction mixture was stirred at room temperature for 30 min. The reaction mixture was quenched with saturated sodium bicarbonate solution. Separated organic layer, aqueous layer extracted with DCM (20 ml).

Combined organic layer washed with water followed by brine solution and dried out with sodium sulfate and concentrated under vacuum to get phenyl (2-methyl-2H-indazol-5-yl)carbamate (1.3 g, 4.82 mmol, 70.9% yield), LCMS (m/z) 268.1 (M+H)+.

Synthesis of Phenyl (5-ethylpyrazin-2-yl)carbamate

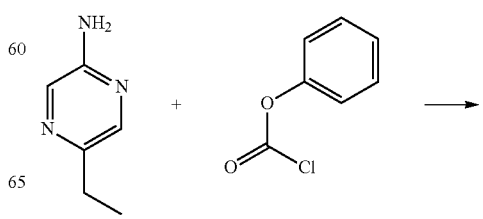

-continued

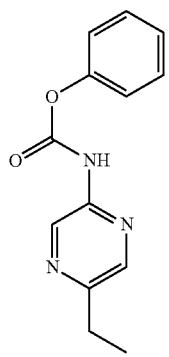

Pyridine (1.051 mL, 12.99 mmol) was added dropwise to a stirred solution of phenyl carbonochloridate (1.324 mL, 10.56 mmol) in dichloromethane (DCM) (20 ml) at room temperature and stirred for 30 minutes. Then 5-ethylpyrazin-2-amine (1 g, 8.12 mmol) dissolved in dichloromethane (DCM) (10 ml) was added dropwise at room temperature and stirred at 50° C. for 16 h. Allowed the reaction mixture to room temperature, diluted with DCM (3×50 mL), washed with water (2×30 mL) and brine (30 mL). Separated the organic layer and dried over sodium sulfate, filtered and concentrated. Residue was purified by column chromatography using silica gel (100-200 mesh) by 10% ethyl acetate in pet ether as eluent to get desired product as off white fluffy solid (1.6 g, 6.58 mmol, 81%), LCMS (m/z) 244.2 (M+H)+.

Synthesis of Phenyl (5-cyclopropylpyrazin-2-yl)carbamate

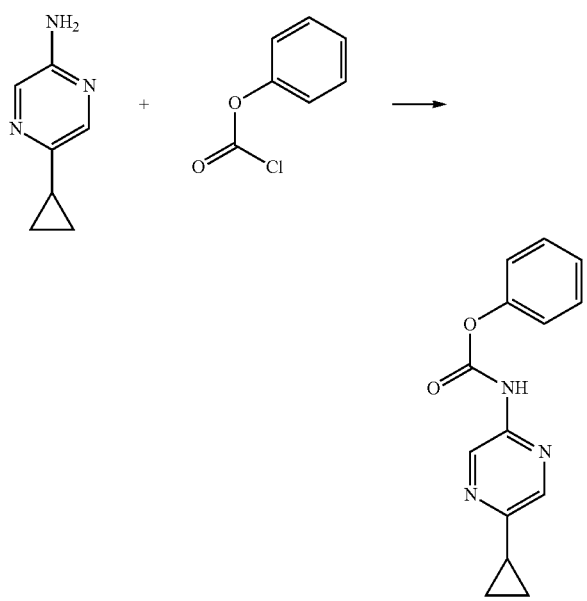

Pyridine (0.598 mL, 7.40 mmol) was added dropwise to a stirred solution of phenyl carbonochloridate (0.928 mL, 7.40 mmol) in dichloromethane (DCM) (15 ml) at 0° C. and stirred at RT for 30 minutes. Then 5-cyclopropylpyrazin-2-amine (1 g, 7.40 mmol) dissolved in dichloromethane (DCM) (5 ml) was added dropwise at 0° C. and stirred at RT for 3 h.

The reaction mixture was diluted with DCM (3×50 mL), washed with water (2×20 mL) and brine (20 mL). Separated the organic layer and dried over sodium sulfate, filtered and concentrated. Residue was purified by column chromatography using silica gel (100-200 mesh). 10% ethyl acetate in pet ether as eluent to give the desired product (1.4 g, 5.31 mmol, 72%) as off white fluffy solid, LCMS (m/z) 256.2 (M+H)+.

Synthesis of phenyl (6-ethoxypyrazin-2-yl)carbamate

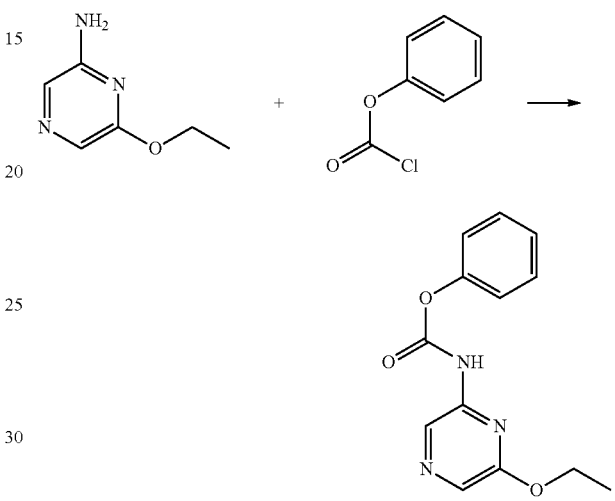

Pyridine (0.930 mL, 11.50 mmol) was added to a solution of phenyl carbonochloridate (1.463 g, 9.34 mmol) in DCM (15 mL) at room temperature and stirred for 20 min, then 6-ethoxypyrazin-2-amine (1.0 g, 7.19 mmol) in DCM (15 mL) was added and continued for another 40 min. The reaction mixture was diluted with DCM (2×20 mL), washed with water (20 mL×2) and brine (10 mL). Organic extracts were dried over Na$_2$SO$_4$ and solvent removed in vacuo to obtain the desired product (1.65 g, 5.22 mmol, 72.6% yield) as a yellow solid, LCMS (m/z) 260.2 (M+H)+.

Synthesis of phenyl pyridazin-3-ylcarbamate

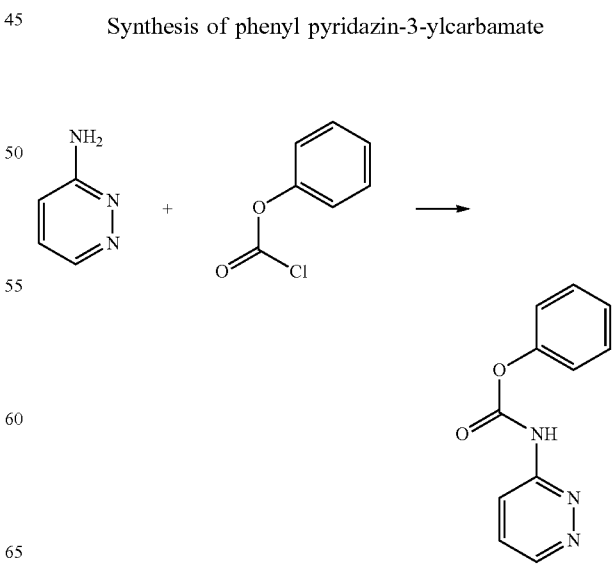

To a solution of phenyl carbonochloridate (1.070 g, 6.83 mmol), pyridine (0.665 g, 8.41 mmol) in dichloromethane (10 ml) stirred under nitrogen at 25° C. was added a suspension of pyridazin-3-amine (0.5 g, 5.26 mmol) in dichloromethane (5 ml) during 5 min. The reaction mixture was stirred at 25° C. for 1 hr. Next, the organic phase was washed with water 3 mL, saturated brine 3 mL, dried over sodium sulfate and concentrated in vacuo to give the crude product as a white solid. The compound was washed with hexane, dried under reduced pressure, LCMS (m/z) 216.2 (M+H)⁺.

Synthesis of phenyl pyrimidin-4-ylcarbamate

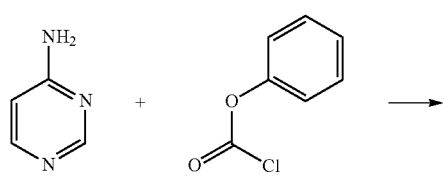

To a solution of phenyl carbonochloridate (1.070 g, 6.83 mmol), pyridine (0.665 g, 8.41 mmol) in DCM (15 ml) stirred under nitrogen at 25° C. was added a suspension of pyrimidin-4-amine (0.5 g, 5.26 mmol) in DCM (5 ml) dropwise during 5 min. The reaction mixture was stirred at 25° C. for 1 hr. The organic phase was washed with water 3 mL, brine 3 mL, dried over sodium sulfate and concentrated under vacuo to give the crude product as a off-white solid. The crude compound was washed with Hexane and then dried under reduced pressure to give the desired product (500 mg, 1.95 mmol, 37%), LCMS (m/z) 215.9 (M+H)⁺.

Synthesis of 2,2-dimethyl-3,6-dihydro-2H-pyran-4-yl trifluoromethanesulfonate

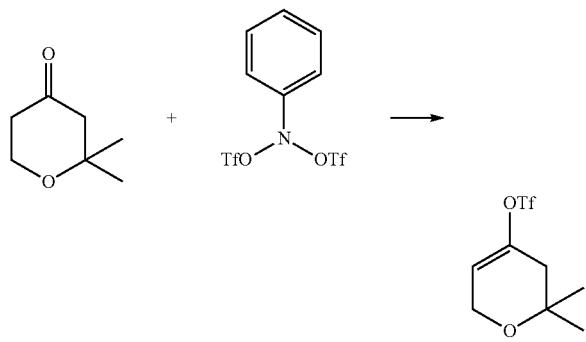

LDA (2.75 mL, 20.29 mmol) was added to a stirred solution of 2,2-dimethyldihydro-2H-pyran-4(3H)-one (2.0 g, 15.60 mmol) in Tetrahydrofuran (THF) (40 mL) at −78° C. and stirred for 20 mins. 1,1,1-trifluoro-N-phenyl-N-((trifluoromethyl)sulfonyl)methanesulfonamide (3.98 mL, 18.73 mmol) was added at −78° C. and stirred at 28° C. for 19 hr. Reaction mixture was quenched with saturated sodium bicarbonate solution, diluted with water (10 mL), extracted with ether (2×30 mL), washed with brine solution (20 mL). Organic layer was separated, dried over Na₂SO₄, filtered and concentrated to get crude product. Crude product was purified by column chromatography using (100-200) silica gel column chromatography and was eluted with 15% EtOAc in Hexane (gradient system) to afford the desired product 2,2-dimethyl-3,6-dihydro-2H-pyran-4-yl trifluoromethanesulfonate (2.4 g, 5.98 mmol, 38.3% yield) as a pale yellow liquid GCMS (m/z): 260 [M+H]⁺.

Synthesis of 4-(2,2-dimethyl-3,6-dihydro-2H-pyran-4-yl)pyridin-2-amine

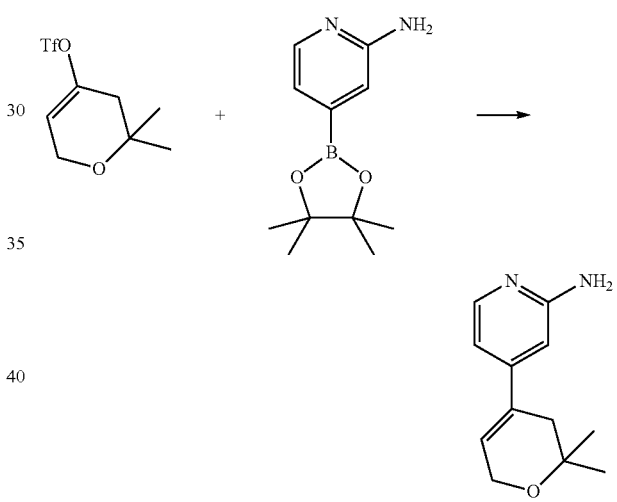

A suspension of 4-(4,4,5,5-tetramethyl-1,3,2-dioxaborolan-2-yl)pyridin-2-amine (1.0 g, 4.54 mmol), 2,2-dimethyl-3,6-dihydro-2H-pyran-4-yl trifluoromethanesulfonate (2.365 g, 9.09 mmol) and tripotassium phosphate (2.89 g, 13.63 mmol) in 1,4-Dioxane (30 mL) stirred and degassed with argon at room temp for 15 mins. PdCl₂(dppf)-CH₂Cl₂ adduct (0.186 g, 0.227 mmol) was added to the reaction mixture. Then the reaction mixture was stirred 4 hr at 90° C. The reaction was monitored by TLC. The reaction mixture was cooled to room temp and filtered through celite and washed with EtOAc (20 ml). Take filtrate and concentrated and dissolved with EtOAc (20 ml). EtOAc layer washed with water (10 ml) followed by brine solution (10 ml) and dried out with Na₂SO₄, filtered and concentrated to get crude product. The crude product was purified by column chromatography using neutral alumina and was eluted with 100% DCM (gradient system) to afford the desired product 4-(2,2-dimethyl-3,6-dihydro-2H-pyran-4-yl)pyridin-2-amine (0.8 g, 3.79 mmol, 83% yield) as a brown solid, LCMS (m/z): 205.2 [M+H]⁺.

Synthesis of 4-(1H-1,2,3-triazol-5-yl)pyridin-2-amine

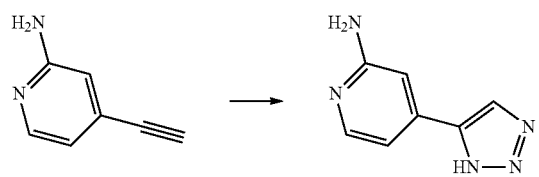

To a stirred suspension of 4-ethynylpyridin-2-amine (350 mg, 2.96 mmol) in TMSN3 (0.5 mL, 3.77 mmol) at 150° C. in microwave. The resulting reaction mixture was stirred for 30 min at same temperature. The progress of the reaction was monitored by TLC. Reaction mixture was filtered, solid compound was washed with DCM (2 ml) and dried to get 4-(1H-1,2,3-triazol-5-yl)pyridin-2-amine (360 mg, 1.832 mmol, 61.8% yield) of light yellow solid, LCMS (m/z): 162.1 [M+H]+.

Synthesis of 3-(2-aminopyridin-4-yl)oxazolidin-2-one

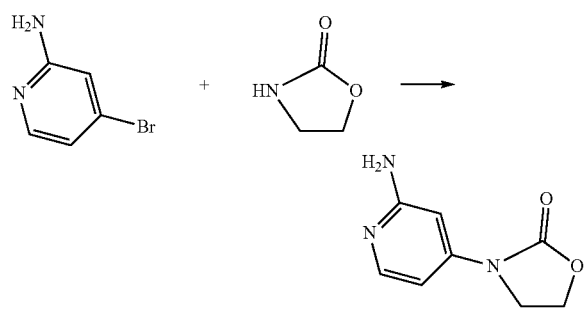

To a stirred solution of 4-bromopyridin-2-amine (1 g, 5.78 mmol) in 1,4-Dioxane (10 ml) was added oxazolidin-2-one (0.755 g, 8.67 mmol), potassium carbonate (1.598 g, 11.56 mmol), copper(I) iodide (0.110 g, 0.578 mmol), N,N'-dimethylethylenediamine (0.102 g, 1.156 mmol) at rt. The resulting reaction mixture was stirred in microwave at 110° C. for 1 hr. The progress of the reaction was monitored by TLC. Reaction mixture solvent was evaporated, diluted with water (10 mL) and stirred for 20 minutes solid was formed, filtered and dried to obtained 3-(2-aminopyridin-4-yl)oxazolidin-2-one (580 mg, 3.11 mmol, 53.8% yield) as pale yellow solid, LCMS (m/z): 180.0 [M+H]+.

Synthesis of 4-(1H-1,2,3-triazol-1-yl)pyridin-2-amine AND 4-(2H-1,2,3-triazol-2-yl)pyridin-2-amine

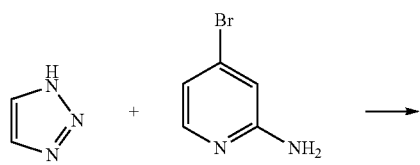

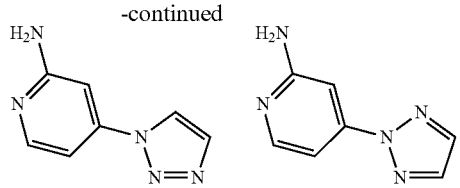

To a solution of 1H-1,2,3-triazole (0.599 g, 8.67 mmol), 4-bromopyridin-2-amine (1 g, 5.78 mmol) in 1,4-Dioxane (10 mL) was added K2CO3 (1.598 g, 11.56 mmol), copper(I) iodide (0.110 g, 0.578 mmol) and N,N dimethyl ethylene diamine (0.126 mL, 1.156 mmol) room temp. The reaction mixture was stirred at 110° C. for 1 hr in MW. The reaction mixture was quenched under with water (30 mL) and extracted with Ethyl acetate (2×50 mL) and followed by brine solution (50 mL) and separated the layer, dried with anhydrous Na2SO4, filtered and concentrated to get crude product. The crude product was purified to afford 4-(1H-1,2,3-triazol-1-yl)pyridin-2-amine (0.1 g, 0.562 mmol, 9.72% yield) as off white solid and 4-(2H-1,2,3-triazol-2-yl)pyridin-2-amine (0.3 g, 1.787 mmol, 30.9% yield) as off white solid, LCMS (m/z): 162.0 [M+H]+.

Synthesis of (E)-2-amino-N-((dimethylamino)methylene)isonicotinamide

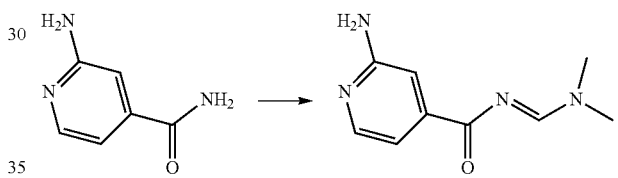

To a stirred solution of 2-aminoisonicotinamide (5 g, 36.5 mmol) in N,N-Dimethylformamide (DMF) (50 mL) was added 1,1-dimethoxy-N,N-dimethylmethanamine (9.76 mL, 72.9 mmol) at rt. The resulting reaction mixture was stirred for 4 hr at 27° C. The progress of the reaction was monitored by TLC. Reaction mixture solvent was evaporated, diluted with EtOAc (5×20 mL) and ice cold water, separated organic layer and concentrated under vacuum to obtained of (E)-2-amino-N-((dimethylamino)methylene)isonicotinamide (4.5 g, 23.41 mmol, 64.2% yield) as off white solid, LCMS (m/z): 193.01 [M+H]+.

Synthesis of 4-(1H-1,2,4-triazol-5-yl)pyridin-2-amine

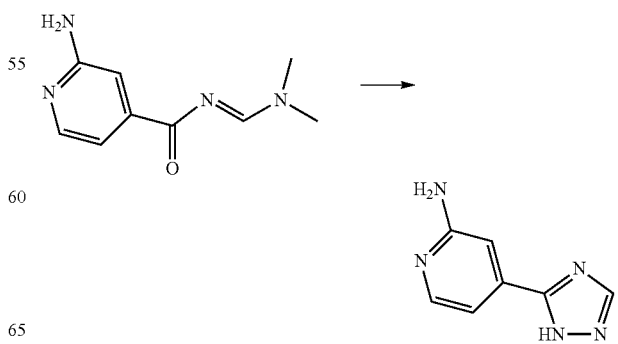

To a stirred suspension of (E)-2-amino-N-((dimethylamino)methylene)isonicotinamide (4 g, 20.81 mmol) in Ethanol (40 mL) was added hydrazine hydrate (1.042 g, 20.81 mmol) at RT. The resulting reaction mixture was stirred for 16 hr at same temperature. The progress of the reaction was monitored by TLC. Reaction mixture was filtered, solid compound was washed with EtOAc (20 ml) and filtrate was dried to get 2 g (LCMS showed 40% desired) of solid compound. The compound was purified by prep HPLC to afford 4-(1H-1,2,4-triazol-5-yl)pyridin-2-amine (750 mg, 4.40 mmol, 21.13% yield) as an brown color solid, LCMS (m/z): 162.0 [M+H]$^+$.

Synthesis of 6-(2-((tetrahydro-2H-pyran-2-yl)oxy)ethoxy)pyridin-2-amine

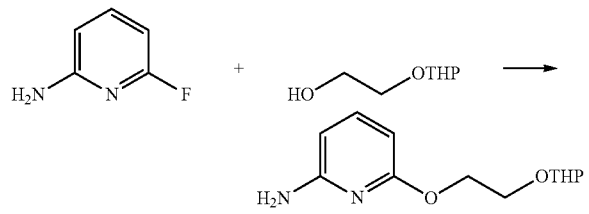

2-((tetrahydro-2H-pyran-2-yl)oxy)ethanol (1.5 g, 10.26 mmol) in N-Methyl-2-pyrrolidone (NMP) (4 mL) was added to a suspension of NaH (0.616 g, 25.7 mmol) at 0° C. and the reaction mixture was stirred for 30 min at 28° C. 6-fluoropyridin-2-amine (1.150 g, 10.26 mmol) was added to the reaction mixture at 0° C., and the reaction mixture was stirred at 120° C. for 16 hr. The reaction mixture was quenched with cold water and extracted with dichloromethane (2×60 mL). The organic layer was washed with water (30 mL) and saturated brine solution (20 mL), dried over anhydrous Na$_2$SO$_4$, filtered and concentrated. Crude was purified by flash chromatography on neutral alumina. Crude was diluted with DCM and absorbed with neutral alumina and eluted with 20-25-% EtOAc in pet ether fractions were collected and concentrated to get 6-(2-((tetrahydro-2H-pyran-2-yl)oxy)ethoxy)pyridin-2-amine (700 mg, 2.66 mmol, 25.9% yield), LCMS (m/z): 239.0 [M+H]$^+$.

Synthesis of 3-((6-aminopyridin-2-yl)oxy)propan-1-ol

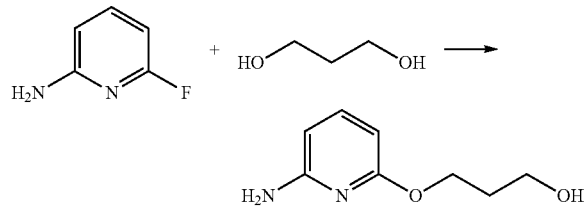

propane-1,3-diol (1.358 g, 17.84 mmol) was added to a stirred solution of NaH (1.070 g, 44.6 mmol) in N-Methyl-2-pyrrolidone (NMP) (5 mL) at 0° C. and stirred for 1 h and followed by addition of 6-fluoropyridin-2-amine (1.0 g, 8.92 mmol) and stirred for 2 h at 80° C.

Reaction mass was cooled to room temperature, slowly added to ice cold water and diluted with ethyl acetate. The separated organic layer was washed with water and brine. The organic layer was dried over Na$_2$SO$_4$, filtered and concentrated to obtain crude compound.

The crude compound was purified by using 100-200 silica gel and eluted in 100% ethyl acetate to afford 3-((6-aminopyridin-2-yl)oxy)propan-1-ol (0.4 g, 1.760 mmol, 19.73% yield) as brown viscous, LCMS (m/z): 169.22 [M+H]$^+$.

Synthesis of 6-(3-((tetrahydro-2H-pyran-2-yl)oxy)propoxy)pyridin-2-amine

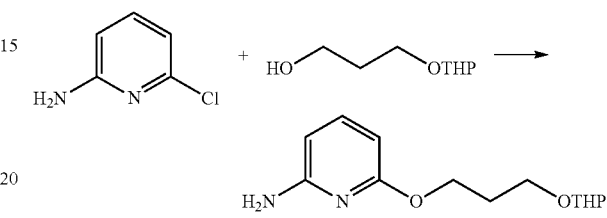

3-((tetrahydro-2H-pyran-2-yl)oxy)propan-1-ol (4.2 g, 26.2 mmol) in 1,4-Dioxane (20 mL) was added to a solution of NaH (1.307 g, 32.7 mmol) in 1,4-Dioxane (20 mL) at 0° C., and the reaction mixture was stirred for 30 min at 28° C. 6-chloropyridin-2-amine (2.8 g, 21.78 mmol) in 1,4-Dioxane (20 mL) was added to the reaction mixture at 0° C., and the reaction mixture was stirred for 10 hr at 100° C. The reaction mixture was partitioned between water (20 mL) and DCM (2×25 mL). DCM layer was washed with saturated NaHCO$_3$ solution, was separated and dried over anhydrous Na$_2$SO$_4$, filtered and filtrate was evaporated to crude 6-(3-((tetrahydro-2H-pyran-2-yl)oxy)propoxy)pyridin-2-amine (5.5 g, 18.12 mmol, 83% yield) as brown oil, LCMS (m/z): 253.2 [M+H]$^+$.

Synthesis of 3-((tetrahydro-2H-pyran-2-yl)oxy)propan-1-ol

p-toluenesulfonic acid monohydrate (0.678 g, 3.57 mmol) was added to a stirred solution of propane-1,3-diol (5.43 g, 71.3 mmol), and 3,4-dihydro-2H-pyran (3 g, 35.7 mmol) in Dichloromethane (DCM) (50 mL) at 0° C. The reaction mixture was stirred for 2 h at 28° C. The reaction mixture was partitioned between water (20 mL) and DCM (2×25 mL). DCM layer was washed with saturated NaHCO$_3$ solution, was separated and dried over anhydrous Na$_2$SO$_4$, filtered and filtrate was evaporated to crude 3-((tetrahydro-2H-pyran-2-yl)oxy)propan-1-ol (4.2 g, 26.2 mmol, 73.5% yield) as colorless oil.

Synthesis of 3-((6-aminopyridin-2-yl)oxy)-2,2-dimethylpropan-1-ol

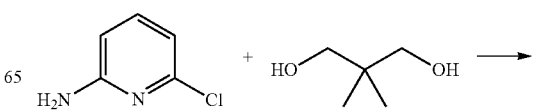

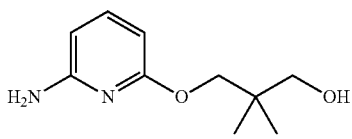

2,2-dimethylpropane-1,3-diol (3.0 g, 28.8 mmol) was added to the stirred solution of NaH (2.304 g, 57.6 mmol) in N-Methyl-2-pyrrolidone (NMP) (25 mL) at 0° C. The reaction mixture was stirred at room temperature for 30 min. 6-chloropyridin-2-amine (4.44 g, 34.6 mmol) was added to the reaction mixture at 0° C. The reaction mixture was stirred at 100° C. for 16 h and progress of the reaction was monitored by TLC. The reaction mixture was cooled to room temperature quenched with ice cold water and extracted with ethyl acetate (3×30 mL). The organic layer was washed with water (30 mL) and saturated brine solution (30 mL), dried over anhydrous $Na_2SO_4$, filtered and concentrated to get crude compound TLC eluent: 50% EtOAc/Hexane, $R_f$: 0.3, UV active. The crude compound was purified by column chromatography using Neutral Alumina and eluted with 5% EtOAc in Petether to obtain pure 3-((6-aminopyridin-2-yl)oxy)-2,2-dimethylpropan-1-ol (1.5 g, 6.79 mmol, 23.56% yield) as off white solid. LCMS: (m/z): 197.16 $[M+H]^+$.

Synthesis of 4-((6-aminopyridin-2-yl)oxy)-2-methylbutan-2-ol

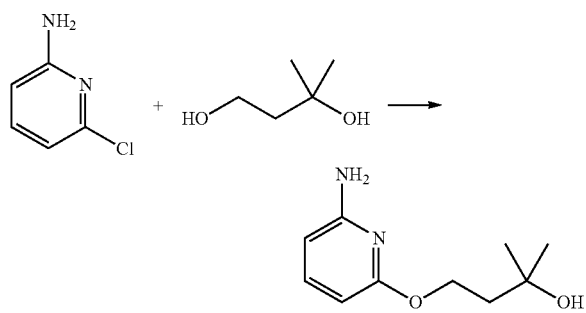

To a stirred suspension of NaH (1.167 g, 29.2 mmol) in N-Methyl-2-pyrrolidone (NMP) (2 mL) under nitrogen at 0° C. was added a solution of 3-methylbutane-1,3-diol (3.04 g, 29.2 mmol) in N-Methyl-2-pyrrolidone (NMP) (2 mL) dropwise during 10 min at 0° C. After 10 min added a solution of 6-chloropyridin-2-amine (2.5 g, 19.45 mmol) in N-Methyl-2-pyrrolidone (NMP) (2 mL) dropwise during 10 min at 0° C. The reaction mixture was heated at 120° C. for 16 hr. Progress of the reaction was monitored by TLC. Reaction mixture was poured into ice water and extracted with EtOAc (3×30 ml), organic solvent was dried over $Na_2SO_4$ and concentrated under vacuum to get crude. The crude was purified by column chromatography by using silica gel (100-200 mesh) by eluting with 50-70% EtOAc in hexane to get 4-((6-aminopyridin-2-yl)oxy)-2-methylbutan-2-ol (1.5 g, 7.51 mmol, 38.6% yield) as an off-white solid, LCMS (m/z): 197.29 $[M+H]^+$.

Synthesis of 3-((6-aminopyrazinopyrazin-2-yl)oxy)-2,2-dimethylpropan-1-ol

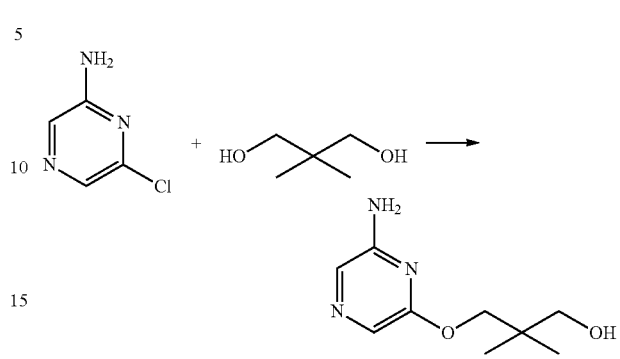

To a stirred suspension of NaH (2.316 g, 57.9 mmol) in 1,4-Dioxane (20 mL) under nitrogen at 0° C. was added a solution of 2,2-dimethylpropane-1,3-diol (4.02 g, 38.6 mmol) in 1,4-Dioxane (20 mL) dropwise during 10 min at 0° C. After 10 min added a solution of 6-chloropyrazin-2-amine (5 g, 38.6 mmol) in 1,4-Dioxane (20 mL) was added dropwise during 10 min at 0° C. The reaction mixture was heated at 120° C. for 48 hr. TLC indicates small amount starting material along with product. Reaction mixture was poured into ice cold water (60 mL), aqueous layer was extracted with EtOAc (2×100 mL). The organic layer was washed with brine (50 mL). The organic layer was dried over $Na_2SO_4$, filtered and concentrated under reduced pressure to obtain crude product. Crude product was purified by column chromatography using 100-200 silica gel as a eluent (0-50% EtOAc in petether) to obtain 3-((6-aminopyrazin-2-yl)oxy)-2,2-dimethylpropan-1-ol (1 g, 4.95 mmol, 12.84% yield), LCMS (m/z): 198.00 $[M+H]^+$.

Synthesis of 3-((6-aminopyrazin-2-yl)oxy)propan-1-ol

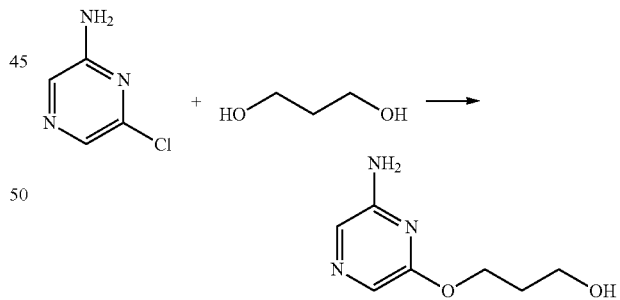

To a suspension of NaH (1.389 g, 34.7 mmol) in NMP (2 mL) was added a solution of propane-1,3-diol (2.64 g, 34.7 mmol) in NMP (2 mL) under Nitrogen at 0° C., the reaction mixture was stirred for 1 h at RT. Then a solution of 6-chloropyrazin-2-amine (3 g, 23.16 mmol) in NMP (6 mL) was added drop by drop over 15 min, at 0° C. and heated at 140° C. for 16 hr. The reaction mixture was cooled to rt, quenched with water (50 mL) and extracted with EtOAc (3×150 mL). The combined organics were washed with brine, dried with anhydrous $Na_2SO_4$, filtered and concentrated to get crude product. The crude was added to a silica gel column and was eluted with (70%) EtOAc/Pet Ether.

Collected fractions were evaporated to obtain compound 3-((6-aminopyrazin-2-yl)oxy)propan-1-ol (1.5 g, 8.21 mmol, 35.5% yield) as Off-white solid, LCMS (m/z): 170.09 [M+H]⁺.

Synthesis of 6-(2-((tetrahydro-2H-pyran-2-yl)oxy)ethoxy)pyrazin-2-amine

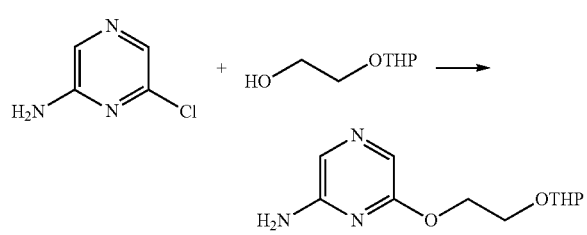

NaH (60%) (0.556 g, 23.16 mmol) was added to a stirred solution of 2-((tetrahydro-2H-pyran-2-yl)oxy)ethanol (3.39 g, 23.16 mmol) in 1,4-Dioxane (100 mL) at 0° C. then stirred at RT for 30 min and 6-chloropyrazin-2-amine (3 g, 23.16 mmol) was added at 0° C. then it was kept at 80° C. for 16 h. The reaction mixture was cooled to RT, and was quenched with ice cold water (50 mL) then partitioned between ice cold water (20 mL×2) and ethyl acetate (20 mL×2). Organic layers were separated and was dried over anhydrous Na₂SO₄, filtered and filtrate was evaporated to get crude compound, then it was purified by column chromatography (using 100-200 silica gel, column eluted at 60% ethyl acetate in hexane) to afford the 6-(2-((tetrahydro-2H-pyran-2-yl)oxy)ethoxy)pyrazin-2-amine (5 g, 20.06 mmol, 87% yield) as gum oil, LCMS (m/z): 240.13 [M+H]⁺.

Synthesis of 4-((6-aminopyrazin-2-yl)oxy)-2-methylbutan-2-ol

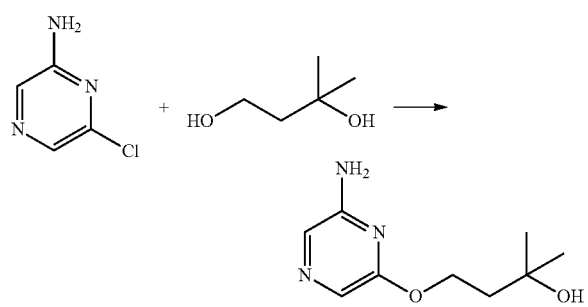

To a stirred suspension of NaH (0.463 g, 11.58 mmol) in 1,4-Dioxane (5.00 mL) under nitrogen at 0° C. was added a solution of 3-methylbutane-1,3-diol (1.206 g, 11.58 mmol) in 1,4-Dioxane (5.00 mL) dropwise during 10 min at 0° C. After 10 min added a solution of 6-chloropyrazin-2-amine (1.0 g, 7.72 mmol) in 1,4-Dioxane (10.00 mL) dropwise during 10 min at 0° C. The reaction mixture was stirred at 100° C. for 16 hr. Progress of the reaction was monitored by TLC. Reaction mixture was poured into ice water and extracted with EtOAc (3×25 ml), organic solvent was dried over Na₂SO₄ and concentrated under vacuum to get crude. The crude was purified by column chromatography by using silica gel (100-200 mesh) by eluting with 50-70% EtOAc in hexane to get 4-((6-aminopyrazin-2-yl)oxy)-2-methylbutan-2-ol (1.0 g, 5.04 mmol, 65.3% yield) as brown solid, LCMS (m/z): 199.08 [M+H]⁺.

Synthesis of (S)-3-bromo-5-((2,2-dimethyl-1,3-dioxolan-4-yl)methoxy)pyridine

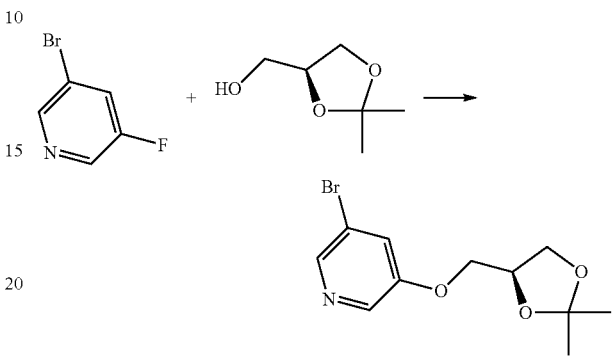

Cesium carbonate (37.0 g, 114 mmol) was taken into multi-neck RB. Then flask was cooled to 0° C. and N-Methyl-2-pyrrolidone (NMP) (100 mL) was added slowly over a period of 3 minutes. The resulting reaction mixture was stirred under nitrogen for 15 min. Then (S)-(2,2-dimethyl-1,3-dioxolan-4-yl)methanol (10 g, 76 mmol) was added dropwise over a period of 5 min at 0° C. This suspension was stirred at room temperature ° C. for 1 h. Suspension became pale yellow solution after added 3-bromo-5-fluoropyridine (7.62 mL, 73.9 mmol). The resulting solution was stirred at 75° C. for 24 hr. Reaction progress was monitored by TLC 40% EtOAc in Hexane. TLC indicated consumption of SM and formation of new spot after 24 h. The reaction mass was cooled to room temperature, diluted with water (500 mL). The aqueous layer was extracted with ethyl acetate (2×300 mL). The organic layer was washed with brine (250 mL), dried over Na₂SO₄ filtered, concentrated under reduced pressure to afford brown oil. The crude product was purified by column chromatography over 100-200 mesh size silica gel. Column was eluted with a gradient of EtOAc/Hexane. Desired compound was eluted with 20% EtOAc in Hexane. Compound fractions containing pure compound were concentrated under reduced pressure to afford (S)-3-bromo-5-((2,2-dimethyl-1,3-dioxolan-4-yl)methoxy)pyridine (10 g, 34.0 mmol, 44.9% yield) as pale yellow viscous oil, LCMS (m/z): 289.99 [M+H]⁺.

Synthesis of (R)-5-((2,2-dimethyl-1,3-dioxolan-4-yl)methoxy)pyridin-3-amine

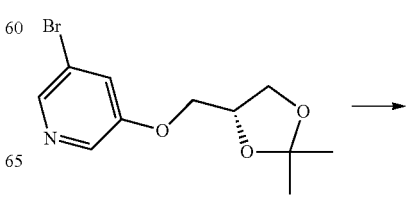

-continued

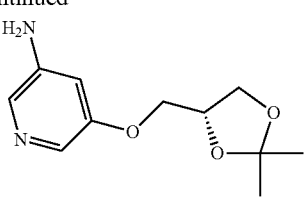

(R)-3-bromo-5-((2,2-dimethyl-1,3-dioxolan-4-yl)methoxy)pyridine (50 g, 174 mmol), liquor ammonia (25 mL, 1155 mmol) were taken in a sealed tube. Then added copper(II) sulfate (5.54 g, 34.7 mmol) at 0° C. The resulting blue solution was heated to 120° C. for 2 hr. The reaction progress was monitored by TLC 10% MeOH in DCM, TLC indicated formation of new spot and consumption of SM after 24 h. After completion, The reaction mass was cooled to room temperature. The reaction mass was brought to pH 10 with 20% NaOH, saturated with NaCl, extracted with ethyl acetate (30 mL*2). The combined organic layer was washed with brine (20 mL), dried over Na$_2$SO$_4$, filtered and concentrated under reduced pressure to afford crude brown solid, which was triturated with diethyl ether and stirred for 4 hours then filtered to afford (R)-5-((2,2-dimethyl-1,3-dioxolan-4-yl)methoxy)pyridin-3-amine (35.4 g, 146 mmol, 84% yield) as pale brown solid, LCMS (m/z): 225.29 [M+H]$^+$.

Synthesis of (S)-5-((2,2-dimethyl-1,3-dioxolan-4-yl)methoxy)pyridin-3-amine

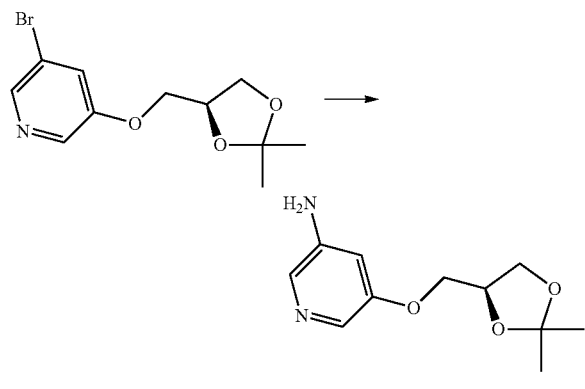

(S)-3-bromo-5-((2,2-dimethyl-1,3-dioxolan-4-yl)methoxy)pyridine (10 g, 34.7 mmol), liquor ammonia (100 mL, 4621 mmol) were taken in a sealed tube. The resulting brown solution was heated to 120° C. for 24 hr. The reaction progress was monitored by TLC 10% MeOH in DCM, TLC indicated formation of new spot and consumption of SM after 24 h. After completion, The reaction mass was cooled to room temperature. The reaction mass was brought to pH 10 with 20% NaOH, saturated with NaCl, extracted with ethyl acetate (30 mL*2). The combined organic layer was washed with brine (20 mL), dried over Na$_2$SO$_4$, filtered and concentrated under reduced pressure to afford the (S)-5-((2,2-dimethyl-1,3-dioxolan-4-yl)methoxy)pyridin-3-amine (6 g, 25.8 mmol, 74.2% yield) as an pale brown solid, LCMS (m/z): 225.10 [M+H]$^+$.

Synthesis of (R)-6-((2,2-dimethyl-1,3-dioxolan-4-yl)methoxy)pyrimidin-4-amine

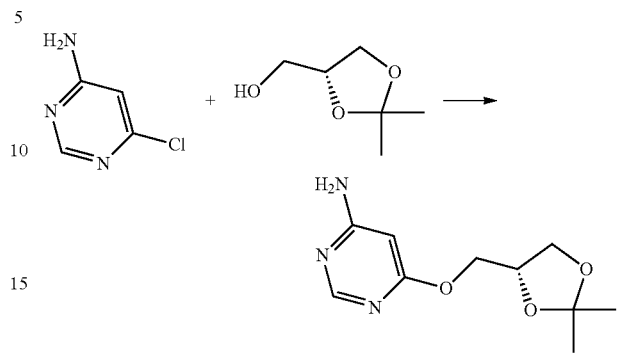

To a suspension of NaH (11.35 g, 473 mmol) in THF (100 mL) was added dropwise a solution of (R)-(2,2-dimethyl-1,3-dioxolan-4-yl)methanol (25 g, 189 mmol) in THF (150 mL) under Nitrogen at 0° C. The resulting suspension was stirred at rt for 1 h. 6-chloropyrimidin-4-amine (19.61 g, 151 mmol) was added to the reaction mixture portion wise at rt and the resulting suspension was heated to 90° C. for 48 hr. After the completion of reaction (monitored by TLC, it shows little bit of starting and new spot observed at polar), reaction mixture was poured into ice water (500 mL) and aqueous layer was extracted with EtOAc (2×1000 mL). Combined organics dried over Na$_2$SO$_4$, filtered and concentrated under reduced pressure to get light brown solid (crude). Crude material was purified by silica gel column (100-200, 3% MeOH in DCM). Fractions containing pure compound were combined and concentrated to afford the desired product (R)-6-((2,2-dimethyl-1,3-dioxolan-4-yl)methoxy)pyrimidin-4-amine (13 g, 53.9 mmol, 28.5% yield) as an off-white solid and also get the impure compound (10 g). LCMS (m/z): 226.17 (M+H)$^+$.

Synthesis of (S)-6-((2,2-dimethyl-1,3-dioxolan-4-yl)methoxy)pyrimidin-4-amine

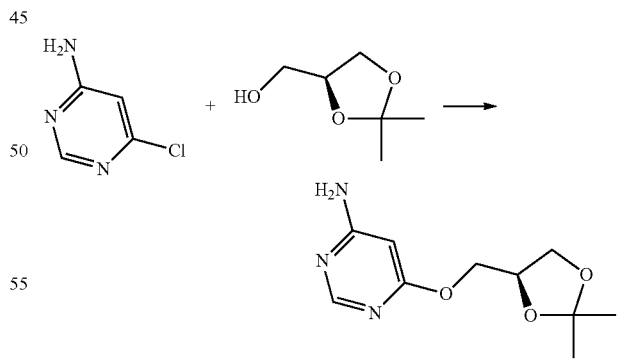

To a suspension of NaH (9.08 g, 378 mmol) in THF (150 mL) was added drop wise a solution of (S)-(2,2-dimethyl-1,3-dioxolan-4-yl)methanol (20 g, 151 mmol) in THF (200 mL) under Nitrogen at 0° C., and the resulting suspension was stirred at rt for 1 h. 6-chloropyrimidin-4-amine (15.68 g, 121 mmol) was added to the reaction mass portion wise at rt and the resulting suspension was heated to 90° C. for 48 hr. After the completion of reaction (monitored by TLC, starting material completely consumed and new spot observed at polar), reaction mass was poured into ice water (200 mL) and extracted with ethyl acetate (2×400 ml). Combined organics dried over Na$_2$SO$_4$, filtered and concentrated under reduced pressure to get light brown solid. The obtained solid was stirred in diethyl ether (200 ml) for 30 min filtered and dried under vacuum to get (S)-6-((2,2-dimethyl-1,3-dioxolan-4-yl)methoxy)pyrimidin-4-amine (13 g, 57.3 mmol, 37.9% yield) as a light brown solid, LCMS (m/z): 225.96 [M+H]$^+$.

Synthesis of 2-((tetrahydro-2H-pyran-4-yl)oxy)pyrimidin-4-amine

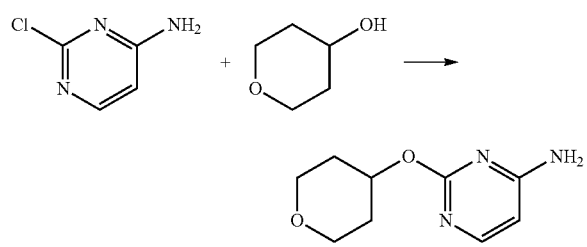

To a solution of tetrahydro-2H-pyran-4-ol (25 g, 245 mmol) in Tetrahydrofuran (THF) (500 mL) stirred under nitrogen, was added NaH (22.52 g, 563 mmol) at 27° C. in 10 mints, after 1 hr was added 2-chloropyrimidin-4-amine (22.20 g, 171 mmol) at 27° C. The reaction mixture was stirred at 85° C. for 36 hr. The progress of reaction was monitored by TLC. TLC indicated a polar spot along with SM. Reaction mass was poured in 200 ml ice cool water, extracted with EtOAc (3×200 ml), combined organic layers dried over Na$_2$SO$_4$ filtered and concentrated under reduced pressure and was purified using column chromatography with (60-120) silica mesh SM was eluted at 50% EtOAc in Hexane and required compound was eluted at 90% EtOAc in Hexane, combined compound fractions concentrated to get 2-((tetrahydro-2H-pyran-4-yl)oxy)pyrimidin-4-amine (9 g, 39.9 mmol, 16.31% yield), LCMS (m/z): 196.00 [M+H]$^+$.

Synthesis of 4-(1-methyl-1H-pyrazol-4-yl)pyrimidin-2-amine

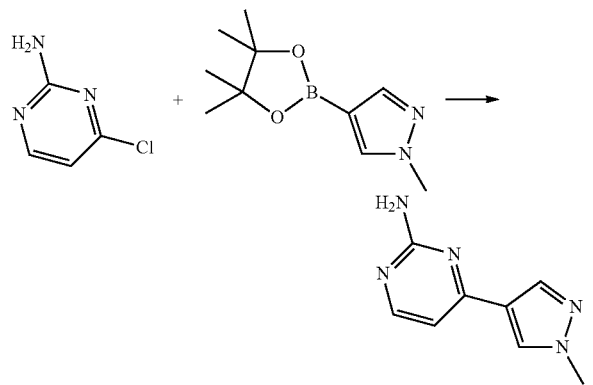

To a degassed solution of 4-chloropyrimidin-2-amine (800 mg, 6.18 mmol), solid 1-methyl-4-(4,4,5,5-tetramethyl-1,3,2-dioxaborolan-2-yl)-1H-pyrazole (1927 mg, 9.26 mmol) and K$_3$PO$_4$ (3932 mg, 18.53 mmol) in 1,4-Dioxane (20 mL), Water (5.00 mL) stirred under at room temp. Then added PdCl$_2$(dppf)-CH$_2$Cl$_2$ adduct (756 mg, 0.926 mmol) and degassed for 5 min. Then reaction mixture was stirred at 80° C. for 15 h 30 min. The reaction mixture was monitored by TLC. The reaction was cooled to RT. The organic phase was evaporated and added water 50 mL and Extracted with Ethyl acetate (3×70 ml) and washed with saturated brine 50 mL dried over Na$_2$SO$_4$ and evaporated in vacuum to give the crude product. The crude compound was purified by flash column chromatography (Neutral alumina, eluent: 90% EtOAc in Pet ether) to afford 4-(1-methyl-1H-pyrazol-4-yl)pyrimidin-2-amine (600 mg, 3.42 mmol, 55.5% yield) as an off white solid, LCMS (m/z): 176.1 [M+H]$^+$.

Synthesis of 4-(2-methyloxazol-5-yl)pyrimidin-2-amine

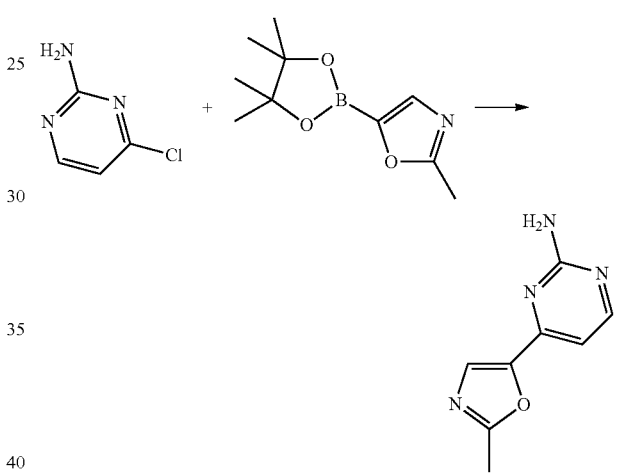

To a stirred solution of 4-chloropyrimidin-2-amine (1.5 g, 11.58 mmol) in 1,4-Dioxane (20 mL) and Water (5 mL) mixture, were added potassium phosphate (3.69 g, 17.37 mmol) and 2-methyl-5-(4,4,5,5-tetramethyl-1,3,2-dioxaborolan-2-yl)oxazole (2.421 g, 11.58 mmol) at Room temperature. The reaction mass was degassed for 15 min with nitrogen, added PdCl$_2$(dppf)-CH$_2$Cl$_2$ adduct (0.095 g, 0.116 mmol) and the resulting reaction mass was stirred for 16 hr at 80° C. under Nitrogen, Progress of the reaction was monitored by TLC, TLC indicated formation of a polar multiple sports and SM was consumed. Reaction mass was concentrated and diluted with 50 ml of water and 60 ml of DCM, pass through Hi-flow bed, separated organic layer, extracted with DCM (2×50 ml), combined organic layers, dried over Na$_2$SO$_4$, filtered and concentrated to get crude compound. The crude product was purified by combiflash chromatography using silica gel column (24 g, 60% EtOAc in pet ether). Column was eluted with a gradient of EtOAc in Hexane. Desired compound was eluted with 60% EtOAc in Hexane. Fractions containing pure compound were concentrated under reduced pressure to afford the 4-(2-methyloxazol-5-yl)pyrimidin-2-amine (1.2 g, 6.66 mmol, 57.5% yield) as an off-white color solid. LCMS (m/z): 177.11 [M+H]$^+$.

Synthesis of (R)-4-((2,2-dimethyl-1,3-dioxolan-4-yl)methoxy)pyrimidin-2-amine

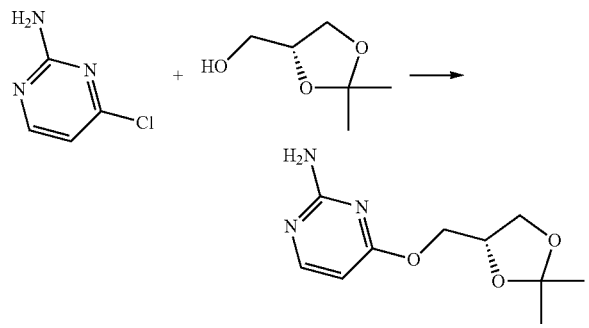

To a suspension of NaH (9.08 g, 378 mmol) in THF (150 mL) was added dropwise a solution of (R)-(2,2-dimethyl-1,3-dioxolan-4-yl)methanol (20 g, 151 mmol) in THF (250 mL) under Nitrogen at 0° C. The resulting suspension was stirred at rt for 1 h. 4-chloropyrimidin-2-amine (15.68 g, 121 mmol) was added to the reaction mixture portion wise at rt and the resulting suspension was heated to 90° C. for 48 hr. After the completion of reaction (monitored by TLC, starting completely consumed and new spot observed at polar), reaction mixture was poured into ice water (250 mL) and aqueous layer was extracted with EtOAc (2×300 mL). Combined organics dried over Na$_2$SO$_4$, filtered and concentrated under reduced pressure to get pale yellow liquid (crude). Obtained crude material was purified by column (100-200 silica gel) by using 0-50% EtOAc-petether to get (R)-4-((2,2-dimethyl-1,3-dioxolan-4-yl)methoxy)pyrimidin-2-amine (13 g, 57.0 mmol, 37.7% yield) as pale yellow solid, LCMS (m/z): 226.20 [M+H]$^+$.

Synthesis of (S)-4-((2,2-dimethyl-1,3-dioxolan-4-yl)methoxy)pyrimidin-2-amine

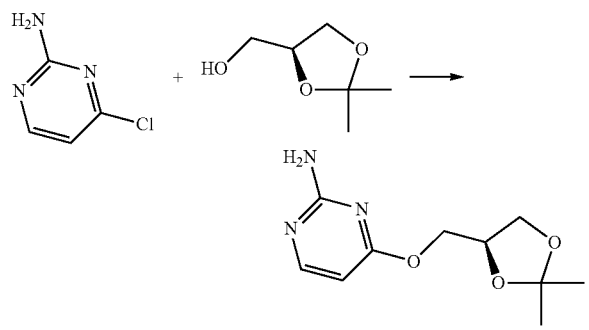

To a suspension of NaH (8.25 g, 189 mmol) in 1,4-Dioxane (200 mL) was added dropwise a solution of (S)-(2,2-dimethyl-1,3-dioxolan-4-yl)methanol (10 g, 76 mmol) in 1,4-Dioxane (50 mL) under Nitrogen at 0° C. The resulting suspension was stirred at rt for 1 h. 4-chloropyrimidin-2-amine (7.84 g, 60.5 mmol) was added to the reaction mixture portion wise at rt and the resulting suspension was heated to 90° C. for 48 hr. The reaction mixture was cooled to 28° C. and was partitioned between water (200 mL) and EtOAc (200 mL).

Organic layer was separated and was dried over anhydrous Na$_2$SO$_4$, filtered and filtrate was evaporated to get crude (TLC eluent: Neat ethyl acetate R$_f$: 0.3; UV active). The crude compound was purified by column chromatography (100-200 mesh silica gel, eluted at 60% Ethyl acetate in hexane) to afford (S)-4-((2,2-dimethyl-1,3-dioxolan-4-yl)methoxy)pyrimidin-2-amine (8.0 g, 35.4 mmol, 46.8% yield) as pale yellow solid LCMS (m/z) 226.30 (M+H)$^+$.

Synthesis of (R)-phenyl (4-((2,2-dimethyl-1,3-dioxolan-4-yl)methoxy)pyrimidin-2-yl)carbamate

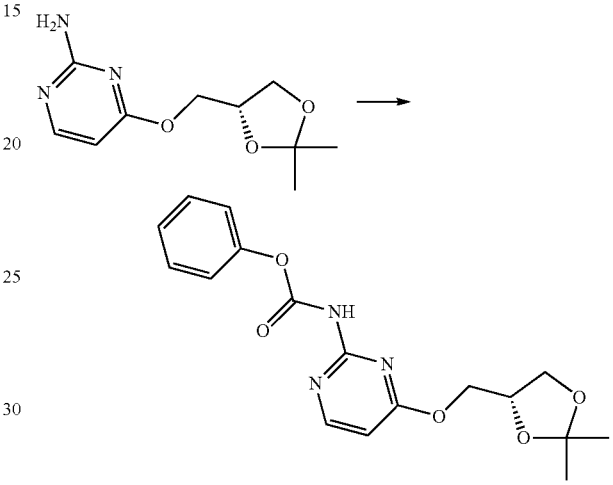

To a solution of phenyl carbonochloridate (2.71 g, 17.31 mmol) and pyridine (1.724 mL, 21.31 mmol) in Dichloromethane (DCM) (50 mL) stirred under nitrogen at room temp was added (R)-4-((2,2-dimethyl-1,3-dioxolan-4-yl)methoxy)pyrimidin-2-amine (3.0 g, 13.32 mmol). The reaction mixture was stirred at 28° C. for 2 hr. The Reaction was monitored by TLC. The reaction mixture was diluted with water (75 mL) extracted with DCM (2×75 mL). The organic layer was separated and dried out with Na$_2$SO$_4$, filtered and concentrated under high vacuum to get crude product. To the Crude product the mixture of Diethyl ether and pentane (3:1) was added and stirred for 10 min and filtered to afford a compound of (R)-phenyl (4-((2,2-dimethyl-1,3-dioxolan-4-yl)methoxy)pyrimidin-2-yl)carbamate (2.5 g, 2.375 mmol, 17.83% yield), LCMS (m/z): 346.21[M+H]$^+$.

Synthesis of 2-(2-((tetrahydro-2H-pyran-2-yl)oxy)ethoxy)pyrimidin-4-amine

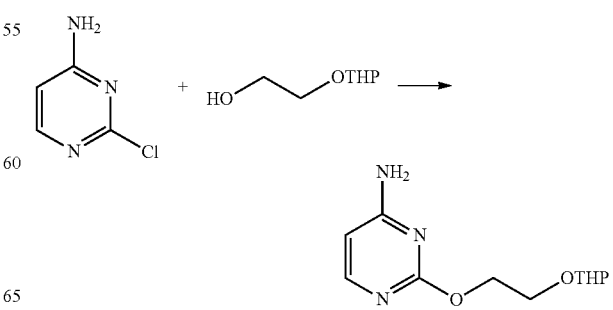

NaH (0.741 g, 30.9 mmol) was added to a stirred solution of 2-((tetrahydro-2H-pyran-2-yl)oxy)ethanol (4.51 g, 30.9 mmol) in 1,4-Dioxane (120 mL) at 0° C. then stirred at RT for 30 min and 2-chloropyrimidin-4-amine (4 g, 30.9 mmol) was added at 0° C. then it was kept at 80° C. for 16 h. The reaction mixture was cooled to RT, and was quenched with ice cold water (50 mL) then partitioned between ice cold water (50 mL×2) and ethyl acetate (50 mL×2). Organic layers were separated and was dried over anhydrous Na$_2$SO$_4$, filtered and filtrate was evaporated to get crude compound then it was purified by column chromatography (using 100-200 silica gel, column eluted at 60% ethyl acetate in hexane) to afford 2-(2-((tetrahydro-2H-pyran-2-yl)oxy) ethoxy)pyrimidin-4-amine (4 g, 16.05 mmol, 52.0% yield) as a gum oil, LCMS (m/z): 239.9 [M+H]$^+$.

Synthesis of 3-((4-aminopyrimidin-2-yl)oxy)-2,2-dimethylpropan-1-ol

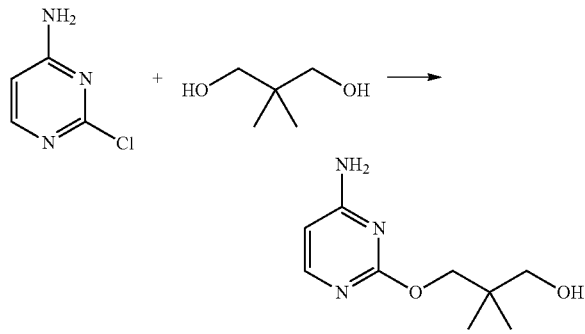

To a stirred suspension of NaH (2.316 g, 57.9 mmol) in Tetrahydrofuran (THF) (20 mL) under nitrogen at 0° C. was added a solution of 2,2-dimethylpropane-1,3-diol (4.02 g, 38.6 mmol) in Tetrahydrofuran (THF) (20 mL) dropwise during 10 min at 0° C. After 10 min added a solution of 2-chloropyrimidin-4-amine (5 g, 38.6 mmol) in Tetrahydrofuran (THF) (20 mL) was added dropwise during 10 min at 0° C. The reaction mixture was heated at 120° C. for 16 hr. TLC indicates small amount starting material along with product. Reaction mixture was poured into ice cold water (60 mL), aqueous layer was extracted with EtOAc (2×100 mL). The organic layer was washed with brine (50 mL). The organic layer was dried over Na$_2$SO$_4$, filtered and concentrated under reduced pressure to obtain crude product.

Crude product was purified by column chromatography using 100-200 silica gel as a eluent (0-50% EtOAc in petether) to get 3-((4-aminopyrimidin-2-yl)oxy)-2,2-dimethylpropan-1-ol (800 mg, 4.04 mmol, 10.47% yield), LCMS (m/z): 198.09 [M+H]$^+$.

Synthesis of 4-((6-aminopyrazin-2-yl)oxy)-2-methylbutan-2-ol

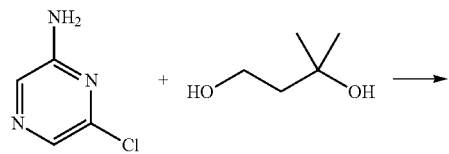

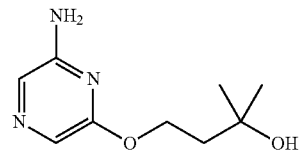

To a stirred suspension of NaH (0.463 g, 11.58 mmol) in 1,4-Dioxane (5.00 mL) under nitrogen at 0° C. was added a solution of 3-methylbutane-1,3-diol (1.206 g, 11.58 mmol) in 1,4-Dioxane (5.00 mL) dropwise during 10 min at 0° C. After 10 min added a solution of 6-chloropyrazin-2-amine (1.0 g, 7.72 mmol) in 1,4-Dioxane (10.00 mL) dropwise during 10 min at 0° C. The reaction mixture was stirred at 100° C. for 16 hr. Progress of the reaction was monitored by TLC. Reaction mixture was poured into ice water and extracted with EtOAc (3×25 ml), organic solvent was dried over Na$_2$SO$_4$ and concentrated under vacuum to get crude. The crude was purified by column chromatography by using silica gel (100-200 mesh) by eluting with 50-70% EtOAc in hexane to get 4-((6-aminopyrazin-2-yl)oxy)-2-methylbutan-2-ol (1.0 g, 5.04 mmol, 65.3% yield) as brown solid, LCMS (m/z): 199.08 [M+H]$^+$.

Synthesis of 4-((4-aminopyrimidin-2-yl)oxy)-2-methylbutan-2-ol

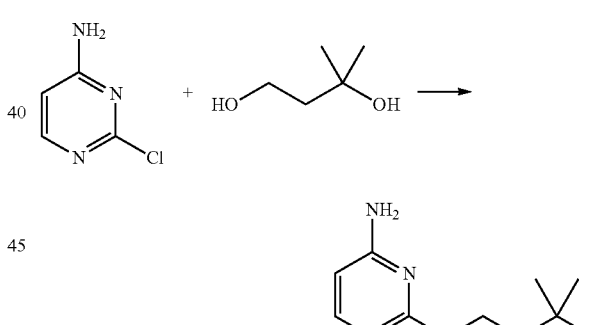

To a stirred suspension of NaH (1.698 g, 42.5 mmol) in 1,4-Dioxane (100 mL) under nitrogen at 0° C. was added a solution of 3-methylbutane-1,3-diol (4.42 g, 42.5 mmol) in 1,4-Dioxane (50 mL) dropwise during 15 min at 0° C. After 10 min added 2-chloropyrimidin-4-amine (5.00 g, 38.6 mmol) portion wise during 15 min at 0° C. The reaction mixture was heated at 100° C. for 16 hr. Progress of the reaction was monitored by TLC. Reaction mixture was poured into ice water, concentrated to get sticky mass as a crude. The crude was purified by column chromatography by using silica gel (60-120 mesh) by eluting with 50-70% EtOAc in hexane to get 4-((4-aminopyrimidin-2-yl)oxy)-2-methylbutan-2-ol (6.3 g, 29.6 mmol, 77% yield) as and off-white solid, LCMS (m/z): 198.30 [M+H]$^+$.

Synthesis of (R)-5-((2,2-dimethyl-1,3-dioxolan-4-yl)methoxy)pyrazin-2-amine

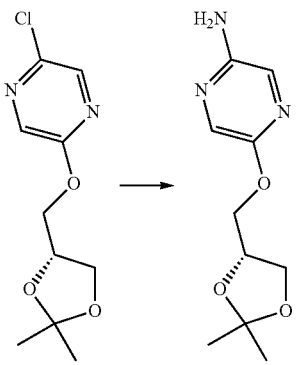 [SMILES: CC1(C)OC[C@@H](COc2cnc(Cl)cn2)O1 ; CC1(C)OC[C@@H](COc2cnc(N)cn2)O1]

To a stirred solution of (R)-2-chloro-5-((2,2-dimethyl-1,3-dioxolan-4-yl)methoxy)pyrazine (12 g, 49.0 mmol) in Tetrahydrofuran (THF) (20 mL) was added ammonium hydroxide (300 mL, 1926 mmol) and copper(II) sulfate (1.566 g, 9.81 mmol) in a sealed tube. Reaction mixture was stirred at 120° C. for 18 hr. Progress of the reaction was monitored by TLC, TLC indicates formation of polar spot along with un-reacted SM. Reaction mixture was diluted with water (300 mL), extracted with EtOAc (3×200 mL), organic layers were combined and washed with water (100 mL), brine solution (100 mL), organic layer dried over anhydrous $Na_2SO_4$, filtered and concentrated under reduced pressure to afford (R)-5-((2,2-dimethyl-1,3-dioxolan-4-yl)methoxy)pyrazin-2-amine (10 g, 3.97 mmol, 8.09% yield) as a yellow oily crude compound, LCMS (m/z): 226.13 $(M+H)^+$.

Synthesis of (S)-2-chloro-5-((2,2-dimethyl-1,3-dioxolan-4-yl)methoxy)pyrazine

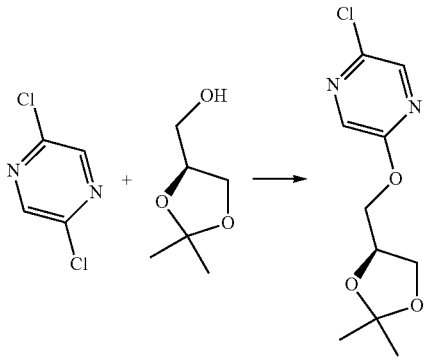

To a suspension of (S)-(2,2-dimethyl-1,3-dioxolan-4-yl)methanol (0.87 g, 67.1 mmol), in N,N-Dimethylformamide (DMF) (50 mL) stirred under nitrogen at 0° C. was added cesium carbonate (32.8 g, 101 mmol), the resulting reaction mixture was stirred at 0° C. for 1 hr. To this added 2,5-dichloropyrazine (10 g, 67.1 mmol). The resulting reaction mixture was stirred at 100° C. for 6 hr. Progress of the reaction was monitored by TLC. TLC indicated starting material was consumed to form new polar spot with 0.3 Rf. The reaction mass was cooled to rt, added water (100 mL) and extracted with Ethyl acetate (100 mL). The organic layer was washed with water (100 mL×2). The organic layer was dried over $Na_2SO_4$ and filtered and concentrated to get crude as light brown liquid. The crude product was added to a silica gel (60-120) column and was eluted with Hex/EtOAc. Collected fractions: 30% EtOAc in Hexane the product was eluted. Concentrated the product fractions to afford (S)-2-chloro-5-((2,2-dimethyl-1,3-dioxolan-4-yl)methoxy)pyrazine (12 g, 47.7 mmol, 71.0% yield) as light brown liquid, LCMS (m/z): 244.90 $[M+H]^+$.

Synthesis of (S)-5-((2,2-dimethyl-1,3-dioxolan-4-yl)methoxy)pyrazin-2-amine

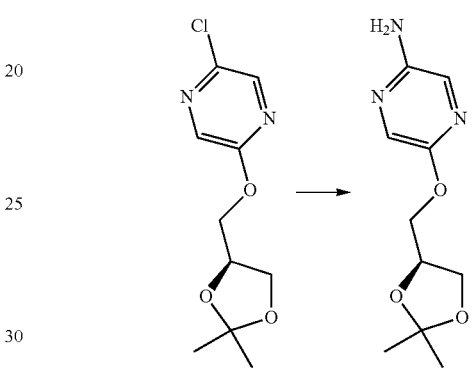

To a solution of (S)-2-chloro-5-((2,2-dimethyl-1,3-dioxolan-4-yl)methoxy)pyrazine (10 g, 40.9 mmol), in Tetrahydrofuran (THF) (10 mL) stirred at room temp was added ammonium hydroxide (63.7 mL, 409 mmol) and copper(II) sulfate (3.26 g, 20.44 mmol) at rt. The reaction mixture was stirred in sealed tube at 130° C. for 2 days. Progress of the reaction was monitored by TLC. TLC indicated starting material was consumed. Cooled the reaction mass to rt, diluted with water (100 mL), Extracted with ethyl acetate (250 mL×2). The organic layer was dried over $Na_2SO_4$, filtered and concentrated to get crude compound as brown sticky compound. The crude product was added to a silica gel column and was eluted with DCM/EtOAc. Collected fractions: 50% EtOAc in petether the product was eluted. Concentrated the product fractions to afford (S)-5-((2,2-dimethyl-1,3-dioxolan-4-yl)methoxy)pyrazin-2-amine (2 g, 8.77 mmol, 21.46% yield)(N35119-51-A2) as light brown solid. NMR: in CDCl3 consistent with, LCMS (m/z): 226.09 $[M+H]^+$.

Synthesis of (S)-6-((2,2-dimethyl-1,3-dioxolan-4-yl)methoxy)pyridazin-3-amine

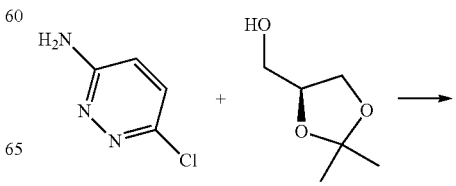

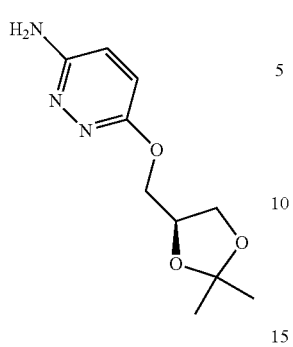

To a suspension of KOtBu (12.99 g, 116 mmol) in 1,4-Dioxane (300 mL) was added dropwise a solution of (S)-(2,2-dimethyl-1,3-dioxolan-4-yl)methanol (4.08 g, 30.9 mmol) in 20 ml under Nitrogen at 0° C. The resulting suspension was stirred at rt for 1 h. 6-chloropyridazin-3-amine (5 g, 38.6 mmol) was added to the reaction mixture portion wise at rt and the resulting suspension was heated to 110° C. for 16 hr. After the completion of reaction (monitored by TLC, it shows little bit of starting and new spot observed at polar), reaction mixture was poured into ice water (50 mL) and aqueous layer was extracted with EtOAc (2×50 mL). Combined organics dried over Na$_2$SO$_4$. LCMS (m/z): 226.19 [M+H]$^+$.

Synthesis of (R)-6-((2,2-dimethyl-1,3-dioxolan-4-yl)methoxy)pyridin-3-amine

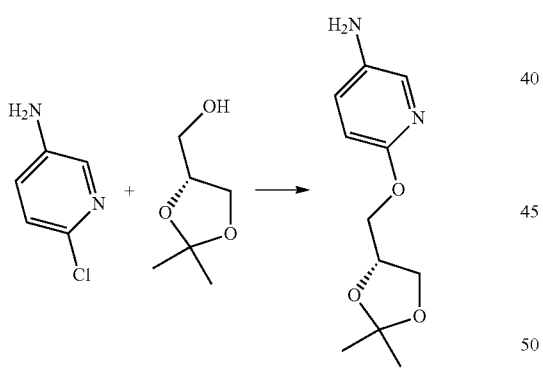

(R)-(2,2-dimethyl-1,3-dioxolan-4-yl)methanol (27.8 g, 210 mmol) was added to a stirred solution of KOtBu (45.8 g, 408 mmol) in NMP (200 mL) at 0° C. then stirred at RT for 1 h and cooled to 0° C., 6-chloropyridin-3-amine (15 g, 117 mmol) was added and heated to 110° C. for 144 h. The reaction mixture cooled to RT and partitioned between water (500 mL×2) and EtOAc (200 mL×4). Organic layers were separated and was dried over anhydrous Na$_2$SO$_4$, filtered and filtrate was evaporated to get crude and purified by column chromatography (using 100-200 silica gel, column eluted at 50% ethyl acetate in hexane) to afford the (R)-6-((2,2-dimethyl-1,3-dioxolan-4-yl)methoxy)pyridin-3-amine (8 g, 35.1 mmol, 30.1% yield) as brown oil, LCMS (m/z): 225.16 [M+H]$^+$.

Synthesis of (S)-6-((2,2-dimethyl-1,3-dioxolan-4-yl)methoxy)pyridin-3-amine

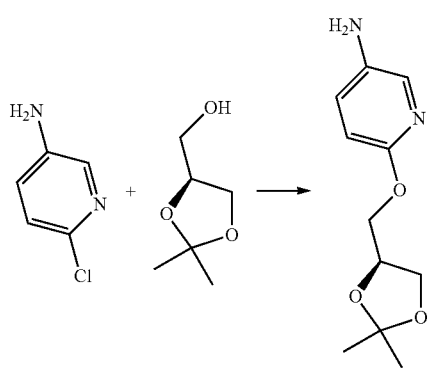

(S)-(2,2-dimethyl-1,3-dioxolan-4-yl)methanol (18.50 g, 140 mmol) was added to a stirred solution of KOtBu (30.5 g, 272 mmol) in NMP (600 mL) at 0° C. then stirred at RT for 1 h and cooled to 0° C., 6-chloropyridin-3-amine (10.0 g, 78 mmol) was added and heated to 110° C. for 88 h. The reaction mixture cooled to RT and partitioned between water (50 mL×2) and EtOAc (100 mL×2). Organic layers were separated and was dried over anhydrous Na$_2$SO$_4$, filtered and filtrate was evaporated to get crude compound as a gum. (TLC: Eluent: 100% ethyl acetate, R$_f$: 0.5; UV active:). The crude product was purified by flash column chromatography (silica-gel: 100-200 mesh) eluted with 50% EtOAc in hexane to afford (S)-6-((2,2-dimethyl-1,3-dioxolan-4-yl)methoxy)pyridin-3-amine (10.0 g, 41.7 mmol, 53.6% yield) as a dark sticky mass, LCMS (m/z) 225.0 (M+H)$^+$.

Synthesis of (R)-5-((2,2-dimethyl-1,3-dioxolan-4-yl)methoxy)pyridin-2-amine (R)-(2,2-dimethyl-1,3-dioxolan-4-yl)methanol (30.7 g, 232 mmol) was added to a stirred solution of KOtBu (70.1 g, 624 mmol) in NMP (800 mL) at 0° C. then stirred at RT for 1 h and cooled to 0° C. then 5-fluoropyridin-2-amine (20 g, 178 mmol) was added and heated to 110° C. for 114 h. The reaction mixture cooled to RT and partitioned between water (500 mL×2) and EtOAc (500 mL×4). Organic layers were separated and was dried over anhydrous Na$_2$SO$_4$, filtered and filtrate was evaporated to get crude compound, then it was purified by column chromatography (using 100-200 silica gel, column eluted at 80% ethyl acetate in hexane) to afford the (R)-5-((2,2-dimethyl-1,3-dioxolan-4-yl)methoxy)pyridin-2-amine (10 g, 40.1 mmol, 22.50% yield) as a brown oil, LCMS: 225.0 (M+H).

Synthesis of (S)-5-((2,2-dimethyl-1,3-dioxolan-4-yl)methoxy)pyridin-2-amine

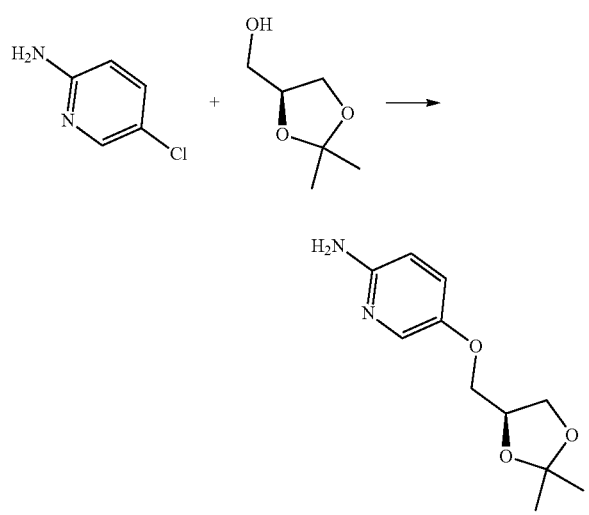

NaH (12.84 g, 268 mmol) was added to a stirred solution of (S)-(2,2-dimethyl-1,3-dioxolan-4-yl)methanol (31.8 g, 241 mmol) in Dimethyl Sulfoxide (DMSO) (100 mL) at 0° C. then stirred at RT for 1 h and cooled to 0° C., 5-fluoropyridin-2-amine (15.0 g, 134 mmol) was added and heated to 110° C. for 60 h. The reaction mixture cooled to RT and partitioned between water (50 mL) and EtOAc (100 mL). Organic layers were separated and was dried over anhydrous Na$_2$SO$_4$, filtered and filtrate was evaporated to get crude compound (TLC: Eluent: 100% ethyl acetate, R$_f$ 0.5; UV active), The crude product was purified by flash column chromatography (silica-gel: 100-200 mesh) eluted with 50% EtOAc in hexane to afford (S)-5-((2,2-dimethyl-1,3-dioxolan-4-yl)methoxy)pyridin-2-amine (7.2 g, 32.1 mmol, 23.99% yield) as a pale yellow sticky, LCMS (m/z): 225.1 (M+H)$^+$.

Synthesis of (R)-2-((2,2-dimethyl-1,3-dioxolan-4-yl)methoxy)pyrimidin-5-amine

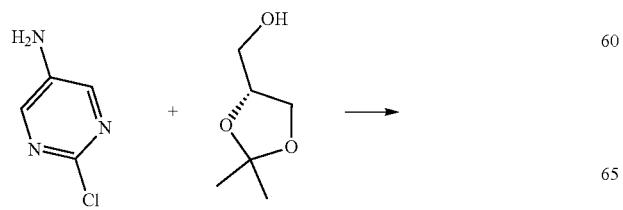

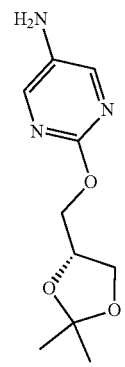

Tetrahydrofuran (75 mL) was added to NaH (5.56 g, 232 mmol) at 0° C., (R)-(2,2-dimethyl-1,3-dioxolan-4-yl)methanol (12.46 mL, 100 mmol) in Tetrahydrofuran (50 mL was added to the reaction mixture at 0° C., and the reaction mixture was stirred for 1 h at 28° C. 2-chloropyrimidin-5-amine (10 g, 77 mmol) in Tetrahydrofuran (25 mL) was added and stirred for 16 hr at 70° C. The reaction mixture was quenched with cold water (30 mL) and extracted with ethyl acetate (3×80 mL). The organic layer was washed with water (2×50 mL) and saturated brine solution (50 mL), dried over anhydrous Na$_2$SO$_4$, filtered and concentrated. The crude compound was purified by column chromatography (Neutral alumina) product was eluted with 40-45% Ethyl acetate in Hexane to afford (R)-2-((2,2-dimethyl-1,3-dioxolan-4-yl)methoxy)pyrimidin-5-amine (6.5 g, 28.3 mmol, 36.6% yield) as pale yellow solid, LCMS (m/z): 226.0 [M+H]$^+$.

Synthesis of (S)-2-((2,2-dimethyl-1,3-dioxolan-4-yl)methoxy)pyrimidin-5-amine

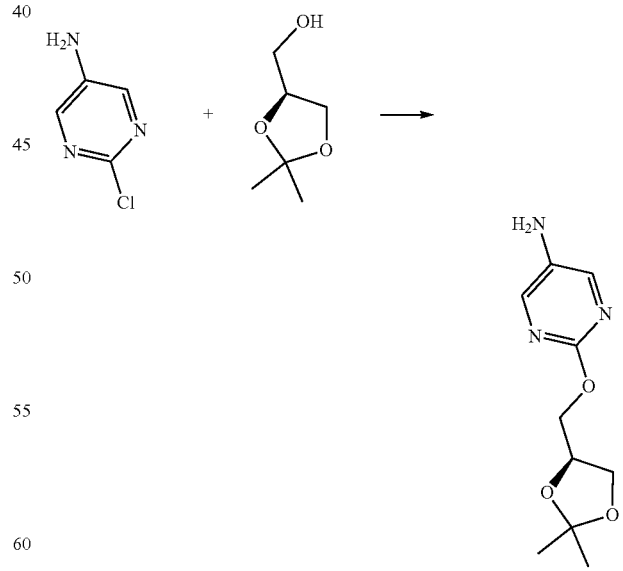

To a suspension of NaH (6.17 g, 154 mmol) in THF (100 ml) was added (S)-(2,2-dimethyl-1,3-dioxolan-4-yl)methanol (13.26 g, 100 mmol) in THF (50 ml) was added to the reaction mixture at 0° C., and the reaction mixture was stirred for 1 h at 25° C. to this 2-chloropyrimidin-5-amine (10 g, 77 mmol) in THF (50 ml) and was added at 0° C. and slowly heated to 80° C. and stirred for 16 hr at 80° C. After completion of the reaction, reaction mixture was quenched with the ammonium chloride (10 ml) and extracted with the ethyl acetate (3×20 ml). The organic layer was separated and washed with the brine and dried over Na$_2$SO$_4$, filtered it and concentrated under reduced pressure to get the crude. This crude was triturated with the diethyl ether to get (S)-2-((2, 2-dimethyl-1,3-dioxolan-4-yl)methoxy)pyrimidin-5-amine (5.0 g, 19.77 mmol, 25.6% yield) as a brown solid, LCMS (m/z): 226.1 [M+H]$^+$.

Synthesis of phenyl benzo[d]oxazol-2-ylcarbamate

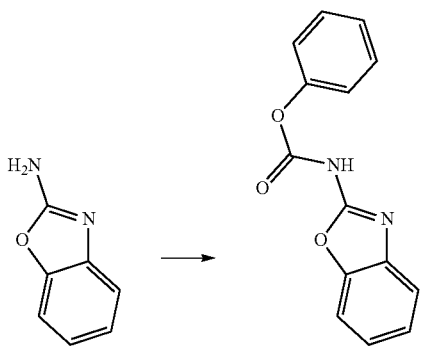 [SMILES: Nc1nc2ccccc2o1 ; O=C(Nc1nc2ccccc2o1)Oc1ccccc1]

To a solution of pyridine (0.965 mL, 11.93 mmol), phenyl carbonochloridate (1.517 g, 9.69 mmol) in Dichloromethane (DCM) (15 mL) stirred under nitrogen at room temp was added benzo[d]oxazol-2-amine (1 g, 7.46 mmol). The reaction mixture was stirred at 30° C. for 3 hr. Reaction was monitored by TLC. The reaction mixture was diluted with water (20 mL), dichloromethane (2×50 mL) and separated the organic layer. The organic layer was washed with saturated brine solution (25 mL), dried over anhydrous Na$_2$SO$_4$, filtered and concentrated. The crude was triturated with 50% ether in hexane and submitted for analysis, LCMS (m/z): 255.19 [M+H]$^+$.

Synthesis of phenyl (4-bromopyridin-2-yl)carbamate

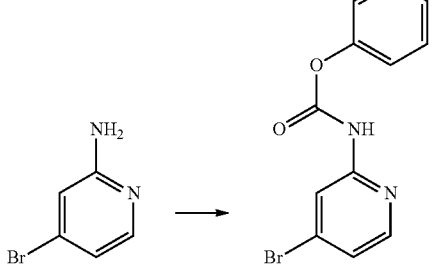

To a mixture of phenyl carbonochloridate (4.98 g, 31.8 mmol) and Py (3.04 mL, 37.6 mmol) in DCM (40 mL) was added dropwise a solution of 4-bromopyridin-2-amine (5 g, 28.9 mmol) in DCM (30 mL) at rt. The resulting solution was stirred at rt for 2 hr. After the completion of reaction (monitored by TLC, Starting material completely consumed and new spot observed at just above of SM), added sat. sodium bicarbonate solution (60 mL) to the reaction mass and the aqueous layer was extracted with DCM (2×70 ML). Combined organic layer was dried over Na$_2$SO$_4$ filtered and concentrated under reduced pressure to get off-white solid. Obtained solid was stirred in petether (50 mL), filtered and dried to get phenyl (4-bromopyridin-2-yl)carbamate (4 g, 6.66 mmol, 23.03% yield) as a white solid, LCMS (m/z): 293.2 (M+H)$^+$.

Synthesis of tert-butyl (2-amino-3,3,3-trifluoropropyl)carbamate

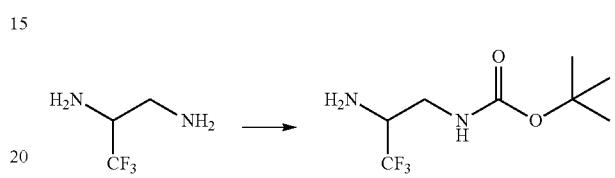

To a solution of 3,3,3-trifluoropropane-1,2-diamine dihydrochloride (1 g, 4.97 mmol), DIPEA (2.61 mL, 14.92 mmol) in Dichloromethane (DCM) (60 mL) stirred under nitrogen at room temperature was added a solution of Boc$_2$O (0.924 mL, 3.98 mmol) in Dichloromethane (DCM) (10 mL) dropwise at room temperature. The reaction mixture was stirred at room temperature for 3 hr. Progress of the reaction was monitored by TLC. TLC indicated formation of a non-polar spot and complete consumption of SM. Reaction mixture was diluted with cold water (50 ml) and extracted with DCM (2×30 ml). The combined organic layer was washed with brine (10 mL), dried over anhydrous Na$_2$SO$_4$, filtered and concentrated under reduced pressure to obtain tert-butyl (2-amino-3,3,3-trifluoropropyl)carbamate (800 mg, 3.51 mmol, 70.5% yield) as colorless oil.

Synthesis of (S)-2-chloro-5-((2, 2-dimethyl-1, 3-dioxolan-4-yl) methyl) pyrazine

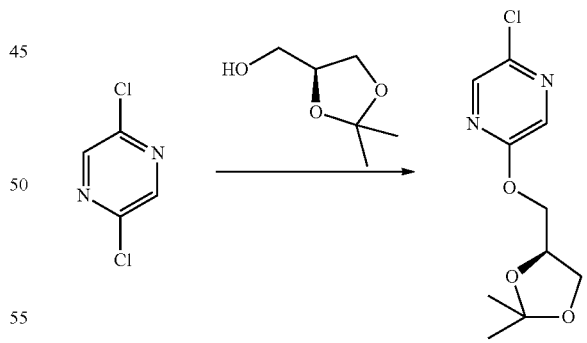

To a stirred solution of cesium carbonate (492 g, 1510 mmol) in DMF (1000 mL) was added (S)-(2, 2-dimethyl-1, 3-dioxolan-4-yl) methanol (133 g, 1007 mmol) at 0° C. The resulting reaction mixture was stirred at room temperature for 30 min. Then a solution of 2, 5-dichloropyrazine (150 g, 1007 mmol) in DMF (500 mL) was added at 0° C. and the resulted reaction mixture was stirred at 100° C. for 4 h. (TLC System: 20% Ethyl acetate in Petether, R$_f$: 0.5, UV active). The reaction mixture was diluted with ice cold water (500 mL), extracted with EtOAc (3×300 mL). The combined organic layer was washed with water (2×200 mL) and brine solution (100 mL), dried over anhydrous Na₂SO₄, filtered and concentrated under reduced pressure to obtain crude compound. The crude compound was purified by flash column chromatography (silica gel: 100-200 mesh, eluent: 10% EtOAc in Hexane) to afford the desired product (S)-2-chloro-5-((2, 2-dimethyl-1, 3-dioxolan-4-yl) methoxy)pyrazine (200 g, 768 mmol, 76% yield) as a yellow liquid. LCMS (m/z): 245.1 [M+H]⁺.

Synthesis of (S)-5-((2,2-dimethyl-1,3-dioxolan-4-yl) methoxy)pyrazin-2-amine

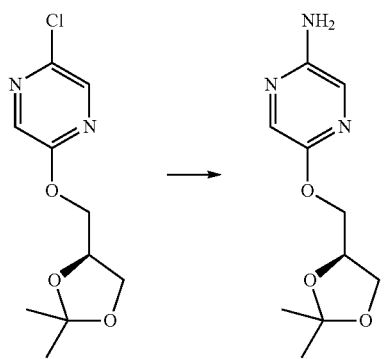 [SMILES: CC1(C)OC[C@H](COc2cnc(Cl)cn2)O1 ; CC1(C)OC[C@H](COc2cnc(N)cn2)O1]

To a stirred solution of (S)-2-chloro-5-((2,2-dimethyl-1, 3-dioxolan-4-yl)methoxy)pyrazine (120 g, 490 mmol) in THF (30 mL) were added ammonium hydroxide (1000 mL, 6420 mmol) and copper(II) sulfate (15.66 g, 98 mmol) in a sealed tube and the result reaction mixture was stirred at 120° C. for 48 h (TLC System: 50% Ethyl acetate in Petether, R_f: 0.4, UV active). The reaction mixture was diluted with water (300 mL), extracted with EtOAc (3×500 mL). The combined organic layer was washed with water (200 mL) and brine solution (200 mL), dried over anhydrous Na₂SO₄, filtered and concentrated under reduced pressure to get crude compound. The crude was purified by flash column chromatography (using 100-200 mesh silicagel and eluted the compound with 40% EtOAc in Hexane) to afford the desired product (S)-5-((2,2-dimethyl-1,3-dioxolan-4-yl)methoxy)pyrazin-2-amine (65 g, 280 mmol, 57.2% yield) as a yellow crystal solid. LCMS (m/z): 226.13 [M+H]⁺.

Synthesis of (R)-2-chloro-5-((2, 2-dimethyl-1, 3-dioxolan-4-yl) methoxy)pyrazine

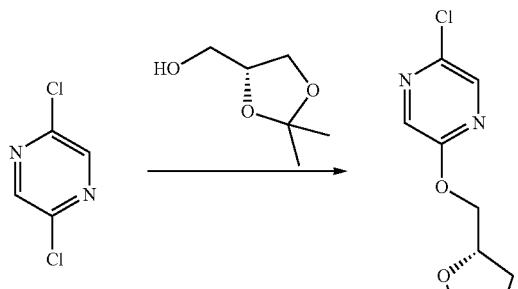

To a stirred suspension of cesium carbonate (32.8 g, 101 mmol) in DMF (100 mL) was added (R)-(2,2-dimethyl-1, 3-dioxolan-4-yl) methanol (8.87 g, 67.1 mmol) at 0° C. and stirred at room temperature for 30 min. Then 2,5-dichloropyrazine (10 g, 67.1 mmol) was added and the resulting reaction mixture was stirred at 100° C. for 4 h. (TLC System: 20% Ethyl acetate in Hexane, R_f: 0.5, UV active). The reaction mixture was diluted with ice cold water (200 mL), extracted with EtOAc (3×100 mL). The combined organic layer was washed with water (2×50 mL) and brine solution (50 mL), dried over anhydrous Na₂SO₄, filtered and concentrated under reduced pressure to afford (R)-2-chloro-5-((2,2-dimethyl-1,3-dioxolan-4-yl)methoxy)pyrazine (12 g, 43.8 mmol, 65.3% yield) as a yellow oily compound. LCMS (m/z): 244.99 [M+H]⁺.

Synthesis of (R)-5-((2, 2-dimethyl-1, 3-dioxolan-4-yl) methoxy) pyrazin-2-amine

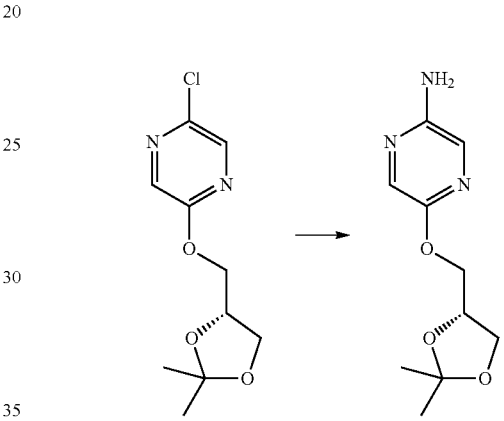

To a stirred solution of (R)-2-chloro-5-((2,2-dimethyl-1, 3-dioxolan-4-yl)methoxy)pyrazine (8 g, 32.7 mmol) in Tetrahydrofuran (10 mL) was added ammonium hydroxide (400 mL, 2568 mmol) and copper(II) sulfate (1.044 g, 6.54 mmol) in a sealed tube and the reaction mixture was stirred at 120° C. for 48 h. (TLC System: 50% Ethyl acetate in Hexane, R_f: 0.4, UV active). The reaction mixture was diluted with water (200 mL), extracted with EtOAc (3×50 mL). The combined organic layer was washed with water (50 mL), brine solution (50 mL), dried over anhydrous Na₂SO₄, filtered and concentrated under reduced pressure to get crude compound. The crude was purified by flash column chromatography (using 100-200 mesh silicagel and eluted the compound with 40% EtOAc in Hexane), pure fraction were collected and concentrated under reduced pressure to afford (R)-5-((2,2-dimethyl-1,3-dioxolan-4-yl) methoxy)pyrazin-2-amine (2 g, 8.65 mmol, 26.4% yield) as a yellow crystal solid. LCMS (m/z): 226.10 [M+H]⁺.

Synthesis of(S)-2-chloro-5-((2,2-dimethyl-1,3-dioxolan-4-yl)methoxy)pyrimidine

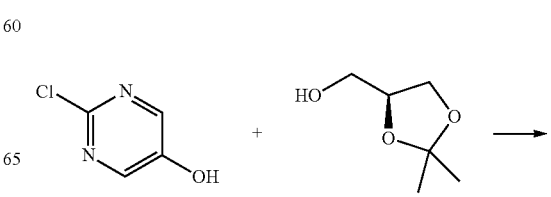

-continued

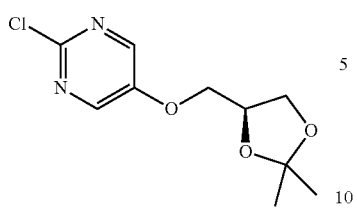

To a stirred solution of 2-chloropyrimidin-5-ol (13 g, 100 mmol) in THF (100 mL) at 0° C. was added (S)-(2,2-dimethyl-1,3-dioxolan-4-yl)methanol (13.16 g, 100 mmol), triphenylphosphine (32.7 g, 124 mmol) followed by DEAD (19.71 mL, 124 mmol) and reaction was stirred at RT for 4 h. (TLC eluting system: 30% EtOAc in pet ether; $R_f$—0.5; UV active). The reaction mixture was quenched with water (50 mL) and extracted into EtOAc (2×75 mL). Organic layer was separated and dried over anhydrous $Na_2SO_4$, filtered and filtrate was evaporated to give crude product. The crude was purified by chromatography (Silicagel, eluent: 20% EtOAc in hexane) to afford (S)-2-chloro-5-((2,2-dimethyl-1,3-dioxolan-4-yl)methoxy)pyrimidine (20 g, 79 mmol, 79% yield) as an off white solid. LCMS (m/z): 245.10; [M+H]$^+$.

Synthesis of (S)-5-((2,2-dimethyl-1,3-dioxolan-4-yl)methoxy)pyrimidin-2-amine

A mixture of (S)-2-chloro-5-((2,2-dimethyl-1,3-dioxolan-4-yl)methoxy)pyrimidine (10 g, 40.9 mmol) and aq. ammonia (66.3 ml, 1226 mmol) in a sealed tube was heated at 120° C. for 24 h. (TLC eluting system: 100% EtOAc; $R_f$—0.2; UV active). The reaction mixture was cooled to RT, quenched with water (50 mL) and extracted into EtOAc (2×75 mL). Organic layer was separated, dried over anhydrous sodium sulphate, filtered and filtrate was evaporated to give crude product as yellow solid. The crude compound was triturated with n-pentane (50 mL) to afford (S)-5-((2,2-dimethyl-1,3-dioxolan-4-yl)methoxy)pyrimidin-2-amine (6.6 g, 28.6 mmol, 70.0% yield) as an off white solid. LCMS (m/z): 226.17; [M+H]$^+$.

Synthesis of (R)-2-chloro-5-((2,2-dimethyl-1,3-dioxolan-4-yl)methoxy)pyrimidine

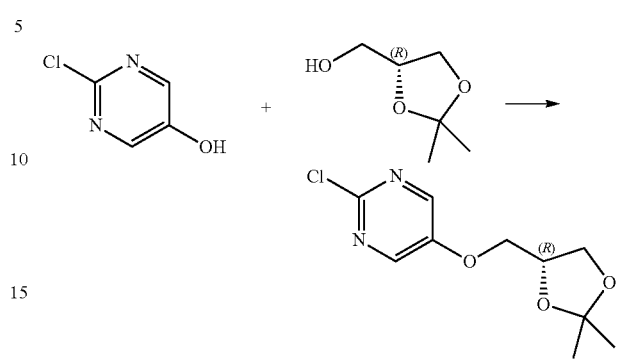

To a stirred solution of 2-chloropyrimidin-5-ol (20 g, 153 mmol) in THF (100 mL) at 0° C. was added (R)-(2,2-dimethyl-1,3-dioxolan-4-yl)methanol (24.30 g, 184 mmol), triphenylphosphine (50.2 g, 192 mmol) followed by DEAD (30.3 mL, 192 mmol) and the reaction was stirred at RT for 12 h. (TLC eluting system: 70% EtOAc in pet ether; $R_f$—0.5; UV active). The reaction mixture was quenched with water (100 mL) and extracted into EtOAc (200 mL). Organic layer was separated and dried over anhydrous $Na_2SO_4$, filtered and filtrate was evaporated to give crude product. The crude was purified by chromatography (Silicagel, eluent: 35% EtOAc in hexane) to afford (R)-2-chloro-5-((2,2-dimethyl-1,3-dioxolan-4-yl)methoxy)pyrimidine (23 g, 91 mmol, 59.5% yield) as a white solid. LCMS (m/z): 245.06; [M+H]$^+$.

Synthesis of (R)-5-((2,2-dimethyl-1,3-dioxolan-4-yl)methoxy)pyrimidin-2-amine

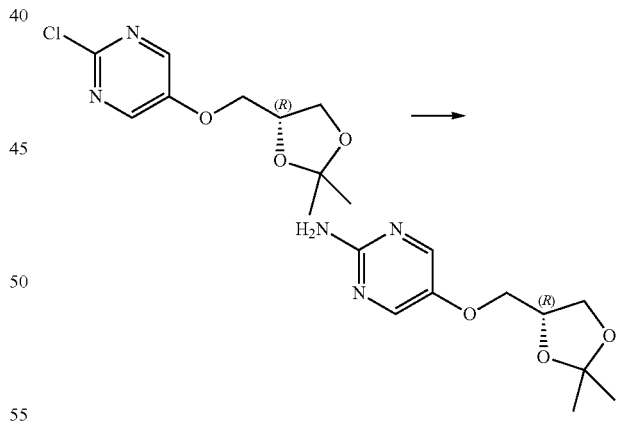

A mixture of (R)-2-chloro-5-((2,2-dimethyl-1,3-dioxolan-4-yl)methoxy)pyrimidine (5 g, 20.44 mmol) and aq. ammonia (50 ml, 924 mmol) in a sealed tube was heated 120° C. for 48 h. (TLC eluting system: 100% EtOAc; $R_f$—0.2; UV active). The reaction mixture was cooled to RT, quenched with water (50 mL) and extracted into DCM (2×75 mL). Organic layer was separated, dried over anhydrous $Na_2SO_4$, filtered and filtrate was evaporated to afford (R)-5-((2,2-dimethyl-1,3-dioxolan-4-yl)methoxy)pyrimidin-2-amine (2.7 g, 11.5 mmol, 57.5% yield) as a pale yellow solid. LCMS (m/z): 226.02; [M+H]$^+$.

Synthesis of (S)-6-((2,2-dimethyl-1,3-dioxolan-4-yl)methoxy)pyridazin-4-amine

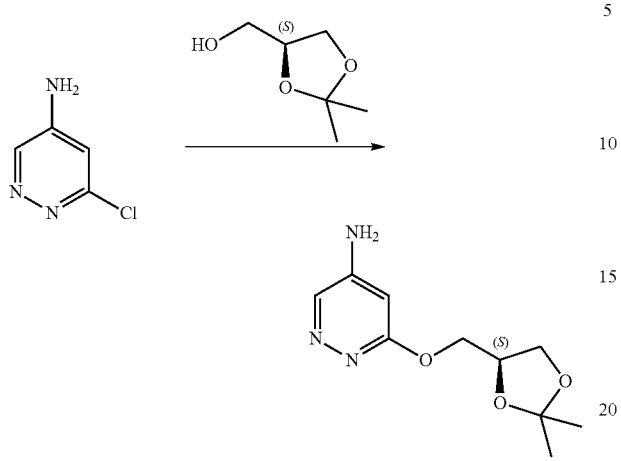

To a stirred suspension of potassium tert-butoxide (3.90 g, 34.7 mmol) in 1,4-Dioxane (50 mL) was added a mixture of (S)-(2,2-dimethyl-1,3-dioxolan-4-yl)methanol (2.75 g, 20.84 mmol) at 0° C. and the reaction mixture was stirred at 25° C. for 1 h. under Nitrogen atmosphere, then 6-chloropyridazin-4-amine (1.5 g, 11.58 mmol) was added to the reaction mixture and the resulted reaction mixture was stirred at 110° C. for 16 h. (TLC System: Neat Ethyl acetate, Rf: 0.3). The reaction mixture was poured in to ice cold water (40 ml) and extracted with EtOAc (2×80 mL). The combined organic layer was washed with brine solution (50 mL), dried over anhydrous Na$_2$SO$_4$, filtered and concentrated under reduced pressure to get crude compound. The crude material was purified by flash column chromatography (Neutral alumina, Eluent: 65% Ethyl acetate in Pet ether) to afford the desired product (S)-6-((2,2-dimethyl-1,3-dioxolan-4-yl)methoxy)pyridazin-4-amine (1.0 g, 4.28 mmol, 37.0% yield) as a white solid. LCMS (m/z): 226.20 [M+H]$^+$.

Synthesis of (R)-6-((2,2-dimethyl-1,3-dioxolan-4-yl)methoxy)pyridazin-4-amine

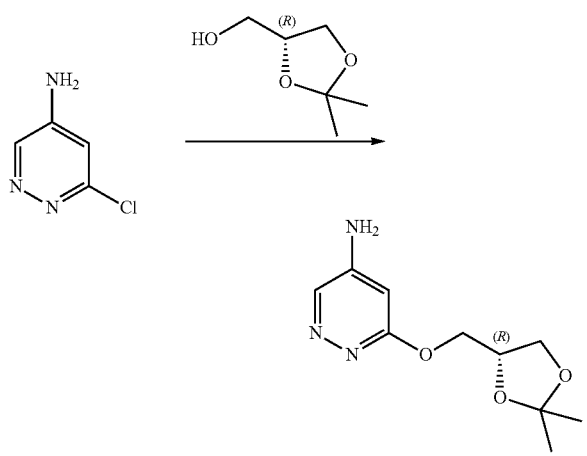

To a stirred suspension of potassium tert-butoxide (7.80 g, 69.5 mmol) in 1,4-Dioxane (50 mL) was added (R)-(2,2-dimethyl-1,3-dioxolan-4-yl)methanol (5.20 mL, 41.7 mmol) at 0° C. and the reaction mixture was stirred at 25° C. for 1 h. under Nitrogen atmosphere. Then 6-chloropyridazin-4-amine (3 g, 23.16 mmol) was added to the reaction mixture and the resulting reaction mixture was stirred at 110° C. for 16 h. (TLC System Ethyl acetate, Rf: 0.3). The reaction mixture was poured into ice cold water (40 ml) and extracted with EtOAc (2×80 mL). The combined organic layer was washed with brine solution (50 mL), dried over anhydrous Na$_2$SO$_4$, filtered and concentrated under reduced pressure to get crude compound. The crude product was purified by flash column chromatography (Neutral alumina, Eluent: 65% Ethyl acetate in Pet ether) to afford the desired product (R)-6-((2,2-dimethyl-1,3-dioxolan-4-yl)methoxy)pyridazin-4-amine (2.2 g, 9.66 mmol, 41.7% yield) as an off white solid. LCMS (m/z): 226.05 [M+H]$^+$, Rt=1.00 min.

COMPOUND EXAMPLES

Example 1

Synthesis of (4S)-7-(3, 3-difluoropyrrolidine-1-carbonyl)-N-(pyridin-2-yl)-3, 4-dihydro-1,4-methanopyrido[2, 3-b] [1, 4] diazepine-5(2H)-carboxamide

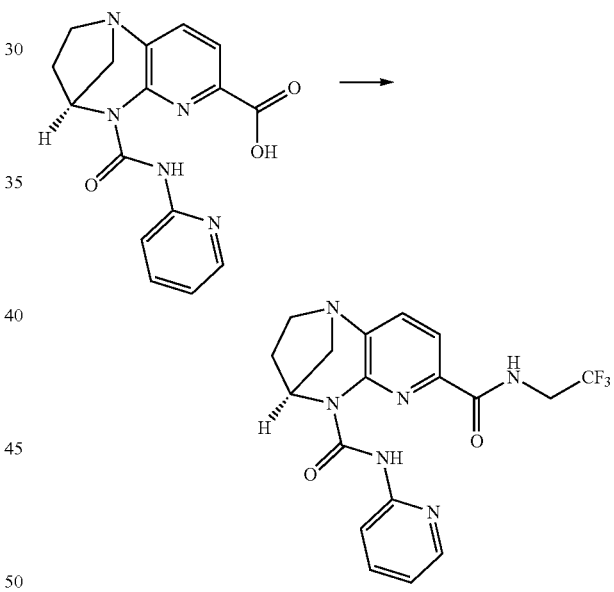

To a stirred solution of (4S)-5-(pyridin-2-ylcarbamoyl)-2,3,4,5-tetrahydro-1,4-methanopyrido[2,3-b][1,4]diazepine-7-carboxylic acid (200 mg, 0.615 mmol) in N,N-dimethylformamide (DMF) (5 mL) were added HATU (351 mg, 0.922 mmol) and DIPEA (0.215 mL, 1.230 mmol). Then 2,2,2-trifluoroethanamine (122 mg, 1.230 mmol) was added and the reaction mixture was stirred at RT for 16 h. Reaction mixture was diluted with 30 ml of water and extracted with EtOAc (2×15 ml). The combined organic layer was dried over anhydrous sodium sulfate and concentrated under reduced pressure to afford crude compound (150 mg). The crude product was purified by flash column chromatography (silica-gel: 100-200 mesh) to afford (4S)-7-(3, 3-difluoropyrrolidine-1-carbonyl)-N-(pyridin-2-yl)-3, 4-dihydro-1,4-methanopyrido[2, 3-b] [1, 4] diazepine-5(2H)-carboxamide (90 mg, 0.221 mmol, 36% yield) as a white solid (TLC: R$_f$ value: 0.25, Neat Ethyl acetate), LCMS (m/z): 407.2 [M+H]$^+$.

$^1$H NMR (400 MHz, DMSO-d$_6$): δ ppm 13.38 (s, 1H), 8.68 (t, J=6.69 Hz, 1H), 8.32-8.37 (m, 1H), 8.00 (dt, J=8.33, 0.99 Hz, 1H), 7.85 (td, J=7.84, 1.86 Hz, 1H), 7.72-7.78 (m, 2H), 7.12 (ddd, J=7.34, 4.93, 1.10 Hz, 1H), 5.42 (dd, J=5.92, 3.07 Hz, 1H), 4.35-4.25 (m, 2H), 3.24-3.17 (m, 3H), 3.01-2.95 (m, 1H), 2.23 (dddd, J=13.76, 9.92, 6.03, 3.84 Hz, 1H), 2.00-1.89 (m, 1H).

Example 2

Synthesis of (4S)—N7-cyclopropyl-N5-(pyridin-2-yl)-3, 4-dihydro-1,4-methano pyrido[2, 3-b][1,4] diazepine-5, 7(2H)-dicarboxamide

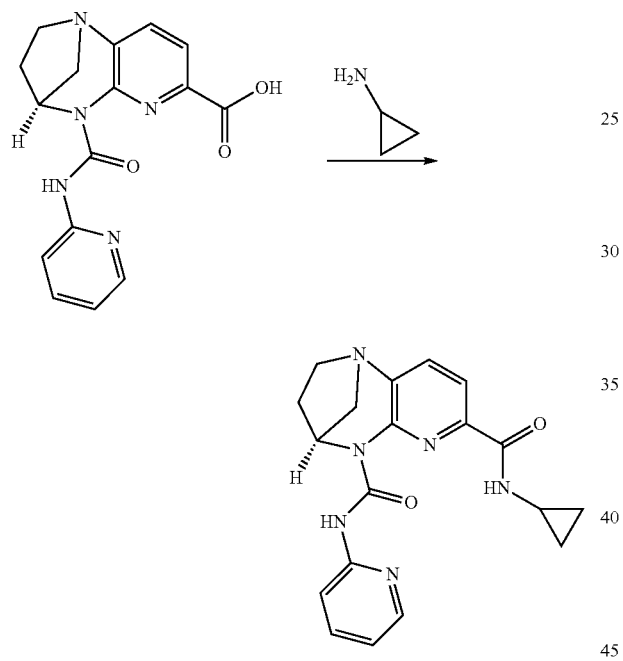

To a solution of (4S)-5-(pyridin-2-ylcarbamoyl)-2,3,4,5-tetrahydro-1,4-methanopyrido[2,3-b][1,4]diazepine-7-carboxylic acid (250 mg, 0.615 mmol) in N,N-Dimethylformamide (DMF) (5 mL) under nitrogen at room temp, HATU (584 mg, 1.537 mmol), DIPEA (0.268 mL, 1.537 mmol) and cyclopropanamine (65.3 mg, 1.153 mmol) was added and stirred at RT for 16 h. Reaction mixture was diluted with ice water and extracted with 2×15 ml of ethyl acetate. The combined organic layer was washed with brine, dried over sodium sulfate and concentrated under reduced pressure to afford crude compound. The crude product was purified by flash column chromatography (100-200 silica gel eluted with 2% of CH$_2$Cl$_2$/MeOH) to afford (4S)—N7-cyclopropyl-N5-(pyridin-2-yl)-3,4-dihydro-1,4-methanopyrido[2,3-b][1,4]diazepine-5,7(2H)-dicarboxamide (140 mg, 0.384 mmol, 50.0% yield) as off white solid. (TLC system: 10% Methanol in DCM. R$_f$ value: 0.35), LCMS: (m/z): 365.28 [M+H]$^+$.

$^1$H NMR (400 MHz, DMSO-d$_6$): δ ppm 13.10 (s, 1H), 8.35-8.27 (m, 1H), 8.11-8.01 (m, 2H), 7.89-7.80 (m, 1H), 7.77-7.60 (m, 2H), 7.14 (ddd, J=7.23, 4.93, 0.99 Hz, 1H), 5.45 (dd, J=5.92, 3.07 Hz, 1H), 3.22-3.01 (m, 3H), 3.01-2.88 (m, 2H), 2.23 (dddd, J=13.67, 9.84, 5.97, 3.84 Hz, 1H), 1.90 (dt, J=13.81, 7.13 Hz, 1H), 0.88-0.79 (m, 2H), 0.78-0.66 (m, 2H).

Example 3

Synthesis of (4S)-7-(3, 3-difluoropyrrolidine-1-carbonyl)-N-(pyridin-2-yl)-3, 4-dihydro-1,4-methanopyrido[2, 3-b] [1, 4] diazepine-5(2H)-carboxamide

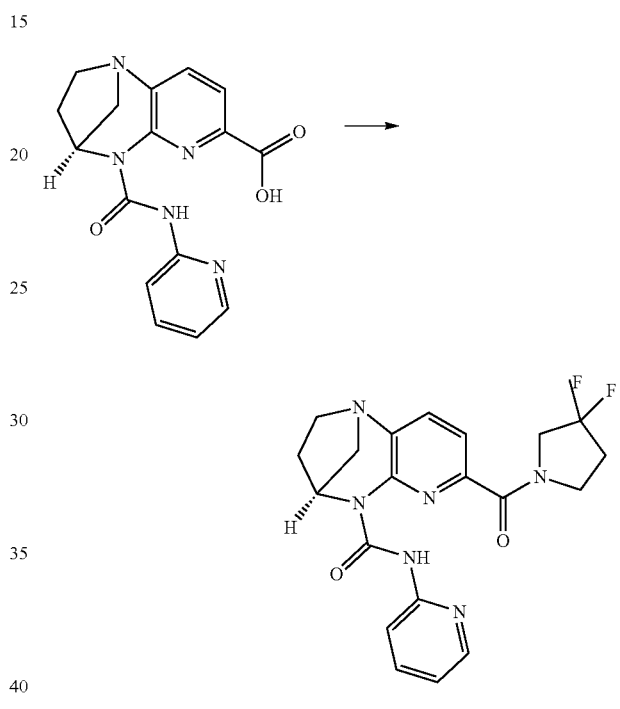

To a stirred solution of (4S)-5-(pyridin-2-ylcarbamoyl)-2,3,4,5-tetrahydro-1,4-methanopyrido[2,3-b][1,4]diazepine-7-carboxylic acid (400 mg, 1.230 mmol) in N,N-Dimethylformamide (DMF) (10 mL) were added HATU (701 mg, 1.844 mmol), DIPEA (0.429 mL, 2.459 mmol) and 3,3-difluoropyrrolidine Hydrochloride (212 mg, 1.475 mmol) at RT. The reaction mixture was stirred at RT for 16 h. Reaction mixture was diluted with 30 ml of water and extracted with EtOAc (2×15 ml). The combined organic layer was dried over anhydrous sodium sulfate and concentrated under reduced pressure to afford the crude compound. The crude mixture was purified by flash column chromatography (silica-gel: 100-200 mesh) to afford (4S)-7-(3,3-difluoropyrrolidine-1-carbonyl)-N-(pyridin-2-yl)-3,4-dihydro-1,4-methanopyrido[2,3-b][1,4]diazepine-5(2H)-carboxamide (110 mg, 0.254 mmol, 20.67% yield) as a white solid (TLC: R$_f$ value: 0.25, Neat Ethyl acetate), LCMS (m/z): 415.15 [M+H]$^+$.

$^1$H NMR (400 MHz, DMSO-d$_6$): δ ppm 12.84 (d, J=10.52 Hz, 1H), 8.38-8.31 (m, 1H), 8.09 (t, J=7.89 Hz, 1H), 7.82-7.74 (m, 1H), 7.70 (dd, J=7.67, 5.48 Hz, 1H), 7.36 (dd, J=7.56, 5.59 Hz, 1H), 7.10 (d, J=6.36 Hz, 1H), 5.49 (dd, J=5.92, 3.29 Hz, 1H), 4.27-3.97 (m, 3H), 3.80 (t, J=7.56 Hz, 1H), 3.19-3.09 (m, 2H), 2.97 (d, J=2.19 Hz, 1H), 2.34-2.14 (m, 3H), 2.01-1.81 (m, 2H).

Example 4

Synthesis of (4S)—N-5-(pyridin-2-yl)-N-7-(tetrahydro-2H-pyran-4-yl)-3, 4-dihydro-1, 4-methanopyrido [2, 3-b] [1, 4] diazepine-5, 7(2H)-dicarboxamide

Example 5

Synthesis of (4S)—N-5-(pyridin-2-yl)-N-7-(tetrahydro-2H-pyran-3-yl)-3, 4-dihydro-1, 4-methanopyrido [2, 3-b] [1, 4] diazepine-5, 7(2H)-dicarboxamide

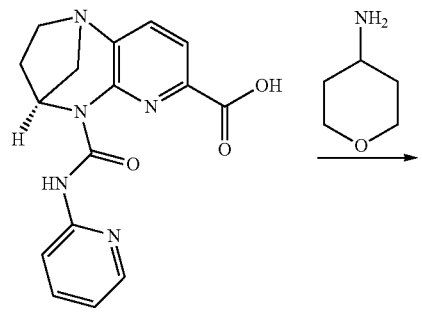

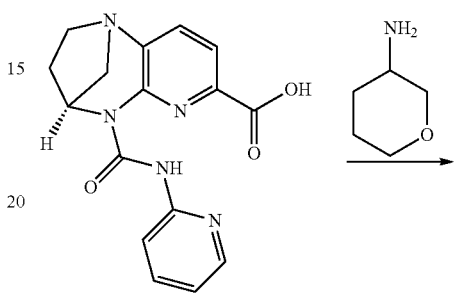

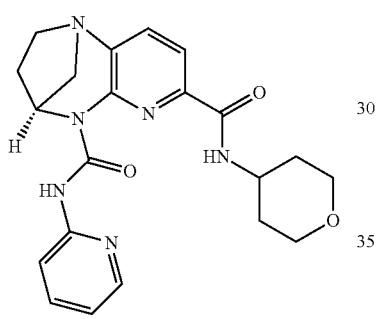

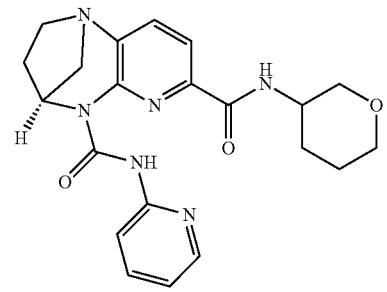

To a solution of (4S)-5-(pyridin-2-ylcarbamoyl)-2,3,4,5-tetrahydro-1,4-methanopyrido[2,3-b][1,4]diazepine-7-carboxylic acid (250 mg, 0.768 mmol) in N,N-Dimethylformamide (DMF) (5 mL) under nitrogen at room temp, HATU (584 mg, 1.537 mmol), DIPEA (0.268 mL, 1.537 mmol) and tetrahydro-2H-pyran-4-amine (117 mg, 1.153 mmol) was added and stirred at RT for 16 h. Reaction mixture was diluted with ice water and extracted with 2×15 ml of ethyl acetate. The combined organic layers were washed with brine, dried over sodium sulfate and concentrated under reduced pressure to afford crude compound. The crude product was purified by flash column chromatography (100-200 silica gel eluted with 2% of $CH_2Cl_2$/MeOH) to afford (4S)—N-5-(pyridin-2-yl)-N-7-(tetrahydro-2H-pyran-4-yl)-3,4-dihydro-1,4-methanopyrido[2,3-b][1,4]diazepine-5,7 (2H)-dicarboxamide (125 mg, 0.298 mmol, 38.8% yield) as an off white solid. (TLC system: 10% Methanol in DCM. $R_f$ value: 0.35), LCMS: (m/z) 409.34 $[M+H]^+$.

$^1$H NMR (400 MHz, DMSO-$d_6$): δ ppm 13.12 (s, 1H), 8.44-8.19 (m, 1H), 8.10 (d, J=8.33 Hz, 1H), 7.95-7.79 (m, 2H), 7.71 (q, J=7.75 Hz, 2H), 7.26-7.04 (m, 1H), 5.47 (dd, J=5.81, 2.96 Hz, 1H), 4.30-4.03 (m, 1H), 3.95 (br d, J=10.30 Hz, 2H), 3.54-3.34 (m, 2H), 3.22-2.83 (m, 4H), 2.33-2.07 (m, 1H), 2.00-1.55 (m, 5H).

To a solution of (4S)-5-(pyridin-2-ylcarbamoyl)-2,3,4,5-tetrahydro-1,4-methanopyrido[2,3-b][1,4]diazepine-7-carboxylic acid (250 mg, 0.768 mmol) in N,N-Dimethylformamide (DMF) (5 mL) under nitrogen at room temp HATU (584 mg, 1.537 mmol), DIPEA (0.268 mL, 1.537 mmol) and tetrahydro-2H-pyran-4-amine (117 mg, 1.153 mmol) was added and stirred at RT for 16 h. Reaction mixture was diluted with ice water and extracted with 2×15 ml of ethyl acetate. The combined organic layers were washed with brine, dried over sodium sulfate and concentrated under reduced pressure to afford crude compound. The crude product was purified by flash column chromatography (100-200 silica gel eluted with 2% of $CH_2Cl2$/MeOH) to afford (4S)—N5-(pyridin-2-yl)-N7-(tetrahydro-2H-pyran-3-yl)-3, 4-dihydro-1,4-methanopyrido[2,3-b][1,4]diazepine-5,7 (2H)-dicarboxamide (240 mg, 0.580 mmol, 75% yield) as off white solid. (TLC system: 10% Methanol in DCM. $R_f$ value: 0.35), LCMS: (m/z): 409.34 $[M+H]^+$.

$^1$H NMR (400 MHz, DMSO-$d_6$): δ ppm 12.98 (br s, 1H), 8.35 (br d, J=4.17 Hz, 1H), 8.11 (d, J=8.33 Hz, 1H), 7.85 (br t, J=7.78 Hz, 1H), 7.80-7.60 (m, 3H), 7.20-7.06 (m, 1H), 5.51-5.41 (m, 1H), 4.01 (ddt, J=13.48, 9.15, 4.80, 4.80 Hz, 1H), 3.93-3.73 (m, 2H), 3.36 (br t, J=10.30 Hz, 1H), 3.29-3.20 (m, 1H), 3.22-3.01 (m, 3H), 3.01-2.89 (m, 1H), 2.33-2.12 (m, 1H), 2.01 (br s, 1H), 1.98-1.83 (m, 1H), 1.81-1.59 (m, 3H).

Example 6

Synthesis of (4S)—N-5-(pyridin-2-yl)-N-7-(tetrahydrofuran-3-yl)-3, 4-dihydro-1, 4-methano pyrido [2, 3-b] [1, 4] diazepine-5, 7(2H)-dicarboxamide

Example 7

Synthesis of (4S)—N-7-cyclobutyl-N-5-(pyridin-2-yl)-3, 4-dihydro-1,4-methanopyrido [2, 3-b] [1, 4] diazepine-5, 7(2H)-dicarboxamide

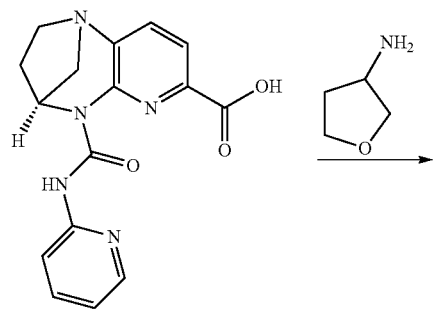

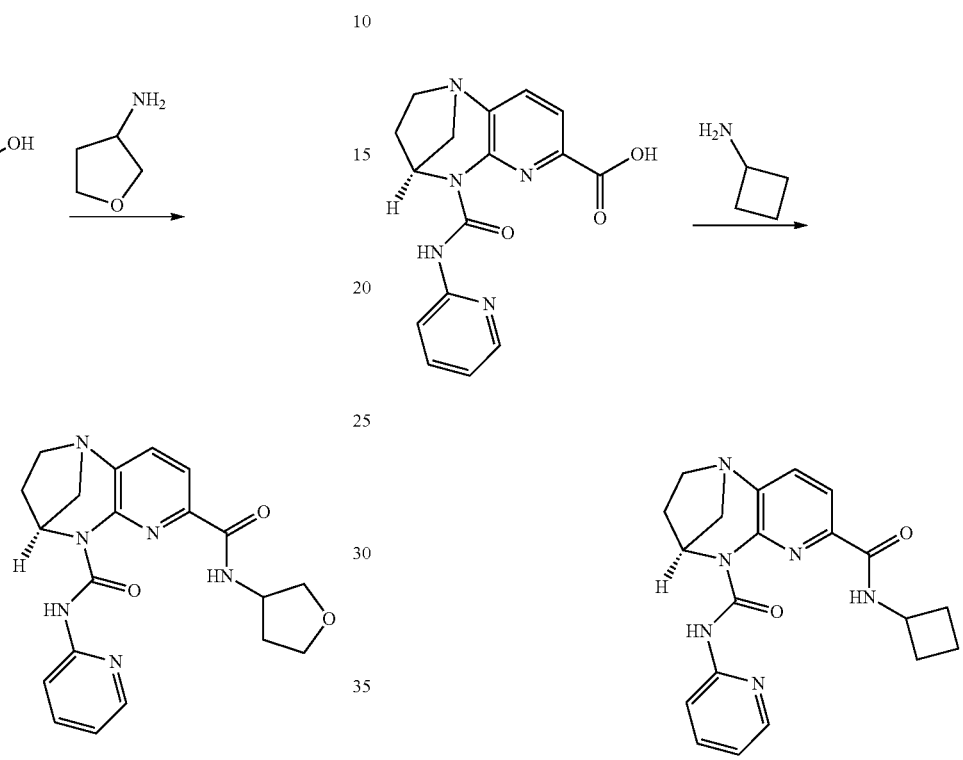

To a solution of (4S)-5-(pyridin-2-ylcarbamoyl)-2,3,4,5-tetrahydro-1,4-methanopyrido[2,3-b][1,4]diazepine-7-carboxylic acid (250 mg, 0.768 mmol) in N,N-Dimethylformamide (DMF) (5 mL) under nitrogen at room temp, HATU (584 mg, 1.537 mmol), DIPEA (0.268 mL, 1.537 mmol) and tetrahydrofuran-3-amine (100 mg, 1.153 mmol) were added and the reaction mixture was stirred at RT for 16 h. The reaction mixture was diluted with ice water and extracted with 2×15 ml of ethyl acetate. The combined organic layer was washed with brine and dried over sodium sulfate and concentrated under reduced pressure to afford crude compound. The crude product was purified by flash column chromatography (100-200 silica gel eluted with 2% of CH$_2$Cl$_2$/MeOH) to afford (4S)—N5-(pyridin-2-yl)-N7-(tetrahydrofuran-3-yl)-3,4-dihydro-1,4-methanopyrido[2,3-b][1,4]diazepine-5,7(2H)-dicarboxamide (140 mg, 0.353 mmol, 45.9% yield) as off white solid. (TLC system: 10% Methanol in DCM. R$_f$ value: 0.35), LCMS (m/z): 395.23 [M+H]$^+$.

$^1$H NMR (400 MHz, DMSO-d$_6$): δ ppm 13.01 (s, 1H), 8.30 (dd, J=4.93, 0.99 Hz, 1H), 7.98-8.17 (m, 2H), 7.93-7.77 (m, 1H), 7.74-7.60 (m, 2H), 7.13 (ddd, J=7.23, 4.93, 0.99 Hz, 1H), 5.48 (dd, J=5.70, 3.07 Hz, 1H), 4.75-4.44 (m, 1H), 4.05-3.55 (m, 4H), 3.23-2.81 (m, 4H), 2.37-2.15 (m, 2H), 2.16-2.05 (m, 1H), 2.16-1.78 (m, 1H).

To a solution of (4S)-5-(pyridin-2-ylcarbamoyl)-2,3,4,5-tetrahydro-1,4-methanopyrido[2,3-b][1,4]diazepine-7-carboxylic acid (250 mg, 0.768 mmol) in N,N-Dimethylformamide (DMF) (5 mL) under nitrogen at room temp, HATU (584 mg, 1.537 mmol), DIPEA (0.268 mL, 1.537 mmol) and cyclobutanamine (82 mg, 1.153 mmol) was added and stirred at RT for 16 h. Reaction was diluted with ice water and extracted with 2×15 ml of ethyl acetate. The combined organic layer was washed with brine, dried over sodium sulfate and concentrated under reduced pressure to afford crude compound. The crude product was purified by flash column chromatography (100-200 silica gel eluted with 2% of CH$_2$Cl$_2$/MeOH) to afford (4S)—N7-cyclobutyl-N5-(pyridin-2-yl)-3,4-dihydro-1,4-methanopyrido[2,3-b][1,4]diazepine-5,7(2H)-dicarboxamide (240 mg, 0.634 mmol, 83% yield) as off white solid. (TLC system: 10% Methanol in DCM. R$_f$ value: 0.35), LCMS (m/z): 379.28 [M+H]$^+$.

$^1$H NMR (400 MHz, DMSO-d$_6$): δ ppm 13.16 (s, 1H), 8.44-8.26 (m, 1H), 8.23-8.02 (m, 2H), 7.99-7.76 (m, 1H), 7.76-7.55 (m, 2H), 7.14-7.08 (m, 1H), 5.47 (dd, J=5.81, 3.18 Hz, 1H), 4.69-4.37 (m, 1H), 3.21-2.85 (m, 4H), 2.41-2.10 (m, 5H), 2.03-1.57 (m, 3H).

Example 8

Synthesis of (4S)—N-5-(pyridin-2-yl)-N-7-(1,1,1-trifluoro-3-hydroxypropan-2-yl)-3,4-dihydro-1,4-methanopyrido[2,3-b][1,4]diazepine-5,7(2H)-dicarboxamide

Example 9

Synthesis of (4S)—N-5-(pyridin-2-yl)-N-7-(1,1,1-trifluoro-3-methoxypropan-2-yl)-3,4-dihydro-1,4-methanopyrido[2,3-b][1,4]diazepine-5,7(2H)-dicarboxamide

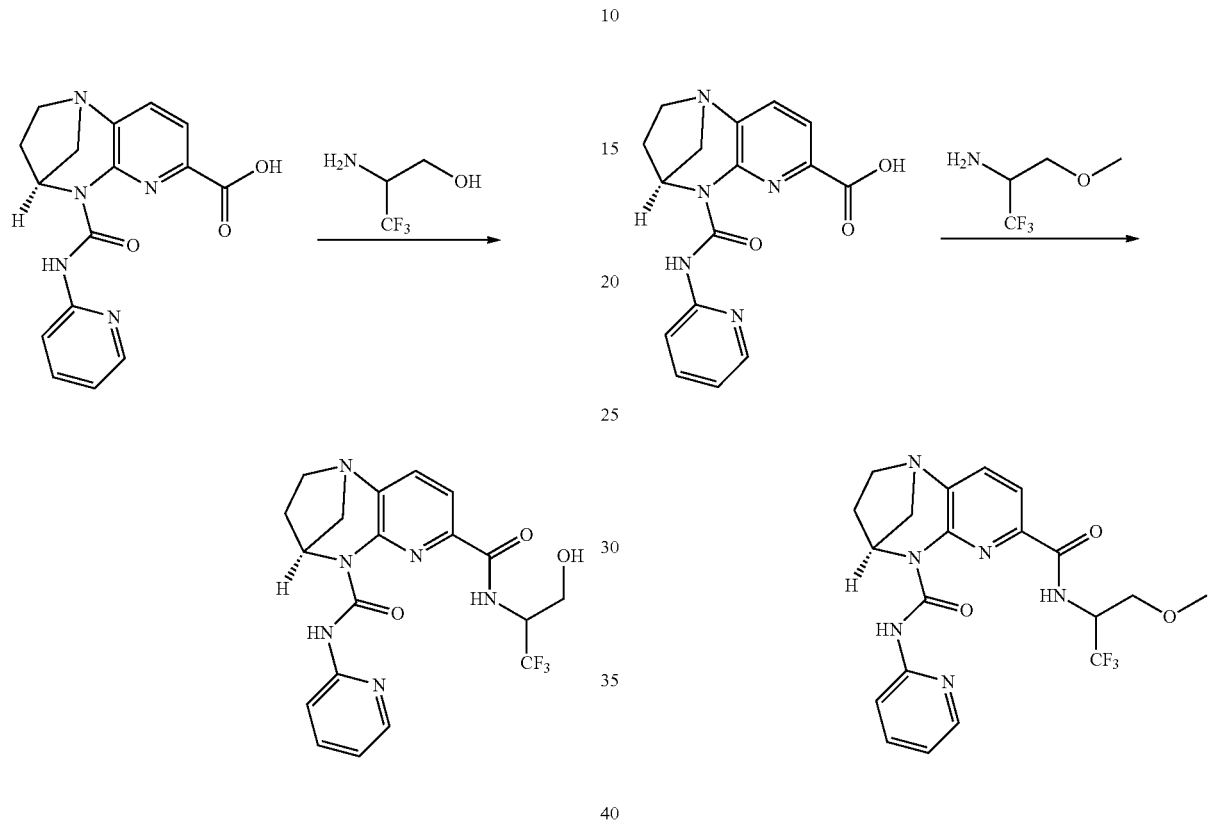

To a solution of (4S)-5-(pyridin-2-ylcarbamoyl)-2,3,4,5-tetrahydro-1,4-methanopyrido[2,3-b][1,4]diazepine-7-carboxylic acid (250 mg, 0.768 mmol) in N,N-Dimethylformamide (DMF) (5 mL) under nitrogen at room temp, HATU (584 mg, 1.537 mmol), DIPEA (0.268 mL, 1.537 mmol) and 2-amino-3,3,3-trifluoropropan-1-ol (149 mg, 1.153 mmol) was added and stirred at RT for 16 h. Reaction mixture was diluted with ice water and extracted with 2×15 ml of ethyl acetate. The combined organic layers were washed with brine, dried over sodium sulfate and concentrated under reduced pressure to afford crude compound. The crude product was purified by flash column chromatography (100-200 silica gel eluted with 3% of $CH_2Cl_2$/MeOH) to afford (4S)—N5-(pyridin-2-yl)-N7-(1,1,1-trifluoro-3-hydroxypropan-2-yl)-3,4-dihydro-1,4 methanopyrido[2,3-b][1,4]diazepine-5,7(2H)-dicarboxamide (300 mg, 0.687 mmol, 89% yield) as off white solid. (TLC system: 10% Methanol in DCM. $R_f$ value: 0.35), LCMS (m/z): 437.27 $[M+H]^+$. $^1H$ NMR (400 MHz, DMSO-$d_6$): δ ppm 12.99 (s, 1H), 8.29-8.14 (m, 2H), 8.18-7.94 (m, 1H), 7.96-7.57 (m, 3H), 7.35-6.92 (m, 1H), 5.48 (dd, J=5.92, 3.07 Hz, 1H), 5.38-5.22 (m, 1H), 4.96-4.80 (m, 1H), 4.02-3.79 (m, 2H), 3.25-3.03 (m, 3H), 3.02-2.88 (m, 1H), 2.33-2.12 (m, 1H), 2.03-1.81 (m, 1H)

To a solution of (4S)-5-(pyridin-2-ylcarbamoyl)-2,3,4,5-tetrahydro-1,4-methanopyrido[2,3-b][1,4]diazepine-7-carboxylic acid (250 mg, 0.768 mmol) in N,N-Dimethylformamide (DMF) (5 mL) under nitrogen at room temp, HATU (584 mg, 1.537 mmol), DIPEA (0.268 mL, 1.537 mmol) and 1,1,1-trifluoro-3-methoxypropan-2-amine (165 mg, 1.153 mmol) was added and stirred at RT for 16 h. Reaction mixture was diluted with ice water and extracted with 2×15 ml of ethyl acetate. The combined organic layer was washed with brine, dried over sodium sulfate and concentrated under reduced pressure to afford crude compound. The crude product was purified by flash column chromatography (100-200 silica gel eluted with 2% of $CH_2Cl2$/MeOH) to afford (4S)—N5-(pyridin-2-yl)-N7-(1,1,1-trifluoro-3-methoxypropan-2-yl)-3,4-dihydro-1,4-methanopyrido[2,3-b][1,4]diazepine-5,7(2H)-dicarboxamide (130 mg, 0.289 mmol, 37.6% yield) as off white solid. (TLC system: 10% Methanol in DCM. $R_f$ value: 0.35), LCMS (m/z): 451.31 $[M+H]^+$.

$^1H$ NMR (400 MHz, DMSO-$d_6$): δ ppm 13.14-12.78 (m, 1H), 8.45-8.16 (m, 2H), 8.08 (d, J=8.33 Hz, 1H), 7.95-7.81 (m, 1H), 7.77 (s, 2H), 7.14 (dd, J=6.91, 5.37 Hz, 1H), 5.64-5.29 (m, 1H), 5.27-4.89 (m, 1H), 3.94-3.78 (m, 2H), 3.29-3.23 (m, 3H), 3.22-2.86 (m, 4H), 2.29-2.12 (m, 1H), 2.03-1.83 (m, 1H).

Example 10

Synthesis of (4S)—N-7-(1-hydroxypropan-2-yl)-N-5-(pyridin-2-yl)-3, 4-dihydro-1, 4-methanopyrido [2, 3-b] [1, 4] diazepine-5, 7(2H)-dicarboxamide

Example 11

Synthesis of (4S)—N-7-(1-methoxypropan-2-yl)-N-5-(pyridin-2-yl)-3,4-dihydro-1, 4-methanopyrido [2, 3-b] [1, 4] diazepine-5, 7(2H)-dicarboxamide

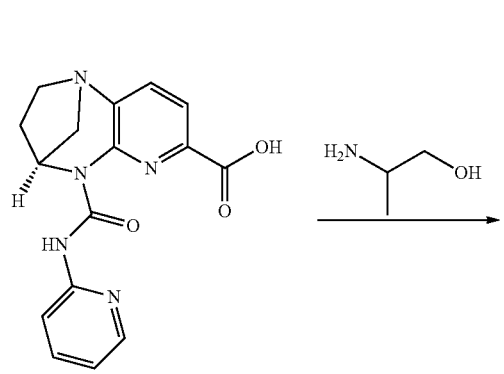

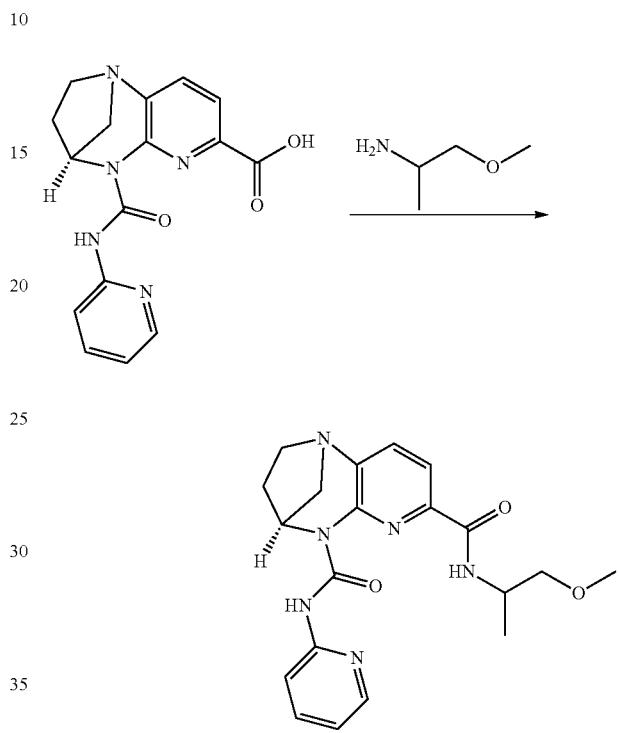

To a solution of (4S)-5-(pyridin-2-ylcarbamoyl)-2,3,4,5-tetrahydro-1,4-methanopyrido[2,3-b][1,4]diazepine-7-carboxylic acid (250 mg, 0.768 mmol) in N,N-Dimethylformamide (DMF) (5 mL) under nitrogen at room temp were added HATU (584 mg, 1.537 mmol), DIPEA (0.268 mL, 1.537 mmol), 2-aminopropan-1-ol (87 mg, 1.153 mmol) and stirred at RT for 16 h. Reaction mixture was diluted with ice water and extracted with 2×15 ml of ethyl acetate. The combined organic layer was washed with brine, dried over sodium sulfate and concentrated under reduced pressure to afford crude compound. The crude product was purified by flash column chromatography (100-200 silica gel eluted with 3% of CH₂Cl2/MeOH) to afford ((4S)—N7-(1-hydroxypropan-2-yl)-N5-(pyridin-2-yl)-3,4-dihydro-1,4-methanopyrido[2,3-b][1,4]diazepine-5,7(2H)-dicarboxamide (135 mg, 0.353 mmol, 45.9% yield) as off white solid. (TLC system: 10% Methanol in DCM. $R_f$ value: 0.35), LCMS (m/z): 383.28 [M+H]⁺.

¹H NMR (400 MHz, DMSO-d₆): δ ppm 13.22-12.90 (m, 1H), 8.30 (dd, J=3.95, 0.88 Hz, 1H), 8.10 (d, J=8.33 Hz, 1H), 7.95-7.57 (m, 4H), 7.22-7.05 (m, 1H), 5.47 (br d, J=2.85 Hz, 1H), 4.79 (br t, J=5.81 Hz, 1H), 4.32-3.92 (m, 1H), 3.69-3.39 (m, 2H), 3.22-2.80 (m, 4H), 2.34-2.12 (m, 1H), 2.04-1.67 (m, 1H), 1.30-1.15 (m, 3H).

To a solution of (4S)-5-(pyridin-2-ylcarbamoyl)-2,3,4,5-tetrahydro-1,4-methanopyrido[2,3-b][1,4]diazepine-7-carboxylic acid (250 mg, 0.768 mmol) in N,N-Dimethylformamide (DMF) (5 mL) under nitrogen at room temp, HATU (584 mg, 1.537 mmol), DIPEA (0.268 mL, 1.537 mmol), 1-methoxypropan-2-amine (103 mg, 1.153 mmol) was added and stirred at RT for 16 h. Reaction mixture was diluted with ice water and extracted with 2×15 ml of ethyl acetate. The combined organic layer was washed with brine, dried over sodium sulfate and concentrated under reduced pressure to afford crude compound. The crude product was purified by flash column chromatography (100-200 silica gel eluted with 2% of CH₂Cl2/MeOH) to afford (4S)—N7-(1-methoxypropan-2-yl)-N5-(pyridin-2-yl)-3,4-dihydro-1,4-methanopyrido[2,3-b][1,4]diazepine-5,7(2H)-dicarboxamide (200 mg, 0.504 mmol, 65.6% yield) as off white solid. (TLC system: 10% Methanol in DCM. $R_f$ value: 0.35), LCMS (m/z): 397 [M+H]⁺.

¹H NMR (400 MHz, DMSO-d₆): δ ppm 13.10 (d, J=5.70 Hz, 1H), 8.31 (br d, J=4.82 Hz, 1H), 8.09 (d, J=8.55 Hz, 1H), 7.94-7.49 (m, 4H), 7.15 (dd, J=6.91, 5.15 Hz, 1H), 5.56-5.27 (m, 1H), 4.55-4.13 (m, 1H), 3.62-3.36 (m, 2H), 3.23 (d, J=4.17 Hz, 3H), 3.20-3.02 (m, 3H), 3.01-2.87 (m, 1H), 2.29-2.13 (m, 1H), 1.99-1.86 (m, 1H), 1.26 (dd, J=6.58, 4.60 Hz, 3H).

Example 12

Synthesis of (4S)—N-7-ethyl-N-5-(pyridin-2-yl)-3,4-dihydro-1,4-methanopyrido [2, 3-b][1,4]diazepine-5, 7(2H)-dicarboxamide

Example 13

Synthesis (4S)—N-7-(2-hydroxyethyl)-N-5-(pyridin-2-yl)-3, 4-dihydro-1, 4-methanopyrido [2, 3-b] [1, 4] diazepine-5, 7(2H)-dicarboxamide

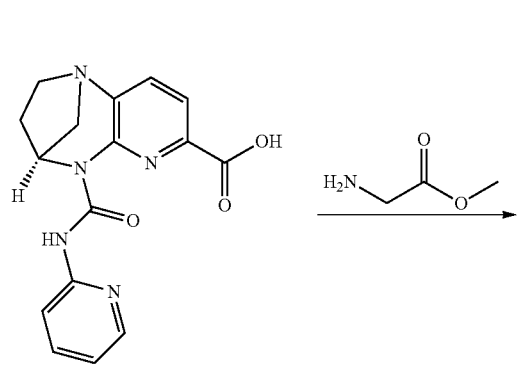

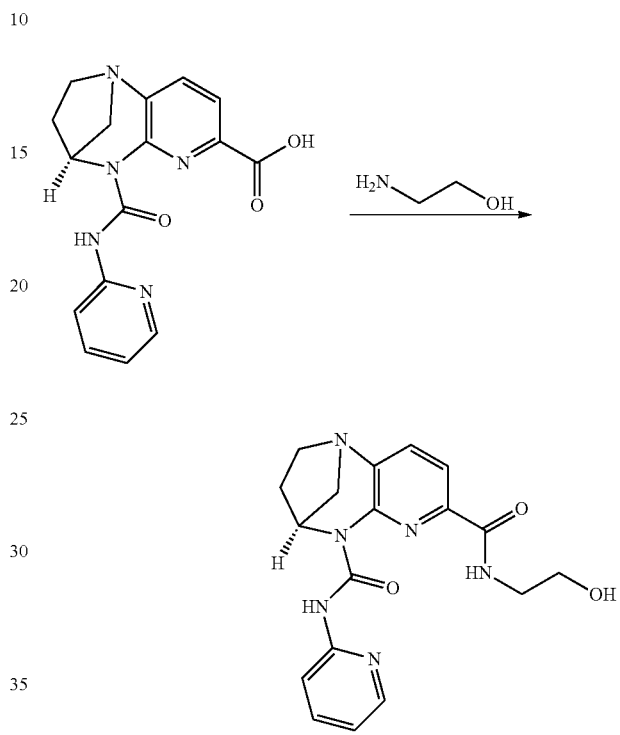

To a solution of (4S)-5-(pyridin-2-ylcarbamoyl)-2,3,4,5-tetrahydro-1,4-methanopyrido[2,3-b][1,4]diazepine-7-carboxylic acid (650 mg, 1.998 mmol) in N,N-Dimethylformamide (DMF) (10 mL) under nitrogen at room temp, HATU (1.51 g, 4.0 mmol), DIPEA (0.7 mL, 4.0 mmol), methyl 2-aminoacetate (267 mg, 3.0 mmol) was added and stirred at RT for 16 h. Reaction mixture was diluted with ice water and extracted with 2×25 ml of ethyl acetate. The combined organic layer was washed with brine, dried over sodium sulfate and concentrated under reduced pressure to afford crude compound. The crude product was purified by flash column chromatography (100-200 silica gel eluted with 2% of CH$_2$C12/MeOH) to afford methyl 2-((4S)-5-(pyridin-2-ylcarbamoyl)-2,3,4,5-tetrahydro-1,4-methanopyrido[2,3-b][1,4]diazepine-7-carboxamido)acetate (400 mg, 1.009 mmol, 50.5% yield) as off white solid. (TLC system: 10% Methanol in DCM. $R_f$ value: 0.35), LCMS (m/z): 397.32 [M+H]$^+$.

$^1$H NMR (400 MHz, DMSO-d$_6$): δ ppm 13.45 (s, 1H), 8.58 (br t, J=5.92 Hz, 1H), 8.25 (d, J=3.95 Hz, 1H), 7.92 (d, J=8.33 Hz, 1H), 7.82-7.52 (m, 3H), 7.03 (dd, J=6.80, 5.26 Hz, 1H), 5.34 (dd, J=5.81, 3.18 Hz, 1H), 4.17 (d, J=6.14 Hz, 2H), 3.59 (s, 3H), 3.19-2.78 (m, 4H), 2.28-2.01 (m, 1H), 1.88 (dt, J=13.87, 6.99 Hz, 1H).

To a solution of (4S)-5-(pyridin-2-ylcarbamoyl)-2,3,4,5-tetrahydro-1,4-methanopyrido[2,3-b][1,4]diazepine-7-carboxylic acid (250 mg, 0.768 mmol) in N,N-Dimethylformamide (DMF) (5 mL) under nitrogen at room temp were added HATU (584 mg, 1.537 mmol), DIPEA (0.268 mL, 1.537 mmol), 2-aminoethanol (70 mg, 1.153 mmol) and stirred at RT for 16 h. Reaction mixture was diluted with ice water and extracted with 2×15 ml of ethyl acetate. The combined organic layers were washed with brine, dried over sodium sulfate and concentrated under reduced pressure to afford crude compound. The crude product was purified by flash column chromatography (100-200 silica gel eluted with 3% of CH$_2$C12/MeOH) to afford (4S)—N7-(2-hydroxyethyl)-N5-(pyridin-2-yl)-3,4-dihydro-1,4-methanopyrido[2,3-b][1,4]diazepine-5,7(2H)-dicarboxamide (195 mg, 0.529 mmol, 68.9% yield) as off white solid. (TLC system: 10% Methanol in DCM. $R_f$ value: 0.3), LCMS (m/z): 369.27 [M+H]$^+$.

$^1$H NMR (400 MHz, DMSO-d$_6$): δ ppm 13.34 (s, 1H), 8.40-8.29 (m, 1H), 8.24 (br t, J=5.81 Hz, 1H), 8.08-7.98 (m, 1H), 7.85 (td, J=7.84, 1.86 Hz, 1H), 7.76-7.59 (m, 2H), 7.13 (ddd, J=7.29, 4.88, 0.99 Hz, 1H), 5.44 (dd, J=5.81, 2.96 Hz, 1H), 4.73 (t, J=5.81 Hz, 1H), 3.66-3.55 (m, 2H), 3.55-3.42 (m, 2H), 3.22-3.01 (m, 3H), 3.03-2.88 (m, 1H), 2.23 (dddd, J=13.70, 9.87, 6.14, 4.06 Hz, 1H), 1.92 (dt, J=13.81, 6.91 Hz, 1H).

Example 14

Synthesis of 2-((4S)-5-(pyridin-2-ylcarbamoyl)-2,3,4,5-tetrahydro-1,4 methano pyrido[2,3-b][1,4]diazepine-7-carboxamido)acetic acid

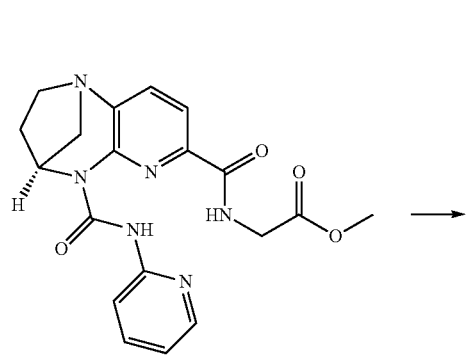

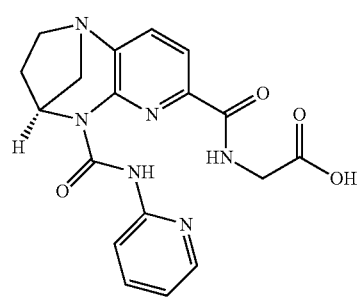

To a stirred solution of Methyl 2-((4S)-5-(pyridin-2-ylcarbamoyl)-2,3,4,5-tetrahydro-1,4-methanopyrido[2,3-b][1,4]diazepine-7-carboxamido)acetate (200 mg, 0.505 mmol) in Tetrahydrofuran (THF) (5 mL) and water (5 mL) was added LiOH.H$_2$O (14.50 mg, 0.605 mmol)) at 0° C. and stirred at RT for 2 h. Tetrahydrofuran was evaporated under reduced pressure to obtain the crude residue and diluted it with water (50 ml) followed by washed it with ethyl acetate (2×40 ml). The aqueous layer was neutralized with NaHCO$_3$ solution and extracted with 5% methanol in DCM (3×15 ml). The combined organic layer was dried over anhydrous sodium sulfate and concentrated under reduced pressure to obtain the crude compound. The crude product was purified by flash column chromatography (silica-gel: 100-200 mesh, eluent: 3% of MeOH in CH$_2$Cl$_2$) to afford 2-((4S)-5-(pyridin-2-ylcarbamoyl)-2,3,4,5-tetrahydro-1,4 methanopyrido[2,3-b][1,4]diazepine-7-carboxamido)acetic acid (135 mg, 0.366 mmol, 72.9%) as a white solid (TLC system: 10% Methanol in DCM. R$_f$: 0.15), LCMS (m/z): 383.31 [M+H]$^+$.

$^1$H NMR (400 MHz, DMSO-d$_6$) δ ppm 13.53 (s, 1H), 12.71 (br s, 1H), 8.55 (t, J=6.03 Hz, 1H), 8.29-8.36 (m, 1H), 7.99 (d, J=8.33 Hz, 1H), 7.89-7.82 (m, 1H), 7.77-7.65 (m, 2H), 7.16-7.06 (m, 1H), 5.42 (dd, J=5.70, 3.07 Hz, 1H), 4.14 (d, J=6.14 Hz, 2H), 3.21-3.08 (m, 3H), 2.98 (dd, J=12.06, 3.07 Hz, 1H), 2.31-2.14 (m, 1H), 2.02-1.89 (m, 1H).

Example 15

Synthesis of (4S)—N-7-neopentyl-N-5-(pyridin-2-yl)-3,4-dihydro-1,4-methanopyrido[2,3-b][1,4]diazepine-5,7(2H)-dicarboxamide

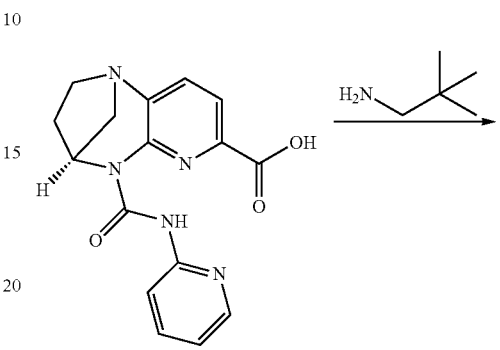

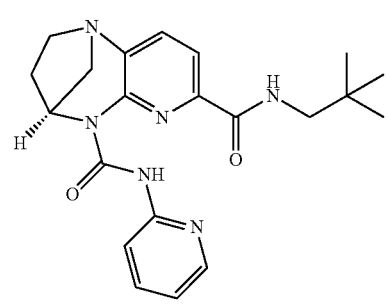

To a stirred solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in N,N-Dimethylformamide (DMF) (5 mL) was added HATU (526 mg, 1.383 mmol) and DIPEA (0.322 ml, 1.844 mmol at RT. To this 2,2-dimethylpropan-1-amine (96 mg, 1.107 mmol) was added and the reaction mixture was stirred at 28° C. for 16 h. (TLC eluent: 5% MeOH in EtOAc, R$_f$: 0.7). The reaction mixture was diluted with water (20 ml) and extracted with EtOAc (2×25 mL). The organic layer was separated and dried over anhydrous Na$_2$SO$_4$, filtered and filtrate was evaporated to obtain the crude compound. The crude compound was purified by flash column chromatography (silica gel: 100-200 mesh, eluent: 70% Ethyl acetate in pet ether) to afford the desired product (4S)—N-7-neopentyl-N-5-(pyridin-2-yl)-3,4-dihydro-1,4-methanopyrido[2,3-b][1,4]diazepine-5,7(2H)-dicarboxamide (170 mg, 0.430 mmol, 46.6% yield) as an off white solid. LCMS (m/z): 395.25 [M+H]$^+$, Rt=2.30 min.

$^1$H NMR (400 MHz, CDCl$_3$): δ ppm 13.38 (s, 1H), 8.28-8.24 (m, 1H), 8.17-8.12 (m, 1H), 8.06 (s, 1H), 7.92 (d, J=7.89 Hz, 1H), 7.75-7.69 (m, 1H), 7.66 (d, J=7.89 Hz, 1H), 7.00 (ddd, J=7.34, 4.93, 1.10 Hz, 1H), 5.65 (dd, J=5.92, 3.29 Hz, 1H), 3.49-3.34 (m, 2H), 3.31-3.19 (m, 2H), 3.16-3.10 (m, 1H), 3.02 (dd, J=12.06, 3.29 Hz, 1H), 2.39-2.26 (m, 1H), 2.13-2.01 (m, 1H), 1.00 (s, 9H).

Example 16

Synthesis of (4S)—N5-(pyridin-2-yl)-N7-((R)-1,1,1-trifluoro-3-hydroxypropan-2-yl)-3,4-dihydro-1,4-methanopyrido[2,3-b][1,4]diazepine-5,7(2H)-dicarboxamide

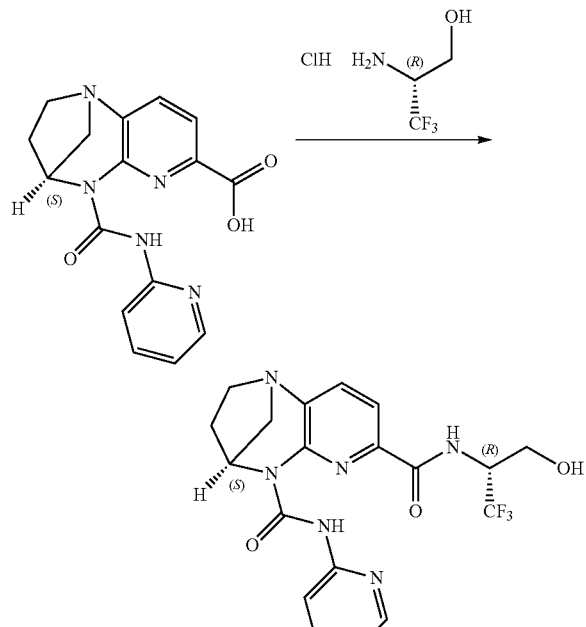

To a stirred solution of (4S)-5-(pyridin-2-ylcarbamoyl)-2,3,4,5-tetrahydro-1,4-methanopyrido[2,3-b][1,4]diazepine-7-carboxylic acid (250 mg, 0.768 mmol) in N,N-Dimethylformamide (DMF) (10 mL) was added HATU (584 mg, 1.537 mmol) and DIPEA (0.268 mL, 1.537 mmol) at room temperature. To this (R)-2-amino-3,3,3-trifluoropropan-1-ol hydrochloride (191 mg, 1.153 mmol) was added and the reaction mixture was stirred at RT for 16 h. (Neat Ethyl acetate. Rf value: 0.25). Reaction mixture was quenched with ice water and extracted with ethyl acetate (2×15 ml). The combined organic layer was washed with brine solution and dried over anhydrous sodium sulfate and concentrated under reduced pressure to obtain crude compound. The crude product was purified by flash column chromatography (100-200 silicagel, Eluent 70% Ethyl acetate in pet ether) and again purified by Prep HPLC (Conditions: MP-A: 5 Mm ammonium bicarbonate (Aq) MP-B: Acetonitrile Column: KROMOSIL C18 (21.2×250) mm 10µ Method: 1/48 10/48 10.1/100 10.2/48 Flow: 20 ml/min Solubility: THF+ACN+MEOH) to afford the desired product (4S)—N5-(pyridin-2-yl)-N7-((R)-1,1, -trifluoro-3-hydroxypropan-2-yl)-3,4-dihydro-1,4-methanopyrido[2,3-b][1,4]diazepine-5,7(2H)-dicarboxamide (80 mg, 0.175 mmol, 22.81% yield) as a white solid. LCMS (m/z): 437.09 [M+H]$^+$, R$_t$=1.79 min.

$^1$H NMR (400 MHz, CDCl$_3$): δ ppm 12.38 (s, 1H), 8.28 (d, J=8.55 Hz, 1H), 8.22 (d, J=4.60 Hz, 1H), 7.87 (d, J=7.89 Hz, 1H), 7.77 (t, J=7.13 Hz, 1H), 7.70 (d, J=7.89 Hz, 1H), 7.63 (d, J=10.08 Hz, 1H), 7.08-7.04 (m, 1H), 5.77 (dd, J=6.25, 3.18 Hz, 1H), 5.16 (t, J=7.13 Hz, 1H), 4.94 (d, J=3.73 Hz, 1H), 4.12-4.03 (m, 2H), 3.31-3.10 (m, 3H), 2.99-3.04 (m, 1H), 2.41-2.27 (m, 1H), 2.04 (dt, J=14.41, 7.15 Hz, 1H).

Example 16A

Synthesis of (4S)—N7-(cyclopropylmethyl)-N5-(pyrazin-2-yl)-3,4-dihydro-1,4-methanopyrido[2,3-b][1,4]diazepine-5,7(2H)-dicarboxamide

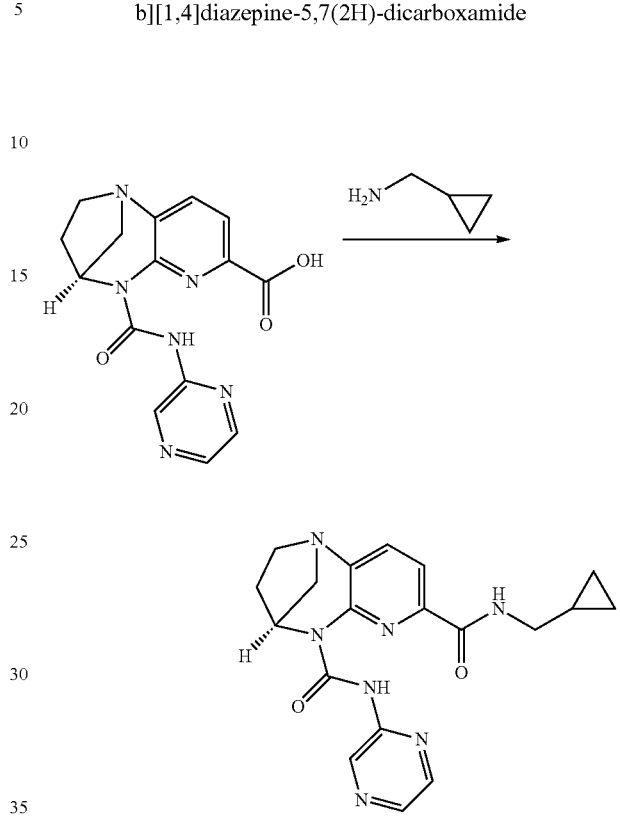

To a stirred solution of (4S)-5-(pyrazin-2-ylcarbamoyl)-2,3,4,5-tetrahydro-1,4-methanopyrido[2,3-b][1,4]diazepine-7-carboxylic acid (500 mg, 1.532 mmol) in DMF (15 mL) 0° C. was added HATU (1165 mg, 3.06 mmol), DIPEA (0.803 mL, 4.60 mmol) and stirred for 30 min. then added cyclopropylmethanamine (218 mg, 3.06 mmol) and the reaction mixture was stirred at RT for 1 h. (TLC system: 10% Methanol in DCM. R$_f$: 0.3). Reaction mixture was cooled RT and quenched with water (50 mL) and the aqueous layer was extracted with EtOAc (2×50 mL). Combined organic layer was dried over anhydrous sodium sulphate, filtered and concentrated under reduced pressure to get crude compound. The crude product was purified by column chromatography (Silica gel column, eluted with 2% of MeOH in CH$_2$Cl$_2$) to afford the desired product (4S)—N7-(cyclopropylmethyl)-N5-(pyrazin-2-yl)-3,4-dihydro-1,4-methanopyrido[2,3-b][1,4]diazepine-5,7(2H)-dicarboxamide (108 mg, 0.284 mmol, 18.56% yield) as a yellow solid. LCMS (m/z): 380.14 [M+H]$^+$, Rt=1.79 min.

$^1$H NMR (400 MHz, CDCl$_3$): δ ppm 13.56 (s, 1H), 9.53 (d, J=1.53 Hz, 1H), 8.34 (d, J=2.19 Hz, 1H), 8.18 (dd, J=2.63, 1.53 Hz, 1H), 7.93 (d, J=7.89 Hz, 1H), 7.83 (br s, 1H), 7.69 (d, J=7.89 Hz, 1H), 5.66 (dd, J=5.92, 3.29 Hz, 1H), 3.36-3.53 (m, 2H), 3.10-3.32 (m, 3H), 2.94-3.09 (m, 1H), 2.21-2.44 (m, 1H), 1.96-2.19 (m, 1H), 1.10-1.34 (m, 1H), 0.43-0.63 (m, 2H), 0.26-0.42 (m, 2H).

Example 17

Synthesis of (4S)—N7-(1-(hydroxymethyl)cyclopropyl)-N5-(pyridin-2-yl)-3,4-dihydro-1,4-methanopyrido[2,3-b][1,4]diazepine-5,7(2H)-dicarboxamide

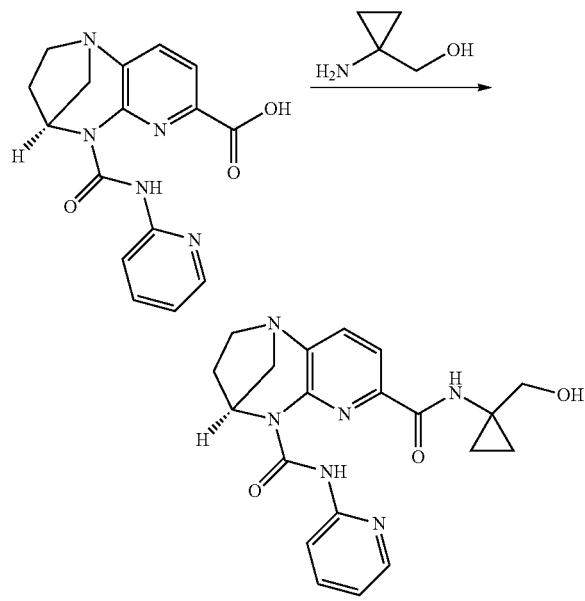

To a solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in DMF (2 mL) under nitrogen at RT was added DIPEA (0.483 mL, 2.77 mmol), HATU (701 mg, 1.844 mmol) and stirred for 10 min, then added (1-aminocyclopropyl)methanol (121 mg, 1.383 mmol) at RT and the resulting reaction mixture was stirred for 16 h. (TLC system 5% Methanol in DCM. Rf value: 0.3.). The reaction was quenched with ice cold water (50 mL) and extracted into ethylacetate (100 mL). The organic layer was separated dried over anhydrous $Na_2SO_4$, filtered and concentrated to get crude compound. The crude was purified by combiflash chromatography (using silica gel column, 2% Methanol in DCM as eluent) to afford the product with 85% purity. This was further purified by preparative HPLC (Column: XTERRA C18 (19×250) mm 10µ; Mobile Phase-A: 5 mM Ammonium Bicarbonate (aq), Mobile Phase-B: Acetonitrile, Method % B/time: 0/20, 1/20, 10/80, 10.5/100; Flow: 18 ml/min; Solubility: ACN+THF) to afford (4S)—N7-(1-(hydroxymethyl)cyclopropyl)-N5-(pyridin-2-yl)-3,4-dihydro-1,4-methanopyrido[2,3-b][1,4]diazepine-5,7(2H)-dicarboxamide (75 mg, 0.189 mmol, 20.53% yield) as an off-white solid. LCMS (m/z): 395.14 [M+H]$^+$, Rt=1.55 min, $^1$H NMR (400 MHz, DMSO-$d_6$): δ ppm 13.09-13.46 (m, 1H), 8.45 (s, 1H), 8.36 (br d, J=4.17 Hz, 1H), 8.03 (d, J=8.11 Hz, 1H), 7.81-7.92 (m, 1H), 7.65-7.78 (m, 2H), 7.10-7.20 (m, 1H), 5.38-5.51 (m, 1H), 4.61-4.71 (m, 1H), 3.57 (d, J=5.92 Hz, 2H), 2.93-3.22 (m, 4H), 2.16-2.29 (m, 1H), 1.91 (dt, J=13.98, 7.15 Hz, 1H), 0.83-0.93 (m, 4H).

Example 18

Synthesis of (4S)—N5-(pyridin-2-yl)-N7-(1,1,1-trifluoro-4-hydroxybutan-2-yl)-3,4-dihydro-1,4-methanopyrido[2,3-b][1,4]diazepine-5,7(2H)-dicarboxamide

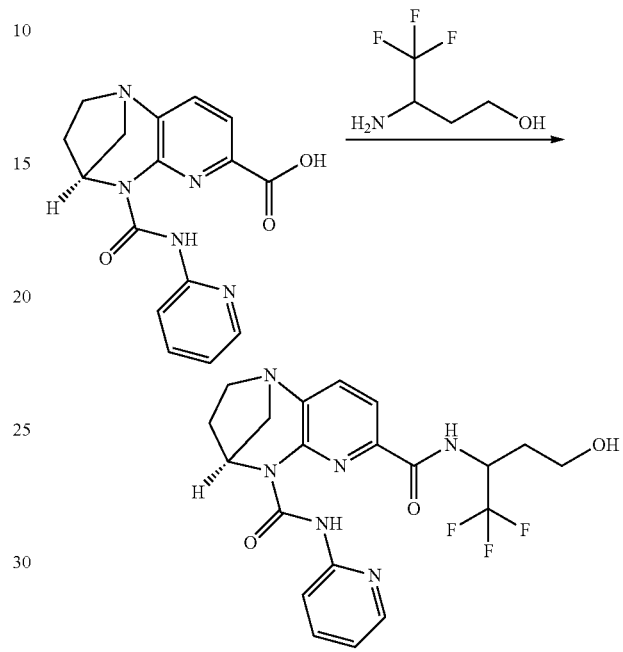

To a stirred solution of (4S)-5-(pyridin-2-ylcarbamoyl)-2,3,4,5-tetrahydro-1,4-methanopyrido[2,3-b][1,4]diazepine-7-carboxylic acid (1 g, 3.07 mmol) in DMF (5 mL) under nitrogen at RT was added DIPEA (1.611 mL, 9.22 mmol), HATU (2.338 g, 6.15 mmol) and stirred for 10 min. then added 3-amino-4,4,4-trifluorobutan-1-ol (0.660 g, 4.61 mmol) to the above reaction mixture and stirred at RT for 16 h. The reaction mixture was poured into ice cold water (100 mL) and extracted with ethylacetate (100 mL). Combined EtOAc extracts were dried over anhydrous $Na_2SO_4$, filtered and concentrated to give crude compound. The crude product was purified by combiflash chromatography (using silicagel column and eluted with 3% Methanol in DCM) to get diastereomeric mixtures of (4S)—N5-(pyridin-2-yl)-N7-(1,1,1-trifluoro-4-hydroxybutan-2-yl)-3,4-dihydro-1,4-methanopyrido[2,3-b][1,4]diazepine-5,7(2H)-dicarboxamide (1.18 g), HPLC purity-91%) as an off white solid. This diastereomeric mixture compound was further separated by chiral SFC (Instrument details: Make/Model: Thar SFC-200; Column Chiralcel OD-H (250×30) mm; CO2—75%, co-solvent (0.5% diethylamine in MeOH)-25%; Flow rate: 80 g/min; Stack time: 3.0 min; Load/inj: 5 mg; Solubility: MeOH).

Peak-1

Collected fractions from chiral SFC was concentrated and the residue was triturated with diethylether (5 mL) to afford (4S)—N5-(pyridin-2-yl)-N7-(1,1,1-trifluoro-4-hydroxybutan-2-yl)-3,4-dihydro-1,4-methanopyrido[2,3-b][1,4]diazepine-5,7(2H)-dicarboxamide (140 mg, 0.309 mmol, 10.07% yield) as an off white solid. LCMS (m/z): 451.09 [M+H]$^+$, Rt=1.86 min.

$^1$H NMR (400 MHz, CDCl$_3$): δ ppm 12.63-13.07 (m, 1H), 8.12-8.26 (m, 3H), 7.92 (d, J=7.89 Hz, 1H), 7.71-7.77 (m, 1H), 7.68 (d, J=7.89 Hz, 1H), 7.04 (ddd, J=7.34 1H), 5.65 (dd, J=6.03, 3.18 Hz, 1H), 5.06-5.21 (m, 1H), 3.77-3.92 (m, 2H), 3.07-3.34 (m, 4H), 2.96-3.06 (m, 1H), 2.22-2.41 (m, 2H), 2.01-2.19 (m, 2H).

Example 19

Synthesis of (4S)—N5-(pyridin-2-yl)-N7-((R)-1,1,1-trifluoropropan-2-yl)-3,4-dihydro-1,4-methanopyrido[2,3-b][1,4]diazepine-5,7(2H)-dicarboxamide

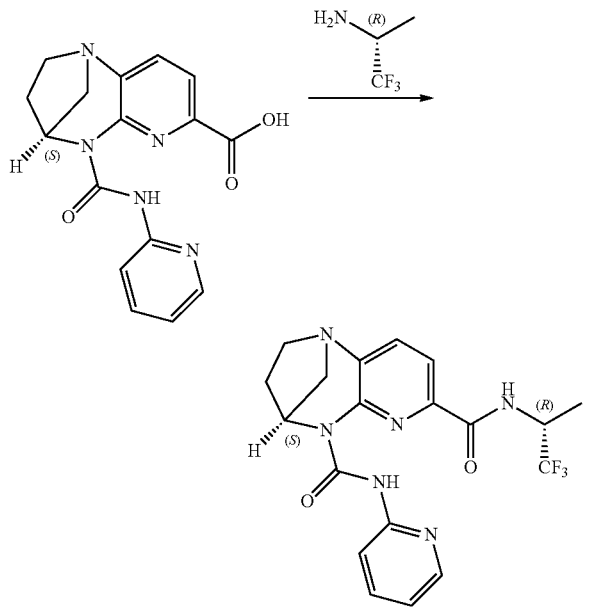

Example 20

Synthesis of (4S)—N7-(2,2-difluorocyclopropyl)-N5-(pyridin-2-yl)-3,4-dihydro-1,4-methanopyrido[2,3-b][1,4]diazepine-5,7(2H)-dicarboxamide

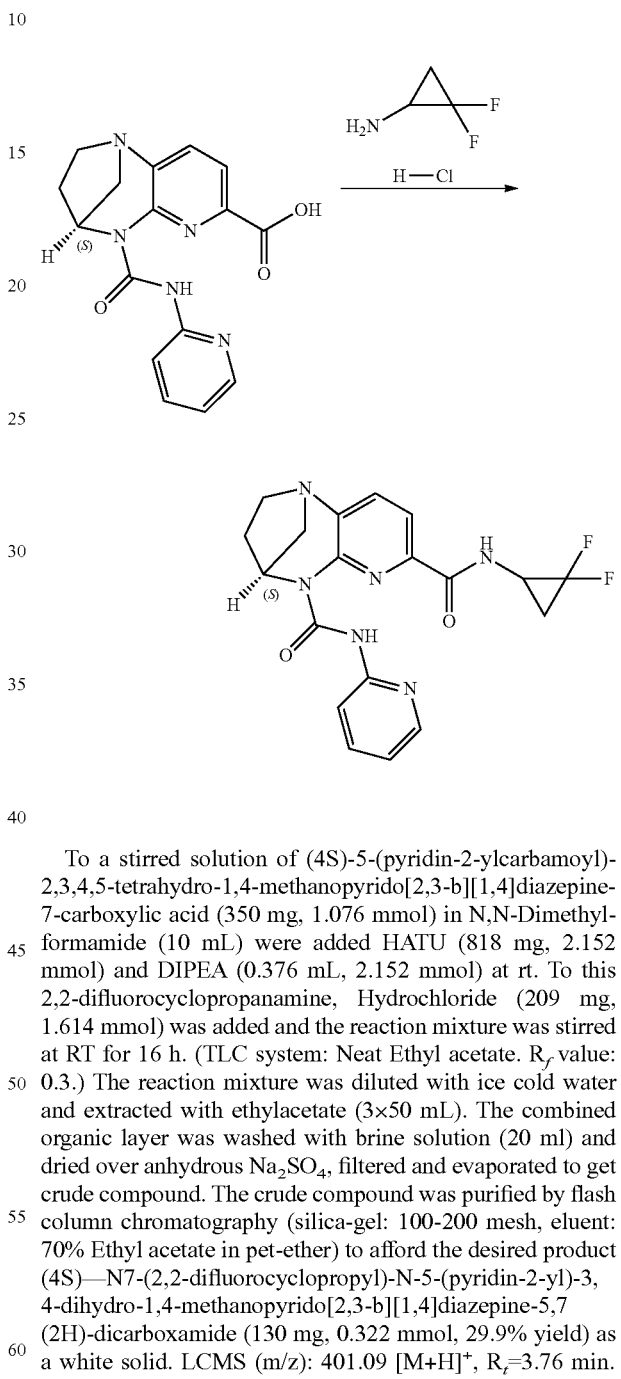

To a stirred solution of (4S)-5-(pyridin-2-ylcarbamoyl)-2,3,4,5-tetrahydro-1,4-methanopyrido[2,3-b][1,4]diazepine-7-carboxylic acid (4 g, 12.30 mmol) in DMF (40 mL) were added DIPEA (6.44 mL, 36.9 mmol), EDC (2.95 g, 15.37 mmol) and HOBT (2.354 g, 15.37 mmol) at RT and stirred under nitrogen for 15 min. Then (R)-1,1,1-trifluoropropan-2-amine (1.668 g, 14.75 mmol) was added and stirred for 16 h at RT. (TLC eluent: 5% MeOH/DCM, R$_f$: 0.4). DMF was distilled off and was partitioned between water (30 mL) and DCM (2×40 mL). The organic layer was separated and dried over anhydrous Na$_2$SO$_4$, filtered and filtrate was evaporated to obtain the crude compound. The crude compound was purified by flash column chromatography (Neutral alumina, Eluent: 55% ethylacetate in Pet ether) to afford the desired product (4S)—N5-(pyridin-2-yl)-N7-((R)-1,1,1-trifluoropropan-2-yl)-3,4-dihydro-1,4-methano pyrido[2,3-b][1,4]diazepine5, 7(2H)-dicarboxamide (1.2 g, 2.84 mmol, 23.06% yield) as a white solid. LCMS (m/z): 421.02 [M+H]$^+$, R$_f$=2.23 min.

$^1$H NMR (400 MHz, CDCl$_3$): δ ppm 13.23 (s, 1H), 8.26 (dd, J=4.93, 0.99 Hz, 1H), 8.15 (dt, J=8.50, 0.90 Hz, 1H), 8.02 (d, J=9.65 Hz, 1H), 7.95 (d, J=7.89 Hz, 1H), 7.76-7.70 (m, 1H), 7.68 (d, J=7.89 Hz, 1H), 7.03 (ddd, J=7.29, 4.99, 1.10 Hz, 1H), 5.65 (dd, J=5.92, 3.29 Hz, 1H), 5.12-4.98 (m, 1H), 3.32-2.97 (m, 4H), 2.40-2.26 (m, 1H), 2.13-2.01 (m, 1H), 1.60 (d, J=7.23 Hz, 3H).

To a stirred solution of (4S)-5-(pyridin-2-ylcarbamoyl)-2,3,4,5-tetrahydro-1,4-methanopyrido[2,3-b][1,4]diazepine-7-carboxylic acid (350 mg, 1.076 mmol) in N,N-Dimethylformamide (10 mL) were added HATU (818 mg, 2.152 mmol) and DIPEA (0.376 mL, 2.152 mmol) at rt. To this 2,2-difluorocyclopropanamine, Hydrochloride (209 mg, 1.614 mmol) was added and the reaction mixture was stirred at RT for 16 h. (TLC system: Neat Ethyl acetate. R$_f$ value: 0.3.) The reaction mixture was diluted with ice cold water and extracted with ethylacetate (3×50 mL). The combined organic layer was washed with brine solution (20 ml) and dried over anhydrous Na$_2$SO$_4$, filtered and evaporated to get crude compound. The crude compound was purified by flash column chromatography (silica-gel: 100-200 mesh, eluent: 70% Ethyl acetate in pet-ether) to afford the desired product (4S)—N7-(2,2-difluorocyclopropyl)-N-5-(pyridin-2-yl)-3,4-dihydro-1,4-methanopyrido[2,3-b][1,4]diazepine-5,7 (2H)-dicarboxamide (130 mg, 0.322 mmol, 29.9% yield) as a white solid. LCMS (m/z): 401.09 [M+H]$^+$, R$_f$=3.76 min.

$^1$H NMR (400 MHz, CDCl$_3$): δ ppm 13.39 (d, J=7.45 Hz, 1H), 8.27 (dt, J=5.04, 0.88 Hz, 2H), 8.11 (dd, J=8.33, 0.66 Hz, 1H), 7.90 (dd, J=7.89, 2.41 Hz, 1H), 7.78-7.56 (m, 2H), 7.08-6.94 (m, 1H), 5.63 (dt, J=5.86, 2.66 Hz, 1H), 3.64-3.41 (m, 1H), 3.29-2.93 (m, 3H), 2.37-2.34 (m, 1H), 2.42-2.22 (m, 1H), 2.11-1.88 (m, 2H), 1.83-1.66 (m, 1H).

Example 21

Synthesis of (4S)—N7-cyclopropyl-N5-(5-fluoro-pyridin-2-yl)-3,4-dihydro-1,4-methanopyrido[2,3-b][1,4]diazepine-5,7(2H)-dicarboxamide

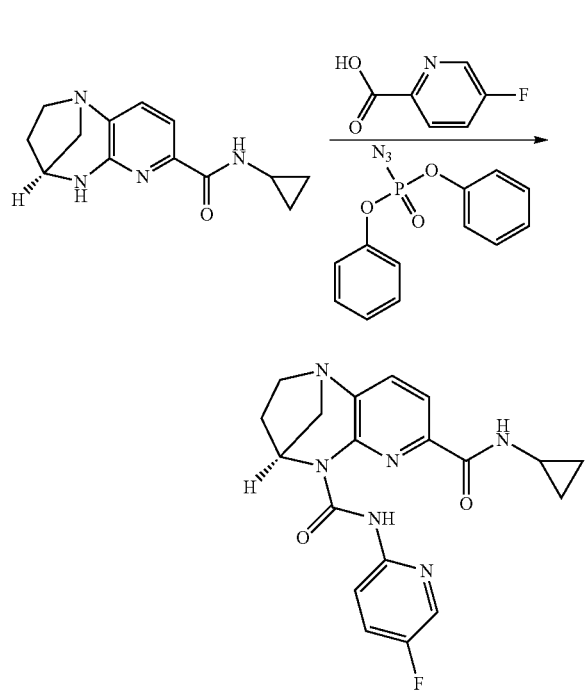

To a stirred solution of 5-fluoropicolinic acid (433 mg, 3.07 mmol) in Chloroform (50 mL) was added TEA (0.856 mL, 6.14 mmol) and diphenyl phosphorazidate (1127 mg, 4.09 mmol) under Nitrogen atmosphere at RT. The resulting reaction mixture was stirred at RT for 10 h. Then (4S)—N-cyclopropyl-2,3,4,5-tetrahydro-1,4-methanopyrido[2,3-b][1,4]diazepine-7-carboxamide (500 mg, 2.047 mmol) was added to the reaction mixture and stirred at 70° C. for 18 h. (TLC system: 10% MeOH in DCM.). Then the reaction mixture was allowed to cool to room temperature and diluted with water (30 mL), extracted with DCM (3×30 mL). The combined organic layer was washed with water (20 mL), brine solution (20 mL), dried over anhydrous $Na_2SO_4$, filtered and concentrated under reduced pressure to afford crude compound. The crude was purified by column chromatography (silica gel: 100-200 mesh, Eluent: 5% MeOH in DCM), obtained yellow semi solid was washed with diethyl ether (10 mL) and n-pentane (10 mL) to afford the desired product (4S)—N7-cyclopropyl-N5-(5-fluoropyridin-2-yl)-3,4-dihydro-1,4-methanopyrido[2,3-b][1,4]diazepine-5,7(2H)-dicarboxamide (260 mg, 0.673 mmol, 32.9% yield) as an off-white solid. LCMS (m/z): 383.04 $[M+H]^+$, $R_t$=2.02 min.

$^1$H NMR (400 MHz, $CDCl_3$): δ ppm 13.36 (s, 1H), 8.20-8.15 (m, 2H), 7.92 (d, J=7.89 Hz, 1H), 7.84 (br s, 1H), 7.65 (d, J=7.89 Hz, 1H), 7.47 (ddd, J=8.99, 7.78, 2.96 Hz, 1H), 5.62-5.60 (m, 1H), 3.28-3.17 (m, 2H), 3.14-3.04 (m, 2H), 3.04-2.98 (m, 1H), 2.37-2.26 (m, 1H), 2.08-1.97 (m, 1H), 0.98-0.90 (m, 2H), 0.84-0.75 (m, 2H).

Example 22

Synthesis of (4S)—N7-cyclopropyl-N5-(4-methyl-pyridin-2-yl)-3,4-dihydro-1,4-methanopyrido[2,3-b][1,4]diazepine-5,7(2H)-dicarboxamide

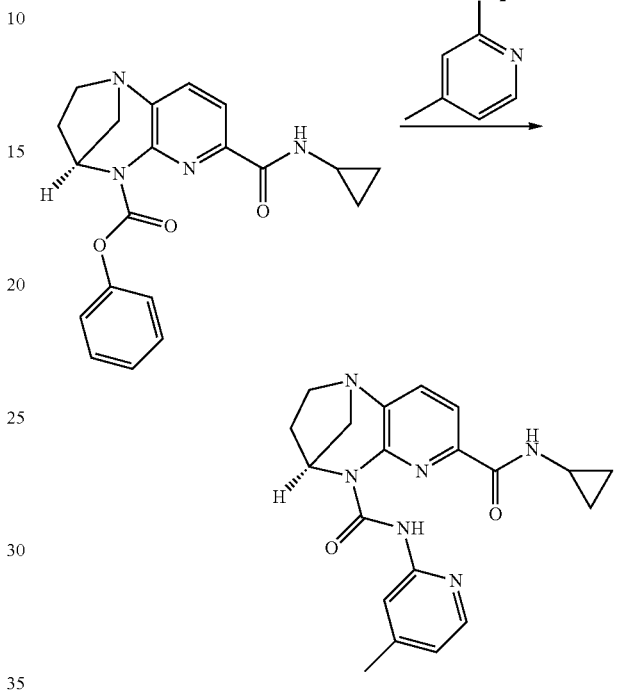

To a stirred solution of 4-methylpyridin-2-amine (297 mg, 2.74 mmol) in THF (20 mL) was added a solution of 1.0 M LiHMDS (2.74 mL, 2.74 mmol) in THF at −78° C. under Nitrogen atmosphere. The resulting reaction mixture was stirred at −78° C. for 30 min. To the reaction mixture, a THF solution of (4S)-phenyl7-(cyclopropylcarbamoyl)-3,4-dihydro-1,4-methanopyrido[2,3-b][1,4]diazepine-5(2H)-carboxylate (20 mL, 500 mg, 1.372 mmol) was added at −78° C. The resulting reaction mixture was warm to room temperature and stirred for 6 h. (TLC system: 5% MeOH in DCM, Rf: 0.5) and quenched with saturated ammonium chloride solution (30 mL), aqueous layer was extracted with EtOAc (3×30 mL). The combined organic layer was washed with water (20 mL), brine solution (20 mL), dried over anhydrous $Na_2SO_4$, faltered and filtrate was concentrated under reduced pressure to obtain crude compound. The crude was purified by flash column chromatography (silica gel: 100-200 mesh, Eluent: 4% MeOH in DCM) and obtained pale yellow semi solid was washed with diethyl ether and n-pentane to afford the desired product (4S)—N7-cyclopropyl-N5-(4-methylpyridin-2-yl)-3,4-dihydro-1,4-methanopyrido[2,3-b][1,4]diazepine-5,7(2H)-dicarboxamide (160 mg, 0.422 mmol, 30.8% yield) as an off-white solid. LCMS (m/z): 379.08 $[M+H]^+$, $R_t$=1.72 min.

$^1$H NMR (400 MHz, $CDCl_3$): δ ppm 13.30 (s, 1H), 8.16 (d, J=5.04 Hz, 1H), 8.05 (br s, 1H), 7.98 (s, 1H), 7.91 (d, J=7.89 Hz, 1H), 7.64 (d, J=7.89 Hz, 1H), 6.86 (dd, J=5.04, 0.66 Hz, 1H), 5.62 (dd, J=5.81, 3.18 Hz, 1H), 3.29-3.15 (m, 2H), 3.15-3.04 (m, 2H), 3.03-2.96 (m, 1H), 2.39 (s, 3H), 2.37-2.26 (m, 1H), 2.09-1.98 (m, 1H), 0.96-0.87 (m, 2H), 0.87-0.81 (m, 2H).

Example 23

Synthesis of (4S)—N5-(1-methyl-2-oxo-1,2-dihydropyridin-3-yl)-N7-(2,2,2-trifluoroethyl)-3,4-dihydro-1,4-methanopyrido[2,3-b][1,4]diazepine-5,7(2H)-dicarboxamide

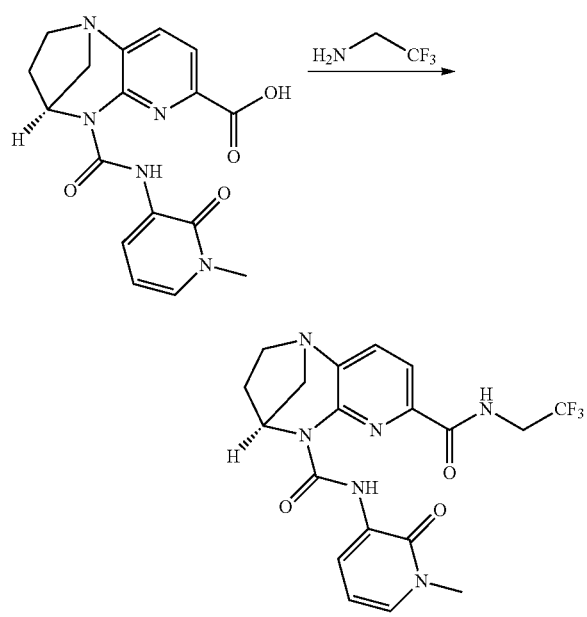

To a suspension of (4S)-5-((1-methyl-2-oxo-1,2-dihydropyridin-3-yl)carbamoyl)-2,3,4,5-tetrahydro-1,4-methanopyrido[2,3-b][1,4]diazepine-7-carboxylic acid (350 mg, 0.985 mmol) in DMF (10 mL) at 0° C. was added HATU (749 mg, 1.970 mmol), DIPEA (0.516 mL, 2.95 mmol) and the resulting mixture was stirred at 0° C. for 20 min. 2,2,2-trifluoroethanamine (146 mg, 1.477 mmol) was added to the above reaction at 0° C. and the reaction mixture was stirred at RT for 16 h. (TLC system: 5% Methanol in DCM. $R_f$: 0.4). The reaction mixture was quenched with water (15 mL) and the aq. layer was extracted with EtOAc (3×20 mL). Combined organic layer was dried over anhydrous sodium sulphate filtered and concentrated under reduced pressure to afford crude compound. The crude product was purified by column chromatography (Silica gel, eluted with 3% of MeOH in $CH_2Cl_2$) to afford (4S)—N5-(1-methyl-2-oxo-1,2-dihydropyridin-3-yl)-N7-(2,2,2-trifluoroethyl)-3,4-dihydro-1,4-methanopyrido[2,3-b][1,4]diazepine-5,7(2H)-dicarboxamide (167 mg, 0.381 mmol, 38.7% yield) as an off-white solid. LCMS (m/z): 437.12 [M+H]$^+$, Rt=2.02 min.

$^1$H NMR (400 MHz, CDCl$_3$): δ ppm 12.23 (s, 1H), 10.10 (br t, J=5.92 Hz, 1H), 8.42 (dd, J=7.45, 1.75 Hz, 1H), 8.01 (d, J=7.89 Hz, 1H), 7.65 (d, J=7.89 Hz, 1H), 7.03 (dd, J=6.80, 1.75 Hz, 1H), 6.33 (t, J=7.04 Hz, 1H), 5.71 (dd, J=6.03, 3.18 Hz, 1H), 4.14-4.33 (m, 2H), 3.63 (s, 3H), 3.06-3.31 (m, 3H), 2.93-3.05 (m, 1H), 2.31 (dddd, J=14.06, 9.89, 5.86, 3.95 Hz, 1H), 1.95-2.17 (m, 1H).

Example 24

Synthesis of (4S)—N7-cyclopropyl-N5-(4-((R)-2,3-dihydroxypropoxy)pyridin-2-yl)-3,4-dihydro-1,4-methanopyrido[2,3-b][1,4]diazepine-5,7(2H)-dicarboxamide

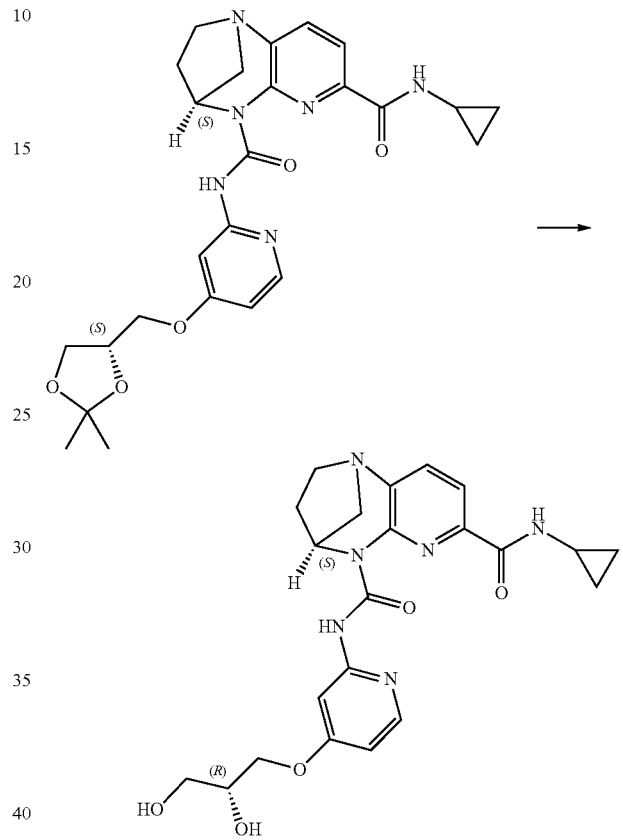

To a stirred solution of (4S)—N7-cyclopropyl-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide (400 mg, 0.809 mmol) in methanol (6 mL) at 0° C. was added aq. HCl (2 mL, 65.8 mmol) slowly over a period of 2 min at 0° C. The resulting reaction mixture was stirred at RT for 16 h. (TLC system: 10% Methanol in DCM. $R_f$: 0.2). Reaction mixture was concentrated in vacuo to afford brown viscous oil. The reaction mass was dissolved in minimum amount of water (4 mL), then neutralized with saturated sodium bicarbonate solution at 0° C. and extracted with 10% MeOH in DCM (2×30 mL). Combined organic layer washed with brine (20 mL), dried over anhydrous Na$_2$SO$_4$, filtered and concentrated under reduced pressure to get crude brown solid. The crude product was purified by column chromatography (silica gel, eluted with 12% of MeOH in CH$_2$Cl$_2$) to afford (4S)—N7-cyclopropyl-N5-(4-((R)-2,3-dihydroxypropoxy)pyridin-2-yl)-3,4-dihydro-1,4-methanopyrido[2,3-b][1,4]diazepine-5,7(2H)-dicarboxamide (150 mg, 0.329 mmol, 40.7% yield) as an off white solid. LC-MS: 455.12 [M+H]$^+$, Rt=1.25 min.

$^1$H NMR (400 MHz, DMSO-d$_6$): δ ppm 13.12 (s, 1H), 8.11 (d, J=5.70 Hz, 1H), 8.06 (br d, J=4.17 Hz, 1H), 7.65-7.74 (m, 3H), 6.75 (dd, J=5.92, 2.41 Hz, 1H), 5.43 (dd, J=5.92, 3.07 Hz, 1H), 5.02 (d, J=5.26 Hz, 1H), 4.68-4.74 (m, 1H), 4.12 (dd, J=9.87, 3.95 Hz, 1H), 3.96 (dd, J=9.76, 6.25 Hz, 1H), 3.79-3.87 (m, 1H), 3.46 (td, J=5.70, 1.97 Hz, 2H), 3.05 (br d, J=12.50 Hz, 3H), 2.92-3.00 (m, 2H), 2.17-2.27 (m, 1H), 1.90 (dt, J=13.87, 6.99 Hz, 1H), 0.79-0.88 (m, 2H), 0.67-0.78 (m, 2H).

Example 25

Synthesis of (4S)—N5-(2-methyloxazol-4-yl)-N7-((R)-1,1,1-trifluoropropan-2-yl)-3,4-dihydro-1,4-methanopyrido[2,3-b][1,4]diazepine-5,7(2H)-dicarboxamide

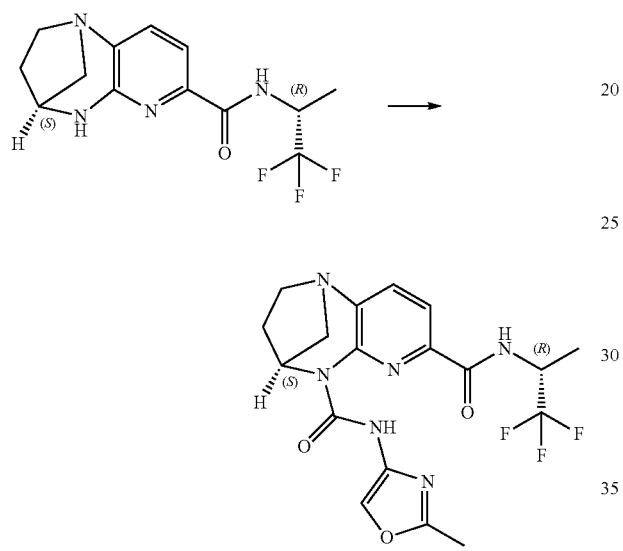

To a stirred solution of 2-methyloxazole-4-carboxylic acid (381 mg, 3.00 mmol) in CHCl$_3$ (20 mL) under nitrogen at RT was added diphenylphosphinyl azide (607 mg, 2.498 mmol) followed by TEA (0.348 mL, 2.498 mmol) and stirred for 10 h. Then added (4S)—N—((R)-1,1,1-trifluoropropan-2-yl)-2,3,4,5-tetrahydro-1,4-methanopyrido[2,3-b][1,4]diazepine-7-carboxamide (750 mg, 2.498 mmol) to the above reaction mixture and heated at 60° C. for 12 h. (TLC eluent: 5% MeOH in DCM R$_f$: 0.3; UV active). Reaction was cooled to RT, then diluted with ice cold water (20 mL) and DCM (20 mL). The organic layer washed with brine (10 mL), dried over anhydrous Na$_2$SO$_4$, filtered and concentrated in vacuo to get crude product. The crude was purified by column chromatography (silica gel, eluted with 5% of MeOH in CH$_2$Cl$_2$) followed by Prep HPLC (Column: phenyl kromosil (150×30) mm 10μ; Mobile Phase-A: 5 mM Ammonium Bicarbonate (Aq), Mobile Phase-B: Acetonitrile; Method: 0/2.3/2.10/50; Flow: 25 ml/min; Solubility: THF+Acetonitrile+Water) to afford (4S)—N5-(2-methyloxazol-4-yl)-N7-((R)-1,1,1-trifluoropropan-2-yl)-3,4-dihydro-1,4-methanopyrido[2,3-b][1,4]diazepine-5,7(2H)-dicarboxamide (125 mg, 0.291 mmol, 11.65% yield) as an off white solid. LC-MS (m/z): 425.10 [M+H]$^+$, Rt=2.12 min.

$^1$H NMR (400 MHz, DMSO-d$_6$): δ ppm 12.20 (s, 1H), 8.48-8.53 (m, 1H), 7.84 (s, 1H), 7.70 (d, J=7.89 Hz, 1H), 7.61 (d, J=7.89 Hz, 1H), 5.41 (dd, J=6.03, 2.96 Hz, 1H), 4.86 (br dd, J=15.78, 7.67 Hz, 1H), 3.00-3.21 (m, 3H), 2.93-2.99 (m, 1H), 2.35 (s, 3H), 2.22 (dddd, J=13.70, 9.87, 6.03, 3.95 Hz, 1H), 1.83-1.92 (m, 1H), 1.49 (d, J=7.02 Hz, 3H).

Example 26

Synthesis of (4S)—N7-((S)-sec-butyl)-N5-(pyridin-2-yl)-3,4-dihydro-1,4-methanopyrido[2,3-b][1,4]diazepine-5,7(2H)-dicarboxamide

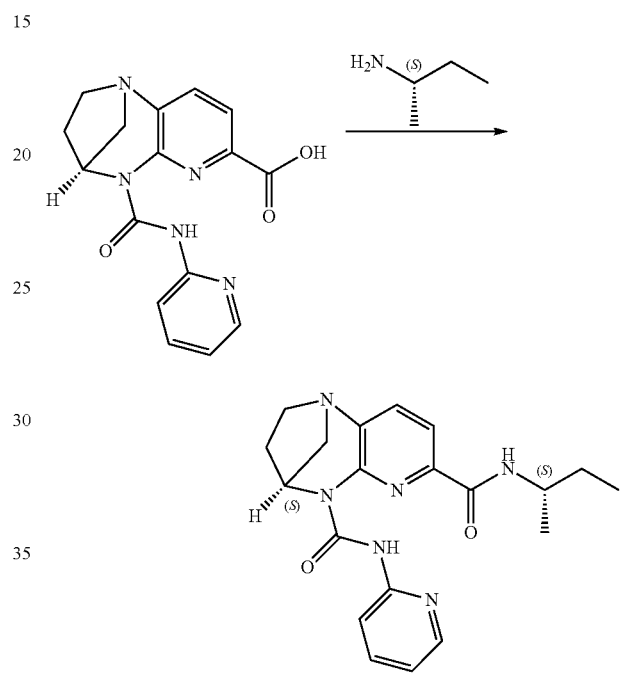

To a stirred solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in DMF (3 mL), under Nitrogen at RT was added DIPEA (0.483 mL, 2.77 mmol), HATU (701 mg, 1.844 mmol) followed by (S)-butan-2-amine (67.4 mg, 0.922 mmol) and the reaction mixture was stirred for 16 h. (TLC system: 5% Methanol in DCM. R$_f$ value: 0.30). Reaction was quenched with ice cold water (50 mL) and extracted into EtOAc (2×100 mL). The combined organic layer was washed with brine (50 mL), dried over Na$_2$SO$_4$, filtered and concentrated to get crude compound. The crude material was purified by combiflash (silica gel, 80% ethyl acetate in hexane). Fractions containing pure compound were combined and concentrated to afford (4S)—N7-((S)-sec-butyl)-N5-(pyridin-2-yl)-3,4-dihydro-1,4-methanopyrido[2,3-b][1,4]diazepine-5,7(2H)-dicarboxamide (91 mg, 0.235 mmol, 25.5% yield) as an off white solid. LCMS (m/z): 381.17 [M+H]$^+$, Rt=2.15 min.

$^1$H NMR (400 MHz, CDCl$_3$): δ ppm 13.29 (s, 1H), 8.26 (d, J=5.09 Hz, 1H), 8.17 (d, J=8.33 Hz, 1H), 7.93 (d, J=7.89 Hz, 1H), 7.58-7.79 (m, 3H), 6.90-7.14 (m, 1H), 5.66 (dd, J=5.92, 3.07 Hz, 1H), 4.18-4.32 (m, 1H), 3.20-3.30 (m, 2H), 3.18 (m, 1H), 2.84-3.07 (m, 1H), 2.18-2.45 (m, 1H), 2.04 (dt, J=14.03, 7.02 Hz, 1H), 1.61-1.83 (m, 2H), 1.34 (d, J=6.80 Hz, 3H), 0.98 (t, J=7.34 Hz, 3H).

Example 27

Synthesis of (4S)—N7-cyclohexyl-N5-(pyridin-2-yl)-3,4-dihydro-1,4-methanopyrido[2,3-b][1,4]diazepine-5,7(2H)-dicarboxamide

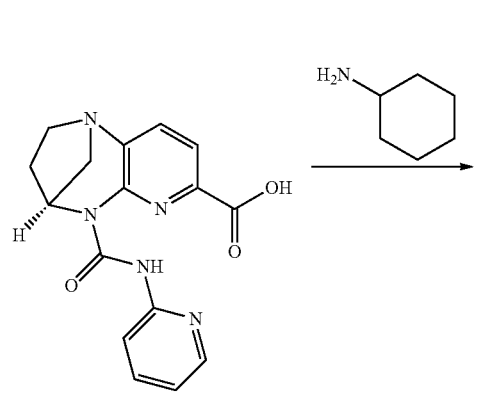

To a stirred solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in DMF (3 mL), under nitrogen at RT was added DIPEA (0.483 mL, 2.77 mmol), HATU (701 mg, 1.844 mmol) followed by cyclohexanamine (137 mg, 1.383 mmol) and resulting reaction mixture was stirred at RT for 16 h. (TLC system: 5% Methanol in DCM. $R_f$ value: 0.30). Reaction was quenched with ice cold water (50 mL) and extracted into EtOAc (2×100 mL). The combined organic layer was washed with brine, dried over $Na_2SO_4$, filtered and concentrated to get crude compound. The crude material was purified by combiflash (using silica gel column 12 g, 75% EtOAc in Hexane). Fractions containing pure compound were combined and concentrated to afford (4S)—N7-cyclohexyl-N5-(pyridin-2-yl)-3,4-dihydro-1,4-methanopyrido[2,3-b][1,4]diazepine-5,7(2H)-dicarboxamide (230 mg, 0.562 mmol, 61.0% yield) as off white solid. LCMS (m/z): 407.14 [M+H]$^+$, Rt=2.39 min.

$^1$H NMR (400 MHz, CDCl$_3$): δ ppm 13.27 (s, 1H), 8.30 (br d, J=3.73 Hz, 1H), 8.18 (d, J=8.33 Hz, 1H), 7.93 (d, J=7.89 Hz, 1H), 7.80 (m, 2H), 7.65 (s, 1H), 6.91-7.15 (m, 1H), 5.66 (dd, J=5.92, 3.07 Hz, 1H), 4.01-4.21 (m, 1H), 3.31 (m, 2H), 3.20 (m, 1H), 3.09 (m, 1H), 2.18-2.41 (m, 1H), 1.94-2.13 (m, 3H), 1.84 (br d, J=12.28 Hz, 3H), 1.76 (br d, J=13.15 Hz, 4H), 1.37-1.64 (m, 1H).

Example 28

Synthesis of (4S)—N7-((1-(hydroxymethyl)cyclopropyl)methyl)-N5-(pyridin-2-yl)-3,4-dihydro-1,4-methanopyrido[2,3-b][1,4]diazepine-5,7(2H)-dicarboxamide

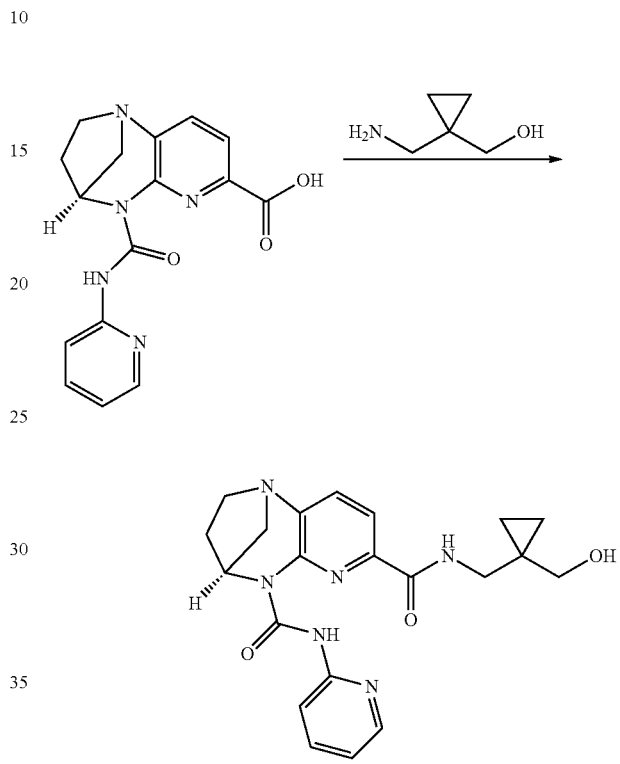

To a stirred solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in DMF (3 mL), under nitrogen at RT was added DIPEA (0.483 mL, 2.77 mmol), HATU (701 mg, 1.844 mmol) and (1-(aminomethyl)cyclopropyl)methanol (112 mg, 1.107 mmol), then the reaction mixture was stirred for 16 h. (TLC system: 5% Methanol in DCM. $R_f$ value: 0.30). Reaction was quenched with ice cold water (80 mL) and extracted into EtOAc (2×100 mL). The combined organic layer was washed with brine, dried over $Na_2SO_4$, filtered and concentrated to get crude compound. The Crude material was purified by combiflash (using silica gel column, 80% EtOAc in Hexane). Fractions containing pure compound were combined and concentrated to afford the desired compound (4S)—N7-((1-(hydroxymethyl)cyclopropyl)methyl)-N5-(pyridin-2-yl)-3,4-dihydro-1,4-methanopyrido[2,3-b][1,4]diazepine-5,7(2H)-dicarboxamide (165 mg, 0.396 mmol, 43.0% yield) as off white solid. LCMS (m/z): 409.14 [M+H]$^+$, Rt=1.62 min.

$^1$H NMR (400 MHz, CDCl$_3$): δ ppm 13.12 (s, 1H), 8.57 (br s, 1H), 8.20-8.37 (m, 1H), 8.14 (d, J=8.33 Hz, 1H), 7.89 (d, J=7.89 Hz, 1H), 7.79 (m, 1H), 7.69 (s, 1H), 6.90-7.15 (m, 1H), 5.63 (dd, J=5.92, 3.07 Hz, 1H), 4.73 (br s, 1H), 3.75 (m, 2H), 3.67 (m, 2H), 3.40 (m, 2H), 3.07 (m, 1H), 2.95-3.09 (m, 1H), 2.22-2.42 (m, 1H), 1.99-2.19 (m, 1H), 0.65-0.55 (m, 2H), 0.45-0.55 (m, 2H).

Example 29

Synthesis of (4S)—N5-(pyridin-2-yl)-N7-((R)-1,1,1-trifluoro-3-methylbutan-2-yl)-3,4-dihydro-1,4-methanopyrido[2,3-b][1,4]diazepine-5,7(2H)-dicarboxamide

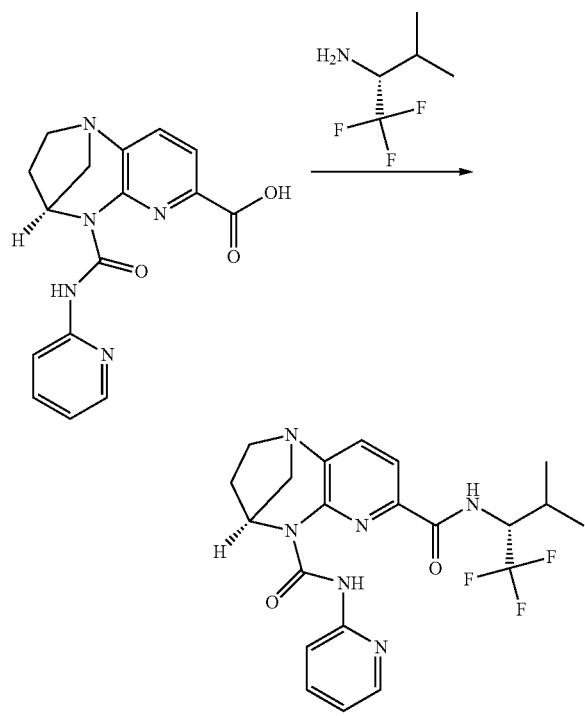

To a stirred solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in DMF) (3 mL, under nitrogen at RT was added DIPEA (0.483 mL, 2.77 mmol), HATU (701 mg, 1.844 mmol) and (R)-1,1,1-trifluoro-3-methylbutan-2-amine (156 mg, 1.107 mmol), then the resulting reaction mixture was stirred for 16 h. (TLC system: 5% Methanol in DCM. $R_f$ value: 0.30). Reaction mass was diluted with 80 mL of ice cold water, extracted with EtOAc (2×100 mL). The combined organic layer was washed with brine (50 mL), dried over $Na_2SO_4$, filtered and concentrated to get crude compound. The crude material was purified by combiflash (using silica gel column, 80% EtOAc in Hexane). Fractions containing pure compound were combined and concentrated to afford the desired compound (4S)—N5-(pyridin-2-yl)-N7-((R)-1,1,1-trifluoro-3-methylbutan-2-yl)-3,4-dihydro-1,4-methanopyrido[2,3-b][1,4]diazepine-5,7(2H)-dicarboxamide (190 mg, 0.423 mmol, 45.9% yield) as off white solid. LCMS (m/z): 449.14 [M+H]$^+$, Rt=2.52 min.

$^1$H NMR (400 MHz, CDCl$_3$): δ ppm 13.12 (s, 1H), 8.57 (br s, 1H), 8.20-8.37 (m, 1H), 8.14 (d, J=8.33 Hz, 1H), 7.89 (d, J=7.89 Hz, 1H), 7.69-7.79 (m, 2H), 7.15 (m, 1H), 5.65 (dd, J=5.92, 3.07 Hz, 1H), 4.67-4.80 (m, 1H), 3.11-3.31 (m, 3H), 3.00-3.05 (m, 1H), 2.30-2.46 (m, 2H), 2.02-2.13 (m, 1H), 1.16-1.21 (m, 3H), 1.08 (d, J=6.80 Hz, 3H).

Example 30

Synthesis of (4S)—N7-((S)-1-hydroxybutan-2-yl)-N5-(pyridin-2-yl)-3,4-dihydro-1,4-methanopyrido[2,3-b][1,4]diazepine-5,7(2H)-dicarboxamide

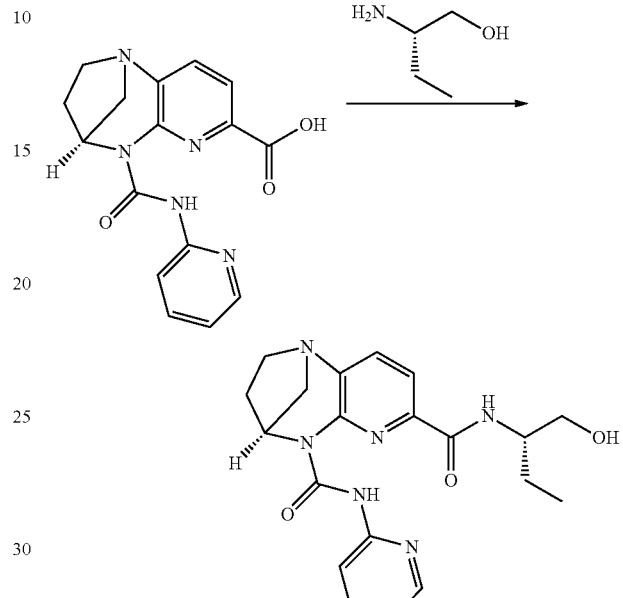

To a stirred solution of (4S)-5-(pyridin-2-ylcarbamoyl)-2,3,4,5-tetrahydro-1,4-methanopyrido[2,3-b][1,4]diazepine-7-carboxylic acid (600 mg, 1.844 mmol) in DMF (6 mL), at RT was added DIPEA (0.966 mL, 5.53 mmol), HATU (1403 mg, 3.69 mmol) and (S)-2-aminobutan-1-ol (164 mg, 1.844 mmol), then the resulting reaction mixture was stirred at RT for 16 h. (TLC system: 5% Methanol in DCM. $R_f$ value: 0.20). Reaction mass was diluted with 50 mL of ice cold water and extracted with EtOAc (2×100 mL). The combined organic layer was washed with brine (80 mL), dried over $Na_2SO_4$, filtered and concentrated to get crude compound. The crude material was purified by combiflash (using silica gel column, 80% EtOAc in Hexane). Fractions containing compound were combined and concentrated to afford the desired compound with 40% pure. Which was further purified by prep HPLC (Column: XBridge C18 (150×19) mm 5μ, Mobile Phase-A: 0.1% Formic acid (aq), Mobile Phase-B: Acetonitrile, Method: Isocratic (A:B)=0/16, 10/16, Flow: 15 ml/min Solubility: THF (excess)+ACN+MeOH) to afford the desired product (4S)—N7-((S)-1-hydroxybutan-2-yl)-N5-(pyridin-2-yl)-3,4-dihydro-1,4-methanopyrido[2,3-b][1,4]diazepine-5,7(2H)-oxamide (80 mg, 0.198 mmol, 10.72% yield) as off white solid. (m/z): 397.12 [M+H]$^+$; Rt=1.67 min.

$^1$H NMR (400 MHz, CDCl$_3$): δ ppm 12.80 (s, 1H), 8.16-8.35 (m, 2H), 7.89 (d, J=7.67 Hz, 1H), 7.61-7.80 (m, 1H), 7.58-7.61 (m, 1H), 7.48 (m, 1H), 6.95-7.05 (m, 1H), 5.72 (dd, J=6.14, 3.29 Hz, 1H), 4.04-4.33 (m, 1H), 3.70-3.95 (m, 3H), 3.08-3.31 (m, 3H), 2.91-3.06 (m, 1H), 2.33 (dddd, J=14.00, 10.00, 6.14, 3.84 Hz, 1H), 1.91-2.11 (m, 1H), 1.62-1.88 (m, 2H), 1.01 (t, J=7.45 Hz, 3H).

Example 31

Synthesis of (4S)—N5-(pyridin-2-yl)-N7-((S)-1,1,1-trifluorobutan-2-yl)-3,4-dihydro-1,4-methanopyrido[2,3-b][1,4]diazepine-5,7(2H)-dicarboxamide

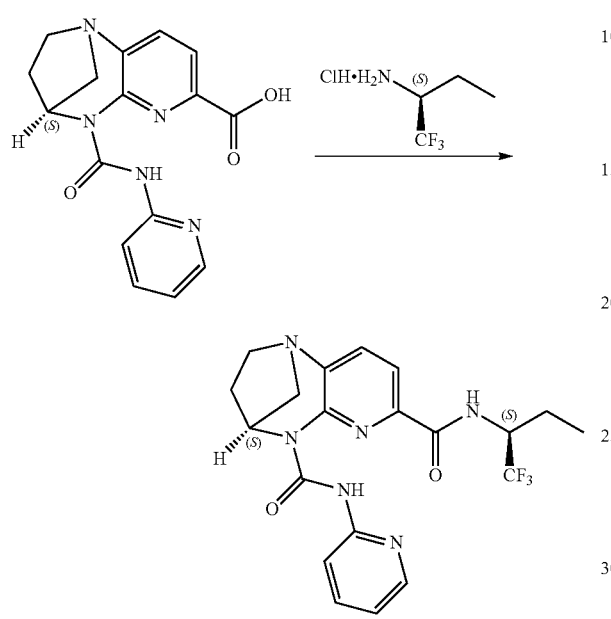

To a stirred solution of (4S)-5-(pyridin-2-ylcarbamoyl)-2,3,4,5-tetrahydro-1,4-methanopyrido[2,3-b][1,4]diazepine-7-carboxylic acid (200 mg, 0.615 mmol) and (S)-1,1,1-trifluorobutan-2-amine hydrochloride (151 mg, 0.922 mmol) in N,N-Dimethylformamide (10 mL) were added HATU (468 mg, 1.230 mmol) and followed by DIPEA (0.215 mL, 1.230 mmol) at room temperature, and stirred it for 18 h. (TLC system: 100% Ethylacetate, Rf value: 0.5). The reaction mixture was diluted with water (25 mL) and extracted with EtOAc (2×50 mL). The combined organic layer was separated and dried over anhydrous $Na_2SO_4$, filtered and filtrate was evaporated to obtain crude compound. The crude product was purified by prep HPLC (Column: XBridge C 18 (75×4.6 mm, 3.5µ), Mobile Phase: A: 0.01 M Ammonium Bicarbonate B: ACN, Gradient: Time/% B: 0/5, 0.8/5, 5/50, 8/95, 12/95, 12.1/5, 15/5, Column Temp: Ambient, Flow Rate: 1.0 ml/min, Diluent: ACN) to afford the desired product (4S)—N5-(pyridin-2-yl)-N7-((S)-1,1,1-trifluorobutan-2-yl)-3,4-dihydro-1,4-methanopyrido[2,3-b][1,4]diazepine-5,7(2H)-dicarboxamide (110 mg, 0.253 mmol, 41.2% yield) as a white solid. LCMS (m/z): 435.03 [M+H]$^+$, $R_t$=2.38 min.

$^1$H NMR (400 MHz, $CDCl_3$): δ ppm 13.26 (br s, 1H), 8.22 (d, J=4.17 Hz, 1H), 8.15 (d, J=8.33 Hz, 1H), 7.96 (d, J=7.89 Hz, 1H), 7.88 (d, J=10.30 Hz, 1H), 7.75-7.63 (m, 2H), 7.02 (dd, J=6.58, 5.04 Hz, 1H), 5.68 (dd, J=5.70, 3.07 Hz, 1H), 4.89-4.78 (m, 1H), 3.31-3.19 (m, 2H), 3.14-3.08 (m, 1H), 3.05-2.97 (m, 1H), 2.40-2.28 (m, 1H), 2.12-1.95 (m, 3H), 1.04 (t, J=7.34 Hz, 3H).

Example 32

Synthesis of (4S)—N7-isopropyl-N5-(pyridin-2-yl)-3,4-dihydro-1,4-methanopyrido[2,3-b][1,4]diazepine-5,7(2H)-dicarboxamide

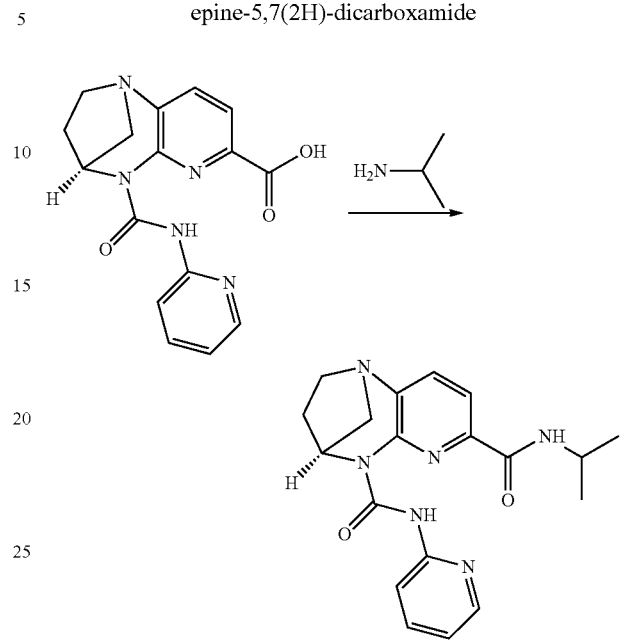

To a solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in DMF (3 mL) at 0° C. under nitrogen was added DIPEA (0.483 mL, 2.77 mmol), HATU (701 mg, 1.844 mmol) and propan-2-amine (109 mg, 1.844 mmol) then the reaction mixture was stirred at RT for 16 h (TLC system: 5% Methanol in DCM. $R_f$ value: 0.2). The reaction was quenched with ice cold water (3 mL) and the resultant solid was filtered, washed and dried under vacuum to afford (4S)—N7-isopropyl-N5-(pyridin-2-yl)-3,4-dihydro-1,4-methanopyrido[2,3-b][1,4]diazepine-5,7(2H)-dicarboxamide (185 mg, 0.501 mmol, 54.4% yield) as an off white solid. LCMS (m/z): 367.13 [M+H]$^+$, Rt=1.95 min.

$^1$H NMR (400 MHz, DMSO-$d_6$): δ ppm 13.11 (s, 1H), 8.31 (br d, J=3.51 Hz, 1H), 8.10 (br d, J=8.11 Hz, 1H), 7.64-7.89 (m, 4H), 6.97-7.23 (m, 1H), 5.47 (br d, J=2.63 Hz, 1H), 4.23 (dq, J=14.17, 6.82 Hz, 1H), 3.01-3.22 (m, 3H), 2.92-3.01 (m, 1H), 2.09-2.29 (m, 1H), 1.93 (dt, J=13.48, 6.85 Hz, 1H), 1.28 (dd, J=6.36, 4.17 Hz, 6H).

Example 33

Synthesis of (4S)—N7-((R)-sec-butyl)-N5-(pyridin-2-yl)-3,4-dihydro-1,4-methanopyrido[2,3-b][1,4]diazepine-5,7(2H)-dicarboxamide

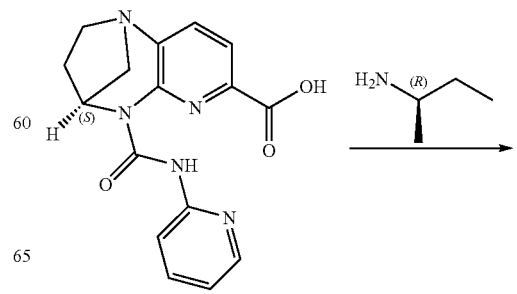

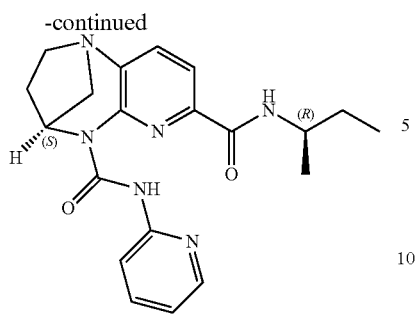

To a suspension of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in DMF (3 mL), under nitrogen at 0° C. was added DIPEA (0.483 mL, 2.77 mmol), HATU (701 mg, 1.844 mmol) and (R)-butan-2-amine (81 mg, 1.107 mmol) and stirred at RT for 4 h. (TLC system: 10% Methanol in DCM. Rf=0.4). The reaction mixture was quenched with cold water (80 mL) and extracted with EtOAc (2×100 mL). Combined organic layer washed with brine (50 mL), dried over sodium sulphate and concentrated under reduced pressure to afford crude compound. The crude material was purified by combiflash chromatography (Silica gel column, 5% methanol in DCM) followed by preparative HPLC (Column: XBridge C 18 (75×4.6 mm, 3.5μ) Mobile Phase-A: 0.01 M Ammonium Bicarbonate, B: CAN; Gradient-Time/% B: 0/5, 0.8/5, 5/50, 8/95, 12/95, 12.1/5, 15/5; Temp: Ambient; Flow Rate: 1.0 ml/min; Diluent: Acetonitrile) to afford (4S)—N7-((R)-sec-butyl)-N5-(pyridin-2-yl)-3,4-dihydro-1,4-methanopyrido[2,3-b][1,4]diazepine-5,7(2H)-dicarboxamide (110 mg, 0.289 mmol, 31.3% yield) as an off white solid. LCMS (m/z): 381.1 [M+H]$^+$, Rt=2.14 min.

$^1$H NMR (400 MHz, DMSO-d$_6$): δ ppm 13.13 (s, 1H), 8.29 (br d, J=3.95 Hz, 1H), 8.10 (d, J=8.33 Hz, 1H), 7.79-7.97 (m, 1H), 7.64-7.79 (m, 3H), 7.14 (dd, J=6.58, 5.04 Hz, 1H), 5.47 (dd, J=5.70, 2.85 Hz, 1H), 4.06 (dt, J=14.52, 7.10 Hz, 1H), 3.29 (s, 4H), 2.09-2.30 (m, 1H), 1.94 (dt, J=13.59, 7.02 Hz, 1H), 1.55-1.79 (m, 2H), 1.26 (d, J=6.58 Hz, 3H), 0.98-1.18 (m, 3H).

Example 34

Synthesis of (4S)—N5-(pyridin-2-yl)-N7-((R)-3,3,3-trifluoro-2-hydroxypropyl)-3,4-dihydro-1,4-methanopyrido[2,3-b][1,4]diazepine-5,7(2H)-dicarboxamide

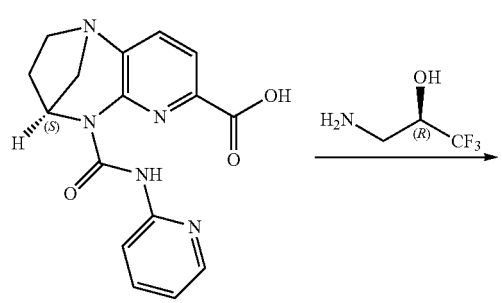

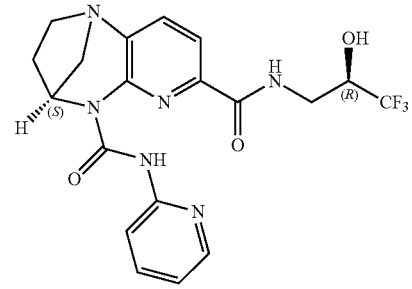

To a suspension of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in DMF (3 mL) under nitrogen at 0° C. was added HATU (701 mg, 1.844 mmol), DIPEA (0.483 mL, 2.77 mmol) and (R)-3-amino-1,1,1-trifluoropropan-2-ol (143 mg, 1.107 mmol) and stirred at RT for 16 h. (TLC system: 10% Methanol in DCM. R$_f$ value: 0.3). The reaction mixture was quenched with cold water (80 mL) and extracted with EtOAc (2×100 mL). Combined organic layer was washed with brine (50 mL), dried over sodium sulphate and concentrated under reduced pressure to afford crude compound. The crude material was purified by combiflash chromatography (Silica gel column, eluent EtOAc) to afford (4S)—N5-(pyridin-2-yl)-N7-((R)-3,3,3-trifluoro-2-hydroxypropyl)-3,4-dihydro-1,4-methanopyrido[2,3-b][1,4]diazepine-5,7(2H)-dicarboxamide (175 mg, 0.400 mmol, 43.4% yield) as a white solid. LCMS (m/z): 437.05 [M+H]$^+$, Rt=1.83 min.

$^1$H NMR (400 MHz, DMSO-d$_6$): δ ppm 13.33 (s, 1H), 8.44 (br t, J=6.03 Hz, 1H), 8.29 (dd, J=4.93, 0.99 Hz, 1H), 8.04 (d, J=8.33 Hz, 1H), 7.80-7.95 (m, 1H), 7.62-7.78 (m, 2H), 7.14 (ddd, J=7.34, 4.93, 1.10 Hz, 1H), 6.51 (d, J=6.58 Hz, 1H), 5.43 (dd, J=5.81, 2.96 Hz, 1H), 4.13-4.37 (m, 1H), 3.77 (dt, J=13.98, 5.40 Hz, 1H), 3.54 (dt, J=13.81, 6.91 Hz, 1H), 3.05-3.28 (m, 3H), 2.83-3.03 (m, 1H), 2.19-2.3 (m, 1H), 1.85-2.02 (m, 1H).

Example 35

Synthesis of (4S)—N7-cyclopentyl-N5-(pyridin-2-yl)-3,4-dihydro-1,4-methanopyrido[2,3-b][1,4]diazepine-5,7(2H)-dicarboxamide

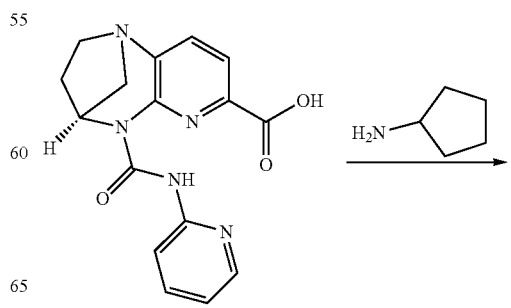

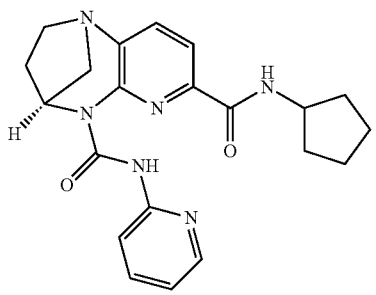

To a stirred solution of (4S)-5-(pyridin-2-ylcarbamoyl)-2,3,4,5-tetrahydro-1,4-methanopyrido[2,3-b][1,4]diazepine-7-carboxylic acid (500 mg, 1.537 mmol) in DMF (4 mL), under nitrogen at 0° C. was added DIPEA (1.342 mL, 7.68 mmol), HATU (1169 mg, 3.07 mmol) and cyclopentanamine (157 mg, 1.844 mmol) and stirred at RT for 16 h (TLC system: 5% Methanol in DCM. $R_f$ value: 0.2). The reaction mixture was quenched with cold water (80 mL) and extracted with EtOAc (2×50 mL). Combined organic layer washed with brine (50 mL), dried over sodium sulphate and concentrated under reduced pressure to afford crude compound. The crude material was purified by combiflash chromatography (Silica gel column, eluent EtOAc) to afford (4S)—N7-cyclopentyl-N5-(pyridin-2-yl)-3,4-dihydro-1,4-methanopyrido[2,3-b][1,4]diazepine-5,7(2H)-dicarboxamide (162 mg, 0.411 mmol, 26.7% yield) as an off white solid. LCMS (m/z): 393.10 [M+H]$^+$, Rt=2.21 min.

$^1$H NMR (400 MHz, DMSO-d$_6$): δ ppm 12.99 (s, 1H), 8.18-8.32 (m, 1H), 8.11 (dt, J=8.39, 0.96 Hz, 1H), 7.78-7.92 (m, 2H), 7.62-7.78 (m, 2H), 7.14 (ddd, J=7.34, 4.93, 1.10 Hz, 1H), 5.48 (dd, J=5.92, 3.07 Hz, 1H), 4.34 (dq, J=14.74, 7.29 Hz, 1H), 3.02-3.22 (m, 3H), 2.89-3.01 (m, 1H), 2.23 (dddd, J=13.70, 9.87, 6.03, 3.73 Hz, 1H), 1.86-2.04 (m, 3H), 1.55-1.81 (m, 6H).

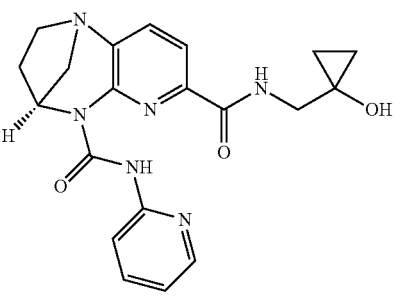

To a stirred solution of (4S)-5-(pyridin-2-ylcarbamoyl)-2,3,4,5-tetrahydro-1,4-methanopyrido[2,3-b][1,4]diazepine-7-carboxylic acid (350 mg, 1.076 mmol) in DMF (3 mL) under nitrogen at 0° C. was added DIPEA (0.564 mL, 3.23 mmol), HATU (818 mg, 2.152 mmol) and 1-(aminomethyl)cyclopropanol (103 mg, 1.183 mmol) and stirred at RT for 16 h. (TLC system: 5% Methanol in DCM. $R_f$ value: 0.2). The reaction mixture was quenched with cold water (50 mL) and extracted with EtOAc (2×80 mL). Combined organic layer was washed with brine (50 mL), dried over sodium sulphate and concentrated under reduced pressure to afford crude compound. The crude material was triturated with acetonitrile then the solid was separated and lyophilized to afford (4S)—N7-((1-hydroxycyclopropyl)methyl)-N5-(pyridin-2-yl)-3,4-dihydro-1,4-methanopyrido[2,3-b][1,4]diazepine-5,7(2H)-dicarboxamide (160 mg, 0.404 mmol, 37.5% yield) as white solid. LCMS (m/z): 395.03 [M+H]$^+$, Rt=1.5 min.

$^1$H NMR (400 MHz, CDCl$_3$): δ ppm 12.94 (s, 1H), 8.24 (d, J=8.12 Hz, 1H), 8.19 (d, J=5.19 Hz, 1H), 8.04 (br s, 1H), 7.87 (d, J=7.89 Hz, 1H), 7.73 (t, J=7.80 Hz, 1H), 7.67 (d, J=7.56 Hz, 1H), 7.02 (ddd, J=7.34, 5.04, 0.99 Hz, 1H), 5.65 (dd, J=5.92, 3.07 Hz, 1H), 5.16 (br s, 1H), 3.60-3.76 (m, 2H), 3.10-3.31 (m, 3H), 2.93-3.08 (m, 1H), 2.21-2.44 (m, 1H), 1.98-2.19 (m, 1H), 0.65-0.77 (m, 2H), −0.04-0.076 (m, 2H).

Example 36

Synthesis of (4S)—N7-((1-hydroxycyclopropyl)methyl)-N5-(pyridin-2-yl)-3,4-dihydro-1,4-methanopyrido[2,3-b][1,4]diazepine-5,7(2H)-dicarboxamide Example 37

Synthesis of (4S)—N7-isobutyl-N5-(pyridin-2-yl)-3,4-dihydro-1,4-methanopyrido[2,3-b][1,4]diazepine-5,7(2H)-dicarboxamide

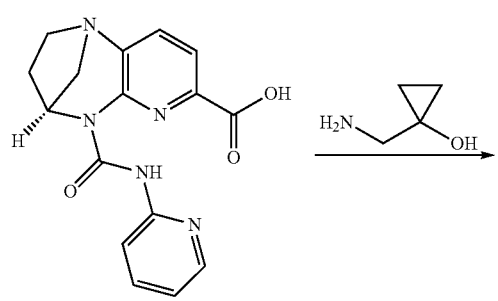

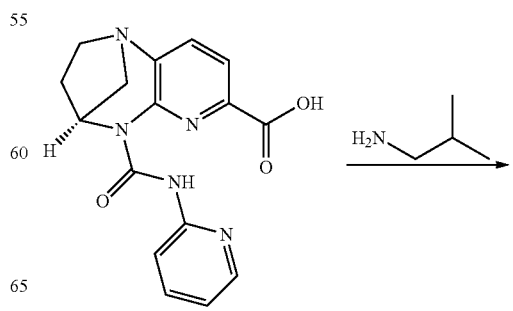

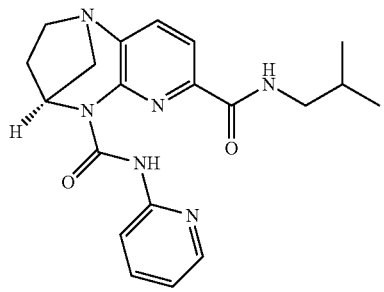

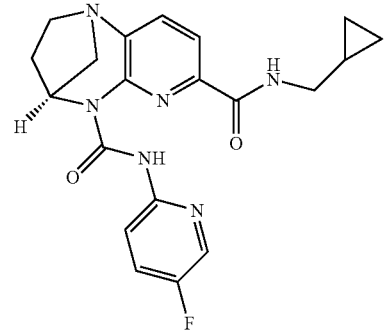

To a suspension of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in DMF (3 mL) under nitrogen at 0° C. was added DIPEA (0.483 mL, 2.77 mmol), HATU (701 mg, 1.844 mmol) and 2-methylpropan-1-amine (67.4 mg, 0.922 mmol) and stirred at RT for 16 h. (TLC system: 5% Methanol in DCM. Rf value: 0.2). The reaction mixture was quenched with cold water (50 mL) and extracted with EtOAc (2×100 mL). Combined organic layer was washed with brine (50 mL), dried over sodium sulphate and concentrated under reduced pressure to get crude compound. The crude material was purified by combiflash chromatography (Silica gel column, eluent EtOAc) to afford (4S)—N7-isobutyl-N5-(pyridin-2-yl)-3,4-dihydro-1,4-methanopyrido[2,3-b][1,4]diazepine-5,7(2H)-dicarboxamide (210 mg, 0.544 mmol, 59.0% yield) as white solid. LCMS (m/z): 381.10 [M+H]+, Rt=2.13 min.

$^1$H NMR (400 MHz, CDCl$_3$): δ ppm 13.43-13.63 (m, 1H), 8.14-8.25 (m, 2H), 8.12 (d, J=8.33 Hz, 1H), 7.91 (d, J=7.89 Hz, 1H), 7.68-7.75 (m, 1H), 7.65 (d, J=7.89 Hz, 1H), 7.01 (ddd, J=7.29, 4.99, 0.88 Hz, 1H), 5.63 (dd, J=6.03, 3.18 Hz, 1H), 3.36-3.42 (m, 2H), 3.10-3.31 (m, 3H), 3.01 (dd, J=12.17, 3.18 Hz, 1H), 2.27-2.37 (m, 1H), 2.01-2.14 (m, 2H), 1.00 (d, J=6.80 Hz, 6H).

To a stirred solution of 5-fluoropicolinic acid (410 mg, 2.90 mmol) in Chloroform (50 mL) was added TEA (0.809 mL, 5.81 mmol) and diphenyl phosphorazidate (1065 mg, 3.87 mmol) at RT under Nitrogen atmosphere, reaction mixture was stirred at rt for 10 h, then (4S)—N-(cyclopropylmethyl)-2,3,4,5-tetrahydro-1,4-methanopyrido[2,3-b][1,4]diazepine-7-carboxamide (500 mg, 1.936 mmol) was added to the reaction mixture and reaction mixture was stirred at 70° C. for 18 h. (TLC 10% MeOH in DCM R$_f$: 0.4; UV active). Reaction mixture was diluted with water (30 mL), extracted with DCM (3×30 mL). The combined organic layer was washed with water (20 mL), brine solution (20 mL) and dried over anhydrous Na$_2$SO$_4$, filtered and concentrated under reduced pressure to get crude compound. The crude was purified by column chromatography (Silicagel: 100-200 mesh, Eluent: 5% MeOH in DCM) to afford a pale yellow sticky compound, which was purified by prep HPLC (Conditions: MP-A: 10 mM Ammonium Bicarbonate (Aq) MP-B: Acetonitrile Column: Kromasil phenyl (150× 25) 10u Method: Isocratic (A:B)=50:50 Flow: 20 ml/min Solubility: ACN) to afford the desired product (4S)—N7-(cyclopropylmethyl)-N5-(5-fluoropyridin-2-yl)-3,4-dihydro-1,4-methanopyrido[2,3-b][1,4]diazepine-5,7(2H)-dicarboxamide (75 mg, 0.187 mmol, 9.66% yield) as a pale brown solid. LCMS (m/z): 397.08 [M+H]+, R$_f$=2.21 min.

$^1$H NMR (400 MHz, DMSO-d$_6$): δ ppm 13.30 (s, 1H), 8.32 (d, J=3.07 Hz, 1H), 8.24-7.98 (m, 2H), 7.82 (td, J=8.71, 2.96 Hz, 1H), 7.76-7.64 (m, 2H), 5.44 (dd, J=6.03, 2.96 Hz, 1H), 3.33-3.27 (m, 2H), 3.24-3.03 (m, 3H), 3.02-2.82 (m, 1H), 2.47-2.30 (m, 1H), 1.93 (dt, J=13.98, 7.15 Hz, 1H), 1.20-1.02 (m, 1H), 0.50-0.37 (m, 2H), 0.35-0.14 (m, 2H).

Example 38

Synthesis of (4S)—N7-(cyclopropylmethyl)-N5-(5-fluoropyridin-2-yl)-3,4-dihydro-1,4-methanopyrido[2,3-b][1,4]diazepine-5,7(2H)-dicarboxamide Example 39

Synthesis of (4S)—N7-(2-fluoroethyl)-N5-(pyridin-2-yl)-3,4-dihydro-1,4-methanopyrido[2,3-b][1,4]diazepine-5,7(2H)-dicarboxamide

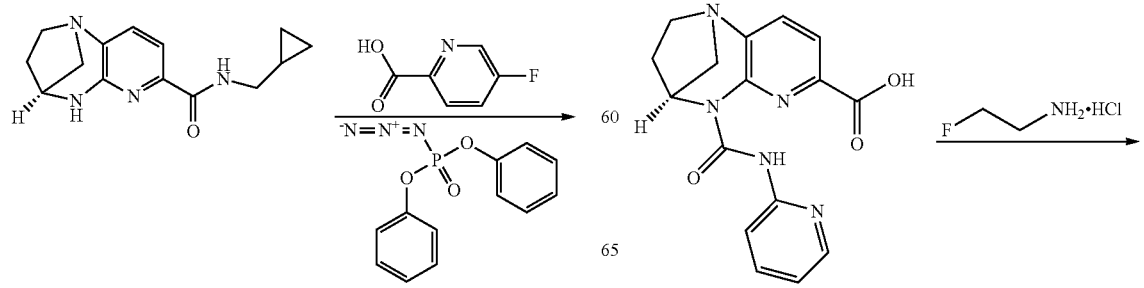

343
-continued

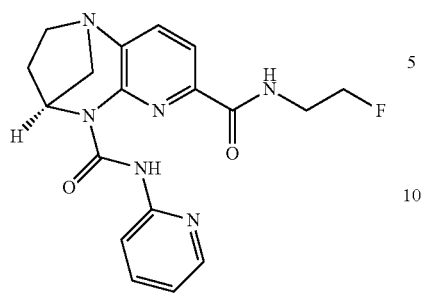

To a solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in DMF (3 mL), under nitrogen at RT was added HATU (701 mg, 1.844 mmol), DIPEA (0.483 mL, 2.77 mmol) and 2-fluoroethanamine hydrochloride (92 mg, 0.922 mmol) and stirred for 16 h. (TLC system: 10% Methanol in DCM. $R_f$ value: 0.40). Reaction mixture was diluted with ice water (20 mL) and extracted with EtOAc (2×30 mL). The combined organic layers were washed with brine (20 mL), dried over sodium sulphate, filtered and concentrated under reduced pressure to afford crude compound. The crude material was purified by combiflash chromatography (using silica gel column, 90% EtOAc in petether) to give (4S)—N7-(2-fluoroethyl)-N5-(pyridin-2-yl)-3,4-dihydro-1,4-methanopyrido[2,3-b][1,4]diazepine-5,7(2H)-dicarboxamide (145 mg, 0.388 mmol, 42.1% yield) as an off white solid. LC-MS (m/z): 371.07 [M+H]$^+$, Rt=1.65 min.

$^1$H NMR (400 MHz, CDCl$_3$): δ ppm 13.62 (s, 1H), 8.48 (br s, 1H), 8.18-8.36 (m, 1H), 8.09 (dt, J=8.33, 0.88 Hz, 1H), 7.88 (d, J=7.89 Hz, 1H), 7.71 (t, J=7.86 Hz, 1H), 7.65 (d, J=7.57 Hz, 1H), 7.01 (ddd, J=7.34, 4.93, 1.10 Hz, 1H), 5.61 (dd, J=5.92, 3.07 Hz, 1H), 4.73 (t, J=5.15 Hz, 1H), 4.61 (t, J=5.04 Hz, 1H), 3.81-3.98 (m, 2H), 3.07-3.30 (m, 3H), 2.88-3.07 (m, 1H), 2.19-2.40 (m, 1H), 1.94-2.18 (m, 1H).

Example 40

Synthesis of (4S)—N7-propyl-N5-(pyridin-2-yl)-3,4-dihydro-1,4-methanopyrido[2,3-b][1,4]diazepine-5,7(2H)-dicarboxamide

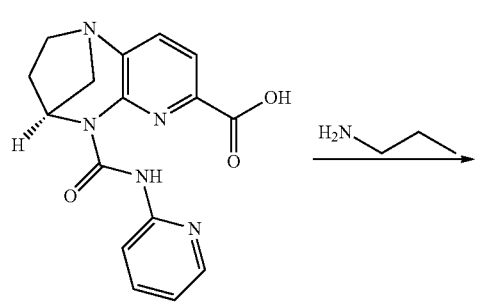

344
-continued

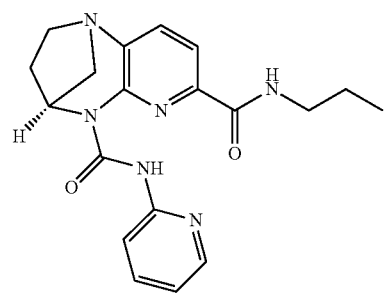

To a solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in DMF (3 mL), under nitrogen at RT was added HATU (701 mg, 1.844 mmol), DIPEA (0.483 mL, 2.77 mmol) and propan-1-amine (54.5 mg, 0.922 mmol) and stirred for 16 h. (TLC system: 10% Methanol in DCM. $R_f$ value: 0.60). Reaction mixture was diluted with ice water (20 mL) and extracted with ethylacetate (2×50 mL). The combined organic layers were washed with brine (25 mL), dried over sodium sulphate, filtered and concentrated under reduced pressure to afford crude compound. The crude material was purified by combiflash chromatography (using silica gel column, 90% EtOAc in pet ether) to afford desired compound (4S)—N7-propyl-N5-(pyridin-2-yl)-3,4-dihydro-1,4-methanopyrido[2,3-b][1,4]diazepine-5,7(2H)-dicarboxamide (118 mg, 0.312 mmol, 33.9% yield) as a pale yellow solid. LC-MS (m/z): 367.11 [M+H]$^+$, Rt=1.95 min.

$^1$H NMR (400 MHz, CDCl$_3$): δ ppm 13.55 (s, 1H), 8.23 (dd, J=4.93, 1.21 Hz, 1H), 8.07-8.18 (m, 2H), 7.90 (d, J=7.89 Hz, 1H), 7.71 (t, J=7.76 Hz, 1H), 7.64 (d, J=7.63 Hz, 1H), 7.01 (td, J=6.14, 0.88 Hz, 1H), 5.62 (dd, J=5.92, 3.29 Hz, 1H), 3.45-3.61 (m, 2H), 3.07-3.30 (m, 3H), 2.96-3.06 (m, 1H), 2.19-2.44 (m, 1H), 1.92-2.17 (m, 1H), 1.64-1.87 (m, 2H), 1.01 (t, J=7.45 Hz, 3H).

Example 41

Synthesis of (4S)—N7-(3-hydroxy-2,2-dimethylpropyl)-N5-(pyridin-2-yl)-3,4-dihydro-1,4-methanopyrido[2,3-b][1,4]diazepine-5,7(2H)-dicarboxamide

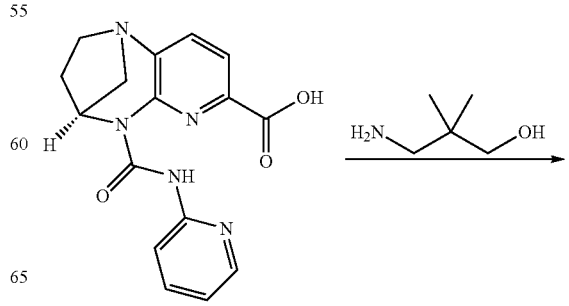

345

-continued

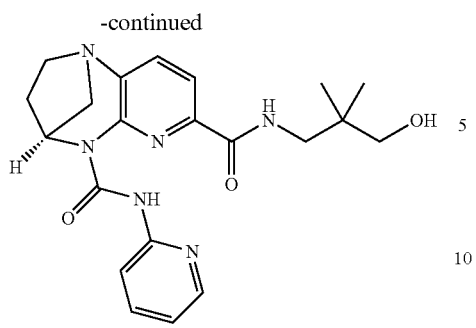

346

-continued

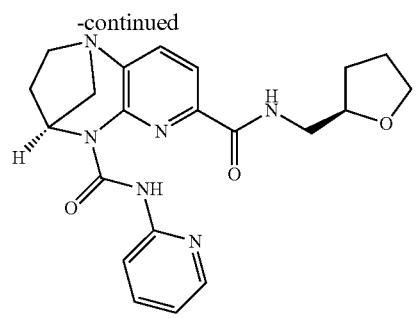

To a solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in DMF (3 mL), under nitrogen at RT was added HATU (491 mg, 1.291 mmol), DIPEA (0.483 mL, 2.77 mmol) and 3-amino-2,2-dimethylpropan-1-ol (95 mg, 0.922 mmol) and stirred for 16 h. (TLC system: 10% Methanol in DCM. $R_f$ value: 0.40). The reaction mixture was diluted with ice water (30 ml) and extracted with EtOAc (2×50 mL). The combined organic layers were washed with brine (25 mL), dried over sodium sulphate, filtered and concentrated under reduced pressure to get the crude compound. The crude material was purified by combiflash chromatography (using silica gel column, 95% EtOAc in pet ether) followed by preparative HPLC (Column: Xbridge (19×150) mm 5μ; Mobile Phase-A: 5 mmol ammonium bicarbonate (Aq), Mobile Phase-B: Acetonitrile; Method: 0/20, 10/50; Flow: 20 ml/min; Solubility: MeOH+Acetonitrile) to afford (4S)—N7-(3-hydroxy-2,2-dimethylpropyl)-N5-(pyridin-2-yl)-3,4-dihydro-1,4-methanopyrido[2,3-b][1,4]diazepine-5,7(2H)-dicarboxamide (95 mg, 0.231 mmol, 25.06% yield) as a white solid, LC-MS (m/z): 411.16 [M+H]$^+$, Rt=1.82 min.

$^1$H NMR (400 MHz, CDCl$_3$): δ ppm 13.31 (s, 1H), 8.47 (br t, J=5.92 Hz, 1H), 8.27 (d, J=5.06 Hz, 1H), 8.12 (d, J=8.33 Hz, 1H), 7.89 (d, J=7.89 Hz, 1H), 7.73 (t, J=7.84 Hz, 1H), 7.66 (d, J=7.64 Hz, 1H), 7.03 (t, J=6.11 Hz, 1H), 5.63 (dd, J=5.92, 3.07 Hz, 1H), 4.75 (t, J=7.34 Hz, 1H), 3.35-3.55 (m, 2H), 3.11-3.31 (m, 5H), 2.96-3.08 (m, 1H), 2.20-2.42 (m, 1H), 1.97-2.18 (m, 1H), 0.99 (d, J=3.29 Hz, 6H).

Example 42

Synthesis of (4S)—N5-(pyridin-2-yl)-N7-(((R)-tetrahydrofuran-2-yl)methyl)-3,4-dihydro-1,4-methanopyrido[2,3-b][1,4]diazepine-5,7(2H)-dicarboxamide

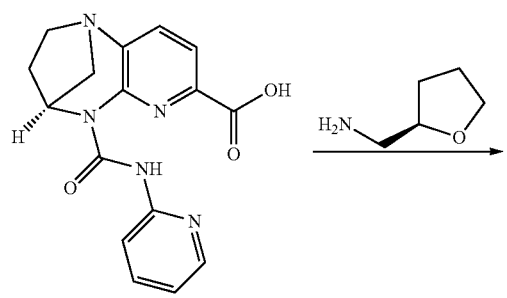

To a solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in N,N-Dimethylformamide (DMF) (3 mL), under nitrogen at room temperature, DIPEA (0.483 mL, 2.77 mmol), HATU (701 mg, 1.844 mmol) and (R)-(tetrahydrofuran-2-yl)methanamine (0.236 mL, 1.844 mmol) and stirred at for 16 h. (TLC system: 10% Methanol in DCM. Rf value: 0.40). Reaction mixture was diluted with ice water (50 ml) and extracted with ETOAc (2×80 mL). The combined organic layers were washed with brine (50 mL), dried over sodium sulphate, filtered and concentrated under reduced pressure to afford crude compound. The crude material was purified by column chromatography (silica gel, 90% ethyl acetate in hexane) followed by preparative HPLC (Column: Durashell phenylhexyl (21.1×150) mm 10μ; Mobile Phase-A: 5 mmol ammonium bicarbonate (Aq), Mobile Phase-B: Acetonitrile; Method: T/% B=0/10, 10/50, 12/50, 12.5/100, 12/100, 12.5/47; Flow: 19 ml/min; Solubility: MeOH+Acetonitrile+THF) to afford the desired product (4S)—N5-(pyridin-2-yl)-N7-(((R)-tetrahydrofuran-2-yl)methyl)-3,4-dihydro-1,4-methanopyrido[2,3-b][1,4]diazepine-5,7(2H)-dicarboxamide (125 mg, 0.298 mmol, 32.4% yield) as white solid, LC-MS (m/z): 409.12 [M+H]$^+$, Rt=1.71 min.

$^1$H NMR (400 MHz, CDCl$_3$): δ ppm 13.57 (s, 1H), 8.19-8.43 (m, 2H), 8.09 (dt, J=8.33, 0.99 Hz, 1H), 7.89 (d, J=7.89 Hz, 1H), 7.58-7.78 (m, 2H), 6.91-7.07 (m, 1H), 5.62 (dd, J=5.92, 3.07 Hz, 1H), 4.18-4.43 (m, 1H), 3.87 (ddd, J=8.28, 7.07, 6.14 Hz, 1H), 3.67-3.79 (m, 2H), 3.60 (dt, J=13.54, 6.28 Hz, 1H), 3.08-3.32 (m, 3H), 2.94-3.07 (m, 1H), 2.18-2.47 (m, 1H), 1.83-2.09 (m, 4H), 1.62-1.79 (m, 1H).

Example 43 (Peak 1)

Example 44 (Peak 2)

Synthesis of (4S)—N7-(2,2-difluorocyclopropyl)-N5-(pyridin-2-yl)-3,4-dihydro-1,4-methanopyrido[2,3-b][1,4]diazepine-5,7(2H)-dicarboxamide

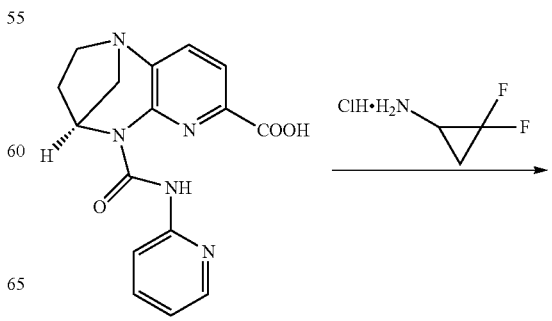

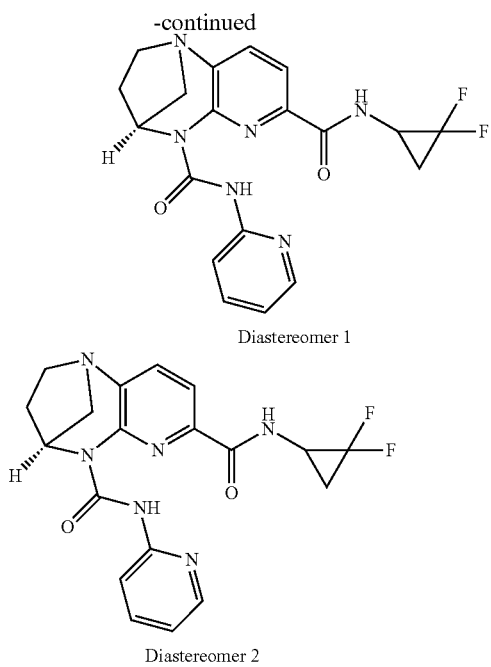

Diastereomer 1

Diastereomer 2

To a solution of (4S)-5-(pyridin-2-ylcarbamoyl)-2,3,4,5-tetrahydro-1,4-methanopyrido[2,3-b][1,4]diazepine-7-carboxylic acid (800 mg, 2.459 mmol) in DMF (10 mL) under nitrogen at RT was added DIPEA (2.147 mL, 12.30 mmol), HATU (1870 mg, 4.92 mmol) and 2,2-difluorocyclopropanamine hydrochloride (319 mg, 2.459 mmol) and stirred for 16 h. Reaction mixture was quenched with ice cold water (40 mL) and extracted with EtOAc (2×50 mL). The combined organic layers were washed with brine (30 mL), dried over sodium sulphate, filtered and concentrated under reduced pressure to afford crude compound. The crude material was purified by combiflash chromatography (using silica gel column, 80% EtOAc in pet ether) to give desired compound as distaereomeric mixtures. The diastereomers were separated by chiral SFC purification (Column: Chiralpak AD-H (250×30) mm, % $CO_2$: 55.0%, % co-solvent: 45.0% (100% Methanol), Total Flow: 90.0 g/min, Back Pressure: 100 bar, UV: 262 nm, Stack time: 2.6 min, Load/inj: 14.0 mg, Solubility: MeOH+Acetonitrile, Instrument details: Thar SFC-200 NEW-2) to afford two single diasteromers with unknown absolute stereochemistry.

Peak 1

(4S)—N7-(2,2-difluorocyclopropyl)-N5-(pyridin-2-yl)-3,4-dihydro-1,4-methanopyrido[2,3-b][1,4]diazepine-5,7(2H)-dicarboxamide (150 mg, 0.373 mmol, 15.19% yield) as white solid. (TLC system: 10% Methanol in DCM. $R_f$ value: 0.50). LC-MS (m/z): 401.04 [M+H]$^+$, Rt=1.90 min.

$^1$H NMR (400 MHz, CDCl$_3$): δ ppm 13.38 (s, 1H), 8.19-8.34 (m, 2H), 8.03-8.19 (m, 1H), 7.90 (d, J=7.89 Hz, 1H), 7.73 (t, J=7.86 Hz, 1H), 7.66 (d, J=8.11 Hz, 1H), 6.92-7.14 (m, 1H), 5.62 (dd, J=5.92, 3.07 Hz, 1H), 3.38-3.65 (m, 1H), 3.08-3.31 (m, 3H), 2.92-3.07 (m, 1H), 2.19-2.44 (m, 1H), 1.87-2.12 (m, 2H), 1.66-1.86 (m, 1H).

Peak 2

(4S)—N7-(2,2-difluorocyclopropyl)-N5-(pyridin-2-yl)-3,4-dihydro-1,4-methanopyrido[2,3-b][1,4]diazepine-5,7(2H)-dicarboxamide (145 mg, 0.358 mmol, 14.57% yield) as white solid. (TLC system: 10% Methanol in DCM. $R_f$ value: 0.50). LC-MS calculated for $C_{19}H_{18}F2N_6O_2$ (m/z): 401.04 [M+H]$^+$, Rt=1.91 min.

$^1$H NMR (400 MHz, CDCl$_3$): δ ppm 13.40 (s, 1H), 8.27 (dt, J=4.99, 0.90 Hz, 2H), 8.12 (d, J=8.33 Hz, 1H), 7.91 (d, J=7.89 Hz, 1H), 7.72 (t, J=7.90 Hz, 1H), 7.66 (d, J=8.08 Hz, 1H), 6.97-7.24 (m, 1H), 5.63 (dd, J=6.03, 3.18 Hz, 1H), 3.40-3.68 (m, 1H), 3.08-3.30 (m, 3H), 2.95-3.07 (m, 1H), 2.19-2.43 (m, 1H), 1.87-2.11 (m, 2H), 1.63-1.84 (m, 1H).

Example 45

Synthesis of (4S)—N7-((R)-3-methylbutan-2-yl)-N5-(pyridin-2-yl)-3,4-dihydro-1,4-methanopyrido[2,3-b][1,4]diazepine-5,7(2H)-dicarboxamide

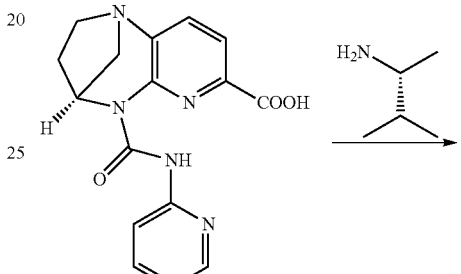

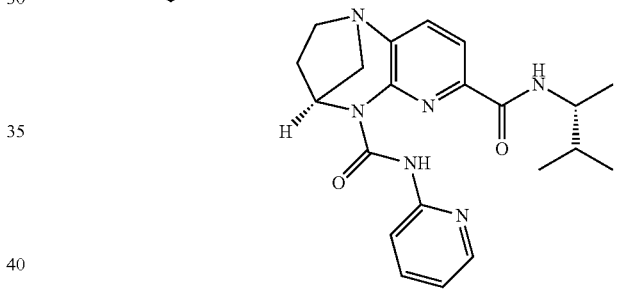

To a solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in DMF (3 mL) under nitrogen at RT was added HATU (701 mg, 1.844 mmol), DIPEA (0.805 mL, 4.61 mmol) followed by (R)-3-methylbutan-2-amine (80 mg, 0.922 mmol) and stirred at RT for 8 h. (TLC system: 5% Methanol in DCM. $R_f$ value: 0.4). Reaction mixture was diluted with ice water (30 ml), and extracted with EtOAc (2×35 mL). The combined organic layers were washed with brine (30 mL), dried over sodium sulphate, filtered and concentrated under reduced pressure to get crude the compound. The crude material was purified by combiflash chromatography (using silica gel column, 85% ethyl acetate in hexane) followed by preparative HPLC (Column: Xterra C18 (19×250) mm 10µ; Mobile Phase-A: 5 mmol ammonium bicarbonate (Aq), Mobile Phase-B: Acetonitrile; Method-35:65; Flow: 18 ml/min; Solubility: Acetonitrile) to afford (4S)—N7-((R)-3-methylbutan-2-yl)-N5-(pyridin-2-yl)-3,4-dihydro-1,4-methanopyrido[2,3-b][1,4]diazepine-5,7(2H)-dicarboxamide (162 mg, 0.411 mmol, 44.5% yield) as a white solid, LC-MS (m/z): 395.18 [M+H]$^+$, Rt=2.31 min.

$^1$H NMR (400 MHz, CDCl$_3$): δ ppm 13.17 (s, 1H), 8.05-8.31 (m, 2H), 7.91 (d, J=7.89 Hz, 1H), 7.55-7.76 (m, 3H), 6.99 (t, J=6.16 Hz, 1H), 5.65 (dd, J=6.03, 3.18 Hz, 1H), 4.09 (dquin, J=9.21, 6.91, 6.91, 6.91, 6.91 Hz, 1H), 3.05-3.28 (m, 3H), 2.88-3.03 (m, 1H), 2.29 (dddd, J=14.09, 9.92, 6.03, 4.17 Hz, 1H), 1.85-2.09 (m, 2H), 1.30 (d, J=6.80 Hz, 3H), 0.96 (dd, J=15.68, 6.69 Hz, 6H).

Example 46

Synthesis of (4S)—N7-((R)-1-cyclopropyl-2,2,2-trifluoroethyl)-N5-(pyridin-2-yl)-3,4-dihydro-1,4-methanopyrido[2,3-b][1,4]diazepine-5,7(2H)-dicarboxamide 1H), 5.53-5.78 (m, 1H), 4.03-4.30 (m, 1H), 3.08-3.31 (m, 3H), 2.93-3.08 (m, 1H), 2.20-2.42 (m, 1H), 1.90-2.14 (m, 1H), 1.41-1.57 (m, 1H), 0.75-0.91 (m, 1H), 0.51-0.71 (m, 2H), 0.30-0.51 (m, 1H).

Example 47

Synthesis of (4S)—N7-(2,2-difluoropropyl)-N5-(pyridin-2-yl)-3,4-dihydro-1,4-methanopyrido[2,3-b][1,4]diazepine-5,7(2H)-dicarboxamide

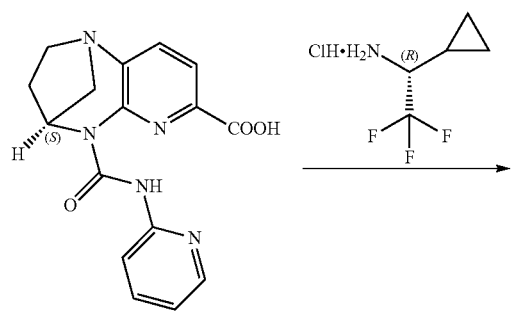

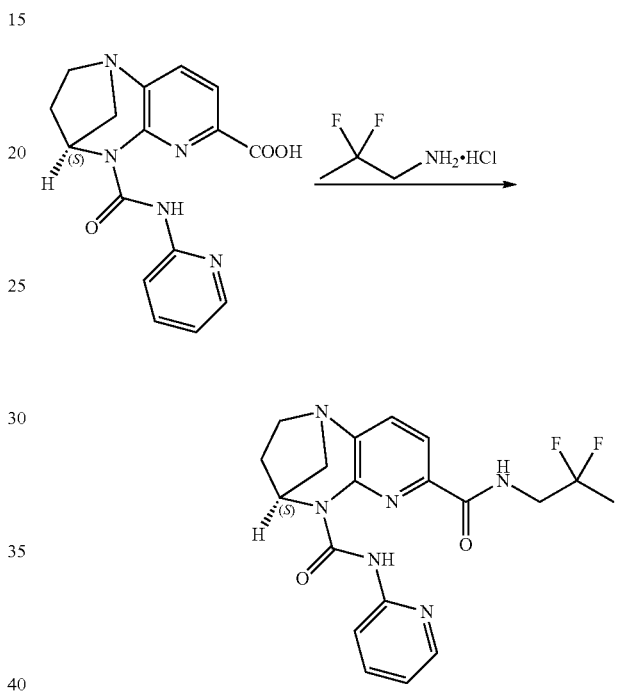

To a solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in DMF (3 mL) under nitrogen at RT was added HATU (701 mg, 1.844 mmol), DIPEA (0.805 mL, 4.61 mmol) and (R)-1-cyclopropyl-2,2,2-trifluoroethanamine hydrochloride (162 mg, 0.922 mmol) and stirred for 8 h. (TLC system: 5% Methanol in DCM. Rf value: 0.4). Reaction mixture was diluted with ice water (20 ml) and extracted with EtOAc (2×25 mL). The combined organic layers were washed with brine (30 mL) dried over sodium sulphate, filtered and concentrated under reduced pressure to get crude compound. The crude material was purified by combiflash chromatography (using silica gel column, 85% ethyl acetate in hexane) followed by preparative HPLC (Column: Xbridge (19×150) mm 10µ; Mobile Phase-A: 5 mmol ammonium bicarbonate (Aq), Mobile Phase-B: Acetonitrile; Method-45:55; Flow: 18 ml/min; Solubility: Acetonitrile) to afford (4S)—N7-((R)-1-cyclopropyl-2,2,2-trifluoroethyl)-N5-(pyridin-2-yl)-3,4-dihydro-1,4-methanopyrido[2,3-b][1,4]diazepine-5,7(2H)-dicarboxamide (158 mg, 0.354 mmol, 38.4% yield) as white solid, LC-MS (m/z): 447.05 [M+H]+, Rt=2.40 min.

$^1$H NMR (400 MHz, CDCl$_3$): δ ppm 13.32 (s, 1H), 8.19-8.27 (m, 2H), 8.10-8.19 (m, 1H), 7.95 (d, J=7.89 Hz, 1H), 7.60-7.79 (m, 2H), 7.01 (ddd, J=7.34, 4.93, 1.10 Hz, To a solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in DMF (3 mL) under nitrogen at RT was added HATU (701 mg, 1.844 mmol), DIPEA (0.805 mL, 4.61 mmol) and 2,2-difluoropropan-1-amine hydrochloride (121 mg, 0.922 mmol) and stirred at RT for 16 h. (TLC system: 5% Methanol in DCM. R$_f$ value: 0.4). The reaction mixture was diluted with ice water (20 ml) and extracted with EtOAc (2×25 mL). Combined organic layers were washed with brine (30 mL), dried over sodium sulphate, filtered and concentrated under reduced pressure to get the crude compound. The crude material was purified by combiflash chromatography (using silica gel column, 80% EtOAc in hexane) to afford the desired product (4S)—N7-(2,2-difluoropropyl)-N5-(pyridin-2-yl)-3,4-dihydro-1,4-methanopyrido[2,3-b][1,4]diazepine-5,7(2H)-dicarboxamide (140 mg, 0.347 mmol, 37.6% yield) as an off white solid. LC-MS (m/z): 403.10 [M+H]+, Rt=1.88 min.

$^1$H NMR (400 MHz, DMSO-d$_6$): δ ppm 13.37 (s, 1H), 8.51 (br t, J=6.58 Hz, 1H), 8.23-8.41 (m, 1H), 8.01 (d, J=8.33 Hz, 1H), 7.84 (td, J=7.84, 1.86 Hz, 1H), 7.67-7.79 (m, 2H), 7.11 (ddd, J=7.29, 4.99, 1.10 Hz, 1H), 5.43 (dd, J=5.81, 2.96 Hz, 1H), 3.91 (td, J=14.41, 6.91 Hz, 2H), 3.04-3.26 (m, 3H), 2.89-3.03 (m, 1H), 2.15-2.39 (m, 1H), 1.94 (dt, J=14.03, 7.02 Hz, 1H), 1.68 (t, J=18.96 Hz, 3H).

Example 48

Synthesis of (4S)—N7-(tert-butyl)-N5-(pyridin-2-yl)-3,4-dihydro-1,4-methanopyrido[2,3-b][1,4]diazepine-5,7(2H)-dicarboxamide

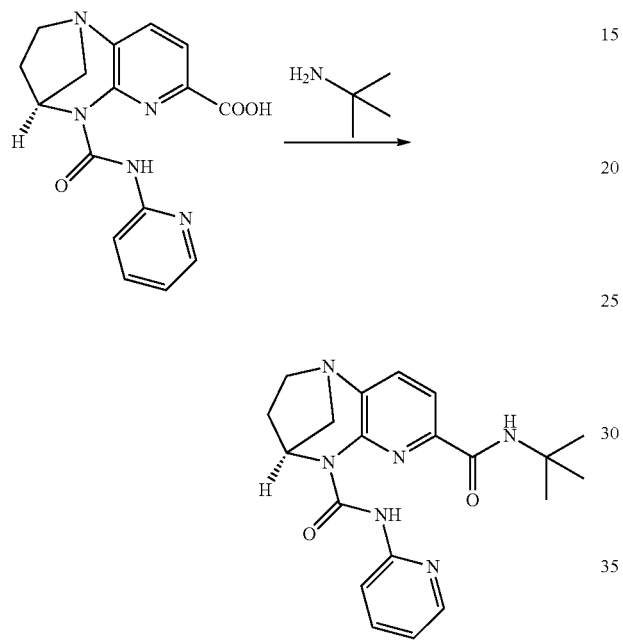

To a solution of (4S)-5-(pyridin-2-ylcarbamoyl)-2,3,4,5-tetrahydro-1,4-methanopyrido[2,3-b][1,4]diazepine-7-carboxylic acid (280 mg, 0.861 mmol) in DMF (3 mL) under nitrogen at RT was added HATU (655 mg, 1.721 mmol), DIPEA (0.601 mL, 3.44 mmol) and 2-methylpropan-2-amine (62.9 mg, 0.861 mmol) and stirred for 16 h. (TLC system: 10% Methanol in DCM. $R_f$ value: 0.35). The reaction mixture was diluted with ice water (30 ml) and extracted with EtOAc (2×30 mL). The combined organic layers were washed with brine (30 mL), dried over sodium sulphate, filtered and concentrated under reduced pressure to get crude compound. The crude material was purified by combiflash chromatography (using silica gel column, 80% EtOAc in hexane). to afford (4S)—N7-(tert-butyl)-N5-(pyridin-2-yl)-3,4-dihydro-1,4-methanopyrido[2,3-b][1,4]diazepine-5,7 (2H)-dicarboxamide (206 mg, 0.538 mmol, 62.5% yield) as a pale yellow solid. LC-MS (m/z): 381.10 [M+H]$^+$, Rt=1.75 min.

$^1$H NMR (400 MHz, CDCl$_3$): δ ppm 12.74 (s, 1H), 8.22 (d, J=4.98 Hz, 1H), 8.18 (d, J=8.33 Hz, 1H), 7.90 (d, J=7.89 Hz, 1H), 7.70 (t, J=7.50 Hz, 1H), 7.64 (d, J=7.56 Hz, 1H), 7.31-7.45 (m, 1H), 7.01 (ddd, J=7.29, 4.88, 0.99 Hz, 1H), 5.68 (dd, J=5.92, 3.29 Hz, 1H), 3.06-3.30 (m, 3H), 2.94-3.05 (m, 1H), 2.22-2.38 (m, 1H), 1.87-2.11 (m, 1H), 1.51-1.67 (m, 9H).

Example 49

Synthesis of (4S)—N7-(2-amino-3,3,3-trifluoropropyl)-N5-(pyridin-2-yl)-3,4-dihydro-1,4-methanopyrido[2,3-b][1,4]diazepine-5,7(2H)-dicarboxamide

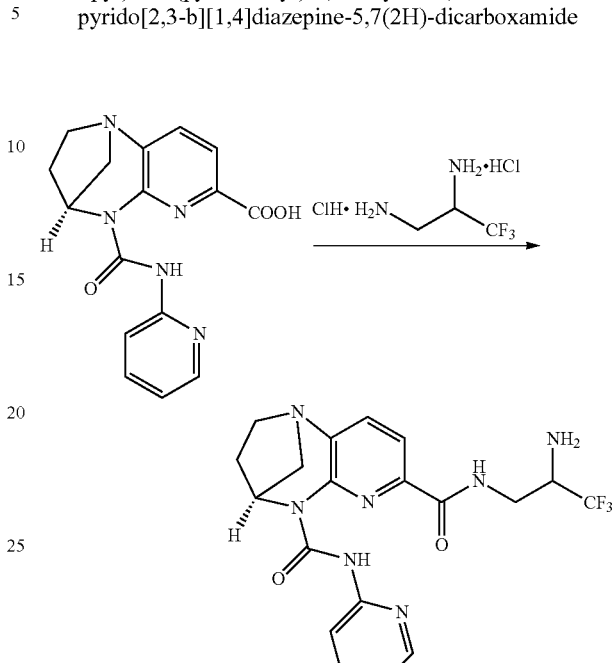

To a solution of (4S)-5-(pyridin-2-ylcarbamoyl)-2,3,4,5-tetrahydro-1,4-methanopyrido[2,3-b][1,4]diazepine-7-carboxylic acid (500 mg, 1.537 mmol) in DMF (5 mL) under nitrogen at RT was added DIPEA (1.342 mL, 7.68 mmol), HATU (1169 mg, 3.07 mmol) and 3,3,3-trifluoropropane-1,2-diamine dihydrochloride (309 mg, 1.537 mmol) and stirred at RT for 16 h. (TLC system: 5% Methanol in DCM. $R_f$ value: 0.40). Reaction mixture was diluted with ice water (20 mL) and extracted with EtOAc (2×30 mL). The combined organic layers were washed with brine (20 mL), dried over sodium sulphate, filtered and concentrated under reduced pressure to afford crude compound. The crude material was purified by combiflash chromatography (using silica gel column, 5% methanol in DCM) to give desired compound as distaereomeric mixtures. The diastereomers were separated by chiral HPLC purification (Column: Chiralpak-IC (250×30) mm, 5u; Mobile phase A: n-Hexane, B: EtOH; Method isocratic: 65:35; Flow: 41 mg/Inj; Instrument details: Make/Model: YMC prep-01) to give to afford two single diasteromers with unknown absolute stereochemistry.

Peak 2

(4S)—N7-(2-amino-3,3,3-trifluoropropyl)-N5-(pyridin-2-yl)-3,4-dihydro-1,4-methanopyrido[2,3-b][1,4]diazepine-5,7(2H)-dicarboxamide (105 mg, 0.237 mmol, 15.42% yield) as an off-white solid. LC-MS (m/z): 436.018 [M+H]$^+$, Rt=1.51 min.

$^1$H NMR (400 MHz, CDCl$_3$): δ ppm 13.46 (s, 1H), 8.19-8.38 (m, 2H), 8.14 (d, J=8.33 Hz, 1H), 7.88 (d, J=7.89 Hz, 1H), 7.73 (t, J=7.79 Hz, 1H), 7.67 (d, J=7.56 Hz, 1H), 6.93-7.14 (m, 1H), 5.62 (dd, J=5.92, 3.29 Hz, 1H), 3.80-4.00 (m, 1H), 3.49-3.75 (m, 2H), 3.09-3.31 (m, 3H), 2.98-3.07 (m, 1H), 2.20-2.43 (m, 1H), 1.97-2.18 (m, 1H), 1.48-1.66 (m, 2H).

Example 50

Synthesis of (4S)—N7-(3-amino-1,1,1-trifluoropropan-2-yl)-N5-(pyridin-2-yl)-3,4-dihydro-4-methanopyrido[2,3-b][1,4]diazepine-5,7(2H)-dicarboxamide

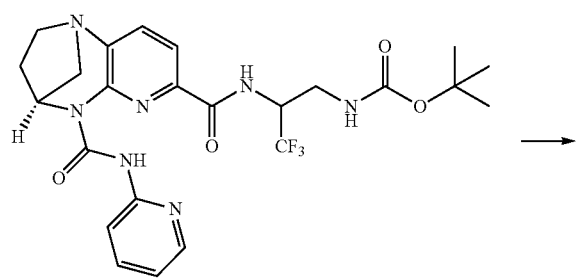

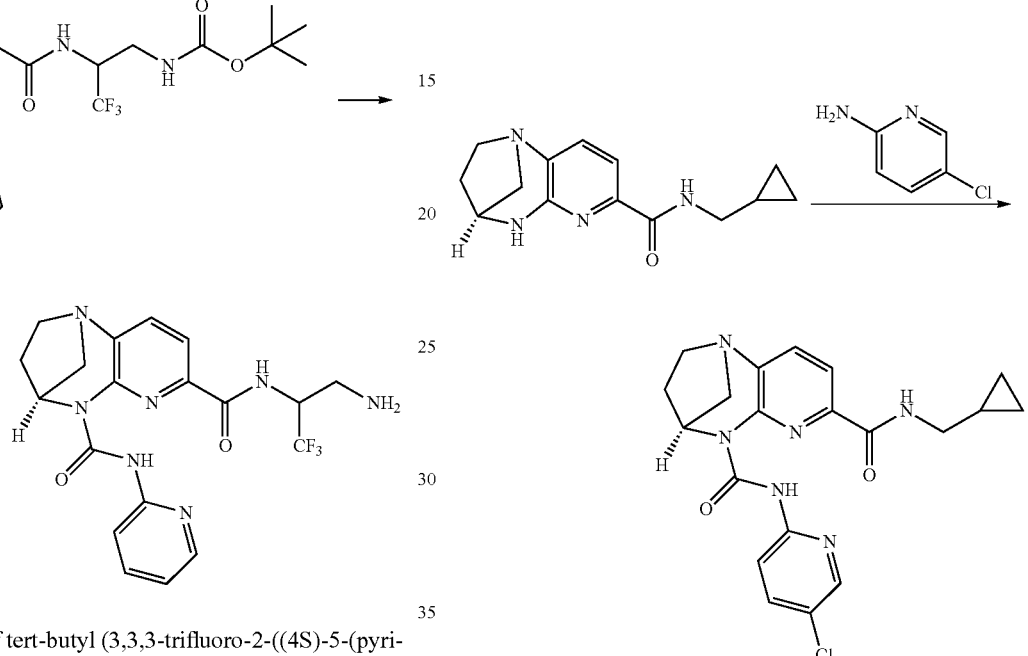

To a solution of tert-butyl (3,3,3-trifluoro-2-((4S)-5-(pyridin-2-ylcarbamoyl)-2,3,4,5-tetrahydro-1,4-methanopyrido[2,3-b][1,4]diazepine-7-carboxamido)propyl)carbamate (1.1 g, 2.054 mmol) in 1,4-Dioxane (15 mL) under nitrogen at RT was added a solution of 4M HCl (10 mL, 40.0 mmol) and stirred for 16 h. (TLC system: 5% Methanol in DCM. $R_f$ value: 0.50). The reaction mixture was concentrated under reduced pressure to remove the methanol and the residue was basified with saturated sodium bicarbonate solution (15 mL) then extracted with DCM (2×50 mL). The combined organic layer was dried over $Na_2SO_4$, filtered and concentrated to give crude compound. The crude material was purified by combiflash chromatography (using silica gel column, 5% MeOH in DCM) to give desired compound as diastereomeric mixtures. The diastereomers were separated by chiral SFC purification (Column: Chiracel OD-H (250× 21) mm, % $CO_2$: 65.0%, % co-solvent: 35.0% (100% Methanol), Total Flow: 60.0 g/min, Back Pressure: 100 bar, UV: 261 nm, Stack time: 2.0 min, Load/inj: 4.0 mg, Solubility: MeOH, Instrument details: Thar SFC-80) to afford two single diasteromers with unknown absolute stereochemistry.

Peak 1

Obtained (4S)—N7-(3-amino-1,1,1-trifluoropropan-2-yl)-N5-(pyridin-2-yl)-3,4-dihydro-1,4-methanopyrido[2,3-b][1,4]diazepine-5,7(2H)-dicarboxamide (190 mg, 0.436 mmol, 21.24% yield) as an off white solid. LC-MS (m/z): 436.011[M+H]$^+$, Rt=1.42 min.

$^1$H NMR (400 MHz, DMSO-$d_6$): δ ppm 12.90 (s, 1H), 8.17-8.39 (m, 2H), 8.10 (d, J=8.55 Hz, 1H), 7.84 (td, J=7.84, 1.86 Hz, 1H), 7.67-7.79 (m, 2H), 7.12 (ddd, J=7.23, 4.93, 0.99 Hz, 1H), 5.50 (dd, J=6.03, 2.96 Hz, 1H), 4.77 (br d, J=7.45 Hz, 1H), 2.96-3.23 (m, 6H), 2.14-2.34 (m, 1H), 1.85-2.01 (m, 1H), 1.75-1.85 (m, 2H).

Example 51

Synthesis of (4S)—N5-(5-chloropyridin-2-yl)-N7-(cyclopropylmethyl)-3,4-dihydro-1,4-methanopyrido[2,3-b][1,4]diazepine-5,7(2H)-dicarboxamide To a stirred solution of (4S)—N-(cyclopropylmethyl)-2,3,4,5-tetrahydro-1,4-methanopyrido[2,3-b][1,4]diazepine-7-carboxamide (600 mg, 2.323 mmol) in THF (30 mL) at RT was added DIPEA (2.028 mL, 11.61 mmol) and triphosgene (551 mg, 1.858 mmol) and stirred for 30 min. Then added 5-chloropyridin-2-amine (299 mg, 2.323 mmol) to the reaction mixture and stirred for 3 h. (TLC system: 5% Methanol in DCM, $R_f$: 0.2). The reaction was poured in to cold water (40 mL) and extracted with ethylacetate (2×50 mL). Combined organic layers were washed with brine (30 mL), dried over anhydrous sodium sulphate, filtered, and concentrated under reduced pressure to get the crude product. The crude material was purified by combiflash chromatography (using silica gel column, 3% methanol in DCM) followed by preparative HPLC (Column: Xbridge (19×150) mm 10μ; Mobile Phase-A: 5 mmol ammonium bicarbonate (Aq), Mobile Phase-B: Acetonitrile; Method: 0/10-2/25/10/55; Solubility: MeOH+THF) to afford the desired product (4S)—N5-(5-chloropyridin-2-yl)-N7-(cyclopropylmethyl)-3,4-dihydro-1,4-methanopyrido[2,3-b][1,4]diazepine-5,7 (2H)-dicarboxamide (150 mg, 0.354 mmol, 15.23% yield) as an off-white solid. LC-MS (m/z): 413.10 [M+H]$^+$, Rt=2.44 min.

$^1$H NMR (400 MHz, CDCl$_3$): δ ppm 13.56 (s, 1H), 8.09-8.22 (m, 2H), 7.88-8.04 (m, 2H), 7.59-7.75 (m, 2H), 5.62 (dd, J=5.81, 3.18 Hz, 1H), 3.35-3.53 (m, 2H), 3.07-3.32 (m, 3H), 2.91-3.07 (m, 1H), 2.23-2.48 (m, 1H), 1.87-2.13 (m, 1H), 1.13-1.30 (m, 1H), 0.46-0.59 (m, 2H), 0.28-0.40 (m, 2H).

Example 52

Synthesis of (4S)—N5-(pyridin-2-yl)-N7-((S)-3,3,3-trifluoro-2-hydroxypropyl)-3,4-dihydro-1,4-methanopyrido[2,3-b][1,4]diazepine-5,7(2H)-dicarboxamide

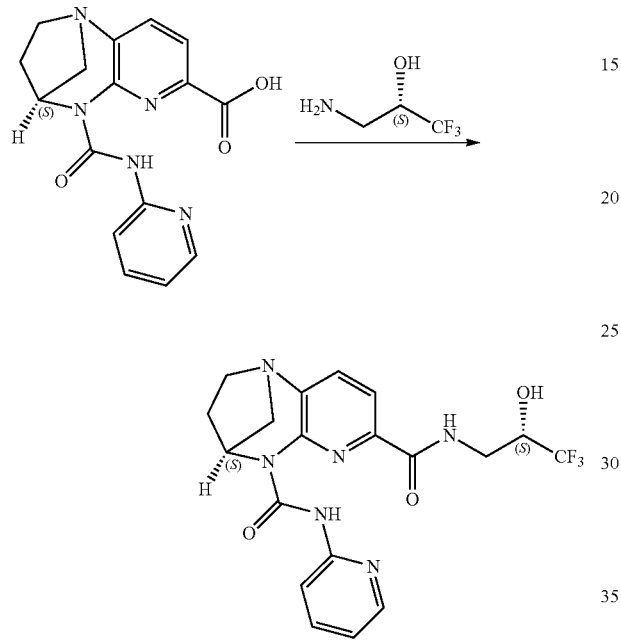

To a solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in DMF (3 mL), under nitrogen at RT was added HATU (701 mg, 1.844 mmol), DIPEA (0.483 mL, 2.77 mmol) and (S)-3-amino-1,1,1-trifluoropropan-2-ol (119 mg, 0.922 mmol) and stirred for 16 h. (TLC system: 10% Methanol in DCM. $R_f$ value: 0.3). The reaction mixture was poured in cold water (30 ml), then stirred for 15 min and the solid formed was filtered, washed with water (10 mL) and dried to give crude product. The crude material was purified by combiflash chromatography (using silica gel column, 6% methanol in DCM) to afford the desired compound (4S)—N5-(pyridin-2-yl)-N7-((S)-3,3,3-trifluoro-2-hydroxypropyl)-3,4-dihydro-1,4-methanopyrido[2,3-b][1,4]diazepine-5,7(2H)-dicarboxamide (140 mg, 0.320 mmol, 34.7% yield) as a white solid, LC-MS (m/z): 437.00 [M+H]$^+$, Rt=1.82 min.

$^1$H NMR (400 MHz, DMSO-d$_6$): δ ppm 13.34 (s, 1H), 8.41 (br t, J=5.81 Hz, 1H), 8.18-8.34 (m, 1H), 8.05 (d, J=8.33 Hz, 1H), 7.86 (td, J=7.89, 1.97 Hz, 1H), 7.64-7.79 (m, 2H), 7.14 (ddd, J=7.34, 4.93, 0.88 Hz, 1H), 6.52 (d, J=6.36 Hz, 1H), 5.44 (dd, J=5.92, 2.85 Hz, 1H), 4.19-4.35 (m, 1H), 3.76 (dt, J=13.65, 5.34 Hz, 1H), 3.56 (dt, J=14.09, 6.88 Hz, 1H), 3.05-3.28 (m, 3H), 2.83-3.03 (m, 1H), 2.19-2.47 (m, 1H), 1.93 (dt, J=13.98, 7.15 Hz, 1H).

Example 53

Synthesis of (4S)—N7-((S)-1-hydroxypropan-2-yl)-N5-(pyridin-2-yl)-3,4-dihydro-1,4-methanopyrido[2,3-b][1,4]diazepine-5,7(2H)-dicarboxamide

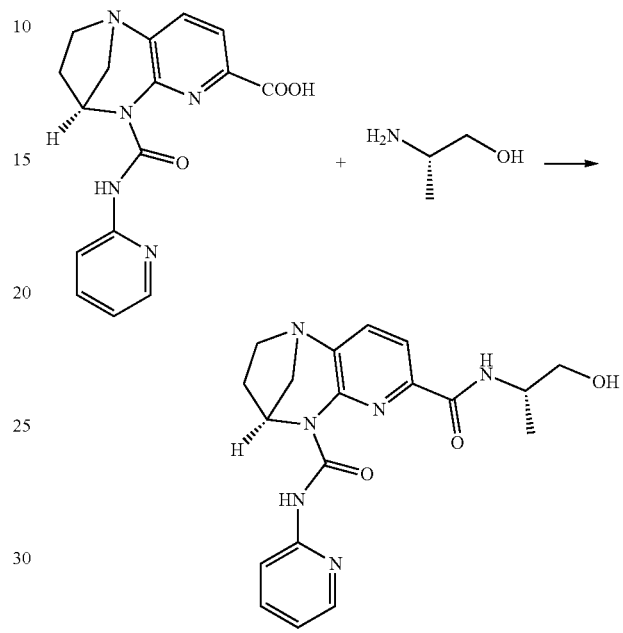

To a stirred solution of (4S)-5-(pyridin-2-ylcarbamoyl)-2,3,4,5-tetrahydro-1,4-methanopyrido[2,3-b][1,4]diazepine-7-carboxylic acid (500 mg, 1.537 mmol) in N,N-dimethylformamide (20 mL) under nitrogen at RT was added (S)-2-aminopropan-1-ol (173 mg, 2.305 mmol), HATU (877 mg, 2.305 mmol) and DIPEA (0.537 mL, 3.07 mmol) stirred for 16 h. (TLC eluting system: 10% MeOH in DCM; $R_f$—0.3; UV active). The reaction mixture was quenched with water (25 mL) and extracted into EtOAc (2×50 mL). Organic layer was separated and dried over anhydrous sodium sulphate, filtered and filtrate was evaporated to get crude compound. The crude was purified by chromatography (GRACE using C-18 reserval column, Mobile phase A: 0.1% Formic Acid in water; B: MeOH, eluent 15% B in A). Combined fractions were concentrated basified with saturated NaHCO$_3$. The aqueous layer was extracted with DCM, DCM layer was dried over anhydrous Na$_2$SO$_4$, filtered and filtrate was evaporated to afford (4S)—N7-((S)-1-hydroxypropan-2-yl)-N5-(pyridin-2-yl)-3,4-dihydro-1,4-methanopyrido[2,3-b][1,4]diazepine-5,7(2H)-dicarboxamide (120 mg, 0.299 mmol, 19.46% yield) as white solid LCMS (m/z): 383.09 [M+H]$^+$, $R_f$=1.52 min.

$^1$H NMR (400 MHz, CDCl$_3$): δ ppm 12.78 (s, 1H), 8.28 (d, J=5.27 Hz, 2H), 7.89 (d, J=7.89 Hz, 1H), 7.71-7.78 (m, 1H), 7.67 (d, J=7.89 Hz, 1H), 7.54-7.61 (m, 1H), 7.04 (ddd, J=7.34, 5.04, 0.99 Hz, 1H), 5.71 (dd, J=6.14, 3.29 Hz, 1H), 4.34-4.45 (m, 1H), 3.84-4.00 (m, 2H), 3.64-3.84 (m, 1H), 3.09-3.32 (m, 3H), 2.98-3.05 (m, 1H), 2.33 (dddd, J=14.11, 10.00, 6.14, 3.95 Hz, 1H), 1.98-2.09 (m, 1H), 1.35 (d, J=6.80 Hz, 3H)

Example 54

Synthesis of (4S)—N7-cyclopropyl-N5-(6-methyl-1H-pyrazolo[3,4-b]pyridin-3-yl)-3,4-dihydro-1,4-methanopyrido[2,3-b][1,4]diazepine-5,7(2H)-dicarboxamide

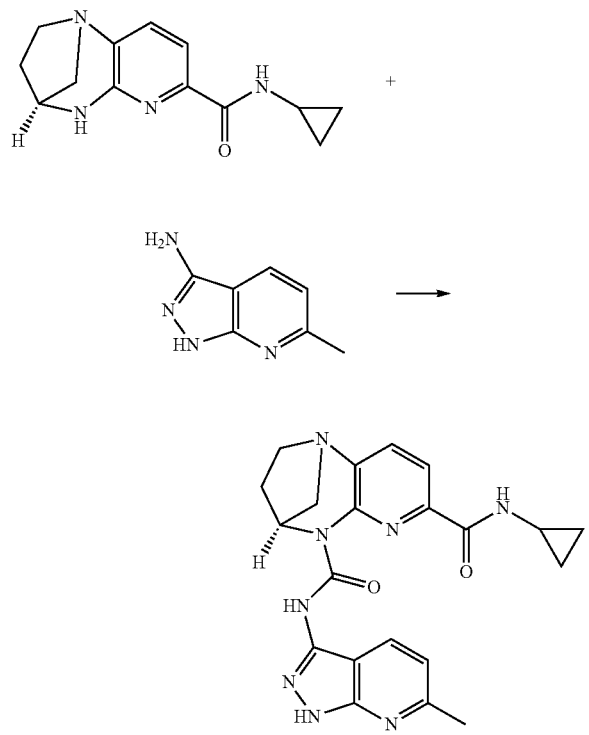 [SMILES: O=C(NC1CC1)c1ccc2c(n1)N[C@H]1CCN2C1 ; Cc1ccc2c(N)n[nH]c2n1 ; Cc1ccc2c(NC(=O)N3c4nc(C(=O)NC5CC5)ccc4N4CC[C@H]3C4)n[nH]c2n1]

To a stirred solution of (4S)—N-cyclopropyl-2,3,4,5-tetrahydro-1,4-methanopyrido[2,3-b][1,4]diazepine-7-carboxamide (500 mg, 2.047 mmol) in THF (25 mL) at RT was added triphosgene (364 mg, 1.228 mmol) and DIPEA (1.787 mL, 10.23 mmol) and stirred for 30 min. then 6-methyl-1H-pyrazolo[3,4-b]pyridin-3-amine (303 mg, 2.047 mmol) was added and reaction mixture was heated to 60° C. for 16 h. The reaction mixture was cooled to room temperature and quenched with water (50 mL) and extracted into EtOAc (2×50 mL). Organic layer was separated, dried over anhydrous sodium sulphate, filtered and filtrate was evaporated to get crude compound. The crude was purified by chromatography (neutral alumina, eluent: 20% ethyl acetate in hexane) to afford (4S)—N7-cyclopropyl-N5-(6-methyl-1H-pyrazolo[3,4-b]pyridin-3-yl)-3,4-dihydro-1,4-methanopyrido[2,3-b][1,4]diazepine-5,7(2H)-dicarboxamide (340 mg, 0.791 mmol, 38.6% yield) as off white solid. LCMS (m/z): 419.16 [M+H]$^+$, R$_t$=1.63 min.

$^1$H NMR (400 MHz, CDCl$_3$): δ ppm 13.13 (s, 1H), 10.92 (s, 1H), 8.73 (d, J=8.33 Hz, 1H), 7.90 (d, J=7.89 Hz, 1H), 7.66 (d, J=7.89 Hz, 1H), 7.38-7.58 (m, 1H), 7.04 (d, J=8.33 Hz, 1H), 5.66 (dd, J=5.81, 3.18 Hz, 1H), 3.13-3.33 (m, 3H), 2.99-3.11 (m, 2H), 2.72 (s, 3H), 2.25-2.41 (m, 1H), 1.97-2.17 (m, 1H), 0.78-0.95 (m, 4H).

Example 55

Synthesis of (4S)—N5-(4-methylpyridin-2-yl)-N7-((R)-1,1,1-trifluoropropan-2-yl)-3,4-dihydro-1,4-methanopyrido[2,3-b][1,4]diazepine-5,7(2H)-dicarboxamide

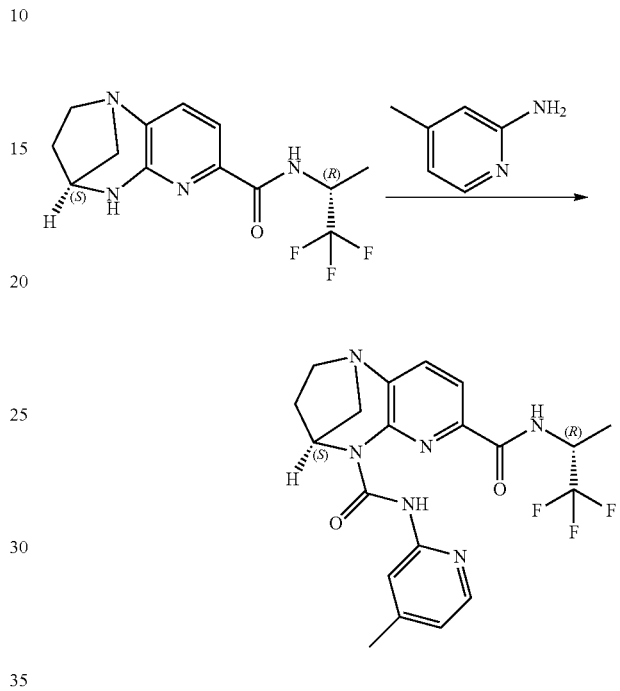

To a stirred solution of (4S)—N—((R)-1,1,1-trifluoropropan-2-yl)-2,3,4,5-tetrahydro-1,4-methanopyrido[2,3-b][1,4]diazepine-7-carboxamide (1 g, 3.33 mmol) in THF (100 mL) at 0° C. was added triethylamine (2.79 mL, 19.98 mmol) followed by triphosgene (0.988 g, 3.33 mmol) and the resulting yellow solution was stirred at RT for 10 min. To the reaction mixture at 0° C. was added 4-methylpyridin-2-amine (1.080 g, 9.99 mmol) solution in THF and heated to 70° C. for 24 h. (TLC eluent: 10% Methanol in DCM Rf: 0.4; UV active). The reaction was cooled to RT and mixture was partitioned between water (100 mL) and EtOAc (300 mL). The organic layer was separated, washed with brine (150 mL), dried over sodium sulphate filtered and concentrated under reduced pressure to get crude brown solid. The crude compound was purified by preparative HPLC (Column: XBridge C 18 (75×4.6 mm, 3.5μ); MP-A: 5 mM Ammonium Bicarbonate, MP-B: Acetonitrile; Method (T/% B): 0/5, 0.8/5, 5/50, 9/98.12/98, 12.1/5, 15/5; Flow: 0.8 mL/min; Solubility: Acetonitrile) to afford (4S)—N5-(4-methylpyridin-2-yl)-N7-((R)-1,1,1-trifluoropropan-2-yl)-3,4-dihydro-1,4-methanopyrido[2,3-b][1,4]diazepine-5,7(2H)-dicarboxamide (235 mg, 0.541 mmol, 16.24% yield) as an off-white fluffy solid. LC-MS (m/z): 435.10 [M+H]$^+$, Rt=2.17 min.

$^1$H NMR (400 MHz, CDCl$_3$): δ ppm 13.20 (s, 1H), 8.02-8.16 (m, 2H), 7.99 (s, 1H), 7.95 (d, J=7.62 Hz, 1H), 7.67 (d, J=7.89 Hz, 1H), 6.85 (dd, J=5.15, 0.77 Hz, 1H), 5.64 (dd, J=5.92, 3.29 Hz, 1H), 4.98-5.15 (m, 1H), 3.09-3.31 (m, 3H), 2.93-3.07 (m, 1H), 2.29-2.40 (m, 4H), 1.91-2.16 (m, 1H), 1.52-1.66 (m, 3H).

Example 56

Synthesis of (4S)—N5-(5-methylpyridin-2-yl)-N7-((R)-1,1,1-trifluoropropan-2-yl)-3,4-dihydro-1,4-methanopyrido[2,3-b][1,4]diazepine-5,7(2H)-dicarboxamide

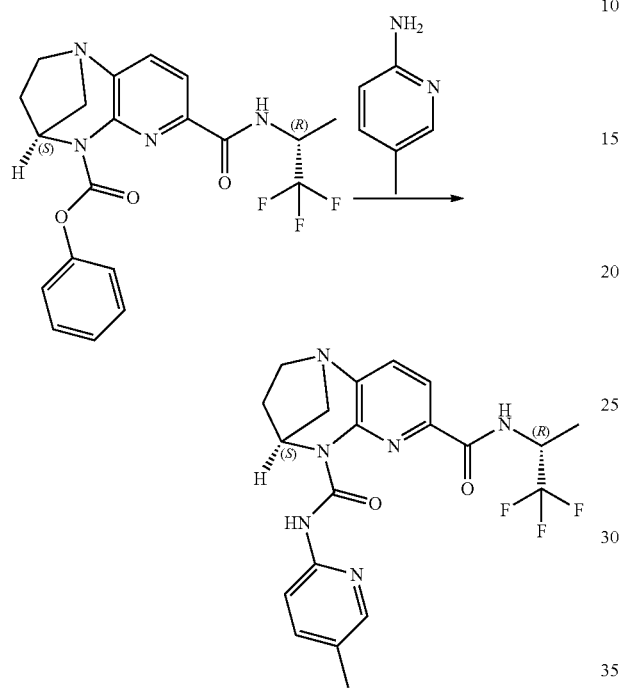

To a stirred solution of 5-methylpyridin-2-amine (309 mg, 2.85 mmol) in THF (80 mL) under nitrogen at −78° C. was added LiHMDS (2.85 mL, 2.85 mmol) drop wisely and stirred for 30 min. Then added (4S)-phenyl-7-(((R)-1,1,1-trifluoropropan-2-yl)carbamoyl)-3,4-dihydro-1,4-methanopyrido[2,3-b][1,4]diazepine-5(2H)-carboxylate (600 mg, 1.427 mmol) at −78° C. and the resulting reaction mixture was stirred at −78° C. for 1 h and at RT for 6 h. (TLC eluent: 5% Methanol in DCM Rf: 0.3; UV active). The reaction mixture was quenched with aqueous NH4Cl (50 mL) and extracted with EtOAc (2×100 mL). Combined organic layer was dried over anhydrous Na2SO4, filtered and concentrated under reduced pressure to obtain crude product. The crude compound was purified by preparative HPLC (Column: XBridge C-18 (75×4.6 mm, 3.5μ); MP-A: 5 mM Ammonium Bicarbonate (Aq), MP-B: Acetonitrile; Method (T/% B): 0/5, 0.8/5, 5/50, 9/98.12/98, 12.1/5, 15/5; Flow: 0.8 ml/min; Solubility: acetonitrile) to afford (4S)—N5-(5-methylpyridin-2-yl)-N7-((R)-1,1,1-trifluoropropan-2-yl)-3,4-dihydro-1,4-methanopyrido[2,3-b][1,4]diazepine-5,7(2H)-dicarboxamide (228 mg, 0.523 mmol, 36.6% yield) as a pale brown solid. LC-MS (m/z): 435.14 [M+H]$^+$, Rt=2.31 min.

$^1$H NMR (400 MHz, CDCl$_3$): δ ppm 13.13 (s, 1H), 7.91-8.11 (m, 4H), 7.66 (d, J=7.89 Hz, 1H), 7.54 (dd, J=8.33, 2.19 Hz, 1H), 5.65 (dd, J=5.92, 3.29 Hz, 1H), 4.98-5.14 (m, 1H), 3.17-3.29 (m, 2H), 3.08-3.14 (m, 1H), 2.99-3.06 (m, 1H), 2.24-2.39 (m, 4H), 1.98-2.21 (m, 1H), 1.52-1.66 (m, 3H).

Example 57

Synthesis of (4S)—N5-(5-fluoro-3-methylpyridin-2-yl)-N7-((R)-1,1,1-trifluoropropan-2-yl)-3,4-dihydro-1,4-methanopyrido[2,3-b][1,4]diazepine-5,7(2H)-dicarboxamide

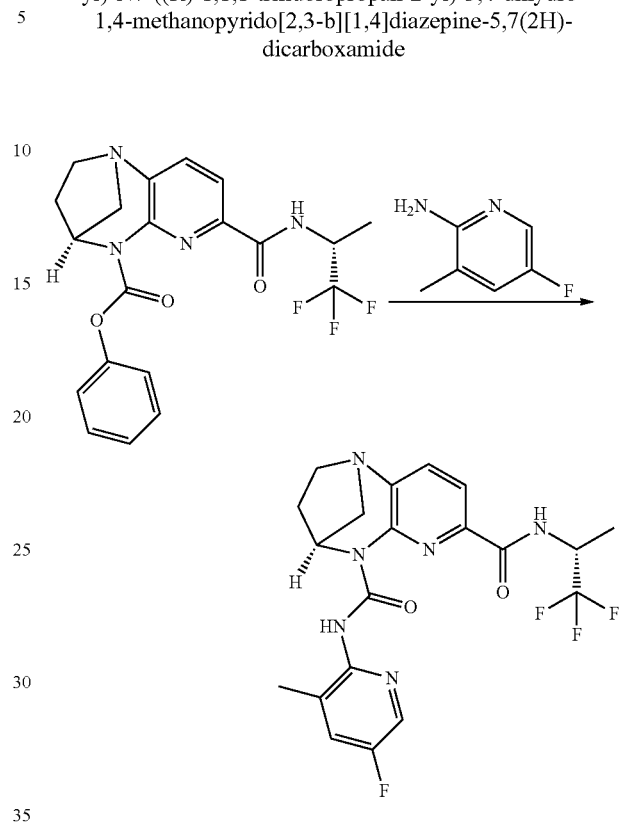

To a stirred solution of 5-fluoro-3-methylpyridin-2-amine (396 mg, 3.14 mmol) in THF (50 mL) at −78° C. under nitrogen was added LiHMDS (3.57 mL, 3.57 mmol) drop wisely and stirred for 30 min. Then added (4S)-phenyl 7-(((R)-1,1,1-trifluoropropan-2-yl)carbamoyl)-3,4-dihydro-1,4-methanopyrido[2,3-b][1,4]diazepine-5(2H)-carboxylate (600 mg, 1.427 mmol) at −78° C. and the resulting reaction mixture was slowly warmed to RT and stirred for 6 h. (TLC eluent: 5% Methanol in DCM Rf: 0.3; UV active). The reaction mixture was quenched with aqueous NH4Cl (50 mL) and the aqueous layer was extracted with EtOAc (2×100 mL). Combined organic layer was dried over anhydrous Na2SO4, filtered and concentrated under reduced pressure to obtain crude product. The crude compound was submitted for preparative HPLC (Column: XBridge C-18 (250×4.6 mm, 5μ); Mobile Phase-A: 5 mM Ammonium Bicarbonate, Mobile Phase-B: Acetonitrile; Method (T/% B): 0/10, 1/10, 10/60, 15/60, 18/98, 20/98, 20.1/10, 25/10; Flow: 1.0 mL/min, Solubility: Acetonitrile) to afford (4S)—N5-(5-fluoro-3-methylpyridin-2-yl)-N7-((R)-1,1,1-trifluoropropan-2-yl)-3,4-dihydro-1,4-methanopyrido[2,3-b][1,4]diazepine-5,7(2H)-dicarboxamide (85 mg, 0.187 mmol, 13.09% yield) as an off-white solid. LC-MS (m/z): 453.15 [M+H]$^+$, Rt=2.01 min.

$^1$H NMR (400 MHz, CDCl$_3$): δ ppm 12.20 (s, 1H), 8.07 (d, J=2.63 Hz, 1H), 7.84 (d, J=7.89 Hz, 1H), 7.56-7.74 (m, 2H), 7.28-7.41 (m, 1H), 5.50 (dd, J=5.92, 3.29 Hz, 1H), 4.87-5.04 (m, 1H), 3.11-3.34 (m, 3H), 3.02 (dd, J=12.06, 3.29 Hz, 1H), 2.42 (s, 3H), 2.30 (qd, J=9.87, 4.38 Hz, 1H), 1.95-2.18 (m, 1H), 1.37 (d, J=7.23 Hz, 3H).

Example 58

Synthesis of (4S)—N7-(1-cyclopropyl-2-hydroxyethyl)-N5-(pyridin-2-yl)-3,4-dihydro-1,4-methanopyrido[2,3-b][1,4]diazepine-5,7(2H)-dicarboxamide

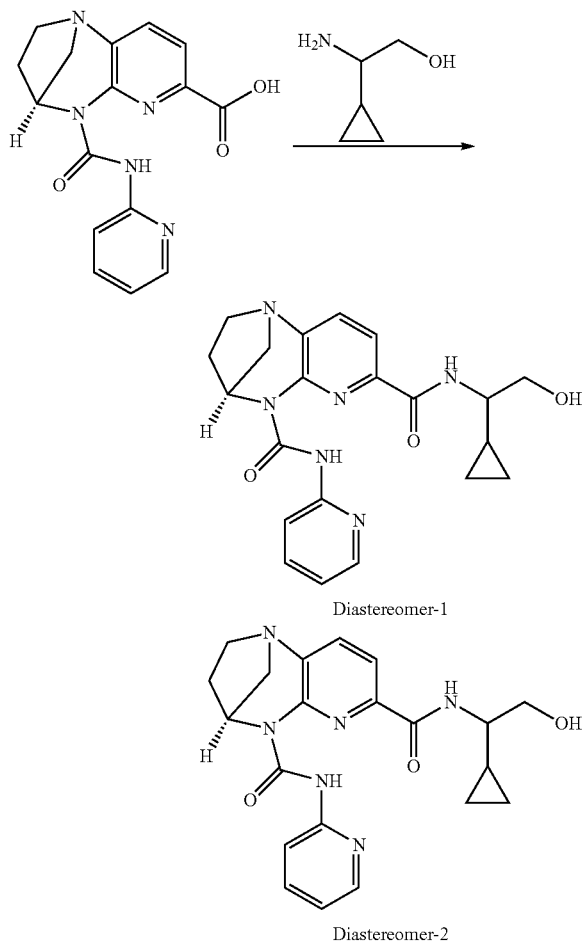

Diastereomer-1

Diastereomer-2

To a stirred suspension of (4S)-5-(pyridin-2-ylcarbamoyl)-2,3,4,5-tetrahydro-1,4-methanopyrido[2,3-b][1,4]diazepine-7-carboxylic acid (800 mg, 2.459 mmol) in DMF (15 mL), under nitrogen at RT was added DIPEA (1.288 mL, 7.38 mmol) and HATU (1870 mg, 4.92 mmol) and stirred for 10 min. 2-amino-2-cyclopropylethanol (298 mg, 2.95 mmol) was added to the above reaction mixture and stirred for 16 h. (TLC eluent: 5% Methanol in DCM $R_f$: 0.4; UV active). The reaction was quenched with cold water (200 mL) and extracted with EtOAc (2×300 mL) and the combined organic layer was dried over $Na_2SO_4$, filtered and concentrated to get crude compound. The crude material was purified by combiflash chromatography (using silica gel column, 5% Methanol in DCM) to afford the desired compound 800 mg (HPLC-94%) as high viscous liquid. Further the diastereomeric mixture was separated by preparative chiral SFC (Thar SFC-200 NEW-2; Chiralcel OX-H (250×30) mm, 5u; % CO2—50.0%; % Co solvent-50.0% (Methanol); Total Flow—100.0 g/min; Back Pressure-100.0 bar; UV-261 nm; Stack time-9.0 min; Load/inj: 45.0 mg; Solubility: Methanol) to give two single unknown dastereomers.

Peak-1

Collected fraction from SFC was concentrated and the residue was triturated with diethyl ether to afford the desired compound (4S)—N7-(1-cyclopropyl-2-hydroxyethyl)-N5-(pyridin-2-yl)-3,4-dihydro-1,4-methanopyrido[2,3-b][1,4]diazepine-5,7(2H)-dicarboxamide (115 mg, 0.280 mmol, 11.39% yield) as off white solid. LC-MS (m/z): 409.18 [M+H]$^+$, Rt=1.71 min.

$^1$H NMR (400 MHz, CDCl$_3$): δ ppm 12.83 (s, 1H), 8.18-8.31 (m, 2H), 7.88 (d, J=7.89 Hz, 1H), 7.62-7.80 (m, 3H), 6.96-7.15 (m, 1H), 5.73 (dd, J=6.14, 3.29 Hz, 1H), 3.80-4.05 (m, 3H), 3.54-3.74 (m, 1H), 3.08-3.31 (m, 3H), 2.92-3.07 (m, 1H), 2.33 (dddd, J=14.11, 9.95, 6.08, 3.84 Hz, 1H), 1.95-2.17 (m, 1H), 1.12-1.32 (m, 1H), 0.57-0.65 (m, 1H), 0.35-0.54 (m, 3H).

Example 59 (Peak 1)

Example 60 (Peak 2)

Synthesis of (4S)—N7-(1-cyclopropyl-2-methoxyethyl)-N5-(pyridin-2-yl)-3,4-dihydro-1,4-methanopyrido[2,3-b][1,4]diazepine-5,7(2H)-dicarboxamide

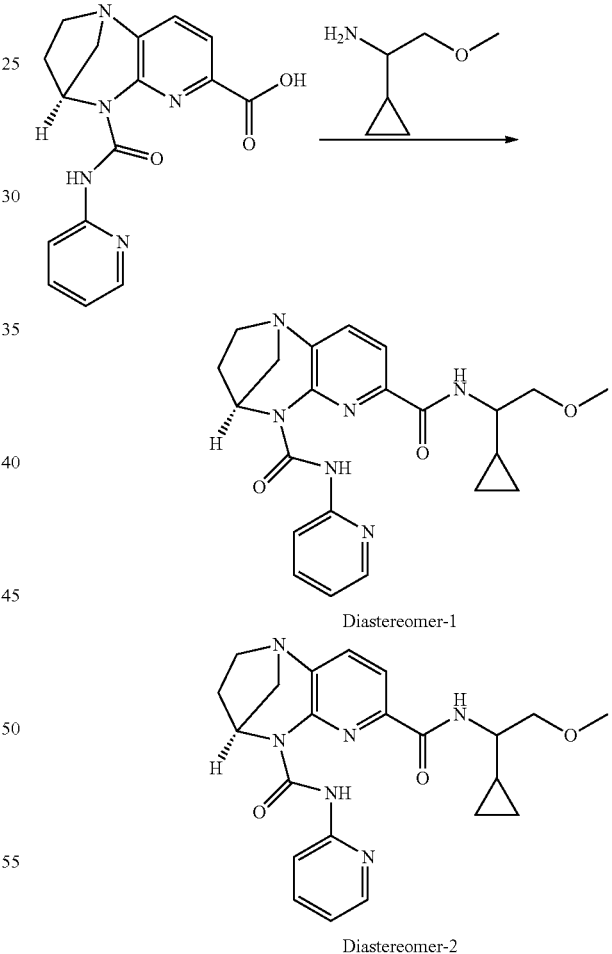

Diastereomer-1

Diastereomer-2

To a suspension of (4S)-5-(pyridin-2-ylcarbamoyl)-2,3,4,5-tetrahydro-1,4-methanopyrido[2,3-b][1,4]diazepine-7-carboxylic acid (800 mg, 2.459 mmol) in DMF (15 ml) under nitrogen at RT was added DIPEA (1.288 mL, 7.38 mmol) and HATU (1870 mg, 4.92 mmol) and stirred or 10 min. 1-cyclopropyl-2-methoxyethanamine (340 mg, 2.95 mmol) was added to the above reaction mixture and stirred at RT for 16 h. (TLC eluent: 5% Methanol in DCM, Rf: 0.5;

UV active). The reaction was quenched with cold water and extracted with EtOAc (2×300 mL). combined organic layer was dried over Na₂SO₄, filtered and concentrated to get crude product. The crude compound was purified by combiflash chromatography (using silica gel column, 5% Methanol in DCM) to afford the desired compound 760 mg (HPLC-96%) as a viscous liquid. Further the diastereomeric mixture was separated by preparative chiral SFC (Thar SFC-200 NEW-2; Chiralcel OD-H (250×21) mm, 5u; % CO2—60.0%; % Co solvent-40.0% (Methanol); Total Flow—600.0 g/min; Back Pressure-100.0 bar; UV-261 nm; Stack time-0.0 min; Load/inj: 14.0 mg; Solubility: Methanol) to give two single unknown dastereomers.

Peak-1

Collected fraction from SFC was concentrated, washed with diethyl ether to afford the desired compound (4S)—N7-(1-cyclopropyl-2-methoxyethyl)-N5-(pyridin-2-yl)-3,4-dihydro-1,4-methanopyrido[2,3-b][1,4]diazepine-5,7(2H)-dicarboxamide (105 mg, 0.247 mmol, 10.05% yield) as an off white solid. LC-MS: 423.15 [M+H]⁺, Rt=2.01 min.

¹H NMR (400 MHz, DMSO-d₆): δ 13.19 (s, 1H), 8.29 (br d, J=4.17 Hz, 1H), 8.09 (d, J=8.33 Hz, 1H), 7.80-7.96 (m, 2H), 7.66-7.80 (m, 2H), 7.10-7.23 (m, 1H), 5.47 (br dd, J=5.59, 2.74 Hz, 1H), 3.53-3.80 (m, 3H), 3.04-3.23 (m, 6H), 2.97 (dd, J=11.84, 3.07 Hz, 1H), 2.11-2.30 (m, 1H), 1.96 (dt, J=13.92, 7.07 Hz, 1H), 1.10 (dtd, J=12.96, 7.99, 7.99, 5.04 Hz, 1H), 0.45-0.61 (m, 1H), 0.21-0.44 (m, 3H).

Peak 2

Collected fraction from SFC was concentrated to afford the desired compound (4S)—N7-(1-cyclopropyl-2-methoxyethyl)-N5-(pyridin-2-yl)-3,4-dihydro-1,4-methanopyrido[2,3-b][1,4]diazepine-5,7(2H)-dicarboxamide (132 mg, 0.311 mmol, 12.63% yield) as an off white solid. LC-MS calculated for C₂₂H₂₆N₆O₃ (m/z): 423.15 [M+H]⁺, Rt=1.99 min.

¹H NMR (400 MHz, DMSO-d₆): δ ppm 13.16 (s, 1H), 8.30 (dt, J=4.93, 0.93 Hz, 1H), 8.09 (d, J=8.33 Hz, 1H), 7.80-7.95 (m, 2H), 7.65-7.80 (m, 2H), 7.15 (ddd, J=7.29, 4.99, 0.88 Hz, 1H), 5.47 (dd, J=5.92, 3.07 Hz, 1H), 3.55-3.78 (m, 3H), 3.06-3.28 (m, 6H), 2.92-3.02 (m, 1H), 2.23 (dddd, J=13.70, 9.87, 6.03, 3.95 Hz, 1H), 1.95 (dt, J=13.76, 7.04 Hz, 1H), 0.98-1.20 (m, 1H), 0.47-0.60 (m, 1H), 0.26-0.44 (m, 3H).

Example 61

Synthesis of (4S)—N5-(pyridin-2-yl)-N7-((S)-1,1,1-trifluorobutan-2-yl)-3,4-dihydro-1,4-methanopyrido[2,3-b][1,4]diazepine-5,7(2H)-dicarboxamide

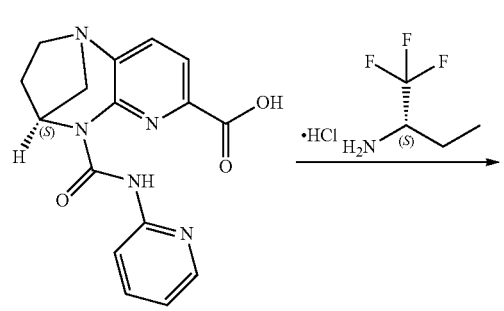

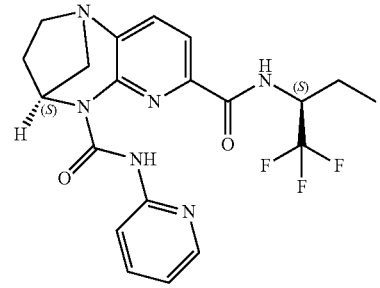

To a stirred solution of (4S)-5-(pyridin-2-ylcarbamoyl)-2,3,4,5-tetrahydro-1,4-methanopyrido[2,3-b][1,4]diazepine-7-carboxylic acid (7 g, 21.52 mmol) in N,N-Dimethylformamide (DMF) (60 mL) were added HATU (16.36 g, 43.0 mmol) and DIPEA (18.79 mL, 108 mmol) at RT. Then (S)-1,1,1-trifluorobutan-2-amine hydrochloride (4.22 g, 25.8 mmol) was added and the reaction mixture was stirred at 28° C. for 16 h. (TLC eluent: 5% MeOH in EtOAc, R$_f$: 0.6). The reaction mixture was diluted with water (60 mL) and extracted with EtOAc (2×120 mL). The combined organic layer was dried over anhydrous Na₂SO₄, filtered and filtrate was evaporated to obtain the crude compound. The crude compound was purified by flash column chromatography (silica gel: 100-200 mesh, eluent: 2% methanol in ethylacetate) to afford the desired product (4S)—N-5-(pyridin-2-yl)-N-7-((S)-1,1,1-trifluorobutan-2-yl)-3,4-dihydro-1,4-methanopyrido[2,3-b][1,4]diazepine-5,7(2H)-dicarboxamide (5 g, 11.44 mmol, 53.2% yield) as an off-white solid. LCMS (m/z): 435.10 [M+H]⁺, Rt=2.39 min.

¹H NMR (400 MHz, CDCl₃): δ ppm 13.25 (s, 1H), 8.22 (d, J=3.95 Hz, 1H), 8.15 (d, J=8.55 Hz, 1H), 7.97 (s, 1H), 7.95-7.84 (m, 1H), 7.76-7.63 (m, 2H), 7.06-6.98 (m, 1H), 5.65 (dd, J=5.92, 3.07 Hz, 1H), 4.89-4.75 (m, 1H), 3.30-3.17 (m, 2H), 3.16-3.10 (m, 1H), 3.06-2.99 (m, 1H), 2.38-2.28 (m, 1H), 2.13-1.95 (m, 3H), 1.05 (t, J=7.34 Hz, 3H).

Example 62

Synthesis of (4S)—N5-(7H-pyrrolo[2,3-d]pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide

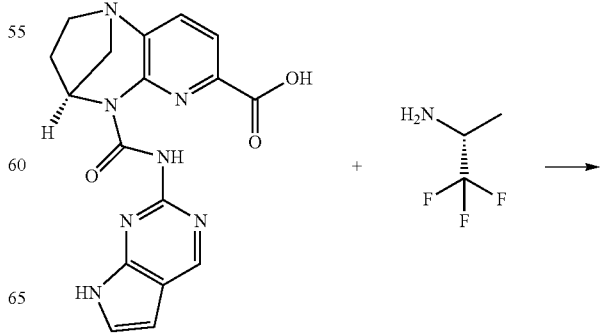

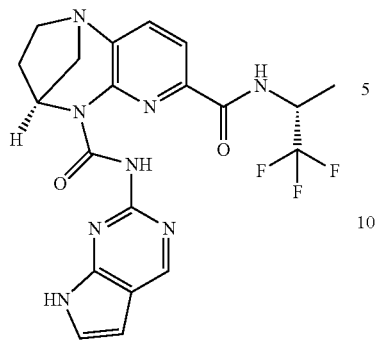

To a stirred solution of (4S)-5-((7H-pyrrolo[2,3-d]pyrimidin-2-yl)carbamoyl)-2,3,4,5-tetrahydro-1,4-methanopyrido[2,3-b][1,4]diazepine-7-carboxylic acid (400 mg, 1.095 mmol) in DMF under nitrogen at 0° C. was added (S)-1,1,1-trifluoropropan-2-amine (186 mg, 1.642 mmol) (20 mL), DIPEA (0.765 mL, 4.38 mmol) and HATU (624 mg, 1.642 mmol) and the mixture was stirred at RT for 16 h. (TLC eluent: 100% EtOAc in Hexane, Rf: 0.3). The reaction mixture was partitioned between ice cold water (40 mL) and EtOAc (100 mL), organic layer was separated, dried over anhydrous $Na_2SO_4$, filtered and filtrate was evaporated to afford crude compound. The crude product was purified by column chromatography (neutral Alumina, 4% MeOH in DCM eluent) to afford (4S)—N5-(7H-pyrrolo[2,3-d]pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide (245 mg, 0.527 mmol, 48.2% yield) as an off white solid. LCMS (m/z): 461.13 [M+H]$^+$, R$_t$=1.59 min $^1$H NMR (400 MHz, CDCl$_3$): δ ppm 13.62 (s, 1H), 11.32 (br s, 1H), 8.76 (s, 1H), 8.21 (br d, J=9.43 Hz, 1H), 7.99 (d, J=7.89 Hz, 1H), 7.71 (d, J=7.89 Hz, 1H), 7.44 (dd, J=3.51, 2.41 Hz, 1H), 6.54 (dd, J=3.73, 1.75 Hz, 1H), 5.76 (dd, J=5.70, 3.07 Hz, 1H), 5.00-5.23 (m, 1H), 3.10-3.40 (m, 3H), 3.00-3.10 (m, 1H), 2.32-2.48 (m, 1H), 2.09-2.22 (m, 1H), 1.57-1.65 (m, 3H).

Example 63

Synthesis of (4S)—N5-(pyrazin-2-yl)-N7-(2,2,2-trifluoroethyl)-3,4-dihydro-1,4-methanopyrido[2,3-b][1,4]diazepine-5,7(2H)-dicarboxamide

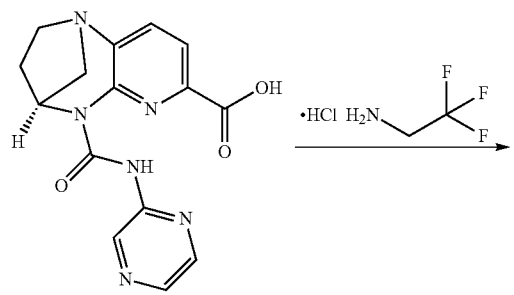

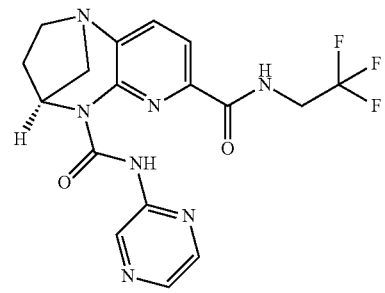

To a stirred solution of (4S)-5-(pyrazin-2-ylcarbamoyl)-2,3,4,5-tetrahydro-1,4-methanopyrido[2,3-b][1,4]diazepine-7-carboxylic acid (25 g, 77 mmol) in DMF (300 mL) were added HATU (43.7 g, 115 mmol), DIPEA (26.8 mL, 153 mmol) and 2,2,2-trifluoroethanamine Hydrochloride (15.57 g, 115 mmol) at room temperature and stirred for 16 h. (TLC eluent: Neat ethyl acetate: R$_f$: 0.3). The reaction mixture was diluted with water (200 mL) and extracted ethylacetate (3×100 mL). The combined organic layer was washed with brine solution (100 mL) and dried over anhydrous $Na_2SO_4$, filtered and evaporated to get crude compound. The crude compound was purified by flash column chromatography (silica-gel: 100-200 mesh, eluent: 2% MeOH in ethyl acetate) to afford the desired compound (4S)—N-5-(pyrazin-2-yl)-N7-(2,2,2-trifluoroethyl)-3,4-dihydro-1,4-methanopyrido[2,3-b][1,4]diazepine-5,7(2H)-dicarboxamide (22 g, 53.9 mmol, 70.4% yield) as a white solid. LCMS (m/z): 408.1 [M+H]$^+$, Rt=1.86 min.

Pd Scavenger Treatment:

The obtained product (22.5 g) was treated with Pd scavenger (13 g, silicycle resin) in ethanol (1.5 L) at 70° C. for 4 h, then it was filtered at hot (around 50° C.) condition and solvent was removed in vacuo to afford the required product.

$^1$H NMR (400 MHz, CDCl$_3$): δ ppm 13.63 (s, 1H), 9.49 (d, J=1.32 Hz, 1H), 8.35 (d, J=2.41 Hz, 1H), 8.25-8.14 (m, 1H), 8.14-8.03 (m, 1H), 7.95 (d, J=7.89 Hz, 1H), 7.71 (d, J=7.89 Hz, 1H), 5.64 (dd, J=5.92, 3.07 Hz, 1H), 4.22-4.16 (m, 2H), 3.37-2.93 (m, 4H), 2.46-2.24 (m, 1H), 2.14-1.94 (m, 1H).

Example 64

Synthesis of (4S)—N5-(6-methyl-1H-pyrazolo[3,4-b]pyridin-3-yl)-N7-(2,2,2-trifluoroethyl)-3,4-dihydro-1,4-methanopyrido[2,3-b][1,4]diazepine-5,7(2H)-dicarboxamide

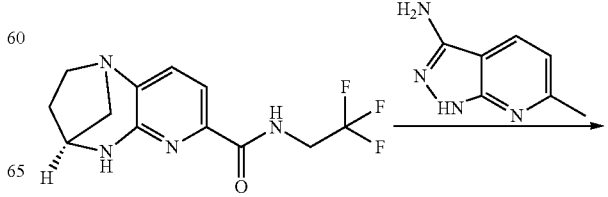

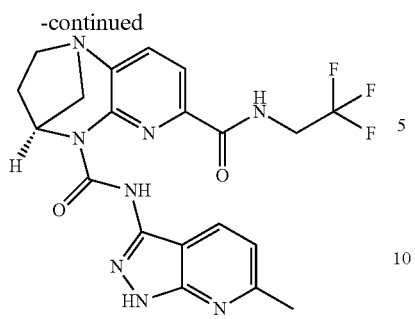

To a stirred solution of (4S)—N-(2,2,2-trifluoroethyl)-2,3,4,5-tetrahydro-1,4-methanopyrido[2,3-b][1,4]diazepine-7-carboxamide (22 g, 77 mmol in Tetrahydrofuran (THF, 200 mL)) were added triphosgene (13.68 g, 46.1 mmol) and DIPEA (67.1 mL, 384 mmol) at 0° C. Then the reaction mixture was stirred at room temperature for 30 min and added 6-methyl-1H-pyrazolo [3, 4-b]pyridin-3-amine (17.08 g, 115 mmol), stirred at 80° C. for 16 h. (TLC eluent: 5% MeOH in DCM: $R_f$—0.4). The reaction mixture was diluted with cold water (100 mL) and extracted with ethyl acetate (2×300 mL). The combined organic layer was dried over anhydrous sodium sulphate and concentrated under reduced pressure to obtain crude compound. The crude compound was purified by flash column chromatography (silica-gel: 100-200 mesh, eluent: 80% EtoAc in Petether) to afford the desired product (4S)—N5-(6-methyl-1H-pyrazolo[3,4-b]pyridin-3-yl)-N7-(2,2,2-trifluoroethyl)-3,4-dihydro-1,4-methanopyrido[2,3-b][1,4]diazepine-5,7(2H)-dicarboxamide (25 g, 54.2 mmol, 70.6% yield) as a white solid. LCMS (m/z): 461.17 [M+H]+, RT=1.75.

Pd Scavenger Treatment:

The obtained product was treated with Pd scavenger (13 g, silicycle resin) in ethanol (1.5 L) at 70° C. for 4 h, then it was filtered at hot (around 50° C.) condition and solvent was removed in vacuo to afford the required product.

$^1$H NMR (400 MHz, CDCl$_3$): δ ppm 13.25 (s, 1H), 10.71 (br s, 1H), 8.76 (d, J=8.33 Hz, 1H), 7.97-7.88 (m, 2H), 7.69 (d, J=7.67 Hz, 1H), 7.04 (d, J=8.55 Hz, 1H), 5.64 (dd, J=5.92, 3.07 Hz, 1H), 4.33-4.14 (m, 2H), 3.32-3.14 (m, 3H), 3.09-3.01 (m, 1H), 2.70 (s, 3H), 2.42-2.30 (m, 1H), 2.11 (dt, J=14.20, 6.82 Hz, 1H).

Example 65

Synthesis of (4S)—N7-(2,2-difluorocyclopropyl)-N5-(6-methyl-1H-pyrazolo[3,4-b]pyridin-3-yl)-3,4-dihydro-1,4-methanopyrido[2,3-b][1,4]diazepine-5,7(2H)-dicarboxamide

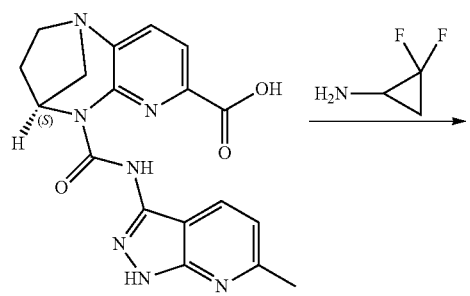

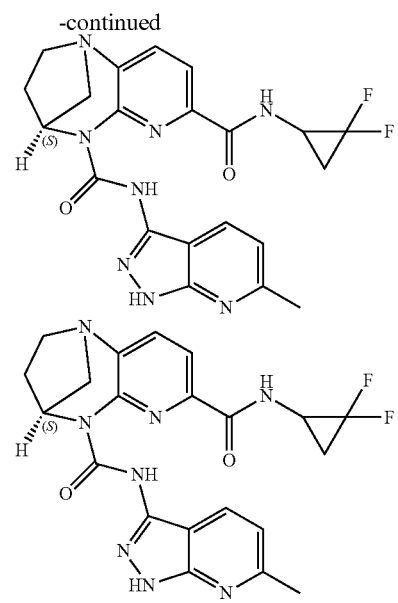

To a stirred solution of (4S)-5-((6-methyl-1H-pyrazolo[3,4-b]pyridin-3-yl)carbamoyl)-2,3,4,5-tetrahydro-1,4-methanopyrido[2,3-b][1,4]diazepine-7-carboxylic acid (500 mg, 1.318 mmol) in DMF (15 mL) were added HATU (601 mg, 1.582 mmol), DIPEA (0.460 mL, 2.64 mmol) and 2,2-difluorocyclopropanamine Hydrochloride (188 mg, 1.450 mmol) at room temperature and stirred for 16 h. (TLC eluent: 10% MeOH in DCM: $R_f$—0.4). The reaction mixture was diluted with ice water (20 mL) and extracted with ethyl acetate (2×50 mL). The combined organic layer was washed with brine solution and dried over anhydrous sodium sulphate, concentrated under reduced pressure to obtain crude compound (N36233-72-A1). The crude product was purified by flash column chromatography (100-200 silicagel using gradient mixture of 2% Methanol in DCM as eluent) to afford diastereomeric mixture of (4S)—N7-(2,2-difluorocyclopropyl)-N5-(6-methyl-1H-pyrazolo[3,4-b]pyridin-3-yl)-3,4-dihydro-1,4-methanopyrido[2,3-b][1,4]diazepine-5,7(2H)-dicarboxamide. This mixture was again purified by SFC (Conditions: Chiralcel OD-H (250×30) mm, 5μ,% CO2: 50.0%,% Co solvent: 50.0% (100% M ETHANOL), total flow: 90.0 g/min, Back Pressure: 100.0 bar, UV: 210 nm, Stack time: 6.0 min, Load/inj: 10.0 mg, Solubility: Methanol+ACN, Total No of injections: 80), separated peaks as peak-I (Fastest eluent) (4S)—N7-(2,2-difluorocyclopropyl)-N5-(6-methyl-1H-pyrazolo[3,4-b]pyridin-3-yl)-3,4-dihydro-1,4-methanopyrido[2,3-b][1,4]diazepine-5,7(2H)-dicarboxamide (200 mg, 0.438 mmol, 33.2% yield) as a pale brown solid. LCMS (m/z): 455.12 [M+H]$^+$, Rt: 1.7 min.

Peak-I (Fastest Eluent)

$^1$H NMR (400 MHz, CDCl$_3$): δ ppm 13.14 (s, 1H), 10.28 (brs, 1H), 8.72 (d, J=8.33 Hz, 1H), 7.89 (d, J=7.89 Hz, 1H), 7.67 (s, 2H), 7.04 (d, J=8.55 Hz, 1H), 5.65 (dd, J=5.70, 3.07 Hz, 1H), 3.68-3.52 (m, 1H), 3.33-3.19 (m, 2H), 3.18-3.11 (m, 1H), 3.09-3.00 (m, 1H), 2.68 (s, 3H), 2.41-2.29 (m, 1H), 2.19-2.03 (m, 1H), 1.90 (dtd, J=13.02, 9.50, 9.50, 6.36 Hz, 1H), 1.78 (ddt, J=14.20, 8.71, 5.43, 5.43 Hz, 1H).

Example 66

Synthesis of (4S)—N5-(pyrimidin-4-yl)-N7-((R)-1,1,1-trifluoropropan-2-yl)-3,4-dihydro-1,4-methanopyrido[2,3-b][1,4]diazepine-5,7(2H)-dicarboxamide

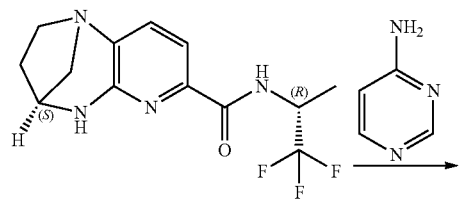

Example 67

Synthesis of (4S)—N5-(5-chloropyridin-2-yl)-N7-cyclopropyl-3,4-dihydro-1,4-methanopyrido[2,3-b][1,4]diazepine-5,7(2H)-dicarboxamide

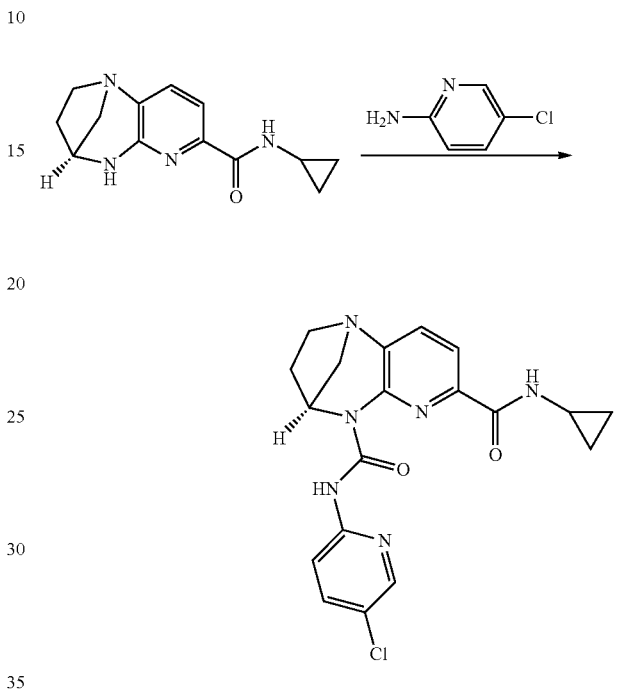

To a stirred solution of (4S)—N—((R)-1,1,1-trifluoropropan-2-yl)-2,3,4,5-tetrahydro-1,4-methanopyrido[2,3-b][1,4]diazepine-7-carboxamide (700 mg, 2.331 mmol) in THF (30 mL) under nitrogen at RT was added triphosgene (692 mg, 2.331 mmol), TEA (1.625 mL, 11.66 mmol) and stirred for 45 min. then added pyrimidin-4-amine (333 mg, 3.50 mmol) and the resulting reaction mixture was stirred at 65° C. for 16 h. (TLC eluent: 5% MeOH in DCM: R$_f$—0.3; UV active). Reaction mixture was quenched with water (40 mL) and the aqueous layer was extracted with EtOAc (2×30 mL). Combined organic layer was dried over anhydrous Na$_2$SO$_4$, filtered and concentrated under reduced pressure to obtain crude product. The crude material was purified by column chromatography (Silica gel, eluent 85% EtOAc in Hexanes) to obtain the desired product (4S)—N5-(pyrimidin-4-yl)-N7-((R)-1,1,1-trifluoropropan-2-yl)-3,4-dihydro-1,4-methanopyrido[2,3-b][1,4]diazepine-5,7(2H)-dicarboxamide (160 mg, 0.380 mmol, 16.28% yield) as white solid. LC-MS (m/z): 422.03 [M+H]$^+$, Rt=1.89 min.

$^1$H NMR (400 MHz, CDCl$_3$): δ ppm 13.50 (s, 1H), 8.82 (d, J=1.10 Hz, 1H), 8.64 (d, J=5.70 Hz, 1H), 8.11 (dd, J=5.70, 1.32 Hz, 1H), 8.00 (d, J=7.89 Hz, 1H), 7.79 (br d, J=9.65 Hz, 1H), 7.72 (d, J=7.89 Hz, 1H), 5.64 (dd, J=5.92, 3.07 Hz, 1H), 4.96-5.15 (m, 1H), 3.18-3.32 (m, 2H), 3.12 (d, J=12.06 Hz, 1H), 3.03 (dd, J=12.28, 3.07 Hz, 1H), 2.20-2.43 (m, 1H), 1.85-2.13 (m, 1H), 1.54-1.63 (m, 3H)

To a stirred solution of (4S)—N-cyclopropyl-2,3,4,5-tetrahydro-1,4-methanopyrido[2,3-b][1,4]diazepine-7-carboxamide (600 mg, 2.456 mmol) in THF (20 mL) under nitrogen at RT was added triphosgene (729 mg, 2.456 mmol), TEA (1.027 mL, 7.37 mmol) and stirred for 45 min. then added a solution of 5-chloropyridin-2-amine (379 mg, 2.95 mmol) in THF (5 mL) and the resulting reaction mixture was stirred at 65° C. for 16 h. (TLC eluent: 5% MeOH in DCM: R$_f$—0.5; UV active). Reaction mixture was quenched with water (25 mL) and the aqueous layer was extracted with EtOAc (2×25 mL). Combined organic layer was dried over anhydrous Na$_2$SO$_4$, filtered and concentrated under reduced pressure to obtain crude product. Crude material was purified by combiflash chromatography (Silica gel column, eluent 2.2% MeOH in DCM). Fraction containing pure compound were combined and concentrated to afford (4S)—N5-(5-chloropyridin-2-yl)-N7-cyclopropyl-3,4-dihydro-1,4-methanopyrido[2,3-b][1,4]diazepine-5,7(2H)-dicarboxamide (310 mg, 0.777 mmol, 31.6% yield) as a white solid. LC-MS (m/z): 399.06 [M+H]$^+$, Rt=2.25 min.

$^1$H NMR (400 MHz, CDCl$_3$): δ ppm 13.29-13.51 (m, 1H), 8.25 (d, J=2.41 Hz, 1H), 8.15 (d, J=8.77 Hz, 1H), 7.92 (d, J=7.89 Hz, 1H), 7.60-7.83 (m, 3H), 5.62 (dd, J=6.03, 3.18 Hz, 1H), 3.17-3.29 (m, 2H), 2.98-3.13 (m, 3H), 2.19-2.39 (m, 1H), 1.92-2.17 (m, 1H), 0.72-1.01 (m, 4H)

Example 68

Synthesis of (4S)—N5-(1H-pyrazol-3-yl)-N7-((R)-1,1,1-trifluoropropan-2-yl)-3,4-dihydro-1,4-methanopyrido[2,3-b][1,4]diazepine-5,7(2H)-dicarboxamide

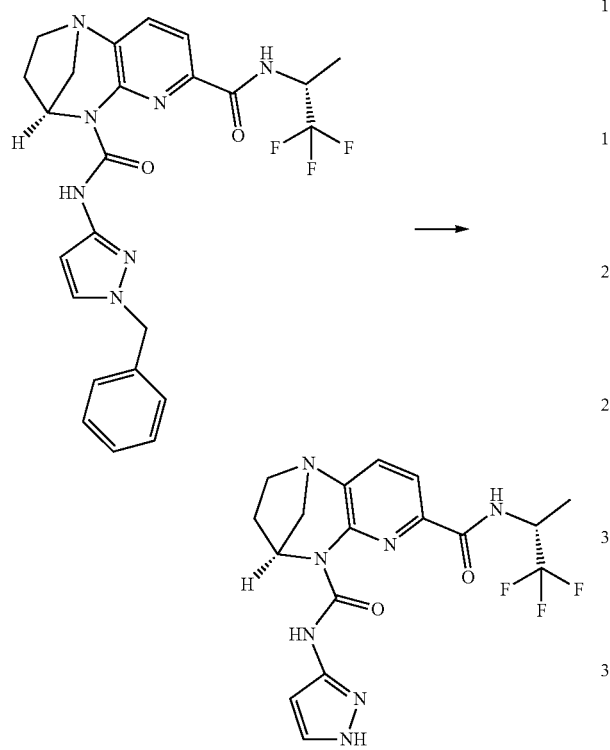

To a stirred solution of (4S)—N5-(1-benzyl-1H-pyrazol-3-yl)-N7-((R)-1,1,1-trifluoropropan-2-yl)-3,4-dihydro-1,4-methanopyrido[2,3-b][1,4]diazepine-5,7(2H)-dicarboxamide (250 mg, 0.501 mmol) in ethanol (5 mL), was added 20% palladium hydroxide on carbon (176 mg, 0.250 mmol) and was stirred under Hydrogen atmosphere at RT for 16 h. (TLC eluent: 5% MeOH in DCM: R$_f$—0.3; UV active). The reaction mixture was filtered on celite bed and filtrate was concentrated under reduced pressure to obtain crude product. Crude material was purified by combiflash chromatography (Silica gel Column, eluent 4% MeOH in DCM) followed by preparative HPLC (Column: XBridge C 18 (250×4.6 mm, 5μ; Mobile Phase: A: 5 mM Ammonium Bicarbonate, B:MeOH:CAN; Gradient: Time/% B: 0/10, 1/10, 10/60, 15/60, 18/98, 20/98, 20.1/10, 25/10; Temp: Ambient; Flow Rate: 1.0 ml/min; Diluent: Acetonitrile) to afford the desired compound (4S)—N5-(1H-pyrazol-3-yl)-N7-((R)-1,1,1-trifluoropropan-2-yl)-3,4-dihydro-1,4-methanopyrido[2,3-b][1,4]diazepine-5,7(2H)-dicarboxamide (27 mg, 0.065 mmol, 13.07% yield) as an off-white solid. LC-MS (m/z): 410.12 [M+H]$^+$, Rt=1.67 min.

$^1$H NMR (400 MHz, CDCl$_3$): δ ppm 12.62 (br s, 1H), 9.60 (br s, 1H), 7.88 (m, J=7.89 Hz, 1H), 7.66 (m, J=7.89 Hz, 1H), 7.36-7.53 (m, 2H), 6.65 (br s, 1H), 5.57-5.83 (m, 1H), 4.97 (dq, J=16.74, 7.21 Hz, 1H), 3.06-3.31 (m, 3H), 2.82-3.06 (m, 1H), 2.20-2.45 (m, 1H), 1.97-2.14 (m, 1H), 1.57 (br d, J=7.02 Hz, 3H).

Example 69

Synthesis of (4S)—N7-(2,2-difluoroethyl)-N5-(5-fluoropyridin-2-yl)-3,4-dihydro-1,4-methanopyrido[2,3-b][1,4]diazepine-5,7(2H)-dicarboxamide

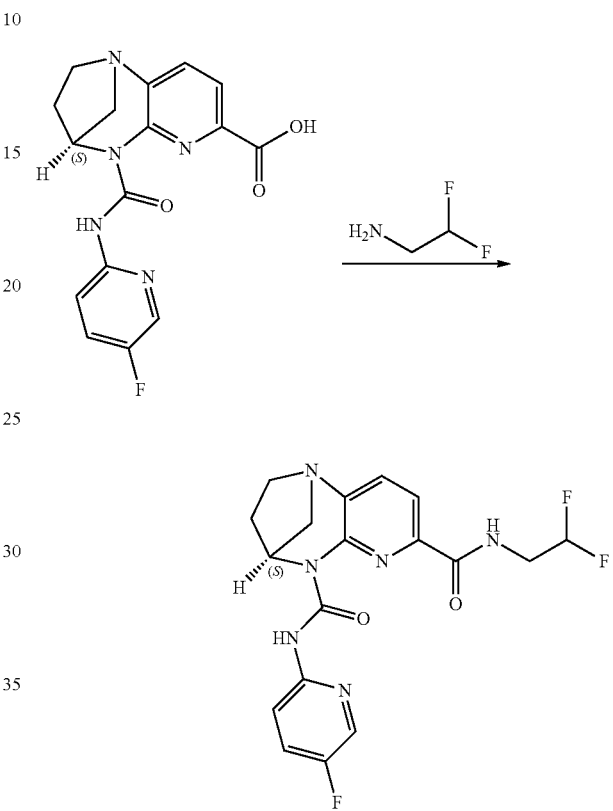

To a stirred solution of (4S)-5-((5-fluoropyridin-2-yl)carbamoyl)-2,3,4,5-tetrahydro-1,4-methanopyrido[2,3-b][1,4]diazepine-7-carboxylic acid (500 mg, 1.456 mmol) in DMF (8 mL) at 0° C. under nitrogen, was added HATU (1108 mg, 2.91 mmol), TEA (0.609 mL, 4.37 mmol) and stirred for 30 min. then added 2,2-difluoroethanamine (177 mg, 2.185 mmol) and the reaction was stirred at RT for 16 h. (TLC eluent: 5% MeOH in DCM: R$_f$—0.4; UV active). Reaction mixture was quenched with water (20 mL) and the resultant solid was filtered, washed with water (10 mL), dried and triturated with diethyl ether (2×10 mL) to afford desired (4S)—N7-(2,2-difluoroethyl)-N5-(5-fluoropyridin-2-yl)-3,4-dihydro-1,4-methanopyrido[2,3-b][1,4]diazepine-5,7(2H)-dicarboxamide (280 mg, 0.687 mmol, 47.2% yield) as an off-white solid. LC-MS (m/z): 407.06 [M+H]$^+$, Rt=2.06 min.

$^1$H NMR (400 MHz, CDCl$_3$): δ ppm 13.48-13.72 (m, 1H), 8.18-8.44 (m, 1H), 8.07-8.18 (m, 2H), 7.89 (d, J=7.89 Hz, 1H), 7.67 (d, J=7.89 Hz, 1H), 7.36-7.58 (m, 1H), 6.14-5.60 (m, 1H), 5.60 (dd, J=5.92, 3.07 Hz, 1H), 3.83-4.01 (m, 2H), 3.08-3.32 (m, 3H), 2.99-3.07 (m, 1H), 2.20-2.45 (m, 1H), 1.95-2.14 (m, 1H).

Example 70

Synthesis of (4S)—N5-(5-fluoropyridin-2-yl)-N7-(2,2,2-trifluoroethyl)-3,4-dihydro-1,4-methanopyrido[2,3-b][1,4]diazepine-5,7(2H)-dicarboxamide

Example 71

Synthesis of (4S)—N5-(5-fluoropyridin-2-yl)-N7-((R)-3,3,3-trifluoro-2-hydroxypropyl)-3,4-dihydro-1,4-methanopyrido[2,3-b][1,4]diazepine-5,7(2H)-dicarboxamide

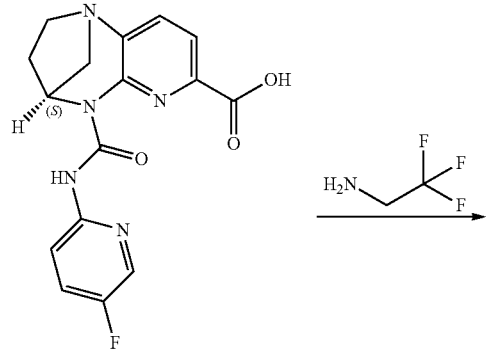

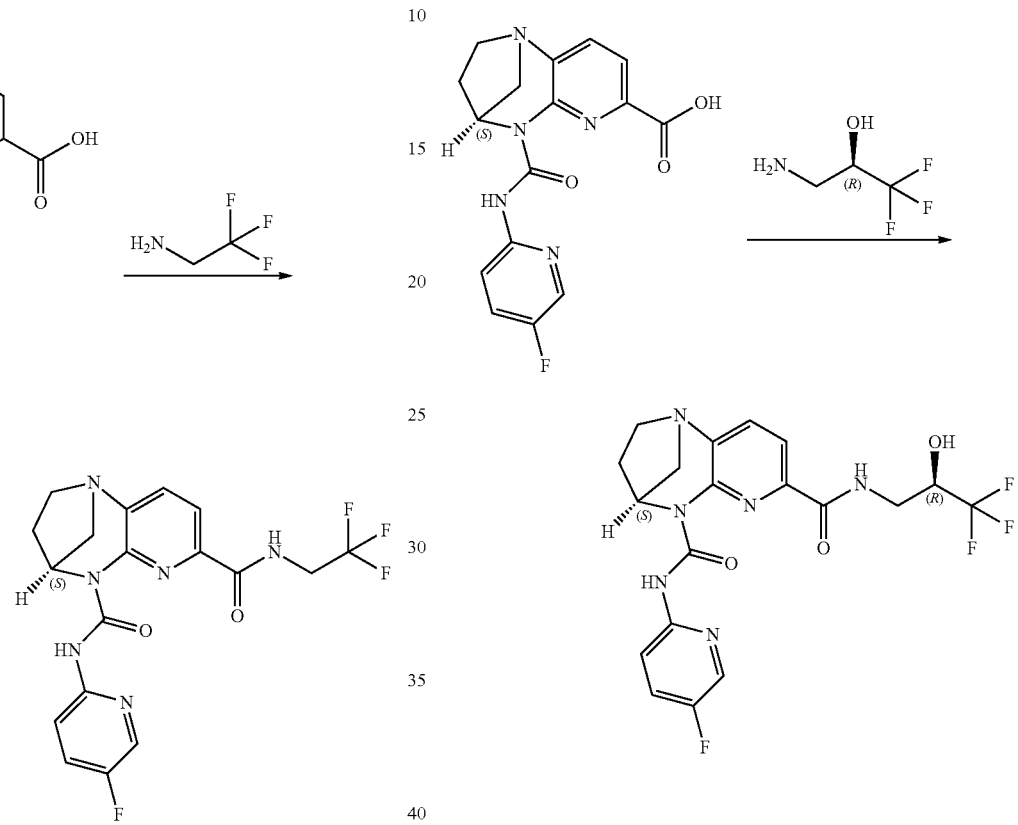

To a stirred solution of (4S)-5-((5-fluoropyridin-2-yl)carbamoyl)-2,3,4,5-tetrahydro-1,4-methanopyrido[2,3-b][1,4]diazepine-7-carboxylic acid (400 mg, 1.165 mmol) in DMF (10 mL) at 0° C. under nitrogen, was added HATU (886 mg, 2.330 mmol), TEA (0.487 mL, 3.50 mmol) and stirred for 30 min. then added 2,2,2-trifluoroethanamine (115 mg, 1.165 mmol) and the reaction mixture was stirred at RT for 16 h. (TLC eluent: 5% MeOH in DCM: $R_f$—0.4; UV active). Reaction mixture was quenched with water (20 mL) and the resultant solid was filtered, washed with water (10 mL), dried and triturated with diethyl ether (2×10 mL) to afford desired (4S)—N5-(5-fluoropyridin-2-yl)-N7-(2,2,2-trifluoroethyl)-3,4-dihydro-1,4-methanopyrido[2,3-b][1,4]diazepine-5,7(2H)-dicarboxamide (190 mg, 0.448 mmol, 38.4% yield) as an off-white solid. LC-MS (m/z): 425.09 [M+H]$^+$, Rt=2.25 min.

$^1$H NMR (400 MHz, CDCl$_3$): δ ppm 13.57 (s, 1H), 8.32 (br t, J=5.70 Hz, 1H), 8.11-8.15 (m, 1H), 8.09 (s, 1H), 7.92 (d, J=7.89 Hz, 1H), 7.68 (d, J=7.89 Hz, 1H), 7.36-7.58 (m, 1H), 5.61 (dd, J=5.92, 3.07 Hz, 1H), 4.13-4.29 (m, 2H), 3.08-3.32 (m, 3H), 2.97-3.08 (m, 1H), 2.21-2.46 (m, 1H), 1.97-2.14 (m, 1H).

To a stirred solution of (4S)-5-((5-fluoropyridin-2-yl)carbamoyl)-2,3,4,5-tetrahydro-1,4-methanopyrido[2,3-b][1,4]diazepine-7-carboxylic acid (400 mg, 1.165 mmol) in DMF (10 mL) at 0° C. under nitrogen, was added HATU (886 mg, 2.330 mmol), TEA (0.487 mL, 3.50 mmol) and stirred for 30 min. then added (R)-3-amino-1,1,1-trifluoropropan-2-ol (150 mg, 1.165 mmol) and the reaction mixture was stirred at RT for 16 h. (TLC eluent: 5% MeOH in DCM: $R_f$—0.4; UV active). Reaction mixture was quenched with water (20 mL) and the resultant solid was filtered, washed with water (10 mL), dried and triturated with diethyl ether (2×10 mL) to afford desired (4S)—N5-(5-fluoropyridin-2-yl)-N7-((R)-3,3,3-trifluoro-2-hydroxypropyl)-3,4-dihydro-1,4-methanopyrido[2,3-b][1,4]diazepine-5,7(2H)-dicarboxamide (255 mg, 0.559 mmol, 48.0% yield) as an off-white solid. LC-MS (m/z): 455.23 [M+H]$^+$, Rt=2.05 min.

$^1$H NMR (400 MHz, CDCl$_3$): δ ppm 13.10 (s, 1H), 8.23 (dd, J=9.21, 4.17 Hz, 1H), 8.08 (d, J=2.85 Hz, 1H), 8.02 (br s, 1H), 7.82 (d, J=7.67 Hz, 1H), 7.67 (d, J=7.67 Hz, 1H), 7.51 (ddd, J=9.21, 7.45, 3.07 Hz, 1H), 5.48-5.69 (m, 2H), 4.17-4.34 (m, 1H), 4.06 (ddd, J=14.09, 6.96, 2.85 Hz, 1H), 3.64 (ddd, J=13.98, 8.60, 5.04 Hz, 1H), 3.18-3.34 (m, 2H), 3.13 (br d, J=12.28 Hz, 1H), 3.04 (dd, J=12.28, 3.07 Hz, 1H), 2.23-2.42 (m, 1H), 1.98-2.20 (m, 1H).

Example 72

Synthesis of (4S)—N5-(5-fluoropyridin-2-yl)-N7-((R)-1,1,1-trifluorobutan-2-yl)-3,4-dihydro-1,4-methanopyrido[2,3-b][1,4]diazepine-5,7(2H)-dicarboxamide

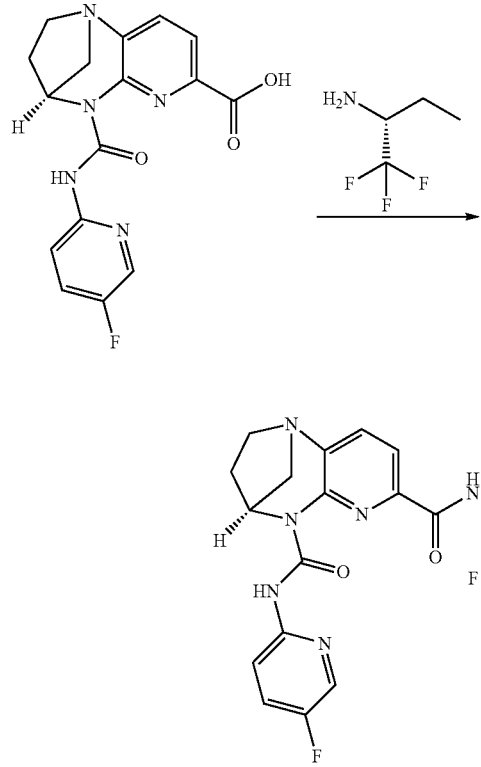

To a stirred solution of (4S)-5-((5-fluoropyridin-2-yl)carbamoyl)-2,3,4,5-tetrahydro-1,4-methanopyrido[2,3-b][1,4]diazepine-7-carboxylic acid (400 mg, 1.165 mmol) in DMF (8 mL) under nitrogen at 0° C. was added HATU (886 mg, 2.330 mmol), TEA (0.487 mL, 3.50 mmol) and stirred for 30 min. then added (R)-1,1,1-trifluorobutan-2-amine (148 mg, 1.165 mmol) and reaction mixture was stirred for 16 h. (TLC eluent: 5% MeOH in DCM: $R_f$—0.4; UV active). Reaction mixture was quenched with water (20 mL) and the resultant solid was filtered, washed with water (10 mL), dried and triturated with diethyl ether (2×10 mL) to afford desired (4S)—N5-(5-fluoropyridin-2-yl)-N7-((R)-1,1,1-trifluorobutan-2-yl)-3,4-dihydro-1,4-methanopyrido[2,3-b][1,4]diazepine-5,7(2H)-dicarboxamide (240 mg, 0.516 mmol, 44.3% yield) as an off-white solid LC-MS (m/z): 453.17 [M+H]$^+$, Rt=2.52 min.

$^1$H NMR (400 MHz, CDCl$_3$): δ ppm 13.25 (s, 1H), 8.19 (dd, J=9.10, 4.06 Hz, 1H), 8.07 (d, J=2.85 Hz, 1H), 7.96 (d, J=7.89 Hz, 1H), 7.65-7.79 (m, 2H), 7.36-7.53 (m, 1H), 5.65 (dd, J=5.92, 3.07 Hz, 1H), 4.77-4.91 (m, 1H), 3.09-3.32 (m, 3H), 2.99-3.07 (m, 1H), 2.23-2.47 (m, 1H), 2.01-2.18 (m, 2H), 1.92 (ddq, J=14.18, 10.98, 7.33, 7.33, 7.33 Hz, 1H), 1.05 (t, J=7.45 Hz, 3H).

Example 73

Synthesis of (4S)—N5-(5-fluoropyridin-2-yl)-N7-neopentyl-3,4-dihydro-1,4-methanopyrido[2,3-b][1,4]diazepine-5,7(2H)-dicarboxamide

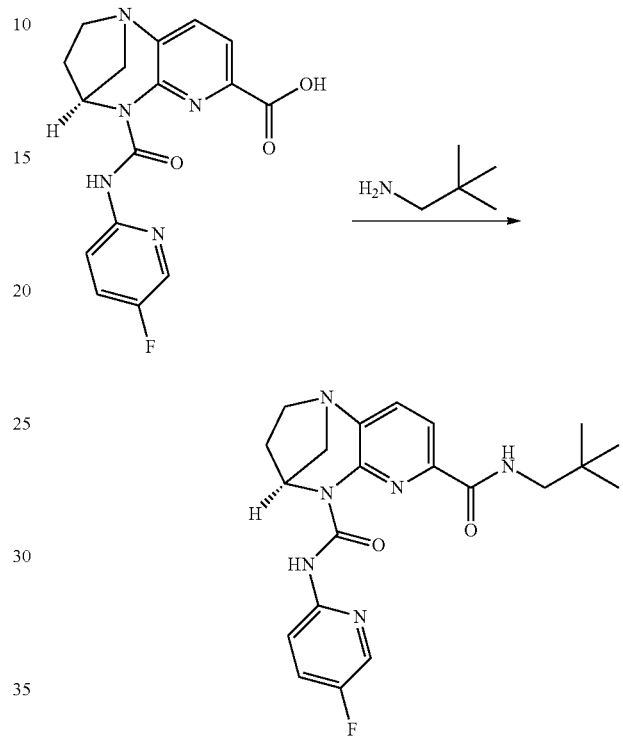

To a stirred solution of (4S)-5-((5-fluoropyridin-2-yl)carbamoyl)-2,3,4,5-tetrahydro-1,4-methanopyrido[2,3-b][1,4]diazepine-7-carboxylic acid (400 mg, 1.165 mmol) in DMF (8 mL) at 0° C. under nitrogen, was added HATU (886 mg, 2.330 mmol), DIPEA (0.610 mL, 3.50 mmol) and 30 min. then added 2,2-dimethylpropan-1-amine (122 mg, 1.398 mmol) and reaction mixture was maintained stirred for 16 h. (TLC eluent: 5% MeOH in DCM: $R_f$—0.4; UV active). Reaction mixture was quenched with water (20 mL) and the resultant solid was filtered, washed with water (10 mL), dried to afford crude compound. The crude was purified by prep HPLC (Column: XBridge C 18 (250×4.6 mm, 5) Mobile Phase: A: 5 mM Ammonium Bicarbonate B: ACN Gradient: Time/% B: 0/10, 1/10, 10/60, 15/60, 18/98, 20/98, 20.1/10, 25/10; Column Temp: Ambient, Flow Rate: 1.0 ml/min Diluent: ACN) to obtain desired product (4S)—N5-(5-fluoropyridin-2-yl)-N7-neopentyl-3,4-dihydro-1,4-methanopyrido[2,3-b][1,4]diazepine-5,7(2H)-dicarboxamide (130 mg, 0.315 mmol, 27.0% yield) as an off-white solid. LC-MS (m/z): 413.19 [M+H]$^+$, Rt=2.49 min.

$^1$H NMR (400 MHz, CDCl$_3$): δ ppm 13.34 (s, 1H), 8.06-8.21 (m, 2H), 7.79-7.99 (m, 2H), 7.66 (d, J=7.89 Hz, 1H), 7.36-7.57 (m, 1H), 5.64 (dd, J=5.92, 3.07 Hz, 1H), 3.39 (qd, J=13.52, 6.80 Hz, 2H), 3.11-3.30 (m, 3H), 2.96-3.07 (m, 1H), 2.33 (dddd, J=14.11, 9.78, 5.81, 4.28 Hz, 1H), 1.99-2.12 (m, 1H), 0.91-1.01 (m, 9H).

Example 74

Synthesis of (4S)—N5-(4-(((S)-2,2-dimethyl-1,3-dioxolan-4-yl)methoxy)pyridin-2-yl)-N7-((R)-1,1,1-trifluoropropan-2-yl)-3,4-dihydro-1,4-methano-pyrido[2,3-b][1,4]diazepine-5,7(2H)-dicarboxamide

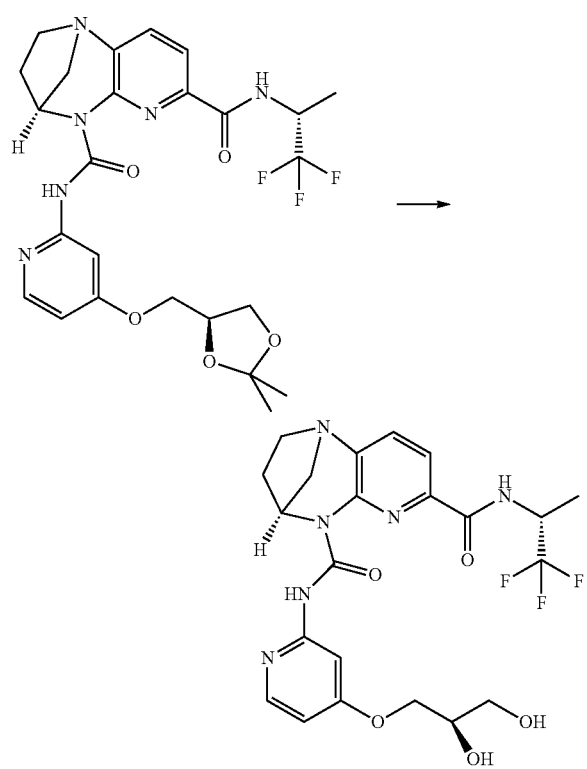

To a stirred solution of (4S)—N5-(4-(((S)-2,2-dimethyl-1,3-dioxolan-4-yl)methoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (10 g, 18.16 mmol) in methanol (50 mL) was added 2 M HCl (9.08 mL, 18.16 mmol) and stirred at RT for 3 h. (TLC eluent: 5% MeOH in DCM: $R_f$—0.2; UV active). Reaction mixture was concentrated to remove methanol and the residue was basified by using saturated NaHCO$_3$ (30 mL). The resultant solid was filtered, dried and triturated with petether (100 mL) to obtain desired product (4S)—N5-(4-((R)-2,3-dihydroxypropoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (9 g, 17.39 mmol, 96% yield) as an white solid. LC-MS (m/z): 510.09 [M]+, Rt=1.83 min.

$^1$H NMR (400 MHz, DMSO-d$_6$): δ ppm 13.01-13.10 (m, 1H), 8.17 (br d, J=9.21 Hz, 1H), 8.06 (d, J=5.92 Hz, 1H), 7.72-7.89 (m, 2H), 7.68 (d, J=2.41 Hz, 1H), 6.74 (dd, J=5.81, 2.30 Hz, 1H), 5.46 (dd, J=5.81, 2.96 Hz, 1H), 4.86-5.09 (m, 2H), 4.73 (br s, 1H), 4.12 (dd, J=9.87, 3.95 Hz, 1H), 3.97 (dd, J=9.87, 6.36 Hz, 1H), 3.83 (br s, 1H), 3.40-3.51 (m, 2H), 3.04-3.28 (m, 3H), 2.93-3.03 (m, 1H), 2.13-2.38 (m, 1H), 1.96 (dt, J=13.87, 7.21 Hz, 1H), 1.53 (d, J=7.23 Hz, 3H).

Example 75

Synthesis of (4S)—N5-(oxazol-2-yl)-N7-((R)-1,1,1-trifluoropropan-2-yl)-3,4-dihydro-1,4-methano-pyrido[2,3-b][1,4]diazepine-5,7(2H)-dicarboxamide

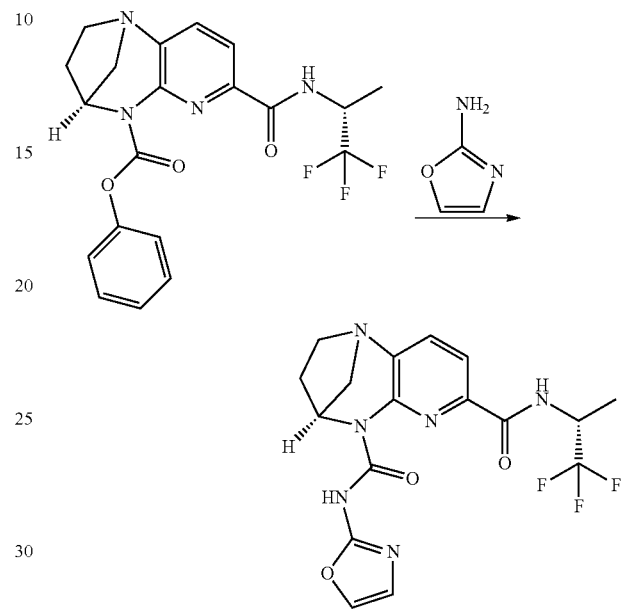

To a stirred solution of oxazol-2-amine (150 mg, 1.784 mmol) in THF (15 mL) at −78° C. under argon, was added LiHMDS (2.379 mL, 2.379 mmol, 1M solution in THF) dropwisely and stirred at −78° C. for 30 min. then added a solution of (4S)-phenyl 7-(((R)-1,1,1-trifluoropropan-2-yl)carbamoyl)-3,4-dihydro-1,4-methanopyrido[2,3-b][1,4]diazepine-5(2H)-carboxylate (500 mg, 1.189 mmol) in THF (5 mL). (TLC eluent: 5% MeOH in DCM; $R_f$—0.2; UV active). The resulting reaction mixture was stirred at −78° C. for 1 h and at RT for 6 h. The reaction mixture was quenched with aqueous NH$_4$Cl (10 mL) and the aqueous layer was extracted with EtOAc (2×20 mL). Combined organic layer was dried over anhydrous Na$_2$SO$_4$, filtered and concentrated under reduced pressure to obtain crude product. The crude material was purified by column chromatography (Silica gel, eluent 2.8% MeOH in DCM), followed by Preparative HPLC (Column: Kromasil phenyl (150×25) mm 10u; Mobile Phase-A: 10 mM Ammonium Bicarbonate (Aq), Mobile Phase-B: Acetonitrile; Method (A:B) 60:40; Flow: 20 ml/min; Solubility: Acetonitrile+MeOH) to afford desired product (4S)—N5-(oxazol-2-yl)-N7-((R)-1,1,1-trifluoropropan-2-yl)-3,4-dihydro-1,4-methanopyrido[2,3-b][1,4]diazepine-5,7(2H)-dicarboxamide (150 mg, 0.364 mmol, 30.6% yield) as an off-white solid. LC-MS (m/z): 411.09 [M+H]$^+$, Rt=1.69 min.

$^1$H NMR (400 MHz, CDCl$_3$): δ ppm 13.47 (s, 1H), 7.92 (d, J=7.89 Hz, 1H), 7.70 (d, J=7.89 Hz, 1H), 7.45 (s, 1H), 7.12-7.25 (m, 1H), 7.00 (s, 1H), 5.65 (dd, J=5.81, 2.96 Hz, 1H), 4.89-5.02 (m, 1H), 3.15-3.31 (m, 2H), 2.97-3.14 (m, 2H), 2.34 (ddt, J=14.44, 8.96, 5.51, 5.51 Hz, 1H), 1.96-2.18 (m, 1H), 1.48-1.62 (m, 3H).

Example 76

Synthesis of (4S)—N5-(6-methyl-1H-pyrazolo[3,4-b]pyridin-3-yl)-N7-((R)-1,1,1-trifluoropropan-2-yl)-3,4-dihydro-1,4-methanopyrido[2,3-b][1,4]diazepine-5,7(2H)-dicarboxamide

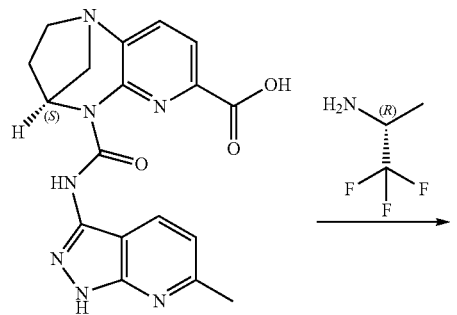

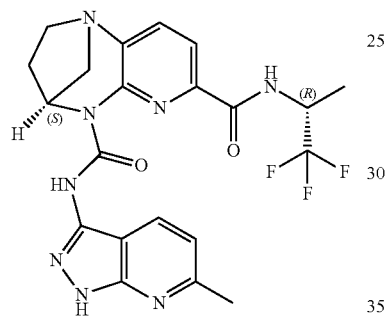

To a stirred solution of (4S)-5-((6-methyl-1H-pyrazolo[3,4-b]pyridin-3-yl)carbamoyl)-2,3,4,5-tetrahydro-1,4-methanopyrido[2,3-b][1,4]diazepine-7-carboxylic acid (750 mg, 1.977 mmol) in DMF (25 mL) at 0° C. was added HATU (2255 mg, 5.93 mmol), DIPEA (1.036 mL, 5.93 mmol) and stirred for 30 min. then added (R)-1,1,1-trifluoropropan-2-amine (224 mg, 1.977 mmol) and reaction mixture was stirred for 16 h. (TLC system: 5% Methanol in DCM. R$_f$: 0.3). Reaction mixture was cooled RT and quenched with water (50 mL) and the aqueous layer was extracted with EtOAc (2×50 mL). Combined organic layer was dried over anhydrous sodium sulphate, filtered and concentrated under reduced pressure to get crude compound. The crude product was purified by column chromatography (Silica gel column, eluted with 2.8% of MeOH in CH$_2$C2) to afford (4S)—N5-(6-methyl-1H-pyrazolo[3,4-b]pyridin-3-yl)-N7-((R)-1,1,1-trifluoropropan-2-yl)-3,4-dihydro-1,4-methanopyrido[2,3-b][1,4]diazepine-5,7(2H)-dicarboxamide (85 mg, 0.179 mmol, 9.05% yield) as a white solid. LCMS (m/z): 475.1 [M+H]$^+$, Rt=1.87 min.

$^1$H NMR (400 MHz, DMSO-d$_6$): δ ppm 12.97 (s, 1H), 12.66 (s, 1H), 8.58 (br d, J=8.99 Hz, 1H), 8.41 (d, J=8.33 Hz, 1H), 7.73 (d, J=7.67 Hz, 1H), 7.63 (d, J=7.89 Hz, 1H), 7.03 (d, J=8.33 Hz, 1H), 5.49 (br dd, J=5.59, 2.74 Hz, 1H), 4.85 (dq, J=15.37, 7.81 Hz, 1H), 3.05-3.27 (m, 3H), 2.83-3.04 (m, 1H), 2.54-2.60 (m, 3H), 2.19-2.46 (m, 1H), 1.96 (dt, J=13.81, 6.91 Hz, 1H), 1.43 (d, J=7.02 Hz, 3H).

Example 77

Synthesis of (4S)—N5-(pyridazin-3-yl)-N7-((R)-1,1,1-trifluoropropan-2-yl)-3,4-dihydro-1,4-methanopyrido[2,3-b][1,4]diazepine-5,7(2H)-dicarboxamide

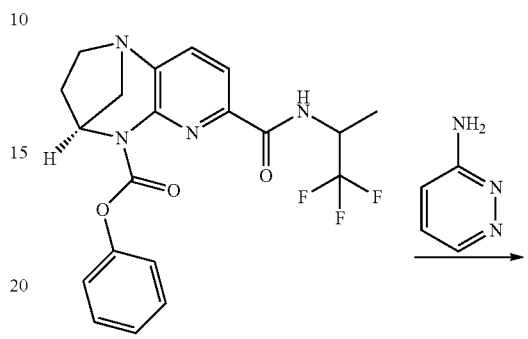

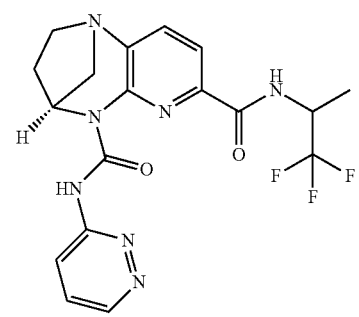

To a stirred solution of pyridazin-3-amine (1.357 g, 14.27 mmol) in THF (30 mL) at −78° C., under argon was added LiHMDS (23.79 mL, 23.79 mmol, 1 M solution in THF) dropwisely and stirred for 30 min. Then added (4S)-phenyl 7-(((R)-1,1,1-trifluoropropan-2-yl)carbamoyl)-3,4-dihydro-1,4-methanopyrido[2,3-b][1,4]diazepine-5(2H)-carboxylate (4 g, 9.52 mmol) at −78° C. and the resulting reaction mixture was stirred at −78° C. for 1 h then slowly warmed to RT and stirred for 6 h. (TLC system: 5% Methanol in DCM. R$_f$: 0.3). The reaction mixture was quenched with aqueous NH$_4$Cl (50 mL) and extracted with EtOAc (2×100 mL), combined organic layer was dried over anhydrous Na$_2$SO$_4$, filtered and concentrated under reduced pressure to obtain crude compound. The crude product was triturated in ethanol (2×30 mL), filtered and dried to afford (4S)—N5-(pyridazin-3-yl)-N7-((R)-1,1,1-trifluoropropan-2-yl)-3,4-dihydro-1,4-methanopyrido[2,3-b][1,4]diazepine-5,7(2H)-dicarboxamide (10.6 g, 24.99 mmol) compound as a white solid. LCMS (m/z): 422.09 [M+H]$^+$, Rt=1.91 min.

$^1$H NMR (400 MHz, CDCl$_3$): δ ppm 13.99 (s, 1H), 8.93 (dd, J=4.82, 1.53 Hz, 1H), 8.39 (dd, J=8.99, 1.53 Hz, 1H), 8.10 (br d, J=9.21 Hz, 1H), 8.00 (d, J=7.89 Hz, 1H), 7.71 (d, J=8.11 Hz, 1H), 7.48 (dd, J=8.99, 4.60 Hz, 1H), 5.66 (dd, J=6.03, 3.18 Hz, 1H), 4.92-5.09 (m, 1H), 3.10-3.32 (m, 3H), 2.95-3.09 (m, 1H), 2.35 (dddd, J=14.20, 9.81, 5.81, 4.17 Hz, 1H), 2.00-2.18 (m, 1H), 1.76 (d, J=7.02 Hz, 3H).

Example 78

Synthesis of (4S)—N7-cyclopropyl-N5-(4-(oxazol-5-yl)pyridin-2-yl)-3,4-dihydro-1,4-methanopyrido[2,3-b][1,4]diazepine-5,7(2H)-dicarboxamide

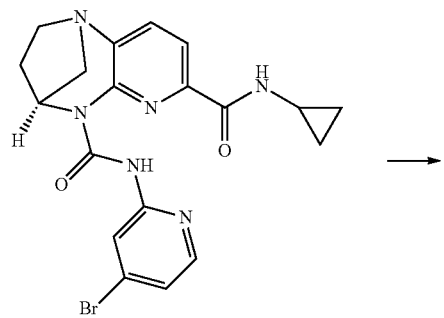

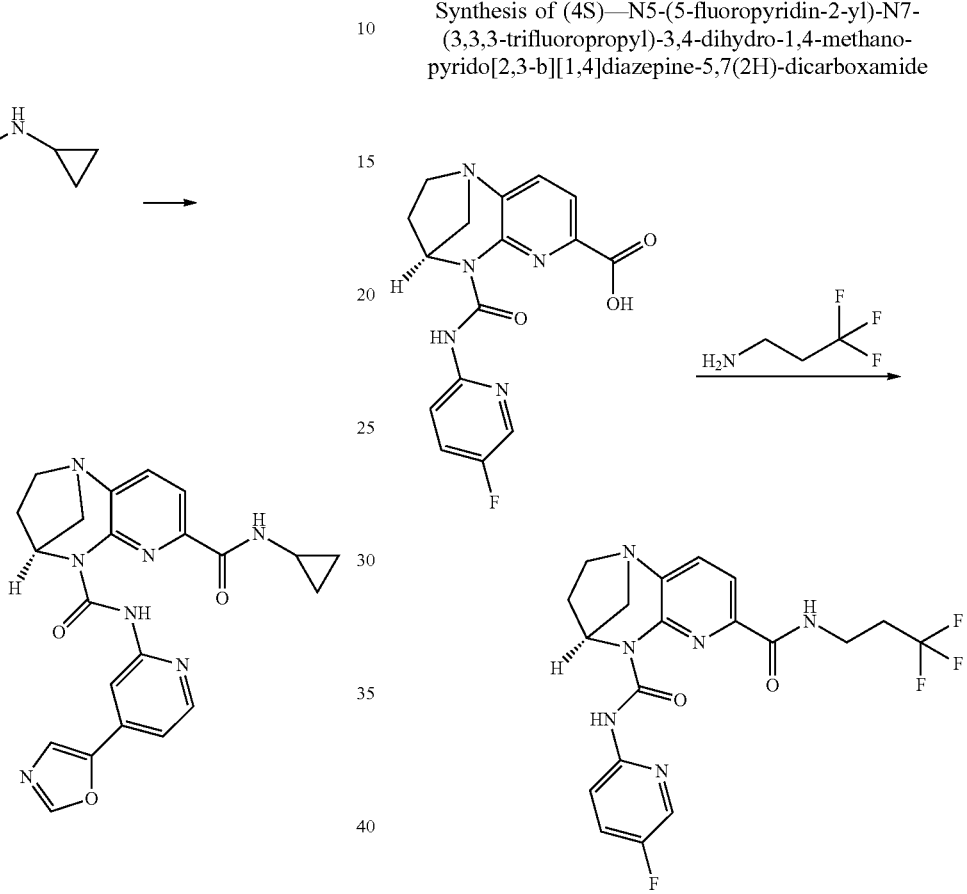

To a mixture of (4S)—N5-(4-bromopyridin-2-yl)-N7-cyclopropyl-3,4-dihydro-1,4-methanopyrido[2,3-b][1,4]diazepine-5,7(2H)-dicarboxamide (500 mg, 1.128 mmol), 5-(4,4,5,5-tetramethyl-1,3-dioxolan-2-yl)oxazole (334 mg, 1.692 mmol) in 1,4-Dioxane (20 mL), water (2 mL) was added potassium acetate (332 mg, 3.38 mmol) and PdCl$_2$(dppf) (124 mg, 0.169 mmol) and the resulting mixture was degassed for 20 min. followed by stirring at 100° C. for 16 h. (TLC system: 5% Methanol in DCM. R$_f$: 0.4). Reaction mixture was cooled to RT and quenched with water (20 mL) and the aqueous layer was extracted with EtOAc (2×30 mL). Combined organic layer was dried over anhydrous sodium sulphate, filtered and concentrated under reduced pressure to get the crude compound. The crude product was purified by column chromatography (Silica gel, eluted with 2.5% of MeOH in CH$_2$Cl$_2$) to afford (4S)—N7-cyclopropyl-N5-(4-(oxazol-5-yl)pyridin-2-yl)-3,4-dihydro-1,4-methanopyrido[2,3-b][1,4]diazepine-5,7(2H)-dicarboxamide (221 mg, 0.495 mmol, 43.9% yield) as a pale yellow solid. LCMS (m/z): 432.1[M+H]$^+$, Rt=1.84 min.

$^1$H NMR (400 MHz, CDCl$_3$): δ ppm 13.49 (s, 1H), 8.45 (s, 1H), 8.36 (d, J=5.26 Hz, 1H), 8.00 (s, 1H), 7.94 (d, J=7.89 Hz, 2H), 7.62-7.73 (m, 2H), 7.29 (d, J=5.35 Hz, 1H), 5.64 (dd, J=5.92, 3.29 Hz, 1H), 3.18-3.30 (m, 2H), 3.00-3.16 (m, 3H), 2.25-2.4 (m, 1H), 1.93-2.12 (m, 1H), 0.79-1.01 (m, 4H).

Example 79

Synthesis of (4S)—N5-(5-fluoropyridin-2-yl)-N7-(3,3,3-trifluoropropyl)-3,4-dihydro-1,4-methanopyrido[2,3-b][1,4]diazepine-5,7(2H)-dicarboxamide To a suspension of (4S)-5-((5-fluoropyridin-2-yl)carbamoyl)-2,3,4,5-tetrahydro-1,4-methanopyrido[2,3-b][1,4]diazepine-7-carboxylic acid (400 mg, 1.165 mmol) in DMF (8 mL) at 0° C. was added HATU (886 mg, 2.330 mmol) followed by DIPEA (0.610 mL, 3.50 mmol) and stirred for 15 min. then added 3,3,3-trifluoropropan-1-amine (198 mg, 1.748 mmol) to the reaction mixture and stirred at RT for 16 h. (TLC system: 5% Methanol in DCM. R$_f$: 0.5). The reaction mixture was quenched with water (40 mL) to give the white precipitation. The solid precipitation was filtered and dried to afford (4S)—N5-(5-fluoropyridin-2-yl)-N7-(3,3,3-trifluoropropyl)-3,4-dihydro-1,4-methanopyrido[2,3-b][1,4]diazepine-5,7(2H)-dicarboxamide (260 mg, 0.591 mmol, 50.8% yield) as an off-white solid. LCMS (m/z): 439.1 [M+H]$^+$, Rt=2.25 min.

$^1$H NMR (400 MHz, CDCl$_3$): δ ppm 13.53 (s, 1H), 8.17 (dd, J=9.10, 4.06 Hz, 2H), 8.08 (d, J=2.85 Hz, 1H), 7.87 (d, J=7.89 Hz, 1H), 7.67 (d, J=7.67 Hz, 1H), 7.43-7.53 (m, 1H), 5.61 (dd, J=5.92, 3.07 Hz, 1H), 3.81 (q, J=6.65 Hz, 2H), 3.17-3.33 (m, 2H), 3.08-3.16 (m, 1H), 2.98-3.06 (m, 1H), 2.49-2.66 (m, 2H), 2.26-2.40 (m, 1H), 1.99-2.14 (m, 1H).

Example 80

Synthesis of (4S)—N5-(5-fluoropyridin-2-yl)-N7-((R)-3-methylbutan-2-yl)-3,4-dihydro-1,4-methanopyrido[2,3-b][1,4]diazepine-5,7(2H)-dicarboxamide

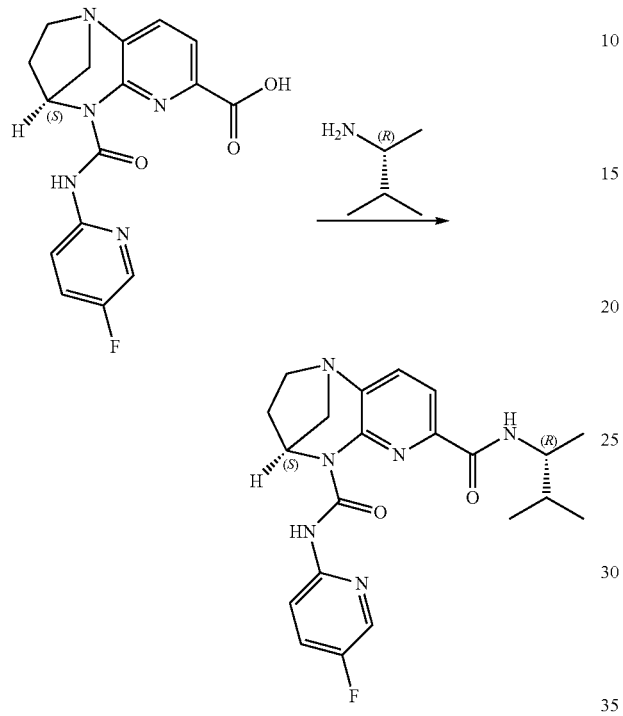

To a suspension of (4S)-5-((5-fluoropyridin-2-yl)carbamoyl)-2,3,4,5-tetrahydro-1,4-methanopyrido[2,3-b][1,4]diazepine-7-carboxylic acid (500 mg, 1.456 mmol) in DMF (8 mL) at 0° C., was added HATU (1108 mg, 2.91 mmol) followed by DIPEA (0.763 mL, 4.37 mmol) and the resulting mixture was stirred for 15 min. then added (R)-3-methylbutan-2-amine (190 mg, 2.185 mmol) the mixture was stirred at RT for 16 h. (TLC system: 5% Methanol in DCM. R$_f$: 0.4). The reaction mixture was quenched with water (20 mL) and the aqueous layer was extracted with EtOAc (2×15 mL). Combined organic layer was dried over anhydrous sodium sulphate, filtered and concentrated to get the crude compound. The crude product was purified by column chromatography (Silica gel column, eluted with 2% of MeOH in CH$_2$C12) followed by prep HPLC (Column: XTERRA rp18 (250×19) mm 10u; Mobile phase-A: 10 Mm Ammonium bicarbonate, Mobile phase-B: Acetonitrile; Method: T/% B: 0/35, 15/35, 15.5/100, 20/100, 20.1/35; Flow: 16 ml/min; Solubility: ACN+THF+Water) to afford (4S)—N5-(5-fluoropyridin-2-yl)-N7-((R)-3-methylbutan-2-yl)-3,4-dihydro-1,4-methanopyrido[2,3-b][1,4]diazepine-5,7(2H)-dicarboxamide (101 mg, 0.245 mmol, 16.80% yield) as a white solid. LCMS (m/z): 413.18 [M+H]$^+$, Rt=2.44 min.

$^1$H NMR (400 MHz, CDCl$_3$): δ ppm 13.20 (s, 1H), 8.22 (dd, J=9.21, 4.17 Hz, 1H), 8.09 (d, J=2.85 Hz, 1H), 7.94 (d, J=7.89 Hz, 1H), 7.66 (d, J=7.89 Hz, 1H), 7.41-7.57 (m, 2H), 5.67 (dd, J=5.92, 3.07 Hz, 1H), 4.07-4.19 (m, 1H), 3.15-3.32 (m, 2H), 3.08-3.14 (m, 1H), 2.97-3.04 (m, 1H), 2.26-2.39 (m, 1H), 2.06 (dt, J=14.14, 6.96 Hz, 1H), 1.86-1.98 (m, 1H), 1.31 (d, J=6.80 Hz, 3H), 0.99 (dd, J=14.91, 6.80 Hz, 6H).

Example 81

Synthesis of (4S)—N5-(5-fluoropyridin-2-yl)-N7-((S)-3,3,3-trifluoro-2-hydroxypropyl)-3,4-dihydro-1,4-methanopyrido[2,3-b][1,4]diazepine-5,7(2H)-dicarboxamide

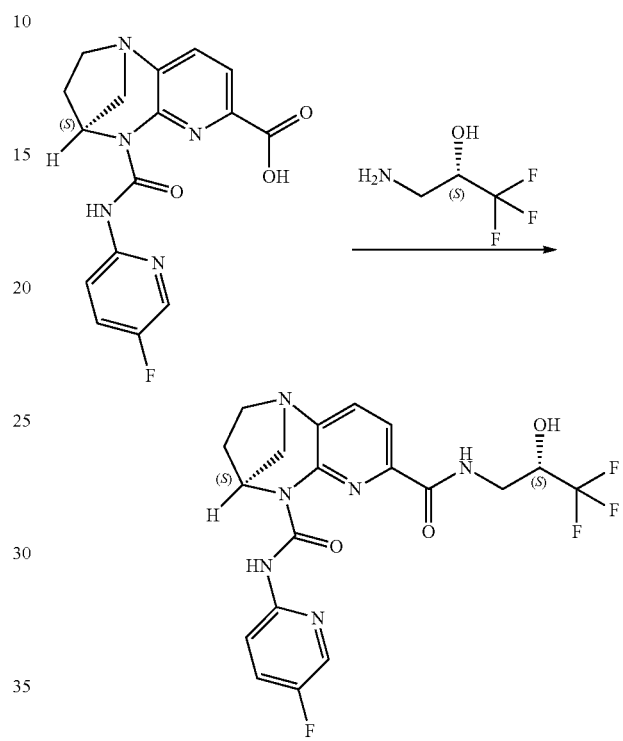

To a suspension of (4S)-5-((5-fluoropyridin-2-yl)carbamoyl)-2,3,4,5-tetrahydro-1,4-methanopyrido[2,3-b][1,4]diazepine-7-carboxylic acid (500 mg, 1.456 mmol) in DMF (10 mL) at 0° C. was added HATU (1108 mg, 2.91 mmol) followed by DIPEA (0.763 mL, 4.37 mmol) and stirred for 15 min. then added (S)-3-amino-1,1,1-trifluoropropan-2-ol (282 mg, 2.185 mmol) to the reaction mixture and stirred at RT for 16 h. (TLC system: 5% Methanol in DCM. R$_f$: 0.4). The reaction mixture was quenched with water (20 mL) and the aqueous layer was extracted with EtOAc (2×15 mL). Combined organic layer was dried over anhydrous sodium sulphate, filtered and concentrated to get the crude compound. The crude product was purified by column chromatography (Silica gel column, eluted with 2.5% of MeOH in CH$_2$C12) to afford (4S)—N5-(5-fluoropyridin-2-yl)-N7-((S)-3,3,3-trifluoro-2-hydroxypropyl)-3,4-dihydro-1,4-methanopyrido[2,3-b][1,4]diazepine-5,7(2H)-dicarboxamide (274 mg, 0.603 mmol, 41.4% yield) as a white solid. LCMS (m/z): 455.1 [M+H]$^+$, Rt=2.05 min.

$^1$H NMR (400 MHz, CDCl$_3$): δ ppm 13.16 (s, 1H), 8.20 (dd, J=9.21, 4.17 Hz, 1H), 8.04-8.14 (m, 2H), 7.84 (d, J=7.89 Hz, 1H), 7.68 (d, J=7.89 Hz, 1H), 7.50 (ddd, J=9.21, 7.45, 2.85 Hz, 1H), 5.65 (dd, J=5.92, 3.07 Hz, 1H), 5.37 (d, J=5.70 Hz, 1H), 4.19-4.32 (m, 1H), 4.00 (ddd, J=14.09, 6.63, 2.74 Hz, 1H), 3.72 (ddd, J=14.14, 8.44, 5.48 Hz, 1H), 3.17-3.32 (m, 2H), 3.09-3.15 (m, 1H), 3.00-3.06 (m, 1H), 2.28-2.39 (m, 1H), 1.97-2.11 (m, 1H).

Example 82

Synthesis of (4S)—N5-(5-fluoropyridin-2-yl)-N7-((R)-1,1,1-trifluoro-3-hydroxypropan-2-yl)-3,4-dihydro-1,4-methanopyrido[2,3-b][1,4]diazepine-5,7(2H)-dicarboxamide

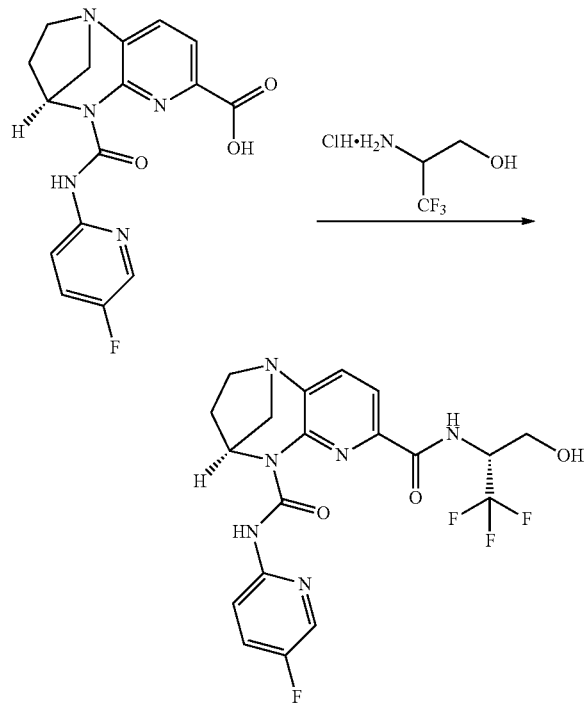

To a stirred suspension of (4S)-5-((5-fluoropyridin-2-yl)carbamoyl)-2,3,4,5-tetrahydro-1,4-methanopyrido[2,3-b][1,4]diazepine-7-carboxylic acid (600 mg, 1.748 mmol) in DMF (8 mL) at 0° C., was added HATU (1329 mg, 3.50 mmol) followed by DIPEA (0.916 mL, 5.24 mmol) and stirred for 15 min. then added Racemic 2-amino-3,3,3-trifluoropropan-1-ol hydrochloride (434 mg, 2.62 mmol) to the reaction mixture and stirred at RT for 16 h. (TLC system: 5% Methanol in DCM. $R_f$: 0.3). The reaction mixture was quenched with water (20 mL) and the aqueous layer was extracted with EtOAc (2×15 mL). Combined organic layer was dried over anhydrous sodium sulphate, filtered and concentrated to get the crude compound. The crude product was purified by column chromatography (Silica gel column, eluted with 2% of MeOH in $CH_2Cl_2$) and separated desired R-diastereomer (confirmed by authentic sample). This was further purified by prep HPLC (Column: kromo phenyl hexyl (150×25) mm×10u); Mobile phase-A: 10 mM Ammonium Bicarbonate (aq), Mobile phase-B: Acetonitrile; Method: 0/47, 8/47, 8.1/100, 12/100, 12.1/47, Flow: 20 ml/min; Solubility: THF+MeOH+CAN) to afford (4S)—N5-(5-fluoropyridin-2-yl)-N7-((R)-1,1,1-trifluoro-3-hydroxypropan-2-yl)-3,4-dihydro-1,4-methanopyrido[2,3-b][1,4]diazepine-5,7(2H)-dicarboxamide as a white solid. LCMS (m/z): 455.25 [M+H]$^+$, Rt=2.08 min.

$^1$H NMR (400 MHz, $CDCl_3$): δ ppm 12.56 (s, 1H), 8.30 (dd, J=9.21, 4.38 Hz, 1H), 8.09 (d, J=2.85 Hz, 1H), 7.88 (d, J=7.89 Hz, 1H), 7.70 (d, J=7.89 Hz, 1H), 7.60 (br d, J=9.87 Hz, 1H), 7.46-7.55 (m, 1H), 5.73 (dd, J=6.25, 3.18 Hz, 1H), 4.90-5.06 (m, 1H), 4.21-4.33 (m, 1H), 4.01-4.15 (m, 2H), 3.07-3.35 (m, 3H), 2.98-3.06 (m, 1H), 2.27-2.42 (m, 1H), 2.04 (dt, J=14.63, 7.48 Hz, 1H)

Example 83

Synthesis of (4S)—N5-(4-(oxazol-5-yl)pyridin-2-yl)-N7-(2,2,2-trifluoroethyl)-3,4-dihydro-1,4-methanopyrido[2,3-b][1,4]diazepine-5,7(2H)-dicarboxamide

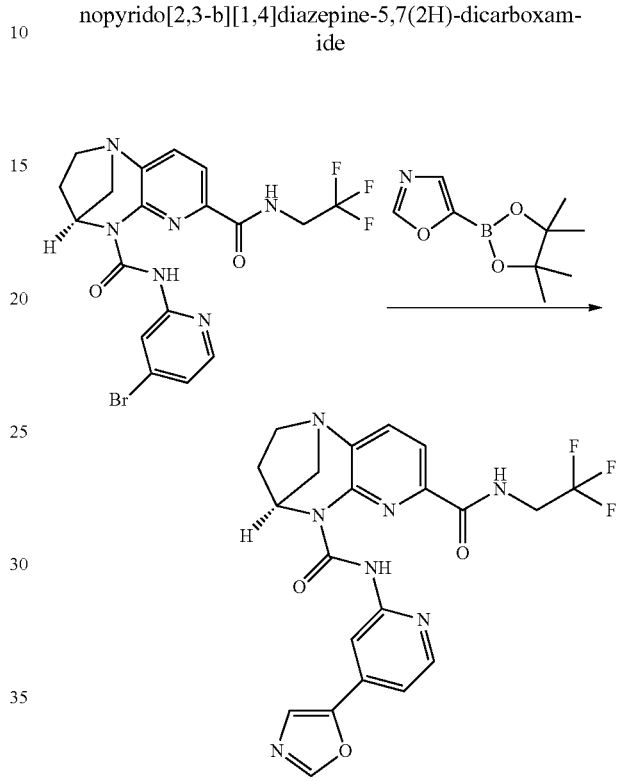

To a mixture of (4S)—N5-(4-bromopyridin-2-yl)-N7-(2,2,2-trifluoroethyl)-3,4-dihydro-1,4-methanopyrido[2,3-b][1,4]diazepine-5,7(2H)-dicarboxamide (500 mg, 1.030 mmol), 5-(4,4,5,5-tetramethyl-1,3,2-dioxaborolan-2-yl)oxazole (305 mg, 1.546 mmol) in 1,4-Dioxane (20 mL), Water (2 mL) was added potassium acetate (303 mg, 3.09 mmol) and $PdCl_2$(dppf) (113 mg, 0.155 mmol) the resulting mixture was degassed for 20 min. then stirred at 100° C. for 16 h. (TLC system: 5% Methanol in DCM. R. 0.4). Reaction mixture was cooled RT and quenched with water (20 mL) and the aqueous layer was extracted with EtOAc (2×30 mL). Combined organic layer was dried over anhydrous sodium sulphate, filtered and concentrated under reduced pressure to get crude compound. The crude product was purified by column chromatography (Silica gel column, eluted with 3% of MeOH in CH2C12) to afford (4S)—N5-(4-(oxazol-5-yl)pyridin-2-yl)-N7-(2,2,2-trifluoroethyl)-3,4-dihydro-1,4-methanopyrido[2,3-b][1,4]diazepine-5,7(2H)-dicarboxamide (258 mg, 0.544 mmol, 52.8% yield) as an off-white solid. LCMS (m/z): 474.05[M+H]$^+$, Rt=2.07 min.

$^1$H NMR (400 MHz, $CDCl_3$): δ ppm 13.75 (s, 1H), 8.48 (br t, J=6.47 Hz, 1H), 8.39 (d, J=0.66 Hz, 1H), 8.28 (d, J=5.26 Hz, 1H), 8.00 (s, 1H), 7.93 (d, J=7.89 Hz, 1H), 7.69 (d, J=7.89 Hz, 1H), 7.63 (s, 1H), 7.27 (d, J=1.53 Hz, 1H), 5.62 (dd, J=5.81, 3.18 Hz, 1H), 4.12-4.33 (m, 2H), 3.10-3.34 (m, 3H), 3.01-3.09 (m, 1H), 2.36 (ddt, J=14.33, 8.96, 5.34, 5.34 Hz, 1H), 2.01-2.15 (m, 1H).

Example 84

Synthesis of (4S)—N5-(4-(1,3-dimethyl-1H-pyrazol-4-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

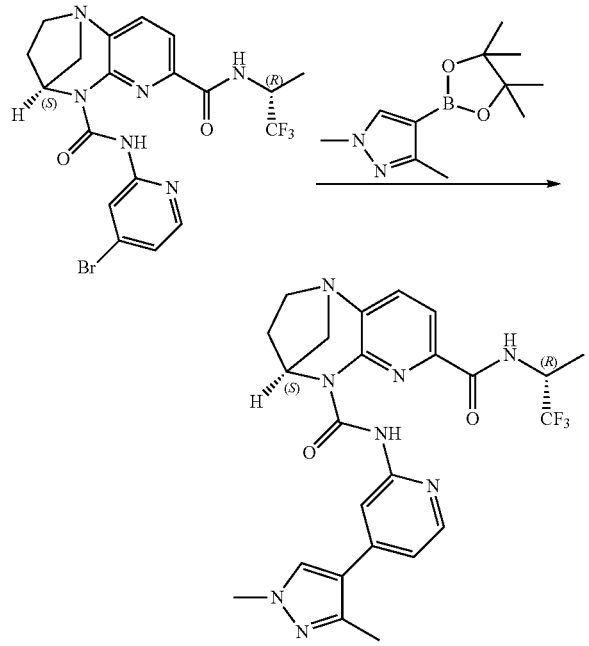

To a mixture of (4S)—N5-(4-bromopyridin-2-yl)-N7-((R)-1,1,1-trifluoropropan-2-yl)-3,4-dihydro-1,4-methanopyrido[2,3-b][1,4]diazepine-5,7(2H)-dicarboxamide (600 mg, 1.202 mmol), 1,3-dimethyl-4-(4,4,5,5-tetramethyl-1,3,2-dioxaborolan-2-yl)-1H-pyrazole (400 mg, 1.803 mmol) in 1,4-Dioxane (20 mL), Water (2.5 mL) was added potassium phosphate tribasic (638 mg, 3.00 mmol) and the resulting mixture was degassed with argon for 15 min. then added dicyclohexyl(2',4',6'-triisopropyl-[1,1'-biphenyl]-2-yl)phosphine (57.3 mg, 0.120 mmol) followed by Pd$_2$(dba)$_3$ (150 mg, 0.164 mmol) and the mixture was stirred at 100° C. for 16 h. (TLC system: 5% Methanol in DCM. R$_f$: 0.4). Reaction mixture was cooled RT and quenched with water (20 mL) and the aqueous layer was extracted with EtOAc (2×30 mL). Combined organic layer was dried over anhydrous sodium sulphate, filtered and concentrated under reduced pressure to get crude compound. The crude product was purified by column chromatography (Silica gel column, eluted with 3% of MeOH in CH$_2$C12) to afford (4S)—N5-(4-(1,3-dimethyl-1H-pyrazol-4-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (245 mg, 0.475 mmol, 39.5% yield) as an off-white solid. LCMS (m/z): 515.17 [M+H]$^+$, Rt=2.03 min.

$^1$H NMR (400 MHz, CDCl$_3$): δ ppm 13.29 (s, 1H), 8.25 (d, J=1.10 Hz, 1H), 8.21 (d, J=5.48 Hz, 1H), 8.10 (br d, J=9.43 Hz, 1H), 7.96 (d, J=7.89 Hz, 1H), 7.64-7.72 (m, 2H), 7.07 (dd, J=5.26, 1.53 Hz, 1H), 5.65 (dd, J=5.92, 3.07 Hz, 1H), 4.99-5.16 (m, 1H), 3.89 (s, 3H), 3.17-3.32 (m, 1H), 3.10-3.17 (m, 1H), 2.99-3.07 (m, 1H), 2.51 (s, 3H), 2.34 (qd, J=9.83, 4.71 Hz, 1H), 2.07 (dt, J=14.14, 6.96 Hz, 1H), 1.62 (d, J=7.23 Hz, 3H)

Example 85

Synthesis of (4S)—N5-(4-(1-methyl-1H-pyrazol-3-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

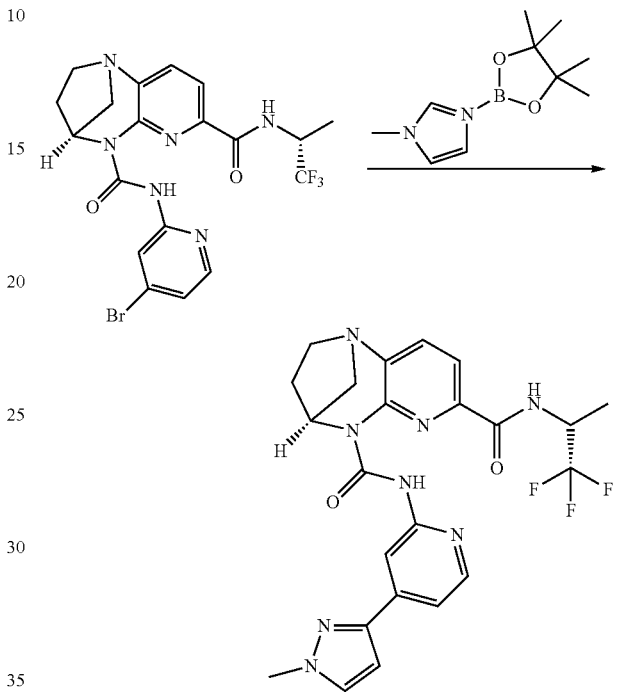

To a mixture of (4S)—N5-(4-bromopyridin-2-yl)-N7-((R)-1,1,1-trifluoropropan-2-yl)-3,4-dihydro-1,4-methanopyrido[2,3-b][1,4]diazepine-5,7(2H)-dicarboxamide (600 mg, 1.202 mmol), 1-methyl-3-(4,4,5,5-tetramethyl-1,3,2-dioxaborolan-2-yl)-1H-pyrazole (375 mg, 1.803 mmol) in 1,4-Dioxane (20 mL), Water (2.5 mL) was added potassium phosphate tribasic (638 mg, 3.00 mmol) and the resulting mixture was degassed with argon for 15 min. Then added dicyclohexyl(2',4',6'-triisopropyl-[1,1'-biphenyl]-2-yl)phosphine (57.3 mg, 0.120 mmol), Pd$_2$(dba)$_3$ (15 mg, 0.016 mmol) to the mixture and stirred at 100° C. for 16 h. (TLC system: 5% Methanol in DCM. R$_f$: 0.4). Reaction mixture was cooled RT and quenched with water (20 mL) and the aqueous layer was extracted with EtOAc (2×30 mL). Combined organic layer was dried over anhydrous sodium sulphate, filtered and concentrated under reduced pressure to get crude compound. The crude product was purified by column chromatography (Silica gel column, eluted with 2% of MeOH in CH$_2$C12) to afford (4S)—N5-(4-(1-methyl-1H-pyrazol-3-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (126 mg, 0.251 mmol, 20.92% yield) as an off-white solid. LCMS (m/z): 501.2 [M+H]$^+$, Rt=2.21 min.

$^1$H NMR (400 MHz, CHCl$_3$): δ ppm 13.41 (s, 1H), 8.29-8.37 (m, 2H), 7.93-8.07 (m, 2H), 7.70 (d, J=7.89 Hz, 1H), 7.55 (d, J=1.97 Hz, 1H), 7.05-7.15 (m, 1H), 6.49 (d, J=1.97 Hz, 1H), 5.64 (dd, J=5.81, 2.96 Hz, 1H), 5.08 (dq, J=16.80, 7.41 Hz, 1H), 3.96-4.12 (s, 3H), 3.18-3.32 (m, 2H), 3.09-3.17 (m, 1H), 3.02 (d, J=3.07 Hz, 1H), 2.27-2.45 (m, 1H), 2.07 (dt, J=14.20, 7.04 Hz, 1H), 1.62 (d, J=7.23 Hz, 3H)

Example 86

Synthesis of (4S)—N5S-(4-(1-methyl-1H-imidazol-5-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

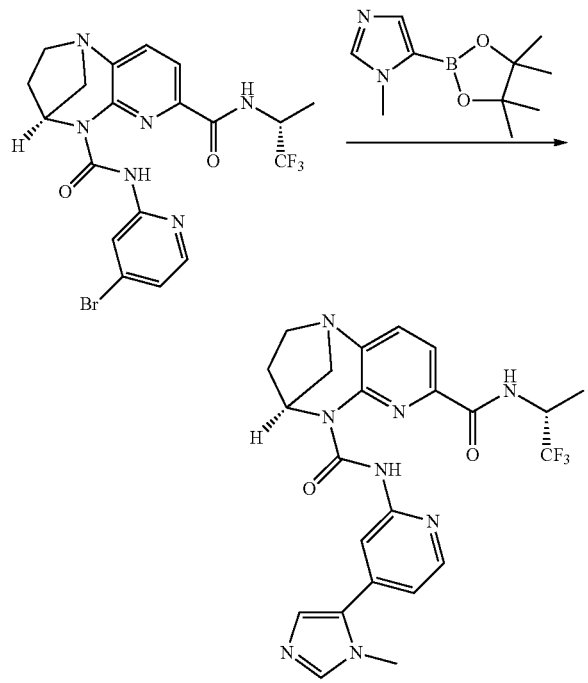

To a mixture of (4S)—N5-(4-bromopyridin-2-yl)-N7-((R)-1,1,1-trifluoropropan-2-yl)-3,4-dihydro-1,4-methanopyrido[2,3-b][1,4]diazepine-5,7(2H)-dicarboxamide (600 mg, 1.202 mmol), 1-methyl-5-(4,4,5,5-tetramethyl-1,3,2-dioxaborolan-2-yl)-1H-imidazole (375 mg, 1.803 mmol) in 1,4-Dioxane (20 mL), water (2 mL) was added potassium phosphate tribasic (638 mg, 3.00 mmol) and the resulting mixture was degassed with argon for 15 min. then added dicyclohexyl(2',4',6'-triisopropyl-[1,1'-biphenyl]-2-yl)phosphine (57.3 mg, 0.120 mmol), Pd$_2$(dba)$_3$ (150 mg, 0.164 mmol) and the mixture was stirred at 100° C. for 16 h. (TLC system: 5% Methanol in DCM. R$_f$: 0.4). Reaction mixture was cooled RT and quenched with water (20 mL) and the aqueous layer was extracted with EtOAc (2×30 mL). Combined organic layer was dried over anhydrous sodium sulphate, filtered and concentrated under reduced pressure to get crude compound. The crude product was purified by column chromatography (Silica gel column, eluted with 2% of MeOH in CH$_2$Cl2) to afford (4S)—N5-(4-(1-methyl-1H-imidazol-5-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (172 mg, 0.331 mmol, 27.6% yield) as an off-white solid. LCMS (m/z): 501.1[M+H]$^+$, Rt=1.57 min.

$^1$H NMR (400 MHz, CDCl$_3$): δ ppm 13.09-13.75 (m, 1H), 8.25-8.32 (m, 2H), 7.94-8.06 (m, 2H), 7.69 (d, J=7.89 Hz, 1H), 7.58 (s, 1H), 7.36 (d, J=1.10 Hz, 1H), 7.10 (dd, J=5.26, 1.75 Hz, 1H), 5.64 (dd, J=5.92, 3.07 Hz, 1H), 5.00-5.16 (m, 1H), 3.85 (s, 3H), 3.18-3.31 (m, 2H), 3.10-3.17 (m, 1H), 3.02 (d, J=3.29 Hz, 1H), 2.29-2.41 (m, 1H), 2.07 (dt, J=14.14, 6.96 Hz, 1H), 1.58-1.66 (m, 3H).

Example 87

Synthesis of (4S)—N5-(4-((S)-2,3-dihydroxypropoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

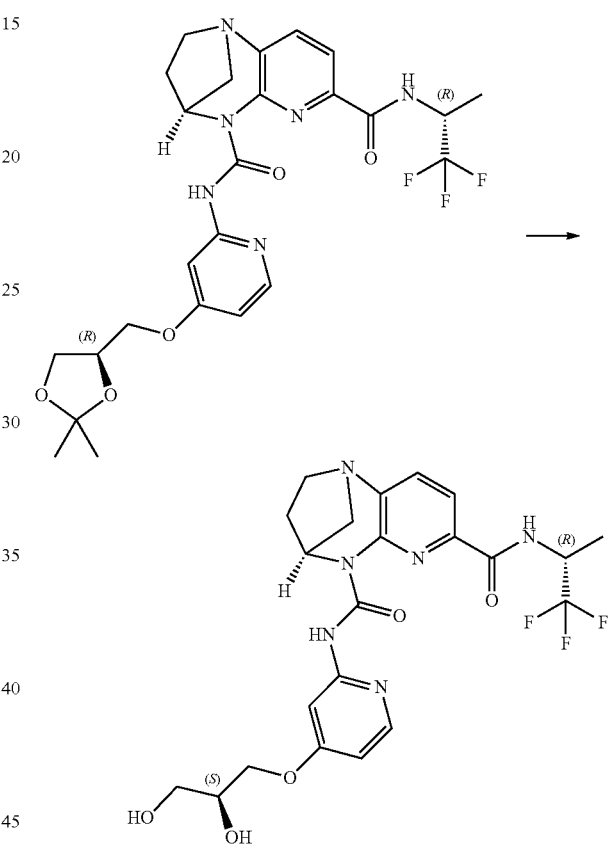

To a stirred solution of (4S)—N5-(4-(((R)-2,2-dimethyl-1,3-dioxolan-4-yl)methoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (350 mg, 0.636 mmol) in methanol (3 mL) at 0° C. was aq. HCl (3 mL, 99 mmol) and stirred for 6 h. (TLC eluent: 10% MeOH in DCM R$_f$: 0.2; UV active). Reaction mixture was concentrated under reduced pressure and the residue was dissolved in water (3 mL), then neutralized with saturated sodium bicarbonate solution and extracted with 10% MeOH in DCM (2×20 mL). The combined organic layer was washed with brine (20 mL), dried over anhydrous Na$_2$SO$_4$, filtered and concentrated under reduced pressure to obtain crude compound. The crude product was purified by column chromatography (silica gel eluted with 10% of MeOH in CH$_2$Cl$_2$) to afford the desired compound (4S)—N5-(4-((S)-2,3-dihydroxypropoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (88 mg, 0.172 mmol, 27.1% yield) as green solid. LC-MS (m/z): 511.17 [M+H]$^+$, Rt=1.49 min.

¹H NMR (400 MHz, DMSO-d₆): δ ppm 13.06 (s, 1H), 8.17 (br d, J=8.99 Hz, 1H), 8.06 (d, J=5.92 Hz, 1H), 7.76 (s, 2H), 7.68 (d, J=2.19 Hz, 1H), 6.74 (dd, J=5.70, 2.41 Hz, 1H), 5.45 (dd, J=5.70, 3.07 Hz, 1H), 5.02 (d, J=5.26 Hz, 1H), 4.98 (br d, J=8.33 Hz, 1H), 4.71 (t, J=5.70 Hz, 1H), 4.12 (dd, J=9.76, 3.84 Hz, 1H), 3.96 (dd, J=9.76, 6.25 Hz, 1H), 3.79-3.87 (m, 1H), 3.43-3.50 (m, 2H), 3.07 (br d, J=12.50 Hz, 3H), 2.88-2.98 (m, 1H), 2.17-2.30 (m, 1H), 1.92-2.02 (m, 1H), 1.52 (d, J=7.02 Hz, 3H).

Example 87

Synthesis of (4S)—N7-(cyclopropylmethyl)-N5-(4-((R)-2,3-dihydroxypropoxy)pyridin-2-yl)-3,4-dihydro-1,4-methanopyrido[2,3-b][1,4]diazepine-5,7(2H)-dicarboxamide

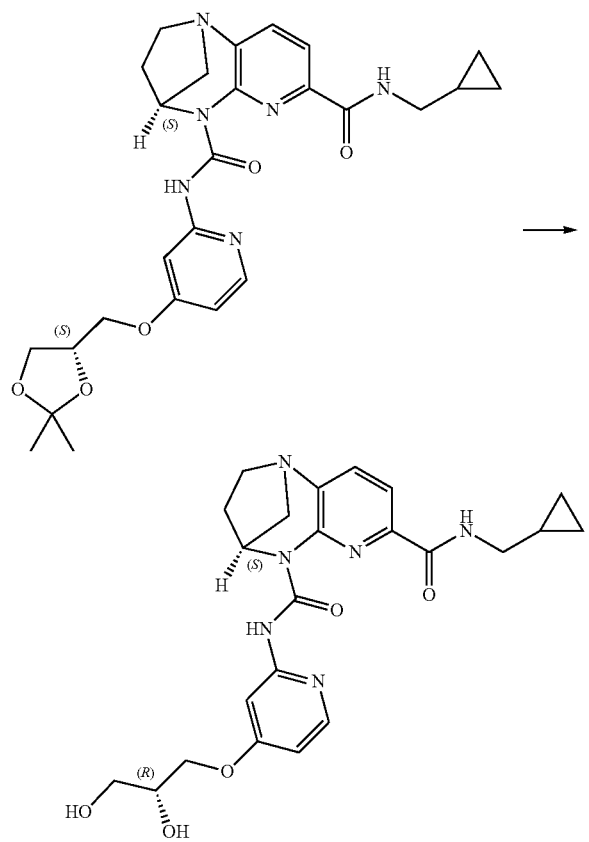

To a stirred solution of (4S)—N7-(cyclopropylmethyl)-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide (520 mg, 1.022 mmol) in methanol (6 mL) at 0° C. was added aq. HCl (3 mL, 99 mmol) and stirred for 5 h. (TLC eluent: Mobile Phase: 10% MeOH in DCM R_f: 0.2; UV active). The reaction mass was concentrated under reduced pressure and the residue was dissolved in water (10 mL) then neutralized with saturated bicarbonate solution and extracted with 10% MeOH in DCM (2×50 mL). The combined organic layer was washed with brine (20 mL), dried over sodium sulphate and filtered concentrated under reduced pressure to afford crude product. The crude solid was suspended in pentane (50 mL) and stirred for 3 h, then filtered and dried under vacuo to get desired compound (4S)—N7-(cyclopropylmethyl)-N5-(4-((R)-2,3-dihydroxypropoxy)pyridin-2-yl)-3,4-dihydro-1,4-methanopyrido[2,3-b][1,4]diazepine-5,7(2H)-dicarboxamide (295 mg, 0.614 mmol, 60.1% yield) as an off white solid. LC-MS (m/z): 469.16 [M+H]⁺, Rt=1.34 min.

¹H NMR (400 MHz, DMSO-d₆): δ ppm 13.41 (s, 1H), 8.24-8.31 (m, 1H), 8.10 (d, J=5.92 Hz, 1H), 7.72 (d, J=4.17 Hz, 2H), 7.64 (d, J=2.41 Hz, 1H), 6.73 (dd, J=5.92, 2.41 Hz, 1H), 5.42 (dd, J=5.70, 3.07 Hz, 1H), 5.02 (d, J=5.26 Hz, 1H), 4.71 (s, 1H), 4.11 (br d, J=3.95 Hz, 1H), 3.97 (dd, J=9.87, 6.36 Hz, 1H), 3.80-3.87 (m, 1H), 3.43-3.51 (m, 2H), 3.31 (s, 2H), 3.07-3.22 (br s, 3H), 2.94-2.99 (m, 1H), 2.22 (dt, J=5.92, 3.84 Hz, 1H), 1.89-2.01 (m, 1H), 1.08-1.19 (m, 1H), 0.41-0.47 (m, 2H), 0.28 (br d, J=4.17 Hz, 2H).

Example 88

Synthesis of (4S)—N7-((R)-1-cyclopropyl-2,2,2-trifluoroethyl)-N5-(4-((R)-2,3-dihydroxypropoxy)pyridin-2-yl)-3,4-dihydro-1,4-methanopyrido[2,3-b][1,4]diazepine-5,7(2H)-dicarboxamide

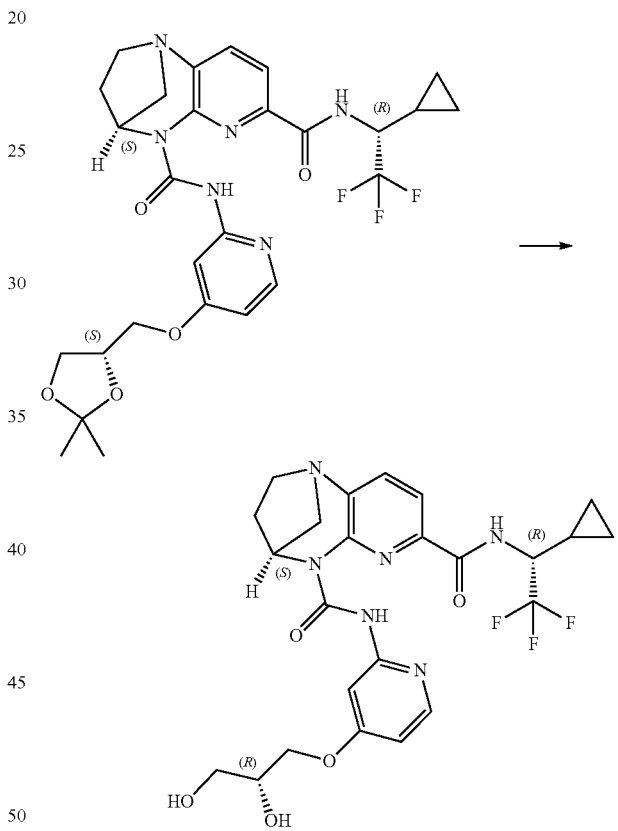

To a stirred solution of (4S)—N7-((R)-1-cyclopropyl-2,2,2-trifluoroethyl)-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide (500 mg, 0.867 mmol) in methanol (7 mL) at 0° C. was 2M HCl (5 mL, 10.00 mmol) and stirred for 5 h. (TLC eluent: Mobile Phase: 10% MeOH in DCM R_f: 0.2; UV active). The reaction mass was concentrated half amount of volume, cooled to 0° C. then neutralised sodium bicarbonate solution and the aqueous layer was extracted with 10% MeOH in DCM (2×40 mL). The combined organic layer was washed with brine (15 mL), dried over sodium sulphate, filtered and concentrated under reduced pressure to afford off white solid. The compound was suspended in Acetonitrile (5 mL) and diethyl ether (10 mL) the resulting white suspension was stirred for 20 min. Then, filtered and dried under vacuo to afford (4S)—N7-((R)-1-cyclopropyl-2,2,2-trifluoroethyl)-

N5-(4-((R)-2,3-dihydroxypropoxy)pyridin-2-yl)-3,4-dihydro-1,4-methanopyrido[2,3-b][1,4]diazepine-5,7(2H)-dicarboxamide (341 mg, 0.620 mmol, 71.5% yield) as off white solid. LC-MS (m/z): 537.20 [M+H]$^+$, Rt=1.62 min.

$^1$H NMR (400 MHz, DMSO-d$_6$): δ ppm 13.16 (s, 1H), 8.26 (d, J=5.70 Hz, 1H), 8.03 (d, J=5.70 Hz, 1H), 7.77 (d, J=3.95 Hz, 2H), 7.67 (d, J=2.19 Hz, 1H), 6.73 (dd, J=5.81, 2.30 Hz, 1H), 5.45 (br dd, J=5.70, 2.85 Hz, 1H), 5.02 (d, J=5.26 Hz, 1H), 4.71 (t, J=5.70 Hz, 1H), 4.22 (br d, J=8.33 Hz, 1H), 4.12 (dd, J=9.87, 3.73 Hz, 1H), 3.97 (dd, J=9.76, 6.25 Hz, 1H), 3.83 (br d, J=4.17 Hz, 1H), 3.41-3.51 (m, 2H), 3.05-3.23 (m, 3H), 2.92-3.02 (m, 1H), 2.15-2.29 (m, 1H), 1.99 (br d, J=2.63 Hz, 1H), 1.36-1.48 (m, 1H), 0.75-0.85 (m, 1H), 0.69 (br dd, J=9.32, 4.93 Hz, 1H), 0.51-0.61 (m, 1H) 0.32 (br dd, J=9.54, 5.15 Hz, 1H).

Example 89

Synthesis of (4S)—N5-(4-((R)-2,3-dihydroxypropoxy)pyridin-2-yl)-N7-(2,2,2-trifluoroethyl)-3,4-dihydro-1,4-methanopyrido[2,3-b][1,4]diazepine-5,7(2H)-dicarboxamide

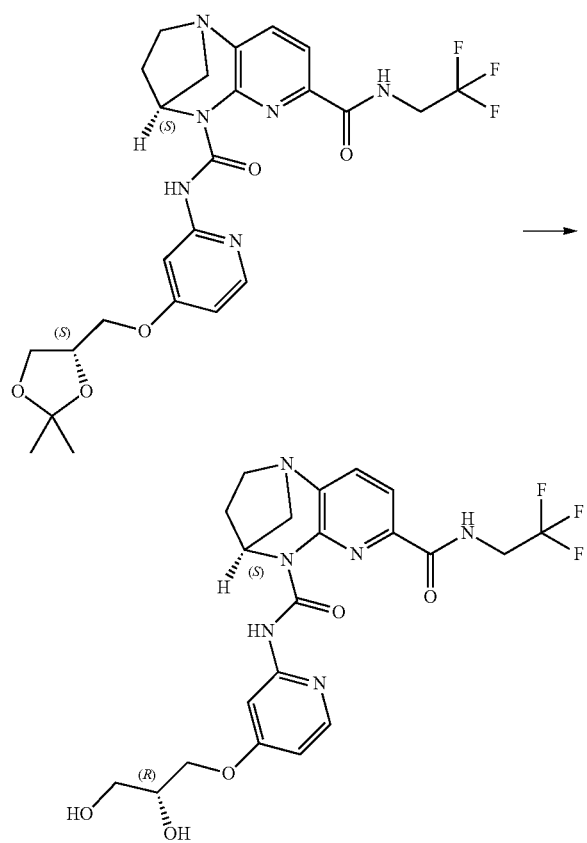

To a stirred solution of (4S)—N5-(4-(((S)-2,2-dimethyl-1,3-dioxolan-4-yl)methoxy)pyridin-2-yl)-N7-(2,2,2-trifluoroethyl)-3,4-dihydro-1,4-methanopyrido[2,3-b][1,4]diazepine-5,7(2H)-dicarboxamide (480 mg, 0.895 mmol) in methanol (8 mL) at 0° C. was added 2M HCl (5 mL, 10.00 mmol and stirred for 5 h. (TLC eluent: Mobile Phase: 10% MeOH in DCM R$_f$: 0.2; UV active). The reaction mass was concentrated half amount of volume, cooled to 0° C. and added neutralised with saturated sodium bicarbonate solution and the aqueous layer was extracted with 10% MeOH in DCM (2×40 mL). The combined organic layer was washed with brine (15 mL), dried over sodium sulphate, filtered and concentrated under reduced pressure to afford off white solid. The compound was suspended in Acetonitrile (5 mL) and diethyl ether (10 mL) the resulting white suspension was stirred for 20 min. Then, filtered and dried under vacuo to afford (4S)—N5-(4-((R)-2,3-dihydroxypropoxy)pyridin-2-yl)-N7-(2,2,2-trifluoroethyl)-3,4-dihydro-1,4-methanopyrido[2,3-b][1,4]diazepine-5,7(2H)-dicarboxamide (340 mg, 0.682 mmol, 76% yield) as off white solid. LC-MS (m/z): 497.20 [M+H]$^+$, Rt=1.62 min.

$^1$H NMR (400 MHz, DMSO-d$_6$): δ ppm 13.46 (s, 1H), 8.71 (br t, J=6.47 Hz, 1H), 8.16 (d, J=5.92 Hz, 1H), 7.75 (d, J=0.88 Hz, 2H), 7.58 (d, J=2.19 Hz, 1H), 6.73 (dd, J=5.92, 2.41 Hz, 1H), 5.40 (dd, J=5.70, 3.07 Hz, 1H), 5.02 (d, J=5.26 Hz, 1H), 4.71 (t, J=5.70 Hz, 1H), 4.30 (br dd, J=9.43, 7.02 Hz, 2H), 4.12 (dd, J=9.87, 3.95 Hz, 1H), 3.97 (dd, J=9.87, 6.36 Hz, 1H), 3.79-3.88 (m, 1H), 3.46 (td, J=5.70, 2.19 Hz, 2H), 3.05-3.24 (m, 3H), 2.95-3.02 (m, 1H), 2.23 (dt, J=6.03, 3.78 Hz, 1H), 1.91-2.01 (m, 1H).

Example 90

Synthesis of (4S)—N5-(4-((R)-2,3-dihydroxypropoxy)pyridin-2-yl)-N7-((R)-1,1,1-trifluorobutan-2-yl)-3,4-dihydro-1,4-methanopyrido[2,3-b][1,4]diazepine-5,7(2H)-dicarboxamide

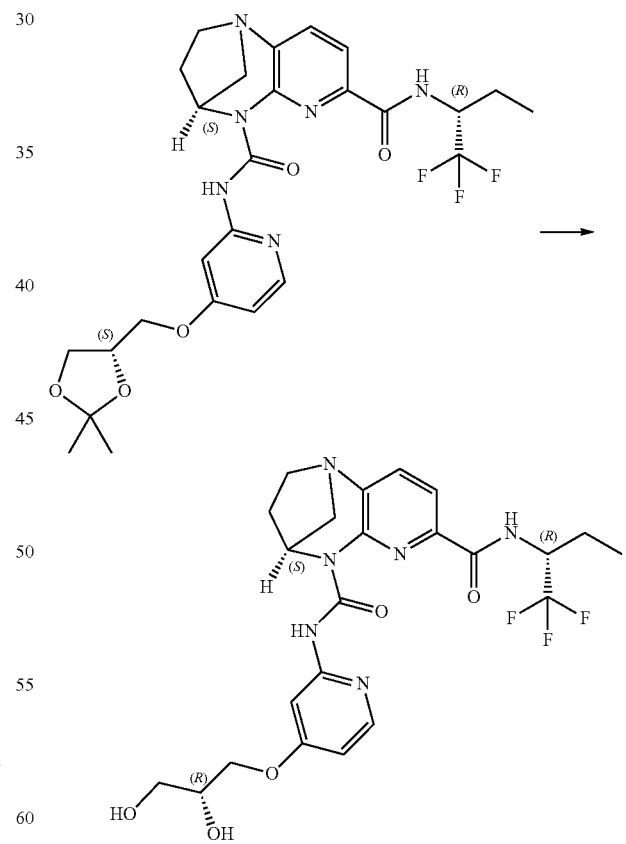

To a stirred solution of (4S)—N5-(4-(((S)-2,2-dimethyl-1,3-dioxolan-4-yl)methoxy)pyridin-2-yl)-N7-((R)-1,1,1-trifluorobutan-2-yl)-3,4-dihydro-1,4-methanopyrido[2,3-b][1,4]diazepine-5,7(2H)-dicarboxamide (320 mg, 0.567 mmol) in methanol (6 mL) at 0° C. under nitrogen was added 2M HCl (5 mL, 10.00 mmol) and stirred for 5 h. (TLC eluent: Mobile Phase: 10% MeOH in DCM R$_f$: 0.2; UV active). The reaction mass was concentrated under reduced pressure, the residue was suspended in water (4 mL) and neutralized with saturated sodium bicarbonate solution then the aqueous layer was extracted with 10% MeOH in DCM (2×50 mL). The combined organic layer was washed with brine (15 mL), dried over sodium sulphate, filtered and concentrated under reduced pressure to afford crude brown solid (380 mg). The crude product was purified by column chromatography (silica gel, eluted with 13% MeOH in CH$_2$Cl$_2$) to afford (4S)—N5-(4-((R)-2,3-dihydroxypropoxy)pyridin-2-yl)-N7-((R)-1,1,1-trifluorobutan-2-yl)-3,4-dihydro-1,4-methanopyrido[2,3-b][1,4]diazepine-5,7(2H)-dicarboxamide (298 mg, 0.568 mmol, 100% yield) as an off white solid. LC-MS (m/z): 525.18 [M+H]$^+$, Rt=1.62 min.

$^1$H NMR (400 MHz, DMSO-d$_6$): δ ppm 13.07 (s, 1H), 8.03 (d, J=5.70 Hz, 2H), 7.77 (d, J=2.41 Hz, 2H), 7.67 (d, J=2.41 Hz, 1H), 6.74 (dd, J=5.92, 2.41 Hz, 1H), 5.43-5.47 (m, 1H), 5.02 (d, J=5.26 Hz, 1H), 4.85-4.65 (m, 2H), 4.10 (br d, J=3.95 Hz, 1H), 3.97 (dd, J=9.87, 6.36 Hz, 1H), 3.79-3.87 (m, 1H), 3.46 (td, J=5.70, 2.19 Hz, 2H), 3.05-3.22 (m, 3H), 2.94-3.00 (m, 1H), 2.22 (dt, J=5.97, 3.92 Hz, 1H), 1.86-2.04 (m, 3H), 0.97 (t, J=7.34 Hz, 3H).

Example 91

Synthesis of (4S)—N5-(4-((R)-2,3-dihydroxypropoxy)pyridin-2-yl)-N7-((S)-3,3,3-trifluoro-2-hydroxypropyl)-3,4-dihydro-1,4-methanopyrido[2,3-b][1,4]diazepine-5,7(2H)-dicarboxamide

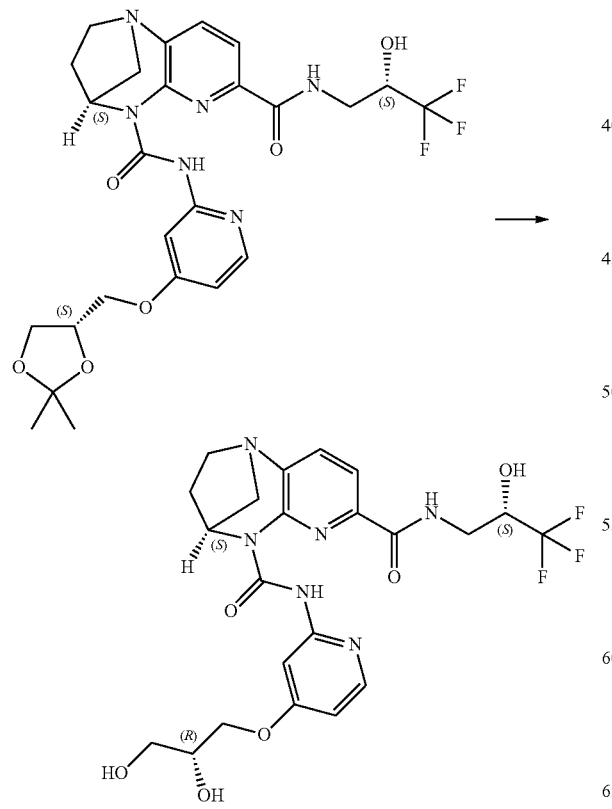

To a stirred solution of (4S)—N5-(4-(((S)-2,2-dimethyl-1,3-dioxolan-4-yl)methoxy)pyridin-2-yl)-N7-((S)-3,3,3-trifluoro-2-hydroxypropyl)-3,4-dihydro-1,4-methanopyrido[2,3-b][1,4]diazepine-5,7(2H)-dicarboxamide (180 mg, 0.318 mmol) in methanol (6 mL) at 0° C. under nitrogen was added 2M HCl (5 mL, 10.00 mmol) and stirred for 5 h. (TLC eluent: Mobile Phase: 10% MeOH in DCM R$_f$: 0.2; UV active). The reaction mass was concentrated under reduced pressure, the residue was taken in water (4 mL) then neutralized with saturated sodium bicarbonate solution and the aqueous layer was extracted with 10% MeOH in DCM (2×50 mL). The combined organic layer was washed with brine (15 mL), dried over sodium sulphate, filtered and concentrated under reduced pressure to get crude solid. The crude product was purified by column chromatography (silica gel, eluted with 13% MeOH in CH$_2$Cl$_2$) to afford (4S)—N5-(4-((R)-2,3-dihydroxypropoxy)pyridin-2-yl)-N7-((S)-3,3,3-trifluoro-2-hydroxypropyl)-3,4-dihydro-1,4-methanopyrido[2,3-b][1,4]diazepine-5,7(2H)-dicarboxamide (100 mg, 0.181 mmol, 57.0% yield) as an off white solid. LC-MS (m/z): 527.16 [M+H]$^+$, Rt=1.30 min.

$^1$H NMR (400 MHz, DMSO-d$_6$): δ ppm 13.35 (s, 1H), 8.44 (s, 1H), 8.08 (d, J=5.70 Hz, 1H), 7.67-7.76 (m, 2H), 7.64 (d, J=2.19 Hz, 1H), 6.76 (dd, J=5.81, 2.30 Hz, 1H), 6.56 (d, J=6.36 Hz, 1H), 5.41-5.46 (m, 1H), 5.02 (d, J=5.26 Hz, 1H), 4.71 (t, J=5.70 Hz, 1H), 4.22-4.32 (m, 1H), 4.12 (dd, J=9.76, 3.84 Hz, 1H), 3.97 (dd, J=9.87, 6.36 Hz, 1H), 3.79-3.88 (m, 1H), 3.69-3.78 (m, 1H), 3.56 (br dd, J=14.03, 7.02 Hz, 2H), 3.46 (td, J=5.70, 2.19 Hz, 1H), 2.94-3.23 (m, 4H), 2.19-2.29 (m, 1H), 1.93 (dt, J=13.65, 7.10 Hz, 1H).

Example 92

Synthesis of (4S)—N5-(4-((R)-2,3-dihydroxypropoxy)pyridin-2-yl)-N7-((R)-1,1,1-trifluoro-3-hydroxypropan-2-yl)-3,4-dihydro-1,4-methanopyrido[2,3-b][1,4]diazepine-5,7(2H)-dicarboxamide

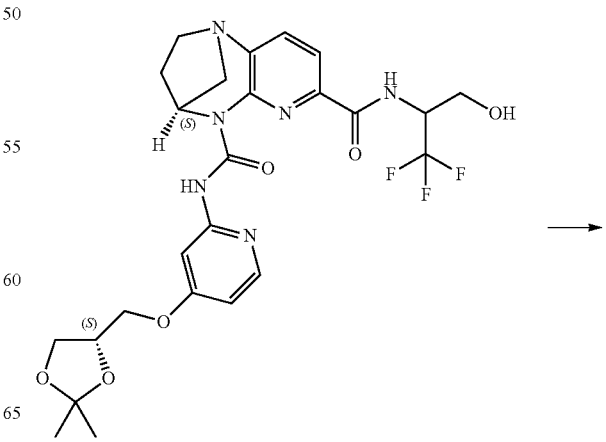

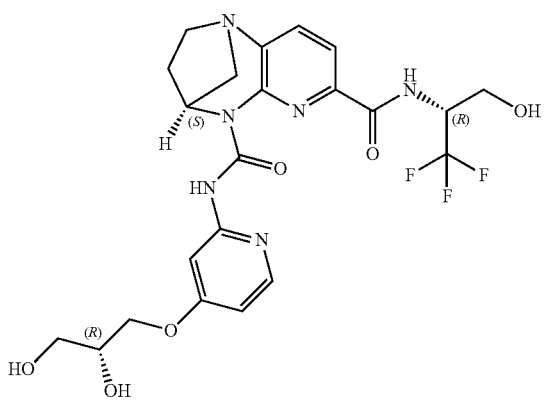

To a stirred solution of (4S)—N5-(4-(((S)-2,2-dimethyl-1,3-dioxolan-4-yl)methoxy)pyridin-2-yl)-N7-(1,1,1-trifluoro-3-hydroxypropan-2-yl)-3,4-dihydro-1,4-methanopyrido[2,3-b][1,4]diazepine-5,7(2H)-dicarboxamide (500 mg, 0.883 mmol) in methanol (2 mL) at 0° C., was added 2M HCl (5 mL, 10.00 mmol) and stirred for 5 h. (TLC eluent: Mobile Phase: 10% MeOH in DCM $R_f$: 0.2; UV active). The reaction mass was concentrated under reduced pressure, neutralized with saturated sodium bicarbonate solution and the aqueous layer was extracted with 10% MeOH in DCM (2×30 mL). The combined organic layer was washed with brine (10 mL), dried over sodium sulphate, filtered and concentrated under reduced pressure to get the product as diastereomeric mixtures. The diastereomers were separated by chiral SFC (Column/dimensions: Luxcellulose-2 (250×30) mm, 5μ; % CO2: 50.0%; % Co solvent: 50.0% (100% METHANOL); Total Flow: 90.0 g/min; Back Pressure: 100.0 bar; UV: 213 nm; Stack time: 7.8 min; Load/inj: 10.0 mg; Solubility: Methanol; Total No of injections: 28; Instrument details: Make/Model: Thar SFC-200 (OLD)) to afford two single diastereomers, of which peak 1 absolute stereochemistry was determined by comparing with the authentic sample.

Peak 1

Obtained (4S)—N5-(4-((R)-2,3-dihydroxypropoxy)pyridin-2-yl)-N7-((R)-1,1,1-trifluoro-3-hydroxypropan-2-yl)-3,4-dihydro-1,4-methanopyrido[2,3-b][1,4]diazepine-5,7 (2H)-dicarboxamide (95 mg, 0.179 mmol, 20.25% yield) as an off white solid. LC-MS (m/z): 527.16 [M+H]$^+$, Rt=1.31 min.

$^1$H NMR (400 MHz, DMSO-d$_6$): δ ppm 13.01 (s, 1H), 8.24 (br d, J=9.21 Hz, 1H), 8.03 (d, J=5.92 Hz, 1H), 7.76 (s, 2H), 7.70 (d, J=2.41 Hz, 1H), 6.75 (dd, J=5.92, 2.41 Hz, 1H), 5.47 (dd, J=5.70, 2.85 Hz, 1H), 5.37 (t, J=6.14 Hz, 1H), 5.02 (d, J=5.26 Hz, 1H), 4.88 (br dd, J=8.22, 5.15 Hz, 1H), 4.71 (t, J=5.59 Hz, 1H), 4.12 (dd, J=9.76, 3.84 Hz, 1H), 3.80-4.00 (m, 4H), 3.41-3.51 (m, 2H), 3.05-3.22 (m, 3H), 2.95-3.02 (m, 1H), 2.23 (br dd, J=9.76, 4.06 Hz, 1H), 1.96 (dt, J=13.81, 7.13 Hz, 1H)

Example 93

Synthesis of (4S)—N5-(7H-pyrrolo[2,3-d]pyrimidin-2-yl)-N7-(2,2,2-trifluoroethyl)-3,4-dihydro-1,4-methanopyrido[2,3-b][1,4]diazepine-5,7(2H)-dicarboxamide To a solution of (4S)-5-((7H-pyrrolo[2,3-d]pyrimidin-2-yl)carbamoyl)-2,3,4,5-tetrahydro-1,4-methanopyrido[2,3-b][1,4]diazepine-7-carboxylic acid (400 mg, 1.095 mmol) in DMF (10 mL) under nitrogen was added 2,2,2-trifluoroethanamine hydrochloride (223 mg, 1.642 mmol), DIPEA (0.765 mL, 4.38 mmol) and HATU (624 mg, 1.642 mmol) and stirred at RT for 16 h. (TLC eluent: 100% EtOAc: $R_f$—0.3; UV active). Water (30 mL) was added to the reaction and stirred for 15 min. to give solid and was filtered through Buchner funnel to give crude product. The crude was triturated with diethylether, to afford (4S)—N5-(7H-pyrrolo[2,3-b]pyrimidin-2-yl)-N7-(2,2,2-trifluoroethyl)-3,4-dihydro-1,4-methanopyrido[2,3-b][1,4]diazepine-5,7 (2H)-dicarboxamide (270 mg, 0.595 mmol, 54.3% yield) as an off white solid. LCMS (m/z): 447.16 [M+H]$^+$, $R_t$=1.51 min.

$^1$H NMR (400 MHz, CDCl$_3$): δ ppm 14.02 (s, 1H), 11.38 (br s, 1H), 8.84 (br t, J=6.36 Hz, 1H), 8.73 (s, 1H), 7.95 (d, J=7.89 Hz, 1H), 7.71 (d, J=7.89 Hz, 1H), 7.46 (dd, J=3.29, 2.41 Hz, 1H), 6.54 (dd, J=3.62, 1.64 Hz, 1H), 5.72 (dd, J=5.70, 3.07 Hz, 1H), 4.34-4.20 (m, 2H), 3.35-3.14 (m, 3H), 3.11-3.03 (m, 1H), 2.38 (qd, J=9.76, 4.71 Hz, 1H), 2.12 (dt, J=14.31, 6.99 Hz, 1H).

Example 94

Synthesis of (4S)—N7-(3-amino-2,2-difluoropropyl)-N5-(pyridin-2-yl)-3,4-dihydro-1,4-methanopyrido[2,3-b][1,4]diazepine-5,7(2H)-dicarboxamide

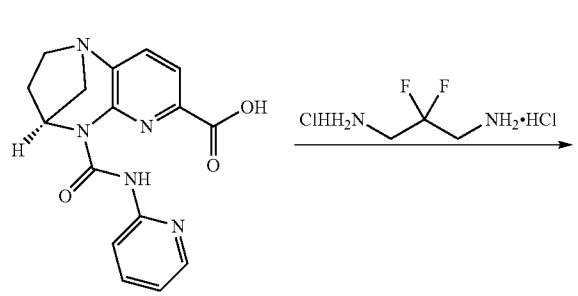

To a stirred suspension of 2,2-difluoropropane-1,3-diamine dihydrochloride (1013 mg, 5.53 mmol) in DMF (30 mL), under nitrogen at RT was added DIPEA (1.611 mL, 9.22 mmol) and stirred until the reaction mixture become clear solution. To this mixture was added (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) and HATU (701 mg, 1.844 mmol) at RT and stirred for 4 h. (TLC system: 5% Methanol in DCM, Rf value: 0.3). Water (100 mL) was added to the reaction mixture and extracted with EtOAc (100 mL). Combined organic extracts were dried over anhydrous $Na_2SO_4$, filtered and concentrated to get crude compound. The crude product was purified by combiflash chromatography (using Silica gel column, eluted with 5% Methanol in DCM) to afford (4S)—N7-(3-amino-2,2-difluoropropyl)-N5-(pyridin-2-yl)-3,4-dihydro-1,4-methanopyrido[2,3-b][1,4]diazepine-5,7(2H)-dicarboxamide (140 mg, 0.328 mmol, 35.5% yield) as an off-white solid. LCMS (m/z): 418.07 $[M+H]^+$, Rt=1.83 min.

$^1$H NMR (400 MHz, DMSO-$d_6$): δ ppm 13.32-13.43 (m, 1H), 8.49 (br t, J=6.47 Hz, 1H), 8.25-8.45 (m, 1H), 7.92-8.04 (m, 1H), 7.84 (td, J=7.78, 1.75 Hz, 1H), 7.69-7.77 (m, 2H), 7.11 (ddd, J=7.29, 4.99, 1.10 Hz, 1H), 5.43 (dd, J=5.81, 2.96 Hz, 1H), 3.84-4.10 (m, 2H), 3.05-3.27 (m, 3H), 2.89-3.02 (m, 3H), 2.23 (dddd, J=13.67, 9.84, 5.97, 3.84 Hz, 1H), 1.77-2.01 (m, 1H), 1.71-1.77 (m, 2H).

Example 95

Synthesis of (4S)—N5-(5-((R)-2,3-dihydroxypropoxy)pyrazin-2-yl)-N7-(2,2,2-trifluoroethyl)-3,4-dihydro-1,4-methanopyrido[2,3-b][1,4]diazepine-5,7(2H)-dicarboxamide

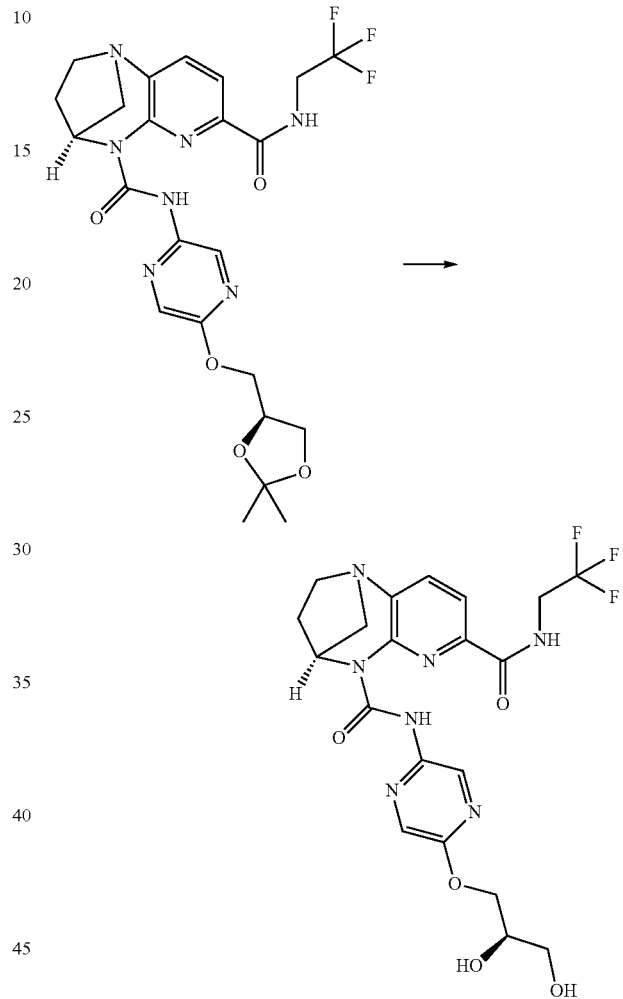

To a solution of (4S)—N5-(5-(((S)-2,2-dimethyl-1,3-dioxolan-4-yl)methoxy)pyrazin-2-yl)-N7-(2,2,2-trifluoroethyl)-3,4-dihydro-1,4-methanopyrido[2,3-b][1,4]diazepine-5,7(2H)-dicarboxamide (370 mg, 0.688 mmol) in methanol (5 mL) at RT was added aq. HCl (5 mL, 10.00 mmol) and stirred for 2 h. (TLC system: 5% Methanol in DCM, Rf value: 0.1). The reaction mixture was concentrated to remove the methanol and the residue was cooled to 0° C., basified with $NaHCO_3$ solution and the aqueous mixture was extracted with DCM (50 mL). Combined DCM extracts were dried over anhydrous $Na_2SO_4$, filtered and concentrated to get crude product. The crude product was purified by combiflash chromatography (using Silicagel column, eluted with 3% Methanol in DCM) to give the product with 80% HPLC purity. This was further purified by preparative HPLC (Column: XBRIDGE C18 (150×19) mm; Mobile Phase A: 5 mM Ammonium bicarbonate, Mobile Phase B: Acetonitrile; % B/Time: 0/10, 2/25, 10/55; Solubility: MeOH+THF) to afford (4S)—N5-(5-((R)-2,3-dihydroxypropoxy)pyrazin-2-yl)-N7-(2,2,2-trifluoroethyl)-3,4-dihydro-1,4-methanopyrido[2,3-b][1,4]diazepine-5,7(2H)-dicarboxamide (90 mg, 0.181 mmol, 26.2% yield) as an off-white solid. LCMS (m/z): 498.18 [M+H]⁺, Rt=1.60 min. ¹H NMR (400 MHz, CDCl₃): δ ppm 13.16-13.59 (m, 1H), 8.92 (d, J=1.10 Hz, 1H), 7.98-8.05 (m, 1H), 7.90-7.96 (m, 2H), 7.69 (d, J=7.89 Hz, 1H), 5.62 (dd, J=5.70, 3.07 Hz, 1H), 4.38-4.54 (m, 2H), 4.07-4.28 (m, 3H), 3.65-3.86 (m, 2H), 2.99-3.32 (m, 5H), 2.20-2.40 (m, 2H), 2.06 (dt, J=14.69, 7.34 Hz, 1H).

Example 96

Synthesis of (4S)—N7-(cyclopropylmethyl)-N5-(pyridazin-3-yl)-3,4-dihydro-1,4-methanopyrido[2,3-b][1,4]diazepine-5,7(2H)-dicarboxamide

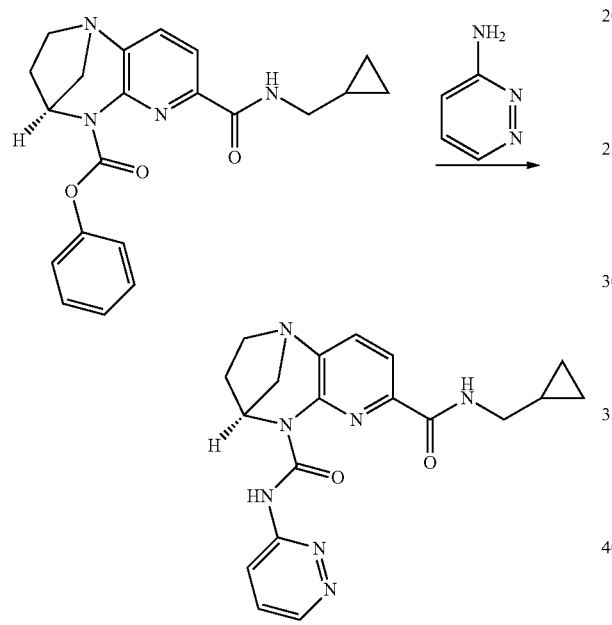

To a stirred solution of pyridazin-3-amine (151 mg, 1.586 mmol) in Tetrahydrofuran (5 mL), was added a solution of 1M LHMDS (2.64 mL, 2.64 mmol) in THF as drop wise at −78° C. After stirring the reaction mixture at −78° C. for 30 min, added a solution of (4S)-phenyl 7-((cyclopropylmethyl)carbamoyl)-3,4-dihydro-1,4-methanopyrido[2,3-b][1,4]diazepine-5(2H)-carboxylate (500 mg, 1.321 mmol) in Tetrahydrofuran (2 mL) as drop wise under nitrogen at −78° C. The resulting reaction mixture was stirred at −78° C. for 1 h. and then at rt for 6 h. (TLC 5% MeOH in DCM R$_f$: 0.3; UV active). The reaction mixture was quenched with aqueous NH₄Cl (10 mL). The aqueous layer was extracted with EtOAc (2×25 mL). The combined organic layer was dried over anhydrous Na₂SO₄, filtered and concentrated under reduced pressure to obtain crude product, which was purified by prep HPLC (conditions: Column: XBRIDGE 150*19 mm, C18 Mobile Phase: 5 mM Ammonium Formate B: ACN MeTHOD: 0/10-2/25/10/55 Solubility: MeOH, THF, water, ACN centrifuge) to afford the desired product (4S)—N7-(cyclopropylmethyl)-N5-(pyridazin-3-yl)-3,4-dihydro-1,4-methanopyrido[2,3-b][1,4]diazepine-5,7(2H)-dicarboxamide (179 mg, 0.471 mmol, 35.7% yield) as a white solid. LCMS (m/z): 380.09 [M+H]⁺, R$_t$=1.73 min.

¹H NMR (400 MHz, DMSO-d₆): δ ppm 13.88 (d, J=1.32 Hz, 1H), 8.97 (dd, J=4.71, 1.43 Hz, 1H), 8.43-8.22 (m, 2H), 7.80-7.68 (m, 3H), 5.44 (dd, J=5.70, 3.07 Hz, 1H), 3.32-3.07 (m, 5H), 2.98 (dd, J=11.95, 3.18 Hz, 1H), 2.35-2.12 (m, 1H), 1.97 (dt, J=13.98, 6.93 Hz, 1H), 1.30-1.06 (m, 1H), 0.47-0.25 (m, 2H), 0.05-0.02 (m, 2H).

Example 97

Synthesis of (4S)—N7-(cyclopropylmethyl)-N5-(pyrimidin-2-yl)-3,4-dihydro-1,4-methanopyrido[2,3-b][1,4]diazepine-5,7(2H)-dicarboxamide

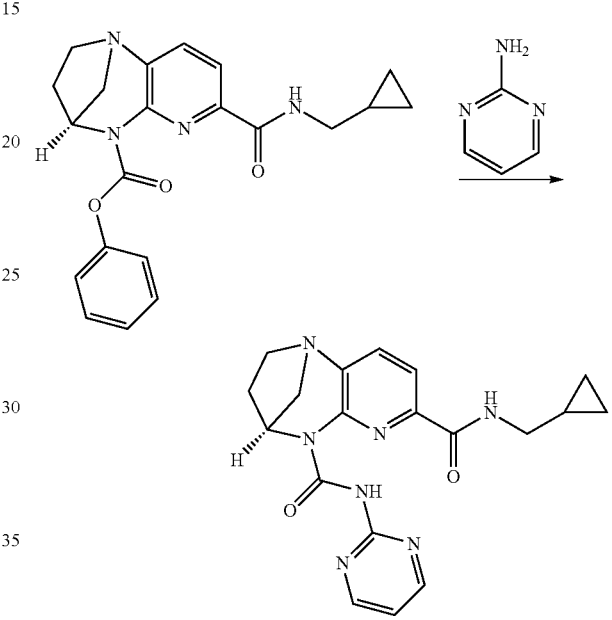

To a stirred solution of pyrimidin-2-amine (151 mg, 1.586 mmol) in Tetrahydrofuran (5 mL), was added a solution of 1M LiHMDS (2.64 mL, 2.64 mmol) in THF as drop wise at −78° C. After stirring the reaction mixture at −78° C. for 30 min, added a solution of (4S)-phenyl 7-((cyclopropylmethyl)carbamoyl)-3,4-dihydro-1,4-methanopyrido[2,3-b][1,4]diazepine-5(2H)-carboxylate (500 mg, 1.321 mmol) in Tetrahydrofuran (2 mL) as drop wise under nitrogen atmosphere at −78° C. The resulting reaction mixture was stirred at −78° C. for 1 h and then at rt for 6 h. (TLC 5% MeOH in DCM R$_f$: 0.3; UV active). The reaction mixture was quenched with aqueous NH₄Cl (10 mL). The aqueous layer was extracted with EtOAc (2×25 mL). The combined organic layer was dried over anhydrous Na₂SO₄, filtered and concentrated under reduced pressure to obtain the crude product which was purified by prep HPLC (conditions: MP-A: 10 mM Ammonium Bicarbonate (Aq) MP-B: Acetonitrile Column: Xterra C18 (250×19 mm), 10U Method: 0/25, 13/25, 13.10/100, 6.00/100, 16.10/25, 19/25 Solubility: ACN+MEOH+THF Flow: 18 ml/min) to afford the desired product (4S)—N7-(cyclopropylmethyl)-N5-(pyrimidin-2-yl)-3,4-dihydro-1,4-methanopyrido[2,3-b][1,4]diazepine-5,7(2H)-dicarboxamide (173 mg, 0.456 mmol, 34.5% yield) as an white solid. LCMS (m/z): 380.13 [M+H]⁺, R$_t$=1.58 min.

¹H NMR (400 MHz, DMSO-d₆): δ ppm 13.50 (s, 1H), 8.68 (d, J=4.82 Hz, 2H), 8.33-8.05 (m, 1H), 7.82-7.57 (m, 2H), 7.20 (t, J=4.82 Hz, 1H), 5.42 (dd, J=5.81, 2.96 Hz, 1H), 3.32-3.05 (m, 5H), 3.00-2.93 (m, 1H), 2.23 (dddd, J=13.54, 9.70, 5.92, 3.73 Hz, 1H), 2.01-1.74 (m, 1H), 1.30-1.04 (m, 1H), 0.53-0.35 (m, 2H), 0.33-0.19 (m, 2H).

Example 98

Synthesis of (4S)—N5-(1-methyl-2-oxo-1,2-dihydropyridin-3-yl)-N7-((R)-1,1,1-trifluoro propan-2-yl)-3,4-dihydro-1,4-methanopyrido[2,3-b][1,4]diazepine-5,7(2H)-dicarboxamide

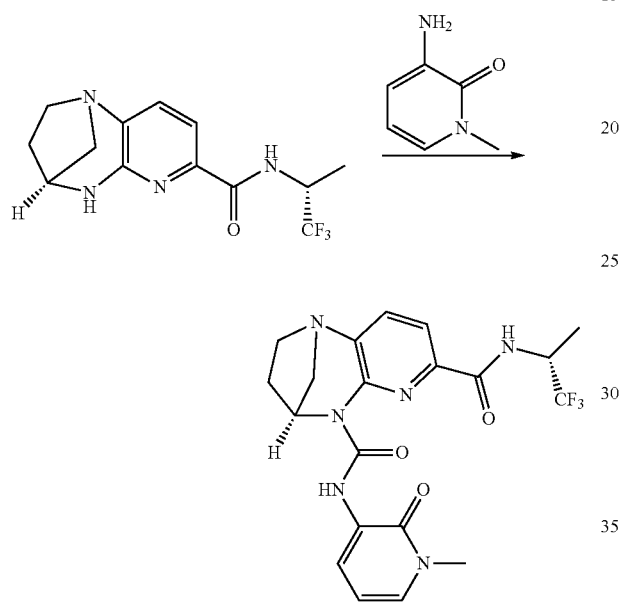

To a stirred solution of (4S)—N—((R)-1,1,1-trifluoropropan-2-yl)-2,3,4,5-tetrahydro-1,4-methanopyrido[2,3-b][1,4]diazepine-7-carboxamide (600 mg, 1.998 mmol) in Tetrahydrofuran (40 mL) were added triphosgene (889 mg, 3.00 mmol) and DIPEA (1.745 mL, 9.99 mmol) at 28° C. The reaction mixture was stirred for 45 min at 28° C. To this 3-amino-1-methylpyridin-2(1H)-one (744 mg, 5.99 mmol) was added to the reaction mixture and stirred at 70° C. for 9 h. (TLC 100% EtOAc R_f: 0.1; UV active). The reaction mixture was cooled to room temperature and was partitioned between water (15 mL) and EtOAc (25 mL). The organic layer was separated and was dried over anhydrous Na_2SO_4, filtered. The filtrate was evaporated to obtain crude which was purified by Prep HPLC (conditions: MP-A: 10 mM Ammonium bicarbonate (Aq) MP-B: Acetonitrile Column: X-terra (250*19 mm) 10μ Solubility: THF+MEOH Method: Time/% B; 0/20, 1/20, 10/85, 10.10/100, 13/100, 13.10/20, 15/20. Flow: 17 ml/min) to afford the desired product (4S)—N5-(1-methyl-2-oxo-1,2-dihydropyridin-3-yl)-N7-((R)-1,1,1-trifluoropropan-2-yl)-3,4-dihydro-1,4-methanopyrido[2,3-b][1,4]diazepine-5,7(2H)-dicarboxamide (135 mg, 0.300 mmol, 15.00% yield) as an off white solid. LCMS (m/z): 451.16 [M+H]+; R_t=2.15 min.

$^1$H NMR (400 MHz, DMSO-d_6): δ ppm 12.19-11.94 (m, 1H), 9.77 (d, J=9.21 Hz, 1H), 8.31 (dd, J=7.56, 1.64 Hz, 1H), 7.90 (d, J=7.89 Hz, 1H), 7.74 (d, J=7.89 Hz, 1H), 7.49 (dd, J=6.80, 1.75 Hz, 1H), 6.43 (t, J=7.13 Hz, 1H), 5.53 (dd, J=5.92, 3.07 Hz, 1H), 5.13-4.93 (m, 1H), 3.61 (s, 3H), 3.02-3.27 (m, 3H), 2.94 (dd, J=11.95, 3.18 Hz, 1H), 2.28-2.15 (m, 1H), 1.99-1.84 (m, 1H), 1.61 (d, J=7.02 Hz, 3H).

Example 99

Synthesis of (4S)—N7-(prop-2-yn-1-yl)-N5-(pyridin-2-yl)-3,4-dihydro-1,4-methanopyrido[2,3-b][1,4]diazepine-5,7(2H)-dicarboxamide

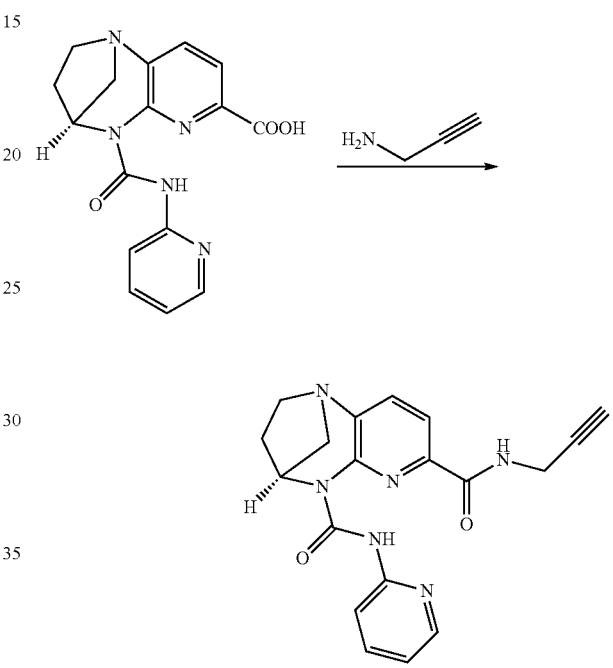

To a stirred solution of (4S)-5-(pyridin-2-ylcarbamoyl)-2,3,4,5-tetrahydro-1,4-methanopyrido[2,3-b][1,4]diazepine-7-carboxylic acid (450 mg, 1.383 mmol), DIPEA (1.208 mL, 6.92 mmol) and HATU (46.8 mg, 0.123 mmol) in N,N-Dimethylformamide (2 mL) was added prop-2-yn-1-amine (76 mg, 1.383 mmol) under nitrogen at room temperature in one charge. The reaction mixture was stirred at room temperature for 16 h. (TLC 5% MeOH\DCM R_f: 0.5; UV active). Reaction mixture was diluted with cold water (30 ml) and extracted with EtOAc (2×50 ml). The combined organic layer was washed with water (30 mL), brine (20 mL), dried over anhydrous Na_2SO_4, filtered and concentrated under reduced pressure to obtain crude product. The crude material was purified by combi-flash (12 g (Reveleris) normal phase, Eluent: 3% methanol in DCM) to afford the desired product (4S)—N7-(prop-2-yn-1-yl)-N5-(pyridin-2-yl)-3,4-dihydro-1,4-methanopyrido[2,3-b][1,4]diazepine-5,7(2H)-dicarboxamide (208 mg, 0.567 mmol, 41.0% yield) as a pale yellow solid. LCMS (m/z): 363.13 [M+H]+, R_t=1.7 min.

$^1$H NMR (400 MHz, DMSO-d_6): δ ppm 13.47 (s, 1H), 8.57 (t, J=5.59 Hz, 1H), 8.41 (dd, J=5.04, 0.88 Hz, 1H), 8.00 (d, J=8.33 Hz, 1H), 7.89-7.65 (m, 3H), 7.13 (ddd, J=7.23, 5.04, 0.88 Hz, 1H), 5.42 (dd, J=5.81, 2.96 Hz, 1H), 4.26 (dd, J=5.81, 2.30 Hz, 2H), 3.22-2.95 (m, 4H), 2.9 (s, 1H), 2.35-2.11 (m, 1H), 2.09-1.87 (m, 1H).

Example 100

Synthesis of (4S)—N7-(1-cyclopropylethyl)-N5-(pyridin-2-yl)-3,4-dihydro-1,4-methanopyrido[2,3-b][1,4]diazepine-5,7(2H)-dicarboxamide

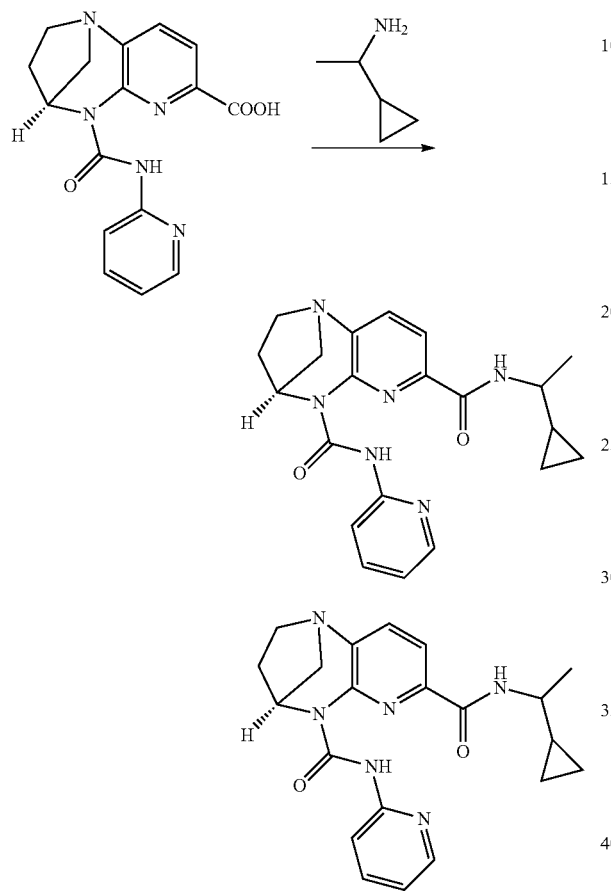

To a stirred solution of (4S)-5-(pyridin-2-ylcarbamoyl)-2,3,4,5-tetrahydro-1,4-methanopyrido[2,3-b][1,4]diazepine-7-carboxylic acid (1 g, 3.07 mmol), DIPEA (2.68 mL, 15.37 mmol) and HATU (46.8 mg, 0.123 mmol) in N,N-Dimethylformamide (2 mL) was added 1-cyclopropylethanamine (0.262 g, 3.07 mmol) under nitrogen at room temperature in one charge. The reaction mixture was stirred at room temperature for 8 h. (TLC 5% MeOH\DCM $R_f$: 0.5; UV active). Reaction mixture was diluted with cold water (30 ml) and extracted with EtOAc (2×50 ml). The combined organic layer was washed with water (30 mL), brine (20 mL), dried over anhydrous $Na_2SO_4$, filtered and concentrated under reduced pressure to obtain crude product. The crude material was purified by combi-flash (12 g (Reveleris) normal phase, Eluent: 5% methanol in DCM) to afford the desired compound (800 mg, HPLC-94%) as an off white solid. This diastereomeric mixture was further separated by SFC (conditions: Column/dimensions: Chiralpak AD-H (250×4.6) mm, 5, % CO: 75.0%, % Co solvent: 25.0% (0.5% Isopropyl amine in IPA), Total Flow: 3.0 g/min, Back Pressure: 100 bar, Temperature: 30.0° C., UV: 259 nm, Solubility: Methanol+DCM (9:1) Total No of injections: 360, Instrument details: Make/Model: Thar SFC-80) to afford two diastereomers.

Peak-1

(fastest eluent) Collected fraction from SFC was concentrated and washed with diethylether (30 mL) to afford (4S)—N7-(1-cyclopropylethyl)-N5-(pyridin-2-yl)-3,4-dihydro-1,4-methanopyrido[2,3-b][1,4]diazepine-5,7(2H)-dicarboxamide (155 mg, 0.387 mmol, 12.58% yield) as a white solid. LCMS (m/z): 393.12 [M+H]$^+$, $R_t$=2.18 min.

$^1$H NMR (400 MHz, CDCl$_3$): δ ppm 13.34 (s, 1H), 8.27 (d, J=4.93 Hz, 1H), 8.18 (dt, J=8.39, 0.96 Hz, 1H), 8.01-7.82 (m, 2H), 7.80-7.58 (m, 2H), 7.02 (ddd, J=7.34, 4.93, 1.10 Hz, 1H), 5.67 (dd, J=5.92, 3.07 Hz, 1H), 3.76-3.65 (m, 1H), 3.31-3.17 (m, 3H), 3.17-3.07 (m, 2H), 2.32 (dd, J=5.81, 4.28 Hz, 1H), 2.18-1.98 (m, 1H), 1.46 (d, J=6.80 Hz, 3H), 1.20-1.03 (m, 1H), 0.68-0.52 (m, 1H), 0.50-0.37 (m, 1H), 0.31 (dt, J=9.65, 4.60 Hz, 1H).

Example 101

Synthesis of (4S)—N7-(1-cyclopropylethyl)-N5-(pyridin-2-yl)-3,4-dihydro-1,4-methanopyrido[2,3-b][1,4]diazepine-5,7(2H)-dicarboxamide

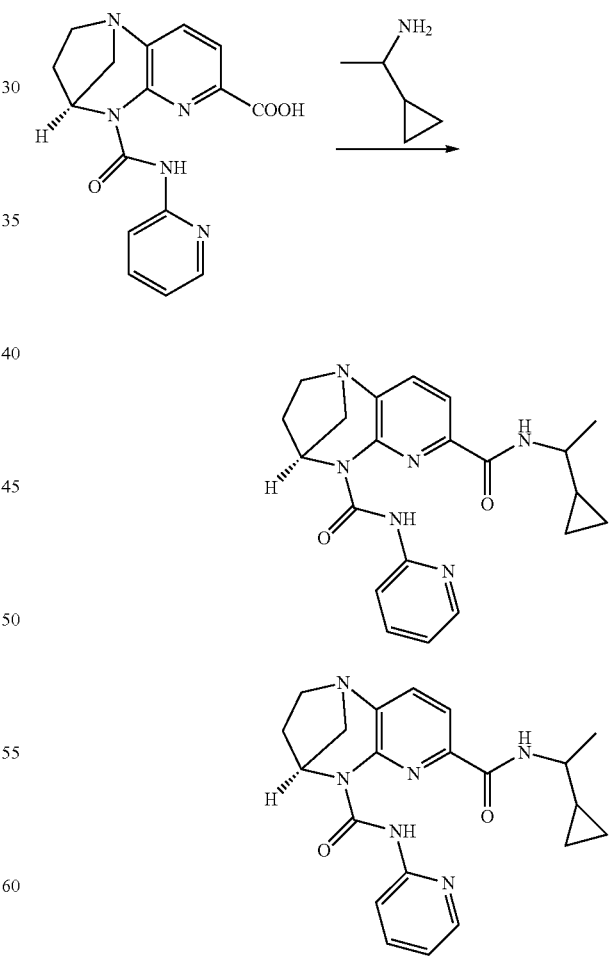

To a stirred solution of (4S)-5-(pyridin-2-ylcarbamoyl)-2,3,4,5-tetrahydro-1,4-methanopyrido[2,3-b][1,4]diazepine- 7-carboxylic acid (1 g, 3.07 mmol), DIPEA (2.68 mL, 15.37 mmol) and HATU (46.8 mg, 0.123 mmol) in N,N-Dimethylformamide (2 mL) was added 1-cyclopropylethanamine (0.262 g, 3.07 mmol) under nitrogen at room temperature in one charge. The reaction mixture was stirred at room temperature for 8 h. (TLC 5% MeOH\DCM $R_f$: 0.5; UV active). Reaction mixture was diluted with cold water (30 ml) and extracted with EtOAc (2×50 ml). The combined organic layer was washed with water (30 mL), brine (20 mL), dried over anhydrous $Na_2SO_4$, filtered and concentrated under reduced pressure to obtain crude product. The crude material was purified by combi-flash (12 g (Reveleris) normal phase, Eluent: 5% methanol in DCM) to afford the desired compound (800 mg, HPLC-94%) as an off white solid. This diastereomeric mixture was further separated by SFC (conditions: Column/dimensions: Chiralpak AD-H (250×4.6) mm, 5µ, % CO: 75.0%, % Co solvent: 25.0% (0.5% Isopropyl amine in IPA), Total Flow: 3.0 g/min, Back Pressure: 100 bar, Temperature: 30.0° C., UV: 259 nm, Solubility: Methanol+DCM (9:1) Total No of injections: 360, Instrument details: Make/Model: Thar SFC-80) to afford two diastereomers.

Peak-2

(Slowest Eluent) Collected fraction from SFC was concentrated and washed with diethylether (30 mL) to afford the desired product ((4S)—N7-(1-cyclopropylethyl)-N5-(pyridin-2-yl)-3,4-dihydro-1,4-methanopyrido[2,3-b][1,4]diazepine-5,7(2H)-dicarboxamide (216 mg, 0.547 mmol, 17.80% yield) as an off white solid. LCMS (m/z): 393.12 [M+H]$^+$, $R_t$=2.17 min.

$^1$H NMR (400 MHz, DMSO-d$_6$): δ ppm 13.18 (s, 1H), 8.40-8.20 (m, 1H), 8.10 (dt, J=8.39, 0.96 Hz, 1H), 7.97-7.79 (m, 2H), 7.79-7.64 (m, 2H), 7.14 (ddd, J=7.34, 4.93, 1.10 Hz, 1H), 5.47 (dd, J=5.92, 3.07 Hz, 1H), 3.63-3.49 (m, 1H), 3.28-3.05 (m, 3H), 3.03-2.83 (m, 1H), 2.23 (dddd, J=13.78, 9.89, 5.81, 3.84 Hz, 1H), 1.94 (dt, J=13.98, 7.15 Hz, 1H), 1.35 (d, J=6.80 Hz, 3H), 1.20-0.99 (m, 1H), 0.52 (tdd, J=8.55, 8.55, 5.15, 3.62 Hz, 1H), 0.43-0.21 (m, 3H).

Example 102

Synthesis of (4S)—N7-(1-cyanoethyl)-N5-(pyridin-2-yl)-3,4-dihydro-1,4-methanopyrido[2,3-b][1,4]diazepine-5,7(2H)-dicarboxamide

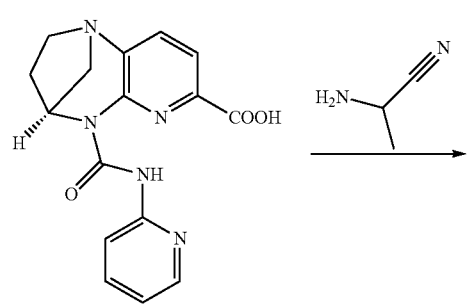

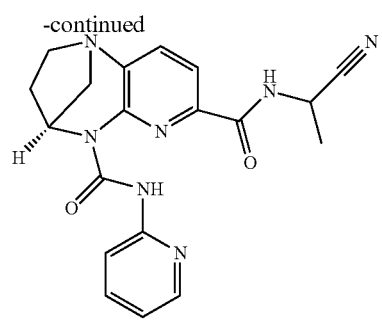

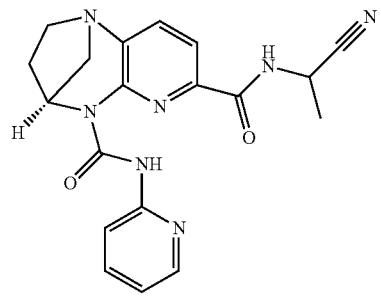

To a stirred solution of (4S)-5-(pyridin-2-ylcarbamoyl)-2,3,4,5-tetrahydro-1,4-methanopyrido[2,3-b][1,4]diazepine-7-carboxylic acid (1.2 g, 3.69 mmol), DIPEA (3.22 mL, 18.44 mmol) and HATU (46.8 mg, 0.123 mmol) in N,N-Dimethylformamide (DMF) (2 mL) was added 2-aminopropanenitrile (0.259 g, 3.69 mmol) under nitrogen at room temperature in one charge. The reaction mixture was stirred at room temperature for 16 h. (TLC 5% MeOH\DCM $R_f$: 0.5; UV active). Reaction mixture was diluted with cold water (30 ml) and extracted with EtOAc (2×50 ml). The combined organic layer was washed with water (30 mL), brine (20 mL), dried over anhydrous $Na_2SO_4$, filtered and concentrated under reduced pressure to obtain crude product. The crude material was purified by combi-flash (12 g (Reveleris) normal phase, Eluent: 3% methanol in DCM) to afford the desired compound (700 mg, HPLC-94%) as an off white solid. This diastereomeric mixture was further separated by SFC (conditions: Column/dimensions: Chiralpak IC (250×4.6) mm, 5µ %, CO2: 60.0%, Co solvent: 40.0% (0.5% DEA MeOH), Total Flow: 4.0 g/min, Back Pressure: 100 bar, Temperature: 30.0° C., UV: 261 nm, Solubility: Methanol, Total No of injections: 25, Instrument details: Make/Model: Thar SFC-200-(OLD)) to obtain two diastereomers.

Peak-1

(fastest eluent) Collected fraction from SFC was concentrated and washed with diethylether to afford the peak-I (4S)—N7-(1-cyanoethyl)-N5-(pyridin-2-yl)-3,4-dihydro-1,4-methanopyrido[2,3-b][1,4]diazepine-5,7(2H)-dicarboxamide (140 mg, 0.371 mmol, 10.05% yield) (N36502-52-A2) as a white solid. LCMS (m/z): 378. 08 [M+H]$^+$, Rt=1.77 min.

$^1$H NMR (400 MHz, DMSO-d$_6$): δ ppm 13.03 (s, 1H), 8.74 (d, J=7.89 Hz, 1H), 8.33 (dd, J=4.93, 0.99 Hz, 1H), 8.08 (d, J=8.33 Hz, 1H), 7.95-7.79 (m, 1H), 7.79-7.64 (m, 2H), 7.13 (dd, J=6.58, 5.04 Hz, 1H), 5.46 (dd, J=5.81, 2.96 Hz, 1H), 5.13 (quin, J=7.29 Hz, 1H), 2.97-3.22 (m, 4H), 2.39-2.16 (m, 1H), 2.00-1.85 (m, 1H), 1.66 (d, J=7.23 Hz, 3H).

Example 103

Synthesis of (4S)—N7-(1-cyanoethyl)-N5-(pyridin-2-yl)-3,4-dihydro-1,4-methanopyrido[2,3-b][1,4]diazepine-5,7(2H)-dicarboxamide

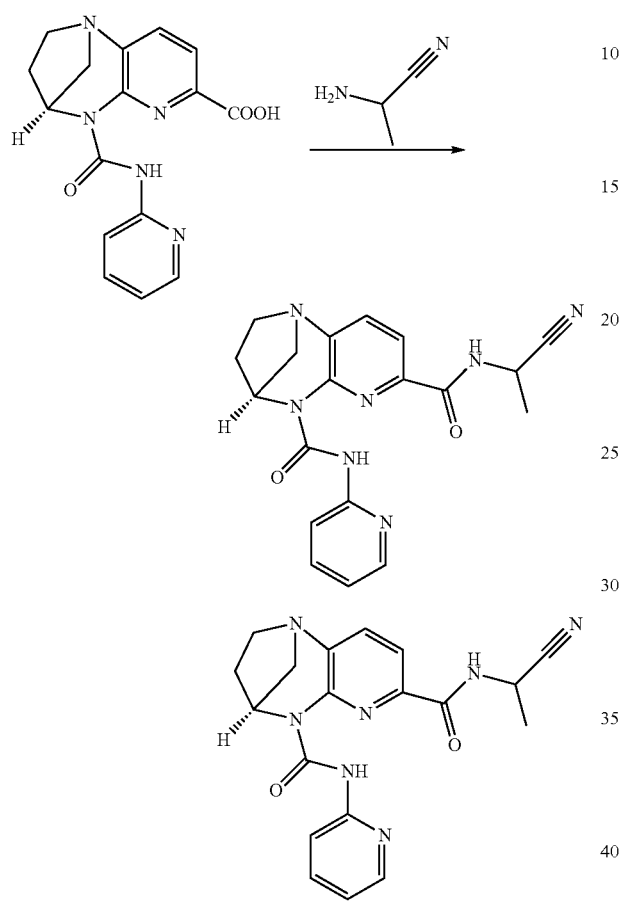

To a stirred solution of (4S)-5-(pyridin-2-ylcarbamoyl)-2,3,4,5-tetrahydro-1,4-methanopyrido[2,3-b][1,4]diazepine-7-carboxylic acid (1.2 g, 3.69 mmol), DIPEA (3.22 mL, 18.44 mmol) and HATU (46.8 mg, 0.123 mmol) in N,N-Dimethylformamide (DMF) (2 mL) was added 2-aminopropanenitrile (0.259 g, 3.69 mmol) under nitrogen at room temperature in one charge. The reaction mixture was stirred at room temperature for 16 h. (TLC 5% MeOH\DCM $R_f$: 0.5; UV active). Reaction mixture was diluted with cold water (30 ml) and extracted with EtOAc (2×50 ml). The combined organic layer was washed with water (30 mL), brine (20 mL), dried over anhydrous $Na_2SO_4$, filtered and concentrated under reduced pressure to obtain crude product. The crude material was purified by combi-flash (12 g (Reveleris) normal phase, Eluent: 3% methanol in DCM) to afford the desired compound (700 mg, HPLC-94%) as an off white solid. This diastereomeric mixture was further separated by SFC (conditions: Column/dimensions: Chiralpak IC (250×4.6) mm, 5µ %, CO2: 60.0%, Co solvent: 40.0% (0.5% DEA MeOH), Total Flow: 4.0 g/min, Back Pressure: 100 bar, Temperature: 30.0° C., UV: 261 nm, Solubility: Methanol, Total No of injections: 25, Instrument details: Make/Model: Thar SFC-200-(OLD)) to obtain two diastereomers.

Peak-2

(slowest eluent) Collected fraction from SFC was concentrated and washed with diethylether to afford the peak-II (4S)—N7-(1-cyanoethyl)-N5-(pyridin-2-yl)-3,4-dihydro-1,4-methanopyrido[2,3-b][1,4]diazepine-5,7(2H)-dicarboxamide (187 mg, 0.494 mmol, 13.38% yield) (N36502-52-B2) as an off white solid (TLC 5% MeOH\DCM $R_f$: 0.5; UV active). LCMS (m/z): 378. 11[M+H]$^+$, Rt=1.76 min.

$^1$H NMR (400 MHz, DMSO-d$_6$): δ ppm 13.04 (s, 1H), 8.83-8.63 (m, 1H), 8.47-8.21 (m, 1H), 8.09 (d, J=8.33 Hz, 1H), 7.96-7.80 (m, 1H), 7.79-7.63 (m, 2H), 7.13 (ddd, J=7.34, 4.93, 1.10 Hz, 1H), 5.47 (dd, J=5.92, 3.07 Hz, 1H), 5.13 (quin, J=7.29 Hz, 1H), 3.22-2.96 (m, 4H), 2.34-2.19 (m, 1H), 2.00-1.74 (m, 1H), 1.66 (d, J=7.02 Hz, 3H).

Example 104

Synthesis (4S)—N7-(2-cyanopropan-2-yl)-N5-(pyridin-2-yl)-3,4-dihydro-1,4-methanopyrido[2,3-b][1,4]diazepine-5,7(2H)-dicarboxamide

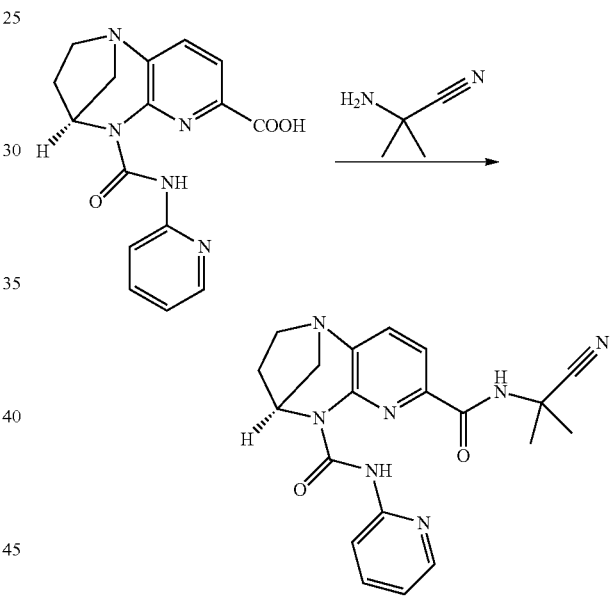

To a stirred solution of (4S)-5-(pyridin-2-ylcarbamoyl)-2,3,4,5-tetrahydro-1,4-methanopyrido[2,3-b][1,4]diazepine-7-carboxylic acid (500 mg, 1.537 mmol), DIPEA (1.342 mL, 7.68 mmol) and HATU (46.8 mg, 0.123 mmol) in N,N-Dimethylformamide (2 mL) was added 2-amino-2-methylpropanenitrile (129 mg, 1.537 mmol) under nitrogen at room temperature in one charge. The reaction mixture was stirred at room temperature for 8 h. (TLC 5% MeOH\DCM $R_f$: 0.5; UV active). Reaction mixture was diluted with cold water (30 ml) and extracted with EtOAc (2×50 ml). The combined organic layer was washed with water (30 mL), brine (20 mL), dried over anhydrous $Na_2SO_4$, filtered and concentrated under reduced pressure to obtain crude product, which was purified by Prep HPLC (conditions: MP-A: 10 Mm Ammonium bicarbonate (Aq) MP-B: Acetonitrile Column: Xbridge (150*19 mm) 5p Method: (T/% B) 0/33, 10/33 Flow: 17 ml/min Solubility: THF+ACN+MeOH) to afford the desired product (4S)—N7-(2-cyanopropan-2-yl)-N5-(pyridin-2-yl)-3,4-dihydro-1,4-methanopyrido[2,3-b][1,4]

diazepine-5,7(2H)-dicarboxamide (202 mg, 0.513 mmol, 33.4% yield) as a white solid. LCMS (m/z): 392.1 [M+H]+, $R_t$=1.88 min.

$^1$H NMR (400 MHz, DMSO-d$_6$): δ ppm 12.77 (s, 1H), 8.50 (s, 1H), 8.38-8.20 (m, 1H), 8.12 (d, J=8.55 Hz, 1H), 7.83 (td, J=7.89, 1.97 Hz, 1H), 7.74 (d, J=7.89 Hz, 1H), 7.64 (d, J=7.89 Hz, 1H), 7.11 (ddd, J=7.34, 4.93, 0.88 Hz, 1H), 5.49 (dd, J=5.92, 2.85 Hz, 1H), 3.22-2.96 (m, 4H), 2.39-2.17 (m, 1H), 1.96-1.77 (m, 1H), 1.63 (s, 6H).

Example 105

Synthesis of (4S)—N7-((R)-but-3-yn-2-yl)-N5-(pyridin-2-yl)-3,4-dihydro-1,4-methanopyrido[2,3-b][1,4]diazepine-5,7(2H)-dicarboxamide

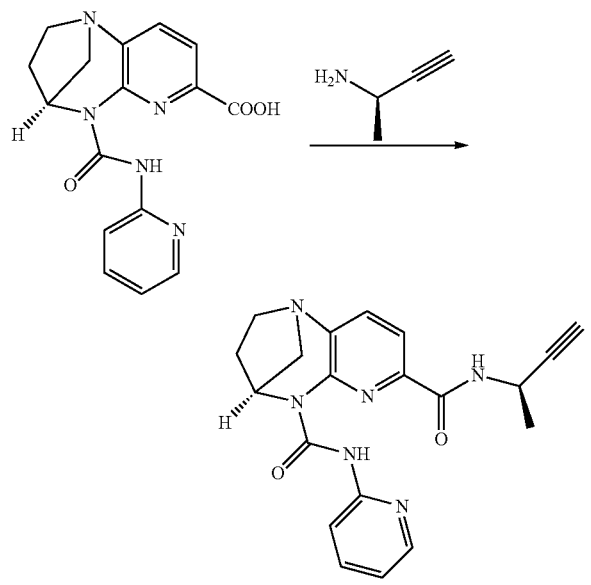

To a stirred solution of (4S)-5-(pyridin-2-ylcarbamoyl)-2,3,4,5-tetrahydro-1,4-methanopyrido[2,3-b][1,4]diazepine-7-carboxylic acid (500 mg, 1.537 mmol), DIPEA (1.342 mL, 7.68 mmol) and HATU (46.8 mg, 0.123 mmol) in N,N-Dimethylformamide (2 mL) was added (R)-but-3-yn-2-amine (106 mg, 1.537 mmol) under nitrogen at room temperature in one charge. The reaction mixture was stirred at room temperature for 8 h. (TLC 5% MeOH\DCM $R_f$: 0.5; UV active). Reaction mixture was diluted with cold water (30 ml) and extracted with EtOAc (2×50 ml). The combined organic layer was washed with water (30 mL), brine (20 mL), dried over anhydrous Na$_2$SO$_4$, filtered and concentrated under reduced pressure to obtain crude product. The crude material was purified by Prep HPLC (conditions: MP-A: 10 Mm Ammonium bicarbonate (Aq) MP-B: Acetonitrile Column: Kinetex C8 (150*30) mm, 5 um. Method: 60:40 Flow: 30 ml/min Solubility: THF+ACN+MEOH) to afford the desired product (4S)—N7-((R)-but-3-yn-2-yl)-N5-(pyridin-2-yl)-3,4-dihydro-1,4-methanopyrido[2,3-b][1,4]diazepine-5,7(2H)-dicarboxamide (233 mg, 0.603 mmol, 39.2% yield) as an off white solid. LCMS (m/z): 377.14 [M+H]+, Rt=1.93 min.

$^1$H NMR (400 MHz, DMSO-d$_6$): δ ppm 13.30 (s, 1H), 8.42-8.24 (m, 2H), 8.05 (d, J=8.33 Hz, 1H), 7.86 (td, J=7.78, 1.97 Hz, 1H), 7.79-7.66 (m, 2H), 7.14 (ddd, J=7.23, 4.93, 0.99 Hz, 1H), 5.45 (dd, J=5.92, 3.07 Hz, 1H), 5.06-4.93 (m, 1H), 3.27-3.05 (m, 3H), 3.02-2.87 (m, 1H), 2.35-2.14 (m, 2H), 1.94 (dt, J=13.87, 7.21 Hz, 1H), 1.53 (d, J=7.02 Hz, 3H).

Example 106

Synthesis of (4S)—N7-benzyl-N5-(pyridin-2-yl)-3,4-dihydro-1,4-methanopyrido[2,3-b][1,4]diazepine-5,7(2H)-dicarboxamide

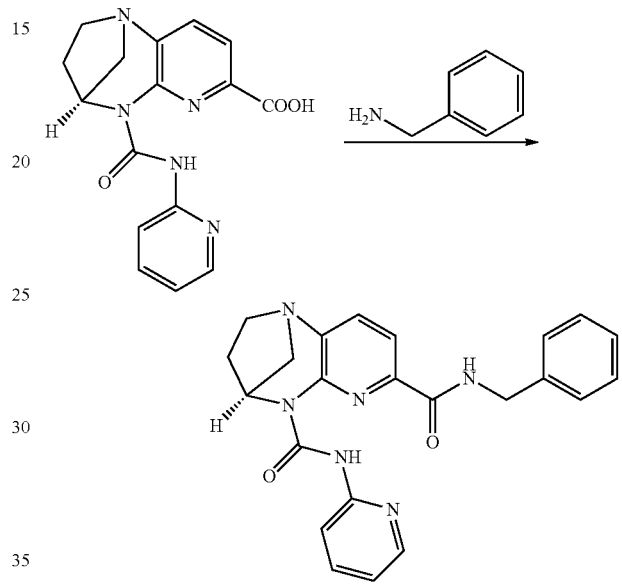

To a stirred solution of (4S)-5-(pyridin-2-ylcarbamoyl)-2,3,4,5-tetrahydro-1,4-methanopyrido[2,3-b][1,4]diazepine-7-carboxylic acid (500 mg, 1.537 mmol), DIPEA (1.342 mL, 7.68 mmol) and HATU (46.8 mg, 0.123 mmol) in N,N-Dimethylformamide (5 mL) was added phenylmethanamine (165 mg, 1.537 mmol) under nitrogen at room temperature in one charge. The reaction mixture was stirred at room temperature for 8 h. (TLC 5% MeOH\DCM $R_f$: 0.5; UV active). Reaction mixture was diluted with cold water (30 ml) and extracted with EtOAc (2×50 ml). The combined organic layer was washed with water (30 mL), brine (20 mL), dried over anhydrous Na$_2$SO$_4$, filtered and concentrated under reduced pressure to obtain crude product, which was purified by Prep HPLC (conditions: MP-A: 0.1% Farmic acid (Aq) MP-B: Acetonitrile Column: Kromasi phenyl (25×150 mm) 10u Method: T/% B=0/10, 1/10, 10/50, 15/55, 15.5/100, 18/100, 18.1/10, 23/10 Flow: 20 ml/min Solubility: ACN+THF+WATER) to afford the desired product (4S)—N7-benzyl-N5-(pyridin-2-yl)-3,4-dihydro-1,4-methanopyrido[2,3-b][1,4]diazepine-5,7(2H)-dicarboxamide (255 mg, 0.614 mmol, 39.9% yield) as a white solid. LCMS (m/z): 415.19 [M+H]+, $R_t$=2.16 min.

$^1$H NMR (400 MHz, DMSO-d$_6$): δ ppm 13.46 (s, 1H), 8.89-8.65 (m, 1H), 8.07-7.92 (m, 2H), 7.85-7.67 (m, 3H), 7.36-7.20 (m, 5H), 7.04 (ddd, J=7.34, 4.93, 0.88 Hz, 1H), 5.42 (dd, J=5.92, 3.07 Hz, 1H), 4.66 (d, J=6.36 Hz, 2H), 3.28-3.05 (m, 3H), 3.03-2.89 (m, 1H), 2.23 (dddd, J=13.73, 9.89, 5.97, 3.95 Hz, 1H), 1.94 (dt, J=13.87, 7.21 Hz, 1H).

Example 107

Synthesis of (4S)—N7-(cyanomethyl)-N5-(pyridin-2-yl)-3,4-dihydro-1,4-methanopyrido[2,3-b][1,4]diazepine-5,7(2H)-dicarboxamide

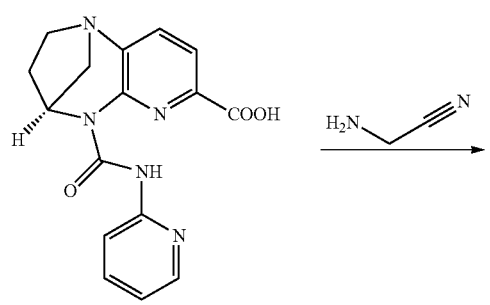

To a stirred solution of (4S)-5-(pyridin-2-ylcarbamoyl)-2,3,4,5-tetrahydro-1,4-methanopyrido[2,3-b][1,4]diazepine-7-carboxylic acid (500 mg, 1.537 mmol), DIPEA (1.342 mL, 7.68 mmol) and HATU (46.8 mg, 0.123 mmol) in N,N-Dimethylformamide (2 mL) was added 2-aminoacetonitrile (86 mg, 1.537 mmol) under nitrogen at room temperature in one charge. The reaction mixture was stirred at room temperature for 8 h. (TLC 5% MeOH\DCM $R_f$: 0.5; UV active). Reaction mixture was diluted with cold water (30 ml) and extracted with EtOAc (2×50 ml). The combined organic layer was washed with water (30 mL), brine (20 mL), dried over anhydrous $Na_2SO_4$, filtered and concentrated under reduced pressure to obtain crude product, which was purified by Prep HPLC (conditions: MP-A: 10 mm Ammonium bicarbonate MP-B: Acetonitrile Column: Kromasil Phenyl Packed (150*25 mm, 10u) Method: isocratic A:B 55:45 Flow: 20 ml/min) to afford the desired product (4S)—N7-(cyanomethyl)-N5-(pyridin-2-yl)-3,4-dihydro-1,4-methanopyrido[2,3-b][1,4]diazepine-5,7(2H)-dicarboxamide (188 mg, 0.500 mmol, 32.5% yield) as an off white solid. LCMS (m/z): 364.07 [M+H]$^+$, $R_t$=1.55 min.

$^1$H NMR (400 MHz, DMSO-$d_6$): δ ppm 13.29 (s, 1H), 8.83 (t, J=5.70 Hz, 1H), 8.52-8.32 (m, 1H), 8.15-7.95 (m, 1H), 7.85 (td, J=7.84, 1.86 Hz, 1H), 7.79-7.62 (m, 2H), 7.13 (ddd, J=7.29, 4.88, 0.99 Hz, 1H), 5.42 (dd, J=5.70, 3.07 Hz, 1H), 4.52 (d, J=6.14 Hz, 2H), 3.28-3.05 (m, 3H), 3.03-2.75 (m, 1H), 2.24 (dddd, J=13.76, 9.87, 5.97, 3.95 Hz, 1H), 1.93 (dt, J=13.98, 7.15 Hz, 1H).

Example 108

Synthesis of (4S)—N5-(pyridin-2-yl)-N7-((trimethylsilyl)methyl)-3,4-dihydro-1,4-methanopyrido[2,3-b][1,4]diazepine-5,7(2H)-dicarboxamide

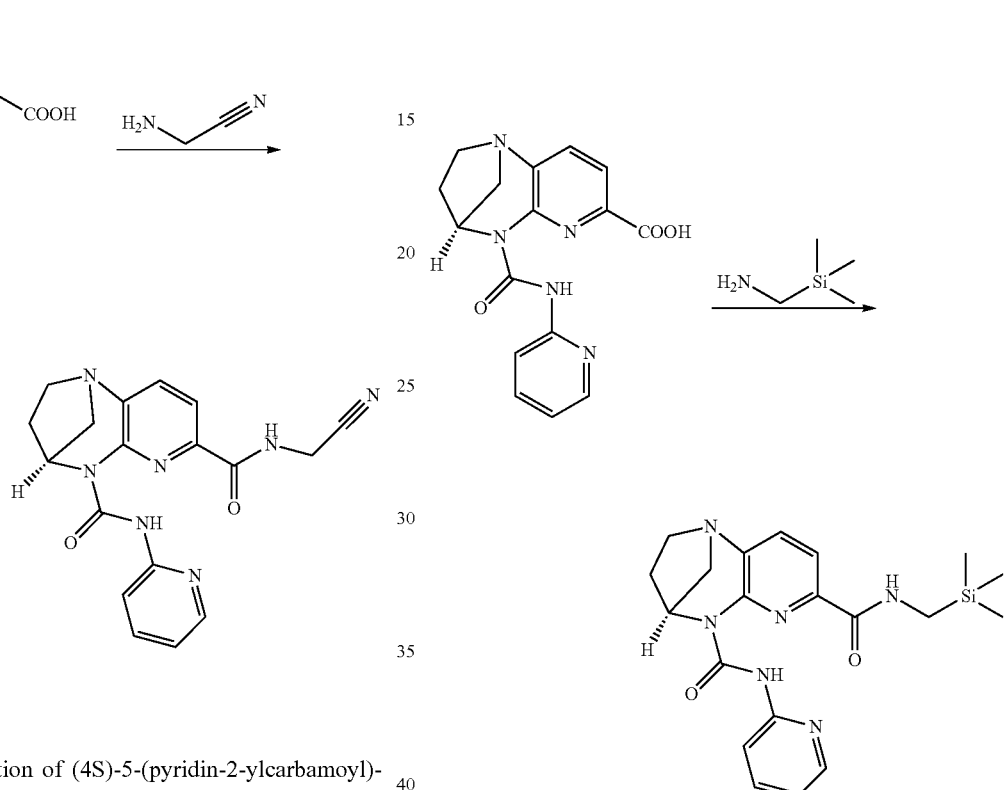

To a stirred solution of (4S)-5-(pyridin-2-ylcarbamoyl)-2,3,4,5-tetrahydro-1,4-methanopyrido[2,3-b][1,4]diazepine-7-carboxylic acid (500 mg, 1.537 mmol), DIPEA (1.342 mL, 7.68 mmol) and HATU (46.8 mg, 0.123 mmol) in N,N-Dimethylformamide (2 mL) was added (trimethylsilyl)methanamine (159 mg, 1.537 mmol) under nitrogen at room temperature in one charge. The reaction mixture was stirred at room temperature for 8 h. (TLC 5% MeOH\DCM $R_f$: 0.5; UV active). Reaction mixture was diluted with cold water (30 ml) and extracted with EtOAc (2×50 ml). The combined organic layer was washed with water (30 mL), brine (20 mL), dried over anhydrous $Na_2SO_4$, filtered and concentrated under reduced pressure to obtain crude product, which was purified by combi-flash (12 g (Reveleris) normal phase, Eluent: 2% methanol in DCM) to afford the desired product (4S)—N5-(pyridin-2-yl)-N7-((trimethylsilyl)methyl)-3,4-dihydro-1,4-methanopyrido[2,3-b][1,4]diazepine-5,7(2H)-dicarboxamide (316 mg, 0.765 mmol, 49.8% yield) as a pale brown solid. LCMS (m/z): 411.12 [M+H]$^+$, Rt=2.34 min.

$^1$H NMR (400 MHz, DMSO-$d_6$): δ ppm 13.49 (s, 1H), 8.41-8.23 (m, 1H), 8.18-7.97 (m, 2H), 7.85 (td, J=7.89, 1.97

Hz, 1H), 7.77-7.60 (m, 2H), 7.13 (ddd, J=7.34, 4.93, 0.88 Hz, 1H), 5.43 (dd, J=5.92, 3.07 Hz, 1H), 3.21-2.94 (m, 5H), 2.29-2.14 (m, 2H), 1.94 (dt, J=13.76, 6.82 Hz, 1H), 0.1 (s, 9H).

Example 109

Synthesis of (4S)—N7-(but-2-yn-1-yl)-N5-(pyridin-2-yl)-3,4-dihydro-1,4-methanopyrido[2,3-b][1,4]diazepine-5,7(2H)-dicarboxamide

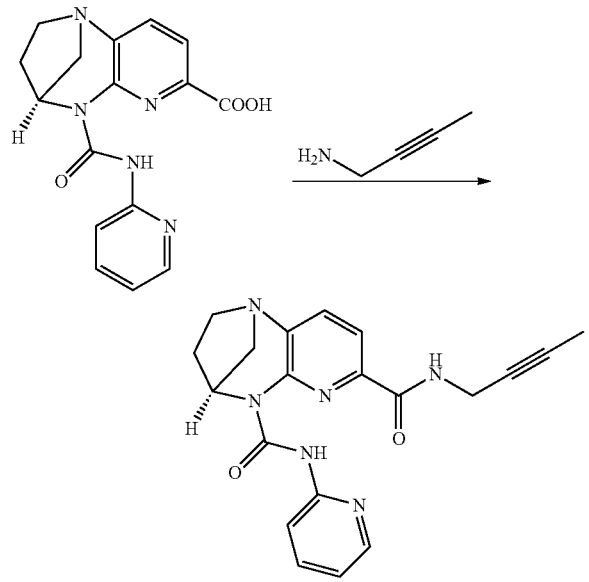

To a stirred solution of (4S)-5-(pyridin-2-ylcarbamoyl)-2,3,4,5-tetrahydro-1,4-methanopyrido[2,3-b][1,4]diazepine-7-carboxylic acid (500 mg, 1.537 mmol), DIPEA (1.342 mL, 7.68 mmol) and HATU (46.8 mg, 0.123 mmol) in N,N-Dimethylformamide (2 mL) was added but-2-yn-1-amine (106 mg, 1.537 mmol) under nitrogen at room temperature in one charge. The reaction mixture was stirred at room temperature for 8 h. (TLC 5% MeOH\DCM R$_f$: 0.5; UV active). Reaction mixture was diluted with cold water (30 ml) and extracted with EtOAc (2×50 ml). The combined organic layer was washed with water (30 mL), brine (20 mL), dried over anhydrous Na$_2$SO$_4$, filtered and concentrated under reduced pressure to obtain crude product, which was purified by combi-flash (12 g (Reveleris) normal phase, Eluent: 5% methanol in DCM) to afford the desired product (4S)—N7-(but-2-yn-1-yl)-N5-(pyridin-2-yl)-3,4-dihydro-1,4-methanopyrido[2,3-b][1,4]diazepine-5,7(2H)-dicarboxamide (315 mg, 0.830 mmol, 54.0% yield) as an off white solid. LCMS (m/z): 377.14 [M+H]$^+$, R$_t$=1.8 min.

$^1$H NMR (400 MHz, DMSO-d$_6$): δ ppm 13.72 (s, 1H), 8.51 (t, J=5.70 Hz, 1H), 8.29-8.40 (m, 1H), 8.00 (d, J=8.33 Hz, 1H), 7.82-7.88 (m, 1H), 7.72 (q, J=7.89 Hz, 2H), 7.14 (ddd, J=7.23, 4.93, 0.99 Hz, 1H), 5.4 (dd, J=5.86, 3.02 Hz, 1H), 4.21 (dd, J=5.70, 2.63 Hz, 2H), 2.81-3.40 (m, 4H), 1.66-2.54 (m, 5H).

Example 110

Synthesis of (4S)—N7-(cyclopropylmethyl)-N5-(4-methylpyridin-2-yl)-3,4-dihydro-1,4-methanopyrido[2,3-b][1,4]diazepine-5,7(2H)-dicarboxamide

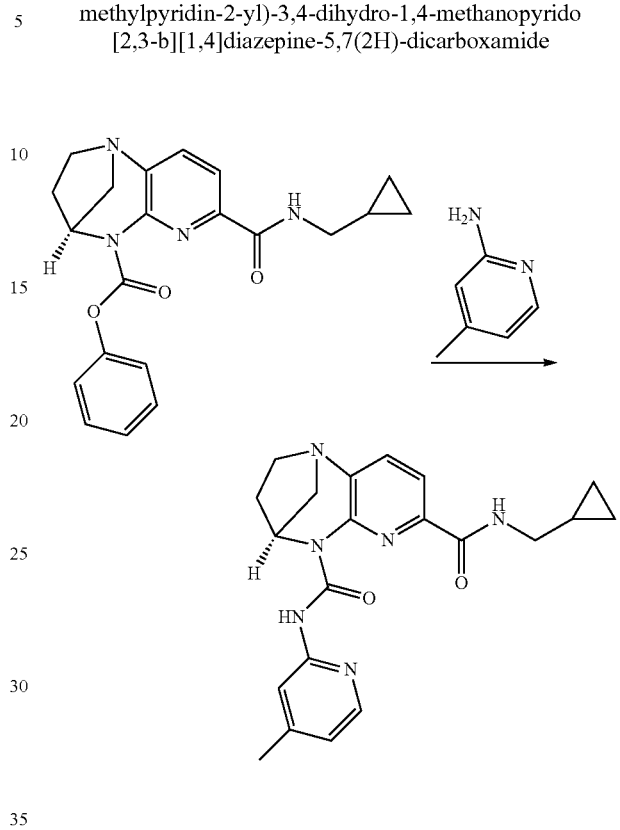

To a stirred solution of 4-methylpyridin-2-amine (189 mg, 1.744 mmol) in Tetrahydrofuran (5 mL), was added a solution of 1M LiHMDS (2.91 mL, 2.91 mmol) in THF drop wise at −78° C. After stirring the reaction mixture at −78° C. for 30 min, added a solution of (4S)-phenyl7-((cyclopropylmethyl)carbamoyl)-3,4-dihydro-1,4-methanopyrido[2,3-b][1,4]diazepine-5(2H)-carboxylate (550 mg, 1.453 mmol) in Tetrahydrofuran (2 mL) drop wise under nitrogen at −78° C. The resulting reaction mixture was stirred at −78° C. for 1 h. and then at rt for 6 h. (TLC 5% MeOH\DCM R$_f$: 0.3; UV active). The reaction mixture was quenched with aqueous NH$_4$Cl (10 mL). The aqueous layer was extracted with EtOAc (2×25 mL). The combined organic layer was dried over anhydrous Na$_2$SO$_4$, filtered and concentrated under reduced pressure to obtain crude product, which was purified by combi-flash (12 g (Reveleris) normal phase, Eluent: 3% methanol in DCM) to afford the desired product (4S)—N7-(cyclopropylmethyl)-N5-(4-methylpyridin-2-yl)-3,4-dihydro-1,4-methanopyrido[2,3-b][1,4]diazepine-5,7(2H)-dicarboxamide (226 mg, 0.553 mmol, 38.0% yield) as a pale yellow solid. LCMS (m/z): 393.12 [M+H]$^+$, Rt=1.92 min.

$^1$H NMR (400 MHz, DMSO-d$_6$): δ ppm 13.35 (s, 1H), 8.29 (t, J=5.92 Hz, 1H), 8.15 (d, J=5.04 Hz, 1H), 7.90 (s, 1H), 7.82-7.60 (m, 2H), 6.97 (dd, J=5.15, 0.77 Hz, 1H), 5.42 (dd, J=5.92, 3.07 Hz, 1H), 3.39-3.31 (m, 2H), 3.28-3.04 (m, 3H), 3.02-2.82 (m, 1H), 2.41 (s, 3H), 2.29-2.07 (m, 1H), 2.06-1.83 (m, 1H), 1.28-1.06 (m, 1H), 0.51-0.35 (m, 2H), 0.35-0.15 (m, 2H).

Example 111

Synthesis of (4S)—N7-(cyclopropylmethyl)-N5-(5-methylpyridin-2-yl)-3,4-dihydro-1,4-methanopyrido[2,3-b][1,4]diazepine-5,7(2H)-dicarboxamide

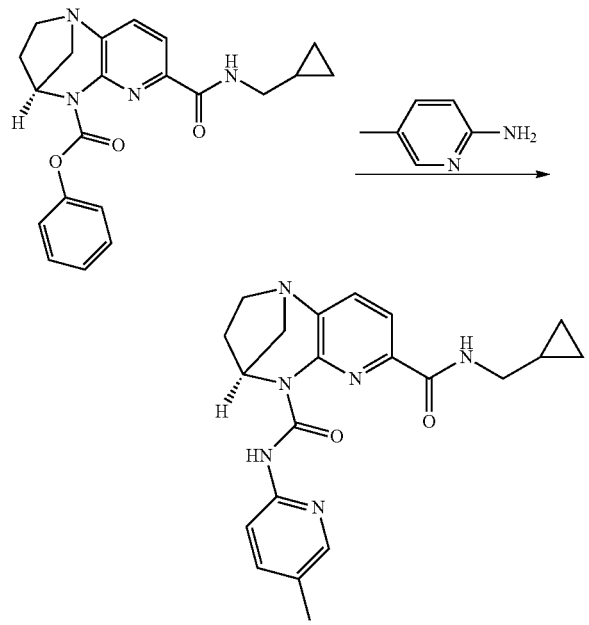

To a stirred solution of 5-methylpyridin-2-amine (171 mg, 1.586 mmol) in Tetrahydrofuran (5 mL), was added a solution of 1M LiHMDS (2.64 mL, 2.64 mmol) in THF drop wise at −78° C. After stirring the reaction mixture at −78° C. for 30 min, added a solution of (4S)-phenyl 7-((cyclopropylmethyl)carbamoyl)-3,4-dihydro-1,4-methanopyrido[2,3-b][1,4]diazepine-5(2H)-carboxylate (500 mg, 1.321 mmol) in Tetrahydrofuran (2 mL), drop wise under nitrogen at −78° C. The resulting reaction mixture was stirred at −78° C. for 1 h and then at rt for 6 h. (TLC 5% MeOH/DCM $R_f$: 0.3; UV active). The reaction mixture was quenched with aqueous $NH_4Cl$ (10 mL). The aqueous layer was extracted with EtOAc (2×25 mL). The combined organic layer was dried over anhydrous $Na_2SO_4$, filtered and concentrated under reduced pressure to obtain crude product which was purified by Prep HPLC (conditions: MP-A: 10 Mm Ammonium bicarbonate (Aq) MP-B: Acetonitrile Column: x-bridge gel (150×19) mm, 10µ Method—T/% B—0.01/10/, 1/10, 10/55 Flow: 19 ml/min Solubility: THF+MeOH) to afford the desired product (4S)—N7-(cyclopropylmethyl)-N5-(5-methylpyridin-2-yl)-3,4-dihydro-1,4-methanopyrido[2,3-b][1,4]diazepine-5,7(2H)-dicarboxamide (89 mg, 0.226 mmol, 17.07% yield) as an off white solid. LCMS (m/z): 393.16 [M+H]$^+$, Rt=2.05 min.

$^1$H NMR (400 MHz, DMSO-$d_6$): δ ppm 13.28 (s, 1H), 8.25 (t, J=5.92 Hz, 1H), 8.18-8.08 (m, 1H), 7.95 (d, J=8.33 Hz, 1H), 7.76-7.62 (m, 3H), 5.43 (dd, J=5.92, 3.07 Hz, 1H), 3.34-3.30 (m, 2H), 3.27-3.04 (m, 3H), 2.96 (dd, J=12.06, 3.29 Hz, 1H), 2.29-2.18 (m, 4H), 1.93 (dt, J=13.70, 6.74 Hz, 1H), 1.21-0.94 (m, 1H), 0.50-0.38 (m, 2H), 0.35-0.22 (m, 2H).

Example 112

Synthesis of (4S)—N7-(cyclopropylmethyl)-N5-(5-fluoro-6-methylpyridin-2-yl)-3,4-dihydro-1,4-methanopyrido[2,3-b][1,4]diazepine-5,7(2H)-dicarboxamide

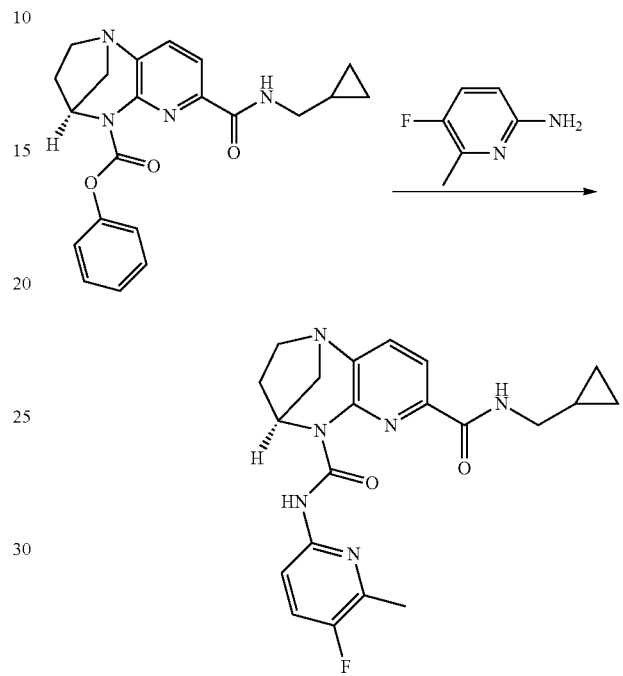

To a stirred solution of 5-fluoro-6-methylpyridin-2-amine (180 mg, 1.427 mmol) in Tetrahydrofuran (5 mL), was added drop wise a solution of 1M LiHMDS (2.378 mL, 2.378 mmol) in THF at −78° C. After stirring the reaction mixture at −78° C. for 30 min, added a solution of (4S)-phenyl 7-((cyclopropylmethyl)carbamoyl)-3,4-dihydro-1,4-methanopyrido[2,3-b][1,4]diazepine-5(2H)-carboxylate (450 mg, 1.189 mmol) in Tetrahydrofuran (2 mL), drop wise under nitrogen at −78° C. The resulting reaction mixture was stirred at −78° C. for 1 h. and then at rt for 6 h. (TLC 5% MeOH\DCM $R_f$: 0.3; UV active). The reaction mixture was quenched with aqueous $NH_4Cl$ (10 mL). The aqueous layer was extracted with EtOAc (2×25 mL). The combined organic layer was dried over anhydrous $Na_2SO_4$, filtered and concentrated under reduced pressure to obtain crude product which was purified by combi-flash (12 g (Reveleris) normal phase, Eluent: 5% methanol in DCM) to afford the desired product (4S)—N7-(cyclopropylmethyl)-N5-(5-fluoro-6-methylpyridin-2-yl)-3,4-dihydro-1,4-methanopyrido[2,3-b][1,4]diazepine-5,7(2H)-dicarboxamide (90 mg, 0.215 mmol, 18.09% yield) as an off white solid. LCMS (m/z): 411.16 [M+H]$^+$, Rt=2.34 min.

$^1$H NMR (400 MHz, DMSO-$d_6$): δ ppm 12.89 (s, 1H), 7.85-8.10 (m, 1H), 7.87-7.92 (m, 1H), 7.57-7.82 (m, 3H), 5.46 (dd, J=5.92, 3.07 Hz, 1H), 3.23-3.43 (m, 2H), 3.02-3.22 (m, 3H), 2.82-3.01 (m, 1H), 2.39 (d, J=2.85 Hz, 3H), 2.08-2.30 (m, 1H), 1.92 (dt, J=14.09, 7.32 Hz, 1H), 1.23 (br s, 1H), 0.19-0.46 (m, 2H), 0.2 (m, 2H).

Example 113

Synthesis of (4S)—N7-(cyclopropylmethyl)-N5-(6-methoxypyrimidin-4-yl)-3,4-dihydro-1,4-methanopyrido[2,3-b][1,4]diazepine-5,7(2H)-dicarboxamide

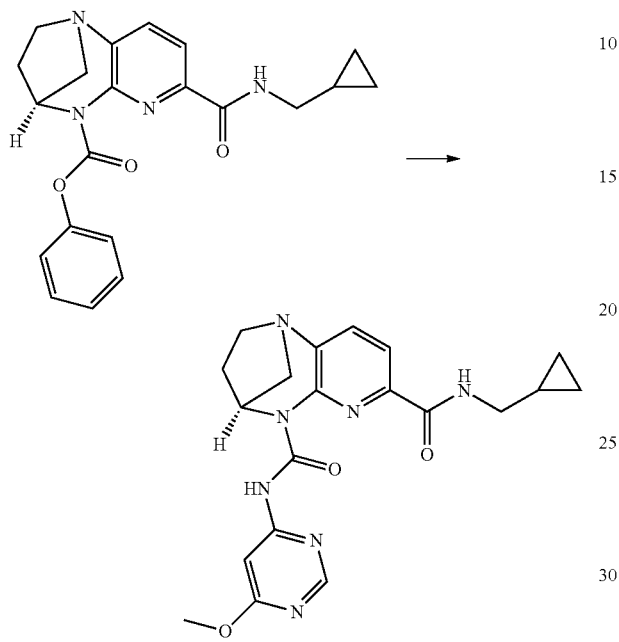

To a stirred solution of 6-methoxypyrimidin-4-amine (198 mg, 1.586 mmol) in Tetrahydrofuran (20 mL), was added drop wise a solution of 1M LiHMDS (2.64 mL, 2.64 mmol) in THF at −78° C. After stirring the reaction mixture at −78° C. for 30 min, added a solution of (4S)-phenyl7-((cyclopropylmethyl)carbamoyl)-3,4-dihydro-1,4-methanopyrido[2,3-b][1,4]diazepine-5(2H)-carboxylate (500 mg, 1.321 mmol) in Tetrahydrofuran (5.00 mL) drop wise under nitrogen at −78° C. The resulting reaction mixture was stirred at −78° C. for 1 h. and then at rt for 6 h. (TLC 5% MeOH\DCM $R_f$: 0.3; UV active). The reaction mixture was quenched with aqueous $NH_4Cl$ (10 mL). The aqueous layer was extracted with EtOAc (2×25 mL). The combined organic layer was dried over anhydrous $Na_2SO_4$, filtered and concentrated under reduced pressure to obtain crude product, which was purified by Prep HPLC (conditions: (conditions: MP-A: 10 mM Ammonium Bicarbonate (Aq) MP-B: Acetonitrile Column: XBridge C18 (150×19 mm), 5u Method: 0/25, 1/25.10/55, 10.5/100, 13.5/100, 14/25, 16.5/25 Solubility: ACN+MEOH+THF Flow: 17 ml/min) to afford the desired product (4S)—N7-(cyclopropylmethyl)-N5-(6-methoxypyrimidin-4-yl)-3,4-dihydro-1,4-methanopyrido[2,3-b][1,4]diazepine-5,7(2H)-dicarboxamide (112 mg, 0.274 mmol, 20.70% yield) as a white solid. LCMS (m/z): 410.12 $[M+H]^+$, Rt=2.11 min.

$^1H$ NMR (400 MHz, DMSO-$d_6$): δ ppm 13.46 (s, 1H), 8.53 (d, J=0.88 Hz, 1H), 8.27-8.06 (m, 1H), 7.81-7.63 (m, 2H), 7.35 (d, J=0.88 Hz, 1H), 5.42 (dd, J=5.92, 3.07 Hz, 1H), 3.93 (s, 3H), 3.32-3.24 (m, 2H), 3.05-3.21 (m, 3H), 3.04-2.82 (m, 1H), 2.22 (dddd, J=13.70, 9.81, 5.97, 3.84 Hz, 1H), 1.94 (dt, J=13.76, 7.04 Hz, 1H), 1.26-1.03 (m, 1H), 0.50-0.38 (m, 2H), 0.34-0.22—(m, 2H).

Example 114

Synthesis of (4S)—N7-(cyclopropylmethyl)-N5-(4-(2-methyloxazol-5-yl)pyridin-2-yl)-3,4-dihydro-1,4-methanopyrido[2,3-b][1,4]diazepine-5,7(2H)-dicarboxamide To a stirred solution of (4S)—N5-(4-bromopyridin-2-yl)-N7-(cyclopropylmethyl)-3,4-dihydro-1,4-methanopyrido[2,3-b][1,4]diazepine-5,7(2H)-dicarboxamide (300 mg, 0.656 mmol) and 2-methyl-5-(4,4,5,5-tetramethyl-1,3,2-dioxaborolan-2-yl)oxazole (165 mg, 0.787 mmol) in 1,4-Dioxane (20 mL) and Water (2 mL) was added potassium acetate (193 mg, 1.968 mmol) and the mixture was purged with argon for 30 min. then added $PdCl_2$(dppf) (72.0 mg, 0.098 mmol) and the mixture was stirred at 80° C. for 16 h. (TLC eluent: 5% Methanol in DCM, $R_f$: 0.2). The reaction mixture was cooled to RT and was partitioned between water (20 mL) and ethyl acetate (2×50 mL). Ethyl acetate layer was separated, dried over anhydrous $Na_2SO_4$, filtered and filtrate was evaporated to afford crude brown liquid. The crude material was purified by combiflash chromatography (using Silica gel column, eluent 2.5% MeOH in DCM) to afford (4S)—N7-(cyclopropylmethyl)-N5-(4-(2-methyloxazol-5-yl)pyridin-2-yl)-3,4-dihydro-1,4-methanopyrido[2,3-b][1,4]diazepine-5,7(2H)-dicarboxamide (70 mg, 0.148 mmol, 22.62% yield) as an off white solid. LCMS (m/z): 460.19 $[M+H]^+$, Rt=2.06 min.

$^1H$ NMR (400 MHz, $CDCl_3$): δ ppm 13.64 (s, 1H), 8.31-8.48 (m, 1H), 8.11-8.30 (m, 2H), 7.92 (d, J=7.89 Hz, 1H), 7.67 (d, J=7.89 Hz, 1H), 7.39-7.57 (m, 1H), 7.10-7.24 (m, 1H), 5.64 (dd, J=5.81, 3.18 Hz, 1H), 3.37-3.58 (m, 2H), 3.09-3.34 (m, 4H), 2.56 (s, 3H), 2.21-2.47 (m, 1H), 1.95-2.20 (m, 1H), 1.17-1.38 (m, 1H), 0.44-0.62 (m, 2H), 0.35 (q, J=4.82 Hz, 2H).

Example 115

Synthesis of (4S)—N5-(4-(2-methyloxazol-5-yl)pyridin-2-yl)-N7-(2,2,2-trifluoroethyl)-3,4-dihydro-1,4-methanopyrido[2,3-b][1,4]diazepine-5,7(2H)-dicarboxamide

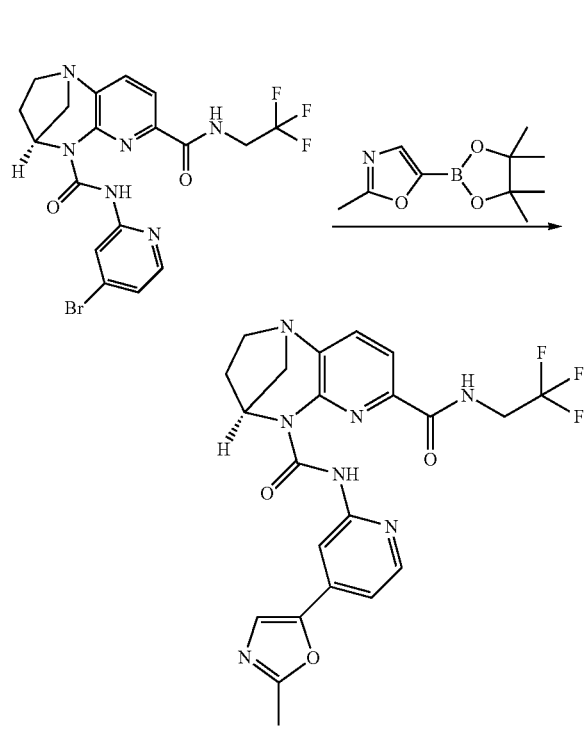

To a stirred solution of (4S)—N5-(4-bromopyridin-2-yl)-N7-(2,2,2-trifluoroethyl)-3,4-dihydro-1,4-methanopyrido[2,3-b][1,4]diazepine-5,7(2H)-dicarboxamide (300 mg, 0.618 mmol) and 2-methyl-5-(4,4,5,5-tetramethyl-1,3-dioxolan-2-yl)oxazole (196 mg, 0.927 mmol) in 1,4-Dioxane (20 mL) and Water (2 mL) was added potassium acetate (182 mg, 1.855 mmol) and the reaction mixture was purged with argon for 30 min. then added $PdCl_2$(dppf) (67.9 mg, 0.093 mmol) and stirred at 100° C. for 5 h. (TLC eluent: 5% Methanol in DCM, $R_f$: 0.2). The reaction mixture was cooled to RT and was partitioned between water (20 mL) and ethyl acetate (2×50 mL). Ethyl acetate layer was separated and was dried over anhydrous $Na_2SO_4$, filtered and filtrate was evaporated to afford crude brown liquid. The crude material was purified by combiflash chromatography (using Silica gel column, 2.5% MeOH in DCM) to afford (4S)—N5-(4-(2-methyloxazol-5-yl)pyridin-2-yl)-N7-(2,2,2-trifluoroethyl)-3,4-dihydro-1,4-methanopyrido[2,3-b][1,4]diazepine-5,7(2H)-dicarboxamide (90 mg, 0.182 mmol, 29.4% yield) as a white solid. LCMS (m/z): 488.13 [M+H]$^+$, Rt=2.10 min.

$^1$H NMR (400 MHz, CDCl$_3$): δ ppm 13.72 (s, 1H), 8.52 (br t, J=6.36 Hz, 1H), 8.29-8.40 (m, 1H), 8.24 (d, J=5.26 Hz, 1H), 7.93 (d, J=7.89 Hz, 1H), 7.69 (d, J=7.89 Hz, 1H), 7.48 (s, 1H), 7.10-7.24 (m, 1H), 5.62 (dd, J=5.81, 3.18 Hz, 1H), 4.10-4.34 (m, 2H), 3.20-3.34 (m, 3H), 3.15 (br d, J=12.06 Hz, 1H), 2.57 (s, 3H), 2.22-2.47 (m, 1H), 1.98-2.21 (m, 1H).

Example 116

Synthesis of (4S)—N7-(2,2-difluoroethyl)-N5-(pyridin-2-yl)-3,4-dihydro-1,4-methanopyrido[2,3-b][1,4]diazepine-5,7(2H)-dicarboxamide

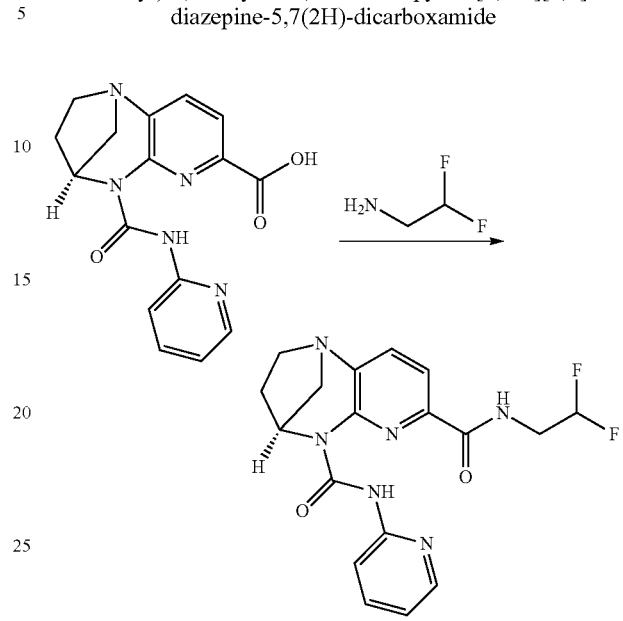

To a stirred solution of (4S)-5-(pyridin-2-ylcarbamoyl)-2,3,4,5-tetrahydro-1,4-methanopyrido[2,3-b][1,4]diazepine-7-carboxylic acid (10 g, 30.7 mmol) in DMF (50 mL), under nitrogen at 0° C. was added DIPEA (26.8 mL, 154 mmol), HATU (23.38 g, 61.5 mmol) and 2,2-difluoroethanamine (2.492 g, 30.7 mmol) and stirred at RT for 16 h. (TLC system: 5% Methanol in DCM. $R_f$ value: 0.2). The reaction mixture was quenched with cold water (50 mL) and the resultant solid was filtered and dried under high vacuum to afford (4S)—N7-(2,2-difluoroethyl)-N5-(pyridin-2-yl)-3,4-dihydro-1,4-methanopyrido[2,3-b][1,4]diazepine-5,7(2H)-dicarboxamide (8.4 g, 21.60 mmol, 70.3% yield) as a white solid. LCMS (m/z): 389.19 [M+H]$^+$, Rt=1.88 min.

$^1$H NMR (400 MHz, CDCl$_3$): δ ppm 13.56-13.74 (m, 1H), 8.51-8.58 (m, 1H), 8.25-8.30 (m, 1H), 8.08 (dt, J=8.33, 0.99 Hz, 1H), 7.88 (d, J=7.89 Hz, 1H), 7.73 (td, J=7.84, 1.86 Hz, 1H), 7.67 (d, J=7.89 Hz, 1H), 7.02 (ddd, J=7.40, 4.99, 0.99 Hz, 1H), 5.78-6.21 (m, 1H), 5.61 (dd, J=5.92, 3.07 Hz, 1H), 3.81-4.06 (m, 2H), 3.09-3.33 (m, 3H), 2.99-3.22 (m, 1H), 2.23-2.47 (m, 1H), 1.98-2.12 (m, 1H).

Example 117

Synthesis of (4S)—N7-(2,2-difluoro-3-hydroxypropyl)-N5-(pyridin-2-yl)-3,4-dihydro-1,4-methanopyrido[2,3-b][1,4]diazepine-5,7(2H)-dicarboxamide

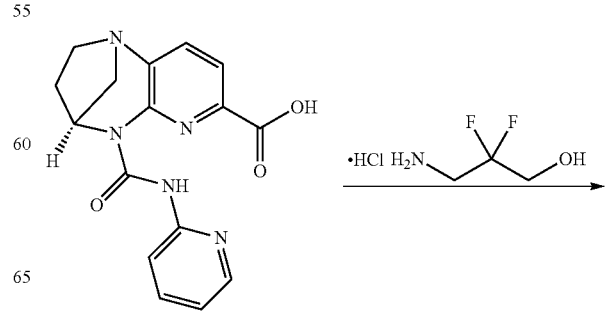

423

-continued

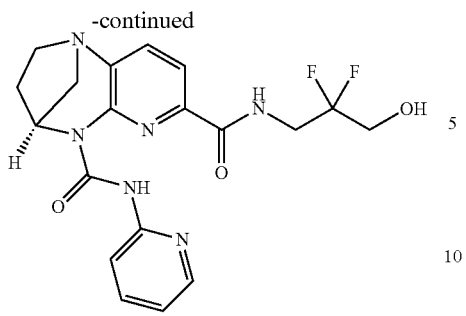

To a solution of (4S)-5-(pyridin-2-ylcarbamoyl)-2,3,4,5-tetrahydro-1,4-methanopyrido[2,3-b][1,4]diazepine-7-carboxylic acid (8 g, 24.59 mmol) in DMF (60 mL) under nitrogen at 0° C., was added DIPEA (21.47 mL, 123 mmol), HATU (18.70 g, 49.2 mmol) and 3-amino-2,2-difluoropropan-1-ol hydrochloride (3.63 g, 24.59 mmol) and stirred at RT for 16 h (TLC system: 5% Methanol in DCM. $R_f$ value: 0.3). The reaction mixture was cooled to RT and was partitioned between water (20 mL) and ethyl acetate (2×50 mL). Ethyl acetate layer was separated and was dried over anhydrous $Na_2SO_4$, filtered and filtrate was evaporated to afford crude brown liquid. The crude material was purified by combiflash chromatography (using Silica gel column, eluent EtOAc) to afford (4S)—N7-(2,2-difluoro-3-hydroxypropyl)-N5-(pyridin-2-yl)-3,4-dihydro-1,4-methanopyrido[2,3-b][1,4]diazepine-5,7(2H)-dicarboxamide (3.629 g, 8.65 mmol, 35.2% yield) as a white solid. LCMS (m/z): 419.15 [M+H]$^+$, Rt=1.53 min.

$^1$H NMR (400 MHz, CDCl$_3$): δ ppm 13.56 (s, 1H), 8.85 (br t, J=6.03 Hz, 1H), 8.31 (dd, J=4.82, 0.88 Hz, 1H), 8.05 (d, J=8.33 Hz, 1H), 7.88 (d, J=7.89 Hz, 1H), 7.73-7.68 (td, J=7.83-8.03 Hz, 2H), 7.03 (ddd, J=7.34, 5.04, 0.77 Hz, 1H), 5.60 (dd, J=5.92, 3.07 Hz, 1H), 4.68 (br t, J=7.56 Hz, 1H), 3.88-4.11 (m, 2H), 3.71 (td, J=12.00, 6.91 Hz, 2H), 3.10-3.36 (m, 3H), 2.84-3.08 (m, 1H), 2.24-2.40 (m, 1H), 1.98-2.17 (m, 1H).

Example 118

Synthesis of (4S)—N5-(5-((S)-2,3-dihydroxypropoxy)pyrazin-2-yl)-N7-(2,2,2-trifluoroethyl)-3,4-dihydro-1,4-methanopyrido[2,3-b][1,4]diazepine-5,7(2H)-dicarboxamide

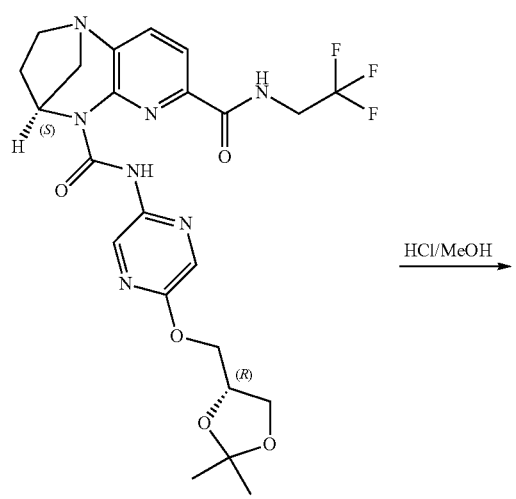

HCl/MeOH →

424

-continued

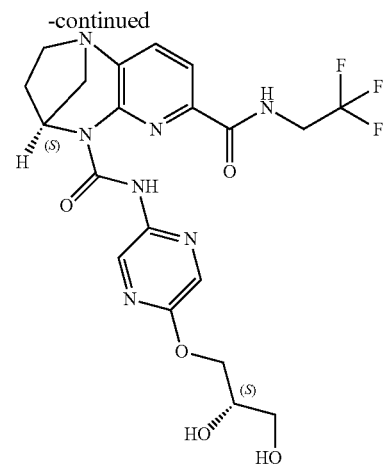

To a stirred solution of (4S)—N5-(5-(((R)-2,2-dimethyl-1,3-dioxolan-4-yl)methoxy)pyrazin-2-yl)-N7-(2,2,2-trifluoroethyl)-3,4-dihydro-1,4-methanopyrido[2,3-b][1,4]diazepine-5,7(2H)-dicarboxamide (520 mg, 0.967 mmol) in Methanol (20 mL) was added aq HCl (3 mL, 6.00 mmol) at room temperature. The resulting reaction mixture was stirred at room temperature for 1 h. (TLC system: 10% MeOH in DCM, $R_f$: 0.5) and concentrated under reduced pressure to remove MeOH, aqueous layer was basified with saturated sodium bicarbonate solution and extracted with DCM (3×30 mL). The combined organic layer was washed with water (20 mL), brine solution (20 mL), dried over anhydrous $Na_2SO_4$, filtered and filtrate was concentrated under reduced pressure, the obtained pale yellow semi solid was washed with Ethanol (10 mL) and n-pentane (10 mL) to afford the desired product (4S)—N5-(5-((S)-2,3-dihydroxypropoxy)pyrazin-2-yl)-N7-(2,2,2-trifluoroethyl)-3,4-dihydro-1,4-methanopyrido[2,3-b][1,4]diazepine-5,7(2H)-dicarboxamide (380 mg, 0.761 mmol, 79% yield) as an off-white solid. LCMS (m/z): 498.10 [M+H]$^+$, $R_f$=1.61 min.

$^1$H NMR (400 MHz, CDCl$_3$): δ ppm 13.38 (s, 1H), 8.92 (d, J=1.54 Hz, 1H), 8.01 (t, J=6.47 Hz, 1H), 7.96-7.90 (m, 2H), 7.69 (d, J=7.89 Hz, 1H), 5.62 (dd, J=5.92, 3.07 Hz, 1H), 4.51-4.41 (m, 2H), 4.29-4.04 (m, 3H), 3.83-3.69 (m, 2H), 3.31-3.17 (m, 2H), 3.15-3.00 (m, 3H), 2.41-2.29 (m, 1H), 2.28-2.20 (m, 1H), 2.14-2.00 (m, 1H).

Example 119

Synthesis of (4S)—N5-(pyrazin-2-yl)-N7-((R)-1,1,1-trifluoro-3-hydroxypropan-2-yl)-3,4-dihydro-1,4-methanopyrido[2,3-b][1,4]diazepine-5,7(2H)-dicarboxamide

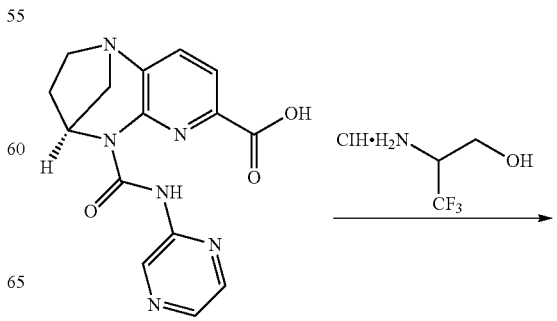

425
-continued

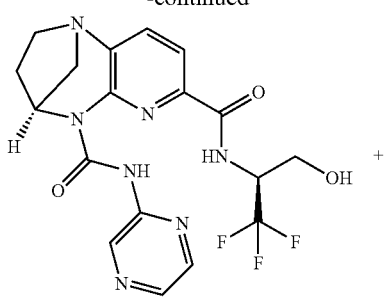

+

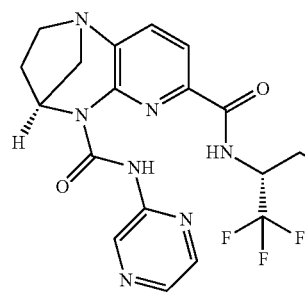

To a stirred solution of (4S)-5-(pyrazin-2-ylcarbamoyl)-2,3,4,5-tetrahydro-1,4-methanopyrido[2,3-b][1,4]diazepine-7-carboxylic acid (11.6 g, 35.5 mmol) in N,N-Dimethylformamide (100 mL) was added HATU (20.28 g, 53.3 mmol) and DIPEA (18.63 mL, 107 mmol) at 0° C. The resulting reaction mixture was stirred at 0° C. for 15 min, then 2-amino-3,3,3-trifluoropropan-1-ol hydrochloride (8.83 g, 53.3 mmol) was added to the reaction mixture. And stirred at rt for 1 h. (TLC system: 10% MeOH in DCM, $R_f$: 0.5) and diluted with ice cold water (500 mL), extracted with EtOAc (3×200 mL). The combined organic layer was washed with ice cold water (3×100 mL), brine solution (100 mL), dried over anhydrous $Na_2SO_4$, filtered and concentrated under reduced pressure to obtain racemic mixture which was purified by Chiral SFC (Conditions: Column/dimensions: Chiralpak IC (250×30) mm, 5µ % CO2: 50.0%, % Co solvent: 50.0% (0.5% Iso propyl amine In IPA), Total Flow: 90.0 g/min, Back Pressure: 100.0 bar, UV: 260 nm, Stack time: 11.5 min, Load/inz: 63.0 mg, Solubility: Methanol+CAN, Total No of injections: 80, Instrument details: Make/Model: Thar SFC-NEW-200-1) to afford the desired products as peak-I and Peak-II. (These peaks were confirmed by matching the chiral HPLC data with known chiral materials data, which were prepared by us earlier).

Peak 2 (Slowest Eluent)

(4S)—N5-(pyrazin-2-yl)-N7-((R)-1,1,1-trifluoro-3-hydroxypropan-2-yl)-3,4-dihydro-1,4-methanopyrido[2,3-b][1,4]diazepine-5,7(2H)-dicarboxamide (3.40 g, 7.74 mmol, 21.78% yield) as an off-white solid. LCMS (m/z): 438.09 $[M+H]^+$, $R_t$=1.69 min.

$^1$H NMR (400 MHz, $CDCl_3$): δ ppm 12.76 (br s, 1H), 9.62 (s, 1H), 8.37 (d, J=2.63 Hz, 1H), 8.18 (br s, 1H), 7.91 (d, J=7.89 Hz, 1H), 7.73 (d, J=7.89 Hz, 1H), 7.58-7.49 (m, 1H), 5.75 (dd, J=6.25, 2.96 Hz, 1H), 5.05-4.94 (m, 1H), 4.13-4.00 (m, 2H), 3.99-3.91 (m, 1H), 3.34-3.09 (m, 3H), 3.07-3.00 (m, 1H), 2.43-2.30 (m, 1H), 2.12-1.97 (m, 1H).

426
Example 120

Synthesis of (4S)—N5-(1-methyl-6-oxo-1,6-dihydropyrimidin-4-yl)-N7-(2,2,2-trifluoroethyl)-3,4-dihydro-1,4-methanopyrido[2,3-b][1,4]diazepine-5,7(2H)-dicarboxamide To a solution of (4S)-5-((1-methyl-6-oxo-1,6-dihydropyrimidin-4-yl)carbamoyl)-2,3,4,5-tetrahydro-1,4-methanopyrido[2,3-b][1,4]diazepine-7-carboxylic acid (350 mg, 0.982 mmol) in DMF (5 mL) at RT was added HATU (747 mg, 1.964 mmol), DIPEA (0.515 mL, 2.95 mmol) followed by 2,2,2-trifluoroethanamine hydrochloride (160 mg, 1.179 mmol) then the reaction mixture was stirred at for 16 h. (TLC system: 5% MeOH in DCM, $R_f$ value: 0.30). The reaction mass was diluted with of ice cold water (80 mL) and extracted with EtOAc (2×100 mL). The combined organic layer was washed with brine (80 mL), dried over $Na_2SO_4$, filtered and concentrated to get crude. The crude material was purified by combiflash chromatography (using silica gel column, 3% methanol in DCM). Fractions containing pure compound were combined and concentrated to afford the desired compound (4S)—N5-(1-methyl-6-oxo-1,6-dihydropyrimidin-4-yl)-N7-(2,2,2-trifluoroethyl)-3,4-dihydro-1,4-methanopyrido[2,3-b][1,4]diazepine-5,7(2H)-dicarboxamide (275 mg, 0.623 mmol, 63.4% yield) as an off white solid. LCMS (m/z): 438.13 $[M+H]^+$, Rt=1.64 min.

$^1$H NMR (400 MHz, $CDCl_3$): δ ppm 13.30 (s, 1H), 8.07 (br t, J=6.14 Hz, 1H), 7.94 (d, J=7.89 Hz, 1H), 7.89 (s, 1H), 7.70 (d, J=7.89 Hz, 1H), 7.14 (s, 1H), 5.61 (dd, J=5.92, 3.07 Hz, 1H), 4.10-4.27 (m, 2H), 3.45 (s, 3H), 3.17-3.28 (m, 2H), 2.99-3.05 (m, 2H), 2.33 (ddt, J=14.36, 8.93, 5.34, 5.34 Hz, 1H), 1.98-2.08 (m, 1H).

Example 121

Synthesis of (4S)—N5-(2-methyl-3-oxo-2,3-dihydropyridazin-4-yl)-N7-(2,2,2-trifluoroethyl)-3,4-dihydro-1,4-methanopyrido[2,3-b][1,4]diazepine-5,7(2H)-dicarboxamide

Example 122

Synthesis of (4S)—N5-(2-methyl-3-oxo-2,3-dihydropyridazin-4-yl)-N7-((R)-1,1,1-trifluoropropan-2-yl)-3,4-dihydro-1,4-methanopyrido[2,3-b][1,4]diazepine-5,7(2H)-dicarboxamide

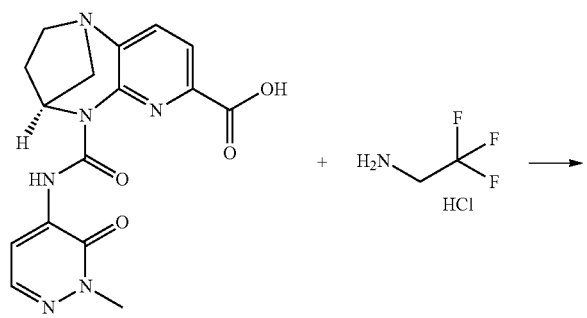

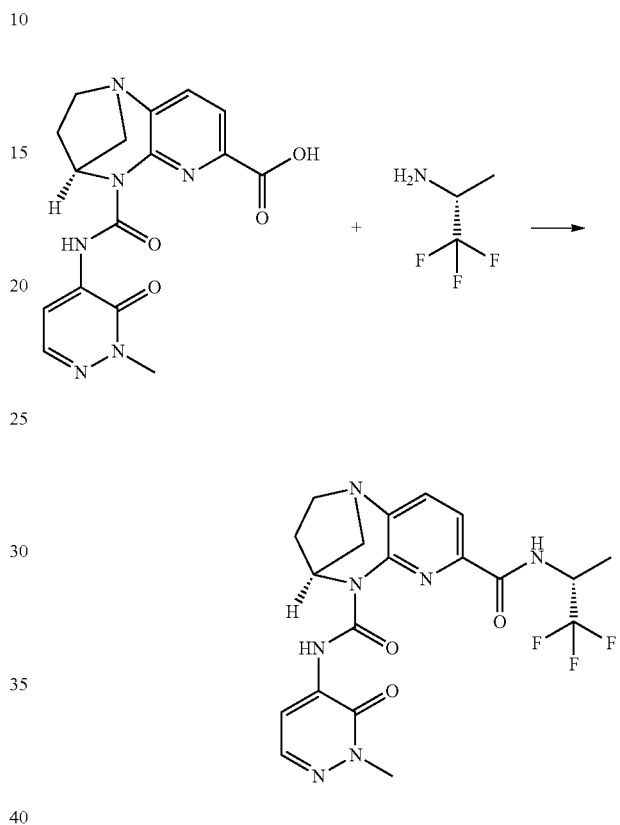

To a stirred solution of (4S)-5-((2-methyl-3-oxo-2,3-dihydropyridazin-4-yl)carbamoyl)-2,3,4,5-tetrahydro-1,4-methanopyrido[2,3-b][1,4]diazepine-7-carboxylic acid (350 mg, 0.982 mmol) in N,N-Dimethylformamide (15 mL) under nitrogen at RT was added 2,2,2-trifluoroethanamine hydrochloride (200 mg, 1.473 mmol), HATU (560 mg, 1.473 mmol) and DIPEA (0.686 mL, 3.93 mmol) and stirred for 16 h. (TLC eluting system: 100% EtOAc; $R_f$—0.4; UV active). The reaction mixture was quenched with water (15 mL) and the resultant solid was filtered, triturated with diethylether to afford (4S)—N5-(2-methyl-3-oxo-2,3-dihydropyridazin-4-yl)-N7-(2,2,2-trifluoroethyl)-3,4-dihydro-1,4-methanopyrido[2,3-b][1,4]diazepine-5,7(2H)-dicarboxamide (160 mg, 0.365 mmol, 37.2% yield) as an off white solid. LCMS (m/z): 438.13; [M+H]$^+$, $R_t$=2.10 min.

$^1$H NMR (400 MHz, CDCl$_3$): δ ppm 12.56 (s, 1H), 9.77-10.03 (m, 1H), 8.13 (d, J=4.82 Hz, 1H), 8.07 (d, J=8.11 Hz, 1H), 7.82 (d, J=4.82 Hz, 1H), 7.69 (d, J=7.89 Hz, 1H), 5.69 (dd, J=5.92, 3.07 Hz, 1H), 4.14-4.35 (m, 2H), 3.86 (s, 3H), 3.08-3.32 (m, 3H), 2.93-3.08 (m, 1H), 2.26-2.42 (m, 1H), 1.97-2.17 (m, 1H).

To a stirred solution of (4S)-5-((2-methyl-3-oxo-2,3-dihydropyridazin-4-yl)carbamoyl)-2,3,4,5-tetrahydro-1,4-methanopyrido[2,3-b][1,4]diazepine-7-carboxylic acid (350 mg, 0.982 mmol) in N,N-Dimethylformamide (15 mL) under nitrogen at RT was added (R)-1,1,1-trifluoropropan-2-amine (111 mg, 0.982 mmol), HATU (560 mg, 1.473 mmol), DIPEA (0.686 mL, 3.93 mmol) and stirred for 16 h. (TLC eluting system: 100% EtOAc; $R_f$—0.4; UV active). The reaction mixture was quenched with water (15 mL) and the resultant solid was filtered, triturated with diethylether to afford (4S)—N5-(2-methyl-3-oxo-2,3-dihydropyridazin-4-yl)-N7-((R)-1,1,1-trifluoropropan-2-yl)-3,4-dihydro-1,4-methanopyrido[2,3-b][1,4]diazepine-5,7(2H)-dicarboxamide (250 mg, 0.551 mmol, 56.1% yield) as an off white solid. LCMS (m/z): 452.17 [M+H]$^+$, $R_t$=2.24 min.

$^1$H NMR (400 MHz, CDCl$_3$): δ ppm 12.55 (s, 1H), 9.60 (br d, J=8.99 Hz, 1H), 8.03-8.18 (m, 2H), 7.81 (d, J=4.82 Hz, 1H), 7.68 (d, J=7.89 Hz, 1H), 5.68 (dd, J=5.92, 3.07 Hz, 1H), 5.12 (br dd, J=16.33, 8.00 Hz, 1H), 3.87 (s, 3H), 3.08-3.30 (m, 3H), 2.89-3.07 (m, 1H), 2.19-2.40 (m, 1H), 1.94-2.09 (m, 1H), 1.65 (d, J=7.23 Hz, 3H).

Example 123

Synthesis of (4S)—N7-cyclopropyl-N5-(4-(2-methyloxazol-5-yl)pyridin-2-yl)-3,4-dihydro-1,4-methanopyrido[2,3-b][1,4]diazepine-5,7(2H)-dicarboxamide

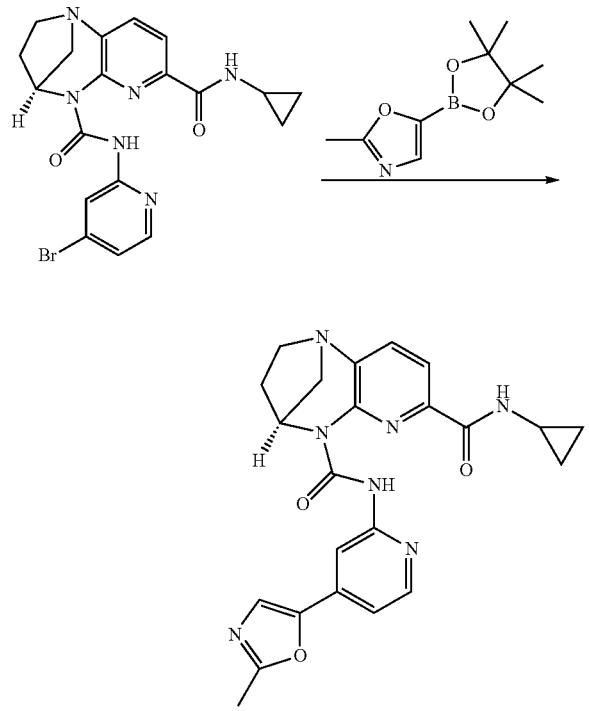

A mixture of (4S)—N5-(4-bromopyridin-2-yl)-N7-cyclopropyl-3,4-dihydro-1,4-methanopyrido[2,3-b][1,4]diazepine-5,7(2H)-dicarboxamide (400 mg, 0.902 mmol), 2-methyl-5-(4,4,5,5-tetramethyl-1,3,2-dioxaborolan-2-yl)oxazole (207 mg, 0.993 mmol) and potassium acetate (177 mg, 1.805 mmol) in 1,4-dioxane (5 mL) and water (2 mL) was degassed by purging argon then added PdCl$_2$(dppf)-CH$_2$Cl$_2$ adduct (36.8 mg, 0.045 mmol) to the above reaction mixture and stirred at 90° C. for 16 h. (TLC system: 5% Methanol in DCM. R$_f$ value: 0.4). The reaction mixture was cooled to 28° C., diluted with water (30 mL) and extracted with ethyl acetate (2×50 mL). The combined organic layer was washed with brine solution (30 mL), dried over anhydrous sodium sulphate, filtered and filtrate was evaporated to give crude compound. The crude material was purified by combiflash chromatography (using silica gel column, 3% methanol in DCM) to afford (4S)—N7-cyclopropyl-N5-(4-(2-methyloxazol-5-yl)pyridin-2-yl)-3,4-dihydro-1,4-methanopyrido[2,3-b][1,4]diazepine-5,7(2H)-dicarboxamide (112 mg, 0.246 mmol, 27.3% yield) as an off-white solid. LC-MS (m/z): 446.15 [M+H]$^+$, Rt=1.91 min.

$^1$H NMR (400 MHz, CDCl$_3$): δ ppm 13.45 (s, 1H), 8.26-8.44 (m, 2H), 7.90-8.00 (m, 2H), 7.66 (d, J=7.89 Hz, 1H), 7.37-7.58 (m, 1H), 7.17-7.20 (m, 1H), 5.64 (dd, J=5.81, 3.18 Hz, 1H), 3.18-3.30 (m, 2H), 3.00-3.16 (m, 3H), 2.51-2.63 (m, 3H), 2.21-2.47 (m, 1H), 1.98-2.17 (m, 1H), 0.79-1.00 (m, 4H).

Example 124

Synthesis of (4S)—N5-(pyridin-2-yl)-N7-(3,3,3-trifluoropropyl)-3,4-dihydro-1,4-methanopyrido[2,3-b][1,4]diazepine-5,7(2H)-dicarboxamide

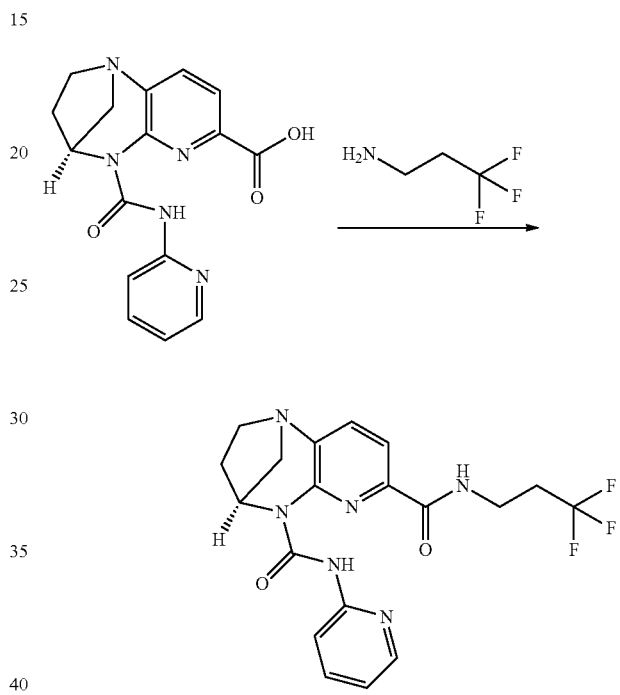

To a solution of (4S)-5-(pyridin-2-ylcarbamoyl)-2,3,4,5-tetrahydro-1,4-methanopyrido[2,3-b][1,4]diazepine-7-carboxylic acid (10 g, 30.7 mmol) in DMF (50 mL) under nitrogen at RT was added DIPEA (16.11 mL, 92 mmol), HATU (23.38 g, 61.5 mmol) and 3,3,3-trifluoropropan-1-amine (4.17 g, 36.9 mmol) and stirred for 16 h. (TLC system: 10% Methanol in DCM. R$_f$ value: 0.4). The reaction mixture was diluted with cold water (100 ml) and the solid formed was filtered, washed with water (50 ml) and dried to give desired product (6 g). The product was taken in 150 ml of ethanol and heated to 80° C. for 30 min. and added palladium scavenger (SilicaMets DMT, 3 g) slowly at 80° C. and stirred for additional 3 h. Reaction suspension was filtered through celite pad and filtrate was concentrated to give (4S)—N5-(pyridin-2-yl)-N7-(3,3,3-trifluoropropyl)-3,4-dihydro-1,4-methanopyrido[2,3-b][1,4]diazepine-5,7(2H)-dicarboxamide (4.6 g, 10.90 mmol, 35.5% yield) as a white solid. LC-MS (m/z): 421.13 [M+H]$^+$, Rt=1.75 min.

$^1$H NMR (400 MHz, CDCl$_3$): δ ppm 13.57 (s, 1H), 8.31-8.56 (m, 1H), 8.23 (d, J=5.17 Hz, 1H), 8.12 (d, J=8.33 Hz, 1H), 7.87 (d, J=7.89 Hz, 1H), 7.73 (t, J=7.83 Hz, 1H), 7.66 (d, J=7.54 Hz, 1H), 6.93-7.14 (m, 1H), 5.61 (dd, J=5.92, 3.07 Hz, 1H), 3.76-3.88 (m, 2H), 3.08-3.32 (m, 3H), 2.95-3.08 (m, 1H), 2.59 (qt, J=10.72, 7.26 Hz, 2H), 2.20-2.44 (m, 1H), 1.93-2.18 (m, 1H).

Example 125

Synthesis of ((4S)—N5-(4-(2-methyloxazol-5-yl)pyridin-2-yl)-N7-((R)-1,1,1-trifluoro-3-hydroxypropan-2-yl)-3,4-dihydro-1,4-methanopyrido[2,3-b][1,4]diazepine-5,7(2H)-dicarboxamide

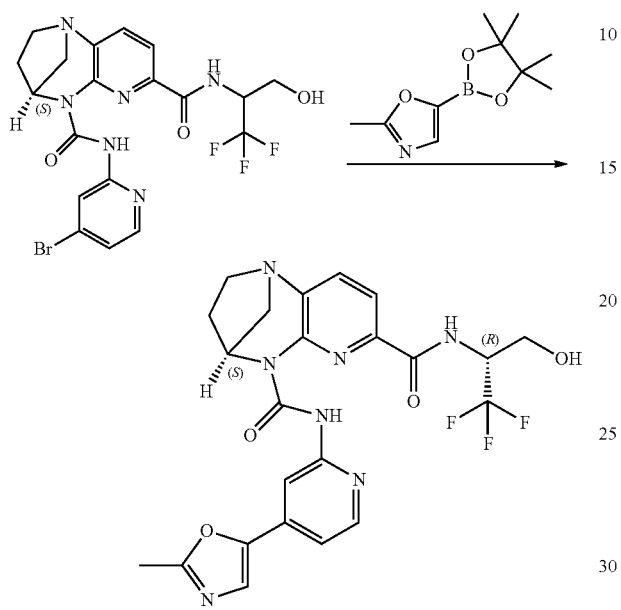

A mixture of (4S)—N5-(4-bromopyridin-2-yl)-N7-(1,1,1-trifluoro-3-hydroxypropan-2-yl)-3,4-dihydro-1,4-methanopyrido[2,3-b][1,4]diazepine-5,7(2H)-dicarboxamide (650 mg, 1.261 mmol), 2-methyl-5-(4,4,5,5-tetramethyl-1,3,2-dioxaborolan-2-yl)oxazole (290 mg, 1.388 mmol) and potassium acetate (248 mg, 2.52 mmol) in 1,4-Dioxane (1 mL) and Water (0.2 mL) was degassed by purging argon for 30 min. then added PdCl$_2$(dppf)-CH$_2$Cl2 adduct (51.5 mg, 0.063 mmol) and heated at 90° C. for 16 h. (TLC system: 5% Methanol in DCM. R$_f$ value: 0.4). The reaction mixture was cooled to RT, diluted with water (50 mL) and extracted with ethyl acetate (2×60 mL). The combined organic layer was washed with brine solution (30 mL), dried over anhydrous sodium sulphate, filtered and filtrate was evaporated to give crude residue. The Crude material was purified by combiflash chromatography (using silica gel column, 5% methanol in DCM) to give desired compound as diastereomeric mixtures. The diastereomers were separated by chiral SFC purification (Column: Lux Cellulose-2 HHhHHh (250×30) mm 5u, % CO2: 50.0%, % co-solvent: 50.0% (0.5% DEA in MeOH), Total Flow: 90.0 g/min, Back Pressure: 100 bar, UV: 269 nm, Stack time: 9.0 min, Load/inj: 36.0 mg, Solubility: MeOH+Acetonitrile+THF, Instrument details: Thar SFC—200) to afford two single diasteromers and Peak 1 was compared with an authentic compound and obsolute chemistry determined.

Peak 1

Obtained (4S)—N5-(4-(2-methyloxazol-5-yl)pyridin-2-yl)-N7-((R)-1,1,1-trifluoro-3-hydroxypropan-2-yl)-3,4-dihydro-1,4-methanopyrido[2,3-b][1,4]diazepine-5,7(2H)-dicarboxamide (90 mg, 0.173 mmol, 13.75% yield) as an off-white solid. LC-MS (m/z): 518.12 [M+H]$^+$, Rt=1.92 min.

1H NMR (400 MHz, CDCl$_3$): δ ppm 12.52 (s, 1H), 8.42-8.62 (m, 1H), 8.23 (dd, J=5.37, 0.77 Hz, 1H), 7.89 (d, J=7.89 Hz, 1H), 7.71 (d, J=7.94 Hz, 1H), 7.62 (br d, J=9.43 Hz, 1H), 7.49 (s, 1H), 7.22-7.27 (m, 1H), 5.77 (dd, J=6.14, 3.29 Hz, 1H), 4.77-5.05 (m, 1H), 4.09 (d, J=5.92 Hz, 2H), 3.09-3.32 (m, 3H), 2.92-3.09 (m, 1H), 2.57 (s, 3H), 2.21-2.46 (m, 1H), 1.98-2.12 (m, 1H).

Example 126

Synthesis of (4S)—N5-(4-(2-methyloxazol-5-yl)pyridin-2-yl)-N7-((S)-1,1,1-trifluoropropan-2-yl)-3,4-dihydro-1,4-methanopyrido[2,3-b][1,4]diazepine-5,7(2H)-dicarboxamide

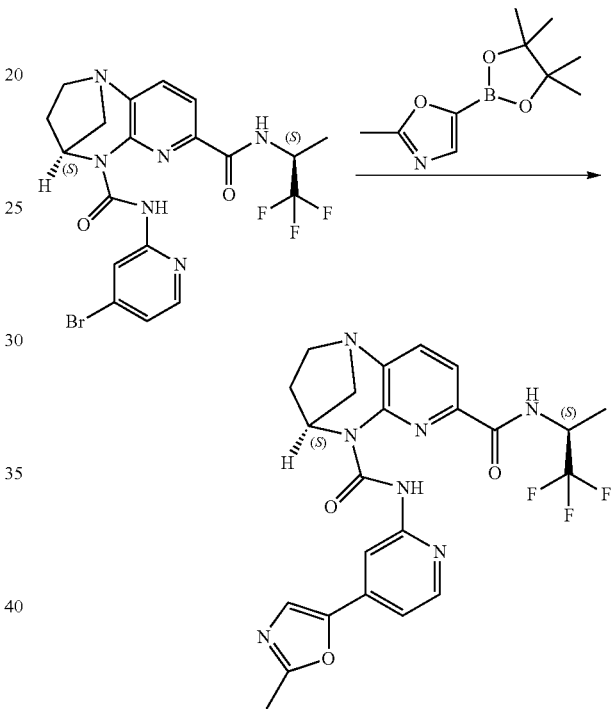

A mixture of (4S)—N5-(4-bromopyridin-2-yl)-N7-((S)-1,1,1-trifluoropropan-2-yl)-3,4-dihydro-1,4-methanopyrido[2,3-b][1,4]diazepine-5,7(2H)-dicarboxamide (450 mg, 0.901 mmol), 2-methyl-5-(4,4,5,5-tetramethyl-1,3,2-dioxaborolan-2-yl)oxazole (264 mg, 1.262 mmol) and potassium acetate (221 mg, 2.253 mmol) in 1,4-Dioxane (5 mL) and Water (2 mL) was degassed by purging argon for 30 min. then added PdCl$_2$(dppf)-CH$_2$Cl$_2$ adduct (73.6 mg, 0.090 mmol) and the reaction mixture was stirred at 90° C. for 16 h. (TLC system: 5% Methanol in DCM. R$_f$ value: 0.4). The reaction mixture was cooled to RT, diluted with water (20 mL) and extracted with ethyl acetate (2×50 mL). The combined organic layer was washed with brine solution (30 mL), dried over anhydrous sodium sulphate, filtered and filtrate was evaporated to give crude residue. The crude material was purified by combiflash chromatography (using silica gel column, 3% methanol in DCM) to give desired pure compound as a solid. The product was taken in 15 ml of ethanol and heated to 80° C. for 30 min. and added palladium scavenger (SilicaMets DMT, 0.5 g) slowly at 80° C. and stirred for additional 3 h. Reaction suspension was filtered through celite pad and filtrate was concentrated to give (4S)—N5-(4-(2-methyloxazol-5-yl)pyridin-2-yl)-N7-((S)-1,1,1-trifluoropropan-2-yl)-3,4-dihydro-1,4-methanopyrido[2,3-b][1,4]diazepine-5,7(2H)-dicarboxamide (160 mg, 0.318 mmol, 35.3% yield) as an off-white solid. LC-MS (m/z): 502.14 [M+H]+, Rt=1.91 min.

¹H NMR (400 MHz, CDCl₃): δ ppm 13.35 (s, 1H), 8.34-8.47 (m, 1H), 8.26 (d, J=5.26 Hz, 1H), 7.83-8.09 (m, 2H), 7.69 (d, J=7.89 Hz, 1H), 7.47 (s, 1H), 7.21 (d, J=5.43 Hz, 1H), 5.68 (dd, J=5.92, 3.07 Hz, 1H), 5.08 (dq, J=16.91, 7.37 Hz, 1H), 3.09-3.33 (m, 3H), 2.94-3.09 (m, 1H), 2.56 (s, 3H), 2.21-2.47 (m, 1H), 1.94-2.20 (m, 1H), 1.53-1.62 (m, 3H)

Example 127

Synthesis of (4S)—N5-(4-(oxazol-5-yl)pyridin-2-yl)-N7-((S)-1,1,1-trifluoropropan-2-yl)-3,4-dihydro-1,4-methanopyrido[2,3-b][1,4]diazepine-5,7(2H)-dicarboxamide

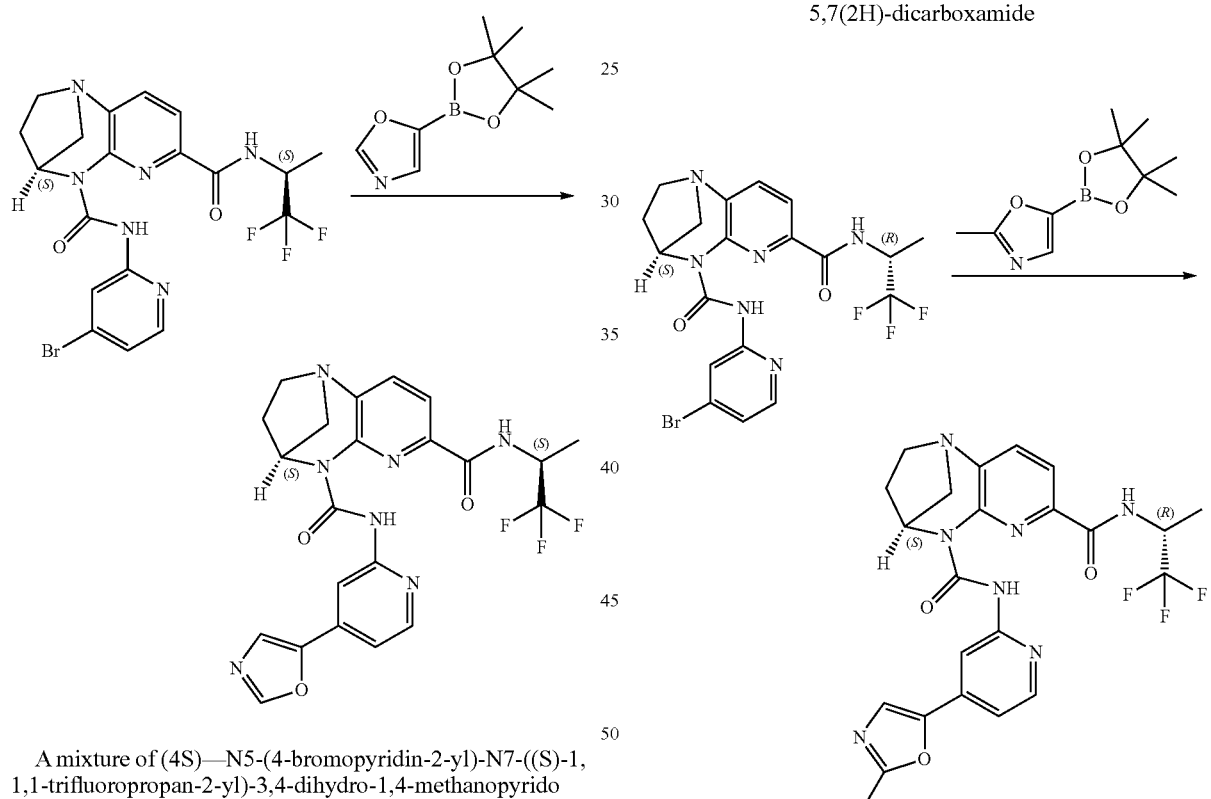

A mixture of (4S)—N5-(4-bromopyridin-2-yl)-N7-((S)-1,1,1-trifluoropropan-2-yl)-3,4-dihydro-1,4-methanopyrido[2,3-b][1,4]diazepine-5,7(2H)-dicarboxamide (450 mg, 0.901 mmol), 5-(4,4,5,5-tetramethyl-1,3,2-dioxaborolan-2-yl)oxazole (246 mg, 1.262 mmol) and potassium acetate (221 mg, 2.253 mmol) in 1,4-Dioxane (5 mL) and Water (2 mL) mixture was degassed by purging argon for 15 min. Then added PdCl₂(dppf)-CH₂Cl₂ adduct (73.6 mg, 0.090 mmol) to the above reaction mixture and heated at 90° C. for 16 h. (TLC system: 5% Methanol in DCM. R_f value: 0.4). The reaction mixture was cooled to RT, diluted with water (20 mL) and extracted with ethyl acetate (2×50 mL). The combined organic layer was washed with brine solution (30 mL), dried over anhydrous sodium sulphate, filtered and filtrate was evaporated to give crude residue. The crude material was purified by combiflash chromatography (using silica gel column, 3% methanol in DCM) to give desired product as a solid. The product was taken in 15 ml of ethanol and heated to 80° C. for 30 min. and added palladium scavenger (SilicaMets DMT, 0.5 g) slowly at 80° C. and stirred for additional 3 h. Reaction suspension was filtered through celite pad and filtrate was concentrated to give (4S)—N5-(4-(oxazol-5-yl)pyridin-2-yl)-N7-((S)-1,1,1-trifluoropropan-2-yl)-3,4-dihydro-1,4-methanopyrido[2,3-b][1,4]diazepine-5,7(2H)-dicarboxamide (162 mg, 0.330 mmol, 36.6% yield) as an off-white solid. LC-MS (m/z): 488.10 [M+H]+, Rt=2.21 min.

¹H NMR (400 MHz, CDCl₃): δ ppm 13.38 (s, 1H), 8.46 (d, J=0.66 Hz, 1H), 8.30 (d, J=5.26 Hz, 1H), 7.91-8.01 (m, 3H), 7.69 (d, J=7.89 Hz, 1H), 7.63 (s, 1H), 7.25-7.29 (m, 1H), 5.69 (dd, J=5.92, 3.07 Hz, 1H), 4.99-5.16 (m, 1H), 3.10-3.33 (m, 3H), 2.95-3.09 (m, 1H), 2.22-2.42 (m, 1H), 1.99-2.20 (m, 1H), 1.51-1.65 (m, 3H).

Example 128

Synthesis of (4S)—N5-(4-(2-methyloxazol-5-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

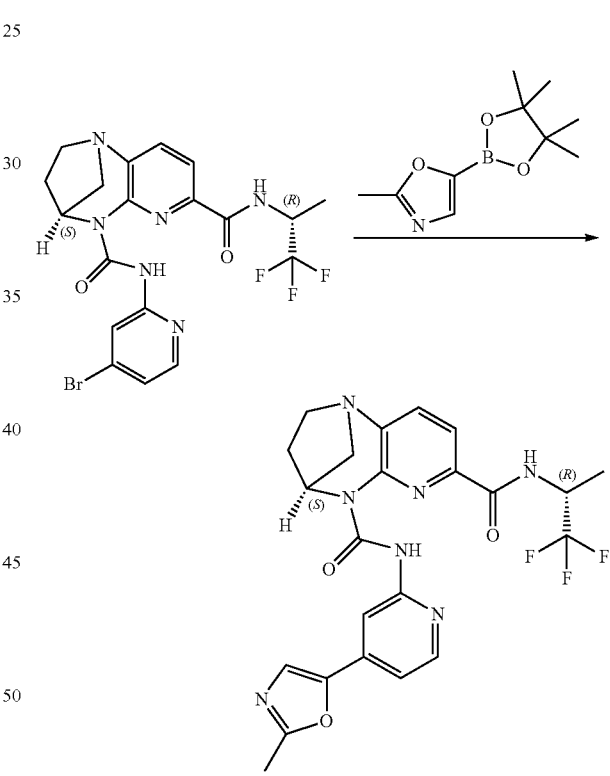

A mixture of (4S)—N5-(4-bromopyridin-2-yl)-N7-((R)-1,1,1-trifluoropropan-2-yl)-3,4-dihydro-1,4-methanopyrido[2,3-b][1,4]diazepine-5,7(2H)-dicarboxamide (400 mg, 0.801 mmol), 2-methyl-5-(4,4,5,5-tetramethyl-1,3,2-dioxaborolan-2-yl)oxazole (184 mg, 0.881 mmol) and potassium acetate (157 mg, 1.602 mmol) in 1,4-Dioxane (5 mL) and Water (2 mL) was degassed by purging argon for 15 min. then added PdCl₂(dppf)-CH₂Cl₂ adduct (32.7 mg, 0.040 mmol) to the above reaction mixture and heated at 90° C. for 16 h. (TLC system: 5% Methanol in DCM. R_f value: 0.4). The reaction mixture was cooled to RT, diluted with water (20 mL) and extracted with ethyl acetate (2×50 mL). The combined organic layer was washed with brine solution (30 mL), dried over anhydrous sodium sulphate, filtered and filtrate was evaporated to give crude residue. The Crude material was purified by combiflash chromatography using silica gel column, 3% methanol in DCM) to give (4S)—N5-(4-(2-methyloxazol-5-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (115 mg, 0.227 mmol, 28.3% yield) as an off-white solid. LC-MS (m/z): 502.14 [M+H]$^+$, Rt=2.25 min.

$^1$H NMR (400 MHz, CDCl$_3$): δ ppm 13.34 (s, 1H), 8.34-8.48 (m, 1H), 8.26 (d, J=5.26 Hz, 1H), 7.86-8.10 (m, 2H), 7.69 (d, J=7.89 Hz, 1H), 7.48 (s, 1H), 7.15-7.25 (m, 1H), 5.66 (dd, J=5.92, 3.07 Hz, 1H), 5.07 (dq, J=16.96, 7.35 Hz, 1H), 3.09-3.33 (m, 3H), 2.94-3.09 (m, 1H), 2.57 (s, 3H), 2.25-2.48 (m, 1H), 2.03-2.22 (m, 1H), 1.52-1.65 (m, 3H).

Example 129

Synthesis of (4S)—N5-(5-fluoropyridin-2-yl)-N7-((R)-1,1,1-trifluoropropan-2-yl)-3,4-dihydro-1,4-methanopyrido[2,3-b][1,4]diazepine-5,7(2H)-dicarboxamide

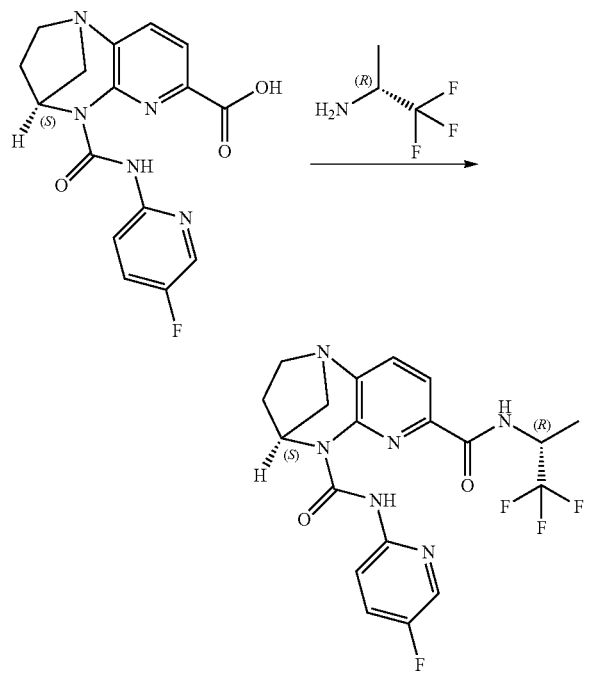

To a stirred solution of (4S)-5-((5-fluoropyridin-2-yl)carbamoyl)-2,3,4,5-tetrahydro-1,4-ethanopyrido[2,3-b][1,4]diazepine-7-carboxylic acid (8.6 g, 25.05 mmol) in DMF (150 mL), under nitrogen at RT was added DIPEA (13.13 mL, 75 mmol), HATU (19.05 g, 50.1 mmol) and stirred for 10 min. Then added (R)-1,1,1-trifluoropropan-2-amine (3.40 g, 30.1 mmol) and the reaction mixture was stirred at RT for 3 h. (TLC eluent: 10% Methanol in DCM, R$_f$: 0.3; UV active). Reaction mixture was quenched with cold water (300 mL) and the resultant solid was filtered, dried and triturated with diethyl ether (2×100 mL) to afford (4S)—N5-(5-fluoropyridin-2-yl)-N7-((R)-1,1,1,1-trifluoropropan-2-yl)-3,4-dihydro-1,4-methanopyrido[2,3-b][1,4]diazepine-5,7(2H)-dicarboxamide (7.8 g, 17.71 mmol, 70.7% yield) as an off white solid. LC-MS (m/z): 439.10 [M+H]$^+$, Rt=2.38 min.

$^1$H NMR (400 MHz, CDCl$_3$): δ ppm 13.23 (s, 1H), 8.19 (dd, J=9.10, 4.06 Hz, 1H), 8.10 (d, J=2.85 Hz, 1H), 7.95 (d, J=7.89 Hz, 1H), 7.84 (br d, J=9.65 Hz, 1H), 7.68 (d, J=7.89 Hz, 1H), 7.36-7.59 (m, 1H), 5.64 (dd, J=5.92, 3.07 Hz, 1H), 4.95-5.16 (m, 1H), 3.07-3.32 (m, 3H), 2.95-3.07 (m, 1H), 2.20-2.40 (m, 1H), 1.96-2.19 (m, 1H), 1.43-1.64 m, 3H).

Example 130

Synthesis of (4S)—N5-(pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide

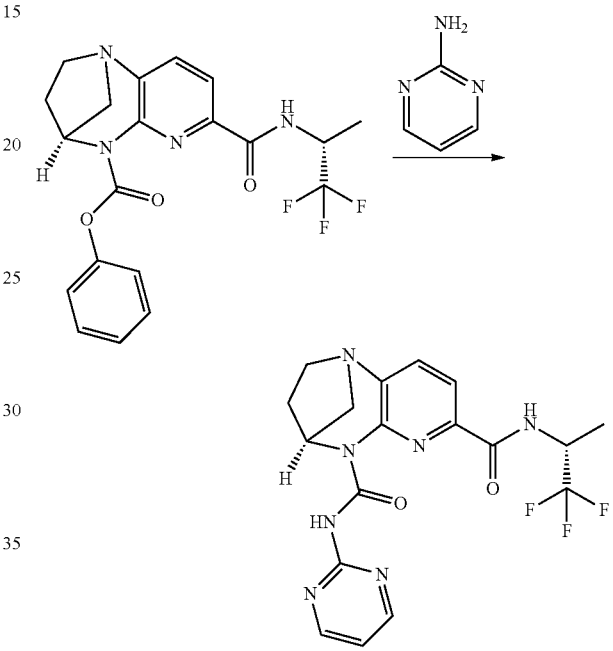

To a stirred solution of pyrimidin-2-amine (3.68 g, 38.7 mmol) in THF (300 mL) under nitrogen at −78° C. was added LiHMDS (44.0 mL, 44.0 mmol) drop wisely and stirred for 30 min, then added (4S)-phenyl 7-(((R)-1,1,1-trifluoropropan-2-yl)carbamoyl)-3,4-dihydro-1,4-methanopyrido[2,3-b][1,4]diazepine-5(2H)-carboxylate (7.4 g, 17.60 mmol) and the resulting reaction mixture was stirred at −78° C. for 1 h and at RT for 6 h. (TLC eluent: 80% EtOAc in pet ether, Rf: 0.1; UV active). The reaction mixture was quenched with aqueous NH$_4$Cl (100 mL) and extracted with EtOAc (2×300 mL). The combined organic layer was dried over anhydrous Na$_2$SO$_4$, filtered and concentrated under reduced pressure to obtain crude product. The crude product was purified by combiflash chromatography (using silica gel column, 60% EtOAc in pet ether) to afford the (4S)—N5-(pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide (4.2 g, 9.94 mmol, 56.5% yield) as an off-white solid. LC-MS (m/z): 422.18 [M+H]$^+$, Rt=1.75 min.

$^1$H NMR (400 MHz, CDCl$_3$): δ ppm 13.61 (s, 1H), 8.63 (d, J=4.82 Hz, 2H), 7.97 (m, J=7.89 Hz, 1H), 7.89 (br d, J=9.43 Hz, 1H), 7.70 (m, J=7.89 Hz, 1H), 7.03 (t, J=4.93 Hz, 1H), 5.72 (dd, J=5.92, 3.07 Hz, 1H), 4.94-5.14 (m, 1H), 3.08-3.29 (m, 3H), 2.94-3.07 (m, 1H), 2.34 (ddt, J=14.33, 8.85, 5.51, 5.51 Hz, 1H), 2.00-2.17 (m, 1H), 1.48-1.65 (m, 3H).

Example 131

Synthesis of (4S)—N5-(4-((2-hydroxyethyl)carbamoyl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

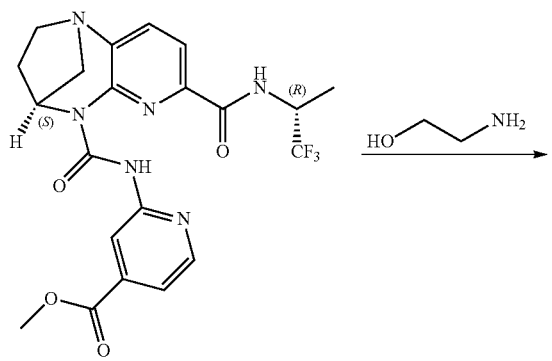

Ethanol amine (1 mL, 0.418 mmol) was added to methyl 2-((4S)-7-(((R)-1,1,1-trifluoropropan-2-yl)carbamoyl)-2,3,4,5-tetrahydro-1,4-methanopyrido[2,3-b][1,4]diazepine-5-carboxamido)isonicotinate (200 mg, 0.418 mmol) in sealed tube and stirred at 70° C. for 1 h. (TLC system: neat ethyl acetate, $R_f$: 0.2). The reaction mixture was cooled to RT and was quenched with ice cold water (10 mL) filtered the obtained solid, washed with water (10 mL×2) and n-pentane (10 mL×2) to afford the desired product (4S)—N5-(4-((2-hydroxyethyl)carbamoyl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (151 mg, 0.295 mmol, 70.5% yield) as an off white solid. LCMS (m/z): 508.20 [M+H]$^+$, Rt=1.74 min.

$^1$H NMR (400 MHz, CDCl$_3$): δ ppm 13.43 (s, 1H), 8.41 (s, 1H), 8.36 (d, J=5.26 Hz, 1H), 7.97 (d, J=7.89 Hz, 1H), 7.89 (d, J=9.65 Hz, 1H), 7.70 (d, J=7.89 Hz, 1H), 7.48 (dd, J=5.26, 1.53 Hz, 1H), 6.99 (d, J=6.58 Hz, 1H), 5.60 (dd, J=5.92, 3.07 Hz, 1H), 5.06 (dq, J=16.77, 7.34 Hz, 1H), 3.87 (t, J=5.04 Hz, 2H), 3.66 (q, J=5.48 Hz, 2H), 3.28-3.21 (m, 2H), 3.15-3.10 (m, 1H), 3.06-3.01 (m, 1H), 2.57 (s, 1H), 2.33 (ddt, J=14.39, 9.07, 5.37, 5.37 Hz, 1H), 2.07 (dt, J=14.41, 6.93 Hz, 1H), 1.59 (d, J=7.02 Hz, 3H).

Example 132

Synthesis of (4S)—N5-(4-(2-hydroxyethoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

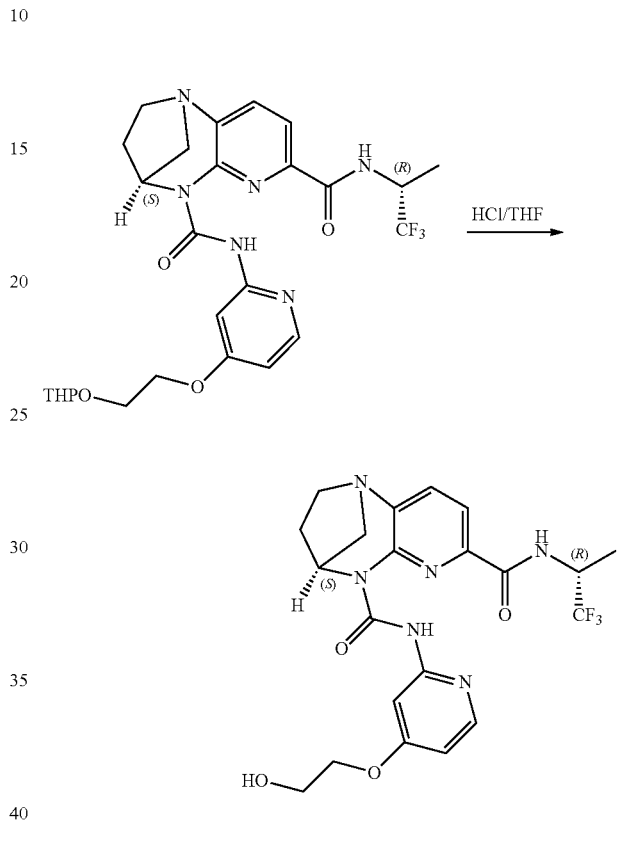

To a stirred solution of (4S)—N5-(4-(2-((tetrahydro-2H-pyran-2-yl)oxy)ethoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (200 mg, 0.354 mmol) in Tetrahydrofuran (THF) (20 mL) was added HCl (1 mL, 32.9 mmol) at 0° C. then stirred at 28° C. for 1 h. (TLC system: neat ethyl acetate, $R_f$: 0.2). The reaction mixture was concentrated in vacuo and the residue was neutralized with saturated NaHCO$_3$ solution and filtered the obtained solid, washed with water (20 mL×3) and n-pentane (10 mL×2) to afford the (4S)—N5-(4-(2-hydroxyethoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (130 mg, 0.271 mmol, 76% yield) as an off white solid. LCMS (m/z): 481.14 [M+H]$^+$, Rt=1.58 min.

$^1$H NMR (400 MHz, CDCl$_3$): δ ppm 13.30 (s, 1H), 8.09-8.05 (m, 2H), 7.96 (d, J=7.89 Hz, 1H), 7.78 (d, J=2.41 Hz, 1H), 7.68 (d, J=7.89 Hz, 1H), 6.60 (dd, J=5.92, 2.41 Hz, 1H), 5.62 (dd, J=5.70, 3.07 Hz, 1H), 5.06 (dd, J=16.77, 7.34 Hz, 1H), 4.23-4.19 (m, 2H), 4.03-3.98 (m, 2H), 3.27-3.21 (m, 2H), 3.15-3.10 (m, 1H), 3.05-3.00 (m, 1H), 2.38-2.28 (m, 1H), 2.11-2.01 (m, 1H), 1.98 (t, J=6.25 Hz, 1H), 1.59 (d, J=7.23 Hz, 3H).

Example 133

Synthesis of (4S)—N5-(3,4-dihydro-2H-pyrano[2,3-c]pyridin-6-yl)-N7-(2,2,2-trifluoroethyl)-3,4-dihydro-1,4-methanopyrido[2,3-b][1,4]diazepine-5,7(2H)-dicarboxamide

Example 134

Synthesis of (4S)—N5-(4-(oxazol-5-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

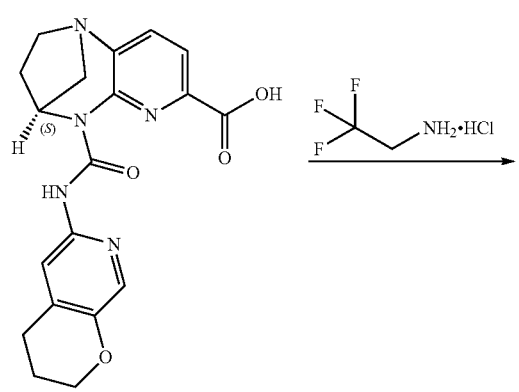

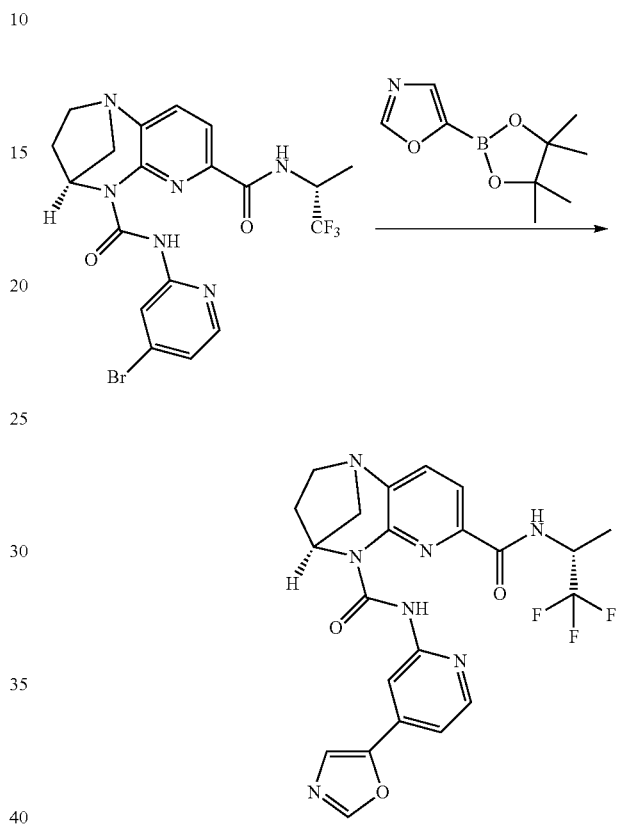

To a solution of (4S)-5-((3,4-dihydro-2H-pyrano[2,3-c]pyridin-6-yl)carbamoyl)-2,3,4,5-tetrahydro-1,4-methanopyrido[2,3-b][1,4]diazepine-7-carboxylic acid (200 mg, 0.524 mmol) in DMF (5 mL) at 0° C. was added HATU (299 mg, 0.787 mmol), DIPEA (0.275 mL, 1.573 mmol) and stirred for 10 min, then added 2,2,2-trifluoroethanamine hydrochloride (142 mg, 1.049 mmol) at 0° C., the resulting solution was stirred at RT for 16 h. (TLC system: 5% Methanol in DCM. $R_f$: 0.5). The reaction mixture was quenched with water (20 mL) to give pale yellow precipitation. The precipitated solid was filtered, dried and triturated with diethyl ether (5 mL) to get (4S)—N5-(3,4-dihydro-2H-pyrano[2,3-c]pyridin-6-yl)-N7-(2,2,2-trifluoroethyl)-3,4-dihydro-1,4-methanopyrido[2,3-b][1,4]diazepine-5,7(2H)-dicarboxamide (156 mg, 0.329 mmol, 62.8% yield) as an off-white solid. LCMS (m/z): 463.07 [M+H]+, Rt=2.17 min.

$^1$H NMR (400 MHz, CDCl$_3$): δ ppm 13.36 (s, 1H), 8.53 (br t, J=6.25 Hz, 1H), 7.88 (d, J=7.89 Hz, 1H), 7.78 (d, J=3.29 Hz, 2H), 7.65 (d, J=7.89 Hz, 1H), 5.58 (dd, J=5.81, 3.18 Hz, 1H), 4.08-4.32 (m, 4H), 3.17-3.31 (m, 2H), 3.09-3.16 (m, 1H), 3.04-3.01 (d, J=3.07 Hz, 1H), 2.78-2.89 (m, 2H), 2.25-2.39 (m, 1H), 1.96-2.13 (m, 3H)

A mixture of (4S)—N5-(4-bromopyridin-2-yl)-N7-((R)-1,1,1-trifluoropropan-2-yl)-3,4-dihydro-1,4-methanopyrido[2,3-b][1,4]diazepine-5,7(2H)-dicarboxamide (450 mg, 0.901 mmol), 5-(4,4,5,5-tetramethyl-1,3,2-dioxaborolan-2-yl)oxazole (267 mg, 1.352 mmol) in 1,4-Dioxane (20 mL), Water (2.5 mL) was degassed for 20 min. then added potassium acetate (265 mg, 2.70 mmol) followed by PdCl$_2$(dppf) (100 mg, 0.137 mmol) and the resulting reaction mixture was stirred at 100° C. for 16 h. (TLC system: 5% Methanol in DCM. $R^1$ 0.4). Reaction mixture was cooled RT and quenched with water (20 mL) and the aqueous layer was extracted with EtOAc (2×30 mL). Combined organic layer was dried over anhydrous sodium sulphate, filtered and concentrated under reduced pressure to get crude compound. The crude product was purified by column chromatography (Silica gel column, eluted with 2.5% of MeOH in CH$_2$Cl$_2$) to afford (4S)—N5-(4-(oxazol-5-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (81 mg, 0.166 mmol, 18.37% yield) as an off-white solid. LCMS (m/z): 488.1 [M+H]+, Rt=2.19 min.

$^1$H NMR (400 MHz, CDCl$_3$): δ ppm 13.37 (s, 1H), 8.42-8.49 (m, 1H), 8.30 (d, J=5.48 Hz, 1H), 7.87-8.10 (m, 3H), 7.69 (d, J=7.89 Hz, 1H), 7.63 (s, 1H), 7.28 (d, J=5.12 Hz, 1H), 5.66 (dd, J=5.92, 3.07 Hz, 1H), 5.07 (dq, J=16.83, 7.47 Hz, 1H), 3.09-3.33 (m, 3H), 2.96-3.09 (m, 1H), 2.26-2.41 (m, 1H), 2.09 (dt, J=14.25, 6.91 Hz, 1H), 1.61 (d, J=7.23 Hz, 3H).

Example 135

Synthesis of (4S)—N5-(4-methoxypyridin-2-yl)-N7-((R)-1,1,1-trifluoropropan-2-yl)-3,4-dihydro-1,4-methanopyrido[2,3-b][1,4]diazepine-5,7(2H)-dicarboxamide

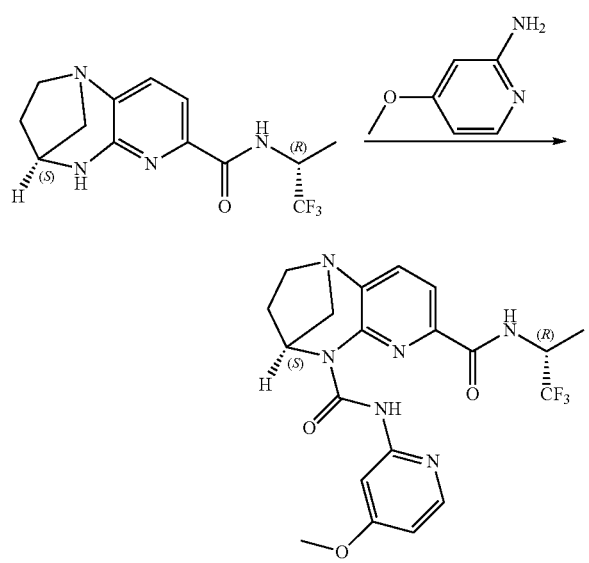

To a stirred solution of (4S)—N—((R)-1,1,1-trifluoropropan-2-yl)-2,3,4,5-tetrahydro-1,4-methanopyrido[2,3-b][1,4]diazepine-7-carboxamide (300 mg, 0.999 mmol) in THF (10 mL) were added triethylamine (0.696 mL, 5.00 mmol) and triphosgene (296 mg, 0.999 mmol) at room temperature and was stirred for 1 h. then 4-methoxypyridin-2-amine (248 mg, 1.998 mmol) was added and stirred at 70° C. for 16 h. (TLC eluent: EtoAc R$_f$: 0.4, UV active). The reaction mixture was allowed to cool to room temperature, diluted with H$_2$O (10 mL), extracted with EtoAc (2×10 mL). The combined organic layer was washed with water (10 mL), brine solution (10 mL) and dried over anhydrous Na$_2$SO$_4$, filtered and concentrated to obtain crude compound. The crude compound was purified by flash column chromatography (Neutral alumina, Eluent: 50% EtoAc in pet ether) to afford the desired product (4S)—N5-(4-methoxypyridin-2-yl)-N7-((R)-1,1,1-trifluoropropan-2-yl)-3,4-dihydro-1,4-methanopyrido[2,3-b][1,4]diazepine-5,7(2H)-dicarboxamide (120 mg, 0.265 mmol, 26.6% yield) as an off-white solid. LCMS (m/z): 451.09 [M+H]$^+$, R$_t$=1.94 min.

$^1$H NMR (400 MHz, CDCl$_3$): δ ppm 13.27 (s, 1H), 8.12-8.01 (m, 2H), 7.95 (d, J=7.89 Hz, 1H), 7.76 (d, J=2.41 Hz, 1H), 7.67 (d, J=7.89 Hz, 1H), 7.26 (s, 1H), 6.58 (dd, J=5.81, 2.30 Hz, 1H), 5.63 (dd, J=5.92, 3.07 Hz, 1H), 5.14-4.97 (m, 1H), 3.90 (s, 2H), 3.28-3.17 (m, 1H), 3.28-3.17 (m, 1H), 3.15-2.98 (m, 2H), 2.39-2.27 (m, 1H), 2.11-2.00 (m, 1H), 1.59 (d, J=7.02 Hz, 3H).

Example 136

Synthesis of (4S)—N5-(4-methoxypyridin-2-yl)-N7-(2,2,2-trifluoroethyl)-3,4-dihydro-1,4-methanopyrido[2,3-b][1,4]diazepine-5,7(2H)-dicarboxamide

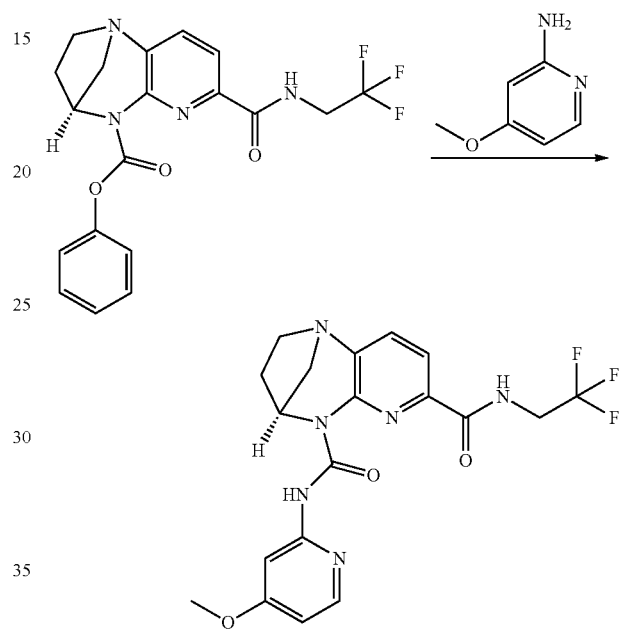

To a stirred solution of 4-methoxypyridin-2-amine (183 mg, 1.477 mmol) in THF (10 mL) at −78° C. under nitrogen was added LiHMDS (1.477 mL, 2.95 mmol, 1 M solution in THF) dropwisely and stirred for 30 min. then added a solution of (4S)-phenyl 7-((2,2,2-trifluoroethyl)carbamoyl)-3,4-dihydro-1,4-methanopyrido[2,3-b][1,4]diazepine-5 (2H)-carboxylate (600 mg, 1.477 mmol) in THF (5 mL). The resulting reaction mixture was stirred at −78° C. for 1 h and at RT for 6 h. (TLC eluent: 5% MeOH in DCM: R$_f$—0.3; UV active). The reaction mixture was quenched with aqueous NH$_4$Cl (10 mL) and aqueous layer was extracted with EtOAc (2×10 mL). Combined organic layer was dried over anhydrous Na$_2$SO$_4$, filtered and concentrated under reduced pressure to obtain crude product. Crude compound was purified by combiflash chromatography (Silica gas column, eluent 2% MeOH in DCM) to obtain desired product (4S)—N5-(4-methoxypyridin-2-yl)-N7-(2,2,2-trifluoroethyl)-3,4-dihydro-1,4-methanopyrido[2,3-b][1,4]diazepine-5,7(2H)-dicarboxamide (160 mg, 0.362 mmol, 24.51% yield) as an off-white solid LC-MS (n/z): 437.15 [M+H]$^+$; Rt=1.76 min.

$^1$H NMR (400 MHz, CDCl$_3$) δ ppm 13.66 (s, 1H), 8.67 (br t, J=6.14 Hz, 1H), 8.02 (d, J=5.70 Hz, 1H), 7.91 (d, J=7.67 Hz, 1H), 7.62-7.71 (m, 2H), 6.56 (dd, J=5.92, 2.41 Hz, 1H), 5.59 (dd, J=6.03, 3.18 Hz, 1H), 4.08-4.30 (m, 2H), 3.90 (s, 3H), 3.18-3.31 (m, 2H), 3.13 (br d, J=12.06 Hz, 1H), 3.03 (dd, J=12.17, 3.18 Hz, 1H), 2.21-2.43 (m, 1H), 1.96-2.18 (m, 1H).

Example 137

Synthesis of (4S)—N5-(4-carbamoylpyridin-2-yl)-N7-((R)-1,1,1-trifluoropropan-2-yl)-3,4-dihydro-1,4-methanopyrido[2,3-b][1,4]diazepine-5,7(2H)-dicarboxamide

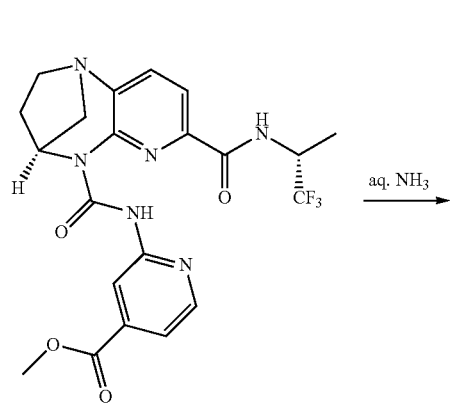

Example 138

Synthesis of (4S)—N5-(3,4-dihydro-2H-pyrano[2,3-c]pyridin-6-yl)-N7-((R)-1,1,1-trifluoropropan-2-yl)-3,4-dihydro-1,4-methanopyrido[2,3-b][1,4]diazepine-5,7(2H)-dicarboxamide

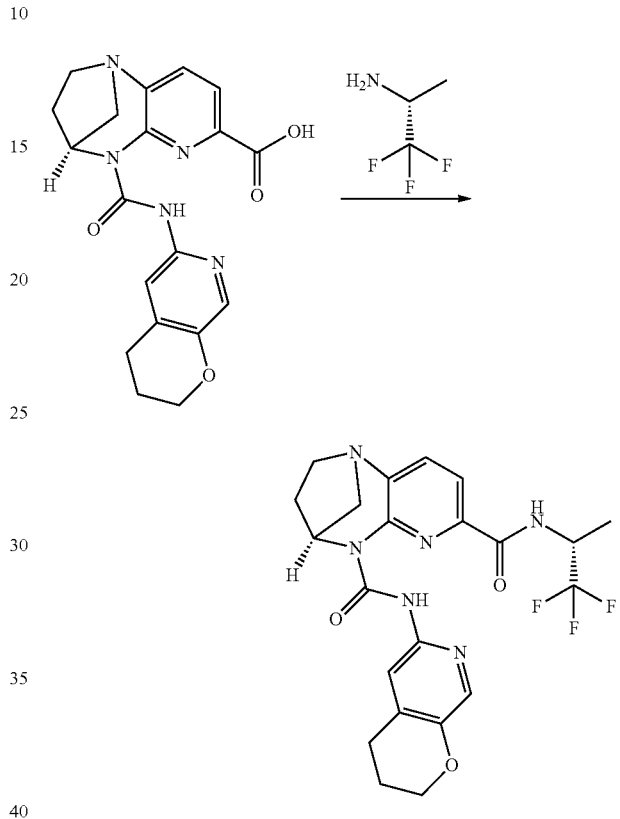

aq. ammonia (2 mL, 0.627 mmol) was added to methyl 2-((4S)-7-(((R)-1,1,1-trifluoropropan-2-yl)carbamoyl)-2,3,4,5-tetrahydro-1,4-methanopyrido[2,3-b][1,4]diazepine-5-carboxamido) isonicotinate (300 mg, 0.627 mmol) in a sealed tube at RT then stirred at 70° C. for 16 h (Neat reaction) (TLC system: neat ethyl acetate; $R_f$: 0.1). The reaction mixture was cooled to RT and was quenched with ice cold water (10 mL) and extracted with ethyl acetate (2×15 mL). The combined organic layer was dried over anhydrous sodium sulphate, filtered and filtrate was evaporated to get crude compound. The crude material was purified by flash column chromatography (100-200 silicagel eluent: 90% ethyl acetate in n-hexane) to afford the desired product (4S)—N5-(4-carbamoylpyridin-2-yl)-N7-((R)-1,1,1-trifluoropropan-2-yl)-3,4-dihydro-1,4-methanopyrido[2,3-b][1,4]diazepine-5,7(2H)-dicarboxamide (103 mg, 0.222 mmol, 35.4% yield) as an off white solid. LCMS (m/z): 464.08 [M+H]+, Rt=1.80 min.

$^1$H NMR (400 MHz, CDCl$_3$): δ ppm 13.44 (s, 1H), 8.47 (d, J=0.88 Hz, 1H), 8.39 (d, J=5.04 Hz, 1H), 7.98 (d, J=7.89 Hz, 1H), 7.89 (d, J=9.43 Hz, 1H), 7.70 (d, J=7.89 Hz, 1H), 7.51 (dd, J=5.15, 1.64 Hz, 1H), 6.28 (s, 1H), 5.64 (dd, J=6.03, 3.18 Hz, 2H), 5.12-5.01 (m, 1H), 3.29-3.22 (m, 2H), 3.16-3.11 (m, 1H), 3.07-3.01 (m, 1H), 2.40-2.30 (m, 1H), 2.07 (dt, J=14.14, 6.96 Hz, 1H), 1.60 (d, J=7.02 Hz, 3H).

To a solution of (4S)-5-((3,4-dihydro-2H-pyrano[2,3-c]pyridin-6-yl)carbamoyl)-2,3,4,5-tetrahydro-1,4-methanopyrido[2,3-b][1,4]diazepine-7-carboxylic acid (200 mg, 0.524 mmol) in DMF (5 mL) at 0° C. was added HATU (239 mg, 0.629 mmol), DIPEA (0.275 mL, 1.573 mmol) and stirred for 10 min. then added (R)-1,1,1-trifluoropropan-2-amine (89 mg, 0.787 mmol) and the resulting solution was stirred at RT for 16 h. (TLC system: 5% Methanol in DCM. $R_f$: 0.4). The reaction mixture was quenched with water (20 mL) to give pale yellow precipitation. The precipitated solid was filtered, dried and triturated with diethyl ether (5 mL) to get (4S)—N5-(3,4-dihydro-2H-pyrano[2,3-c]pyridin-6-yl)-N7-((R)-1,1,1-trifluoropropan-2-yl)-3,4-dihydro-1,4-methanopyrido[2,3-b][1,4]diazepine-5,7(2H)-dicarboxamide (52 mg, 0.107 mmol, 20.42% yield) as an off-white solid. LCMS (m/z): 477.3 [M+H]+, Rt=2.36 min.

$^1$H NMR (400 MHz, CDCl$_3$): δ ppm 13.01 (s, 1H), 7.97 (br d, J=9.21 Hz, 1H), 7.93 (s, 1H), 7.85 (s, 1H), 7.81 (s, 1H), 7.65 (d, J=7.89 Hz, 1H), 5.63 (dd, J=5.92, 3.29 Hz, 1H), 5.04 (dq, J=16.94, 7.44 Hz, 1H), 4.16-4.26 (m, 2H), 3.16-3.30 (m, 2H), 3.08-3.15 (m, 1H), 2.98-3.05 (m, 1H), 2.84 (t, J=6.58 Hz, 2H), 2.25-2.39 (m, 1H), 1.98-2.13 (m, 3H), 1.57 (d, J=7.02 Hz, 3H)

Example 139

Synthesis of (4S)—N5-(6-methyl-1H-pyrazolo[3,4-b]pyridin-3-yl)-N7-((R)-1,1,1-trifluoro-3-hydroxypropan-2-yl)-3,4-dihydro-1,4-methanopyrido[2,3-b][1,4]diazepine-5,7(2H)-dicarboxamide

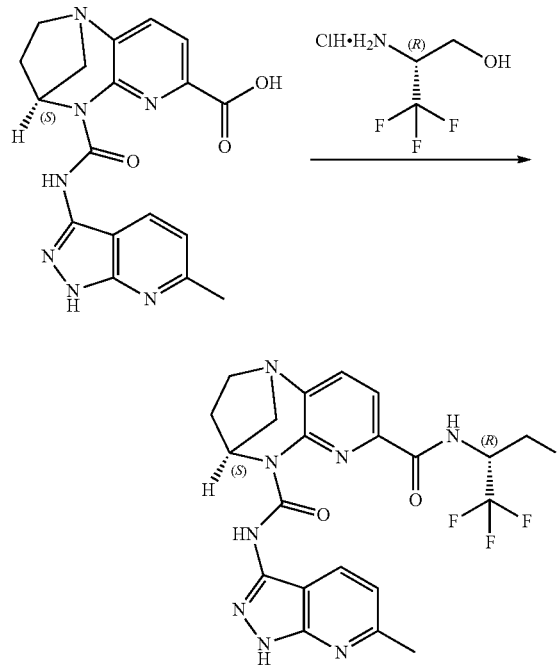

To a stirred solution of (4S)-5-((6-methyl-1H-pyrazolo[3,4-b]pyridin-3-yl)carbamoyl)-2,3,4,5-tetrahydro-1,4-methanopyrido[2,3-b][1,4]diazepine-7-carboxylic acid (650 mg, 1.713 mmol) in DMF (20 mL) at 0° C. was added HATU (1954 mg, 5.14 mmol), DIPEA (0.898 mL, 5.14 mmol) and stirred for 15 min. then added (R)-2-amino-3,3,3-trifluoropropan-1-ol (332 mg, 2.57 mmol) reaction mixture was stirred for 16 h. (TLC system: 10% Methanol in DCM. $R_f$: 0.4). Reaction mixture was quenched with water was (50 mL) and extracted in to EtOAc (2×35 mL). Combined organic layer was dried over $Na_2SO_4$, filtered and concentrated to get crude compound. The crude product was purified by column chromatography (Silica gel, eluted with 2.5% of MeOH in $CH_2Cl_2$) to afford (4S)—N5-(6-methyl-1H-pyrazolo[3,4-b]pyridin-3-yl)-N7-((R)-1,1,1-trifluoro-3-hydroxypropan-2-yl)-3,4-dihydro-1,4-methanopyrido[2,3-b][1,4]diazepine-5,7(2H)-dicarboxamide (122 mg, 0.248 mmol, 14.50% yield) as a white solid. LCMS (m/z): 491 [M+H]$^+$, Rt=1.72 min.

HNMR $^1$H NMR (400 MHz, DMSO-d$_6$): δ ppm 13.00 (s, 1H), 12.62 (s, 1H), 8.54 (br d, J=8.99 Hz, 1H), 8.41 (d, J=8.55 Hz, 1H), 7.74 (d, J=7.89 Hz, 1H), 7.66 (d, J=7.89 Hz, 1H), 7.03 (d, J=8.55 Hz, 1H), 5.49 (dd, J=5.92, 3.07 Hz, 1H), 5.22 (t, J=6.25 Hz, 1H), 4.69-4.85 (m, 1H), 3.83 (t, J=6.25 Hz, 2H), 3.06-3.27 (m, 3H), 2.84-3.05 (m, 1H), 2.57 (s, 3H), 2.20-2.47 (m, 1H), 1.97 (dt, J=13.76, 7.04 Hz, 1H).

Example 140

Synthesis of (4S)—N5-(5H-pyrrolo[3,2-d]pyrimidin-2-yl)-N7-(2,2,2-trifluoroethyl)-3,4-dihydro-1,4-methanopyrido[2,3-b][1,4]diazepine-5,7(2H)-dicarboxamide

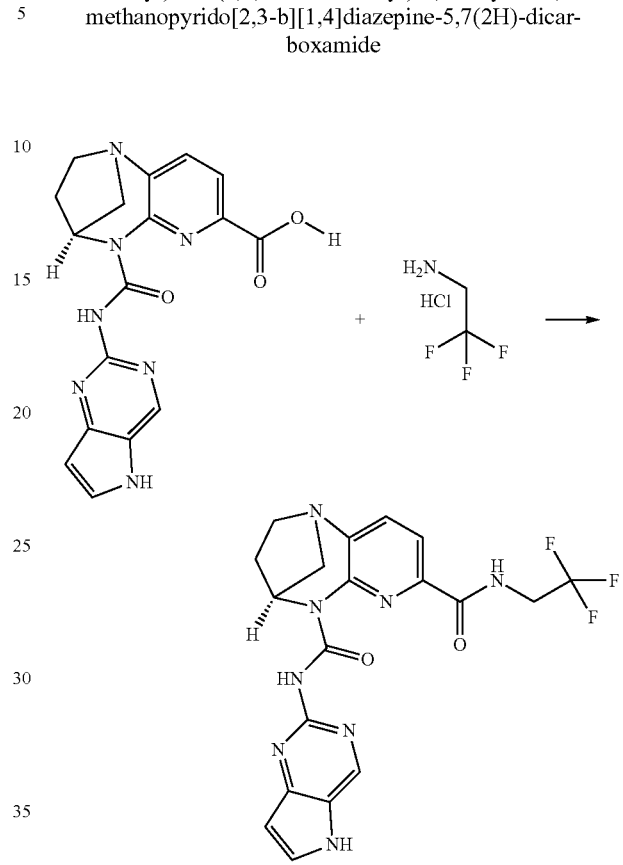

To a stirred solution of (4S)-5-((5H-pyrrolo[3,2-d]pyrimidin-2-yl)carbamoyl)-2,3,4,5-tetrahydro-1,4-methanopyrido[2,3-b][1,4]diazepine-7-carboxylicacid (400 mg, 1.095 mmol), in DMF (10 mL) under nitrogen at 0° C. was added 2,2,2-trifluoroethanamine hydrochloride (223 mg, 1.642 mmol), HATU (624 mg, 1.642 mmol), DIPEA (0.956 mL, 5.47 mmol) and stirred at RT for 16 h. (TLC eluent: 100% EtOAc, $R_f$: 0.2, UV active). The reaction mixture was diluted with water (20 mL) and extracted into DCM (30 mL). Combined organic extracts were dried over anhydrous $Na_2SO_4$, filtered and filtrate was evaporated to afford crude product. The crude product was purified by reverse phase chromatography (Using Grace chromatography C-18 column, Mobile phase A: 0.1% Formic Acid in water; B: Acetonitrile; eluted at 20% B in A). Subsequently the fractions were concentrated and the residue was basified with saturated NaHCO$_3$ then extracted with DCM (2×10 mL). Combined extracts were was dried over anhydrous $Na_2SO_4$, filtered and concentrated to afford pure (4S)—N5-(5H-pyrrolo[3,2-d]pyrimidin-2-yl)-N7-(2,2,2-trifluoroethyl)-3,4-dihydro-1,4-methanopyrido[2,3-b][1,4]diazepine-5,7(2H)-dicarboxamide (160 mg, 0.357 mmol, 32.6% yield) as a white solid. LCMS (m/z): 447.16 [M+H]$^+$, $R_t$=1.46 min.

$^1$H NMR (400 MHz, DMSO-d$_6$): δ ppm 13.52-13.23 (m, 1H), 11.72 (br s, 1H), 9.05-8.73 (m, 2H), 7.88 (t, J=2.74 Hz, 1H), 7.79-7.67 (m, 2H), 6.49 (br s, 1H), 5.42 (dd, J=5.92, 2.85 Hz, 1H), 4.48-4.25 (m, 2H), 3.25-3.04 (m, 3H), 3.02-2.94 (m, 1H), 2.29-2.17 (m, 1H), 2.00-1.87 (m, 1H)

Example 141

Synthesis of (4S)—N5-(6-((R)-2,3-dihydroxypropoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

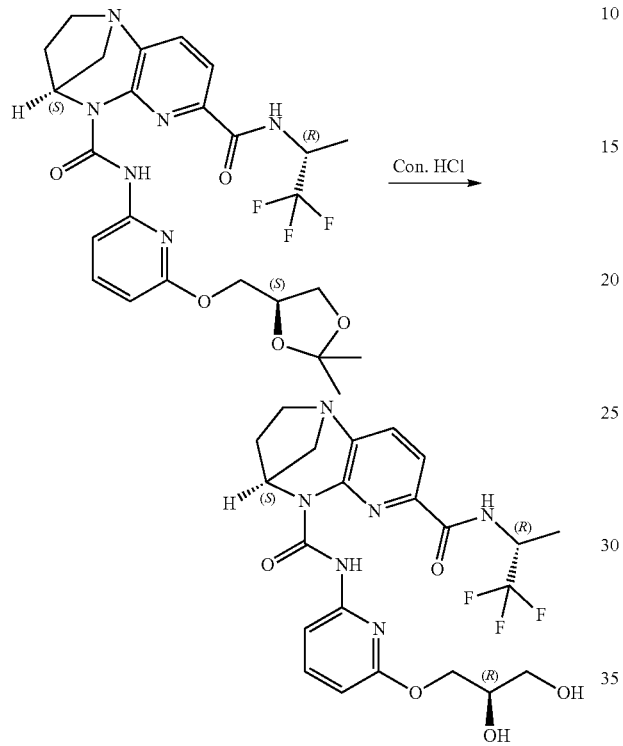

To a suspension of (4S)—N5-(6-(((S)-2,2-dimethyl-1,3-dioxolan-4-yl)methoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (0.23 g, 0.418 mmol) in Methanol (8 mL) at 0° C., HCl (1.2 mL, 39.5 mmol) was added and stirred for 2 h at RT. (TLC system: 10% Methanol in DCM. Rf value: 0.4.). The reaction mixture was quenched with saturated NaHCO₃ solution (30 mL) and extracted with ethyl acetate (2×30 ml). The combined organic layer was washed with brine solution, dried over anhydrous sodium sulphate and concentrated under reduced pressure to afford crude compound. The crude product was purified by flash column chromatography (100-200 silicagel eluted with 8% of MeOH in CH₂Cl₂), compound further purified by prep HPLC (Column: XBridge C 18 (75×4.6 mm, 3.54), Mobile Phase: A: 5 mM Ammonium Bicarbonate B: CAN Gradient: Time/% B: 0/5, 0.8/5, 5/50, 9/98, 12/98, 12.1/5, 15/5 Column Temp: Ambient, Flow Rate: 0.8 ml/min) to afford the desired product (4S)—N5-(6-((R)-2,3-dihydroxypropoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (93 mg, 0.181 mmol, 43.2% yield) as an off-white solid. LCMS (m/z): 511.2 [M+H]⁺, Rt=1.70 min.

¹H NMR (400 MHz, DMSO-d₆): δ ppm 12.56 (s, 1H), 8.70 (d, J=8.99 Hz, 1H), 7.75-7.66 (m, 2H), 7.59 (d, J=7.89 Hz, 2H), 6.54-6.37 (m, 1H), 5.46 (dd, J=6.03, 2.96 Hz, 1H), 4.91-4.73 (m, 2H), 4.54 (t, J=5.70 Hz, 1H), 4.25-4.04 (m, 2H), 3.76 (dq, J=10.55, 5.40 Hz, 1H), 3.43 (tq, J=10.82, 5.57 Hz, 2H), 3.22-2.99 (m, 3H), 3.05-2.83 (m, 1H), 2.33-2.09 (m, 1H), 1.90 (dt, J=14.25, 7.13 Hz, 1H), 1.41 (d, J=7.02 Hz, 3H).

Example 142

Synthesis of (4S)—N7-((S)-but-3-yn-2-yl)-N5-(pyridin-2-yl)-3,4-dihydro-1,4-methanopyrido[2,3-b][1,4]diazepine-5,7(2H)-dicarboxamide

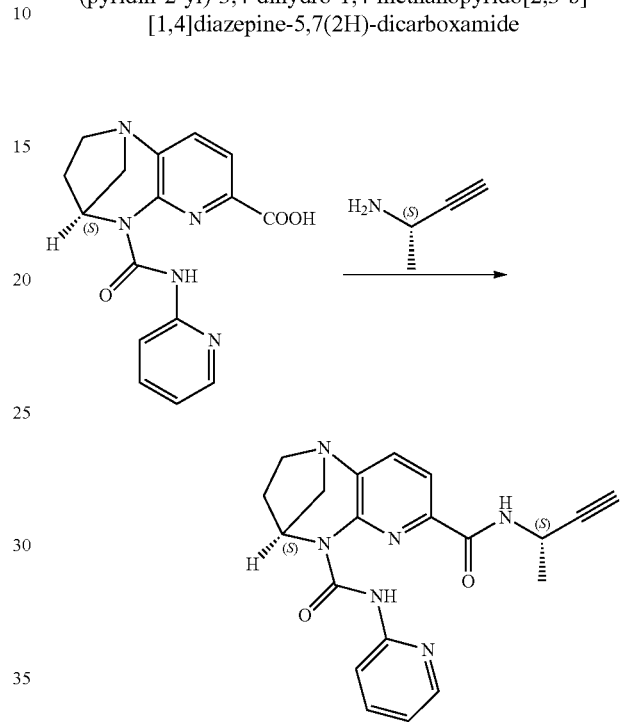

To a stirred solution of (4S)-5-(pyridin-2-ylcarbamoyl)-2,3,4,5-tetrahydro-1,4-methanopyrido[2,3-b][1,4]diazepine-7-carboxylic acid (500 mg, 1.537 mmol), DIPEA (1.342 mL, 7.68 mmol) and HATU (46.8 mg, 0.123 mmol) in DMF (5 mL) was added (S)-but-3-yn-2-amine (106 mg, 1.537 mmol) at room temperature and the reaction mixture was stirred for 16 h. at room temperature (TLC 5% MeOH\DCM R_f: 0.5; UV active). Reaction mixture was diluted with cold water (30 ml) and extracted with EtOAc (2×50 ml). The combined organic layer was washed with water (30 mL), brine (20 mL), dried over anhydrous Na₂SO₄, filtered and concentrated under reduced pressure to obtain crude product. The crude material was purified by combi-flash chromatography (12 g (Reveleris) normal phase, Eluent: 3% methanol in DCM) to afford the desired product (4S)—N7-((S)-but-3-yn-2-yl)-N5-(pyridin-2-yl)-3,4-dihydro-1,4-methanopyrido[2,3-b][1,4]diazepine-5,7(2H)-dicarboxamide (102 mg, 0.270 mmol, 17.59% yield) as an off white solid. LCMS (m/z): 377.26 [M+H]⁺. R_t=1.93 min.

¹H NMR (400 MHz, DMSO-d₆): δ ppm 13.31 (s, 1H), 8.23-8.48 (m, 2H), 8.05 (d, J=8.33 Hz, 1H), 7.86 (td, J=7.89, 1.97 Hz, 1H), 7.66-7.79 (m, 2H), 7.14 (ddd, J=7.23, 4.93, 0.99 Hz, 1H), 5.45 (dd, J=5.92, 3.07 Hz, 1H), 4.93-5.07 (m, 1H), 3.04-3.25 (m, 4H), 2.88-3.02 (m, 1H), 2.23 (dddd, J=13.78, 9.89, 5.92, 3.73 Hz, 1H), 1.94 (dt, J=13.65, 6.88 Hz, 1H), 1.52 (d, J=6.80 Hz, 3H)

Example 143

Synthesis of (4S)—N5-(5-carbamoylpyridin-2-yl)-N7-(2,2,2-trifluoroethyl)-3,4-dihydro-1,4-methanopyrido[2,3-b][1,4]diazepine-5,7(2H)-dicarboxamide

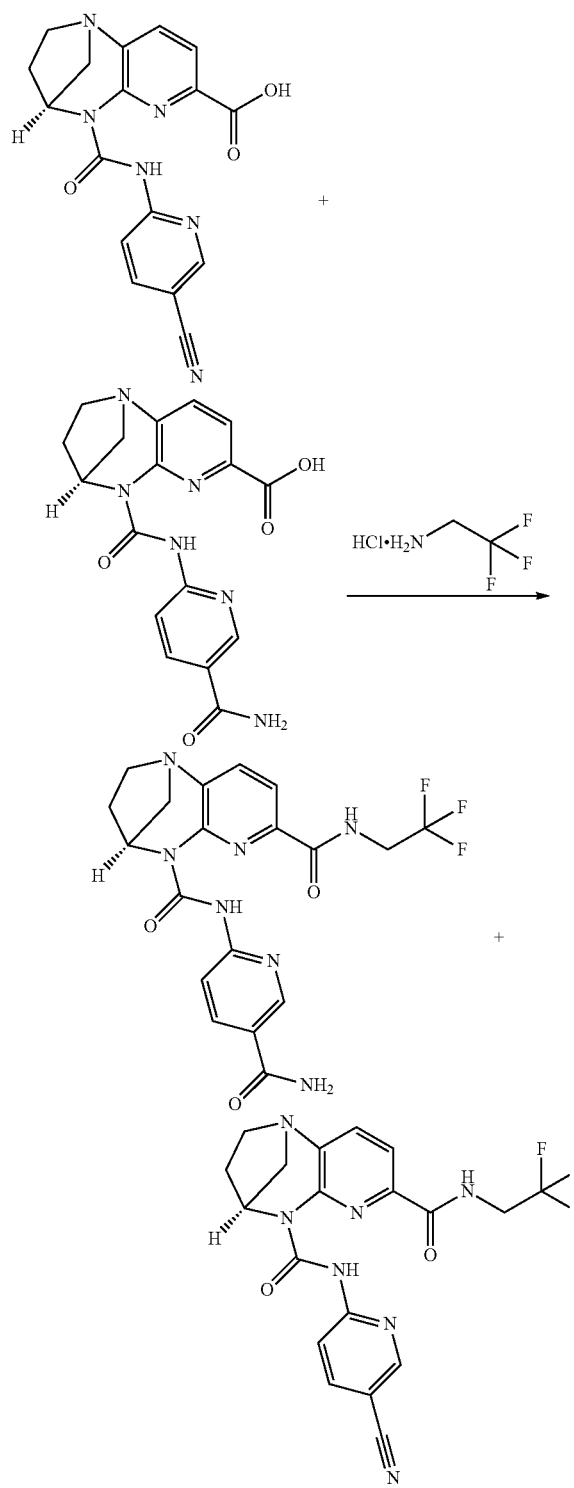

To a stirred solution of (4S)-5-((5-cyanopyridin-2-yl)carbamoyl)-2,3,4,5-tetrahydro-1,4-methanopyrido[2,3-b][1,4]diazepine-7-carboxylic acid (2.5 g, 7.14 mmol) and (4S)-5-((5-carbamoylpyridin-2-yl)carbamoyl)-2,3,4,5-tetrahydro-1,4-methanopyrido[2,3-b][1,4]diazepine-7-carboxylic acid in N,N-Dimethylformamide (DMF) (40 mL) was added HATU (4.07 g, 10.70 mmol) and TEA (2.98 mL, 21.41 mmol) at 0° C. under Nitrogen atmosphere and stirred at 0° C. for 15 min. Then 2,2,2-trifluoroethanamine hydrochloride (1.451 g, 10.70 mmol) was added to the reaction mixture and stirred at room temperature for 4 h. Reaction mixture was diluted with ice cold water and stirred for 10 min, filtered the solid which was precipitate out and dried well to get crude mixture of compounds. The crude mixture was purified by flash column chromatography (using 100-200 mesh silica gel and eluted the upper spot with 3% MeOH in DCM) to obtain a mixture with 90% purity which was again purified by flash column chromatography (Silicagel: 230-400 mesh, Eluent: 5% MeOH in DCM) to afford a pale brown solid, which was washed with Ethanol and n-pentane to afford the desired product (4S)—N5-(5-carbamoylpyridin-2-yl)-N7-(2,2,2-trifluoroethyl)-3,4-dihydro-1,4-methanopyrido[2,3-b][1,4]diazepine-5,7(2H)-dicarboxamide (420 mg, 0.918 mmol, 12.87% yield) as an off-white solid. LCMS (m/z): 450.15 [M+H]$^+$ R$_f$=1.66 min.

$^1$HNMR (400 MHz, DMSO-d$_6$): δ ppm 13.54 (s, 1H), 8.84 (d, J=1.97 Hz, 1H), 8.66 (t, J=6.47 Hz, 1H), 8.29 (dd, J=8.77, 2.19 Hz, 1H), 8.16-7.92 (m, 2H), 7.86-7.67 (m, 2H), 7.45 (br s, 1H), 5.44 (dd, J=5.70, 2.85 Hz, 1H), 4.42-4.21 (m, 2H), 3.27-3.06 (m, 3H), 3.04-2.83 (m, 1H), 2.34-2.17 (m, 1H), 2.10-1.85 (m, 1H).

Example 144

Synthesis of (4S)—N5-(6-((S)-2,3-dihydroxypropoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

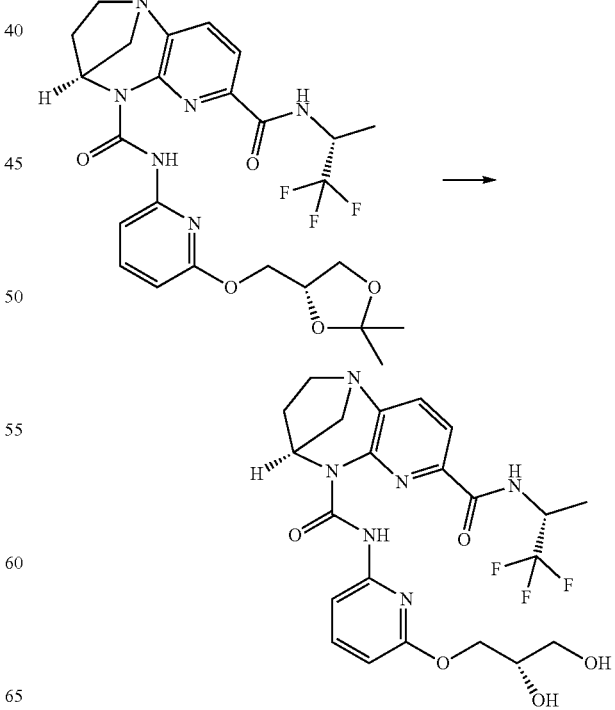

To a stirred solution of (4S)—N5-(6-(((R)-2,2-dimethyl-1,3-dioxolan-4-yl)methoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (0.48 g, 0.872 mmol) in Methanol (10 mL) was added hydrochloric acid (1.2 mL, 0.872 mmol) at 0° C. and stirred the reaction mixture at 25° C. for 4 h. (TLC system: 10% MeOH in DCM, Rf: 0.4). The reaction mixture was quenched with saturated NaHCO$_3$ solution (25 mL) and extracted with EtOAc (3×30 mL). The combined organic layer was washed with brine solution (2×20 mL), dried over anhydrous Na$_2$SO$_4$, filtered and concentrated to obtain crude product. The crude product was purified by flash column chromatography (100-200 silica gel: Eluent: 5% MeOH/CH$_2$Cl$_2$) to afford the desired product (4S)—N5-(6-((S)-2,3-dihydroxypropoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (230 mg, 0.438 mmol, 50.2% yield) as an off-white solid. LCMS (m/z): 511.27 [M+H]$^+$, R$_t$=1.80 min.

$^1$H NMR (400 MHz, DMSO-d$_6$): δ ppm 12.58 (s, 1H), 8.72 (d, J=8.77 Hz, 1H), 7.78-7.68 (m, 1H), 7.62-7.53 (m, 2H), 6.50 (d, J=7.89 Hz, 1H), 5.46 (dd, J=6.03, 2.96 Hz, 1H), 4.91-4.73 (m, 2H), 4.55 (t, J=5.70 Hz, 1H), 4.25 (dd, J=10.96, 4.60 Hz, 1H), 4.11 (dd, J=10.85, 6.25 Hz, 1H), 3.87-3.67 (m, 1H), 3.48-3.34 (m, 2H), 3.22-3.01 (m, 3H), 2.99-2.87 (m, 2H), 2.30-2.14 (m, 1H), 2.01-1.80 (m, 1H), 1.40 (d, J=7.02 Hz, 3H).

Example 145

Synthesis of (4S)—N7-(cyclopropylmethyl)-N5-(3,4-dihydro-2H-pyrano[2,3-c]pyridin-6-yl)-3,4-dihydro-1,4-methanopyrido[2,3-b][1,4]diazepine-5,7(2H)-dicarboxamide

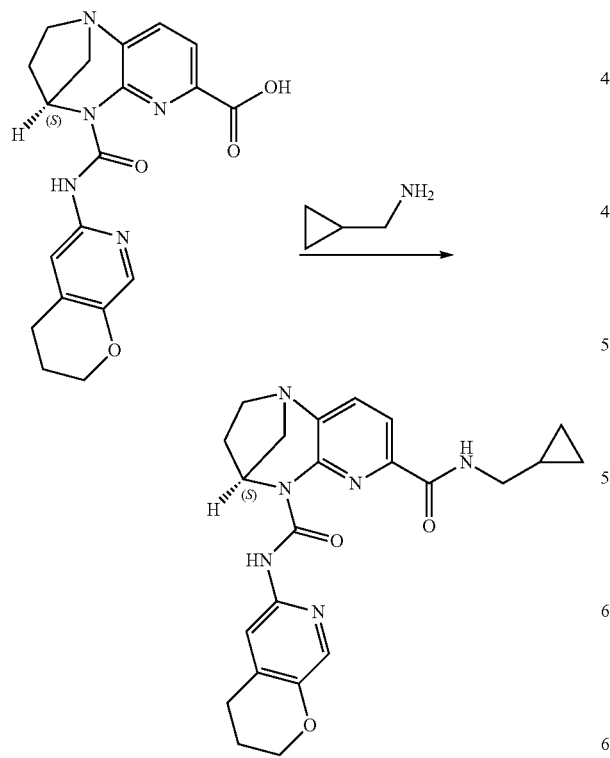

To a stirred solution of (4S)-5-((3,4-dihydro-2H-pyrano[2,3-c]pyridin-6-yl)carbamoyl)-2,3,4,5-tetrahydro-1,4-methanopyrido[2,3-b][1,4]diazepine-7-carboxylic acid (190 mg, 0.498 mmol) in DMF (5 mL) at 0° C. was added HATU (284 mg, 0.747 mmol), DIPEA (0.261 mL, 1.495 mmol) and followed by cyclopropyl methanamine (70.9 mg, 0.996 mmol) and the resulting solution was stirred at RT for 16 h. (TLC eluent: 5% MeOH in DCM: R$_f$—0.4; UV active). To the reaction mixture was added ice cold water (20 mL) and the resultant solid was filtered, dried to obtain off-white solid. The obtained compound was triturated in diethyl ether (5 mL), filtered and dried in vacuo to afford (4S)—N7-(cyclopropylmethyl)-N5-(3,4-dihydro-2H-pyrano[2,3-c]pyridin-6-yl)-3,4-dihydro-1,4-methanopyrido[2,3-b][1,4]diazepine-5,7(2H)-dicarboxamide (83 mg, 0.186 mmol, 37.4% yield) as an off-white solid. LCMS (m/z): 435.27 [M+H]$^+$, R$_t$=2.31 min.

$^1$H NMR (400 MHz, CDCl$_3$): δ ppm 13.28 (s, 1H), 8.19 (br s, 1H), 7.82-7.93 (m, 2H), 7.77 (s, 1H), 7.63 (d, J=7.89 Hz, 1H), 5.60 (dd, J=5.81, 3.18 Hz, 1H), 4.09-4.25 (m, 2H), 3.37-3.50 (m, 2H), 3.16-3.32 (m, 2H), 3.09-3.15 (m, 1H), 2.97-3.05 (m, 1H), 2.84 (t, J=6.47 Hz, 2H), 2.31 (qd, J=9.76, 4.71 Hz, 1H), 1.98-2.12 (m, 3H), 1.15-1.29 (m, 1H), 0.45-0.55 (m, 2H), 0.29-0.38 (m, 2H).

Example 146

Synthesis of (4S)—N5-(5-(methylsulfonyl)pyridin-2-yl)-N7-(2,2,2-trifluoroethyl)-3,4-dihydro-1,4-methanopyrido[2,3-b][1,4]diazepine-5,7(2H)-dicarboxamide

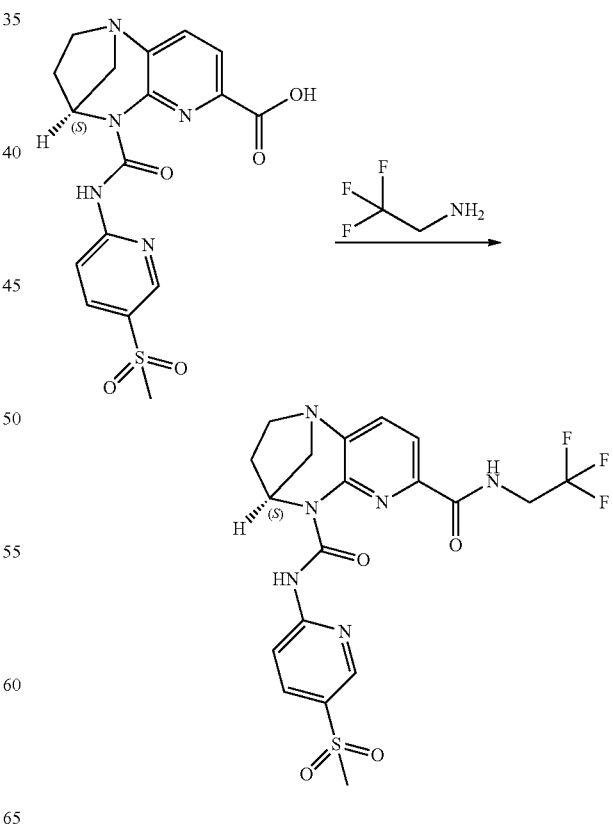

To a stirred solution of 4(S)-5-((5-(methylsulfonyl)pyridin-2-yl)carbamoyl)-2,3,4,5-tetrahydro-1,4-methanopyrido

[2,3-b][1,4]diazepine-7-carboxylic acid (750 mg, 1.859 mmol), in DMF (5 mL) at 0° C. was added DIPEA (0.325 mL, 1.859 mmol), HATU (1414 mg, 3.72 mmol) and stirred for 20 min. then added 2,2,2-trifluoroethanamine (184 mg, 1.859 mmol) and stirred at RT for 16 h. (TLC eluent: 5% MeOH in DCM: $R_f$—0.5; UV active). To the reaction mixture was added ice cold water (10 mL) and extracted with ethylacetate (15 mL). Combined organic layer was dried over anhydrous $Na_2SO_4$, filtered and concentrated under reduced pressure to obtain crude compound. The crude compound was purified by preparative HPLC (Column: XBridge [250×30 mm, 1u]; Mobile Phase A: 10 mM Ammonium Bicarbonate (Aq); Mobile Phase B: Acetonitrile: Methanol (1:1); Method: T/% B=0/50, 14/50, 14.5/100, 19/100, 19.5/50; Flow: 25 ml/min; Solubility: ACN+THF+$H_2O$) to afford (4S)—N5-(5-(methylsulfonyl)pyridin-2-yl)-N7-(2,2,2-trifluoroethyl)-3,4-dihydro-1,4-methanopyrido[2,3-b][1,4]diazepine-5,7(2H)-dicarboxamide (190 mg, 0.391 mmol, 21.05% yield) as an off white solid. LCMS (m/z): 485.11 $[M+H]^+$, $R_t$=1.93 min.

$^1$HNMR (400 MHz, DMSO-$d_6$): δ ppm 13.6 (s, 1H), 8.81 (d, J=1.75 Hz, 1H), 8.57-8.68 (m, 1H), 8.29-8.36 (m, 1H), 8.21 (br d, J=8.55 Hz, 1H), 7.75 (q, J=7.82 Hz, 2H), 5.45 (dd, J=5.81, 2.96 Hz, 1H), 4.30 (br d, J=9.65 Hz, 2H), 3.29 (br s, 3H), 3.07-3.24 (m, 3H), 2.95-3.04 (m, 1H), 2.16-2.32 (m, 1H), 1.90-2.02 (m, 1H)

Example 147

Synthesis of Synthesis of (4S)—N5-(5H-pyrrolo[3,2-d]pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide

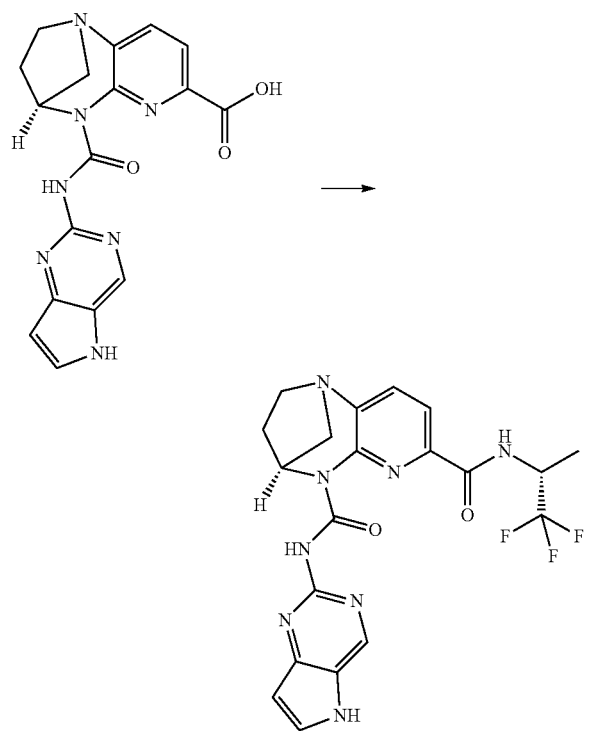

To a stirred solution of (4S)-5-((5H-pyrrolo[3,2-d]pyrimidin-2-yl)carbamoyl)-2,3,4,5-tetrahydro-1,4-methanopyrido [2,3-b][1,4]diazepine-7-carboxylic acid (500 mg, 1.369 mmol), in DMF (5 mL) under nitrogen at 0° C. was added (R)-1,1,1-trifluoropropan-2-amine (232 mg, 2.053 mmol), HATU (781 mg, 2.053 mmol), DIPEA (1.195 mL, 6.84 mmol) and stirred at RT for 16 h. (TLC eluent: 100% EtOAc, $R_f$: 0.2, UV active). The reaction mixture was diluted with water (20 mL) and extracted into EtOAc (50 mL). Combined organic extracts were dried over anhydrous $Na_2SO_4$, filtered and filtrate was evaporated to afford crude product. The crude product was purified by reverse phase chromatography (Using Grace chromatography C-18 column, Mobile phase A: 0.1% Formic Acid in water; B: Acetonitrile; eluted at 22% B in A). Subsequently the fractions were concentrated and the residue was basified with saturated $NaHCO_3$ then extracted with DCM (2×20 mL). Combined extracts were was dried over anhydrous $Na_2SO_4$, filtered and concentrated to afford pure (4S)—N5-(5H-pyrrolo[3,2-d]pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide (278 mg, 0.600 mmol, 43.8% yield) as a white solid. LCMS (m/z): 461.13 $[M+H]^+$, $R_t$=1.53 min.

$^1$H NMR (400 MHz, $CDCl_3$): δ ppm 13.37 (s, 1H), 10.31 (br s, 1H), 8.73 (s, 1H), 8.05 (br d, J=9.21 Hz, 1H), 7.95 (d, J=7.89 Hz, 1H), 7.68 (d, J=7.89 Hz, 1H), 7.64 (t, J=2.85 Hz, 1H), 6.57 (br s, 1H), 5.76 (dd, J=5.70, 2.85 Hz, 1H), 5.15-5.02 (m, 1H), 3.30-3.18 (m, 2H), 3.16-3.10 (m, 1H), 3.06-2.99 (m, 1H), 2.39-2.26 (m, 1H), 2.08 (dt, J=14.36, 7.29 Hz, 1H), 1.67-1.56 (m, 3H)

Example 148

Synthesis of (4S)—N5-(4-(2-methylthiazol-5-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

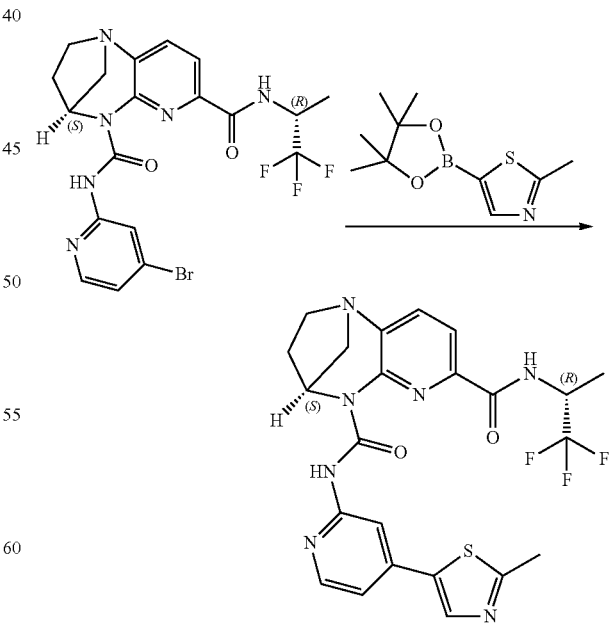

To a stirred solution of (4S)—N5-(4-bromopyridin-2-yl)-N7-((R)-1,1,1-trifluoropropan-2-yl)-3,4-dihydro-1,4-methanopyrido[2,3-b][1,4]diazepine-5,7(2H)-dicarboxamide (350 mg, 0.701 mmol) and 2-methyl-5-(4,4,5,5-tetramethyl-1,3,2-dioxaborolan-2-yl)thiazole (237 mg, 1.052 mmol) in 1,4-Dioxane (12 mL) and water (2 mL) was added potassium phosphate dibasic (366 mg, 2.103 mmol), dicyclohexyl(2',4',6'-triisopropyl-[1,1'-biphenyl]-2-yl)phosphine (33.4 mg, 0.070 mmol) were added and degassed with Argon for 15 min. then added $Pd_2(dba)_3$ (15 mg, 0.016 mmol) and the resulting mixture was stirred under microwave at 100° C. for 1 h. (TLC eluent: 5% MeOH in DCM, $R_f$—0.4; UV active). Reaction was cooled to RT, water (120 mL) was added and the aqueous layer was extracted with ethylacetate (2×100 mL). Combined organic layer was dried over sodium sulphate, filtered and concentrated under reduced pressure to get crude compound. Crude compound was purified by preparative HPLC (Column: XBridge C 18 (75×4.6 mm, 3.5μ); Mobile Phase: A: mM Ammonium Bicarbonate B: CAN; Gradient: Time/% B: 0/5, 0.8/5, 5/50, 9/98, 12/98, 12.1/5, 15/5; Column Temp: Ambient; Flow Rate: 0.8 ml/min; Diluent: CAN) Pure fractions were collected, concentrated and the precipitate was filtered and dried to afford (4S)—N5-(4-(2-methylthiazol-5-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (60 mg, 0.116 mmol, 16.48% yield) as an off-white solid. LCMS (m/z): 518.12 [M+H]$^+$, $R_t$=2.41 min.

$^1$H NMR (400 MHz, DMSO-$d_6$): δ ppm 13.10 (s, 1H), 8.18-8.30 (m, 4H), 7.71-7.80 (m, 2H), 7.41-7.48 (m, 1H), 5.49 (dd, J=5.81, 2.96 Hz, 1H), 4.91-5.04 (m, 1H), 3.29 (s, 3H), 2.95-3.03 (m, 1H), 2.73 (s, 3H), 2.17-2.31 (m, 1H), 1.91-2.05 (m, 1H), 1.53 (d, J=7.02 Hz, 3H).

Example 149

Synthesis of (4S)—N5-(5-((R)-2,3-dihydroxypropoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

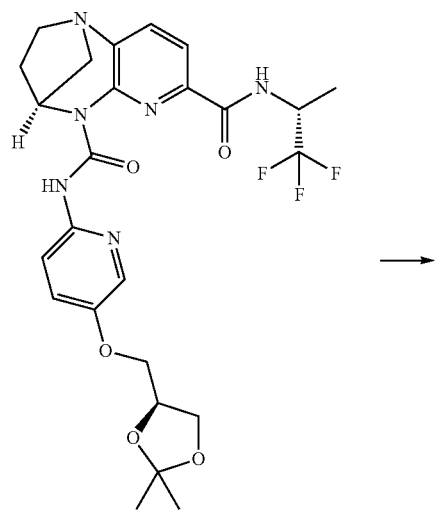

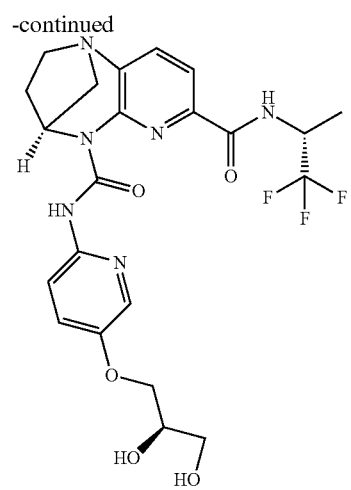

To a solution of (4S)—N5-(5-(((S)-2,2-dimethyl-1,3-dioxolan-4-yl)methoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (330 mg, 0.599 mmol) in THF (10 mL) was added aq. HCL (1 mL, 32.9 mmol) and stirred at RT for 2 h. (TLC system: 100% ethylacetate, Rf value: 0.1). The reaction mixture was concentrated and the residue was neutralized with aq. NaHCO$_3$ solution, and extracted with ethylacetate (2×20 mL). The organic layer was dried over anhydrous sodium sulphate, filtered and concentrated. The crude compound was triturated with diethyl ether (2×20 mL), dried under vacuum to afford (4S)—N5-(5-((R)-2,3-dihydroxypropoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (195 mg, 0.379 mmol, 63.2% yield) as an off-white solid. LCMS (m/z): 511.21, Rt=1.68 min.

$^1$H NMR (400 MHz, CDCl$_3$): δ ppm 13.08 (s, 1H), 8.10 (d, J=9.21 Hz, 1H), 7.99-7.86 (m, 3H), 7.67 (d, J=7.89 Hz, 1H), 7.32 (dd, J=8.99, 3.07 Hz, 1H), 5.64 (dd, J=5.81, 3.18 Hz, 1H), 5.11-4.98 (m, 1H), 4.17-4.03 (m, 3H), 3.91-3.73 (m, 2H), 3.30-3.16 (m, 2H), 3.15-3.08 (m, 1H), 3.05-2.97 (m, 1H), 2.63 (br s, 1H), 2.38-2.26 (m, 1H), 2.06 (dt, J=14.14, 6.96 Hz, 2H), 1.62-1.54 (m, 3H).

Example 150

Synthesis of (4S)—N5-(4-(dimethylcarbamoyl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

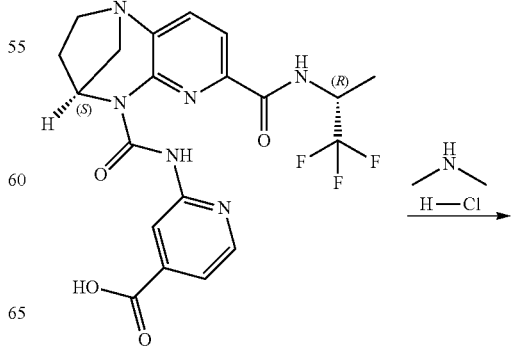

457

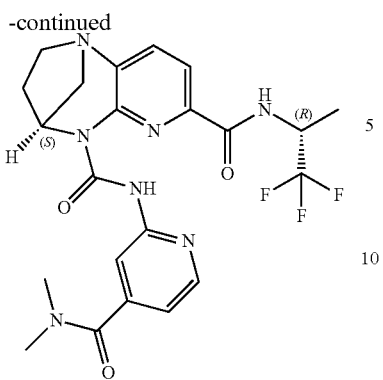

To a suspension of 2-((4S)-7-(((R)-1,1,1-trifluoropropan-2-yl)carbamoyl)-2,3,4,5-tetrahydro-1,4-methanopyrido[2,3-b][1,4]diazepine-5-carboxamido)isonicotinic acid (200 mg, 0.431 mmol) in Tetrahydrofuran (15 mL) were added N-ethyl-N-isopropylpropan-2-amine (0.376 mL, 2.153 mmol) followed by 2-(3H-[1,2,3]triazolo[4,5-b]pyridin-3-yl)-1,1,3,3-tetramethylisouronium hexafluorophosphate(V) (328 mg, 0.861 mmol) and dimethylamine hydrochloride (88 mg, 1.077 mmol) at room temperature then stirred at the same temperature for 16 h (TLC system: Neat ethyl acetate: $R_f$: 0.1; UV active). The solvent was removed under reduced pressure and the obtain residue was partitioned between water (30 mL) and EtOAc (30 mL×2). The combined organic layer was dried over anhydrous $Na_2SO_4$, filtered and filtrate was evaporated to obtain crude compound. The crude material was purified by flash column chromatography (Silica gel: 100-200 Mesh, Eluent: 80% ethyl acetate in n-hexane) to afford the desired product (4S)—N5-(4-(dimethylcarbamoyl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (138 mg, 0.280 mmol, 65.0% yield) as an off white solid. LCMS (m/z): 492.27 [M+H]⁺, Rt=1.97 min.

¹H NMR (400 MHz, CDCl₃): δ ppm 13.36 (s, 1H), 8.31 (d, J=5.04 Hz, 1H), 8.19-8.17 (m, 1H), 7.97 (d, J=7.89 Hz, 1H), 7.93 (d, J=9.65 Hz, 1H), 7.69 (d, J=7.89 Hz, 1H), 7.05 (dd, J=5.04, 1.53 Hz, 1H), 5.63 (dd, J=5.92, 3.07 Hz, 1H), 5.06 (dq, J=16.77, 7.34 Hz, 1H), 3.29-3.20 (m, 2H), 3.15-3.10 (m, 4H), 3.06-2.98 (m, 4H), 2.39-2.28 (m, 1H), 2.11-2.01 (m, 1H), 1.59 (d, J=7.02 Hz, 3H).

458

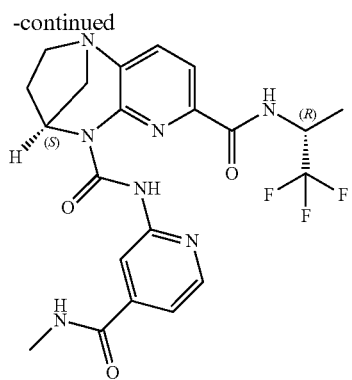

To a suspension of 2-((4S)-7-(((R)-1,1,1-trifluoropropan-2-yl)carbamoyl)-2,3,4,5-tetrahydro-1,4-methanopyrido[2,3-b][1,4]diazepine-5-carboxamido)isonicotinic acid (200 mg, 0.431 mmol) in Tetrahydrofuran (15 mL), were added N-ethyl-N-isopropylpropan-2-amine (0.376 mL, 2.153 mmol), 2-(3H-[1,2,3]triazolo[4,5-b]pyridin-3-yl)-1,1,3,3-tetramethylisouronium hexafluorophosphate (V) (328 mg, 0.861 mmol) and methanamine hydrochloride (72.7 mg, 1.077 mmol) at room temperature and stirred for 16 h. (TLC system: Neat ethyl acetate: $R_f$: 0.1; UV active). The organic solvent was removed under reduced pressure and partitioned between water (30 mL) and EtOAc (30 mL×2). The combined organic layer was dried over anhydrous $Na_2SO_4$, filtered and filtrate was evaporated to get crude. The crude product was purified by flash column chromatography (silicagel: 100-200 Mesh, Eluent: 80% ethyl acetate in n-hexane) to afford the desired product (4S)—N5-(4-(methylcarbamoyl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (55 mg, 0.114 mmol, 26.5% yield) as an off white solid. LCMS (m/z): 478.23 [M+H]⁺, Rt=1.90 min.

¹H NMR (400 MHz, CDCl₃): δ ppm 13.42 (s, 1H), 8.41-8.35 (m, 2H), 7.98 (d, J=7.89 Hz, 1H), 7.90 (d, J=9.43 Hz, 1H), 7.70 (d, J=8.11 Hz, 1H), 7.50 (dd, J=5.04, 1.53 Hz, 1H), 6.37 (br s, 1H), 5.63 (dd, J=5.81, 2.96 Hz, 1H), 5.06 (dt, J=9.37, 7.37 Hz, 1H), 3.28-3.22 (m, 2H), 3.17-3.11 (m, 1H), 3.07-3.02 (m, 4H), 2.39-2.30 (m, 1H), 2.07 (dt, J=14.20, 6.82 Hz, 1H), 1.60 (s, 3H).

Example 151

Synthesis of (4S)—N5-(4-(methylcarbamoyl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

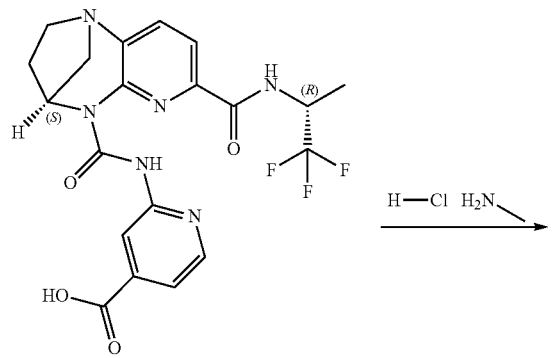

Example 152

Synthesis of (4S)—N5-(4-(hydrazinecarbonyl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

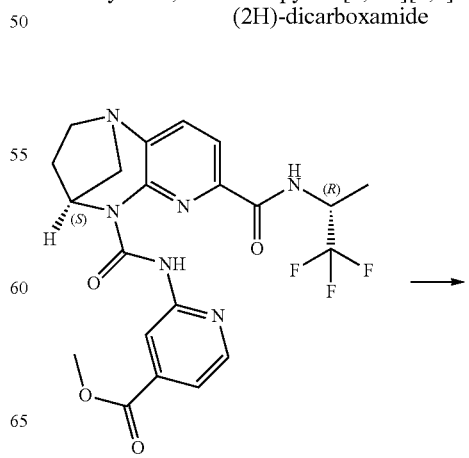

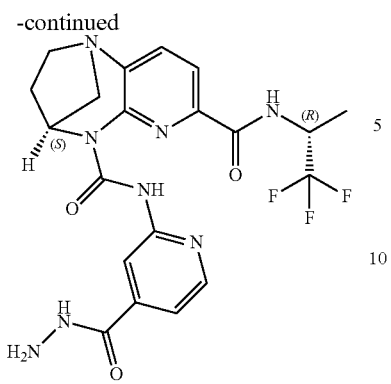

To a solid of methyl 2-((4S)-7-(((R)-1,1,1-trifluoropropan-2-yl)carbamoyl)-2,3,4,5-tetrahydro-1,4-methanopyrido[2,3-b][1,4]diazepine-5-carboxamido)isonicotinate (200 mg, 0.418 mmol) was added hydrazine hydrate (3 ml, 96 mmol) at room temperature in a sealed tube and stirred at 50° C. for 16 h. (TLC eluent: neat ethyl acetate; R$_f$: 0.1; UV active). The reaction mixture was cooled to room temperature and was quenched with ice cold water (10 mL) then partitioned between ice cold water (20 mL) and ethyl acetate (15 mL×2). The combined organic layer was dried over anhydrous Na$_2$SO$_4$, filtered and filtrate was evaporated to obtain crude product. The crude material was purified by flash column chromatography (Silica gel; 100-200 Mesh, Eluent: 90% ethyl acetate in hexane) to afford the desired product (4S)—N5-(4-(hydrazinecarbonyl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (184 mg, 0.381 mmol, 91% yield) as an off white solid. LCMS (m/z): 479.17 [M+H]$^+$, Rt=1.71 min.

$^1$H NMR (400 MHz, CDCl$_3$): δ ppm 13.43 (s, 1H), 8.42 (s, 1H), 8.38 (d, J=5.26 Hz, 1H), 7.97 (d, J=7.89 Hz, 1H), 7.88 (d, J=9.65 Hz, 1H), 7.70 (d, J=8.11 Hz, 2H), 7.45 (dd, J=5.26, 1.53 Hz, 1H), 5.63 (dd, J=5.92, 3.07 Hz, 1H), 5.06 (dt, J=9.48, 7.32 Hz, 1H), 4.16 (s, 2H), 3.30-3.20 (m, 2H), 3.16-3.10 (m, 1H), 3.07-3.01 (m, 1H), 2.34 (ddt, J=14.31, 8.88, 5.51, 5.51 Hz, 1H), 2.11-2.02 (m, 1H), 1.59 (d, J=7.02 Hz, 3H).

Example 153

Synthesis of (4S)—N5-(5-((S)-2,3-dihydroxypropoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

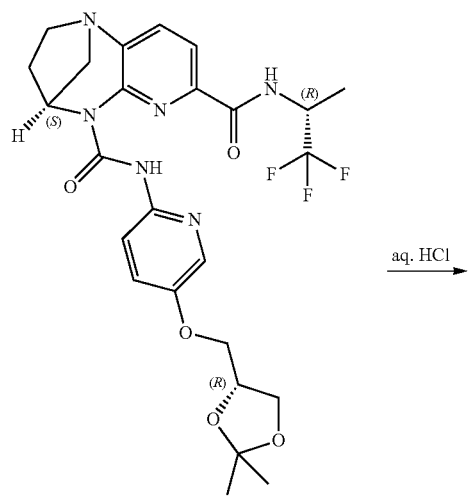

aq. HCl →

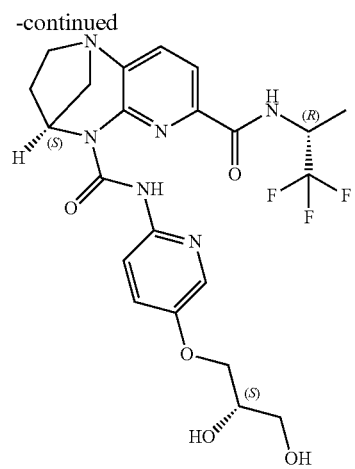

To a solution of (4S)—N5-(5-(((R)-2,2-dimethyl-1,3-dioxolan-4-yl)methoxy)pyridin-2-yl)-dihydroxypropoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (400 mg, 0.727 mmol) in Tetrahydrofuran (10 mL), Hydrochloric acid (1 mL, 32.9 mmol) was added at 0° C. then stirred at room temperature for 2 h. (TLC system: neat ethyl acetate; R$_f$: 0.1; UV active). The solvent was removed under reduced pressure and neutralized with saturated sodium bicarbonate solution, filtered the obtain solid and washed with n-pentane (10 mL×3) to afford the desired product (4S)—N5-(5-((S)-2,3-dihydroxypropoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (256 mg, 0.500 mmol, 68.9% yield) as an off white solid. LCMS (m/z): 511.17 [M+H]$^+$, Rt=1.70 min.

$^1$H NMR (400 MHz, CDCl$_3$): δ ppm 13.09 (s, 1H), 8.11 (d, J=8.99 Hz, 1H), 7.97-7.88 (m, 3H), 7.32 (dd, J=9.10, 2.96 Hz, 1H), 7.32 (dd, J=9.10, 2.96 Hz, 1H) 5.64 (dd, J=5.92, 3.07 Hz, 1H), 5.05 (dq, J=16.85, 7.39 Hz, 1H), 4.18-4.07 (m, 3H), 3.91-3.75 (m, 2H), 3.29-3.16 (m, 2H), 3.14-2.99 (m, 2H), 2.59 (d, J=4.38 Hz, 1H), 2.37-2.28 (m, 1H), 2.11-1.96 (m, 2H), 1.59 (d, J=7.23 Hz, 3H).

Example 154

Synthesis of (4S)—N5-(4-((S)-2,3-dihydroxypropoxy)pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide

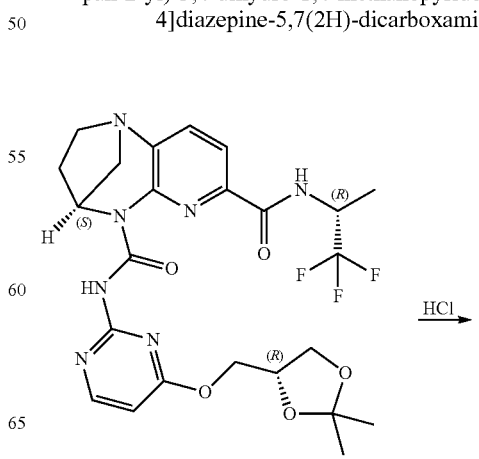

HCl →

461

-continued

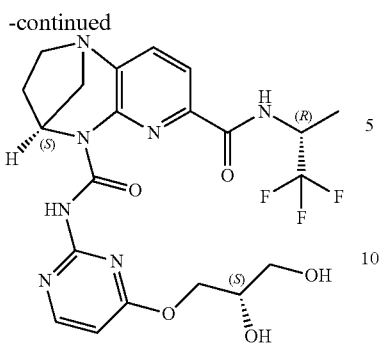

To a stirred solution of (4S)—N5-(4-(((R)-2,2-dimethyl-1,3-dioxolan-4-yl)methoxy)pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide (0.320 g, 0.580 mmol) in Methanol (10 mL) at 0° C. was added hydrochloric acid (1 mL, 0.580 mmol) and stirred the reaction mixture at 25° C. for 4 h. (TLC system: 10% MeOH in DCM, $R_f$: 0.4). The reaction mixture was quenched with saturated NaHCO$_3$ solution (25 mL) and extracted with EtOAc (3×30 mL). The combined organic layer was washed with brine solution (2×20 mL) and dried with anhydrous Na$_2$SO$_4$, filtered and concentrated to obtain crude product. The crude product was purified by flash column chromatography (100-200 silica gel: Eluent: 5% MeOH/CH$_2$Cl$_2$) to afford the desired product (4S)—N5-(4-((S)-2,3-dihydroxypropoxy)pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide (102 mg, 0.191 mmol, 32.9% yield) as an off-white solid. LCMS (m/z): 512.22 [M+H]$^+$, $R_t$=1.59 min.

$^1$H NMR (400 MHz, DMSO-d$_6$): δ ppm 13.11 (s, 1H), 8.44-8.17 (m, 2H), 7.78-7.60 (m, 2H), 6.61 (d, J=5.70 Hz, 1H), 5.44 (dd, J=5.70, 3.07 Hz, 1H), 5.08-4.82 (m, 2H), 4.66 (t, J=5.81 Hz, 1H), 4.45-4.26 (m, 2H), 3.82 (dd, J=10.08, 5.04 Hz, 1H), 3.56-3.32 (m, 2H), 3.04 (s, 1H), 3.23-2.85 (m, 2H), 2.96-2.83 (m, 1H), 2.30-2.13 (m, 1H), 1.94 (dt, J=13.76, 7.04 Hz, 1H), 1.45 (d, J=7.02 Hz, 2H), 1.24 (s, 1H).

Example 155

Synthesis of (4S)—N5-(6-((R)-2,3-dihydroxypropoxy)pyrazin-2-yl)-N7-((R)-1,1,1-trifluoropropan-2-yl)-3,4-dihydro-1,4-methanopyrido[2,3-b][1,4]diazepine-5,7(2H)-dicarboxamide

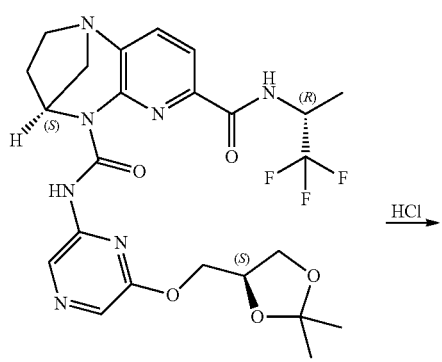

462

-continued

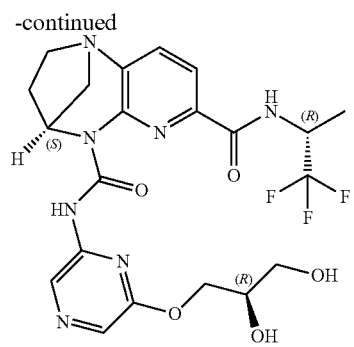

To a stirred solution of (4S)—N5-(6-(((S)-2,2-dimethyl-1,3-dioxolan-4-yl)methoxy)pyrazin-2-yl)-N7-((R)-1,1,1-trifluoropropan-2-yl)-3,4-dihydro-1,4-methanopyrido[2,3-b][1,4]diazepine-5,7(2H)-dicarboxamide (0.4 g, 0.725 mmol) in Methanol (15 mL) at 0° C. was added hydrochloric acid (1.2 mL, 0.725 mmol) and stirred the reaction mixture at 25° C. for 4 h. (TLC system: 10% MeOH in DCM, Rf: 0.4). The reaction mixture was quenched with saturated NaHCO$_3$ solution (30 mL) and extracted with EtOAc (3×30 mL). The combined organic layer was washed with brine solution (2×20 mL), dried over anhydrous Na$_2$SO$_4$, filtered and concentrated to get crude product. The crude product was purified by flash column chromatography (silica gel: 100-200 Mesh, Eluent; 5% MeOH/CH$_2$Cl$_2$) to afford the desired product (4S)—N5-(6-((R)-2,3-dihydroxypropoxy)pyrazin-2-yl)-N7-((R)-1,1,1-trifluoropropan-2-yl)-3,4-dihydro-1,4-methanopyrido[2,3-b][1,4]diazepine-5,7(2H)-dicarboxamide (168 mg, 0.324 mmol, 44.7% yield) as a pale yellow solid. LCMS (m/z): 512.22 [M+H]$^+$, $R_t$=1.56 min.

$^1$H NMR (400 MHz, DMSO-d$_6$): δ ppm 12.80 (s, 1H), 8.94-8.73 (m, 2H), 7.99 (s, 1H), 7.79-7.47 (m, 2H), 5.56-5.38 (m, 1H), 4.98-4.71 (m, 1H), 4.71-4.65 (m, 1H), 4.59 (t, J=5.70 Hz, 1H), 4.38-4.16 (m, 2H), 3.88-3.68 (m, 1H), 3.50-3.36 (m, 2H), 3.22-3.02 (m, 3H), 2.97 (dd, J=12.17, 3.18 Hz, 1H), 2.34-2.11 (m, 1H), 2.02-1.75 (m, 1H), 1.54-1.08 (m, 3H).

Example 156

Synthesis of (4S)—N5-(4-(2-methyloxazol-5-yl)pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide

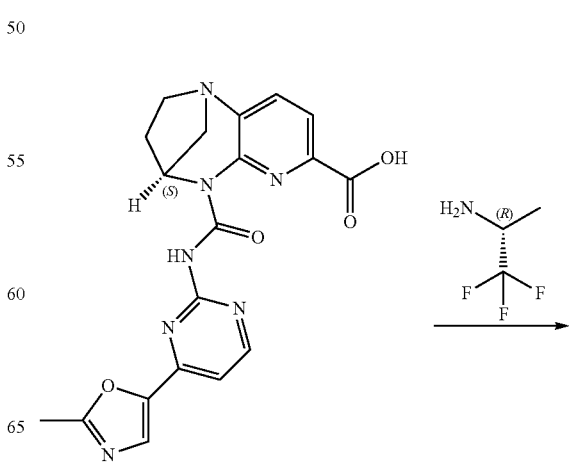

463

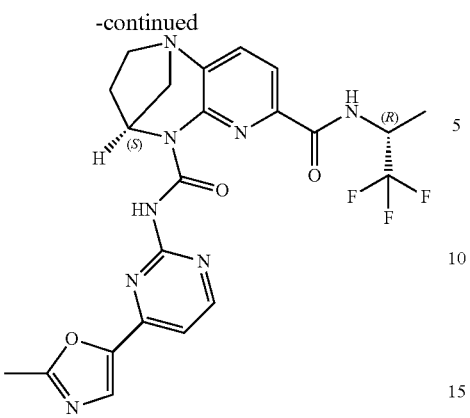

To a stirred solution of 4(S)-5-((4-(2-methyloxazol-5-yl) pyrimidin-2-yl)carbamoyl)-2,3,4,5-tetrahydro-1,4-methano-pyrido[2,3-b][1,4]diazepine-7-carboxylic acid (240 mg, 0.589 mmol) in DMF (10 mL) at 0° C. was added HATU (448 mg, 1.178 mmol) and DIPEA (0.309 mL, 1.767 mmol) and stirred for 10 min, then added (R)-1,1,1-trifluoropropan-2-amine (100 mg, 0.884 mmol) to the reaction mixture at 0° C. and the resulting solution was stirred at RT for 4 h. (TLC eluent: 5% MeOH in DCM, R$_f$—0.3; UV active). To the reaction mixture was added ice cold water (20 mL) and extracted into ethylacetate (50 mL). The separated organic layer was dried over anhydrous Na$_2$SO$_4$, filtered and concentrated under reduced pressure to obtain crude compound. The crude compound was purified by combiflash chromatography (silica gel column and was eluted in 5% MeOH in DCM) to afford (4S)—N5-(4-(2-methyloxazol-5-yl)pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide (50 mg, 0.098 mmol, 16.65% yield) as an off-white solid. LCMS (m/z): 503.14 [M+H]$^+$, R$_t$=1.89 min.

$^1$H NMR (400 MHz, CDCl$_3$): δ ppm 13.57 (s, 1H), 8.53 (d, J=5.04 Hz, 1H), 7.97 (d, J=7.89 Hz, 1H), 7.83-7.93 (m, 2H), 7.70 (d, J=7.89 Hz, 1H), 7.23-7.28 (m, 1H), 5.73 (dd, J=5.92, 3.07 Hz, 1H), 5.07 (dt, J=9.26, 7.43 Hz, 1H), 3.17-3.37 (m, 2H), 2.96-3.16 (m, 2H), 2.60 (s, 3H), 2.23-2.48 (m, 1H), 2.00-2.17 (m, 1H), 1.47-1.64 (m, 3H).

Example 157

Synthesis of (4S)—N5-(4-(2-methyloxazol-5-yl) pyrimidin-2-yl)-N7-(2,2,2-trifluoroethyl)-3,4-di-hydro-1,4-methanopyrido[2,3-b][1,4]diazepine-5,7 (2H)-dicarboxamide

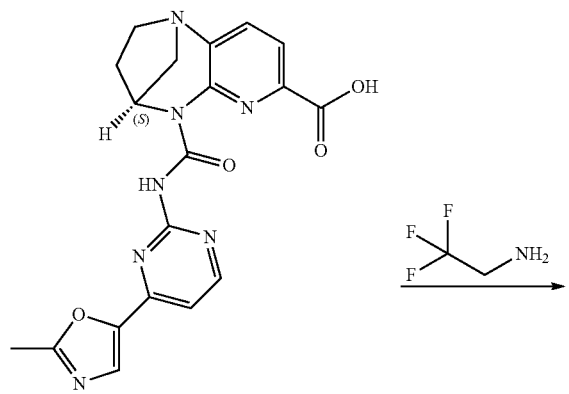

464

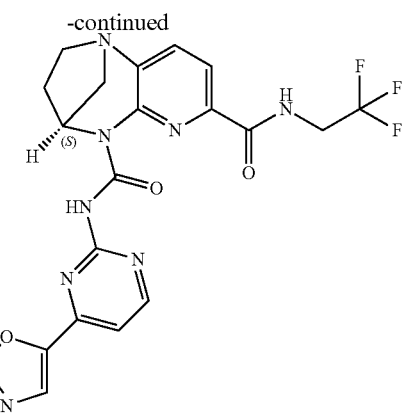

To a stirred solution of (4S)-5-((4-(2-methyloxazol-5-yl) pyrimidin-2-yl)carbamoyl)-2,3,4,5-tetrahydro-1,4-methano-pyrido[2,3-b][1,4]diazepine-7-carboxylic acid (240 mg, 0.589 mmol) in DMF (10 mL) at 0° C. was added HATU (448 mg, 1.178 mmol) and DIPEA (0.309 mL, 1.767 mmol) and stirred for 10 min. Then added 2,2,2-trifluoroethan-amine (88 mg, 0.884 mmol) at 0° C. and the resulting solution was stirred at RT for 4 h. (TLC eluent: 5% MeOH in DCM, R$_f$—0.3; UV active). To the reaction mixture was added ice cold water (20 mL) and extracted into ethylacetate (50 mL). The separated organic layer was dried over anhydrous Na$_2$SO$_4$, filtered and concentrated under reduced pressure to obtain crude compound. The crude compound was purified by combiflash chromatography (Silica gel column and was eluted in 5% MeOH in DCM) to obtain desired compound. The desired product was triturated with diethyl ether (2×5 ml) to afford (4S)—N5-(4-(2-methylox-azol-5-yl)pyrimidin-2-yl)-N7-(2,2,2-trifluoroethyl)-3,4-di-hydro-1,4-methanopyrido[2,3-b][1,4]diazepine-5,7(2H)-di-carboxamide (44 mg, 0.089 mmol, 15.14% yield) as an off-white solid. LCMS (m/z): 489.14 [M+H]$^+$, R$_t$=1.78 min.

$^1$H NMR (400 MHz, CDCl$_3$): δ ppm 13.86 (s, 1H), 8.53 (d, J=5.26 Hz, 1H), 8.31 (br t, J=6.14 Hz, 1H), 7.94 (d, J=7.89 Hz, 1H), 7.86 (s, 1H), 7.70 (d, J=7.89 Hz, 1H), 7.10-7.25 (m, 1H), 5.71 (dd, J=5.59, 2.96 Hz, 1H), 4.12-4.31 (m, 2H), 3.18-3.30 (m, 2H), 3.01-3.15 (m, 2H), 2.60 (s, 3H), 2.22-2.49 (m, 1H), 2.08 (dt, J=14.85, 7.37 Hz, 1H).

Example 158

Synthesis of (4S)—N5-(5-cyanopyridin-2-yl)-N7-(2, 2,2-trifluoroethyl)-3,4-dihydro-1,4-methanopyrido[2, 3-b][1,4]diazepine-5,7(2H)-dicarboxamide

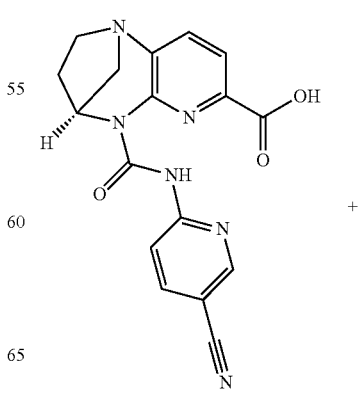

465

-continued

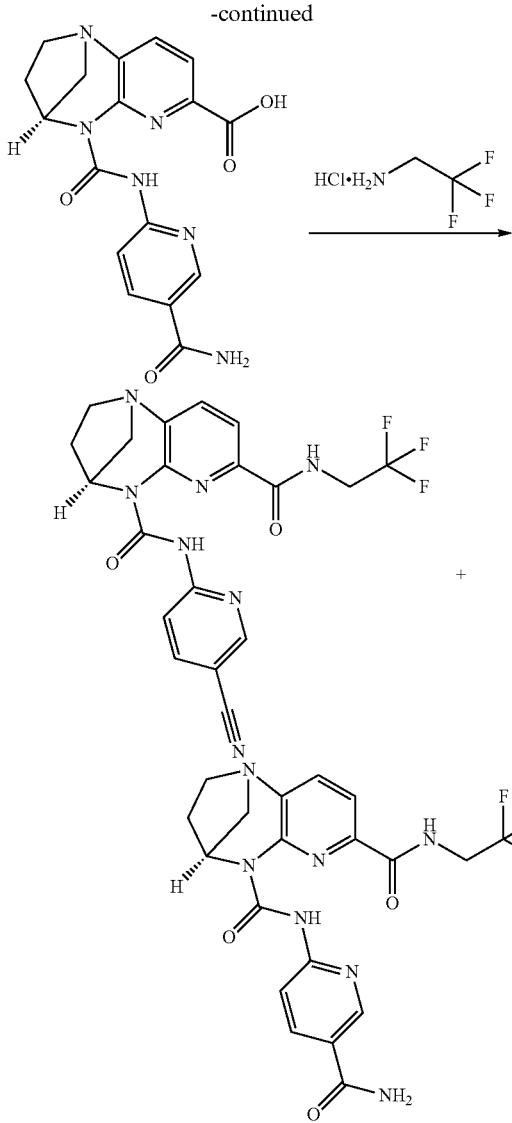

466

(5-cyanopyridin-2-yl)-N7-(2,2,2-trifluoroethyl)-3,4-dihydro-1,4-methanopyrido[2,3-b][1,4]diazepine-5,7(2H)-dicarboxamide (230 mg, 0.528 mmol, 7.41% yield) (N36561-77-A3) as an off-white solid. LCMS (nm/z): 432.11 [M+H]$^+$, Rt=2.14.

$^1$H NMR (400 MHz, DMSO-d$_6$): δ ppm 13.66 (s, 1H), 8.82 (d, J=1.75 Hz, 1H), 8.60 (t, J=6.58 Hz, 1H), 8.31 (dd, J=8.77, 2.19 Hz, 1H), 8.16 (d, J=8.77 Hz, 1H), 7.76 (q, J=7.89 Hz, 2H), 5.43 (dd, J=5.81, 2.96 Hz, 1H), 4.42-4.21 (m, 2H), 3.28-3.06 (m, 3H), 3.04-2.90 (m, 1H), 2.24 (dddd, J=13.73, 9.78, 5.86, 3.73 Hz, 1H), 1.96 (dt, J=13.98, 7.15 Hz, 1H).

Example 159

Synthesis of (4S)—N7-cyclopropyl-N5-(3,4-dihydro-2H-pyrano[2,3-c]pyridin-6-yl)-3,4-dihydro-1,4-methanopyrido[2,3-b][1,4]diazepine-5,7(2H)-dicarboxamide

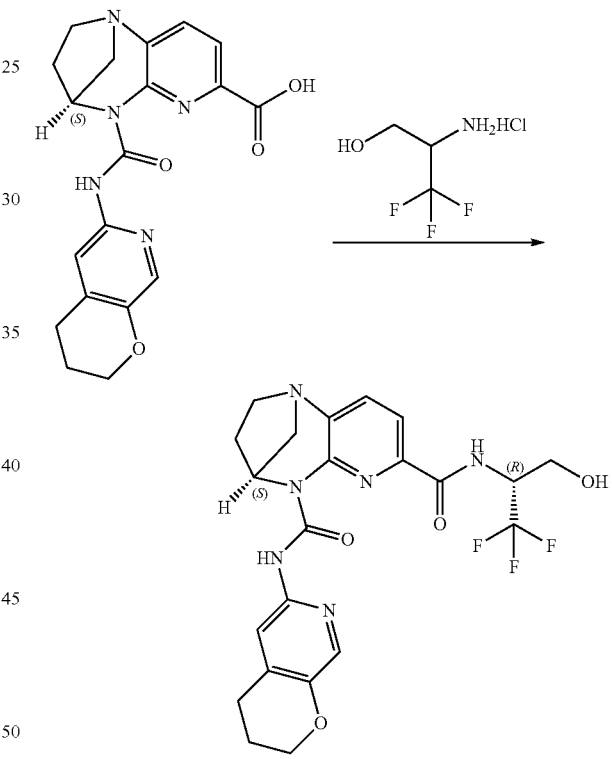

To a stirred solution of (4S)-5-((5-cyanopyridin-2-yl)carbamoyl)-2,3,4,5-tetrahydro-1,4-methanopyrido[2,3-b][1,4]diazepine-7-carboxylic acid (2.5 g, 7.14 mmol) and (4S)-5-((5-carbamoylpyridin-2-yl)carbamoyl)-2,3,4,5-tetrahydro-1,4-methanopyrido[2,3-b][1,4]diazepine-7-carboxylic acid in N,N-Dimethylformamide (DMF) (40 mL) was added HATU (4.07 g, 10.70 mmol) and TEA (2.98 mL, 21.41 mmol) at 0° C. under Nitrogen atmosphere and stirred at 0° C. for 15 min. Then 2,2,2-trifluoroethanamine hydrochloride (1.451 g, 10.70 mmol) was added to the reaction mixture and stirred at room temperature for 4 h. (TLC System: 10% MeOH/DCM, R$_f$ value: 0.5, UV active). Then the reaction mixture was diluted with ice cold water and stirred for 10 min, filtered the solid which was precipitate out and dried well to get crude mixture of compounds. The crude mixture was purified by flash column chromatography (using 100-200 mesh silica gel and eluted the upper spot with 3% MeOH in DCM) to obtain a mixture with 90% purity which was again purified by flash column chromatography (Silicagel: 230-400 mesh, Eluent: 3% MeOH in DCM) to obtain the non-polar compound as a pale yellow semi solid which was washed with ethanol (10 mL) and n-pentane (10 mL) to afford the desired product (4S)—N5-

To a stirred solution of (4S)-5-((3,4-dihydro-2H-pyrano[2,3-c]pyridin-6-yl)carbamoyl)-2,3,4,5-tetrahydro-1,4-methanopyrido[2,3-b][1,4]diazepine-7-carboxylic acid (190 mg, 0.498 mmol) in DMF (5 mL) at 0° C. was added HATU (284 mg, 0.747 mmol) and DIPEA (0.261 mL, 1.495 mmol) and stirred for 10 min. Then added 2-amino-3,3,3-trifluoropropan-1-ol hydrochloride (124 mg, 0.747 mmol) at 0° C. and the resulting solution was stirred at RT for 16 h. (TLC eluent: 5% MeOH in DCM: R$_f$—0.4; UV active). Ice cold water (20 mL) was added to the reaction mixture and extracted with ethylacetate (50 mL). Combined organic layer was dried over anhydrous Na$_2$SO$_4$, filtered and concentrated under reduced pressure to get crude diastereomeric mixture as a light brown solid. The diastereoisomers were separated by combiflash chromatography (silica gel column and was eluted in 2% MeOH in DCM), the to afford desired (4S)—N5-(3,4-dihydro-2H-pyrano[2,3-c]pyridin-6-yl)-N7-((R)-1,1,1-trifluoro-3-hydroxypropan-2-yl)-3,4-dihydro-1,4-methanopyrido[2,3-b][1,4]diazepine-5,7(2H)-dicarboxamide (40 mg, 0.078 mmol, 15.61% yield) as an off-white solid. The absolute stereochemistry at amine center was confirmed with authentic sample Chiral HPLC retention time is 2.46 min. [Column: YMC AMYLOSE-C (4.6×250 mm) 5 um; Co-solvent: 0.5% DEA in METHANOL; Total flow: 4 g/mn; % of Co-Solvent: 40%; Temperature: 30° C.; ABPR: 100 bar; UV: 265 nm] LCMS (m/z): 493.17 [M+H]$^+$, R$_t$=1.99 min.

$^1$H NMR (400 MHz, CDCl$_3$): δ ppm 12.14 (s, 1H), 7.97 (s, 1H), 7.84 (d, J=7.67 Hz, 1H), 7.77 (s, 1H), 7.68 (d, J=7.89 Hz, 1H), 7.61 (br d, J=8.99 Hz, 1H), 5.74 (dd, J=6.14, 3.07 Hz, 1H), 5.24 (br s, 1H), 4.82-4.98 (m, 1H), 4.17-4.25 (m, 2H), 4.05 (br s, 2H), 3.07-3.32 (m, 3H), 2.95-3.05 (m, 1H), 2.77-2.91 (m, 2H), 2.24-2.41 (m, 1H), 1.95-2.14 (m, 3H)

Example 160

Synthesis of (4S)—N7-cyclopropyl-N5-(3,4-dihydro-2H-pyrano[2,3-c]pyridin-6-yl)-3,4-dihydro-1,4-methanopyrido[2,3-b][1,4]diazepine-5,7(2H)-dicarboxamide

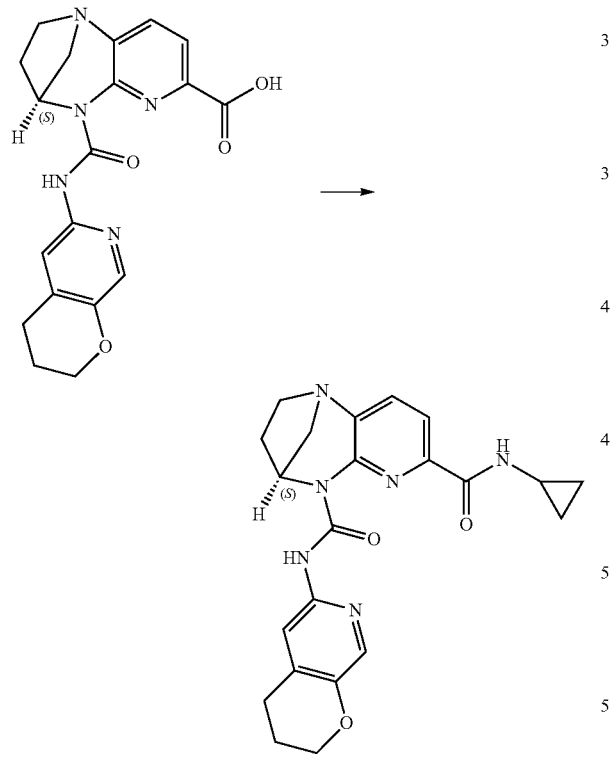

To a stirred solution of (4S)-5-((3,4-dihydro-2H-pyrano[2,3-c]pyridin-6-yl)carbamoyl)-2,3,4,5-tetrahydro-1,4-methanopyrido[2,3-b][1,4]diazepine-7-carboxylic acid (200 mg, 0.524 mmol) in DMF (5 mL) at 0° C. was added HATU (299 mg, 0.787 mmol) and DIPEA (0.275 mL, 1.573 mmol). and stirred for 10 min. then added cyclopropanamine (59.9 mg, 1.049 mmol) and the resulting solution was stirred at RT for 16 h. (TLC eluent: 5% MeOH in DCM: R$_f$—0.5; UV active). Ice cold water (20 mL) was added to the above reaction mixture and the resultant solid was filtered and dried in vacuo to obtain an off-white solid. The solid was triturated with diethyl ether (5 mL), filtered and dried in vacuo to afford (4S)—N7-cyclopropyl-N5-(3,4-dihydro-2H-pyrano[2,3-c]pyridin-6-yl)-3,4-dihydro-1,4-methanopyrido[2,3-b][1,4]diazepine-5,7(2H)-dicarboxamide (96 mg, 0.227 mmol, 43.3% yield) as an off-white solid. LCMS (m/z): 421.17 [M+H]$^+$, R$_t$=2.0 min.

$^1$H NMR (400 MHz, CDCl$_3$): δ ppm 13.10 (s, 1H), 7.94 (br s, 1H), 7.82-7.92 (m, 3H), 7.62 (d, J=7.89 Hz, 1H), 5.60 (dd, J=5.81, 2.96 Hz, 1H), 4.18-4.25 (m, 2H), 3.15-3.29 (m, 2H), 3.03-3.14 (m, 2H), 2.95-3.03 (m, 1H), 2.79-2.89 (m, 2H), 2.24-2.36 (m, 1H), 1.97-2.10 (m, 3H), 0.79-0.96 (m, 4H)

Example 161

Synthesis of (4S)—N5-(4-(2-hydroxyethoxy)pyridin-2-yl)-N7-(2,2,2-trifluoroethyl)-3,4-dihydro-1,4-methanopyrido[2,3-b][1,4]diazepine-5,7(2H)-dicarboxamide

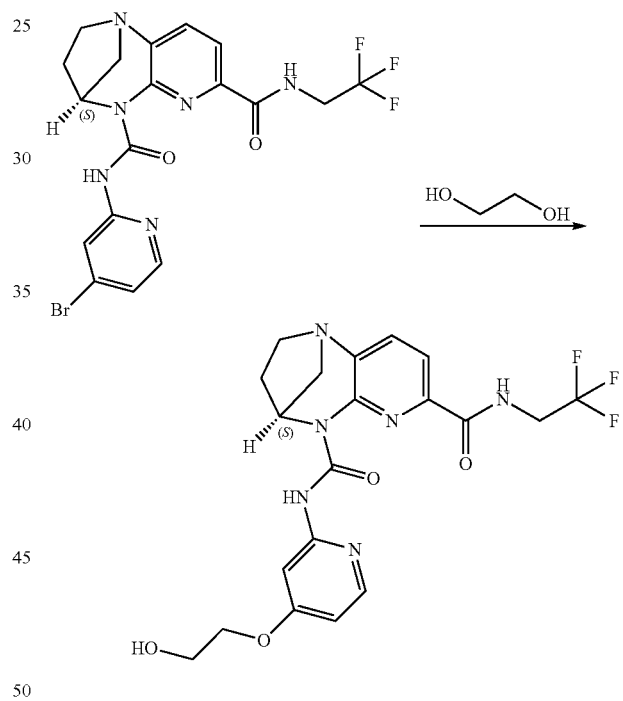

To a stirred solution of (4S)—N5-(4-bromopyridin-2-yl)-N7-(2,2,2-trifluoroethyl)-3,4-dihydro-1,4-methanopyrido[2,3-b][1,4]diazepine-5,7(2H)-dicarboxamide (1 g, 2.061 mmol), dicyclohexyl(2',4',6'-triisopropyl-[1,1'-biphenyl]-2-yl)phosphine (0.295 g, 0.618 mmol) and ethylene glycol (0.345 mL, 6.18 mmol) in 1,4-Dioxane (3 mL) was degassed by purging nitrogen for 20 min. then added potassium phosphate tribasic (1.077 g, 6.18 mmol) followed by Pd$_2$(dba)$_3$ (0.189 g, 0.206 mmol). The resulting reaction mixture was stirred at 100° C. in sealed tube for 1 h. (TLC eluent: 5% MeOH in DCM, R$_f$—0.2; UV active). Reaction mixture was cooled to RT and water (20 mL) was added and the aqueous layer was extracted with EtOAc (2×50 mL). Organic layer was dried over sodium sulphate, filtered and concentrated under reduced pressure to get crude compound. Crude compound was purified by column chromatography (silica gel 100-200 mesh, 3% MeOH in DCM) followed by preparative HPLC (Column: Xbridge [150×19 mm 5u], Mobile Phase-A: 10 mM aq. Ammonium bicarbonate; Mobile Phase-B: Acetonitrile; Method: 0/10, 1/10, 10/50, 12.0/50, 12.1/100, 18/100, 18.1/10, 21/10; Flow: 16 ml/min; Solubility: ACN+THF+MeOH) to afford (4S)—N5-(4-(2-hydroxyethoxy)pyridin-2-yl)-N7-(2,2,2-trifluoroethyl)-3,4-dihydro-1,4-methanopyrido[2,3-b][1,4]diazepine-5,7(2H)-dicarboxamide (135 mg, 0.287 mmol, 13.90% yield) as a white solid. LCMS (m/z): 467.14 [M+H]$^+$, R$_f$=1.49 min.

$^1$H NMR (400 MHz, CDCl$_3$): δ ppm 13.67 (s, 1H), 8.64 (br t, J=6.47 Hz, 1H), 8.04 (d, J=5.92 Hz, 1H), 7.91 (d, J=7.89 Hz, 1H), 7.70 (s, 1H), 7.67 (d, J=7.71 Hz, 1H), 6.59 (dd, J=5.92, 2.41 Hz, 1H), 5.58 (dd, J=5.92, 3.07 Hz, 1H), 4.11-4.30 (m, 4H), 3.92-4.08 (m, 2H), 3.08-3.31 (m, 3H), 2.94-3.08 (m, 1H), 2.20-2.39 (m, 1H), 1.92-2.12 (m, 2H)

crude product was purified by flash column chromatography (100-200 silica gel: Eluent: 5% MeOH/CH$_2$Cl$_2$) to afford the desired product (4S)—N5-(6-((S)-2,3-dihydroxypropoxy)pyrimidin-4-yl)-N7-((R)-1,1,1-trifluoropropan-2-yl)-3,4-dihydro-1,4-methanopyrido[2,3-b][1,4]diazepine-5,7(2H)-dicarboxamide (190 mg, 0.354 mmol, 39.0% yield) as an off-white solid. LCMS (m/z): 512.26 [M+H], R$_f$=4.29 min.

$^1$H NMR (400 MHz, DMSO-d$_6$): δ ppm 13.09 (s, 1H), 8.43 (d, J=0.88 Hz, 1H), 8.25 (d, J=8.99 Hz, 1H), 7.84-7.63 (m, 2H), 7.39 (d, J=0.88 Hz, 1H), 5.45 (dd, J=5.92, 2.85 Hz, 1H), 5.05-4.85 (m, 2H), 4.66 (t, J=5.70 Hz, 1H), 4.38 (dd, J=10.85, 4.06 Hz, 1H), 4.22 (dd, J=10.85, 6.47 Hz, 1H), 3.88-3.72 (m, 1H), 3.48-3.33 (m, 2H), 3.19-2.86 (m, 4H), 2.35-2.15 (m, 1H), 2.05-1.82 (m, 1H), 1.50 (d, J=7.02 Hz, 3H).

Example 162

Synthesis of (4S)—N5-(6-((S)-2,3-dihydroxypropoxy)pyrimidin-4-yl)-N7-((R)-1,1,1-trifluoropropan-2-yl)-3,4-dihydro-1,4-methanopyrido[2,3-b][1,4]diazepine-5,7(2H)-dicarboxamide Example 163

Synthesis of (4S)—N5-(1H-pyrazolo[3,4-b]pyridin-3-yl)-N7-((R)-1,1,1-trifluoropropan-2-yl)-3,4-dihydro-1,4-methanopyrido[2,3-b][1,4]diazepine-5,7(2H)-dicarboxamide

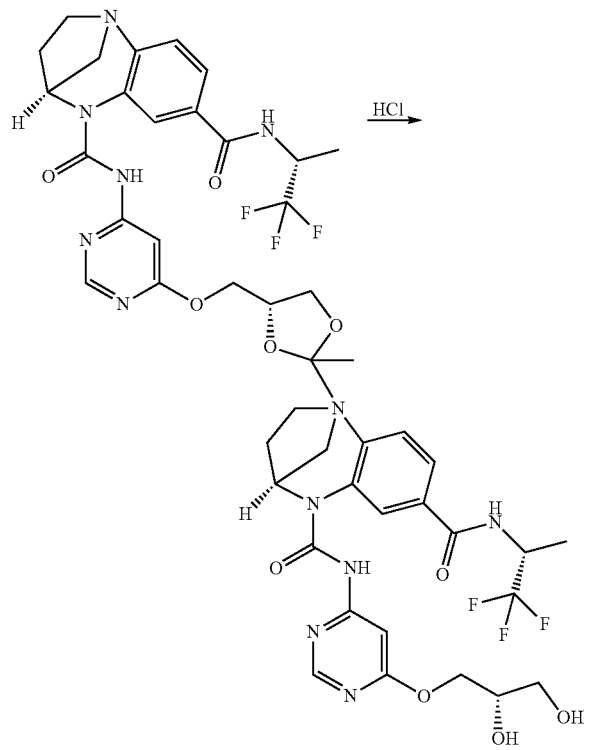

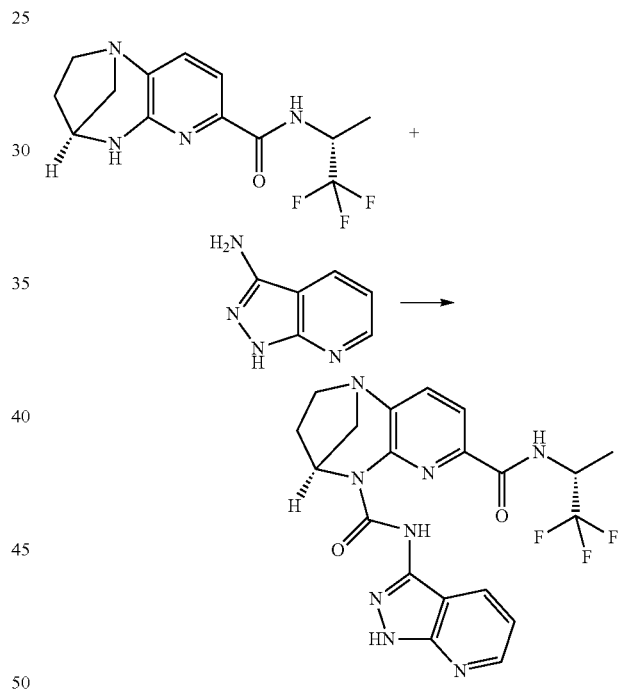

To a stirred solution of (4S)—N5-(6-(((R)-2,2-dimethyl-1,3-dioxolan-4-yl)methoxy)pyrimidin-4-yl)-N7-((R)-1,1,1-trifluoropropan-2-yl)-3,4-dihydro-1,4-methanopyrido[2,3-b][1,4]diazepine-5,7(2H)-dicarboxamide (0.5 g, 0.907 mmol) in Methanol (10 mL) was added hydrochloric acid (0.1 mL, 0.907 mmol) at 0° C. and stirred the reaction mixture at 25° C. for 4 h. (TLC system: 10% MeOH in DCM, Rf: 0.4). The reaction mixture was quenched with saturated NaHCO$_3$ solution (25 mL) and extracted with EtOAc (3×30 mL). The combined organic layer was washed with brine solution (2×20 mL), dried over anhydrous Na$_2$SO$_4$, filtered and concentrated to get crude product. The To a stirred solution of (4S)—N—((R)-1,1,1-trifluoropropan-2-yl)-2,3,4,5-tetrahydro-1,4-methanopyrido[2,3-b][1,4]diazepine-7-carboxamide (400 mg, 1.332 mmol) in THF (15 mL) at 0° C. under nitrogen was added TEA (807 mg, 7.99 mmol) and Triphosgene (395 mg, 1.332 mmol) and stirred at RT for 1 h. Then added a solution of 1H-pyrazolo [3,4-b]pyridin-3-amine (357 mg, 2.66 mmol) in THF (5 mL) and stirred at 70° C. for 16 h. (TLC system: 5% MeOH in DCM, Rf value: 0.5). Reaction mixture was cooled to RT, diluted with water (25 mL) and extracted with ethyl acetate (2×25 mL). Combined organic layer was dried over anhydrous sodium sulphate, filtered and concentrated. Crude compound was purified by flash column chromatography (silica-gel 100-200 mesh, eluted with 3% methanol in DCM) followed by Preparative HPLC (Column: XBridge C 18 (75×4.6 mm, 3.5μ), Mobile Phase: A: 5 mM Ammonium Bicarbonate; B: Acetonitrile; Gradient: Time/% B: 0/5, 0.8/5, 5/50, 9/98, 12/98, 12.1/5, 15/5; Column Temp: Ambient, Flow Rate: 0.8 ml/min, Diluent: acetonitrile) to afford (4S)—N5-(1H-pyrazolo[3,4-b]pyridin-3-yl)-N7-((R)-1,1,1-trifluoropropan-2-yl)-3,4-dihydro-1,4-methanopyrido[2,3-b][1,4]diazepine-5,7(2H)-dicarboxamide (110 mg, 0.239 mmol, 61.4% yield) as an off white solid. LCMS (m/z) =461.13 [M+H]⁺, Rt=1.78 min.

$^1$H NMR (400 MHz, DMSO-$d_6$): δ ppm 13.21 (s, 1H), 12.70 (s, 1H), 8.61 (br d, J=8.99 Hz, 1H), 8.42-8.56 (m, 2H), 7.74 (d, J=7.89 Hz, 1H), 7.64 (d, J=7.89 Hz, 1H), 7.16 (dd, J=8.22, 4.49 Hz, 1H), 5.49 (dd, J=5.81, 2.96 Hz, 1H), 4.85 (dq, J=15.62, 7.65 Hz, 1H), 3.07-3.25 (m, 3H), 2.96-3.04 (m, 1H), 2.15-2.34 (m, 1H), 1.97 (dt, J=13.98, 6.93 Hz, 1H), 1.42 (d, J=7.02 Hz, 3H)

Example 164

Synthesis of (4S)—N5-(4-ethynylpyridin-2-yl)-N7-(2,2,2-trifluoroethyl)-3,4-dihydro-1,4-methanopyrido[2,3-b][1,4]diazepine-5,7(2H)-dicarboxamide ing silica gel column, 50% EtOAc in Hexane) to afford the desired compound (4S)—N5-(4-ethynylpyridin-2-yl)-N7-(2,2,2-trifluoroethyl)-3,4-dihydro-1,4-methanopyrido[2,3-b][1,4]diazepine-5,7(2H)-dicarboxamide (170 mg, 0.392 mmol, 33.7% yield) as an off-white solid. LCMS (m/z): 431.07[M+H]⁺, R$_f$=2.33 min.

$^1$H NMR (400 MHz, CDCl$_3$): δ ppm 13.66 (s, 1H), 8.44 (br t, J=6.14 Hz, 1H), 8.09-8.31 (m, 2H), 7.92 (d, J=7.89 Hz, 1H), 7.68 (d, J=7.89 Hz, 1H), 7.07 (dd, J=5.04, 1.32 Hz, 1H), 5.61 (dd, J=5.81, 3.18 Hz, 1H), 4.10-4.32 (m, 2H), 3.11-3.32 (m, 4H), 2.97-3.09 (m, 1H), 2.20-2.43 (m, 1H), 2.06 (dt, J=14.31, 6.99 Hz, 1H).

Example 165

Synthesis of (4S)—N5-(4-(2-oxooxazolidin-3-yl)pyridin-2-yl)-N7-((R)-1,1,1-trifluoro propan-2-yl)-3,4-dihydro-1,4-methanopyrido[2,3-b][1,4]diazepine-5,7(2H)-dicarboxamide

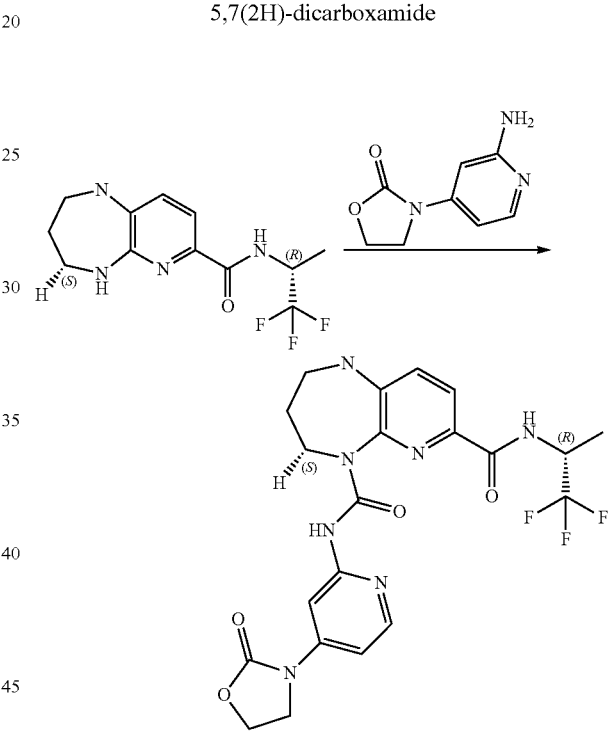

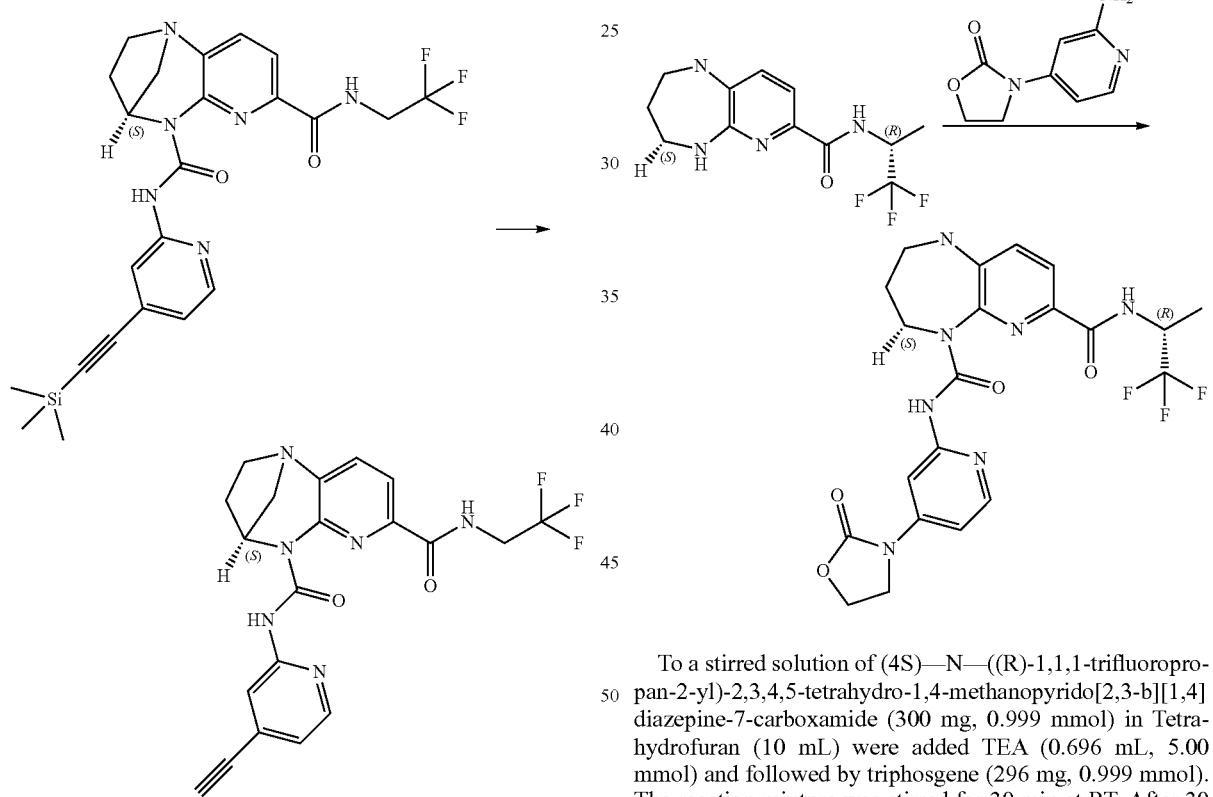

To a stirred solution of (4S)—N7-(2,2,2-trifluoroethyl)-N5-(4-((trimethylsilyl)ethynyl)pyridin-2-yl)-3,4-dihydro-1,4-methanopyrido[2,3-b][1,4]diazepine-5,7(2H)-dicarboxamide (700 mg, 1.393 mmol) in Methanol (20 mL) under nitrogen at RT was added potassium fluoride (202 mg, 3.48 mmol) and stirred for 3 h. (TLC eluent: 70% EtOAc in Hexane: R$_f$—0.3; UV active). methanol was evapourated and the reaction mixture was diluted with water (10 ml) and extracted with ethylacetate (20 ml). The organic layer was dried over anhydrous Na$_2$SO$_4$, filtered and concentrated under reduced pressure to get crude compound. The crude compound was purified by combiflash chromatography (us- To a stirred solution of (4S)—N—((R)-1,1,1-trifluoropropan-2-yl)-2,3,4,5-tetrahydro-1,4-methanopyrido[2,3-b][1,4]diazepine-7-carboxamide (300 mg, 0.999 mmol) in Tetrahydrofuran (10 mL) were added TEA (0.696 mL, 5.00 mmol) and followed by triphosgene (296 mg, 0.999 mmol). The reaction mixture was stirred for 30 min at RT. After 30 min 3-(2-aminopyridin-4-yl) oxazolidin-2-one (269 mg, 1.499 mmol) was added. The resulting reaction mixture was stirred at 80° C. for 24 h. (TLC system: 5% MeOH in DCM, Rf: 0.3). Reaction mixture was poured in ice cold water (20 mL), extracted with EtOAc (2×20 mL). The combined organic layer was washed with brine (10 mL) and dried over anhydrous Na$_2$SO$_4$, filtered and concentrated under reduced pressure to obtain crude compound. The crude material was purified by flash column chromatography (100-200 silica mesh, Eluent: 4% MeOH in DCM) to afford the desired product (4S)—N5-(4-(2-oxooxazolidin-3-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (38 mg, 0.074 mmol, 7.45% yield) as an off-white solid. LCMS (m/z): 506.17 [M+H]⁺, R_f=1.97 min.

¹H NMR (400 MHz, DMSO-d₆): δ ppm 13.07 (s, 1H), 8.32 (d, J=1.53 Hz, 1H), 8.25-8.07 (m, 2H), 7.76 (s, 2H), 7.36 (dd, J=5.81, 2.08 Hz, 1H), 5.46 (d, J=2.41 Hz, 1H), 4.98 (dd, J=15.35, 7.45 Hz, 1H), 4.49 (t, J=8.00 Hz, 2H), 4.09 (t, J=7.89 Hz, 2H), 3.27-2.92 (m, 4H), 2.46-2.23 (m, 1H), 2.29-2.11 (m, 1H), 1.53 (d, J=7.02 Hz, 3H).

Example 166

Synthesis of (4S)—N5-(7H-purin-2-yl)-N7-((R)-1,1,1-trifluoropropan-2-yl)-3,4-dihydro-1,4-methanopyrido[2,3-b][1,4]diazepine-5,7(2H)-dicarboxamide

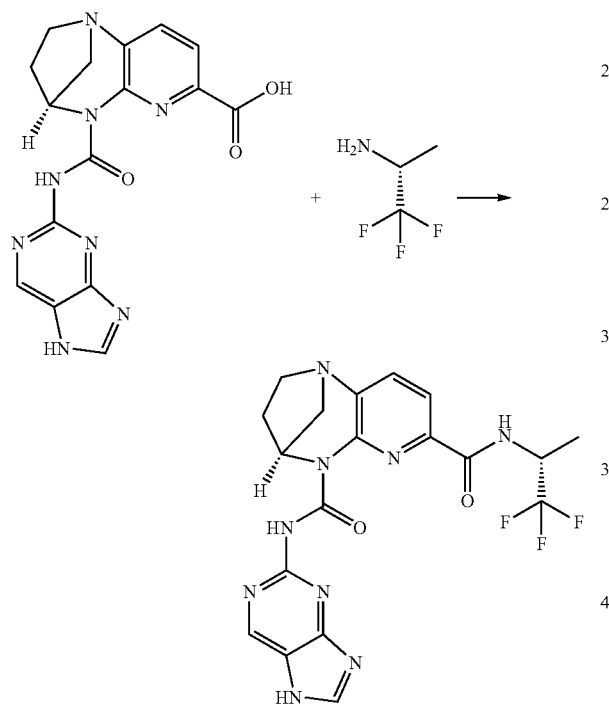

To a stirred solution of (4S)-5-((7H-purin-2-yl)carbamoyl)-2,3,4,5-tetrahydro-1,4-methanopyrido[2,3-b][1,4]diazepine-7-carboxylic acid (120 mg, 0.328 mmol), HATU (187 mg, 0.491 mmol) in N,N-Dimethylformamide (DMF) (10 mL) were added DIPEA (0.229 mL, 1.310 mmol) and (R)-1,1,1-trifluoropropan-2-amine (37.0 mg, 0.328 mmol). The reaction mixture was stirred at room temperature for 16 h. (TLC System: 10% MeOH in DCM: R_f—0.3; UV active). Then poured into water (20 mL) and extracted with EtOAc (3×10 mL). The combined organic layer was washed with brine (2×10 mL) solution dried over anhydrous Na₂SO₄, filtered and evaporated to obtain crude compound. The crude was purified by GRACE system purification (C-18 reserval column, Eluent: A: 0.1% Formic Acid in water; B: MeOH) to afford the desired product (4S)—N5-(7H-purin-2-yl)-N7-((R)-1,1,1-trifluoropropan-2-yl)-3,4-dihydro-1,4-methanopyrido[2,3-b][1,4]diazepine-5,7(2H)-dicarboxamide (75 mg, 0.162 mmol, 49.5% yield) as an off-white solid. LCMS (m/z): 462.10 [M+H]⁺; R_f=1.55 min.

¹H NMR (400 MHz, CDCl₃): δ ppm 13.95 (s, 1H), 13.75 (s, 1H), 8.99 (s, 1H), 8.61 (s, 1H), 8.21-8.00 (m, 2H), 7.75 (d, J=7.89 Hz, 1H), 5.76 (dd, J=5.81, 2.74 Hz, 1H), 5.22- 5.09 (m, 1H), 3.39-3.03 (m, 4H), 2.43 (td, J=14.20, 5.59 Hz, 1H), 2.15 (dt, J=14.25, 6.91 Hz, 1H), 1.64 (d, J=7.23 Hz, 3H).

Example 167

Synthesis of (4S)—N5-(4-acetamidopyridin-2-yl)-N7-(2,2,2-trifluoroethyl)-3,4-dihydro-1,4-methanopyrido[2,3-b][1,4]diazepine-5,7(2H)-dicarboxamide

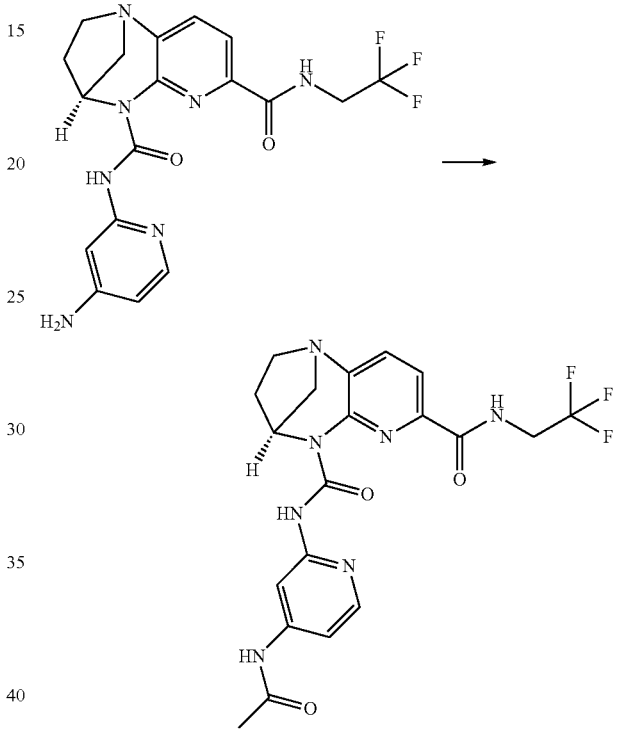

To a stirred solution of (4S)—N5-(4-aminopyridin-2-yl)-N7-(2,2,2-trifluoroethyl)-3,4-dihydro-1,4-methanopyrido[2,3-b][1,4]diazepine-5,7(2H)-dicarboxamide (400 mg, 0.949 mmol) in DCM (20 mL) at 0° C. under nitrogen was added Ac₂O (0.448 mL, 4.75 mmol), Et₃N (0.794 mL, 5.70 mmol) and stirred at RT for 65 h. (TLC eluent: 5% MeOH in DCM R_f—0.2; UV active). The reaction mixture was diluted with water (30 mL) and extracted into DCM (2×30 mL). Combined organic extracts were dried over anhydrous sodium sulphate, filtered and filtrate was evaporated to get crude product. The crude compound was purified by column chromatography (neutral alumina, eluent: 80-85% ethyl acetate in hexane). Collected fractions were concentrated under reduce pressure to afford desired product (4S)—N5-(4-acetamidopyridin-2-yl)-N7-(2,2,2-trifluoroethyl)-3,4-dihydro-1,4-methanopyrido[2,3-b][1,4]diazepine-5,7(2H)-dicarboxamide (230 mg, 0.493 mmol, 51.9% yield) as an off white solid. LCMS (m/z): 464.15 [M+H]⁺, R_f=1.61 min.

¹H NMR (400 MHz, CDCl₃): δ ppm 13.66 (s, 1H), 8.56 (t, J=6.36 Hz, 1H), 8.13 (d, J=5.70 Hz, 1H), 7.91 (d, J=7.89 Hz, 1H), 7.83 (d, J=1.97 Hz, 1H), 7.72-7.65 (m, 2H), 7.42 (s, 1H), 5.58 (dd, J=5.92, 3.29 Hz, 1H), 4.30-4.12 (m, 2H), 3.31-3.09 (m, 3H), 3.07-2.97 (m, 1H), 2.40-2.27 (m, 1H), 2.21 (s, 3H), 2.11-1.97 (m, 1H).

Example 168

Synthesis of (4S)—N5-(5-(methylcarbamoyl)pyridin-2-yl)-N7-(2,2,2-trifluoroethyl)-3,4-dihydro-1,4-methanopyrido[2,3-b][1,4]diazepine-5,7(2H)-dicarboxamide

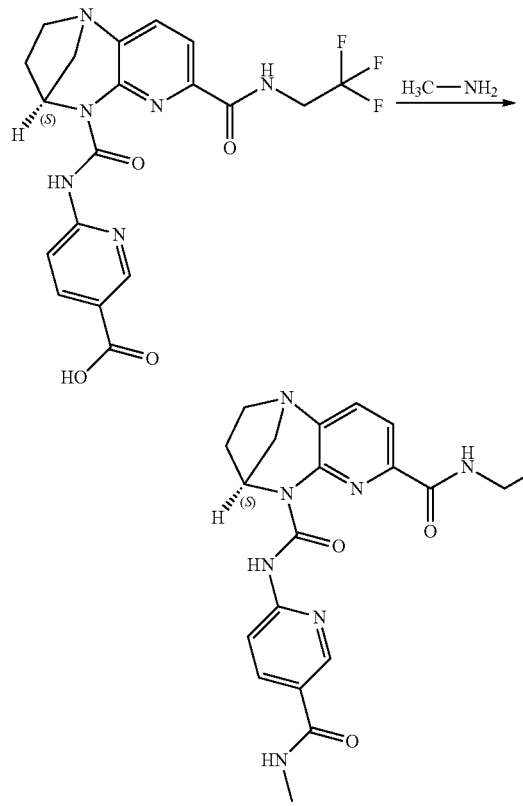

To a stirred solution of 6-((4S)-7-((2,2,2-trifluoroethyl)carbamoyl)-2,3,4,5-tetrahydro-1,4-methanopyrido[2,3-b][1,4]diazepine-5-carboxamido)nicotinic acid (600 mg, 1.332 mmol), in DMF (5 mL) at 0° C. was added DIPEA (0.233 mL, 1.332 mmol), HATU (1013 mg, 2.66 mmol) and stirred for 20 min. Methanamine (10 mL, 50.0 mmol) was added to the above reaction mixture and stirred at RT for 16 h. (TLC eluent: 5% MeOH in DCM: $R_f$—0.5; UV active). The reaction mixture was partitioned between water (50 mL) and EtOAc (50 mL) then organic layer was separated, dried over anhydrous sodium sulphate, filtered and filtrate was evaporated to get crude compound. Crude material was purified by column chromatography (Silica gel 100-200 mesh, 3% MeOH in DCM). Fractions containing pure compound were combined and concentrated to afford (4S)—N5-(5-(methylcarbamoyl)pyridin-2-yl)-N7-(2,2,2-trifluoroethyl)-3,4-dihydro-1,4-methanopyrido[2,3-b][1,4]diazepine-5,7(2H)-dicarboxamide (40 mg, 0.086 mmol, 6.46% yield) as an off white solid. LCMS (m/z): 464.15[M+H]$^+$, $R_t$=1.77 min.

$^1$H NMR (400 MHz, CDCl$_3$): δ ppm 13.49 (s, 1H), 8.76-8.83 (m, 1H), 8.65 (t, J=6.47 Hz, 1H), 8.48 (br d, J=4.60 Hz, 1H), 8.25 (dd, J=8.66, 2.30 Hz, 1H), 8.06 (dd, J=8.77, 0.66 Hz, 1H), 7.71-7.81 (m, 2H), 5.44 (dd, J=5.92, 3.07 Hz, 1H), 4.24-4.38 (m, 2H), 3.29 (s, 3H), 2.95-3.03 (m, 1H), 2.80 (d, J=4.38 Hz, 3H), 2.22 (br s, 1H), 1.93-2.03 (m, 1H).

Example 169

Synthesis of (4S)—N5-(6-(2-methyloxazol-5-yl)pyrimidin-4-yl)-N7-(2,2,2-trifluoroethyl)-3,4-dihydro-1,4-methanopyrido[2,3-b][1,4]diazepine-5,7(2H)-dicarboxamide

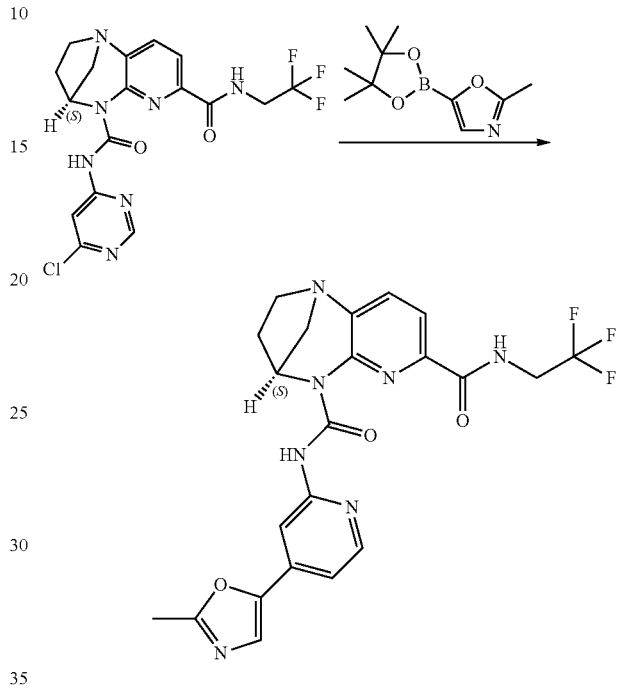

To a stirred solution of (4S)—N5-(6-chloropyrimidin-4-yl)-N7-(2,2,2-trifluoroethyl)-3,4-dihydro-1,4-methanopyrido[2,3-b][1,4]diazepine-5,7(2H)-dicarboxamide (400 mg, 0.905 mmol) and 2-methyl-5-(4,4,5,5-tetramethyl-1,3,2-dioxaborolan-2-yl)oxazole (246 mg, 1.177 mmol) in 1,4-Dioxane (10 mL) and water (1 mL) at RT was added potassium acetate (178 mg, 1.811 mmol) and the mixture was degassed for 15 min with nitrogen, then added PdCl$_2$(dppf)-CH$_2$Cl$_2$ adduct (73.9 mg, 0.091 mmol) and the reaction was stirred at 90° C. for 16 h. (TLC eluent: 5% MeOH in DCM: $R_f$—0.4; UV active). Reaction mixture was cooled to RT and water (80 mL) was added then the aqueous layer was extracted with ethylacetate (2×50 mL). Combined organic layer was dried over sodium sulphate, filtered and concentrated under reduced pressure to get crude compound. The crude product was purified by chromatography (silica gel 100-200, using 3% MeOH in DCM) to afford (4S)—N5-(6-(2-methyloxazol-5-yl)pyrimidin-4-yl)-N7-(2,2,2-trifluoroethyl)-3,4-dihydro-1,4-methanopyrido[2,3-b][1,4]diazepine-5,7(2H)-dicarboxamide (110 mg, 0.222 mmol, 24.50% yield) as a white solid. LCMS (m/z): 489.14[M+H]$^+$, $R_t$=1.97 min.

$^1$H NMR (400 MHz, DMSO-d$_6$): δ ppm 13.52 (s, 1H), 8.84 (d, J=1.10 Hz, 1H), 8.64 (br t, J=6.47 Hz, 1H), 8.22 (d, J=1.10 Hz, 1H), 7.65-7.88 (m, 3H), 5.43 (dd, J=5.70, 2.85 Hz, 1H), 4.27 (dt, J=17.70, 8.58 Hz, 2H), 2.95-3.22 (m, 4H), 2.57 (s, 3H), 2.20-2.34 (m, 1H), 1.99 (dt, J=13.70, 6.96 Hz, 1H).

Example 170

Synthesis of (4S)—N5-(1H-pyrazolo[3,4-c]pyridin-5-yl)-N7-((R)-1,1,1-trifluoropropan-2-yl)-3,4-dihydro-1,4-methanopyrido[2,3-b][1,4]diazepine-5,7(2H)-dicarboxamide

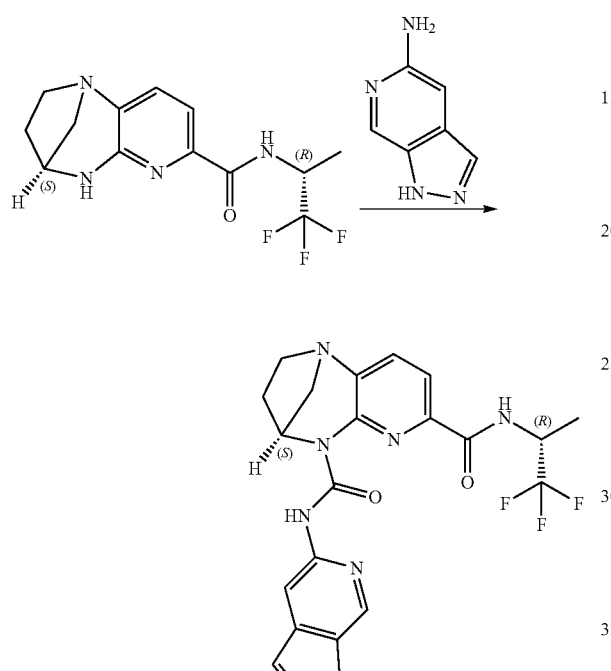

To a stirred solution of (4S)—N—((R)-1,1,1-trifluoropropan-2-yl)-2,3,4,5-tetrahydro-1,4-methanopyrido[2,3-b][1,4]diazepine-7-carboxamide (0.3 g, 0.999 mmol) in THF (25 mL) under nitrogen at RT was added Et$_3$N (0.696 mL, 5.00 mmol), triphosgene (0.296 g, 0.999 mmol) and stirred for 1 h. then 1H-pyrazolo[3,4-c]pyridin-5-amine (0.335 g, 2.498 mmol) was added and reaction mixture was heated at 65° C. for 16 h. (TLC eluent: 100% EtOAc: R$_f$—0.3; UV active). The reaction mixture was cooled to room temperature, concentrated in vacuo and the residue was partitioned between water (50 mL) and EtOAc (50 mL). Organic layer was separated and dried over anhydrous sodium sulphate, filtered and filtrate was evaporated to get crude compound. The crude product was purified by flash column chromatography (neutral alumina, eluent: 70% ethyl acetate in hexane) to afford (4S)—N5-(1H-pyrazolo[3,4-c]pyridin-5-yl)-N7-((R)-1,1,1-trifluoropropan-2-yl)-3,4-dihydro-1,4-methanopyrido[2,3-b][1,4]diazepine-5,7(2H)-dicarboxamide (0.085 g, 0.183 mmol, 18.33% yield) as an off white solid. LCMS (m/z): 461.17.10 [M+H]$^+$, R$_t$=1.91 min.

$^1$H NMR (400 MHz, CDCl$_3$): δ ppm 13.19 (br s, 1H), 10.12-10.67 (m, 1H), 8.72 (s, 1H), 8.50 (s, 1H), 7.83-8.24 (m, 3H), 7.68 (br d, J=7.67 Hz, 1H), 5.70 (br s, 1H), 4.98-5.30 (m, 1H), 2.96-3.41 (m, 4H), 2.35 (br d, J=5.48 Hz, 1H), 2.02-2.18 (m, 1H), 1.39-1.75 (m, 3H).

Example 171

Synthesis (4S)—N7-benzyl-N5-(4-((R)-2,3-dihydroxypropoxy)pyridin-2-yl)-3,4-dihydro-1,4-methanopyrido[2,3-b][1,4]diazepine-5,7(2H)-dicarboxamide

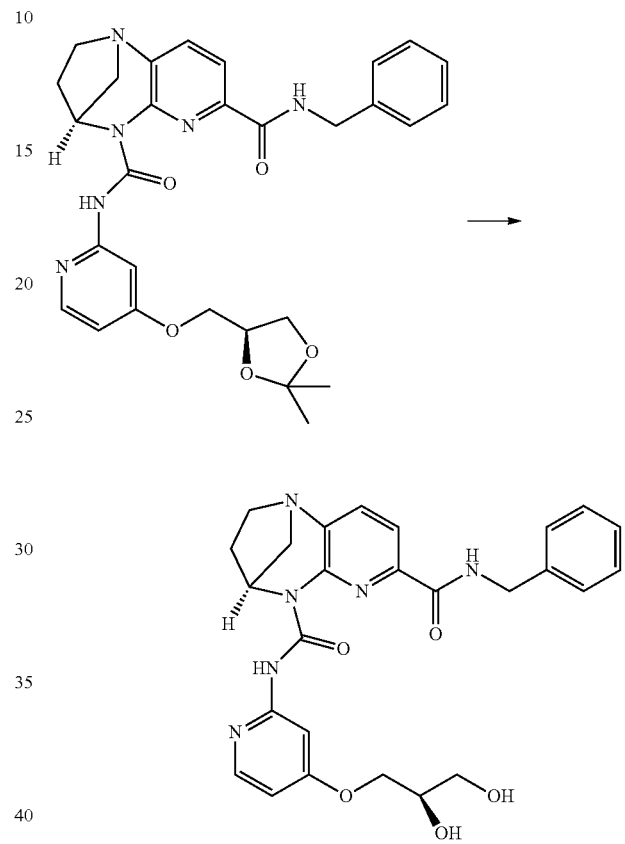

To a stirred solution of (4S)—N7-benzyl-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide (350 mg, 0.643 mmol) in methanol (10 mL) at RT was added 2M HCl (0.5 mL, 1.000 mmol) and stirred for 3 h. (TLC system: 5% MeOH in DCM, Rf value: 0.2). Reaction mixture was concentrated to remove methanol completely and basified the reaction mixture with saturated NaHCO$_3$ (15 mL) solution. The resultant solid was filtered, washed with water (20 mL) and dried under high vacuum to obtain the desired product (4S)—N7-benzyl-N5-(4-((R)-2,3-dihydroxypropoxy)pyridin-2-yl)-3,4-dihydro-1,4-methanopyrido[2,3-b][1,4]diazepine-5,7(2H)-dicarboxamide (142 mg, 0.276 mmol, 43.0% yield) as an off-white solid. LCMS (m/z): 505.20 [M+H]$^+$, Rt=1.53 min.

$^1$H NMR (400 MHz, CDCl$_3$): δ ppm 13.71 (s, 1H), 8.73 (br t, J=5.81 Hz, 1H), 7.92 (d, J=7.89 Hz, 1H), 7.55-7.76 (m, 3H), 7.43 (d, J=7.23 Hz, 2H), 7.19-7.35 (m, 3H), 6.47 (dd, J=5.81, 2.30 Hz, 1H), 5.57 (dd, J=5.81, 2.96 Hz, 1H), 4.69-4.83 (m, 2H), 4.00-4.25 (m, 3H), 3.79-3.96 (m, 2H), 3.00-3.31 (m, 4H), 2.50-2.65 (m, 1H), 2.18-2.38 (m, 1H), 1.90-2.18 (m, 2H)

Example 172

Synthesis of (4S)—N5-(5-isopropylpyridin-2-yl)-N7-(2,2,2-trifluoroethyl)-3,4-dihydro-1,4-methanopyrido[2,3-b][1,4]diazepine-5,7(2H)-dicarboxamide

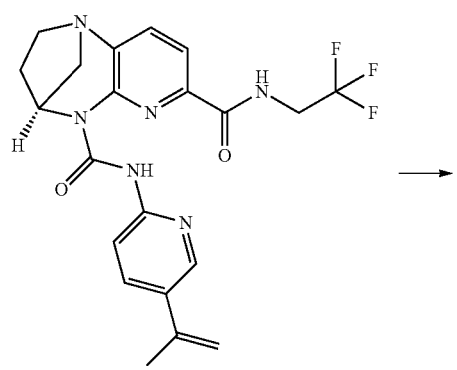

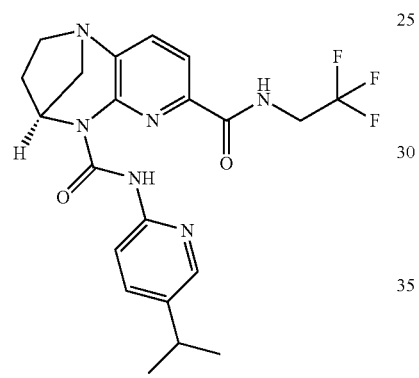

To a stirred solution of (4S)—N5-(5-(prop-1-en-2-yl)pyridin-2-yl)-N7-(2,2,2-trifluoroethyl)-3,4-dihydro-1,4-methanopyrido[2,3-b][1,4]diazepine-5,7(2H)-dicarboxamide (400 mg, 0.896 mmol) in ethanol (5 mL) was flushed with nitrogen for 3 min, then added Pd—C (95 mg, 0.090 mmol) under nitrogen condition. The reaction mass was stirred under Hydrogen balloon at RT for 16 h. (TLC system 5% Methanol in DCM. Rf value 0.6.) The reaction mass was filtered through celite bed, washed with ethanol (30 mL) and concentrated under reduced pressure to afford pale brown viscous oil. This was further purified by preparative HPLC (XTerra RP18 (250×19 mm, 10u; Mobile Phase-A: 10 mM Ammonium Bicarbonate (aq), Mobile Phase-B: Acetonitrile; Method % B/time: 0/60, 8.4/60, 8.5/100, 12.5/100, 12.6/60, 16/60; Flow: 18 ml/min; Solubility: Methanol+ACN+THF) to afford (4S)—N5-(5-isopropylpyridin-2-yl)-N7-(2,2,2-trifluoroethyl)-3,4-dihydro-1,4-methanopyrido[2,3-b][1,4]diazepine-5,7(2H)-dicarboxamide (310 mg, 0.682 mmol, 76% yield) as an off-white solid. LCMS (m/z): 449.32 [M+H]+, Rt=2.47 min.

$^1$H NMR (400 MHz, DMSO-d$_6$): δ ppm 13.27 (s, 1H), 8.61-8.77 (m, 1H), 8.23 (d, J=2.19 Hz, 1H), 7.92 (d, J=8.55 Hz, 1H), 7.70-7.81 (m, 3H), 5.41 (dd, J=5.92, 3.29 Hz, 1H), 4.31 (br d, J=8.99 Hz, 2H), 3.05-3.23 (m, 3H), 2.89-3.02 (m, 2H), 2.18-2.30 (m, 1H), 1.88-2.00 (m, 1H), 1.22 (d, J=6.80 Hz, 6H).

Example 173

Synthesis of (4S)—N5-(5-((R)-2,3-dihydroxypropoxy)pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide

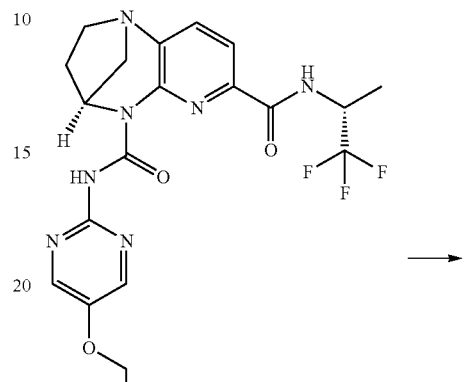

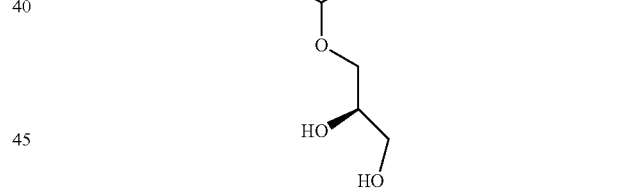

To a stirred solution of (4S)—N5-(5-(((S)-2,2-dimethyl-1,3-dioxolan-4-yl)methoxy)pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide (250 mg, 0.453 mmol) in methanol (50 mL) at 0° C. was added aq. HCl (0.567 mL, 6.80 mmol) and stirred at RT for 1 h (TLC eluent system: 100% EtOAc, R$_f$: 0.4, UV active). The reaction mixture was concentrated under reduced pressure and the residue was basified with saturated sodium bicarbonate solution (till pH-8-9) and the precipitated solid was filtered, dried to afford the crude product. Crude compound was triturated with diethyl ether (5 mL) to afford (4S)—N5-(5-((R)-2,3-dihydroxypropoxy)pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide (153 mg, 0.298 mmol, 65.7% yield) as white solid. LCMS (m/z): 512.18 [M+H]+, R$_t$=1.55 min.

$^1$H NMR (400 MHz, CDCl$_3$): δ ppm 13.45 (s, 1H), 8.34 (s, 2H), 7.95 (d, J=7.89 Hz, 1H), 7.79 (br d, J=9.65 Hz, 1H), 7.52-7.73 (m, 1H), 5.70 (br dd, J=5.81, 2.96 Hz, 1H), 5.05 (br dd, J=15.35, 8.11 Hz, 1H), 4.03-4.27 (m, 3H), 3.87 (br d, J=3.73 Hz, 1H), 3.67-3.84 (m, 1H), 2.91-3.37 (m, 4H), 2.63 (br d, J=3.73 Hz, 1H), 2.21-2.41 (m, 1H), 1.95-2.17 (m, 2H), 1.54-1.60 (m, 3H).

Example 174

Synthesis of (4S)—N5-(5-cyclopropylpyridin-2-yl)-N7-(2,2,2-trifluoroethyl)-3,4-dihydro-1,4-methanopyrido[2,3-b][1,4]diazepine-5,7(2H)-dicarboxamide

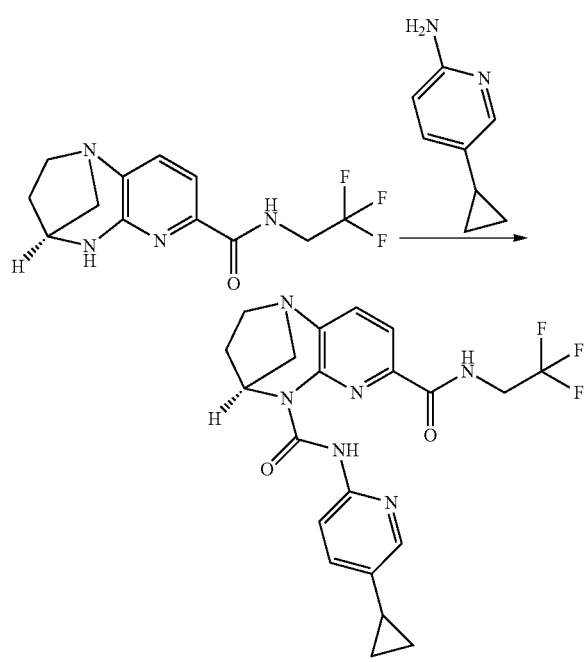

To a stirred solution of (4S)—N-(2,2,2-trifluoroethyl)-2,3,4,5-tetrahydro-1,4-methanopyrido[2,3-b][1,4]diazepine-7-carboxamide (800 mg, 2.79 mmol) in THF (10 mL) at RT under nitrogen atmosphere was added triphosgene (829 mg, 2.79 mmol) and TEA (1.169 mL, 8.38 mmol) and stirred for 1 h. Then added a solution of 5-cyclopropylpyridin-2-amine (450 mg, 3.35 mmol) in THF (10 mL) and the resulting reaction mixture was stirred at 80° C. for 16 h. (TLC system 5% Methanol in DCM. Rf value: 0.6). The reaction mixture was cooled to RT, diluted with water (100 mL) and extracted with EtOAc (3×100 mL). Combined organic layers were dried over anhydrous $Na_2SO_4$, filtered and concentrated under reduced pressure to get crude compound. The crude product was purified by combiflash chromatography (silica gel column and was eluted with $CH_2Cl_2$/MeOH) followed by preparative HPLC. (Column: Sunfire (150×19) mm, 5u; MobilePhase-A: 10 mm Ammonium Bicarbonate, Mobile Phase-B: Acetonitrile; Method (T/% B): 0/60, 10/60, 10.1/100, 13/100, 13.1/60; Flow: 18 ml/min; Solubility: Acetonitrile+THF+MeOH) to afford (4S)—N5-(5-cyclopropylpyridin-2-yl)-N7-(2,2,2-trifluoroethyl)-3,4-dihydro-1,4-methanopyrido[2,3-b][1,4]diazepine-5,7(2H)-dicarboxamide (65 mg, 0.145 mmol, 5.18% yield) as an off-white solid. LCMS (m/z): 447.31[M+H]$^+$, Rt=2.34 min.

$^1$H NMR (400 MHz, DMSO-$d_6$): δ ppm 13.28 (s, 1H) 8.65 (br t, J=6.58 Hz, 1H), 8.19 (d, J=2.19 Hz, 1H), 7.88 (d, J=8.55 Hz, 1H), 7.64-7.78 (m, 2H), 7.50 (dd, J=8.44, 2.30 Hz, 1H), 5.40 (dd, J=5.59, 3.18 Hz, 1H), 4.23-4.39 (m, 2H), 3.03-3.23 (m, 3H), 2.89-3.00 (m, 1H), 2.14-2.30 (m, 1H), 1.83-2.05 (m, 2H), 0.90-1.06 (m, 2H), 0.61-0.75 (m, 2H).

Example 175

Synthesis of (4S)—N5-(5-methyl-7H-pyrrolo[2,3-d]pyrimidin-2-yl)-N7-((R)-1,1,1-trifluoro propan-2-yl)-3,4-dihydro-1,4-methanopyrido[2,3-b][1,4]diazepine-5,7(2H)-dicarboxamide

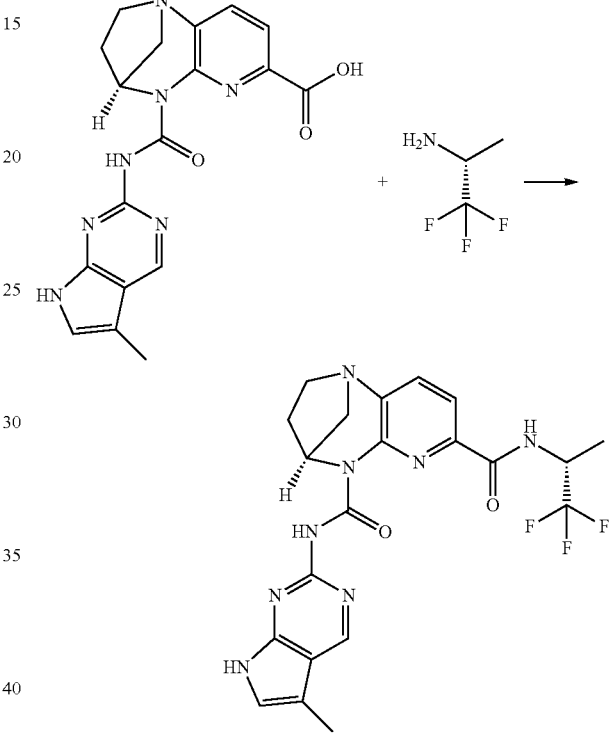

To a stirred solution of (4S)-5-((5-methyl-7H-pyrrolo[2,3-d]pyrimidin-2-yl)carbamoyl)-2,3,4,5-tetrahydro-1,4-methanopyrido[2,3-b][1,4]diazepine-7-carboxylic acid (250 mg, 0.659 mmol), HATU (376 mg, 0.988 mmol) in N,N-Dimethylformamide (10 mL) were added DIPEA (0.460 mL, 2.64 mmol) and (R)-1,1,1-trifluoropropan-2-amine (74.5 mg, 0.659 mmol) at 0° C. and the reaction mixture was stirred at room temperature for 16 h. (TLC System: 10% MeOH in DCM: R$_f$—0.3; UV active). The reaction mixture was poured into water (30 mL) and extracted with EtOAc (3×20 mL). The combined organic layer was washed with brine solution dried over anhydrous $Na_2SO_4$, filtered and evaporated to obtain crude compound. The crude was purified by GRACE (C-18 reverse column, Eluent: 70% of MeOH in 0.1% Formic Acid in water) to afford the desired product (4S)—N5-(5-methyl-7H-pyrrolo[2,3-d]pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide (105 mg, 0.219 mmol, 33.3% yield) as an off white solid. LCMS (m/z): 475.14 [M+H]$^+$; R$_t$=1.67 min.

$^1$H NMR (400 MHz, CDCl$_3$): δ ppm 13.54 (s, 1H), 10.57 (s, 1H), 8.65 (s, 1H), 8.18 (d, J=9.43 Hz, 1H), 7.98 (d, J=7.89 Hz, 1H), 7.70 (d, J=7.89 Hz, 1H), 7.09 (s, 1H), 5.75 (dd, J=5.81, 2.96 Hz, 1H), 5.18-5.04 (m, 1H), 3.33-3.11 (m, 3H), 3.09-3.01 (m, 1H), 2.42-2.30 (m, 4H), 2.12 (dt, J=14.25, 7.34 Hz, 1H), 1.69-1.54 (m, 3H).

Example 176

Synthesis of (4S)—N5-(5-methyl-7H-pyrrolo[2,3-d]pyrimidin-2-yl)-N7-(2,2,2-trifluoro ethyl)-3,4-dihydro-1,4-methanopyrido[2,3-b][1,4]diazepine-5,7(2H)-dicarboxamide

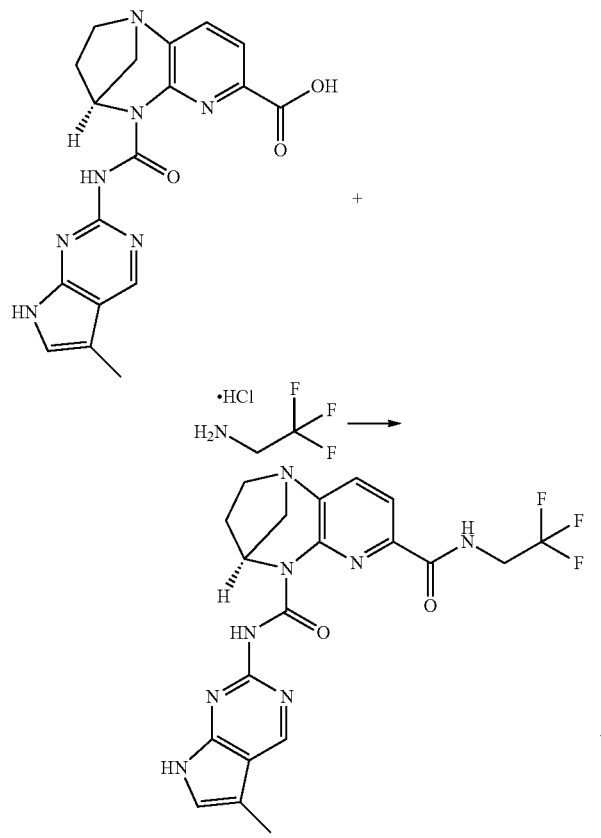

To a stirred solution of (4S)-5-((5-methyl-7H-pyrrolo[2,3-d]pyrimidin-2-yl)carbamoyl)-2,3,4,5-tetrahydro-1,4-methanopyrido[2,3-b][1,4]diazepine-7-carboxylic acid (250 mg, 0.659 mmol), HATU (376 mg, 0.988 mmol) in N,N-Dimethylformamide (10 mL) were added DIPEA (0.460 mL, 2.64 mmol) and 2,2,2-trifluoroethanamine hydrochloride (89 mg, 0.659 mmol) at 0° C. The reaction mixture was stirred at room temperature for 16 h. (TLC System: 10% MeOH in DCM: R$_f$—0.3; UV active). Then the reaction mixture was poured into water (20 mL) and extracted with EtOAc (3×20 mL). The combined organic layer was washed with brine solution and dried over anhydrous Na$_2$SO$_4$, filtered and evaporated to obtain crude compound. The crude compound was purified by GRACE (C-18 reserval column, Eluent: 50% of MeOH in 0.1% Formic Acid in water) to afford the desired product (4S)—N5-(5-methyl-7H-pyrrolo[2,3-d]pyrimidin-2-yl)-N7-(2,2,2-trifluoroethyl)-3,4-dihydro-1,4-methanopyrido[2,3-b][1,4]diazepine-5,7(2H)-dicarboxamide (150 mg, 0.312 mmol, 47.3% yield) as an off-white solid. LCMS (m/z): 461.13 [M+H]$^+$; R$_t$=1.59 min.

$^1$H NMR (400 MHz, CDCl$_3$): δ ppm 13.95 (s, 1H), 10.55 (br s, 1H), 8.82 (t, J=6.47 Hz, 1H), 8.63 (s, 1H), 7.94 (d, J=7.89 Hz, 1H), 7.70 (d, J=7.89 Hz, 1H), 7.10 (s, 1H), 5.72 (dd, J=5.70, 2.85 Hz, 1H), 4.34-4.22 (m, 2H), 3.32-3.14 (m, 3H), 3.09-3.03 (m, 1H), 2.43-2.31 (m, 4H), 2.12 (dt, J=14.47, 7.23 Hz, 1H).

Example 177

Synthesis of (4S)—N5-(5-((S)-2,3-dihydroxypropoxy)pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide

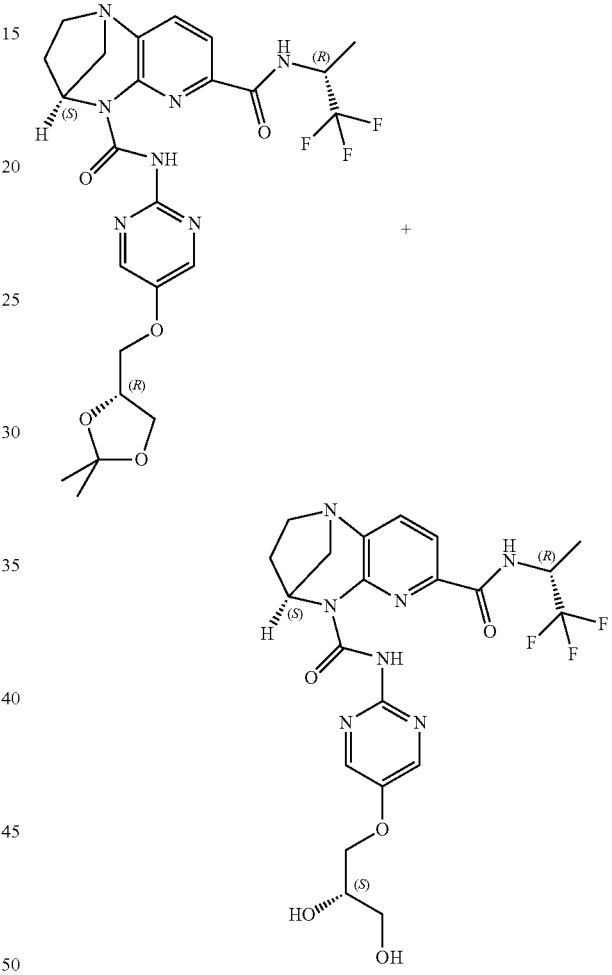

To a stirred solution of (4S)—N5-(5-(((R)-2,2-dimethyl-1,3-dioxolan-4-yl)methoxy)pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide (250 mg, 0.453 mmol) in methanol (10 mL) was added hydrochloric acid (4 ml, 132 mmol) at 0° C. and the reaction mixture was stirred at 30° C. for 2 h. (TLC eluent: 10% MeOH in DCM: R$_f$—0.15; UV active). Then evaporated the solvent and neutralized with saturated NaHCO$_3$ solution and filtered the obtained solid, washed with water and diethyl ether to afford the desired product (4S)—N5-(5-((S)-2,3-dihydroxypropoxy)pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide (120 mg, 0.226 mmol, 49.9% yield) as a pale brown solid. LCMS (m/z): 512.18 [M+H]$^+$; Rt=1.54 min.

¹H NMR (400 MHz, DMSO-d₆): δ ppm 12.90 (s, 1H), 8.40 (s, 2H), 8.31 (br d, J=8.99 Hz, 1H), 7.77-7.64 (m, 2H), 5.44 (dd, J=5.81, 3.18 Hz, 1H), 5.01 (d, J=5.26 Hz, 1H), 4.96-4.84 (m, 1H), 4.69 (t, J=5.70 Hz, 1H), 4.15 (dd, J=9.98, 3.84 Hz, 1H), 4.03 (dd, J=10.08, 6.14 Hz, 1H), 3.85-3.75 (m, 1H), 3.50-3.40 (m, 2H), 3.23-2.91 (m, 4H), 2.29-2.17 (m, 1H), 1.91 (dt, J=13.92, 7.07 Hz, 1H), 1.44 (d, J=7.02 Hz, 3H).

Example 178

Synthesis of (4S)—N7-allyl-N5-(4-(((R)-2,3-dihydroxypropoxy)pyridin-2-yl)-3,4-dihydro-1,4-methanopyrido[2,3-b][1,4]diazepine-5,7(2H)-dicarboxamide

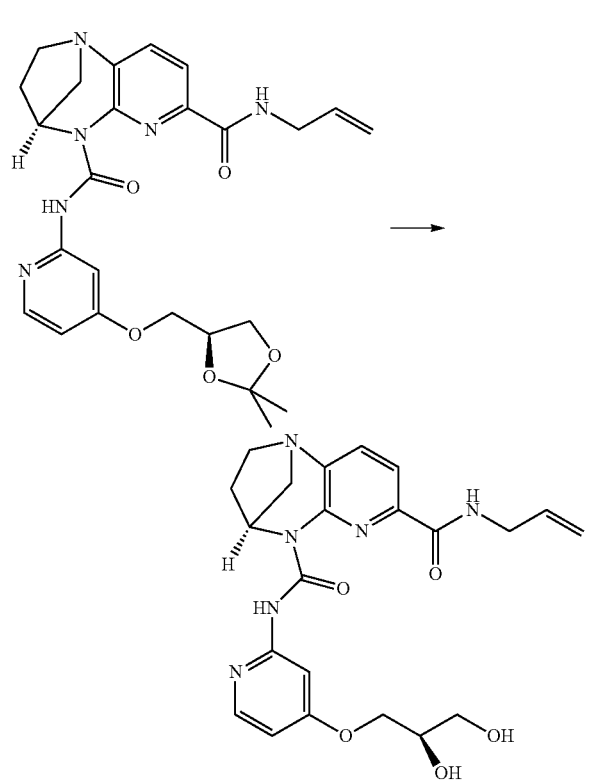

To a stirred solution of (4S)—N7-allyl-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide (500 mg, 1.011 mmol) in methanol (10 mL) at RT was added 2M HCl (0.75 mL, 1.500 mmol) and stirred for 3 h. (TLC system: 5% MeOH in DCM, Rf value: 0.2). Reaction mixture was concentrated to remove methanol completely and basified the reaction mixture with saturated NaHCO₃ (15 mL) solution. The resultant solid was filtered, washed with water (20 mL) and dried under high vacuum to get the crude compound as a solid. The solid product was triturated with diethylether (10 mL), filtered and dried to afford (4S)—N7-allyl-N5-(4-((R)-2,3-dihydroxypropoxy)pyridin-2-yl)-3,4-dihydro-1,4-methanopyrido[2,3-b][1,4]diazepine-5,7(2H)-dicarboxamide (400 mg, 0.877 mmol, 87% yield) as an off-white solid. LCMS (m/z): 455.19 [M+H]⁺, Rt=1.24 min. 1H NMR (400 MHz, CDCl₃): δ ppm 13.68 (s, 1H), 8.36 (br s, 1H), 8.02 (d, J=5.92 Hz, 1H), 7.90 (d, J=7.89 Hz, 1H), 7.57-7.79 (m, 2H), 6.56 (dd, J=5.81, 2.30 Hz, 1H), 5.84-6.11 (m, 1H), 5.57 (br dd, J=5.81, 2.96 Hz, 1H), 5.23-5.43 (m, 1H), 5.17 (br d, J=10.08 Hz, 1H), 4.07-4.27 (m, 5H), 3.85 (br d, J=10.08 Hz, 1H), 3.76 (br d, J=10.08 Hz, 1H), 3.08-3.32 (m, 3H), 2.86-3.08 (m, 1H), 2.69 (br s, 1H), 2.32 (ddt, J=14.47, 9.48, 5.01, 5.01 Hz, 1H), 2.15 (br s, 1H), 2.05 (dt, J=14.36, 7.29 Hz, 1H).

Example 179

Synthesis of (4S)—N7-allyl-N5-(pyridin-2-yl)-3,4-dihydro-1,4-methanopyrido[2,3-b][1,4]diazepine-5,7(2H)-dicarboxamide

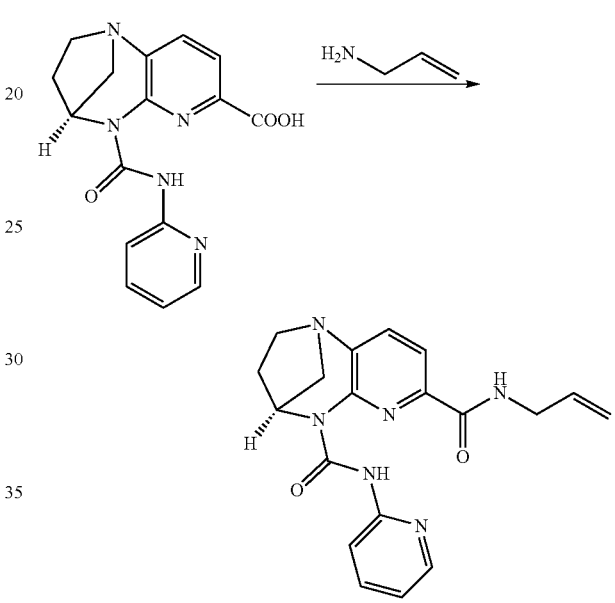

To a stirred solution of (4S)-5-(pyridin-2-ylcarbamoyl)-2,3,4,5-tetrahydro-1,4-methanopyrido[2,3-b][1,4]diazepine-7-carboxylic acid (500 mg, 1.537 mmol) in Pyridine (5 mL), EDC (884 mg, 4.61 mmol) was added at 0° C. under Nitrogen atmosphere and stirred for 50 min. at 0° C. then prop-2-en-1-amine (176 mg, 3.07 mmol) was added and the reaction mixture was stirred at room temperature for 16 h. (TLC 10% MeOH\DCM R_f: 0.5; UV active). After 16 h. Water (100 ml) was added to the reaction mixture and extracted with Ethylacetate (2×50 ml). The combined organic layer was concentrated to obtain crude compound. The crude material was purified by flash column chromatography (Silicagel: 100-200 Mesh, Eluent: 3% MeOH/DCM) to afford the desired product (4S)—N7-allyl-N5-(pyridin-2-yl)-3,4-dihydro-1,4-methanopyrido[2,3-b][1,4]diazepine-5,7(2H)-dicarboxamide (87 mg, 0.235 mmol, 15.32% yield) as a brown solid. LCMS (m/z): 365.18 [M+H]⁺, R_t=1.79 min.

¹H NMR (400 MHz, CDCl₃): δ ppm 13.65 (s, 1H), 8.34 (s, 1H), 8.22 (d, J=5.23 Hz, 1H), 8.09 (d, J=8.33 Hz, 1H), 7.91 (d, J=7.89 Hz, 1H), 7.71 (t, J=7.84 Hz, 2H), 7.00 (ddd, J=7.34, 4.93, 0.88 Hz, 1H), 6.08-5.95 (m, 1H), 5.62 (dd, J=5.92, 3.29 Hz, 1H), 5.43-5.25 (m, 1H), 5.18 (dd, J=10.19, 1.43 Hz, 1H), 4.29-4.13 (m, 2H), 3.33-3.08 (m, 3H), 3.08-2.95 (m, 1H), 2.47-2.21 (m, 1H), 2.18-1.93 (m, 1H).

Example 180

Synthesis of (4S)—N5-(4-((2-hydroxyethyl)carbamoyl)pyridin-2-yl)-N7-(2,2,2-trifluoroethyl)-3,4-dihydro-1,4-methanopyrido[2,3-b][1,4]diazepine-5,7(2H)-dicarboxamide

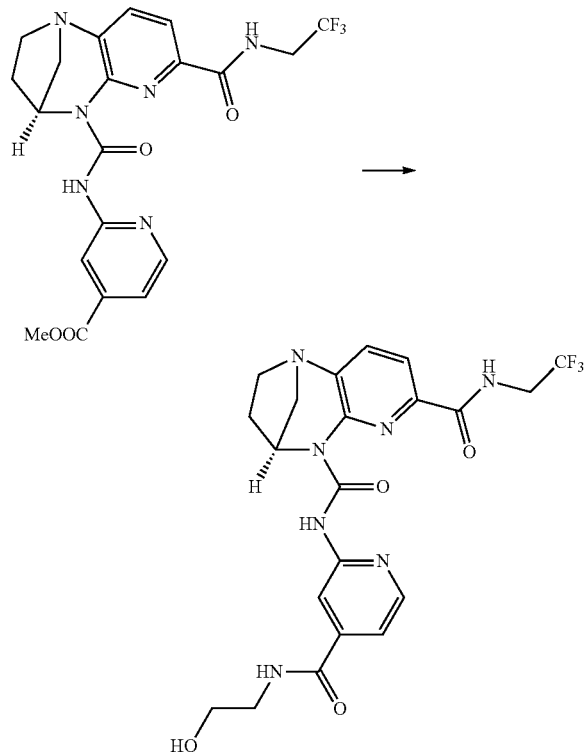

The mixture of methyl 2-((4S)-7-((2,2,2-trifluoroethyl)carbamoyl)-2,3,4,5-tetrahydro-1,4-methanopyrido[2,3-b][1,4]diazepine-5-carboxamido)isonicotinate (400 mg, 0.861 mmol) and ethanol amine (1 mL, 0.861 mmol) was stirred at 90° C. in sealed tube for 2 h. (TLC EtOAC $R_f$: 0.5; UV active) and the reaction mixture was allowed to cool to room temperature, diluted with ice cold water (10 mL) and filtered the obtain solid, dried and triturated with Ethanol to obtain pure compound (4S)—N5-(4-((2-hydroxyethyl)carbamoyl)pyridin-2-yl)-N7-(2,2,2-trifluoroethyl)-3,4-dihydro-1,4-methanopyrido[2,3-b][1,4]diazepine-5,7(2H)-dicarboxamide (101 mg, 0.205 mmol, 23.76% yield) as a white solid. LCMS (m/z): 494.18 [M+H]$^+$. $R_t$=1.65 min.

$^1$H NMR (400 MHz, CDCl$_3$): δ ppm 13.79 (s, 1H), 8.46-8.23 (m, 2H), 7.93 (d, J=7.89 Hz, 1H), 7.70 (d, J=7.89 Hz, 1H), 7.46 (dd, J=5.04, 1.75 Hz, 1H), 7.14-6.86 (m, 1H), 5.56 (dd, J=5.92, 3.07 Hz, 1H), 4.22 (dtd, J=15.24, 8.99, 8.99, 6.25 Hz, 2H), 3.87 (br s, 2H), 3.75-3.57 (m, 2H), 3.34-3.18 (m, 3H), 3.14 (br d, J=12.06 Hz, 1H), 3.04 (dd, J=12.28, 3.07 Hz, 1H), 2.67 (br s, 1H), 2.42-2.19 (m, 1H), 2.18-1.98 (m, 1H).

$^1$H NMR (400 MHz, DMSO-d$_6$) δ ppm 13.20 (s, 1H), 13.03 (s, 1H), 8.59 (d, J=9.21 Hz, 1H), 8.31-8.50 (m, 1H), 7.61-7.83 (m, 2H), 7.03 (d, J=8.33 Hz, 1H), 5.29 (t, J=6.36 Hz, 1H), 4.72-4.96 (m, 2H), 3.86 (t, J=6.25 Hz, 2H), 3.25-3.42 (m, 3H), 2.89 (br d, J=13.81 Hz, 1H), 2.57 (s, 3H), 2.01-2.27 (m, 2H), 1.77-2.01 (m, 2H).

Example 181

Synthesis of (4S)—N5-(1H-pyrrolo[2,3-c]pyridin-5-yl)-N7-((R)-1,1,1-trifluoropropan-2-yl)-3,4-dihydro-1,4-methanopyrido[2,3-b][1,4]diazepine-5,7(2H)-dicarboxamide

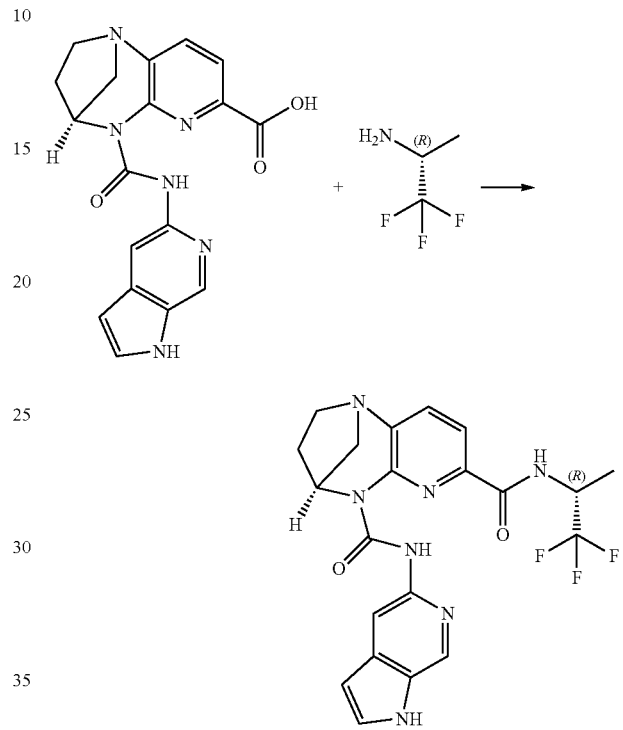

To a stirred solution of (4S)-5-((1H-pyrrolo[2,3-c]pyridin-5-yl)carbamoyl)-2,3,4,5-tetrahydro-1,4-methanopyrido[2,3-b][1,4]diazepine-7-carboxylic acid (600 mg, 1.647 mmol) in DMF (15 mL) at 0° C. were added DIPEA (1.438 mL, 8.23 mmol), HATU (939 mg, 2.470 mmol) and (R)-1,1,1-trifluoropropan-2-amine (279 mg, 2.470 mmol) and stirred at RT for 16 h. (TLC eluent: 100% Ethyl acetate; $R_f$=0.3; UV active). The reaction mixture was diluted with water (30 mL) and stirred for 15 min. The precipitated solid was filtered through Buchner Funnel, washed with water and dried under reduced pressure to get crude product. The crude compound was purified by column chromatography (neutral alumina, eluent: 80% ethyl acetate in hexane) to afford desired product (4S)—N5-(1H-pyrrolo[2,3-c]pyridin-5-yl)-N7-((R)-1,1,1-trifluoropropan-2-yl)-3,4-dihydro-1,4-methanopyrido[2,3-b][1,4]diazepine-5,7(2H)-dicarboxamide (280 mg, 0.608 mmol, 36.9% yield) as an off-white solid. LCMS (m/z): 460.16 [M+H]$^+$; $R_t$=1.57 min.

$^1$H NMR (400 MHz, CDCl$_3$): δ ppm 13.07 (s, 1H), 8.47 (s, 1H), 8.39-8.29 (m, 2H), 8.21 (br d, J=9.65 Hz, 1H), 7.93 (d, J=7.89 Hz, 1H), 7.66 (d, J=7.89 Hz, 1H), 7.42-7.33 (m, 1H), 6.57 (ddd, J=3.01, 2.03, 0.88 Hz, 1H), 5.69 (dd, J=5.92, 3.07 Hz, 1H), 5.18-5.03 (m, 1H), 3.29-3.17 (m, 2H), 3.16-3.10 (m, 1H), 3.06-2.99 (m, 1H), 2.39-2.28 (m, 1H), 2.14-2.03 (m, 1H), 1.64 (d, J=7.02 Hz, 3H).

Example 182

Synthesis of (4S)—N5-(4-(1H-1,2,3-triazol-1-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

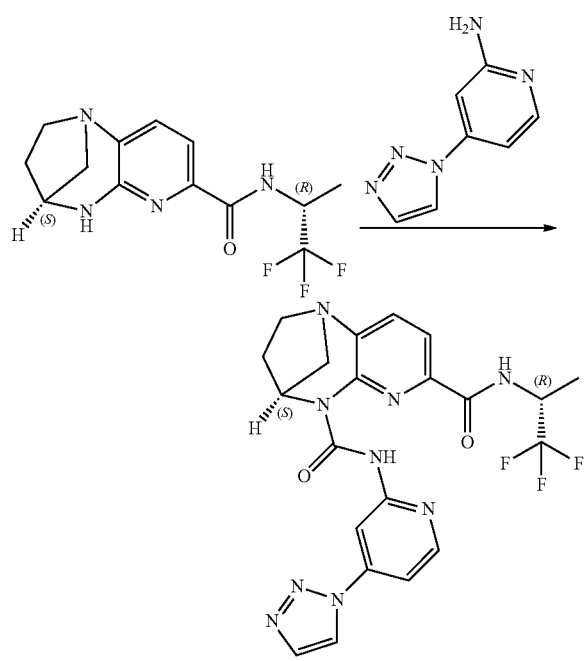

To a solution of (4S)—N—((R)-1,1,1-trifluoropropan-2-yl)-2,3,4,5-tetrahydro-1,4-methanopyrido[2,3-b][1,4]diazepine-7-carboxamide (75 mg, 0.250 mmol) in Tetrahydrofuran (10 mL) were added triethylamine (0.174 mL, 1.249 mmol) followed by triphosgene (74.1 mg, 0.250 mmol) at 0° C. in sealed tube and stirred for 1 h. at room temperature then 4-(1H-1,2,3-triazol-1-yl)pyridin-2-amine (60.4 mg, 0.375 mmol) was added and stirred at 70° C. for 15 h. (TLC system: 100% ethyl acetate, $R_f$: 0.4; UV active). The reaction mixture was cooled to room temperature and was diluted with water (20 mL) and extracted with EtOAc (20 mL×2). The combined organic layer was dried over anhydrous $Na_2SO_4$, filtered and filtrate was evaporated to get crude, then it was purified by flash column chromatography (Silica gel: 100-200 Mesh, Eluent: 90% ethyl acetate in n-hexane) to afford the desired product (4S)—N5-(4-(1H-1,2,3-triazol-1-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (41 mg, 0.081 mmol, 32.3% yield) as an off white solid. LCMS (m/z): 488.20 [M+H]$^+$, Rt=2.13 min.

$^1$H NMR (400 MHz, CDCl$_3$): δ ppm 13.54 (s, 1H), 8.54 (d, J=1.97 Hz, 1H), 8.40 (d, J=5.48 Hz, 1H), 8.21 (d, J=1.32 Hz, 1H), 7.99 (d, J=7.89 Hz, 1H), 7.92-7.89 (m, 2H), 7.73-7.68 (m, 2H), 5.65 (dd, J=5.92, 3.07 Hz, 1H), 5.08 (dt, J=9.48, 7.43 Hz, 1H), 3.29-3.23 (m, 2H), 3.17-3.12 (m, 1H), 3.07-3.02 (m, 1H), 2.41-2.31 (m, 1H), 2.13-2.04 (m, 1H), 1.61 (d, J=7.02 Hz, 3H).

Example 183

Synthesis of (4S)—N7-(2,2-difluoropropyl)-N5-(4-((R)-2,3-dihydroxypropoxy)pyridin-2-yl)-3,4-dihydro-1,4-methanopyrido[2,3-b][1,4]diazepine-5,7(2H)-dicarboxamide

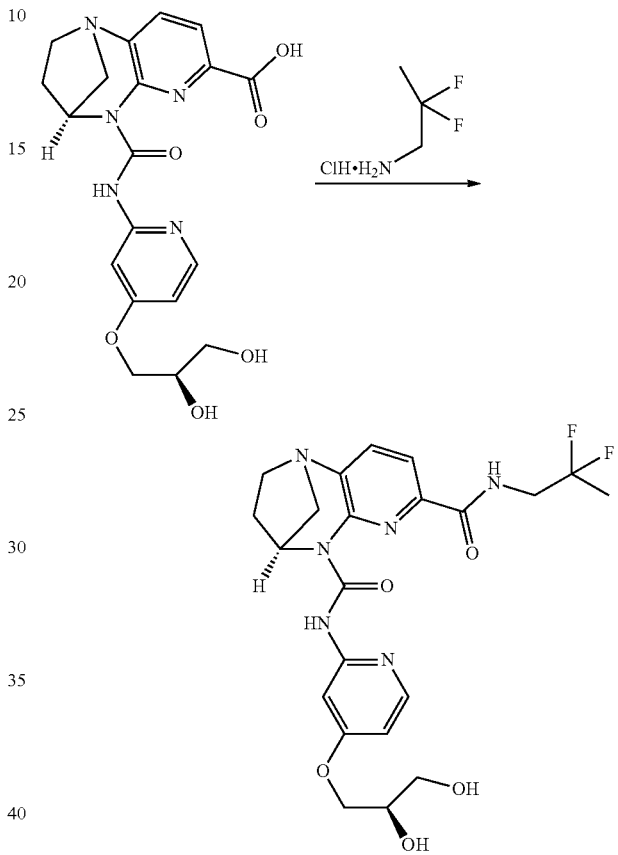

To a solution of (4S)-5-((4-((R)-2,3-dihydroxypropoxy)pyridin-2-yl)carbamoyl)-2,3,4,5-tetrahydro-1,4-methanopyrido[2,3-b][1,4]diazepine-7-carboxylic acid (800 mg, 1.926 mmol) and 2,2-difluoropropan-1-amine hydrochloride (380 mg, 2.89 mmol) in DMF (20 mL) at RT, was added HATU (879 mg, 2.311 mmol) followed by DIPEA (0.673 mL, 3.85 mmol) and stirred for 18 h. (TLC system: 100% Ethylacetate, Rf value: 0.4). The reaction mixture was partitioned between water (30 mL) and EtOAc (100 mL). Organic layer was separated, dried over anhydrous $Na_2SO_4$, filtered and filtrate was evaporated to get crude product. The crude compound was purified by preparative HPLC (Column: XBridge C18 (75×4.6 mm, 3.5µ), Mobile Phase-A: 0.01 M Ammonium Bicarbonate Mobile Phase-B: ACN, Gradient: Time/% B: 0/5, 0.8/5, 5/50, 8/95, 12/95, 12.1/5, 15/5, Column Temp: Ambient, Flow Rate: 1.0 ml/min, Diluent: ACN) to afford (4S)—N7-(2,2-difluoropropyl)-N5-(4-((R)-2,3-dihydroxypropoxy)pyridin-2-yl)-3,4-dihydro-1,4-methanopyrido[2,3-b][1,4]diazepine-5,7(2H)-dicarboxamide (90 mg, 0.178 mmol, 9.26% yield) as an off white solid. LCMS (m/z): 493.21 [M+H]$^+$, Rt=1.38 min.

$^1$H NMR (400 MHz, CDCl$_3$): δ ppm 13.42 (s, 1H), 8.53 (br t, J=6.25 Hz, 1H), 8.13 (d, J=5.92 Hz, 1H), 7.78-7.70 (m, 2H), 7.59 (d, J=2.19 Hz, 1H), 6.72 (dd, J=5.92, 2.41 Hz, 1H), 5.41 (dd, J=5.59, 2.96 Hz, 1H), 5.02 (d, J=5.26 Hz, 1H), 4.71 (br t, J=5.59 Hz, 1H), 4.11 (dd, J=9.87, 3.73 Hz, 1H), 4.02-3.78 (m, 4H), 3.53-3.43 (m, 2H), 3.22-3.05 (m, 3H), 3.02-2.92 (m, 1H), 2.27-2.14 (m, 1H), 2.01-1.92 (m, 1H), 1.67 (t, J=18.96 Hz, 3H).

Example 184

Synthesis of (4S)—N5-(4-((R)-2,3-dihydroxypropoxy)pyridin-2-yl)-N7-((R)-2,2,2-trifluoro-1-phenylethyl)-3,4-dihydro-1,4-methanopyrido[2,3-b][1,4]diazepine-5,7(2H)-dicarboxamide

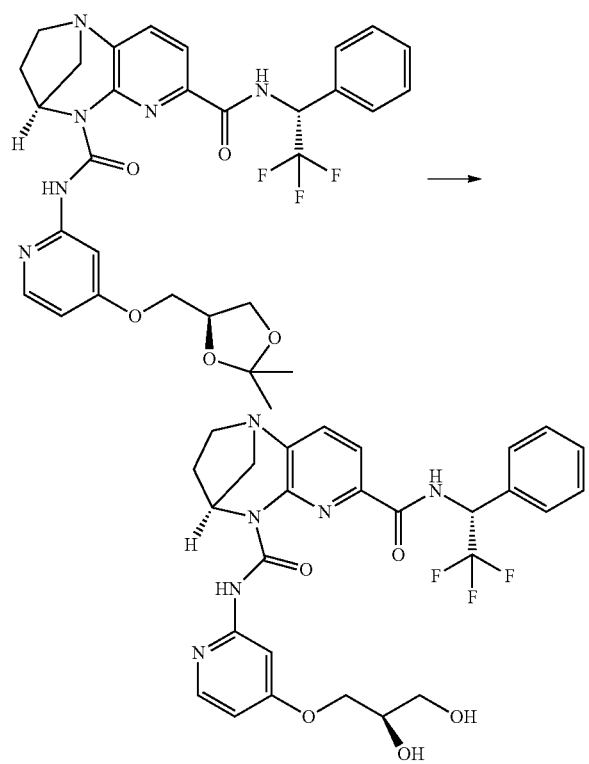

To a stirred solution of (4S)—N5-(4-(((S)-2,2-dimethyl-1,3-dioxolan-4-yl)methoxy)pyridin-2-yl)-N7-((R)-2,2,2-trifluoro-1-phenylethyl)-3,4-dihydro-1,4-methanopyrido[2,3-b][1,4]diazepine-5,7(2H)-dicarboxamide (450 mg, 0.735 mmol) in methanol (10 mL) at RT was added 2M HCl (0.5 mL, 1.000 mmol) and stirred for 3 h. (TLC eluent: 5% MeOH in DCM R$_f$: 0.2; UV active). The reaction mixture was concentrated to remove methanol completely and basified the reaction mixture with saturated NaHCO$_3$ (15 mL) solution. The resultant solid was filtered, washed with water (20 mL) and dried under high vacuum to obtain crude product. The crude was triturated with diethylether (5 ml) and pentane (10 mL) to afford (4S)—N5-(4-((R)-2,3-dihydroxypropoxy)pyridin-2-yl)-N7-((R)-2,2,2-trifluoro-1-phenylethyl)-3,4-dihydro-1,4-methanopyrido[2,3-b][1,4]diazepine-5,7(2H)-dicarboxamide (320 mg, 0.557 mmol, 76% yield) as an off-white solid. LCMS (m/z): 573.27 [M+H]$^+$; Rt=1.83 min.

1H NMR (400 MHz, CDCl$_3$): δ ppm 13.20 (s, 1H), 8.56 (br d, J=9.65 Hz, 1H), 7.99 (d, J=7.89 Hz, 1H), 7.91 (d, J=5.92 Hz, 1H), 7.73-7.83 (m, 3H), 7.68 (d, J=7.89 Hz, 1H), 7.31-7.41 (m, 3H), 6.55 (dd, J=5.81, 2.30 Hz, 1H), 6.04-6.25 (m, 1H), 5.64 (dd, J=5.59, 2.96 Hz, 1H), 4.05-4.27 (m, 3H), 3.85 (br d, J=11.62 Hz, 1H), 3.76 (br d, J=11.84 Hz, 1H), 3.17-3.35 (m, 2H), 3.11 (br d, J=12.06 Hz, 1H), 3.02 (dd, J=12.28, 3.07 Hz, 1H), 2.59 (br s, 1H), 2.34 (dt, J=9.81, 4.85 Hz, 1H), 1.87-2.15 (m, 2H)

Example 185

Synthesis of (4S)—N5-(1-methyl-4-oxo-1,4-dihydropyridin-3-yl)-N7-(2,2,2-trifluoroethyl)-3,4-dihydro-1,4-methanopyrido[2,3-b][1,4]diazepine-5,7(2H)-dicarboxamide

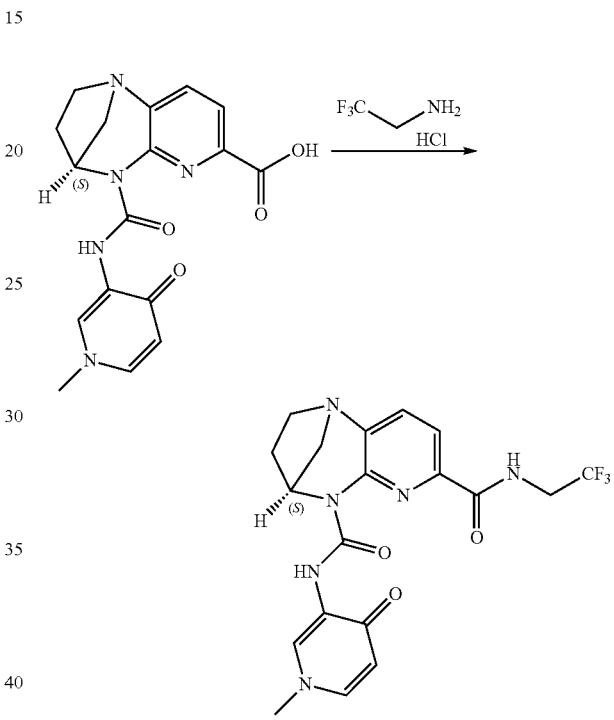

To a stirred solution of (4S)-5-((1-methyl-4-oxo-1,4-dihydropyridin-3-yl)carbamoyl)-2,3,4,5-tetrahydro-1,4-methanopyrido[2,3-b][1,4]diazepine-7-carboxylic acid (250 mg, 0.704 mmol) in DMF (5 mL), under nitrogen at 0° C. was added HATU (401 mg, 1.055 mmol), DIPEA (0.614 mL, 3.52 mmol) and 2,2,2-trifluoroethanamine hydrochloride (114 mg, 0.844 mmol) and stirred at room temperature for 16 h. (TLC eluent: 100% EtOAc: R$_f$—0.3; UV active). The reaction mixture was partitioned between water (50 mL) and EtOAc (50 mL). Organic layer was separated and dried over anhydrous sodium sulphate, filtered and filtrate was evaporated to get crude compound. The crude product was triturated with diethyl ether to afford (4S)—N5-(1-methyl-4-oxo-1,4-dihydropyridin-3-yl)-N7-(2,2,2-trifluoroethyl)-3,4-dihydro-1,4-methanopyrido[2,3-b][1,4]diazepine-5,7(2H)-dicarboxamide (180 mg, 0.411 mmol, 58.4% yield) as an off-white solid. LCMS (m/z): 437.16[M+H]$^+$, R$_t$=1.72 min.

1H NMR (400 MHz, CDCl$_3$): δ ppm 12.25 (s, 1H), 10.33 (br s, 1H), 8.77 (d, J=2.41 Hz, 1H), 8.01 (d, J=7.89 Hz, 1H), 7.64 (d, J=7.89 Hz, 1H), 7.38-7.24 (m, 1H), 6.47 (d, J=7.23 Hz, 1H), 5.65 (dd, J=5.59, 3.18 Hz, 1H), 4.38-4.13 (m, 2H), 3.77 (s, 3H), 3.30-3.09 (m, 3H), 2.91-3.03 (m, 1H), 2.38-2.27 (m, 1H), 2.03 (dt, J=14.31, 7.21 Hz, 1H).

Example 186

Synthesis of (4S)—N5-(4-(2-aminoethoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

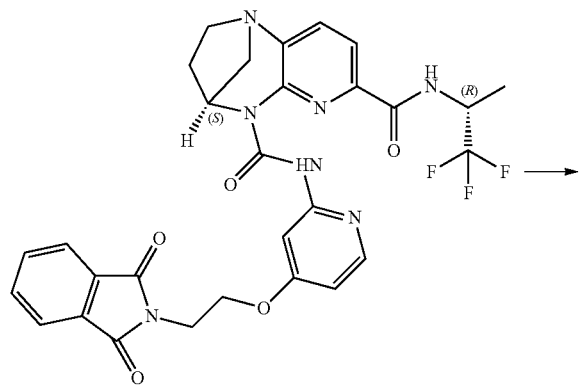

To a stirred solution of (4S)—N5-(4-(2-(1,3-dioxoisoindolin-2-yl)ethoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (300 mg, 0.492 mmol) in Tetrahydrofuran (10 mL) was added hydrazine hydrate (1 mL, 31.9 mmol) at room temperature and stirred at RT for 16 h. (TLC system: neat ethyl acetate; $R_f$: 0.1; UV active). The reaction mixture was diluted with water (20 mL) and extracted with ethyl acetate (2×20 mL). The combined organic layer was washed with saturated brine (20 mL) solution and dried over anhydrous $Na_2SO_4$, filtered and filtrate was evaporated to obtain crude, then it was purified by flash column chromatography (Silicagel: 100-200 Mesh, Eluent: 90% ethyl acetate in n-hexane) to afford the desired product (4S)—N5-(4-(2-aminoethoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (180 mg, 0.372 mmol, 76% yield) as an off white solid. LCMS (m/z): 480.1 [M+H]$^+$, Rt=3.43 min.

$^1$H NMR (400 MHz, CDCl$_3$): δ ppm 13.27 (s, 1H), 8.05 (d, J=5.92 Hz, 2H), 7.95 (d, J=7.89 Hz, 1H), 7.76 (d, J=2.41 Hz, 1H), 7.67 (d, J=7.89 Hz, 1H), 6.59 (dd, J=5.92, 2.41 Hz, 1H), 5.62 (dd, J=5.92, 3.07 Hz, 1H), 5.11-5.00 (m, 1H), 4.11 (t, J=5.15 Hz, 2H), 3.27-3.08 (m, 7H), 3.05-2.99 (m, 1H), 2.38-2.27 (m, 1H), 2.11-2.02 (m, 1H), 1.59 (d, J=7.02 Hz, 3H).

Example 187

Synthesis of (4S)—N5-(4-((R)-2,3-dihydroxypropoxy)pyridin-2-yl)-N7-(3-fluorobenzyl)-3,4-dihydro-1,4-methanopyrido[2,3-b][1,4]diazepine-5,7(2H)-dicarboxamide

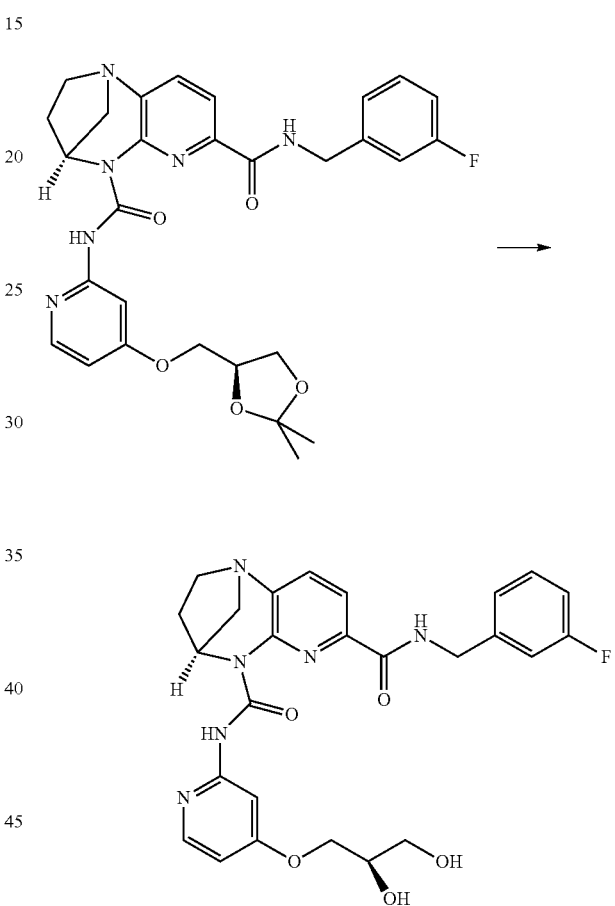

To a stirred solution of (4S)—N5-(4-(((S)-2,2-dimethyl-1,3-dioxolan-4-yl)methoxy)pyridin-2-yl)-N7-(3-fluorobenzyl)-3,4-dihydro-1,4-methanopyrido[2,3-b][1,4]diazepine-5,7(2H)-dicarboxamide (400 mg, 0.711 mmol) in methanol (10 mL) at 0° C. was added HCl (0.216 mL, 7.11 mmol) and stirred for 3 h. (TLC System: $R_f$—0.1, EtOAc, UV active) The reaction mixture was concentrated under reduced pressure to give residue. The residue was neutralized with saturated sodium bicarbonate solution to afford solid product, filtered and dried to obtain (4S)—N5-(4-((R)-2,3-dihydroxypropoxy)pyridin-2-yl)-N7-(3-fluorobenzyl)-3,4-dihydro-1,4-methanopyrido[2,3-b][1,4]diazepine-5,7(2H)-dicarboxamide (250 mg, 0.474 mmol, 66.6% yield) as an Off white solid. LCMS (m/z): 523.27 [M+H]$^+$, Rt=1.62 min.

¹H NMR (400 MHz, CDCl₃): δ ppm 13.72 (s, 1H), 8.77 (br t, J=6.03 Hz, 1H), 7.91 (d, J=7.89 Hz, 1H), 7.72-7.64 (m, 3H), 7.30-7.26 (m, 2H), 7.13 (br d, J=9.87 Hz, 1H), 6.92 (td, J=8.28, 2.30 Hz, 1H), 6.49 (dd, J=5.92, 2.41 Hz, 1H), 5.57 (dd, J=5.92, 3.07 Hz, 1H), 4.81-4.68 (m, 2H), 4.19-4.09 (m, 3H), 3.86-3.69 (m, 2H), 3.31-3.21 (m, 3H), 3.18-3.10 (m, 1H), 2.61 (br s, 1H), 2.40-2.28 (m, 1H), 2.13-1.98 (m, 2H)

Example 188

Synthesis of (4S)—N5-(1-methyl-4-oxo-1,4-dihydropyridin-3-yl)-N7-((R)-1,1,1-trifluoropropan-2-yl)-3,4-dihydro-1,4-methanopyrido[2,3-b][1,4]diazepine-5,7(2H)-dicarboxamide

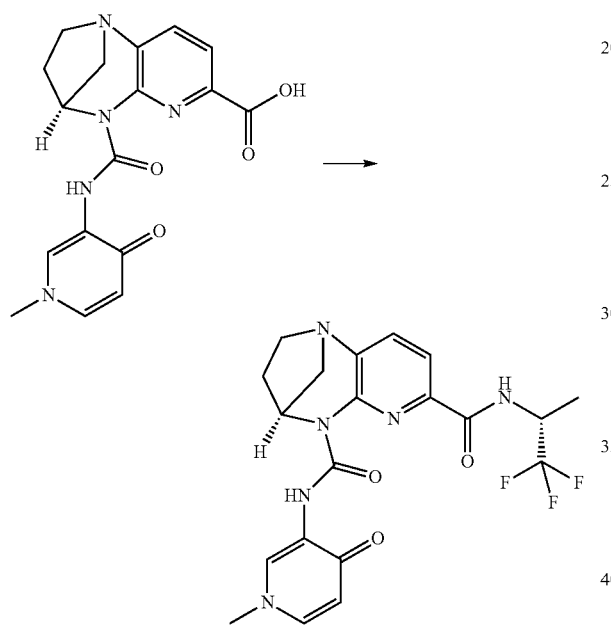

To a solution of (4S)-5-((1-methyl-4-oxo-1,4-dihydropyridin-3-yl)carbamoyl)-2,3,4,5-tetrahydro-1,4-methanopyrido[2,3-b][1,4]diazepine-7-carboxylic acid (250 mg, 0.704 mmol) in DMF (2.5 mL) at 25° C. was added (R)-1,1,1-trifluoropropan-2-amine hydrochloride (137 mg, 0.915 mmol), DIPEA (0.184 mL, 1.055 mmol) and HATU (401 mg, 1.055 mmol) and stirred at RT for 2 h. (TLC system: 10% MeOH in DCM, Rf value: 0.5). Reaction mixture was quenched with water (40 mL) and stirred for 15 min. the resultant solid was filtered and triturated with diethyl ether (20 mL), n-pentane (25 mL) and dried to afford (4S)—N5-(1-methyl-4-oxo-1,4-dihydropyridin-3-yl)-N7-((R)-1,1,1-trifluoropropan-2-yl)-3,4-dihydro-1,4-methanopyrido[2,3-b][1,4]diazepine-5,7(2H)-dicarboxamide (185 mg, 0.400 mmol, 56.9% yield) as an off white solid. LCMS (m/z)=451.20 [M+H]⁺, Rt=1.86 min.

¹H NMR (400 MHz, CDCl₃): δ ppm 12.30 (s, 1H), 10.01 (br d, J=8.99 Hz, 1H), 8.67 (d, J=2.19 Hz, 1H), 8.04 (d, J=7.89 Hz, 1H), 7.63 (d, J=7.89 Hz, 1H), 7.16-7.40 (m, 1H), 6.44 (d, J=7.23 Hz, 1H), 5.63 (dd, J=6.03, 3.18 Hz, 1H), 4.97-5.14 (m, 1H), 3.76 (s, 3H), 3.05-3.30 (m, 3H), 2.89-3.03 (m, 1H), 2.20-2.34 (m, 1H), 2.03 (dt, J=14.36, 7.29 Hz, 1H), 1.67 (d, J=7.02 Hz, 3H)

Example 189

Synthesis of (4S)—N5-(6-((R)-2,3-dihydroxypropoxy)pyrimidin-4-yl)-N7-((R)-1,1,1-trifluoropropan-2-yl)-3,4-dihydro-1,4-methanopyrido[2,3-b][1,4]diazepine-5,7(2H)-dicarboxamide

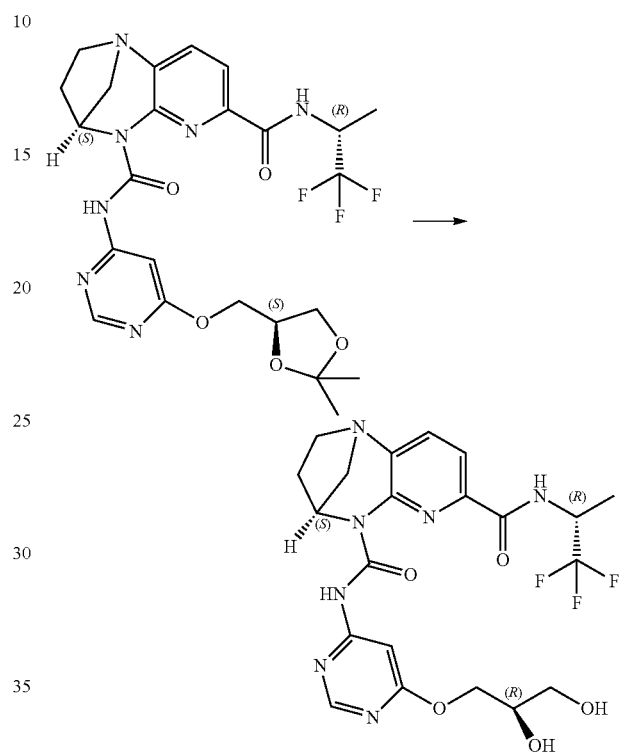

To a stirred solution of 4(S)—N5-(6-(((S)-2,2-dimethyl-1,3-dioxolan-4-yl)methoxy)pyrimidin-4-yl)-N7-((R)-1,1,1-trifluoropropan-2-yl)-3,4-dihydro-1,4-methanopyrido[2,3-b][1,4]diazepine-5,7(2H)-dicarboxamide (0.14 g, 0.254 mmol) in methanol (5 mL) at 0° C. was added aq. HCl (0.304 mL, 10.00 mmol, 36%) and stirred for 3 h. (TLC eluent: 5% MeOH in DCM: R_f—0.2; UV active). Reaction mixture was basified by adding saturated sodium bicarbonate solution (till pH-8-9) then concentrated. The residue was diluted with water (10 mL) and extracted into EtOAc (2×25 mL). Combined organic extracts were dried over anhydrous Na₂SO₄, filtered and filtrate was evaporated to give crude product. The crude was triturated with diethyl ether (10 mL) to afford the desired product (4S)—N5-(6-((R)-2,3-dihydroxypropoxy)pyrimidin-4-yl)-N7-((R)-1,1,1-trifluoropropan-2-yl)-3,4-dihydro-1,4-methanopyrido[2,3-b][1,4]diazepine-5,7(2H)-dicarboxamide (0.085 g, 0.166 mmol, 65.4% yield) as an off-white solid. LCMS (m/z): 512.25 [M+H]⁺, R_f=1.76 min.

¹H NMR (400 MHz, CDCl₃): δ ppm 13.44 (s, 1H), 8.41 (s, 1H), 7.99 (d, J=7.89 Hz, 1H), 7.81 (br d, J=9.43 Hz, 1H), 7.71 (d, J=7.89 Hz, 1H), 7.53 (d, J=0.88 Hz, 1H), 5.62 (dd, J=5.81, 2.96 Hz, 1H), 5.06 (dq, J=16.83, 7.25 Hz, 1H), 4.40-4.61 (m, 2H), 4.02-4.13 (m, 1H), 3.62-3.82 (m, 2H), 3.20-3.35 (m, 3H), 2.97-3.16 (m, 2H), 2.43 (t, J=6.25 Hz, 1H), 2.26-2.37 (m, 1H), 2.05 (dt, J=14.52, 7.10 Hz, 1H), 1.52-1.63 (m, 3H).

Example 190

Synthesis of (4S)—N5-(isothiazol-3-yl)-N7-((R)-1,1,1-trifluoropropan-2-yl)-3,4-dihydro-1,4-methanopyrido[2,3-b][1,4]diazepine-5,7(2H)-dicarboxamide

Example 191

Synthesis of (4S)—N5-(thiazol-2-yl)-N7-((R)-1,1,1-trifluoropropan-2-yl)-3,4-dihydro-1,4-methanopyrido[2,3-b][1,4]diazepine-5,7(2H)-dicarboxamide

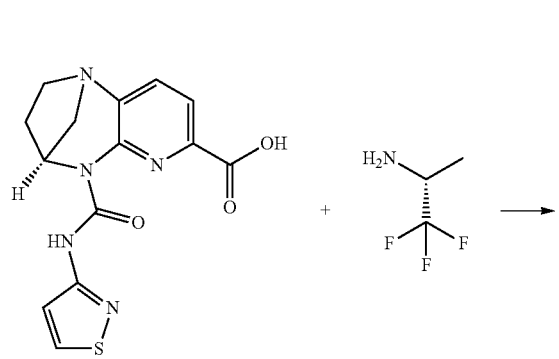

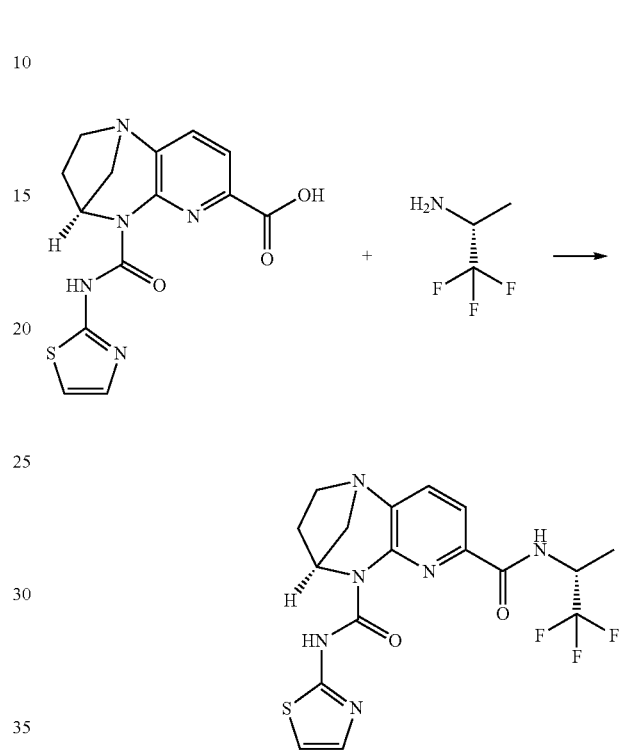

To a stirred solution of (4S)-5-(isothiazol-3-ylcarbamoyl)-2,3,4,5-tetrahydro-1,4-methanopyrido[2,3-b][1,4]diazepine-7-carboxylic acid (400 mg, 1.207 mmol) in DMF (15 mL) under nitrogen at RT was added (R)-1,1,1-trifluoropropan-2-amine (137 mg, 1.207 mmol), HATU (689 mg, 1.811 mmol) and DIPEA (1.265 mL, 7.24 mmol) then stirred for 16 h. (TLC eluting system: 10% MeOH in DCM; $R_f$—0.3; UV active). The reaction mixture was quenched with water (15 mL) and extracted into EtOAc (2×15 mL). Combined organic layer was separated, dried over anhydrous sodium sulphate, filtered and filtrate was evaporated to get the crude product. The crude was purified by chromatography (GRACE using C-18 reserval column, Mobile phase A: 0.1% Formic Acid in water; B: ACN, eluent 28% B in A). Combined fractions were concentrated basified with saturated $NaHCO_3$. The aqueous layer was extracted with DCM and the DCM layer was dried over anhydrous $Na_2SO_4$, filtered and filtrate was evaporated to afford (4S)—N5-(isothiazol-3-yl)-N7-((R)-1,1,1-trifluoropropan-2-yl)-3,4-dihydro-1,4-methanopyrido[2,3-b][1,4]diazepine-5,7(2H)-dicarboxamide (230 mg, 0.536 mmol, 44.4% yield) as off white solid. LCMS (m/z): 427.15 [M+H]$^+$, $R_t$=2.22 min.

$^1$H NMR (400 MHz, CDCl$_3$): δ ppm 13.46 (s, 1H), 8.63 (d, J=4.8 Hz, 1H), 7.94 (d, J=7.9 Hz, 1H), 7.80 (d, J=4.8 Hz, 1H), 7.68 (d, J=7.9 Hz, 1H), 7.64-7.56 (m, 1H), 5.62 (dd, J=3.0, 6.0 Hz, 1H), 5.00 (td, J=7.2, 9.5 Hz, 1H), 3.31-3.07 (m, 3H), 3.07-2.95 (m, 1H), 2.48-2.20 (m, 1H), 2.19-2.00 (m, 1H), 1.59 (d, J=7.2 Hz, 3H).

To a stirred solution of (4S)-5-(thiazol-2-ylcarbamoyl)-2,3,4,5-tetrahydro-1,4-methanopyrido[2,3-b][1,4]diazepine-7-carboxylic acid (270 mg, 0.815 mmol) in DMF (15 mL) under nitrogen at RT was added (R)-1,1,1-trifluoropropan-2-amine (92 mg, 0.815 mmol), HATU (465 mg, 1.222 mmol) and DIPEA (0.854 mL, 4.89 mmol) stirred for 16 h. (TLC eluting system: 10% MeOH in DCM; $R_f$—0.3; UV active). The reaction mixture was quenched with water (15 mL) and extracted into EtOAc (2×15 mL). Organic layer was separated and dried over anhydrous sodium sulphate, filtered and filtrate was evaporated to get crude product. The crude compound was purified by chromatography (GRACE using C-18 reserval column, Mobile phase A: 0.1% Formic Acid in water; B: ACN, eluent 34% B in A). Combined fractions were concentrated and basified with saturated $NaHCO_3$. The aqueous layer was extracted with DCM the DCM layer was separated, dried over anhydrous $Na_2SO_4$, filtered and filtrate was evaporated to afford (4S)—N5-(thiazol-2-yl)-N7-((R)-1,1,1-trifluoropropan-2-yl)-3,4-dihydro-1,4-methanopyrido[2,3-b][1,4]diazepine-5,7(2H)-dicarboxamide (32 mg, 0.074 mmol, 9.09% yield) as an off white solid. LCMS (m/z): 427.15 [M+H]$^+$, $R_t$=2.18 min.

$^1$H NMR (400 MHz, CDCl$_3$): δ ppm 13.89 (s, 1H), 7.95 (d, J=7.9 Hz, 1H), 7.71 (d, J=7.9 Hz, 1H), 7.52-7.33 (m, 2H), 6.95 (d, J=3.5 Hz, 1H), 5.64 (dd, J=3.0, 5.8 Hz, 1H), 5.10-4.90 (m, 1H), 3.35-3.09 (m, 3H), 3.09-2.83 (m, 1H), 2.48-2.26 (m, 1H), 2.20-1.96 (m, 1H), 1.64 (d, J=7.2 Hz, 3H).

Example 192

Synthesis of (4S)—N5-(3H-imidazo[4,5-c]pyridin-6-yl)-N7-((R)-1,1,1-trifluoropropan-2-yl)-3,4-dihydro-1,4-methanopyrido[2,3-b][1,4]diazepine-5,7(2H)-dicarboxamide

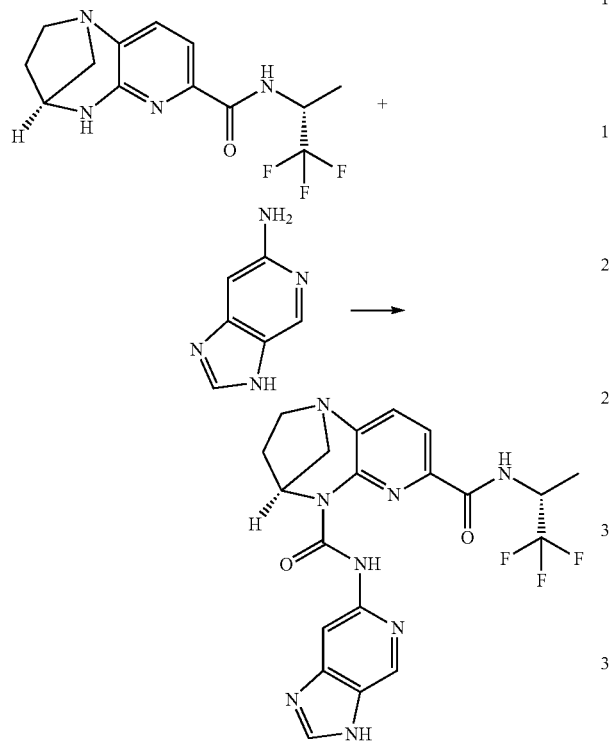

To a stirred solution of (4S)—N—((R)-1,1,1-trifluoropropan-2-yl)-2,3,4,5-tetrahydro-4-methanopyrido[2,3-b][1,4]diazepine-7-carboxamide (300 mg, 0.999 mmol) in THF (30 mL) at RT was added TEA (0.836 mL, 5.99 mmol) and triphosgene (296 mg, 0.999 mmol) and stirred for 1 h. then added 3H-imidazo[4,5-c]pyridin-6-amine (134 mg, 0.999 mmol) and the reaction mixture was heated at 65° C. for 16 h. (TLC eluent: 100% EtOAc; $R_f$—0.2; UV active). The reaction mixture was cooled to RT, concentrated in vacuo and the residue was partitioned between water (20 mL) and DCM (2×30 mL). Organic layer was separated and dried over anhydrous sodium sulphate, filtered and filtrate was evaporated to get crude product. The crude compound was purified by chromatography (Grace Instrument, C-18 reserval column, Mobile phase A: 0.1% Formic Acid in water; B: ACN, the product was eluted with 20% B in A) and the compound fractions were concentrated, basified with saturated solution of $NaHCO_3$ and aqueous layer was extracted with DCM. The DCM layer was dried over anhydrous $Na_2SO_4$, filtered and evaporated to afford pure (4S)—N5-(3H-imidazo[4,5-c]pyridin-6-yl)-N7-((R)-1,1,1-trifluoropropan-2-yl)-3,4-dihydro-1,4-methanopyrido[2,3-b][1,4]diazepine-5,7(2H)-dicarboxamide (36 mg, 0.078 mmol, 7.82% yield) as a white solid. LCMS (m/z): 461.17 [M+H]$^+$, $R_t$=1.64 min.

$^1$H NMR (400 MHz, DMSO-d6): δ ppm 13.04 (br s, 1H), 12.75 (br s, 1H), 8.59 (br s, 1H), 8.33 (br s, 2H), 8.24 (br s, 1H), 7.76 (br s, 2H), 5.50 (br s, 1H), 5.01 (br s, 1H), 3.20-2.89 (m, 4H), 2.24 (br s, 1H), 1.98 (br s, 1H), 1.59 (br d, J=6.4 Hz, 3H).

Example 193

Synthesis of (4S)—N5-(6-((R)-2,3-dihydroxypropoxy)pyridazin-3-yl)-N7-((R)-1,1,1-trifluoro propan-2-yl)-3,4-dihydro-1,4-methanopyrido[2,3-b][1,4]diazepine-5,7(2H)-dicarboxamide

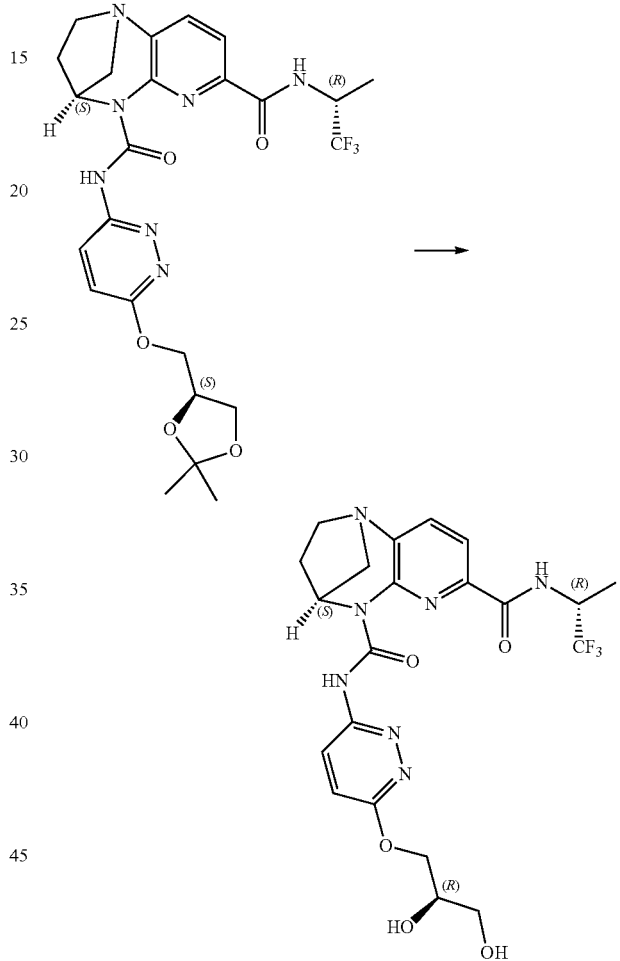

To a stirred solution of (4S)—N5-(6-(((S)-2,2-dimethyl-1,3-dioxolan-4-yl)methoxy)pyridazin-3-yl)-N7-((R)-1,1,1-trifluoropropan-2-yl)-3,4-dihydro-1,4-methanopyrido[2,3-b][1,4]diazepine-5,7(2H)-dicarboxamide (150 mg, 0.272 mmol) in Methanol (5 mL) was added HCl (1.5 mL, 9.00 mmol) at 0° C. and the reaction mixture was stirred at room temperature for 2 h. (TLC eluent: 5% MeOH in DCM, Rf: 0.3). The reaction mixture was concentrated in vacuo and the residue was neutralized with sodium bicarbonate solution and extracted with ethyl acetate (2×30 mL). The combined organic layer was dried over anhydrous sodium sulphate and concentrated under reduced pressure to afford the desired product (4S)—N5-(6-((R)-2,3-dihydroxypropoxy)pyridazin-3-yl)-N7-((R)-1,1,1-trifluoropropan-2-yl)-3,4-dihydro-1,4-methanopyrido[2,3-b][1,4]diazepine-5,7(2H)-dicarboxamide (101 mg, 0.195 mmol, 71.7% yield) as a brown solid. LCMS (m/z): 512.18 [M+H]$^+$, Rt=1.68 min.

¹H NMR (400 MHz, CDCl₃): δ ppm 13.81 (s, 1H), 8.40 (d, J=9.43 Hz, 1H), 7.97 (d, J=7.89 Hz, 2H), 7.70 (d, J=7.89 Hz, 1H), 7.10 (d, J=9.43 Hz, 1H), 5.62 (dd, J=6.14, 3.07 Hz, 1H), 5.13-4.93 (m, 1H), 4.68-4.50 (m, 2H), 4.14-4.07 (m, 1H), 3.82-3.66 (m, 2H), 3.49 (s, 1H), 3.32-3.09 (m, 3H), 3.06-3.00 (m, 1H), 2.40-2.28 (m, 2H), 2.13-1.98 (m, 1H), 1.69 (d, J=7.23 Hz, 3H).

Example 194

Synthesis of (4S)—N5-(5-((R)-2,3-dihydroxypropoxy)pyrazin-2-yl)-N7-((R)-1,1,1-trifluoropropan-2-yl)-3,4-dihydro-1,4-methanopyrido[2,3-b][1,4]diazepine-5,7(2H)-dicarboxamide

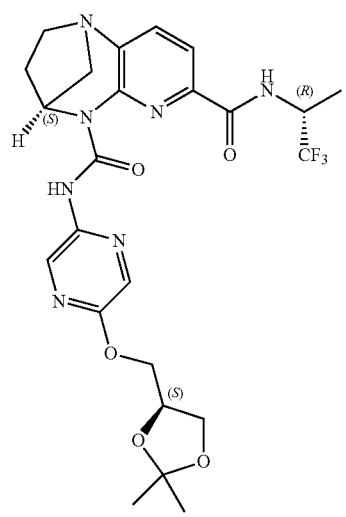

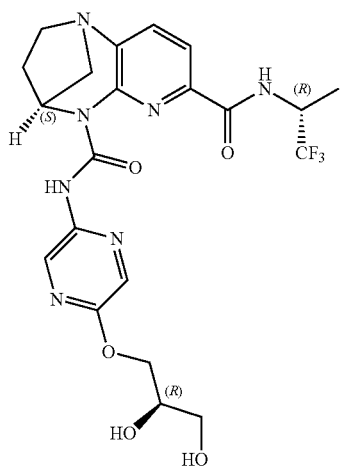

To a stirred solution of (4S)—N5-(5-(((S)-2,2-dimethyl-1,3-dioxolan-4-yl)methoxy)pyrazin-2-yl)-N7-((R)-1,1,1-trifluoropropan-2-yl)-3,4-dihydro-1,4-methanopyrido[2,3-b][1,4]diazepine-5,7(2H)-dicarboxamide (500 mg, 0.907 mmol) in Tetrahydrofuran (10 mL) at 0° C., was added hydrochloric acid (2 mL, 395 mmol) drop wise over a period of 5 min. Then the reaction mixture was stirred at 30° C. for 30 min (TLC: ethyl acetate, R_f=0.3, UV active). The organic solvent from the reaction mixture was evaporated completely under reduced pressure and obtained crude was neutralized with sodium bicarbonate solution (15 mL) and extracted with EtOAc (100 mL×2). The combined organic layer was washed with brine solution (50 mL) and dried over anhydrous Na₂SO₄, filtered and filtrate was evaporated to get crude. The crude was triturated with n-pentane (2×20 mL) and filtered through a Buchner funnel, rinsed with n-pentane to afford the desired product (4S)—N5-(5-((R)-2,3-dihydroxypropoxy)pyrazin-2-yl)-N7-((R)-1,1,1-trifluoropropan-2-yl)-3,4-dihydro-1,4-methanopyrido[2,3-b][1,4]diazepine-5,7(2H)-dicarboxamide (245 mg, 0.466 mmol, 51.4% yield) as an off white solid. LCMS: (m/z): 512.25 [M+H]⁺, Rt=1.72 min.

¹H NMR (400 MHz, CDCl₃): δ ppm 13.11 (s, 1H), 8.97 (d, J=1.32 Hz, 1H), 7.98-7.88 (m, 2H), 7.69 (d, J=7.89 Hz, 1H), 7.61-7.60 (s, 1H), 5.65 (dd, J=5.81, 3.18 Hz, 1H), 5.04 (dq, J=16.85, 7.24 Hz, 1H), 4.55-4.39 (m, 2H), 4.11 (d, J=4.17 Hz, 1H), 3.85-3.69 (m, 2H), 3.29-3.20 (m, 2H), 3.13-2.94 (m, 3H), 2.44-2.31 (m, 2H), 2.10-2.00 (m, 1H), 1.56 (s, 3H).

Example 195

Synthesis of (4S)—N5-(4-((R)-2,3-dihydroxypropoxy)pyridin-2-yl)-N7-(thiazol-2-ylmethyl)-3,4-dihydro-1,4-methanopyrido[2,3-b][1,4]diazepine-5,7(2H)-dicarboxamide

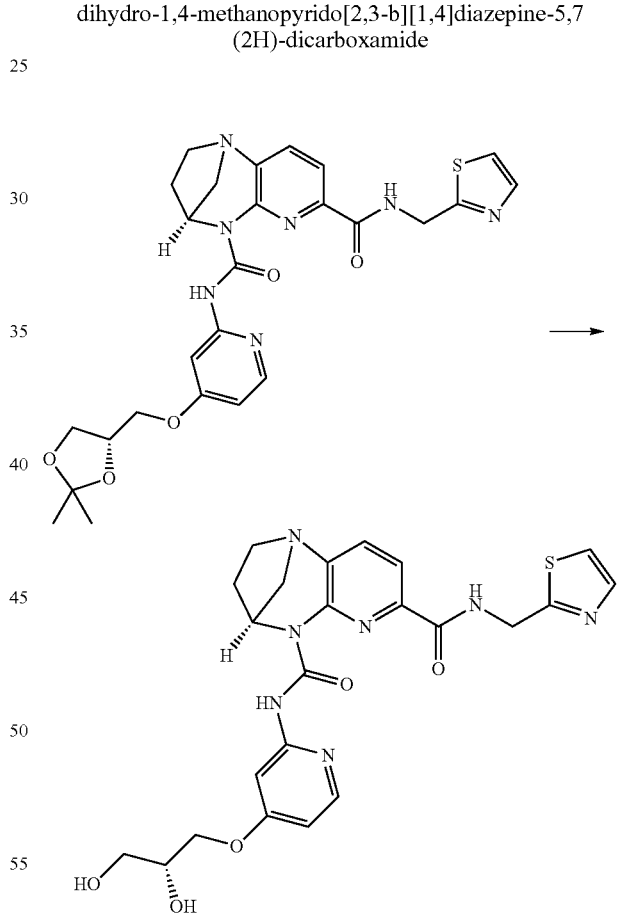

To a stirred solution of (4S)—N5-(4-(((S)-2,2-dimethyl-1,3-dioxolan-4-yl)methoxy)pyridin-2-yl)-N7-(thiazol-2-ylmethyl)-3,4-dihydro-1,4-methanopyrido[2,3-b][1,4]diazepine-5,7(2H)-dicarboxamide (300 mg, 0.544 mmol) in methanol (5 mL) at 0° C. was added aq. HCl (0.459 mL, 5.44 mmol) and the reaction mixture was stirred for 2 h. (TLC eluent: 100% EtOAc: R_f=0.2; UV active). The reaction mixture was basified with saturated sodium bicarbonate solution (till pH-8-9) and solvent was evaporated under reduced pressure. The residue was diluted with water (5 mL) and extracted into dichloromethane (2×50 mL). Combined organic extracts were dried over anhydrous sodium sulphate, filtered and filtrate was evaporated in vacuo and the crude product was triturated with pentane (2×10 mL) to afford (4S)—N5-(4-((R)-2,3-dihydroxypropoxy)pyridin-2-yl)-N7-(thiazol-2-ylmethyl)-3,4-dihydro-1,4-methanopyrido[2,3-b][1,4]diazepine-5,7(2H)-dicarboxamide (204 mg, 0.395 mmol, 72.7% yield) as an off-white solid. LCMS (m/z): 512.22 [M+H]+, R$_f$=1.33 min.

$^1$H NMR (400 MHz, DMSO-d6): δ ppm 14.03-13.05 (m, 1H), 9.10 (br s, 1H), 7.95 (br d, J=5.5 Hz, 1H), 7.82-7.67 (m, 3H), 7.66-7.50 (m, 2H), 6.67 (br d, J=4.2 Hz, 1H), 5.39 (br s, 1H), 4.95 (br d, J=5.3 Hz, 4H), 4.10 (br d, J=6.1 Hz, 1H), 4.02-3.89 (m, 1H), 3.81 (br s, 1H), 3.46 (br s, 2H), 3.23-3.04 (m, 3H), 2.98 (br d, J=10.3 Hz, 1H), 2.36-2.12 (m, 1H), 2.06-1.80 (m, 1H)

Example 196

Synthesis of (4S)—N7-(2-amino-3,3,3-trifluoropropyl)-N5-(4-((R)-2,3-dihydroxypropoxy)pyridin-2-yl)-3,4-dihydro-1,4-methanopyrido[2,3-b][1,4]diazepine-5,7(2H)-dicarboxamide

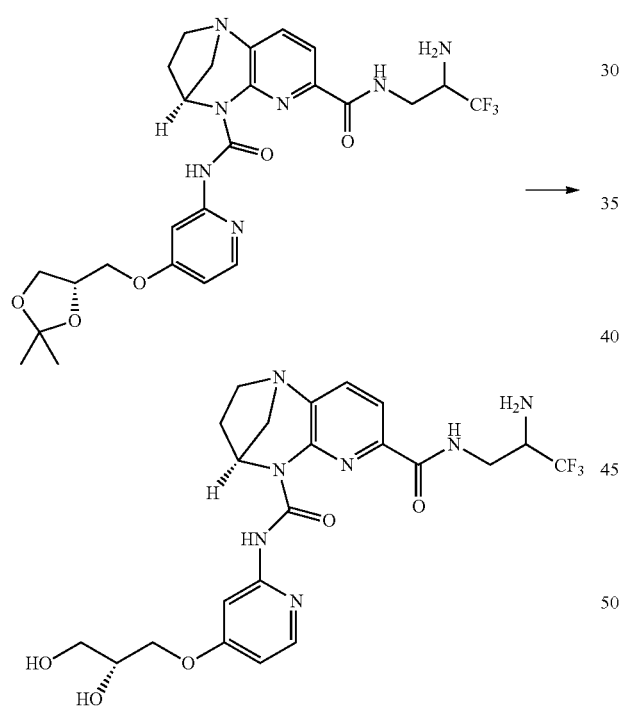

To a solution of fastest eluting isomer in chiral SFC of (4S)—N7-(2-amino-3,3,3-trifluoropropyl)-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide (500 mg, 0.884 mmol) in methanol (10 mL) at RT was added aq. HCl (0.077 mL, 0.884 mmol) and stirred for 2 h. (TLC system: 10% methanol in DCM, Rf value: 0.1). The solvent was evaporated and neutralized with saturated aq. NaHCO$_3$ solution (50 mL). Precipitated solid was filtered and dried to afford (4S)—N7-(2-amino-3,3,3-trifluoropropyl)-N5-(4-((R)-2,3-dihydroxypropoxy)pyridin-2-yl)-3,4-dihydro-1,4-methanopyrido[2,3-b][1,4]diazepine-5,7(2H)-dicarboxamide (355 mg, 0.668 mmol, 76% yield) as off white solid. LCMS (m/z): 526.26[M+H]+, Rt=1.21 min.

$^1$H NMR (400 MHz, DMSO-d$_6$): δ ppm 13.18 (s, 1H), 8.44 (br t, J=6.03 Hz, 1H), 8.10 (d, J=5.92 Hz, 1H), 7.75-7.68 (m, 1H), 7.69-7.62 (m, 2H), 6.82-6.67 (m, 1H), 5.43 (dd, J=5.59, 2.96 Hz, 1H), 5.05 (br s, 1H), 4.74 (br s, 1H), 4.12 (dd, J=9.87, 3.95 Hz, 1H), 3.96 (dd, J=9.76, 6.25 Hz, 1H), 3.83 (br s, 1H), 3.76-3.53 (m, 2H), 3.51-3.30 (m, 3H), 3.25-3.03 (m, 3H), 3.01-2.93 (m, 1H), 2.28-2.11 (m, 3H), 2.01-1.85 (m, 1H).

Example 197

Synthesis of (4S)—N7-(2-amino-3,3,3-trifluoropropyl)-N5-(6-methyl-1H-pyrazolo-[3,4-b]pyridin-3-yl)-3,4-dihydro-1,4-methanopyrido-[2,3-b][1,4]diazepine-5,7(2H)-dicarboxamide

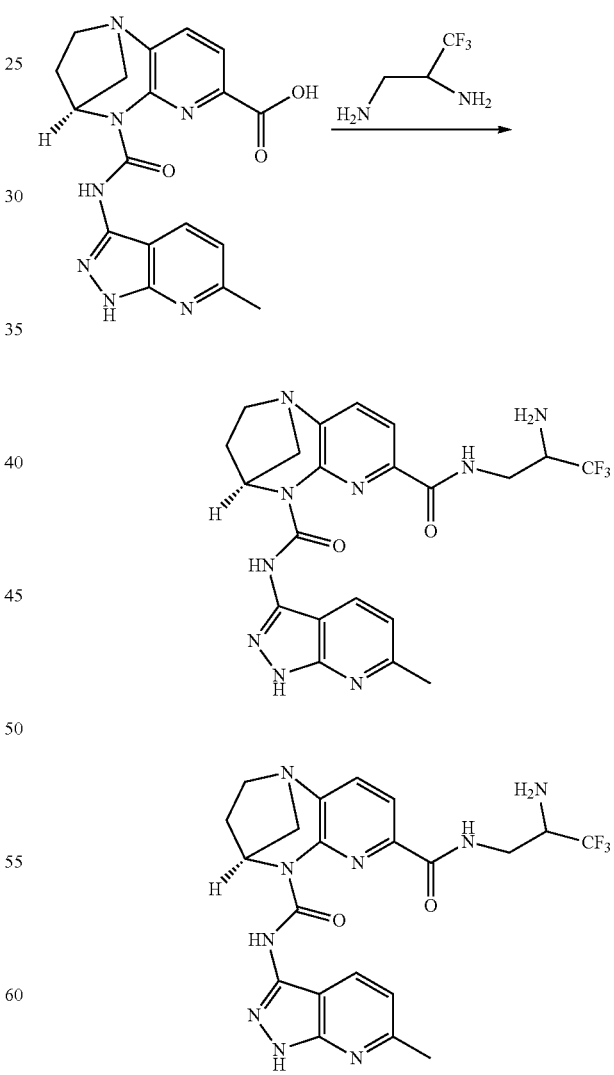

To a solution of (4S)-5-((6-methyl-1H-pyrazolo[3,4-b]pyridin-3-yl)carbamoyl)-2,3,4,5-tetrahydro-1,4-methanopyrido[2,3-b][1,4]diazepine-7-carboxylic acid (1.00 g, 2.64 mmol) in DMF (50 mL) at RT was added HATU (1.002 g, 2.64 mmol), DIPEA (1.381 mL, 7.91 mmol) followed by 3,3,3-trifluoropropane-1,2-diamine (0.405 g, 3.16 mmol) and the reaction was stirred for 16 h. (TLC system: 10% Methanol in DCM, Rf value: 0.5). The reaction mixture was diluted with cold water (100 mL) and stirred for 15 min at RT. The precipitated solid was filtered and dried under vacuum to afford diastereomeric mixtures of (4S)—N7-(2-amino-3,3,3-trifluoropropyl)-N5-(6-methyl-1H-pyrazolo[3,4-b]pyridin-3-yl)-3,4-dihydro-1,4-methanopyrido[2,3-b][1,4]diazepine-5,7(2H)-dicarboxamide. The diastereomers were separated by Chiral SFC (Column/dimensions: Chiralcel OD-H (250×21 mm, 5µ), % CO2: 60.0, % Co-solvent: 40.0 (0.5% DEA in methanol), Total Flow: 70.0 g/min, Back Pressure: 100.0 bar, UV: 216 nm, Stack time: 4.0 min, Load/Inj: 4.0 mg, Solubility: Methanol, Total No of injections: 200, Instrument details: Thar SFC-80) to afford two single isomers.

Peak 1: The fractions of fastest eluting isomer were concentrated and then triturated with diethylether to afford (4S)—N7-(2-amino-3,3,3-trifluoropropyl)-N5-(6-methyl-1H-pyrazolo[3,4-b]pyridin-3-yl)-3,4-dihydro-1,4-methanopyrido[2,3-b][1,4]diazepine-5,7(2H)-dicarboxamide (150 mg, 0.294 mmol, 11.17% yield) as an off white solid. LCMS (m/z): 490.22 [M+1]⁺, Rt=1.49 min.

¹H NMR (400 MHz, DMSO-d₆): δ ppm 13.07-12.86 (m, 1H), 12.74 (s, 1H), 8.54 (br s, 1H), 8.44 (br d, J=7.89 Hz, 1H), 7.72 (br d, J=7.89 Hz, 1H), 7.60 (br d, J=7.67 Hz, 1H), 6.93-7.08 (m, 1H), 5.48 (br s, 1H), 3.65 (br d, J=12.72 Hz, 2H), 3.55 (br s, 1H), 3.20-3.04 (m, 4H), 2.57 (s, 3H), 2.36-2.16 (m, 1H), 2.07 (br s, 3H).

Example 198

Synthesis (4S)—N7-(2-amino-3,3,3-trifluoropropyl)-N5-(pyrimidin-2-yl)-3,4-dihydro-1,4-methanopyrido[2,3-b][1,4]diazepine-5,7(2H)-dicarboxamide

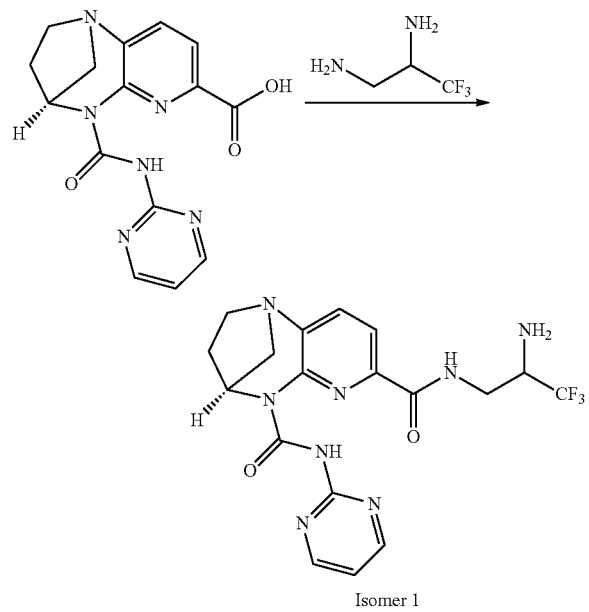

Isomer 1

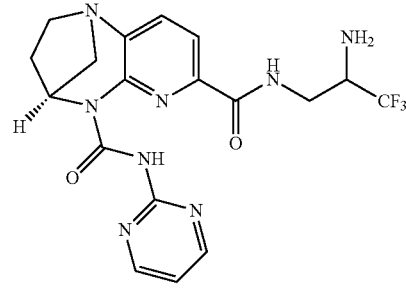

Isomer 2

To a stirred solution of (4S)-5-(pyrimidin-2-ylcarbamoyl)-2,3,4,5-tetrahydro-1,4-methanopyrido[2,3-b][1,4]diazepine-7-carboxylic acid (4 g, 12.26 mmol) in DMF (20 mL), at RT under nitrogen was added was added HATU (6.99 g, 18.39 mmol) followed by DIPEA (6.42 mL, 36.8 mmol) and stirred 10 min, then added solid 3,3,3-trifluoropropane-1,2-diamine (1.884 g, 14.71 mmol) in one charge and reaction mixture was stirred at RT for 16 h. (TLC system: 5% Methanol in DCM. R_f value: 0.3). Reaction mixture was poured in to cold water (60 mL) and extracted with EtOAc (2×100 mL). Combined organic layer was dried over anhydrous Na₂SO₄, filtered and concentrated under reduced pressure to obtain crude product. The crude compound was purified by chromatography (Grace instrument, C-18 reserval column, Mobile phase A: 0.1% formic acid in water; B: acetonitrile, eluted with 30% B in A). Combined product fractions were concentrated and basified with saturated NaHCO₃ solution and the aqueous layer was extracted with DCM. Combined DCM layer was dried over anhydrous Na₂SO₄, filtered and evaporated to afford desired product as distaereomeric mixtures (1.5 g, LCMS-92%). The diastereomers were separated by chiral SFC purification (Column/dimensions: Chiralpak-IE (250×30) mm, 5u; mobile phase-A: 0.2% isopropylamine in n-Hexane; mobile phase-B: Ethanol; Method-Isocratic 20:80 (A:B); Flow: 40 ml/min; Temperature: Ambient; Wave length: 264 nm; Run Time: 33 min; Stacking time: 17 min Solubility: Ethanol with slightly DCM added; Loadability/Inj: 13.21 mg/Inj; Total injections: 114; Instrument details: YMC prep-02) afforded two single isomers with unknown absolute stereochemistry. Fractions of fast eluting isomer were concentrated and further purified by chromatography (Grace instrument, C-18 reserval column, Mobile phase A: 0.1% formic acid in water; B: acetonitrile, eluted with 32% B in A) to afford (4S)—N7-(2-amino-3,3,3-trifluoropropyl)-N5-(pyrimidin-2-yl)-3,4-dihydro-1,4-methanopyrido[2,3-b][1,4]diazepine-5,7(2H)-dicarboxamide (150 mg, 0.343 mmol, 2.80% yield) obtained as an off-white solid. LC-MS (m/z): 437.27 [M+H]⁺, Rt=1.29 min.

¹H NMR (400 MHz, DMSO-d₆): δ ppm 13.31 (s, 1H), 8.67 (d, J=4.82 Hz, 2H), 8.45 (br t, J=6.03 Hz, 1H), 7.55-7.81 (m, 2H), 7.21 (t, J=4.82 Hz, 1H), 5.43 (dd, J=5.59, 2.74 Hz, 1H), 3.71 (dt, J=13.32, 5.29 Hz, 1H), 3.56 (br d, J=4.17 Hz, 1H), 3.38 (dt, J=13.76, 7.04 Hz, 1H), 3.03-3.22 (m, 3H), 2.93-3.00 (m, 1H), 2.18-2.29 (m, 1H), 2.12 (br d, J=7.23 Hz, 2H), 1.91 (dt, J=13.92, 7.07 Hz, 1H).

Example 199

Synthesis (4S)—N5-(4-((R)-2,3-dihydroxypropoxy)pyridin-2-yl)-N7-(thiazol-4-ylmethyl)-3,4-dihydro-1,4-methanopyrido[2,3-b][1,4]diazepine-5,7(2H)-dicarboxamide

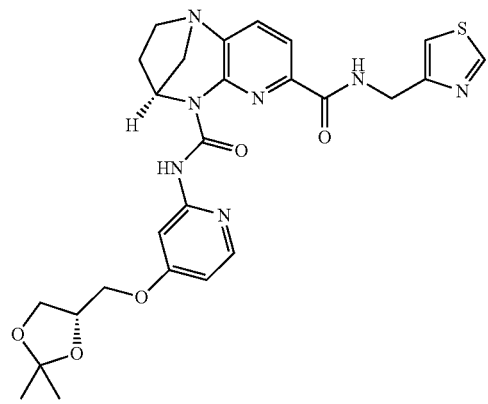

To a stirred solution of (4S)—N5-(4-(((S)-2,2-dimethyl-1,3-dioxolan-4-yl)methoxy)pyridin-2-yl)-N7-(thiazol-4-ylmethyl)-3,4-dihydro-1,4-methanopyrido[2,3-b][1,4]diazepine-5,7(2H)-dicarboxamide (250 mg, 0.453 mmol) in methanol (10 mL) at 0° C. was added aq. HCl (3 mL, 99 mmol) and stirred for 2 h. (TLC eluent: 10% MeOH&DCM: $R_f$—0.2; UV active). The reaction mixture was basified with saturated sodium bicarbonate solution (till pH-8-9) and solvent was evaporated under reduced pressure. The resultent solid was filtered and washed with water to afford the desired product (4S)—N5-(4-((R)-2,3-dihydroxypropoxy)pyridin-2-yl)-N7-(thiazol-4-ylmethyl)-3,4-dihydro-1,4-methanopyrido[2,3-b][1,4]diazepine-5,7(2H)-dicarboxamide (104 mg, 0.202 mmol, 44.6% yield) as an off-white solid. LCMS (m/z): 512.22 [M+H]$^+$, $R_t$=1.28 min.

$^1$H NMR: (400 MHz, CDCl$_3$): δ ppm 13.76 (s, 1H), 8.91 (br t, J=5.8 Hz, 1H), 8.75 (d, J=2.2 Hz, 1H), 7.97-7.87 (m, 1H), 7.91 (d, J=7.9 Hz, 1H), 7.84 (d, J=5.7 Hz, 1H), 7.69-7.62 (m, 1H), 7.33-7.28 (m, 1H), 6.50 (dd, J=2.4, 5.7 Hz, 1H), 5.56 (dd, J=3.1, 5.9 Hz, 1H), 4.96 (dd, J=1.9, 6.0 Hz, 2H), 4.22-4.09 (m, 3H), 3.89-3.80 (m, 1H), 3.78-3.70 (m, 1H), 3.31-3.17 (m, 1H), 3.16-3.08 (m, 1H), 3.04 (d, J=3.1 Hz, 1H), 3.01 (d, J=3.3 Hz, 1H), 2.58 (br s, 1H), 2.38-2.26 (m, 1H), 2.11-1.96 (m, 2H)

Example 200

Synthesis (4S)—N7-(1-hydroxy-2-methylpropan-2-yl)-N5-(pyridin-2-yl)-3,4-dihydro-1,4-methanopyrido[2,3-b][1,4]diazepine-5,7(2H)-dicarboxamide

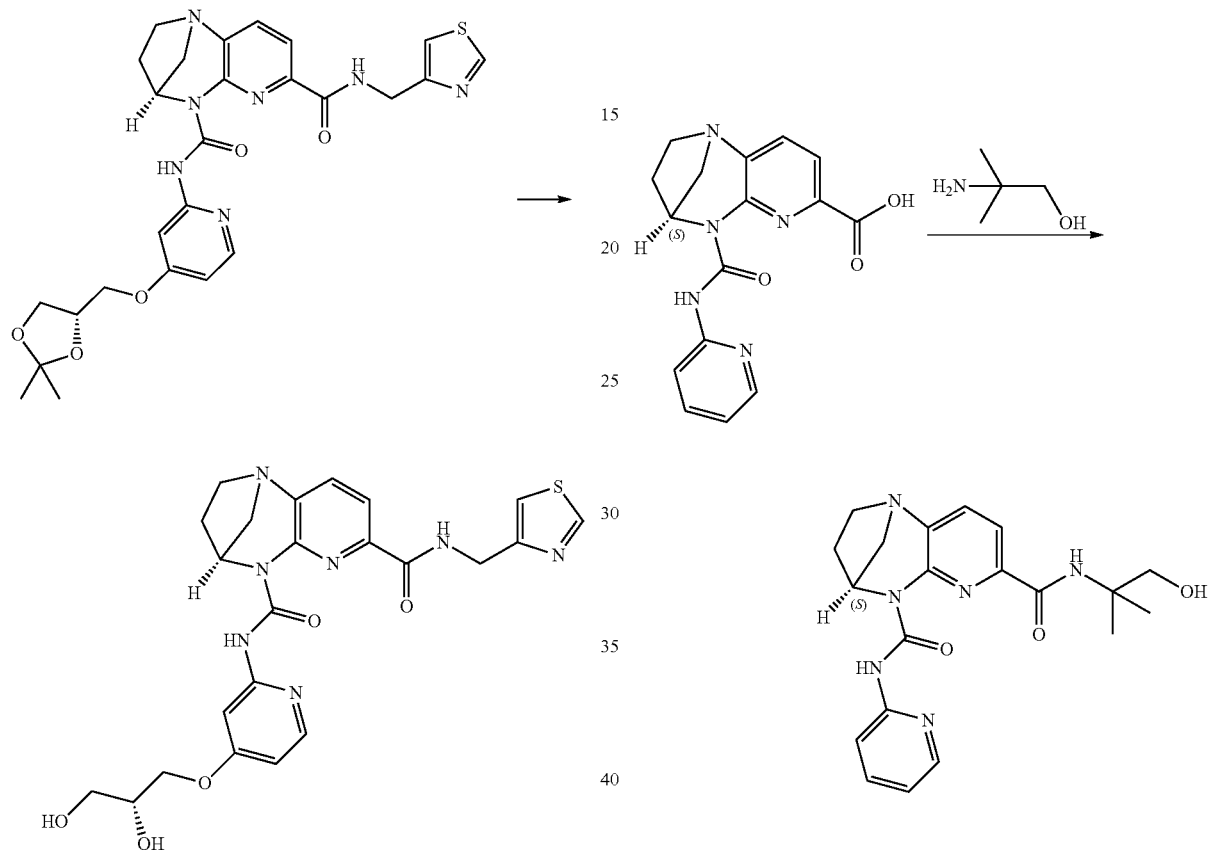

To a stirred solution of (4S)-5-(pyridin-2-ylcarbamoyl)-2,3,4,5-tetrahydro-1,4-methanopyrido[2,3-b][1,4]diazepine-7-carboxylic acid (400 mg, 1.230 mmol) in DMF (4 mL) at 0° C. was added HATU (935 mg, 2.459 mmol) and DIPEA (1.074 mL, 6.15 mmol) and stirred for 10 min. Then added 2-amino-2-methylpropan-1-ol (219 mg, 2.459 mmol) at 0° C. and the resulting solution was stirred at RT for 16 h. (TLC eluent: 5% MeOH in DCM, $R_f$—0.2; UV active). To the reaction mixture was added ice cold water (20 mL) and extracted into ethylacetate (50 mL). The separated organic layer was dried over anhydrous Na$_2$SO$_4$, filtered and concentrated under reduced pressure to obtain crude compound. Crude material was purified by combiflash chromatography (silica gel column, eluent EtOAc). Fraction containing pure compound were combined and concentration to afford the desired compound, which was dissolved in water (25 mL) and ACN (25 mL), kept for lyophilization to give (4S)—N7-(1-hydroxy-2-methylpropan-2-yl)-N5-(pyridin-2-yl)-3,4-dihydro-1,4-methanopyrido[2,3-b][1,4]diazepine-5,7(2H)-dicarboxamide (255 mg, 0.616 mmol, 50.1% yield) as an white solid. LCMS (m/z): 397.03 [M+H]$^+$, $R_t$=1.67 min.

¹H NMR (400 MHz, DMSO-d₆): δ ppm 12.65 (s, 1H), 8.18-8.33 (m, 1H), 8.04-8.15 (m, 1H), 7.61-7.88 (m, 3H), 7.40-7.52 (m, 1H), 7.00-7.20 (m, 1H), 5.37-5.56 (m, 1H), 4.84 (t, J=5.92 Hz, 1H), 3.61 (d, J=6.14 Hz, 2H), 3.02-3.24 (m, 3H), 2.85-3.00 (m, 1H), 2.23 (dddd, J=13.67, 9.84, 5.97, 3.84 Hz, 1H), 1.86-2.09 (m, 1H), 1.34-1.56 (m, 6H)

Example 201

Synthesis of (4S)-7-(2, 2-dimethylhydrazinecarbonyl)-N-(pyridin-2-yl)-3, 4-dihydro-1, 4-methanopyrido[2,3-b][1,4]diazepine-5(2H)-carboxamide

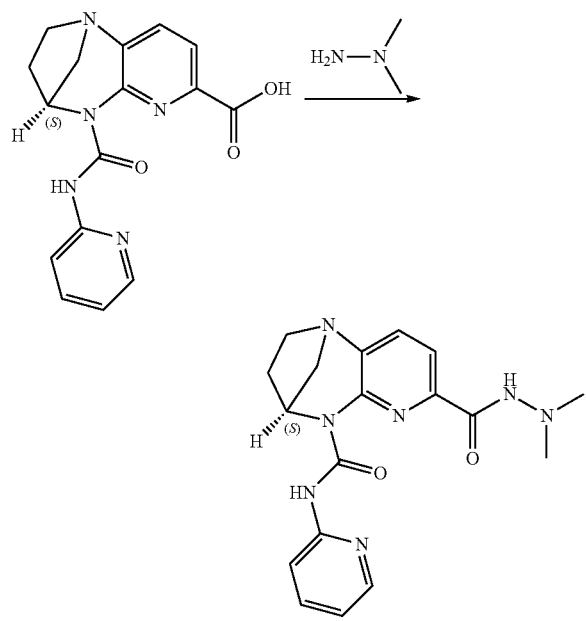

To a stirred solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in DMF (3 mL) at 0° C. was added HATU (701 mg, 1.844 mmol) and DIPEA (0.483 mL, 2.77 mmol) and stirred for 10 min. Then added 1,1-dimethylhydrazine (0.140 mL, 1.844 mmol) in one charge at 0° C. and the resulting solution was stirred at RT for 16 h. (TLC eluent: 5% MeOH in DCM, R_f—0.4; UV active). The reaction mixture was diluted with 50 mL of ice cold water to get solid, which was filtered and dried to get (4S)-7-(2,2-dimethylhydrazinecarbonyl)-N-(pyridin-2-yl)-3,4-dihydro-1,4-methanopyrido[2,3-b][1,4]diazepine-5(2H)-carboxamide (149 mg, 0.403 mmol, 43.7% yield) as an off white solid. LCMS (m/z): 368.10 [M+H]⁺, R_t=1.47 min.

¹H NMR (400 MHz, CDCl₃): δ ppm 13.31 (s, 1H), 8.76 (s, 1H), 8.33 (dd, J=4.93, 0.99 Hz, 1H), 8.18 (d, J=8.33 Hz, 1H), 7.96 (d, J=7.89 Hz, 1H), 7.74 (t, J=7.83 Hz, 1H), 7.65 (d, J=7.89 Hz, 1H), 6.93-7.17 (m, 1H), 5.65 (dd, J=5.92, 3.07 Hz, 1H), 3.20-3.31 (m, 2H), 3.06-3.20 (m, 1H), 2.85-3.05 (m, 1H), 2.82 (s, 6H), 2.19-2.41 (m, 1H), 1.97-2.17 (m, 1H).

Example 202

Synthesis of (4S)—N7-(2-hydroxy-2-methylpropyl)-N5-(pyridin-2-yl)-3, 4-dihydro-1, 4-methanopyrido[2, 3-b][1, 4] diazepine-5,7(2H)-dicarboxamide

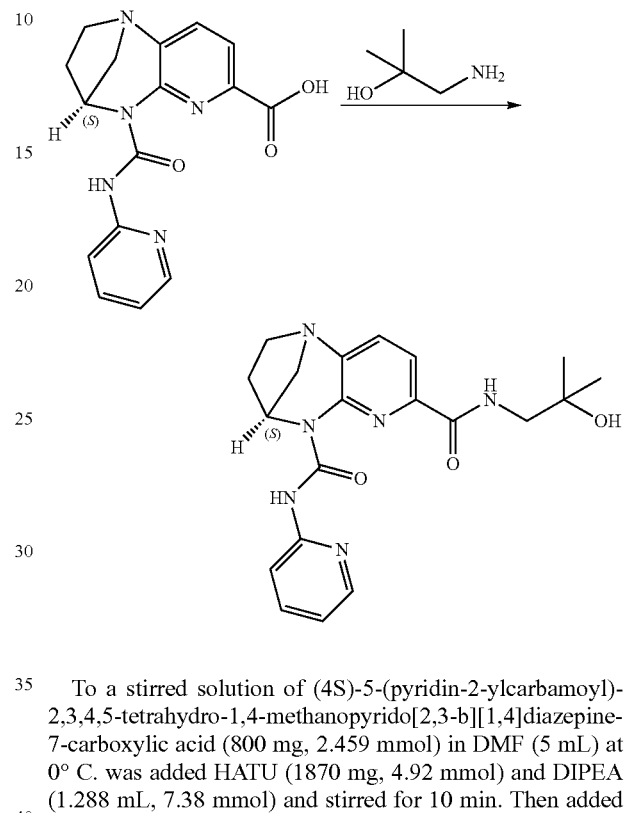

To a stirred solution of (4S)-5-(pyridin-2-ylcarbamoyl)-2,3,4,5-tetrahydro-1,4-methanopyrido[2,3-b][1,4]diazepine-7-carboxylic acid (800 mg, 2.459 mmol) in DMF (5 mL) at 0° C. was added HATU (1870 mg, 4.92 mmol) and DIPEA (1.288 mL, 7.38 mmol) and stirred for 10 min. Then added 1-amino-2-methylpropan-2-ol (219 mg, 2.459 mmol) at 0° C. and the resulting solution was stirred at RT for 16 h. (TLC eluent: 10% MeOH in DCM, R_f—0.5; UV active). Reaction mixture was poured in to cold water (30 ml), the aqueous layer was extracted with EtOAc (2×35 ml), combined organic layer was dried over anhydrous Na₂SO₄, filtered and concentrated under reduced pressure to obtain crude compound. Crude was purified by combiflash chromatography (using silica gel column, 95% ethyl acetate in hexane) to get desired compound with 90% purity which was further purified by prep HPLC (Column: XBridge [(150×19) mm 5µ]; mobile phase-A: 10 mM Ammonium Bicarbonate (Aq), mobile phase-B: Acetonitrile; Method—T % B 0/10, 10/60, 10.1/10, 15/10; Flow: 19 ml/min; Solubility: THF+ACN) to afford (4S)—N7-(2-hydroxy-2-methylpropyl)-N5-(pyridin-2-yl)-3,4-dihydro-1,4-methanopyrido[2,3-b][1,4]diazepine-5,7(2H)-dicarboxamide (120 mg, 0.302 mmol, 12.27% yield) as a white solid. LCMS (m/z): 397.12 [M+H]⁺, R_t=1.56 min.

¹H NMR (400 MHz, CDCl₃): δ ppm 13.02 (s, 1H), 8.29 (ddd, J=5.04, 1.97, 0.88 Hz, 1H), 8.21 (dt, J=8.33, 0.88 Hz, 1H), 8.04 (br s, 1H), 7.88 (d, J=7.89 Hz, 1H), 7.61-7.79 (m, 2H), 6.93-7.12 (m, 1H), 5.65 (dd, J=5.92, 3.07 Hz, 1H), 4.32 (br s, 1H), 3.48-3.68 (m, 2H), 3.08-3.33 (m, 3H), 2.94-3.08 (m, 1H), 2.23-2.42 (m, 1H), 1.99-2.13 (m, 1H), 1.33 (d, J=2.85 Hz, 6H).

Example 203

Synthesis of (4S)—N7-((R)-2-hydroxypropyl)-N5-(pyridin-2-yl)-3,4-dihydro-1,4-methanopyrido[2,3-b][1,4]diazepine-5,7(2H)-dicarboxamide

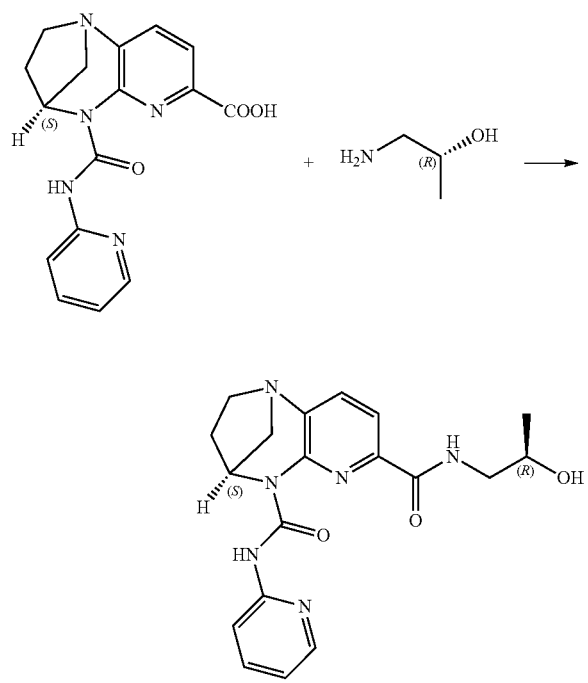

Example 204

Synthesis of (4S)—N7-cyclopropyl-N5-(pyrimidin-2-yl)-3,4-dihydro-1,4-methanopyrido[2,3-b][1,4]diazepine-5,7(2H)-dicarboxamide

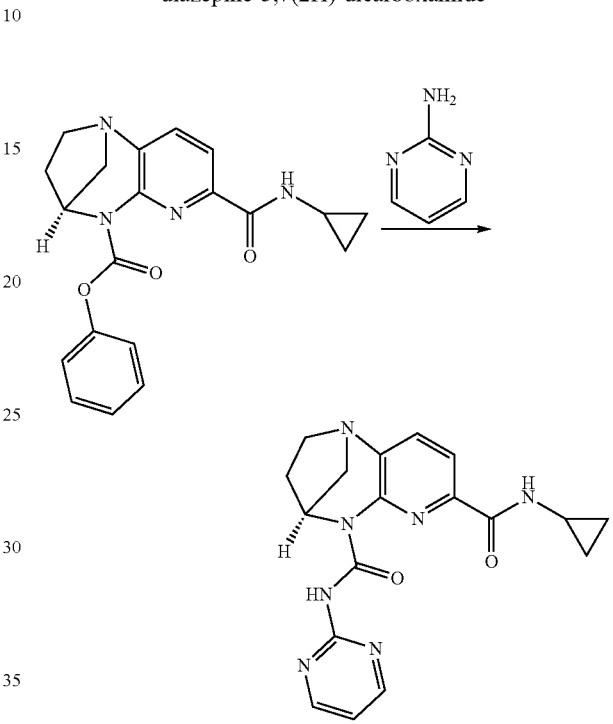

To a stirred solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) and (R)-1-aminopropan-2-ol (104 mg, 1.383 mmol) in N,N-Dimethylformamide (10 mL) was added DIPEA (0.805 mL, 4.61 mmol) followed by HATU (701 mg, 1.844 mmol) at RT then stirred at the same temperature for 16 h. (TLC solvent: 5% MeOH in EtOAc, $R_f$: 0.5; UV active).

The reaction mixture was partitioned between ice cold water (10 mL) and ethyl acetate (15 mL×2). The combined organic layer was dried over anhydrous $Na_2SO_4$, filtered and filtrate was evaporated to get crude and it was purified by Prep HPLC (Column: XBridge C 18 (75×4.6 mm, 3.5µ), Mobile Phase: A: 0.01 M Ammonium Bicarbonate B: ACN; Gradient: Time/% B: 0/5, 0.8/5, 5/50, 8/95, 12/95, 12.1/5, 15/5: Column Temp: Ambient, Flow Rate: 1.0 ml/min: Diluent: ACN) to afford the desired product (4S)—N7-((R)-2-hydroxypropyl)-N5-(pyridin-2-yl)-3,4-dihydro-1,4-methanopyrido[2,3-b][1,4]diazepine-5,7(2H)-dicarboxamide (120 mg, 0.311 mmol, 33.8% yield) as an off white solid. LCMS (m/z): 383.09 [M+H]⁺, Rt=1.46 min.

¹H NMR (400 MHz, CDCl₃): δ ppm 13.08 (s, 1H), 8.30-8.25 (m, 1H), 8.21-8.17 (m, 1H), 8.03 (br s, 1H), 7.87 (d, J=7.89 Hz, 1H), 7.77-7.70 (m, 1H), 7.66 (d, J=7.89 Hz, 1H), 7.03 (ddd, J=7.29, 4.99, 1.10 Hz, 1H), 5.67 (dd, J=6.03, 3.18 Hz, 1H), 4.23 (br s, 1H), 4.15-4.08 (m, 1H), 3.74 (ddd, J=13.70, 6.47, 2.85 Hz, 1H), 3.42 (ddd, J=13.70, 8.00, 5.70 Hz, 1H), 3.32-3.09 (m, 3H), 3.06-2.99 (m, 1H), 2.39-2.28 (m, 1H), 2.10-2.02 (m, 1H), 1.30 (d, J=6.36 Hz, 3H).

To a stirred solution of pyrimidin-2-amine (157 mg, 1.647 mmol) in THF (20 mL), was added a solution of 1M LiHMDS (2.74 mL, 2.74 mmol) dropwise at −78° C. under nitrogen and stirred for 30 min, then added a solution of (4S)-phenyl 7-(cyclopropylcarbamoyl)-3,4-dihydro-1,4-methanopyrido[2,3-b][1,4]diazepine-5(2H)-carboxylate (500 mg, 1.372 mmol) in THF (5 mL). The resulting reaction mixture was stirred at −78° C. for 1 h and at RT for 6 h. (TLC system: 5% MeOH in DCM, Rf value: 0.3). Reaction mixture was quenched with aq. NH₄Cl (10 mL) and the aqueous layer was extracted with EtOAc (2×20 mL). Combined organic layer was dried over anhydrous $Na_2SO_4$, filtered and concentrated under reduced pressure to obtain crude product. The crude material was purified by combi-flash chromatography (Silicagel, eluent 2.8% MeOH in DCM) to afford (4S)—N7-cyclopropyl-N5-(pyrimidin-2-yl)-3,4-dihydro-1,4-methanopyrido[2,3-b][1,4]diazepine-5,7(2H)-dicarboxamide (280 mg, 0.761 mmol, 55.5% yield) as an off-white solid. LCMS (m/z): 366.09 [M+H]⁺, Rt=1.43 min ¹H NMR (400 MHz, CDCl₃): δ ppm 13.74 (s, 1H), 8.65 (d, J=4.82 Hz, 2H), 7.80-8.02 (m, 2H), 7.66 (d, J=7.89 Hz, 1H), 7.04 (t, J=4.93 Hz, 1H), 5.70 (dd, J=5.92, 3.29 Hz, 1H), 3.16-3.28 (m, 2H), 2.98-3.13 (m, 3H), 2.19-2.43 (m, 1H), 1.94-2.15 (m, 1H), 0.73-0.99 (m, 4H)

Example 205

Synthesis of (4S)—N7-cyclopropyl-N5-(5-fluoro-6-methylpyridin-2-yl)-3,4-dihydro-1,4-methanopyrido[2,3-b][1,4]diazepine-5,7(2H)-dicarboxamide

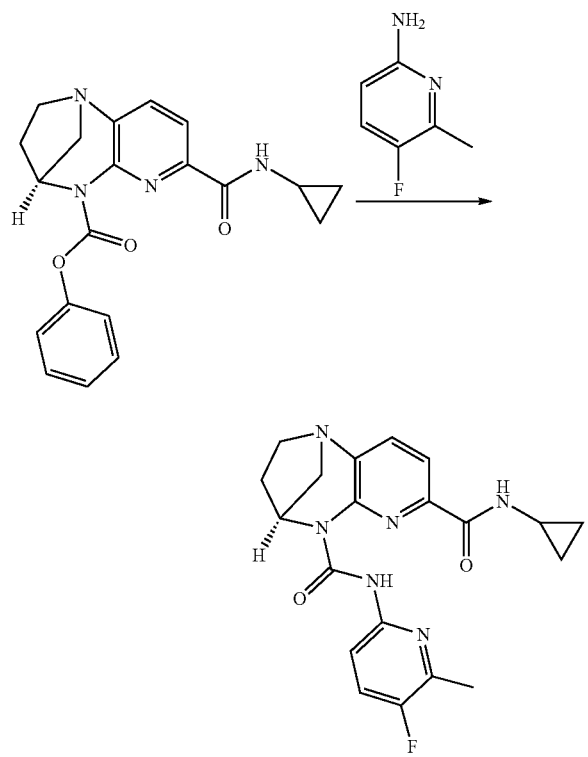

To a stirred solution of 5-fluoro-6-methylpyridin-2-amine (346 mg, 2.74 mmol) in Tetrahydrofuran (20 mL) was added a solution of 1.0 M LiHMDS (2.74 mL, 2.74 mmol) in THF at −78° C. under Nitrogen atmosphere. The resulting reaction mixture was stirred at −78° C. for 30 min. To the reaction mixture was added a solution of (4S)-phenyl 7-(cyclopropylcarbamoyl)-3,4-dihydro-1,4-methanopyrido[2,3-b][1,4]diazepine-5(2H)-carboxylate (500 mg, 1.372 mmol) in Tetrahydrofuran (10 mL) at −78° C. The resulting reaction mixture was warm to room temperature and stirred at RT for 6 h. (TLC system: 5% MeOH in DCM, Rf: 0.5). The reaction mixture was quenched with saturated ammonium chloride solution (30 mL), aqueous layer was extracted with EtOAc (3×30 mL). The combined organic layer was washed with water (20 mL), brine solution (20 mL) and dried over anhydrous $Na_2SO_4$, filtered and concentrated under reduced pressure to obtain crude compound. The crude was purified by flash column chromatography (silica gel: 100-200 mesh, Eluent: 4% MeOH in DCM) to afford sticky solid. The sticky solid was washed with a mixture of diethyl ether (5 ml) and n-pentane (10 mL), filtered and dried well to afford the desired product (4S)—N7-cyclopropyl-N5-(5-fluoro-6-methylpyridin-2-yl)-3,4-dihydro-1,4-methanopyrido[2,3-b][1,4]diazepine-5,7(2H)-dicarboxamide (220 mg, 0.552 mmol, 40.2% yield) as an off-white solid. LCMS (m/z): 397.08 [M+H]+, $R_t$=2.09 min.

$^1$H NMR (400 MHz, $CDCl_3$): δ ppm 12.80 (s, 1H), 8.00 (dd, J=8.99, 3.51 Hz, 1H), 7.91 (d, J=7.89 Hz, 1H), 7.71 (br s, 1H), 7.64 (d, J=7.89 Hz, 1H), 7.37 (t, J=8.66 Hz, 1H), 5.64 (dd, J=5.92, 3.07 Hz, 1H), 3.25-3.14 (m, 2H), 3.12-3.05 (m, 1H), 3.03-2.96 (m, 1H), 2.95-2.86 (m, 1H), 2.51 (d, J=2.85 Hz, 3H), 2.37-2.25 (m, 1H), 2.07-1.96 (m, 1H), 0.96-0.89 (m, 2H), 0.77-0.68 (m, 2H).

Example 206

Synthesis of (4S)—N7-cyclobutyl-N5-(pyrazin-2-yl)-3,4-dihydro-1,4-methanopyrido[2,3-b][1,4]diazepine-5,7(2H)-dicarboxamide

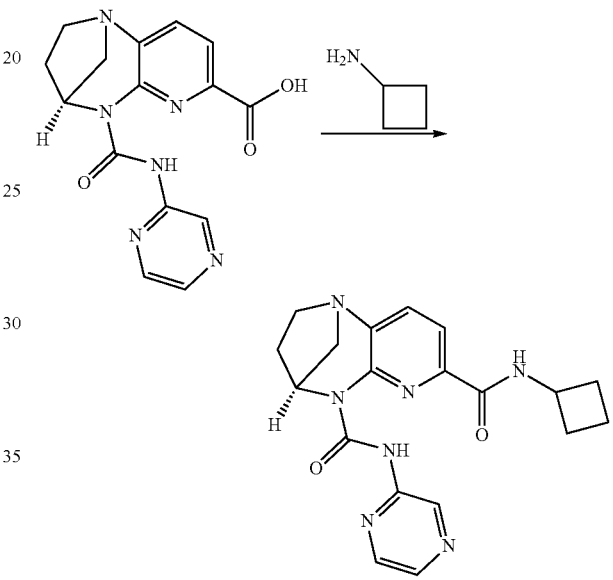

To a stirred solution of (4S)-5-(pyrazin-2-ylcarbamoyl)-2,3,4,5-tetrahydro-1,4-methanopyrido[2,3-b][1,4]diazepine-7-carboxylic acid (500 mg, 1.532 mmol) in DMF (10 mL), was added HATU (874 mg, 2.298 mmol) followed by TEA (0.641 mL, 4.60 mmol) and the reaction mixture was stirred at RT for 15 min. Then added cyclobutanamine (218 mg, 3.06 mmol) and reaction was stirred at RT for 16 h. (TLC eluent: 5% MeOH in DCM, $R_f$: 0.4; UV active). Water (25 mL) was added to the reaction mixture and extracted with EtOAc (2×30 mL). The combined organic extracts were dried over anhydrous $Na_2SO_4$, filtered and concentrated under reduced pressure to obtain crude product. The crude was purified by column chromatography (silicagel, eluent 0.5-1.5% MeOH in DCM) to afford (4S)—N7-cyclobutyl-N5-(pyrazin-2-yl)-3,4-dihydro-1,4-methanopyrido[2,3-b][1,4]diazepine-5,7(2H)-dicarboxamide (450 mg, 1.183 mmol, 77% yield) as a white solid. LCMS (m/z): 380.11 [M+H]+; Rt=1.83 min.

$^1$H NMR (400 MHz, $CDCl_3$): δ ppm 13.44 (s, 1H), 9.54 (d, J=1.53 Hz, 1H), 8.35 (d, J=2.63 Hz, 1H), 8.23 (dd, J=2.52, 1.64 Hz, 1H), 7.90 (d, J=7.89 Hz, 1H), 7.74 (br d, J=7.02 Hz, 1H), 7.65 (d, J=7.89 Hz, 1H), 5.65 (dd, J=5.92, 3.07 Hz, 1H), 4.62-4.84 (m, 1H), 3.08-3.28 (m, 3H), 2.94-3.05 (m, 1H), 2.40-2.48 (m, 2H), 2.16-2.37 (m, 3H), 1.95-2.11 (m, 1H), 1.73-1.92 (m, 2H).

Example 207

Synthesis of (4S)—N5-(pyridin-2-yl)-N7-((S)-1,1,1-trifluoropropan-2-yl)-3,4-dihydro-1,4-methanopyrido[2,3-b][1,4]diazepine-5,7(2H)-dicarboxamide

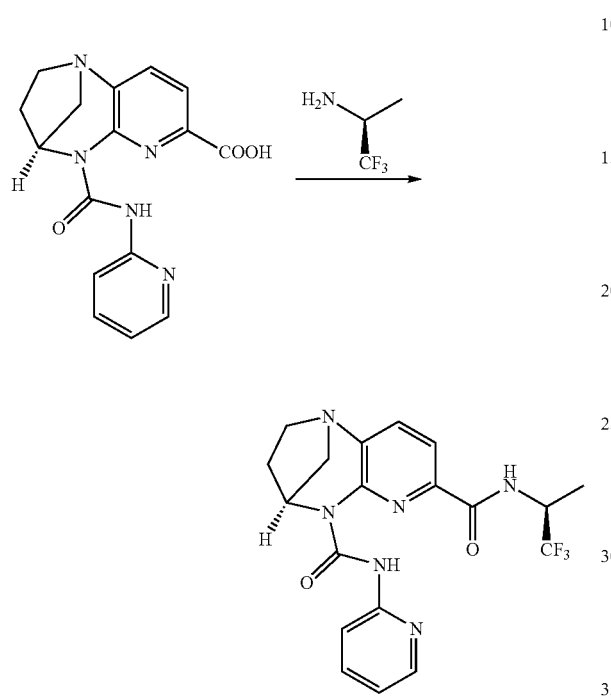

To a stirred solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in DMF (10 mL) were added HATU (701 mg, 1.844 mmol) and DIPEA (0.322 mL, 1.844 mmol) under nitrogen atmosphere at 0° C. To this reaction mixture (S)-1,1,1-trifluoropropan-2-amine, Hydrochloride (207 mg, 1.383 mmol) was added and the reaction mixture was stirred at room temperature for 16 h. (TLC system: Neat Ethyl acetate. Rf value: 0.25). The reaction mixture was diluted with ice water (10 mL) and extracted with ethyl acetate (2×25 ml). The combined organic layer was washed with brine solution (15 ml) and dried over sodium sulphate and concentrated under reduced pressure to afford crude compound. The crude product was purified by flash column chromatography (silicagel: 100-200 Mesh, Eluent: 70% Ethyl acetate in pet ether) to afford pure compound (4S)—N5-(pyridin-2-yl)-N7-((S)-1,1,1-trifluoropropan-2-yl)-3,4-dihydro-1,4-methanopyrido[2,3-b][1,4]diazepine-5,7(2H)-dicarboxamide (190 mg, 0.450 mmol, 48.8% yield) as an off white solid. LCMS (m/z): 421.06 [M+H]+, R$_t$=3.44 min.

$^1$H NMR (400 MHz, CDCl$_3$): δ ppm 13.25 (s, 1H), 8.33-8.19 (m, 1H), 8.20-8.08 (m, 1H), 8.04-7.87 (m, 2H), 7.68-7.65 (m, 2H), 7.05-6.96 (m, 1H), 5.75-5.60 (m, 1H), 5.16-4.92 (m, 1H), 3.34-3.16 (m, 2H), 3.16-3.07 (m, 1H), 3.07-2.95 (m, 1H), 2.40-2.24 (m, 1H), 2.10-1.95 (m, 1H), 1.64-1.48 (m, 3H).

Example 208

Synthesis of (4S)—N5-(pyridin-2-yl)-N7-(((S)-tetrahydrofuran-2-yl)methyl)-3,4-dihydro-1,4-methanopyrido[2,3-b][1,4]diazepine-5,7(2H)-dicarboxamide

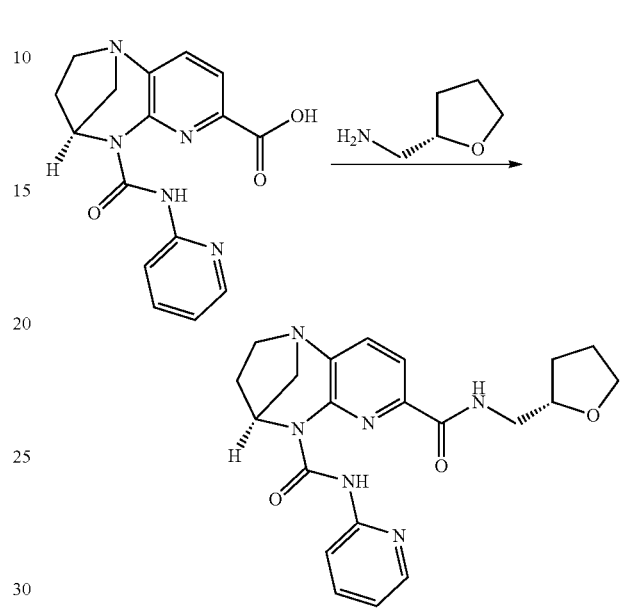

To a stirred solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in N,N-Dimethylformamide (3 mL) were added DIPEA (0.483 mL, 2.77 mmol) and HATU (701 mg, 1.844 mmol) at room temperature and stirred it for 10 min. at room temperature. Then added (S)-(tetrahydrofuran-2-yl) methanamine (0.236 mL, 1.844 mmol) at 24-27° C. The resulting reaction mixture was stirred at room temperature for 16 h. (TLC 5% MeOH\DCM R$_f$; 0.5; UV active). Reaction mixture was poured in ice-cold water (50 mL) and extracted with EtOAc (2×80 mL). The combined organic layer was washed with brine (50 mL) dried over anhydrous Na$_2$SO$_4$, filtered and concentrated under reduced pressure to obtain crude material. The crude material was purified by flash column chromatography (silica gel: 100-200 mesh, Eluent; 90% ethyl acetate in hexane) to afford the desired compound with 75% purity which was further purified by prep HPLC (conditions; MP-A: 5 Mm ammonium bicarbonate (Aq) MP-B: Acetonitrile Column: Xbridge (150×30) mm 5μ Method: 65:35 isocratic Flow: 19 ml/min Solubility: THF+CAN+MEOH) to afford the desired product (4S)—N5-(pyridin-2-yl)-N7-(((S)-tetrahydrofuran-2-yl)methyl)-3,4-dihydro-1,4-methanopyrido[2,3-b][1,4]diazepine-5,7(2H)-dicarboxamide (128 mg, 0.313 mmol, 33.9% yield) as a white solid. LCMS (m/z): 409.15 [M+H]+, Rt=1.75 min.

$^1$H NMR (400 MHz, CDCl$_3$): δ ppm 13.57 (s, 1H), 8.39-8.22 (m, 1H), 8.09 (d, J=8.33 Hz, 1H), 7.89 (d, J=7.89 Hz, 1H), 7.76-7.60 (m, 1H), 7.6 (d, J=7.89 Hz, 1H), 7.07-6.95 (m, 1H), 5.61 (dd, J=5.92, 3.29 Hz, 1H), 4.23 (dd, J=6.58, 5.48 Hz, 1H), 4.04-3.81 (m, 1H), 3.78-3.66 (m, 2H), 3.59 (dt, J=13.32, 6.39 Hz, 1H), 3.37-3.17 (m, 3H), 3.13 (d, J=12.28 Hz, 1H), 2.37-2.23 (m, 1H), 2.08-1.83 (m, 5H), 1.82-1.64 (m, 1H).

Example 209

Synthesis of (4S)—N7-(4-hydroxy-2-methylbutan-2-yl)-N5-(pyridin-2-yl)-3, 4-dihydro-1, 4-methanopyrido[2, 3-b][1, 4] diazepine-5, 7(2H)-dicarboxamide

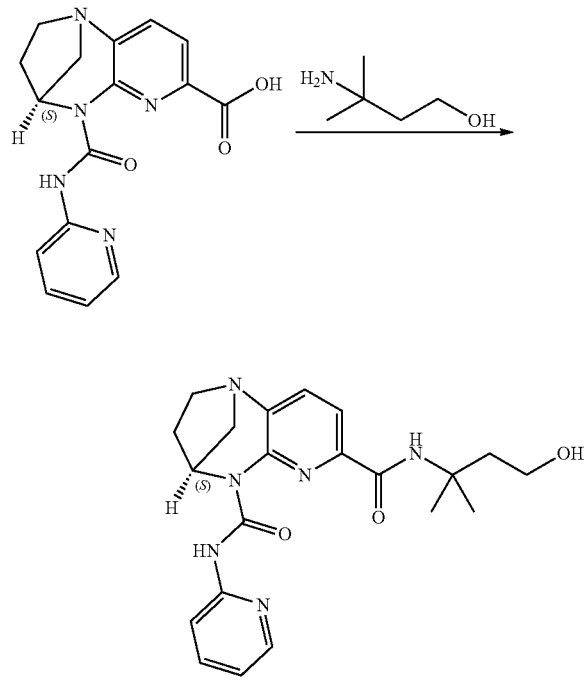

To a stirred solution of (4S)-5-(pyridin-2-ylcarbamoyl)-2,3,4,5-tetrahydro-1,4-methanopyrido[2,3-b][1,4]diazepine-7-carboxylic acid (500 mg, 1.537 mmol) in DMF (4 mL) at 0° C. was added HATU (1169 mg, 3.07 mmol) and DIPEA (0.805 mL, 4.61 mmol), and stirred for 10 min. Then added 3-amino-3-methylbutan-1-ol (174 mg, 1.691 mmol) at 0° C. and the resulting solution was stirred at RT for 16 h. (TLC eluent: 5% MeOH in DCM, $R_f$—0.2; UV active). Reaction mixture was diluted in EtOAc (100 mL), washed with water (50 mL) and brine. The separated organic layer was dried over anhydrous $Na_2SO_4$, then filtered and concentrated under reduced pressure to crude product. Crude material was purified by combiflash chromatography (Silica gel column, eluent 5% methanol in DCM) to obtain desired compound with 87% purity which was further purified by prep HPLC (Column: XBridge C18 (150×4.6 mm, 3.5μ); Mobile Phase: A: 5 mM Ammonium Bicarbonate; B: ACN, Gradient: Time/% B: 0/10, 1/10, 10/50, 15/50, 18/98, 20/98, 20.1/10, 25/10; Column Temp: Ambient; Flow Rate: 0.8 ml/min; Diluent: ACN) to give desired compound as a color less gum. The product was dissolved in water (25 mL) and ACN (20 mL), kept for lyophilization to give (4S)—N7-(4-hydroxy-2-methylbutan-2-yl)-N5-(pyridin-2-yl)-3,4-dihydro-1,4-methanopyrido[2,3-b][1,4]diazepine-5,7(2H)-dicarboxamide (120 mg, 0.291 mmol, 18.94% yield) as a white solid. LCMS (m/z): 411.16 [M+H]$^+$, $R_t$=1.71 min.

$^1$H NMR (400 MHz, DMSO-d$_6$): δ ppm 12.64 (s, 1H), 8.29 (br d, J=3.95 Hz, 1H), 8.10 (d, J=8.33 Hz, 1H), 7.76-7.96 (m, 1H), 7.59-7.75 (m, 3H), 7.12 (dd, J=6.91, 5.37 Hz, 1H), 5.47 (dd, J=5.92, 3.07 Hz, 1H), 4.41 (br s, 1H), 3.43-3.67 (m, 2H), 3.02-3.27 (m, 3H), 2.81-3.00 (m, 1H), 2.14-2.47 (m, 3H), 1.86-2.13 (m, 1H), 1.46 (s, 6H)

Example 210

Synthesis of (4S)—N7-((1r,3S)-3-hydroxycyclobutyl)-N5-(pyridin-2-yl)-3,4-dihydro-1,4-methanopyrido[2,3-b][1,4]diazepine-5,7(2H)-dicarboxamide

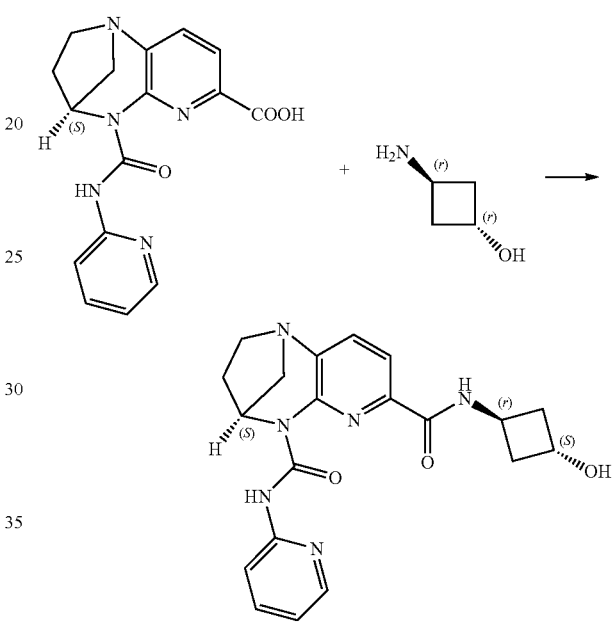

To a suspension of (4S)-5-(pyridin-2-ylcarbamoyl)-2,3,4,5-tetrahydro-1,4-methano pyrido[2,3-b][1,4]diazepine-7-carboxylic acid (300 mg, 0.922 mmol) and (1r,3r)-3-aminocyclobutanol hydrochloride (171 mg, 1.383 mmol) in N,N-Dimethylformamide (10 mL) were added DIEA (0.805 mL, 4.61 mmol) followed by HATU (701 mg, 1.844 mmol) at RT then stirred at the same temperature for 16 h. (TLC system: 5% MeOH in ethyl acetate; $R_f$: 0.5; UV active). The reaction mixture was partitioned between ice cold water (20 mL) and ethyl acetate (20 mL×2). The combined organic layer was dried over anhydrous $Na_2SO_4$, filtered and filtrate was evaporated to get crude compound then it was purified by flash column chromatography (using 100-200 silica gel, column eluted at 5% MeOH in ethyl acetate) to afford the desired product (4S)—N7-((1r,3S)-3-hydroxycyclobutyl)-N5-(pyridin-2-yl)-3,4-dihydro-1,4-methanopyrido[2,3-b][1,4]diazepine-5,7(2H)-dicarboxamide (122 mg, 0.303 mmol, 32.8% yield) as an off white solid. LCMS (m/z): 395.07 [M+H]$^+$, Rt=1.47 min.

$^1$H NMR (400 MHz, CDCl$_3$): δ ppm 13.19 (s, 1H), 8.27-8.20 (m, 2H), 7.98 (d, J=6.80 Hz, 1H), 7.91 (d, J=7.89 Hz, 1H), 7.71-7.76 (m, 1H), 7.65 (d, J=7.89 Hz, 1H), 7.04 (ddd, J=7.29, 4.99, 0.88 Hz, 1H), 5.67 (dd, J=5.92, 3.07 Hz, 1H), 4.86-4.77 (m, 1H), 4.73-4.67 (m, 1H), 3.27-3.20 (m, 2H), 3.15-3.10 (m, 1H), 3.04-2.99 (m, 2H), 2.70-2.61 (m, 2H), 2.52-2.45 (m, 2H), 2.37-2.29 (m, 1H), 2.05 (dt, J=14.09, 6.88 Hz, 1H).

Example 211

Synthesis of (4S)—N7-((S)-2-hydroxypropyl)-N5-(pyridin-2-yl)-3,4-dihydro-1,4-methanopyrido[2,3-b][1,4]diazepine-5,7(2H)-dicarboxamide

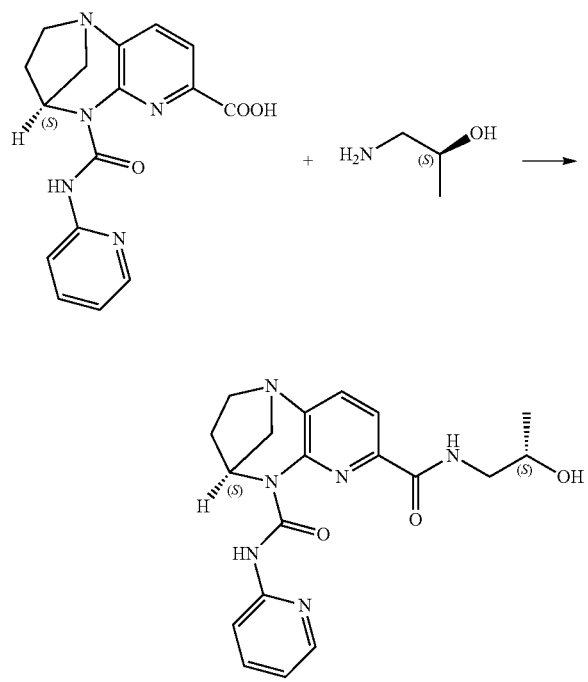

To a stirred solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) and (S)-1-aminopropan-2-ol (104 mg, 1.383 mmol) in N,N-Dimethylformamide (5 mL) were added DIPEA (0.805 mL, 4.61 mmol) followed by HATU (701 mg, 1.844 mmol) at RT then stirred at the same temperature for 16 h. (TLC system: Neat ethyl acetate $R_f$: 0.2, UV active). The reaction mixture was partitioned between ice cold water (10 mL) and ethyl acetate (15 mL×2). The combined organic layer was dried over anhydrous $Na_2SO_4$, filtered and filtrate was evaporated to get crude. It was purified by prep HPLC (Conditions: Column: XBridge C 18 (75×4.6 mm, 3.5): Mobile Phase: A: 0.01 M Ammonium Bicarbonate B: ACN: Gradient: Time/% B: 0/5, 0.8/5, 5/50, 8/95, 12/95, 12.1/5, 15/5: Column Temp: Ambient, Flow Rate: 1.0 ml/min: Diluent: ACN) to afford the desired product (4S)—N7-((S)-2-hydroxypropyl)-N5-(pyridin-2-yl)-3,4-dihydro-1,4-methanopyrido[2,3-b][1,4]diazepine-5,7(2H)-dicarboxamide (143 mg, 0.371 mmol, 40.2% yield) as an off white solid. LCMS (m/z): 383.09 $[M+H]^+$, Rt=1.48 min.

$^1$H NMR (400 MHz, $CDCl_3$): δ ppm 13.05 (s, 1H), 8.27 (d, J=3.73 Hz, 1H), 8.21 (d, J=8.55 Hz, 1H), 8.00 (s, 1H), 7.86 (d, J=7.89 Hz, 1H), 7.77-7.71 (m, 1H), 7.66 (d, J=7.67 Hz, 1H), 7.03 (ddd, J=7.29, 5.10, 0.99 Hz, 1H), 5.61 (dd, J=5.92, 3.07 Hz, 1H), 4.38 (br s, 1H), 4.15-4.06 (m, 1H), 3.78 (ddd, J=13.70, 6.91, 2.85 Hz, 1H), 3.34 (ddd, J=13.59, 8.33, 5.26 Hz, 1H), 3.39-3.20 (m, 2H), 3.16-3.11 (m, 1H), 3.06-3.00 (m, 1H), 2.34 (ddt, J=14.22, 8.69, 5.54, 5.54 Hz, 1H), 2.12-2.01 (m, 1H), 1.30 (d, J=6.36 Hz, 3H)

Example 212

Synthesis of (4S)—N7-methyl-N5-(pyridin-2-yl)-3,4-dihydro-1,4-methanopyrido[2,3-b][1,4]diazepine-5,7(2H)-dicarboxamide To a stirred solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in N,N-Dimethylformamide (10 mL) were added DIPEA (0.322 mL, 1.844 mmol) followed by HATU (701 mg, 1.844 mmol) at room temperature and stirred for 1 h. Then methanamine (43.0 mg, 1.383 mmol) was added to the reaction mixture and stirred for 16 h. (TLC System: $R_f$: 0.6, 5% methanol in DCM). Reaction mixture was diluted with water (30 mL), extracted with ethylacetate (2×40 mL). The combined organic layer was washed with brine solution (20 mL) and dried over anhydrous sodium sulphate, filtered and concentrated to obtain crude compound. The crude compound was purified by flash column chromatography (silica gel: 100-200 mesh, Eluent: 2% methanol in DCM) to afford the desired product (4S)—N7-methyl-N5-(pyridin-2-yl)-3,4-dihydro-1,4-methanopyrido[2,3-b][1,4]diazepine-5,7(2H)-dicarboxamide (110 mg, 0.316 mmol, 34.3% yield) as an off-white solid. LCMS (m/z): 339.1 $[M+H]^+$ Rt=1.54 min.

$^1$H NMR (400 MHz, $CDCl_3$): δ ppm 13.72 (s, 1H), 8.35-8.18 (m, 2H), 8.10 (d, J=8.33 Hz, 1H), 7.88 (d, J=7.89 Hz, 1H), 7.79-7.71 (m, 1H), 7.65 (d, J=7.89 Hz, 1H), 7.02 (dd, J=6.80, 5.26 Hz, 1H), 5.60 (dd, J=5.81, 3.18 Hz, 1H), 3.30-3.10 (m, 6H), 3.05-2.99 (m, 1H), 2.37-2.26 (m, 1H), 2.05 (dt, J=14.41, 7.37 Hz, 1H).

Example 213

Synthesis of 6-((4S)-7-((2,2,2-trifluoroethyl)carbamoyl)-2,3,4,5-tetrahydro-1,4-methanopyrido[2,3-b][1,4]diazepine-5-carboxamido)nicotinic acid

Example 214

Synthesis of (4S)—N7-(2-hydroxy-3-methoxypropyl)-N5-(pyridin-2-yl)-3,4-dihydro-1,4-methanopyrido[2,3-b][1,4]diazepine-5,7(2H)-dicarboxamide

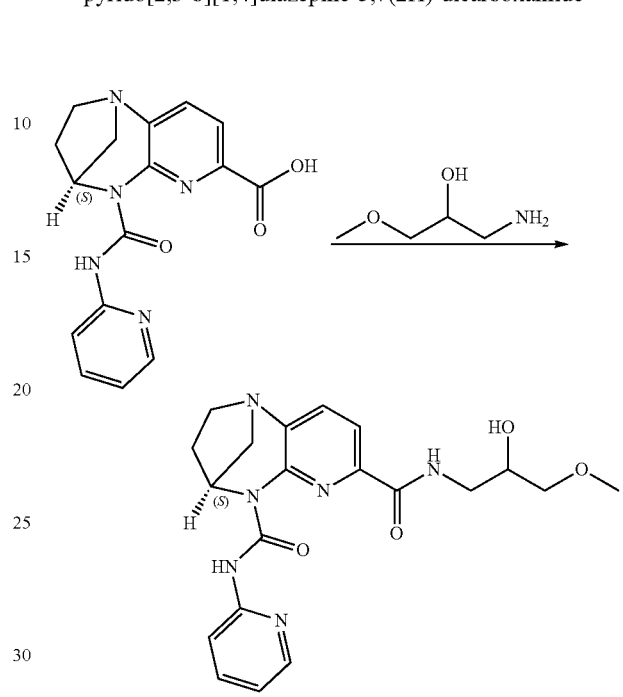

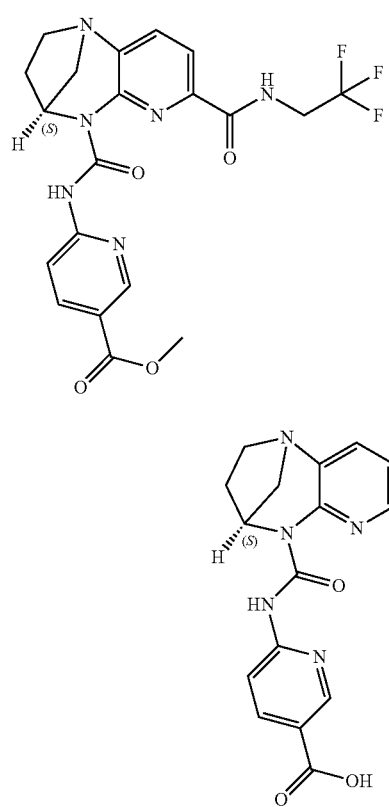

To a stirred solution of methyl 6-((4S)-7-((2,2,2-trifluoroethyl)carbamoyl)-2,3,4,5-tetrahydro-1,4-methanopyrido[2,3-b][1,4]diazepine-5-carboxamido)nicotinate (2.7 g, 5.81 mmol) in THF (20 mL), Methanol (20 mL) and Water (6.00 mL) at 0° C. under nitrogen was added LiOH (0.139 g, 5.81 mmol) in one portion and stirred at RT for 16 h. (TLC eluent: 5% MeOH in DCM, R$_f$—0.2; UV active). The reaction mixture was concentrated to half volume and diluted with cold water, then neutralized with citric acid. During the process precipitated pale brown solid was filtered and dried under vacuum to obtain the crude compound. The crude product was purified by chromatography (silica gel, eluting with 5% MeOH in DCM) to afford 6-((4S)-7-((2,2,2-trifluoroethyl)carbamoyl)-2,3,4,5-tetrahydro-1,4-methanopyrido[2,3-b][1,4]diazepine-5-carboxamido)nicotinic acid (900 mg, 1.942 mmol, 33.4% yield) as a pale brown solid. LCMS (m/z): 451.12 [M+H]$^+$, R$_t$=1.84 min.

$^1$H NMR (400 MHz, DMSO-d$_6$): δ ppm 13.61 (s, 1H), 13.08-13.25 (m, 1H), 8.86 (d, J=1.75 Hz, 1H), 8.61 (br t, J=6.36 Hz, 1H), 8.32 (dd, J=8.77, 2.19 Hz, 1H), 8.12 (d, J=8.55 Hz, 1H), 7.73-7.81 (m, 2H), 5.44 (dd, J=5.81, 2.96 Hz, 1H), 4.25-4.41 (m, 2H), 3.06-3.23 (m, 3H), 2.96-3.03 (m, 1H), 2.18-2.34 (m, 1H), 1.97 (dt, J=14.20, 7.26 Hz, 1H)

To a stirred solution of (4S)-5-(pyridin-2-ylcarbamoyl)-2,3,4,5-tetrahydro-1,4-methanopyrido[2,3-b][1,4]diazepine-7-carboxylic acid (800 mg, 2.459 mmol), in DMF (4 mL) at 0° C. was added HATU (1870 mg, 4.92 mmol) and DIPEA (1.288 mL, 7.38 mmol) and stirred for 10 min. Then added 1-amino-3-methoxypropan-2-ol (284 mg, 2.71 mmol) at 0° C. and the resulting solution was stirred at RT for 16 h. (TLC eluent: 5% MeOH in DCM, R$_f$—0.2; UV active). Reaction mixture was poured in to ice cold water (40 ml), extracted with EtOAc (2×60 mL), combined organic layer was dried over anhydrous Na$_2$SO$_4$, filtered and concentrated under reduced pressure to obtain crude compound. The resulting crude material was purified by combiflash chromatography (silica gel column, 5% MeOH in DCM) to afford the diastereomeric mixture (500 mg, HPLC-91%) as a high viscous liquid. This diastereomeric mixture was further separated by chiral SFC (Column/dimensions: Lux Amylose-2 (250×30) mm; % CO$_2$: 50.0%; % Co solvent: 50.0% (100% MeOH); Total Flow: 70.0 g/min; Back Pressure: 100.0 bar; UV: 259 nm; Stack time: 10.50 min; Load/Inj: 26 mg; Solubility: MeOH: Instrument details: Thar SFC-80) to give two single unknown enantiomers. The fastest eluting fraction from SFC was concentrated, washed with diethylether to give 180 mg desired peak alone with aliphatic impurities, which was further purified by combiflash chromatography (Silica gel column, 5% MeOH in DCM) followed by lyophilisation to afford the desired compound (4S)—N7-(2-hydroxy-3-methoxypropyl)-N5-(pyridin-2-yl)-3,4-dihydro-1,4-methanopyrido[2,3-b][1,4]diazepine-5,7(2H)-dicarboxamide (128 mg, 0.303 mmol, 12.32% yield) as an off white solid. LCMS (m/z): 413.14 [M+H]$^+$, R$_t$=1.45 min.

$^1$H NMR (400 MHz, CDCl$_3$): δ ppm 13.24 (s, 1H), 8.11-8.35 (m, 3H), 7.86 (d, J=7.89 Hz, 1H), 7.59-7.78 (m, 2H), 6.90-7.15 (m, 1H), 5.65 (dd, J=6.03, 3.18 Hz, 1H), 4.06-4.33 (m, 2H), 3.82 (ddd, J=13.87, 6.52, 3.73 Hz, 1H), 3.43-3.64 (m, 3H), 3.37 (s, 3H), 3.10-3.30 (m, 3H), 2.94-3.07 (m, 1H), 2.33 (dddd, J=14.03, 9.81, 5.97, 4.17 Hz, 1H), 1.99-2.13 (m, 1H).

Example 215

Synthesis of (4S)—N7-cyclopropyl-N5-(5-methyl-pyridin-2-yl)-3,4-dihydro-1,4-methanopyrido[2,3-b][1,4]diazepine-5,7(2H)-dicarboxamide

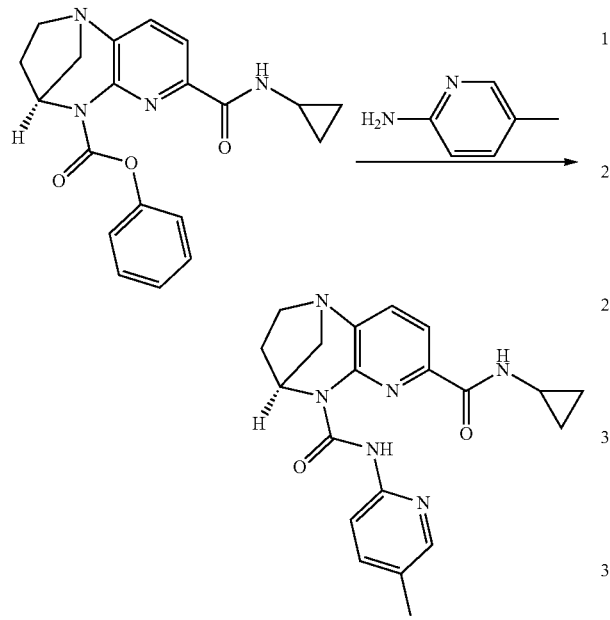

To a stirred solution of 5-methylpyridin-2-amine (297 mg, 2.74 mmol) in Tetrahydrofuran (THF) (20 mL) was added a solution of 1.0 M LiHMDS (2.74 mL, 2.74 mmol) in THF at −78° C. under Nitrogen atmosphere. The resulting reaction mixture was stirred at −78° C. for 30 min. To the reaction mixture was added a solution of (4S)-phenyl 7-(cyclopropylcarbamoyl)-3,4-dihydro-1,4-methanopyrido[2,3-b][1,4]diazepine-5(2H)-carboxylate (500 mg, 1.372 mmol) in Tetrahydrofuran (10 mL) at −78° C. The resulting reaction mixture was warm to room temperature and stirred for 6 h. (TLC system: 5% MeOH in DCM, Rf: 0.5). The reaction mixture was quenched with saturated ammonium chloride solution (30 mL), aqueous layer was extracted with EtOAc (3×30 mL). The combined organic layer was washed with water (20 mL), brine solution (20 mL), dried over anhydrous $Na_2SO_4$, filtered and concentrated under reduced pressure to obtain crude compound. The crude compound was purified by column chromatography (silica gel 100-200 mesh, Eluent: 4% MeOH in DCM) to afford sticky solid. The sticky solid was washed with a mixture of diethyl ether (5 mL) and n-pentane (15 mL), to afford the desired product (4S)—N7-cyclopropyl-N5-(5-methylpyridin-2-yl)-3,4-dihydro-1,4-methanopyrido[2,3-b][1,4]diazepine-5,7(2H)-dicarboxamide (315 mg, 0.830 mmol, 60.5% yield) as an off-white solid. LCMS (m/z): 379.12 [M+H]$^+$, $R_t$=1.89 min.

$^1$H NMR (400 MHz, CDCl$_3$): δ ppm 13.24 (br s, 1H), 8.12 (s, 1H), 8.06-7.95 (m, 2H), 7.91 (d, J=7.89 Hz, 1H), 7.64 (d, J=7.67 Hz, 1H), 7.59-7.43 (m, 1H), 5.63 (dd, J=5.70, 3.07 Hz, 1H), 3.28-3.07 (m, 4H), 3.04-2.97 (m, 1H), 2.40-2.24 (m, 4H), 2.13-1.92 (m, 1H), 1.00-0.81 (m, 4H).

Example 216

Synthesis of (4S)—N7-cyclopropyl-N5-(1-methyl-2-oxo-1,2-dihydropyridin-3-yl)-3,4-dihydro-1,4-methanopyrido[2,3-b][1,4]diazepine-5,7(2H)-dicarboxamide

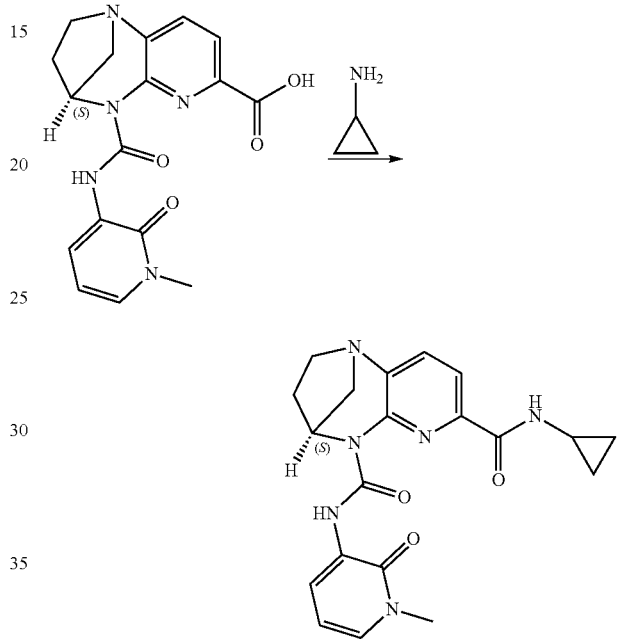

To a stirred solution of (4S)-5-((1-methyl-2-oxo-1,2-dihydropyridin-3-yl)carbamoyl)-2,3,4,5-tetrahydro-1,4-methanopyrido[2,3-b][1,4]diazepine-7-carboxylic acid (350 mg, 0.985 mmol) in DMF (3.5 mL) at 0° C. was added HATU (749 mg, 1.970 mmol), DIPEA (0.516 ml, 2.95 mmol) and stirred for 10 min. then added cyclopropanamine (67.5 mg, 1.182 mmol) and the resulting solution was stirred at RT for 16 h. (TLC eluent: 5% MeOH in DCM: $R_f$—0.3; UV active). The reaction mixture was diluted with ice cold water (80 mL), extracted with EtOAc (2×100 ml). Combined organic layer were dried over anhydrous $Na_2SO_4$, filtered and concentrated to get crude product. Crude material was purified by combiflash chromatography (Silica gel column, eluent 100% EtOAc) to afford (4S)—N7-cyclopropyl-N5-(1-methyl-2-oxo-1,2-dihydropyridin-3-yl)-3,4-dihydro-1,4-methanopyrido[2,3-b][1,4]diazepine-5,7(2H)-dicarboxamide (250 mg, 0.623 mmol, 63.3% yield) as an off white solid. LCMS (m/z): 395.10 [M+H]$^+$, $R_t$=1.73 min.

$^1$H NMR (400 MHz, CDCl$_3$): δ ppm 12.20 (s, 1H), 9.46 (br s, 1H), 8.38 (dd, J=7.56, 1.64 Hz, 1H), 8.04 (d, J=7.89 Hz, 1H), 7.63 (d, J=7.89 Hz, 1H), 7.03 (dd, J=6.80, 1.53 Hz, 1H), 6.31 (t, J=7.13 Hz, 1H), 5.70 (dd, J=6.03, 3.18 Hz, 1H), 3.69 (s, 3H), 3.11-3.28 (m, 4H), 2.98 (d, J=3.29 Hz, 1H), 2.24-2.34 (m, 1H), 2.00 (dt, J=14.36, 7.29 Hz, 1H), 0.91-0.97 (m, 2H), 0.78-0.86 (m, 2H)

Example 217

Synthesis of (4S)—N5-(2-(dimethylamino)-2-oxo-ethyl)-N7-((R)-1,1,1-trifluoropropan-2-yl)-3,4-dihydro-1,4-methanopyrido[2,3-b][1,4]diazepine-5,7(2H)-dicarboxamide

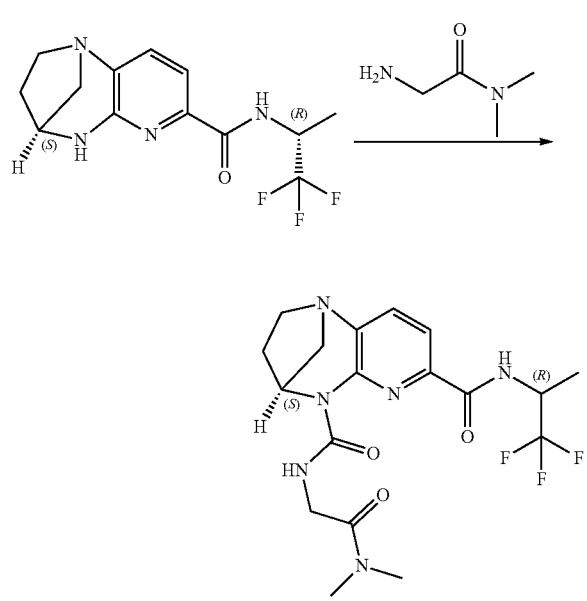

To a stirred solution of (4S)—N—((R)-1,1,1-trifluoropropan-2-yl)-2,3,4,5-tetrahydro-1,4-methanopyrido[2,3-b][1,4]diazepine-7-carboxamide (1 g, 3.33 mmol) in Tetrahydrofuran (40 mL) was added TEA (2.321 mL, 16.65 mmol) at 0° C. and stirred for 10 min. Then added triphosgene (0.988 g, 3.33 mmol) in one portion at 0° C. The resulting yellow suspension was stirred for 45 min at room temperature. After 45 min. the THF (4 mL) solution of 2-amino-N,N-dimethylacetamide (0.340 g, 3.33 mmol) was added at 0° C. over a period of 5 min. The resulting yellow suspension was stirred at 70° C. for 24 h. (TLC 10% MeOH\DCM $R_f$: 0.4; UV active) and cooled to room temperature, diluted with water (20 mL), extracted with ethyl acetate (30 mL×2). The combined organic layer was washed with brine (15 mL), dried over anhydrous sodium sulphate filtered, concentrated under reduced pressure to get the crude product. The crude material was purified by prep HPLC (conditions: MP-A: 10 mM Ammonium Bicarbonate (Aq) MP-B: Acetonitrile Column: Kromasil phenyl (150×25) 10u Method: Isocratic (A:B)=50:50 Flow: 20 ml/min Solubility: ACN) to afford the desired product (4S)—N5-(2-(dimethylamino)-2-oxoethyl)-N7-((R)-1,1,1-trifluoropropan-2-yl)-3,4-dihydro-1,4-methanopyrido[2,3-b][1,4]diazepine-5,7(2H)-dicarboxamide as an off white solid. LCMS (m/z): 429.09 [M+H]$^+$, Rt=1.86 min.

$^1$H NMR (400 MHz, DMSO-d$_6$): δ ppm 10.14 (t, J=3.62 Hz, 1H), 9.13 (d, J=9.21 Hz, 1H), 7.65-7.92 (m, 2H), 5.45 (dd, J=5.92, 2.63 Hz, 1H), 5.09-4.85 (m, 1H), 4.24 (d, J=3.29 Hz, 2H), 3.30-3.12 (m, 1H), 3.08-2.88 (m, 4H), 2.9-2.50 (dt, J=3.67, 1.78 Hz, 5H), 2.25-2.10 (m, 1H), 1.82 (dt, J=13.76, 7.04 Hz, 1H), 1.52 (d, J=7.23 Hz, 3H).

Example 218

Synthesis of (4S)—N7-(3-hydroxypropyl)-N5-(pyridin-2-yl)-3,4-dihydro-1,4-methanopyrido[2,3-b][1,4]diazepine-5,7(2H)-dicarboxamide

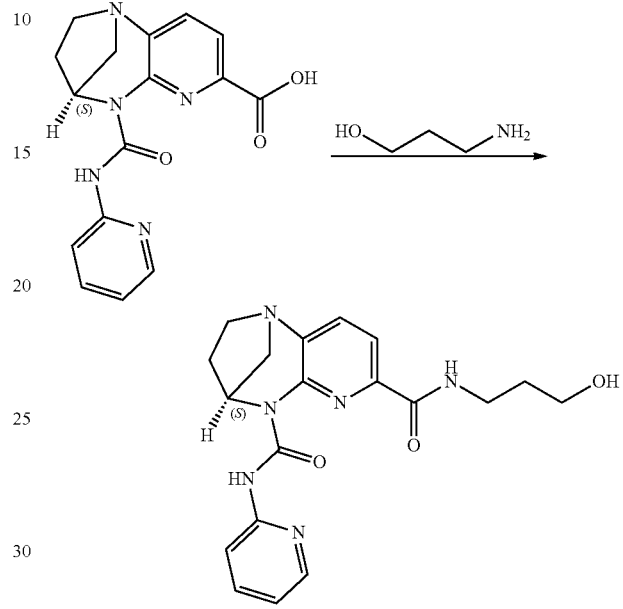

To a stirred solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in DMF (3 mL) at 0° C. was added HATU (701 mg, 1.844 mmol), DIPEA (0.483 mL, 2.77 mmol) and stirred for 10 min. Then added 3-aminopropan-1-ol (76 mg, 1.014 mmol) at 0° C. and the resulting solution was stirred at RT for 16 h. (TLC eluent: 5% MeOH in DCM: $R_f$—0.2; UV active). Reaction mixture was diluted with EtOAc (100 mL) and washed with water (50 mL), The organic layer was separated, dried over anhydrous Na$_2$SO$_4$, then filtered and concentrated under reduced pressure to give the crude product. Crude material was purified by combiflash chromatography (using silica gel column, eluent 5% methanol in DCM) to get desired compound with 90% purity which was further purified by prep HPLC (Column: XBridge C18 (150×4.6 mm, 3.5μ); Mobile Phase-A: 0.01 mM Ammonium Bicarbonate; B-CAN; Gradient-Time/% B: 0/5, 0.8/5, 5/50, 8/95, 12/95, 12.5/5, 15/5; Column temp: Ambient, Flow Rate: 0.8 ml/min, Diluent: ACN) to give desired compound as colourless oil. This was dissolved in water (25 mL) and ACN (10 mL) and kept for lyophilization to afford (4S)—N7-(3-hydroxypropyl)-N5-(pyridin-2-yl)-3,4-dihydro-1,4-methanopyrido[2,3-b][1,4]diazepine-5,7(2H)-dicarboxamide (110 mg, 0.284 mmol, 30.8% yield) as an off white solid. LCMS (m/z): 383.12 [M+H]$^+$, $R_t$=2.94 min.

$^1$H NMR (400 MHz, CDCl$_3$): δ ppm 13.42 (br s, 1H), 8.47 (br s, 1H), 8.22-8.33 (m, 1H), 8.11 (d, J=8.33 Hz, 1H), 7.87 (d, J=7.89 Hz, 1H), 7.58-7.81 (m, 2H), 7.03 (ddd, J=7.29, 4.99, 0.88 Hz, 1H), 5.61 (dd, J=5.92, 3.07 Hz, 1H), 3.68-3.89 (m, 5H), 3.11-3.30 (m, 3H), 2.98-3.06 (m, 1H), 2.20-2.42 (m, 1H), 1.83-2.10 (m, 3H).

Example 219

Synthesis of (4S)—N7-(cyclopropylmethyl)-N5-(pyrimidin-4-yl)-3,4-dihydro-1,4-methano pyrido[2,3-b][1,4]diazepine-5,7(2H)-dicarboxamide

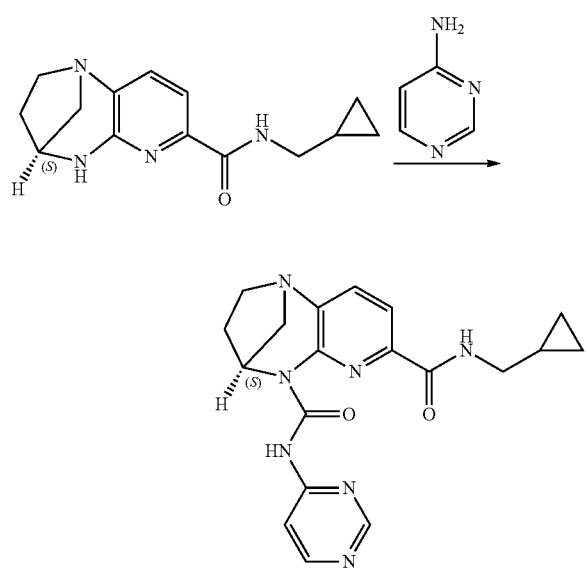

To a stirred solution of (4S)—N-(cyclopropylmethyl)-2,3,4,5-tetrahydro-1,4-methanopyrido[2,3-b][1,4]diazepine-7-carboxamide (600 mg, 2.323 mmol) in Tetrahydrofuran (5 mL) was added Triphosgene (689 mg, 2.323 mmol) followed by TEA (1.295 mL, 9.29 mmol). After stirring the reaction mixture at RT for 45 min, added pyrimidin-4-amine (265 mg, 2.79 mmol) in Tetrahydrofuran (2.5 mL) under nitrogen. The resulting reaction mixture was stirred at 65° C. for 12 h. (TLC: 5% MeOH\DCM R$_f$: 0.4; UV active). Then Water (10 mL) was added to the reaction mixture. The aqueous layer was extracted with EtOAc (2×5 mL), the combined organic layer was dried over anhydrous Na$_2$SO$_4$, filtered and concentrated under reduced pressure to obtain desired crude product which was purified by prep HPLC (conditions: MP-A: 10 mM Ammonium Bicarbonate (Aq) MP-B: Acetonitrile Column: Krom phenyl (150*25) 10u Method: Isocratic (A:B)=55:45 Flow: 20 ml/min Solubility: ACN+MEOH) to afford the desired product (4S)—N7-(cyclopropylmethyl)-N5-(pyrimidin-4-yl)-3,4-dihydro-1,4-methanopyrido[2,3-b][1,4]diazepine-5,7(2H)-dicarboxamide (91 mg, 0.236 mmol, 10.14% yield) as a pale pink solid. LCMS (m/z): 380.09 [M+H]$^+$, Rt=1.73 min.

$^1$H NMR (400 MHz, DMSO-d$_6$): δ ppm 13.48 (s, 1H), 8.85 (d, J=1.10 Hz, 1H), 8.69 (d, J=5.70 Hz, 1H), 8.38-8.11 (m, 1H), 8.04 (dd, J=5.70, 1.32 Hz, 1H), 7.81-7.63 (m, 2H), 5.44 (d, J=5.92, 3.07 Hz, 1H), 3.33-3.25 (m, 2H), 3.22-3.06 (m, 3H), 2.97 (dd, J=12.06, 3.29 Hz, 1H), 2.38-2.10 (m, 1H), 2.09-1.85 (m, 1H), 1.34 (br s, 1H), 0.51-0.39 (m, 2H), 0.34-0.20 (m, 2H).

Example 220

Synthesis of (4S)—N5-(1-methyl-1H-indazol-4-yl)-N7-(2,2,2-trifluoroethyl)-3,4-dihydro-1,4-methanopyrido[2,3-b][1,4]diazepine-5,7(2H)-dicarboxamide

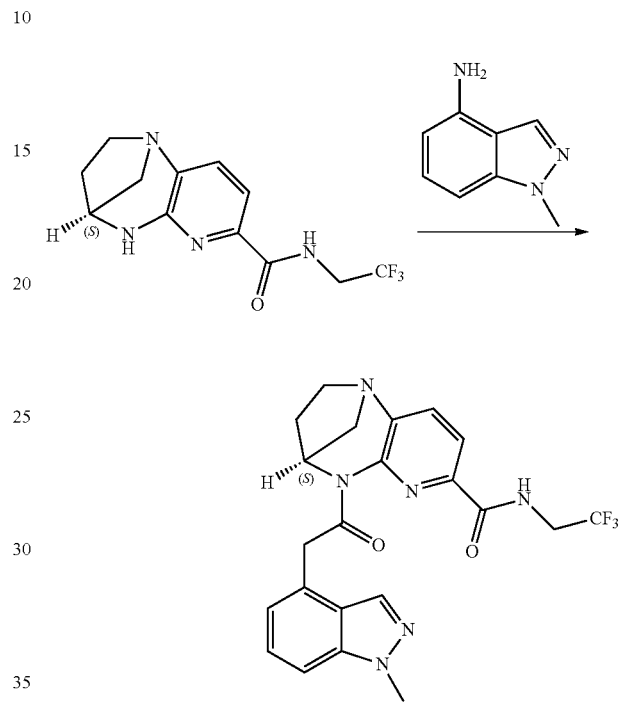

To a stirred solution of (4S)—N-(2,2,2-trifluoroethyl)-2,3,4,5-tetrahydro-1,4-methanopyrido[2,3-b][1,4]diazepine-7-carboxamide (400 mg, 1.397 mmol) in Tetrahydrofuran (15 mL) were added triphosgene (249 mg, 0.838 mmol) and DIPEA (1.220 mL, 6.99 mmol) under nitrogen atmosphere at 0° C. and then the reaction mixture was stirred at 30° C. for 30 min. and added 1-methyl-1H-indazol-4-amine (308 mg, 2.096 mmol), the reaction mixture was stirred at 70° C. for 15 h. (TLC System: 10% MeOH/DCM, R$_f$—0.4). Then the reaction mixture was poured in to the cold water (40 mL) and extracted with ethyl acetate (2×80 mL). The combined organic layer was dried over anhydrous sodium sulphate and concentrated under reduced pressure to obtain crude compound. The crude compound was purified by flash column chromatography (silicagel: 100-200 mesh, 3% MeOH in DCM) to afford the desired product (4S)—N5-(1-methyl-1H-indazol-4-yl)-N7-(2,2,2-trifluoroethyl)-3,4-dihydro-1,4-methanopyrido[2,3-b][1,4]diazepine-5,7(2H)-dicarboxamide (310 mg, 0.646 mmol, 46.2% yield) as a yellow solid. LCMS (m/z): 460.09 [M+H]$^+$, R$_t$=1.86 min.

$^1$H NMR (400 MHz, CDCl$_3$): δ ppm 11.82 (s, 1H), 8.00 (d, J=1.10 Hz, 1H), 7.83 (d, J=7.67 Hz, 1H), 7.63-7.73 (m, 2H), 7.40 (t, J=8.00 Hz, 1H), 7.17 (d, J=8.33 Hz, 1H), 6.97-7.05 (m, 1H), 5.72 (dd, J=5.92, 3.07 Hz, 1H), 4.12-3.89 (m, 5H), 3.33-3.12 (m, 3H), 3.08-3.00 (m, 1H), 2.41-2.31 (m, 1H), 2.12 (dt, J=14.14, 6.96 Hz, 1H).

Example 221

Synthesis of (4S)—N7-(2,2-difluorocyclopropyl)-N5-(6-methyl-1H-pyrazolo[3,4-b]pyridin-3-yl)-3,4-dihydro-1,4-methanopyrido[2,3-b][1,4]diazepine-5,7(2H)-dicarboxamide

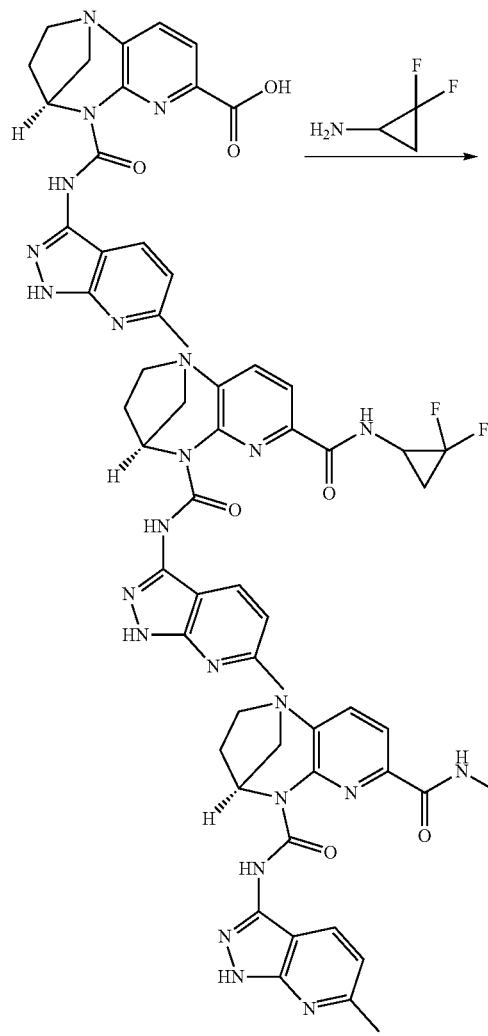

To a solution of (4S)-5-((6-methyl-1H-pyrazolo[3,4-b]pyridin-3-yl)carbamoyl)-2,3,4,5-tetrahydro-1,4-methanopyrido[2,3-b][1,4]diazepine-7-carboxylic acid (500 mg, 1.318 mmol) in N,N-Dimethylformamide (15 mL) were added HATU (601 mg, 1.582 mmol) and DIPEA (0.460 mL, 2.64 mmol) at room temperature. To this 2,2-difluorocyclopropanamine, Hydrochloride (188 mg, 1.450 mmol) was added and the reaction mixture was stirred at RT for 16 h. (TLC system: 10% Methanol in DCM. Rf value: 0.4). Reaction mixture was quenched with water (50 mL) and extracted with ethyl acetate (2×25 mL). The combined organic layer was washed with brine solution (10 mL) and dried over anhydrous sodium sulphate and concentrated under reduced pressure to afford crude compound. The crude product was purified by flash column chromatography (using 100-200 silica gel column and was eluted with 2% Methanol in DCM) to afford mixture of diastereomers and was submitted for SFC separation to afford as peak-I and Peak-II.

Peak-II: (4S)—N7-(2,2-difluorocyclopropyl)-N5-(6-methyl-1H-pyrazolo[3,4-b]pyridin-3-yl)-3,4-dihydro-1,4-methanopyrido[2,3-b][1,4]diazepine-5,7(2H)-dicarboxamide (215 mg, 0.469 mmol, 35.6% yield) as pale brown solid. LCMS (m/z): 455.12 [M+H]$^+$, Rt=1.69 min.

$^1$H NMR (400 MHz, CDCl$_3$): δ ppm 13.14 (m, 1H), 10.47 (d, J=12.28 Hz, 1H), 8.72 (d, J=8.33 Hz, 1H), 7.88 (d, J=7.89 Hz, 1H), 7.67 (s, 2H), 7.04 (d, J=8.55 Hz, 1H), 5.63 (dd, J=5.70, 3.07 Hz, 1H), 3.60 (d, J=8.55 Hz, 1H), 3.34-3.11 (m, 2H), 3.10-2.97 (m, 1H), 2.69 (s, 3H), 2.76-2.61 (m, 1H), 2.46-2.22 (m, 1H), 2.19-2.00 (m, 1H), 1.97-1.83 (m, 1H), 1.74-1.72 (m, 1H).

Example 222

Synthesis of (4S)—N7-cyclopropyl-N5-(pyrazin-2-yl)-3,4-dihydro-1,4-methanopyrido[2,3-b][1,4]diazepine-5,7(2H)-dicarboxamide

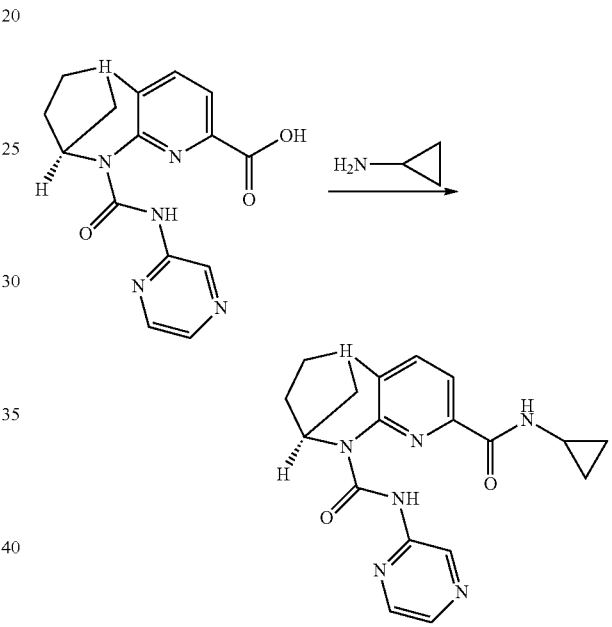

To a stirred solution of (4S)-5-(pyrazin-2-ylcarbamoyl)-2,3,4,5-tetrahydro-1,4-methanopyrido[2,3-b][1,4]diazepine-7-carboxylic acid (500 mg, 1.532 mmol) in DMF (10 mL) at RT under nitrogen, was added HATU (874 mg, 2.298 mmol) followed by TEA (0.641 mL, 4.60 mmol) and stirred for 15 min. Then added cyclopropanamine (175 mg, 3.06 mmol) and the reaction was stirred at RT for 16 h. (TLC eluent: 5% MeOH in DCM, R$_f$: 0.4; UV active). Water (25 mL) was added to the reaction mixture and extracted with EtOAc (2×30 mL). Combined organic layers were dried over anhydrous Na$_2$SO$_4$, filtered and concentrated under reduced pressure to obtain crude product. The crude was purified by column chromatography (silicagel, eluent 0.5-1.5% MeOH in DCM) followed by preparative HPLC (Column: Xbridge (30×250) mm 5µ; MP-A: 5 Mm ammonium bicarbonate (Aq), MP-B: Acetonitrile; Method: 0/23, 10/50; Flow: 20 ml/min; Solubility: MeOH+Acetonitrile) to afford (4S)—N7-cyclopropyl-N5-(pyrazin-2-yl)-3,4-dihydro-1,4-methanopyrido[2,3-b][1,4]diazepine-5,7(2H)-dicarboxamide (130 mg, 0.355 mmol, 23.19% yield) as off-white solid. LCMS (m/z): 366.01 [M+H]$^+$; Rt=1.65 min.

$^1$H NMR (400 MHz, CDCl$_3$): δ ppm 13.44 (s, 1H), 9.52 (d, J=1.53 Hz, 1H), 8.36 (d, J=2.63 Hz, 1H), 8.25 (dd, J=2.52, 1.64 Hz, 1H), 7.94 (d, J=7.89 Hz, 1H), 7.68 (d, J=7.89 Hz, 2H), 5.65 (dd, J=5.92, 3.07 Hz, 1H), 3.00-3.30 (m, 5H), 2.22-2.42 (m, 1H), 1.94-2.18 (m, 1H), 0.75-1.00 (m, 4H).

Example 223

Synthesis of (4S)—N7-(3-amino-1,1,1-trifluoropropan-2-yl)-N5-(pyridin-2-yl)-3,4-dihydro-1,4-methanopyrido[2,3-b][1,4]diazepine-5,7(2H)-dicarboxamide

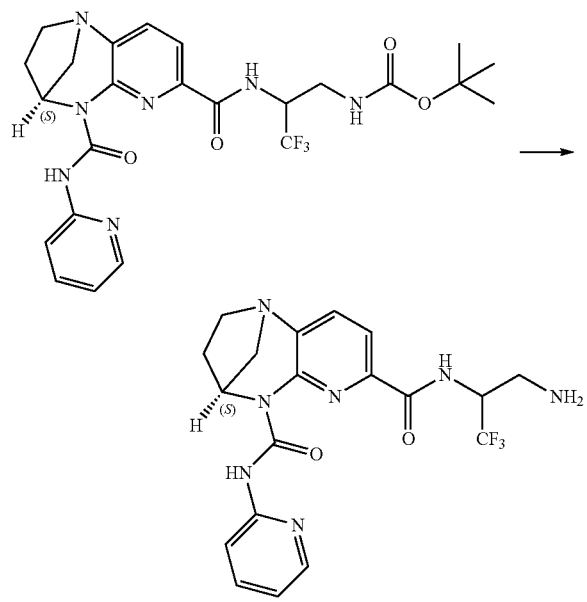

To a stirred solution of tert-butyl (3,3,3-trifluoro-2-((4S)-5-(pyridin-2-ylcarbamoyl)-2,3,4,5-tetrahydro-1,4-methanopyrido[2,3-b][1,4]diazepine-7-carboxamido)propyl)carbamate (1.1 g, 2.054 mmol) in 1,4-Dioxane (15 mL) at RT, under nitrogen was added a solution of 4M HCl (10 mL, 40.0 mmol) in one charge and stirred for 4 h. (TLC eluent: 10% MeOH in EtOAc: $R_f$—0.5; UV active). Reaction mixture was concentrated under reduced pressure, added saturated sodium bicarbonate (15 mL) solution and extracted with DCM (2×50 mL). The combined organic layers were dried over anhydrous $Na_2SO_4$, filtered and concentrated to obtain crude compound. Crude material was purified by combiflash chromatography (Silica gel column, 5% MeOH in DCM) to afford the diasteromeric mixture (800 mg, HPLC-94%) as high viscous liquid. This diastereomeric mixture was further separated by chiral SFC (Column/dimensions: Chiralcel OD-H (250×21 mm); % $CO_2$: 65.0; % Co-solvent: 35.0 (100% MeOH); Total Flow: 60.0 g/min; Back Pressure: 100.0 bar; UV: 261 nm; Stack time: 2.0 min; Load/inj: 4.0 mg; Solubility: MeOH; Total No of injections: 220; Instrument details: Make/Model: Thar SFC-80) to give two single unknown enantiomers. Slowest eluting fractions from SFC was concentrated followed by lyophilisation afforded (4S)—N7-(3-amino-1,1,1-trifluoropropan-2-yl)-N5-(pyridin-2-yl)-3,4-dihydro-1,4-methanopyrido[2,3-b][1,4]diazepine-5,7(2H)-dicarboxamide (188 mg, 0.432 mmol, 21.02% yield) as off white solid. LCMS (m/z): 436.11 [M+H]⁺, $R_t$=1.42 min.

¹H NMR (400 MHz, DMSO-d₆): δ ppm 12.94 (s, 1H), 8.17-8.36 (m, 2H), 8.11 (d, J=8.33 Hz, 1H), 7.84 (td, J=7.84, 1.86 Hz, 1H), 7.65-7.79 (m, 2H), 7.12 (ddd, J=7.34, 4.93, 0.88 Hz, 1H), 5.47 (dd, J=5.81, 2.96 Hz, 1H), 4.68-4.87 (m, 1H), 2.96-3.23 (m, 6H), 2.14-2.34 (m, 1H), 1.92 (dt, J=14.03, 7.02 Hz, 1H), 1.81 (br s, 2H).

Example 224

Synthesis of (4S)—N5-(pyridin-3-yl)-N7-((S)-1,1,1-trifluoro-3-hydroxypropan-2-yl)-3,4-dihydro-1,4-methanopyrido[2,3-b][1,4]diazepine-5,7(2H)-dicarboxamide

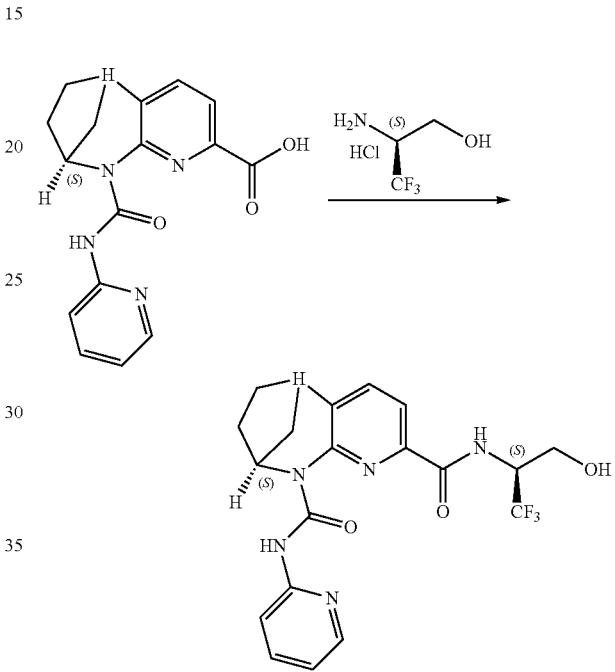

To a stirred solution of (4S)-5-(pyridin-3-ylcarbamoyl)-2,3,4,5-tetrahydro-1,4-methanopyrido[2,3-b][1,4]diazepine-7-carboxylic acid (400 mg, 1.230 mmol) in DMF (10 mL) at 0° C. was added HATU (935 mg, 2.459 mmol) and DIPEA (0.644 mL, 3.69 mmol) and stirred for 20 min. Then added (S)-2-amino-3,3,3-trifluoropropan-1-ol hydrochloride (305 mg, 1.844 mmol) and the resulting solution was stirred at RT for 16 h. (TLC eluent: 10% MeOH in DCM: $R_f$—0.5; UV active). Reaction mixture was diluted with EtOAc (100 mL) and washed with water (50 mL). The separated the organic layer was dried over anhydrous $Na_2SO_4$, filtered and concentrated under reduced pressure to give the crude product. Crude was purified by combiflash chromatography (silica gel column, 3.5% MeOH in DCM) followed by preparative HPLC (Column: PHENOMENEX PHYNY HEXYL (21.2× 250); mobile phase-A: 5 mM Ammonium Bicarbonate (Aq); mobile phase-B: Acetonitrile; Method: 98:2; Flow: 19 ml/min; Solubility: Water) to afford (4S)—N5-(pyridin-3-yl)-N7-((S)-1,1,1-trifluoro-3-hydroxypropan-2-yl)-3,4-dihydro-1,4-methanopyrido[2,3-b][1,4]diazepine-5,7(2H)-dicarboxamide (87 mg, 0.198 mmol, 16.11% yield) as a white solid. LCMS (m/z): 437.08 [M+H]⁺, $R_t$=1.3 min.

¹H NMR (400 MHz, DMSO-d₆): δ ppm 12.72 (s, 1H), 9.08 (d, J=8.99 Hz, 1H), 8.86 (d, J=2.63 Hz, 1H), 8.25 (dd, J=4.60, 1.10 Hz, 1H), 8.10 (dt, J=8.39, 1.84 Hz, 1H), 7.63-7.80 (m, 2H), 7.34 (dd, J=8.33, 4.60 Hz, 1H), 5.47 (dd, J=5.92, 2.85 Hz, 1H), 5.18 (t, J=6.03 Hz, 1H), 4.77-4.94 (m, 1H), 3.69-3.87 (m, 2H), 3.04-3.27 (m, 3H), 2.91-3.02 (m, 1H), 2.16-2.32 (m, 1H), 1.81-1.96 (m, 1H).

Example 225

Synthesis of 2-((4S)-7-(((R)-1,1,1-trifluoropropan-2-yl)carbamoyl)-2,3,4,5-tetrahydro-1,4-methanopyrido[2,3-b][1,4]diazepine-5-carboxamido)isonicotinic acid

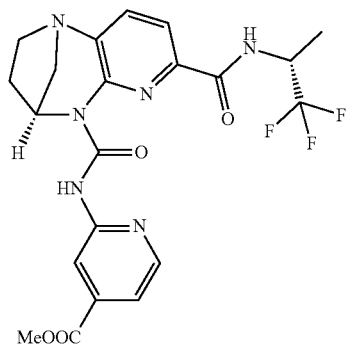

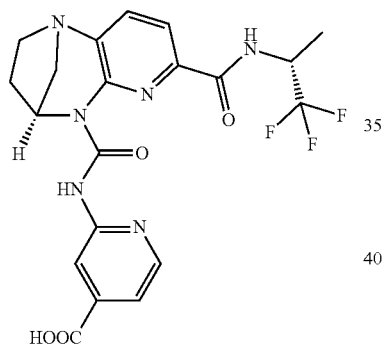

To a stirred solution of methyl 2-((4S)-7-(((R)-1,1,1-trifluoropropan-2-yl)carbamoyl)-2,3,4,5-tetrahydro-1,4-methanopyrido[2,3-b][1,4]diazepine-5-carboxamido)isonicotinate (800 mg, 1.672 mmol) in Tetrahydrofuran (15 mL) and Water (10 mL) was added LiOH (60.1 mg, 2.508 mmol) at RT stirred for 2 h. (TLC system: neat ethyl acetate; R$_f$: 0.2; UV active). The organic solvent was removed and neutralized with 5% HCl then filtered the obtain solid and washed with n-pentane (10 mL×3) to afford the desired product 2-((4S)-7-(((R)-1,1,1-trifluoropropan-2-yl)carbamoyl)-2,3,4,5-tetrahydro-1,4-methanopyrido[2,3-b][1,4]diazepine-5-carboxamido)isonicotinic acid (600 mg, 1.283 mmol, 77% yield) as an off white solid. LCMS (m/z): 465.15 [M+H]$^+$, Rt=1.97 min.

$^1$H NMR (400 MHz, DMSO-d$_6$): δ ppm 13.65 (br s, 1H), 13.14 (s, 1H), 8.58 (s, 1H), 8.42 (d, J=5.04 Hz, 1H), 8.23 (d, J=8.99 Hz, 1H), 7.79-7.71 (m, 2H), 7.55 (dd, J=5.04, 1.32 Hz, 1H), 5.48 (dd, J=5.81, 2.96 Hz, 1H), 4.96 (dq, J=15.84, 7.65 Hz, 1H), 3.23-3.06 (m, 3H), 3.03-2.95 (m, 1H), 2.29-2.18 (m, 1H), 1.97 (dt, J=13.98, 7.15 Hz, 1H), 1.51 (d, J=7.02 Hz, 3H).

Example 226

Synthesis of (4S)—N5-(4-((R)-2,3-dihydroxypropoxy)pyridin-2-yl)-N7-(pyridin-3-ylmethyl)-3,4-dihydro-1,4-methanopyrido[2,3-b][1,4]diazepine-5,7(2H)-dicarboxamide

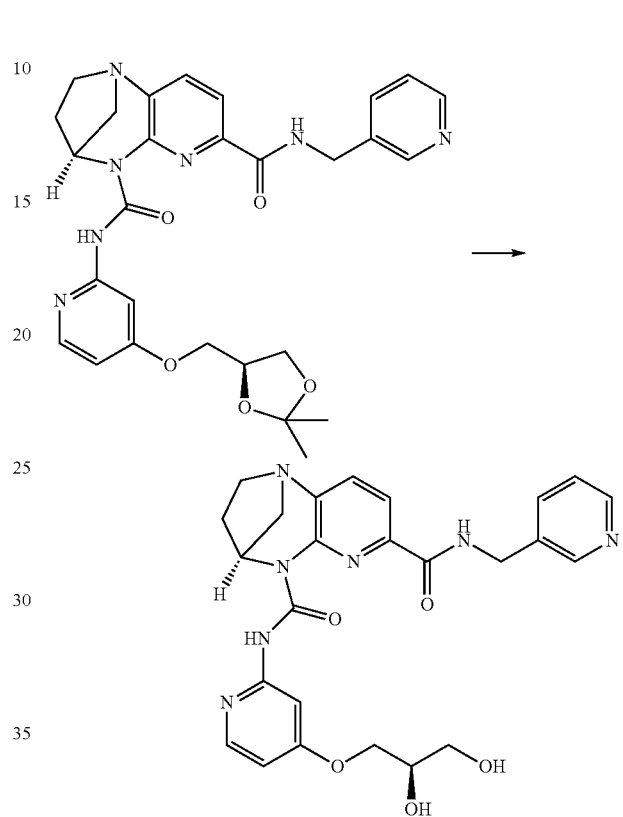

To a solution of (4S)—N5-(4-(((S)-2,2-dimethyl-1,3-dioxolan-4-yl)methoxy)pyridin-2-yl)-N7-(pyridin-3-ylmethyl)-3,4-dihydro-1,4-methanopyrido[2,3-b][1,4]diazepine-5,7(2H)-dicarboxamide (500 mg, 0.916 mmol) in methanol (10 mL) at RT was added aq. HCL (0.080 mL, 0.916 mmol) and stirred for 2 h. (TLC system: 100% ethylacetate, Rf value: 0.2). The reaction mixture was partitioned between saturated aq. NaHCO$_3$ solution (50 mL) and DCM (50 mL). Organic layer was separated and was dried over anhydrous Na$_2$SO$_4$, filtered and filtrate was evaporated to get crude product. The crude compound was triturated with diethylether (2×30 mL) and the resulting solid was filtered and dried to afford (4S)—N5-(4-((R)-2,3-dihydroxypropoxy)pyridin-2-yl)-N7-(pyridin-3-ylmethyl)-3,4-dihydro-1,4-methanopyrido[2,3-b][1,4]diazepine-5,7(2H)-dicarboxamide (260 mg, 0.506 mmol, 55.3% yield) as an off white solid. LCMS (m/z): 506.24[M+H]$^+$, Rt=1.13 min.

$^1$H NMR (400 MHz, CDCl$_3$): δ ppm 13.67 (s, 1H), 8.76 (br t, J=5.92 Hz, 1H), 8.69 (d, J=1.75 Hz, 1H), 8.49 (dd, J=4.82, 1.32 Hz, 1H), 7.90 (d, J=7.89 Hz, 1H), 7.78 (brd, J=7.67 Hz, 1H), 7.73-7.65 (m, 3H), 7.22 (dd, J=7.89, 4.82 Hz, 1H), 6.50 (dd, J=5.92, 2.41 Hz, 1H), 5.57 (dd, J=5.70, 3.07 Hz, 1H), 4.80-4.74 (m, 2H), 4.17-4.09 (m, 3H), 3.88-3.80 (m, 1H), 3.79-3.69 (m, 1H), 3.28-3.18 (m, 2H), 3.16-3.09 (m, 1H), 3.06-2.98 (m, 1H), 2.64 (br s, 1H), 2.38-2.26 (m, 1H), 2.13-1.99 (m, 2H).

Example 227

Synthesis of (4S)—N5-(4-(2-(dimethylamino)ethoxy)pyridin-2-yl)-N7-(2,2,2-trifluoroethyl)-3,4-dihydro-1,4-methanopyrido[2,3-b][1,4]diazepine-5,7(2H)-dicarboxamide

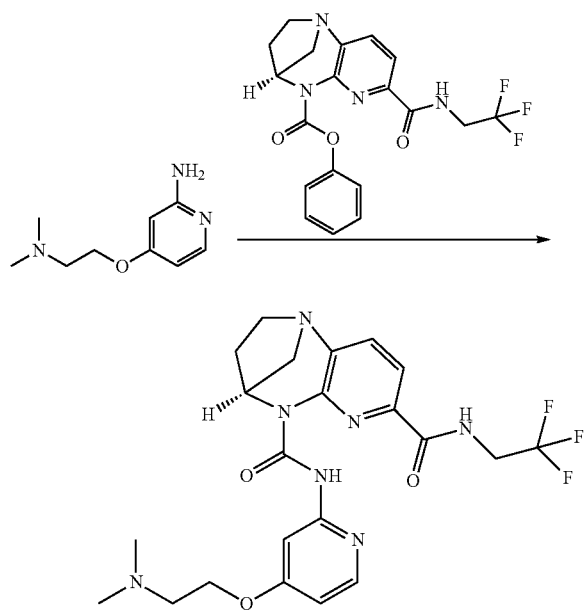

To a stirred solution of 4-(2-(dimethylamino)ethoxy)pyridin-2-amine (400 mg, 2.207 mmol) in Tetrahydrofuran (20 mL) was added a solution of 1.0 M LiHMDS (4.41 mL, 4.41 mmol) in THF at −78° C. under Nitrogen atmosphere. The resulting reaction mixture was stirred at −78° C. for 30 min. To the reaction mixture was added a solution of (4S)-phenyl7-((2,2,2-trifluoroethyl)carbamoyl)-3,4-dihydro-1,4-methanopyrido[2,3-b][1,4]diazepine-5(2H)-carboxylate (897 mg, 2.207 mmol) in Tetrahydrofuran (20 mL) at −78° C. The resulting reaction mixture was warm to room temperature and stirred at RT for 6 h. (TLC system: 5% MeOH in DCM, Rf: 0.4). The reaction mixture was quenched with saturated ammonium chloride solution (30 mL), aqueous layer was extracted with EtOAc (3×30 mL). The combined organic layer was washed with water (20 mL), brine solution (20 mL), dried over anhydrous Na₂SO₄. filtered and concentrated under reduced pressure to obtain crude compound. The crude was purified by column chromatography (silica gel: 100-200 mesh, Eluent: 4% MeOH in DCM) and followed by purified it through Prep-HPLC (Prep-HPLC condition: MP-A: 0.1% Triflouro Acetic Acid (Aq) MP-B: Acetonitrile Column: Sun fire C18 (150*19 mm*10u) Method: 0/10, 1/10, 7/25, 7.5/100, 10/100, 10.5/10, 15/10 Solubility: ACN+THF+WATER+FA Flow: 18 ml/min.) to afford the desired product (4S)—N5-(4-(2-(dimethylamino)ethoxy)pyridin-2-yl)-N7-(2,2,2-trifluoroethyl)-3,4-dihydro-1,4-methanopyrido[2,3-b][1,4]diazepine-5,7(2H)-dicarboxamide (370 mg, 0.748 mmol, 33.9% yield) as a white solid. LCMS (m/z): 494.18 [M+H]⁺, R=1.32 min.

¹H NMR (400 MHz, CDCl₃): δ 13.65 (s, 1H), 8.67 (t, J=6.5 Hz, 1H), 8.01 (d, J=5.8 Hz, 1H), 7.91 (d, J=7.9 Hz, 1H), 7.71-7.63 (m, 2H), 6.60 (dd, J=5.9, 2.4 Hz, 1H), 5.58 (dd, J=6.0, 3.1 Hz, 1H), 4.20 (dt, J=13.9, 5.7 Hz, 4H), 3.31-3.19 (m, 2H), 3.18-3.08 (m, 1H), 3.03 (dd, J=12.2, 3.2 Hz, 1H), 2.76 (t, J=5.5 Hz, 2H), 2.35 (s, 7H), 2.06 (dt, J=14.1, 7.0 Hz, 1H).

Example 228

Synthesis of (4S)—N7-methoxy-N5-(pyridin-2-yl)-3,4-dihydro-1,4-methanopyrido[2,3-b][1,4]diazepine-5,7(2H)-dicarboxamide

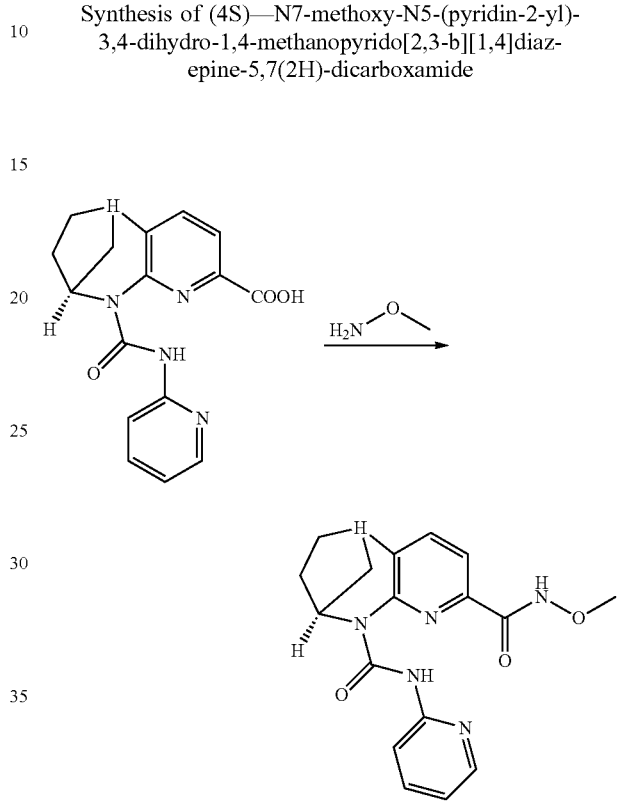

To a stirred solution of (4S)-5-(pyridin-2-ylcarbamoyl)-2,3,4,5-tetrahydro-1,4-methanopyrido[2,3-b][1,4]diazepine-7-carboxylic acid (500 mg, 1.537 mmol), DIPEA (1.342 mL, 7.68 mmol) and HATU (46.8 mg, 0.123 mmol) in N,N-Dimethylformamide (2 mL), was added O-methylhydroxylamine (72.3 mg, 1.537 mmol) at room temperature and reaction mixture was stirred at room temperature for 8 h. (TLC 5% MeOH\DCM Rf: 0.5; UV active). Reaction mixture was diluted with cold water (30 ml) and extracted with EtOAc (2×50 ml). The combined organic layer was washed with water (30 mL), brine (20 mL) and dried over anhydrous Na₂SO₄, filtered and concentrated under reduced pressure to obtain crude product and which was purified by combi-flash to afford the desired product (4S)—N7-methoxy-N5-(pyridin-2-yl)-3,4-dihydro-1,4-methanopyrido[2,3-b][1,4]diazepine-5,7(2H)-dicarboxamide (167 mg, 0.471 mmol, 30.7% yield) as a white solid. LCMS (m/z): 355.1 [M+H]⁺, Rt=1.42 min.

¹H NMR (400 MHz, DMSO-d₆): δ ppm 12.96 (s, 1H), 11.50 (s, 1H), 8.44-8.19 (m, 1H), 8.05 (d, J=8.55 Hz, 1H), 7.84 (t, J=7.81 Hz, 1H), 7.71 (d, J=7.52 Hz, 1H), 7.57 (d, J=7.89 Hz, 1H), 7.12 (ddd, J=7.29, 4.88, 0.99 Hz, 1H), 5.43 (dd, J=5.92, 3.07 Hz, 1H), 3.8 (s, 3H), 3.21-2.95 (m, 4H), 2.36-2.13 (m, 1H), 1.97-1.84 (m, 1H).

Example 229

Synthesis of (4S)—N7-cyclopropyl-N5-(pyridazin-3-yl)-3,4-dihydro-1,4-methanopyrido[2,3-b][1,4]diazepine-5,7(2H)-dicarboxamide

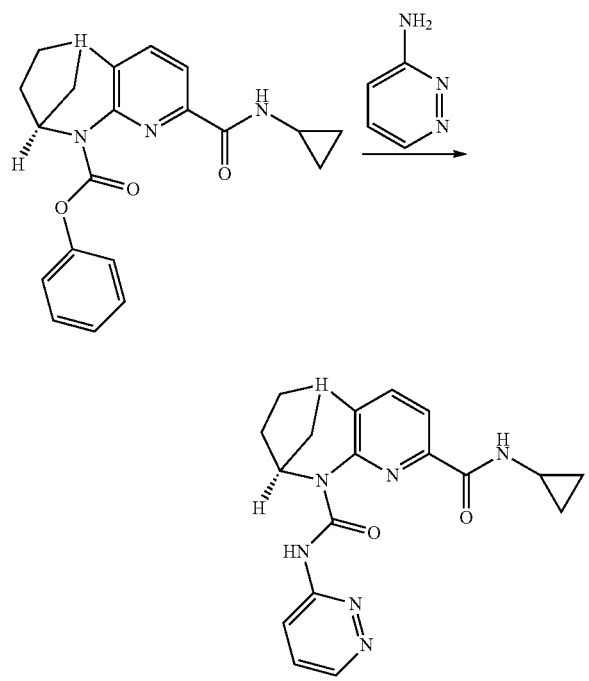

To a stirred solution of pyridazin-3-amine (196 mg, 2.058 mmol) in THF (5 mL), was added a solution of 1M LiHMDS (2.74 mL, 2.74 mmol) dropwise at −78° C. and stirred for 30 min, then added a solution of (4S)-phenyl 7-(cyclopropylcarbamoyl)-3,4-dihydro-1,4-methanopyrido[2,3-b][1,4]diazepine-5(2H)-carboxylate (500 mg, 1.372 mmol) in THF (5 mL) under nitrogen at −78° C. The resulting reaction mixture was stirred at −78° C. for 1 h and at RT for 6 h. (TLC eluent: 5% MeOH in DCM, $R_f$ 0.3; UV active). The reaction mixture was quenched with aq. NH$_4$Cl (10 mL) and the aqueous layer was extracted with EtOAc (2×25 mL). Combined organic layer was dried over anhydrous Na$_2$SO$_4$, filtered and concentrated under reduced pressure to obtain desired crude product. The crude material was purified by combiflash chromatography (Silicagel, eluent 0.5-2.5% MeOH in DCM) and the resulted compound was triturated with pentane (2×10 mL) and dried under high vacuum to afford (4S)—N7-cyclopropyl-N5-(pyridazin-3-yl)-3,4-dihydro-1,4-methanopyrido[2,3-b][1,4]diazepine-5,7(2H)-dicarboxamide (380 mg, 1.039 mmol, 76% yield) as off-white solid. LCMS (m/z): 366.01 [M+H]$^+$; Rt=1.65 min.

$^1$H NMR (400 MHz, CDCl$_3$): δ ppm 14.0 (s, 1H), 8.94 (dd, J=4.82, 1.53 Hz, 1H), 8.40 (dd, J=8.99, 1.53 Hz, 1H), 7.85-8.07 (m, 2H), 7.69 (d, J=7.89 Hz, 1H), 7.49 (dd, J=8.99, 4.82 Hz, 1H), 5.61 (dd, J=6.03, 3.18 Hz, 1H), 3.09-3.31 (m, 4H), 2.97-3.08 (m, 1H), 2.19-2.44 (m, 1H), 1.96-2.12 (m, 1H), 0.87-1.11 (m, 4H).

Example 230

Synthesis of (4S)—N—((R)-sec-butyl)-7-(3-(trifluoromethyl)phenyl)-3,4-dihydro-1,4-methanopyrido[2,3-b][1,4]diazepine-5(2H)-carboxamide, Hydrochloride

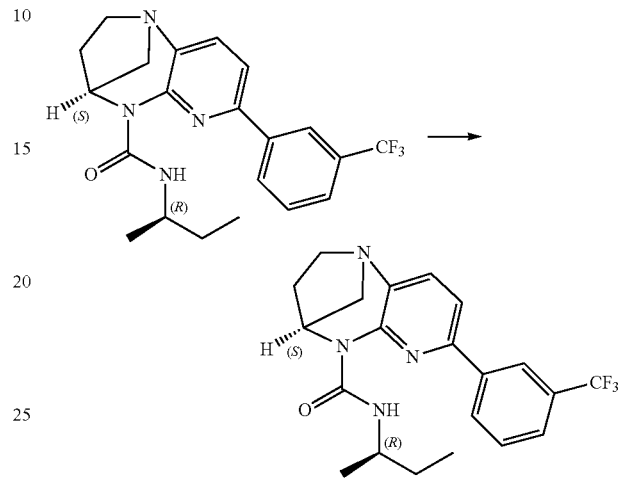

To a stirred suspension of (4S)—N—((R)-sec-butyl)-7-(3-(trifluoromethyl)phenyl)-3,4-dihydro-1,4-methanopyrido[2,3-b][1,4]diazepine-5(2H)-carboxamide (150 mg, 0.371 mmol) in diethylether (10 mL) under nitrogen at 0° C. was added 2.0 M HCl in diethylether (0.185 mL, 0.371 mmol) and stirred at RT for 1 h. (TLC System: 5% MeOH in DCM, $R_f$—0.2, UV active). The solvent was evaporated under reduced pressure and crude was triturated with diethylether (2×10 mL) to afford the desired product (4S)—N—((R)-sec-butyl)-7-(3-(trifluoromethyl)phenyl)-3,4-dihydro-1,4-methanopyrido[2,3-b][1,4]diazepine-5(2H)-carboxamide, Hydrochloride (115 mg, 0.254 mmol, 68.4% yield) as an off white solid. LCMS (m/z): 405.12 [M+H]$^+$, $R_t$=2.58 min.

$^1$H NMR (400 MHz, DMSO-d$_6$): δ ppm 9.97 (d, J=7.89 Hz, 1H) 8.18 (d, J=7.89 Hz, 1H) 8.13-8.05 (m, 1H) 7.99 (d, J=8.11 Hz, 1H) 7.95-7.77 (m, 1H) 7.71 (d, J=8.11 Hz, 1H) 5.54 (dd, J=5.59, 3.18 Hz, 1H) 3.82-3.76 (m, 2H) 3.61-3.41 (m, 4H) 2.42-2.38 (m, 1H) 2.16-2.00 (m, 1H) 1.52 (quin, J=7.18 Hz, 2H) 1.15 (d, J=6.58 Hz, 3H) 0.92-0.81 (m, 3H).

Example 231

Synthesis of (4S)—N5-(1H-benzo[d]imidazol-5-yl)-N7-(2,2,2-trifluoroethyl)-3,4-dihydro-1,4-methanopyrido[2,3-b][1,4]diazepine-5,7(2H)-dicarboxamide

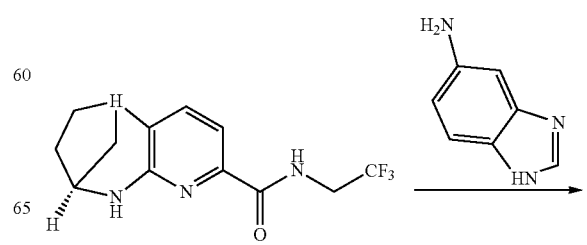

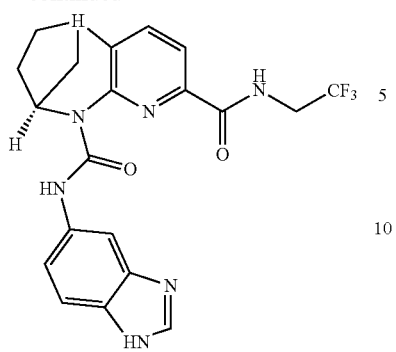

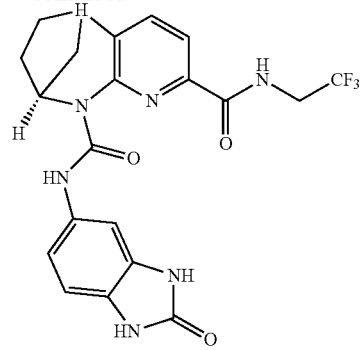

To a solution of (4S)—N-(2,2,2-trifluoroethyl)-2,3,4,5-tetrahydro-1,4-methanopyrido[2,3-b][1,4]diazepine-7-carboxamide (500 mg, 1.747 mmol), Triethylamine (1.217 mL, 8.73 mmol) and triphosgene (518 mg, 1.747 mmol) in Tetrahydrofuran (50 mL) was added 1H-benzo[d]imidazol-5-amine (349 mg, 2.62 mmol). The reaction mixture was stirred at 70° C. for 16 h. (TLC: Eluent: 10% methanol in DCM, $R_f$: 0.4). The reaction mixture was cooled to RT and was partitioned between water (100 mL) and EtOAc (2×50 mL). The combined organic layer was separated and was dried over anhydrous $Na_2SO_4$, filtered and filtrate was evaporated to get crude material (625 mg). The crude compound was purified by Prep. HPLC (Conditions: Column: XBridge C 18 (250×4.6 mm, 5) Mobile Phase: A: 5 mM Ammonium Bicarbonate B: ACN, Gradient: Time/% B: 0/10, 1/10, 10/60, 15/60, 18/98, 20/98, 20.1/10, 25/10, Column Temp: Ambient, Flow Rate: 1.0 mL/min, Diluent: ACN) to afford the desired product (4S)—N5-(1H-benzo[d]imidazol-5-yl)-N7-(2,2,2-trifluoroethyl)-3,4-dihydro-1,4-methanopyrido[2,3-b][1,4]diazepine-5,7(2H)-dicarboxamide (90 mg, 0.199 mmol, 11.39% yield) as an off white solid. LCMS (m/z): 446.09 [M+H]$^+$, $R_t$=1.34 min.

$^1$H NMR (400 MHz, DMSO-d$_6$): δ ppm 12.35 (m, 1H), 12.06 (s, 1H), 9.00 (s, 1H), 8.10-7.97 (m, 2H), 7.69-7.63 (m, 1H), 7.60-7.55 (m, 1H), 7.50-7.24 (m, 2H), 5.48 (d, J=2.85 Hz, 1H), 4.19-4.06 (m, 2H), 3.21-3.00 (m, 4H), 2.30-2.15 (m, 1H), 1.95-1.88 (m, 1H).

To a stirred solution of (4S)—N-(2,2,2-trifluoroethyl)-2,3,4,5-tetrahydro-1,4-methanopyrido[2,3-b][1,4]diazepine-7-carboxamide (500 mg, 1.747 mmol) in Tetrahydrofuran (50 mL) were added Triethylamine (1.704 mL, 12.23 mmol) and triphosgene (518 mg, 1.747 mmol) under nitrogen at 28° C. for 3 h. Then 5-amino-1H-benzo[d]imidazol-2(3H)-one (782 mg, 5.24 mmol) was added and the resulted reaction mixture was stirred at 70° C. for 16 h. (TLC Eluent: 10% methanol in DCM, $R_f$: 0.3). The reaction mixture was cooled to RT and was poured into water (100 mL) and filtered the obtain solid, dried under vacuum to get crude material. The crude material was purified by prep HPLC (Conditions: Column: X-Bridge C 18 (75×4.6 mm, 3.5.) Mobile Phase: A: 5 mM Ammonium Bicarbonate B: ACN Gradient: Time/% B: 0/5, 0.8/5, 5/50, 9/98, 12/98, 12.1/5, 15/5 Column Temp: Ambient, Flow Rate: 0.8 ml/min, Diluent: CAN) to afford the desired product (4S)—N5-(2-oxo-2,3-dihydro-1H-benzo[d]imidazol-5-yl)-N7-(2,2,2-trifluoroethyl)-3,4-dihydro-1,4-methanopyrido[2,3-b][1,4]diazepine-5,7(2H)-dicarboxamide (120 mg, 0.254 mmol, 14.53% yield) as a pale yellow solid. LCMS (m/z): 462.07 [M+H]$^+$, $R_t$=1.50 min.

$^1$H NMR (400 MHz, DMSO-d$_6$): δ ppm: 12.37 (s, 1H), 10.57 (s, 1H), 10.43 (s, 1H), 9.31 (br t, J=5.81 Hz, 1H), 7.69 (d, J=7.67 Hz, 1H), 7.60 (d, J=7.89 Hz, 1H), 7.55 (d, J=1.53 Hz, 1H), 7.02 (dd, J=8.33, 1.75 Hz, 1H), 6.81 (d, J=8.33 Hz, 1H), 5.43 (dd, J=5.48, 2.85 Hz, 1H), 4.14 (dd, J=15.24, 9.32 Hz, 2H), 3.21-2.93 (m, 4H), 2.27-2.18 (m, 1H), 1.94-1.84 (m, 1H).

Example 232

Synthesis of (4S)—N5-(2-oxo-2,3-dihydro-1H-benzo[d]imidazol-5-yl)-N7-(2,2,2-trifluoroethyl)-3,4-dihydro-1,4-methanopyrido[2,3-b][1,4]diazepine-5,7(2H)-dicarboxamide Example 233

Synthesis of (4S)—N7-(2-amino-3,3,3-trifluoropropyl)-N5-(6-methyl-1H-pyrazolo-[3,4-b]pyridin-3-yl)-3,4-dihydro-1,4-methanopyrido-[2,3-b][1,4]diazepine-5,7(2H)-dicarboxamide

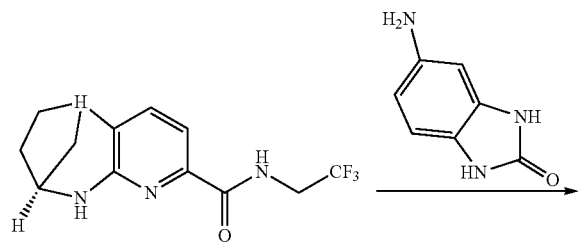

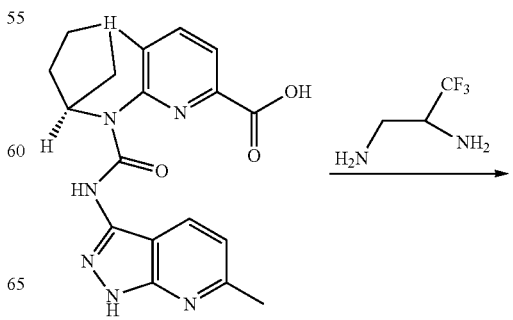

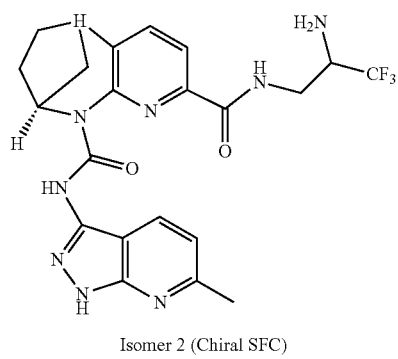

Isomer 2 (Chiral SFC)

To a solution of (4S)-5-(((6-methyl-1H-pyrazolo[3,4-b]pyridin-3-yl)carbamoyl)-2,3,4,5-tetrahydro-1,4-methanopyrido[2,3-b][1,4]diazepine-7-carboxylic acid (1.00 g, 2.64 mmol) in DMF (50 mL) at RT was added HATU (1.002 g, 2.64 mmol), DIPEA (1.381 mL, 7.91 mmol) and 3,3,3-trifluoropropane-1,2-diamine (0.405 g, 3.16 mmol) and stirred for 16 h. (TLC system: 10% Methanol in DCM, Rf value: 0.5). The reaction mixture diluted with cold water (100 mL) and stirred for 15 min at RT. The resultant solid was filtered and dried under vacuum to afford (4S)—N7-(2-amino-3,3,3-trifluoropropyl)-N5-(6-methyl-1H-pyrazolo[3,4-b]pyridin-3-yl)-3,4-dihydro-1,4-methanopyrido[2,3-b][1,4]diazepine-5,7(2H)-dicarboxamide as diasteriomeric mixture. The diastereomers were separated by preparative chiral SFC (Column: Chiralcel OD-H (250×21) mm, 5μ, % $CO_2$: 60.0, % Co-solvent: 40.0 (0.5% DEA in methanol), Total Flow: 70.0 g/min, Back Pressure: 100.0 bar, UV: 216 nm, Stack time: 4.0 min, Load/Inj: 4.0 mg, Solubility: Methanol; Total No of injections: 200, Instrument details: Thar SFC-80) to give two single isomers. Slowest eluting fractions from chiral SFC were concentrated and triturated with diethylether to afford (4S)—N7-(2-amino-3,3,3-trifluoropropyl)-N5-(6-methyl-1H-pyrazolo-[3,4-b]-pyridin-3-yl)-3,4-dihydro-1,4-methanopyrido[2,3-b][1,4]diazepine-5,7(2H)-dicarboxamide (80 mg, 0.157 mmol, 5.95% yield) as an off white solid. LCMS (m/z): 253.91 [M+H]$^+$, Rt=1.81 min.

$^1$H NMR (400 MHz, DMSO-d$_6$): δ ppm 12.98 (br s, 1H), 12.74 (s, 1H), 8.56 (br t, J=5.81 Hz, 1H), 8.44 (d, J=8.33 Hz, 1H), 7.72 (d, J=7.67 Hz, 1H), 7.60 (d, J=7.67 Hz, 1H), 7.03 (d, J=8.33 Hz, 1H), 5.47 (dd, J=5.70, 3.07 Hz, 1H), 3.77-3.59 (m, 1H), 3.57-3.47 (m, 1H), 3.34-3.22 (m, 5H), 3.06-3.15 (m, 1H), 2.57 (m, 4H), 2.34-2.20 (m, 1H), 1.95 (dt, J=14.20, 7.26 Hz, 1H).

Example 234

Synthesis of (4S)—N5-(6-((S)-2,3-dihydroxypropoxy)pyridazin-3-yl)-N7-((R)-1,1,1-trifluoropropan-2-yl)-3,4-dihydro-1,4-methanopyrido[2,3-b][1,4]diazepine-5,7(2H)-dicarboxamide

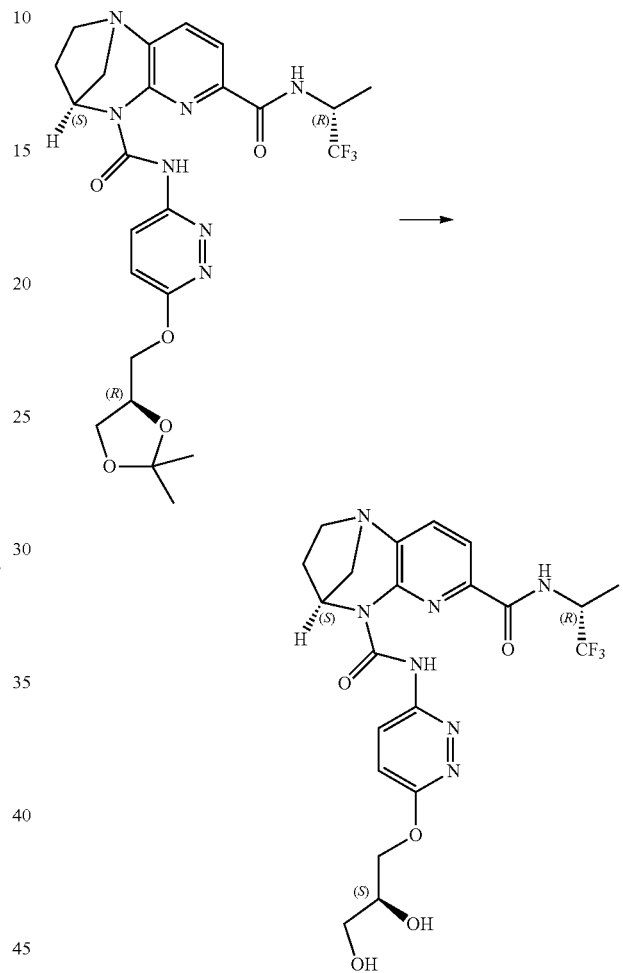

To a stirred solution of (4S)—N5-(6-(((R)-2,2-dimethyl-1,3-dioxolan-4-yl)methoxy)pyridazin-3-yl)-N7-((R)-1,1,1-trifluoropropan-2-yl)-3,4-dihydro-1,4-methanopyrido[2,3-b][1,4]diazepine-5,7(2H)-dicarboxamide (300 mg, 0.544 mmol) in Methanol (5 mL) was added hydrochloric acid (0.017 mL, 0.544 mmol) at 0° C. drop wise over a period of 5 min. Then the reaction mixture was stirred at RT for 1 h. (TLC eluent: 5% MeOH in DCM: R$_f$—0.1; UV active). The reaction mixture was evaporated and neutralized with sodium bicarbonate solution and filtered the obtain solid, washed with diethylether (20 ml) and pentane (20 ml) to afford the desired compound (4S)—N5-(6-((S)-2,3-dihydroxypropoxy)pyridazin-3-yl)-N7-((R)-1,1,1-trifluoropropan-2-yl)-3,4-dihydro-1,4-methanopyrido[2,3-b][1,4]diazepine-5,7(2H)-dicarboxamide (100 mg, 0.191 mmol, 35.1% yield) as an off white solid. LCMS (m/z): 512.29 [M+H]$^+$, Rt=1.67 min.

$^1$H NMR (400 MHz, CDCl$_3$): δ ppm 13.78 (s, 1H), 8.39 (d, J=9.65 Hz, 1H), 7.96 (d, J=7.89 Hz, 2H), 7.69 (d, J=7.89 Hz, 1H), 7.10 (d, J=9.43 Hz, 1H), 5.61 (dd, J=5.92, 3.07 Hz, 1H), 5.04-4.92 (m, 1H), 4.68-4.52 (m, 2H), 4.18-4.08 (m, 1H), 3.82-3.67 (m, 2H), 3.51 (d, J=5.04 Hz, 1H), 3.29-3.20 (m, 2H), 3.16-3.08 (m, 1H), 3.08-3.00 (m, 1H), 2.38-2.26 (m, 2H), 2.06 (dt, J=14.36, 7.07 Hz, 1H), 1.68 (d, J=7.23 Hz, 3H).

Example 235

Synthesis (4S)—N7-(2-amino-3,3,3-trifluoropropyl)-N5-(pyrimidin-2-yl)-3,4-dihydro-1,4-methanopyrido[2,3-b][1,4]diazepine-5,7(2H)-dicarboxamide

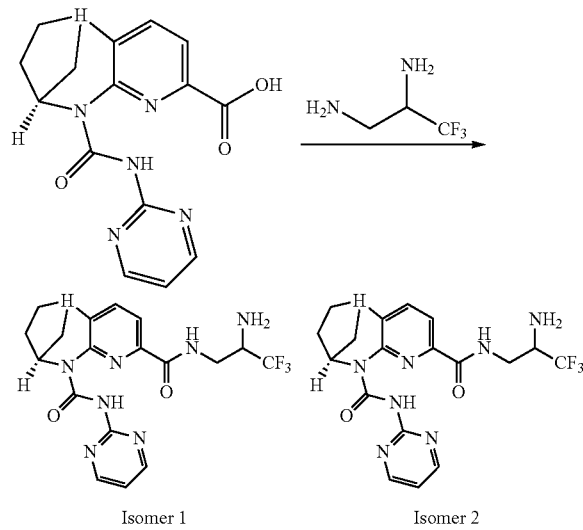

To a stirred solution of (4S)-5-(pyrimidin-2-ylcarbamoyl)-2,3,4,5-tetrahydro-1,4-methanopyrido[2,3-b][1,4]diazepine-7-carboxylic acid (4 g, 12.26 mmol) in DMF (20 mL) at RT under nitrogen, was added HATU (6.99 g, 18.39 mmol), DIPEA (6.42 mL, 36.8 mmol) and stirred for 10 min. then added solid 3,3,3-trifluoropropane-1,2-diamine (1.884 g, 14.71 mmol) in one charge and the reaction mixture was stirred for 16 h. (TLC system: 5% Methanol in DCM. $R_f$ value: 0.3). Water (60 mL) was added to the reaction and extracted with EtOAc (2×100 mL), organic layer separated, washed with brine (2×100 mL), dried over anhydrous $Na_2SO_4$, filtered and concentrated under reduced pressure to obtain crude product. The crude compound was purified by chromatography (GRACE instrument, C-18 reserval column, Mobile phase A: 0.1% Formic Acid in water; B: acetonitrile, the product was eluted at 30% B in A). Collected compound fractions were concentrated and basified with saturated $NaHCO_3$ solution. The aqueous layer was extracted with DCM and separated DCM layer was dried over anhydrous $Na_2SO_4$, filtered and evaporated to afford as distaereomeric mixtures (1.5 g, LCMS-92%). The diastereomers were separated by chiral SFC purification (Column/dimensions: Chiralpak-IE (250×30) mm, 5u; Mobile Phase: A: 0.2% Ipamine in n-Hexane B: Ethanol; Isocratic: 20:80 (A:B); Flow: 40 ml/min; Temperature: Ambient; Wave length: 264 nm; Run Time: 33 min; Stacking time: 17 min; Solubility: Ethanol with slightly DCM added; Load ability/Inj: 13.21 mg/Inj; Total No of injections: 114; Instrument details: Make/Model: YMC prep-02) to afford two single isomers with unknown absolute stereochemistry. Peak 2: Slow eluting fractions from Chiral SFC were concentrated to afford (4S)—N7-(2-amino-3,3,3-trifluoropropyl)-N5-(pyrimidin-2-yl)-3,4-dihydro-1,4-methanopyrido[2,3-b][1,4]diazepine-5,7(2H)-dicarboxamide (130 mg, 0.295 mmol, 2.407% yield) as an off white solid. LC-MS (m/z): 437.20 [M+H]$^+$. Rt=1.27 min.

$^1$H NMR (400 MHz, DMSO-d$_6$): δ ppm 13.16-13.59 (m, 1H), 8.67 (d, J=4.82 Hz, 2H), 8.44 (br t, J=5.81 Hz, 1H), 7.71-7.76 (m, 1H), 7.63-7.69 (m, 1H), 7.21 (t, J=4.82 Hz, 1H), 5.43 (dd, J=5.92, 3.07 Hz, 1H), 3.68 (dt, J=13.15, 5.26 Hz, 1H), 3.50-3.60 (m, 1H), 3.36-3.47 (m, 1H), 3.03-3.23 (m, 3H), 2.94-3.01 (m, 1H), 2.18-2.32 (m, 1H), 2.12 (br d, J=7.23 Hz, 2H), 1.91 (dt, J=14.09, 7.32 Hz, 1H)

Example 236

Synthesis of (4S)—N7-(3-fluorobenzyl)-N5-(pyridin-2-yl)-3,4-dihydro-1,4-methanopyrido[2,3-b][1,4]diazepine-5,7(2H)-dicarboxamide

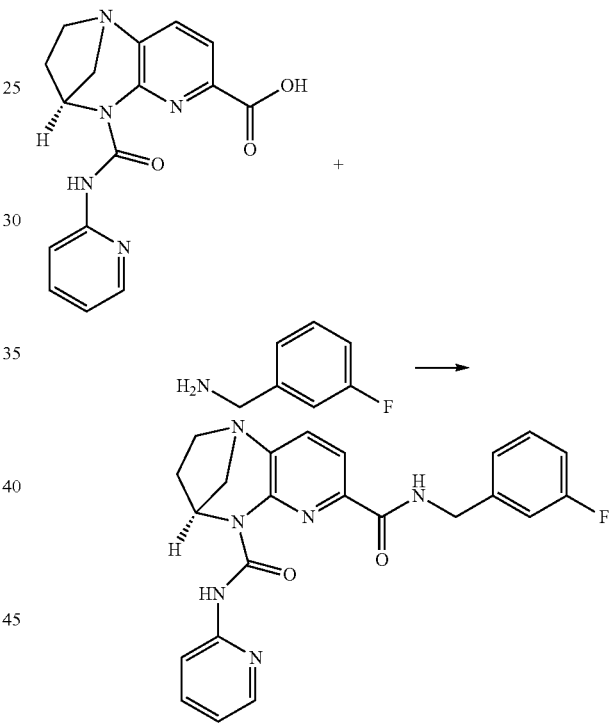

To a stirred solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in DMF (5 mL) at RT, was added (3-fluorophenyl)methanamine (115 mg, 0.922 mmol) and DIPEA (0.966 mL, 5.53 mmol) and stirred for 16 h. (TLC eluting system: 10% MeOH in DCM; R$_f$—0.3; UV active). The reaction mixture was cooled to RT, quenched with water (20 mL) and extracted into EtOAc (2×25 mL). Organic layer was separated and dried over anhydrous sodium sulphate, filtered and filtrate was evaporated to get crude compound. The crude was purified by chromatography (GRACE using C-18 reserval column, Mobile phase A: 0.1% Formic Acid in water; B: acetonitrile, eluent 28% B in A). Combined fractions were concentrated basified with saturated NaHCO$_3$ solution. The aqueous layer was extracted with DCM and separated DCM layer was dried over anhydrous Na$_2$SO$_4$, filtered and filtrate was evaporated to afford (4S)—N7-(3-fluorobenzyl)-N5-(pyridin-2-yl)-3,4-dihydro-1,4-methanopyrido[2,3-b][1,4]diazepine-5,7(2H)-dicarboxamide (170 mg, 0.386 mmol, 41.8% yield) as an off white solid. LCMS (m/z): 433.16 [M+H]$^+$, R$_t$=2.26 min.

$^1$H NMR (400 MHz, CDCl$_3$): δ ppm 13.68 (br s, 1H), 8.74 (br s, 1H), 8.07 (br d, J=8.1 Hz, 1H), 7.99-7.80 (m, 2H), 7.80-7.58 (m, 2H), 7.32-7.19 (m, 2H), 7.15 (br d, J=9.2 Hz, 1H), 7.11-6.85 (m, 2H), 5.61 (br s, 1H), 4.77 (br d, J=4.8 Hz, 2H), 3.38-3.19 (m, 2H), 3.19-3.08 (m, 1H), 3.08-2.82 (m, 1H), 2.33 (br d, J=5.5 Hz, 1H), 2.19-1.98 (m, 1H).

Example 237

Synthesis of (4S)—N5-(pyrazin-2-yl)-N7-((R)-1,1,1-trifluoropropan-2-yl)-3,4-dihydro-1,4-methanopyrido[2,3-b][1,4]diazepine-5,7(2H)-dicarboxamide

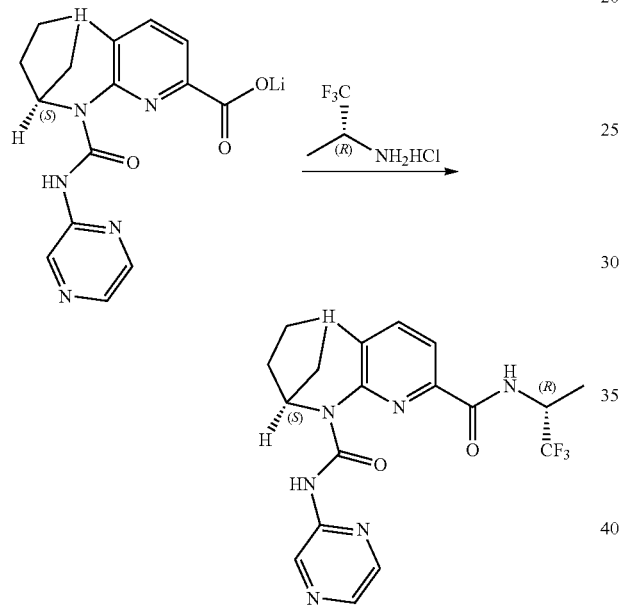

To a stirred solution of lithium (4S)-5-(pyrazin-2-ylcarbamoyl)-2,3,4,5-tetrahydro-1,4-methanopyrido[2,3-b][1,4]diazepine-7-carboxylate (440 mg, 1.324 mmol) and (R)-1,1,1-trifluoropropan-2-amine hydrochloride (594 mg, 3.97 mmol) in DMF (15 mL) were added DIPEA (1.156 mL, 6.62 mmol) and HATU (1007 mg, 2.65 mmol) at 0° C. then stirred at room temp for 16 h. (TLC eluent: Neat ethyl acetate: R$_f$: 0.3; UV active). The reaction mixture solvent was removed by under reduced pressure and diluted with water, extracted with EtOAc (40 ml×2). The combined organic layer was dried over anhydrous Na$_2$SO$_4$ and filtered, filtrate was evaporated to get crude compound, then it was purified by Prep HPLC (Conditions: MP-A: 10 Mm Ammonium Bicarbonate (Aq) MP-B: Acetonitrile Column: KINETEX PHENYL HEXYL (150*30 MM)*5u Method:—0/10, 1/10, 10/50, 15/60, Flow: 30 ml/min Solubility: MeoH+Acetonitrile+THF) to afford the pure compound (4S)—N5-(pyrazin-2-yl)-N7-((R)-1,1,1-trifluoropropan-2-yl)-3,4-dihydro-1,4-methanopyrido[2,3-b][1,4]diazepine-5,7(2H)-dicarboxamide (95 mg, 0.224 mmol, 16.90% yield) as an off white solid. LCMS (m/z): 422.15 [M+H]$^+$, Rt=2.02 min.

$^1$H NMR (400 MHz, CDCl$_3$): δ ppm 13.34 (s, 1H), 9.53 (d, J=1.53 Hz, 1H), 8.35 (d, J=2.63 Hz, 1H), 8.20 (dd, J=2.41, 1.53 Hz, 1H), 7.98 (d, J=7.89 Hz, 1H), 7.71 (d, J=8.11 Hz, 2H), 5.67 (dd, J=6.14, 3.07 Hz, 1H), 5.05 (dt, J=9.65, 7.34 Hz, 1H), 3.29-3.20 (m, 2H), 3.15-3.01 (m, 2H), 2.41-2.31 (m, 1H), 2.13-2.02 (m, 1H), 1.58 (d, J=2.19 Hz, 3H).

Example 238

Synthesis of (4S)—N5-(5-fluoro-4-methylpyridin-2-yl)-N7-((R)-1,1,1-trifluoropropan-2-yl)-3,4-dihydro-1,4-methanopyrido[2,3-b][1,4]diazepine-5,7(2H)-dicarboxamide

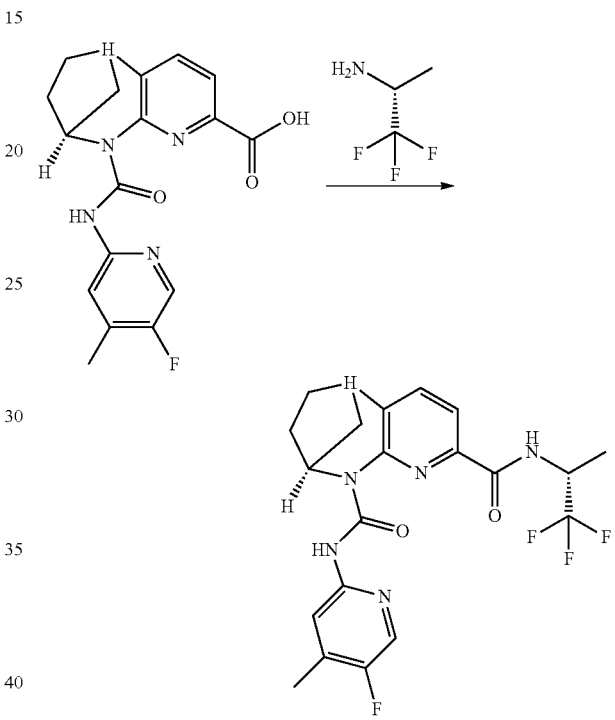

To a stirred solution of (4S)-5-((5-fluoro-4-methylpyridin-2-yl)carbamoyl)-2,3,4,5-tetrahydro-1,4-methanopyrido[2,3-b][1,4]diazepine-7-carboxylic acid (400 mg, 1.119 mmol) in pyridine (10 mL) under nitrogen at RT, was added EDC.HCl (429 mg, 2.239 mmol) and was stirred for 15 min. then added (R)-1,1,1-trifluoropropan-2-amine (152 mg, 1.343 mmol) and stirring continued for 16 h. (TLC system: 5% MeOH in DCM, Rf value=0.5). The reaction mixture was concentrated under vacuum to obtain crude compound. The crude product was purified by chromatography (GRACE instrument, C-18 reserval column; Mobile phase A: 0.1% Formic Acid in water; B: acetonitrile; the product was eluted at 95% B in A) and collected fractions were concentrated and basified with saturated NaHCO$_3$ solution. The resultant solid was filtered and washed with water (10 mL), dried under high vacuum to afford (4S)—N5-(5-fluoro-4-methylpyridin-2-yl)-N7-((R)-1,1,1-trifluoropropan-2-yl)-3,4-dihydro-1,4-methanopyrido[2,3-b][1,4]diazepine-5,7(2H)-dicarboxamide (210 mg, 0.464 mmol, 41.4% yield) as an off-white solid. LCMS (m/z): 453.14, Rt=2.59.

$^1$H NMR (400 MHz, CDCl$_3$): δ ppm 13.17 (s, 1H), 8.06 (d, J=5.70 Hz, 1H), 7.98 (s, 1H), 7.95 (d, J=7.89 Hz, 1H), 7.89 (br d, J=9.43 Hz, 1H), 7.67 (d, J=7.89 Hz, 1H), 5.63 (dd, J=5.92, 3.07 Hz, 1H), 4.97-5.11 (m, 1H), 3.17-3.28 (m, 2H), 3.09-3.14 (m, 1H), 3.00-3.06 (m, 1H), 2.28-2.37 (m, 4H), 2.00-2.11 (m, 1H), 1.57 (d, J=7.23 Hz, 3H).

Example 239

Synthesis of (4S)—N5-(3,5-difluoropyridin-2-yl)-N7-((R)-1,1,1-trifluoropropan-2-yl)-3,4-dihydro-1,4-methanopyrido[2,3-b][1,4]diazepine-5,7(2H)-dicarboxamide

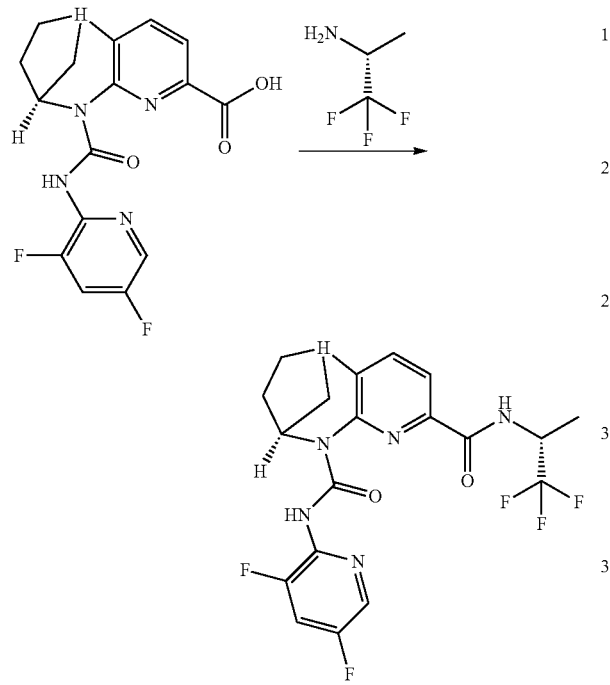

To a stirred solution of (4S)-5-((3,5-difluoropyridin-2-yl)carbamoyl)-2,3,4,5-tetrahydro-1,4-methanopyrido[2,3-b][1,4]diazepine-7-carboxylic acid (600 mg, 1.661 mmol) in pyridine (10 mL) under nitrogen at RT, was added EDC.HCl (637 mg, 3.32 mmol) and stirred for 15 min. then added (R)-1,1,1-trifluoropropan-2-amine (188 mg, 1.661 mmol) and stirring continued for 16 h. (TLC system: 5% MeOH in DCM, Rf value=0.5). The reaction mixture was concentrated under vacuum to give crude product. The crude product was purified by chromatography (GRACE instrument, C-18 reserval column, Mobile phase A: 0.1% Formic Acid in water; B: Acetonitrile, the product was eluted at 80% B in A) and collected fractions were concentrated then the product was basified with saturated NaHCO₃ solution. The obtained solid was filtered and washed with water (10 mL) and dried under high vacuum to afford pure (4S)—N5-(3,5-difluoropyridin-2-yl)-N7-((R)-1,1,1-trifluoropropan-2-yl)-3,4-dihydro-1,4-methanopyrido[2,3-b][1,4]diazepine-5,7(2H)-dicarboxamide (360 mg, 0.784 mmol, 47.2% yield) as an off-white solid. LCMS (m/z): 457.17, Rt=1.98.

$^1$H NMR (400 MHz, CDCl₃): δ ppm 12.29 (s, 1H), 8.15 (d, J=2.63 Hz, 1H), 7.87 (d, J=7.89 Hz, 1H), 7.68 (d, J=7.89 Hz, 1H), 7.29-7.44 (m, 2H), 5.62 (dd, J=5.92, 3.07 Hz, 1H), 4.87-5.03 (m, 1H), 3.12-3.30 (m, 3H), 3.00-3.05 (m, 1H), 2.26-2.40 (m, 1H), 2.01-2.15 (m, 1H), 1.42 (d, J=7.02 Hz, 3H).

Example 240

Synthesis of (4S)—N5-(4-((R)-2,3-dihydroxypropoxy)pyridin-2-yl)-N7-(4-fluorobenzyl)-3,4-dihydro-1,4-methanopyrido[2,3-b][1,4]diazepine-5,7(2H)-dicarboxamide

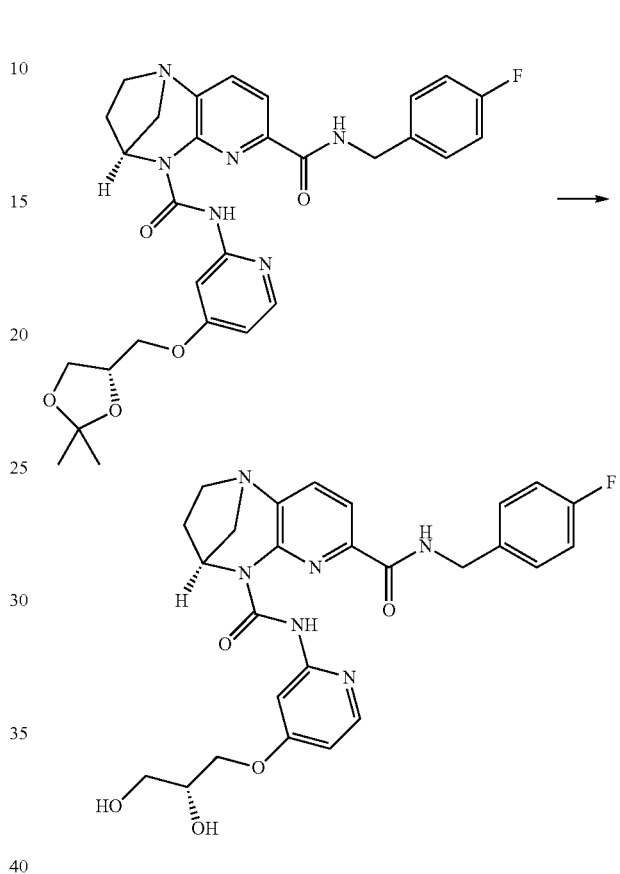

To a stirred solution of (4S)—N5-(4-(((S)-2,2-dimethyl-1,3-dioxolan-4-yl)methoxy)pyridin-2-yl)-N7-(4-fluorobenzyl)-3,4-dihydro-1,4-methanopyrido[2,3-b][1,4]diazepine-5,7(2H)-dicarboxamide (300 mg, 0.533 mmol) in methanol (15 mL) at 0° C., was added HCl (0.081 mL, 2.67 mmol) and stirred at RT for 1 h. The reaction mixture was concentrated under reduced pressure and the residue was neutralized with saturated sodium bicarbonate solution (30 mL). The aqueous layer was extracted with DCM (2×150 mL). Combined organic extracts were washed with brine (100 mL) dried over sodium sulphate and concentrated under reduced pressure. The resultant solid was triturated with n-pentane and diethylether to get pure afford (4S)—N5-(4-((R)-2,3-dihydroxypropoxy)pyridin-2-yl)-N7-(4-fluorobenzyl)-3,4-dihydro-1,4-methanopyrido[2,3-b][1,4]diazepine-5,7(2H)-dicarboxamide (125 mg, 0.237 mmol, 44.5% yield) as an off white solid. LCMS (m/z): 523.27 [M+H]⁺. Rt=1.60 min.

$^1$H NMR (400 MHz, DMSO-d₆): δ ppm 13.48 (s, 1H), 8.82 (t, J=6.3 Hz, 1H), 7.90 (d, J=5.8 Hz, 1H), 7.78-7.67 (m, 2H), 7.59 (d, J=2.4 Hz, 1H), 7.48-7.39 (m, 2H), 7.13 (t, J=8.9 Hz, 2H), 6.67 (dd, J=5.9, 2.4 Hz, 1H), 5.41 (dd, J=6.0, 3.0 Hz, 1H), 5.01 (d, J=5.2 Hz, 1H), 4.70 (t, J=5.6 Hz, 1H), 4.63 (d, J=6.3 Hz, 2H), 4.10 (dd, J=9.9, 3.8 Hz, 1H), 3.95 (dd, J=9.9, 6.3 Hz, 1H), 3.81 (q, J=5.3 Hz, 1H), 3.45 (td, J=5.7, 2.3 Hz, 2H), 3.13-3.04 (m, 3H), 2.97 (dd, J=11.8, 3.2 Hz, 1H), 2.21 (d, J=6.5 Hz, 1H), 1.94 (dt, J=14.5, 7.6 Hz, 1H).

Example 241

Synthesis of (4S)—N5-(pyridin-2-yl)-N7-(1-(trifluoromethyl) cyclopropyl)-3,4-dihydro-1,4-methanopyrido [2,3-b][1,4]diazepine-5,7(2H)-dicarboxamide

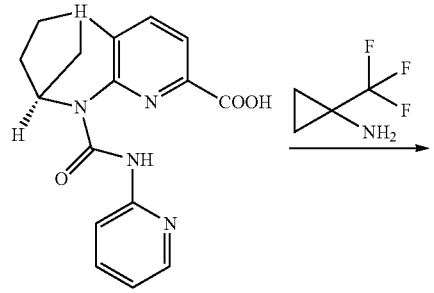

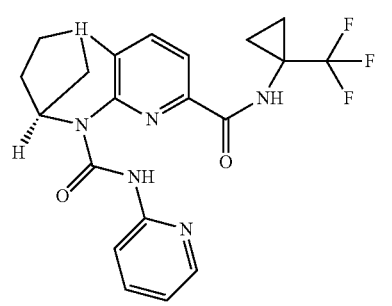

To a stirred solution of (4S)-5-(pyridin-2-ylcarbamoyl)-2,3,4,5-tetrahydro-1,4-methanopyrido[2,3-b][1,4]diazepine-7-carboxylic acid (500 mg, 1.537 mmol) in Pyridine (5 mL) was added EDC (884 mg, 4.61 mmol) at 0° C. and stirred for 50 min. then 1-(trifluoromethyl)cyclopropanamine (385 mg, 3.07 mmol) was added and the reaction was stirred at room temp for 16 h. (TLC: 10% Methanol in DCM, $R_f$ value: 0.3, UV active).

Reaction mixture was diluted with water and extracted with Ethyl acetate (2×50 ml). The combined organic layer was washed with brine solution (50 mL) and dried over anhydrous $Na_2SO_4$, filtered and filtrate was evaporated to get crude compound. The crude product was purified by flash column chromatography (using 100-200 silica gel, compound eluted at 2% Methanol in DCM) to afford the desired product (4S)—N5-(pyridin-2-yl)-N7-(1-(trifluoromethyl)cyclopropyl)-3,4-dihydro-1,4-methanopyrido[2,3-b][1,4]diazepine-5,7(2H)-dicarboxamide (140 mg, 0.317 mmol, 20.64% yield) as an off white solid. LCMS: (m/z): 433.01[M+H]$^+$, Rt=2.23 min.

$^1$H NMR (400 MHz, CDCl$_3$): δ ppm 13.60 (br s, 1H), 8.78 (s, 1H), 8.28 (d, J=4.60 Hz, 1H), 8.08 (d, J=8.33 Hz, 1H), 7.91 (d, J=7.89 Hz, 1H), 7.81-7.59 (m, 2H), 7.03 (dd, J=6.80, 5.04 Hz, 1H), 5.61 (dd, J=5.81, 3.40 Hz, 1H), 3.32-3.18 (m, 3H), 3.03 (dd, J=12.17, 3.18 Hz, 1H), 2.44-2.19 (m, 1H), 2.12-1.96 (m, 1H), 1.58-1.56 (m, 2H), 1.44-1.33 (br s, 2H).

Example 242

Synthesis of (4S)—N7-(2,2-difluorocyclopropyl)-N5-(5-fluoropyridin-2-yl)-3,4-dihydro-1,4-methanopyrido[2,3-b][1,4]diazepine-5,7(2H)-dicarboxamide

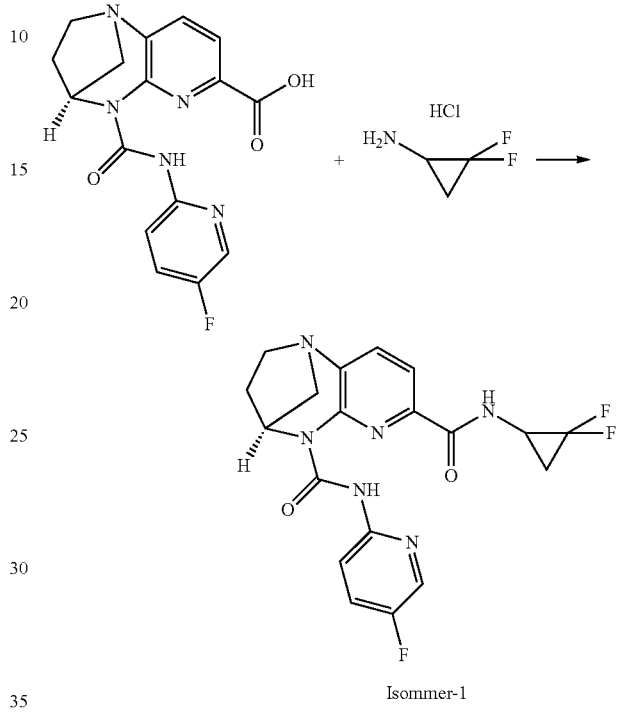

Isommer-1

To a stirred solution of (4S)-5-((5-fluoropyridin-2-yl) carbamoyl)-2,3,4,5-tetrahydro-1,4-methanopyrido[2,3-b][1,4]diazepine-7-carboxylicacid (1.4 g, 4.08 mmol) in DMF (15 mL) at 0° C. was added HATU (2.326 g, 6.12 mmol), DIPEA (3.56 mL, 20.39 mmol) followed by 2,2-difluorocyclopropanamine hydrochloride (0.792 g, 6.12 mmol). The reaction mixture was stirred at RT for 4 h. (TLC eluent: 100% EtOAc: $R_f$—0.3; UV active). The reaction mixture was diluted with cold water and extracted in to DCM (2×50 mL). Organic layer was separated, dried over anhydrous sodium sulphate, filtered and filtrate was evaporated to get crude product. The crude was purified by chromatography (GRACE using C-18 reserval column, Mobile phase A: 0.1% Formic Acid in water; B: ACN, eluent 45-50% B in A) and combined fractions were concentrated basified with saturated NaHCO$_3$ solution. The compound was extracted in to DCM and DCM layer was separated, dried over anhydrous Na$_2$SO$_4$, filtered and filtrate was evaporated to afford diastereomeric mixtures of the desired compound. Diastereomeric mixtures was separated by chiral SFC (Column/dimensions: Chiralcel OJ-H (250×30) mm, 5µ; % CO2: 80.0; % Co-solvent: 20.0 (100% Methanol); Total Flow: 90.0 g/min; Back Pressure: 100.0 bar; UV: 261 nm; Stack time: 4.5 min; Load/Inj: 14.0 mg; Solubility: Methanol+DCM; Total No of injections: 100; Instrument detail: Thar SFC-200-002), to give two single isomers. Isomer-1: Fastest eluting fractions from chiral SFC were concentrated and the solid was triturated with pentane to give (4S)—N7-(2,2-difluorocyclopropyl)-N5-(5-fluoropyridin-2-yl)-3,4-dihydro-1,4-methanopyrido[2,3-b][1,4]diazepine-5,7(2H)-dicarboxamide (320 mg, 0.764 mmol, 18.74% yield) as an off white solid. LCMS (m/z): 419.16 [M+H]$^+$, R$_t$=2.16 min.

$^1$H NMR (400 MHz, CDCl$_3$): δ ppm 13.35 (s, 1H), 8.19-8.10 (m, 2H), 8.05 (s, 1H), 7.90 (d, J=7.8 Hz, 1H), 7.67 (d, J=7.7 Hz, 1H), 7.47 (ddd, J=9.1, 7.6, 3.0 Hz, 1H), 5.62 (dd, J=6.0, 3.2 Hz, 1H), 3.60-3.48 (m, 1H), 3.32-3.15 (m, 3H), 3.16-3.07 (m, 1H), 2.39-2.26 (m, 1H), 2.11-1.90 (m, 2H), 1.71 (ddt, J=14.0, 8.9, 5.4 Hz, 1H).

Example 243

Synthesis of (4S)—N7-(2,2-difluorocyclopropyl)-N5-(5-fluoropyridin-2-yl)-3,4-dihydro-1,4-methanopyrido[2,3-b][1,4]diazepine-5,7(2H)-dicarboxamide

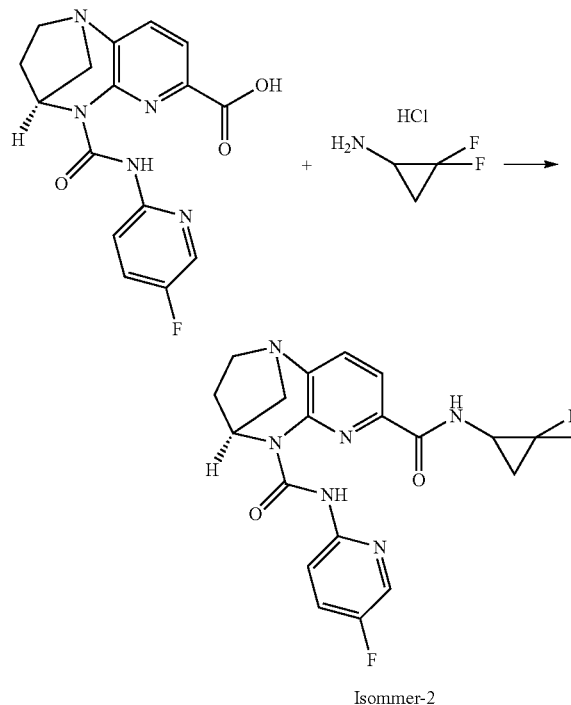

Isommer-2

To a stirred solution of (4S)-5-((5-fluoropyridin-2-yl)carbamoyl)-2,3,4,5-tetrahydro-1,4-methanopyrido[2,3-b][1,4]diazepine-7-carboxylicacid (1.4 g, 4.08 mmol) in DMF (15 mL) at 0° C. was added HATU (2.326 g, 6.12 mmol), DIPEA (3.56 mL, 20.39 mmol) followed by 2,2-difluorocyclopropanamine hydrochloride (0.792 g, 6.12 mmol). The reaction mixture was stirred at RT for 4 h. (TLC eluent: 100% EtOAc: R$_f$—0.3; UV active). The reaction mixture was diluted with cold water and extracted in to DCM (2×50 mL). Organic layer was separated, dried over anhydrous sodium sulphate, filtered and filtrate was evaporated to get crude product. The crude was purified by chromatography (GRACE using C-18 reserval column, Mobile phase A: 0.1% Formic Acid in water; B: ACN, eluent 45-50% B in A) and combined fractions were concentrated basified with saturated NaHCO$_3$ solution. The compound was extracted in to DCM and DCM layer was separated, dried over anhydrous Na$_2$SO$_4$, filtered and filtrate was evaporated to afford diastereomeric mixtures of the desired compound. Diastereomeric mixtures was separated by chiral SFC (Column/dimensions: Chiralcel OJ-H (250×30) mm, 5μ; % CO$_2$: 80.0; % Co-solvent: 20.0 (100% Methanol); Total Flow: 90.0 g/min; Back Pressure: 100.0 bar; UV: 261 nm; Stack time: 4.5 min; Load/Inj: 14.0 mg; Solubility: Methanol+DCM; Total No of injections: 100; Instrument detail: Thar SFC-200-002), to give two single isomers. Isomer-2: Slowest eluting fractions from chiral SFC were concentrated and solid was triturated with pentane to give (4S)—N7-(2,2-difluorocyclopropyl)-N5-(5-fluoropyridin-2-yl)-3,4-dihydro-1,4-methanopyrido[2,3-b][1,4]diazepine-5,7(2H)-dicarboxamide (320 mg, 0.764 mmol, 18.74% yield) as an off white solid. LCMS (m/z): 419.13 [M+H]$^+$, R$_t$=2.15 min.

$^1$H NMR (400 MHz, CDCl$_3$): δ ppm 13.37 (s, 1H), 8.19-8.09 (m, 2H), 8.05 (s, 1H), 7.91 (d, J=7.9 Hz, 1H), 7.67 (d, J=7.9 Hz, 1H), 7.47 (ddd, J=9.0, 7.7, 3.0 Hz, 1H), 5.62 (dd, J=6.0, 3.1 Hz, 1H), 3.61-3.46 (m, 1H), 3.31-3.15 (m, 3H), 3.16-3.07 (m, 1H), 2.33 (dddd, J=13.9, 9.3, 6.0, 4.6 Hz, 1H), 2.11-1.90 (m, 2H), 1.76-1.63 (m, 1H).

Example 244

Synthesis of (4S)—N5-(4-((R)-2,3-dihydroxypropoxy)pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide

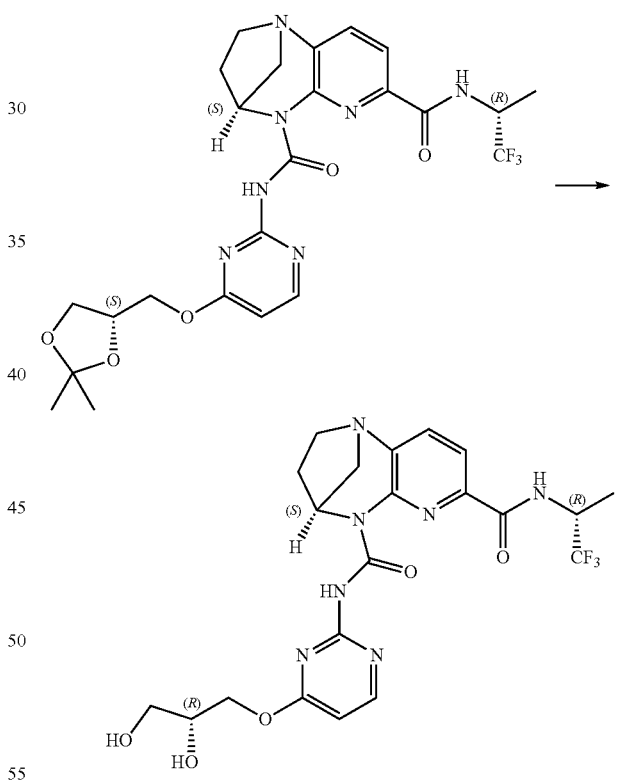

To a stirred solution of (4S)—N5-(4-(((S)-2,2-dimethyl-1,3-dioxolan-4-yl)methoxy)pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide (500 mg, 0.907 mmol) in Methanol (30 mL) was added hydrochloric acid (2 ml, 23.70 mmol), drop wise over a period of 5 min. and the reaction mixture was stirred at RT for 1 h. (TLC system: EtoAC, Rf value: 0.1). The reaction mixture was concentrated under reduced pressure and neutralized the obtain residue with saturated NaHCO$_3$ solution, extracted with 5% MeOH in DCM and concentrated under reduced pressure, triturated with n-pentane (2×20 mL) to afford pure product (4S)—N5-(4-((R)-2,3-dihydroxypropoxy)pyrimidin-2-yl)-N7-((R)-1,1,1-trifluoropropan-2-yl)-3,4-dihydro-1,4-methanopyrido[2,3-b][1,4]diazepine-5,7(2H)-dicarboxamide (380 mg, 0.714 mmol, 79% yield) as a white solid. LCMS (m/z): 512.25 [M+H]+, Rt=1.60 min.

¹H NMR (400 MHz, CDCl₃): δ 13.80 (s, 1H), 8.22 (d, J=5.7 Hz, 1H), 8.03-7.91 (m, 2H), 7.70 (dd, J=7.9, 1.0 Hz, 1H), 6.50 (dd, J=5.8, 1.0 Hz, 1H), 5.71 (dd, J=6.1, 3.1 Hz, 1H), 5.14-4.99 (m, 1H), 4.73 (dd, J=12.2, 4.7 Hz, 1H), 4.60 (dd, J=12.2, 4.2 Hz, 1H), 4.45 (d, J=6.0 Hz, 1H), 3.96 (dt, J=5.9, 4.5 Hz, 1H), 3.70-3.62 (m, 2H), 3.43 (dd, J=7.5, 6.4 Hz, 1H), 3.29-3.14 (m, 2H), 3.08 (d, J=12.2 Hz, 1H), 3.00 (dd, J=12.2, 3.2 Hz, 1H), 2.32 (ddd, J=15.6, 9.2, 4.4 Hz, 1H), 2.04 (dt, J=15.2, 7.7 Hz, 1H), 1.53 (s, 3H).

Example 245

Synthesis of (4S)—N7-(2,2-difluorocyclopropyl)-N5-(4-((R)-2,3-dihydroxypropoxy) pyridin-2-yl)-3,4-dihydro-1,4-methanopyrido[2,3-b][1,4]diazepine-5,7(2H)-dicarboxamide

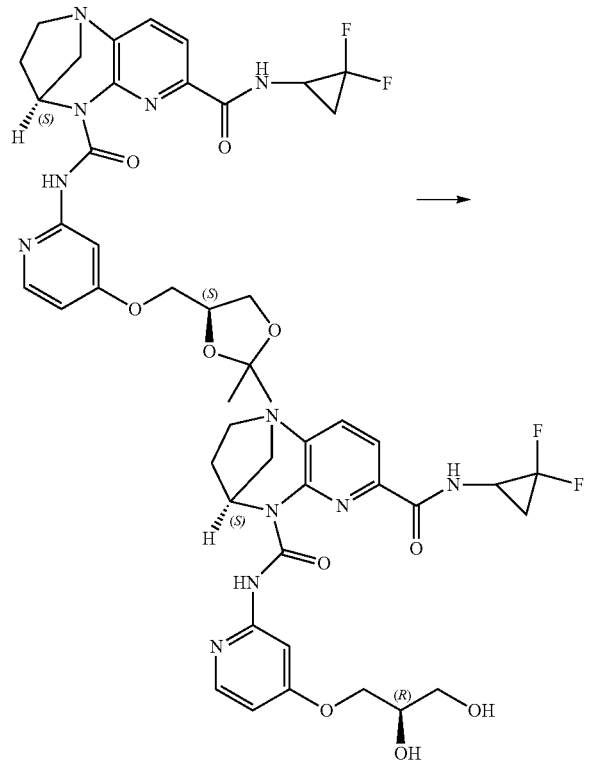

To a stirred solution of (4S)—N7-(2,2-difluorocyclopropyl)-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide (160 mg, 0.302 mmol) in Methanol (10 mL) was added hydrochloric acid (0.018 mL, 0.603 mmol) at 0° C., drop wise over a period of 5 min. and the reaction mixture was stirred at room temperature for 2 h. (TLC eluent: 5% MeOH in DCM: R<sub>f</sub>—0.1; UV active) then evaporated the solvent. The reaction mixture was neutralized with sodium bicarbonate solution and filtered the obtain solid, dried and triturated with diethylether (20 ml) and n-pentane (20 ml) to afford the desired compound (4S)—N7-(2,2-difluorocyclopropyl)-N5-(4-((R)-2,3-dihydroxypropoxy)pyridin-2-yl)-3,4-dihydro-1,4-methanopyrido[2,3-b][1,4]diazepine-5,7(2H)-dicarboxamide (50 mg, 0.102 mmol, 33.7% yield) as an off white solid. LCMS (m/z): 491.19 [M+H]+, Rt=1.33 min.

¹H NMR (400 MHz, CDCl₃): δ 13.44 (s, 1H), 8.28 (s, 1H), 8.07 (d, J=5.8 Hz, 1H), 7.91 (d, J=7.9 Hz, 1H), 7.74 (d, J=2.4 Hz, 1H), 7.67 (d, J=7.9 Hz, 1H), 6.60 (dd, J=5.9, 2.4 Hz, 1H), 5.59 (dd, J=5.9, 3.1 Hz, 1H), 4.17 (dd, J=15.5, 4.7 Hz, 3H), 4.17 (s, 1H), 3.85 (d, J=11.5 Hz, 1H), 3.76 (d, J=11.7 Hz, 1H), 3.53 (d, J=8.8 Hz, 1H), 3.24 (dt, J=9.3, 5.0 Hz, 2H), 3.12 (d, J=12.2 Hz, 1H), 3.02 (dd, J=12.2, 3.2 Hz, 1H), 2.54 (s, 1H), 2.33 (ddt, J=14.3, 9.8, 5.3 Hz, 1H), 2.11-1.87 (m, 3H).

Example 246

Synthesis of (4S)—N7-(3,3-difluorocyclobutyl)-N5-(pyridin-2-yl)-3,4-dihydro-1,4-methanopyrido[2,3-b][1,4]diazepine-5,7(2H)-dicarboxamide

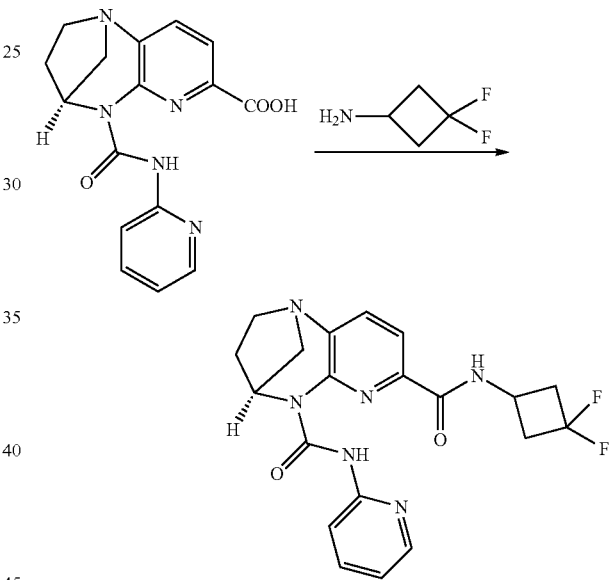

To a stirred solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in DMF (10 mL) were added HATU (701 mg, 1.844 mmol) and DIPEA (0.322 mL, 1.844 mmol) and stirred under nitrogen atmosphere at room temperature. To this reaction mixture 3,3-difluorocyclobutanamine (148 mg, 1.383 mmol) was added and the reaction mixture was stirred at room temperature for 16 h. (TLC eluent: Neat Ethyl acetate: R<sub>f</sub>—0.25; UV active). Reaction mixture was diluted with ice water and extracted with ethyl acetate (2×15 mL). The combined organic layer was washed with brine solution and dried over anhydrous sodium sulphate, filtered and concentrated under reduced pressure to afford crude compound. The crude product was purified by flash column chromatography (100-200 silicagel eluting at 70% Ethyl acetate in pet ether) to afford the desired product (4S)—N7-(3,3-difluorocyclobutyl)-N5-(pyridin-2-yl)-3,4-dihydro-1,4-methanopyrido[2,3-b][1,4]diazepine-5,7(2H)-dicarboxamide (270 mg, 0.640 mmol, 69.4% yield) as a white solid. LCMS (m/z): 415.04 [M+H]+, R<sub>t</sub>=2.1 min.

¹H NMR (400 MHz, CDCl₃): δ ppm 13.18 (s, 1H), 8.33-8.30 (m, 1H), 8.21 (dt, J=8.44, 0.93 Hz, 1H), 8.03 (d, J=7.45 Hz, 1H), 7.90-7.89 (m, 1H), 7.74 (ddd, J=8.50, 7.29, 1.53 Hz, 1H), 7.74 (d, J=7.67 Hz, 1H), 7.06 (ddd, J=7.40, 4.99, 0.99 Hz, 1H), 5.67 (dd, J=6.03, 3.18 Hz, 1H), 4.72-4.61 (m, 1H), 3.30-2.83 (m, 8H), 2.38-2.28 (m, 1H), 2.10-1.99 (m, 1H).

Example 247

Synthesis of (4S)—N5-(3-methylpyridin-2-yl)-N7-((R)-1,1,1-trifluoropropan-2-yl)-3,4-dihydro-1,4-methanopyrido[2,3-b][1,4]diazepine-5,7(2H)-dicarboxamide

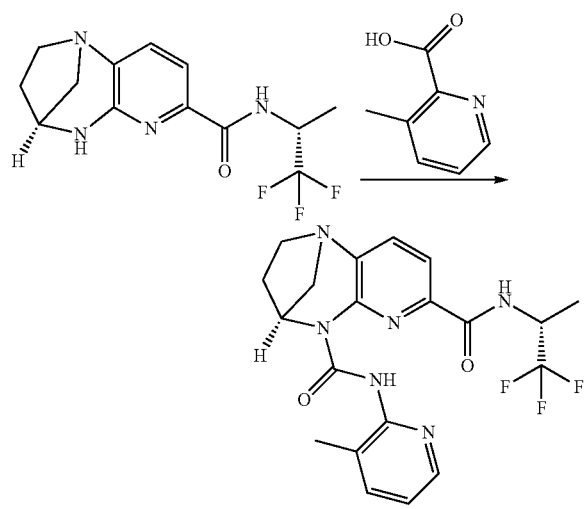

To a solution of 3-methylpicolinic acid (411 mg, 3.00 mmol) in chloroform (100 mL) were added TEA (0.836 mL, 5.99 mmol) followed by diphenyl phosphorazidate (1100 mg, 4.00 mmol) and stirred at 25° C. for 10 h. Then added (4S)—N—((R)-1,1,1-trifluoropropan-2-yl)-2,3,4,5-tetrahydro-1,4-methanopyrido[2,3-b][1,4]diazepine-7-carboxamide (600 mg, 1.998 mmol) to the above reaction mixture and stirred at 80° C. for 16 h. (TLC system: 80% ethylacetate in hexane, Rf value: 0.2). Reaction was cooled to RT then added water (100 mL) and extracted with DCM (3×100 mL). Combined organic layer was washed with brine (100 mL), dried over sodium sulphate filtered and concentrated under reduced pressure to get crude product. The crude compound was purified by preparative HPLC (Column: XBridge C 18 (150×4.6 mm, 3.5μ; MP-A: 5 mM Ammonium Bicarbonate (Aq), MP-B: Acetonitrile, Method (T/% B): 0/10, 1/10, 10/60, 15/60, 18/98, 20/98, 20.1/10, 25/10; Flow: 1.0 ml/min; Solubility: Acetonitrile) to afford (4S)—N5-(3-methylpyridin-2-yl)-N7-((R)-1,1,1-trifluoropropan-2-yl)-3,4-dihydro-1,4-methanopyrido[2,3-b][1,4]diazepine-5,7(2H)-dicarboxamide (92 mg, 0.211 mmol, 10.57% yield) as an off-white solid. LCMS (m/z): 435.10 [M+H]⁺, Rt=1.52 min.

¹H NMR (400 MHz, CDCl₃): δ ppm 12.33 (s, 1H), 8.23 (dd, J=4.82, 1.32 Hz, 1H), 7.85 (d, J=7.89 Hz, 2H), 7.71-7.56 (m, 2H), 7.12 (dd, J=7.67, 4.82 Hz, 1H), 5.51 (dd, J=5.92, 3.07 Hz, 1H), 5.02-4.79 (m, 1H), 3.30-3.11 (m, 3H), 3.02 (dd, J=12.06, 3.29 Hz, 1H), 2.42 (s, 3H), 2.38-2.21 (m, 1H), 2.19-1.92 (m, 1H), 1.39 (d, J=7.23 Hz, 3H).

Example 248

Synthesis of (4S)—N5-(pyridin-2-yl)-N7-(1,1,1-trifluoro-4-hydroxybutan-2-yl)-3,4-dihydro-1,4-methanopyrido[2,3-b][1,4]diazepine-5,7(2H)-dicarboxamide

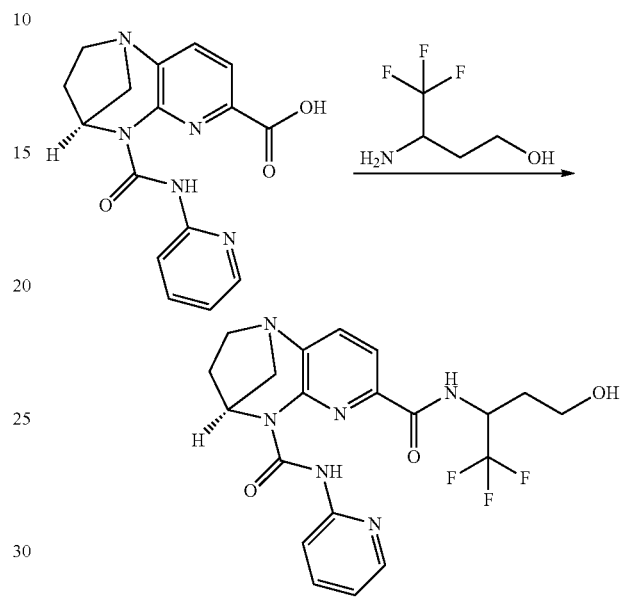

To a stirred solution of (4S)-5-(pyridin-2-ylcarbamoyl)-2,3,4,5-tetrahydro-1,4-methanopyrido[2,3-b][1,4]diazepine-7-carboxylic acid (1 g, 3.07 mmol) in DMF (5 mL) under nitrogen at RT, was added DIPEA (1.611 mL, 9.22 mmol), HATU (2.338 g, 6.15 mmol) and stirred for 10 min. then added 3-amino-4,4,4-trifluorobutan-1-ol (0.660 g, 4.61 mmol) to the above reaction mixture and stirred at RT for 16 h. The reaction mixture was poured into ice cold water (100 mL) and extracted with ethylacetate (100 mL). Combined EtOAc extracts were dried over anhydrous Na₂SO₄, filtered and concentrated to give crude compound. The crude product was purified by combiflash chromatography (using silicagel column and eluted with 3% Methanol in DCM) to get diastereomeric mixtures of (4S)—N5-(pyridin-2-yl)-N7-(1,1,1-trifluoro-4-hydroxybutan-2-yl)-3,4-dihydro-1,4-methanopyrido[2,3-b][1,4]diazepine-5,7(2H)-dicarboxamide (1.18 g), HPLC purity-91%) as an off white solid. This diastereomeric mixture was further separated by chiral SFC (Instrument details: Make/Model: Thar SFC-200; Column Chiralcel OD-H (250×30) mm; C₀₂₋₇₅%, co-solvent (0.5% diethylamine in MeOH)-25%; Flow rate: 80 g/min; Stack time: 3.0 min; Load/inj: 5 mg; Solubility: MeOH) to give two single isomers. Peak-2: The slowest fractions from SFC were collected and concentrated then the residue was triturated with diethylether (5 mL) to afford (4S)—N5-(pyridin-2-yl)-N7-(1,1,1-trifluoro-4-hydroxybutan-2-yl)-3,4-dihydro-1,4-methanopyrido[2,3-b][1,4]diazepine-5,7(2H)-dicarboxamide (240 mg, 0.520 mmol, 16.90% yield) as off white solid. LCMS (m/z): 451.12 [M+H]⁺, Rt=1.83 min.

¹H NMR (400 MHz, CDCl₃): δ ppm 12.66-13.15 (m, 1H), 8.21 (br d, J=3.95 Hz, 1H), 8.08-8.18 (m, 2H), 7.92 (d, J=7.67 Hz, 1H), 7.70-7.76 (m, 1H), 7.68 (d, J=7.89 Hz, 1H), 7.00-7.08 (m, 1H), 5.66 (dd, J=5.70, 3.07 Hz, 1H), 5.08-5.21

(m, 1H), 3.76-3.89 (m, 2H), 3.18-3.30 (m, 2H), 3.08-3.15 (m, 1H), 2.98-3.06 (m, 1H), 2.22-2.41 (m, 2H), 1.98-2.18 (m, 2H).

Example 249

Synthesis of (4S)—N7-(2-amino-3,3,3-trifluoropropyl)-N5-(pyridin-2-yl)-3,4-dihydro-1,4-methanopyrido[2,3-b][1,4]diazepine-5,7(2H)-dicarboxamide

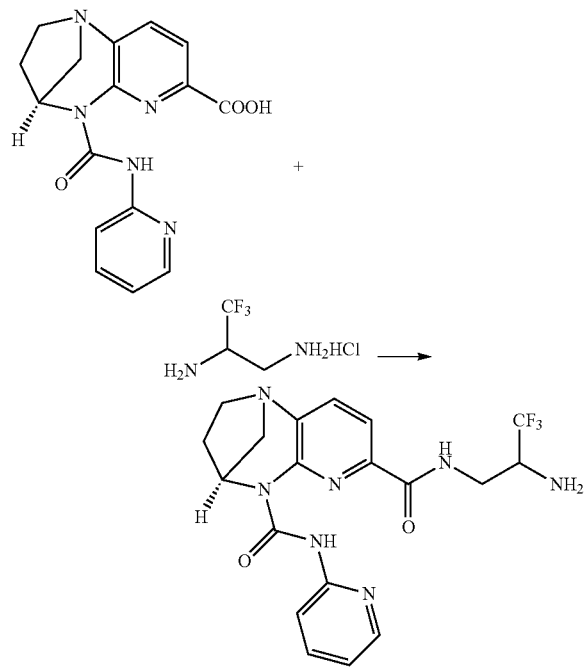

To a solution of (4S)-5-(pyridin-2-ylcarbamoyl)-2,3,4,5-tetrahydro-1,4-methanopyrido[2,3-b][1,4]diazepine-7-carboxylic acid (500 mg, 1.537 mmol) in DMF (5 mL) under nitrogen at RT, was added DIPEA (1.342 mL, 7.68 mmol), HATU (1169 mg, 3.07 mmol) and stirred for 15 min. then added 3,3,3-trifluoropropane-1,2-diamine dihydrochloride (309 mg, 1.537 mmol) in one charge. The reaction mixture was stirred at RT for 16 h. (TLC system: 5% Methanol in DCM, Rf: 0.4). Reaction mixture was diluted with cold water (20 mL) and extracted with EtOAc (2×30 mL). Combined organic extracts were washed with brine (20 mL) solution, dried over anhydrous Na$_2$SO$_4$, filtered and concentrated under reduced pressure to obtain crude product. Crude compound was purified by combiflash chromatography (silicagel, eluted with 5% methanol in DCM) to obtain desired compound as a diastereomeric mixtures. Diastereomers were separated by chiral SFC (Column/dimensions: CHIRALPAK-IC (250×30) mm, 5u, Mobile Phase-A: n-Hexane, Mobile Phase-B: Ethanol, Isocratic: 65:35, Total Flow: 41.0 ml/min, Temperature: Ambient, Wave length: 262 nm, Solubility: Ethanol, Loadability/Inj: 41 mg/Inj, Total No of injections: 10, Instrument details: YMC prep-01) to afford two single isomers with unknown absolute stereochemistry at amine center. Peak-1: Fast eluting fractions from SFC was concentrated and purified further by combiflash chromatography (Silicagel, eluted with 5% methanol in DCM) to afford (4S)—N7-(2-amino-3,3,3-trifluoropropyl)-N5-(pyridin-2-yl)-3,4-dihydro-1,4-methanopyrido[2,3-b][1,4]diazepine-5,7(2H)-dicarboxamide (108 mg, 0.243 mmol, 15.83% yield) as an off-white solid. LCMS (m/z): 436.18[M+H]$^+$. Rt=1.51 min.

$^1$H NMR (400 MHz, CDCl$_3$): δ ppm 13.47 (s, 1H), 8.32 (br s, 1H), 8.07-8.28 (m, 2H), 7.87 (d, J=7.89 Hz, 1H), 7.73 (t, J=7.84 Hz, 1H), 7.67 (d, J=8.11 Hz, 1H), 6.91-7.13 (m, 1H), 5.62 (dd, J=5.92, 3.07 Hz, 1H), 3.79-3.96 (m, 1H), 3.63-3.75 (m, 2H), 3.09-3.30 (m, 3H), 3.00-3.07 (m, 1H), 2.19-2.42 (m, 1H), 1.98-2.17 (m, 1H).

Example 250

Synthesis of (4S)—N5-(isoxazol-3-yl)-N7-((R)-1,1,1-trifluoropropan-2-yl)-3,4-dihydro-1,4-methanopyrido[2,3-b][1,4]diazepine-5,7(2H)-dicarboxamide

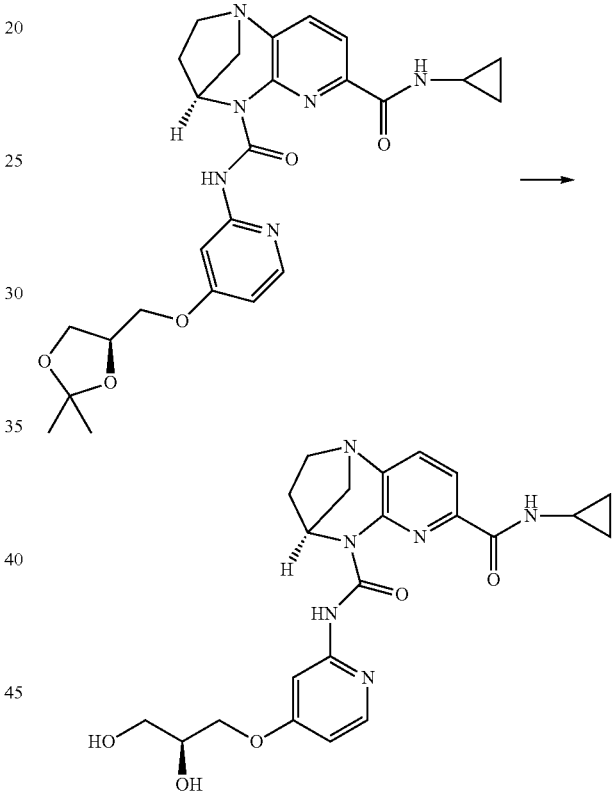

To a solution of (4S)—N7-cyclopropyl-N5-(4-(((R)-2,2-dimethyl-1,3-dioxolan-4-yl)methoxy)-pyridin-2-yl)-3,4-dihydro-1,4-methanopyrido[2,3-b][1,4]-diazepine-5,7(2H)-dicarboxamide (950 mg, 1.921 mmol) in methanol (3 mL) under nitrogen at 0° C., was added HCl (3 mL, 99 mmol) and stirred at RT for 5 h. (TLC system: 10% MeOH in DCM. Rf value: 0.2). Reaction mixture was concentrated under reduced pressure and the residue was taken in water (3 mL), then neutralized with saturated sodium bicarbonate solution. The aq. Layer was extracted with 10% MeOH in DCM (20 mL). Combined organic layer was washed with brine (20 mL), dried over anhydrous Na$_2$SO$_4$, filtered and concentrated under reduced pressure to get the crude product. The crude was purified by combiflash chromatography (Silicagel, eluted with 10% methanol in DCM) to afford the desired compound (4S)—N7-cyclopropyl-N5-(4-((S)-2,3-dihydroxypropoxy)pyridin-2-yl)-3,4-dihydro-1,4-methanopyrido[2,3-b][1,4]diazepine-5,7(2H)-dicarboxamide (510 mg, 1.110 mmol, 57.8% yield) as a white solid. LCMS (m/z): 455.19 [M+H]+. Rt=1.24 min.

¹H NMR (400 MHz, DMSO-d₆): δ ppm 13.12 (s, 1H), 8.11 (d, J=5.92 Hz, 1H), 8.06 (br d, J=4.17 Hz, 1H), 7.73 (s, 1H), 7.71 (s, 1H), 7.68 (s, 1H), 6.74 (dd, J=5.92, 2.41 Hz, 1H), 5.43 (dd, J=5.81, 2.96 Hz, 1H), 5.02 (br d, J=5.04 Hz, 1H), 4.71 (br s, 1H), 4.12 (dd, J=9.76, 3.84 Hz, 1H), 3.96 (dd, J=9.87, 6.36 Hz, 1H), 3.83 (br d, J=4.38 Hz, 1H), 3.47 (br d, J=3.95 Hz, 2H), (br d, J=12.28 Hz, 3H), 3.00-2.93 (m, 2H), 2.27-2.17 (m, 1H), 1.91 (dt, J=13.87, 7.21 Hz, 1H), 0.87-0.79 (m, 2H), 0.77-0.70 (m, 2H)

Example 251

Synthesis of (4S)—N5-(isoxazol-3-yl)-N7-((R)-1,1, 1-trifluoropropan-2-yl)-3,4-dihydro-1,4-methano-pyrido[2,3-b][1,4]diazepine-5,7(2H)-dicarboxamide

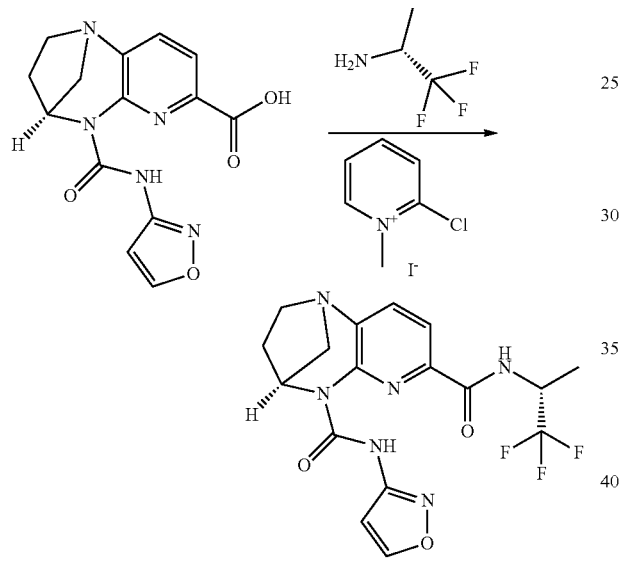

To a solution of (4S)-5-(isoxazol-3-ylcarbamoyl)-2,3,4,5-tetrahydro-1,4-methanopyrido[2,3-b][1,4]diazepine-7-carboxylic acid (900 mg, 2.85 mmol) in THF (60 mL) were added TEA (1.194 mL, 8.56 mmol) followed by 2-chloro-1-methylpyridin-1-ium iodide (1459 mg, 5.71 mmol) and stirred for 10 min, then added (R)-1,1,1-trifluoropropan-2-amine (484 mg, 4.28 mmol) and stirred at RT for 16 h. (TLC system: 80% ethylacetate in hexane, Rf value: 0.3). Water (80 ml) was added to the reaction mixture and extracted with EtOAc (2×100 ml), the separated organic layer was washed with brine (80 mL) and dried over anhydrous Na₂SO₄, filtered and concentrated to get crude product. The crude product was purified by combiflash chromatography (Silicage, eluted with 60% EtOAc in Hexane) to afford (4S)—N5-(isoxazol-3-yl)-N7-((R)-1,1,1-trifluoropropan-2-yl)-3,4-dihydro-1,4-methanopyrido[2,3-b][1,4]diazepine-5,7 (2H)-dicarboxamide (395 mg, 0.959 mmol, 33.6% yield) as an off-white solid. LCMS (m/z): 411.12 [M+H]+, Rt=1.96 min.

¹H NMR (400 MHz, CDCl₃): δ ppm 12.99 (s, 1H), 8.29 (d, J=1.75 Hz, 1H), 7.92 (m, J=7.89 Hz, 1H), 7.70 (m, J=7.89 Hz, 1H), 7.25-7.10 (m, 1H), 6.98 (d, J=1.75 Hz, 1H), 5.62 (dd, J=6.03, 2.96 Hz, 1H), 5.01-4.87 (m, 1H), 3.30-3.08 (m, 3H), 3.07-2.97 (m, 1H), 2.42-2.21 (m, 1H), 2.19-1.97 (m, 1H), 1.62 (d, J=7.02 Hz, 3H).

Example 252

Synthesis of (4S)-9-methyl-N5-(4-(2-methyloxazol-5-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

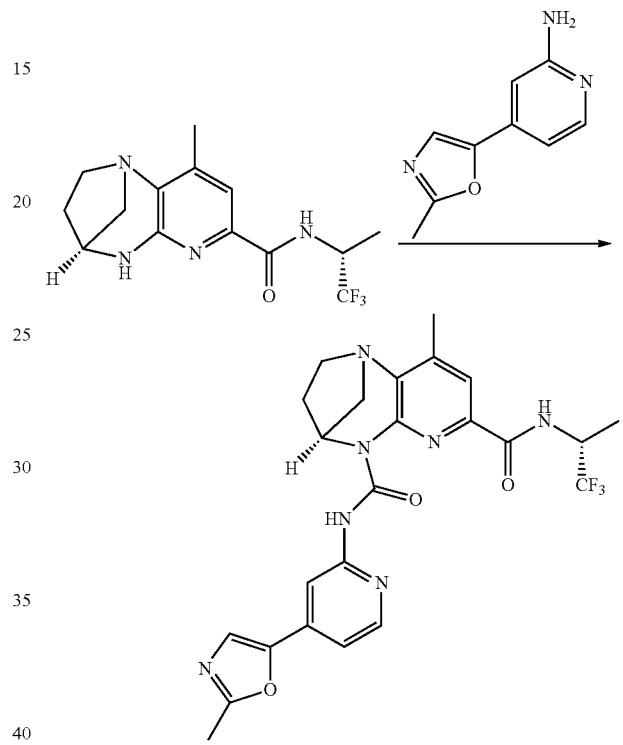

To a stirred solution of (4S)-9-methyl-N—((R)-1,1,1-trifluoropropan-2-yl)-2,3,4,5-tetrahydro-1,4-methanopyrido [2,3-b][1,4]diazepine-7-carboxamide (500 mg, 1.591 mmol) in THF (50 ml) were added triphosgene (283 mg, 0.954 mmol) and DIPEA (1.389 mL, 7.95 mmol) at 0° C. and stirred to RT for 1 h. Then 4-(2-methyloxazol-5-yl)pyridin-2-amine (418 mg, 2.386 mmol) was added sub sequentially at 75° C. for 16 h. (TLC System;—80% EtOAc in Pet-Ether, Rf:—0.4). The reaction was allowed to cool to room temperature and poured in saturated NaHCO₃ solution (30 mL), extracted with ethyl acetate (2×100 mL). The combined organic layer was dried over anhydrous Na₂SO₄ and concentrated under reduced pressure to obtain crude compound. The crude product was purified by flash column chromatography (Silica gel: Neutral alumina, Eluent: 30% Ethyl acetate in Petether) to afford the desired product (4S)-9-methyl-N5-(4-(2-methyloxazol-5-yl)pyridin-2-yl)-N7-((R)-1,1,1-trifluoropropan-2-yl)-3,4-dihydro-1,4-methanopyrido [2,3-b][1,4]diazepine-5,7(2H)-dicarboxamide (230 mg, 0.442 mmol, 27.8% yield) as a white solid. LCMS (m/z): 516.21 [M+H]+, Rt=2.57 min.

¹H NMR (400 MHz, DMSO-d₆): δ ppm 13.24 (s, 1H), 8.34 (s, 1H), 8.28 (d, J=5.26 Hz, 1H), 8.16 (d, J=8.99 Hz, 1H), 7.82 (s, 1H), 7.70 (s, 1H), 7.40 (dd, J=5.26, 1.53 Hz, 1H), 5.49 (d, J=5.70 Hz, 1H), 4.97 (dq, J=15.70, 7.77 Hz, 1H), 3.18-2.95 (m, 4H), 2.54 (s, 3H), 2.45 (s, 3H), 2.31-2.17 (m, 1H), 2.00-1.91 (m, 1H), 1.52 (d, J=7.23 Hz, 3H).

Example 253

Synthesis of (4S)—N7-(2-methylbut-3-yn-2-yl)-N5-(pyridin-2-yl)-3, 4-dihydro-1, 4-methanopyrido [2, 3-b] [1, 4] diazepine-5, 7(2H)-dicarboxamide

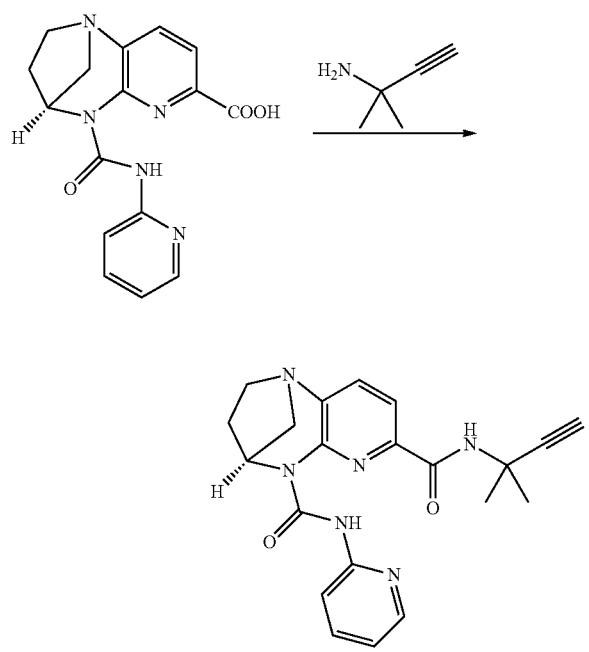

To a stirred solution of (4S)-5-(pyridin-2-ylcarbamoyl)-2,3,4,5-tetrahydro-1,4-methanopyrido[2,3-b][1,4]diazepine-7-carboxylic acid (500 mg, 1.537 mmol) in DMF (2 mL) were added DIPEA (1.342 mL, 7.68 mmol), HATU (46.8 mg, 0.123 mmol) and 2-methylbut-3-yn-2-amine (128 mg, 1.537 mmol) under nitrogen at RT. The reaction mixture was stirred at RT for 8 h. (TLC eluent: 5% MeOH in DCM: R$_f$—0.5; UV active). Reaction mixture was diluted with cold water and extracted with ethyl acetate (2×50 ml). The combined organic layer was washed with brine solution (20 mL), dried over anhydrous Na$_2$SO$_4$, filtered and concentrated under reduced pressure to get crude product. The crude compound was purified by combi flash chromatography (normal phase column 12 g, eluent: 5% methanol in DCM) to afford semi pure compound, which was again purified by Prep HPLC (Conditions: MP-A: 10 Mm Ammonium bicarbonate (Aq) MP-B: Acetonitrile Column: Xbridge (150*19 mm) 5. Method: (T/% B) 0/10, 10/60 Flow: 17 ml/min. Solubility: THF+ACN+MeOH) to afford pure compound (4S)—N7-(2-methylbut-3-yn-2-yl)-N5-(pyridin-2-yl)-3,4-dihydro-1,4-methanopyrido[2,3-b][1,4]diazepine-5,7(2H)-dicarboxamide (206 mg, 0.524 mmol, 34.1% yield) as a pale green solid. LCMS (m/z): 391.18 [M+H]$^+$, R$_t$=2.02 min.

$^1$H NMR (400 MHz, DMSO-d$_6$): δ ppm 12.75 (s, 1H), 8.25 (d, J=5.11 Hz, 1H), 8.17-8.04 (m, 1H), 7.91 (s, 1H), 7.83 (t, J=7.45 Hz, 1H), 7.77-7.60 (m, 2H), 7.11 (ddd, J=7.34, 4.93, 1.10 Hz, 1H), 5.48 (dd, J=5.92, 3.07 Hz, 1H), 2.94-3.20 (m, 4H), 2.76-2.53 (m, 1H), 2.38-2.15 (m, 1H), 2.08-1.84 (m, 1H), 1.71 (s, 6H).

Example 254

Synthesis of (4S)—N7-methyl-N5-(pyridin-2-yl)-N7-(2,2,2-trifluoroethyl)-3,4-dihydro-1,4-methanopyrido[2,3-b][1,4]diazepine-5,7(2H)-dicarboxamide

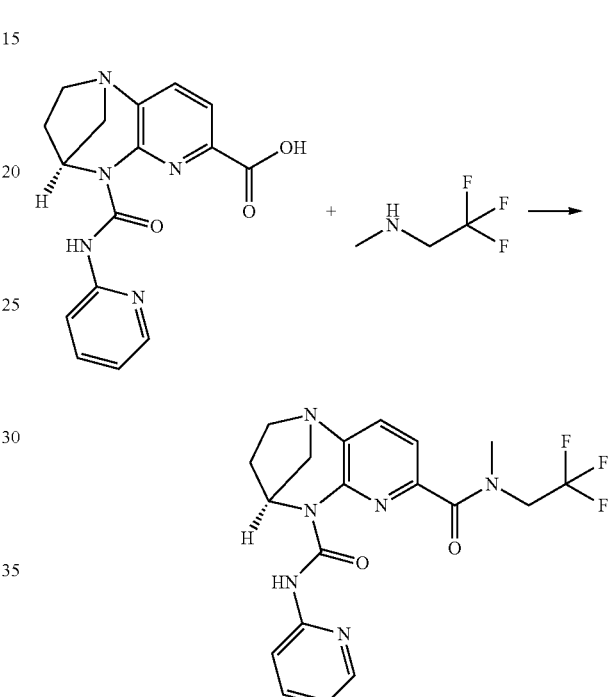

To a stirred solution (4S)-5-(pyridin-2-ylcarbamoyl)-2,3,4,5-tetrahydro-1,4-methanopyrido[2,3-b][1,4]diazepine-7-carboxylic acid (500 mg, 1.537 mmol) in THF (20 mL) under nitrogen at RT, was added DIPEA (0.805 mL, 4.61 mmol), HATU (877 mg, 2.305 mmol) and 2,2,2-trifluoro-N-methylethanamine (226 mg, 1.998 mmol) and stirred for 16 h. (TLC eluent: 10% MeOH in DCM, R$_f$: 0.5, UV active). The reaction mixture was diluted with water (50 mL) and extracted with ethylacetate, organic extracts were washed with brine (100 mL) dried over anhydrous Na$_2$SO$_4$, filtered and evaporated to get crude product. The crude compound was purified by column chromatography (neutral alumina, eluted with ethylacetate) to get solid compound. The solid was triturated with diethylether and pentane to afford (4S)—N7-methyl-N5-(pyridin-2-yl)-N7-(2,2,2-trifluoroethyl)-3,4-dihydro-1,4-methanopyrido[2,3-b][1,4]diazepine-5,7(2H)-dicarboxamide (208 mg, 0.493 mmol, 32.1% yield) as an off-white solid. LCMS (m/z): 421.10 [M+H]$^+$, R$_t$=1.80 min.

$^1$H NMR (400 MHz, CDCl$_3$): δ ppm 12.79 (s, 1H), 8.26 (d, J=3.73 Hz, 1H), 8.13 (d, J=8.33 Hz, 1H), 7.60-7.77 (m, 2H), 7.34 (br d, J=7.89 Hz, 1H), 6.89-7.07 (m, 1H), 5.68 (s, 1H), 4.12-4.54 (m, 2H), 3.11-3.49 (m, 6H), 2.93-3.07 (m, 1H), 2.24-2.38 (m, 1H), 1.96-2.12 (m, 1H)

Example 255

Synthesis of (4S)—N7-cyclopropyl-N5-(2-methyl-oxazol-4-yl)-3,4-dihydro-1,4-methanopyrido[2,3-b][1,4]diazepine-5,7(2H)-dicarboxamide

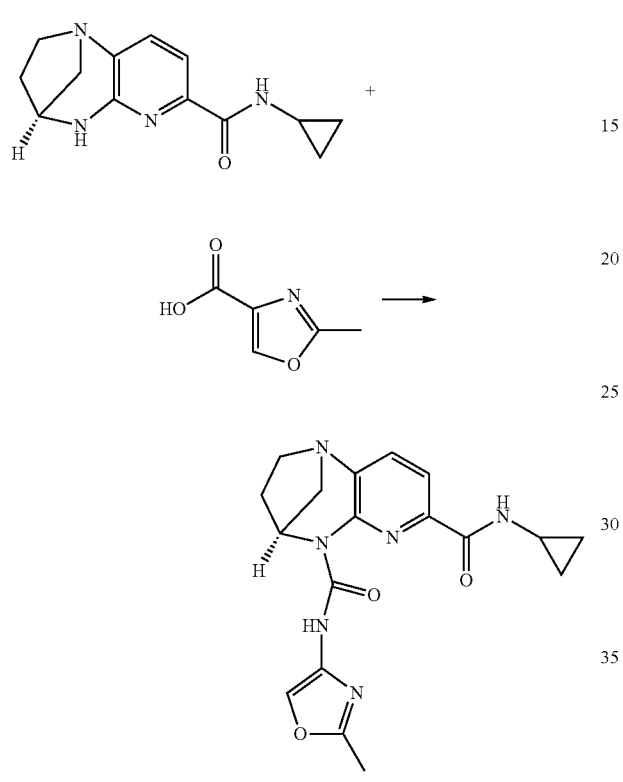

To a solution of 2-methyloxazole-4-carboxylic acid (375 mg, 2.95 mmol) in CHCl₃ (50 mL), was added diphenyl phosphorazidate (811 mg, 2.95 mmol) and TEA (0.685 mL, 4.91 mmol) then the reaction mixture stirred at RT for 10 h. Then added (4S)—N-cyclopropyl-2,3,4,5-tetrahydro-1,4-methanopyrido-[2,3-b][1,4]-diazepine-7-carboxamide (600 mg, 2.456 mmol) and to the above reaction and stirred at 60° C. for 12 h. (TLC system: 10% Methanol in DCM, Rf value: 0.4). Water (50 mL) was added to the reaction and extracted with DCM (2×50 mL), organic layer was separated washed with brine solution (10 mL), filtered and concentrated under reduced pressure to afford crude product. The crude material was purified by combiflash chromatography (Silicagel, 5% MeOH in DCM) to afford the desired compound (4S)—N7-cyclopropyl-N5-(2-methyloxazol-4-yl)-3,4-dihydro-1,4-methanopyrido[2,3-b][1,4]diazepine-5,7(2H)-dicarboxamide (230 mg, 0.613 mmol, 24.96% yield) as an yellow solid. LCMS (m/z): 369.11 [M+H]⁺, Rt=1.77 min.

¹H NMR (400 MHz, CDCl₃): δ ppm 12.45 (s, 1H), 7.87 (d, J=7.89 Hz, 1H), 7.76 (s, 1H), 7.63 (d, J=7.89 Hz, 1H), 7.22 (br s, 1H), 5.58 (dd, J=5.92, 3.07 Hz, 1H), 3.05-3.30 (m, 4H), 2.96-3.02 (m, 1H), 2.39-2.49 (m, 3H), 2.24-2.35 (m, 1H), 1.94-2.08 (m, 1H), 0.85-1.04 (m, 4H).

Example 256

Synthesis of (4S)—N7-((1H-tetrazol-5-yl)methyl)-N5-(4-((R)-2,3-dihydroxypropoxy)pyridin-2-yl)-3,4-dihydro-1,4-methanopyrido[2,3-b][1,4]diazepine-5,7(2H)-dicarboxamide

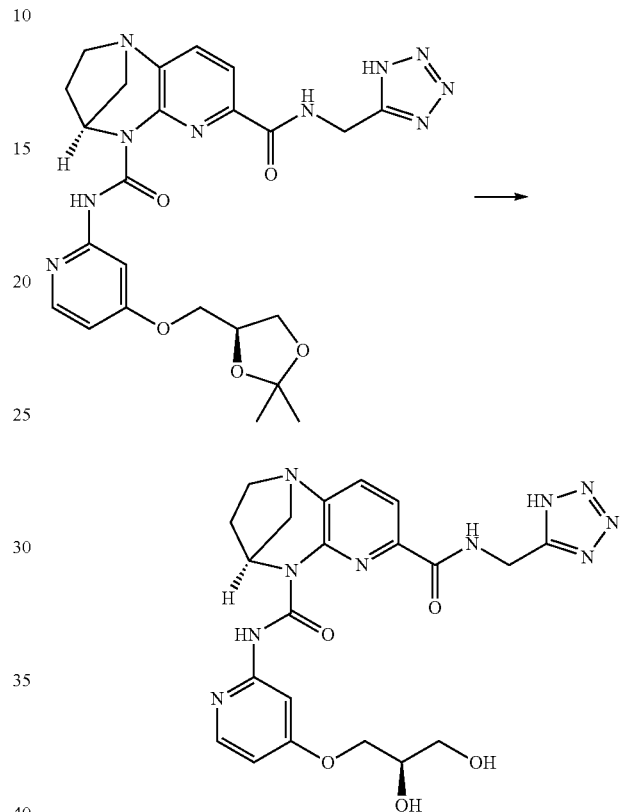

To a stirred solution of (4S)—N7-((1H-tetrazol-5-yl)methyl)-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide (200 mg, 0.373 mmol) in methanol (10 mL) at 0° C. was added aq. HCl (0.057 mL, 1.864 mmol) and stirred for 4 h. (TLC eluting system: 10% MeOH in DCM; Rf—0.3; UV active). The reaction mixture was concentrated and the residue was basified with saturated NaHCO₃ solution and volatiles were removed under vacuum. The crude was taken in 10% MeOH in DCM and resultant solids are filtered and the filtrate was evaporated to afford (4S)—N7-((1H-tetrazol-5-yl)methyl)-N5-(4-((R)-2,3-dihydroxypropoxy)pyridin-2-yl)-3,4-dihydro-1,4-methanopyrido[2,3-b][1,4]diazepine-5,7(2H)-dicarboxamide (130 mg, 0.255 mmol, 68.3% yield) as off white solid. LCMS (m/z): 494.9 [M–H]⁺. Rt=2.45 min.

¹H NMR (400 MHz, DMSO-d6): δ ppm 13.59-13.52 (m, 1H), 8.49 (q, J=6.0 Hz, 1H), 7.91-7.79 (m, 1H), 7.79-7.66 (m, 2H), 7.49 (d, J=2.2 Hz, 1H), 6.59 (dt, J=2.6, 6.0 Hz, 1H), 5.40 (br d, J=3.1 Hz, 1H), 4.83-4.63 (m, 3H), 4.22-3.58 (m, 3H), 3.53-3.39 (m, 1H), 3.38-3.33 (m, 1H), 3.17 (br d, J=5.0 Hz, 1H), 3.13-3.03 (m, 2H), 2.96 (br dd, J=3.3, 12.1 Hz, 1H), 2.27-2.13 (m, 1H), 2.00-1.87 (m, 1H).

Example 257

Synthesis of (4S)—N5-(pyridin-2-yl)-3,4-dihydro-1,4-methanopyrido[2,3-b][1,4]diazepine-5,7(2H)-dicarboxamide

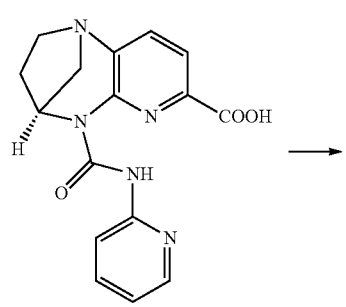

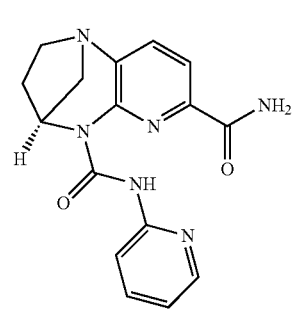

To a solution of (4S)-5-(pyridin-2-ylcarbamoyl)-2,3,4,5-tetrahydro-1,4-methanopyrido[2,3-b][1,4]diazepine-7-carboxylic acid (200 mg, 0.615 mmol) in DMF (2 mL) under nitrogen at RT, was added DIPEA (0.537 mL, 3.07 mmol), HATU (46.8 mg, 0.123 mmol) followed by ammonium chloride (32.9 mg, 0.615 mmol) and the reaction mixture was stirred for 16 h. (TLC system: 5% Methanol in DCM. Rf value: 0.5). Reaction mixture was diluted with cold water (30 mL) and extracted with ethylacetate (2×50 mL). Combined organic layers were washed with brine (30 mL), dried over anhydrous sodium sulphate and concentrated under reduced pressure to afford crude compound. Crude product was purified by combiflash chromatography (Silicagel, 5% methanol in DCM) to afford the desired compound (4S)—N5-(pyridin-2-yl)-3,4-dihydro-1,4-methanopyrido-[2,3-b][1,4]-diazepine-5,7(2H)-dicarboxamide (95 mg, 0.292 mmol, 47.5% yield) as a white solid. LCMS (m/z): 325.05 [M+H]$^+$. Rt=1.31 min.

$^1$H NMR (400 MHz, DMSO-d$_6$): δ ppm 13.40 (s, 1H), 8.25 (dt, J=4.88, 0.96 Hz, 1H), 8.07-7.90 (m, 2H), 7.84 (t, J=7.86 Hz, 1H), 7.78-7.66 (m, 3H), 7.11 (ddd, J=7.29, 4.99, 0.66 Hz, 1H), 5.44 (dd, J=5.81, 3.18 Hz, 1H), 3.28-3.05 (m, 3H), 3.02-2.89 (m, 1H), 2.23 (dddd, J=13.76, 9.92, 5.92, 3.73 Hz, 1H), 1.93 (dt, J=13.81, 7.13 Hz, 1H).

Example 258

Synthesis of (4S)—N7, N7-dimethyl-N5-(pyridin-2-yl)-3, 4-dihydro-1,4-methanopyrido [2, 3-b] [1, 4] diazepine-5, 7(2H)-dicarboxamide

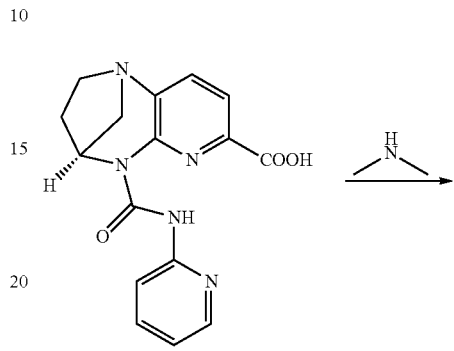

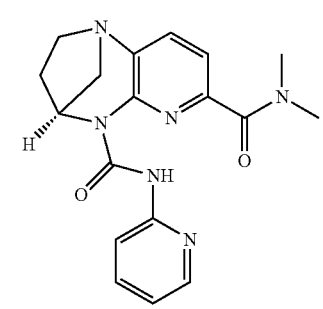

To a stirred solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) in DMF (15 mL) were added HATU (701 mg, 1.844 mmol) and DIPEA (0.322 mL, 1.844 mmol) at room temperature and stirred for 1 h. Then dimethyl amine (62.4 mg, 1.383 mmol) was added to the reaction mixture and stirred at RT for 16 h. (TLC eluent: 20% Methanol in ethyl acetate: R$_f$—0.6; UV active). Reaction mixture was diluted with ice water, extracted with ethyl acetate (2×30 mL). The combined organic layer was washed with brine solution (20 mL), dried over anhydrous sodium sulphate, filtered and concentrated to get crude compound. The crude compound was purified by flash column chromatography (100-200 silicagel eluted with 2% of Methanol in DCM) to afford the desired compound (4S)—N7,N7-dimethyl-N5-(pyridin-2-yl)-3,4-dihydro-1,4-methanopyrido[2,3-b][1,4]diazepine-5,7(2H)-dicarboxamide (130 mg, 0.362 mmol, 39.2% yield) as an off white solid. LCMS (m/z): 353.18 [M+H]$^+$, R$_t$=1.36 min.

$^1$H NMR (400 MHz, CDCl$_3$): δ ppm 12.93 (s, 1H), 8.32-8.21 (m, 1H), 8.14 (d, J=8.33 Hz, 1H), 7.71-7.62 (m, 1H), 7.59 (d, J=7.89 Hz, 1H), 7.31 (d, J=7.89 Hz, 1H), 6.97 (ddd, J=7.29, 4.88, 0.99 Hz, 1H), 5.67 (dd, J=6.03, 3.18 Hz, 1H), 3.27-3.10 (m, 9H), 3.00 (dd, J=12.06, 3.29 Hz, 1H), 2.31 (dddd, J=14.09, 9.98, 5.97, 3.95 Hz, 1H), 2.07-1.98 (m, 1H)

Example 259

Synthesis (4S)—N5-(4-(dimethylcarbamoyl)pyridin-2-yl)-N7-(2,2,2-trifluoroethyl)-3,4-dihydro-1,4-methanopyrido[2,3-b][1,4]diazepine-5,7(2H)-dicarboxamide

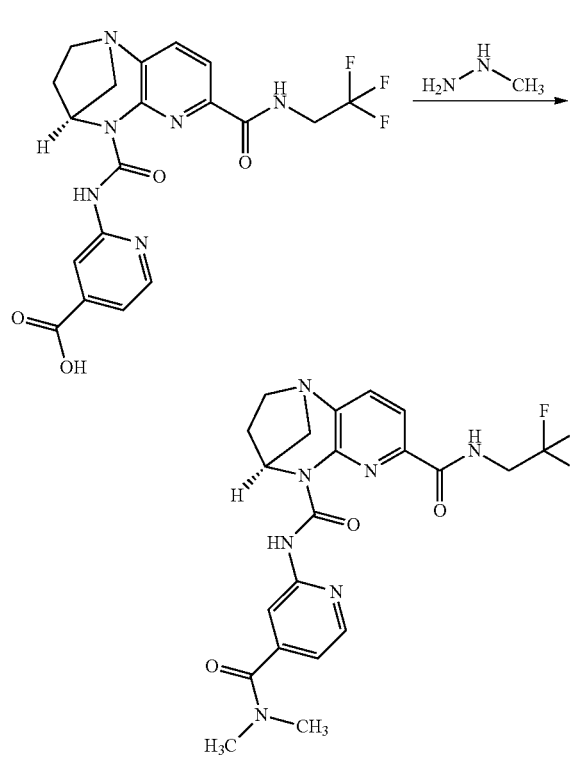

Example 260

Synthesis of (4S)—N7-(2,2-difluorocyclopropyl)-N5-(5-((R)-2,3-dihydroxypropoxy)pyrazin-2-yl)-3,4-dihydro-1,4-methanopyrido[2,3-b][1,4]diazepine-5,7(2H)-dicarboxamide

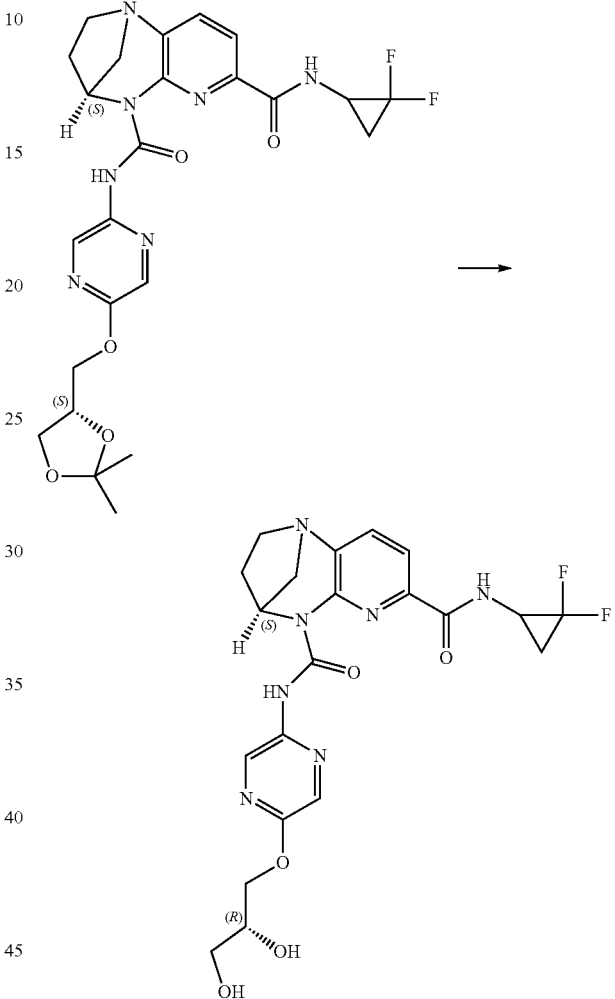

To a stirred solution of 2-((4S)-7-((2,2,2-trifluoroethyl)carbamoyl)-2,3,4,5-tetrahydro-1,4-methanopyrido[2,3-b][1,4]diazepine-5-carboxamido)isonicotinic acid (400 mg, 0.888 mmol) in DMF (8 mL) under nitrogen at 0° C., was added HATU (338 mg, 0.888 mmol) followed by TEA (0.124 mL, 0.888 mmol) and stirred for 30 min. then added dimethylamine (40.0 mg, 0.888 mmol) and the reaction was stirred for 16 h. (TLC system: 5% Methanol in DCM. $R_f$ value: 0.4). Water (20 mL) was added to the reaction mixture and aqueous layer was extracted with EtOAc (2×20 mL). Combined organic layer was dried over anhydrous $Na_2SO_4$, filtered and concentrated under reduced pressure to obtain crude product. Crude compound was purified by combiflash chromatography (Silicagel, eluent 2% MeOH in DCM) to afford desired product (4S)—N5-(4-(dimethylcarbamoyl)pyridin-2-yl)-N7-(2,2,2-trifluoroethyl)-3,4-dihydro-1,4-methanopyrido[2,3-b][1,4]diazepine-5,7(2H)-dicarboxamide (200 mg, 0.414 mmol, 46.6% yield) as an off-white solid. LC-MS (m/z): 478.20 [M+H]$^+$. Rt=1.85 min.

$^1$H NMR (400 MHz, CDCl$_3$): δ ppm 13.73 (s, 1H), 8.44 (br t, J=6.25 Hz, 1H), 8.29 (d, J=4.82 Hz, 1H), 8.12 (s, 1H), 7.93 (d, J=7.89 Hz, 1H), 7.69 (d, J=7.89 Hz, 1H), 7.04 (dd, J=5.04, 1.10 Hz, 1H), 5.60 (dd, J=5.81, 2.96 Hz, 1H), 4.10-4.32 (m, 2H), 3.09-3.28 (m, 6H), 2.91-3.09 (m, 4H), 2.20-2.42 (m, 1H), 1.93-2.18 (m, 1H).

To a stirred solution of (4S)—N7-(2,2-difluorocyclopropyl)-N5-(5-(((S)-2,2-dimethyl-1,3-dioxolan-4-yl)methoxy)pyrazin-2-yl)-3,4-dihydro-1,4-methanopyrido[2,3-b][1,4]diazepine-5,7(2H)-dicarboxamide (200 mg, 0.376 mmol) in Methanol (5 mL) was added hydrochloric acid (0.023 mL, 0.753 mmol) dropwise at 0° C. over a period of 5 min. Then the reaction mixture was stirred at RT for 2 h. (TLC eluent: 5% MeOH in DCM: $R_f$—0.1; UV active) and evaporated the solvent. The obtained residue was neutralized with sodium bicarbonate solution, filtered the obtain solid and triturated with the mixture (1:1) of diethyl ether (20 ml) and n-pentane (20 ml) to afford the desired product (4S)—N7-(2,2-difluorocyclopropyl)-N5-(5-((R)-2,3-dihydroxypropoxy)pyrazin-2-yl)-3,4-dihydro-1,4-methanopyrido[2,3-b][1,4]diazepine-5,7(2H)-dicarboxamide (125 mg, 0.252 mmol, 67.0% yield) as an off white solid. LCMS (m/z): 492.24 [M+H]$^+$, $R_t$=1.56 min.

$^1$H NMR (400 MHz, CDCl$_3$): δ 13.19 (s, 1H), 8.94 (d, J=1.5 Hz, 1H), 7.98 (d, J=1.5 Hz, 1H), 7.90 (d, J=7.9 Hz,

1H), 7.78 (s, 1H), 7.68 (d, J=7.9 Hz, 1H), 5.63 (dd, J=6.0, 3.1 Hz, 1H), 4.53-4.39 (m, 2H), 4.11 (d, J=5.6 Hz, 1H), 3.79 (q, J=5.6, 4.7 Hz, 2H), 3.72 (q, J=6.2, 5.6 Hz, 1H), 3.56 (d, J=7.7 Hz, 2H), 3.24 (s, 2H), 3.29-3.16 (m, 1H), 3.11 (d, J=12.6 Hz, 2H), 2.34 (td, J=9.2, 4.5 Hz, 2H), 1.66 (ddt, J=14.2, 8.9, 5.8 Hz, 1H).

Example 261

Synthesis of (4S)-9-hydroxy-N5-(pyridin-2-yl)-N7-(2,2,2-trifluoroethyl)-3,4-dihydro-1,4-methanopyrido[2,3-b][1,4]diazepine-5,7(2H)-dicarboxamide

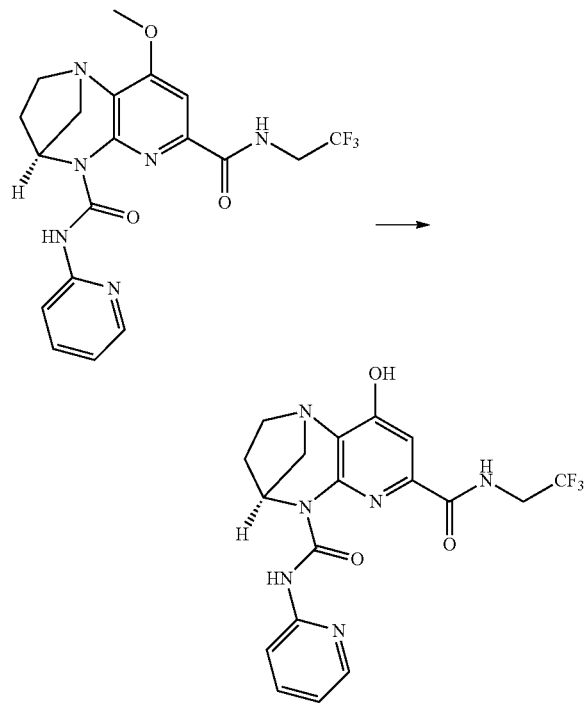

To a stirred solution of (4S)-9-methoxy-N5-(pyridin-2-yl)-N7-(2,2,2-trifluoroethyl)-3,4-dihydro-1,4-methanopyrido[2,3-b][1,4]diazepine-5,7(2H)-dicarboxamide (200 mg, 0.458 mmol) in Chloroform (15 mL) was added BBr₃ (0.260 mL, 2.75 mmol) under nitrogen at −75° C. The reaction mixture was stirred at 60° C. for 16 h. (TLC eluent: 5% Methanol in DCM. Rf: 0.2; UV active). The reaction mixture was cooled to 10° C., quenched with NaHCO₃ solution and extracted with 10% Methanol in DCM (2×20 mL). The combined organic layer was dried over anhydrous Na₂SO₄, filtered and concentrated to obtain crude compound. The crude compound was purified by flash column chromatography (using neutral alumina eluted at 2% MeOH in DCM) to afford the desired compound (4S)-9-hydroxy-N5-(pyridin-2-yl)-N7-(2,2,2-trifluoroethyl)-3,4-dihydro-1,4-methanopyrido[2,3-b][1,4]diazepine-5,7(2H)-dicarboxamide (50 mg, 0.114 mmol, 24.85% yield) as an off white solid. LCMS (m/z): 423.12[M+H]⁺, R$_t$=1.96.

¹H NMR (400 MHz, CDCl₃): δ 13.65 (s, 1H), 8.51 (s, 1H), 8.22 (d, J=4.9 Hz, 1H), 8.06 (d, J=8.3 Hz, 1H), 7.72 (t, J=7.9 Hz, 1H), 7.58 (s, 1H), 7.00 (t, J=6.1 Hz, 1H), 5.64 (d, J=5.8 Hz, 1H), 4.20 (q, J=8.3 Hz, 2H), 3.18 (t, J=7.5 Hz, 2H), 3.13-2.99 (m, 2H), 2.37 (dd, J=13.9, 7.1 Hz, 1H), 2.11 (dt, J=14.7, 7.8 Hz, 1H).

Example 262

Peak-II: Synthesis of (4S)—N7-(2,2-difluorocyclopropyl)-N5-(4-(2-hydroxyethoxy)pyridin-2-yl)-3,4-dihydro-1,4-methanopyrido[2,3-b][1,4]diazepine-5,7(2H)-dicarboxamide

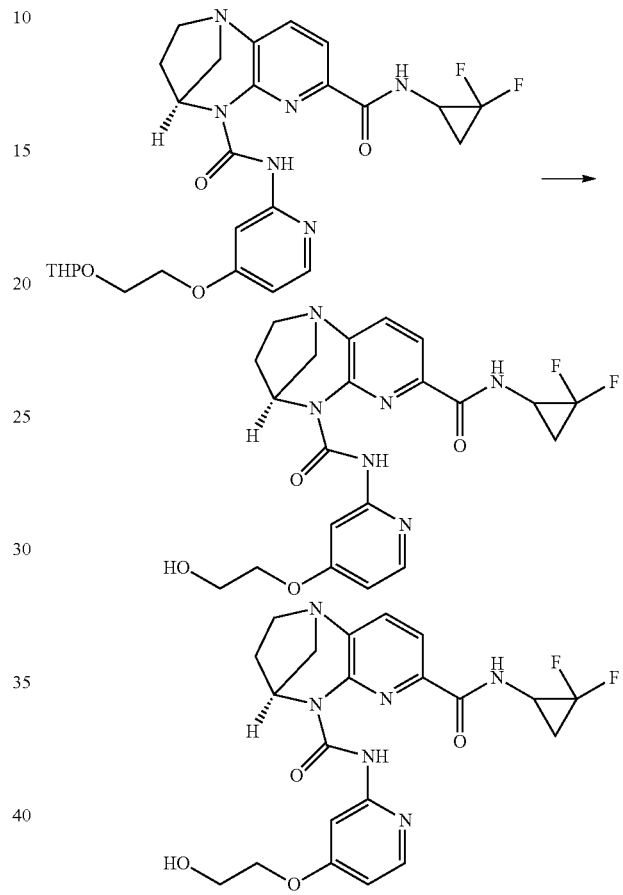

To a stirred solution of (4S)—N7-(2,2-difluorocyclopropyl)-N5-(4-(2-((tetrahydro-2H-pyran-2-yl)oxy)ethoxy)pyridin-2-yl)-3,4-dihydro-1,4-methanopyrido[2,3-b][1,4]diazepine-5,7(2H)-dicarboxamide (550 mg, 1.010 mmol) in THF (10 mL) was added HCl (2.0 mL, 24.00 mmol) at RT. The resulting reaction mixture was stirred at RT for 2 h. (TLC eluent: Neat ethyl acetate, R$_f$—0.3, UV active). THF was concentrated under reduced pressure to obtain the residue, which was basified with saturated sodium bicarbonate solution (30 mL), extracted with DCM (3×30 mL). The combined organic layer was washed with brine solution (20 mL) and dried over anhydrous Na₂SO₄, filtered and concentrated under reduced pressure to obtain crude compound. The crude compound was triturated with 1:3 of diethyl ether and pentane to obtain racemic mixture (380 mg). The racemic mixture was separated by Chiral SFC (SFC Conditions: Column/dimensions: Column/dimensions: (R, R)Whelk-01 (250×30) mm, 5μ, % CO2: 55.0%, % Co solvent: 45.0% (100% Methanol), Total Flow: 100.0 g/min, Back Pressure: 100.0 bar, UV: 267 nm, Stack time: 11.0 min, Load/Inj: 6.5 mg, Solubility: Methanol, Total No of injections: 50, Instrument details: Make/Model: Thar SFC-200-005) as peak-I and peak-II. Peak-II: (4S)—N7-(2,2-difluorocyclopropyl)-N5-(4-(2-hydroxyethoxy)pyridin-2-yl)-3,4-dihydro-1,4-methanopyrido[2,3-b][1,4]diazepine-5,7(2H)-dicarboxamide (47 mg, 0.097 mmol, 9.65% yield) as an off white solid. LCMS (m/z): 461.24[M+H]⁺, $R_t$=1.41 min.

¹H NMR (400 MHz, CDCl₃): δ ppm 13.45 (s, 1H), 8.29 (br s, 1H), 8.07 (d, J=5.92 Hz, 1H), 7.91 (d, J=7.89 Hz, 1H), 7.74 (d, J=2.19 Hz, 1H), 7.66 (d, J=7.89 Hz, 1H), 6.61 (dd, J=5.81, 2.30 Hz, 1H), 5.60 (dd, J=5.81, 3.18 Hz, 1H), 4.31-4.10 (m, 2H), 4.00 (br s, 2H), 3.67-3.40 (m, 1H), 3.38-3.17 (m, 3H), 3.02 (dd, J=12.28, 3.29 Hz, 1H), 2.53-2.24 (m, 1H), 2.17-2.00 (m, 3H), 2.00-1.85 (m, 1H)

Example 263

Peak-I: (4S)—N7-(2,2-difluorocyclopropyl)-N5-(4-(2-hydroxyethoxy)pyridin-2-yl)-3,4-dihydro-1,4-methanopyrido[2,3-b][1,4]diazepine-5,7(2H)-dicarboxamide

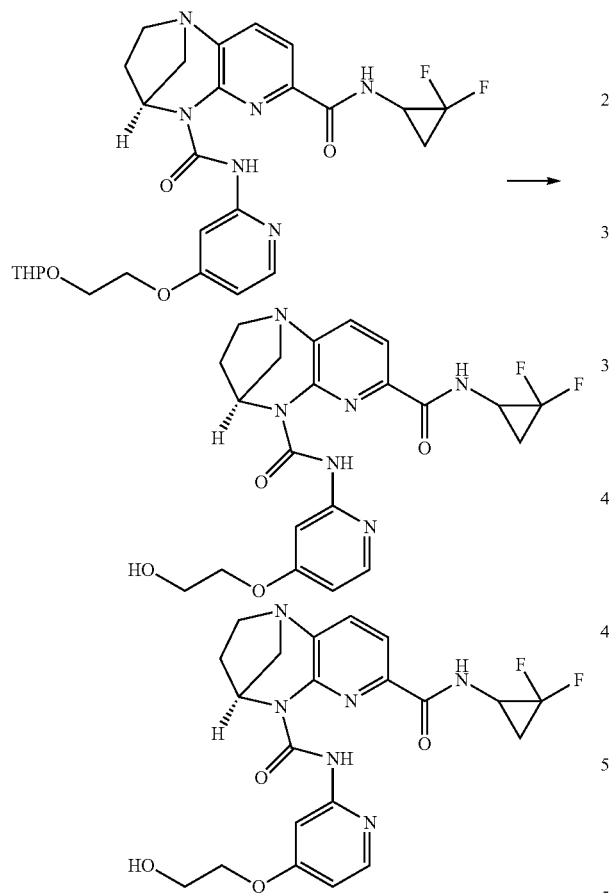

To a stirred solution of (4S)—N7-(2,2-difluorocyclopropyl)-N5-(4-(2-((tetrahydro-2H-pyran-2-yl)oxy)ethoxy)pyridin-2-yl)-3,4-dihydro-1,4-methanopyrido[2,3-b][1,4]diazepine-5,7(2H)-dicarboxamide (550 mg, 1.010 mmol) in THF (10 mL) was added HCl (2.0 mL, 24.00 mmol) at RT. The resulting reaction mixture was stirred at RT for 2 h. (TLC eluent: Neat ethyl acetate, $R_f$=0.3, UV active). THF was concentrated under reduced pressure to obtain the residue, which was basified with saturated sodium bicarbonate solution (30 mL), extracted with DCM (3×30 mL). The combined organic layer was washed with brine solution (20 mL) and dried over anhydrous Na₂SO₄, filtered and concentrated under reduced pressure to obtain crude compound. The crude compound was triturated with 1:3 of diethyl ether and pentane to obtain racemic mixture (380 mg). The racemic mixture was separated by Chiral SFC (SFC Conditions: Column/dimensions: Column/dimensions: (R, R)Whelk-01 (250×30) mm, 5μ, % CO2: 55.0%, % Co solvent: 45.0% (100% Methanol), Total Flow: 100.0 g/min, Back Pressure: 100.0 bar, UV: 267 nm, Stack time: 11.0 min, Load/Inj: 6.5 mg, Solubility: Methanol, Total No of injections: 50, Instrument details: Make/Model: Thar SFC-200-005) as peak-I and peak-II. Peak-I: (4S)—N7-(2,2-difluorocyclopropyl)-N5-(4-(2-hydroxyethoxy)pyridin-2-yl)-3,4-dihydro-1,4-methanopyrido[2,3-b][1,4]diazepine-5,7(2H)-dicarboxamide (51 mg, 0.109 mmol, 10.78% yield) as an off white solid. LCMS (m/z): 461.24 [M+H]⁺, $R_t$=1.41 min.

¹H NMR (400 MHz, CDCl₃): δ ppm 13.43 (s, 1H), 8.30 (br s, 1H), 8.07 (d, J=5.70 Hz, 1H), 7.90 (d, J=7.89 Hz, 1H), 7.74 (d, J=2.41 Hz, 1H), 7.66 (d, J=7.89 Hz, 1H), 6.61 (dd, J=5.92, 2.41 Hz, 1H), 5.59 (dd, J=6.03, 2.96 Hz, 1H), 4.23-4.18 (m, 2H), 4.03-3.97 (m, 2H), 3.52 (d, J=6.80 Hz, 1H), 3.27-3.18 (m, 3H), 3.00 (d, J=3.07 Hz, 1H), 2.37-2.27 (m, 1H), 2.09-1.90 (m, 3H), 1.81-1.72 (m, 1H).

Example 264

Synthesis of (4S)—N5-(4-(((S)-tetrahydrofuran-3-yl)carbamoyl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

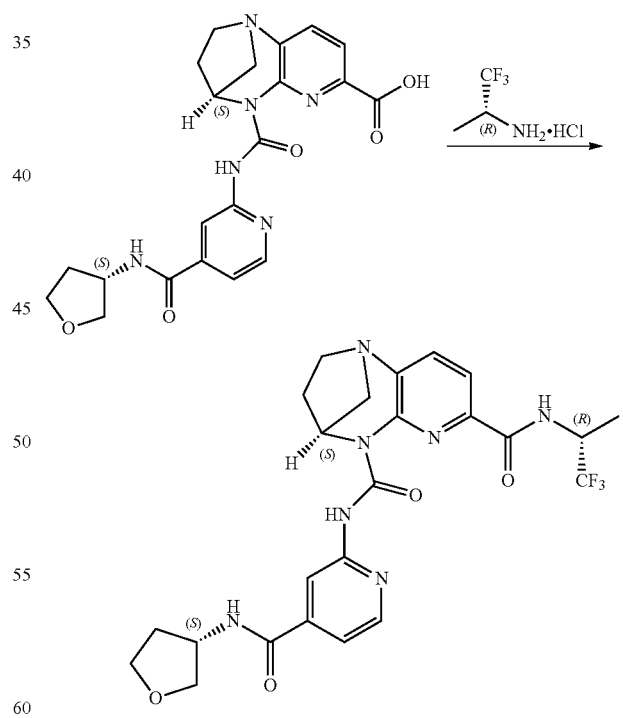

To a stirred suspension of (4S)-5-((4-(((S)-tetrahydrofuran-3-yl)carbamoyl)pyridin-2-yl)carbamoyl)-2,3,4,5-tetrahydro-1,4-methanopyrido[2,3-b][1,4]diazepine-7-carboxylic acid (390 mg, 0.890 mmol) in DMF (15 mL) were added HATU (676 mg, 1.779 mmol) and DIPEA (0.466 mL, 2.67 mmol) at RT. After 2 min (R)-1,1,1-trifluoropropan-2-amine hydrochloride (160 mg, 1.067 mmol) was added. The resulting reaction mixture was stirred at RT for 16 h. (TLC eluent: 10% methanol in DCM, $R_f$—0.2; UV active). DMF was concentrated under vacuum and diluted with ice cold water, extracted with ethyl acetate (3×25 mL). The combined organic layer was washed with brine solution (25 mL) and dried over anhydrous sodium sulphate, filtered and concentrated under reduced pressure to get crude compound. The crude compound was purified by flash column chromatography (60-120 silica gel, eluted at neat ethyl acetate) obtained gummy solid, which was with 87% purity. Further purified by reverse phase combi flash (12 g silica gel column, eluted at 35% water in MeOH) to afford pure compound (4S)—N5-(4-(((S)-tetrahydrofuran-3-yl)carbamoyl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (101 mg, 0.187 mmol, 21.06% yield) as an off white solid. LCMS (m/z): 534.25 [M+H]$^+$, $R_t$=1.95 min.

$^1$H NMR (400 MHz, CDCl$_3$): δ ppm 13.44 (s, 1H), 8.41-8.33 (m, 2H), 7.98 (d, J=7.89 Hz, 1H), 7.90 (d, J=9.87 Hz, 1H), 7.70 (d, J=7.89 Hz, 1H), 7.47 (dd, J=5.26, 1.53 Hz, 1H), 6.51 (d, J=7.02 Hz, 1H), 5.63 (dd, J=5.81, 3.18 Hz, 1H), 5.15-4.98 (m, 1H), 4.79-4.67 (m, 1H), 4.08-3.98 (m, 1H), 3.93 (dd, J=9.65, 5.48 Hz, 1H), 3.88-3.78 (m, 2H), 3.34-3.18 (m, 2H), 3.18-3.08 (m, 1H), 3.08-2.99 (m, 1H), 2.48-2.28 (m, 2H), 2.16-1.90 (m, 2H), 1.59 (d, J=7.23 Hz, 3H).

Example 265

Synthesis of 2-((2-((4S)-7-(((R)-1,1,1-trifluoropropan-2-yl)carbamoyl)-2,3,4,5-tetrahydro-1,4-methanopyrido[2,3-b][1,4]diazepine-5-carboxamido)pyridin-4-yl)oxy)acetic acid

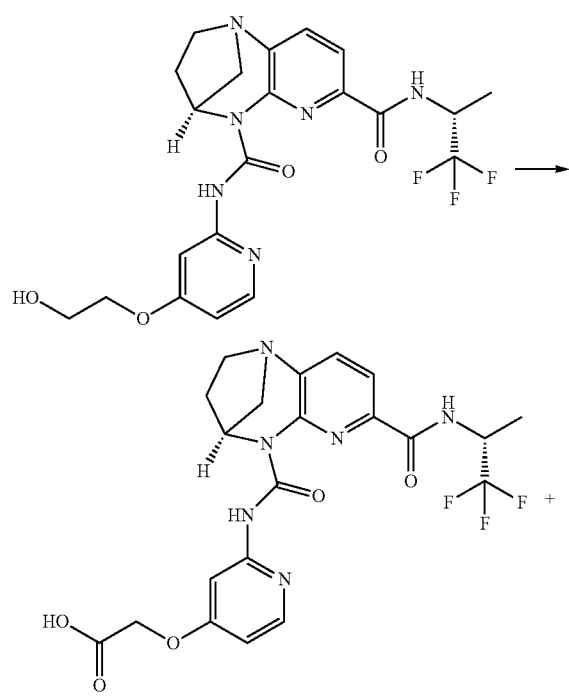

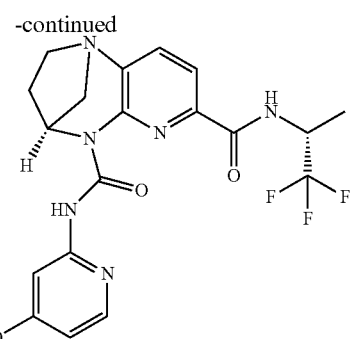

To a stirred solution of (4S)—N5-(4-(2-hydroxyethoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (1 g, 2.081 mmol) in Acetone (25 mL) was added 4 mL of freshly prepared Jones reagent and stirred for 16 h. at RT. (TLC eluent: 10% MeOH in DCM: $R_f$—0.1 (polar compound), $R_f$—0.3 (non-polar compound); UV active). Evaporated the acetone and basified the obtain residue with saturated sodium bicarbonate solution and extracted with 10% MeOH in DCM (3×30 mL). The combined organic layer was washed with brine solution (30 mL), dried over anhydrous Na$_2$SO$_4$, filtered and evaporated under reduced pressure to obtain crude compound. The crude was purified by Prep-HPLC (Prep HPLC conditions: MP-A: 10 mM Ammonium bicarbonate (aq) MP-B: Acetonitrile Column: Kromasil (250*21.2 mm) 10p Method % of 0.01/38, 2.5/38, 8/80, 8.5/100, 13/100, 13.2/38, Solubility: THF+Acetonitrile+Methonal Flow: 20 ml/min, Temperature: Ambient) and isolated two compounds. Polar compound (N38152-41-A2) 2-((2-((4S)-7-(((R)-1,1,1-trifluoropropan-2-yl)carbamoyl)-2,3,4,5-tetrahydro-1,4-methanopyrido[2,3-b][1,4]diazepine-5-carboxamido)pyridin-4-yl)oxy)acetic acid (117 mg, 0.233 mmol, 11.20% yield) as an off white solid. LCMS (m/z): 495.19 [M+H]$^+$; $R_t$=1.67 min.

$^1$H NMR (400 MHz, DMSO-d$_6$): δ 12.98 (s, 1H), 8.18 (d, J=9.2 Hz, 1H), 7.97 (d, J=5.8 Hz, 1H), 7.75 (d, J=1.2 Hz, 2H), 7.53 (d, J=2.3 Hz, 1H), 6.56 (dd, J=5.9, 2.4 Hz, 1H), 5.46 (dd, J=6.1, 3.0 Hz, 1H), 4.97 (m, J=15.2, 7.6 Hz, 1H), 4.18 (s, 2H), 3.23-3.02 (m, 3H), 2.96 (dd, J=12.0, 3.3 Hz, 1H), 2.29-2.16 (m, 1H), 1.95 (dt, J=14.6, 7.9 Hz, 1H), 1.52 (d, J=7.1 Hz, 3H).

Example 266

Synthesis of (4S)—N5-(4-(3-hydroxypropoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

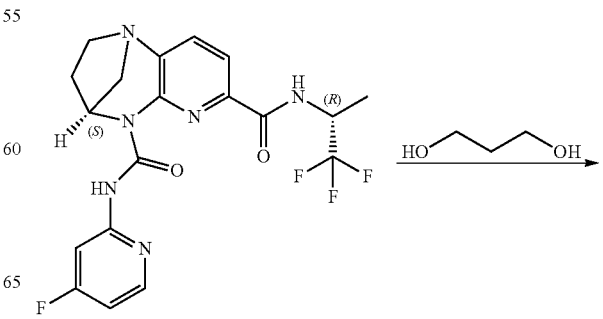

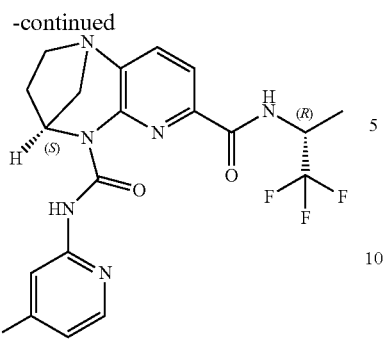

To a stirred solution of sodium 3-hydroxypropan-1-olate [it was prepared by in situ added (697 mg, 29.0) NaH to stirred solution of 1,3-dihydroxy propanol (1.1 g, 14.46 mmol) in THF (10 mL) at 0° C.] was added (4S)—N5-(4-fluoropyridin-2-yl)-N7-((R)-1,1,1-trifluoropropan-2-yl)-3,4-dihydro-1,4-methanopyrido[2,3-b][1,4]diazepine-5,7(2H)-dicarboxamide (640 mg, 1.460 mmol) at 0° C. then stirred at 70° C. for 3 days in sealed tube (TLC eluent: Neat ethyl acetate: $R_f$: 0.2; UV active). The reaction mixture was cooled to RT then quenched with cold ammonium chloride solution (20 mL) and extracted with ethyl acetate (20 mL), dried over anhydrous $Na_2SO_4$, filtered and filtrate was evaporated to get crude compound. The crude compound was purified by flash column chromatography (using 100-200 silicagel, column eluted at 50% ethyl acetate in n-hexane) to afford the desired compound (4S)—N5-(4-(3-hydroxypropoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (65 mg, 0.129 mmol, 8.82% yield) as an off white solid. LCMS (m/z): 495.22 [M+H]$^+$; $R_t$=1.69 min.

$^1$H NMR (400 MHz, CDCl$_3$): δ 13.26 (s, 1H), 8.06 (dd, J=15.0, 7.7 Hz, 3H), 7.95 (dd, J=7.9, 0.9 Hz, 1H), 7.77 (d, J=2.3 Hz, 1H), 7.67 (dd, J=7.9, 0.9 Hz, 1H), 6.57 (dd, J=5.9, 2.4 Hz, 1H), 5.62 (dd, J=6.1, 3.1 Hz, 1H), 5.06 (dq, J=15.6, 7.5 Hz, 1H), 4.25 (t, J=6.0 Hz, 2H), 3.87 (t, J=6.0 Hz, 2H), 3.28-3.18 (m, 3H), 3.02 (dd, J=12.2, 3.2 Hz, 1H), 2.33 (ddt, J=14.5, 10.2, 5.4 Hz, 1H), 2.08 (p, J=6.1 Hz, 3H), 1.59 (d, J=7.1 Hz, 3H).

Example 267

Synthesis 2-((4S)-7-((2,2,2-trifluoroethyl)carbamoyl)-2,3,4,5-tetrahydro-1,4-methanopyrido[2,3-b][1,4]diazepine-5-carboxamido)isonicotinic acid

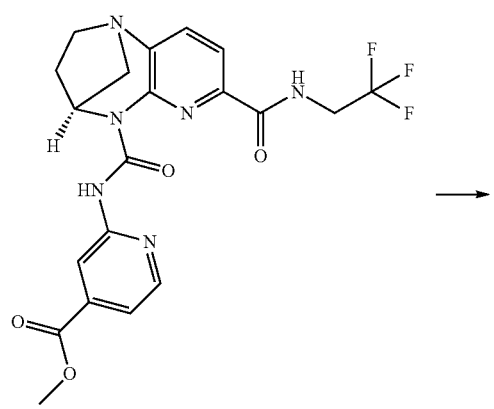

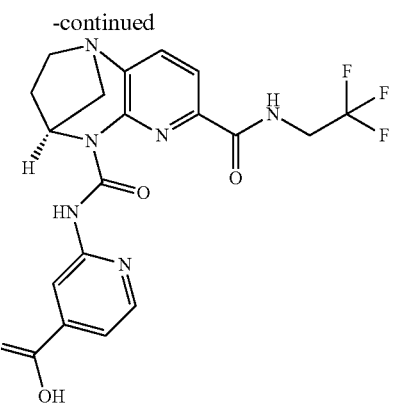

To a stirred solution of methyl 2-((4S)-7-((2,2,2-trifluoroethyl)carbamoyl)-2,3,4,5-tetrahydro-1,4-methanopyrido[2,3-b][1,4]diazepine-5-carboxamido)isonicotinate (1.5 g, 3.23 mmol) in THF (15 mL) and Water (5 mL) at RT, was added LiOH (0.232 g, 9.69 mmol) and stirred for 16 h. (TLC system: 5% Methanol in DCM. $R_f$ value: 0.1). Reaction mixture was concentrated and acidified with aq. HCl. Resultant solid was filtered and the solid was purified by preparative HPLC (Column: kinetex C 8 (150×30) mm, 5 um; Mobile phase A: 10 Mm ammonium bicarbonate (aq) Mobile phase B: Acetonitrile; Isocratic: 65:35 (A:B); Flow: 30 mL/min; Solubility: acetonitrile+MeOH+THF+water+formic acid). Fraction containing pure compound was evapourated under reduce pressure followed by lypholyzation afforded 2-((4S)-7-((2,2,2-trifluoroethyl)carbamoyl)-2,3,4,5-tetrahydro-1,4-methanopyrido[2,3-b][1,4]diazepine-5-carboxamido)isonicotinic acid (110 mg, 0.243 mmol, 7.52% yield) as an off-white solid. LC-MS (m/z): 451.09 [M+H]$^+$, Rt=1.85 min.

$^1$H NMR (400 MHz, DMSO-d$_6$): δ ppm 14.45-13.50 (br, 1H), 13.45 (s, 2H), 8.65 (br t, J=6.47 Hz, 1H), 8.40-8.56 (m, 2H), 7.65-7.84 (m, 2H), 7.54 (br d, J=4.82 Hz, 1H), 5.44 (dd, J=5.70, 2.85 Hz, 1H), 4.12-4.38 (m, 2H), 3.06-3.26 (m, 3H), 2.78-3.05 (m, 1H), 2.19-2.47 (m, 1H), 1.96 (dt, J=13.98, 7.15 Hz, 1H)

Example 268

Synthesis of (4S)—N5-(4-(2-(dimethylamino)ethoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

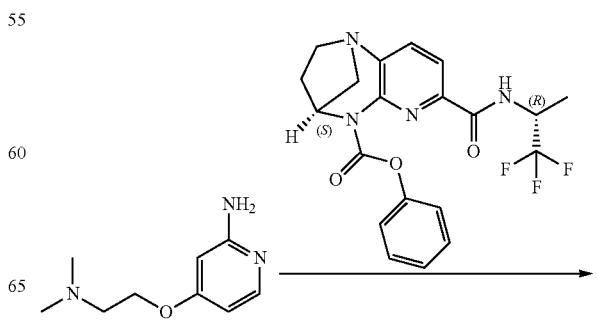

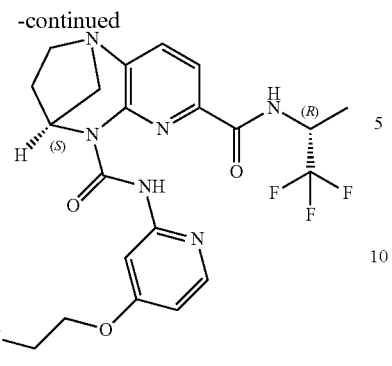

To a stirred solution of 4-(2-(dimethylamino)ethoxy)pyridin-2-amine (400 mg, 2.207 mmol) in THF (10 mL) was added 1.0 M LiHMDS (4.41 mL, 4.41 mmol) in THF at −78° C. under Nitrogen atmosphere. The resulting reaction mixture was stirred at −78° C. for 30 min. To the reaction mixture was added a solution of (4S)-phenyl 7-(((R)-1,1,1-trifluoropropan-2-yl)carbamoyl)-3,4-dihydro-1,4-methanopyrido[2,3-b][1,4]diazepine-5(2H)-carboxylate (928 mg, 2.207 mmol) in Tetrahydrofuran (20 mL) at −78° C. The resulting reaction mixture was warmed to room temperature and stirred for 6 h. (TLC system: 5% MeOH in DCM, Rf: 0.4) and quenched with saturated ammonium chloride solution (40 mL), extracted with EtOAc (3×30 mL). The combined organic layer was washed with water (20 mL), brine solution (20 mL), dried over anhydrous $Na_2SO_4$, filtered and filtrate was concentrated under reduced pressure to afford crude compound. The crude was purified by flash column chromatography (silica gel: 100-200 mesh, Eluent: 4% MeOH in DCM) and obtained pale yellow semi solid was washed with n-pentane (10 mL) to afford the desired product (4S)—N5-(4-(2-(dimethylamino)ethoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (280 mg, 0.548 mmol, 24.81% yield) as an off-white solid. LCMS (m/z): 508.18 [M+H]$^+$, $R_t$=1.45 min.

1H NMR (400 MHz, CDCl$_3$): ppm 13.27 (s, 1H), 8.13-8.00 (m, 2H), 7.95 (d, J=7.89 Hz, 1H), 7.76 (d, J=2.41 Hz, 1H), 7.67 (d, J=7.89 Hz, 1H), 6.62 (dd, J=5.81, 2.30 Hz, 1H), 5.62 (dd, J=5.81, 3.18 Hz, 1H), 5.12-4.96 (m, 1H), 4.21 (t, J=5.48 Hz, 2H), 3.33-3.17 (m, 2H), 3.12 (d, J=12.06 Hz, 1H), 3.02 (dd, J=12.17, 3.18 Hz, 1H), 2.85 (t, J=5.48 Hz, 2H), 2.43 (s, 6H), 2.40-2.21 (m, 1H), 2.07 (d, J=7.23 Hz, 1H), 1.59 (d, J=7.02 Hz, 3H).

Example 269

Synthesis of (4S)—N5-(5-fluoro-6-methylpyridin-2-yl)-N7-((R)-1,1,1-trifluoropropan-2-yl)-3,4-dihydro-1,4-methanopyrido[2,3-b][1,4]diazepine-5,7(2H)-dicarboxamide

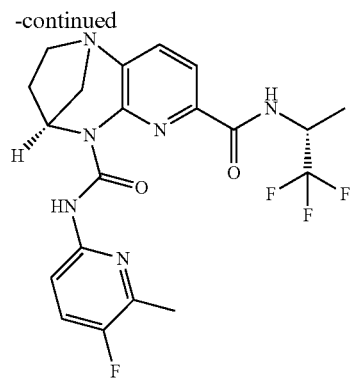

To a stirred solution of 5-fluoro-6-methylpyridin-2-amine (180 mg, 1.427 mmol) in THF (20 mL) under nitrogen at −78° C. added a solution of LiHMDS (2.379 mL, 2.379 mmol, 1 M in THF) dropwisely and stirred at −78° C. for 30 min. then added a solution of (4S)-phenyl 7-(((R)-1,1,1-trifluoropropan-2-yl)carbamoyl)-3,4-dihydro-1,4-methanopyrido[2,3-b][1,4]diazepine-5(2H)-carboxylate (500 mg, 1.189 mmol) in THF (5.00 mL) and the resulting reaction mixture was stirred at −78° C. for 1 h and at RT for 6 h. (TLC eluent: 5% MeOH in DCM: $R_f$—0.3; UV active). The reaction mixture was quenched with aqueous NH$_4$Cl (10 mL) and aqueous layer was extracted with EtOAc (2×25 mL), combined organic layer was dried over anhydrous $Na_2SO_4$, filtered and concentrated under reduced pressure to obtain crude product. The crude material was purified by column chromatography (Silicagel, eluent 0.5-2.5% MeOH in DCM). Fraction containing pure compound were combined and concentrated to afford (4S)—N5-(5-fluoro-6-methylpyridin-2-yl)-N7-((R)-1,1,1-trifluoropropan-2-yl)-3,4-dihydro-1,4-methanopyrido[2,3-b][1,4]diazepine-5,7 (2H)-dicarboxamide (190 mg, 0.420 mmol, 35.3% yield) as light brown solid. LC-MS (m/z): 453.10 [M+H]$^+$, Rt=2.35 min.

$^1$H NMR (400 MHz, CDCl$_3$): δ ppm 11.88 (s, 1H), 8.03 (dd, J=8.99, 3.51 Hz, 1H), 7.93 (m, J=7.89 Hz, 1H), 7.67 (m, J=7.89 Hz, 1H), 7.27-7.42 (m, 2H), 5.70 (dd, J=5.92, 3.29 Hz, 1H), 4.98 (dq, J=16.88, 7.38 Hz, 1H), 3.05-3.31 (m, 3H), 2.94-3.05 (m, 1H), 2.42 (d, J=2.85 Hz, 3H), 2.20-2.39 (m, 1H), 1.97-2.18 (m, 1H), 1.51-1.60 (m, 3H).

Example 270

Synthesis of (4S)—N7-(2,2-difluorocyclopropyl)-N5-(pyridazin-3-yl)-3,4-dihydro-1,4-methanopyrido[2,3-b][1,4]diazepine-5,7(2H)-dicarboxamide

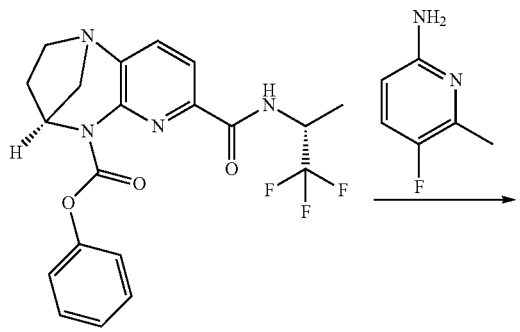

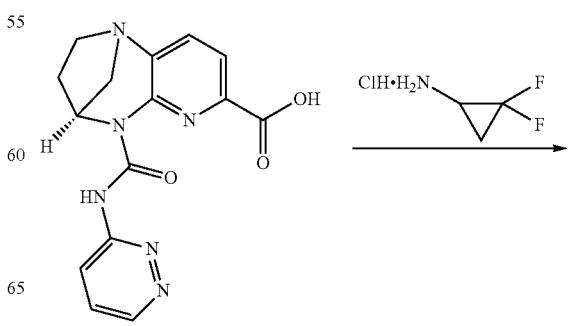

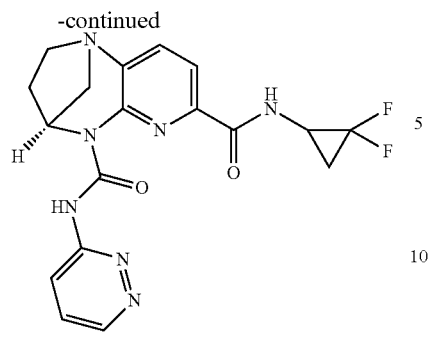

Isomer 2

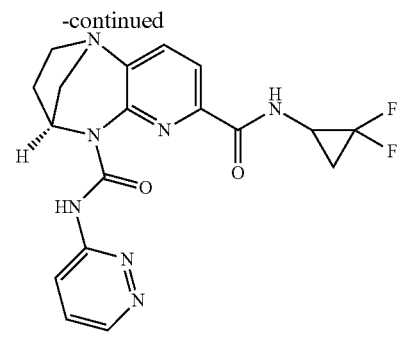

Isomer 1

To a stirred solution of (4S)-5-(pyridazin-3-ylcarbamoyl)-2,3,4,5-tetrahydro-1,4-methanopyrido[2,3-b][1,4]diazepine-7-carboxylic acid (1.15 g, 3.52 m mol) in DMF (15 mL) under argon, at 0° C. was added HATU (2.010 g, 5.29 m mol) followed by DIPEA (3.08 mL, 17.62 mmol) and stirred for 20 min. then added 2,2-difluorocyclopropanamine hydrochloride (0.878 g, 5.29 mmol) and reaction mixture was stirred at RT for 5 h. (TLC System: Rf—0.6, EtOAc). The reaction mixture was partitioned between water (80 mL) and EtOAc (2×150 mL) and organic layer separated, dried over anhydrous $Na_2SO_4$, filtered and filtrate was evaporated to get crude compound. The crude was purified by chromatography (GRACE instrument, C-18 reserval column, Mobile phase A: 0.1% Formic Acid in water; B: Acetonitrile, the product was eluted at 35-40% B in A) to afford desired compound (650 mg) as diastereomeric mixture. The diastereomers were separated by chiral SFC (Chiralpak IC (250× 30) mm, 5μ; % CO2: 55.0; % Co-solvent [100% MeOH]: 45; Total Flow: 100 g/min; Back Pressure: 100 bar; UV: 260 nm; Stack time: 8.5 min; Load/Inj: 17.5 mg; Solubility: MeOH+ DCM; Total No. of Injections: 40; Instrument: Thar SFC-200-005) to give two single isomers. Peak-2: Combined fractions of slowest eluting isomer from chiral SFC were concentrated and triturated with pentane to give (4S)—N7-(2,2-difluorocyclopropyl)-N5-(pyridazin-3-yl)-3,4-dihydro-1,4-methanopyrido[2,3-b][1,4]diazepine-5,7(2H)-dicarboxamide (195 mg, 0.479 mmol, 13.59% yield) as an off white solid. LCMS (m/z) 402.17 $[M+H]^+$. Rt=1.74 min.

$^1$H NMR (400 MHz, $CDCl_3$): δ ppm 14.13 (s, 1H), 8.91 (dd, J=4.71, 1.42 Hz, 1H), 8.38 (dd, J=8.99, 1.53 Hz, 1H), 8.09 (br s, 1H), 7.97 (d, J=7.89 Hz, 1H), 7.70 (d, J=7.89 Hz, 1H), 7.53-7.41 (m, 1H), 5.60 (dd, J=5.81, 3.18 Hz, 1H), 3.75-3.63 (m, 1H), 3.32-3.19 (m, 2H), 3.17-3.10 (m, 1H), 3.07-2.98 (m, 1H), 2.54-2.42 (m, 1H), 2.40-2.28 (m, 1H), 2.13-1.99 (m, 1H), 1.98-1.85 (m, 1H).

Example 271

Synthesis of (4S)—N7-(2,2-difluorocyclopropyl)-N5-(pyridazin-3-yl)-3,4-dihydro-1,4-methanopyrido[2,3-b][1,4]diazepine-5,7(2H)-dicarboxamide

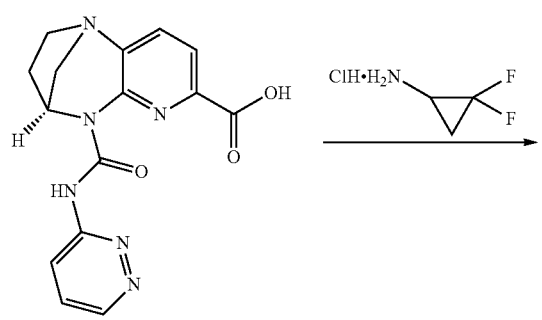

To a stirred solution of (4S)-5-(pyridazin-3-ylcarbamoyl)-2,3,4,5-tetrahydro-1,4-methanopyrido[2,3-b][1,4]diazepine-7-carboxylic acid (1.15 g, 3.52 m mol) in DMF (15 mL) under argon, at 0° C. was added HATU (2.010 g, 5.29 m mol) followed by DIPEA (3.08 mL, 17.62 mmol) and stirred for 20 min. then added 2,2-difluorocyclopropanamine hydrochloride (0.878 g, 5.29 mmol) and reaction mixture was stirred at RT for 5 h. (TLC System: $R_f$—0.6, EtOAc). The reaction mixture was partitioned between water (80 mL) and EtOAc (2×150 mL) and organic layer separated, dried over anhydrous $Na_2SO_4$, filtered and filtrate was evaporated to get crude compound. The crude was purified by chromatography (GRACE instrument, C-18 reserval column, Mobile phase A: 0.1% Formic Acid in water; B: Acetonitrile, the product was eluted at 35-40% B in A) to afford desired compound (650 mg) as diastereomeric mixture. The diastereomers were separated by chiral SFC (Chiralpak IC (250× 30) mm, 5μ; % CO2: 55.0; % Co-solvent [100% MeOH]: 45; Total Flow: 100 g/min; Back Pressure: 100 bar; UV: 260 nm; Stack time: 8.5 min; Load/Inj: 17.5 mg; Solubility: MeOH+ DCM; Total No. of Injections: 40; Instrument: Thar SFC-200-005) to give two single isomers. Peak-1: Combined fractions of fastest eluting isomer from chiral SFC, were concentrated and triturated with pentane to give (4S)—N7-(2,2-difluorocyclopropyl)-N5-(pyridazin-3-yl)-3,4-dihydro-1,4-methanopyrido[2,3-b][1,4]diazepine-5,7(2H)-dicarboxamide (265 mg, 0.657 mmol, 18.63% yield) as an off white solid. LCMS (m/z): 402.17 $[M+H]^+$. Rt=1.74 min.

$^1$H NMR (400 MHz, $CDCl_3$): δ ppm 14.13 (s, 1H), 8.91 (dd, J=4.71, 1.42 Hz, 1H), 8.38 (dd, J=8.99, 1.32 Hz, 1H), 8.09 (br s, 1H), 7.97 (d, J=7.89 Hz, 1H), 7.70 (d, J=7.89 Hz, 1H), 7.55-7.44 (m, 1H), 5.62 (dd, J=5.92, 3.29 Hz, 1H), 3.79-3.66 (m, 1H), 3.34-3.18 (m, 2H), 3.17-3.09 (m, 1H), 3.08-2.98 (m, 1H), 2.53-2.40 (m, 1H), 2.40-2.26 (m, 1H), 2.14-2.01 (m, 1H), 1.97-1.84 (m, 1H).

Example 272

Synthesis of (4S)—N7-(2,2-difluorocyclopropyl)-N5-(pyrazin-2-yl)-3,4-dihydro-1,4-methanopyrido[2,3-b][1,4]diazepine-5,7(2H)-dicarboxamide

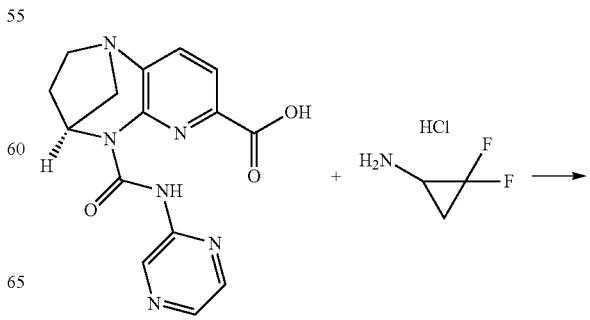

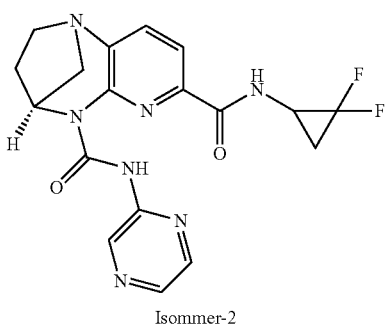

Isommer-2

To a stirred solution of (4S)-5-(pyrazin-2-ylcarbamoyl)-2,3,4,5-tetrahydro-1,4-methanopyrido[2,3-b][1,4]diazepine-7-carboxylic acid (1.1 g, 3.37 mmol) in DMF (15 mL) at 0° C. was added HATU (1.923 g, 5.06 mmol), DIPEA (2.94 mL, 16.86 mmol) and 2,2-difluorocyclopropanamine hydrochloride (0.524 g, 4.05 mmol) and stirred at RT for 4 h. (TLC eluent: 2% MeOH in EtOAc: $R_f$—0.3; UV active). The reaction mixture was diluted with cold water and extracted with DCM (2×50 mL). Organic layer was separated and dried over anhydrous sodium sulphate, filtered and filtrate was evaporated to get crude. The crude was purified by chromatography (GRACE using C-18 reserval column, Mobile phase A: 0.1% Formic Acid in water; B: ACN, eluent 35-40% B in A). Combined fractions were concentrated and basified with saturated aqueous solution of $NaHCO_3$. The aqueous layer was extracted with DCM, DCM layer was dried over anhydrous $Na_2SO_4$, filtered and filtrate was evaporated to afford diastereomeric mixtures of the desired compound. The Diastereomeric mixture was separated by chiral SFC (Chiral cel OJ-H (250×21) mm, 5μ; % CO2: 65.0; % Co-solvent [100% MeOH]: 35; Total Flow: 60 g/min; Back Pressure: 100 bar; UV: 258 nm; Stack time: 2.6 min; Load/Inj: 12.3 mg; Solubility: MeOH; Total No. of Injections: 100; Instrument: Thar SFC-80) to give two single isomers. Isomer-2: Combined fractions of slowest eluting isomer from chiral SFC were concentrated, triturated with pentane to give (4S)—N7-(2,2-difluorocyclopropyl)-N5-(pyrazin-2-yl)-3,4-dihydro-1,4-methanopyrido[2,3-b][1,4]diazepine-5,7(2H)-dicarboxamide (320 mg, 0.770 mmol, 22.85% yield) as an off white solid. LCMS (m/z): 402.14 [M+H]$^+$, $R_t$=2.87 min.

$^1$H NMR (400 MHz, $CDCl_3$): δ ppm 13.45 (s, 1H), 9.50 (d, J=1.53 Hz, 1H), 8.36 (d, J=2.63 Hz, 1H), 8.23 (dd, J=2.41, 1.53 Hz, 1H), 7.82-8.00 (m, 2H), 7.70 (d, J=7.89 Hz, 1H), 5.65 (dd, J=6.03, 3.18 Hz, 1H), 3.49-3.64 (m, 1H), 3.17-3.31 (m, 2H), 3.01-3.15 (m, 2H), 2.28-2.41 (m, 1H), 1.89-2.13 (m, 2H), 1.61-1.76 (m, 1H).

Example 273

Synthesis of (4S)—N7-(2,2-difluorocyclopropyl)-N5-(pyrazin-2-yl)-3,4-dihydro-1,4-methanopyrido[2,3-b][1,4]diazepine-5,7(2H)-dicarboxamide

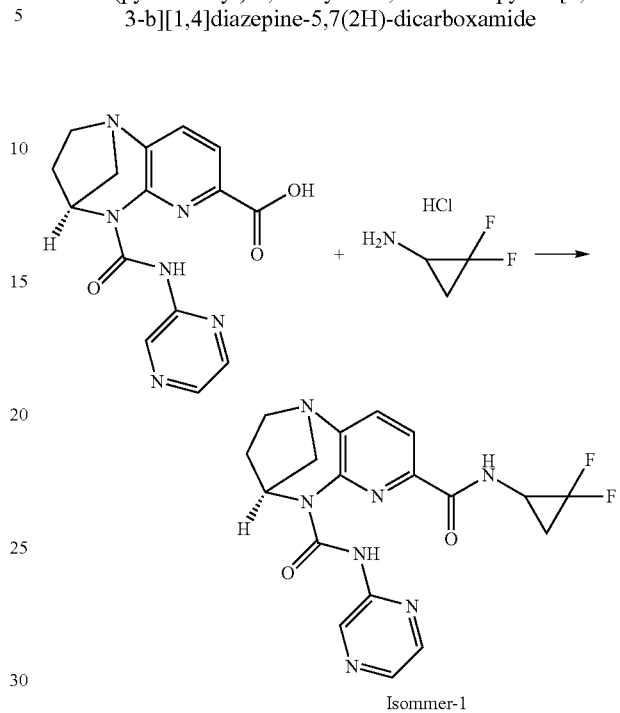

Isommer-1

To a stirred solution of (4S)-5-(pyrazin-2-ylcarbamoyl)-2,3,4,5-tetrahydro-1,4-methanopyrido[2,3-b][1,4]diazepine-7-carboxylic acid (1.1 g, 3.37 mmol) in DMF (15 mL) at 0° C. was added HATU (1.923 g, 5.06 mmol), DIPEA (2.94 mL, 16.86 mmol) and 2,2-difluorocyclopropanamine hydrochloride (0.524 g, 4.05 mmol) and stirred at RT for 4 h. (TLC eluent: 2% MeOH in EtOAc: $R_f$—0.3; UV active). The reaction mixture was diluted with cold water and extracted with DCM (2×50 mL). Organic layer was separated and dried over anhydrous sodium sulphate, filtered and filtrate was evaporated to get crude. The crude was purified by chromatography (GRACE using C-18 reserval column, Mobile phase A: 0.1% Formic Acid in water; B: ACN, eluent 35-40% B in A). Combined fractions were concentrated and basified with saturated aqueous solution of $NaHCO_3$. The aqueous layer was extracted with DCM, DCM layer was dried over anhydrous $Na_2SO_4$, filtered and filtrate was evaporated to afford diastereomeric mixtures of the desired compound. The Diastereomeric mixture was separated by chiral SFC (Chiral cel OJ-H (250×21) mm, 5; % $CO_2$: 65.0; % Co-solvent [100% MeOH]: 35; Total Flow: 60 g/min; Back Pressure: 100 bar; UV: 258 nm; Stack time: 2.6 min; Load/Inj: 12.3 mg; Solubility: MeOH; Total No. of Injections: 100; Instrument: Thar SFC-80) to give two single isomers. Isomer-1: Combined fractions of fastest eluting isomer from chiral SFC were concentrated and triturated with pentane to give (4S)—N7-(2,2-difluorocyclopropyl)-N5-(pyrazin-2-yl)-3,4-dihydro-1,4-methanopyrido[2,3-b][1,4]diazepine-5,7(2H)-dicarboxamide (340 mg, 0.841 mmol, 24.95% yield) as an off white solid. LCMS (m/z): 402.14 [M+H]$^+$, $R_t$=2.87 min.

$^1$H NMR (400 MHz, $CDCl_3$): δ ppm 13.42 (s, 1H), 9.50 (d, J=1.53 Hz, 1H), 8.36 (d, J=2.63 Hz, 1H), 8.23 (dd, J=2.41, 1.53 Hz, 1H), 7.82-8.02 (m, 2H), 7.70 (d, J=7.89 Hz, 1H), 5.65 (dd, J=6.03, 3.18 Hz, 1H), 3.43-3.69 (m, 1H), 3.19-3.31 (m, 2H), 3.10-3.16 (m, 1H), 2.99-3.08 (m, 1H), 2.28-2.41 (m, 1H), 1.89-2.13 (m, 2H), 1.61-1.76 (m, 1H).

Example 274

Peak-I: Synthesis of (4S)—N7-(2,2-difluorocyclopropyl)-N5-(4-methoxypyridin-2-yl)-3,4-dihydro-1,4-methanopyrido[2,3-b][1,4]diazepine-5,7(2H)-dicarboxamide Peak-II: Synthesis of (4S)—N7-(2,2-difluorocyclopropyl)-N5-(4-methoxypyridin-2-yl)-3,4-dihydro-1,4-methanopyrido[2,3-b][1,4]diazepine-5,7(2H)-dicarboxamide

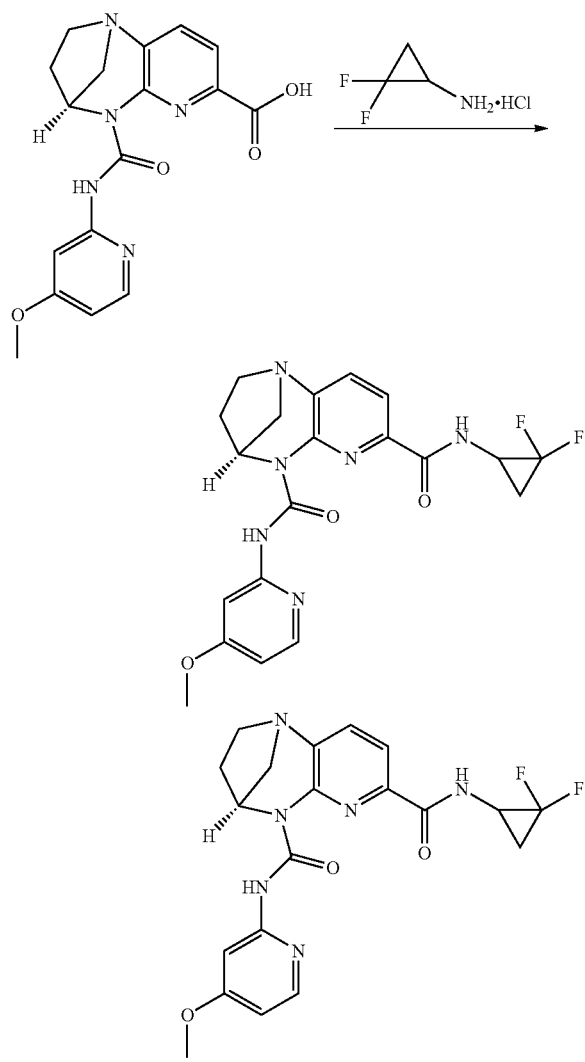

To a stirred solution of (4S)-5-((4-methoxypyridin-2-yl)carbamoyl)-2,3,4,5-tetrahydro-1,4-methanopyrido[2,3-b][1,4]diazepine-7-carboxylic acid (1.50 g, 4.22 mmol) in pyridine (10 mL, 124 mmol) was added EDC.HCl (2.428 g, 12.66 mmol) under nitrogen atmosphere at RT and stirred for 30 min. then 2,2-difluorocyclopropanamine hydrochloride (0.547 g, 4.22 mmol) was added and stirred for 16 h. (TLC eluent: 5% MeOH in DCM, $R_f$: 0.4, UV active).

Pyridine was evaporated under reduced pressure and diluted with ice water, extracted with ethyl acetate (3×20 mL). The combined organic layer was dried over anhydrous $Na_2SO_4$, filtered and concentrated to obtain crude compound. The crude compound was purified by flash column chromatography (using neutral alumina eluted with 1% MeOH in DCM) to afford mixture of compounds (550 mg). The mixture was separated by Chiral SFC as peak-I and peak-II.

SFC Conditions:

Column/dimensions: Chiralpak AD-H (250×30) mm, 5R, % CO2: 50.0%, % CO solvent: 50.0% (100% Methanol), Total Flow: 70.0 g/min, Back Pressure: 100.0 bar, UV: 267 nm, Stack time: 6.6 min, Load/Inj: 16.0 mg, Solubility: Methanol, Total No of injections: 35, Instrument details: Make/Model: Thar SFC-80.

Peak-I (4S)—N7-(2,2-difluorocyclopropyl)-N5-(4-methoxypyridin-2-yl)-3,4-dihydro-1,4-methanopyrido[2,3-b][1,4]diazepine-5,7(2H)-dicarboxamide (199 mg, 0.460 mmol, 10.89% yield) as an off-white solid. LCMS (m/z): 431.18 [M+H]$^+$, $R_t$=1.72 min.

$^1$H NMR (400 MHz, CDCl$_3$): δ 13.42 (s, 1H), 8.33 (s, 1H), 8.05 (d, J=5.9 Hz, 1H), 7.90 (dd, J=7.9, 0.6 Hz, 1H), 7.75-7.62 (m, 1H), 7.26 (s, 1H), 6.58 (ddd, J=5.9, 2.4, 0.6 Hz, 1H), 5.60 (dd, J=6.0, 3.2 Hz, 1H), 3.90 (d, J=0.5 Hz, 3H), 3.23 (dt, J=9.2, 4.6 Hz, 1H), 3.22-3.08 (m, 3H), 3.02 (dd, J=12.2, 3.3 Hz, 1H), 2.33 (ddt, J=14.1, 9.9, 5.3 Hz, 1H), 2.11-1.87 (m, 2H), 1.77 (ddt, J=14.0, 8.7, 5.5 Hz, 1H).

Peak-II (4S)—N7-(2,2-difluorocyclopropyl)-N5-(4-methoxypyridin-2-yl)-3,4-dihydro-1,4-methanopyrido[2,3-b][1,4]diazepine-5,7(2H)-dicarboxamide (186 mg, 0.428 mmol, 10.14% yield) as an off-white solid. LCMS (m/z): 431.18 [M+H]$^+$, $R_t$=1.73 min.

$^1$H NMR (400 MHz, CDCl$_3$): δ 13.44 (s, 1H), 8.32 (s, 1H), 8.05 (d, J=5.8 Hz, 1H), 7.90 (d, J=7.9 Hz, 1H), 7.75-7.63 (m, 2H), 6.58 (dd, J=5.8, 2.4 Hz, 1H), 5.61 (dd, J=5.9, 3.2 Hz, 1H), 3.90 (s, 3H), 3.51 (t, J=9.3 Hz, 1H), 3.23 (dd, J=9.3, 7.0 Hz, 3H), 3.02 (dd, J=12.2, 3.2 Hz, 1H), 2.32 (ddt, J=14.4, 9.9, 5.6 Hz, 1H), 2.05 (dt, J=14.7, 7.6 Hz, 1H), 1.93 (s, 1H), 1.83-1.69 (m, 1H).

Example 275

Synthesis of (4S)-5-((1-oxidopyridin-2-yl)carbamoyl)-7-((2,2,2-trifluoroethyl)carbamoyl)-2,3,4,5-tetrahydro-1H-1,4-methanopyrido[2,3-b][1,4]diazepine 1-oxide

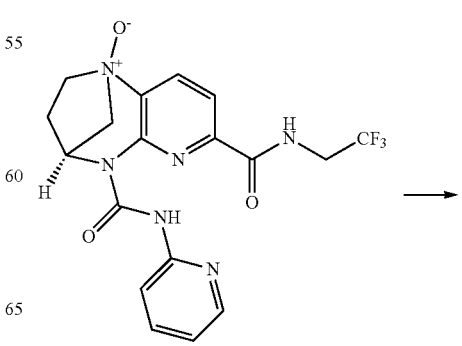

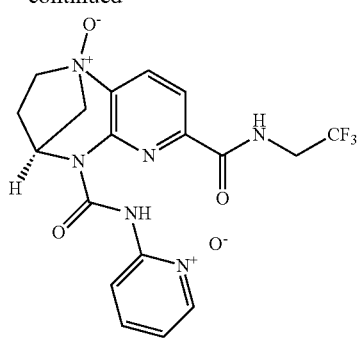

To a stirred solution of (4S)-5-(pyridin-2-ylcarbamoyl)-7-((2,2,2-trifluoroethyl)carbamoyl)-2,3,4,5-tetrahydro-1H-1,4-methanopyrido[2,3-b][1,4]diazepine1-oxide (100 mg, 0.237 mmol) in Chloroform (10 mL) was added m-CPBA (123 mg, 0.710 mmol) portion wise over a period of 10 min at 0° C., then the reaction mixture was stirred at RT for 16 h. (TLC eluent: 20% MeOH in DCM: $R_f$—0.1; UV active). The reaction mixture was poured in to the water and extracted with DCM (2×25 mL). The combined organic layer was washed with brine solution (20 mL), dried over anhydrous sodium sulphate and concentrated under reduced pressure to get crude compound. The crude compound was purified by column chromatography (100-200 silicagel eluted with 5% of Methanol in DCM) to afford the desired product (4S)-5-((1-oxidopyridin-2-yl)carbamoyl)-7-((2,2,2-trifluoroethyl)carbamoyl)-2,3,4,5-tetrahydro-1H-1,4-methanopyrido[2,3-b][1,4]diazepine 1-oxide (45 mg, 0.101 mmol, 42.5% yield) as an off white solid. LCMS (m/z): 439.06 [M+H]$^+$, $R_f$=1.45 min.

$^1$H NMR (400 MHz, DMSO-d$_6$): δ ppm 13.05 (s, 1H), 10.09 (t, J=6.47 Hz, 1H), 8.98 (d, J=8.11 Hz, 1H), 8.51 (dd, J=6.47, 0.99 Hz, 1H), 8.41 (dd, J=8.55, 1.53 Hz, 1H), 8.09 (d, J=8.11 Hz, 1H), 7.65-7.57 (m, 1H), 7.28-7.20 (m, 1H), 5.60 (dd, J=6.58, 3.95 Hz, 1H), 4.32-4.17 (m, 2H), 3.94 (dd, J=11.07, 3.84 Hz, 2H), 3.79 (d, J=11.18 Hz, 1H), 3.68 (d, J=7.02 Hz, 1H), 2.79-2.69 (m, 1H), 2.28-2.17 (m, 1H).

Example 276

Synthesis of (4S)-5-(2-(pyridin-2-yl)acetyl)-N—((R)-1,1,1-trifluoropropan-2-yl)-2,3,4,5-tetrahydro-1,4-methanopyrido[2,3-b][1,4]diazepine-7-carboxamide

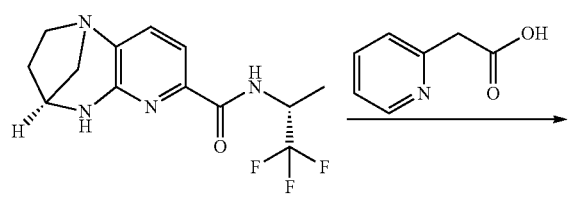

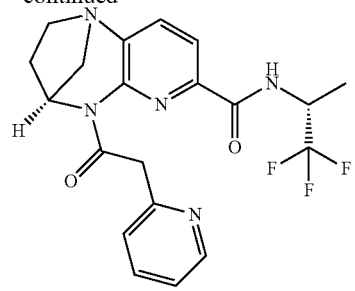

To a solution of (4S)—N—((R)-1,1,1-trifluoropropan-2-yl)-2,3,4,5-tetrahydro-1,4-methanopyrido[2,3-b][1,4]diazepine-7-carboxamide (600 mg, 1.998 mmol) in acetonitrile (50 mL) were added 2-(pyridin-2-yl)acetic acid (411 mg, 3.00 mmol) followed by phosphorus trichloride (0.350 mL, 4.00 mmol) and the reaction mixture was stirred in sealed tube at 100° C. for 16 h. (TLC system: 80% ethylacetate in hexane, Rf value: 0.1). The reaction mixture was cooled to RT, basified with saturated NaHCO$_3$ solution and extracted with DCM (2×100 mL). Combined organic layer was dried over anhydrous sodium sulphate, filtered and concentrated to get crude product. The crude compound was purified by preparative HPLC (Column: XBridge C18 (250×4.6 mm, 5μ); MP-A: 5 mM Ammonium Bicarbonate (aq), MP-B: ACN; Method (T/% B): 0/10, 1/10, 10/60, 15/60, 18/98, 20/98, 20.1/10, 25/10; Flow: 1.0 ml/min; Solubility: Acetonitrile) to afford (4S)-5-(2-(pyridin-2-yl)acetyl)-N—((R)-1,1,1-trifluoropropan-2-yl)-2,3,4,5-tetrahydro-1,4-methanopyrido[2,3-b][1,4]diazepine-7-carboxamide (200 mg, 0.467 mmol, 23.36% yield) as a pale yellow solid. LCMS (m/z): 420.05 [M+H]$^+$, Rt=1.60 min.

$^1$H NMR (400 MHz, CDCl$_3$): δ ppm: 9.87 (br d, J=8.99 Hz, 1H), 8.40-8.53 (m, 1H), 7.84 (d, J=7.89 Hz, 1H), 7.66 (td, J=7.67, 1.75 Hz, 1H), 7.55 (d, J=7.89 Hz, 1H), 7.44 (d, J=7.89 Hz, 1H), 7.15-7.20 (m, 1H), 5.69 (dd, J=6.25, 3.18 Hz, 1H), 4.77-5.00 (m, 3H), 3.06-3.25 (m, 2H), 2.87-3.05 (m, 2H), 2.15-2.36 (m, 1H), 1.72-1.98 (m, 1H), 1.48 (d, J=7.23 Hz, 3H).

Example 277

Synthesis of (4S)—N-(5-chloropyridin-2-yl)-7-(N-(2,2,2-trifluoroethyl)sulfamoyl)-3,4-dihydro-1,4-methanopyrido[2,3-b][1,4]diazepine-5(2H)-carboxamide

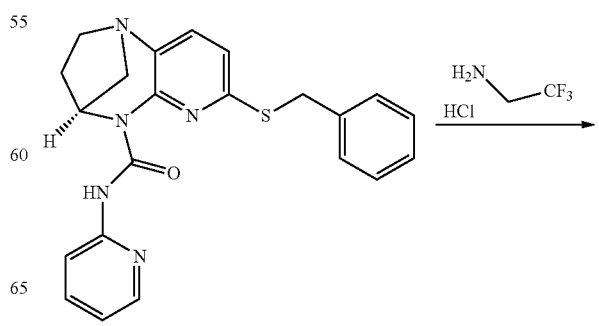

-continued

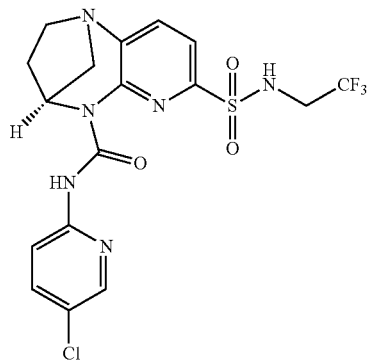

To a stirred mixture of (4S)-7-(benzylthio)-N-(pyridin-2-yl)-3,4-dihydro-1,4-methanopyrido[2,3-b][1,4]diazepine-5(2H)-carboxamide (1 g, 2.478 mmol) in water (25 mL), DCM (10 mL) and aq. HCl (0.4 mL, 13.16 mmol) at 0° C. was added sodium hypochlorite solution (12 mL, 2.478 mmol, 9% aq. solution) and was stirred for 30 min. (TLC eluting system: 5% MeOH in DCM; $R_f$—0.5; UV active). The reaction mixture was cooled to RT, quenched with cold water (20 mL) and extracted into DCM (2×20 mL). Organic layer was separated and dried over anhydrous sodium sulphate, filtered and filtrate was evaporated to get crude compound as brown liquid. The obtained brown liquid was dissolved in THF (30 mL) and was added DIPEA (0.433 mL, 2.478 mmol) and 2,2,2-trifluoroethanamine hydrochloride (1.008 g, 7.43 mmol). The resulting mixture was stirred at 75° C. for 16 h. The reaction mixture was cooled to RT, quenched with water (10 mL) and extracted into EtOAc (2×20 mL). Organic layer was separated and dried over anhydrous sodium sulphate, filtered and filtrate was evaporated to get crude compound as a pale brown liquid. The crude compound was purified by preparative HPLC (Column: X-Bridge C-18 (150×4.6 mm, 3.5 µm); Mobile Phase A: 10 mM Ammonium Acetate, B: 100% Acetonitrile; Gradient: Time/% B: 0/5, 1.5/5, 3/15, 7/55, 10/95, 15/95, 17/5, 20/5; Column Temp: Ambient; Flow Rate: 1.0 ml/min; Diluent: 70:30 Acetonitrile:$H_2O$) to afford (4S)—N-(5-chloropyridin-2-yl)-7-(N-(2,2,2-trifluoroethyl)sulfamoyl)-3,4-dihydro-1,4-methanopyrido[2,3-b][1,4]diazepine-5(2H)-carboxamide (57 mg, 0.118 mmol, 4.75% yield) as a pale yellow solid. LCMS (m/z): 477.04 [M+H]$^+$, $R_t$=2.35 min.

$^1$H NMR (400 MHz, $CDCl_3$): δ ppm 13.71 (s, 1H), 8.20 (d, J=2.41 Hz, 1H), 8.11 (d, J=8.77 Hz, 1H), 7.66-7.74 (m, 2H), 7.57 (d, J=7.89 Hz, 1H), 7.41-7.52 (m, 1H), 5.57 (dd, J=5.81, 2.96 Hz, 1H), 3.59-3.74 (m, 2H), 3.20-3.31 (m, 2H), 3.02-3.16 (m, 2H), 2.29-2.41 (m, 1H), 2.02-2.15 (m, 1H).

Example 278

Synthesis of (4S)-2,2,2-trifluoroethyl 5-(pyridin-2-ylcarbamoyl)-2,3,4,5-tetrahydro-1,4-methanopyrido[2,3-b][1,4]diazepine-7-carboxylate

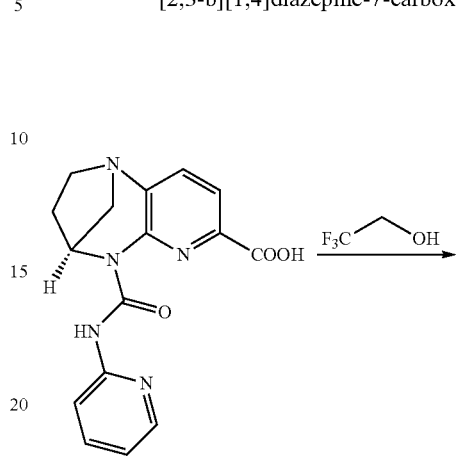

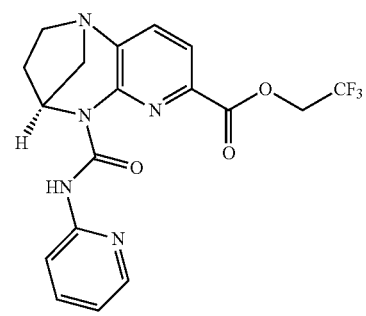

To a stirred solution of (4S)-5-(pyridin-2-ylcarbamoyl)-2,3,4,5-tetrahydro-1,4-methanopyrido[2,3-b][1,4]diazepine-7-carboxylic acid (300 mg, 0.922 mmol) and 2,2,2-trifluoroethanol (138 mg, 1.383 mmol) in DMF (10 mL) at room temp were added DIPEA (0.805 mL, 4.61 mmol) and HATU (701 mg, 1.844 mmol), then stirred at room temperature for 16 h. (TLC eluent: 5% MeOH in ethyl acetate: $R_f$—0.5; UV active). The reaction mixture was diluted with cold water and extracted with ethyl acetate (15 mL×2). The combined organic layer was dried over anhydrous $Na_2SO_4$, filtered and filtrate was evaporated to get crude compound. The crude was purified by flash column chromatography (100-200 silicagel, column eluted at 1% MeOH in ethyl acetate) to afford pure compound (4S)-2,2,2-trifluoroethyl5-(pyridin-2-ylcarbamoyl)-2,3,4,5-tetrahydro-1,4-methanopyrido[2,3-b][1,4]diazepine-7-carboxylate (115 mg, 0.281 mmol, 30.5% yield) as an off white solid. LCMS (m/z): 408.07 [M+H]$^+$, $R_t$=1.87 min.

$^1$H NMR (400 MHz, $CDCl_3$): δ ppm 13.08 (s, 1H), 8.43-8.29 (m, 1H), 8.17-8.01 (m, 1H), 7.79 (d, J=7.89 Hz, 1H), 7.72-7.65 (m, 1H), 7.63 (d, J=7.89 Hz, 1H), 6.99 (ddd, J=7.29, 4.88, 0.99 Hz, 1H), 5.69 (dd, J=6.03, 3.18 Hz, 1H), 4.83 (q, J=8.33 Hz, 2H), 3.29-2.99 (m, 4H), 2.39-2.28 (m, 1H), 2.11-2.00 (m, 1H).

Example 279

Synthesis of (4S)-8-chloro-N5-(pyridin-2-yl)-N7-(2,2,2-trifluoroethyl)-3,4-dihydro-1,4-methanopyrido[2,3-b][1,4]diazepine-5,7(2H)-dicarboxamide

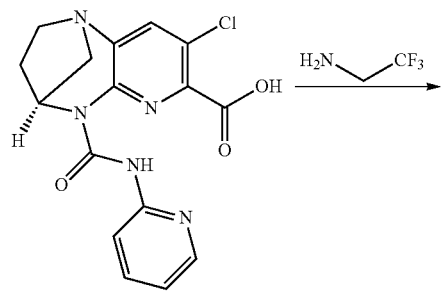

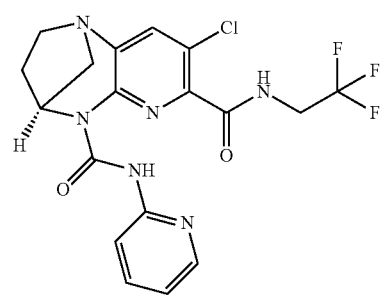

To a stirred solution of (4S)-8-chloro-5-(pyridin-2-ylcarbamoyl)-2,3,4,5-tetrahydro-1,4-methanopyrido[2,3-b][1,4]diazepine-7-carboxylic acid (500 mg, 1.390 mmol) in DMF (10 mL) were added HATU (1057 mg, 2.78 mmol), DIPEA (0.485 mL, 2.78 mmol) and 2,2,2-trifluoroethanamine Hydrochloride (283 mg, 2.085 mmol) and the reaction mixture was stirred at room temp for 16 h. (TLC eluent: Neat ethyl acetate; R$_f$: 0.23). The reaction mixture was diluted with ice cold water and extracted with ethylacetate (3×50 mL). The combined organic layer was washed with brine solution (20 ml) and dried over anhydrous Na$_2$SO$_4$, filtered and evaporated to get crude compound. The crude compound was purified by flash column chromatography (silicagel: 100-200 mesh, eluent: 70% Ethyl acetate in petether) to afford the desired product (4S)-8-chloro-N5-(pyridin-2-yl)-N7-(2,2,2-trifluoroethyl)-3,4-dihydro-1,4-methanopyrido[2,3-b][1,4]diazepine-5,7(2H)-dicarboxamide (280 mg, 0.626 mmol, 45.1% yield) as an off white solid. LCMS (m/z): 441.04 [M+H]$^+$, R$_t$=1.98 min.

$^1$H NMR (400 MHz, CDCl$_3$): δ ppm 12.93 (s, 1H), 8.27 (t, J=5.92 Hz, 1H), 8.23 (dd, J=4.93, 0.99 Hz, 1H), 8.17 (br s, 1H), 8.08 (d, J=8.33 Hz, 1H), 7.69-7.79 (m, 1H), 7.66 (s, 1H), 6.93-7.11 (m, 1H), 5.59 (dd, J=5.92, 3.07 Hz, 1H), 4.06-4.36 (m, 2H), 3.14-3.32 (m, 1H), 3.07-3.17 (m, 1H), 2.95-3.06 (m, 1H), 2.23-2.42 (m, 1H), 1.98-2.12 (m, 1H).

Example 280

Synthesis of (4S)-8-chloro-N5-(pyridin-2-yl)-N7-((R)-1,1,1-trifluoropropan-2-yl)-3,4-dihydro-1,4-methanopyrido[2,3-b][1,4]diazepine-5,7(2H)-dicarboxamide

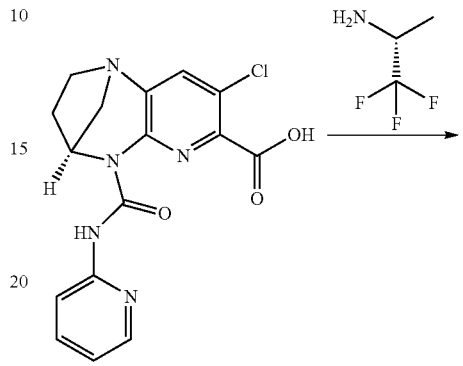

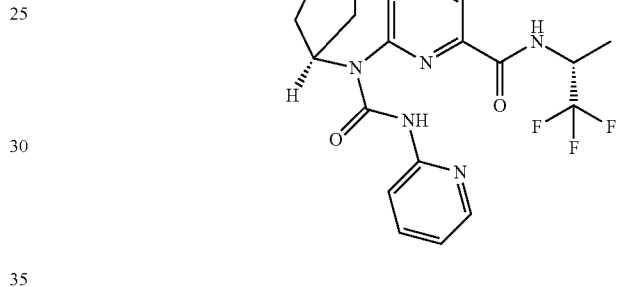

To a stirred solution of (4S)-8-chloro-5-(pyridin-2-ylcarbamoyl)-2,3,4,5-tetrahydro-1,4-methanopyrido[2,3-b][1,4]diazepine-7-carboxylic acid (250 mg, 0.695 mmol) in DMF (2.5 mL), under nitrogen at RT was added DIPEA (0.364 mL, 2.085 mmol), HATU (528 mg, 1.390 mmol) and (R)-1,1,1-trifluoropropan-2-amine (94 mg, 0.834 mmol) then the resulting reaction mixture was stirred for 16 h. (TLC system: 5% Methanol in DCM. R$_f$ value: 0.30). Reaction mass was quenched with ice cold water (80 mL) and extracted into EtOAc (2×100 mL). The combined organic layer was washed with brine, dried over Na$_2$SO$_4$, filtered and concentrated to get crude compound. The crude material was purified by combiflash (using silica gel column, 85% EtOAc in Hexane). Fractions containing pure compound were combined and concentrated to afford the desired compound with 93% purity which was further purified by prep HPLC (Column: XBridge C18 (150×19) mm 5μ, Mobile Phase-A: 10 mM Ammonium Bicarbonate (Aq), Mobile Phase-B: Acetonitrile, Method: Isocratic (A:B)=65:35, Flow: 18 ml/min Solubility: THF+ACN) to afford the desired product (4S)-8-chloro-N5-(pyridin-2-yl)-N7-((R)-1,1,1-trifluoropropan-2-yl)-3,4-dihydro-1,4-methanopyrido[2,3-b][1,4]diazepine-5,7(2H)-dicarboxamide (65 mg, 0.143 mmol, 20.51% yield) as off white solid. LCMS (m/z): 455.05 [M+H]$^+$, Rt=2.06 min.

$^1$H NMR (400 MHz, CDCl$_3$): δ ppm 12.44 (s, 1H), 8.24 (dt, J=4.93, 0.93 Hz, 1H), 8.13 (dt, J=8.39, 0.96 Hz, 1H), 7.72 (td, J=7.84, 1.64 Hz, 1H), 7.67 (s, 1H), 7.63 (br d, J=9.65 Hz, 1H), 7.03 (ddd, J=7.40, 4.99, 0.99 Hz, 1H), 5.62 (dd, J=5.92, 3.07 Hz, 1H), 4.96-5.14 (m, 1H), 3.17-3.28 (m, 2H), 3.07-3.13 (m, 1H), 2.98-3.04 (m, 1H), 2.26-2.43 (m, 1H), 2.01-2.11 (m, 1H), 1.59 (d, J=7.02 Hz, 3H).

Example 281

Synthesis of (4S)-8-chloro-N5-(4-(2-methyloxazol-5-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

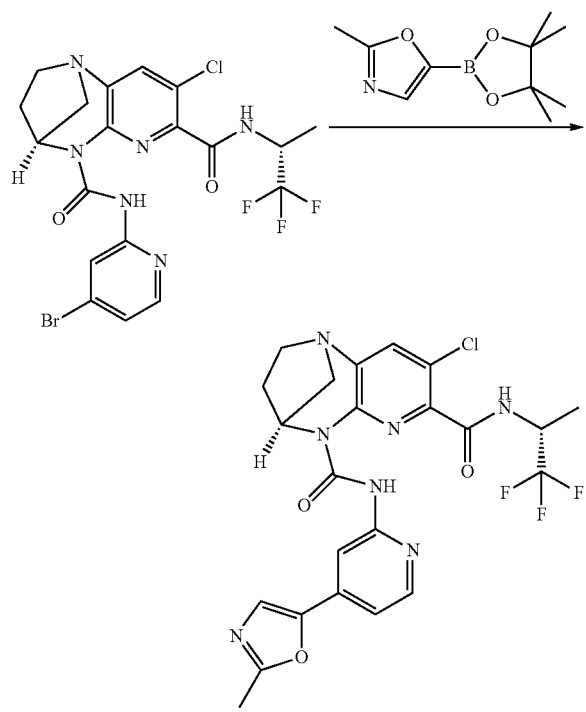

To a solution (4S)—N5-(4-bromopyridin-2-yl)-8-chloro-N7-((R)-1,1,1-trifluoropropan-2-yl)-3,4-dihydro-1,4-methanopyrido[2,3-b][1,4]diazepine-5,7(2H)-dicarboxamide (500 mg, 0.937 mmol) in 1,4-Dioxane (10 mL) and water (2.5 mL) was added Potassium acetate (184 mg, 1.874 mmol) and 2-methyl-5-(4,4,5,5-tetramethyl-1,3,2-dioxaborolan-2-yl)oxazole (215 mg, 1.030 mmol) and the reaction mixture was purged with argon for 30 min. then added $PdCl_2$(dppf)-$CH_2Cl_2$ adduct (38.3 mg, 0.047 mmol) and stirred at 90° C. for 5 h. (TLC system: 5% MeOH in DCM, $R_f$ value: 0.30). The reaction mixture was cooled to RT, concentrated in vacuo and the residue was partitioned between water (40 mL) and EtOAc (80 mL). Organic layer was separated and dried over anhydrous $Na_2SO_4$, filtered and filtrate was evaporated to get crude compound. The crude material was purified by combiflash chromatography (using silica gel column, 1% methanol in DCM). Fractions containing pure compound were combined and concentrated to afford the desired compound (4S)-8-chloro-N5-(4-(2-methyloxazol-5-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (60 mg, 0.108 mmol, 11.56% yield as an off white solid. LCMS (m/z): 536.12 [M+H]$^+$, Rt=2.15 min.

$^1$H NMR (400 MHz, $CDCl_3$): δ ppm 12.42-12.67 (m, 1H), 8.31-8.47 (m, 1H), 8.25 (d, J=5.04 Hz, 1H), 7.69 (s, 1H), 7.55-7.65 (m, 1H), 7.39-7.55 (m, 1H), 7.19-7.28 (m, 1H), 5.63 (dd, J=5.81, 2.96 Hz, 1H), 5.06 (dq, J=16.80, 7.48 Hz, 1H), 3.16-3.34 (m, 2H), 2.93-3.08 (m, 2H), 2.56 (s, 3H), 2.26-2.48 (m, 1H), 2.03-2.23 (m, 1H), 1.52-1.64 (m, 3H).

Example 282

Synthesis of (4S)-8-chloro-N5-(4-(oxazol-5-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

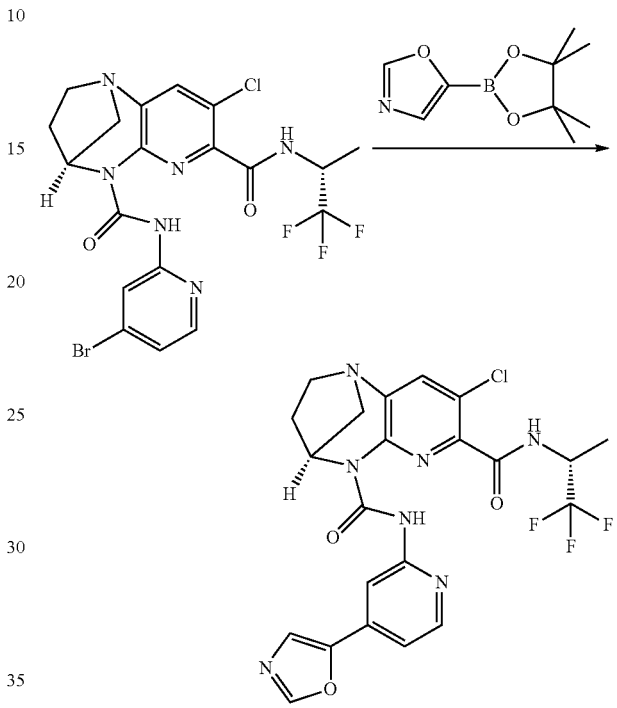

To a solution of (4S)—N5-(4-bromopyridin-2-yl)-8-chloro-N7-((R)-1,1,1-trifluoropropan-2-yl)-3,4-dihydro-1,4-methanopyrido[2,3-b][1,4]diazepine-5,7(2H)-dicarboxamide (600 mg, 1.124 mmol) in 1,4-Dioxane (12 mL) and water (3 mL) was added Potassium acetate (276 mg, 2.81 mmol), 5-(4,4,5,5-tetramethyl-1,3,2-dioxaborolan-2-yl)oxazole (263 mg, 1.349 mmol) and the reaction mixture was purged with argon for 30 min. then added $PdCl_2$(dppf)-$CH_2Cl_2$ adduct (55.1 mg, 0.067 mmol) and stirred at 90° C. for 5 h. (TLC system: 5% MeOH in DCM, $R_f$ value: 0.30). The reaction mixture was cooled to RT, concentrated in vacuo and the residue was partitioned between water (50 mL) and EtOAc (90 mL). Organic layer was separated and dried over anhydrous $Na_2SO_4$, filtered and filtrate was evaporated to get crude compound. The crude material was purified by combiflash chromatography (using silica gel column, 2% methanol in DCM). Fractions containing pure compound were combined and concentrated to afford the desired compound (4S)-8-chloro-N5-(4-(oxazol-5-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (75 mg, 0.143 mmol, 12.70% yield) as off white solid LCMS (m/z): 522.15 [M+H]$^+$, Rt=4.78 min.

$^1$H NMR (400 MHz, $CDCl_3$): δ ppm 12.45-12.77 (m, 1H), 8.44 (s, 1H), 8.29 (d, J=5.26 Hz, 1H), 8.00 (s, 1H), 7.69 (s, 1H), 7.53-7.60 (m, 2H), 7.24-7.34 (m, 1H), 5.63 (dd, J=5.81, 3.18 Hz, 1H), 4.93-5.17 (m, 1H), 3.17-3.32 (m, 2H), 2.99-3.15 (m, 2H), 2.28-2.42 (m, 1H), 2.01-2.17 (m, 1H), 1.60 (br, 3H).

Example 283

Synthesis of (4S)—N5-(4-((R)-2,3-dihydroxy-propoxy)pyridin-2-yl)-8-fluoro-N7-((R)-1,1,1-trifluoropropan-2-yl)-3,4-dihydro-1,4-methanopyrido[2,3-b][1,4]diazepine-5,7(2H)-dicarboxamide

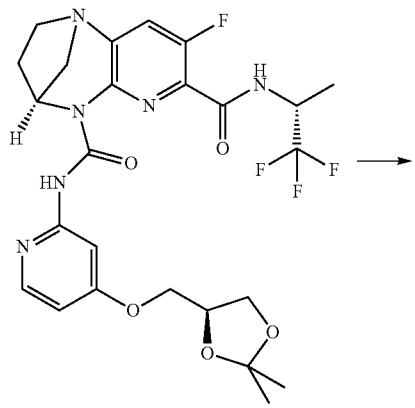

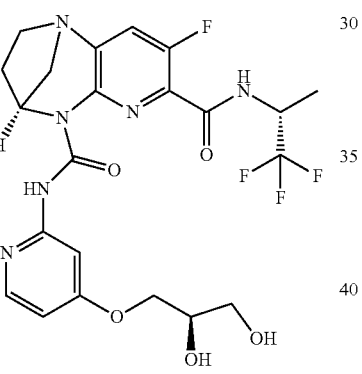

To a stirred solution of (4S)—N5-(4-(((S)-2,2-dimethyl-1,3-dioxolan-4-yl)methoxy)pyridin-2-yl)-8-fluoro-N7-((R)-1,1,1-trifluoropropan-2-yl)-3,4-dihydro-1,4-methanopyrido[2,3-b][1,4]diazepine-5,7(2H)-dicarboxamide (130 mg, 0.229 mmol) in methanol (10 mL) at RT was added 2M HCl (0.6 mL, 1.200 mmol) and stirred for 3 h. (TLC eluent: 5% Methanol in DCM, Rf: 0.2; UV active). Reaction mixture was concentrated to remove methanol and the residue was basified using saturated of solution of NaHCO$_3$ (3 mL). The resultant solid was filtered, dried and triturated with pet ether (10 mL) to afford (4S)—N5-(4-((R)-2,3-dihydroxypropoxy)pyridin-2-yl)-8-fluoro-N7-((R)-1,1,1-trifluoropropan-2-yl)-3,4-dihydro-1,4-methanopyrido[2,3-b][1,4]diazepine-5,7(2H)-dicarboxamide (105 mg, 0.196 mmol, 86% yield) as an off-white solid. LC-MS (m/z): 529.25 [M+H]$^+$, Rt=1.40 min.

$^1$H NMR (400 MHz, DMSO-d$_6$): δ ppm 12.43 (s, 1H), 8.79 (br d, J=8.77 Hz, 1H), 8.04 (br d, J=5.92 Hz, 1H), 7.56-7.84 (m, 2H), 6.71 (br d, J=4.17 Hz, 1H), 5.47 (br s, 1H), 5.01 (br d, J=4.82 Hz, 1H), 4.86 (br dd, J=15.46, 7.56 Hz, 1H), 4.70 (br t, J=5.48 Hz, 1H), 4.10 (br dd, J=9.65, 3.51 Hz, 1H), 3.88-4.01 (m, 1H), 3.82 (br d, J=4.82 Hz, 1H), 3.33-3.54 (m, 2H), 3.19-3.27 (m, 1H), 3.04-3.18 (m, 2H), 2.98 (br d, J=9.87 Hz, 1H), 2.25 (br d, J=5.70 Hz, 1H), 1.88 (br dd, J=13.92, 6.91 Hz, 1H), 1.46 (br d, J=7.23 Hz, 3H).

Example 284

Synthesis of (4S)-8-methoxy-N5-(pyridin-2-yl)-N7-(2,2,2-trifluoroethyl)-3,4-dihydro-1,4-methanopyrido[2,3-b][1,4]diazepine-5,7(2H)-dicarboxamide

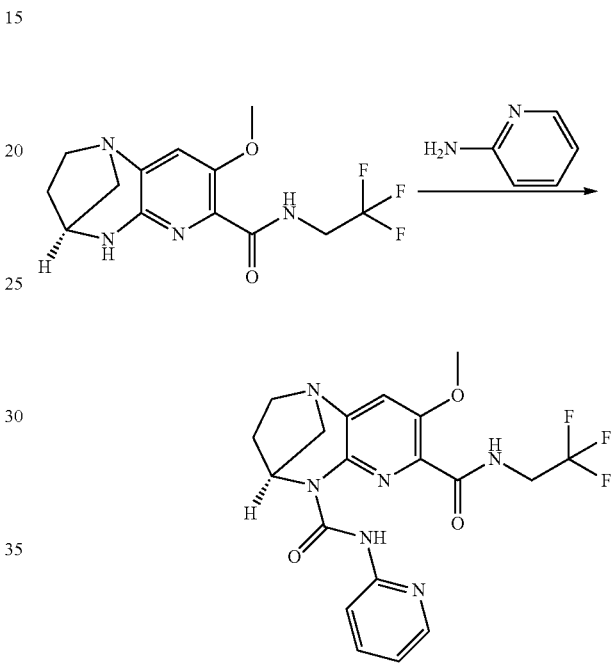

To a stirred solution of (4S)-8-methoxy-N-(2,2,2-trifluoroethyl)-2,3,4,5-tetrahydro-1,4-methanopyrido[2,3-b][1,4]diazepine-7-carboxamide (690 mg, 2.182 mmol) in Tetrahydrofuran (THF, 30 mL) were added triphosgene (647 mg, 2.182 mmol) and DIPEA (1.905 mL, 10.91 mmol) at 0° C. and the reaction mixture was stirred for 30 min at room temperature. Then pyridin-2-amine (246 mg, 2.62 mmol) was added and stirred at 80° C. for 16 h. (TLC system: R$_f$: 0.4, EtOAc). The reaction mixture was allowed to cool to room temperature and quenched with water (100 ml), extracted with ethylacetate (2×250 ml). The combined organic layer was dried over anhydrous sodium sulphate and concentrated under reduced pressure to obtain crude compound. The crude product was purified by flash column chromatography (silica-gel: 100-200 mesh, eluent: Neat ethyl acetate) to afford the desired product (4S)-8-methoxy-N-5-(pyridin-2-yl)-N-7-(2,2,2-trifluoroethyl)-3,4-dihydro-1,4-methanopyrido[2,3-b][1,4]diazepine-5,7(2H)-dicarboxamide (423 mg, 0.952 mmol, 43.6% yield) as a pale yellow solid. LCMS (m/z): 437.1 [M+H]$^+$, R$_t$=1.51 min.

$^1$H NMR (400 MHz, DMSO-d$_6$): δ ppm 12.70 (s, 1H), 8.81 (t, J=6.47 Hz, 1H), 8.28 (dd, J=4.82, 1.10 Hz, 1H), 8.02 (d, J=8.33 Hz, 1H), 7.84-7.69 (m, 1H), 7.55 (s, 1H), 7.12-7.00 (m, 1H), 5.45 (dd, J=5.92, 3.07 Hz, 1H), 4.23-4.02 (m, 2H), 3.79 (s, 3H), 3.34 (br s, 1H), 3.15-3.02 (m, 2H), 3.00-2.90 (m, 1H), 2.28-2.19 (m, 1H), 1.92-1.79 (m, 1H).

Example 285

Synthesis of (4S)-8-hydroxy-N5-(pyridin-2-yl)-N7-(2,2,2-trifluoroethyl)-3,4-dihydro-1,4-methanopyrido[2,3-b][1,4]diazepine-5,7(2H)-dicarboxamide

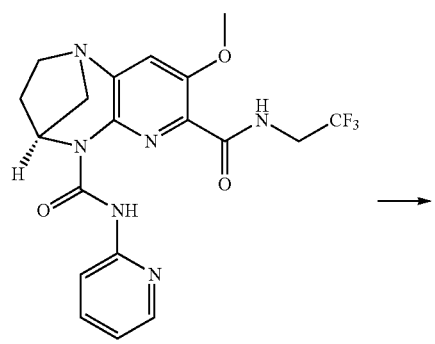

Example 286

Synthesis of (4S)-9-methoxy-N5-(pyridin-2-yl)-N7-(2,2,2-trifluoroethyl)-3,4-dihydro-1,4-methanopyrido[2,3-b][1,4]diazepine-5,7(2H)-dicarboxamide

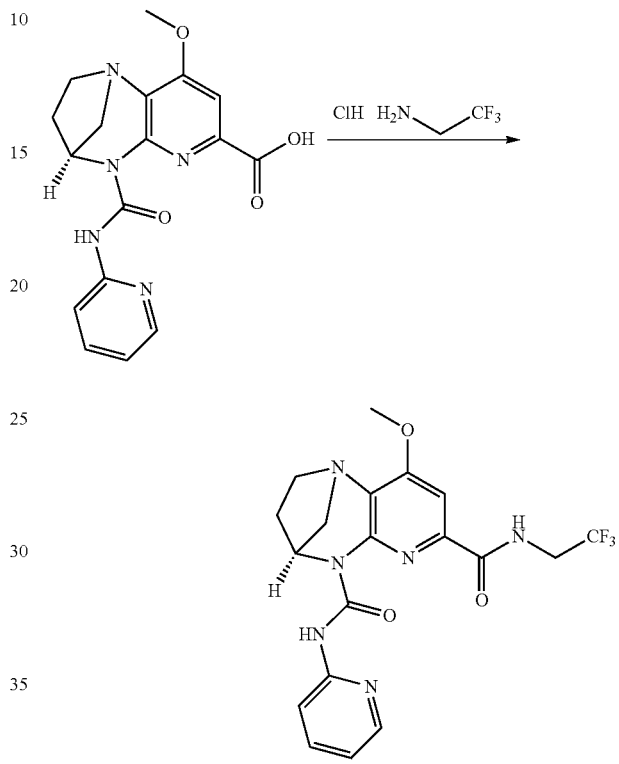

To a stirred solution of (4S)-8-methoxy-N5-(pyridin-2-yl)-N7-(2,2,2-trifluoroethyl)-3,4-dihydro-1,4-methanopyrido[2,3-b][1,4]diazepine-5,7(2H)-dicarboxamide (270 mg, 0.619 mmol) in DCM (20 mL), under nitrogen at −78° C. was added BBr$_3$ (0.175 m L, 1.856 m mol) and stirred for 16 h at RT. (TLC: Rf value: 0.5, EtOAc, UV active). The reaction mixture was quenched with of aq. NaHCO$_3$ (100 mL) solution and extracted with DCM (250 mL). The organic layer was dried over sodium sulphate and concentrated under reduced pressure to obtain crude product. The crude compound was purified by flash column chromatography (silica-gel: 100-200 mesh, eluted with 80% ethylacetate in petether) to afford (4S)-8-hydroxy-N5-(pyridin-2-yl)-N7-(2,2,2-trifluoroethyl)-3,4-dihydro-1,4-methanopyrido[2,3-b][1,4]diazepine-5,7(2H)-dicarboxamide (169 mg, 0.393 mmol, 63.5% yield) as an off white solid. LCMS (m/z): 423.14 [M+H]$^+$, Rt=2.48 in.

$^1$H NMR (400 MHz, CDCl$_3$): δ ppm 13.48 (s, 1H), 11.69 (s, 1H), 8.68 (br t, J=6.47 Hz, 1H), 8.20 (dd, J=4.93, 0.99 Hz, 1H), 8.07 (dt, J=8.33, 0.99 Hz, 1H), 7.72 (td, J=7.89, 1.97 Hz, 1H), 7.26 (s, 1H), 7.00 (ddd, J=7.29, 4.99, 1.10 Hz, 1H), 5.55 (dd, J=5.92, 3.29 Hz, 1H), 4.20 (qd, J=8.92, 6.80 Hz, 2H), 3.32-3.20 (m, 2H), 3.14 (br d, J=12.06 Hz, 1H), 2.98 (dd, J=12.28, 3.29 Hz, 1H), 2.31 (ddt, J=14.17, 8.58, 5.73, 5.73 Hz, 1H), 2.12-1.96 (m, 1H)

To a stirred solution of (4S)-9-methoxy-5-(pyridin-2-ylcarbamoyl)-2,3,4,5-tetrahydro-1,4-methanopyrido[2,3-b][1,4]diazepine-7-carboxylic acid (300 mg, 0.844 mmol) in DMF (10 mL) were added DIPEA (0.737 mL, 4.22 mmol) and HATU (482 mg, 1.266 mmol) at 0° C. and stirred for 30 min. Then 2,2,2-trifluoroethanamine hydrochloride (172 mg, 1.266 mmol) was added and the reaction mixture was stirred at 28° C. for 16 h. (TLC system: 5% MeOH in DCM, Rf: 0.4). The reaction mixture was quenched with cool water (25 mL) and extracted with EtOAc (3×30 mL). The combined organic layer was washed with brine solution (2×20 mL), dried with anhydrous Na$_2$SO$_4$, filtered and concentrated to get crude product. The crude product was purified by flash column chromatography (100-200 silica gel: Eluent: 1% MeOH/CH$_2$Cl$_2$) to afford the desired product (4S)-9-methoxy-N5-(pyridin-2-yl)-N7-(2,2,2-trifluoroethyl)-3,4-dihydro-1,4-methanopyrido[2,3-b][1,4]diazepine-5,7(2H)-dicarboxamide (120 mg, 0.274 mmol, 32.4% yield) as an off-white solid. LCMS (m/z): 437.19 [M+H]$^+$, R$_t$=2.00 min.

$^1$H NMR (400 MHz, CDCl$_3$): δ ppm 13.72 (s, 1H), 8.70-8.58 (m, 1H), 8.22 (d, J=4.17 Hz, 1H), 8.07 (d, J=8.33 Hz, 1H), 7.80-7.70 (m, 1H), 7.63 (s, 1H), 7.00 (dd, J=7.34, 4.93 Hz, 1H), 5.63 (d, J=5.92 Hz, 1H), 4.33-4.17 (m, 2H), 4.06 (s, 3H), 3.30-3.19 (m, 2H), 3.08 (s, 2H), 2.32 (dddd, J=14.03, 9.87, 5.92, 3.95 Hz, 1H), 2.11-1.96 (m, 1H).

Example 287

Synthesis of (4S)-9-methyl-N5-(pyridin-2-yl)-N7-(2,2,2-trifluoroethyl)-3,4-dihydro-1,4-methanopyrido[2,3-b][1,4]diazepine-5,7(2H)-dicarboxamide

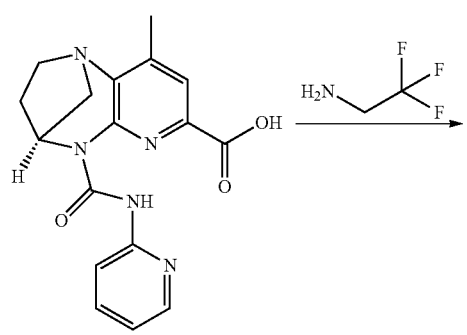

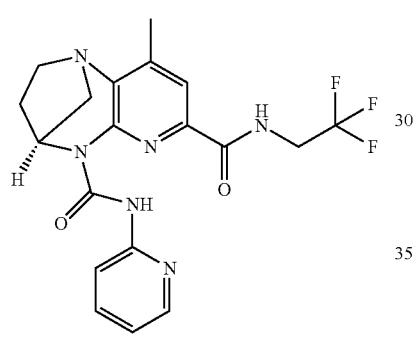

To a stirred solution of (4S)-9-methyl-5-(pyridin-2-ylcarbamoyl)-2,3,4,5-tetrahydro-1,4-methanopyrido[2,3-b][1,4]diazepine-7-carboxylic acid (1 g, 2.95 mmol) in Tetrahydrofuran (80 mL) were added DIPEA (1.544 mL, 8.84 mmol) and HATU (1.681 g, 4.42 mmol) at room temperature, stirred for 1 h. Then 2,2,2-trifluoroethanamine Hydrochloride (0.599 g, 4.42 mmol) was added and stirred at room temperature for 16 h. (TLC system: EtoAc, Rf: 0.6). Reaction mixture was poured in ice water (100 mL) and extracted with EtOAc (2×250 mL). The combined organic layer was dried over anhydrous $Na_2SO_4$, filtered and concentrated under reduced pressure to obtain crude product. The crude compound was purified by flash column chromatography (Neutral alumina column, Eluent: 10% EtoAc in Pet Ether) to afford the desired product (4S)-9-methyl-N5-(pyridin-2-yl)-N7-(2,2,2-trifluoroethyl)-3,4-dihydro-1,4-methanopyrido[2,3-b][1,4]diazepine-5,7(2H)-dicarboxamide (620 mg, 1.465 mmol, 49.7% yield) as a white solid. LCMS (m/z): 421.14 [M+H]$^+$, $R_t$=2.33 min.

$^1$H NMR (400 MHz, CDCl$_3$): δ ppm 13.80 (s, 1H), 8.57 (t, J=6.36 Hz, 1H), 8.23 (d, J=4.17 Hz, 1H), 8.08 (d, J=8.33 Hz, 1H), 7.81 (s, 1H), 7.76-7.64 (m, 1H), 7.00 (ddd, J=7.29, 4.99, 0.88 Hz, 1H), 5.61 (dd, J=6.03, 2.52 Hz, 1H), 4.30-4.14 (m, 2H), 3.20-3.09 (m, 2H), 3.08-2.98 (m, 2H), 2.49 (s, 3H), 2.39-2.24 (m, 1H), 2.03 (dt, J=14.74, 7.43 Hz, 1H).

Example 288

Synthesis of (4S)-9-methyl-N5-(pyridin-2-yl)-N7-((R)-1,1,1-trifluoropropan-2-yl)-3,4-dihydro-1,4-methanopyrido[2,3-b][1,4]diazepine-5,7(2H)-dicarboxamide

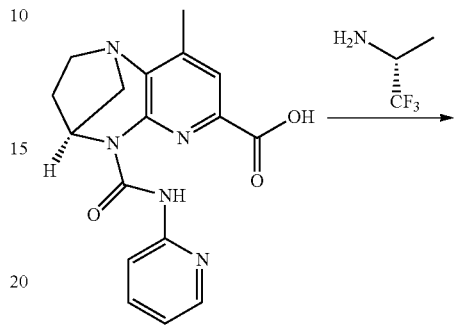

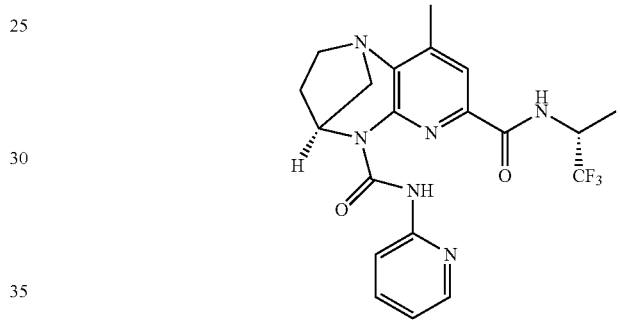

To a stirred solution of (4S)-9-methyl-5-(pyridin-2-ylcarbamoyl)-2,3,4,5-tetrahydro-1,4-methanopyrido[2,3-b][1,4]diazepine-7-carboxylic acid (230 mg, 0.678 mmol) in Tetrahydrofuran (50 mL) were added HATU (387 mg, 1.017 mmol) and DIPEA (0.355 mL, 2.033 mmol) at room temperature and stirred for 1 h. at room temperature. Then (R)-1,1,1-trifluoropropan-2-amine Hydrochloride (152 mg, 1.017 mmol) was added and stirred at 27° C. for 16 h. (TLC system: EtoAc, Rf: 0.5). The reaction mixture was poured in ice water (100 mL) and extracted with EtOAc (2×250 mL). The combined organic layer was dried over anhydrous $Na_2SO_4$, filtered and concentrated under reduced pressure to obtain crude compound. The obtained crude was purified by flash column chromatography (Neutral alumina column, Eluent: 10% EtoAc in Pet Ether) to afford the desired product (4S)-9-methyl-N5-(pyridin-2-yl)-N7-((R)-1,1,1-trifluoropropan-2-yl)-3,4-dihydro-1,4-methanopyrido[2,3-b][1,4]diazepine-5,7(2H)-dicarboxamide (90 mg, 0.207 mmol, 30.5% yield) as a white solid. LCMS (m/z): 435.18 [M+H]$^+$, $R_t$=2.54 min.

$^1$H NMR (400 MHz, CDCl$_3$): δ ppm 13.40 (br s, 1H), 8.25 (d, J=4.17 Hz, 1H), 8.15 (d, J=8.55 Hz, 1H), 8.01 (d, J=9.43 Hz, 1H), 7.85 (s, 1H), 7.75-7.65 (m, 1H), 7.01 (dd, J=6.47, 5.15 Hz, 1H), 5.65 (dd, J=5.81, 2.30 Hz, 1H), 5.13-5.00 (m, 1H), 3.19-3.09 (m, 2H), 3.07-2.99 (m, 2H), 2.49 (s, 3H), 2.38-2.26 (m, 1H), 2.03 (dt, J=14.47, 7.45 Hz, 1H), 1.60 (d, J=7.02 Hz, 3H).

Example 289

Synthesis of (4S)-9-methyl-N5-(6-methyl-1H-pyrazolo[3,4-b]pyridin-3-yl)-N7-((R)-1,1,1-trifluoropropan-2-yl)-3,4-dihydro-1,4-methanopyrido[2,3-b][1,4]diazepine-5,7(2H)-dicarboxamide

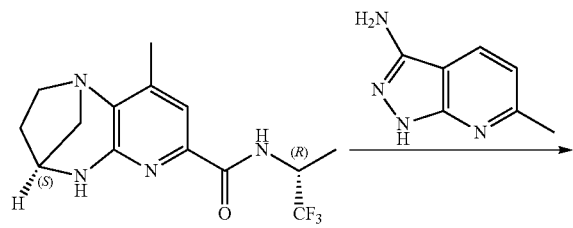

To a stirred solution of (4S)-9-methyl-N—((R)-1,1,1-trifluoropropan-2-yl)-2,3,4,5-tetrahydro-1,4-methanopyrido[2,3-b][1,4]diazepine-7-carboxamide (500 mg, 1.591 mmol) in Tetrahydrofuran (50 ml) were added triphosgene (283 mg, 0.954 mmol) and DIPEA (1.389 mL, 7.95 mmol) at room temperature. Then the reaction mixture was stirred for 4 h. at RT. After 4 h. 6-methyl-1H-pyrazolo [3,4-b]pyridin-3-amine (354 mg, 2.386 mmol) was added and stirred at 75° C. for 16 h. (TLC system: Neat EtOAc, Rf: 0.5). Then the reaction mixture was allowed to cool to room temperature and poured in saturated NaHCO₃ solution (50 mL), extracted with EtOAc (2×200 mL). The combined organic layer was dried over anhydrous Na₂SO₄, filtered and concentrated under reduced pressure to obtain the crude product. The crude material was purified by flash column chromatography (Neutral alumina, Eluent: 30% EtoAc in Pet Ether) to afford the desired product (4S)-9-methyl-N5-(6-methyl-1H-pyrazolo[3,4-b]pyridin-3-yl)-N7-((R)-1,1,1-trifluoropropan-2-yl)-3,4-dihydro-1,4-methanopyrido[2,3-b][1,4]diazepine-5,7(2H)-dicarboxamide (350 mg, 0.716 mmol, 45.0% yield) as a white solid. LCMS (m/z): 489.21 [M+H]⁺, R$_t$=2.16 min.

¹H NMR (400 MHz, CDCl₃): δ ppm 13.24 (s, 1H), 10.31-10.11 (m, 1H), 8.72 (s, 1H), 7.81 (s, 1H), 7.62 (d, J=9.21 Hz, 1H), 7.03 (d, J=8.33 Hz, 1H), 5.65 (dd, J=6.14, 2.85 Hz, 1H), 4.99 (dq, J=16.72, 7.36 Hz, 1H), 3.22-3.01 (m, 4H), 2.67 (s, 3H), 2.50 (s, 3H), 2.40-2.27 (m, 1H), 2.14-2.02 (m, 1H), 1.56 (d, J=7.02 Hz, 3H).

Example 290

Synthesis of (4S)—N5-(5-((S)-2,3-dihydroxypropoxy)pyridin-2-yl)-9-methyl-N7-((R)-1,1,1-trifluoropropan-2-yl)-3,4-dihydro-1,4-methanopyrido[2,3-b][1,4]diazepine-5,7(2H)-dicarboxamide

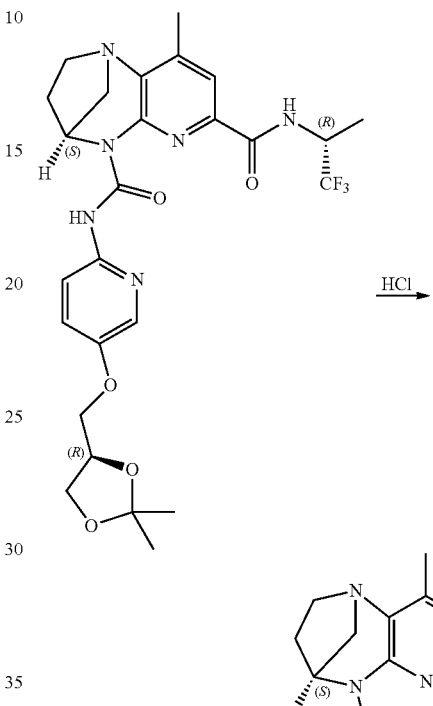

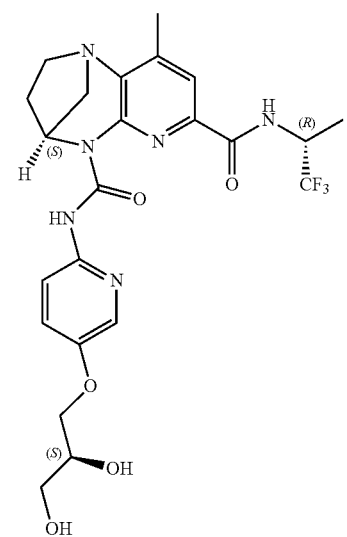

To a stirred solution of (4S)—N5-(5-(((R)-2,2-dimethyl-1,3-dioxolan-4-yl)methoxy)pyridin-2-yl)-9-methyl-N7-((R)-1,1,1-trifluoropropan-2-yl)-3,4-dihydro-1,4-methanopyrido[2,3-b][1,4]diazepine-5,7(2H)-dicarboxamide (500 mg, 0.886 mmol) in Methanol (30 mL) at room temperature was added hydrochloric acid (2 ml, 23.70 mmol) and the reaction mixture was stirred at RT for 1 h. (TLC system: Neat EtOAc, Rf: 0.3). After 1 h. the reaction mixture was concentrated under reduced pressure and quenched it with NaHCO₃ solution (30 mL), extracted with 5% MeOH in DCM (2×50 mL). the combined organic layer was dried over anhydrous Na₂SO₄ and concentrated under reduced pressure to obtain semi solid, which was washing with pentane (2×20 mL) and dried to afford the desired product (4S)—N5-(5-((S)-2,3-dihydroxypropoxy)pyridin-2-yl)-9-methyl-N7-((R)-1,1,1-trifluoropropan-2-yl)-3,4-dihydro-1,4-methanopyrido[2,3-b][1,4]diazepine-5,7(2H)-dicarboxamide (360 mg, 0.683 mmol, 77% yield) as a white solid. LCMS (m/z): 525.25 [M+H]⁺, $R_f$=1.95 min.

¹H NMR (400 MHz, CDCl₃): δ ppm 13.26 (s, 1H), 8.11 (d, J=8.99 Hz, 1H), 7.96 (d, J=2.85 Hz, 1H), 7.88 (d, J=9.43 Hz, 1H), 7.83 (s, 1H), 7.31 (dd, J=8.99, 3.07 Hz, 1H), 5.64 (dd, J=5.70, 2.41 Hz, 1H), 5.05 (dq, J=16.74, 7.28 Hz, 1H), 4.20-4.05 (m, 3H), 3.94-3.73 (m, 2H), 3.20-3.08 (m, 2H), 3.07-2.97 (m, 2H), 2.54 (d, J=4.60 Hz, 1H), 2.48 (s, 3H), 2.36-2.26 (m, 1H), 2.11-1.97 (m, 1H), 1.92 (t, J=5.92 Hz, 1H), 1.58 (d, J=7.23 Hz, 3H).

Example 291

Synthesis of (4S)—N5-(4-((R)-2,3-dihydroxypropoxy)pyridin-2-yl)-8-methyl-N7-((R)-1,1,1-trifluoropropan-2-yl)-3,4-dihydro-1,4-methanopyrido[2,3-b][1,4]diazepine-5,7(2H)-dicarboxamide ¹H NMR (400 MHz, CDCl₃): δ ppm 12.87 (s, 1H), 8.05 (d, J=5.92 Hz, 1H), 7.87 (br d, J=9.87 Hz, 1H), 7.78 (d, J=2.19 Hz, 1H), 7.47 (s, 1H), 6.59 (dd, J=5.81, 2.30 Hz, 1H), 5.58 (dd, J=5.81, 3.18 Hz, 1H), 4.88-5.14 (m, 1H), 4.02-4.27 (m, 3H), 3.69-3.91 (m, 2H), 3.15-3.27 (m, 2H), 3.06-3.14 (m, 1H), 2.96-3.07 (m, 1H), 2.66 (s, 4H), 2.24-2.38 (m, 1H), 1.97-2.09 (m, 2H), 1.62-1.46 (s, 3H).

Example 292

Synthesis of (4S)—N5-(4-((R)-2,3-dihydroxypropoxy)pyridin-2-yl)-9-methyl-N7-((R)-1,1,1-trifluoropropan-2-yl)-3,4-dihydro-1,4-methanopyrido[2,3-b][1,4]diazepine-5,7(2H)-dicarboxamide

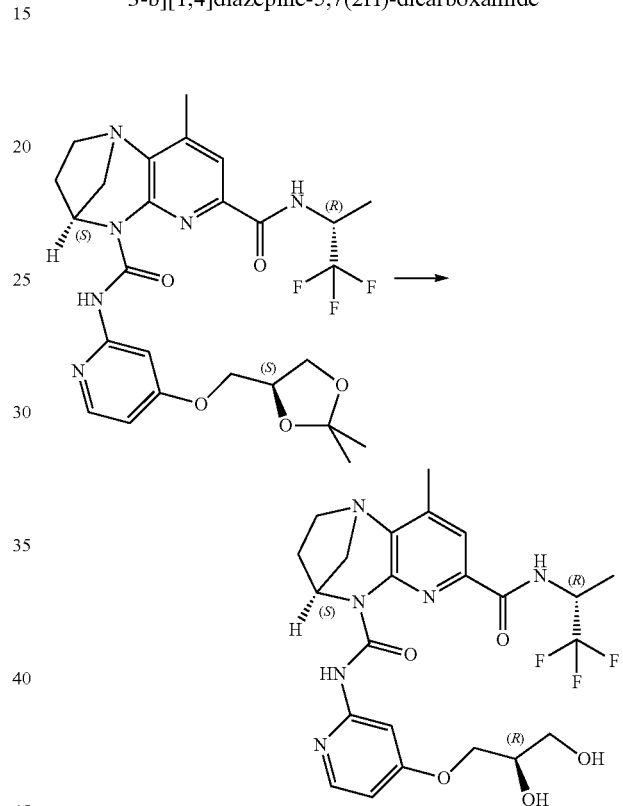

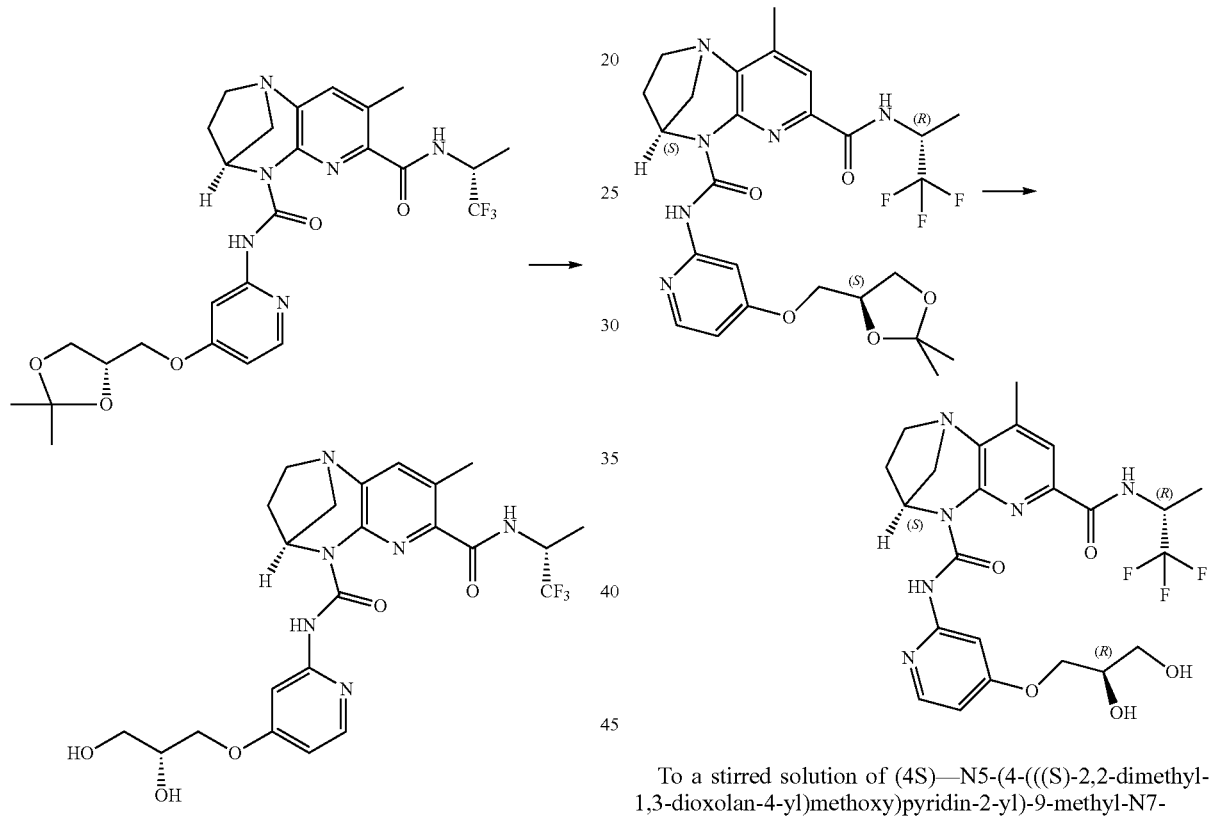

To a stirred solution of (4S)—N5-(4-(((S)-2,2-dimethyl-1,3-dioxolan-4-yl)methoxy)pyridin-2-yl)-8-methyl-N7-((R)-1,1,1-trifluoropropan-2-yl)-3,4-dihydro-1,4-methanopyrido[2,3-b][1,4]diazepine-5,7(2H)-dicarboxamide (250 mg, 0.443 mmol) in methanol (10 mL) at 0° C. was added aq. HCl (1.50 mL, 18.00 mmol) and stirred under nitrogen at RT for 1 h. (TLC eluent: 5% MeOH in DCM $R_f$—0.2; UV active). The reaction mixture was basified with saturated sodium bicarbonate solution (till pH-8-9) at 0° C. and the solvent was evaporated under reduced pressure. The residue was diluted with water and precipitated solid was filtered to afford crude product. The crude was triturated with diethylether to afford (4S)—N5-(4-((R)-2,3-dihydroxypropoxy)pyridin-2-yl)-8-methyl-N7-((R)-1,1,1-trifluoropropan-2-yl)-3,4-dihydro-1,4-methanopyrido[2,3-b][1,4]diazepine-5,7(2H)-dicarboxamide (160 mg, 0.305 mmol, 68.8% yield) as an off white solid. LCMS (m/z): 525.58 [M+H]⁺, $R_f$=1.48 min.

To a stirred solution of (4S)—N5-(4-(((S)-2,2-dimethyl-1,3-dioxolan-4-yl)methoxy)pyridin-2-yl)-9-methyl-N7-((R)-1,1,1-trifluoropropan-2-yl)-3,4-dihydro-1,4-methanopyrido[2,3-b][1,4]diazepine-5,7(2H)-dicarboxamide (250 mg, 0.443 mmol) in Methanol (30 mL) was added hydrochloric acid (1 ml, 11.85 mmol), drop wise over a period of 5 min. and the resulted reaction mixture was stirred at RT for 1 h. (TLC system: EtOAc, Rf value: 0.3). The reaction mixture was concentrated under reduced pressure and the obtained residue was neutralized with saturated NaHCO₃ solution, extracted with 5% MeOH in DCM and concentrated under reduced pressure and triturated with n-pentane (2×20 mL) to afford the desired product (4S)—N5-(4-((R)-2,3-dihydroxypropoxy)pyridin-2-yl)-9-methyl-N7-((R)-1,1,1-trifluoropropan-2-yl)-3,4-dihydro-1,4-methanopyrido[2,3-b][1,4]diazepine-5,7(2H)-dicarboxamide (180 mg, 0.342 mmol, 77% yield) as a white solid. LCMS (m/z): 525.28 [M+H]⁺, Rt=1.70 min.

¹H NMR (400 MHz, CDCl₃): δ ppm 13.46 (s, 1H), 8.06 (d, J=5.92 Hz, 2H), 7.85 (s, 1H), 7.77 (d, J=2.19 Hz, 1H), 6.59 (dd, J=5.70, 2.41 Hz, 1H), 5.61 (d, J=3.29 Hz, 1H), 5.11-5.02 (m, 1H), 4.22-4.11 (m, 3H), 3.70-3.88 (m, 2H), 3.22-3.02 (m, 4H), 2.49 (s, 3H), 2.32 (qd, J=9.76, 4.49 Hz, 1H), 2.03 (dt, J=14.63, 7.48 Hz, 3H), 1.57 (s, 3H).

Example 293

Synthesis of (4S)-9-methyl-N5-(4-(2-methyloxazol-5-yl)pyridin-2-yl)-N7-(2,2,2-trifluoroethyl)-3,4-dihydro-1,4-methanopyrido[2,3-b][1,4]diazepine-5,7(2H)-dicarboxamide

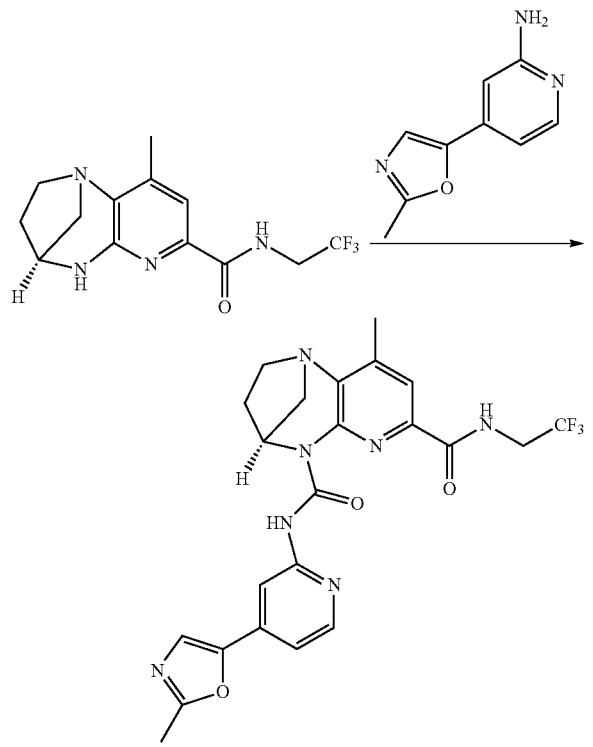

To a stirred solution of (4S)-9-methyl-N-(2,2,2-trifluoroethyl)-2,3,4,5-tetrahydro-1,4-methanopyrido[2,3-b][1,4]diazepine-7-carboxamide (500 mg, 1.665 mmol) in THF (50 ml) were added triphosgene (296 mg, 0.999 mmol) and DIPEA (1.454 mL, 8.33 mmol) at 0° C. and stirred to RT for 1 h. then 4-(2-methyloxazol-5-yl)pyridin-2-amine (438 mg, 2.498 mmol) was added and the resulted reaction mixture was stirred at 75° C. for 16 h. (TLC System: 100% EtOAc, Rf:—0.4). The reaction mixture was allowed to cool to room temperature and poured in saturated NaHCO₃ solution (30 mL), extracted with ethyl acetate (2×100 mL). The combined organic layer was dried over anhydrous Na₂SO₄ and concentrated under reduced pressure to obtain crude material. The crude product was purified by flash column chromatography (using Neutral alumina and was eluted with 30% Ethylacetate in Petether) Collected fractions are evaporated to afford the desired product (4S)-9-methyl-N5-(4-(2-methyloxazol-5-yl)pyridin-2-yl)-N7-(2,2,2-trifluoroethyl)-3,4-dihydro-1,4-methanopyrido[2,3-b][1,4]diazepine-5,7(2H)-dicarboxamide (329 mg, 0.656 mmol, 39.4% yield) as a white solid. LCMS (m/z): 502.24 [M+H]⁺, Rt=2.41 min.

¹H NMR (400 MHz, CDCl₃): δ ppm 13.90 (s, 1H), 8.50 (t, J=6.69 Hz, 1H), 8.33 (d, J=0.66 Hz, 1H), 8.23 (d, J=5.26 Hz, 1H), 7.82 (s, 1H), 7.47 (s, 1H), 7.19 (dd, J=5.26, 1.53 Hz, 1H), 5.62 (dd, J=5.81, 2.52 Hz, 1H), 4.29-4.17 (m, 2H), 3.24-2.99 (m, 4H), 2.56 (s, 3H), 2.50 (s, 3H), 2.41-2.29 (m, 1H), 2.11-2.00 (m, 1H).

Example 294

Synthesis of (4S)—N5-(4-((R)-2,3-dihydroxypropoxy)pyridin-2-yl)-9-methyl-N7-(2,2,2-trifluoroethyl)-3,4-dihydro-1,4-methanopyrido[2,3-b][1,4]diazepine-5,7(2H)-dicarboxamide

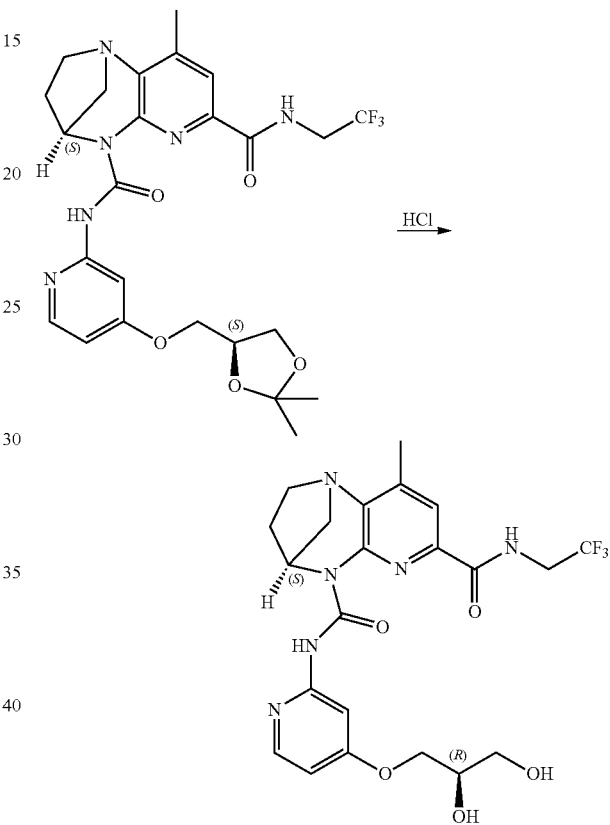

To a stirred solution of (4S)—N5-(4-(((S)-2,2-dimethyl-1,3-dioxolan-4-yl)methoxy)pyridin-2-yl)-9-methyl-N7-(2,2,2-trifluoroethyl)-3,4-dihydro-1,4-methanopyrido[2,3-b][1,4]diazepine-5,7(2H)-dicarboxamide (200 mg, 0.363 mmol) in Methanol (30 mL) at room temperature was added hydrochloric acid (1.5 ml, 17.77 mmol). The reaction mixture was stirred at RT for 1 h. (TLC system: Neat EtOAc, Rf: 0.2). The reaction mixture was concentrated under reduced pressure and quenched with NaHCO₃ (30 mL) solution followed by extracted with 5% MeOH in DCM (2×50 mL). The combined organic layer was dried over anhydrous sodium sulphate and concentrated under reduced pressure to obtain semi solid, which was washed with n-pentane (2×20 mL) and dried to afford the desired product (4S)—N5-(4-((R)-2,3-dihydroxypropoxy)pyridin-2-yl)-9-methyl-N7-(2,2,2-trifluoroethyl)-3,4-dihydro-1,4-methanopyrido[2,3-b][1,4]diazepine-5,7(2H)-dicarboxamide (150 mg, 0.293 mmol, 81% yield) as a white solid. LCMS (m/z): 511.21 [M+H]⁺, R$_t$=1.59 min.

¹H NMR (400 MHz, CDCl₃): δ ppm 13.85 (s, 1H), 8.60 (t, J=6.14 Hz, 1H), 8.03 (d, J=5.92 Hz, 1H), 7.81 (s, 1H), 7.70 (d, J=2.41 Hz, 1H), 6.57 (dd, J=5.81, 2.30 Hz, 1H), 5.58 (d, J=2.19 Hz, 1H), 4.27-4.06 (m, 5H), 3.91-3.70 (m, 2H), 3.22-2.98 (m, 4H), 2.58 (br s, 1H), 2.49 (s, 3H), 2.32 (qd, J=9.57, 5.04 Hz, 1H), 2.11-1.96 (m, 2H).

Example 295

Synthesis of (4S)-5-(pyridin-2-ylcarbamoyl)-7-((2,2,2-trifluoroethyl)carbamoyl)-2,3,4,5-tetrahydro-1H-1,4-methanopyrido[2,3-b][1,4]diazepine 1-oxide

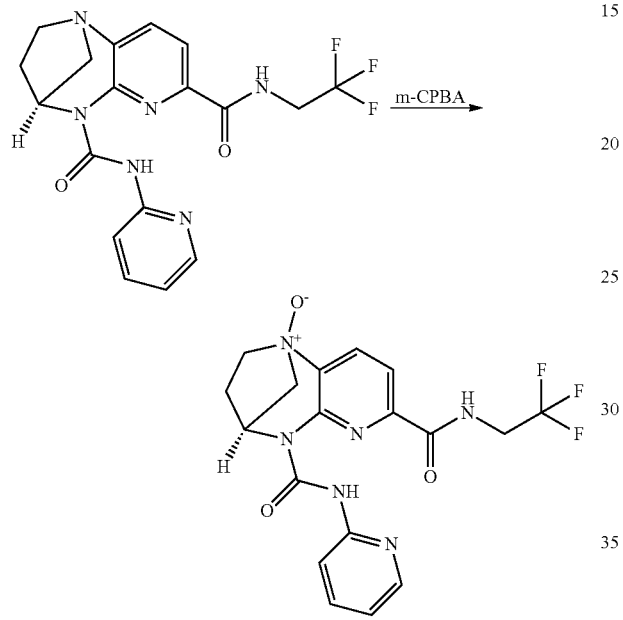

To a stirred solution of (4S)—N5-(pyridin-2-yl)-N7-(2,2,2-trifluoroethyl)-3,4-dihydro-1,4-methanopyrido[2,3-b][1,4]diazepine-5,7(2H)-dicarboxamide (500 mg, 1.230 mmol) in Chloroform (20 mL) was added m-CPBA (212 mg, 1.230 mmol) portion wise over a period of 10 min at 0° C., then the reaction mixture was stirred at 28° C. for 16 h. (TLC system: 10% MeOH in DCM, R$_f$ 0.5). The reaction mixture was diluted with ice water (40 mL) and extracted with EtOAc (2×40 mL). The combined organic layer was separated and dried over anhydrous sodium sulphate, filtered and filtrate was evaporated to get crude compound. The crude product was purified by flash column chromatography (100-200 silicagel, eluent: 5% MeOH in DCM,) to afford the desired product (4S)-5-(pyridin-2-ylcarbamoyl)-7-((2,2,2-trifluoroethyl)carbamoyl)-2,3,4,5-tetrahydro-1H-1,4-methanopyrido[2,3-b][1,4]diazepine 1-oxide (350 mg, 0.829 mmol, 67.3% yield) as an off white solid. LCMS (m/z): 423.11[M+H]$^+$, Rt=1.59 min.

$^1$H NMR (400 MHz, CDCl$_3$): δ ppm 13.15 (s, 1H), 9.09 (d, J=8.11 Hz, 1H), 8.55 (t, J=6.69 Hz, 1H), 8.26 (d, J=4.17 Hz, 1H), 8.16 (d, J=8.11 Hz, 1H), 8.04 (d, J=8.33 Hz, 1H), 7.81-7.73 (m, 1H), 7.11-7.06 (m, 1H), 5.82 (dd, J=6.80, 3.95 Hz, 1H), 4.37-4.15 (m, 2H), 4.10 (dd, J=11.40, 3.95 Hz, 1H), 4.06-3.97 (m, 2H), 3.79 (d, J=11.62 Hz, 1H), 2.97-2.85 (m, 1H), 2.33-2.21 (m, 1H).

Example 296

Synthesis of (4S)—N5-(4-(1H-1,2,3-triazol-5-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

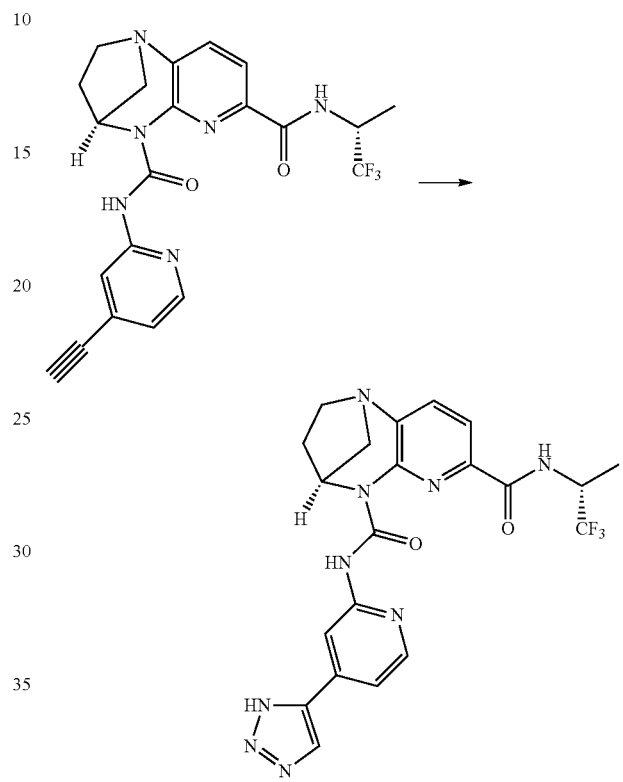

The suspension of (4S)—N5-(4-ethynylpyridin-2-yl)-N7-((R)-1,1,1-trifluoropropan-2-yl)-3,4-dihydro-1,4-methanopyrido[2,3-b][1,4]diazepine-5,7(2H)-dicarboxamide (600 mg, 1.350 mmol) in TMSN$_3$ (5 mL, 37.7 mmol) was stirred at 80° C. in microwave for 30 min. (TLC eluent: 10% MeOH in DCM, R$_f$: 0.2, UV active). The reaction mixture was concentrated under reduced pressure and diluted with 10% MeOH in DCM (15 mL), washed with water and dried over anhydrous sodium sulphate, filtered and concentrated under vacuo to get crude product with (36% of LCMS 260 mg). The crude compound was purified by prep HPLC (Prep HPLC conditions. Method: MP-A: 10 Mm Ammonium Bicarbonate MP-B: Acetonitrile Column: xbridge C18 (150*19) mm, 5u Method:—t/% B): 0/10, 1/10, 9/45, Flow: 15 ml/min Solubility: Acetonitrile+THF+MeOH) to afford (4S)—N5-(4-(1H-1,2,3-triazol-5-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (40 mg, 0.082 mmol, 6.07% yield) as an off white solid. LCMS (m/z): 488.17 [M+H]$^+$, R$_t$=2.00.

$^1$H NMR (400 MHz, CDCl$_3$): δ ppm 13.38 (s, 1H), 8.60 (s, 1H), 8.33 (d, J=5.26 Hz, 1H), 8.18 (s, 1H), 8.06-7.95 (m, 2H), 7.70 (d, J=7.89 Hz, 1H), 7.59-7.49 (m, 1H), 5.68 (dd, J=5.92, 3.07 Hz, 1H), 5.15-4.98 (m, 1H), 3.33-3.13 (m, 3H), 3.08-3.00 (m, 1H), 2.45-2.28 (m, 1H), 2.10 (dt, J=14.25, 7.13 Hz, 1H), 1.62 (d, J=7.23 Hz, 3H).

Example 297

Synthesis of (4S)—N5-(4-(isopropylcarbamoyl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

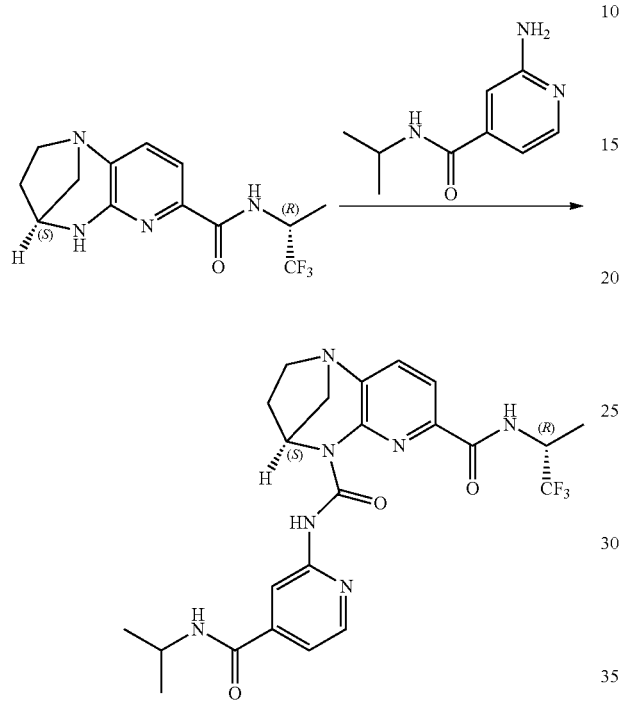

To a stirred solution of (4S)—N—((R)-1,1,1-trifluoropropan-2-yl)-2,3,4,5-tetrahydro-1,4-methanopyrido[2,3-b][1,4]diazepine-7-carboxamide (300 mg, 0.999 mmol) in THF (15 mL) were added triphosgene (296 mg, 0.999 mmol) and TEA (0.836 mL, 5.99 mmol) at 10° C. and stirred for 30 min at RT, then 2-amino-N-isopropylisonicotinamide (269 mg, 1.499 mmol) at RT and the reaction mixture was stirred at 80° C. for 16 h. (TLC eluent: Neat ethyl acetate, $R_f$—0.3; UV active). The reaction mixture was cooled to RT and diluted with water and extracted with ethyl acetate (3×50 mL). The combined organic layer was washed with saturated brine solution (25 mL), dried over anhydrous sodium sulphate, filtered and concentrated to get crude compound. The crude product was purified by flash column chromatography (using 100-200 silica gel, eluted at 80% ethyl acetate in pet ether) to afford the desired product (4S)—N5-(4-(isopropylcarbamoyl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (39 mg, 0.077 mmol, 7.70% yield). LCMS (m/z): 506.17 [M+H]$^+$, $R_t$=2.15 min.

$^1$H NMR (400 MHz, CDCl$_3$): δ ppm 13.43 (s, 1H), 8.35 (d, J=2.41 Hz, 2H), 8.05-7.85 (m, 2H), 7.70 (d, J=7.89 Hz, 1H), 7.56-7.39 (m, 1H), 6.09 (d, J=7.89 Hz, 1H), 5.64 (dd, J=6.03, 2.96 Hz, 1H), 5.19-4.95 (m, 1H), 4.42-4.15 (m, 1H), 3.37-2.95 (m, 4H), 2.48-2.24 (m, 1H), 2.16-1.95 (m, 1H), 1.60 (s, 3H), 1.29 (d, J=6.58 Hz, 6H).

Example 298

Peak-II: Synthesis of (4S)—N7-(2,2-difluorocyclopropyl)-N5-(6-methoxypyrimidin-4-1)-3,4-dihydro-1,4-methanopyrido[2,3-b][1,4]diazepine-5,7(2H)-dicarboxamide

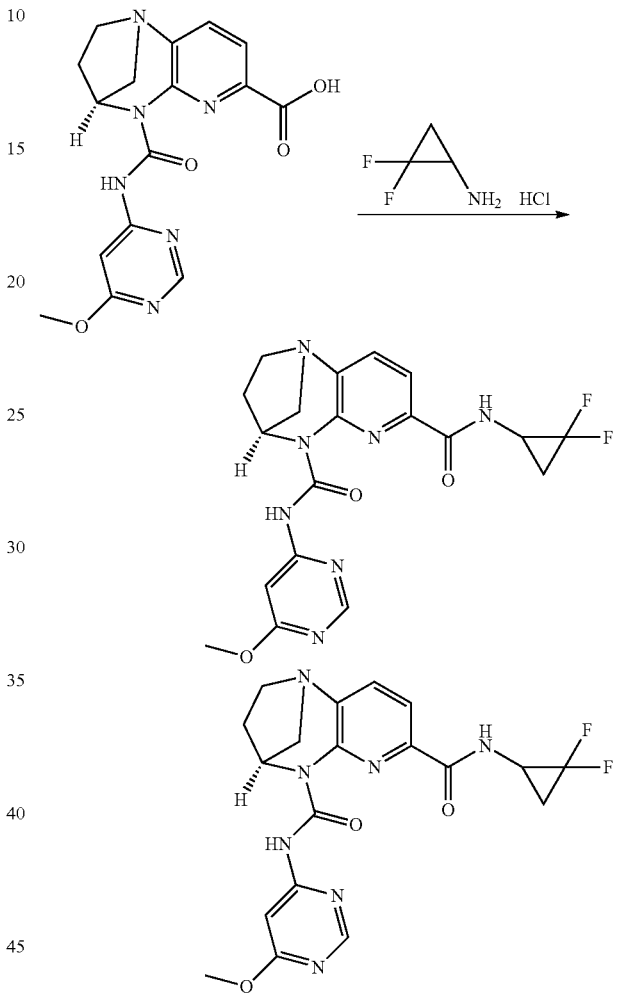

To a stirred solution of (4S)-5-((6-methoxypyrimidin-4-yl)carbamoyl)-2,3,4,5-tetrahydro-1,4-methanopyrido[2,3-b][1,4]diazepine-7-carboxylic acid (600 mg, 1.684 mmol in DMF (10 mL) were added DIPEA (1.470 mL, 8.42 mmol), HATU (1280 mg, 3.37 mmol) and 2,2-difluorocyclopropanamine hydrochloride (218 mg, 1.684 mmol) at RT and stirred the reaction mixture for 16 h. (TLC eluent: 5% MeOH in DCM, $R_f$: 0.1, UV active). The reaction mixture was diluted with water and extracted with ethyl acetate (2×100 mL). The combined organic layer was washed with brine solution (50 mL) and dried over anhydrous Na$_2$SO$_4$, filtered and filtrate was evaporated to get crude compound. The crude product was purified by flash column chromatography (using 100-200 silica gel eluted with 2% Methanol in DCM) to afford the desired compound as diastereomeric mixture and submitted for Chiral SFC (Chiral SFC conditions: Column/dimensions: Chiralpak AD-H (250×21) mm, 5μ, % CO solvent: 40.0%, % CO$_2$ solvent: 60.0% (100% Methanol), Total Flow: 60.0 g/min, Back Pressure: 100.0 bar, UV: 210 nm, Stack time: 5.8 min, Load/inj: 5.0 mg, Solubility: Methanol+DCM, Total No of injections: 60, Instrument details: Make/Model: Thar SFC-80). separated as peak-I and peak-II.

Peak-I (N38241-48-A2)

(4S)—N7-(2,2-difluorocyclopropyl)-N5-(6-methoxypyrimidin-4-yl)-3,4-dihydro-1,4-methanopyrido[2,3-b][1,4]diazepine-5,7(2H)-dicarboxamide (79 mg, 0.181 mmol, 10.73% yield) as a white solid. LCMS (m/z): 432.16 [M+H]+, Rt=2.08 min.

$^1$H NMR (400 MHz, CDCl$_3$): δ ppm 13.49 (s, 1H), 8.46 (s, 1H), 8.08 (br s, 1H), 7.93 (d, J=7.89 Hz, 1H), 7.72 (s, 1H), 7.43 (s, 1H), 5.68-5.51 (m, 1H), 4.00 (s, 3H), 3.61-3.43 (m, 1H), 3.26 (t, J=7.56 Hz, 3H), 3.19-2.98 (m, 1H), 2.45-2.22 (m, 1H), 2.13-1.98 (m, 2H), 1.81-1.63 (m, 1H).

Example 299

Synthesis of (4S)—N5-(4-ethynylpyridin-2-yl)-N7-((R)-1,1,1-trifluoropropan-2-yl)-3,4-dihydro-1,4-methanopyrido[2,3-b][1,4]diazepine-5,7(2H)-dicarboxamide 100-200 silica gel, column eluted at 80% ethyl acetate in n-hexane) and again purified by prep HPLC (Prep HPLC conditions: MP-A:—10 mM Ammonium Bicarbonate (Aq) MP-B: Acetonitrile Column: Xterra RP18 (19*250 mm) 10μ Method: B: 0/10, 1/10, 10/55, 11/5, 13/5 Flow: 19 ml/min Temperature: Ambient Solubility: THF+MeOH to afford pure compound (4S)—N5-(4-ethynylpyridin-2-yl)-N7-((R)-1,1,1-trifluoropropan-2-yl)-3,4-dihydro-1,4-methanopyrido[2,3-b][1,4]diazepine-5,7(2H)-dicarboxamide (720 mg, 1.604 mmol, 31.1% yield) as an off white solid. LCMS (m/z): 445.19[M+H]+, R=2.5 min.

$^1$H NMR (400 MHz, CDCl$_3$): δ 13.28 (s, 1H), 8.31-8.25 (m, 1H), 8.24-8.18 (m, 1H), 7.94 (dd, J=14.5, 8.7 Hz, 2H), 7.68 (dd, J=7.9, 0.7 Hz, 1H), 7.08 (dd, J=5.1, 1.4 Hz, 1H), 5.64 (dd, J=6.0, 3.1 Hz, 1H), 5.13-4.98 (m, 1H), 3.30-3.19 (m, 3H), 3.22-3.07 (m, 1H), 3.03 (dd, J=12.2, 3.2 Hz, 1H), 2.40-2.27 (m, 1H), 2.06 (dt, J=14.4, 7.3 Hz, 1H), 1.58 (d, J=7.1 Hz, 3H).

Example 300

Synthesis of (4S)—N5-(5-methylpyridazin-3-yl)-N7-((R)-1,1,1-trifluoropropan-2-yl)-3,4-dihydro-1,4-methanopyrido[2,3-b][1,4]diazepine-5,7(2H)-dicarboxamide

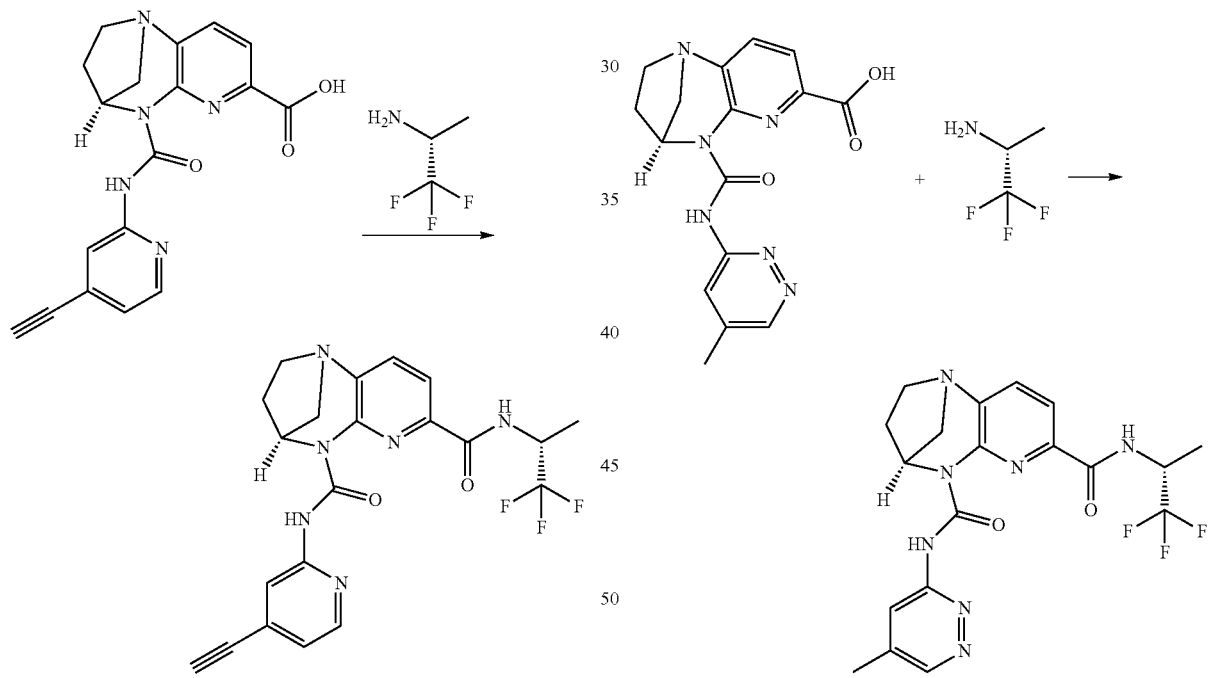

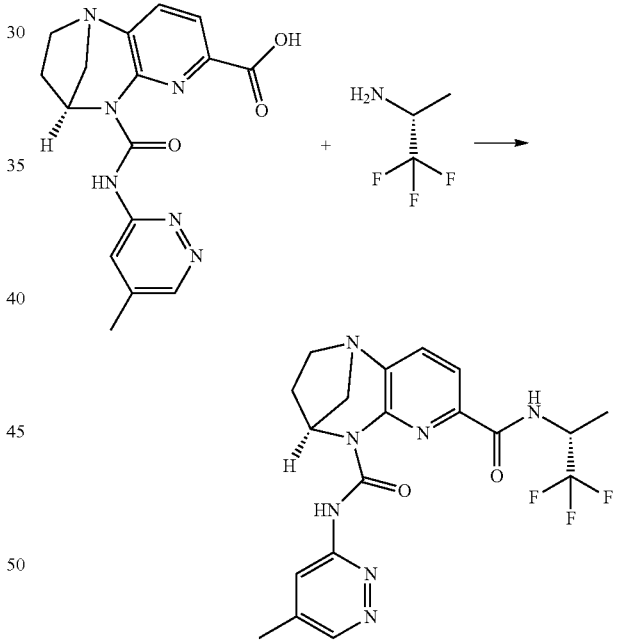

To a stirred solution of (4S)-5-((4-ethynylpyridin-2-yl)carbamoyl)-2,3,4,5-tetrahydro-1,4-methanopyrido[2,3-b][1,4]diazepine-7-carboxylic acid (1.8 g, 5.15 mmol) in DMF (10 mL) were added DIEA (4.50 mL, 25.8 mmol) and HATU (3.92 g, 10.31 mmol) were added, followed by (R)-1,1,1-trifluoropropan-2-amine (1.165 g, 10.31 mmol) was added at 0° C. then stirred at RT for 16 h. (TLC eluent: Neat ethyl acetate: R$_f$: 0.3; UV active). The reaction mixture was removed under vacuum. It was partitioned between water and ethyl acetate (2×20 mL). The combined organic layer was separated and was dried over anhydrous Na$_2$SO$_4$, filtered and filtrate was evaporated to get crude compound, then it was purified by flash column chromatography (using To a stirred solution of (4S)-5-((5-methylpyridazin-3-yl)carbamoyl)-2,3,4,5-tetrahydro-1,4-methanopyrido[2,3-b][1,4]diazepine-7-carboxylic acid (200 mg, 0.588 mmol) in DMF (5 mL) under nitrogen at RT was added (R)-1,1,1-trifluoropropan-2-amine (66.5 mg, 0.588 mmol), HATU (335 mg, 0.881 mmol) followed by DIPEA (0.616 mL, 3.53 mmol), and the reaction mixture was stirred at RT for 16 h. (TLC eluent: 10% MeOH & DCM: R$_f$—0.3; UV active). Water (15 mL) was added to the reaction mixture and extracted into EtOAc (2×15 mL). Combined organic layer was separated, dried over anhydrous sodium sulphate, filtered and filtrate was evaporated to get crude compound and the crude was purified by chromatography (GRACE using C-18 reserval column, Mobile phase A: 0.1% Formic Acid in water; B: ACN, eluent 28% B in A). Combined fractions were concentrated, basified with saturated NaHCO$_3$ solution, then extracted with DCM, DCM layer was dried over anhydrous Na$_2$SO$_4$, filtered and filtrate was evaporated to afford ((4S)—N5-(5-methylpyridazin-3-yl)-N7-((R)-1,1,1-trifluoropropan-2-yl)-3,4-dihydro-1,4-methanopyrido[2,3-b][1,4]diazepine-5,7(2H)-dicarboxamide (44 mg, 0.100 mmol, 16.95% yield) as an off white solid. LCMS (m/z): 436.22 [M+H]$^+$, R$_t$=2.08 min.

$^1$H NMR (400 MHz, CDCl$_3$): δ 13.90 (s, 1H), 8.77 (d, J=2.0 Hz, 1H), 8.21 (s, 1H), 8.14 (d, J=9.4 Hz, 1H), 7.99 (d, J=7.8 Hz, 1H), 7.70 (d, J=7.9 Hz, 1H), 5.64 (dd, J=6.2, 3.2 Hz, 1H), 5.02 (dt, J=16.1, 7.8 Hz, 1H), 3.30-3.19 (m, 1H), 3.18-3.09 (m, 1H), 3.04 (dd, J=12.2, 3.3 Hz, 1H), 2.39 (s, 3H), 2.33 (dq, J=10.0, 5.7, 5.2 Hz, 1H), 2.07 (dt, J=14.8, 7.7 Hz, 1H), 1.75 (d, J=7.1 Hz, 3H), 1.26 (s, 1H).

Example 301

Synthesis of (4S)—N5-(4-hydroxypyridin-2-yl)-N7-((R)-1,1,1-trifluoropropan-2-yl)-3,4-dihydro-1,4-methanopyrido[2,3-b][1,4]diazepine-5,7(2H)-dicarboxamide

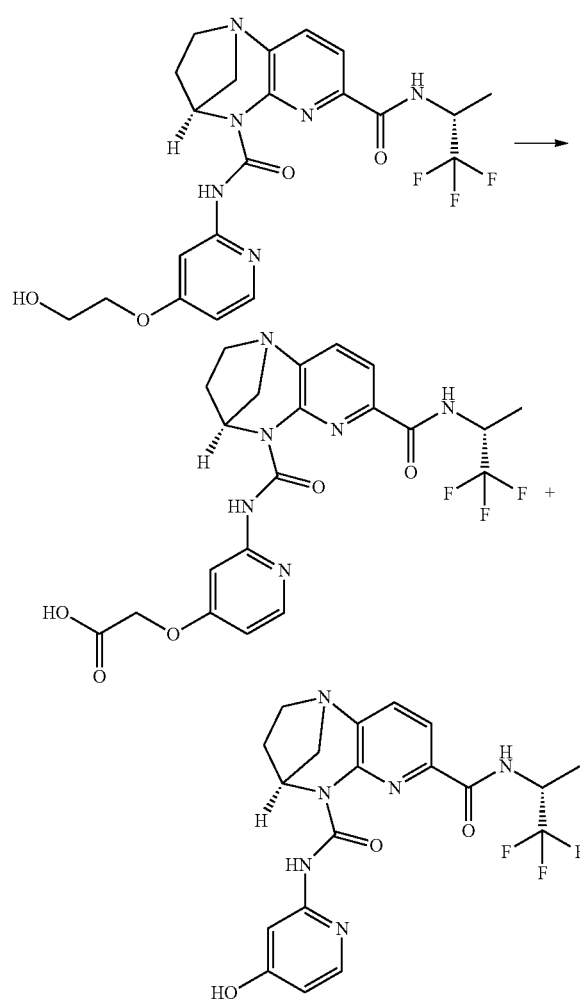

To a stirred solution of (4S)—N5-(4-(2-hydroxyethoxy)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (1 g, 2.081 mmol) in Acetone (25 mL) was added 4 mL of freshly prepared Jones reagent and stirred for 16 h. at RT. (TLC eluent: 10% MeOH in DCM: R$_f$—0.1 (polar compound), R$_f$—0.3 (non-polar compound); UV active). Evaporated the acetone and basified the obtain residue with saturated sodium bicarbonate solution and extracted with 10% MeOH in DCM (3×30 mL). The combined organic layer was washed with brine solution (30 mL), dried over anhydrous Na$_2$SO$_4$, filtered and evaporated under reduced pressure to obtain crude compound. The crude was purified by Prep-HPLC (Prep HPLC conditions: MP-A: 10 mM Ammonium bicarbonate (aq) MP-B: Acetonitrile Column: Kromasil (250*21.2 mm) 10p Method % of 0.01/38, 2.5/38, 8/80, 8.5/100, 13/100, 13.2/38, Solubility: THF+Acetonitrile+Methonal Flow: 20 ml/min, Temperature: Ambient) and isolated two compounds. Non polar compound (N38152-41-B2) (4S)—N5-(4-hydroxypyridin-2-yl)-N7-((R)-1,1,1-trifluoropropan-2-yl)-3,4-dihydro-1,4-methanopyrido[2,3-b][1,4]diazepine-5,7(2H)-dicarboxamide (121 mg, 0.276 mmol, 13.28% yield) as an off white solid. LCMS (m/z): 437.20 [M+H]; R$_t$=1.53 min.

$^1$H NMR (400 MHz, CDCl$_3$): δ 13.38 (s, 1H), 8.12 (d, J=9.4 Hz, 1H), 8.06 (d, J=5.8 Hz, 1H), 7.98 (d, J=7.9 Hz, 1H), 7.81 (s, 1H), 7.70 (d, J=7.9 Hz, 1H), 7.62 (s, 1H), 6.58 (d, J=5.6 Hz, 1H), 5.56 (dd, J=6.0, 3.1 Hz, 1H), 5.12-5.01 (m, 1H), 3.25 (dd, J=9.1, 6.9 Hz, 3H), 3.05 (dd, J=12.2, 3.3 Hz, 1H), 2.39 (tt, J=9.8, 5.5 Hz, 1H), 2.08 (dt, J=14.7, 7.8 Hz, 1H), 1.59 (d, J=7.1 Hz, 3H).

Example 302

Synthesis of (4S)—N5-(4-(3,4-dihydroxybutyl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

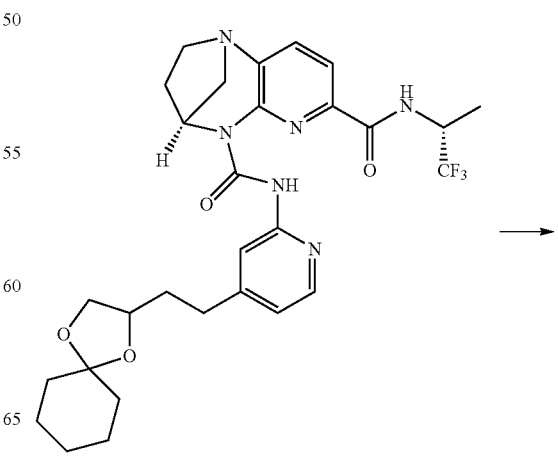

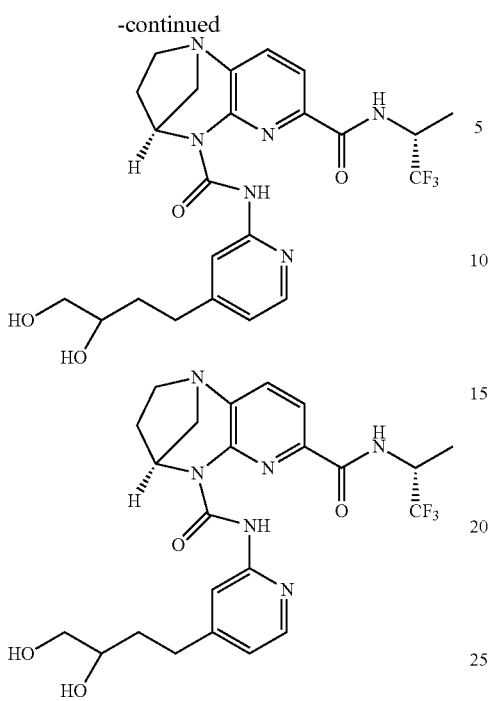

2.93-2.68 (m, 2H), 2.33 (ddt, J=14.5, 9.9, 5.3 Hz, 1H), 2.18 (s, 1H), 2.06 (dt, J=14.5, 7.5 Hz, 1H), 1.82 (q, J=7.8 Hz, 3H), 1.60 (d, J=7.1 Hz, 3H).

Example 303

Peak-II: Synthesis of (4S)—N7-(2, 2-difluorocyclopropyl)-N5-(6-methoxypyrimidin-4-yl)-3,4-dihydro-1,4-methanopyrido [2,3-b][1,4]diazepine-5,7(2H)-dicarboxamide

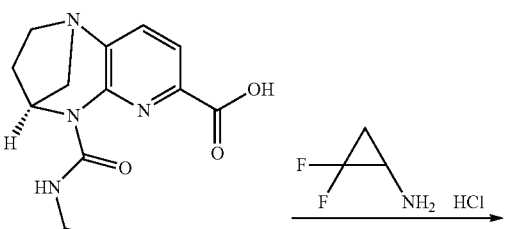

To a stirred solution of (4S)—N5-(4-(2-(1,4-dioxaspiro [4.5]decan-2-yl)ethyl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (600 mg, 1.019 mmol) in Methanol (10 mL) was added HCl (2 mL, 24.00 mmol) at RT. The resulting reaction mixture was stirred at RT for 6 h. (TLC eluent: 10% MeOH in DCM, $R_f$: 0.5). The Reaction mixture was concentrated under vacuum and obtained residue was basified with saturated sodium bicarbonate solution, extracted with DCM (3×30 mL). The combined organic layer was washed with brine solution (20 mL), dried over anhydrous $Na_2SO_4$, filtered and concentrated under reduced pressure to obtain crude compound. The crude compound was purified by flash column chromatography (using 100-200 silica gel eluted at 6% MeOH in DCM) to afford racemic compound (500 mg). The racemic compound was submitted for Chiral SFC (Chiral SFC conditions: Column/dimensions: Lux Amylose-2 (250×30) mm, 5% CO2: 50.0%, % CO solvent: 50.0%, (100% IPA), Total Flow: 60.0 g/min, Back Pressure: 100.0 bar, UV: 263 nm, Stack time: 3.9 min, Load/inj: 4.6 mg, Solubility: IPA, Total No of injections: 120, Instrument details: Make/Model: Thar SFC-80). separated as peak-I and peak-II.

Peak-I (4S)—N5-(4-(3,4-dihydroxybutyl)pyridin-2-yl)-N7-((R)-1,1,1-trifluoropropan-2-yl)-3,4-dihydro-1,4-methanopyrido [2,3-b][1,4]diazepine-5,7(2H)-dicarboxamide (142 mg, 0.278 mmol, 27.3% yield) as an off-white solid. LCMS (m/z): 509.30[M+H]$^+$, $R_t$=1.65.

$^1$H NMR (400 MHz, CDCl$_3$): δ 13.23 (s, 1H), 8.14 (d, J=5.1 Hz, 1H), 8.05 (d, J=9.2 Hz, 2H), 7.95 (d, J=8.0 Hz, 1H), 7.67 (d, J=7.9 Hz, 1H), 6.89 (dd, J=5.2, 1.5 Hz, 1H), 5.63 (dd, J=5.9, 3.1 Hz, 1H), 5.06 (dq, J=15.1, 7.3 Hz, 1H), 3.77-3.65 (m, 2H), 3.49 (t, J=9.3 Hz, 1H), 3.28-3.17 (m, 2H), 3.17-3.08 (m, 1H), 3.02 (dd, J=12.1, 3.2 Hz, 1H),

To a stirred solution of (4S)-5-((6-methoxypyrimidin-4-yl)carbamoyl)-2,3,4,5-tetrahydro-1,4-methanopyrido[2,3-b] [1,4]diazepine-7-carboxylic acid (600 mg, 1.684 mmol in DMF (10 mL) were added DIPEA (1.470 mL, 8.42 mmol), HATU (1280 mg, 3.37 mmol) and 2,2-difluorocyclopropanamine hydrochloride (218 mg, 1.684 mmol) at RT and stirred the reaction mixture for 16 h. (TLC eluent: 5% MeOH in DCM, $R_f$: 0.1, UV active). The reaction mixture was diluted with water and extracted with ethyl acetate (2×100 mL). The combined organic layer was washed with brine solution (50 mL) and dried over anhydrous $Na_2SO_4$, filtered and filtrate was evaporated to get crude compound. The crude product was purified by flash column chromatography (using 100-200 silica gel eluted with 2% Methanol in DCM) to afford the desired compound as diastereomeric mixture and submitted for Chiral SFC (Chiral SFC conditions: Column/dimensions: Chiralpak AD-H (250×21) mm, 5μ, % CO solvent: 40.0%, % $CO_2$ solvent: 60.0% (100% Methanol), Total Flow: 60.0 g/min, Back Pressure: 100.0 bar, UV: 210 nm, Stack time: 5.8 min, Load/inj: 5.0 mg, Solubility: Methanol+DCM, Total No of injections: 60, Instrument details: Make/Model: Thar SFC-80). separated as peak-I and peak-II.

Peak-II (N38241-48-B2)

(4S)—N7-(2,2-difluorocyclopropyl)-N5-(6-methoxypyrimidin-4-yl)-3,4-dihydro-1,4-methanopyrido[2,3-b][1,4]diazepine-5,7(2H)-dicarboxamide (86 mg, 0.198 mmol, 11.78% yield) as a white solid. LCMS (m/z): 432.16 $[M+H]^+$, $R_t$=2.07 min.

$^1$H NMR (400 MHz, $CDCl_3$): δ ppm 13.65-13.33 (m, 1H), 8.46 (s, 1H), 8.08 (br s, 1H), 7.93 (d, J=7.89 Hz, 1H), 7.70 (s, 1H), 7.45-7.38 (m, 1H), 5.65-5.56 (m, 1H), 4.10-3.89 (m, 3H), 3.73-3.38 (m, 1H), 3.31-2.90 (m, 3H), 3-2.8 (m, 1H), 2.46-2.15 (m, 1H), 2.08-1.82 (m, 2H), 1.81-1.51 (m, 1H).

Example 304

Synthesis of (4S)—N5-(4-(ethylcarbamoyl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

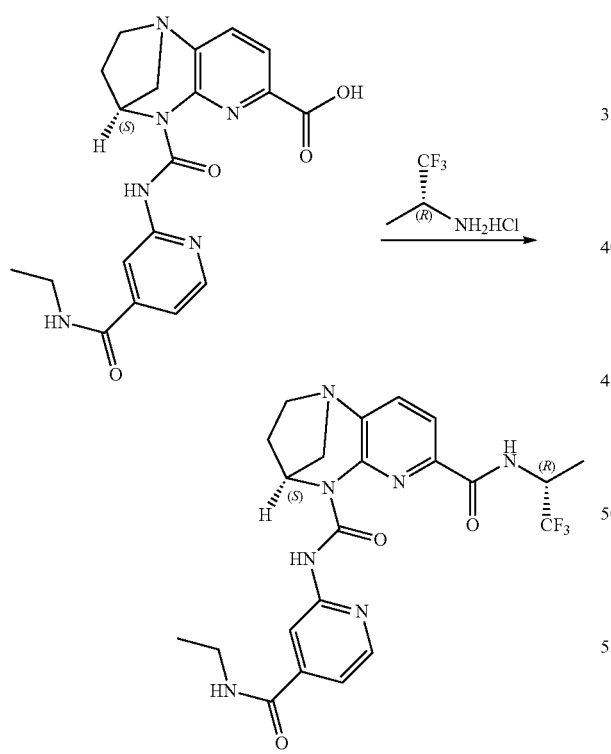

To a stirred solution of (4S)-5-((4-(ethylcarbamoyl)pyridin-2-yl)carbamoyl)-2,3,4,5-tetrahydro-1,4-methanopyrido[2,3-b][1,4]diazepine-7-carboxylic acid (400 mg, 1.009 mmol) in DMF (10 mL) were added TEA (0.703 mL, 5.05 mmol) and HATU (767 mg, 2.018 mmol) followed by (R)-1,1,1-trifluoropropan-2-amine hydrochloride (453 mg, 3.03 mmol) at 0° C. then stirred at RT for 16 h. (TLC eluent: Neat ethyl acetate: $R_f$: 0.3; UV active). The reaction mixture was evaporated under vacuum and partitioned between water and ethyl acetate (2×10 mL). The combined organic layer was separated and dried over anhydrous $Na_2SO_4$, filtered and filtrate was evaporated to afford crude compound. The crude was triturated with n-pentane (15 ml) to afford pure compound (4S)—N5-(4-(ethylcarbamoyl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (240 mg, 0.474 mmol, 47.0% yield) as an off white solid. LCMS (m/z): 492.20 $[M+H]^+$, $R_t$=2.03 min.

$^1$H NMR (400 MHz, $CDCl_3$): δ 13.44 (s, 1H), 8.43-8.33 (m, 2H), 7.98 (d, J=7.9 Hz, 1H), 7.90 (d, J=9.6 Hz, 1H), 7.70 (d, J=7.9 Hz, 1H), 7.50 (dd, J=5.2, 1.6 Hz, 1H), 6.34 (s, 1H), 5.63 (dd, J=6.0, 3.1 Hz, 1H), 5.14-4.98 (m, 1H), 3.58-3.45 (m, 2H), 3.33-3.20 (m, 2H), 3.14 (d, J=12.3 Hz, 1H), 3.04 (dd, J=12.3, 3.3 Hz, 1H), 2.35 (ddt, J=14.3, 9.9, 5.4 Hz, 1H), 2.08 (dt, J=14.7, 7.7 Hz, 1H), 1.65-1.49 (m, 3H), 1.28 (t, J=7.3 Hz, 3H).

Example 305

Synthesis of (4S)—N5-(4-(cyclopropylcarbamoyl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

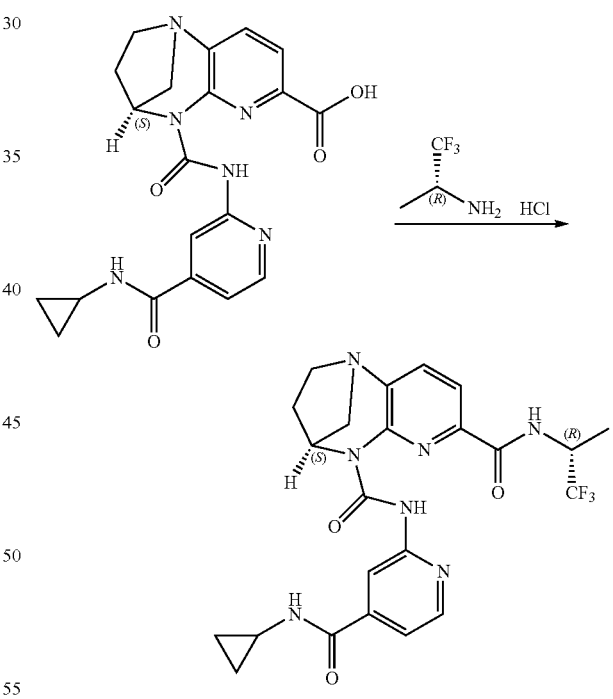

To a stirred solution of (4S)-5-((4-(cyclopropylcarbamoyl)pyridin-2-yl)carbamoyl)-2,3,4,5-tetrahydro-1,4-methanopyrido[2,3-b][1,4]diazepine-7-carboxylic acid (600 mg, 1.469 mmol) in DMF (15 mL) were added HATU (838 mg, 2.204 mmol) and DIPEA (0.770 mL, 4.41 mmol) at RT and stirred for 30 min. To this (R)-1,1,1-trifluoropropan-2-amine hydrochloride (330 mg, 2.204 mmol) was added and stirred for 16 h. at RT (TLC eluent: Neat ethyl acetate, $R_f$: 0.2, UV active). The reaction mixture was diluted with ice water and extracted with ethyl acetate (2×100 mL). The combined organic layer was washed with saturated brine solution (50 mL) and dried over anhydrous Na$_2$SO$_4$, filtered and filtrate was evaporated to get crude compound. The crude product was purified by flash column chromatography (using 100-200 silica gel eluted at 80% ethyl acetate in n-hexane) to afford the desired product (4S)—N5-(4-(cyclopropylcarbamoyl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (60 mg, 0.119 mmol, 8.10% yield). LCMS (m/z): 504.19[M+H]$^+$, R$_t$=2.07 min.

$^1$H NMR (400 MHz, CDCl$_3$): δ 13.43 (s, 1H), 8.39-8.30 (m, 2H), 7.98 (d, J=7.9 Hz, 1H), 7.90 (d, J=9.5 Hz, 1H), 7.70 (d, J=7.9 Hz, 1H), 7.49 (dd, J=5.2, 1.6 Hz, 1H), 6.42 (s, 1H), 5.63 (dd, J=5.9, 3.2 Hz, 1H), 5.07-5.03 (m, 1H), 3.25 (s, 3H), 3.13 (d, J=12.3 Hz, 1H), 2.91 (dt, J=7.1, 3.5 Hz, 1H), 2.29-2.25 (m, 1H), 2.14-2.03 (m, 1H), 1.59 (d, J=7.1 Hz, 3H), 0.90 (q, J=6.9 Hz, 2H), 0.67 (s, 2H).

Example 306

Synthesis of (4S)—N7-(2,2-difluorocyclopropyl)-N5-(4-((R)-2,3-dihydroxypropoxy) pyridin-2-yl)-3,4-dihydro-1,4-methanopyrido[2,3-b][1,4]diazepine-5,7(2H)-dicarboxamide

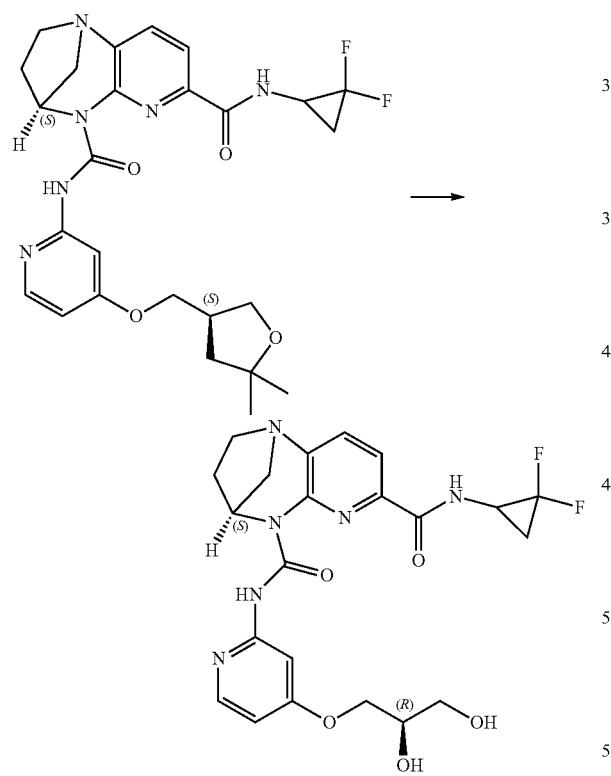

To a stirred solution of (4S)—N7-(2,2-difluorocyclopropyl)-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide (220 mg, 0.415 mmol) in Methanol (10 mL) was added hydrochloric acid (0.025 mL, 0.829 mmol) at 0° C., drop wise over a period of 5 min. and the reaction mixture was stirred at room temp for 2 h. (TLC eluent: 5% MeOH in DCM: R$_f$—0.1; UV active) then evaporated the solvent. The reaction mixture was neutralized with sodium bicarbonate solution and filtered the obtain solid, triturated with diethylether (20 ml) and n-pentane (20 ml) to afford pure compound (4S)—N7-(2,2-difluorocyclopropyl)-N5-(4-((R)-2,3-dihydroxypropoxy)pyridin-2-yl)-3,4-dihydro-1,4-methanopyrido[2,3-b][1,4]diazepine-5,7(2H)-dicarboxamide (100 mg, 0.204 mmol, 49.1% yield) as an off white solid. LCMS (m/z): 491.23 [M+H]$^+$, Rt=1.33 min.

$^1$H NMR (400 MHz, CDCl$_3$): δ 13.42 (s, 1H), 8.31 (s, 1H), 8.07 (d, J=5.9 Hz, 1H), 7.90 (d, J=7.9 Hz, 1H), 7.73 (d, J=2.4 Hz, 1H), 7.67 (d, J=7.9 Hz, 1H), 6.61 (dd, J=6.0, 2.4 Hz, 1H), 5.58 (dd, J=6.1, 3.1 Hz, 1H), 4.24-4.12 (m, 3H), 3.81-3.72 (m, 1H), 3.51 (s, 1H), 3.24 (s, 2H), 3.28-3.15 (m, 1H), 3.13 (d, J=12.3 Hz, 1H), 3.02 (dd, J=12.2, 3.2 Hz, 1H), 2.61 (s, 1H), 2.33 (ddt, J=14.4, 10.1, 5.5 Hz, 1H), 2.11-2.02 (m, 3H), 2.05-1.87 (m, 1H).

Example 307

Synthesis of (4S)—N5-(4-morpholinopyridin-2-yl)-N7-((R)-1,1,1-trifluoropropan-2-yl)-3,4-dihydro-1,4-methanopyrido[2,3-b][1,4]diazepine-5,7(2H)-dicarboxamide

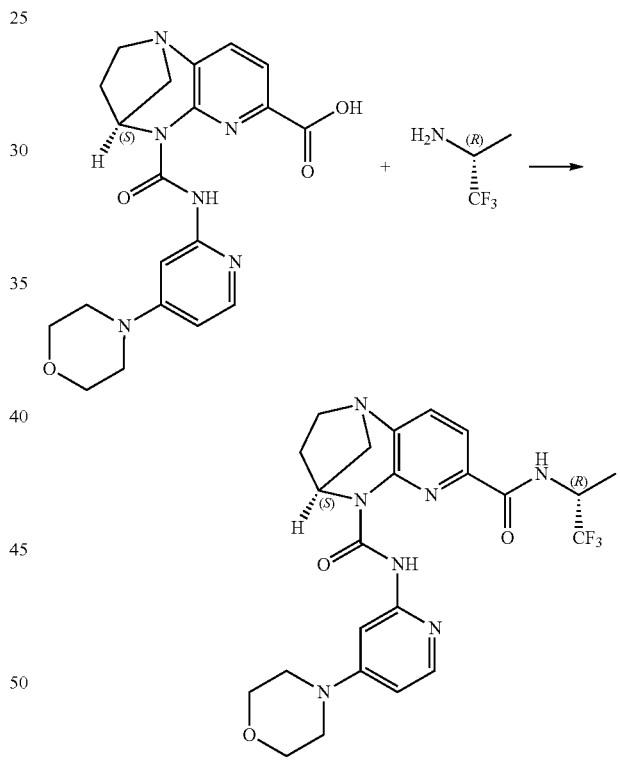

To a stirred solution of (4S)-5-((4-morpholinopyridin-2-yl)carbamoyl)-2,3,4,5-tetrahydro-1,4-methanopyrido[2,3-b][1,4]diazepine-7-carboxylic acid (300 mg, 0.731 mmol), HATU (417 mg, 1.096 mmol) in N,N-Dimethylformamide (10 mL) was added DIPEA (0.511 mL, 2.92 mmol) at rt and followed by (R)-1,1,1-trifluoropropan-2-amine hydrochloride (164 mg, 1.096 mmol) was added to the reaction mixture at 0° C. The reaction mixture was stirred at 28° C. for 16 h. (TLC eluent: 10% MeOH in DCM: R$_f$—0.3; UV active). The reaction mixture was poured in to water (30 mL) and extracted with EtOAc (3×20 mL). The combined organic layer was washed with brine solution, dried over anhydrous Na$_2$SO$_4$, filtered and filtrate was evaporated to get crude compound. The crude compound was purified by column chromatography (Silica gel: Neutral alumina, Eluent: 30% EtOAc in pet ether) to afford the desired product (4S)—N5-(4-morpholinopyridin-2-yl)-N7-((R)-1,1,1-trifluoropropan-2-yl)-3,4-dihydro-1,4-methanopyrido[2,3-b][1,4]diazepine-5,7(2H)-dicarboxamide (215 mg, 0.419 mmol, 57.3% yield) as an off white solid. LCMS (m/z): 506.28 [M+H]$^+$, R$_f$=1.65 min.

$^1$H NMR (400 MHz, CDCl$_3$): δ 13.18 (s, 1H), 8.18 (d, J=9.5 Hz, 1H), 7.99-7.91 (m, 2H), 7.70-7.62 (m, 2H), 6.43 (dd, J=6.1, 2.5 Hz, 1H), 5.60 (dd, J=6.0, 3.1 Hz, 1H), 5.05 (dp, J=9.2, 7.3 Hz, 1H), 3.87-3.80 (m, 4H), 3.36 (dd, J=5.9, 4.0 Hz, 4H), 3.30-3.07 (m, 3H), 3.02 (dd, J=12.1, 3.2 Hz, 1H), 2.39-2.25 (m, 1H), 2.13-2.00 (m, 1H), 1.60 (s, 3H).

Example 308

Synthesis of (4S)—N5-(4-(2H-tetrazol-5-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

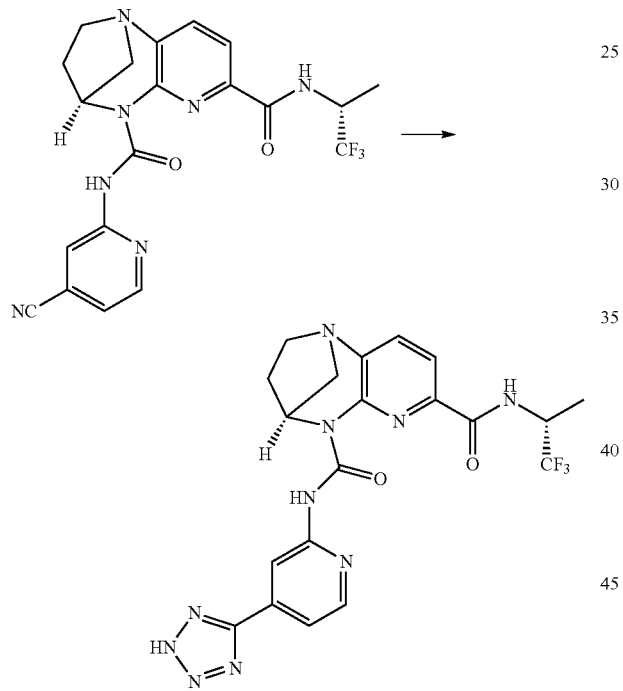

To a solution of (4S)—N5-(4-cyanopyridin-2-yl)-N7-((R)-1,1,1-trifluoropropan-2-yl)-3,4-dihydro-1,4-methanopyrido[2,3-b][1,4]diazepine-5,7(2H)-dicarboxamide (400 mg, 0.898 mmol) in 1,4-Dioxane (10 mL) at 0° C. was added azidotributylstannane (2.465 mL, 8.98 mmol) and stirred in a sealed tube at 110° C. for 16 h. (TLC system: 20% MeOH in DCM, Rf value: 0.5). The reaction mixture was cooled to RT and concentrated under reduced pressure and residue was triturated with diethylether (15 mL) and pentane (2×25 ml). The resultant crude was purified by column chromatography (Grace C-18: eluted with 50% MeOH in 1% aq ammonium bicarbonate) to afford (4S)—N5-(4-(2H-tetrazol-5-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (50 mg, 0.101 mmol, 11.28% yield) as an off white solid. LCMS (m/z): 489.25 [M+H]$^+$. Rt=1.95 min.

$^1$H NMR (400 MHz, DMSO-d$_6$): δ ppm 13.17 (s, 1H), 8.79 (s, 1H), 8.45 (d, J=5.26 Hz, 1H), 8.26 (br d, J=8.99 Hz, 1H), 7.69-7.80 (m, 3H), 5.51 (dd, J=6.03, 2.96 Hz, 1H), 4.91-5.04 (m, 1H), 3.07-3.24 (m, 4H), 2.16-2.44 (m, 1H), 1.91-2.16 (m, 1H), 1.54 (d, J=7.02 Hz, 3H)

Example 309

Synthesis of (4S)—N5-(4-((2-hydroxyethyl)amino)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

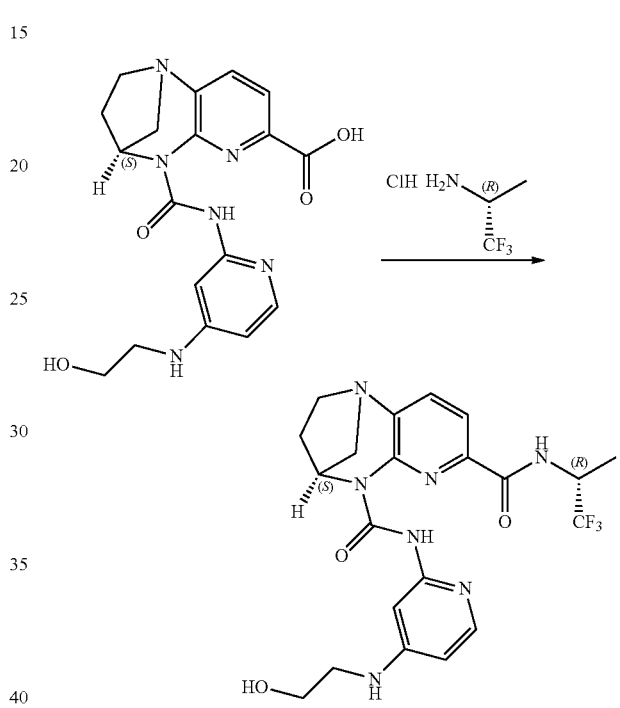

To a stirred solution of (4S)-5-((4-((2-hydroxyethyl)amino)pyridin-2-yl)carbamoyl)-2,3,4,5-tetrahydro-1,4-methanopyrido[2,3-b][1,4]diazepine-7-carboxylic acid (400 mg, 1.041 mmol), HATU (594 mg, 1.561 mmol) and DIPEA (0.545 mL, 3.12 mmol) in DMF (15 mL) was added (R)-1,1,1-trifluoropropan-2-amine hydrochloride (233 mg, 1.561 mmol) at room temperature and stirred the reaction mixture at room temp for 16 h. (TLC: neat ethyl acetate, R$_f$ value: 0.2, UV active). The reaction mixture was diluted with water and extracted with EtOAc (100 mL×2). The combined organic layer was washed with saturated brine solution (50 mL) and dried over anhydrous Na$_2$SO$_4$, filtered and filtrate was evaporated to get crude compound. The crude product was purified by flash column chromatography (using 100-200 silica gel, compound eluted at 80% ethyl acetate in n-hexane) to afford the desired product (4S)—N5-(4-((2-hydroxyethyl)amino)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (50 mg, 0.102 mmol, 9.77% yield) as an off white solid. LCMS (m/z): 480.21 [M+H]$^+$, Rt=1.45 min.

$^1$H NMR (400 MHz, DMSO-d$_6$): δ ppm 12.87 (s, 1H), 8.2-8.1 (s, 1H), 7.81-7.63 (m, 3H), 7.28 (s, 1H), 6.70 (s, 1H), 6.32 (d, J=4.60 Hz, 1H), 5.43 (dd, J=5.70, 2.85 Hz, 1H), 5.06-4.95 (m, 1H), 4.74 (t, J=5.37 Hz, 1H), 3.56 (q, J=5.99

Hz, 2H), 3.21-2.99 (m, 5H), 2.98-2.84 (m, 1H), 2.26-2.15 (m, 1H), 2.02-1.88 (m, 1H), 1.52 (d, J=7.02 Hz, 3H).

Example 310

Synthesis of (4S)—N5-(3,5-difluoropyridin-2-yl)-N7-((R)-1,1,1-trifluoropropan-2-yl)-3,4-dihydro-1,4-methanopyrido[2,3-b][1,4]diazepine-5,7(2H)-dicarboxamide

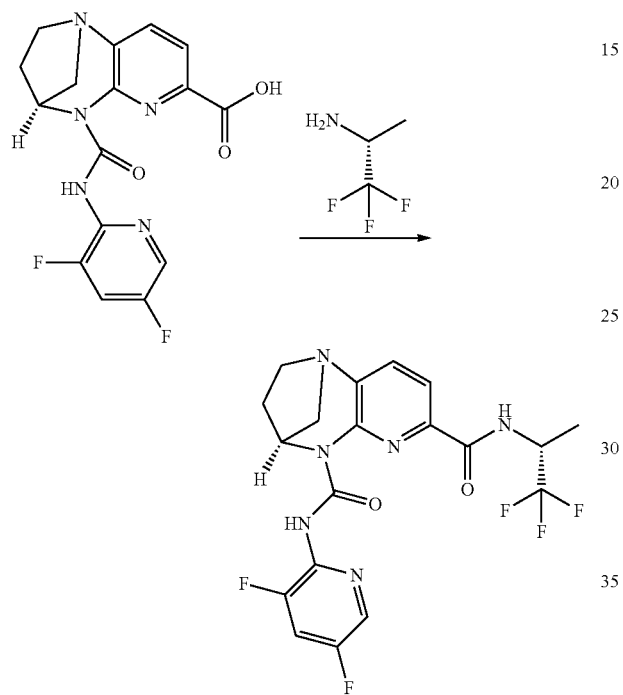

To a stirred solution of (4S)-5-((3,5-difluoropyridin-2-yl)carbamoyl)-2,3,4,5-tetrahydro-1,4-methanopyrido[2,3-b][1,4]diazepine-7-carboxylic acid (600 mg, 1.661 mmol) in pyridine (10 mL) under nitrogen at RT, was added EDC.HCl (637 mg, 3.32 mmol) and stirred for 15 min. then added (R)-1,1,1-trifluoropropan-2-amine (188 mg, 1.661 mmol) and stirring continued for 16 h. (TLC system: 5% MeOH in DCM, Rf value=0.5). The reaction mixture was concentrated under vacuum to give crude product. The crude product was purified by chromatography (GRACE instrument, C-18 reserval column, Mobile phase A: 0.1% Formic Acid in water; B: Acetonitrile, the product was eluted at 80% B in A) and collected fractions were concentrated then the product was basified with saturated NaHCO₃ solution. The obtained solid was filtered and washed with water (10 mL) and dried under high vacuum to afford pure (4S)—N5-(3,5-difluoropyridin-2-yl)-N7-((R)-1,1,1-trifluoropropan-2-yl)-3,4-dihydro-1,4-methanopyrido[2,3-b][1,4]diazepine-5,7(2H)-dicarboxamide (360 mg, 0.784 mmol, 47.2% yield) as an off-white solid. LCMS (m/z): 457.17, Rt=1.98.

$^1$H NMR (400 MHz, CDCl₃): δ ppm 12.29 (s, 1H), 8.15 (d, J=2.63 Hz, 1H), 7.87 (d, J=7.89 Hz, 1H), 7.68 (d, J=7.89 Hz, 1H), 7.29-7.44 (m, 2H), 5.62 (dd, J=5.92, 3.07 Hz, 1H), 4.87-5.03 (m, 1H), 3.12-3.30 (m, 3H), 3.00-3.05 (m, 1H), 2.26-2.40 (m, 1H), 2.01-2.15 (m, 1H), 1.42 (d, J=7.02 Hz, 3H).

Example 311

Synthesis of (4S)—N5-(4-((2-hydroxyethyl)amino)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

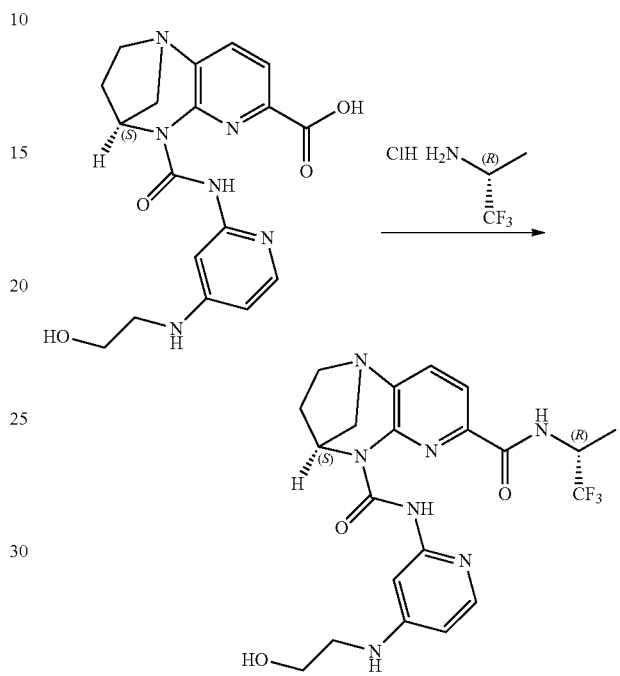

To a stirred solution of (4S)-5-((4-((2-hydroxyethyl)amino)pyridin-2-yl)carbamoyl)-2,3,4,5-tetrahydro-1,4-methanopyrido[2,3-b][1,4]diazepine-7-carboxylic acid (400 mg, 1.041 mmol), HATU (594 mg, 1.561 mmol) and DIPEA (0.545 mL, 3.12 mmol) in DMF (15 mL) was added (R)-1,1,1-trifluoropropan-2-amine hydrochloride (233 mg, 1.561 mmol) at room temperature and stirred the reaction mixture at room temp for 16 h. (TLC: neat ethyl acetate, R$_f$ value: 0.2, UV active). The reaction mixture was diluted with water and extracted with EtOAc (100 mL×2). The combined organic layer was washed with saturated brine solution (50 mL) and dried over anhydrous Na₂SO₄, filtered and filtrate was evaporated to get crude compound. The crude product was purified by flash column chromatography (using 100-200 silica gel, compound eluted at 80% ethyl acetate in n-hexane) to afford the desired product (4S)—N5-(4-((2-hydroxyethyl)amino)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (50 mg, 0.102 mmol, 9.77% yield) as an off white solid. LCMS (m/z): 480.21 [M+H]⁺, Rt=1.45 min.

$^1$H NMR (400 MHz, DMSO-d₆): δ ppm 12.87 (s, 1H), 8.2-8.1 (s, 1H), 7.81-7.63 (m, 3H), 7.28 (s, 1H), 6.70 (s, 1H), 6.32 (d, J=4.60 Hz, 1H), 5.43 (dd, J=5.70, 2.85 Hz, 1H), 5.06-4.95 (m, 1H), 4.74 (t, J=5.37 Hz, 1H), 3.56 (q, J=5.99 Hz, 2H), 3.21-2.99 (m, 5H), 2.98-2.84 (m, 1H), 2.26-2.15 (m, 1H), 2.02-1.88 (m, 1H), 1.52 (d, J=7.02 Hz, 3H).

Example 312

Synthesis of (4S)—N5-(4-morpholinopyridin-2-yl)-N7-((R)-1,1,1-trifluoropropan-2-yl)-3,4-dihydro-1,4-methanopyrido[2,3-b][1,4]diazepine-5,7(2H)-dicarboxamide

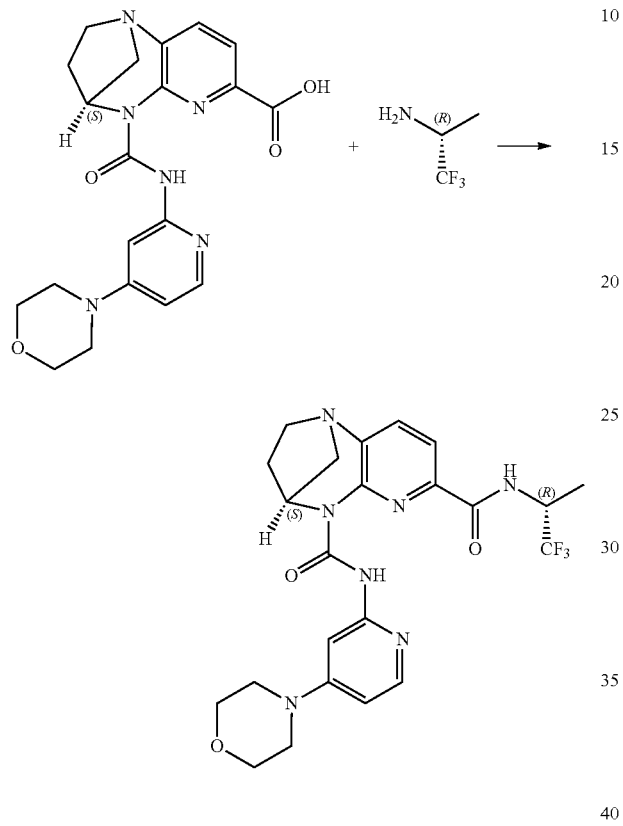

To a stirred solution of (4S)-5-((4-morpholinopyridin-2-yl)carbamoyl)-2,3,4,5-tetrahydro-1,4-methanopyrido[2,3-b][1,4]diazepine-7-carboxylic acid (300 mg, 0.731 mmol), HATU (417 mg, 1.096 mol) in N,N-Dimethylformamide (10 mL) was added DIPEA (0.511 mL, 2.92 mmol) at rt and followed by (R)-1,1,1-trifluoropropan-2-amine hydrochloride (164 mg, 1.096 mmol) was added to the reaction mixture at 0° C. The reaction mixture was stirred at 28° C. for 16 h. (TLC eluent: 10% MeOH in DCM: $R_f$—0.3; UV active). The reaction mixture was poured in to water (30 mL) and extracted with EtOAc (3×20 mL). The combined organic layer was washed with brine solution, dried over anhydrous $Na_2SO_4$, filtered and filtrate was evaporated to get crude compound. The crude compound was purified by column chromatography (Silica gel: Neutral alumina, Eluent: 30% EtOAc in pet ether) to afford the desired product (4S)—N5-(4-morpholinopyridin-2-yl)-N7-((R)-1,1,1-trifluoropropan-2-yl)-3,4-dihydro-1,4-methanopyrido[2,3-b][1,4]diazepine-5,7(2H)-dicarboxamide (215 mg, 0.419 mol, 57.3% yield) as an off white solid. LCMS (m/z): 506.28 [M+H]$^+$, $R_f$=1.65 min.

$^1$H NMR (400 MHz, $CDCl_3$): δ 13.18 (s, 1H), 8.18 (d, J=9.5 Hz, 1H), 7.99-7.91 (m, 2H), 7.70-7.62 (m, 2H), 6.43 (dd, J=6.1, 2.5 Hz, 1H), 5.60 (dd, J=6.0, 3.1 Hz, 1H), 5.05 (dp, J=9.2, 7.3 Hz, 1H), 3.87-3.80 (m, 4H), 3.36 (dd, J=5.9, 4.0 Hz, 4H), 3.30-3.07 (m, 3H), 3.02 (dd, J=12.1, 3.2 Hz, 1H), 2.39-2.25 (m, 1H), 2.13-2.00 (m, 1H), 1.60 (s, 3H).

Example 313

Synthesis of (4S)—N5-(4-(2H-tetrazol-5-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide To a solution of (4S)—N5-(4-cyanopyridin-2-yl)-N7-((R)-1,1,1-trifluoropropan-2-yl)-3,4-dihydro-1,4-methanopyrido[2,3-b][1,4]diazepine-5,7(2H)-dicarboxamide (400 mg, 0.898 mmol) in 1,4-Dioxane (10 mL) at 0° C. was added azidotributylstannane (2.465 mL, 8.98 mmol) and stirred in a sealed tube at 110° C. for 16 h. (TLC system: 20% MeOH in DCM, Rf value: 0.5). The reaction mixture was cooled to RT and concentrated under reduced pressure and residue was triturated with diethylether (15 mL) and pentane (2×25 ml). The resultant crude was purified by column chromatography (Grace C-18: eluted with 50% MeOH in 1% aq ammonium bicarbonate) to afford (4S)—N5-(4-(2H-tetrazol-5-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (50 mg, 0.101 mmol, 11.28% yield) as an off white solid. LCMS (m/z): 489.25 [M+H]$^+$. Rt=1.95 min.

$^1$H NMR (400 MHz, DMSO-$d_6$): δ ppm 13.17 (s, 1H), 8.79 (s, 1H), 8.45 (d, J=5.26 Hz, 1H), 8.26 (br d, J=8.99 Hz, 1H), 7.69-7.80 (m, 3H), 5.51 (dd, J=6.03, 2.96 Hz, 1H), 4.91-5.04 (m, 1H), 3.07-3.24 (m, 4H), 2.16-2.44 (m, 1H), 1.91-2.16 (m, 1H), 1.54 (d, J=7.02 Hz, 3H)

Example 314

Synthesis of (4S)—N5-(4-((2-hydroxyethyl)amino)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

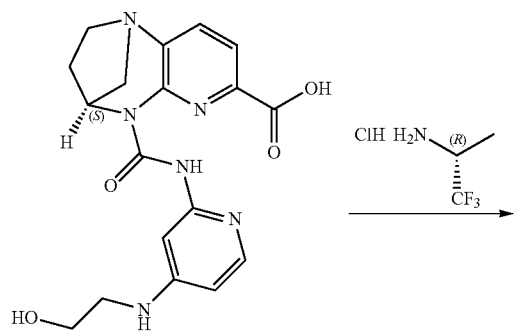

To a stirred solution of (4S)-5-((4-((2-hydroxyethyl)amino)pyridin-2-yl)carbamoyl)-2,3,4,5-tetrahydro-1,4-methanopyrido[2,3-b][1,4]diazepine-7-carboxylic acid (400 mg, 1.041 mmol), HATU (594 mg, 1.561 mmol) and DIPEA (0.545 mL, 3.12 mmol) in DMF (15 mL) was added (R)-1,1,1-trifluoropropan-2-amine hydrochloride (233 mg, 1.561 mmol) at room temperature and stirred the reaction mixture at room temp for 16 h. (TLC: neat ethyl acetate, $R_f$ value: 0.2, UV active). The reaction mixture was diluted with water and extracted with EtOAc (100 mL×2). The combined organic layer was washed with saturated brine solution (50 mL) and dried over anhydrous $Na_2SO_4$, filtered and filtrate was evaporated to get crude compound. The crude product was purified by flash column chromatography (using 100-200 silica gel, compound eluted at 80% ethyl acetate in n-hexane) to afford the desired product (4S)—N5-(4-((2-hydroxyethyl)amino)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (50 mg, 0.102 mmol, 9.77% yield) as an off white solid. LCMS (m/z): 480.21 [M+H]$^+$, Rt=1.45 min.

$^1$H NMR (400 MHz, DMSO-d$_6$): δ ppm 12.87 (s, 1H), 8.2-8.1 (s, 1H), 7.81-7.63 (m, 3H), 7.28 (s, 1H), 6.70 (s, 1H), 6.32 (d, J=4.60 Hz, 1H), 5.43 (dd, J=5.70, 2.85 Hz, 1H), 5.06-4.95 (m, 1H), 4.74 (t, J=5.37 Hz, 1H), 3.56 (q, J=5.99 Hz, 2H), 3.21-2.99 (m, 5H), 2.98-2.84 (m, 1H), 2.26-2.15 (m, 1H), 2.02-1.88 (m, 1H), 1.52 (d, J=7.02 Hz, 3H).

Example 315

Synthesis of (4S)—N7-allyl-N5-(4-((R)-2,3-dihydroxypropoxy)pyridin-2-yl)-3,4-dihydro-1,4-methanopyrido[2,3-b][1,4]diazepine-5,7(2H)-dicarboxamide

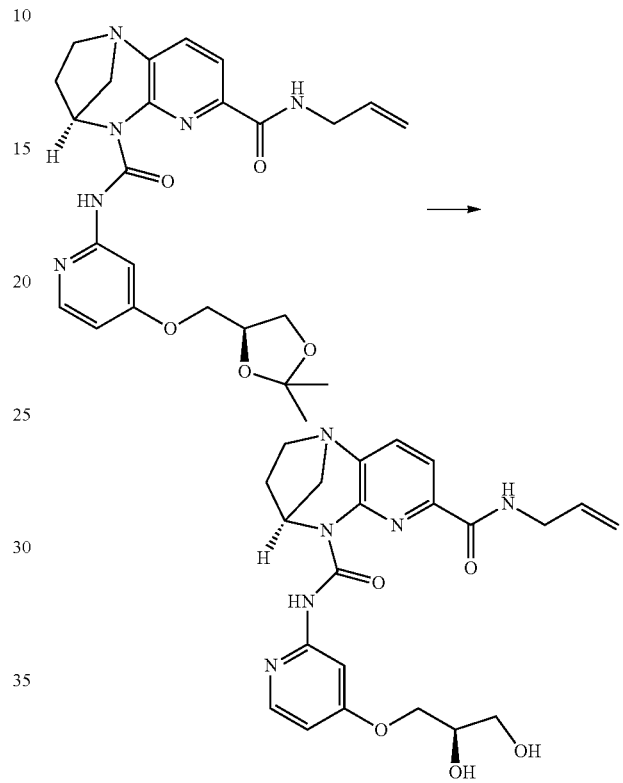

To a stirred solution of (4S)—N7-allyl-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide (500 mg, 1.011 mmol) in methanol (10 mL) at RT was added 2M HCl (0.75 mL, 1.500 mmol) and stirred for 3 h. (TLC system: 5% MeOH in DCM, Rf value: 0.2). Reaction mixture was concentrated to remove methanol completely and basified the reaction mixture with saturated $NaHCO_3$ (15 mL) solution. The resultant solid was filtered, washed with water (20 mL) and dried under high vacuum to get the crude compound as a solid. The solid product was triturated with diethylether (10 mL), filtered and dried to afford (4S)—N7-allyl-N5-(4-((R)-2,3-dihydroxypropoxy)pyridin-2-yl)-3,4-dihydro-1,4-methanopyrido[2,3-b][1,4]diazepine-5,7(2H)-dicarboxamide (400 mg, 0.877 mmol, 87% yield) as an off-white solid. LCMS (m/z): 455.19 [M+H]s, Rt=1.24 min $^1$H NMR (400 MHz, CDCl$_3$): δ ppm 13.68 (s, 1H), 8.36 (br s, 1H), 8.02 (d, J=5.92 Hz, 1H), 7.90 (d, J=7.89 Hz, 1H), 7.57-7.79 (m, 2H), 6.56 (dd, J=5.81, 2.30 Hz, 1H), 5.84-6.11 (m, 1H), 5.57 (br dd, J=5.81, 2.96 Hz, 1H), 5.23-5.43 (m, 1H), 5.17 (br d, J=10.08 Hz, 1H), 4.07-4.27 (m, 5H), 3.85 (br d, J=10.08 Hz, 1H), 3.76 (br d, J=10.08 Hz, 1H), 3.08-3.32 (m, 3H), 2.86-3.08 (m, 1H), 2.69 (br s, 1H), 2.32 (ddt, J=14.47, 9.48, 5.01, 5.01 Hz, 1H), 2.15 (br s, 1H), 2.05 (dt, J=14.36, 7.29 Hz, 1H).

Example 316

Synthesis of (4S)-8-chloro-N5-(6-methyl-1H-pyrazolo[3,4-b]pyridin-3-yl)-N7-((R)-1,1,1-trifluoropropan-2-yl)-3,4-dihydro-1,4-methanopyrido[2,3-b][1,4]diazepine-5,7(2H)-dicarboxamide

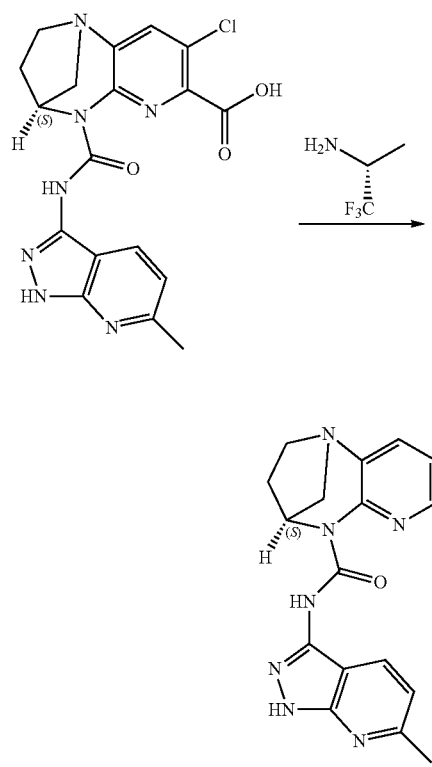

To a stirred solution of (4S)-8-chloro-5-(((6-methyl-1H-pyrazolo[3,4-b]pyridin-3-yl)carbamoyl)-2,3,4,5-tetrahydro-1,4-methanopyrido[2,3-b][1,4]diazepine-7-carboxylic acid (850 mg, 2.054 mmol) in pyridine (25 mL), at 0° C. under nitrogen was added EDC (1181 mg, 6.16 mmol) followed by (R)-1,1,1-trifluoropropan-2-amine (465 mg, 4.11 mmol) and stirred for 2 h. (TLC eluent: 10% MeOH in DCM, R$_f$—0.3; UV active). Water (100 ml) was added to the reaction mixture and compound was extracted with Ethylacetate (2×50 ml). Combined ethylacetate layer was dried oven anhydrous sodium sulfate and concentrated to get crude compound. Crude compound was purified by chromatography (silica gel 100-200 mesh, eluent 3.5% of MeOH in DCM) to get pure (4S)-8-chloro-N5-(6-methyl-1H-pyrazolo[3,4-b]pyridin-3-yl)-N7-((R)-1,1,1-trifluoropropan-2-yl)-3,4-dihydro-1,4-methanopyrido[2,3-b][1,4]diazepine-5,7(2H)-dicarboxamide (223 mg, 0.434 mmol, 21.12% yield) as an off white solid. LCMS (m/z): 509.1 [M+H]$^+$, R$_t$=1.88 min $^1$H NMR (400 MHz, DMSO-d6): δ ppm 12.97 (s, 1H), 12.27 (s, 1H), 9.26 (br d, J=8.99 Hz, 1H), 8.32 (d, J=8.33 Hz, 1H), 7.82 (s, 1H), 7.02 (d, J=8.55 Hz, 1H), 5.50 (dd, J=5.81, 2.96 Hz, 1H), 4.67-4.85 (m, 1H), 3.07-3.28 (m, 3H), 2.84-3.05 (m, 1H), 2.53-2.60 (m, 3H), 2.10-2.36 (m, 1H), 1.91 (dt, J=14.09, 7.32 Hz, 1H), 1.34 (d, J=7.02 Hz, 3H)

Example 317

Synthesis of (4S)—N7-(2-amino-3,3,3-trifluoropropyl)-N5-(4-((R)-2,3-dihydroxypropoxy)pyridin-2-yl)-3,4-dihydro-1,4-methanopyrido[2,3-b][1,4]diazepine-5,7(2H)-dicarboxamide

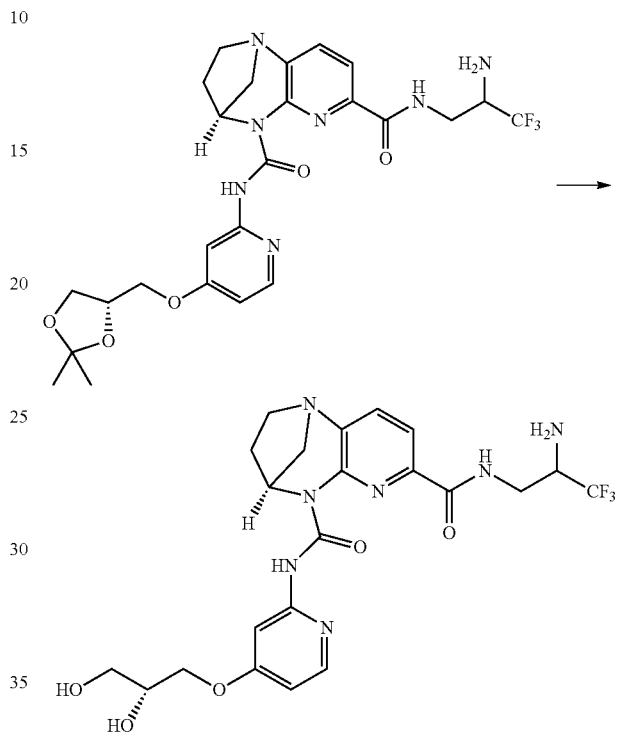

To a solution of slowest eluting isomer in chiral SFC of (4S)—N7-(2-amino-3,3,3-trifluoropropyl)-N5-(4-(((S)-2,2-dimethyl-1,3-dioxolan-4-yl)methoxy)pyridin-2-yl)-3,4-dihydro-1,4-methanopyrido[2,3-b][1,4]diazepine-5,7(2H)-dicarboxamide (500 mg, 0.884 mmol) in methanol (10 mL) at RT was added aq. HCl (0.077 mL, 0.884 mmol) and stirred for 2 h. (TLC system: 10% methanol in DCM, Rf value: 0.1). The reaction mixture was partitioned between saturated aq. NaHCO$_3$ solution (50 mL) and DCM (50 mL). Organic layer was separated, dried over anhydrous Na$_2$SO$_4$, filtered and filtrate was evaporated to get crude product. The crude compound was purified by flash column chromatography (Silica gel: 100-200 mesh, 10% methanol in DCM) to afford (4S)—N7-(2-amino-3,3,3-trifluoropropyl)-N5-(4-((R)-2,3-dihydroxypropoxy)pyridin-2-yl)-3,4-dihydro-1,4-methanopyrido[2,3-b][1,4]diazepine-5,7(2H)-dicarboxamide (240 mg, 0.450 mmol, 50.9% yield) as a white solid. LCMS (m/z): 526.29[M+H]$^+$, Rt=1.21 min.

$^1$H NMR (400 MHz, DMSO-d$_6$): δ ppm 13.18 (s, 1H), 8.43 (br t, J=5.70 Hz, 1H), 8.09 (d, J=5.70 Hz, 1H), 7.77-7.72 (m, 1H), 7.70-7.64 (m, 2H), 6.75 (dd, J=5.81, 2.30 Hz, 1H), 5.43 (dd, J=5.70, 3.07 Hz, 1H), 5.02 (d, J=5.26 Hz, 1H), 4.71 (t, J=5.70 Hz, 1H), 4.12 (dd, J=9.87, 3.73 Hz, 1H), 3.97 (dd, J=9.87, 6.14 Hz, 1H), 3.83 (br dd, J=9.65, 5.48 Hz, 1H), 3.74-3.56 (m, 2H), 3.51-3.38 (m, 3H), 3.22-3.02 (m, 3H), 3.00-2.94 (m, 1H), 2.29-2.10 (m, 3H), 1.98-1.84 (m, 1H).

Example 318

Synthesis of (4S)—N5-(6-(2-methyloxazol-5-yl)pyrimidin-4-yl)-N7-((R)-1,1,1-trifluoropropan-2-yl)-3,4-dihydro-1,4-methanopyrido[2,3-b][1,4]diazepine-5,7(2H)-dicarboxamide

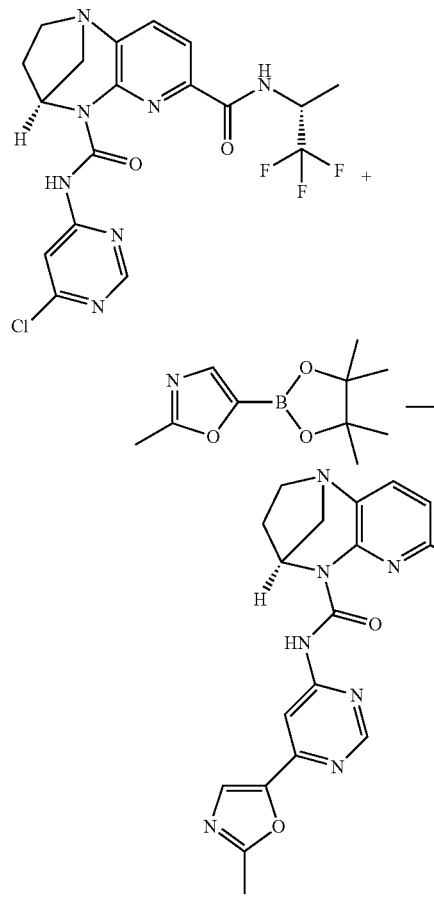

To a solution of (4S)—N5-(6-chloropyrimidin-4-yl)-N7-((R)-1,1,1-trifluoropropan-2-yl)-3,4-dihydro-1,4-methanopyrido[2,3-b][1,4]diazepine-5,7(2H)-dicarboxamide (500 mg, 1.097 mmol), 2-methyl-5-(4,4,5,5-tetramethyl-1,3,2-dioxaborolan-2-yl)oxazole (275 mg, 1.316 mmol) in 1,4-Dioxane (10 mL), Water (2.500 mL) under nitrogen at RT was added tripotassium phosphate (699 mg, 3.29 mmol) and the reaction mixture was degassed for 15 min by purging nitrogen then added PdCl$_2$(dppf)-CH$_2$Cl2 adduct (90 mg, 0.110 mmol) and heated at 80° C. for 2 hr. (TLC system: 5% Methanol in DCM, Rf: 0.3). The reaction mixture was cooled to RT and water (50 mL) was added and stirred 10 min. The resultant solid was filtered and dried to get the crude compound as an off-white solid. The crude compound was purified by preparative HPLC (Column: Kinetex phenyl hexyl (150×30 mm) 5u; mobile phase-A: 10 Mm Ammonium Bicarbonate (Aq), mobile phase-B: Acetonitrile; Method: 0/10, 1/10, 8/50, 11.5/50; Flow: 30 ml/min; Solubility: MeOH+Acetonitrile+THF+DMSO) to afford (4S)—N5-(6-(2-methyloxazol-5-yl)pyrimidin-4-yl)-N7-((R)-1,1,1-trifluoropropan-2-yl)-3,4-dihydro-1,4-methanopyrido[2,3-b][1,4]diazepine-5,7(2H)-dicarboxamide (55 mg, 0.109 mmol, 9.97% yield) as an off-white solid. LCMS (m/z): 503.22 [M+H]$^+$, Rt=2.14 min.

$^1$H NMR (400 MHz, TFA-d): δ 9.21 (s, 1H), 8.73 (s, 1H), 8.60 (br s, 1H), 8.56-8.37 (m, 1H), 8.20 (br d, J=8.3 Hz, 1H), 6.06 (br s, 1H), 5.19-5.03 (m, 1H), 4.61-4.00 (m, 4H), 3.33-2.86 (m, 4H), 2.86-2.62 (m, 1H), 1.65 (br d, J=7.0 Hz, 3H).

Example 319

Synthesis of (4S)—N5-(1-methyl-5-(2-methyloxazol-5-yl)-2-oxo-1,2-dihydropyridin-3-yl)-N7-((R)-1,1,1-trifluoropropan-2-yl)-3,4-dihydro-1,4-methanopyrido[2,3-b][1,4]diazepine-5,7(2H)-dicarboxamide

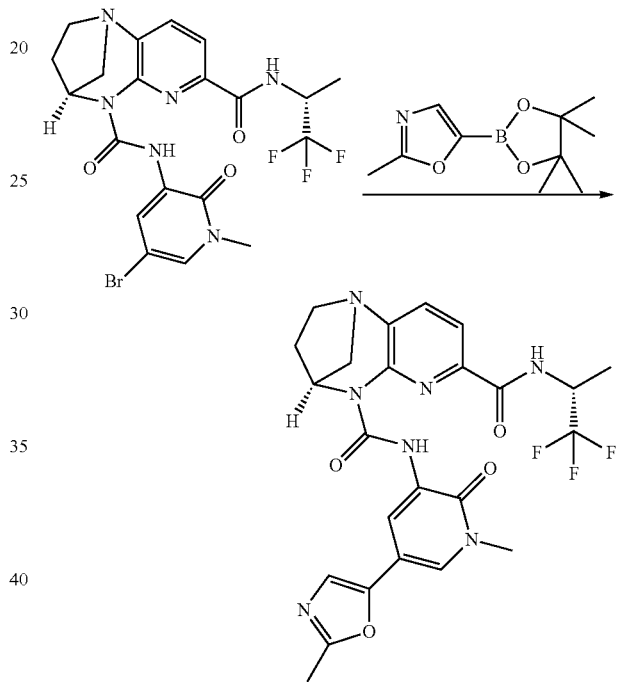

To a stirred solution of (4S)—N5-(5-bromo-1-methyl-2-oxo-1,2-dihydropyridin-3-yl)-N7-((R)-1,1,1-trifluoropropan-2-yl)-3,4-dihydro-1,4-methanopyrido[2,3-b][1,4]diazepine-5,7(2H)-dicarboxamide (800 mg, 1.511 mmol) and 2-methyl-5-(4,4,5,5-tetramethyl-1,3,2-dioxaborolan-2-yl)oxazole (474 mg, 2.267 mmol) in 1,4-Dioxane (24 mL) and Water (6 mL) was added K$_3$PO$_4$ (962 mg, 4.53 mmol). The resulting reaction mixture was degassed for 15 min. with Nitrogen. Then PdCl$_2$(dppf) (111 mg, 0.151 mmol) was added to the reaction mixture and again degassed for 5 min. The resulting reaction mixture was stirred at 100° C. for 18 h. (TLC system: 10% MeOH in DCM, R$_f$: 0.6). After 18 h. the reaction mixture was diluted with water (30 mL) and extracted with EtOAc (3×30 mL). The combined organic layer was washed with water (30 mL), brine solution (20 mL), dried over anhydrous Na$_2$SO$_4$, filtered and concentrated under reduced pressure to obtain crude compound. The crude was purified by flash column chromatography (Silica gel: 100-200 mesh, Eluent: 4% MeOH in DCM), the obtained solid was washed with mixture of diethyl ether (10 mL) and n-pentane (20 mL), filtered and dried well, to afford the desired product (4S)—N5-(1-methyl-5-(2-methyloxazol-5-yl)-2-oxo-1,2-dihydropyridin-3-yl)-N7-((R)-1,1,1-trifluoropropan-2-yl)-3,4-dihydro-1,4-methanopyrido[2,3-b][1,4]diazepine-5,7(2H)-dicarboxamide (204 mg, 0.372 mmol, 24.64% yield) as an off-white solid. LCMS (m/z): 532.27 [M+H]$^+$, R$_t$=2.22 min.

NMR (400 MHz, CDCl$_3$): δ 12.30 (s, 1H), 9.65 (d, J=9.3 Hz, 1H), 8.64 (d, J=2.3 Hz, 1H), 8.09 (d, J=8.0 Hz, 1H), 7.67 (d, J=8.0 Hz, 1H), 7.38 (d, J=2.3 Hz, 1H), 7.11 (s, 1H), 5.70 (dd, J=6.0, 3.2 Hz, 1H), 5.13 (dq, J=15.4, 7.7 Hz, 1H), 3.70 (s, 3H), 3.28-3.18 (m, 2H), 3.17-3.07 (m, 1H), 3.00 (dd, J=12.2, 3.3 Hz, 1H), 2.51 (s, 3H), 2.33 (ddt, J=14.4, 9.9, 5.1 Hz, 1H), 2.05 (dt, J=14.6, 7.7 Hz, 1H), 1.65 (d, J=7.1 Hz, 3H).

Example 320

Synthesis of (4S)—N5-(4-acetamidopyridin-2-yl)-N7-((R)-1,1,1-trifluoropropan-2-yl)-3,4-dihydro-1,4-methanopyrido[2,3-b][1,4]diazepine-5,7(2H)-dicarboxamide

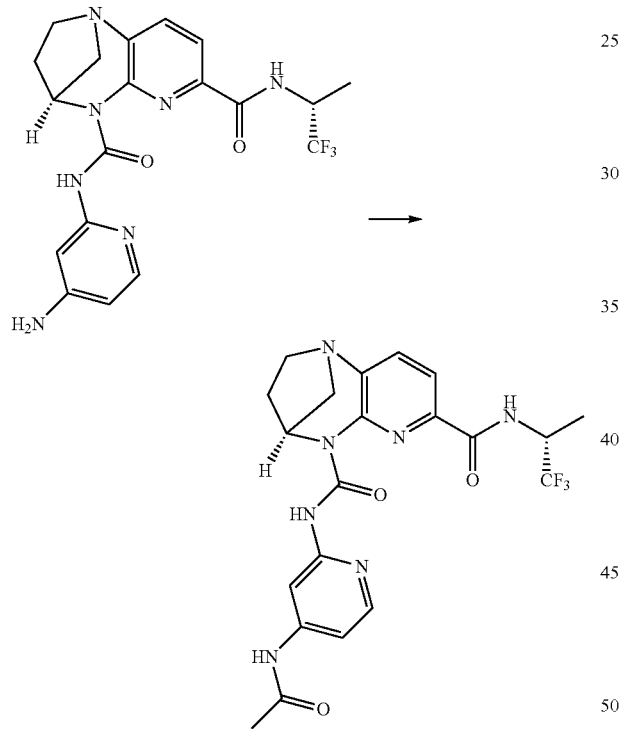

To a stirred solution of (4S)—N5-(4-aminopyridin-2-yl)-N7-((R)-1,1,1-trifluoropropan-2-yl)-3,4-dihydro-1,4-methanopyrido[2,3-b][1,4]diazepine-5,7(2H)-dicarboxamide (600 mg, 1.378 mmol) in Dichloromethane (30 mL) was added Ac$_2$O (0.780 mL, 8.27 mmol) and Et$_3$N (1.152 mL, 8.27 mmol) under nitrogen atmosphere at 0° C. and stirred the reaction mixture at RT for 65 h. (TLC: neat ethyl acetate, Rf value: 0.2, UV active). The reaction mixture was diluted with water (100 mL) and extracted with EtOAc (100 mL×2). The combined organic layer was washed with brine solution (50 mL) and dried over anhydrous Na$_2$SO$_4$, filtered and filtrate was evaporated to get crude. The crude product was purified by flash column chromatography (Silica gel: 100-200 Mesh, Eluent: 60% ethyl acetate in n-hexane) to afford the desired product (4S)—N5-(4-acetamidopyridin-2-yl)-N7-((R)-1,1,1-trifluoropropan-2-yl)-3,4-dihydro-1,4-methanopyrido[2,3-b][1,4]diazepine-5,7(2H)-dicarboxamide (160 mg, 0.331 mmol, 24.04% yield) as an off white solid. LCMS: (m/z): 478.2 [M+H]$^+$, Rt=1.87 min.

$^1$H NMR (400 MHz, CDCl$_3$): δ ppm 13.28 (s, 1H), 8.15 (d, J=4.60 Hz, 1H), 8.04-7.82 (m, 2H), 7.75-7.61 (m, 2H), 7.42 (s, 1H), 5.63 (s, 1H), 5.05 (d, J=7.23 Hz, 1H), 3.86-3.67 (m, 1H), 3.30-2.93 (m, 4H), 2.32 (s, 1H), 2.21 (s, 3H), 2.06 (d, J=7.45 Hz, 1H), 1.59 (d, J=6.14 Hz, 3H).

Example 321

Synthesis of (4S)—N5-(4-(1H-pyrazol-4-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

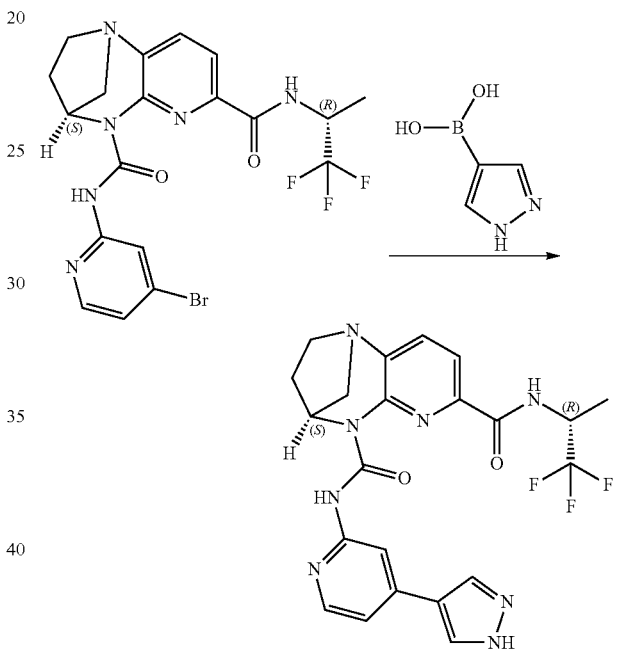

To a stirred solution of (4S)—N5-(4-bromopyridin-2-yl)-N7-((R)-1,1,1-trifluoropropan-2-yl)-3,4-dihydro-1,4-methanopyrido[2,3-b][1,4]diazepine-5,7(2H)-dicarboxamide (0.3 g, 0.601 mmol) in 1,4-Dioxane (5 mL) and Water (1 mL) at RT, in sealed tube was added (1H-pyrazol-4-yl) boronic acid (0.134 g, 1.202 mmol) and tripotassium phosphate (0.255 g, 1.202 mmol) and the reaction mixture was degassed for 4 min. Then added Pd$_2$(dba)$_3$ (0.055 g, 0.060 mmol) followed by X-phos (0.029 g, 0.060 mmol) and stirred at 100° C. for 16 h. (TLC eluent: 5% MeOH in DCM: R$_f$—0.2; UV active). The reaction mixture was cooled to room temperature, solvent evaporated under reduced pressure to get crude compound. The crude product was purified by column chromatography (using neutral alumina and eluted in 50% ethylacetate in hexane) to afford (4S)—N5-(4-(1H-pyrazol-4-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (0.1 g, 0.204 mmol, 33.9% yield) as pale yellow solid. LCMS (m/z): 487.20 [M+H]$^+$, R$_t$=1.90 min.

$^1$H NMR (400 MHz, CDCl$_3$): δ ppm 13.30 (s, 1H), 10.49 (br s, 1H), 8.33 (d, J=0.9 Hz, 1H), 8.22 (d, J=5.3 Hz, 1H), 8.10-7.92 (m, 3H), 7.69 (d, J=7.9 Hz, 1H), 7.71 (d, J=7.9 Hz, 1H), 7.26 (s, 1H), 5.65 (dd, J=3.1, 5.9 Hz, 1H), 5.21-4.99 (m, 1H), 3.41-3.11 (m, 3H), 3.02 (s, 1H), 2.42-2.22 (m, 1H), 2.09 (td, J=7.1, 14.3 Hz, 1H), 1.69-1.69 (m, 3H).

Example 322

Synthesis of (4S)—N5-(4-(1H-1,2,4-triazol-5-yl) pyridin-2-yl)-N7-((R)-1,1,1-trifluoro propan-2-yl)-3,4-dihydro-1,4-methanopyrido[2,3-b][1,4]diazepine-5,7(2H)-dicarboxamide

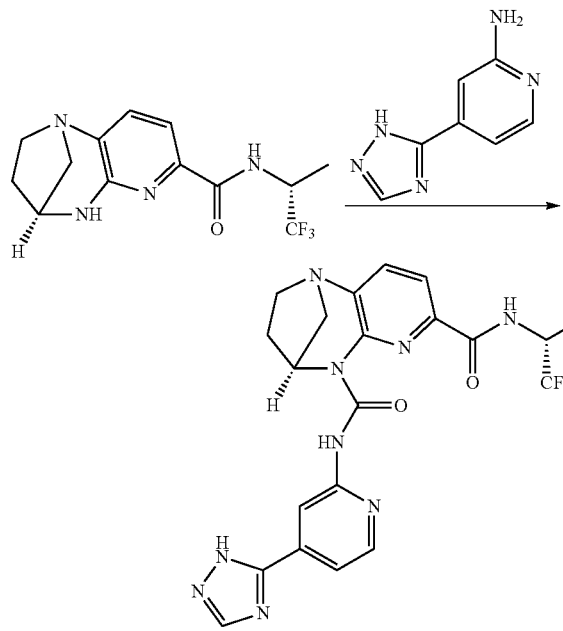

To a stirred solution of (4S)—N—((R)-1,1,1-trifluoropropan-2-yl)-2,3,4,5-tetrahydro-1,4-methanopyrido[2,3-b][1,4]diazepine-7-carboxamide (700 mg, 2.331 mmol) in Tetrahydrofuran (15 mL) were added TEA (1.625 mL, 11.66 mmol) and followed by triphosgene (692 mg, 2.331 mmol) at RT and stirred for 45 min. Then 4-(1H-1,2,4-triazol-5-yl) pyridin-2-amine (451 mg, 2.80 mmol) was added to the reaction mixture at 28° C. and stirred at 80° C. for 16 h. (TLC system: 5% MeOH\DCM. $R_f$ value: 0.3, UV) and the reaction mixture was allowed to cool to room temperature, diluted with water (25 mL), extracted with ethyl acetate (5×30 mL). The combined organic layer was washed with brine solution (20 mL), dried over anhydrous sodium sulphate, filtered and concentrated to afford crude compound. The crude compound was purified by Prep HPLC (Conditions: MP-A: 10 mM Ammonium Bicarbonate (aq), MP-B: Acetonitrile, Column: kromasil C18 (250×21.2 mm) 10u, Flow: 20 ml/min, Method: % of B/time 0/35, 15/35, 15.1/100, 20/100, 20.1/35, 24/35 Solubility: MEOH+ACN+THF) to afford the desired product (4S)—N5-(4-(1H-1,2,4-triazol-5-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (47 mg, 0.096 mmol, 4.12% yield) as an off white solid. LCMS (m/z): 488.24 [M+H]$^+$, $R_t$=1.92 min.

$^1$H NMR (400 MHz, DMSO-$d_6$): δ ppm 14.51 (s, 1H), 13.12 (s, 1H), 8.76 (s, 1H), 8.65 (s, 1H), 8.35 (d, J=4.82 Hz, 1H), 8.23 (d, J=9.43 Hz, 1H), 7.76 (s, 2H), 7.72-7.67 (m, 1H), 5.50 (dd, J=6.03, 2.74 Hz, 1H), 4.98 (dd, J=16.11, 7.34 Hz, 1H), 3.22-3.04 (m, 3H), 3.03-2.95 (m, 1H), 2.24 (d, J=9.65 Hz, 1H), 2.03-1.95 (m, 1H), 1.54 (d, J=7.02 Hz, 3H).

Example 323

Synthesis of (4S)—N5-(4-(1H-pyrazol-3-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

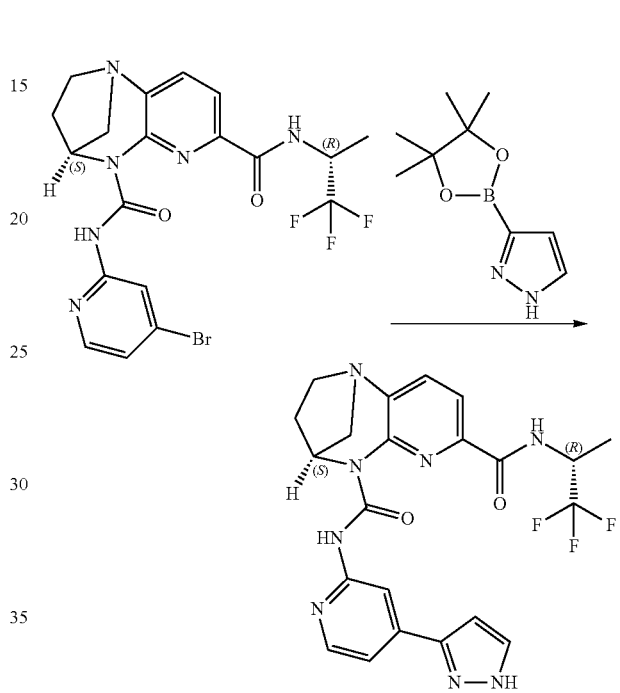

To a stirred solution of (4S)—N5-(4-bromopyridin-2-yl)-N7-((R)-1,1,1-trifluoropropan-2-yl)-3,4-dihydro-1,4-methanopyrido[2,3-b][1,4]diazepine-5,7(2H)-dicarboxamide (0.34 g, 0.681 mmol) in 1,4-Dioxane (10 mL) and Water (2 mL) at RT, in sealed tube was added 3-(4,4,5,5-tetramethyl-1,3,2-dioxaborolan-2-yl)-1H-pyrazole (0.264 g, 1.362 mmol) and tripotassium phosphate (0.361 g, 1.702 mmol) and the reaction mixture was degassed for 4 min. Then added Pd$_2$(dba)$_3$ (0.062 g, 0.068 mmol) followed by X-phos (0.032 g, 0.068 mmol) stirred at 100° C. for 16 h. (TLC eluent: 100% EtOAc: $R_f$—0.3; UV active). The reaction mixture was cooled to RT and solvent evaporated under reduced pressure to get crude product. The crude compound was purified by column chromatography (using neutral alumina and eluted in 75% ethylacetate in hexane) to afford (4S)—N5-(4-(1H-pyrazol-3-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (0.09 g, 0.182 mmol, 26.8% yield) as an off white solid. LCMS (m/z): 487.20 [M+H]$^+$, $R_t$=2.07 min.

$^1$H NMR (400 MHz, CDCl$_3$): δ ppm 13.31 (s, 1H), 10.50 (s, 1H), 8.53 (s, 1H), 8.28 (d, J=5.3 Hz, 1H), 8.09-7.93 (m, 1H), 7.75-7.61 (m, 1H), 7.54-7.46 (m, 2H), 7.26 (s, 1H), 6.83 (d, J=2.4 Hz, 1H), 5.67 (dd, J=3.2, 6.0 Hz, 1H), 5.13-5.02 (m, 1H), 3.29-3.18 (m, 2H), 3.17-3.10 (m, 1H), 3.05 (d, J=3.1 Hz, 1H), 2.34 (td, J=4.9, 9.9 Hz, 1H), 2.09 (td, J=7.1, 14.1 Hz, 1H), 1.62 (d, J=7.0 Hz, 3H).

Example 324

Synthesis of (4S)—N5-(4-(methylsulfonamido)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

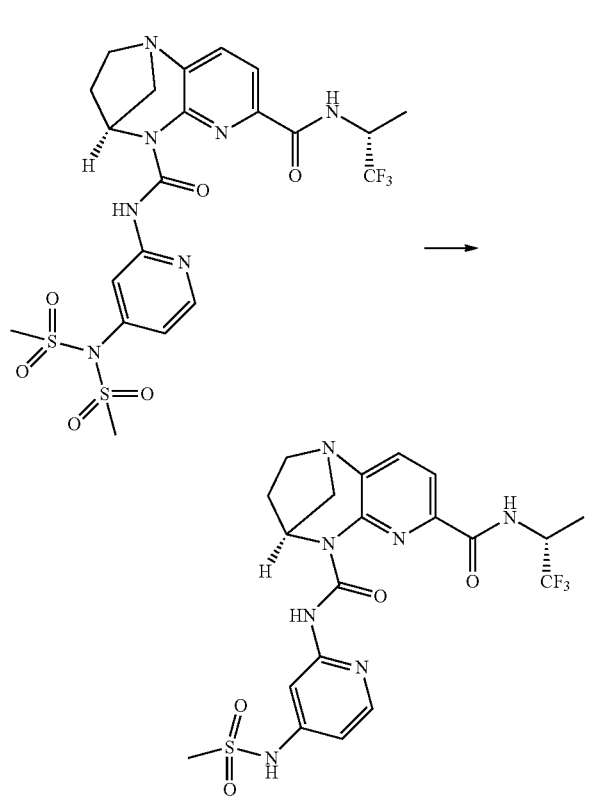

To a stirred solution of (4S)—N5-(4-(N-(methylsulfonyl)methylsulfonamido)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (200 mg, 0.338 mmol) in 1,4-Dioxane (5 mL) was added 2N NaOH solution (5 mL, 10.00 mmol) at 0° C. and stirred the reaction mixture at RT for 5 h. (TLC: neat ethyl acetate, $R_f$ value: 0.3, UV active). The reaction mixture was diluted with water (30 mL) and extracted with EtOAc (2×50 mL). The combined organic layer was washed with saturated brine solution (50 mL) and dried over anhydrous $Na_2SO_4$, filtered and filtrate was evaporated to get crude. The crude product was purified by flash column chromatography (Silica gel: 100-200 Mesh, Eluent: 80% ethyl acetate in n-hexane) to afford the desired product (4S)—N5-(4-(methylsulfonamido)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (50 mg, 0.094 mmol, 27.8% yield) as an off white solid. LCMS (m/z): 514.16 [M+H]$^+$, Rt=1.9 min.

$^1$H NMR (400 MHz, CDCl$_3$): δ ppm 13.37 (s, 1H), 8.15 (d, J=5.70 Hz, 1H), 8.07-7.76 (m, 3H), 7.69 (d, J=7.89 Hz, 1H), 7.02-6.77 (m, 2H), 5.63 (dd, J=5.81, 2.96 Hz, 1H), 5.15-4.94 (m, 1H), 3.29-3.19 (m, 2H), 3.16-3.08 (m, 3H), 3.07-3.06 (d, 1H), 3.06-2.97 (m, 1H), 2.39-2.25 (m, 1H), 2.12-1.94 (m, 1H), 1.58-1.46 (m, 3H).

Example 325

Synthesis of (4S)—N5-(4-(2-cyclopropylthiazol-5-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide

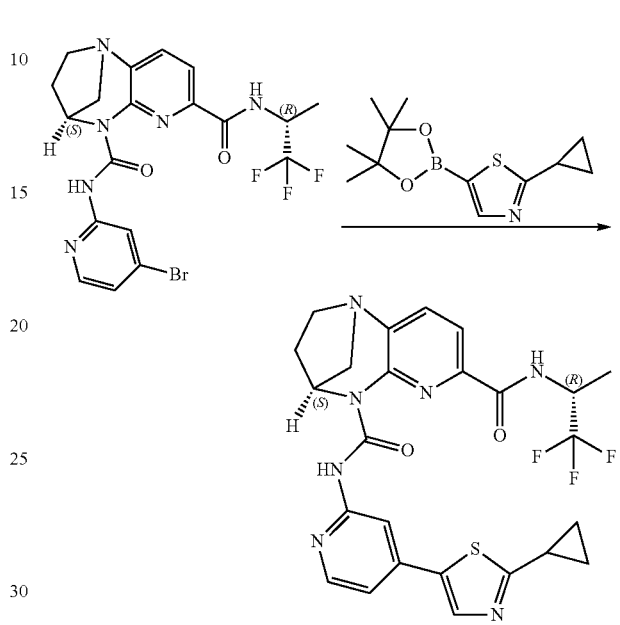

To a stirred solution of (4S)—N5-(4-bromopyridin-2-yl)-N7-((R)-1,1,1-trifluoropropan-2-yl)-3,4-dihydro-1,4-methanopyrido[2,3-b][1,4]diazepine-5,7(2H)-dicarboxamide (150 mg, 0.300 mmol) and 2-cyclopropyl-5-(4,4,5,5-tetramethyl-1,3,2-dioxaborolan-2-yl)thiazole (113 mg, 0.451 mmol) in 1,4-Dioxane (3 mL) and Water (0.5 mL) was added potassium carbonate (125 mg, 0.901 mmol), dicyclohexyl(2',4',6'-triisopropyl-[1,1'-biphenyl]-2-yl)phosphine (14.32 mg, 0.030 mmol) and the resulting mixture was degassed by purging argon for 45 min. then added Pd(OAc)$_2$ (33.7 mg, 0.150 mmol) and stirred at 100° C. for 1 h in MW-150 mW. (TLC eluent: 5% MeOH in DCM, $R_f$—0.3, UV active). Reaction mixture was cooled to room temperature then added water (80 mL) to the reaction and the aqueous layer was extracted with ethyl acetate (2×50 mL). Combined organic layer was dried over sodium sulphate, filtered and concentrated under reduced pressure to get crude compound. Crude compound was purified chromatography (Silicagel 100-200, eluted in 2% MeOH in DCM) to afford (4S)—N5-(4-(2-cyclopropylthiazol-5-yl)pyridin-2-yl)-N7-((R)-1,1,1-trifluoropropan-2-yl)-3,4-dihydro-1,4-methanopyrido[2,3-b][1,4]diazepine-5,7(2H)-dicarboxamide (8 mg, 0.014 mmol, 4.81% yield) compound as pale yellow solid. LCMS (m/z): 544.1.10[M+H]$^+$, R$_t$=2.68 min.

$^1$H NMR (400 MHz, CDCl$_3$): δ ppm 13.33 (s, 1H), 8.32 (s, 1H), 8.21 (d, J=5.26 Hz, 1H), 7.93-8.04 (m, 3H), 7.69 (d, J=7.89 Hz, 1H), 7.14 (dd, J=5.37, 1.43 Hz, 1H), 5.66 (brdd, J=5.70, 3.07 Hz, 1H), 4.99-5.16 (m, 1H), 3.19-3.32 (m, 2H), 3.09-3.17 (m, 1H), 2.99-3.08 (m, 1H), 2.26-2.44 (m, 2H), 2.08 (dt, J=14.31, 7.43 Hz, 1H), 1.60 (d, J=7.02 Hz, 3H), 1.08-1.29 (m, 4H)

Example 326. Full-Length SIRT1 Production

Full-length human SIRT1 (hSIRT1) proteins were expressed with a C-terminal His$_6$ tag and purified as described in Hubbard. et al. (2013) Science 339, 1216. Each cell paste was resuspended in buffer A (50 mM Tris-HCl pH 7.5, 250 mM NaCl, 25 mM imidazole, and 0.1 mM TCEP) with 1,000 U Benzonase nuclease (Sigma Aldrich) supplemented with complete, EDTA-free Protease Inhibitor Cocktail Tablets (Roche) on ice. Cells were disrupted by pulse sonication with 50% on and 50% off for 12 minutes total at 40 W. Insoluble debris was removed by centrifugation. Clarified supernatant was directly loaded onto a 1 mL HisTrap FF Crude column (GE Lifesciences). After washing with buffer A, SIRT1 was eluted with buffer B (50 mM Tris-HCl pH 7.5, 250 mM NaCl, 500 mM imidazole and 0.1 mM TCEP). Protein was further purified by size exclusion chromatography in buffer C (50 mM Tris-HCl pH 7.5, 300 mM NaCl, 0.1 mM TCEP) using a Hi-load Superdex 200 16/60 column (GE Lifesciences). Enzyme concentrations were determined by Bradford assay using BSA as a standard. Final protein purity was assessed by gel densitometry. Proteins were confirmed by LC/MS. All proteins were greater than 90% pure.

Example 327. SIRT1 Deacetylation Reactions

SIRT1 deacetylation reactions were performed in reaction buffer (50 mM HEPES-NaOH, pH 7.5, 150 mM NaCl, 1 mM DTT, and 1% DMSO) at 25° C. monitoring either nicotinamide production using the continuous PNC1/GDH coupled assay (Smith, B. C. et al. (2009) Anal Biochem 394, 101) or O-acetyl ADP ribose (OAcADPr) production by mass spectrometry (Hubbard. et al. (2013) Science 339, 1216). Final concentrations of the PNC1/GDH coupling system components used were 20 units/mL bovine GDH (Sigma-Aldrich), 1 uM yeast PNC1, 3.4 mM α-ketoglutarate, and 220 µM NADH or NADPH. An extinction coefficient of 6.22 mM$^{-1}$cm$^{-}$ and a pathlength of 0.81 cm was used to convert the absorbance at 340 nm to product concentration for the 150 uL reactions used. Assays monitoring OAcADPr production were performed in reaction buffer with 0.05% BSA and time points were taken by quenching the deacetylation reaction with a stop solution which gave a final concentration of 1% formic acid and 5 mM nicotinamide. Quenched reactions were diluted 5-fold with 1:1 acetonitrile:methanol and spun at 5,000×g for 10 minutes to precipitate protein before being analyzed with an Agilent RapidFire 200 High-Throughput Mass Spectrometry System (Agilent, Wakefield, Mass.) coupled to an ABSciex API 4000 mass spectrometer fitted with an electrospray ionization source. The p53-based Ac-p53(W5) (Ac-RHKK$^{Ac}$W—NH$_2$) and TAMRA (Ac-EE-K(biotin)-GQST-SSHSK(Ac)NleSTEG-K(5TMR)-EE-NH$_2$) peptides were obtained from American Century Peptide and Biopeptide, Inc, respectively.). Substrate K$_M$ determinations were performed by varying one substrate concentration at a fixed, saturating concentration of the second substrate. SIRT1 activation and inhibition assays were run in reaction buffer with 0.05% BSA at 25° C. and analyzed using the OAcADPr assay. Enzyme and compound were pre-incubated for 20 minutes before addition of substrates. For the activation screen of full-length hSIRT1, compounds were tested in duplicate with a dose response. In order to be sensitive to KM-modulating activators, substrate concentrations of approximately one-tenth their K$_M$ values were used. The dose-dependence of five compounds was tested and the fold-activation data were described by Eq. 1

$$\frac{v_x}{v_0} = b + \frac{RV_{max} - b}{1 + \frac{EC_{50}}{[X]_0}}$$ (Eq. 1)

where $v_x/v_o$ is the ratio of the reaction rate in the presence ($v_x$) versus absence ($v_o$) of activator (X), $RV_{max}$ is the relative velocity at infinite activator concentration, $EC_{50}$ is the concentration of activator required to produce one-half $RV_{max}$ and b is the minimum value of $v_x/v_o$.

Example 328. Biochemical Activity

Mass spectrometry based assays were used to identify modulators of SIRT1 activity. The TAMRA based assay utilized a peptide having 20 amino acid residues as follows: Ac-EE-K(biotin)-GQSTSSHSK(Ac)NleSTEG-K(5TMR)-EE-NH$_2$ (SEQ ID NO: 1), wherein K(Ac) is an acetylated lysine residue and Nle is a norleucine. The peptide was labeled with the fluorophore 5TMR (excitation 540 nm/emission 580 nm) at the C-terminus. The sequence of the peptide substrate was based on p53 with several modifications. In addition, the methionine residue naturally present in the sequence was replaced with the norleucine because the methionine may be susceptible to oxidation during synthesis and purification. The Trp based assay utilized a peptide having an amino acid residues as follows: Ac-R—H—K—K(Ac)-W—NH2 (SEQ ID NO: 2).

The TAMRA based mass spectrometry assay was conducted as follows: 0.5 µM peptide substrate and 120 µM (βNAD$^+$ was incubated with 10 nM SIRT1 for 25 minutes at 25° C. in a reaction buffer (50 mM Tris-acetate pH 8, 137 mM NaCl, 2.7 mM KCl, 1 mM MgCl$_2$, 5 mM DTT, 0.05% BSA). The SIRT1 protein was obtained by cloning the SirT1 gene into a T7-promoter containing vector, which was then transformed and expressed in BL21(DE3) bacterial cells. Test compound was added at varying concentrations to this reaction mixture and the resulting reactions were monitored. After the 25 minute incubation with SIRT1, 10 µL of 10% formic acid was added to stop the reaction. The resulting reactions were sealed and frozen for later mass spec analysis. Determination of the amount of deacetylated substrate peptide formed (or, alternatively, the amount of O-acetyl-ADP-ribose (OAADPR) generated) by the sirtuin-mediated NAD-dependent deacetylation reaction allowed for the precise measurement of relative SIRT1 activity in the presence of varying concentrations of the test compound versus control reactions lacking the test compound.

The Trp mass spectrometry assay was conducted as follows. 0.5 µM peptide substrate and 120 µM βNAD$^+$ were incubated with 10 nM SIRT1 for 25 minutes at 25° C. in a reaction buffer (50 mM HEPES pH 7.5, 1500 mM NaCl, 1 mM DTT, 0.05% BSA). The SIRT1 protein was obtained by cloning the SirT1 gene into a T7-promoter containing vector, which was then expressed in BL21(DE3) bacterial cells and purified as described in further detail below. Test compound was added at varying concentrations to this reaction mixture and the resulting reactions were monitored. After the 25 minute incubation with SIRT1, 10 µL of 10% formic acid was added to stop the reaction. The resulting reactions were sealed and frozen for later mass spec analysis. The relative SIRT1 activity was then determined by measuring the amount of O-acetyl-ADP-ribose (OAADPR) formed (or, alternatively, the amount of deacetylated Trp peptide generated) by the NAD-dependent sirtuin deacetylation reaction in the presence of varying concentrations of the test compound versus control reactions lacking the test compound. The degree to which the test agent activated deacetylation by SIRT1 was expressed as $EC_{1.5}$ (i.e., the concentration of compound required to increase SIRT1 activity by 50% over the control lacking test compound), and Percent Maximum Activation (i.e., the maximum activity relative to control (100%) obtained for the test compound).

A control for inhibition of sirtuin activity was conducted by adding 1 μL of 500 mM nicotinamide as a negative control at the start of the reaction (e.g., permits determination of maximum sirtuin inhibition). A control for activation of sirtuin activity was conducted using 10 nM of sirtuin protein, with 1 μL of DMSO in place of compound, to determine the amount of deacetylation of the substrate at a given time point within the linear range of the assay. This time point was the same as that used for test compounds and, within the linear range, the endpoint represents a change in velocity.

For the above assay, SIRT1 protein was expressed and purified as follows. The SirT1 gene was cloned into a T7-promoter containing vector and transformed into BL21 (DE3). The protein was expressed by induction with 1 mM IPTG as an N-terminal His-tag fusion protein at 18° C. overnight and harvested at 30,000×g. Cells were lysed with lysozyme in lysis buffer (50 mM Tris-HCl, 2 mM Tris[2-carboxyethyl]phosphine (TCEP), 10 μM $ZnCl_2$, 200 mM NaCl) and further treated with sonication for 10 min for complete lysis. The protein was purified over a Ni-NTA column (Amersham) and fractions containing pure protein were pooled, concentrated and run over a sizing column (Sephadex S200 26/60 global). The peak containing soluble protein was collected and run on an Ion-exchange column (MonoQ). Gradient elution (200 mM-500 mM NaCl) yielded pure protein. This protein was concentrated and dialyzed against dialysis buffer (20 mM Tris-HCl, 2 mM TCEP) overnight. The protein was aliquoted and frozen at −80° C. until further use.

Sirtuin-modulating compounds of Formula (I) that activated SIRT1 were identified using the assay described above and are shown below in Table 1. The $EC_{1.5}$ values represent the concentration of test compounds that result in 150% activation of SIRT1.

The $EC_{1.5}$ values for the activating compounds of Formula (I) are represented by A ($EC_{1.5}$<1 μM), B ($EC_{1.5}$ 1-25 μM), C ($EC_{1.5}$>25 μM). The percent maximum fold activation is represented by A (Fold activation≥150%) or B (Fold Activation<150%). "NT" means not tested; "ND" means not determinable. The compound numbering in the table starts with compound number 10, and parenthetic numbering (#) corresponding to the STAC numbering system in Examples 90-106 (i.e., compound no. 68 is also STAC 1, so it is shown as 68(1), and further STACs: 546(3), 444(4), 314(5), 816(7), 76(8), and 81(9)).

It is noted that compounds of the present invention have been named by two different chemical nomenclature conventions as generated by two different chemical drawing and/or chemical naming computer programs, i.e., generated by Chem Axon (JChem-Excel) and Cambridge Soft (ChemDraw®), respective companies.

TABLE 1

| Example number | Structure | Chemical Name: Generated by CHemAxon | TRP Activity | TRP MAX RESP |
|---|---|---|---|---|
| 1 | 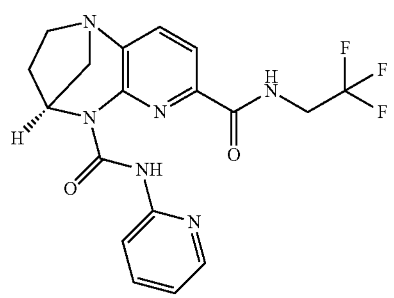 [SMILES: O=C(NCC(F)(F)F)c1ccc2c(n1)N(C(=O)Nc1ccccn1)[C@H]1CCN2C1] | (9S)-8-N-(pyridin-2-yl)-5-N-(2,2,2-trifluoroethyl)-1,6,8-triazatricyclo[7.2.1.0$^{2,7}$]dodeca-2(7),3,5-triene-5,8-dicarboxamide | A | A |
| 2 | 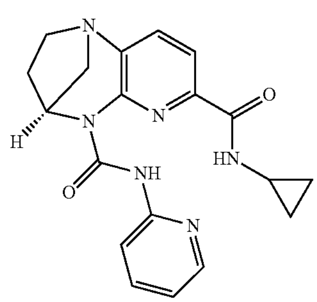 [SMILES: O=C(NC1CC1)c1ccc2c(n1)N(C(=O)Nc1ccccn1)[C@H]1CCN2C1] | (9S)-5-N-cyclopropyl-8-N-(pyridin-2-yl)-1,6,8-triazatricyclo[7.2.1.0$^{2,7}$]dodeca-2(7),3,5-triene-5,8-dicarboxamide | A | A |

TABLE 1-continued

| Example number | Structure | Chemical Name: Generated by CHemAxon | TRP Activity | TRP MAX RESP |
| --- | --- | --- | --- | --- |
| 3 | 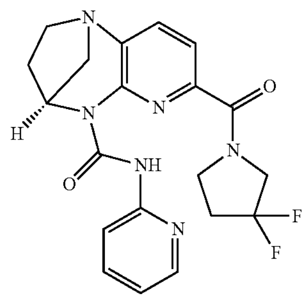 [SMILES: O=C(c1ccc2c(n1)N(C(=O)Nc1ccccn1)[C@H]1CCN2C1)N1CCC(F)(F)C1] | (9S)-5-(3,3-difluoropyrrolidine-1-carbonyl)-N-(pyridin-2-yl)-1,6,8-triazatricyclo[7.2.1.0$^{2,7}$]dodeca-2(7),3,5-triene-8-carboxamide | B | A |
| 4 | 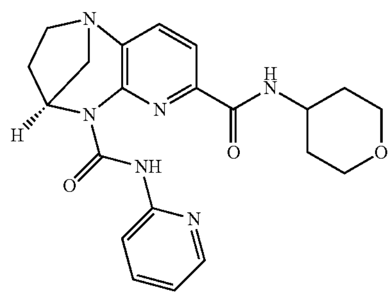 [SMILES: O=C(NC1CCOCC1)c1ccc2c(n1)N(C(=O)Nc1ccccn1)[C@H]1CCN2C1] | (9S)-5-N-(oxan-4-yl)-8-N-(pyridin-2-yl)-1,6,8-triazatricyclo[7.2.1.0$^{2,7}$]dodeca-2(7),3,5-triene-5,8-dicarboxamide | B | A |
| 5 | 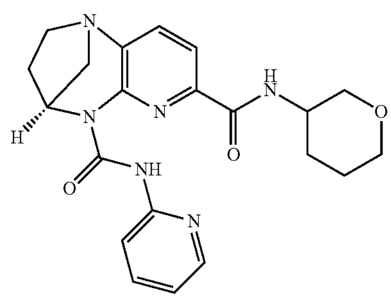 [SMILES: O=C(NC1CCCOC1)c1ccc2c(n1)N(C(=O)Nc1ccccn1)[C@H]1CCN2C1] | (9S)-5-N-(oxan-3-yl)-8-N-(pyridin-2-yl)-1,6,8-triazatricyclo[7.2.1.0$^{2,7}$]dodeca-2(7),3,5-triene-5,8-dicarboxamide | B | A |
| 6 | 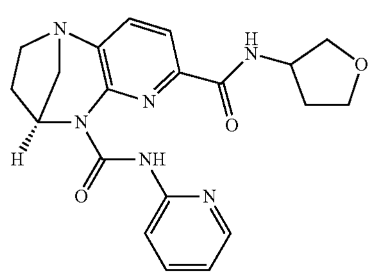 [SMILES: O=C(NC1CCOC1)c1ccc2c(n1)N(C(=O)Nc1ccccn1)[C@H]1CCN2C1] | (9S)-5-N-(oxolan-3-yl)-8-N-(pyridin-2-yl)-1,6,8-triazatricyclo[7.2.1.0$^{2,7}$]dodeca-2(7),3,5-triene-5,8-dicarboxamide | B | A |
| 7 | 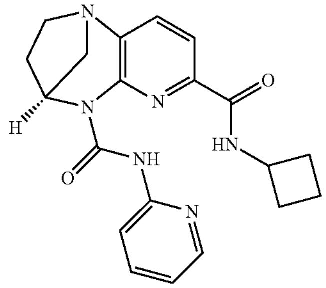 [SMILES: O=C(NC1CCC1)c1ccc2c(n1)N(C(=O)Nc1ccccn1)[C@H]1CCN2C1] | (9S)-5-N-cyclobutyl-8-N-(pyridin-2-yl)-1,6,8-triazatricyclo[7.2.1.0$^{2,7}$]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 8 | 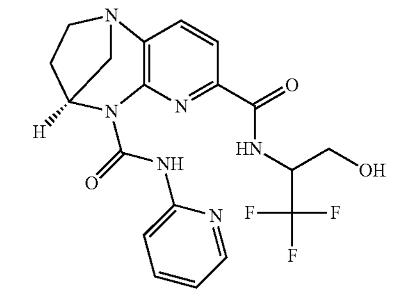 [SMILES: O=C(NC(CO)C(F)(F)F)c1ccc2c(n1)N(C(=O)Nc1ccccn1)[C@H]1CCN2C1] | (9S)-8-N-(pyridin-2-yl)-5-N-(1,1,1-trifluoro-3-hydroxypropan-2-yl)-1,6,8-triazatricyclo[7.2.1.0$^{2,7}$]dodeca-2(7),3,5-triene-5,8-dicarboxamide | A | A |
| 9 | 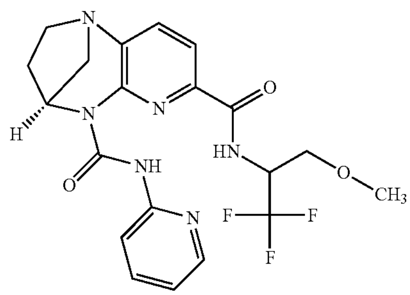 [SMILES: COCC(NC(=O)c1ccc2c(n1)N(C(=O)Nc1ccccn1)[C@H]1CCN2C1)C(F)(F)F] | (9S)-8-N-(pyridin-2-yl)-5-N-(1,1,1-trifluoro-3-methoxypropan-2-yl)-1,6,8-triazatricyclo[7.2.1.0$^{2,7}$]dodeca-2(7),3,5-triene-5,8-dicarboxamide | A | A |
| 10 | 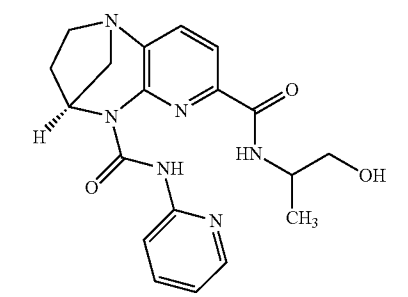 [SMILES: CC(CO)NC(=O)c1ccc2c(n1)N(C(=O)Nc1ccccn1)[C@H]1CCN2C1] | (9S)-5-N-(1-hydroxypropan-2-yl)-8-N-(pyridin-2-yl)-1,6,8-triazatricyclo[7.2.1.0$^{2,7}$]dodeca-2(7),3,5-triene-5,8-dicarboxamide | B | A |
| 11 | 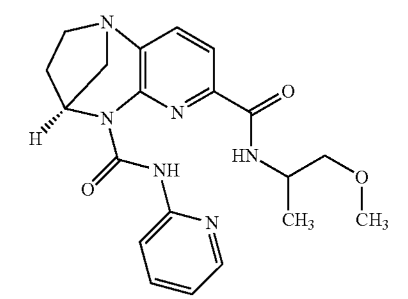 [SMILES: COCC(C)NC(=O)c1ccc2c(n1)N(C(=O)Nc1ccccn1)[C@H]1CCN2C1] | (9S)-5-N-(1-methoxypropan-2-yl)-8-N-(pyridin-2-yl)-1,6,8-triazatricyclo[7.2.1.0$^{2,7}$]dodeca-2(7),3,5-triene-5,8-dicarboxamide | B | A |
| 12 | 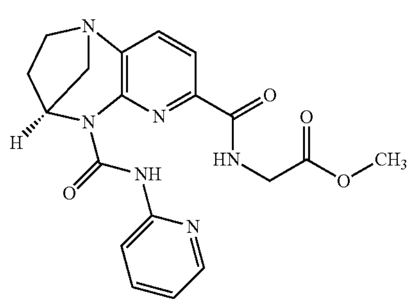 [SMILES: COC(=O)CNC(=O)c1ccc2c(n1)N(C(=O)Nc1ccccn1)[C@H]1CCN2C1] | methyl 2-{[(9S)-8-[(pyridin-2-yl)carbamoyl]-1,6,8-triazatricyclo[7.2.1.0$^{2,7}$]dodeca-2(7),3,5-trien-5-yl]formamido}acetate | B | A |

TABLE 1-continued

| Example number | Structure | Chemical Name: Generated by CHemAxon | TRP Activity | TRP MAX RESP |
|---|---|---|---|---|
| 13 | 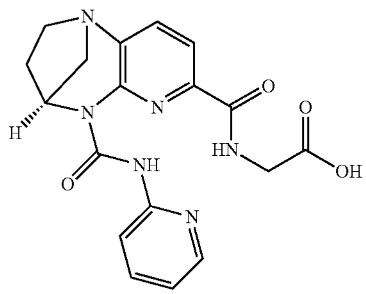 [SMILES: O=C(O)CNC(=O)c1ccc2c(n1)N(C(=O)Nc1ccccn1)[C@H]1CCN2C1] | (9S)-5-N-(2-hydroxyethyl)-8-N-(pyridin-2-yl)-1,6,8-triazatricyclo[7.2.1.0$^{2,7}$]dodeca-2(7),3,5-triene-5,8-dicarboxamide | B | A |
| 14 | 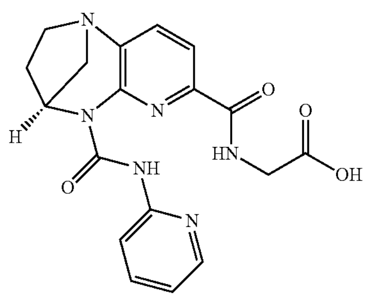 [SMILES: O=C(O)CNC(=O)c1ccc2c(n1)N(C(=O)Nc1ccccn1)[C@H]1CCN2C1] | 2-{[(9S)-8-[(pyridin-2-yl)carbamoyl]-1,6,8-triazatricyclo[7.2.1.0$^{2,7}$]dodeca-2(7),3,5-trien-5-yl]formamido}acetic acid | C | B |
| 15 | 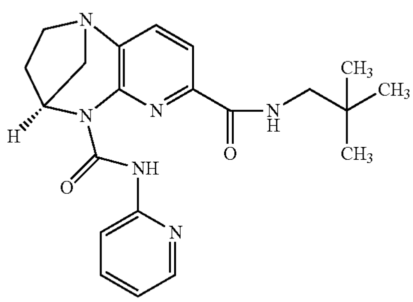 [SMILES: CC(C)(C)CNC(=O)c1ccc2c(n1)N(C(=O)Nc1ccccn1)[C@H]1CCN2C1] | (9S)-5-N-(2,2-dimethylpropyl)-8-N-(pyridin-2-yl)-1,6,8-triazatricyclo[7.2.1.0$^{2,7}$]dodeca-2(7),3,5-triene-5,8-dicarboxamide | A | A |
| 16 | 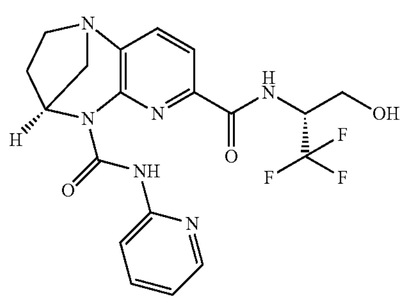 [SMILES: O=C(N[C@H](CO)C(F)(F)F)c1ccc2c(n1)N(C(=O)Nc1ccccn1)[C@H]1CCN2C1] | (9S)-8-N-(pyridin-2-yl)-5-N-[(2R)-1,1,1-trifluoro-3-hydroxypropan-2-yl]-1,6,8-triazatricyclo[7.2.1.0$^{2,7}$]dodeca-2(7),3,5-triene-5,8-dicarboxamide | A | A |
| 17 | 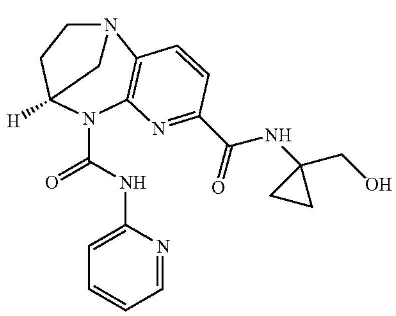 [SMILES: O=C(NC1(CO)CC1)c1ccc2c(n1)N(C(=O)Nc1ccccn1)[C@H]1CCN2C1] | (9S)-5-N-[1-(hydroxymethyl)cyclopropyl]-8-N-(pyridin-2-yl)-1,6,8-triazatricyclo[7.2.1.0$^{2,7}$]dodeca-2(7),3,5-triene-5,8-dicarboxamide | B | A |

TABLE 1-continued

| Example number | Structure | Chemical Name: Generated by CHemAxon | TRP Activity | TRP MAX RESP |
|---|---|---|---|---|
| 18 | ISOMER 1 | (9S)-8-N-(pyridin-2-yl)-5-N-[(2S)-1,1,1-trifluoro-4-hydroxybutan-2-yl]-1,6,8-triazatricyclo[7.2.1.0$^{2,7}$]dodeca-2(7),3,5-triene-5,8-dicarboxamide | A | A |
| 19 | 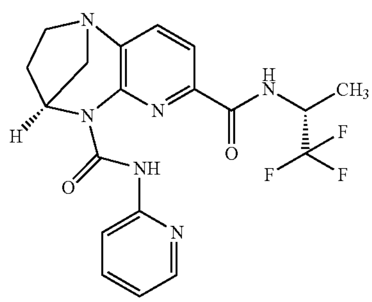 [SMILES: C[C@@H](NC(=O)c1ccc2c(n1)N(C(=O)Nc1ccccn1)[C@H]1CCN2C1)C(F)(F)F] | (9S)-8-N-(pyridin-2-yl)-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | A |
| 20 | 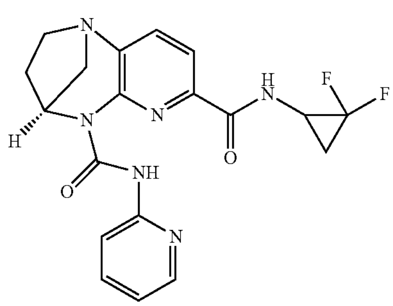 [SMILES: O=C(NC1CC1(F)F)c1ccc2c(n1)N(C(=O)Nc1ccccn1)[C@H]1CCN2C1] | (9S)-5-N-(2,2-difluorocyclopropyl)-8-N-(pyridin-2-yl)-1,6,8-triazatricyclo[7.2.1.0$^{2,7}$]dodeca-2(7),3,5-triene-5,8-dicarboxamide | A | A |
| 21 | 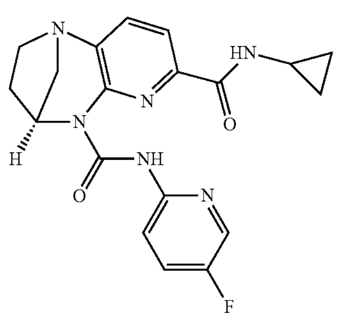 [SMILES: O=C(NC1CC1)c1ccc2c(n1)N(C(=O)Nc1ccc(F)cn1)[C@H]1CCN2C1] | (9S)-5-N-cyclopropyl-8-N-(5-fluoropyridin-2-yl)-1,6,8-triazatricyclo[7.2.1.0$^{2,7}$]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 22 | 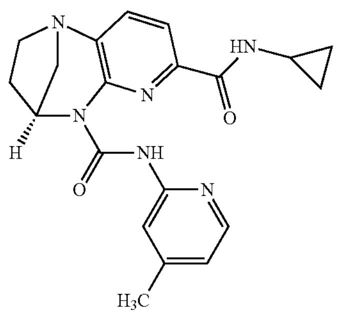 [SMILES: Cc1ccnc(NC(=O)N2c3nc(C(=O)NC4CC4)ccc3N3CC[C@H]2C3)c1] | (9S)-5-N-cyclopropyl-8-N-(4-methylpyridin-2-yl)-1,6,8-triazatricyclo[7.2.1.0²,⁷]dodeca-2(7),3,5-triene-5,8-dicarboxamide | B | A |
| 23 | 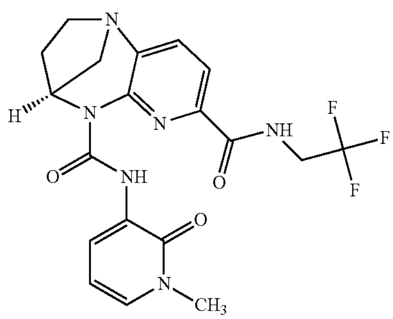 [SMILES: Cn1cccc(NC(=O)N2c3nc(C(=O)NCC(F)(F)F)ccc3N3CC[C@H]2C3)c1=O] | (9S)-8-N-(1-methyl-2-oxo-1,2-dihydropyridin-3-yl)-5-N-(2,2,2-trifluoroethyl)-1,6,8-triazatricyclo[7.2.1.0²,⁷]dodeca-2,4,6-triene-5,8-dicarboxamide | A | A |
| 24 | 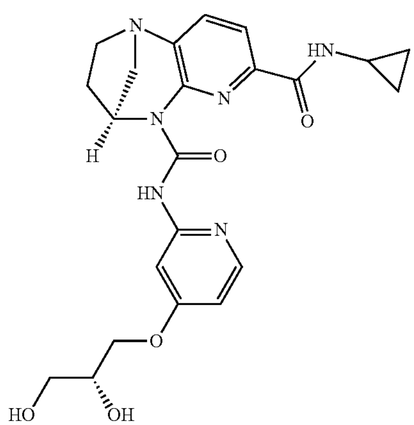 [SMILES: O=C(NC1CC1)c1ccc2c(n1)N(C(=O)Nc1cc(OC[C@H](O)CO)ccn1)[C@H]1CCN2C1] | (9S)-5-N-cyclopropyl-8-N-{4-[(2R)-2,3-dihydroxypropoxy]pyridin-2-yl}-1,6,8-triazatricyclo[7.2.1.0²,⁷]dodeca-2(7),3,5-triene-5,8-dicarboxamide | B | A |
| 25 | 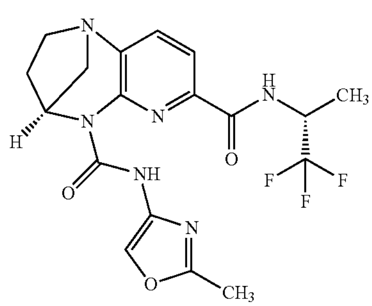 [SMILES: Cc1nc(NC(=O)N2c3nc(C(=O)N[C@H](C)C(F)(F)F)ccc3N3CC[C@H]2C3)co1] | (9S)-8-N-(2-methyl-1,3-oxazol-4-yl)-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 26 | 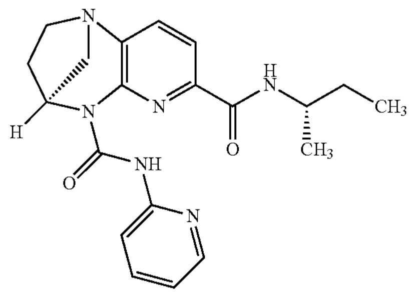 [SMILES: CC[C@H](C)NC(=O)c1ccc2c(n1)N(C(=O)Nc1ccccn1)[C@H]1CCN2C1] | (9S)-5-N-[(2S)-butan-2-yl]-8-N-(pyridin-2-yl)-1,6,8-triazatricyclo[7.2.1.0$^{2,7}$]dodeca-2(7),3,5-triene-5,8-dicarboxamide | A | A |
| 27 | 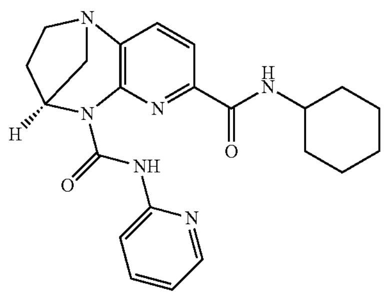 [SMILES: O=C(NC1CCCCC1)c1ccc2c(n1)N(C(=O)Nc1ccccn1)[C@H]1CCN2C1] | (9S)-5-N-cyclohexyl-8-N-(pyridin-2-yl)-1,6,8-triazatricyclo[7.2.1.0$^{2,7}$]dodeca-2(7),3,5-triene-5,8-dicarboxamide | A | A |
| 28 | 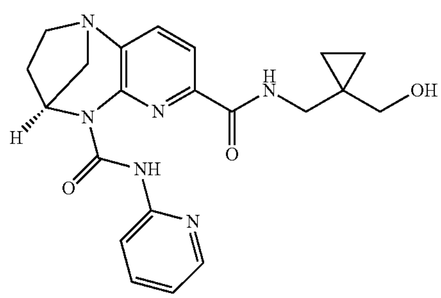 [SMILES: O=C(NCC1(CO)CC1)c1ccc2c(n1)N(C(=O)Nc1ccccn1)[C@H]1CCN2C1] | (9S)-5-N-{[1-(hydroxymethyl)cyclopropyl]methyl}-8-N-(pyridin-2-yl)-1,6,8-triazatricyclo[7.2.1.0$^{2,7}$]dodeca-2(7),3,5-triene-5,8-dicarboxamide | B | A |
| 29 | 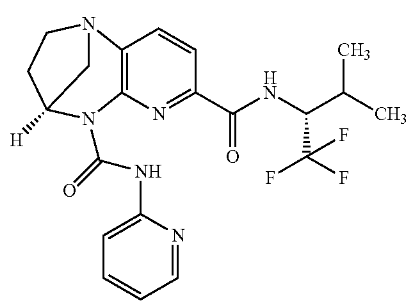 [SMILES: CC(C)[C@@H](NC(=O)c1ccc2c(n1)N(C(=O)Nc1ccccn1)[C@H]1CCN2C1)C(F)(F)F] | (9S)-8-N-(pyridin-2-yl)-5-N-[(2R)-1,1,1-trifluoro-3-methylbutan-2-yl]-1,6,8-triazatricyclo[7.2.1.0$^{2,7}$]dodeca-2(7),3,5-triene-5,8-dicarboxamide | A | A |
| 30 | 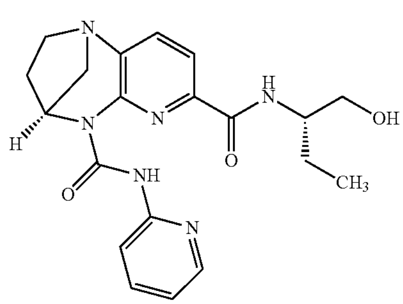 [SMILES: CC[C@@H](CO)NC(=O)c1ccc2c(n1)N(C(=O)Nc1ccccn1)[C@H]1CCN2C1] | (9S)-5-N-[(2S)-1-hydroxybutan-2-yl]-8-N-(pyridin-2-yl)-1,6,8-triazatricyclo[7.2.1.0$^{2,7}$]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 31 | 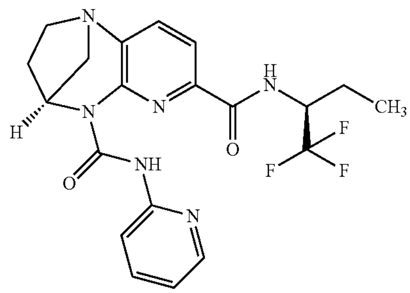 [SMILES: CC[C@H](NC(=O)c1ccc2c(n1)N(C(=O)Nc1ccccn1)[C@H]1CCN2C1)C(F)(F)F] | (9S)-8-N-(pyridin-2-yl)-5-N-[(2S)-1,1,1-trifluorobutan-2-yl]-1,6,8-triazatricyclo[7.2.1.0²,⁷]dodeca-2(7),3,5-triene-5,8-dicarboxamide | A | A |
| 32 | 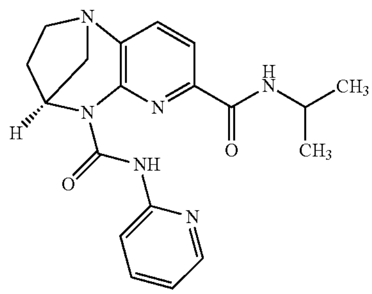 [SMILES: CC(C)NC(=O)c1ccc2c(n1)N(C(=O)Nc1ccccn1)[C@H]1CCN2C1] | (9S)-5-N-(propan-2-yl)-8-N-(pyridin-2-yl)-1,6,8-triazatricyclo[7.2.1.0²,⁷]dodeca-2(7),3,5-triene-5,8-dicarboxamide | A | A |
| 33 | 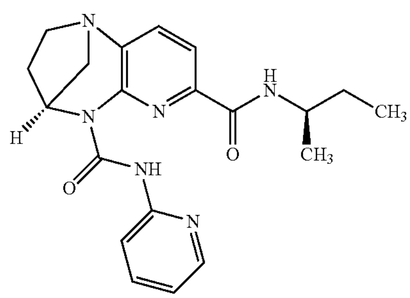 [SMILES: CC[C@@H](C)NC(=O)c1ccc2c(n1)N(C(=O)Nc1ccccn1)[C@H]1CCN2C1] | (9S)-5-N-[(2R)-butan-2-yl]-8-N-(pyridin-2-yl)-1,6,8-triazatricyclo[7.2.1.0²,⁷]dodeca-2(7),3,5-triene-5,8-dicarboxamide | A | A |
| 34 | 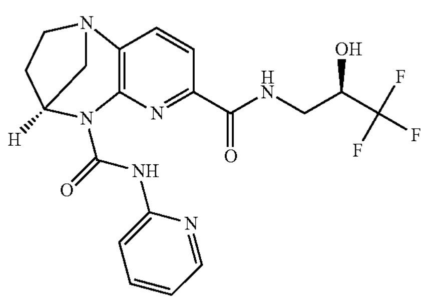 [SMILES: O=C(NC[C@@H](O)C(F)(F)F)c1ccc2c(n1)N(C(=O)Nc1ccccn1)[C@H]1CCN2C1] | (9S)-8-N-(pyridin-2-yl)-5-N-[(2R)-3,3,3-trifluoro-2-hydroxypropyl]-1,6,8-triazatricyclo[7.2.1.0²,⁷]dodeca-2(7),3,5-triene-5,8-dicarboxamide | A | A |
| 35 | 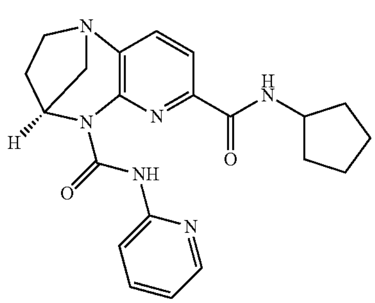 [SMILES: O=C(NC1CCCC1)c1ccc2c(n1)N(C(=O)Nc1ccccn1)[C@H]1CCN2C1] | (9S)-5-N-cyclopentyl-8-N-(pyridin-2-yl)-1,6,8-triazatricyclo[7.2.1.0²,⁷]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 36 | 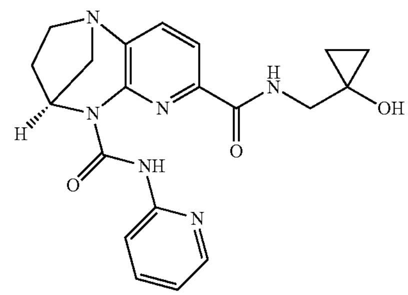 [SMILES: O=C(NCC1(O)CC1)c1ccc2c(n1)N(C(=O)Nc1ccccn1)[C@H]1CCN2C1] | (9S)-5-N-[(1-hydroxycyclopropyl)methyl]-8-N-(pyridin-2-yl)-1,6,8-triazatricyclo[7.2.1.0$^{2,7}$]dodeca-2(7),3,5-triene-5,8-dicarboxamide | B | A |
| 37 | 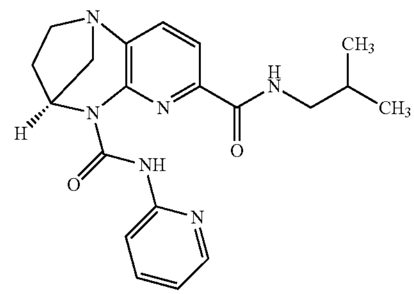 [SMILES: CC(C)CNC(=O)c1ccc2c(n1)N(C(=O)Nc1ccccn1)[C@H]1CCN2C1] | (9S)-5-N-(2-methylpropyl)-8-N-(pyridin-2-yl)-1,6,8-triazatricyclo[7.2.1.0$^{2,7}$]dodeca-2(7),3,5-triene-5,8-dicarboxamide | A | A |
| 38 | 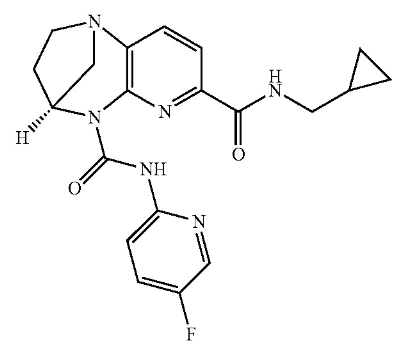 [SMILES: O=C(NCC1CC1)c1ccc2c(n1)N(C(=O)Nc1ccc(F)cn1)[C@H]1CCN2C1] | (9S)-5-N-(cyclopropylmethyl)-8-N-(5-fluoropyridin-2-yl)-1,6,8-triazatricyclo[7.2.1.0$^{2,7}$]dodeca-2(7),3,5-triene-5,8-dicarboxamide | A | A |
| 39 | 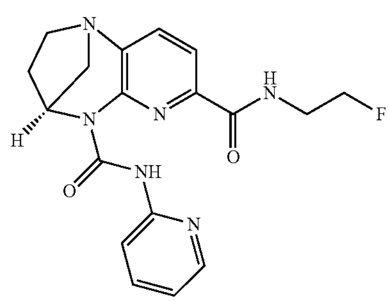 [SMILES: O=C(NCCF)c1ccc2c(n1)N(C(=O)Nc1ccccn1)[C@H]1CCN2C1] | (9S)-5-N-(2-fluoroethyl)-8-N-(pyridin-2-yl)-1,6,8-triazatricyclo[7.2.1.0$^{2,7}$]dodeca-2(7),3,5-triene-5,8-dicarboxamide | A | A |
| 40 | 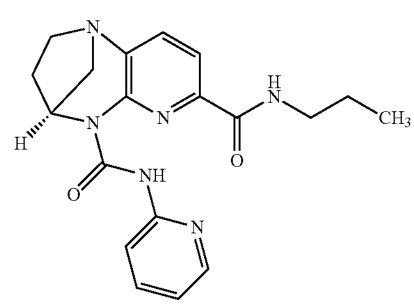 [SMILES: CCCNC(=O)c1ccc2c(n1)N(C(=O)Nc1ccccn1)[C@H]1CCN2C1] | (9S)-5-N-propyl-8-N-(pyridin-2-yl)-1,6,8-triazatricyclo[7.2.1.0$^{2,7}$]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 41 | 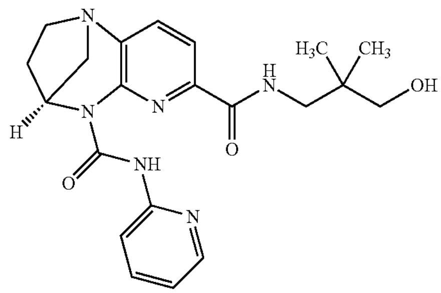 [SMILES: CC(C)(CO)CNC(=O)c1ccc2c(n1)N(C(=O)Nc1ccccn1)[C@H]1CCN2C1] | (9S)-5-N-(3-hydroxy-2,2-dimethylpropyl)-8-N-(pyridin-2-yl)-1,6,8-triazatricyclo[7.2.1.0$^{2,7}$]dodeca-2(7),3,5-triene-5,8-dicarboxamide | B | A |
| 42 | 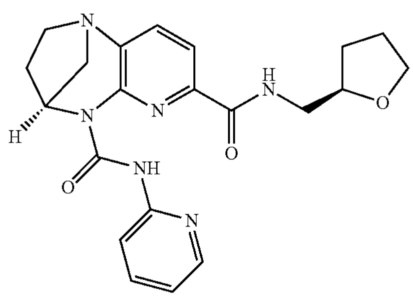 [SMILES: O=C(NC[C@H]1CCCO1)c1ccc2c(n1)N(C(=O)Nc1ccccn1)[C@H]1CCN2C1] | (9S)-5-N-[(2R)-oxolan-2-ylmethyl]-8-N-(pyridin-2-yl)-1,6,8-triazatricyclo[7.2.1.0$^{2,7}$]dodeca-2(7),3,5-triene-5,8-dicarboxamide | B | A |
| 43 | ISOMER 1 | (9S)-5-N-[(1R)-2,2-difluorocyclopropyl]-8-N-(pyridin-2-yl)-1,6,8-triazatricyclo[7.2.1.0$^{2,7}$]dodeca-2(7),3,5-triene-5,8-dicarboxamide | A | A |
| 44 | ISOMER 2 | (9S)-5-N-[(1R)-2,2-difluorocyclopropyl]-8-N-(pyridin-2-yl)-1,6,8-triazatricyclo[7.2.1.0$^{2,7}$]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 45 | 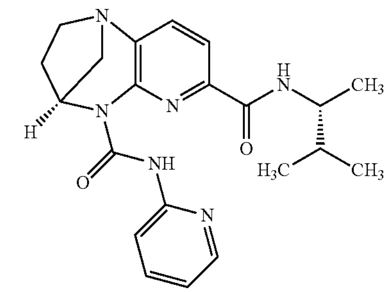 [SMILES: CC(C)[C@@H](C)NC(=O)c1ccc2c(n1)N(C(=O)Nc1ccccn1)[C@H]1CCN2C1] | (9S)-5-N-[(2R)-3-methylbutan-2-yl]-8-N-(pyridin-2-yl)-1,6,8-triazatricyclo[7.2.1.0$^{2,7}$]dodeca-2(7),3,5-triene-5,8-dicarboxamide | A | A |
| 46 | 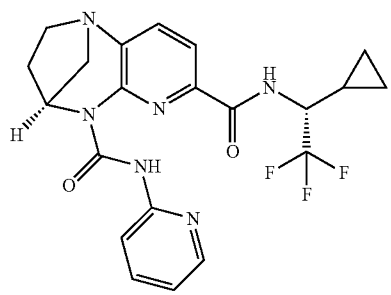 [SMILES: O=C(N[C@H](C1CC1)C(F)(F)F)c1ccc2c(n1)N(C(=O)Nc1ccccn1)[C@H]1CCN2C1] | (9S)-5-N-[(1R)-1-cyclopropyl-2,2,2-trifluoroethyl]-8-N-(pyridin-2-yl)-1,6,8-triazatricyclo[7.2.1.0$^{2,7}$]dodeca-2(7),3,5-triene-5,8-dicarboxamide | A | A |
| 47 | 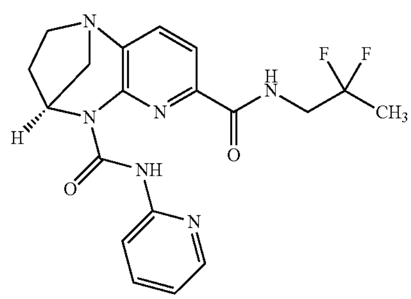 [SMILES: CC(F)(F)CNC(=O)c1ccc2c(n1)N(C(=O)Nc1ccccn1)[C@H]1CCN2C1] | (9S)-5-N-(2,2-difluoropropyl)-8-N-(pyridin-2-yl)-1,6,8-triazatricyclo[7.2.1.0$^{2,7}$]dodeca-2(7),3,5-triene-5,8-dicarboxamide | A | A |
| 48 | 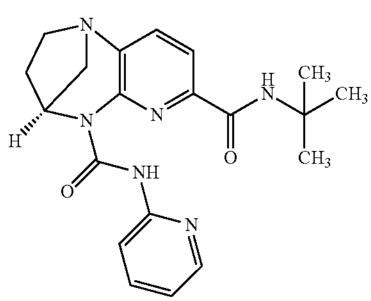 [SMILES: CC(C)(C)NC(=O)c1ccc2c(n1)N(C(=O)Nc1ccccn1)[C@H]1CCN2C1] | (9S)-5-N-tert-butyl-8-N-(pyridin-2-yl)-1,6,8-triazatricyclo[7.2.1.0$^{2,7}$]dodeca-2(7),3,5-triene-5,8-dicarboxamide | B | A |
| 49 | ISOMER 2 | (9S)-5-N-[(2S)-2-amino-3,3,3-trifluoropropyl]-8-N-(pyridin-2-yl)-1,6,8-triazatricyclo[7.2.1.0$^{2,7}$]dodeca-2(7),3,5-triene-5,8-dicarboxamide | B | A |

| Example number | Structure | Chemical Name: Generated by CHemAxon | TRP Activity | TRP MAX RESP |
|---|---|---|---|---|
| 50 | ISOMER 1 | (9S)-5-N-[(2S)-3-amino-1,1,1-trifluoropropan-2-yl]-8-N-(pyridin-2-yl)-1,6,8-triazatricyclo[7.2.1.0²,⁷]dodeca-2(7),3,5-triene-5,8-dicarboxamide | A | A |
| 51 | 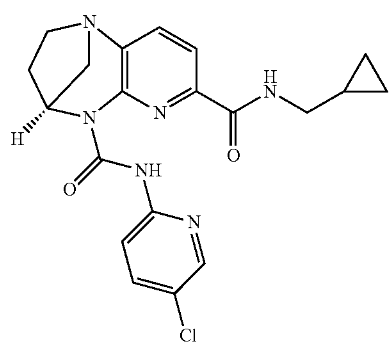 [SMILES: O=C(NCC1CC1)c1ccc2c(n1)N(C(=O)Nc1ccc(Cl)cn1)[C@H]1CCN2C1] | (9S)-8-N-(5-chloropyridin-2-yl)-5-N-(cyclopropylmethyl)-1,6,8-triazatricyclo[7.2.1.0²,⁷]dodeca-2(7),3,5-triene-5,8-dicarboxamide | A | A |
| 52 | 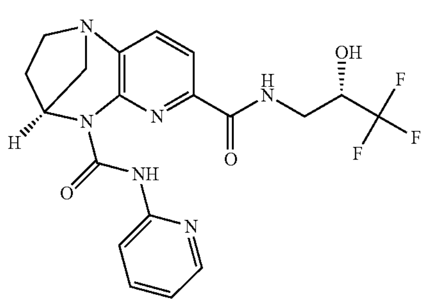 [SMILES: O=C(NC[C@H](O)C(F)(F)F)c1ccc2c(n1)N(C(=O)Nc1ccccn1)[C@H]1CCN2C1] | (9S)-8-N-(pyridin-2-yl)-5-N-[(2S)-3,3,3-trifluoro-2-hydroxypropyl]-1,6,8-triazatricyclo[7.2.1.0²,⁷]dodeca-2(7),3,5-triene-5,8-dicarboxamide | A | A |
| 53 | 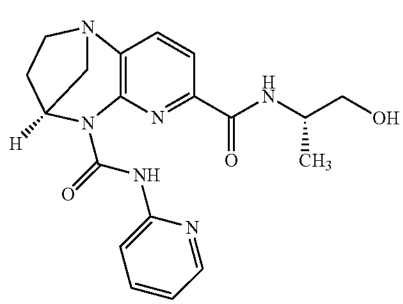 [SMILES: C[C@@H](CO)NC(=O)c1ccc2c(n1)N(C(=O)Nc1ccccn1)[C@H]1CCN2C1] | (9S)-5-N-[(2S)-1-hydroxypropan-2-yl]-8-N-(pyridin-2-yl)-1,6,8-triazatricyclo[7.2.1.0²,⁷]dodeca-2(7),3,5-triene-5,8-dicarboxamide | B | A |

TABLE 1-continued

| Example number | Structure | Chemical Name: Generated by CHemAxon | TRP Activity | TRP MAX RESP |
|---|---|---|---|---|
| 54 | 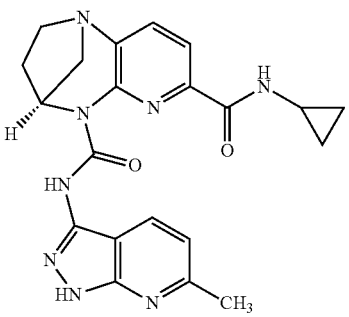 [SMILES: Cc1ccc2c(NC(=O)N3c4nc(C(=O)NC5CC5)ccc4N4CC[C@H]3C4)n[nH]c2n1] | (9S)-5-N-cyclopropyl-8-N-{6-methyl-1H-pyrazolo[3,4-b]pyridin-3-yl}-1,6,8-triazatricyclo[7.2.1.0²,⁷]dodeca-2(7),3,5-triene-5,8-dicarboxamide | B | A |
| 55 | 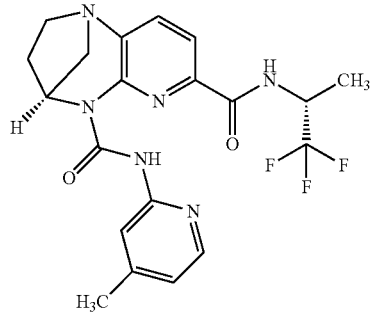 [SMILES: Cc1ccnc(NC(=O)N2c3nc(C(=O)N[C@H](C)C(F)(F)F)ccc3N3CC[C@H]2C3)c1] | (9S)-8-N-(4-methylpyridin-2-yl)-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |
| 56 | 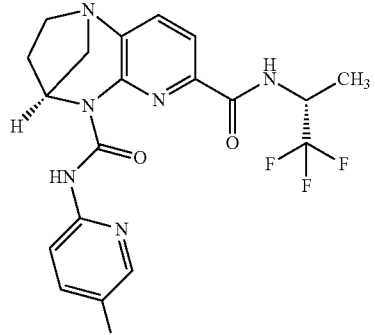 | (9S)-8-N-(5-methylpyridin-2-yl)-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |
| 57 | 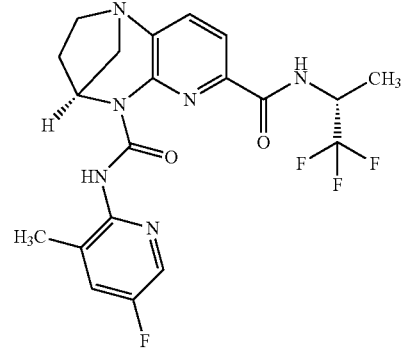 [SMILES: Cc1cc(F)cnc1NC(=O)N1c2nc(C(=O)N[C@H](C)C(F)(F)F)ccc2N2CC[C@H]1C2] | (9S)-8-N-(5-fluoro-3-methylpyridin-2-yl)-5-N-[(2R)-1,1,1-trifluoropropan-2-yl]-1,6,8-triazatricyclo[7.2.1.0²,⁷]dodeca-2(7),3,5-triene-5,8-dicarboxamide | B | A |

TABLE 1-continued

| Example number | Structure | Chemical Name: Generated by CHemAxon | TRP Activity | TRP MAX RESP |
|---|---|---|---|---|
| 58 | 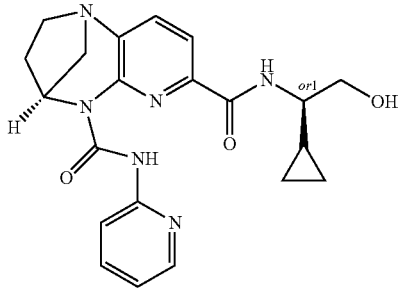 ISOMER 1 | (9S)-5-N-[(1R)-1-cyclopropyl-2-hydroxyethyl]-8-N-(pyridin-2-yl)-1,6,8-triazatricyclo[7.2.1.0²,⁷]dodeca-2(7),3,5-triene-5,8-dicarboxamide | A | A |
| 59 | 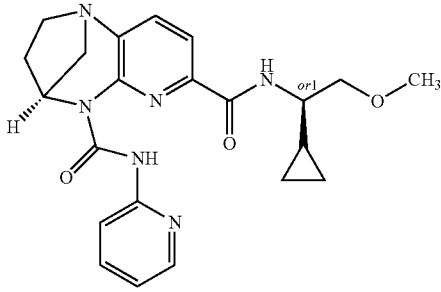 ISOMER 1 | (9S)-5-N-[(1R)-1-cyclopropyl-2-methoxyethyl]-8-N-(pyridin-2-yl)-1,6,8-triazatricyclo[7.2.1.0²,⁷]dodeca-2(7),3,5-triene-5,8-dicarboxamide | A | A |
| 60 | 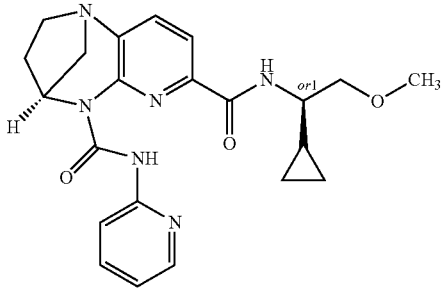 ISOMER 2 | (9S)-5-N-[(1R)-1-cyclopropyl-2-methoxyethyl]-8-N-(pyridin-2-yl)-1,6,8-triazatricyclo[7.2.1.0²,⁷]dodeca-2(7),3,5-triene-5,8-dicarboxamide | A | A |
| 61 | 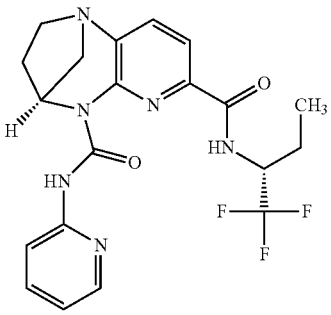 [SMILES: CC[C@@H](NC(=O)c1ccc2c(n1)N(C(=O)Nc1ccccn1)[C@H]1CCN2C1)C(F)(F)F] | (9S)-8-N-(pyridin-2-yl)-5-N-[(2R)-1,1,1-trifluorobutan-2-yl]-1,6,8-triazatricyclo[7.2.1.0²,⁷]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 62 | 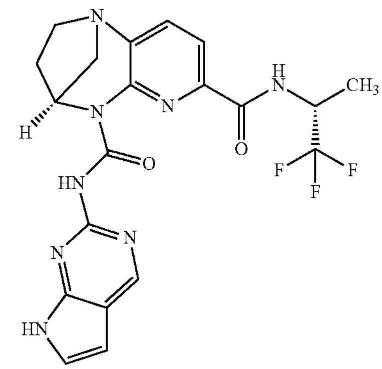 [SMILES: C[C@@H](NC(=O)c1ccc2c(n1)N(C(=O)Nc1ncc3cc[nH]c3n1)[C@H]1CCN2C1)C(F)(F)F] | (9S)-8-N-{7H-pyrrolo[2,3-d]pyrimidin-2-yl}-5-N-[(2R)-1,1,1-trifluoropropan-2-yl]-1,6,8-triazatricyclo[7.2.1.0²,⁷]dodeca-2,4,6-triene-5,8-dicarboxamide | A | A |
| 63 | 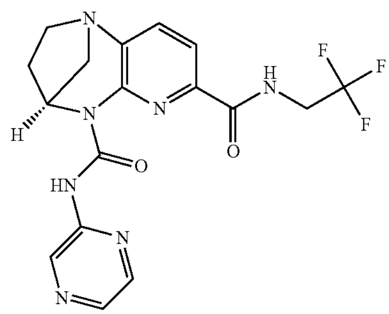 [SMILES: O=C(NCC(F)(F)F)c1ccc2c(n1)N(C(=O)Nc1cnccn1)[C@H]1CCN2C1] | (9S)-8-N-(pyrazin-2-yl)-5-N-(2,2,2-trifluoroethyl)-1,6,8-triazatricyclo[7.2.1.0²,⁷]dodeca-2(7),3,5-triene-5,8-dicarboxamide | A | A |
| 64 | 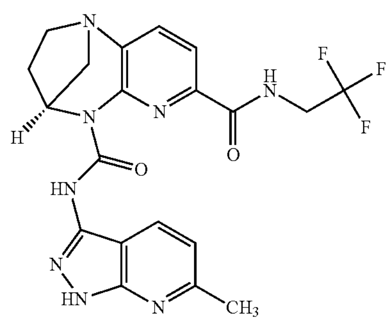 [SMILES: Cc1ccc2c(NC(=O)N3c4nc(C(=O)NCC(F)(F)F)ccc4N4CC[C@H]3C4)n[nH]c2n1] | (9S)-8-N-{6-methyl-1H-pyrazolo[3,4-b]pyridin-3-yl}-5-N-(2,2,2-trifluoroethyl)-1,6,8-triazatricyclo[7.2.1.0²,⁷]dodeca-2(7),3,5-triene-5,8-dicarboxamide | A | A |
| 65 | ISOMER 1 | (9S)-5-N-[(1R)-2,2-difluorocyclopropyl]-8-N-{6-methyl-1H-pyrazolo[3,4-b]pyridin-3-yl}-1,6,8-triazatricyclo[7.2.1.0²,⁷]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 66 | 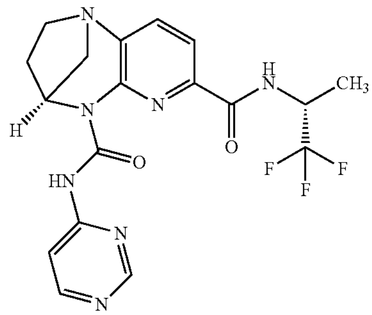 [SMILES: C[C@@H](NC(=O)c1ccc2c(n1)N(C(=O)Nc1ccncn1)[C@H]1CCN2C1)C(F)(F)F] | (9S)-8-N-(pyrimidin-4-yl)-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |
| 67 | 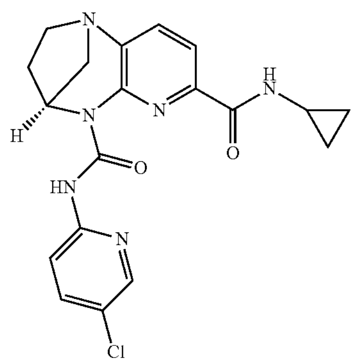 [SMILES: O=C(NC1CC1)c1ccc2c(n1)N(C(=O)Nc1ccc(Cl)cn1)[C@H]1CCN2C1] | (9S)-8-N-(5-chloropyridin-2-yl)-5-N-cyclopropyl-1,6,8-triazatricyclo[7.2.1.0²,⁷]dodeca-2(7),3,5-triene-5,8-dicarboxamide | B | A |
| 68 | 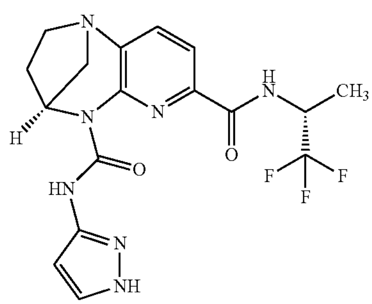 [SMILES: C[C@@H](NC(=O)c1ccc2c(n1)N(C(=O)Nc1cc[nH]n1)[C@H]1CCN2C1)C(F)(F)F] | (9S)-8-N-(1H-pyrazol-3-yl)-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |
| 69 | 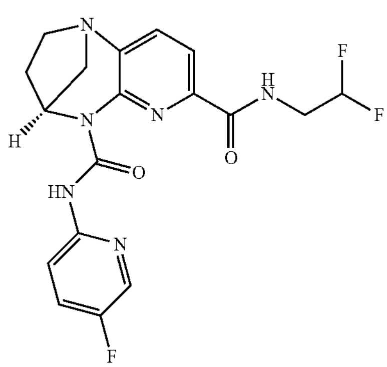 [SMILES: O=C(NCC(F)F)c1ccc2c(n1)N(C(=O)Nc1ccc(F)cn1)[C@H]1CCN2C1] | (9S)-5-N-(2,2-difluoroethyl)-8-N-(5-fluoropyridin-2-yl)-1,6,8-triazatricyclo[7.2.1.0²,⁷]dodeca-2,4,6-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 70 | 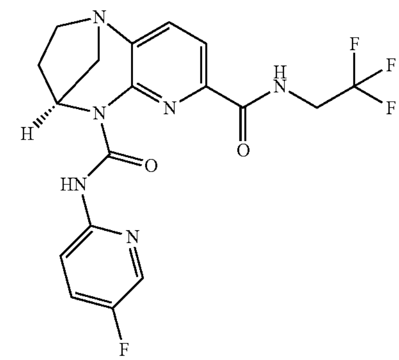 [SMILES: O=C(NCC(F)(F)F)c1ccc2c(n1)N(C(=O)Nc1ccc(F)cn1)[C@H]1CCN2C1] | (9S)-8-N-(5-fluoropyridin-2-yl)-5-N-(2,2,2-trifluoroethyl)-1,6,8-triazatricyclo[7.2.1.0²,⁷]dodeca-2,4,6-triene-5,8-dicarboxamide | A | A |
| 71 | 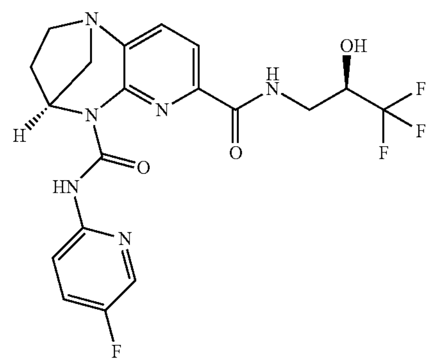 [SMILES: O=C(NC[C@@H](O)C(F)(F)F)c1ccc2c(n1)N(C(=O)Nc1ccc(F)cn1)[C@H]1CCN2C1] | (9S)-8-N-(5-fluoropyridin-2-yl)-5-N-[(2R)-3,3,3-trifluoro-2-hydroxypropyl]-1,6,8-triazatricyclo[7.2.1.0²,⁷]dodeca-2,4,6-triene-5,8-dicarboxamide | A | A |
| 73 | 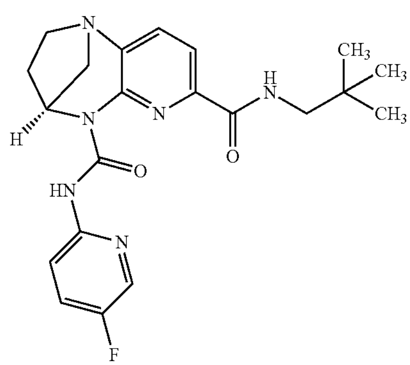 [SMILES: CC(C)(C)CNC(=O)c1ccc2c(n1)N(C(=O)Nc1ccc(F)cn1)[C@H]1CCN2C1] | (9S)-5-N-(2,2-dimethylpropyl)-8-N-(5-fluoropyridin-2-yl)-1,6,8-triazatricyclo[7.2.1.0²,⁷]dodeca-2,4,6-triene-5,8-dicarboxamide | A | A |
| 74 | 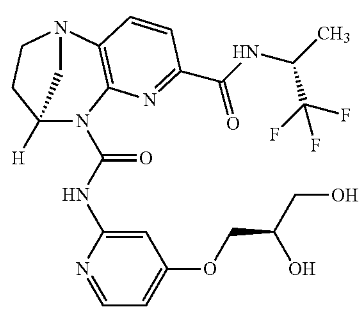 [SMILES: C[C@@H](NC(=O)c1ccc2c(n1)N(C(=O)Nc1cc(OC[C@H](O)CO)ccn1)[C@H]1CCN2C1)C(F)(F)F] | (9S)-8-N-{4-[(2R)-2,3-dihydroxypropoxy]pyridin-2-yl}-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 75 | 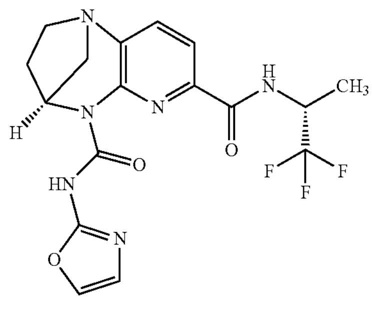 [SMILES: C[C@@H](NC(=O)c1ccc2c(n1)N(C(=O)Nc1ncco1)[C@H]1CCN2C1)C(F)(F)F] | (9S)-8-N-(1,3-oxazol-2-yl)-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | A |
| 76 | 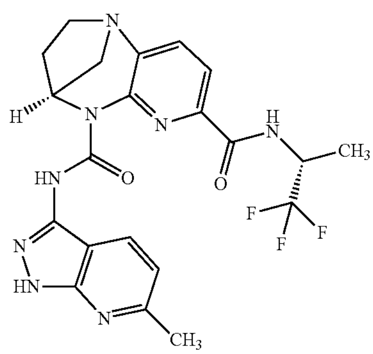 [SMILES: Cc1ccc2c(NC(=O)N3c4nc(C(=O)N[C@H](C)C(F)(F)F)ccc4N4CC[C@H]3C4)n[nH]c2n1] | (9S)-8-N-{6-methyl-1H-pyrazolo[3,4-b]pyridin-3-yl}-5-N-[(2R)-1,1,1-trifluoropropan-2-yl]-1,6,8-triazatricyclo[7.2.1.0$^{2,7}$]dodeca-2,4,6-triene-5,8-dicarboxamide | A | A |
| 77 | 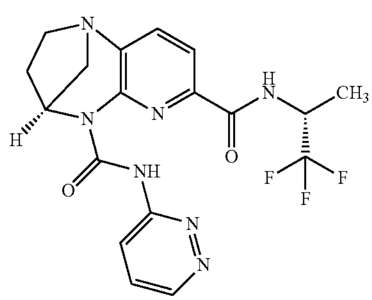 [SMILES: C[C@@H](NC(=O)c1ccc2c(n1)N(C(=O)Nc1cccnn1)[C@H]1CCN2C1)C(F)(F)F] | (9S)-8-N-(pyridazin-3-yl)-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | A |
| 78 | 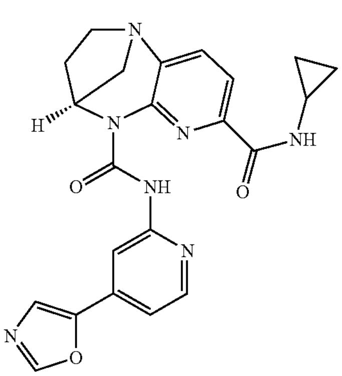 [SMILES: O=C(NC1CC1)c1ccc2c(n1)N(C(=O)Nc1cc(-c3cnco3)ccn1)[C@H]1CCN2C1] | (9S)-5-N-cyclopropyl-8-N-[4-(1,3-oxazol-5-yl)pyridin-2-yl]-1,6,8-triazatricyclo[7.2.1.0$^{2,7}$]dodeca-2,4,6-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 79 | 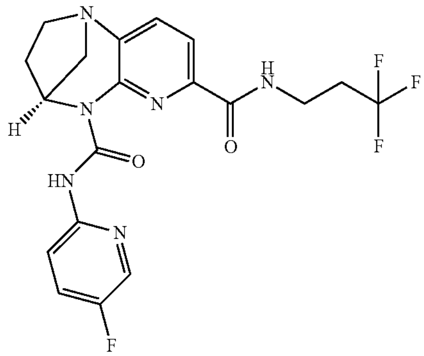 [SMILES: O=C(NCCC(F)(F)F)c1ccc2c(n1)N(C(=O)Nc1ccc(F)cn1)[C@H]1CCN2C1] | (9S)-8-N-(5-fluoropyridin-2-yl)-5-N-(3,3,3-trifluoropropyl)-1,6,8-triazatricyclo[7.2.1.0²,⁷]dodeca-2,4,6-triene-5,8-dicarboxamide | A | A |
| 80 | 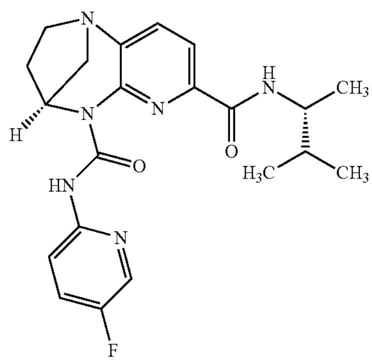 [SMILES: CC(C)[C@@H](C)NC(=O)c1ccc2c(n1)N(C(=O)Nc1ccc(F)cn1)[C@H]1CCN2C1] | (9S)-8-N-(5-fluoropyridin-2-yl)-5-N-[(2R)-3-methylbutan-2-yl]-1,6,8-triazatricyclo[7.2.1.0²,⁷]dodeca-2,4,6-triene-5,8-dicarboxamide | A | A |
| 81 | 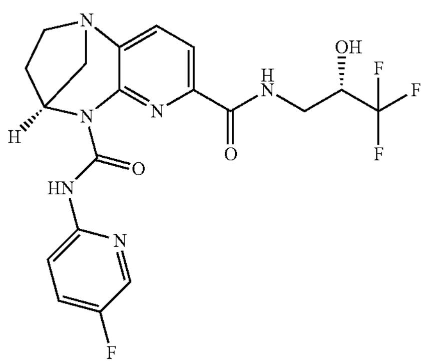 [SMILES: O=C(NC[C@H](O)C(F)(F)F)c1ccc2c(n1)N(C(=O)Nc1ccc(F)cn1)[C@H]1CCN2C1] | (9S)-8-N-(5-fluoropyridin-2-yl)-5-N-[(2S)-3,3,3-trifluoro-2-hydroxypropyl]-1,6,8-triazatricyclo[7.2.1.0²,⁷]dodeca-2,4,6-triene-5,8-dicarboxamide | A | A |
| 82 | 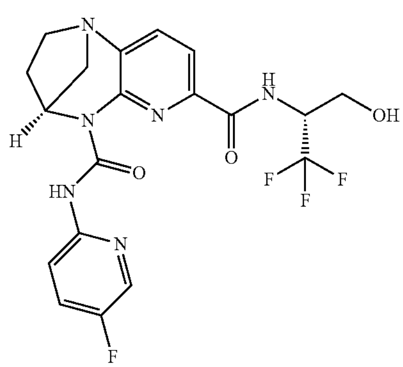 [SMILES: O=C(N[C@H](CO)C(F)(F)F)c1ccc2c(n1)N(C(=O)Nc1ccc(F)cn1)[C@H]1CCN2C1] | (9S)-8-N-(5-fluoropyridin-2-yl)-5-N-[(2R)-1,1,1-trifluoro-3-hydroxypropan-2-yl]-1,6,8-triazatricyclo[7.2.1.0²,⁷]dodeca-2,4,6-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 83 | 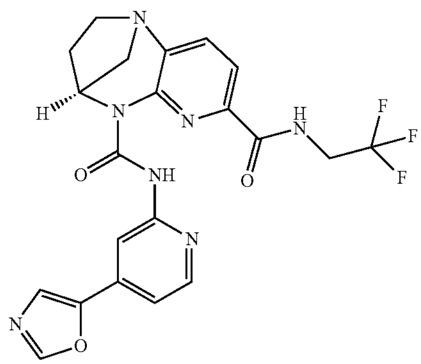 [SMILES: O=C(NCC(F)(F)F)c1ccc2c(n1)N(C(=O)Nc1cc(-c3cnco3)ccn1)[C@H]1CCN2C1] | (9S)-8-N-[4-(1,3-oxazol-5-yl)pyridin-2-yl]-5-N-(2,2,2-trifluoroethyl)-1,6,8-triazatricyclo[7.2.1.0$^{2,7}$]dodeca-2,4,6-triene-5,8-dicarboxamide | A | A |
| 84 | 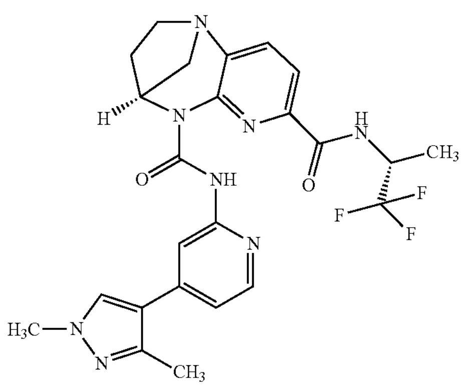 [SMILES: Cc1nn(C)cc1-c1ccnc(NC(=O)N2c3nc(C(=O)N[C@H](C)C(F)(F)F)ccc3N3CC[C@H]2C3)c1] | (9S)-8-N-[4-(1,3-dimethyl-1H-pyrazol-4-yl)pyridin-2-yl]-5-N-[(2R)-1,1,1-trifluoropropan-2-yl]-1,6,8-triazatricyclo[7.2.1.0$^{2,7}$]dodeca-2,4,6-triene-5,8-dicarboxamide | A | A |
| 85 | 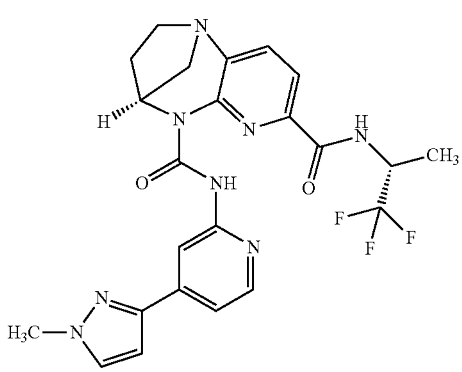 [SMILES: C[C@@H](NC(=O)c1ccc2c(n1)N(C(=O)Nc1cc(-c3ccn(C)n3)ccn1)[C@H]1CCN2C1)C(F)(F)F] | (9S)-8-N-[4-(1-methyl-1H-pyrazol-3-yl)pyridin-2-yl]-5-N-[(2R)-1,1,1-trifluoropropan-2-yl]-1,6,8-triazatricyclo[7.2.1.0$^{2,7}$]dodeca-2,4,6-triene-5,8-dicarboxamide | A | A |
| 86 | 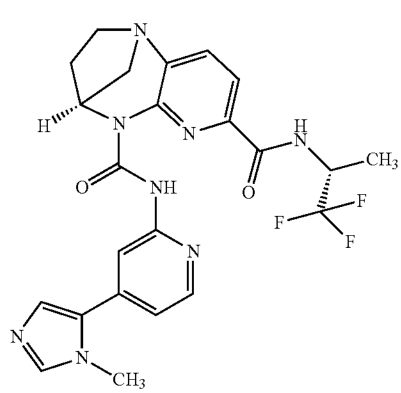 [SMILES: C[C@@H](NC(=O)c1ccc2c(n1)N(C(=O)Nc1cc(-c3cncn3C)ccn1)[C@H]1CCN2C1)C(F)(F)F] | (9S)-8-N-[4-(1-methyl-1H-imidazol-5-yl)pyridin-2-yl]-5-N-[(2R)-1,1,1-trifluoropropan-2-yl]-1,6,8-triazatricyclo[7.2.1.0$^{2,7}$]dodeca-2,4,6-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 87 | | (9S)-5-N-(cyclopropylmethyl)-8-N-{4-[(2R)-2,3-dihydroxypropoxy]pyridin-2-yl}-1,6,8-triazatricyclo[7.2.1.0$^{2,7}$]dodeca-2(7),3,5-triene-5,8-dicarboxamide | A | A |
| 87 | | (9S)-8-N-{4-[(2S)-2,3-dihydroxypropoxy]pyridin-2-yl}-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | A |
| 88 | 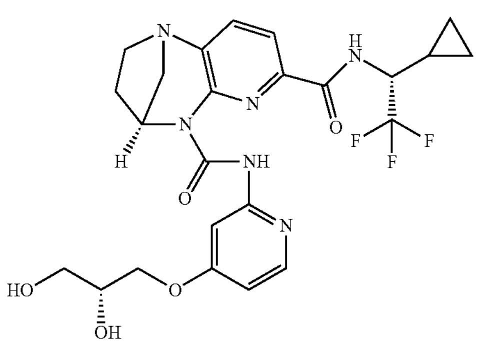 [SMILES: O=C(N[C@H](C1CC1)C(F)(F)F)c1ccc2c(n1)N(C(=O)Nc1cc(OC[C@H](O)CO)ccn1)[C@H]1CCN2C1] | (9S)-5-N-[(1R)-1-cyclopropyl-2,2,2-trifluoroethyl]-8-N-{4-[(2R)-2,3-dihydroxypropoxy]pyridin-2-yl}-1,6,8-triazatricyclo[7.2.1.0$^{2,7}$]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 89 | 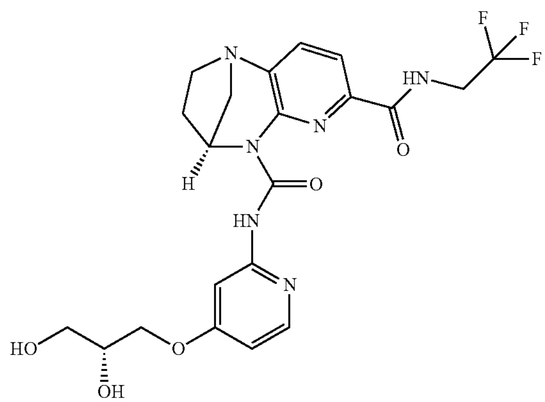 [SMILES: O=C(NCC(F)(F)F)c1ccc2c(n1)N(C(=O)Nc1cc(OC[C@H](O)CO)ccn1)[C@H]1CCN2C1] | (9S)-8-N-{4-[(2R)-2,3-dihydroxypropoxy]pyridin-2-yl}-5-N-(2,2,2-trifluoroethyl)-1,6,8-triazatricyclo[7.2.1.0²,⁷]dodeca-2(7),3,5-triene-5,8-dicarboxamide | A | A |
| 90 | 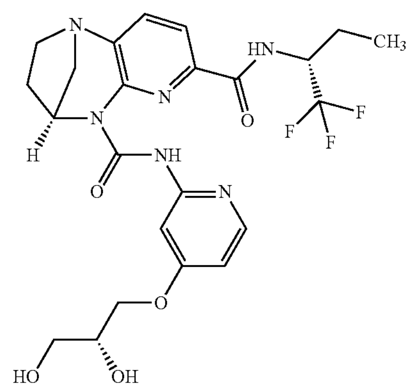 [SMILES: CC[C@@H](NC(=O)c1ccc2c(n1)N(C(=O)Nc1cc(OC[C@H](O)CO)ccn1)[C@H]1CCN2C1)C(F)(F)F] | (9S)-8-N-{4-[(2R)-2,3-dihydroxypropoxy]pyridin-2-yl}-5-N-[(2R)-1,1,1-trifluorobutan-2-yl]-1,6,8-triazatricyclo[7.2.1.0²,⁷]dodeca-2(7),3,5-triene-5,8-dicarboxamide | A | A |
| 91 | 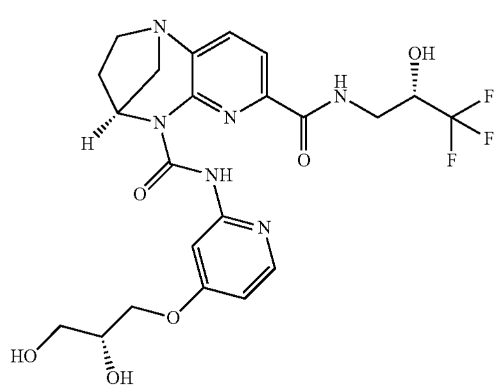 [SMILES: O=C(NC[C@H](O)C(F)(F)F)c1ccc2c(n1)N(C(=O)Nc1cc(OC[C@H](O)CO)ccn1)[C@H]1CCN2C1] | (9S)-8-N-{4-[(2R)-2,3-dihydroxypropoxy]pyridin-2-yl}-5-N-[(2S)-3,3,3-trifluoro-2-hydroxypropyl]-1,6,8-triazatricyclo[7.2.1.0²,⁷]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 92 | 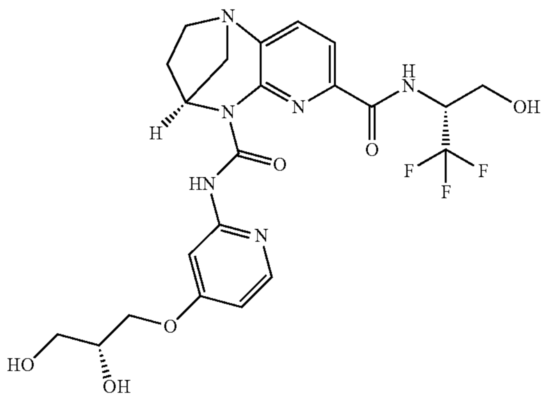 [SMILES: O=C(N[C@H](CO)C(F)(F)F)c1ccc2c(n1)N(C(=O)Nc1cc(OC[C@H](O)CO)ccn1)[C@H]1CCN2C1] | (9S)-8-N-{4-[(2R)-2,3-dihydroxypropoxy]pyridin-2-yl}-5-N-[(2R)-1,1,1-trifluoro-3-hydroxypropan-2-yl]-1,6,8-triazatricyclo[7.2.1.0²,⁷]dodeca-2(7),3,5-triene-5,8-dicarboxamide | A | A |
| 93 | 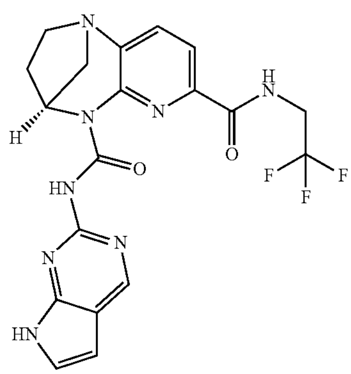 [SMILES: O=C(NCC(F)(F)F)c1ccc2c(n1)N(C(=O)Nc1ncc3cc[nH]c3n1)[C@H]1CCN2C1] | (9S)-8-N-{7H-pyrrolo[2,3-d]pyrimidin-2-yl}-5-N-(2,2,2-trifluoroethyl)-1,6,8-triazatricyclo[7.2.1.0²,⁷]dodeca-2,4,6-triene-5,8-dicarboxamide | A | A |
| 94 | 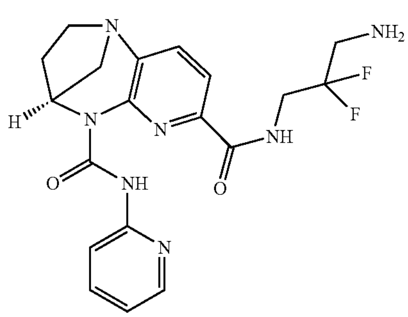 [SMILES: NCC(F)(F)CNC(=O)c1ccc2c(n1)N(C(=O)Nc1ccccn1)[C@H]1CCN2C1] | (9S)-5-N-(3-amino-2,2-difluoropropyl)-8-N-(pyridin-2-yl)-1,6,8-triazatricyclo[7.2.1.0²,⁷]dodeca-2(7),3,5-triene-5,8-dicarboxamide | B | A |

TABLE 1-continued

| Example number | Structure | Chemical Name: Generated by CHemAxon | TRP Activity | TRP MAX RESP |
|---|---|---|---|---|
| 95 | 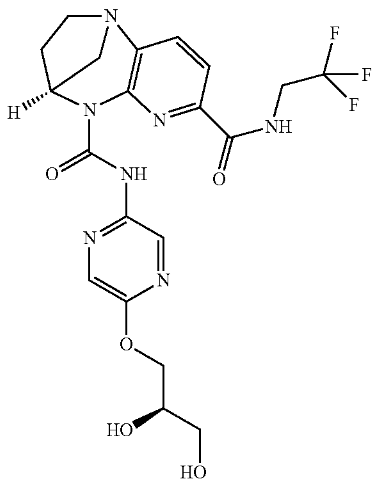 [SMILES: O=C(NCC(F)(F)F)c1ccc2c(n1)N(C(=O)Nc1cnc(OC[C@H](O)CO)cn1)[C@H]1CCN2C1] | (9S)-8-N-{5-[(2R)-2,3-dihydroxypropoxy]pyrazin-2-yl}-5-N-(2,2,2-trifluoroethyl)-1,6,8-triazatricyclo[7.2.1.0$^{2,7}$]dodeca-2(7),3,5-triene-5,8-dicarboxamide | A | A |
| 96 | 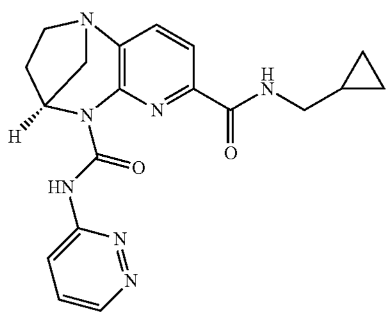 [SMILES: O=C(NCC1CC1)c1ccc2c(n1)N(C(=O)Nc1cccnn1)[C@H]1CCN2C1] | (9S)-5-N-(cyclopropylmethyl)-8-N-(pyridazin-3-yl)-1,6,8-triazatricyclo[7.2.1.0$^{2,7}$]dodeca-2(7),3,5-triene-5,8-dicarboxamide | A | A |
| 97 | 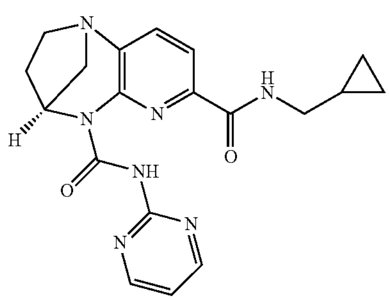 [SMILES: O=C(NCC1CC1)c1ccc2c(n1)N(C(=O)Nc1ncccn1)[C@H]1CCN2C1] | (9S)-5-N-(cyclopropylmethyl)-8-N-(pyrimidin-2-yl)-1,6,8-triazatricyclo[7.2.1.0$^{2,7}$]dodeca-2(7),3,5-triene-5,8-dicarboxamide | A | A |
| 98 | 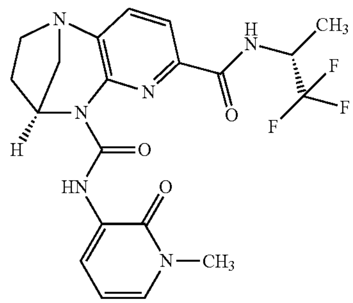 [SMILES: C[C@@H](NC(=O)c1ccc2c(n1)N(C(=O)Nc1cccn(C)c1=O)[C@H]1CCN2C1)C(F)(F)F] | (9S)-8-N-(1-methyl-2-oxo-1,2-dihydropyridin-3-yl)-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 99 | 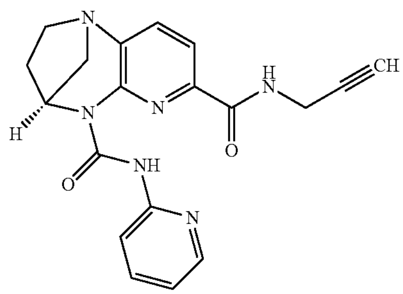 [SMILES: C#CCNC(=O)c1ccc2c(n1)N(C(=O)Nc1ccccn1)[C@H]1CCN2C1] | (9S)-5-N-(prop-2-yn-1-yl)-8-N-(pyridin-2-yl)-1,6,8-triazatricyclo[7.2.1.0²,⁷]dodeca-2(7),3,5-triene-5,8-dicarboxamide | A | A |
| 100 | ISOMER 2 | (9S)-5-N-[(1S)-1-cyclopropylethyl]-8-N-(pyridin-2-yl)-1,6,8-triazatricyclo[7.2.1.0²,⁷]dodeca-2(7),3,5-triene-5,8-dicarboxamide | A | A |
| 101 | ISOMER 1 | (9S)-5-N-[(1S)-1-cyclopropylethyl]-8-N-(pyridin-2-yl)-1,6,8-triazatricyclo[7.2.1.0²,⁷]dodeca-2(7),3,5-triene-5,8-dicarboxamide | A | A |
| 102 | ISOMER 2 | (9S)-5-N-[(1R)-1-cyanoethyl]-8-N-(pyridin-2-yl)-1,6,8-triazatricyclo[7.2.1.0²,⁷]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 103 | ISOMER 1 | (9S)-5-N-[(1R)-1-cyanoethyl]-8-N-(pyridin-2-yl)-1,6,8-triazatricyclo[7.2.1.0²,⁷]dodeca-2(7),3,5-triene-5,8-dicarboxamide | A | A |
| 104 | 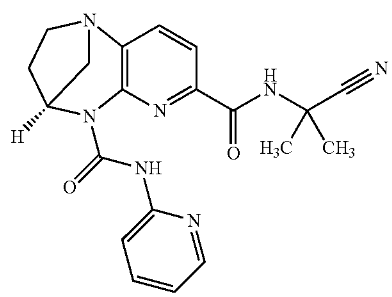 [SMILES: CC(C)(C#N)NC(=O)c1ccc2c(n1)N(C(=O)Nc1ccccn1)[C@H]1CCN2C1] | (9S)-5-N-(1-cyano-1-methylethyl)-8-N-(pyridin-2-yl)-1,6,8-triazatricyclo[7.2.1.0²,⁷]dodeca-2(7),3,5-triene-5,8-dicarboxamide | B | A |
| 105 | 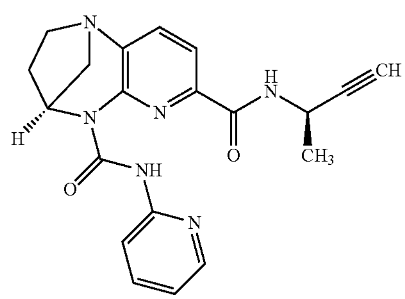 [SMILES: C#C[C@@H](C)NC(=O)c1ccc2c(n1)N(C(=O)Nc1ccccn1)[C@H]1CCN2C1] | (9S)-5-N-[(2R)-but-3-yn-2-yl]-8-N-(pyridin-2-yl)-1,6,8-triazatricyclo[7.2.1.0²,⁷]dodeca-2(7),3,5-triene-5,8-dicarboxamide | A | A |
| 106 | 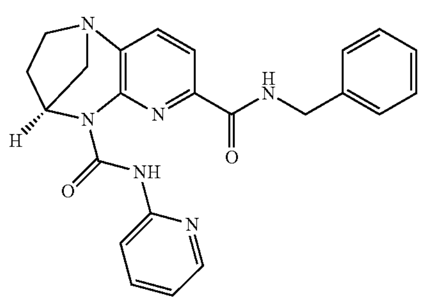 [SMILES: O=C(NCc1ccccc1)c1ccc2c(n1)N(C(=O)Nc1ccccn1)[C@H]1CCN2C1] | (9S)-5-N-benzyl-8-N-(pyridin-2-yl)-1,6,8-triazatricyclo[7.2.1.0²,⁷]dodeca-2(7),3,5-triene-5,8-dicarboxamide | A | A |
| 107 | 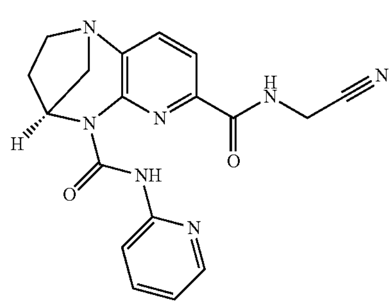 [SMILES: N#CCNC(=O)c1ccc2c(n1)N(C(=O)Nc1ccccn1)[C@H]1CCN2C1] | (9S)-5-N-(cyanomethyl)-8-N-(pyridin-2-yl)-1,6,8-triazatricyclo[7.2.1.0²,⁷]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 108 | 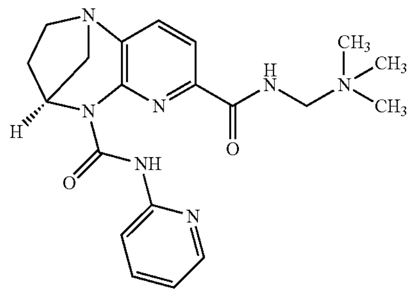 | (9S)-8-N-(pyridin-2-yl)-5-N-[(trimethylsilyl)methyl]-1,6,8-triazatricyclo[7.2.1.0$^{2,7}$]dodeca-2(7),3,5-triene-5,8-dicarboxamide | A | A |
| 109 | 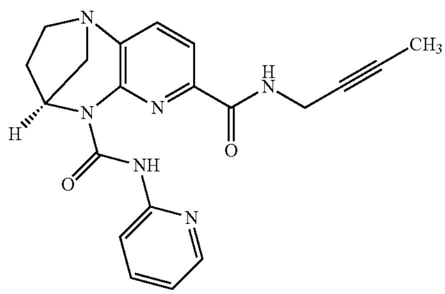 [SMILES: CC#CCNC(=O)c1ccc2c(n1)N(C(=O)Nc1ccccn1)[C@H]1CCN2C1] | (9S)-5-N-(but-2-yn-1-yl)-8-N-(pyridin-2-yl)-1,6,8-triazatricyclo[7.2.1.0$^{2,7}$]dodeca-2(7),3,5-triene-5,8-dicarboxamide | A | A |
| 110 | 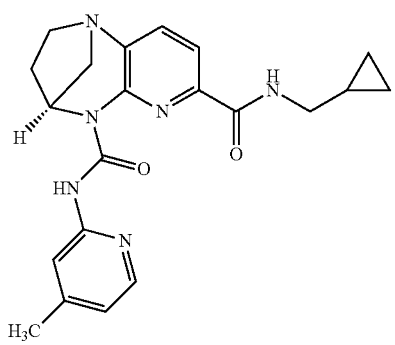 [SMILES: Cc1ccnc(NC(=O)N2c3nc(C(=O)NCC4CC4)ccc3N3CC[C@H]2C3)c1] | (9S)-5-N-(cyclopropylmethyl)-8-N-(4-methylpyridin-2-yl)-1,6,8-triazatricyclo[7.2.1.0$^{2,7}$]dodeca-2(7),3,5-triene-5,8-dicarboxamide | A | A |
| 111 | 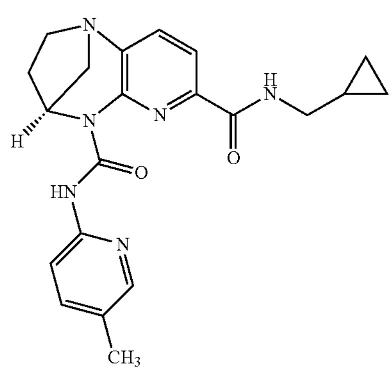 [SMILES: Cc1ccc(NC(=O)N2c3nc(C(=O)NCC4CC4)ccc3N3CC[C@H]2C3)nc1] | (9S)-5-N-(cyclopropylmethyl)-8-N-(5-methylpyridin-2-yl)-1,6,8-triazatricyclo[7.2.1.0$^{2,7}$]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 112 | 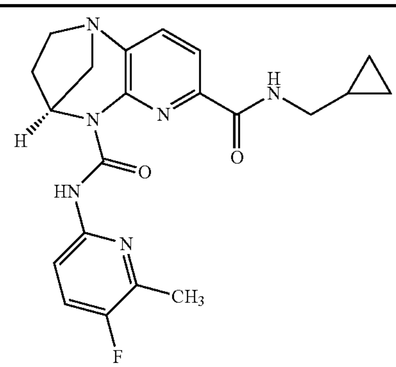 | (9S)-5-N-(cyclopropylmethyl)-8-N-(5-fluoro-6-methylpyridin-2-yl)-1,6,8-triazatricyclo[7.2.1.0$^{2,7}$]dodeca-2(7),3,5-triene-5,8-dicarboxamide | A | A |
| 113 | 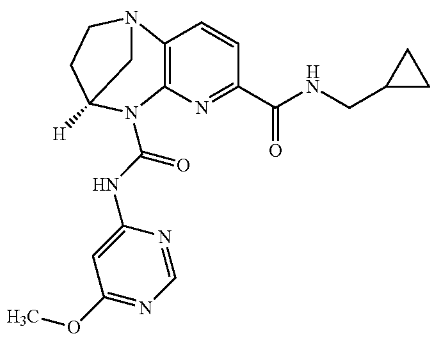 [SMILES: COc1cc(NC(=O)N2c3nc(C(=O)NCC4CC4)ccc3N3CC[C@H]2C3)ncn1] | (9S)-5-N-(cyclopropylmethyl)-8-N-(6-methoxypyrimidin-4-yl)-1,6,8-triazatricyclo[7.2.1.0$^{2,7}$]dodeca-2(7),3,5-triene-5,8-dicarboxamide | B | A |
| 114 | 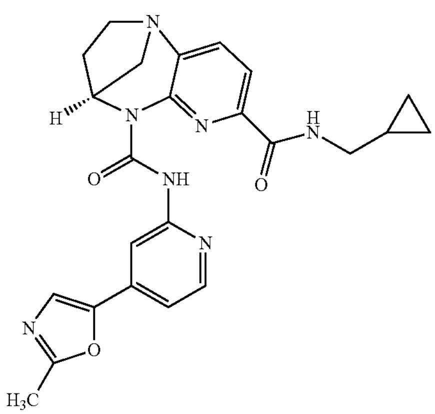 [SMILES: Cc1ncc(-c2ccnc(NC(=O)N3c4nc(C(=O)NCC5CC5)ccc4N4CC[C@H]3C4)c2)o1] | (9S)-5-N-(cyclopropylmethyl)-8-N-[4-(2-methyl-1,3-oxazol-5-yl)pyridin-2-yl]-1,6,8-triazatricyclo[7.2.1.0$^{2,7}$]dodeca-2,4,6-triene-5,8-dicarboxamide | B | A |
| 115 | 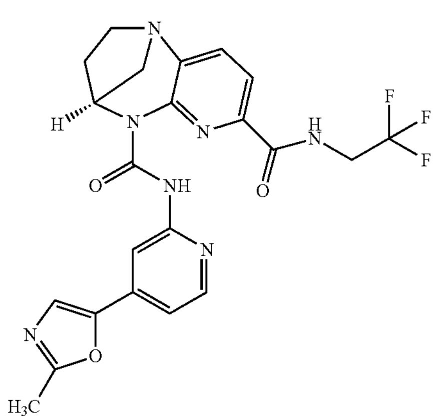 [SMILES: Cc1ncc(-c2ccnc(NC(=O)N3c4nc(C(=O)NCC(F)(F)F)ccc4N4CC[C@H]3C4)c2)o1] | (9S)-8-N-[4-(2-methyl-1,3-oxazol-5-yl)pyridin-2-yl]-5-N-(2,2,2-trifluoroethyl)-1,6,8-triazatricyclo[7.2.1.0$^{2,7}$]dodeca-2,4,6-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 116 | 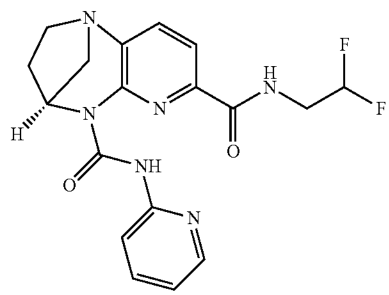 [SMILES: O=C(NCC(F)F)c1ccc2c(n1)N(C(=O)Nc1ccccn1)[C@H]1CCN2C1] | (9S)-5-N-(2,2-difluoroethyl)-8-N-(pyridin-2-yl)-1,6,8-triazatricyclo[7.2.1.0$^{2,7}$]dodeca-2(7),3,5-triene-5,8-dicarboxamide | A | A |
| 117 | 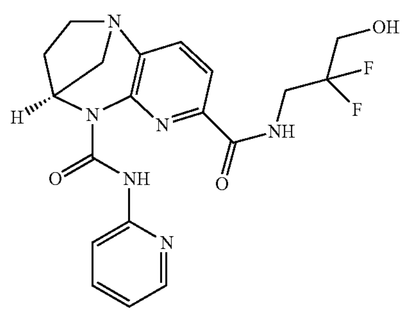 [SMILES: O=C(NCC(F)(F)CO)c1ccc2c(n1)N(C(=O)Nc1ccccn1)[C@H]1CCN2C1] | (9S)-5-N-(2,2-difluoro-3-hydroxypropyl)-8-N-(pyridin-2-yl)-1,6,8-triazatricyclo[7.2.1.0$^{2,7}$]dodeca-2(7),3,5-triene-5,8-dicarboxamide | A | A |
| 118 | 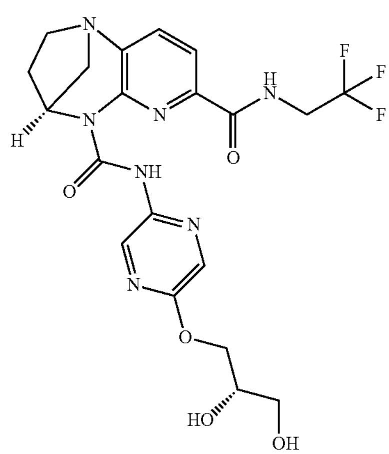 [SMILES: O=C(NCC(F)(F)F)c1ccc2c(n1)N(C(=O)Nc1cnc(OC[C@@H](O)CO)cn1)[C@H]1CCN2C1] | (9S)-8-N-{5-[(2S)-2,3-dihydroxypropoxy]pyrazin-2-yl}-5-N-(2,2,2-trifluoroethyl)-1,6,8-triazatricyclo[7.2.1.0$^{2,7}$]dodeca-2(7),3,5-triene-5,8-dicarboxamide | B | A |
| 119 | 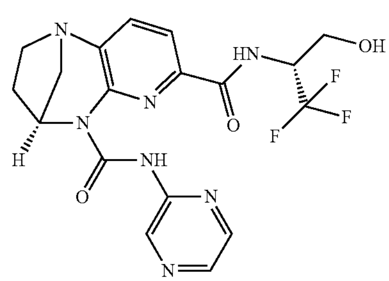 [SMILES: O=C(N[C@H](CO)C(F)(F)F)c1ccc2c(n1)N(C(=O)Nc1cnccn1)[C@H]1CCN2C1] | (9S)-8-N-(pyrazin-2-yl)-5-N-[(2R)-1,1,1-trifluoro-3-hydroxypropan-2-yl]-1,6,8-triazatricyclo[7.2.1.0$^{2,7}$]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 120 | 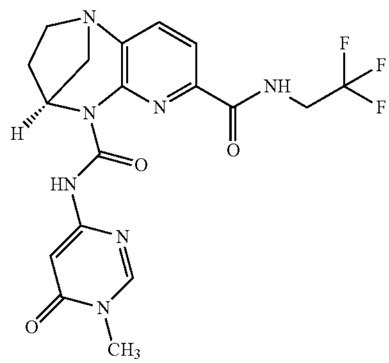 [SMILES: Cn1cnc(NC(=O)N2c3nc(C(=O)NCC(F)(F)F)ccc3N3CC[C@H]2C3)cc1=O] | (9S)-8-N-(1-methyl-6-oxo-1,6-dihydropyrimidin-4-yl)-5-N-(2,2,2-trifluoroethyl)-1,6,8-triazatricyclo[7.2.1.0²,⁷]dodeca-2(7),3,5-triene-5,8-dicarboxamide | B | A |
| 121 | 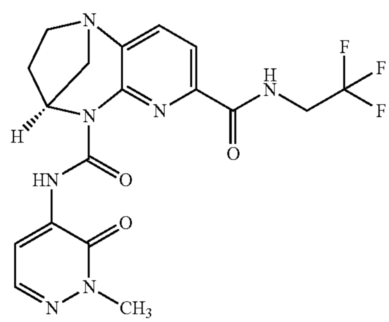 [SMILES: Cn1nccc(NC(=O)N2c3nc(C(=O)NCC(F)(F)F)ccc3N3CC[C@H]2C3)c1=O] | (9S)-8-N-(2-methyl-3-oxo-2,3-dihydropyridazin-4-yl)-5-N-(2,2,2-trifluoroethyl)-1,6,8-triazatricyclo[7.2.1.0²,⁷]dodeca-2,4,6-triene-5,8-dicarboxamide | A | A |
| 122 | 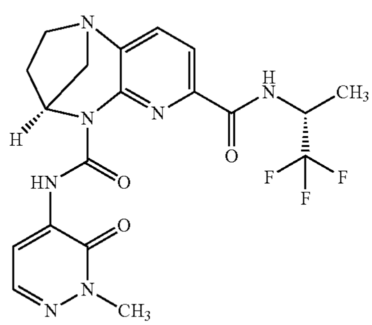 [SMILES: C[C@@H](NC(=O)c1ccc2c(n1)N(C(=O)Nc1ccnn(C)c1=O)[C@H]1CCN2C1)C(F)(F)F] | (9S)-8-N-(2-methyl-3-oxo-2,3-dihydropyridazin-4-yl)-5-N-[(2R)-1,1,1-trifluoropropan-2-yl]-1,6,8-triazatricyclo[7.2.1.0²,⁷]dodeca-2,4,6-triene-5,8-dicarboxamide | A | A |
| 123 | 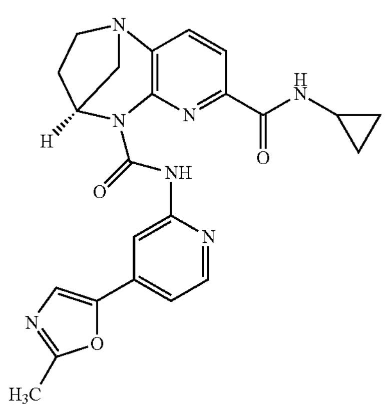 [SMILES: Cc1ncc(-c2ccnc(NC(=O)N3c4nc(C(=O)NC5CC5)ccc4N4CC[C@H]3C4)c2)o1] | (9S)-5-N-cyclopropyl-8-N-[4-(2-methyl-1,3-oxazol-5-yl)pyridin-2-yl]-1,6,8-triazatricyclo[7.2.1.0²,⁷]dodeca-2(7),3,5-triene-5,8-dicarboxamide | B | A |

TABLE 1-continued

| Example number | Structure | Chemical Name: Generated by CHemAxon | TRP Activity | TRP MAX RESP |
|---|---|---|---|---|
| 124 | 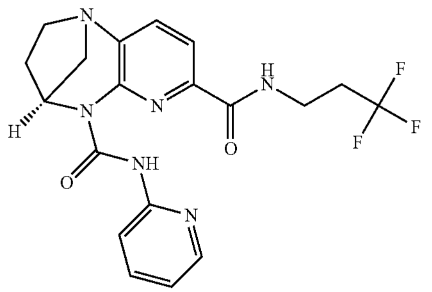 [SMILES: O=C(NCCC(F)(F)F)c1ccc2c(n1)N(C(=O)Nc1ccccn1)[C@H]1CCN2C1] | (9S)-8-N-(pyridin-2-yl)-5-N-(3,3,3-trifluoropropyl)-1,6,8-triazatricyclo[7.2.1.0²,⁷]dodeca-2(7),3,5-triene-5,8-dicarboxamide | A | A |
| 125 | 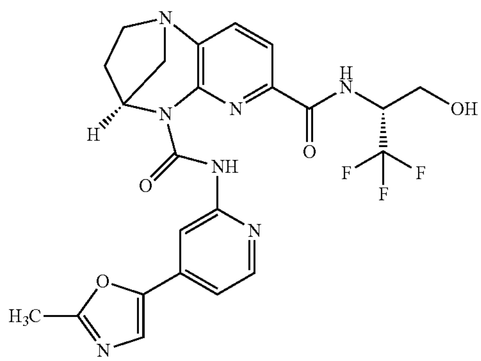 [SMILES: Cc1ncc(-c2ccnc(NC(=O)N3c4nc(C(=O)N[C@H](CO)C(F)(F)F)ccc4N4CC[C@H]3C4)c2)o1] | (9S)-8-N-[4-(2-methyl-1,3-oxazol-5-yl)pyridin-2-yl]-5-N-[(2R)-1,1,1-trifluoro-3-hydroxypropan-2-yl]-1,6,8-triazatricyclo[7.2.1.0²,⁷]dodeca-2(7),3,5-triene-5,8-dicarboxamide | A | A |
| 126 | 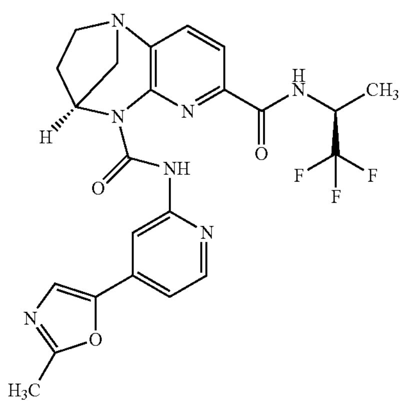 [SMILES: Cc1ncc(-c2ccnc(NC(=O)N3c4nc(C(=O)N[C@@H](C)C(F)(F)F)ccc4N4CC[C@H]3C4)c2)o1] | (9S)-8-N-[4-(2-methyl-1,3-oxazol-5-yl)pyridin-2-yl]-5-N-[(2S)-1,1,1-trifluoropropan-2-yl]-1,6,8-triazatricyclo[7.2.1.0²,⁷]dodeca-2(7),3,5-triene-5,8-dicarboxamide | B | A |
| 127 | 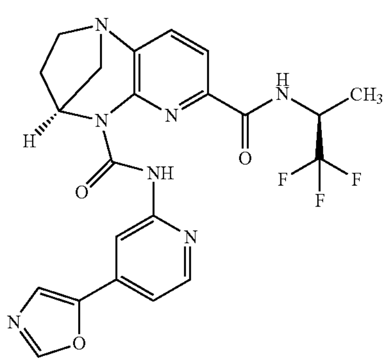 [SMILES: C[C@H](NC(=O)c1ccc2c(n1)N(C(=O)Nc1cc(-c3cnco3)ccn1)[C@H]1CCN2C1)C(F)(F)F] | (9S)-8-N-[4-(1,3-oxazol-5-yl)pyridin-2-yl]-5-N-[(2S)-1,1,1-trifluoropropan-2-yl]-1,6,8-triazatricyclo[7.2.1.0²,⁷]dodeca-2(7),3,5-triene-5,8-dicarboxamide | B | A |

TABLE 1-continued

| Example number | Structure | Chemical Name: Generated by CHemAxon | TRP Activity | TRP MAX RESP |
|---|---|---|---|---|
| 128 | 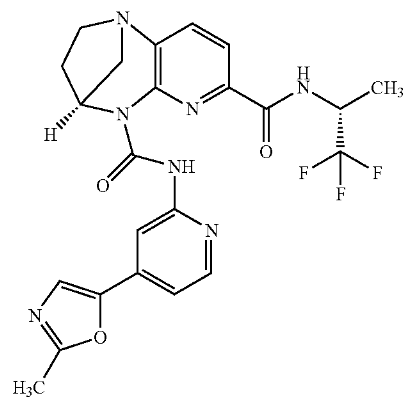 [SMILES: Cc1ncc(-c2ccnc(NC(=O)N3c4nc(C(=O)N[C@H](C)C(F)(F)F)ccc4N4CC[C@H]3C4)c2)o1] | (9S)-8-N-[4-(2-methyl-1,3-oxazol-5-yl)pyridin-2-yl]-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | A |
| 129 | 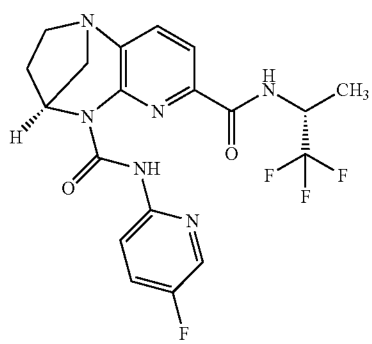 [SMILES: C[C@@H](NC(=O)c1ccc2c(n1)N(C(=O)Nc1ccc(F)cn1)[C@H]1CCN2C1)C(F)(F)F] | (9S)-8-N-(5-fluoropyridin-2-yl)-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | A |
| 130 | 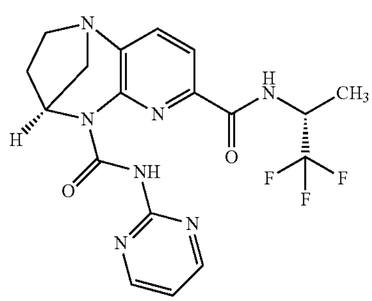 [SMILES: C[C@@H](NC(=O)c1ccc2c(n1)N(C(=O)Nc1ncccn1)[C@H]1CCN2C1)C(F)(F)F] | (9S)-8-N-(pyrimidin-2-yl)-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | A |
| 131 | 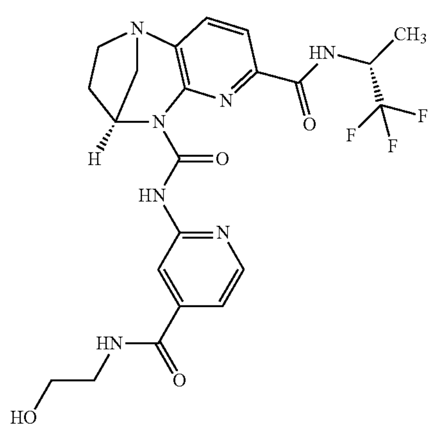 [SMILES: C[C@@H](NC(=O)c1ccc2c(n1)N(C(=O)Nc1cc(C(=O)NCCO)ccn1)[C@H]1CCN2C1)C(F)(F)F] | (9S)-8-N-{4-[(2-hydroxyethyl)carbamoyl]pyridin-2-yl}-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 132 | 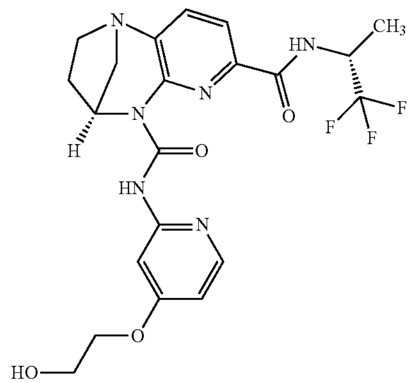 [SMILES: C[C@@H](NC(=O)c1ccc2c(n1)N(C(=O)Nc1cc(OCCO)ccn1)[C@H]1CCN2C1)C(F)(F)F] | (9S)-8-N-[4-(2-hydroxyethoxy)pyridin-2-yl]-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |
| 133 | 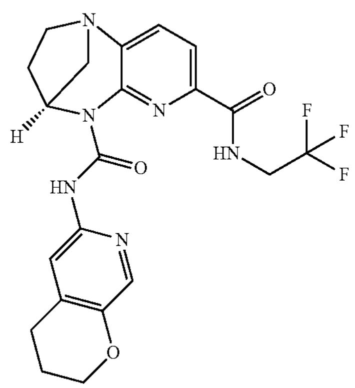 [SMILES: O=C(NCC(F)(F)F)c1ccc2c(n1)N(C(=O)Nc1cc3c(cn1)OCCC3)[C@H]1CCN2C1] | (9S)-8-N-{2H,3H,4H-pyrano[2,3-c]pyridin-6-yl}-5-N-(2,2,2-trifluoroethyl)-1,6,8-triazatricyclo[7.2.1.0²,⁷]dodeca-2,4,6-triene-5,8-dicarboxamide | A | A |
| 134 | 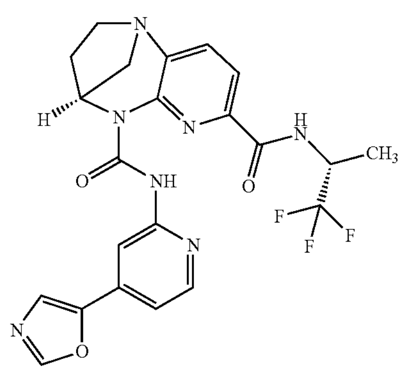 [SMILES: C[C@@H](NC(=O)c1ccc2c(n1)N(C(=O)Nc1cc(-c3cnco3)ccn1)[C@H]1CCN2C1)C(F)(F)F] | (9S)-8-N-[4-(1,3-oxazol-5-yl)pyridin-2-yl]-5-N-[(2R)-1,1,1-trifluoropropan-2-yl]-1,6,8-triazatricyclo[7.2.1.0²,⁷]dodeca-2,4,6-triene-5,8-dicarboxamide | A | A |
| 135 | 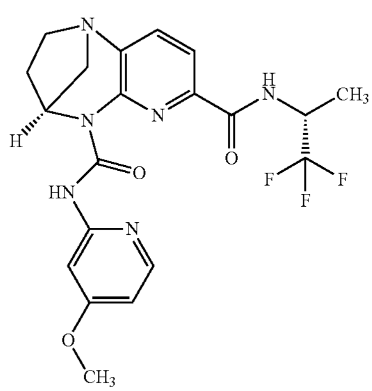 [SMILES: COc1ccnc(NC(=O)N2c3nc(C(=O)N[C@H](C)C(F)(F)F)ccc3N3CC[C@H]2C3)c1] | (9S)-8-N-(4-methoxypyridin-2-yl)-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 136 | 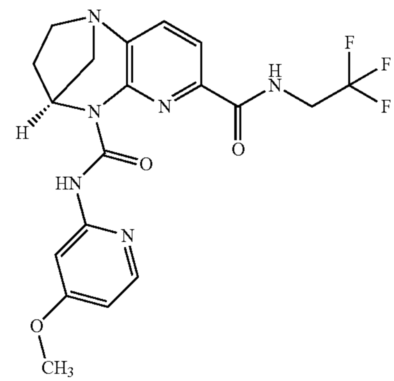 [SMILES: COc1ccnc(NC(=O)N2c3nc(C(=O)NCC(F)(F)F)ccc3N3CC[C@H]2C3)c1] | (9S)-8-N-(4-methoxypyridin-2-yl)-5-N-(2,2,2-trifluoroethyl)-1,6,8-triazatricyclo[7.2.1.0²,⁷]dodeca-2(7),3,5-triene-5,8-dicarboxamide | A | A |
| 137 | 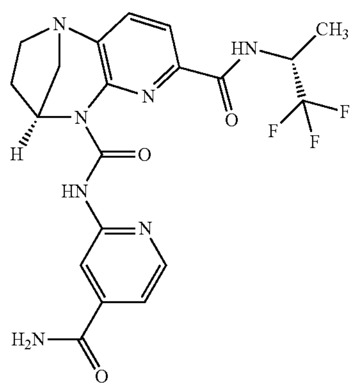 [SMILES: C[C@@H](NC(=O)c1ccc2c(n1)N(C(=O)Nc1cc(C(N)=O)ccn1)[C@H]1CCN2C1)C(F)(F)F] | (9S)-8-N-(4-carbamoylpyridin-2-yl)-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |
| 138 | 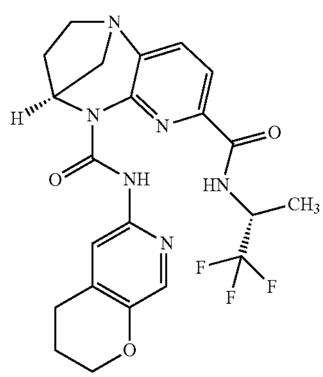 [SMILES: C[C@@H](NC(=O)c1ccc2c(n1)N(C(=O)Nc1cc3c(cn1)OCCC3)[C@H]1CCN2C1)C(F)(F)F] | (9S)-8-N-{2H,3H,4H-pyrano[2,3-c]pyridin-6-yl}-5-N-[(2R)-1,1,1-trifluoropropan-2-yl]-1,6,8-triazatricyclo[7.2.1.0²,⁷]dodeca-2,4,6-triene-5,8-dicarboxamide | A | A |
| 139 | 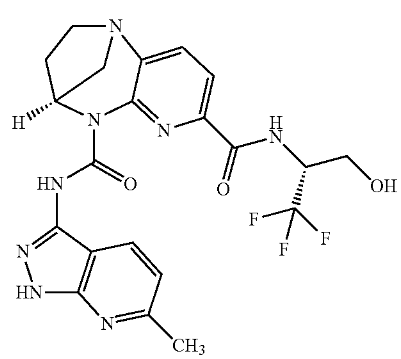 [SMILES: Cc1ccc2c(NC(=O)N3c4nc(C(=O)N[C@H](CO)C(F)(F)F)ccc4N4CC[C@H]3C4)n[nH]c2n1] | (9S)-8-N-{6-methyl-1H-pyrazolo[3,4-b]pyridin-3-yl}-5-N-[(2R)-1,1,1-trifluoro-3-hydroxypropan-2-yl]-1,6,8-triazatricyclo[7.2.1.0²,⁷]dodeca-2,4,6-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 140 | 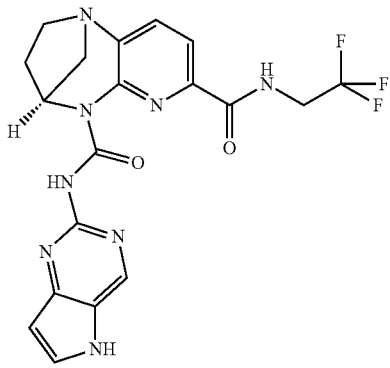 [SMILES: O=C(NCC(F)(F)F)c1ccc2c(n1)N(C(=O)Nc1ncc3[nH]ccc3n1)[C@H]1CCN2C1] | (9S)-8-N-{5H-pyrrolo[3,2-d]pyrimidin-2-yl}-5-N-(2,2,2-trifluoroethyl)-1,6,8-triazatricyclo[7.2.1.0²,⁷]dodeca-2,4,6-triene-5,8-dicarboxamide | A | A |
| 141 | 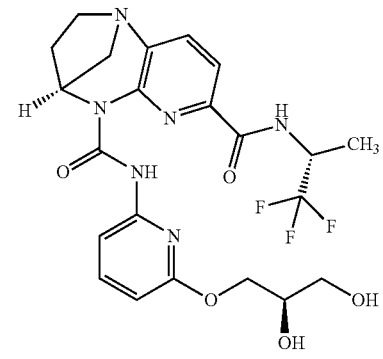 [SMILES: C[C@@H](NC(=O)c1ccc2c(n1)N(C(=O)Nc1cccc(OC[C@H](O)CO)n1)[C@H]1CCN2C1)C(F)(F)F] | (9S)-8-N-{6-[(2R)-2,3-dihydroxypropoxy]pyridin-2-yl}-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |
| 142 | 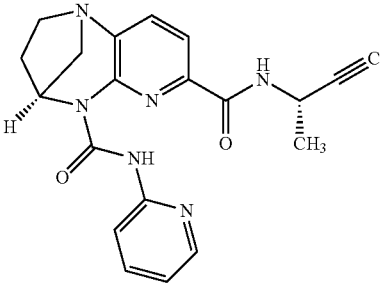 | (9S)-5-N-[(2S)-but-3-yn-2-yl]-8-N-(pyridin-2-yl)-1,6,8-triazatricyclo[7.2.1.0²,⁷]dodeca-2(7),3,5-triene-5,8-dicarboxamide | A | A |
| 143 | 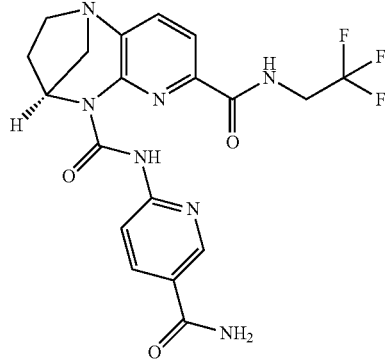 [SMILES: NC(=O)c1ccc(NC(=O)N2c3nc(C(=O)NCC(F)(F)F)ccc3N3CC[C@H]2C3)nc1] | (9S)-8-N-(5-carbamoylpyridin-2-yl)-5-N-(2,2,2-trifluoroethyl)-1,6,8-triazatricyclo[7.2.1.0²,⁷]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 144 | 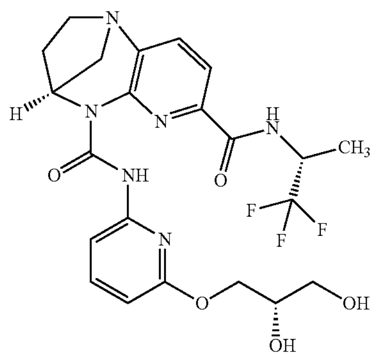 [SMILES: C[C@@H](NC(=O)c1ccc2c(n1)N(C(=O)Nc1cccc(OC[C@@H](O)CO)n1)[C@H]1CCN2C1)C(F)(F)F] | (9S)-8-N-{6-[(2S)-2,3-dihydroxypropoxy]pyridin-2-yl}-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |
| 145 | 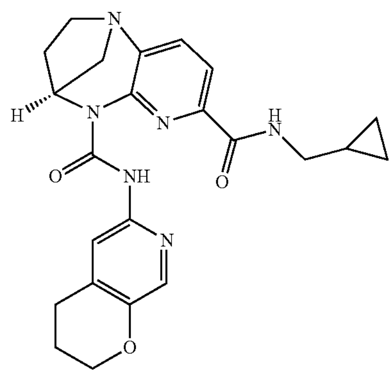 [SMILES: O=C(NCC1CC1)c1ccc2c(n1)N(C(=O)Nc1cc3c(cn1)OCCC3)[C@H]1CCN2C1] | (9S)-5-N-(cyclopropylmethyl)-8-N-{2H,3H,4H-pyrano[2,3-c]pyridin-6-yl}-1,6,8-triazatricyclo[7.2.1.0²,⁷]dodeca-2,4,6-triene-5,8-dicarboxamide | A | A |
| 146 | 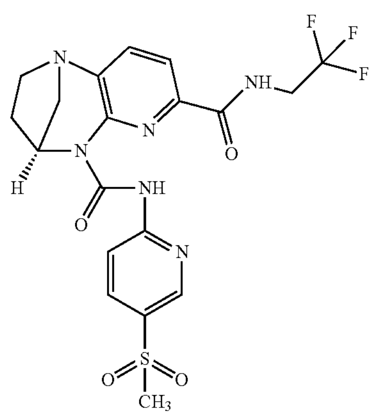 [SMILES: CS(=O)(=O)c1ccc(NC(=O)N2c3nc(C(=O)NCC(F)(F)F)ccc3N3CC[C@H]2C3)nc1] | (9S)-8-N-(5-methanesulfonylpyridin-2-yl)-5-N-(2,2,2-trifluoroethyl)-1,6,8-triazatricyclo[7.2.1.0²,⁷]dodeca-2(7),3,5-triene-5,8-dicarboxamide | B | A |
| 147 | 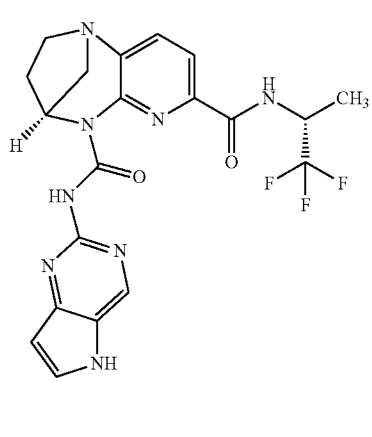 [SMILES: C[C@@H](NC(=O)c1ccc2c(n1)N(C(=O)Nc1ncc3[nH]ccc3n1)[C@H]1CCN2C1)C(F)(F)F] | (9S)-8-N-{5H-pyrrolo[3,2-d]pyrimidin-2-yl}-5-N-[(2R)-1,1,1-trifluoropropan-2-yl]-1,6,8-triazatricyclo[7.2.1.0²,⁷]dodeca-2,4,6-triene-5,8-dicarboxamide | A | A |

| Example number | Structure | Chemical Name: Generated by CHemAxon | TRP Activity | TRP MAX RESP |
|---|---|---|---|---|
| 148 | 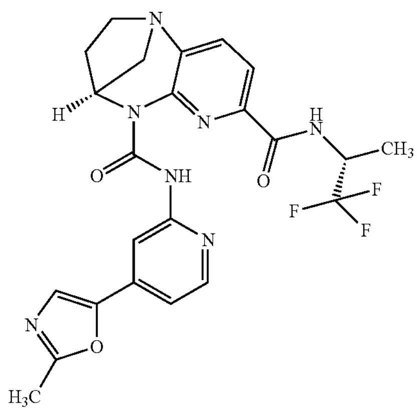 [SMILES: Cc1ncc(-c2ccnc(NC(=O)N3c4nc(C(=O)N[C@H](C)C(F)(F)F)ccc4N4CC[C@H]3C4)c2)o1] | (9S)-8-N-[4-(2-methyl-1,3-thiazol-5-yl)pyridin-2-yl]-5-N-[(2R)-1,1,1-trifluoropropan-2-yl]-1,6,8-triazatricyclo[7.2.1.0²,⁷]dodeca-2,4,6-triene-5,8-dicarboxamide | A | A |
| 149 | 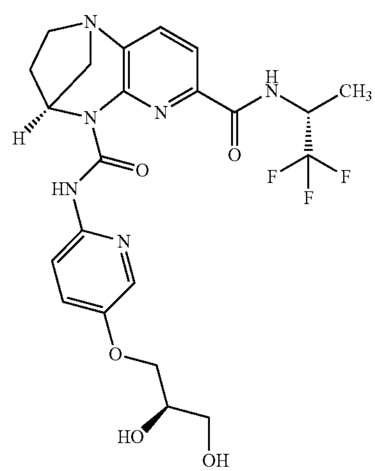 [SMILES: C[C@@H](NC(=O)c1ccc2c(n1)N(C(=O)Nc1ccc(OC[C@H](O)CO)cn1)[C@H]1CCN2C1)C(F)(F)F] | (9S)-8-N-{5-[(2R)-2,3-dihydroxypropoxy]pyridin-2-yl}-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |
| 150 | 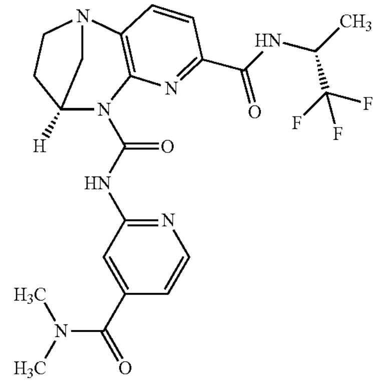 [SMILES: C[C@@H](NC(=O)c1ccc2c(n1)N(C(=O)Nc1cc(C(=O)N(C)C)ccn1)[C@H]1CCN2C1)C(F)(F)F] | (9S)-8-N-[4-(dimethylcarbamoyl)pyridin-2-yl]-5-N-[(2R)-1,1,1-trifluoropropan-2-yl]-1,6,8-triazatricyclo[7.2.1.0²,⁷]dodeca-2(7),3,5-triene-5,8-dicarboxamide | B | A |

TABLE 1-continued

| Example number | Structure | Chemical Name: Generated by CHemAxon | TRP Activity | TRP MAX RESP |
|---|---|---|---|---|
| 151 | 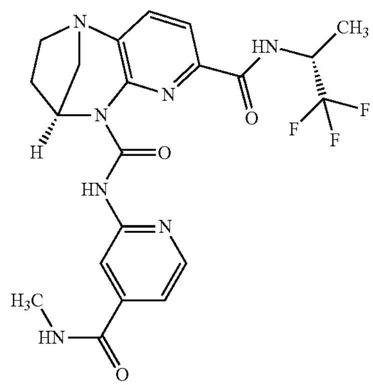 | (9S)-8-N-[4-(methylcarbamoyl)pyridin-2-yl]-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |
| 152 | 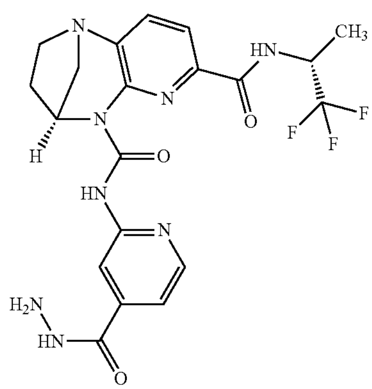 [SMILES: CNC(=O)c1ccnc(NC(=O)N2c3nc(C(=O)N[C@H](C)C(F)(F)F)ccc3N3CC[C@H]2C3)c1] | (9S)-8-N-[4-(hydrazinecarbonyl)pyridin-2-yl]-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |
| 153 | 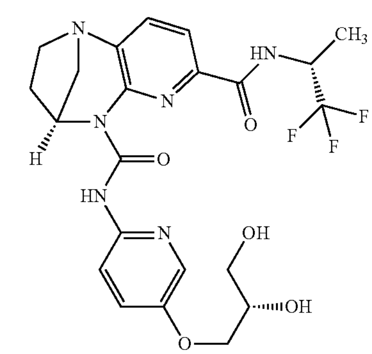 [SMILES: C[C@@H](NC(=O)c1ccc2c(n1)N(C(=O)Nc1ccc(OC[C@@H](O)CO)cn1)[C@H]1CCN2C1)C(F)(F)F] | (9S)-8-N-{5-[(2S)-2,3-dihydroxypropoxy]pyridin-2-yl}-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |
| 154 | 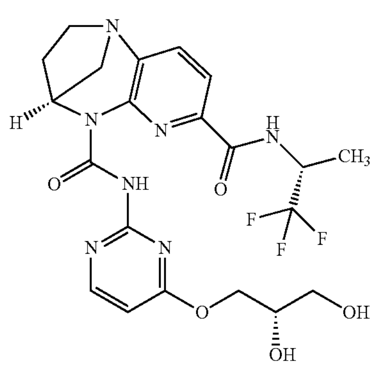 [SMILES: C[C@@H](NC(=O)c1ccc2c(n1)N(C(=O)Nc1nccc(OC[C@@H](O)CO)n1)[C@H]1CCN2C1)C(F)(F)F] | (9S)-8-N-{4-[(2S)-2,3-dihydroxypropoxy]pyrimidin-2-yl}-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 155 | 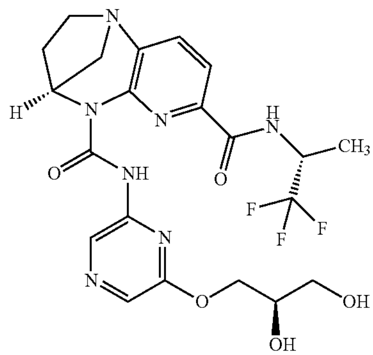 [SMILES: C[C@@H](NC(=O)c1ccc2c(n1)N(C(=O)Nc1cncc(OC[C@H](O)CO)n1)[C@H]1CCN2C1)C(F)(F)F] | (9S)-8-N-{6-[(2R)-2,3-dihydroxypropoxy]pyrazin-2-yl}-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | A |
| 156 | 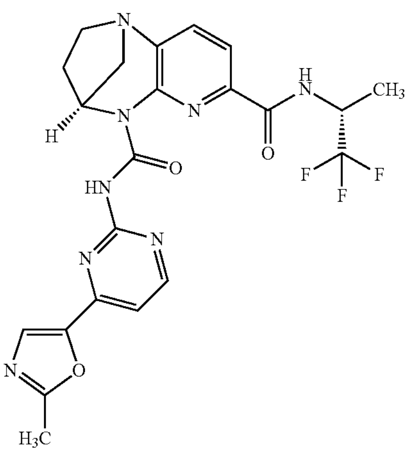 [SMILES: Cc1ncc(-c2ccnc(NC(=O)N3c4nc(C(=O)N[C@H](C)C(F)(F)F)ccc4N4CC[C@H]3C4)n2)o1] | (9S)-8-N-[4-(2-methyl-1,3-oxazol-5-yl)pyrimidin-2-yl]-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | A |
| 157 | 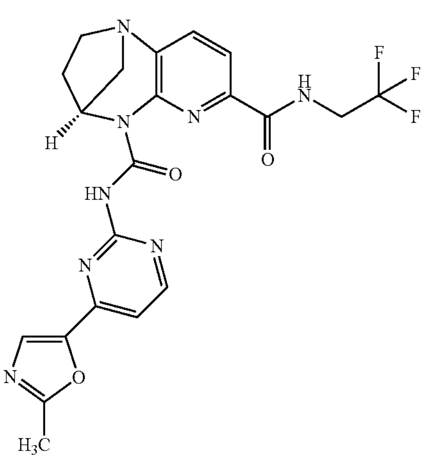 [SMILES: Cc1ncc(-c2ccnc(NC(=O)N3c4nc(C(=O)NCC(F)(F)F)ccc4N4CC[C@H]3C4)n2)o1] | (9S)-8-N-[4-(2-methyl-1,3-oxazol-5-yl)pyrimidin-2-yl]-5-N-(2,2,2-trifluoroethyl)-1,6,8-triazatricyclo[7.2.1.0$^{2,7}$]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 158 | 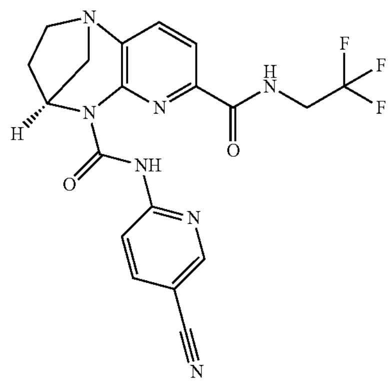 [SMILES: N#Cc1ccc(NC(=O)N2c3nc(C(=O)NCC(F)(F)F)ccc3N3CC[C@H]2C3)nc1] | (9S)-8-N-(5-cyanopyridin-2-yl)-5-N-(2,2,2-trifluoroethyl)-1,6,8-triazatricyclo[7.2.1.0²,⁷]dodeca-2(7),3,5-triene-5,8-dicarboxamide | A | A |
| 159 | 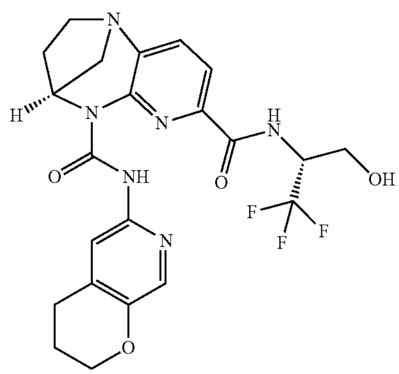 [SMILES: O=C(N[C@H](CO)C(F)(F)F)c1ccc2c(n1)N(C(=O)Nc1cc3c(cn1)OCCC3)[C@H]1CCN2C1] | (9S)-8-N-{2H,3H,4H-pyrano[2,3-c]pyridin-6-yl}-5-N-[(2R)-1,1,1-trifluoro-3-hydroxypropan-2-yl]-1,6,8-triazatricyclo[7.2.1.0²,⁷]dodeca-2,4,6-triene-5,8-dicarboxamide | A | A |
| 160 | 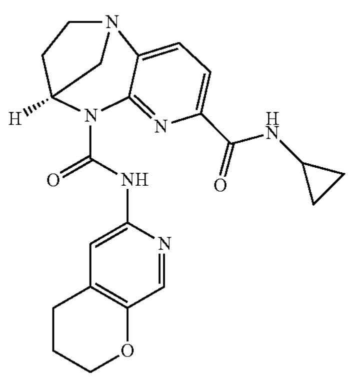 [SMILES: O=C(NC1CC1)c1ccc2c(n1)N(C(=O)Nc1cc3c(cn1)OCCC3)[C@H]1CCN2C1] | (9S)-5-N-cyclopropyl-8-N-{2H,3H,4H-pyrano[2,3-c]pyridin-6-yl}-1,6,8-triazatricyclo[7.2.1.0²,⁷]dodeca-2,4,6-triene-5,8-dicarboxamide | A | A |
| 161 | 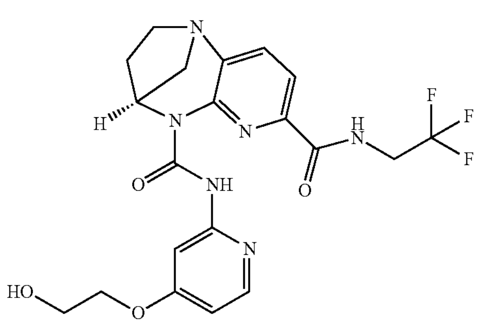 [SMILES: O=C(NCC(F)(F)F)c1ccc2c(n1)N(C(=O)Nc1cc(OCCO)ccn1)[C@H]1CCN2C1] | (9S)-8-N-[4-(2-hydroxyethoxy)pyridin-2-yl]-5-N-(2,2,2-trifluoroethyl)-1,6,8-triazatricyclo[7.2.1.0²,⁷]dodeca-2,4,6-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 162 | 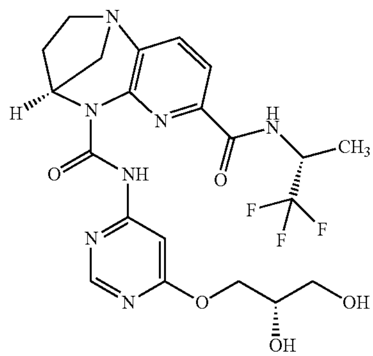 [SMILES: C[C@@H](NC(=O)c1ccc2c(n1)N(C(=O)Nc1cc(OC[C@@H](O)CO)ncn1)[C@H]1CCN2C1)C(F)(F)F] | (9S)-8-N-{6-[(2S)-2,3-dihydroxypropoxy]pyrimidin-4-yl}-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |
| 163 | 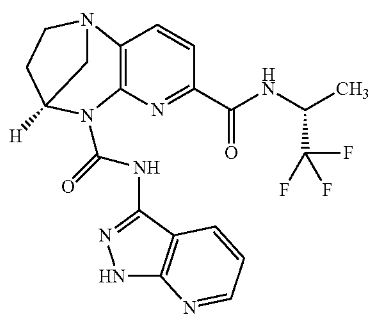 [SMILES: C[C@@H](NC(=O)c1ccc2c(n1)N(C(=O)Nc1n[nH]c3ncccc13)[C@H]1CCN2C1)C(F)(F)F] | (9S)-8-N-{1H-pyrazolo[3,4-b]pyridin-3-yl}-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |
| 164 | 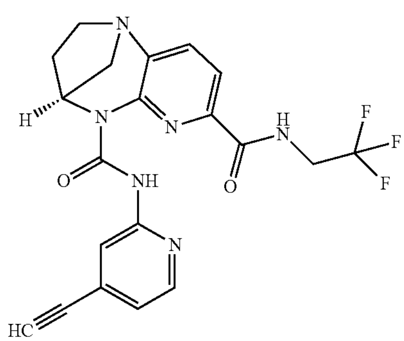 [SMILES: C#Cc1ccnc(NC(=O)N2c3nc(C(=O)NCC(F)(F)F)ccc3N3CC[C@H]2C3)c1] | (9S)-8-N-(4-ethynylpyridin-2-yl)-5-N-(2,2,2-trifluoroethyl)-1,6,8-triazatricyclo[7.2.1.0²,⁷]dodeca-2,4,6-triene-5,8-dicarboxamide | A | A |
| 165 | 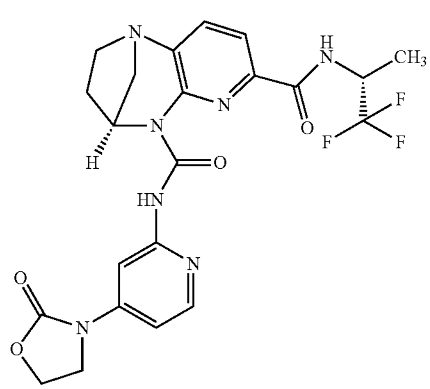 [SMILES: C[C@@H](NC(=O)c1ccc2c(n1)N(C(=O)Nc1cc(N3CCOC3=O)ccn1)[C@H]1CCN2C1)C(F)(F)F] | (9S)-8-N-[4-(2-oxo-1,3-oxazolidin-3-yl)pyridin-2-yl]-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 166 | 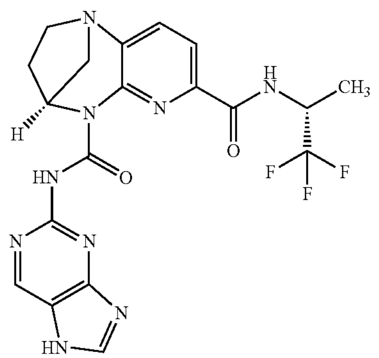 [SMILES: C[C@@H](NC(=O)c1ccc2c(n1)N(C(=O)Nc1ncc3[nH]cnc3n1)[C@H]1CCN2C1)C(F)(F)F] | (9S)-8-N-(7H-purin-2-yl)-5-N-[(2R)-1,1,1-trifluoropropan-2-yl]-1,6,8-triazatricyclo[7.2.1.0$^{2,7}$]dodeca-2,4,6-triene-5,8-dicarboxamide | A | A |
| 167 | 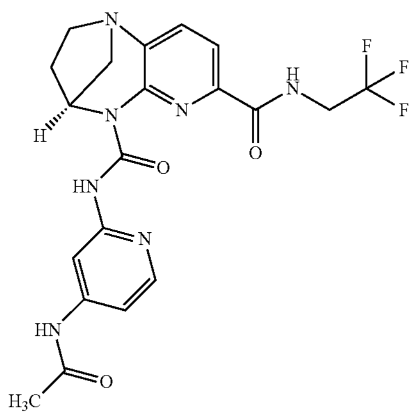 [SMILES: CC(=O)Nc1ccnc(NC(=O)N2c3nc(C(=O)NCC(F)(F)F)ccc3N3CC[C@H]2C3)c1] | (9S)-8-N-(4-acetamidopyridin-2-yl)-5-N-(2,2,2-trifluoroethyl)-1,6,8-triazatricyclo[7.2.1.0$^{2,7}$]dodeca-2,4,6-triene-5,8-dicarboxamide | A | A |
| 168 | 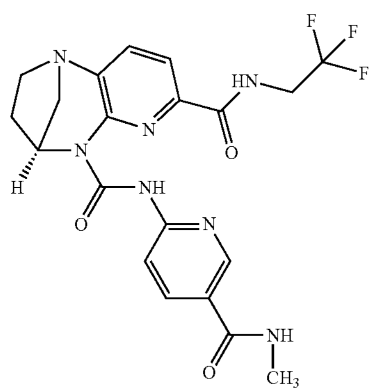 [SMILES: CNC(=O)c1ccc(NC(=O)N2c3nc(C(=O)NCC(F)(F)F)ccc3N3CC[C@H]2C3)nc1] | (9S)-8-N-[5-(methylcarbamoyl)pyridin-2-yl]-5-N-(2,2,2-trifluoroethyl)-1,6,8-triazatricyclo[7.2.1.0$^{2,7}$]dodeca-2(7),3,5-triene-5,8-dicarboxamide | A | A |
| 169 | 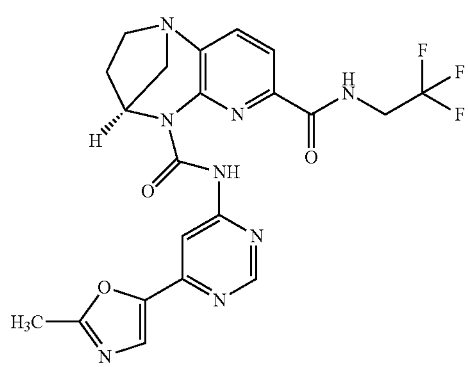 [SMILES: Cc1ncc(-c2cc(NC(=O)N3c4nc(C(=O)NCC(F)(F)F)ccc4N4CC[C@H]3C4)ncn2)o1] | (9S)-8-N-[6-(2-methyl-1,3-oxazol-5-yl)pyrimidin-4-yl]-5-N-(2,2,2-trifluoroethyl)-1,6,8-triazatricyclo[7.2.1.0$^{2,7}$]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 170 | 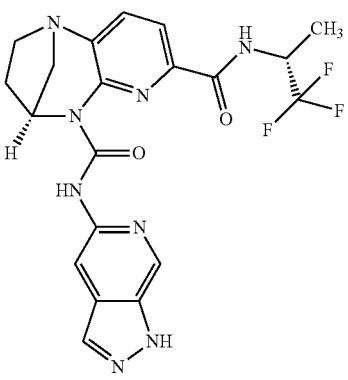 [SMILES: C[C@@H](NC(=O)c1ccc2c(n1)N(C(=O)Nc1cc3cn[nH]c3cn1)[C@H]1CCN2C1)C(F)(F)F] | (9S)-8-N-{1H-pyrazolo[3,4-c]pyridin-5-yl}-5-N-[(2R)-1,1,1-trifluoropropan-2-yl]-1,6,8-triazatricyclo[7.2.1.0²,⁷]dodeca-2,4,6-triene-5,8-dicarboxamide | A | A |
| 171 | 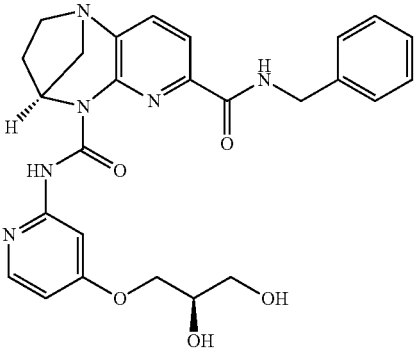 [SMILES: O=C(NCc1ccccc1)c1ccc2c(n1)N(C(=O)Nc1cc(OC[C@H](O)CO)ccn1)[C@H]1CCN2C1] | (9S)-5-N-benzyl-8-N-{4-[(2R)-2,3-dihydroxypropoxy]pyridin-2-yl}-1,6,8-triazatricyclo[7.2.1.0²,⁷]dodeca-2(7),3,5-triene-5,8-dicarboxamide | A | A |
| 172 | 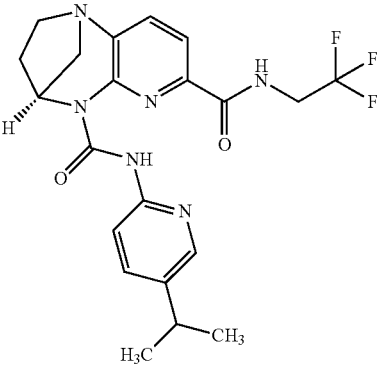 [SMILES: CC(C)c1ccc(NC(=O)N2c3nc(C(=O)NCC(F)(F)F)ccc3N3CC[C@H]2C3)nc1] | (9S)-8-N-[5-(propan-2-yl)pyridin-2-yl]-5-N-(2,2,2-trifluoroethyl)-1,6,8-triazatricyclo[7.2.1.0²,⁷]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 173 | 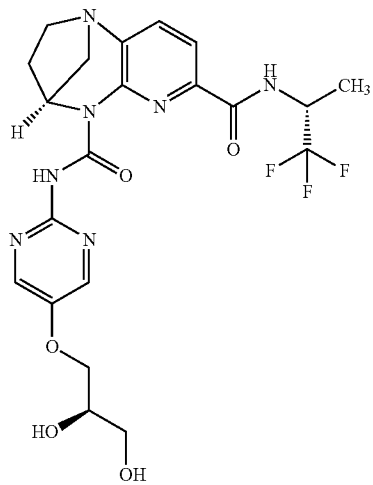 [SMILES: C[C@@H](NC(=O)c1ccc2c(n1)N(C(=O)Nc1ncc(OC[C@H](O)CO)cn1)[C@H]1CCN2C1)C(F)(F)F] | (9S)-8-N-{5-[(2R)-2,3-dihydroxypropoxy]pyrimidin-2-yl}-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | A |
| 174 | 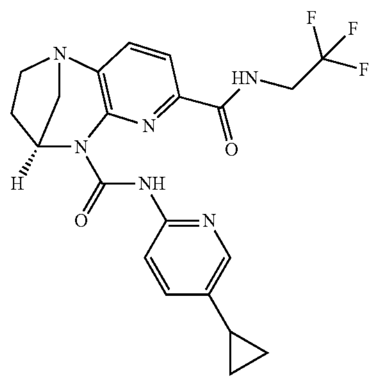 [SMILES: O=C(NCC(F)(F)F)c1ccc2c(n1)N(C(=O)Nc1ccc(C3CC3)cn1)[C@H]1CCN2C1] | (9S)-8-N-(5-cyclopropylpyridin-2-yl)-5-N-(2,2,2-trifluoroethyl)-1,6,8-triazatricyclo[7.2.1.0$^{2,7}$]dodeca-2(7),3,5-triene-5,8-dicarboxamide | A | A |
| 175 | 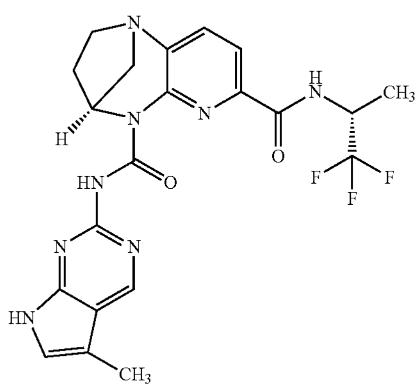 [SMILES: Cc1c[nH]c2nc(NC(=O)N3c4nc(C(=O)N[C@H](C)C(F)(F)F)ccc4N4CC[C@H]3C4)ncc12] | (9S)-8-N-{5-methyl-7H-pyrrolo[2,3-d]pyrimidin-2-yl}-5-N-[(2R)-1,1,1-trifluoropropan-2-yl]-1,6,8-triazatricyclo[7.2.1.0$^{2,7}$]dodeca-2,4,6-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 176 | 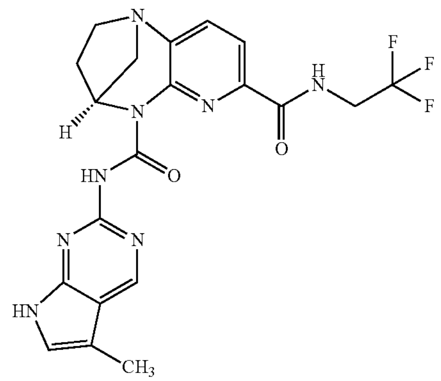 [SMILES: Cc1c[nH]c2nc(NC(=O)N3c4nc(C(=O)NCC(F)(F)F)ccc4N4CC[C@H]3C4)ncc12] | (9S)-8-N-{5-methyl-7H-pyrrolo[2,3-d]pyrimidin-2-yl}-5-N-(2,2,2-trifluoroethyl)-1,6,8-triazatricyclo[7.2.1.0$^{2,7}$]dodeca-2,4,6-triene-5,8-dicarboxamide | A | A |
| 177 | 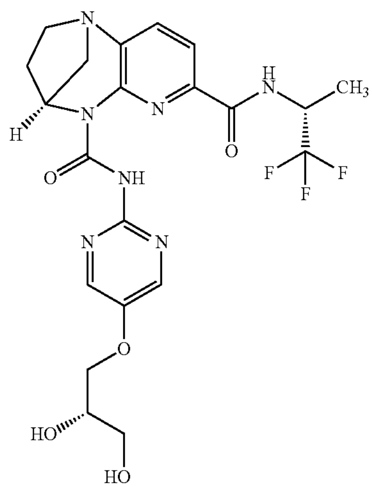 [SMILES: C[C@@H](NC(=O)c1ccc2c(n1)N(C(=O)Nc1ncc(OC[C@@H](O)CO)cn1)[C@H]1CCN2C1)C(F)(F)F] | (9S)-8-N-{5-[(2S)-2,3-dihydroxypropoxy]pyrimidin-2-yl}-5-N-[(2R)-1,1,1-trifluoropropan-2-yl]-1,6,8-triazatricyclo[7.2.1.0$^{2,7}$]dodeca-2(7),3,5-triene-5,8-dicarboxamide | B | A |
| 178 | 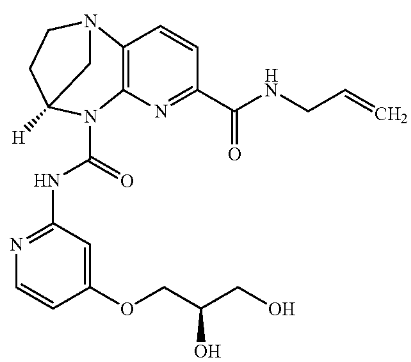 [SMILES: C=CCNC(=O)c1ccc2c(n1)N(C(=O)Nc1cc(OC[C@H](O)CO)ccn1)[C@H]1CCN2C1] | (9S)-8-N-{4-[(2R)-2,3-dihydroxypropoxy]pyridin-2-yl}-5-N-(prop-2-en-1-yl)-1,6,8-triazatricyclo[7.2.1.0$^{2,7}$]dodeca-2(7),3,5-triene-5,8-dicarboxamide | B | A |
| 179 | 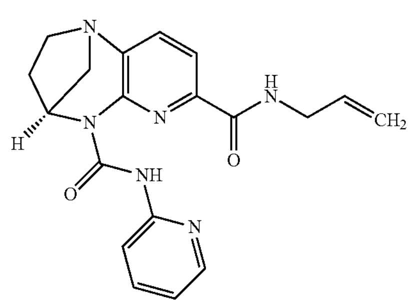 [SMILES: C=CCNC(=O)c1ccc2c(n1)N(C(=O)Nc1ccccn1)[C@H]1CCN2C1] | (9S)-5-N-(prop-2-en-1-yl)-8-N-(pyridin-2-yl)-1,6,8-triazatricyclo[7.2.1.0$^{2,7}$]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 180 | 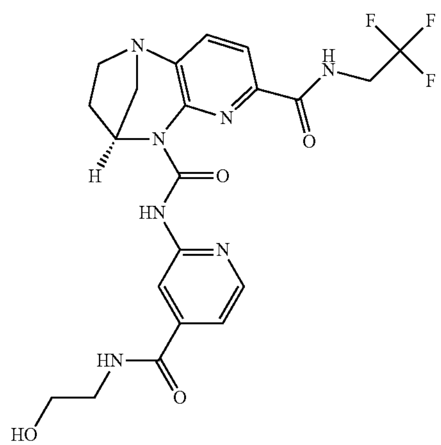 [SMILES: O=C(NCCO)c1ccnc(NC(=O)N2c3nc(C(=O)NCC(F)(F)F)ccc3N3CC[C@H]2C3)c1] | (9S)-8-N-{4-[(2-hydroxyethyl)carbamoyl]pyridin-2-yl}-5-N-(2,2,2-trifluoroethyl)-1,6,8-triazatricyclo[7.2.1.0$^{2,7}$]dodeca-2(7),3,5-triene-5,8-dicarboxamide | A | A |
| 181 | 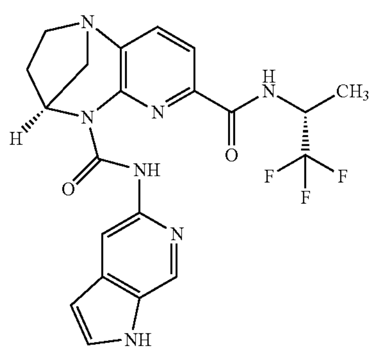 [SMILES: C[C@@H](NC(=O)c1ccc2c(n1)N(C(=O)Nc1cc3cc[nH]c3cn1)[C@H]1CCN2C1)C(F)(F)F] | (9S)-8-N-{1H-pyrrolo[2,3-c]pyridin-5-yl}-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | A |
| 182 | 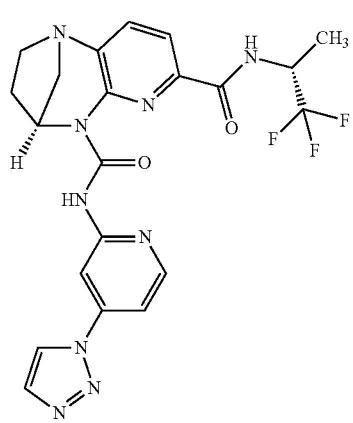 [SMILES: C[C@@H](NC(=O)c1ccc2c(n1)N(C(=O)Nc1cc(-n3ccnn3)ccn1)[C@H]1CCN2C1)C(F)(F)F] | (9S)-8-N-[4-(1H-1,2,3-triazol-1-yl)pyridin-2-yl]-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 183 | 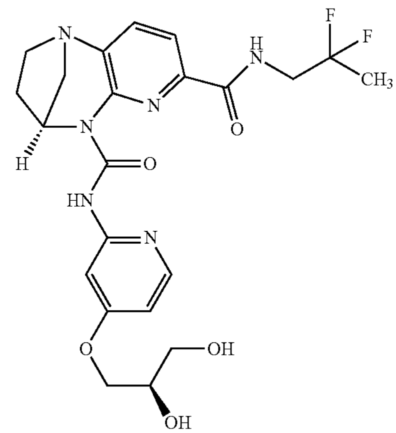 [SMILES: CC(F)(F)CNC(=O)c1ccc2c(n1)N(C(=O)Nc1cc(OC[C@H](O)CO)ccn1)[C@H]1CCN2C1] | (9S)-5-N-(2,2-difluoropropyl)-8-N-{4-[(2R)-2,3-dihydroxypropoxy]pyridin-2-yl}-1,6,8-triazatricyclo[7.2.1.0²,⁷]dodeca-2(7),3,5-triene-5,8-dicarboxamide | B | A |
| 184 | 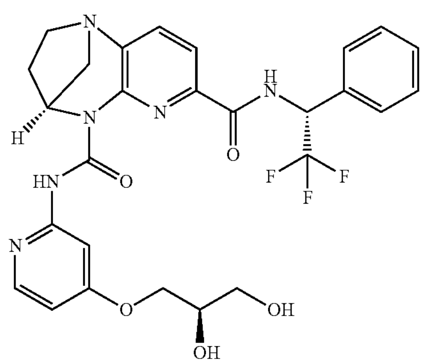 [SMILES: O=C(N[C@H](c1ccccc1)C(F)(F)F)c1ccc2c(n1)N(C(=O)Nc1cc(OC[C@H](O)CO)ccn1)[C@H]1CCN2C1] | (9S)-8-N-{4-[(2R)-2,3-dihydroxypropoxy]pyridin-2-yl}-5-N-[(1R)-2,2,2-trifluoro-1-phenylethyl]-1,6,8-triazatricyclo[7.2.1.0²,⁷]dodeca-2(7),3,5-triene-5,8-dicarboxamide | A | A |
| 185 | 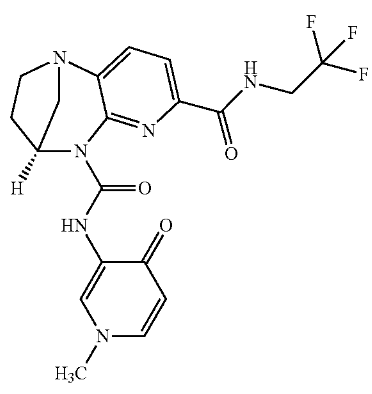 [SMILES: Cn1ccc(=O)c(NC(=O)N2c3nc(C(=O)NCC(F)(F)F)ccc3N3CC[C@H]2C3)c1] | (9S)-8-N-(1-methyl-4-oxo-1,4-dihydropyridin-3-yl)-5-N-(2,2,2-trifluoroethyl)-1,6,8-triazatricyclo[7.2.1.0²,⁷]dodeca-2,4,6-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 186 | 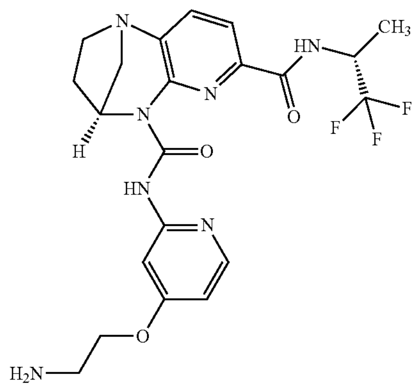 [SMILES: C[C@@H](NC(=O)c1ccc2c(n1)N(C(=O)Nc1cc(OCCN)ccn1)[C@H]1CCN2C1)C(F)(F)F] | (9S)-8-N-[4-(2-aminoethoxy)pyridin-2-yl]-5-N-[(2R)-1,1,1-trifluoropropan-2-yl]-1,6,8-triazatricyclo[7.2.1.0²,⁷]dodeca-2(7),3,5-triene-5,8-dicarboxamide | B | A |
| 187 | 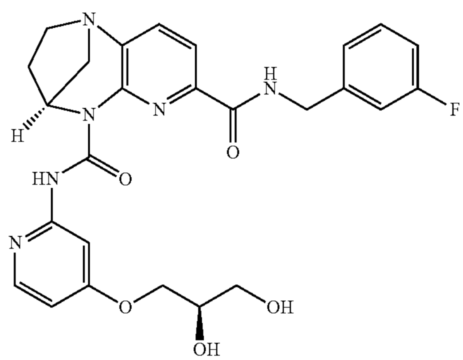 [SMILES: O=C(NCc1cccc(F)c1)c1ccc2c(n1)N(C(=O)Nc1cc(OC[C@H](O)CO)ccn1)[C@H]1CCN2C1] | (9S)-8-N-{4-[(2R)-2,3-dihydroxypropoxy]pyridin-2-yl}-5-N-[(3-fluorophenyl)methyl]-1,6,8-triazatricyclo[7.2.1.0²,⁷]dodeca-2(7),3,5-triene-5,8-dicarboxamide | A | A |
| 188 | 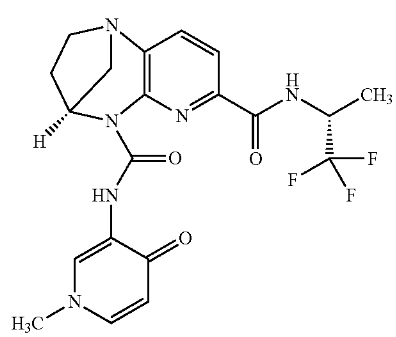 [SMILES: C[C@@H](NC(=O)c1ccc2c(n1)N(C(=O)Nc1cn(C)ccc1=O)[C@H]1CCN2C1)C(F)(F)F] | (9S)-8-N-(1-methyl-4-oxo-1,4-dihydropyridin-3-yl)-5-N-[(2R)-1,1,1-trifluoropropan-2-yl]-1,6,8-triazatricyclo[7.2.1.0²,⁷]dodeca-2(7),3,5-triene-5,8-dicarboxamide | B | A |
| 189 | 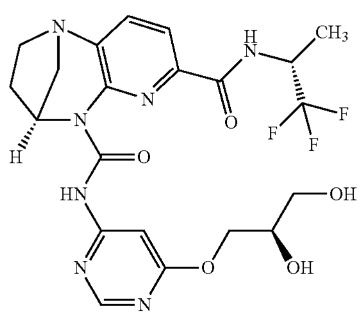 [SMILES: C[C@@H](NC(=O)c1ccc2c(n1)N(C(=O)Nc1cc(OC[C@H](O)CO)ncn1)[C@H]1CCN2C1)C(F)(F)F] | (9S)-8-N-{6-[(2R)-2,3-dihydroxypropoxy]pyrimidin-4-yl}-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 190 | 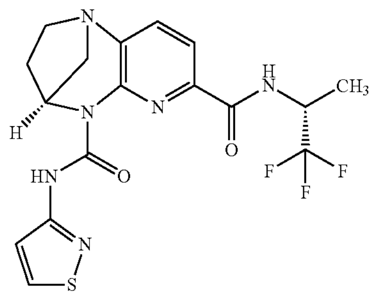 [SMILES: C[C@@H](NC(=O)c1ccc2c(n1)N(C(=O)Nc1ccsn1)[C@H]1CCN2C1)C(F)(F)F] | (9S)-8-N-(1,2-thiazol-3-yl)-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |
| 191 | 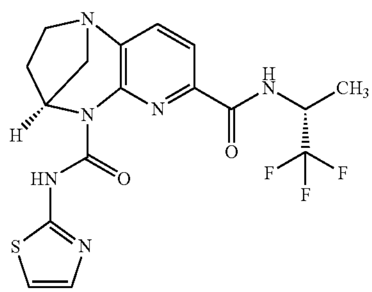 [SMILES: C[C@@H](NC(=O)c1ccc2c(n1)N(C(=O)Nc1nccs1)[C@H]1CCN2C1)C(F)(F)F] | (9S)-8-N-(1,3-thiazol-2-yl)-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |
| 192 | 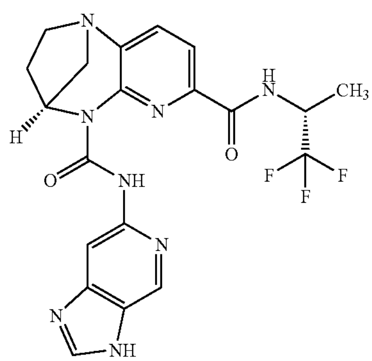 [SMILES: C[C@@H](NC(=O)c1ccc2c(n1)N(C(=O)Nc1cc3nc[nH]c3cn1)[C@H]1CCN2C1)C(F)(F)F] | (9S)-8-N-{3H-imidazo[4,5-c]pyridin-6-yl}-5-N-[(2R)-1,1,1-trifluoropropan-2-yl]-1,6,8-triazatricyclo[7.2.1.0²,⁷]dodeca-2,4,6-triene-5,8-dicarboxamide | A | A |
| 193 | 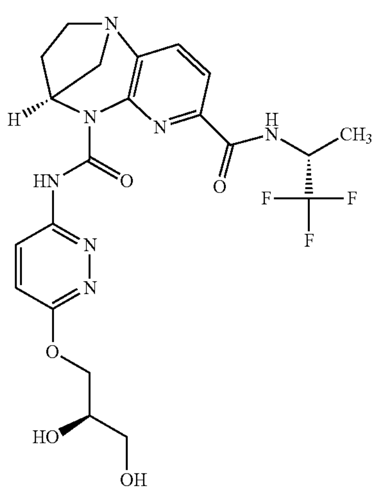 [SMILES: C[C@@H](NC(=O)c1ccc2c(n1)N(C(=O)Nc1ccc(OC[C@H](O)CO)nn1)[C@H]1CCN2C1)C(F)(F)F] | (9S)-8-N-{6-[(2R)-2,3-dihydroxypropoxy]pyridazin-3-yl}-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 194 | 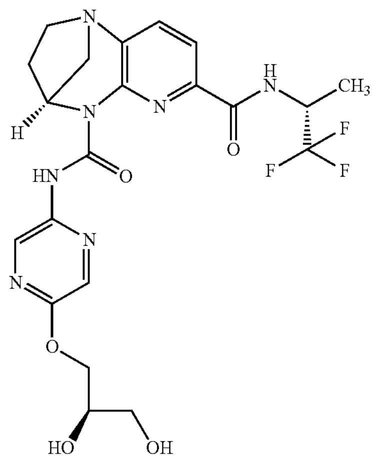 [SMILES: C[C@@H](NC(=O)c1ccc2c(n1)N(C(=O)Nc1cnc(OC[C@H](O)CO)cn1)[C@H]1CCN2C1)C(F)(F)F] | (9S)-8-N-{5-[(2R)-2,3-dihydroxypropoxy]pyrazin-2-yl}-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |
| 195 | 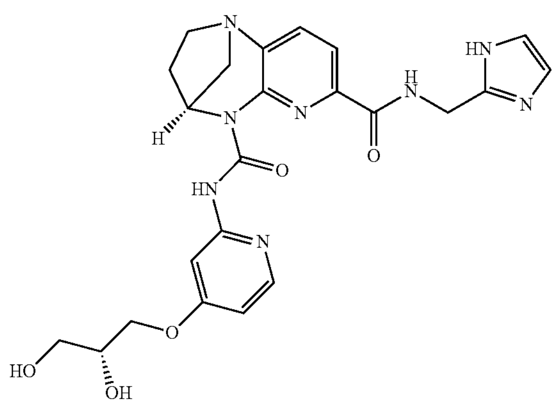 [SMILES: O=C(NCc1ncc[nH]1)c1ccc2c(n1)N(C(=O)Nc1cc(OC[C@H](O)CO)ccn1)[C@H]1CCN2C1] | (9S)-8-N-{4-[(2R)-2,3-dihydroxypropoxy]pyridin-2-yl}-5-N-(1H-imidazol-2-ylmethyl)-1,6,8-triazatricyclo[7.2.10²,⁷]dodeca-2,4,6-triene-5,8-dicarboxamide | B | A |
| 196 | ISOMER 1 | (9S)-5-N-[(2R)-2-amino-3,3,3-trifluoropropyl]-8-N-{4-[(2R)-2,3-dihydroxypropoxy]pyridin-2-yl}-1,6,8-triazatricyclo[7.2.1.0²,⁷]dodeca-2(7),3,5-triene-5,8-dicarboxamide | B | A |

TABLE 1-continued

| Example number | Structure | Chemical Name: Generated by CHemAxon | TRP Activity | TRP MAX RESP |
|---|---|---|---|---|
| 197 | 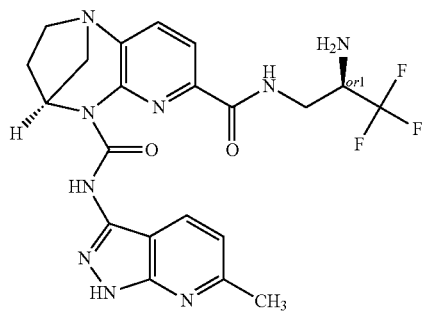 ISOMER 1 | (9S)-5-N-[(2R)-2-amino-3,3,3-trifluoropropyl]-8-N-{6-methyl-1H-pyrazolo[3,4-b]pyridin-3-yl}-1,6,8-triazatricyclo[7.2.1.0$^{2,7}$]dodeca-2(7),3,5-triene-5,8-dicarboxamide | B | A |
| 198 | 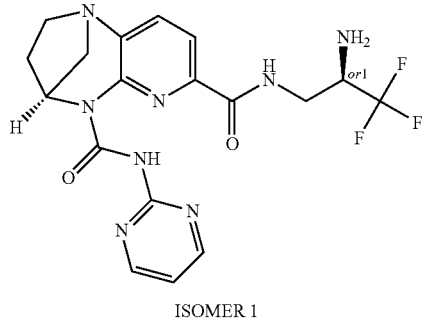 [SMILES: N[C@H](CNC(=O)c1ccc2c(n1)N(C(=O)Nc1ncccn1)[C@H]1CCN2C1)C(F)(F)F] ISOMER 1 | (9S)-5-N-[(2R)-2-amino-3,3,3-trifluoropropyl]-8-N-(pyrimidin-2-yl)-1,6,8-triazatricyclo[7.2.1.0$^{2,7}$]dodeca-2,4,6-triene-5,8-dicarboxamide | B | A |
| 199 | 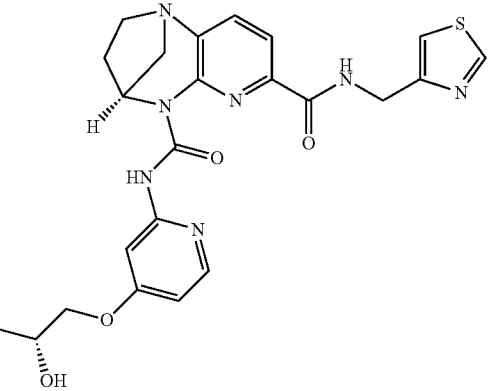 | (9S)-8-N-{4-[(2R)-2,3-dihydroxypropoxy]pyridin-2-yl}-5-N-(1,3-thiazol-4-ylmethyl)-1,6,8-triazatricyclo[7.2.1.0$^{2,7}$]dodeca-2(7),3,5-triene-5,8-dicarboxamide | B | A |
| 200 | 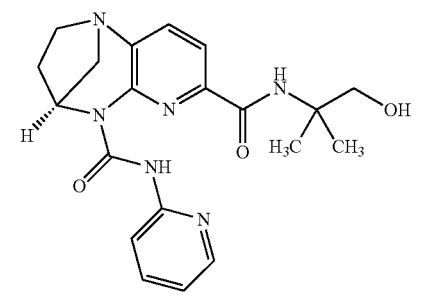 [SMILES: CC(C)(CO)NC(=O)c1ccc2c(n1)N(C(=O)Nc1ccccn1)[C@H]1CCN2C1] | (9S)-5-N-(1-hydroxy-2-methylpropan-2-yl)-8-N-(pyridin-2-yl)-1,6,8-triazatricyclo[7.2.1.0$^{2,7}$]dodeca-2(7),3,5-triene-5,8-dicarboxamide | B | A |

TABLE 1-continued

| Example number | Structure | Chemical Name: Generated by CHemAxon | TRP Activity | TRP MAX RESP |
|---|---|---|---|---|
| 201 | 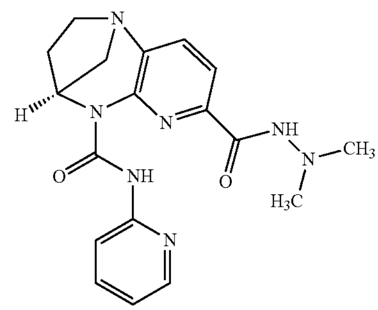 [SMILES: CN(C)NC(=O)c1ccc2c(n1)N(C(=O)Nc1ccccn1)[C@H]1CCN2C1] | (9S)-5-(N',N'-dimethylhydrazinecarbonyl)-N-(pyridin-2-yl)-1,6,8-triazatricyclo[7.2.1.0²,⁷]dodeca-2(7),3,5-triene-8-carboxamide | B | A |
| 202 | 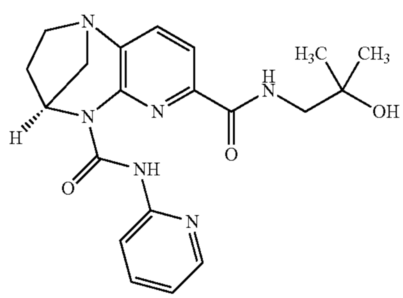 [SMILES: CC(C)(O)CNC(=O)c1ccc2c(n1)N(C(=O)Nc1ccccn1)[C@H]1CCN2C1] | (9S)-5-N-(2-hydroxy-2-methylpropyl)-8-N-(pyridin-2-yl)-1,6,8-triazatricyclo[7.2.1.0²,⁷]dodeca-2(7),3,5-triene-5,8-dicarboxamide | B | A |
| 203 | 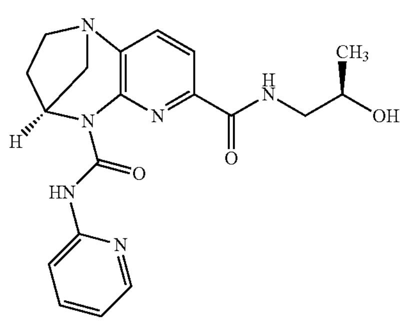 [SMILES: C[C@@H](O)CNC(=O)c1ccc2c(n1)N(C(=O)Nc1ccccn1)[C@H]1CCN2C1] | (9S)-5-N-[(2R)-2-hydroxypropyl]-8-N-(pyridin-2-yl)-1,6,8-triazatricyclo[7.2.1.0²,⁷]dodeca-2(7),3,5-triene-5,8-dicarboxamide | B | A |
| 204 | 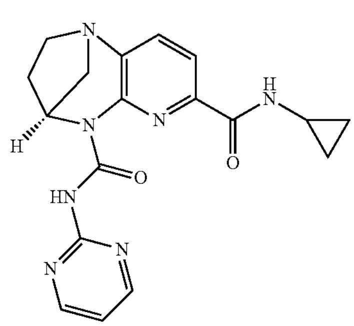 [SMILES: O=C(NC1CC1)c1ccc2c(n1)N(C(=O)Nc1ncccn1)[C@H]1CCN2C1] | (9S)-5-N-cyclopropyl-8-N-(pyrimidin-2-yl)-1,6,8-triazatricyclo[7.2.1.0²,⁷]dodeca-2(7),3,5-triene-5,8-dicarboxamide | B | A |

TABLE 1-continued

| Example number | Structure | Chemical Name: Generated by CHemAxon | TRP Activity | TRP MAX RESP |
|---|---|---|---|---|
| 205 | 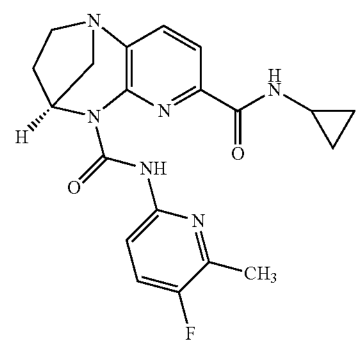 [SMILES: Cc1nc(NC(=O)N2c3nc(C(=O)NC4CC4)ccc3N3CC[C@H]2C3)ccc1F] | (9S)-5-N-cyclopropyl-8-N-(5-fluoro-6-methylpyridin-2-yl)-1,6,8-triazatricyclo[7.2.1.0$^{2,7}$]dodeca-2(7),3,5-triene-5,8-dicarboxamide | B | A |
| 206 | 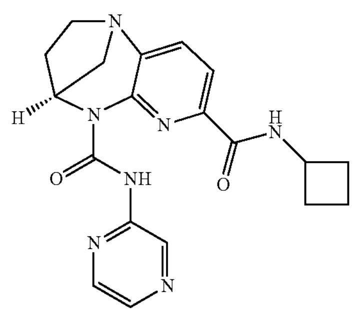 [SMILES: O=C(NC1CCC1)c1ccc2c(n1)N(C(=O)Nc1cnccn1)[C@H]1CCN2C1] | (9S)-5-N-cyclobutyl-8-N-(pyrazin-2-yl)-1,6,8-triazatricyclo[7.2.1.0$^{2,7}$]dodeca-2,4,6-triene-5,8-dicarboxamide | B | A |
| 207 | 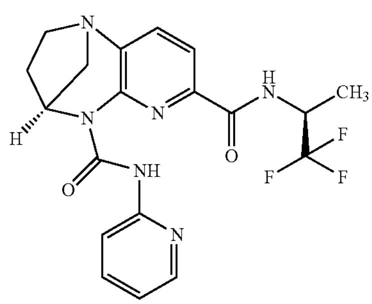 [SMILES: C[C@H](NC(=O)c1ccc2c(n1)N(C(=O)Nc1ccccn1)[C@H]1CCN2C1)C(F)(F)F] | (9S)-8-N-(pyridin-2-yl)-5-N-[(2S)-1,1,1-trifluoropropan-2-yl]-1,6,8-triazatricyclo[7.2.1.0$^{2,7}$]dodeca-2(7),3,5-triene-5,8-dicarboxamide | B | A |
| 208 | 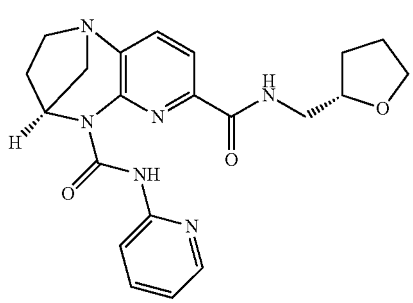 [SMILES: O=C(NC[C@@H]1CCCO1)c1ccc2c(n1)N(C(=O)Nc1ccccn1)[C@H]1CCN2C1] | (9S)-5-N-[(2S)-oxolan-2-ylmethyl]-8-N-(pyridin-2-yl)-1,6,8-triazatricyclo[7.2.1.0$^{2,7}$]dodeca-2(7),3,5-triene-5,8-dicarboxamide | B | A |

TABLE 1-continued

| Example number | Structure | Chemical Name: Generated by CHemAxon | TRP Activity | TRP MAX RESP |
|---|---|---|---|---|
| 209 | 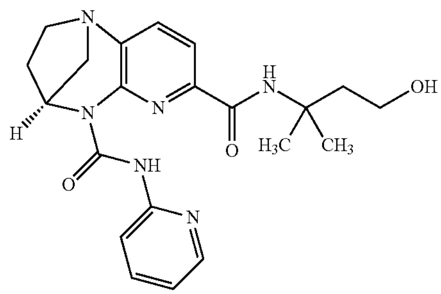 [SMILES: CC(C)(CCO)NC(=O)c1ccc2c(n1)N(C(=O)Nc1ccccn1)[C@H]1CCN2C1] | (9S)-5-N-(4-hydroxy-2-methylbutan-2-yl)-8-N-(pyridin-2-yl)-1,6,8-triazatricyclo[7.2.1.0$^{2,7}$]dodeca-2(7),3,5-triene-5,8-dicarboxamide | B | A |
| 210 | 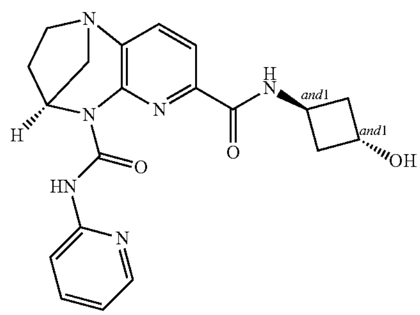 [SMILES: O=C(N[C@H]1C[C@H](O)C1)c1ccc2c(n1)N(C(=O)Nc1ccccn1)[C@H]1CCN2C1] | (9S)-8-N-(pyridin-2-yl)-5-N-[(1r,3r)-3-hydroxycyclobutyl]-1,6,8-triazatricyclo[7.2.1.0$^{2,7}$]dodeca-2(7),3,5-triene-5,8-dicarboxamide | B | A |
| 211 | 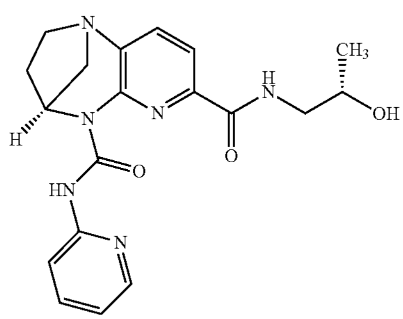 [SMILES: C[C@H](O)CNC(=O)c1ccc2c(n1)N(C(=O)Nc1ccccn1)[C@H]1CCN2C1] | (9S)-5-N-[(2S)-2-hydroxypropyl]-8-N-(pyridin-2-yl)-1,6,8-triazatricyclo[7.2.1.0$^{2,7}$]dodeca-2(7),3,5-triene-5,8-dicarboxamide | B | A |
| 212 | 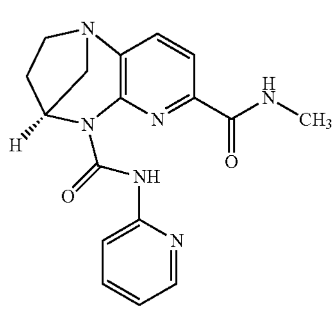 [SMILES: CNC(=O)c1ccc2c(n1)N(C(=O)Nc1ccccn1)[C@H]1CCN2C1] | (9S)-5-N-methyl-8-N-(pyridin-2-yl)-1,6,8-triazatricyclo[7.2.1.0$^{2,7}$]dodeca-2(7),3,5-triene-5,8-dicarboxamide | B | A |

TABLE 1-continued

| Example number | Structure | Chemical Name: Generated by CHemAxon | TRP Activity | TRP MAX RESP |
|---|---|---|---|---|
| 213 | 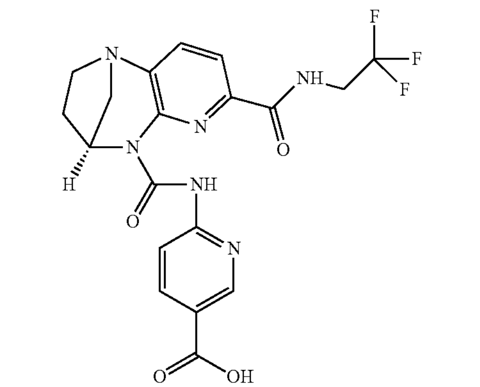 [SMILES: O=C(O)c1ccc(NC(=O)N2c3nc(C(=O)NCC(F)(F)F)ccc3N3CC[C@H]2C3)nc1] | 6-{[(9S)-5-[(2,2,2-trifluoroethyl)carbamoyl]-1,6,8-triazatricyclo[7.2.1.0²,⁷]dodeca-2(7),3,5-triene-8-carbonyl]amino}pyridine-3-carboxylic acid | B | A |
| 214 | ISOMER 1 | (9S)-5-N-[(2R)-2-hydroxy-3-methoxypropyl]-8-N-(pyridin-2-yl)-1,6,8-triazatricyclo[7.2.1.0²,⁷]dodeca-2(7),3,5-triene-5,8-dicarboxamide | B | A |
| 215 | 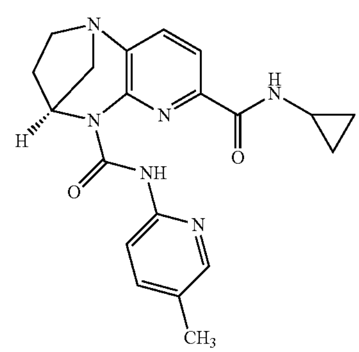 [SMILES: Cc1ccc(NC(=O)N2c3nc(C(=O)NC4CC4)ccc3N3CC[C@H]2C3)nc1] | (9S)-5-N-cyclopropyl-8-N-(5-methylpyridin-2-yl)-1,6,8-triazatricyclo[7.2.1.0²,⁷]dodeca-2(7),3,5-triene-5,8-dicarboxamide | B | A |
| 216 | 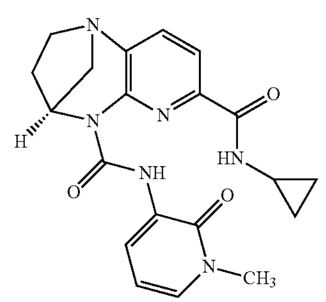 [SMILES: Cn1cccc(NC(=O)N2c3nc(C(=O)NC4CC4)ccc3N3CC[C@H]2C3)c1=O] | (9S)-5-N-cyclopropyl-8-N-(1-methyl-2-oxo-1,2-dihydropyridin-3-yl)-1,6,8-triazatricyclo[7.2.1.0²,⁷]dodeca-2(7),3,5-triene-5,8-dicarboxamide | B | A |

TABLE 1-continued

| Example number | Structure | Chemical Name: Generated by CHemAxon | TRP Activity | TRP MAX RESP |
|---|---|---|---|---|
| 217 | 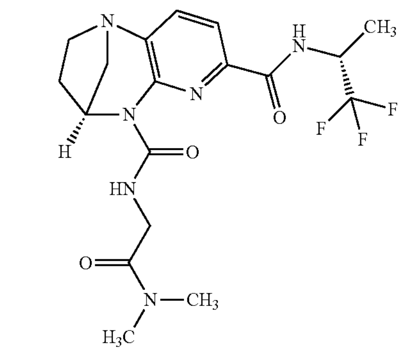 [SMILES: C[C@@H](NC(=O)c1ccc2c(n1)N(C(=O)NCC(=O)N(C)C)[C@H]1CCN2C1)C(F)(F)F] | (9S)-8-N-[(dimethylcarbamoyl)methyl]-5-N-[(2R)-1,1,1-trifluoropropan-2-yl]-1,6,8-triazatricyclo[7.2.1.0$^{2,7}$]dodeca-2(7),3,5-triene-5,8-dicarboxamide | B | A |
| 218 | 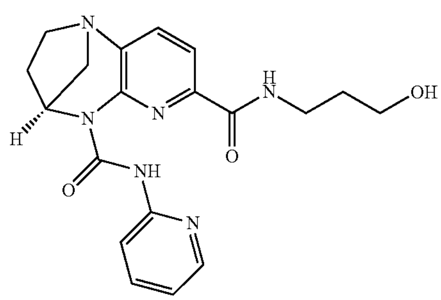 [SMILES: O=C(NCCCO)c1ccc2c(n1)N(C(=O)Nc1ccccn1)[C@H]1CCN2C1] | (9S)-5-N-(3-hydroxypropyl)-8-N-(pyridin-2-yl)-1,6,8-triazatricyclo[7.2.1.0$^{2,7}$]dodeca-2(7),3,5-triene-5,8-dicarboxamide | B | A |
| 219 | 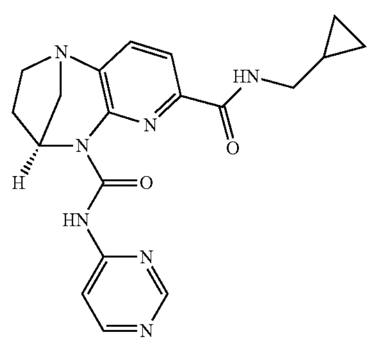 [SMILES: O=C(NCC1CC1)c1ccc2c(n1)N(C(=O)Nc1ccncn1)[C@H]1CCN2C1] | (9S)-5-N-(cyclopropylmethyl)-8-N-(pyrimidin-4-yl)-1,6,8-triazatricyclo[7.2.1.0$^{2,7}$]dodeca-2(7),3,5-triene-5,8-dicarboxamide | B | A |
| 220 | 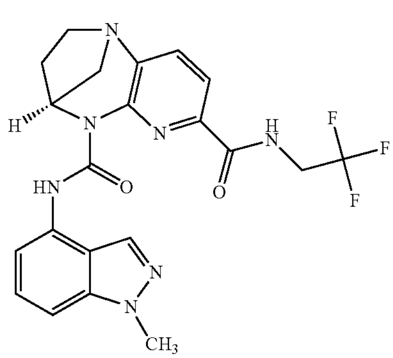 [SMILES: Cn1ncc2c(NC(=O)N3c4nc(C(=O)NCC(F)(F)F)ccc4N4CC[C@H]3C4)cccc21] | (9S)-8-N-(1-methyl-1H-indazol-4-yl)-5-N-(2,2,2-trifluoroethyl)-1,6,8-triazatricyclo[7.2.1.0$^{2,7}$]dodeca-2(7),3,5-triene-5,8-dicarboxamide | B | A |

TABLE 1-continued

| Example number | Structure | Chemical Name: Generated by CHemAxon | TRP Activity | TRP MAX RESP |
|---|---|---|---|---|
| 221 | ISOMER 2 | (9S)-5-N-[(1R)-2,2-difluorocyclopropyl]-8-N-{6-methyl-1H-pyrazolo[3,4-b]pyridin-3-yl}-1,6,8-triazatricyclo[7.2.1.0²,⁷]dodeca-2(7),3,5-triene-5,8-dicarboxamide | B | A |
| 222 | 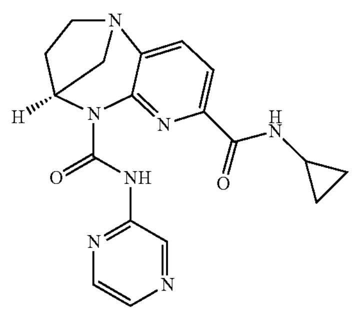 [SMILES: O=C(NC1CC1)c1ccc2c(n1)N(C(=O)Nc1cnccn1)[C@H]1CCN2C1] | (9S)-5-N-cyclopropyl-8-N-(pyrazin-2-yl)-1,6,8-triazatricyclo[7.2.1.0²,⁷]dodeca-2,4,6-triene-5,8-dicarboxamide | B | A |
| 223 | ISOMER 2 | (9S)-5-N-[(2S)-3-amino-1,1,1-trifluoropropan-2-yl]-8-N-(pyridin-2-yl)-1,6,8-triazatricyclo[7.2.1.0²,⁷]dodeca-2(7),3,5-triene-5,8-dicarboxamide | B | A |
| 224 | 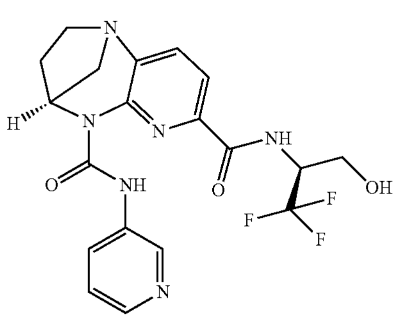 [SMILES: O=C(N[C@@H](CO)C(F)(F)F)c1ccc2c(n1)N(C(=O)Nc1cccnc1)[C@H]1CCN2C1] | (9S)-8-N-(pyridin-3-yl)-5-N-[(2S)-1,1,1-trifluoro-3-hydroxypropan-2-yl]-1,6,8-triazatricyclo[7.2.1.0²,⁷]dodeca-2,4,6-triene-5,8-dicarboxamide | B | A |

| Example number | Structure | Chemical Name: Generated by CHemAxon | TRP Activity | TRP MAX RESP |
|---|---|---|---|---|
| 225 | 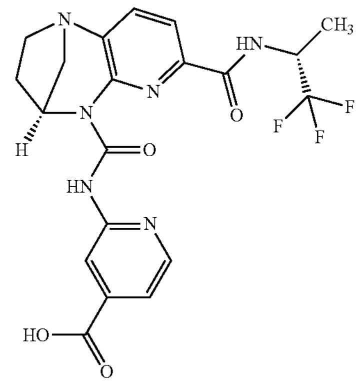 [SMILES: C[C@@H](NC(=O)c1ccc2c(n1)N(C(=O)Nc1cc(C(=O)O)ccn1)[C@H]1CCN2C1)C(F)(F)F] | 2-{[(9S)-5-{[(2R)-1,1,1-trifluoropropan-2-yl]carbamoyl}-1,6,8-triazatricyclo[7.2.1.0$^{2,7}$]dodeca-2(7),3,5-triene-8-carbonyl]amino}pyridine-4-carboxylic acid | B | A |
| 226 | 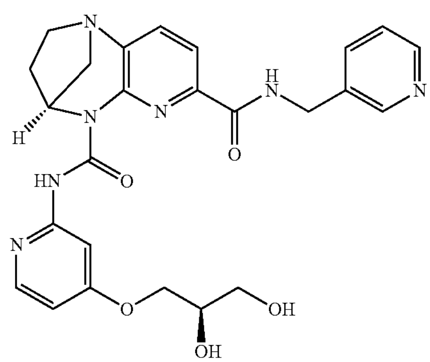 [SMILES: O=C(NCc1cccnc1)c1ccc2c(n1)N(C(=O)Nc1cc(OC[C@H](O)CO)ccn1)[C@H]1CCN2C1] | (9S)-8-N-{4-[(2R)-2,3-dihydroxypropoxy]pyridin-2-yl}-5-N-(pyridin-3-ylmethyl)-1,6,8-triazatricyclo[7.2.1.0$^{2,7}$]dodeca-2(7),3,5-triene-5,8-dicarboxamide | B | A |
| 227 | 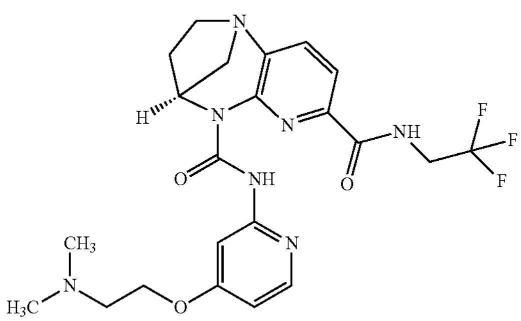 [SMILES: CN(C)CCOc1ccnc(NC(=O)N2c3nc(C(=O)NCC(F)(F)F)ccc3N3CC[C@H]2C3)c1] | (9S)-8-N-{4-[2-(dimethylamino)ethoxy]pyridin-2-yl}-5-N-(2,2,2-trifluoroethyl)-1,6,8-triazatricyclo[7.2.1.0$^{2,7}$]dodeca-2(7),3,5-triene-5,8-dicarboxamide | B | A |
| 228 | 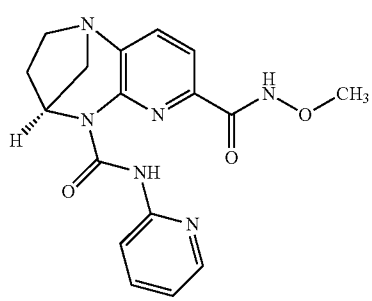 [SMILES: CONC(=O)c1ccc2c(n1)N(C(=O)Nc1ccccn1)[C@H]1CCN2C1] | (9S)-5-N-methoxy-8-N-(pyridin-2-yl)-1,6,8-triazatricyclo[7.2.1.0$^{2,7}$]dodeca-2(7),3,5-triene-5,8-dicarboxamide | B | A |

TABLE 1-continued

| Example number | Structure | Chemical Name: Generated by CHemAxon | TRP Activity | TRP MAX RESP |
| --- | --- | --- | --- | --- |
| 229 | 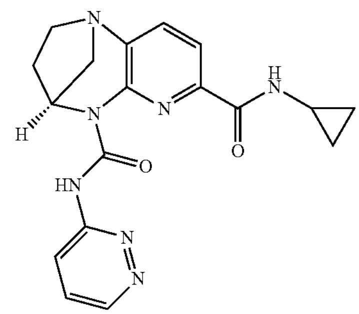 [SMILES: O=C(NC1CC1)c1ccc2c(n1)N(C(=O)Nc1cccnn1)[C@H]1CCN2C1] | (9S)-5-N-cyclopropyl-8-N-(pyridazin-3-yl)-1,6,8-triazatricyclo[7.2.1.0$^{2,7}$]dodeca-2(7),3,5-triene-5,8-dicarboxamide | B | A |
| 231 | 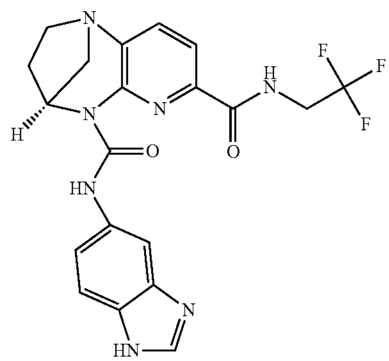 [SMILES: O=C(NCC(F)(F)F)c1ccc2c(n1)N(C(=O)Nc1ccc3[nH]cnc3c1)[C@H]1CCN2C1] | (9S)-8-N-(1H-1,3-benzodiazol-5-yl)-5-N-(2,2,2-trifluoroethyl)-1,6,8-triazatricyclo[7.2.1.0$^{2,7}$]dodeca-2(7),3,5-triene-5,8-dicarboxamide | B | A |
| 232 | 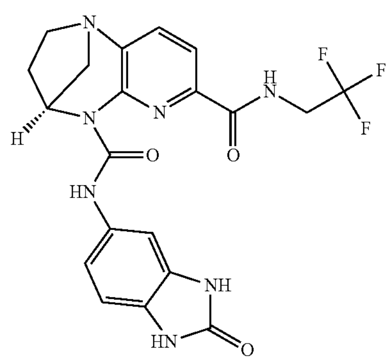 [SMILES: O=C(NCC(F)(F)F)c1ccc2c(n1)N(C(=O)Nc1ccc3[nH]c(=O)[nH]c3c1)[C@H]1CCN2C1] | (9S)-8-N-(2-oxo-2,3-dihydro-1H-1,3-benzodiazol-5-yl)-5-N-(2,2,2-trifluoroethyl)-1,6,8-triazatricyclo[7.2.1.0$^{2,7}$]dodeca-2(7),3,5-triene-5,8-dicarboxamide | C | B |
| 233 | ISOMER 2 | (9S)-5-N-[(2R)-2-amino-3,3,3-trifluoropropyl]-8-N-{6-methyl-1H-pyrazolo[3,4-b]pyridin-3-yl}-1,6,8-triazatricyclo[7.2.1.0$^{2,7}$]dodeca-2(7),3,5-triene-5,8-dicarboxamide | B | A |

TABLE 1-continued

| Example number | Structure | Chemical Name: Generated by CHemAxon | TRP Activity | TRP MAX RESP |
|---|---|---|---|---|
| 234 | 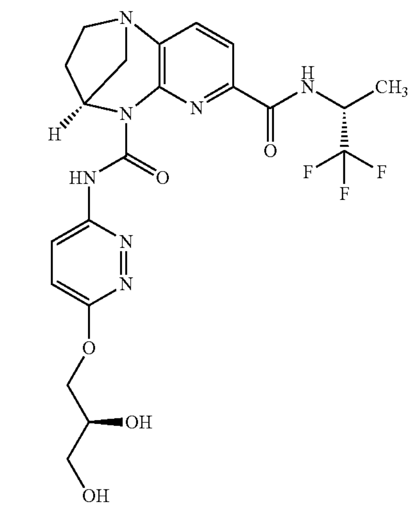 [SMILES: C[C@@H](NC(=O)c1ccc2c(n1)N(C(=O)Nc1ccc(OC[C@@H](O)CO)nn1)[C@H]1CCN2C1)C(F)(F)F] | (9S)-8-N-{6-[(2S)-2,3-dihydroxypropoxy]pyridazin-3-yl}-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |
| 235 | ISOMER 2 | (9S)-5-N-[(2R)-2-amino-3,3,3-trifluoropropyl]-8-N-(pyrimidin-2-yl)-1,6,8-triazatricyclo[7.2.1.0²,⁷]dodeca-2,4,6-triene-5,8-dicarboxamide | A | A |
| 236 | 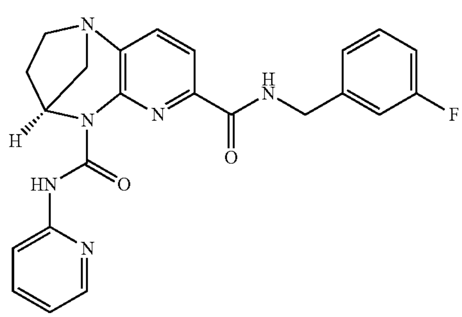 [SMILES: O=C(NCc1cccc(F)c1)c1ccc2c(n1)N(C(=O)Nc1ccccn1)[C@H]1CCN2C1] | (9S)-5-N-[(3-fluorophenyl)methyl]-8-N-(pyridin-2-yl)-1,6,8-triazatricyclo[7.2.1.0²,⁷]dodeca-2(7),3,5-triene-5,8-dicarboxamide | A | A |
| 237 | 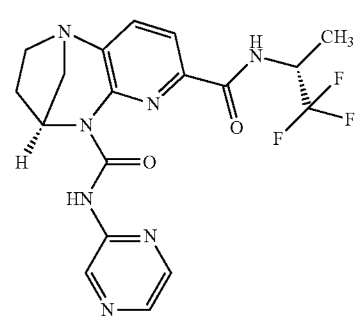 [SMILES: C[C@@H](NC(=O)c1ccc2c(n1)N(C(=O)Nc1cnccn1)[C@H]1CCN2C1)C(F)(F)F] | (9S)-8-N-(pyrazin-2-yl)-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 238 | 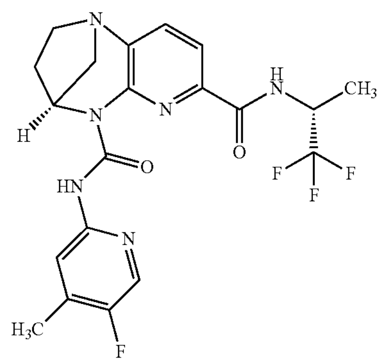 [SMILES: Cc1cc(NC(=O)N2c3nc(C(=O)N[C@H](C)C(F)(F)F)ccc3N3CC[C@H]2C3)ncc1F] | (9S)-8-N-(5-fluoro-4-methylpyridin-2-yl)-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | A |
| 239 | 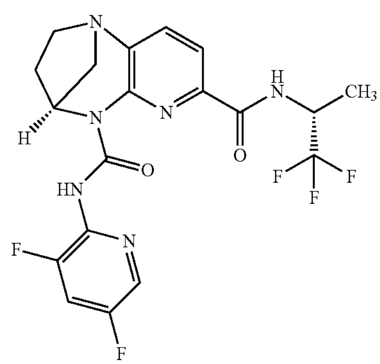 [SMILES: C[C@@H](NC(=O)c1ccc2c(n1)N(C(=O)Nc1ncc(F)cc1F)[C@H]1CCN2C1)C(F)(F)F] | (9S)-8-N-(3,5-difluoropyridin-2-yl)-5-N-[(2R)-1,1,1-trifluoropropan-2-yl]-1,6,8-triazatricyclo[7.2.1.0$^{2,7}$]dodeca-2(7),3,5-triene-5,8-dicarboxamide | B | A |
| 240 | 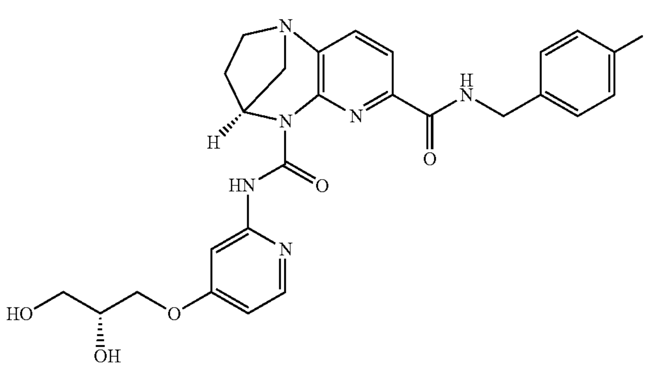 | (9S)-8-N-{4-[(2R)-2,3-dihydroxypropoxy]pyridin-2-yl}-5-N-[(4-fluorophenyl)methyl]-1,6,8-triazatricyclo[7.2.1.0$^{2,7}$]dodeca-2(7),3,5-triene-5,8-dicarboxamide | A | A |
| 241 | 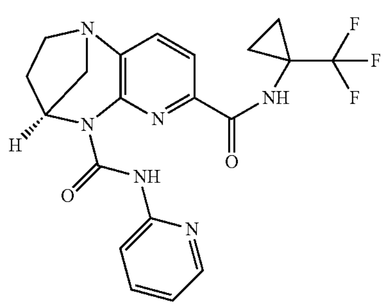 [SMILES: O=C(NC1(C(F)(F)F)CC1)c1ccc2c(n1)N(C(=O)Nc1ccccn1)[C@H]1CCN2C1] | (9S)-8-N-(pyridin-2-yl)-5-N-[1-(trifluoromethyl)cyclopropyl]-1,6,8-triazatricyclo[7.2.1.0$^{2,7}$]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 242 | ISOMER 1 | (9S)-5-N-[(1R)-2,2-difluorocyclopropyl]-8-N-(5-fluoropyridin-2-yl)-1,6,8-triazatricyclo[7.2.1.0$^{2,7}$]dodeca-2(7),3,5-triene-5,8-dicarboxamide | A | A |
| 243 | ISOMER 2 | (9S)-5-N-[(1R)-2,2-difluorocyclopropyl]-8-N-(5-fluoropyridin-2-yl)-1,6,8-triazatricyclo[7.2.1.0$^{2,7}$]dodeca-2(7),3,5-triene-5,8-dicarboxamide | A | A |
| 244 | 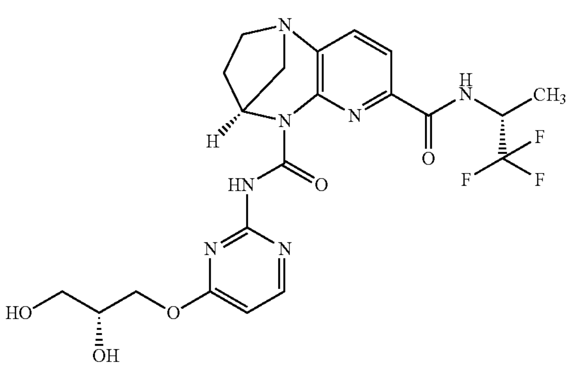 [SMILES: C[C@@H](NC(=O)c1ccc2c(n1)N(C(=O)Nc1nccc(OC[C@H](O)CO)n1)[C@H]1CCN2C1)C(F)(F)F] | (9S)-8-N-{4-[(2R)-2,3-dihydroxypropoxy]pyrimidin-2-yl}-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 245 | 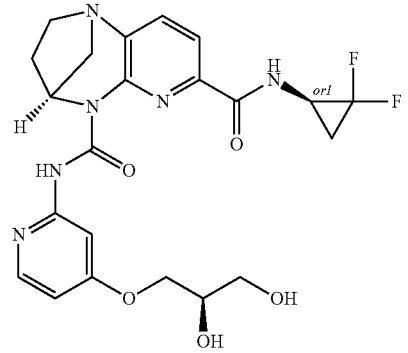 ISOMER 2 | (9S)-5-N-[(1R)-2,2-difluorocyclopropyl]-8-N-{4-[(2R)-2,3-dihydroxypropoxy]pyridin-2-yl}-1,6,8-triazatricyclo[7.2.1.0²,⁷]dodeca-2(7),3,5-triene-5,8-dicarboxamide | A | A |
| 246 | 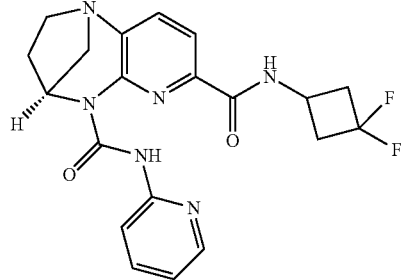 [SMILES: O=C(NC1CC(F)(F)C1)c1ccc2c(n1)N(C(=O)Nc1ccccn1)[C@H]1CCN2C1] | (9S)-5-N-(3,3-difluorocyclobutyl)-8-N-(pyridin-2-yl)-1,6,8-triazatricyclo[7.2.1.0²,⁷]dodeca-2(7),3,5-triene-5,8-dicarboxamide | A | A |
| 247 | 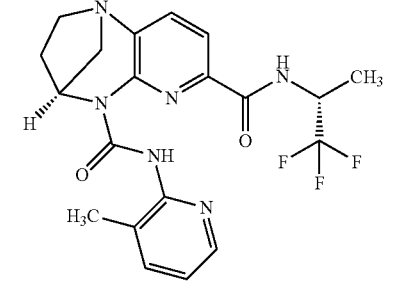 [SMILES: Cc1cccnc1NC(=O)N1c2nc(C(=O)N[C@H](C)C(F)(F)F)ccc2N2CC[C@H]1C2] | (9S)-8-N-(3-methylpyridin-2-yl)-5-N-[(2R)-1,1,1-trifluoropropan-2-yl]-1,6,8-triazatricyclo[7.2.1.0²,⁷]dodeca-2(7),3,5-triene-5,8-dicarboxamide | B | A |
| 248 | 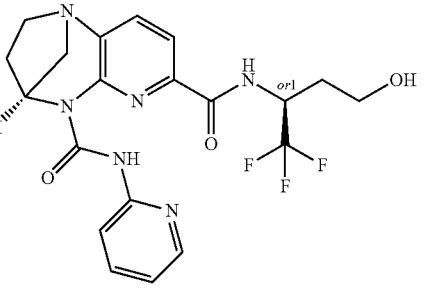 ISOMER 2 | (9S)-8-N-(pyridin-2-yl)-5-N-[(2S)-1,1,1-trifluoro-4-hydroxybutan-2-yl]-1,6,8-triazatricyclo[7.2.1.0²,⁷]dodeca-2(7),3,5-triene-5,8-dicarboxamide | B | A |

TABLE 1-continued

| Example number | Structure | Chemical Name: Generated by CHemAxon | TRP Activity | TRP MAX RESP |
|---|---|---|---|---|
| 249 | ISOMER 1 | (9S)-5-N-[(2S)-2-amino-3,3,3-trifluoropropyl]-8-N-(pyridin-2-yl)-1,6,8-triazatricyclo[7.2.1.0$^{2,7}$]dodeca-2(7),3,5-triene-5,8-dicarboxamide | B | A |
| 250 | 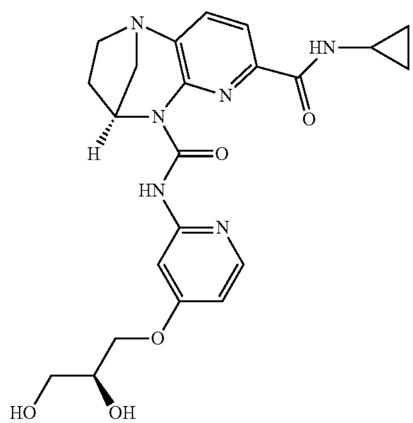 [SMILES: O=C(NC1CC1)c1ccc2c(n1)N(C(=O)Nc1cc(OC[C@@H](O)CO)ccn1)[C@H]1CCN2C1] | (9S)-5-N-cyclopropyl-8-N-{4-[(2S)-2,3-dihydroxypropoxy]pyridin-2-yl}-1,6,8-triazatricyclo[7.2.1.0$^{2,7}$]dodeca-2(7),3,5-triene-5,8-dicarboxamide | A | A |
| 251 | 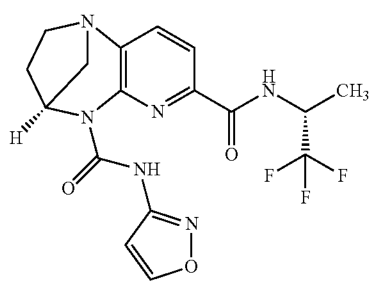 [SMILES: C[C@@H](NC(=O)c1ccc2c(n1)N(C(=O)Nc1ccon1)[C@H]1CCN2C1)C(F)(F)F] | (9S)-8-N-(1,2-oxazol-3-yl)-5-N-[(2R)-1,1,1-trifluoropropan-2-yl]-1,6,8-triazatricyclo[7.2.1.0$^{2,7}$]dodeca-2(7),3,5-triene-5,8-dicarboxamide | B | A |
| 252 | 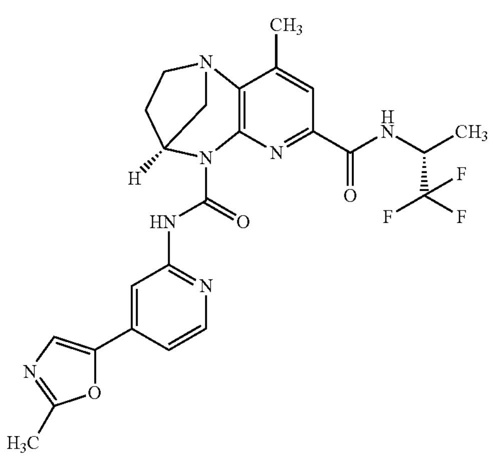 [SMILES: Cc1ncc(-c2ccnc(NC(=O)N3c4nc(C(=O)N[C@H](C)C(F)(F)F)cc(C)c4N4CC[C@H]3C4)c2)o1] | (9S)-3-methyl-8-N-[4-(2-methyl-1,3-oxazol-5-yl)pyridin-2-yl]-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | B |

TABLE 1-continued

| Example number | Structure | Chemical Name: Generated by CHemAxon | TRP Activity | TRP MAX RESP |
|---|---|---|---|---|
| 253 | 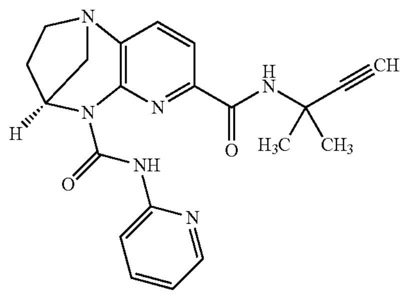 [SMILES: C#CC(C)(C)NC(=O)c1ccc2c(n1)N(C(=O)Nc1ccccn1)[C@H]1CCN2C1] | (9S)-5-N-(2-methylbut-3-yn-2-yl)-8-N-(pyridin-2-yl)-1,6,8-triazatricyclo[7.2.1.0$^{2,7}$]dodeca-2(7),3,5-triene-5,8-dicarboxamide | B | A |
| 254 | 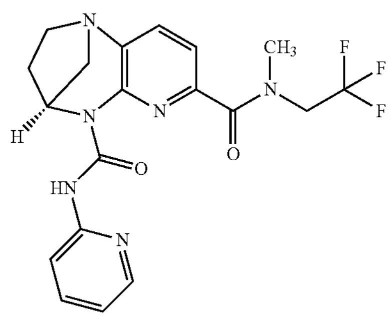 [SMILES: CN(CC(F)(F)F)C(=O)c1ccc2c(n1)N(C(=O)Nc1ccccn1)[C@H]1CCN2C1] | (9S)-5-N-methyl-8-N-(pyridin-2-yl)-5-N-(2,2,2-trifluoroethyl)-1,6,8-triazatricyclo[7.2.1.0$^{2,7}$]dodeca-2(7),3,5-triene-5,8-dicarboxamide | B | A |
| 255 | 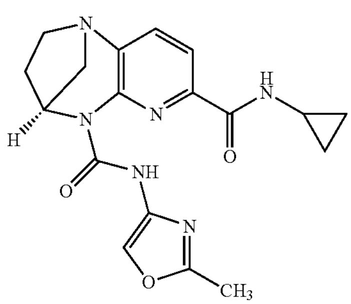 [SMILES: Cc1nc(NC(=O)N2c3nc(C(=O)NC4CC4)ccc3N3CC[C@H]2C3)co1] | (9S)-5-N-cyclopropyl-8-N-(2-methyl-1,3-oxazol-4-yl)-1,6,8-triazatricyclo[7.2.1.0$^{2,7}$]dodeca-2(7),3,5-triene-5,8-dicarboxamide | B | A |
| 256 | 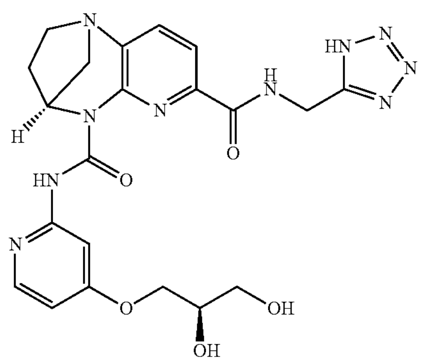 [SMILES: O=C(NCc1nnn[nH]1)c1ccc2c(n1)N(C(=O)Nc1cc(OC[C@H](O)CO)ccn1)[C@H]1CCN2C1] | (9S)-8-N-{4-[(2R)-2,3-dihydroxypropoxy]pyridin-2-yl}-5-N-(1H-1,2,3,4-tetrazol-5-ylmethyl)-1,6,8-triazatricyclo[7.2.1.0$^{2,7}$]dodeca-2(7),3,5-triene-5,8-dicarboxamide | B | A |

TABLE 1-continued

| Example number | Structure | Chemical Name: Generated by ChemAxon | TRP Activity | TRP MAX RESP |
|---|---|---|---|---|
| 257 | 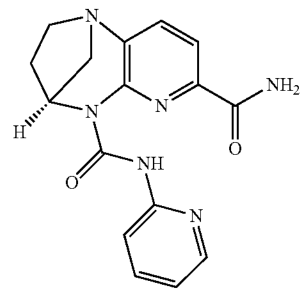 [SMILES: NC(=O)c1ccc2c(n1)N(C(=O)Nc1ccccn1)[C@H]1CCN2C1] | (9S)-8-N-(pyridin-2-yl)-1,6,8-triazatricyclo[7.2.1.0²,⁷]dodeca-2(7),3,5-triene-5,8-dicarboxamide | B | A |
| 258 | 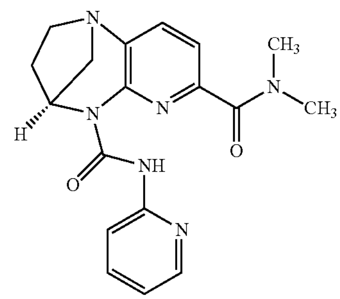 [SMILES: CN(C)C(=O)c1ccc2c(n1)N(C(=O)Nc1ccccn1)[C@H]1CCN2C1] | (9S)-5-N,5-N-dimethyl-8-N-(pyridin-2-yl)-1,6,8-triazatricyclo[7.2.1.0²,⁷]dodeca-2(7),3,5-triene-5,8-dicarboxamide | C | B |
| 259 | 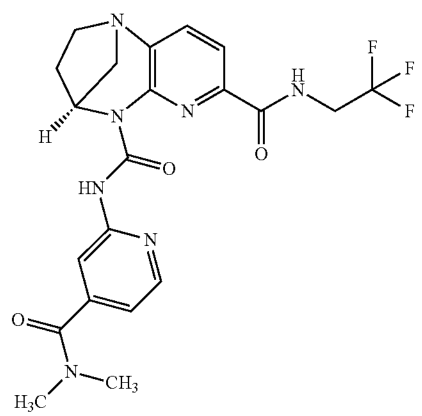 [SMILES: CN(C)C(=O)c1ccnc(NC(=O)N2c3nc(C(=O)NCC(F)(F)F)ccc3N3CC[C@H]2C3)c1] | (9S)-8-N-[4-(dimethylcarbamoyl)pyridin-2-yl]-5-N-(2,2,2-trifluoroethyl)-1,6,8-triazatricyclo[7.2.1.0²,⁷]dodeca-2(7),3,5-triene-5,8-dicarboxamide | B | A |
| 260 | ISOMER 2 | (9S)-5-N-[(1R)-2,2-difluorocyclopropyl]-8-N-{5-[(2R)-2,3-dihydroxypropoxy]pyrazin-2-yl}-1,6,8-triazatricyclo[7.2.1.0²,⁷]dodeca-2(7),3,5-triene-5,8-dicarboxamide | B | A |

TABLE 1-continued

| Example number | Structure | Chemical Name: Generated by CHemAxon | TRP Activity | TRP MAX RESP |
|---|---|---|---|---|
| 261 | 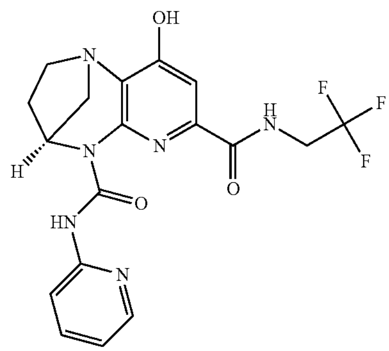 [SMILES: O=C(NCC(F)(F)F)c1cc(O)c2c(n1)N(C(=O)Nc1ccccn1)[C@H]1CCN2C1] | (9S)-3-hydroxy-8-N-(pyridin-2-yl)-5-N-(2,2,2-trifluoroethyl)-1,6,8-triazatricyclo[7.2.1.0²,⁷]dodeca-2(7),3,5-triene-5,8-dicarboxamide | A | A |
| 262 | ISOMER 2 | (9S)-5-N-[(1R)-2,2-difluorocyclopropyl]-8-N-[4-(2-hydroxyethoxy)pyridin-2-yl]-1,6,8-triazatricyclo[7.2.1.0²,⁷]dodeca-2(7),3,5-triene-5,8-dicarboxamide | A | A |
| 263 | ISOMER 1 | (9S)-5-N-[(1R)-2,2-difluorocyclopropyl]-8-N-[4-(2-hydroxyethoxy)pyridin-2-yl]-1,6,8-triazatricyclo[7.2.1.0²,⁷]dodeca-2(7),3,5-triene-5,8-dicarboxamide | B | A |
| 264 | 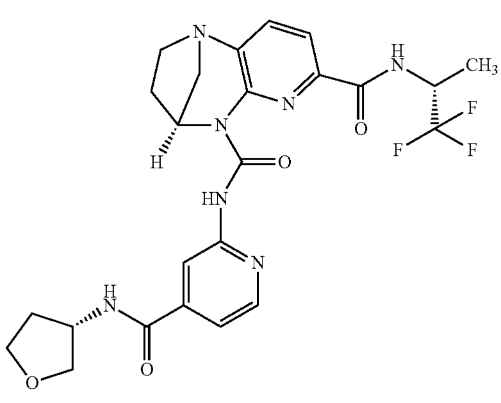 [SMILES: C[C@@H](NC(=O)c1ccc2c(n1)N(C(=O)Nc1cc(C(=O)N[C@H]3CCOC3)ccn1)[C@H]1CCN2C1)C(F)(F)F] | (9S)-8-N-(4-{[(3S)-oxolan-3-yl]carbamoyl}pyridin-2-yl)-5-N-[(2R)-1,1,1-trifluoropropan-2-yl]-1,6,8-triazatricyclo[7.2.1.0²,⁷]dodeca-2(7),3,5-triene-5,8-dicarboxamide | C | B |

TABLE 1-continued

| Example number | Structure | Chemical Name: Generated by CHemAxon | TRP Activity | TRP MAX RESP |
|---|---|---|---|---|
| 265 | 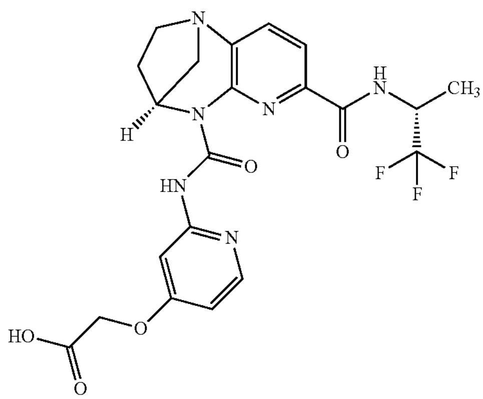 [SMILES: C[C@@H](NC(=O)c1ccc2c(n1)N(C(=O)Nc1cc(OCC(=O)O)ccn1)[C@H]1CCN2C1)C(F)(F)F] | 2-[(2-{[(9S)-5-{[(2R)-1,1,1-trifluoropropan-2-yl]carbamoyl}-1,6,8-triazatricyclo[7.2.1.0²,⁷]dodeca-2(7),3,5-triene-8-carbonyl]amino}pyridin-4-yl)oxy]acetic acid | B | A |
| 266 | 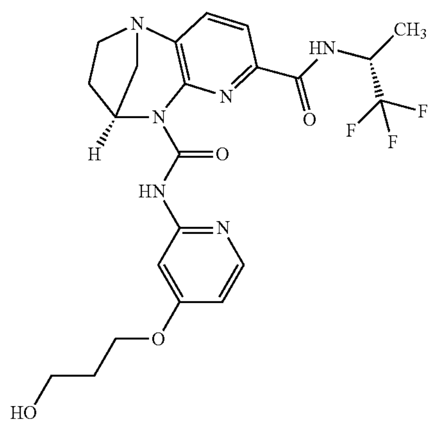 [SMILES: C[C@@H](NC(=O)c1ccc2c(n1)N(C(=O)Nc1cc(OCCCO)ccn1)[C@H]1CCN2C1)C(F)(F)F] | (9S)-8-N-[4-(3-hydroxypropoxy)pyridin-2-yl]-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |
| 267 | 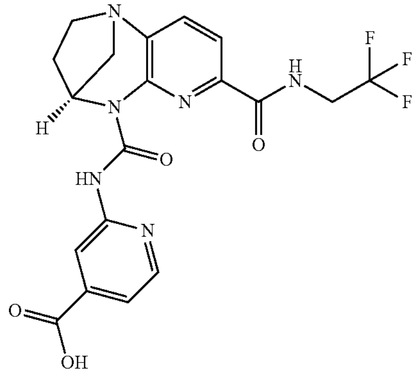 [SMILES: O=C(O)c1ccnc(NC(=O)N2c3nc(C(=O)NCC(F)(F)F)ccc3N3CC[C@H]2C3)c1] | 2-{[(9S)-5-[(2,2,2-trifluoroethyl)carbamoyl]-1,6,8-triazatricyclo[7.2.1.0²,⁷]dodeca-2(7),3,5-triene-8-carbonyl]amino}pyridine-4-carboxylic acid | B | A |

TABLE 1-continued

| Example number | Structure | Chemical Name: Generated by CHemAxon | TRP Activity | TRP MAX RESP |
|---|---|---|---|---|
| 268 | 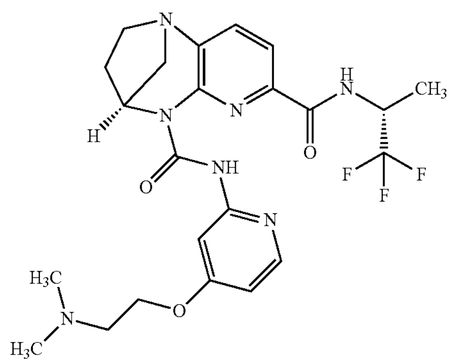 [SMILES: C[C@@H](NC(=O)c1ccc2c(n1)N(C(=O)Nc1cc(OCCN(C)C)ccn1)[C@H]1CCN2C1)C(F)(F)F] | (9S)-8-N-{4-[2-(dimethylamino)ethoxy]pyridin-2-yl}-5-N-[(2R)-1,1,1-trifluoropropan-2-yl]-1,6,8-triazatricyclo[7.2.1.0²,⁷]dodeca-2(7),3,5-triene-5,8-dicarboxamide | B | A |
| 269 | 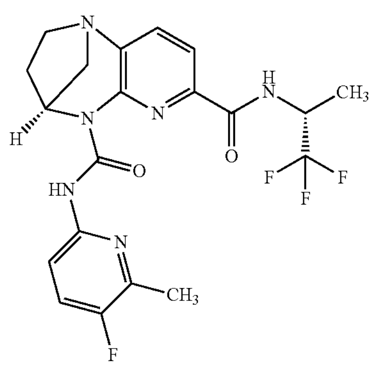 [SMILES: Cc1nc(NC(=O)N2c3nc(C(=O)N[C@H](C)C(F)(F)F)ccc3N3CC[C@H]2C3)ccc1F] | (9S)-8-N-(5-fluoro-6-methylpyridin-2-yl)-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |
| 270 | ISOMER 2 | (9S)-5-N-[(1R)-2,2-difluorocyclopropyl]-8-N-(pyridazin-3-yl)-1,6,8-triazatricyclo[7.2.1.0²,⁷]dodeca-2,4,6-triene-5,8-dicarboxamide | A | A |
| 271 | ISOMER 1 | (9S)-5-N-[(1R)-2,2-difluorocyclopropyl]-8-N-(pyridazin-3-yl)-1,6,8-triazatricyclo[7.2.1.0²,⁷]dodeca-2,4,6-triene-5,8-dicarboxamide | B | A |

TABLE 1-continued

| Example number | Structure | Chemical Name: Generated by CHemAxon | TRP Activity | TRP MAX RESP |
|---|---|---|---|---|
| 272 | ISOMER 2 | (9S)-5-N-[(1R)-2,2-difluorocyclopropyl]-8-N-(pyrazin-2-yl)-1,6,8-triazatricyclo[7.2.1.0²,⁷]dodeca-2(7),3,5-triene-5,8-dicarboxamide | A | A |
| 273 | ISOMER 1 | (9S)-5-N-[(1R)-2,2-difluorocyclopropyl]-8-N-(pyrazin-2-yl)-1,6,8-triazatricyclo[7.2.1.0²,⁷]dodeca-2(7),3,5-triene-5,8-dicarboxamide | B | A |
| 274 | ISOMER 1 | (9S)-5-N-[(1R)-2,2-difluorocyclopropyl]-8-N-(4-methoxypyridin-2-yl)-1,6,8-triazatricyclo[7.2.1.0²,⁷]dodeca-2(7),3,5-triene-5,8-dicarboxamide | B | A |
| 275 | 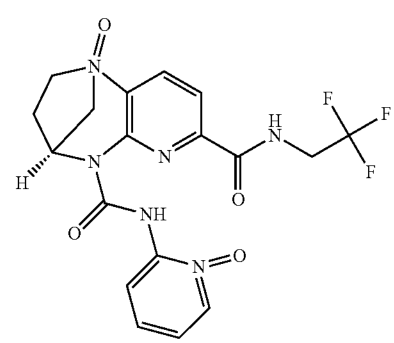 [SMILES: O=C(NCC(F)(F)F)c1ccc2c(n1)N(C(=O)Nc1cccc[n+]1[O-])[C@H]1CC[N+]2([O-])C1] | (9S)-1-oxo-8-N-(1-oxo-1λ⁵-pyridin-2-yl)-5-N-(2,2,2-trifluoroethyl)-1λ⁵,6,8-triazatricyclo[7.2.1.0²,⁷]dodeca-2(7),3,5-triene-5,8-dicarboxamide | C | A |

TABLE 1-continued

| Example number | Structure | Chemical Name: Generated by CHemAxon | TRP Activity | TRP MAX RESP |
|---|---|---|---|---|
| 276 | 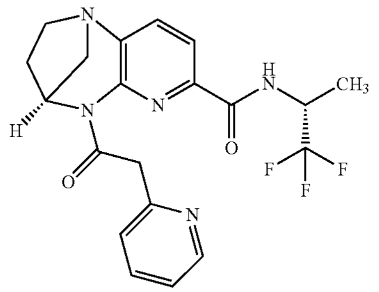 [SMILES: C[C@@H](NC(=O)c1ccc2c(n1)N(C(=O)Cc1ccccn1)[C@H]1CCN2C1)C(F)(F)F] | (9S)-8-[2-(pyridin-2-yl)acetyl]-N-[(2R)-1,1,1-trifluoropropan-2-yl]-1,6,8-triazatricyclo[7.2.1.0$^2$,$^7$]dodeca-2(7),3,5-triene-5-carboxamide | C | B |
| 277 | 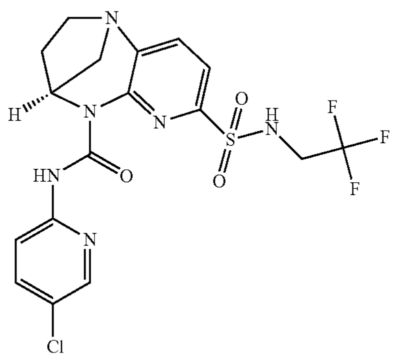 [SMILES: O=C(Nc1ccc(Cl)cn1)N1c2nc(S(=O)(=O)NCC(F)(F)F)ccc2N2CC[C@H]1C2] | (9S)-N-(5-chloropyridin-2-yl)-5-[(2,2,2-trifluoroethyl)sulfamoyl]-1,6,8-triazatricyclo[7.2.1.0$^2$,$^7$]dodeca-2,4,6-triene-8-carboxamide | C | B |
| 278 | 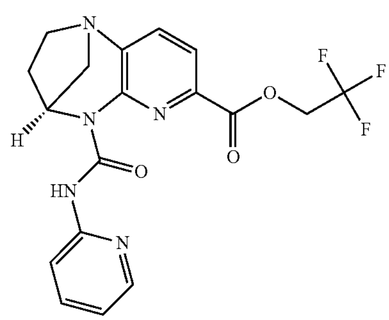 [SMILES: O=C(OCC(F)(F)F)c1ccc2c(n1)N(C(=O)Nc1ccccn1)[C@H]1CCN2C1] | 2,2,2-trifluoroethyl (9S)-8-[(pyridin-2-yl)carbamoyl]-1,6,8-triazatricyclo[7.2.1.0$^2$,$^7$]dodeca-2(7),3,5-triene-5-carboxylate | B | A |
| 279 | 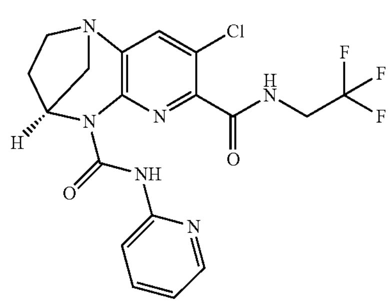 [SMILES: O=C(NCC(F)(F)F)c1nc2c(cc1Cl)N1CC[C@@H](C1)N2C(=O)Nc1ccccn1] | (9S)-4-chloro-8-N-(pyridin-2-yl)-5-N-(2,2,2-trifluoroethyl)-1,6,8-triazatricyclo[7.2.1.0$^2$,$^7$]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 280 | 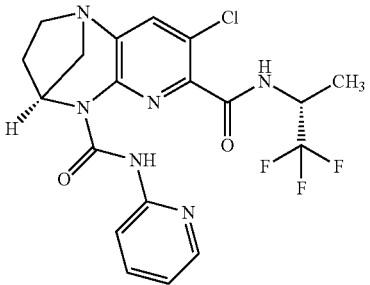 [SMILES: C[C@@H](NC(=O)c1nc2c(cc1Cl)N1CC[C@@H](C1)N2C(=O)Nc1ccccn1)C(F)(F)F] | (9S)-4-chloro-8-N-(pyridin-2-yl)-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |
| 281 | 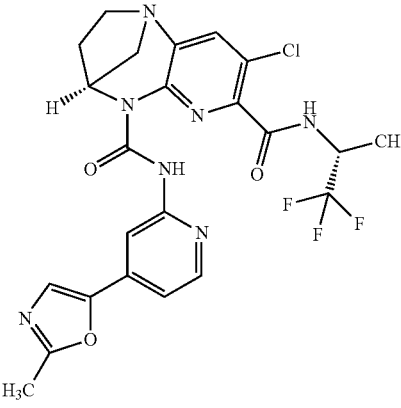 | (9S)-4-chloro-8-N-[4-(2-methyl-1,3-oxazol-5-yl)pyridin-2-yl]-5-N-[(2R)-1,1,1-trifluoropropan-2-yl]-1,6,8-triazatricyclo[7.2.1.0²,⁷]dodeca-2,4,6-triene-5,8-dicarboxamide | B | A |
| 282 | 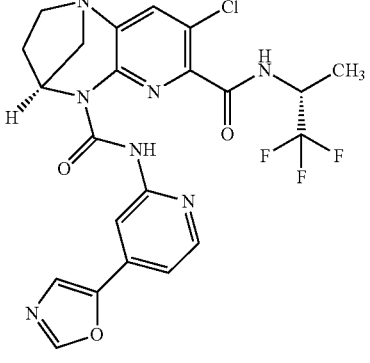 | (9S)-4-chloro-8-N-[4-(1,3-oxazol-5-yl)pyridin-2-yl]-5-N-[(2R)-1,1,1-trifluoropropan-2-yl]-1,6,8-triazatricyclo[7.2.1.0²,⁷]dodeca-2,4,6-triene-5,8-dicarboxamide | A | A |
| 283 | 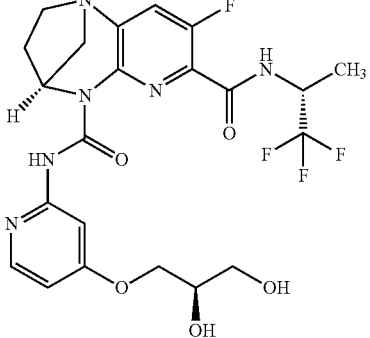 | (9S)-8-N-{4-[(2R)-2,3-dihydroxypropoxy]pyridin-2-yl}-4-fluoro-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 284 | 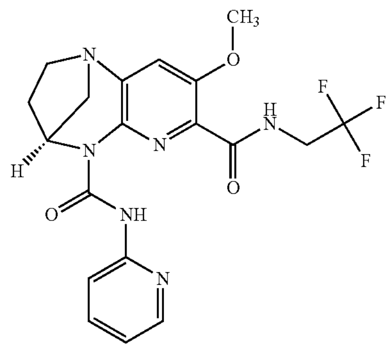 [SMILES: COc1cc2c(nc1C(=O)NCC(F)(F)F)N(C(=O)Nc1ccccn1)[C@H]1CCN2C1] | (9S)-4-methoxy-8-N-(pyridin-2-yl)-5-N-(2,2,2-trifluoroethyl)-1,6,8-triazatricyclo[7.2.1.0$^{2,7}$]dodeca-2(7),3,5-triene-5,8-dicarboxamide | A | A |
| 285 | 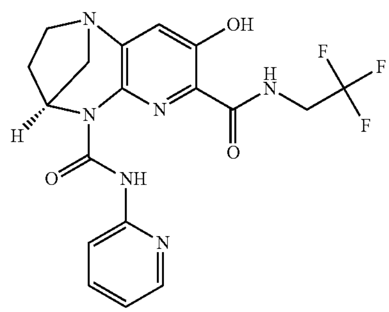 [SMILES: O=C(NCC(F)(F)F)c1nc2c(cc1O)N1CC[C@@H](C1)N2C(=O)Nc1ccccn1] | (9S)-4-hydroxy-8-N-(pyridin-2-yl)-5-N-(2,2,2-trifluoroethyl)-1,6,8-triazatricyclo[7.2.1.0$^{2,7}$]dodeca-2(7),3,5-triene-5,8-dicarboxamide | A | A |
| 286 | 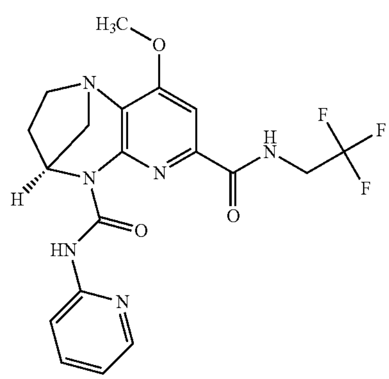 [SMILES: COc1cc(C(=O)NCC(F)(F)F)nc2c1N1CC[C@@H](C1)N2C(=O)Nc1ccccn1] | (9S)-3-methoxy-8-N-(pyridin-2-yl)-5-N-(2,2,2-trifluoroethyl)-1,6,8-triazatricyclo[7.2.1.0$^{2,7}$]dodeca-2(7),3,5-triene-5,8-dicarboxamide | A | A |
| 287 | 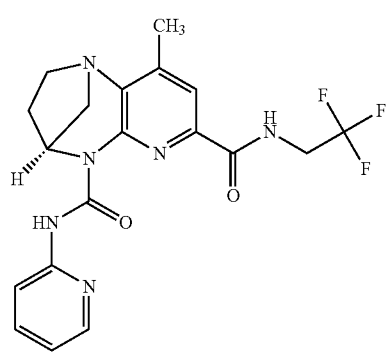 [SMILES: Cc1cc(C(=O)NCC(F)(F)F)nc2c1N1CC[C@@H](C1)N2C(=O)Nc1ccccn1] | (9S)-3-methyl-8-N-(pyridin-2-yl)-5-N-(2,2,2-trifluoroethyl)-1,6,8-triazatricyclo[7.2.1.0$^{2,7}$]dodeca-2(7),3,5-triene-5,8-dicarboxamide | A | A |

TABLE 1-continued

| Example number | Structure | Chemical Name: Generated by CHemAxon | TRP Activity | TRP MAX RESP |
|---|---|---|---|---|
| 288 | 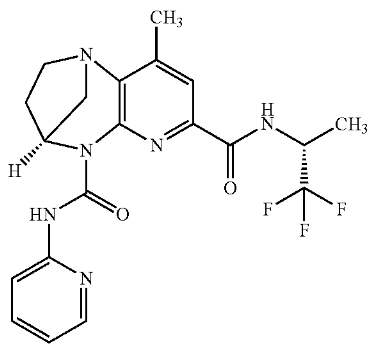 [SMILES: Cc1cc(C(=O)N[C@H](C)C(F)(F)F)nc2c1N1CC[C@@H](C1)N2C(=O)Nc1ccccn1] | (9S)-3-methyl-8-N-(pyridin-2-yl)-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |
| 289 | 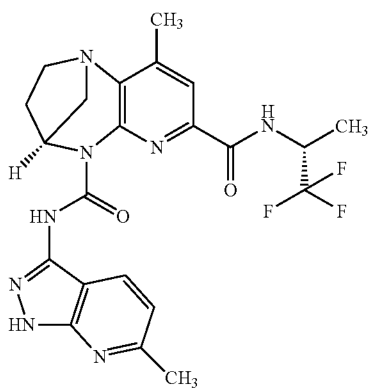 [SMILES: Cc1ccc2c(NC(=O)N3c4nc(C(=O)N[C@H](C)C(F)(F)F)cc(C)c4N4CC[C@H]3C4)n[nH]c2n1] | (9S)-3-methyl-8-N-{6-methyl-1H-pyrazolo[3,4-b]pyridin-3-yl}-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |
| 290 | 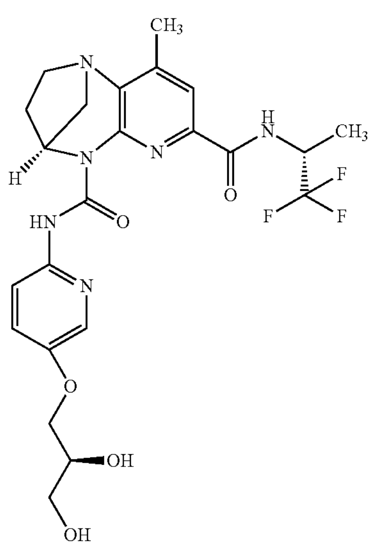 [SMILES: Cc1cc(C(=O)N[C@H](C)C(F)(F)F)nc2c1N1CC[C@@H](C1)N2C(=O)Nc1ccc(OC[C@@H](O)CO)cn1] | (9S)-8-N-{5-[(2S)-2,3-dihydroxypropoxy]pyridin-2-yl}-3-methyl-5-N-[(2R)-1,1,1-trifluoropropan-2-yl]-1,6,8-triazatricyclo[7.2.1.0²,⁷]dodeca-2(7),3,5-triene-5,8-dicarboxamide | A | A |

TABLE 1-continued

| Example number | Structure | Chemical Name: Generated by CHemAxon | TRP Activity | TRP MAX RESP |
| --- | --- | --- | --- | --- |
| 291 | 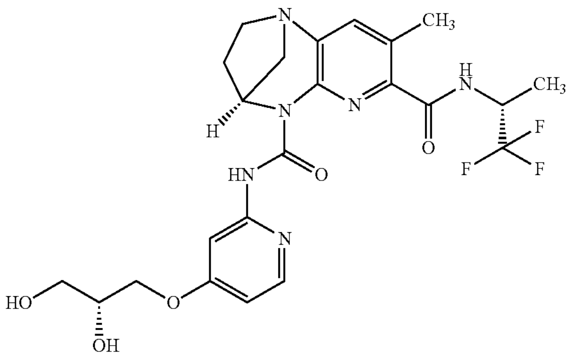 [SMILES: Cc1cc2c(nc1C(=O)N[C@H](C)C(F)(F)F)N(C(=O)Nc1cc(OC[C@H](O)CO)ccn1)[C@H]1CCN2C1] | (9S)-8-N-{4-[(2R)-2,3-dihydroxypropoxy]pyridin-2-yl}-4-methyl-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | B |
| 292 | 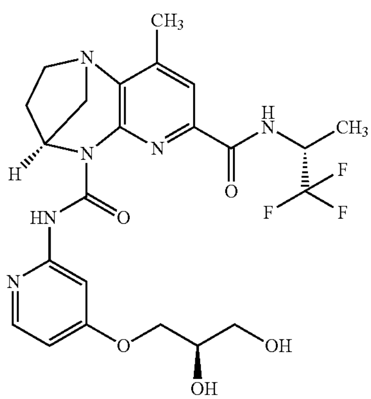 [SMILES: Cc1cc(C(=O)N[C@H](C)C(F)(F)F)nc2c1N1CC[C@@H](C1)N2C(=O)Nc1cc(OC[C@H](O)CO)ccn1] | (9S)-8-N-{4-[(2R)-2,3-dihydroxypropoxy]pyridin-2-yl}-3-methyl-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | B |
| 293 | 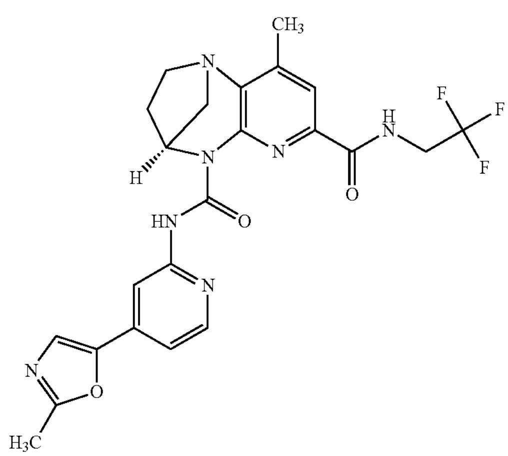 [SMILES: Cc1ncc(-c2ccnc(NC(=O)N3c4nc(C(=O)NCC(F)(F)F)cc(C)c4N4CC[C@H]3C4)c2)o1] | (9S)-3-methyl-8-N-[4-(2-methyl-1,3-oxazol-5-yl)pyridin-2-yl]-5-N-(2,2,2-trifluoroethyl)-1,6,8-triazatricyclo[7.2.1.0$^{2,7}$]dodeca-2(7),3,5-triene-5,8-dicarboxamide | A | B |

TABLE 1-continued

| Example number | Structure | Chemical Name: Generated by CHemAxon | TRP Activity | TRP MAX RESP |
|---|---|---|---|---|
| 294 | 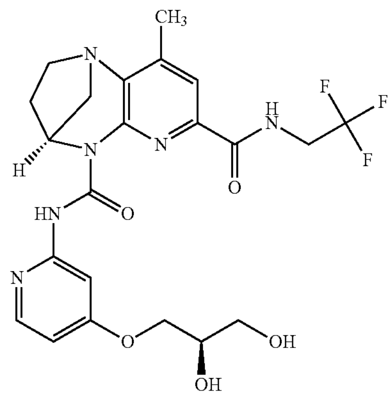 [SMILES: Cc1cc(C(=O)NCC(F)(F)F)nc2c1N1CC[C@@H](C1)N2C(=O)Nc1cc(OC[C@H](O)CO)ccn1] | (9S)-8-N-{4-[(2R)-2,3-dihydroxypropoxy]pyridin-2-yl}-3-methyl-5-N-(2,2,2-trifluoroethyl)-1,6,8-triazatricyclo[7.2.1.0$^{2,7}$]dodeca-2(7),3,5-triene-5,8-dicarboxamide | A | B |
| 295 | 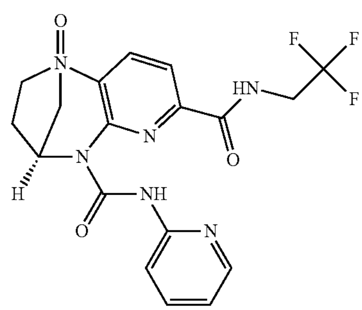 [SMILES: O=C(NCC(F)(F)F)c1ccc2c(n1)N(C(=O)Nc1ccccn1)[C@H]1CC[N+]2([O-])C1] | (9S)-1-oxo-8-N-(pyridin-2-yl)-5-N-(2,2,2-trifluoroethyl)-1$\lambda^5$,6,8-triazatricyclo[7.2.1.0$^{2,7}$]dodeca-2(7),3,5-triene-5,8-dicarboxamide | B | A |
| 296 | 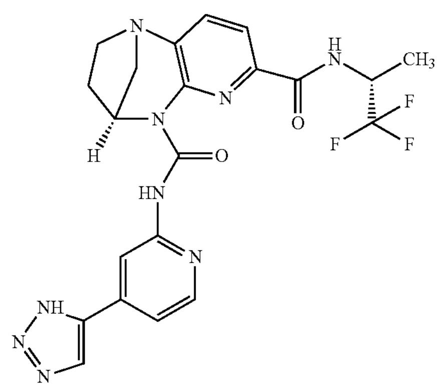 [SMILES: C[C@@H](NC(=O)c1ccc2c(n1)N(C(=O)Nc1cc(-c3cnn[nH]3)ccn1)[C@H]1CCN2C1)C(F)(F)F] | (9S)-8-N-[4-(1H-1,2,3-triazol-5-yl)pyridin-2-yl]-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | B |
| 297 | 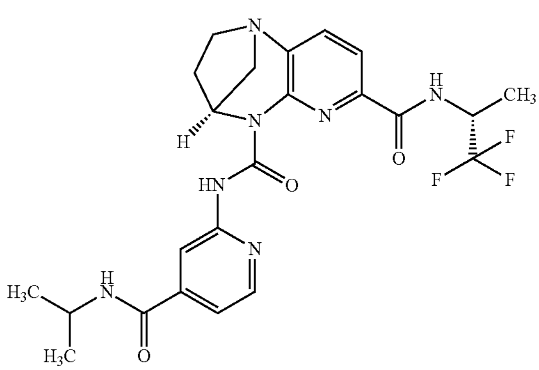 [SMILES: CC(C)NC(=O)c1ccnc(NC(=O)N2c3nc(C(=O)N[C@H](C)C(F)(F)F)ccc3N3CC[C@H]2C3)c1] | (9S)-8-N-{4-[(propan-2-yl)carbamoyl]pyridin-2-yl}-5-N-[(2R)-1,1,1-trifluoropropan-2-yl]-1,6,8-triazatricyclo[7.2.1.02,7]dodeca-2(7),3,5-triene-5,8-dicarboxamide | A | B |

TABLE 1-continued

| Example number | Structure | Chemical Name: Generated by CHemAxon | TRP Activity | TRP MAX RESP |
|---|---|---|---|---|
| 298 | ISOMER 1 | (9S)-5-N-[(1R)-2,2-difluorocyclopropyl]-8-N-(6-methoxypyrimidin-4-yl)-1,6,8-triazatricyclo[7.2.1.0²,⁷]dodeca-2(7),3,5-triene-5,8-dicarboxamide | B | B |
| 299 | 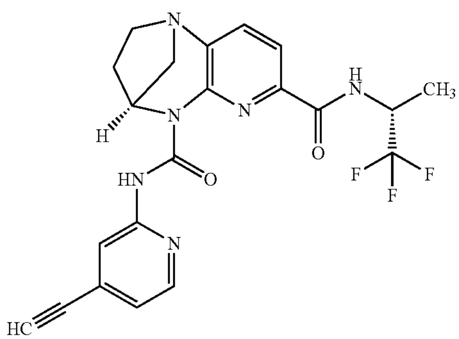 [SMILES: C#Cc1ccnc(NC(=O)N2c3nc(C(=O)N[C@H](C)C(F)(F)F)ccc3N3CC[C@H]2C3)c1] | (9S)-8-N-(4-ethynylpyridin-2-yl)-5-N-[(2R)-1,1,1-trifluoropropan-2-yl]-1,6,8-triazatricyclo[7.2.1.0²,⁷]dodeca-2(7),3,5-triene-5,8-dicarboxamide | A | B |
| 300 | 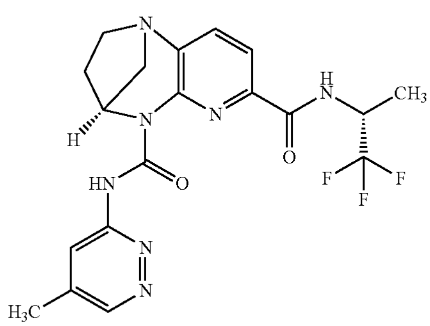 [SMILES: Cc1cnnc(NC(=O)N2c3nc(C(=O)N[C@H](C)C(F)(F)F)ccc3N3CC[C@H]2C3)c1] | (9S)-8-N-(5-methylpyridazin-3-yl)-5-N-[(2R)-1,1,1-trifluoropropan-2-yl]-1,6,8-triazatricyclo[7.2.1.0²,⁷]dodeca-2(7),3,5-triene-5,8-dicarboxamide | A | B |
| 301 | 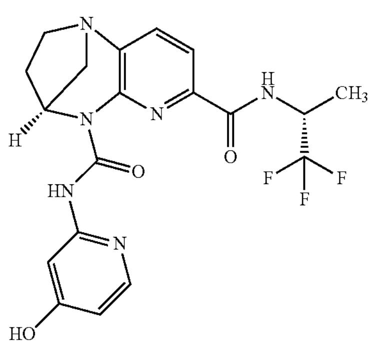 [SMILES: C[C@@H](NC(=O)c1ccc2c(n1)N(C(=O)Nc1cc(O)ccn1)[C@H]1CCN2C1)C(F)(F)F] | (9S)-8-N-(4-hydroxypyridin-2-yl)-5-N-[(2R)-1,1,1-trifluoropropan-2-yl]-1,6,8-triazatricyclo[7.2.1.0²,⁷]dodeca-2(7),3,5-triene-5,8-dicarboxamide | A | B |

TABLE 1-continued

| Example number | Structure | Chemical Name: Generated by CHemAxon | TRP Activity | TRP MAX RESP |
|---|---|---|---|---|
| 302 | ISOMER 1 | (9S)-8-N-{4-[(3R)-3,4-dihydroxybutyl]pyridin-2-yl}-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | B |
| 303 | ISOMER 2 | (9S)-5-N-[(1R)-2,2-difluorocyclopropyl]-8-N-(6-methoxypyrimidin-4-yl)-1,6,8-triazatricyclo[7.2.1.0$^{2,7}$]dodeca-2(7),3,5-triene-5,8-dicarboxamide | A | B |
| 304 | 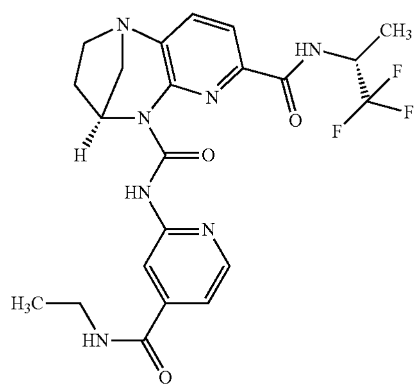 [SMILES: CCNC(=O)c1ccnc(NC(=O)N2c3nc(C(=O)N[C@H](C)C(F)(F)F)ccc3N3CC[C@H]2C3)c1] | (9S)-8-N-[4-(ethylcarbamoyl)pyridin-2-yl]-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | B |
| 305 | 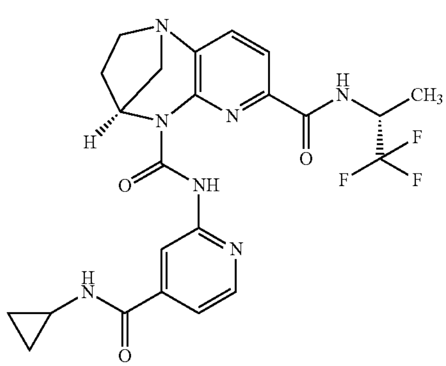 [SMILES: C[C@@H](NC(=O)c1ccc2c(n1)N(C(=O)Nc1cc(C(=O)NC3CC3)ccn1)[C@H]1CCN2C1)C(F)(F)F] | (9S)-8-N-[4-(cyclopropylcarbamoyl)pyridin-2-yl]-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | B |

TABLE 1-continued

| Example number | Structure | Chemical Name: Generated by CHemAxon | TRP Activity | TRP MAX RESP |
|---|---|---|---|---|
| 306 | ISOMER 1 | (9S)-5-N-[(1R)-2,2-difluorocyclopropyl]-8-N-{4-[(2R)-2,3-dihydroxypropoxy]pyridin-2-yl}-1,6,8-triazatricyclo[7.2.1.0$^{2,7}$]dodeca-2(7),3,5-triene-5,8-dicarboxamide | B | B |
| 307 | 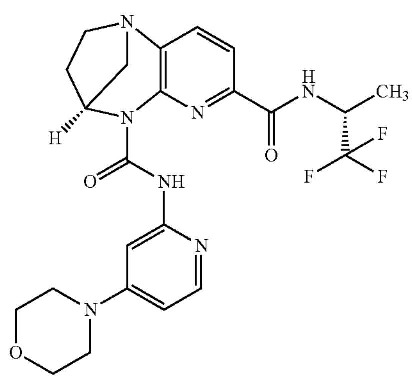 [SMILES: C[C@@H](NC(=O)c1ccc2c(n1)N(C(=O)Nc1cc(N3CCOCC3)ccn1)[C@H]1CCN2C1)C(F)(F)F] | (9S)-8-N-[4-(morpholin-4-yl)pyridin-2-yl]-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | B |
| 308 | 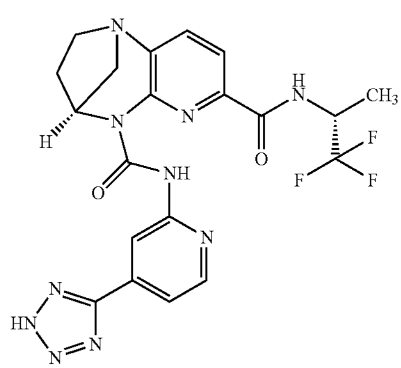 [SMILES: C[C@@H](NC(=O)c1ccc2c(n1)N(C(=O)Nc1cc(-c3nn[nH]n3)ccn1)[C@H]1CCN2C1)C(F)(F)F] | (9S)-8-N-[4-(2H-1,2,3,4-tetrazol-5-yl)pyridin-2-yl]-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | B |
| 309 | 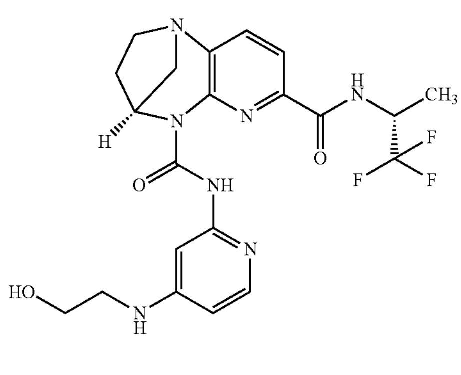 [SMILES: C[C@@H](NC(=O)c1ccc2c(n1)N(C(=O)Nc1cc(NCCO)ccn1)[C@H]1CCN2C1)C(F)(F)F] | (9S)-8-N-{4-[(2-hydroxyethyl)amino]pyridin-2-yl}-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | B |

TABLE 1-continued

| Example number | Structure | Chemical Name: Generated by CHemAxon | TRP Activity | TRP MAX RESP |
|---|---|---|---|---|
| 310 | 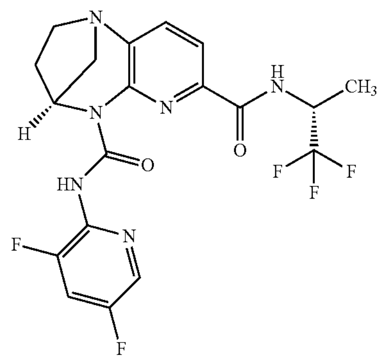 [SMILES: C[C@@H](NC(=O)c1ccc2c(n1)N(C(=O)Nc1ncc(F)cc1F)[C@H]1CCN2C1)C(F)(F)F] | (9S)-8-N-(3,5-difluoropyridin-2-yl)-5-N-[(2R)-1,1,1-trifluoropropan-2-yl]-1,6,8-triazatricyclo[7.2.1.0$^{2,7}$]dodeca-2(7),3,5-triene-5,8-dicarboxamide | B | B |
| 311 | 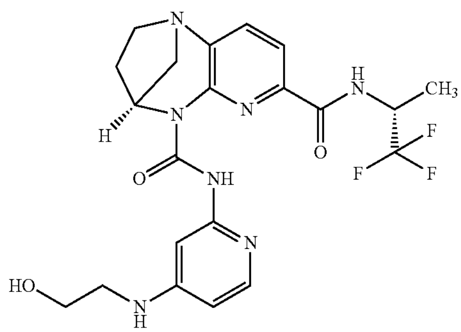 [SMILES: C[C@@H](NC(=O)c1ccc2c(n1)N(C(=O)Nc1cc(NCCO)ccn1)[C@H]1CCN2C1)C(F)(F)F] | (9S)-8-N-{4-[(2-hydroxyethyl)amino]pyridin-2-yl}-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | B |
| 312 | 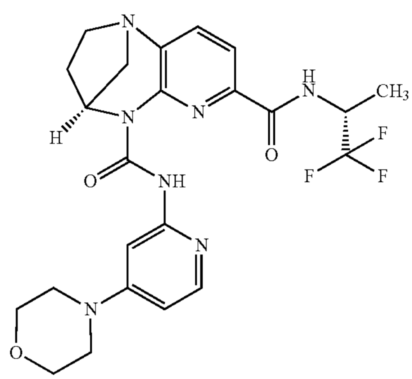 [SMILES: C[C@@H](NC(=O)c1ccc2c(n1)N(C(=O)Nc1cc(N3CCOCC3)ccn1)[C@H]1CCN2C1)C(F)(F)F] | (9S)-8-N-[4-(morpholin-4-yl)pyridin-2-yl]-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | B |
| 313 | 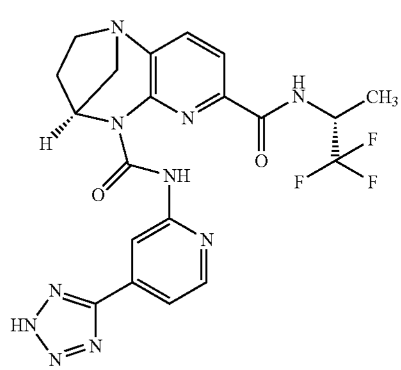 [SMILES: C[C@@H](NC(=O)c1ccc2c(n1)N(C(=O)Nc1cc(-c3nn[nH]n3)ccn1)[C@H]1CCN2C1)C(F)(F)F] | (9S)-8-N-[4-(2H-1,2,3,4-tetrazol-5-yl)pyridin-2-yl]-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | B |

TABLE 1-continued

| Example number | Structure | Chemical Name: Generated by CHemAxon | TRP Activity | TRP MAX RESP |
|---|---|---|---|---|
| 314 | 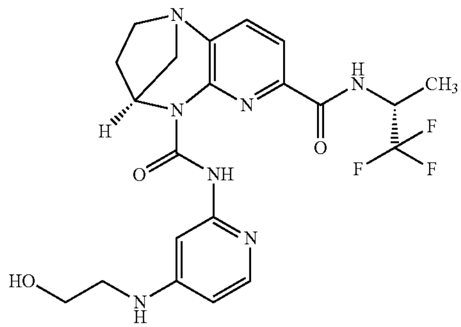 [SMILES: C[C@@H](NC(=O)c1ccc2c(n1)N(C(=O)Nc1cc(NCCO)ccn1)[C@H]1CCN2C1)C(F)(F)F] | (9S)-8-N-{4-[(2-hydroxyethyl)amino]pyridin-2-yl}-5-N-[(2R)-1,1,1-trifluoropropan-2-yl]-1,6,8-triazatricyclo[7.2.1.0²,⁷]dodeca-2(7),3,5-triene-5,8-dicarboxamide | A | B |
| 315 | 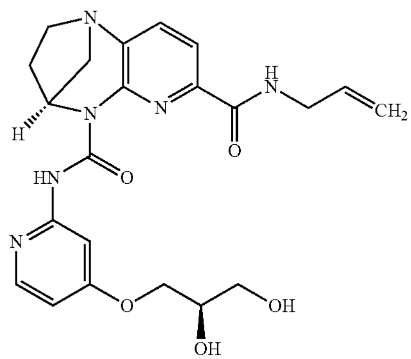 [SMILES: C=CCNC(=O)c1ccc2c(n1)N(C(=O)Nc1cc(OC[C@H](O)CO)ccn1)[C@H]1CCN2C1] | (9S)-8-N-{4-[(2R)-2,3-dihydroxypropoxy]pyridin-2-yl}-5-N-(prop-2-en-1-yl)-1,6,8-triazatricyclo[7.2.1.0²,⁷]dodeca-2(7),3,5-triene-5,8-dicarboxamide | B | B |
| 316 | 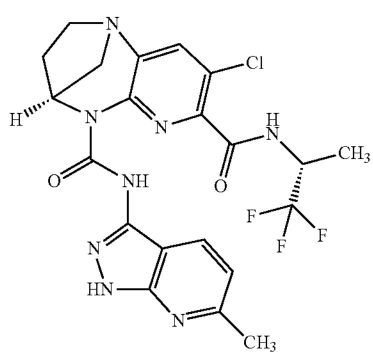 [SMILES: Cc1ccc2c(NC(=O)N3c4nc(C(=O)N[C@H](C)C(F)(F)F)c(Cl)cc4N4CC[C@H]3C4)n[nH]c2n1] | (9S)-4-chloro-8-N-{6-methyl-1H-pyrazolo[3,4-b]pyridin-3-yl}-5-N-[(2R)-1,1,1-trifluoropropan-2-yl]-1,6,8-triazatricyclo[7.2.1.0²,⁷]dodeca-2,4,6-triene-5,8-dicarboxamide | B | B |
| 317 | 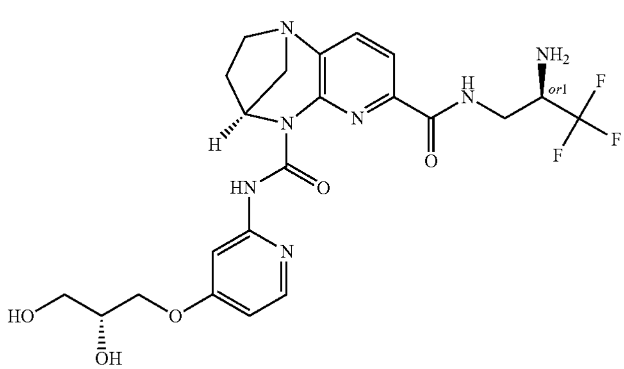 | (9S)-5-N-[(2R)-2-amino-3,3,3-trifluoropropyl]-8-N-{4-[(2R)-2,3-dihydroxypropoxy]pyridin-2-yl}-1,6,8-triazatricyclo[7.2.1.0²,⁷]dodeca-2(7),3,5-triene-5,8-dicarboxamide | B | B |

TABLE 1-continued

| Example number | Structure | Chemical Name: Generated by CHemAxon | TRP Activity | TRP MAX RESP |
|---|---|---|---|---|
| 318 | 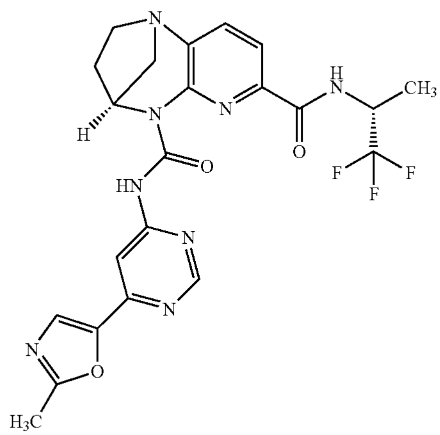 [SMILES: Cc1ncc(-c2cc(NC(=O)N3c4nc(C(=O)N[C@H](C)C(F)(F)F)ccc4N4CC[C@H]3C4)ncn2)o1] | (9S)-8-N-[6-(2-methyl-1,3-oxazol-5-yl)pyrimidin-4-yl]-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | B |
| 319 | 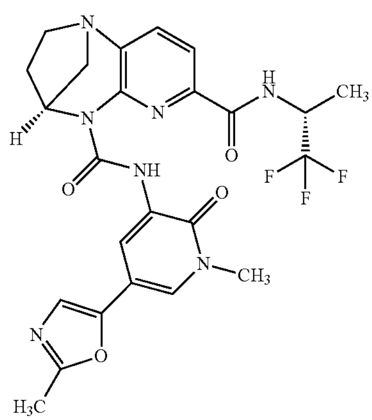 [SMILES: Cc1ncc(-c2cc(NC(=O)N3c4nc(C(=O)N[C@H](C)C(F)(F)F)ccc4N4CC[C@H]3C4)c(=O)n(C)c2)o1] | (9S)-8-N-[1-methyl-5-(2-methyl-1,3-oxazol-5-yl)-2-oxo-1,2-dihydropyridin-3-yl]-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | B |
| 320 | 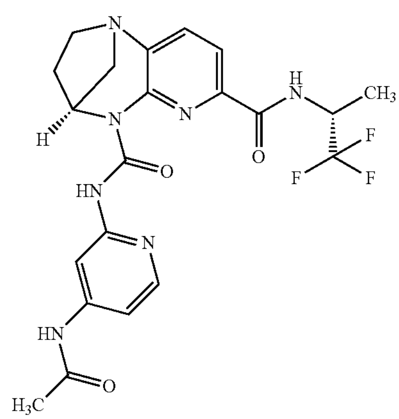 [SMILES: CC(=O)Nc1ccnc(NC(=O)N2c3nc(C(=O)N[C@H](C)C(F)(F)F)ccc3N3CC[C@H]2C3)c1] | (9S)-8-N-(4-acetamidopyridin-2-yl)-5-N-[(2R)-1,1,1-trifluoropropan-2-yl]-1,6,8-triazatricyclo[7.2.1.0$^{2,7}$]dodeca-2,4,6-triene-5,8-dicarboxamide | A | B |

TABLE 1-continued

| Example number | Structure | Chemical Name: Generated by CHemAxon | TRP Activity | TRP MAX RESP |
|---|---|---|---|---|
| 321 | 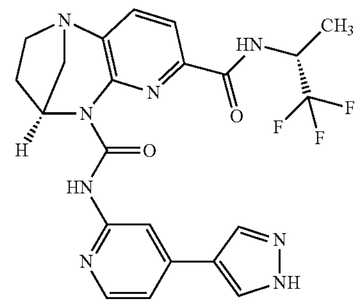 [SMILES: C[C@@H](NC(=O)c1ccc2c(n1)N(C(=O)Nc1cc(-c3cn[nH]c3)ccn1)[C@H]1CCN2C1)C(F)(F)F] | (9S)-8-N-[4-(1H-pyrazol-4-yl)pyridin-2-yl]-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | B |
| 322 | 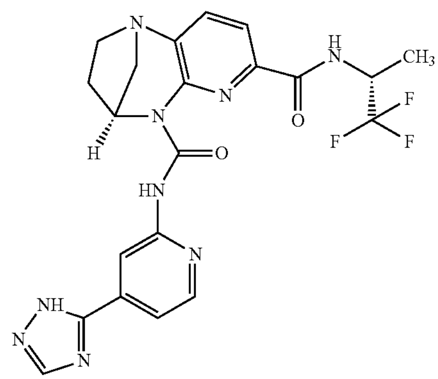 [SMILES: C[C@@H](NC(=O)c1ccc2c(n1)N(C(=O)Nc1cc(-c3ncn[nH]3)ccn1)[C@H]1CCN2C1)C(F)(F)F] | (9S)-8-N-[4-(1H-1,2,4-triazol-5-yl)pyridin-2-yl]-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | B |
| 323 | 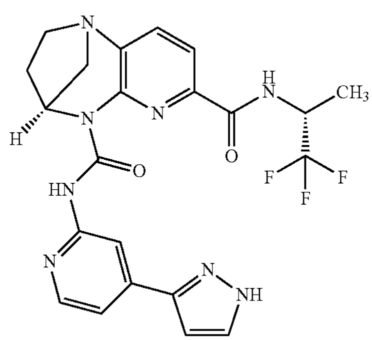 [SMILES: C[C@@H](NC(=O)c1ccc2c(n1)N(C(=O)Nc1cc(-c3cc[nH]n3)ccn1)[C@H]1CCN2C1)C(F)(F)F] | (9S)-8-N-[4-(1H-pyrazol-3-yl)pyridin-2-yl]-5-N-[(2R)-1,1,1-trifluoropropan-2-yl]-1,6,8-triazatricyclo[7.2.1.0$^{2,7}$]dodeca-2(7),3,5-triene-5,8-dicarboxamide | A | B |
| 324 | 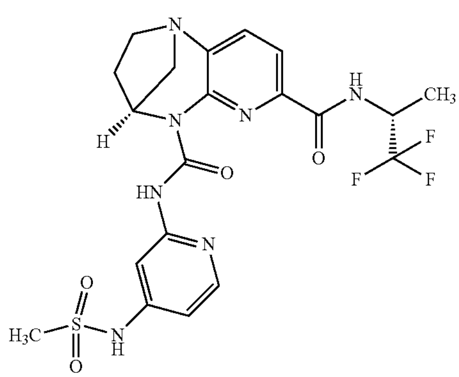 [SMILES: C[C@@H](NC(=O)c1ccc2c(n1)N(C(=O)Nc1cc(NS(C)(=O)=O)ccn1)[C@H]1CCN2C1)C(F)(F)F] | (9S)-8-N-(4-methanesulfonamidopyridin-2-yl)-5-N-[(2R)-1,1,1-trifluoropropan-2-yl]-1,6,8-triazatricyclo[7.2.1.0$^{2,7}$]dodeca-2,4,6-triene-5,8-dicarboxamide | A | B |

TABLE 1-continued

| Example number | Structure | Chemical Name: Generated by CHemAxon | TRP Activity | TRP MAX RESP |
|---|---|---|---|---|
| 325 | 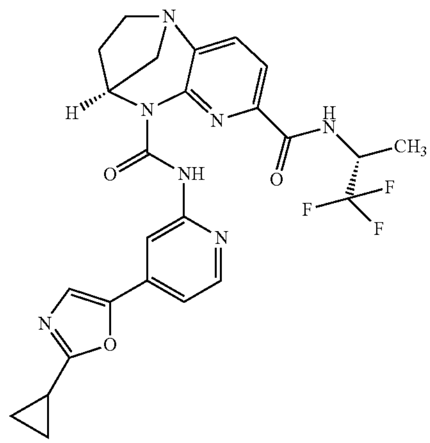 [SMILES: C[C@@H](NC(=O)c1ccc2c(n1)N(C(=O)Nc1cc(-c3cnc(C4CC4)o3)ccn1)[C@H]1CCN2C1)C(F)(F)F] | (9S)-8-N-[4-(2-cyclopropyl-1,3-thiazol-5-yl)pyridin-2-yl]-5-N-[(2R)-1,1,1-trifluoropropan-2-yl]-1,6,8-triazatricyclo[7.2.1.0$^{2,7}$]dodeca-2,4,6-triene-5,8-dicarboxamide | A | B |

Example 326

The present invention relates to Sirtuin Modulators, which are known in the scientific literature for being useful for increasing lifespan of a cell, and in treating and/or preventing a wide variety of diseases and disorders, which include, but are not limited to, for example, diseases or disorders related to aging or stress, diabetes, obesity, neurodegenerative diseases, cardiovascular disease, blood clotting disorders, inflammation, cancer, and/or flushing as well as diseases or disorders that would benefit from increased mitochondrial activity.

In addition to therapeutic potential, structural and biophysical studies of SIRT1 activity and activation by small molecule sirtuin modulators would be useful in advancing understanding of the biological function of sirtuins, mechanism of action of sirtuin activation and to aid in development of assays that identify novel sirtuin modulators.

Based on the foregoing, the following literature references, respectively, are cited to demonstrate the utility of compounds of the present invention as Sirtuin Modulators and its interconnection with various diseases as exemplified or disclosed in the following references:

1. Marcia C. Haigis and David A. Sinclair, Mammalian Sirtuins: Biological Insights and Disease Relevance, *Annu Rev Pathol.* 2010; 5: 253-295.

Haigis and Sinclair teach:

"Aging is accompanied by a decline in the healthy function of multiple organ systems, leading to increased incidence and mortality from diseases such as type II diabetes mellitus, neurodegenerative diseases, cancer, and cardiovascular disease. Historically, researchers have focused on investigating individual pathways in isolated organs as a strategy to identify the root cause of a disease, with hopes of designing better drugs. Studies of aging in yeast led to the of a family of conserved enzymes known as the sirtuins, which affect multiple pathways that increase the life span and the overall health of organisms. Since the discovery of the first known mammalian sirtuin, SIRT1, 10 years ago, there have been major advances in our understanding of the enzymology of sirtuins, their regulation, and their ability to broadly improve mammalian physiology and health span. This review summarizes and discusses the discovery advances of the past decade and the challenges that will confront the field in the coming years (see, ABSTRACT, therein and reference)."

2. Gizem Donmezl et. al., SIRT1 and SIRT2: emerging targets in neurodegeneration, EMBO Mol Med (2013) 5, 344-352.

Gizem Donmezl et. al., teaches:

"Sirtuins are NAD-dependent protein deacetylases known to have protective effects against age-related diseases such as cancer, diabetes, cardiovascular and neurodegenerative diseases. In mammals, there are seven sirtuins (SIRT1-7), which display diversity in subcellular localization and function. While SIRT1 has been extensively investigated due to its initial connection with lifespan extension and involvement in calorie restriction, important biological and therapeutic roles of other sirtuins have only recently been recognized. Here, we review the potential roles and effects of SIRT1 and SIRT2 in neurodegenerative diseases. We discuss different functions and targets of SIRT1 and SIRT2 in a variety of neurodegenerative diseases including Alzheimer's disease (AD), Parkinson's disease (PD) and Huntington's Disease (HD). We also cover the role of SIRT1 in neuronal differentiation due to the possible implications in neurodegenerative conditions, and conclude with an outlook on the potential therapeutic value of SIRT1 and SIRT2 in these disorders (see, ABSTRACT, therein and reference)."

3. Bracke et al., Targeted silencing of DEFB4 in a bioengineered skin-humanized mouse model for psoriasis: development of siRNA SECosome-based novel therapies; *Exp Dermatol.* 2014 March; 23(3):199-201. doi: 10.1111/exd.12321.

In particular, Bracke et al. teaches

"Psoriasis is a complex inflammatory skin disease that presents a wide variety of clinical manifestations. Human β defensin-2 (hBD-2) is highly up-regulated in psoriatic lesions and has been defined as a biomarker for disease activity. We explored the potential benefits of targeting hBD-2 by topical application of DEFB4-siRNA-containing SECosomes in a bioengineered skin-humanized mouse model for psoriasis. A significant improvement in the psoriatic phenotype was observed by histological examination, with a normalization of the skin architecture and a reduction in the number and size of blood vessels in the dermal compartment. Treatment leads to the recovery of transglutaminase activity, filaggrin expression and stratum corneum appearance to the levels similar to those found in normal regenerated human skin. The availability of a reliable skin-humanized mouse model for psoriasis in conjunction with the use of the SECosome technology may provide a valuable preclinical tool for identifying potential therapeutic targets for this disease."

4. Karline Guilloteau et al., Skin Inflammation Induced by the Synergistic Action of IL-17A, IL-22 Recapitulates Some Features of Psoriasis Oncostatin M, IL-1a, and TNF-α, *J Immunol* 2010; 184:5263-5270.

Guilloteau et al. teaches:

"Keratinocytes play a crucial role in the regulation of skin inflammation, responding to environmental and immune cells stimuli. They produce soluble factors that can act in an autocrine or paracrine manner on immune cells or directly on aggressors. A screening of the activities of 36 cytokines on keratinocyte gene expression identified IL-17A, IL-22, oncostatin M, TNF-a, and IL-1a as potent cytokines in inducing cutaneous inflammation. These five proinflammatory cytokines synergistically increased production of CXCL8 and b-defensin 2 (BD2). In addition, ex vivo studies on human skin explants demonstrated upregulation of BD2, S100A7, and CXCL8 expression in response to the same combination of cytokines. In vivo intradermal injection of these five cytokines in mouse increased CXCL1, CXCL2, CXCL3, S100A9, and BD3 expression, associated with neutrophil infiltration. We confirmed and extended this synergistic effect using quantitative real-time PCR analysis and observed increased expression of nine chemokines and 12 antimicrobial peptides. Production of CXCL, CXCL5, and CXCL8 by keratinocytes stimulated in the presence of this cytokine combination was associated with increased neutrophil chemotactic activity. Similarly, high production of BD2, BD3, and S100A7 was associated with an increased antimicrobial activity. Finally, the transcriptional profile observed in this in vitro model of inflammatory keratinocytes correlated with the one of lesional psoriatic skin. Our results demonstrate the important potentiating activities of IL-17A, IL-22, oncostatin M, TNF-a, and IL-1a on keratinocytes. This is particularly interesting in the context of psoriasis where these cytokines are overexpressed and could synergize to play an important role in upregulation of chemokines and antimicrobial peptides production. The Journal of Immunology, 2010, 184: 5263-5270 (see, ABSTRACT, therein and reference)".

Example 327

Description of Assays:
PBMC Assay
Sirtuin 1 (Sirt1) is a homolog of silent information regulator 2 (Sir2) and a member of the NAD dependent class III histone deacetylase. Sirt1 deacetylates lysine residues on histones, transcription factors and nonhistone proteins. Sirt1 has been shown to be involved in aging, cell cycle regulation, apoptosis, metabolic modulation and inflammation. The activation of Sirt1 causes deacetylation at lysine 310 of RelA/p65 subunit of nuclear factor kB (NF-kB) transcriptional factor which inhibits NF-kB transcription and down-regulates levels of TNFalpha. TNFalpha is a pleitotropic cytokine that is mainly produced by macrophages and monocytes. TNFalpha is closely involved in immune defense and chronic inflammation including Psoriasis. The expression of type-I cytokines such as TNFa was known to be increased in psoriatic skin and it plays important role in the etiology of psoriasis (Uyemura K et al, 1993, J. Invest Dermatol, 101, p701). Importantly, anti-TNF agent has been in clinical use for psoriasis. Therefore, Sirt1 activators that induce a reduction in TNFa expression in inflammatory cells should have therapeutic effect in moderate to severe psoriatic patients.

A PBMC/TNFalpha cell based assay was developed to identify activators of Sirt1 that inhibit the release of TNFalpha in response to lipopolysaccharide (LPS) stimulation of peripheral blood mononuclear cells (PBMC's). Briefly, PBMC's were stimulated by LPS, leading to an increase in the production of TNFalpha secretion. TNFalpha protein level was measured by TNFalpha HTRF (homogeneous time resolved fluorescence) kit (CisBio, Inc). Cell lysis and TNFalpha detection were performed according to manufacturer's instructions. Sirt1 activators were tested in the presence of LPS to evaluate their inhibitory effect on TNFa release and IC50 were determined in a dose-response experiment.

Beta-Defensin 2 (bD2) Assay
Sirtuin is a family of NAD-dependent deacetylases which have broad physiological functions and have been implicated in a number of autoimmune and metabolic disorders including rheumatoid arthritis and type I diabetes. Substrates of SIRT1 are diverse and include inflammatory components with well established roles in innate and adaptive immune response such as NF☐B, AP-1, FOXO, and p53.

Psoriasis is a chronic inflammatory skin disorder induced by genetic, autoimmune, and environmental factors. Lesions are characterized by hyperproliferation of keratinocytes in the epidermis and infiltration of inflammatory cells resulting in chronic erythmatous plaques covered by white scales. Previous studies have shown that SIRT1 can impede the effects of IL-22, a key cytokine in psoriasis, through direct inhibition of STAT3 acetylation (Sestito et al, 2011). In addition, both SIRT1 overexpression and resveratrol treatment (SIRT1 activation) can induce keratinocyte differentiation (Blander et al, 2009).

Beta-defensin 2 (bD2) is an antimicrobial peptide that can be secreted from the epithelia where it acts as a chemoattractant for memory T-cells, immature dendritic cells, and neutrophils. As such, bD2 is a major part of the inflammatory response in the skin. Not only is bD2 induced in lesional epidermal cells of psoriasis patients compared to normal skin, but it is also a serum biomarker for disease severity in psoriasis patients (Jansen et al, 2009; Kamsteeg et al 2009). In addition, bD2 may be genetically linked to psoriasis as a recent study uncovered a significant association between increased beta-defensin gene copy number and psoriasis risk (Hollox et al, 2008). Of note, topical delivery of bD2 siRNA resulted in recovery of normal skin architecture and protein expression in a bioengineered skin-humanized mouse model for psoriasis (Bracke et al, 2014).

An in vitro keratinocyte inflammation assay generated to mimic psoriatic inflammation was previously described (Guilloteau et al, 2010; Teng et al 2014). In these studies, a cytokine cocktail of IL-1alpha, IL-17A, IL-22, OSM, and TNFalpha (referred to as "M5") was found to synergize to produce a "psoriasiform" transcriptional profile in primary human keratinocytes in vitro. In these studies, bD2 was one of the strongest responders to the induction of keratinocyte inflammation.

Therefore, this assay was further developed in order to assess the efficacy of SIRT1 activator compounds for the topical psoriasis program. Specifically, conditions were optimized for an immortalized human keratinocyte cell line (HaCaT) treated in vitro with the M5 cytokine combination to induce psoriatic inflammation (as in reference above). In a 48 hour time frame, bD2 secretion, as measured by a bD2 ELISA assay (Alpha Diagnostics), is significantly increased compared to unstimulated keratinocytes. This bD2 induction can be suppressed with treatment of compounds known to suppress psoriatic inflammation or, importantly, with a subset of SIRT1 activators. In parallel, cytotoxicity over the length of the 48 hour assay is ascertained by a CellTiter-Glo Luminescent Cell Viability Assay (Promega) to determine whether toxicity might play a role in bD2 response.

REFERENCES

Blander G, Bhimavarapu A, Mammone T, Maes D, Elliston K, Reich C, Matsui M S, Guarente L, Loureiro J J. SIRT1 promotes differentiation of normal human keratinocytes. *J Invest Dermatol.* 2009 January; 129(1):41-9.

Bracke S, Carretero M, Guerrero-Aspizua S, Desmet E, Illera N, Navarro M, Lambert J, Del Rio M. Targeted silencing of DEFB4 in a bioengineered skin-humanized mouse model for psoriasis: development of siRNA SECosome-based novel therapies. *Exp Dermatol.* 2014 March; 23(3):199-201.

Guilloteau K, Paris I, Pedretti N, Boniface K, Juchaux F, Huguier V, Guillet G, Bernard F X, Lecron J C, Morel F. Skin Inflammation Induced by the Synergistic Action of IL-17A, IL-22, Oncostatin M, IL-1alpha, and TNFalpha Recapitulates Some Features of Psoriasis. J Immunol. 2010 Mar. 24.

Jansen P A, Rodijk-Olthuis D, Hollox E J, Kamsteeg M, Tjabringa G S, de Jongh G J, van Vlijmen-Willems I M, Bergboer J G, van Rossum M M, de Jong E M, den Heijer M, Evers A W, Bergers M, Armour J A, Zeeuwen P L, Schalkwijk J. Beta-defensin-2 protein is a serum biomarker for disease activity in psoriasis and reaches biologically relevant concentrations in lesional skin. *PLoS One.* 2009; 4(3):e4725.

Kamsteeg M, Jansen P A, van Vlijmen-Willems I M, van Erp P E, Rodijk-Olthuis D, van der Valk P G, Feuth T, Zeeuwen P L, Schalkwijk J. Molecular diagnostics of psoriasis, atopic dermatitis, allergic contact dermatitis and irritant contact dermatitis. *Br J Dermatol.* 2010 March; 162(3):568-78.

Sestito R, Madonna S, Scarponi C, Cianfarani F, Failla C M, Cavani A, Girolomoni G, Albanesi C. STAT3-dependent effects of IL-22 in human keratinocytes are counterregulated by sirtuin 1 through a direct inhibition of STAT3 acetylation. *FASEB J.* 2011 March; 25(3):916-27.

Teng X, Hu Z, Wei X, Wang Z, Guan T, Liu N, Liu X, Ye N, Deng G, Luo C, Huang N, Sun C, Xu M, Zhou X, Deng H, Edwards C K 3rd, Chen X, Wang X, Cui K, Wei Y, Li J. IL-37 ameliorates the inflammatory process in psoriasis by suppressing proinflammatory cytokine production. *J Immunol.* 2014 Feb. 15; 192(4):1815-23.

Psoriasis & IL-17

Psoriasis is a chronic, relapsing, inflammatory autoimmune skin disorder with a multi-factorial pathogenesis influenced by genetic, environmental, and immunopathologic factors (Griffiths C E et al., Lancet 2007; 370:263-71). Psoriasis is characterized by recurrent episodes of raised, well-demarcated erythematous oval plaques with adherent silvery scales. Histologically, the hallmark of psoriasis is the presence of a thickened nucleated keratinocyte layer, with exaggeration of the rete pegs, caused by hyperproliferation of keratinocytes and dermal infiltration by activated T cells, neutrophils, and dendritic cells (Schon M P N. Engl. J. Med. 352: 1899-1912).

An accumulating body of evidence suggests psoriasis as a Th17-mediated disease, driven by its signature cytokines IL-17 A, IL-17 F and IL-22. IL-22 induces proliferation of keratinocytes, whereas IL-17A stimulates keratinocytes to secrete chemokines and other proinflammatory mediators that recruit additional inflammatory cells, including neutrophils, dendritic cells, and innate lymphoid cells (Martin D A et al, J Invest Dermatol 2013; 133:17-26).

The clinical validation of the IL-17 pathway in mediating psoriasis is demonstrated by successful Ph3 studies that show significant improvement of disease using monoclonal antibody therapy targeting IL-17 (Langley et al., NEJM 2014). In addition, global transcription profiling in psoriasis lesions following IL-17 inhibition suppressed multiple inflammatory factors from keratinocytes and leukocyte subsets to similar levels as observed in non-lesional skin (Russell et al., J Immunol 2014, 192: 3828-3836). Taken together, these findings support the role of IL-17 in mediating psoriasis pathogenesis.

Method (Ex Vivo Skin Assay)

Stimulation of skin-resident immune cells in ex vivo human skin explants using a Th17 cytokine cocktail results in a dramatic upregulation of Th17 related cytokines (IL-17A, IL-17F and IL-22), which establishes this system as a human tissue-based model for psoriasis. The ability of test compounds to modulate the expression of IL-17A, IL-17 F and IL-22 was assessed using the ex vivo skin culture method post stimulation with Th17 cytokine cocktail. Briefly, ex vivo human skin obtained from abdominoplasty surgery was processed to remove fat and the tissue was dermatomed to ~750 microns. Dermatomed skin was then cleaned in two serial rinses of 5-10 minutes each in room temperature PBS containing an antibiotic/antimycotic solution. The skin section was cut with disposable single-use biopsy punches to 10 mm diameter round sections, which were then placed in the upper chamber of a 0.4 μm PCF membrane transwell (Millicell #PIHP01250) containing 30 μl of a 64% bovine collagen solution (Organogenesis, #200-055) prepared with Cornification media. The skin samples were allowed to set on the collagen solution for 30 min at 37° C. in a humidified chamber. The skin samples on transwells were transferred to 6-well plates (1 sample per well) and the lower chamber was filled with 1 ml complete media (Cornification Media).

On the first day following abdominoplasty surgery, skin explants were cultured in Cornification media and allowed to incubate overnight at 37° C. Specifically, human skin explants (N=3 per condition) were stimulated with the Th17 cocktail (CD3, 1 μg/ml, CD28, 2 μg/ml, IL-1b, 10 ng/ml, IL-6, 5 ng/ml, TGFb, 1 ng/ml, IL-21, 10 ng/ml, anti-IL-4, 1 µg/ml and anti-INFg, 1 µg/ml). Test compound at 1,3 and 10 uM was added at the same time as Th17 cocktail. Tissue was harvested 24 hrs after Th17 activation and RNA was isolated for transcript quantification (IL-17A, IL-17F, IL-22) using qPCR.

Total RNA was isolated from ~40 mg of tissue using Qiagen's Mini RNA Isolation kit (Cat #74106). Briefly, tissue was minced and homogenized in the Precellys-24 machine using 300 µl of RLT buffer supplemented with 1% 2-Beta-Mercapto-Ethanol at 6300 rpm for 30 seconds for 10 cycles with a 2-minute ice break. 490 µl of water containing 10 µl Proteinase K was added to the homogenate and digested at 55° C. for 15 minutes. Digested tissue was spun down for 3 minutes at 10,000 G to pellet cell debris and the supernatant was used for RNA isolation using Qiagen's RNeasy mini columns according to manufacturer's protocol. Total RNA was quantified using Nanodrop 2000 and analyzed on Agilent bioanalyser (files attached). 1.4 µg of RNA was used as template in a 20 µl PCR volume using Invitrogen SuperScript VILO cDNA Synthesis kit (#11754-050) to create a cDNA template. Then cDNA was diluted 1:25 for the subsequent qPCR with the specific TaqMan probe for each gene to be quantified. RNA levels of gene of interest's relative expression were calculated using the Delta Delta CT formula.

EQUIVALENTS

The present invention provides among other things sirtuin-modulating compounds and methods or uses thereof. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

What is claimed is:

1. A compound or pharmaceutically acceptable salt thereof, selected from

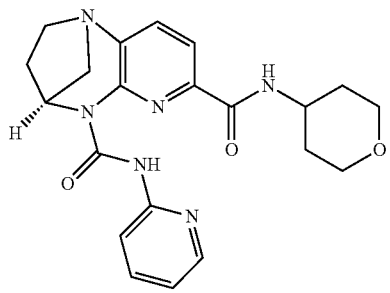

(9S)-5-N-(oxan-4-yl)-8-N-(pyridin-2-yl)-
1,6,8-triazatricyclo[7.2.1.0$^{2,7}$]dodeca-2(7),3,
5-triene-5,8-dicarboxamide -continued

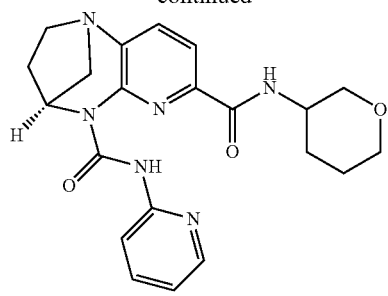

(9S)-5-N-(oxan-3-yl)-8-N-(pyridin-2-yl)-
1,6,8-triazatricyclo[7.2.1.0$^{2,7}$]dodeca-2(7),3,
5-triene-5,8-dicarboxamide

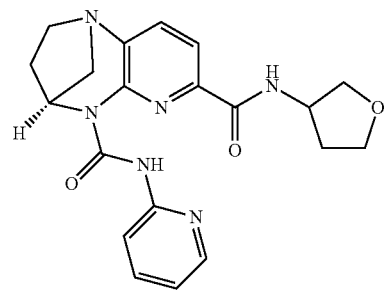

(9S)-5-N-(oxolan-3-yl)-8-N-(pyridin-2-yl)-
1,6,8-triazatricyclo[7.2.1.0$^{2,7}$]dodeca-2(7),3,
5-triene-5,8-dicarboxamide

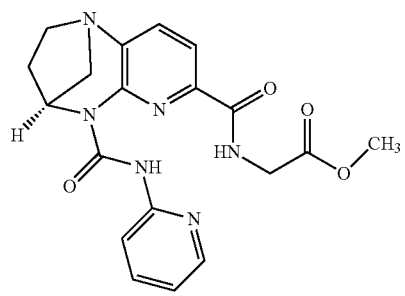

methyl 2-{[(9S)-8-[(pyridin-2-yl)carbamoyl]-
1,6,8-triazatricyclo[7.2.1.0$^{2,7}$]dodeca-2(7),3,
5-trien-5-yl]formamido}acetate

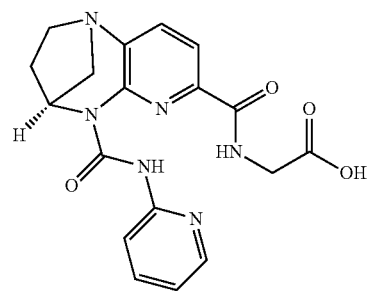

2-{[(9S)-8-[(pyridin-2-yl)carbamoyl]-
1,6,8-triazatricyclo[7.2.1.0$^{2,7}$]dodeca-2(7),3,
5-trien-5-yl]formamido}acetic acid -continued

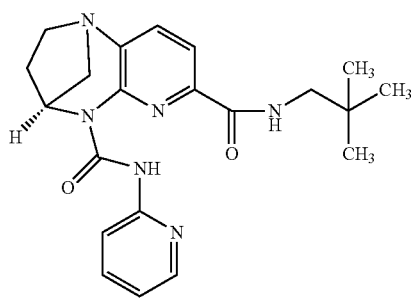

(9S)-5-N-(2,2-dimethylpropyl)-8-N-(pyridin-2-yl)-
1,6,8-triazatricyclo[7.2.1.0²,⁷]dodeca-2(7),3,
5-triene-5,8-dicarboxamide

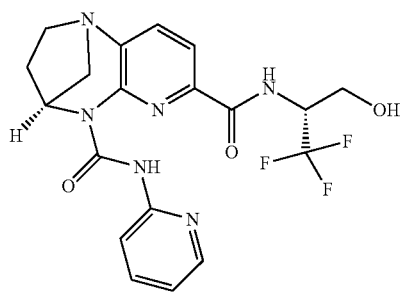

(9S)-8-N-(pyridin-2-yl)-5-N-[(2R)-1,1,1-trifluoro-3-
hydroxypropan-2-yl]-1,6,8-triazatricyclo[7.2.1.0²,⁷]
dodeca-2(7),3,5-triene-5,8-dicarboxamide

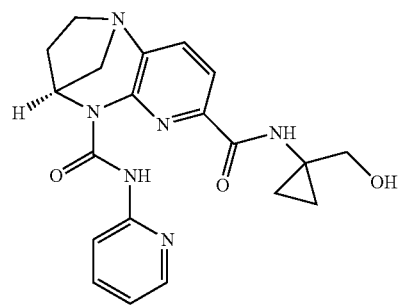

(9S)-5-N-[1-(hydroxymethyl)cyclopropyl]-8-N-(pyridin-2-yl)-
1,6,8-triazatricyclo[7.2.1.0²,⁷]dodeca-2(7),3,
5-triene-5,8-dicarboxamide

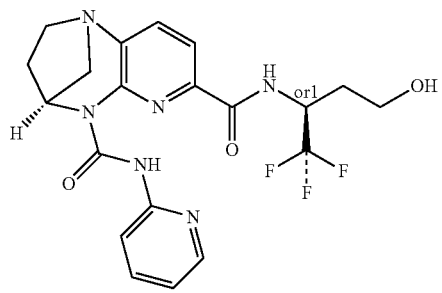

ISOMER 1
(9S)-8-N-(pyridin-2-yl)-5-N-[(2S)-1,1,1-trifluoro-4-
hydroxybutan-2-yl]-1,6,8-triazatricyclo[7.2.1.0²,⁷]
dodeca-2(7),3,5-triene-5,8-dicarboxamide -continued

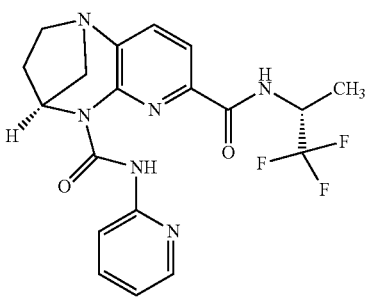

(9S)-8-N-(pyridin-2-yl)-5-N-[(2R)-1,1,1-trifluoropropan-2-yl]-
1,6,8-triazatricyclo[7.2.1.0²,⁷]
dodeca-2(7),3,5-triene-5,8-dicarboxamide

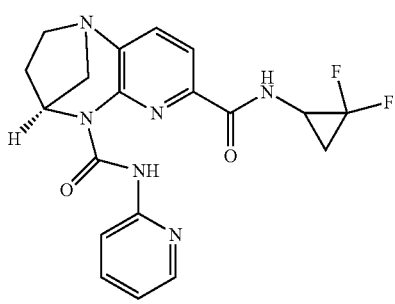

(9S)-5-N-(2,2-difluorocyclopropyl)-8-N-(pyridin-2-yl)-
1,6,8-triazatricyclo[7.2.1.0²,⁷]dodeca-
2(7),3,5-triene-5,8-dicarboxamide

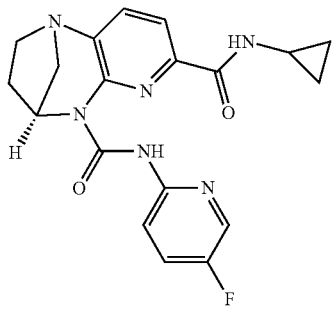

(9S)-5-N-cyclopropyl-8-N-(5-fluoropyridin-2-yl)-
1,6,8-triazatricyclo[7.2.1.0²,⁷]dodeca-2(7),3,
5-triene-5,8-dicarboxamide

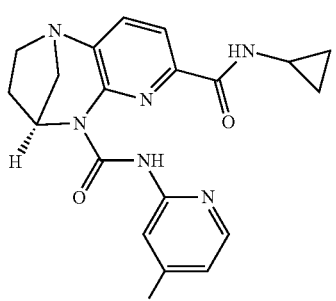

(9S)-5-N-cyclopropyl-8-N-(4-methylpyridin-2-yl)-
1,6,8-triazatricyclo[7.2.1.0²,⁷]dodeca-2(7),3,
5-triene-5,8-dicarboxamide

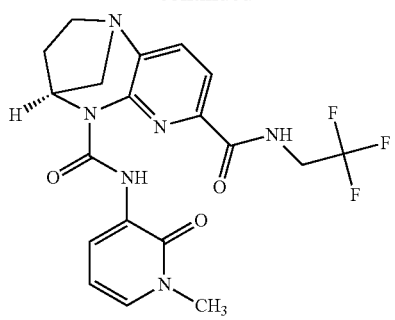

(9S)-8-N-(1-methyl-2-oxo-1,2-dihydropyridin-3-yl)-5-N-(2,2,2-trifluoroethyl)-1,6,8-triazatricyclo[7.2.1.0²,⁷]dodeca-2,4,6-triene-5,8-dicarboxamide

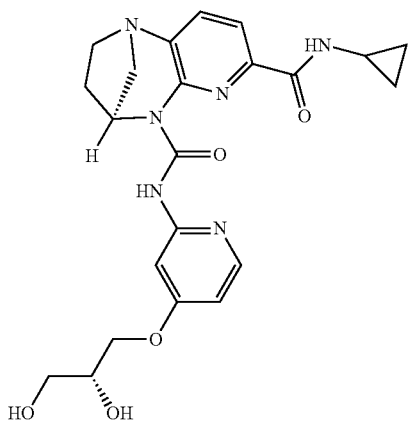

(9S)-5-N-cyclopropyl-8-N-{4-[(2R)-2,3-dihydroxypropoxy]pyridin-2-yl}-1,6,8-triazatricyclo[7.2.1.0²,⁷]dodeca-2(7),3,5-triene-5,8-dicarboxamide

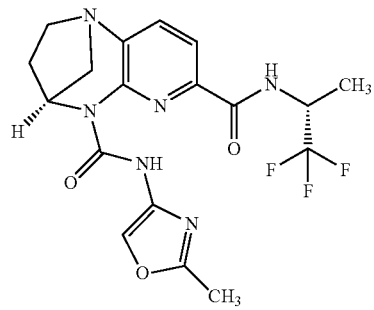

(9S)-8-N-(2-methyl-1,3-oxazol-4-yl)-5-N-[(2R)-1,1,1-trifluoropropan-2-yl]-1,6,8-triazatricyclo[7.2.1.0²,⁷]dodeca-2(7),3,5-triene-5,8-dicarboxamide

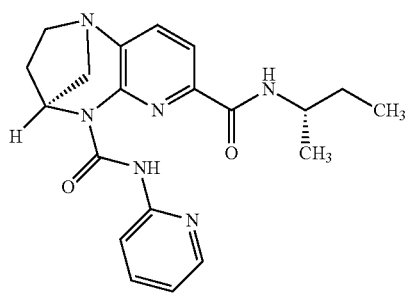

(9S)-5-N-[(2S)-butan-2-yl]-8-N-(pyridin-2-yl)-1,6,8-triazatricyclo[7.2.1.0²,⁷]dodeca-2(7),3,5-triene-5,8-dicarboxamide

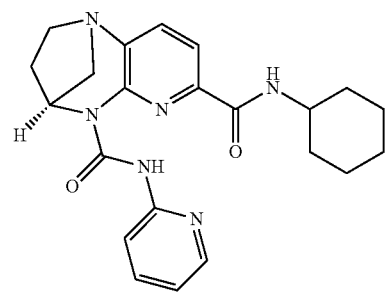

(9S)-5-N-cyclohexyl-8-N-(pyridin-2-yl)-1,6,8-triazatricyclo[7.2.1.0²,⁷]dodeca-2(7),3,5-triene-5,8-dicarboxamide

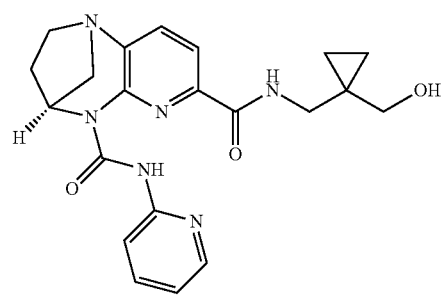

(9S)-5-N-{[1-(hydroxymethyl)cyclopropyl]methyl}-8-N-(pyridin-2-yl)-1,6,8-triazatricyclo[7.2.1.0²,⁷]dodeca-2(7),3,5-triene-5,8-dicarboxamide

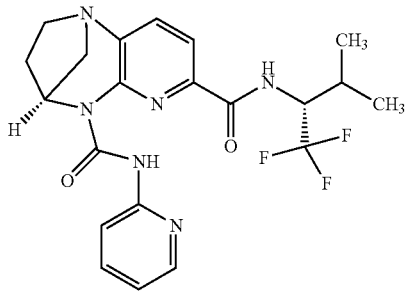

(9S)-8-N-(pyridin-2-yl)-5-N-[(2R)-1,1,1-trifluoro-3-methylbutan-2-yl]-1,6,8-triazatricyclo[7.2.1.0²,⁷]dodeca-2(7),3,5-triene-5,8-dicarboxamide

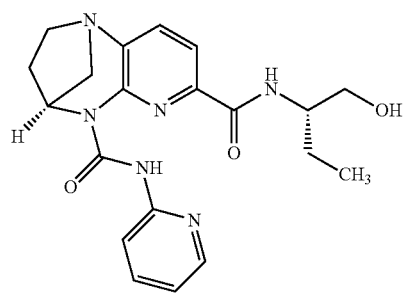

(9S)-5-N-[(2S)-1-hydroxybutan-2-yl]-8-N-(pyridin-2-yl)-1,6,8-triazatricyclo[7.2.1.0²,⁷]dodeca-2(7),3,5-triene-5,8-dicarboxamide

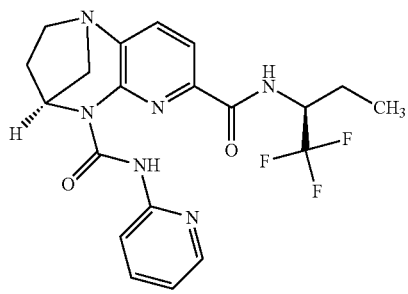

(9S)-8-N-(pyridin-2-yl)-5-N-[(2S)-1,1,1-
trifluorobutan-2-yl]-1,6,8-triazatricyclo
[7.2.1.0²,⁷]dodeca-2(7),3,5-triene-5,8-dicarboxamide

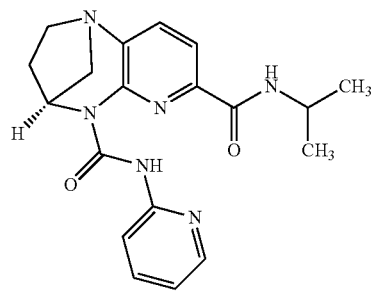

(9S)-5-N-(propan-2-yl)-8-N-(pyridin-2-yl)-1,6,8-
triazatricyclo[7.2.1.0²,⁷]dodeca-2(7),3,
5-triene-5,8-dicarboxamide

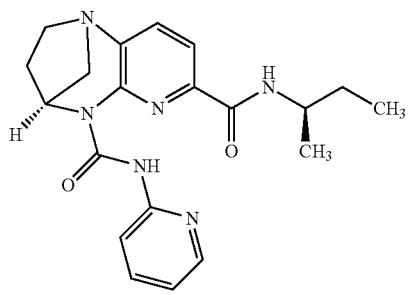

(9S)-5-N-[(2R)-butan-2-yl]-8-N-(pyridin-2-yl)-1,6,8-
triazatricyclo[7.2.1.0²,⁷]dodeca-2(7),3,
5-triene-5,8-dicarboxamide

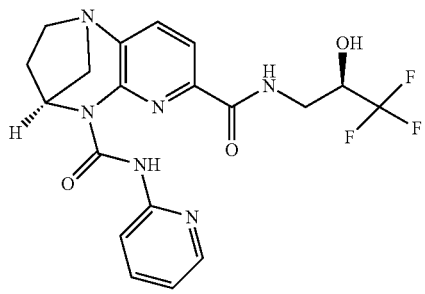

(9S)-8-N-(pyridin-2-yl)-5-N-[(2R)-3,3,3-trifluoro-
2-hydroxypropyl]-1,6,8-triazatricyclo[7.2.1.0²,⁷]dodeca-
2(7),3,5-triene-5,8-dicarboxamide

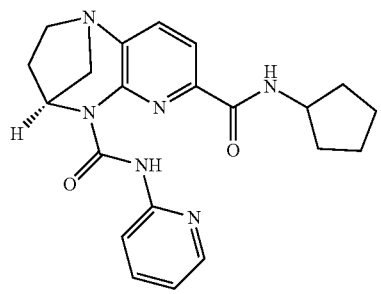

(9S)-5-N-cyclopentyl-8-N-(pyridin-2-yl)-
1,6,8-triazatricyclo[7.2.1.0²,⁷]dodeca-
2(7),3,5-triene-5,8-dicarboxamide

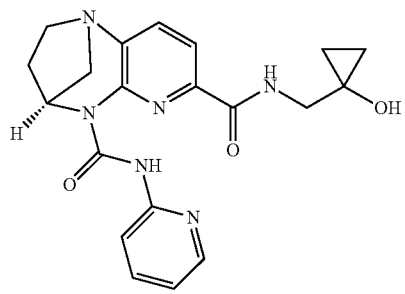

(9S)-5-N-[(1-hydroxycyclopropyl)methyl]-8-N-
(pyridin-2-yl)-1,6,8-triazatricyclo[7.2.1.0²,⁷]dodeca-
2(7),3,5-triene-5,8-dicarboxamide

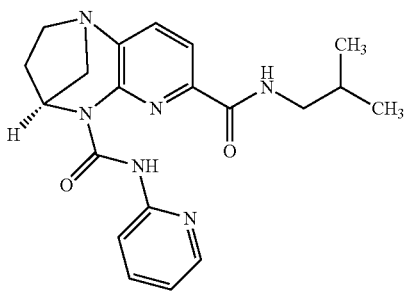

(9S)-5-N-(2-methylpropyl)-8-N-(pyridin-2-yl)-1,6,8-
triazatricyclo[7.2.1.0²,⁷]dodeca-2(7),3,
5-triene-5,8-dicarboxamide

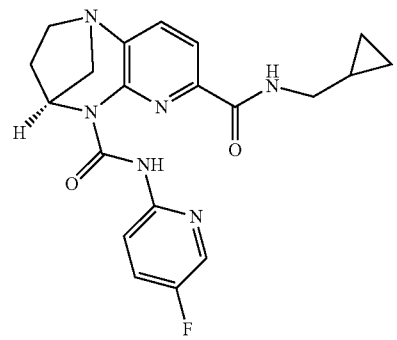

(9S)-5-N-(cyclopropylmethyl)-8-N-(5-fluoropyridin-2-
yl)-1,6,8-triazatricyclo[7.2.1.0²,⁷]dodeca-
2(7),3,5-triene-5,8-dicarboxamide -continued

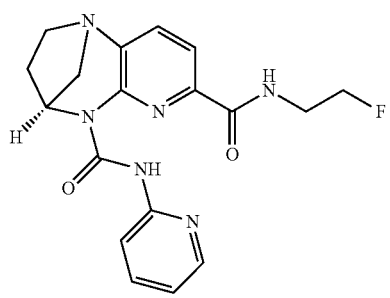

(9S)-5-N-(2-fluoroethyl)-8-N-(pyridin-2-yl)-
1,6,8-triazatricyclo[7.2.1.0²,⁷]dodeca-
2(7),3,5-triene-5,8-dicarboxamide

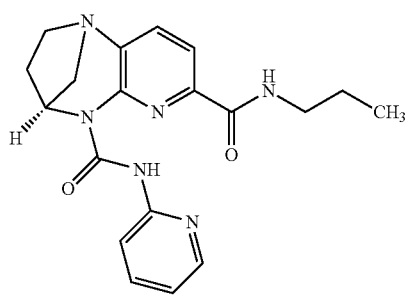

(9S)-5-N-propyl-8-N-(pyridin-2-yl)-1,6,8-
triazatricyclo[7.2.1.0²,⁷]dodeca-
2(7),3,5-triene-5,8-dicarboxamide

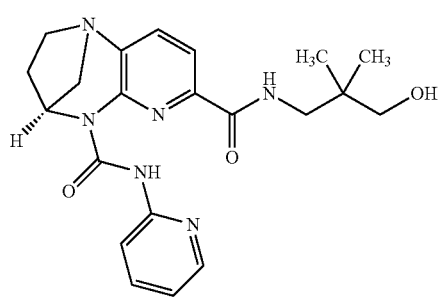

(9S)-5-N-(3-hydroxy-2,2-dimethylpropyl)-8-N-
(pyridin-2-yl)-1,6,8-triazatricyclo[7.2.1.0²,⁷]dodeca-
2(7),3,5-triene-5,8-dicarboxamide

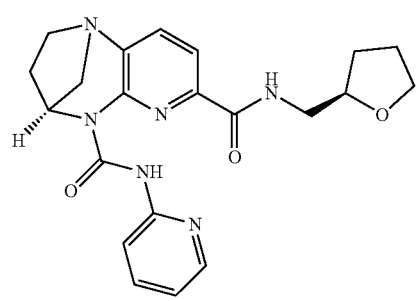

(9S)-5-N-[(2R)-oxolan-2-ylmethyl]-8-N-
(pyridin-2-yl)-1,6,8-triazatricyclo[7.2.1.0²,⁷]dodeca-
2(7),3,5-triene-5,8-dicarboxamide -continued

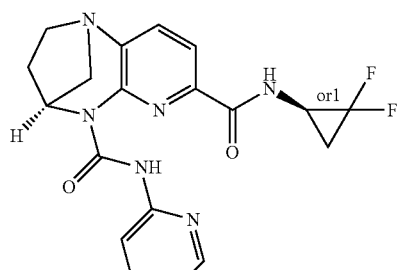

ISOMER 1

(9S)-5-N-[(1R)-2,2-difluorocyclopropyl]-8-N-(pyridin-
2-yl)-1,6,8-triazatricyclo[7.2.1.0²,⁷]dodeca-
2(7),3,5-triene-5,8-dicarboxamide

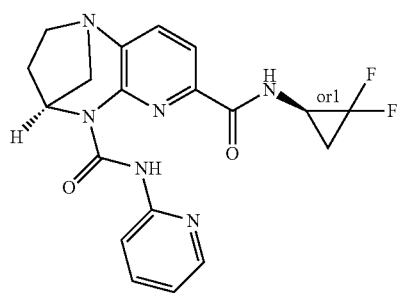

ISOMER 2

(9S)-5-N-[(1R)-2,2-difluorocyclopropyl]-8-N-(pyridin-
2-yl)-1,6,8-triazatricyclo[7.2.1.0²,⁷]dodeca-
2(7),3,5-triene-5,8-dicarboxamide

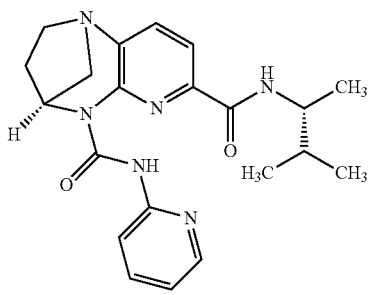

(9S)-5-N-[(2R)-3-methylbutan-2-yl]-8-N-(pyridin-2-
yl)-1,6,8-triazatricyclo[7.2.1.0²,⁷]dodeca-
2(7),3,5-triene-5,8-dicarboxamide

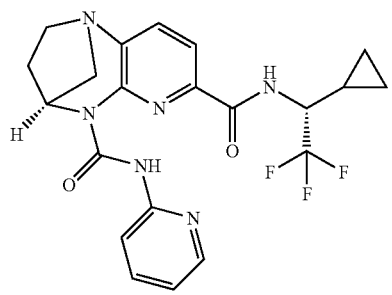

(9S)-5-N-[(1R)-1-cyclopropyl-2,2,2-trifluoroethyl]-8-
N-(pyridin-2-yl)-1,6,8-triazatricyclo[7.2.1.0²,⁷]dodeca-
2(7),3,5-triene-5,8-dicarboxamide

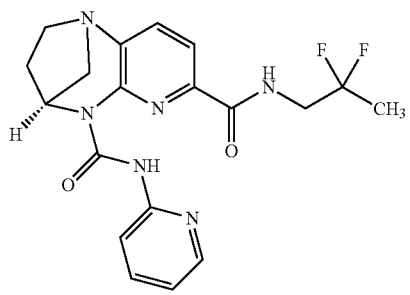

(9S)-5-N-(2,2-difluoropropyl)-8-N-(pyridin-2-yl)-1,6,8-
triazatricyclo[7.2.1.0²,⁷]dodeca-
2(7),3,5-triene-5,8-dicarboxamide

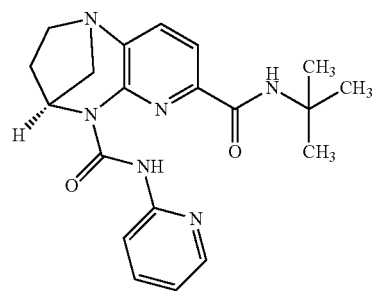

(9S)-5-N-tert-butyl-8-N-(pyridin-2-yl)-
1,6,8-triazatricyclo[7.2.1.0²,⁷]dodeca-
2(7),3,5-triene-5,8-dicarboxamide

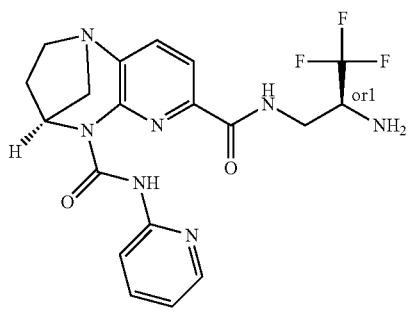

ISOMER 2

(9S)-5-N-[(2S)-2-amino-3,3,3-trifluoropropyl]-8-N-
(pyridin-2-yl)-1,6,8-triazatricyclo[7.2.1.0²,⁷]dodeca-
2(7),3,5-triene-5,8-dicarboxamide

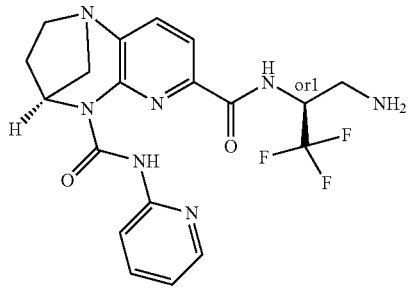

ISOMER 1

(9S)-5-N-[(2S)-3-amino-1,1,1-trifluoropropan-2-yl]-8-N-
(pyridin-2-yl)-1,6,8-triazatricyclo[7.2.1.0²,⁷]dodeca-
2(7),3,5-triene-5,8-dicarboxamide

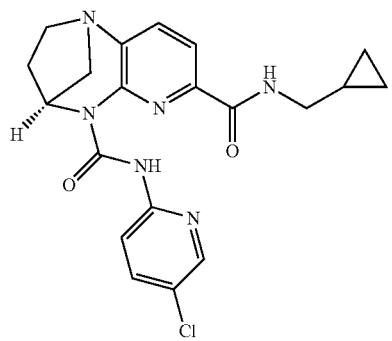

(9S)-8-N-(5-chloropyridin-2-yl)-5-N-
(cyclopropylmethyl)-1,6,8-triazatricyclo[7.2.1.0²,⁷]dodeca-
2(7),3,5-triene-5,8-dicarboxamide

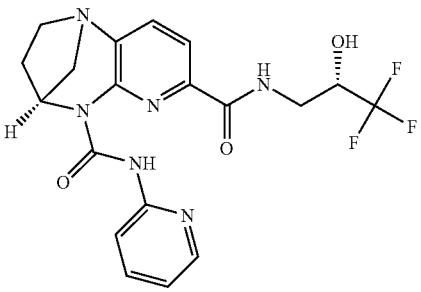

(9S)-8-N-(pyridin-2-yl)-5-N-[(2S)-3,3,3-trifluoro-2-
hydroxypropyl]-1,6,8-triazatricyclo[7.2.1.0²,⁷]dodeca-
2(7),3,5-triene-5,8-dicarboxamide

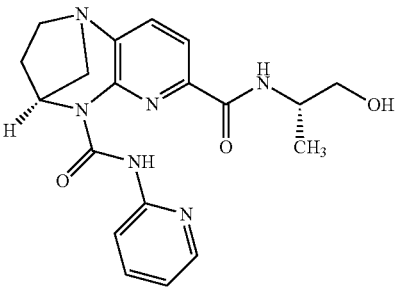

(9S)-5-N-[(2S)-1-hydroxypropan-2-yl]-8-N-(pyridin-2-
yl)-1,6,8-triazatricyclo[7.2.1.0²,⁷]dodeca-
2(7),3,5-triene-5,8-dicarboxamide

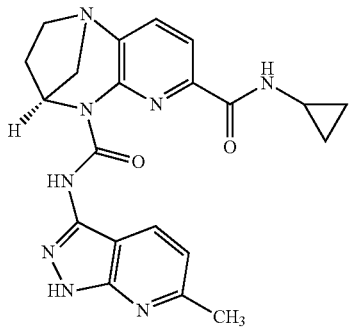

(9S)-5-N-cyclopropyl-8-N-{6-methyl-1H-
pyrazolo[3,4-b]pyridin-3-yl}-1,6,8-triazatricyclo
[7.2.1.0²,⁷]dodeca-2(7),3,5-triene-5,8-dicarboxamide

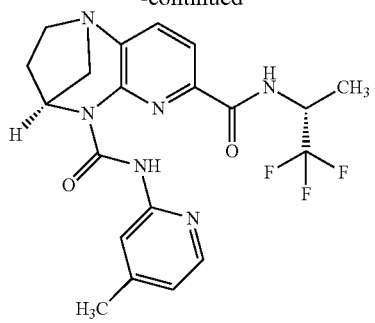

(9S)-8-N-(4-methylpyridin-2-yl)-5-N-[(2R)-1,1,1-trifluoropropan-2-yl]-1,6,8-triazatricyclo[7.2.1.0²,⁷]dodeca-2(7),3,5-triene-5,8-dicarboxamide

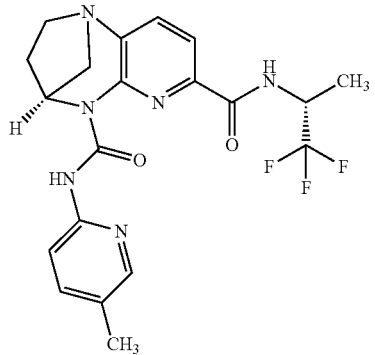

(9S)-8-N-(5-methylpyridin-2-yl)-5-N-[(2R)-1,1,1-trifluoropropan-2-yl]-1,6,8-triazatricyclo[7.2.1.0²,⁷]dodeca-2(7),3,5-triene-5,8-dicarboxamide

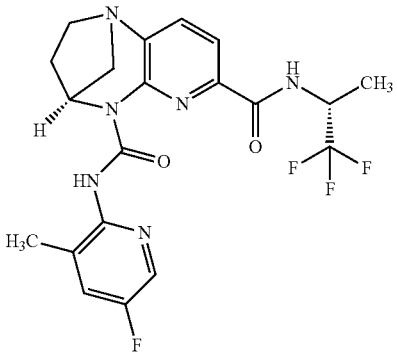

(9S)-8-N-(5-fluoro-3-methylpyridin-2-yl)-5-N-[(2R)-1,1,1-trifluoropropan-2-yl]-1,6,8-triazatricyclo[7.2.1.0²,⁷]dodeca-2(7),3,5-triene-5,8-dicarboxamide

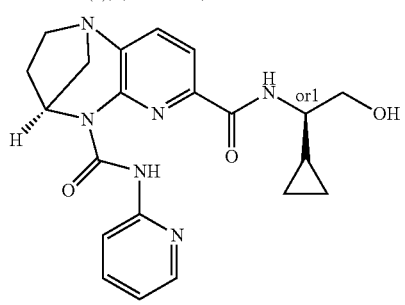

ISOMER 1

(9S)-5-N-[(1R)-1-cyclopropyl-2-hydroxyethyl]-8-N-(pyridin-2-yl)-1,6,8-triazatricyclo[7.2.1.0²,⁷]dodeca-2(7),3,5-triene-5,8-dicarboxamide

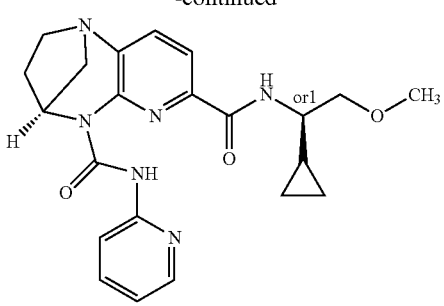

ISOMER 1

(9S)-5-N-[(1R)-1-cyclopropyl-2-methoxyethyl]-8-N-(pyridin-2-yl)-1,6,8-triazatricyclo[7.2.1.0²,⁷]dodeca-2(7),3,5-triene-5,8-dicarboxamide

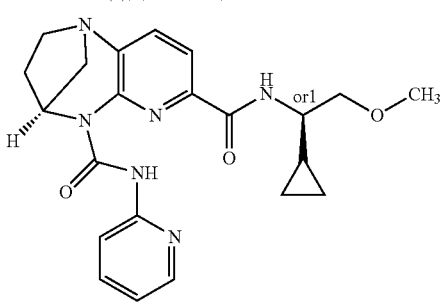

ISOMER 2

(9S)-5-N-[(1R)-1-cyclopropyl-2-methoxyethyl]-8-N-(pyridin-2-yl)-1,6,8-triazatricyclo[7.2.1.0²,⁷]dodeca-2(7),3,5-triene-5,8-dicarboxamide

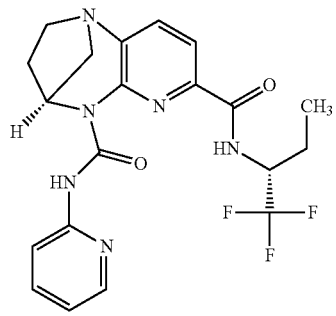

(9S)-8-N-(pyridin-2-yl)-5-N-[(2R)-1,1,1-trifluorobutan-2-yl]-1,6,8-triazatricyclo[7.2.1.0²,⁷]dodeca-2(7),3,5-triene-5,8-dicarboxamide

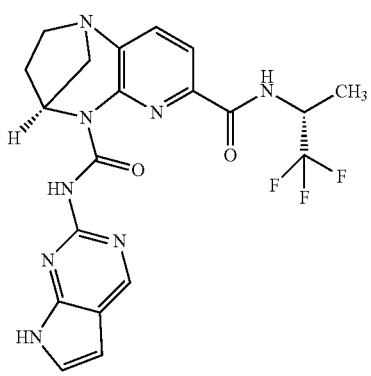

(9S)-8-N-{7H-pyrrolo[2,3-d]pyrimidin-2-yl}-5-N-[(2R)-1,1,1-trifluorobutan-2-yl]-1,6,8-triazatricyclo[7.2.1.0²,⁷]dodeca-2,4,6-triene-5,8-dicarboxamide

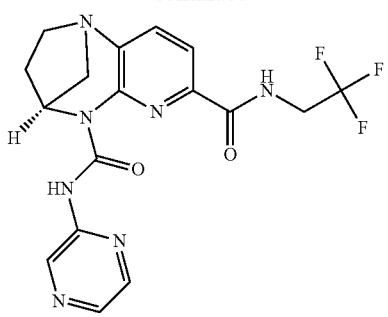

(9S)-8-N-(pyrazin-2-yl)-5-N-(2,2,2-trifluoroethyl)-1,6,8-triazatricyclo[7.2.1.0²,⁷]dodeca-2(7),3,5-triene-5,8-dicarboxamide

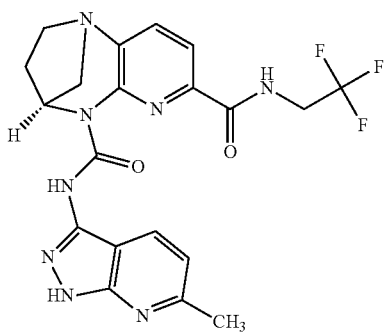

(9S)-8-N-{6-methyl-1H-pyrazolo[3,4-b]pyridin-3-yl}-5-N-(2,2,2-trifluoroethyl)-1,6,8-triazatricyclo[7.2.1.0²,⁷]dodeca-2(7),3,5-triene-5,8-dicarboxamide

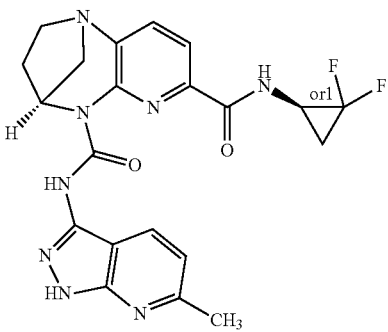

ISOMER 1
(9S)-5-N-[(1R)-2,2-difluorocyclopropyl]-8-N-{6-methyl-1H-pyrazolo[3,4-b]pyridin-3-yl}-1,6,8-triazatricyclo[7.2.1.0²,⁷]dodeca-2(7),3,5-triene-5,8-dicarboxamide

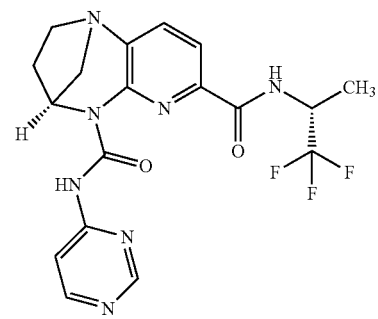

(9S)-8-N-(pyrimidin-4-yl)-5-N-[(2R)-1,1,1-trifluoropropan-2-yl]-1,6,8-triazatricyclo[7.2.1.0²,⁷]dodeca-2(7),3,5-triene-5,8-dicarboxamide

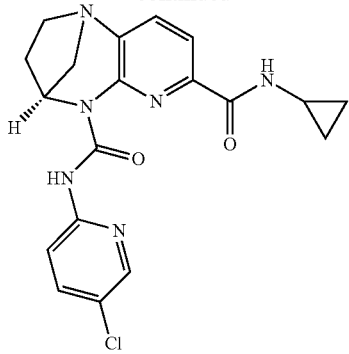

(9S)-8-N-(5-chloropyridin-2-yl)-5-N-cyclopropyl-1,6,8-triazatricyclo[7.2.1.0²,⁷]dodeca-2(7),3,5-triene-5,8-dicarboxamide

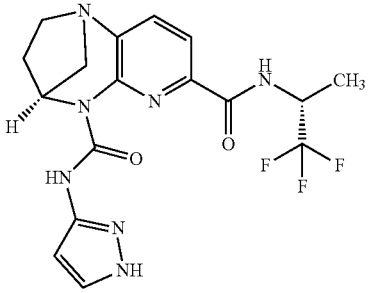

(9S)-8-N-(1H-pyrazol-3-yl)-5-N-[(2R)-1,1,1-trifluoropropan-2-yl]-1,6,8-triazatricyclo[7.2.1.0²,⁷]dodeca-2(7),3,5-triene-5,8-dicarboxamide

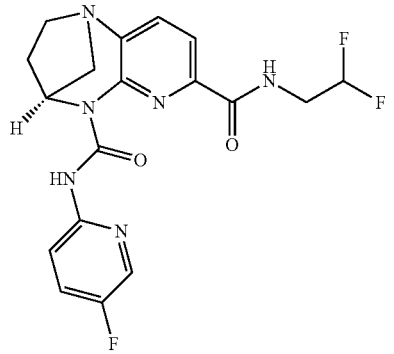

(9S)-5-N-(2,2-difluoroethyl)-8-N-(5-fluoropyridin-2-yl)-1,6,8-triazatricyclo[7.2.1.0²,⁷]dodeca-2,4,6-triene-5,8-dicarboxamide

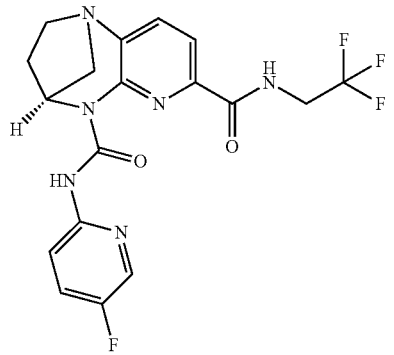

(9S)-8-N-(5-fluoropyridin-2-yl)-5-N-(2,2,2-trifluoroethyl)-1,6,8-triazatricyclo[7.2.1.0²,⁷]dodeca-2,4,6-triene-5,8-dicarboxamide -continued

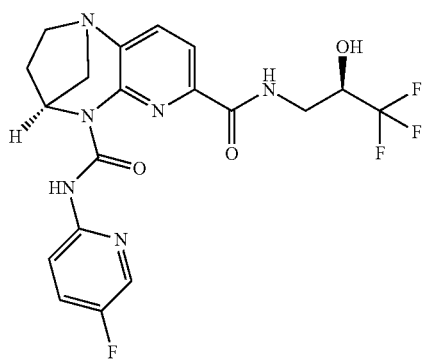

(9S)-8-N-(5-fluoropyridin-2-yl)-5-N-[(2R)-3,3,3-trifluoro-
2-hydroxypropyl]-1,6,8-triazatricyclo[7.2.1.0²,⁷]dodeca-
2,4,6-triene-5,8-dicarboxamide

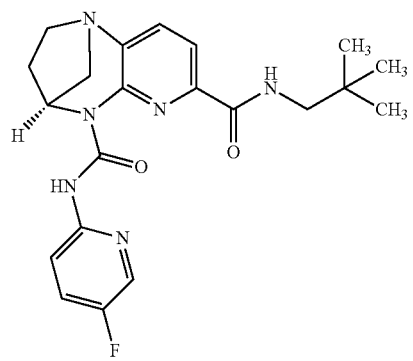

(9S)-5-N-(2,2-dimethylpropyl)-8-N-(5-fluoropyridin-2-yl)-
1,6,8-triazatricyclo[7.2.1.0²,⁷]dodeca-
2,4,6-triene-5,8-dicarboxamide

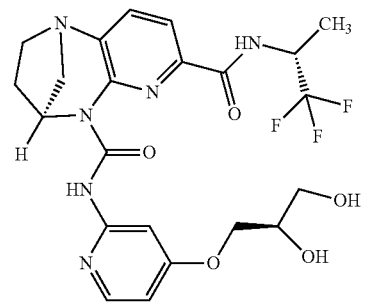

(9S)-8-N-{4-[(2R)-2,3-dihydroxypropoxy]pyridin-2-yl}-
5-N-[(2R)-1,1,1-trifluoropropan-2yl]-1,6,8-triazatricyclo
[7.2.1.0²,⁷]dodeca-2(7),3,5-triene-5,8-dicarboxamide

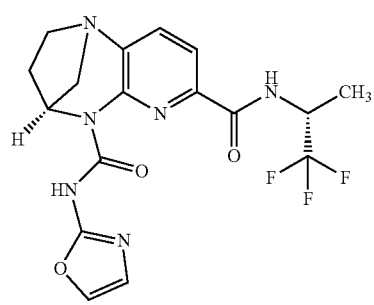

(9S)-8-N-(1,3-oxazol-2-yl)-5-N-[(2R)-1,1,1-
trifluoropropan-2-yl]-1,6,8-triazatricyclo[7.2.1.0²,⁷]dodeca-
2(7),3,5-triene-5,8-dicarboxamide -continued

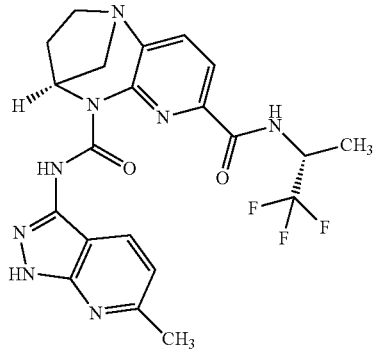

(9S)-8-N-{6-methyl-1H-pyrazolo[3,4-b]pyridin-3-yl}-
5-N-[(2R)-1,1,1-trifluoropropan-2-yl]-1,6,8-triazatricyclo
[7.2.1.0²,⁷]dodeca-2,4,6-triene-5,8-dicarboxamide

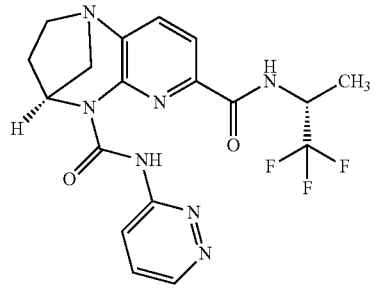

(9S)-8-N-(pyridazin-3-yl)-5-N-[(2R)-1,1,1-trifluoropropan-
2-yl]-1,6,8-triazatricyclo[7.2.1.0²,⁷]dodeca-
2(7),3,5-triene-5,8-dicarboxamide

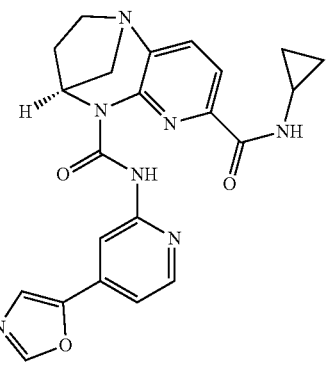

(9S)-5-N-cyclopropyl-8-N-[4-(1,3-oxazol-5yl)
pyridin-2-yl]-1,6,8-triazatricyclo
[7.2.1.0²,⁷]dodeca-2,4,6-triene-5,8-dicarboxamide

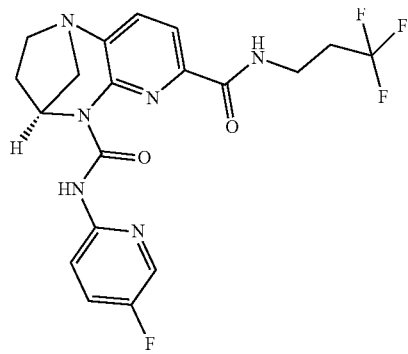

(9S)-8-N-(5-fluoropyridin-2-yl)-5-N-(3,3,3-
trifluoropropyl)-1,6,8-triazatricyclo[7.2.1.0²,⁷]dodeca-
2,4,6-triene-5,8-dicarboxamide

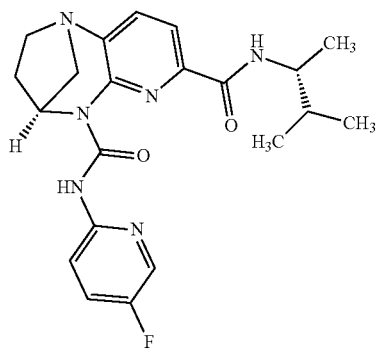

(9S)-8-N-(5-fluoropyridin-2-yl)-5-N-[(2R)-3-methylbutan-2-yl]-1,6,8-triazatricyclo[7.2.1.0²,⁷]dodeca-2,4,6-triene-5,8-dicarboxamide

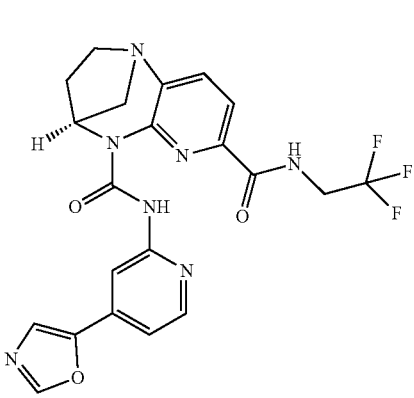

(9S)-8-N-[4-(1,3-oxazol-5-yl)pyridin-2-yl]-5-N-(2,2,2-trifluoroethyl)-1,6,8-triazatricyclo[7.2.1.0²,⁷]dodeca-2,4,6-triene-5,8-dicarboxamide

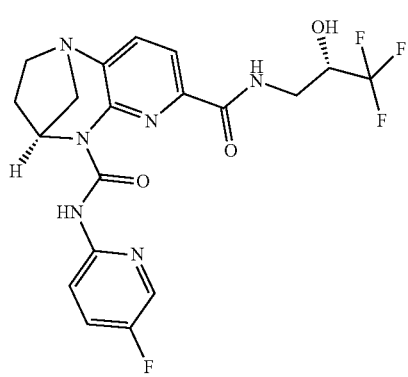

(9S)-8-N-(5-fluoropyridin-2-yl)-5-N-[(2S)-3,3,3-trifluoro-2-hydroxypropyl]-1,6,8-triazatricyclo[7.2.1.0²,⁷]dodeca-2,4,6-triene-5,8-dicarboxamide

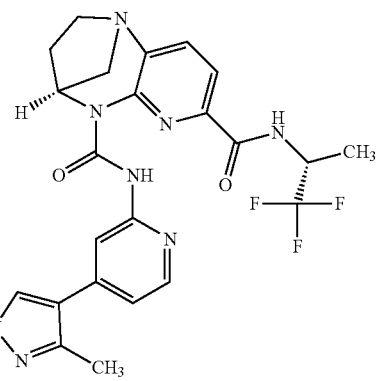

(9S)-8-N-[4-(1,3-dimethyl-1H-pyrazol-4-yl)pyridin-2-yl]-5-N-[(2R)-1,1,1-trifluoropropan-2-yl]-1,6,8-triazatricyclo[7.2.1.0²,⁷]dodeca-2,4,6-triene-5,8-dicarboxamide

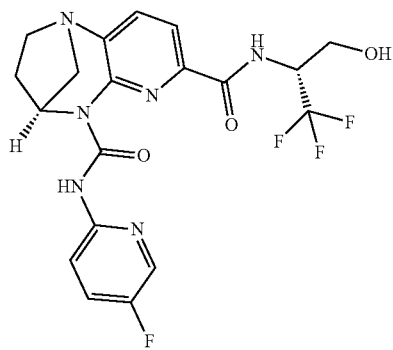

(9S)-8-N-(5-fluoropyridin-2-yl)-5-N-[(2R)-1,1,1-trifluoro-3-hydroxypropan-2-yl]-1,6,8-triazatricyclo[7.2.1.0²,⁷]dodeca-2,4,6-triene-5,8-dicarboxamide

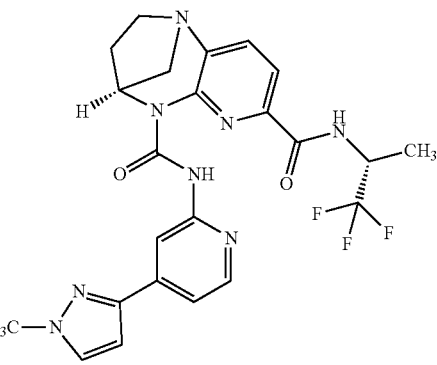

(9S)-8-N-[4-(1-methyl-1H-pyrazol-3-yl)pyridin-2-yl]-5-N-[(2R)-1,1,1-trifluoropropan-2-yl]-1,6,8-triazatricyclo[7.2.1.0²,⁷]dodeca-2,4,6-triene-5,8-dicarboxamide

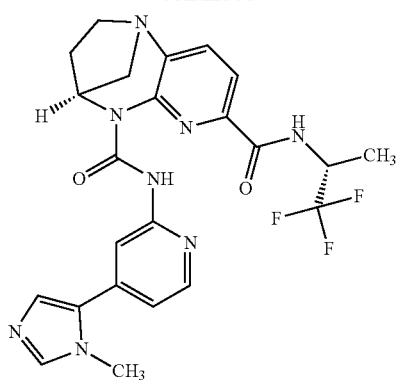

(9S)-8-N-[4-(1-methyl-1H-imidazol-5-yl)pyridin-2-yl]-5-N-[(2R)-1,1,1-trifluoropropan-2-yl]-1,6,8-triazatricyclo[7.2.1.0²,⁷]dodeca-2,4,6-triene-5,8-dicarboxamide

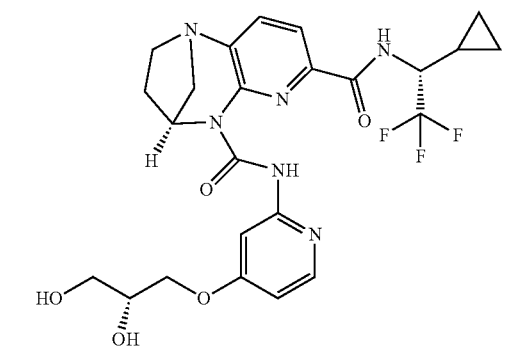

(9S)-5-N-[(1R)-1-cyclopropyl-2,2,2-trifluoroethyl]-8-N-{4-[(2R)-2,3-dihydroxypropoxy]pyridin-2-yl}-1,6,8-triazatricyclo[7.2.1.0²,⁷]dodeca-2(7),3,5-triene-5,8-dicarboxamide

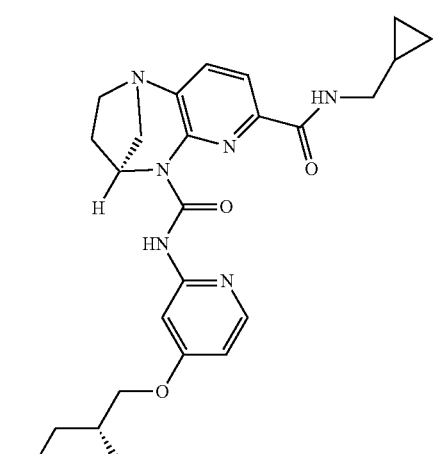

(9S)-5-N-(cyclopropylmethyl)-8-N-{4-[(2R)-2,3-dihydroxypropoxy]pyridin-2-yl}-1,6,8-triazatricyclo[7.2.1.0²,⁷]dodeca-2(7),3,5-triene-5,8-dicarboxamide

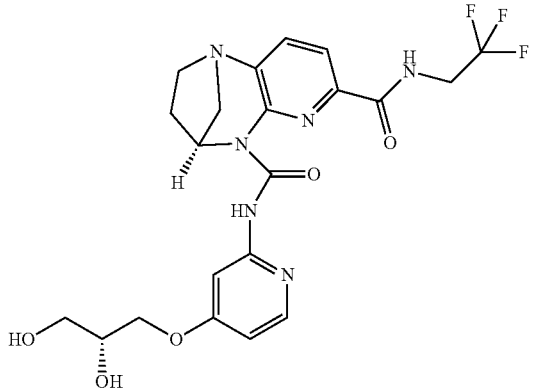

(9S)-8-N-{4-[(2R)-2,3-dihydroxypropoxy]pyridin-2-yl}-5-N-(2,2,2-trifluoroethyl)-1,6,8-triazatricyclo[7.2.1.0²,⁷]dodeca-2(7),3,5-triene-5,8-dicarboxamide

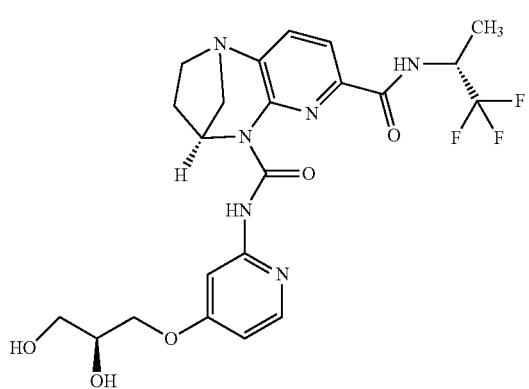

(9S)-8-N-{4-[(2S)-2,3-dihydroxypropoxy]pyridin-2-yl}-5-N-[(2R)-1,1,1-trifluoropropan-2-yl]-1,6,8-triazatricyclo[7.2.1.0²,⁷]dodeca-2(7),3,5-triene-5,8-dicarboxamide

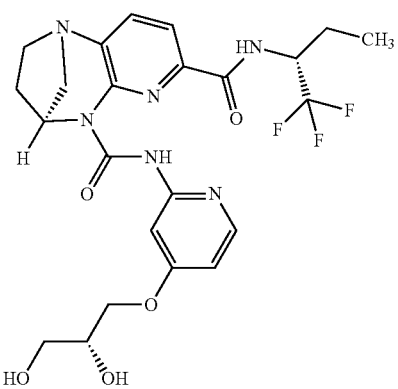

(9S)-8-N-{4-[(2R)-2,3-dihydroxypropoxy]pyridin-2-yl}-5-N-[(2R)-1,1,1-trifluorobutan-2-yl]-1,6,8-triazatricyclo[7.2.1.0²,⁷]dodeca-2(7),3,5-triene-5,8-dicarboxamide

833

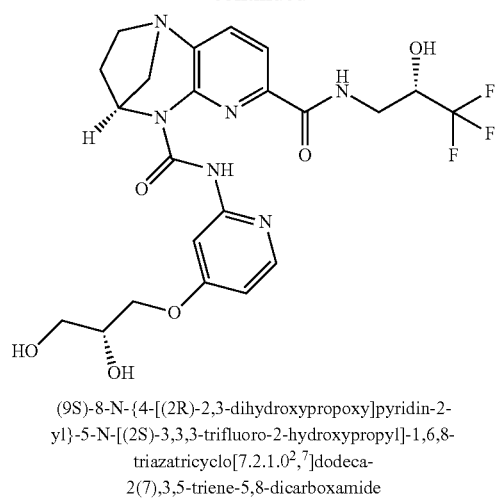

(9S)-8-N-{4-[(2R)-2,3-dihydroxypropoxy]pyridin-2-yl}-5-N-[(2S)-3,3,3-trifluoro-2-hydroxypropyl]-1,6,8-triazatricyclo[7.2.1.0²,⁷]dodeca-2(7),3,5-triene-5,8-dicarboxamide

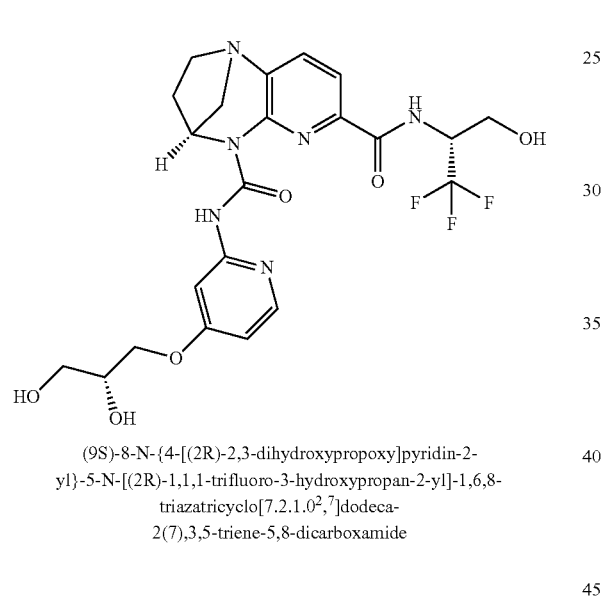

(9S)-8-N-{4-[(2R)-2,3-dihydroxypropoxy]pyridin-2-yl}-5-N-[(2R)-1,1,1-trifluoro-3-hydroxypropan-2-yl]-1,6,8-triazatricyclo[7.2.1.0²,⁷]dodeca-2(7),3,5-triene-5,8-dicarboxamide

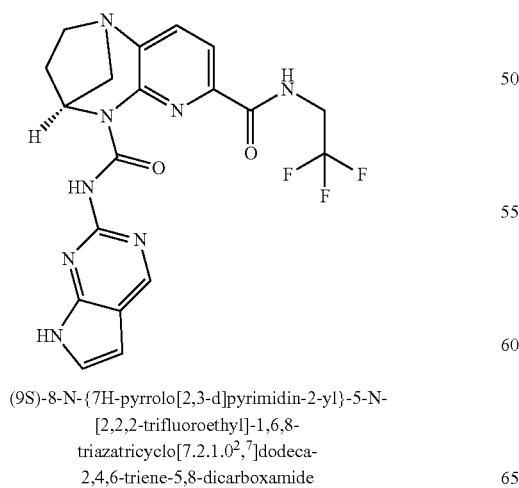

(9S)-8-N-{7H-pyrrolo[2,3-d]pyrimidin-2-yl}-5-N-[2,2,2-trifluoroethyl]-1,6,8-triazatricyclo[7.2.1.0²,⁷]dodeca-2,4,6-triene-5,8-dicarboxamide

834

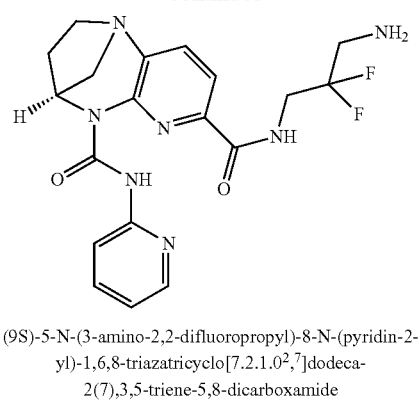

(9S)-5-N-(3-amino-2,2-difluoropropyl)-8-N-(pyridin-2-yl)-1,6,8-triazatricyclo[7.2.1.0²,⁷]dodeca-2(7),3,5-triene-5,8-dicarboxamide

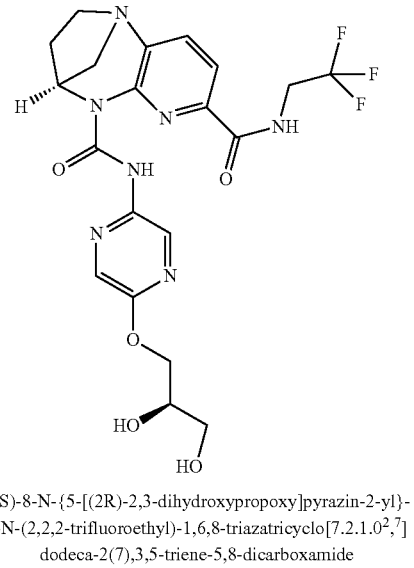

(9S)-8-N-{5-[(2R)-2,3-dihydroxypropoxy]pyrazin-2-yl}-5-N-(2,2,2-trifluoroethyl)-1,6,8-triazatricyclo[7.2.1.0²,⁷]dodeca-2(7),3,5-triene-5,8-dicarboxamide

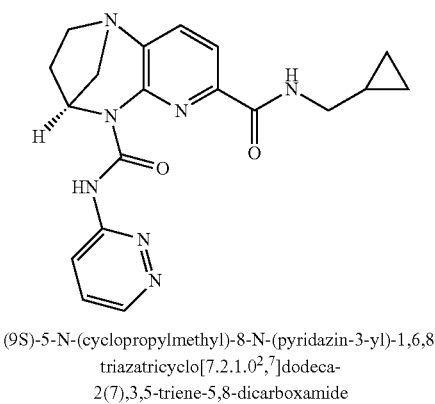

(9S)-5-N-(cyclopropylmethyl)-8-N-(pyridazin-3-yl)-1,6,8-triazatricyclo[7.2.1.0²,⁷]dodeca-2(7),3,5-triene-5,8-dicarboxamide

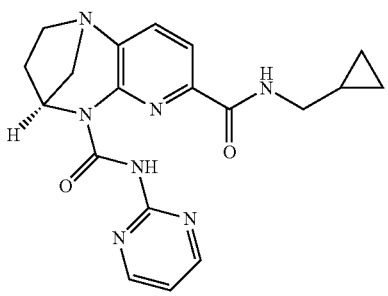

(9S)-5-N-(cyclopropylmethyl)-8-N-(pyrimidin-2-yl)-1,6,8-triazatricyclo[7.2.1.0²,⁷]dodeca-2(7),3,5-triene-5,8-dicarboxamide

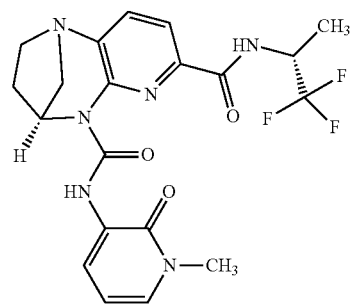

(9S)-8-N-(1-methyl-2-oxo-1,2-dihydropyridin-3-yl)-5-N-[(2R)-1,1,1-trifluoropropan-2-yl]-1,6,8-triazatricyclo[7.2.1.0²,⁷]dodeca-2(7),3,5-triene-5,8-dicarboxamide

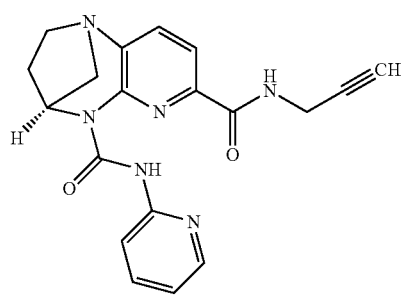

(9S)-5-N-(prop-2-yn-1-yl)-8-N-(pyridin-2-yl)-1,6,8-triazatricyclo[7.2.1.0²,⁷]dodeca-2(7),3,5-triene-5,8-dicarboxamide

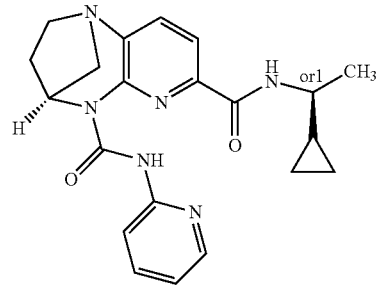

ISOMER 2

(9S)-5-N-[(1S)-1-cyclopropylethyl]-8-N-(pyridin-2-yl)-1,6,8-triazatricyclo[7.2.1.0²,⁷]dodeca-2(7),3,5-triene-5,8-dicarboxamide

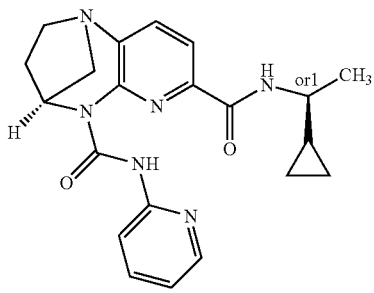

ISOMER 1

(9S)-5-N-[(1S)-1-cyclopropylethyl]-8-N-(pyridin-2-yl)-1,6,8-triazatricyclo[7.2.1.0²,⁷]dodeca-2(7),3,5-triene-5,8-dicarboxamide

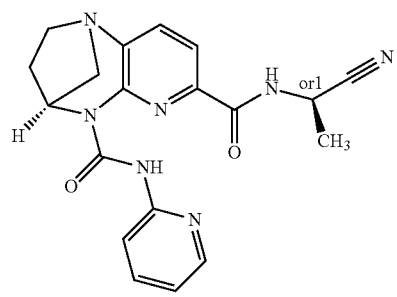

ISOMER 2

(9S)-5-N-[(1R)-1-cyanoethyl]-8-N-(pyridin-2-yl)-1,6,8-triazatricyclo[7.2.1.0²,⁷]dodeca-2(7),3,5-triene-5,8-dicarboxamide

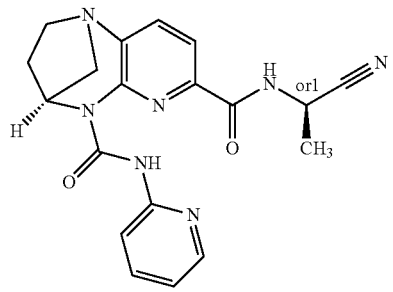

ISOMER 1

(9S)-5-N-[(1R)-1-cyanoethyl]-8-N-(pyridin-2-yl)-1,6,8-triazatricyclo[7.2.1.0²,⁷]dodeca-2(7),3,5-triene-5,8-dicarboxamide

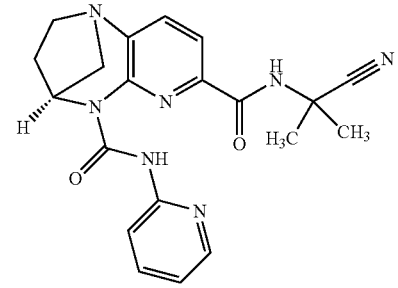

(9S)-5-N-(cyano-1-methylethyl)-8-N-(pyridin-2-yl)-1,6,8-triazatricyclo[7.2.1.0²,⁷]dodeca-2(7),3,5-triene-5,8-dicarboxamide

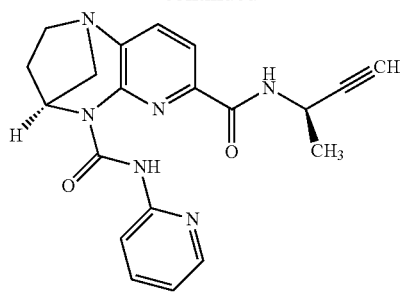

(9S)-5-N-[(2R)-but-3-yn-2-yl]-8-N-(pyridin-2-yl)-1,6,8-triazatricyclo[7.2.1.0²,⁷]dodeca-2(7),3,5-triene-5,8-dicarboxamide

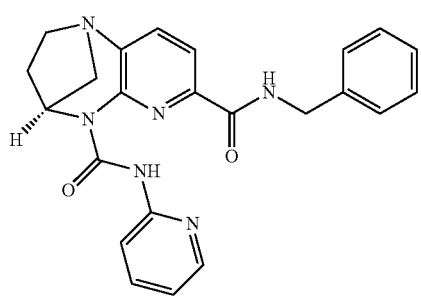

(9S)-5-N-benzyl-8-N-(pyridin-2-yl)-1,6,8-triazatricyclo[7.2.1.0²,⁷]dodeca-2(7),3,5-triene-5,8-dicarboxamide

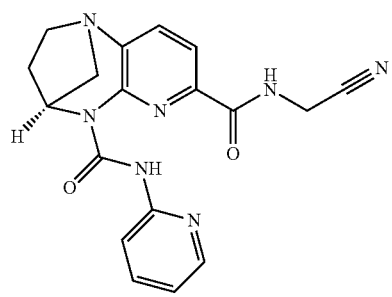

(9S)-5-N-(cyanomethyl)-8-N-(pyridin-2-yl)-1,6,8-triazatricyclo[7.2.1.0²,⁷]dodeca-2(7),3,5-triene-5,8-dicarboxamide

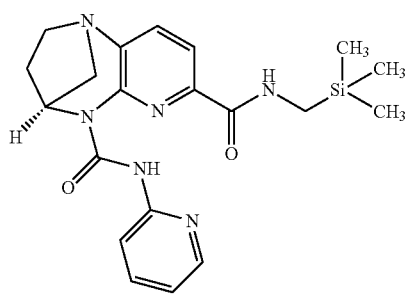

(9S)-8-N-(pyridin-2-yl)-5-N-[(trimethylsilyl)methyl]-1,6,8-triazatricyclo[7.2.1.0²,⁷]dodeca-2(7),3,5-triene-5,8-dicarboxamide

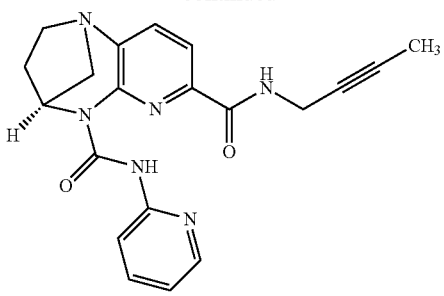

(9S)-5-N-(but-2-yn-1-yl)-8-N-(pyridin-2-yl)-1,6,8-triazatricyclo[7.2.1.0²,⁷]dodeca-2(7),3,5-triene-5,8-dicarboxamide

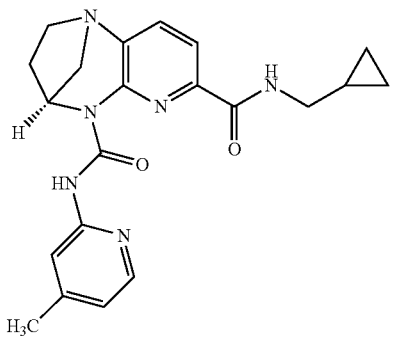

(9S)-5-N-(cyclopropylmethyl)-8-N-(4-methylpyridin-2-yl)-1,6,8-triazatricyclo[7.2.1.0²,⁷]dodeca-2(7),3,5-triene-5,8-dicarboxamide

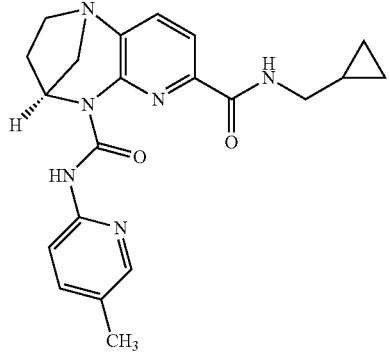

(9S)-5-N-(cyclopropylmethyl)-8-N-(5-methylpyridin-2-yl)-1,6,8-triazatricyclo[7.2.1.0²,⁷]dodeca-2(7),3,5-triene-5,8-dicarboxamide

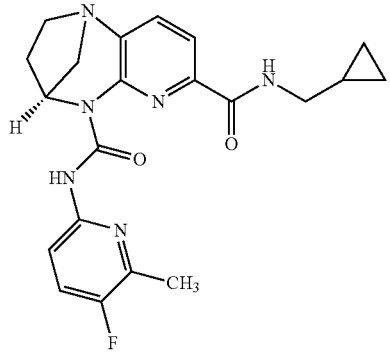

(9S)-5-N-(cyclopropylmethyl)-8-N-(5-fluoro-6-methylpyridin-2-yl)-1,6,8-triazatricyclo[7.2.1.0²,⁷]dodeca-2(7),3,5-triene-5,8-dicarboxamide

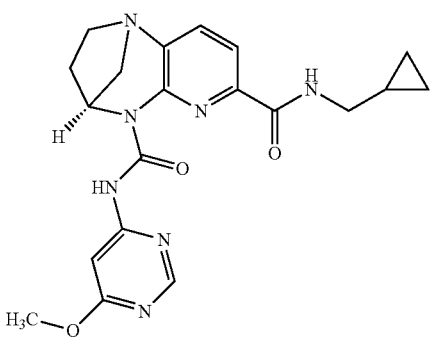

(9S)-5-N-(cyclopropylmethyl)-8-N-(6-methoxypyrimidin-4-yl)-
1,6,8-triazatricyclo[7.2.1.0²,⁷]dodeca-
2(7),3,5-triene-5,8-dicarboxamide

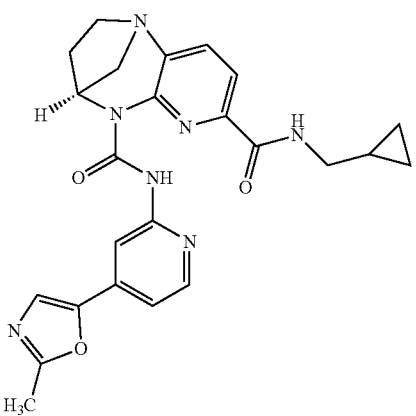

(9S)-5-N-(cyclopropylmethyl)-8-N-[4-(2-methyl-1,3-oxazol-5-
yl)pyridin-2-yl]-1,6,8-triazatricyclo[7.2.1.0²,⁷]dodeca-
2,4,6-triene-5,8-dicarboxamide

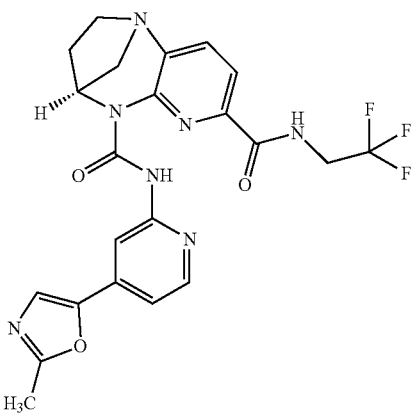

(9S)-8-N-[4-(2-methyl-1,3-oxazol-5-yl)pyridin-2-yl]-
5-N-(2,2,2-trifluoroethyl)-1,6,8-triazatricyclo[7.2.1.0²,⁷]
dodeca-2,4,6-triene-5,8-dicarboxamide

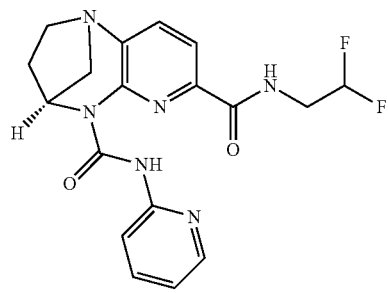

(9S)-5-N-(2,2-difluoroethyl)-8-N-(pyridin-2-yl)-
1,6,8-triazatricyclo[7.2.1.0²,⁷]dodeca-
2(7),3,5-triene-5,8-dicarboxamide

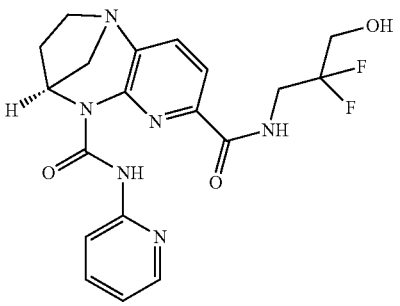

(9S)-5-N-(2,2-difluoro-3-hydroxypropyl)-8-N-(pyridin-2-yl)-
1,6,8-triazatricyclo[7.2.1.0²,⁷]dodeca-
2(7),3,5-triene-5,8-dicarboxamide

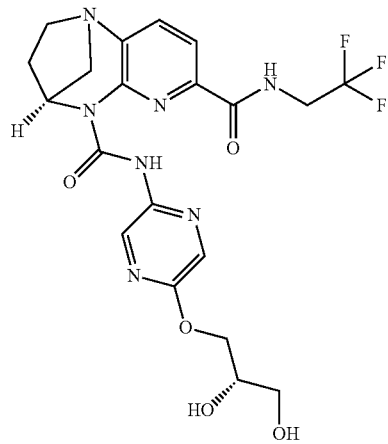

(9S)-8-N-{5-[(2S)-2,3-dihydroxypropoxy]pyrazin-2-yl}-
5-N-(2,2,2-trifluoroethyl)-1,6,8-triazatricyclo[7.2.1.0²,⁷]
dodeca-2(7),3,5-triene-5,8-dicarboxamide

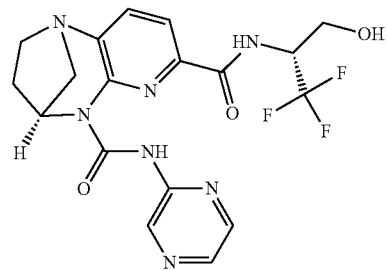

(9S)-8-N-(pyrazin-2-yl)-5-N-[(2R)-1,1,1-trifluoro-
3-hydroxypropan-2-yl]-1,6,8-triazatricyclo[7.2.1.0²,⁷]
dodeca-2(7),3,5-triene-5,8-dicarboxamide 841
-continued

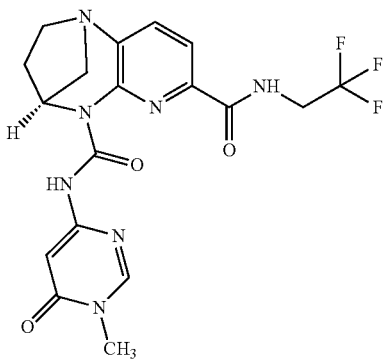

(9S)-8-N-(1-methyl-6-oxo-1,6-dihydropyrimidin-4-yl)-
5-N-(2,2,2-trifluoroethyl)-1,6,8-triazatricyclo[7.2.1.0²,⁷]
dodeca-2(7),3,5-triene-5,8-dicarboxamide

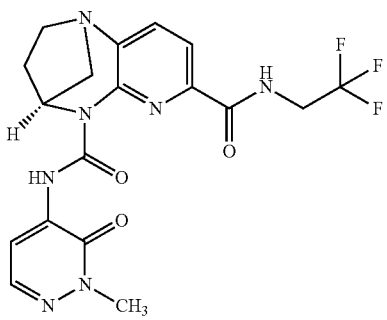

(9S)-8-N-(2-methyl-3-oxo-2,3-dihydropyridazin-4-yl)-
5-N-(2,2,2-trifluoroethyl)-1,6,8-triazatricyclo[7.2.1.0²,⁷]
dodeca-2,4,6-triene-5,8-dicarboxamide

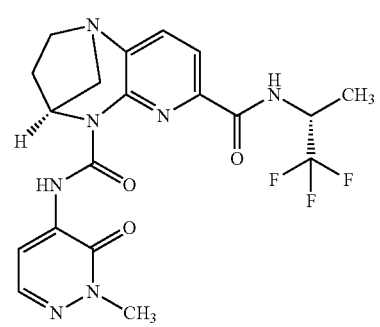

(9S)-8-N-(2-methyl-3-oxo-2,3-dihydropyridazin-4-yl)-
5-N-[(2R)-1,1,1-trifluoropropan-2-yl]-1,6,8-triazatricyclo
[7.2.1.0²,⁷]dodeca-2,4,6-triene-5,8-dicarboxamide 842
-continued

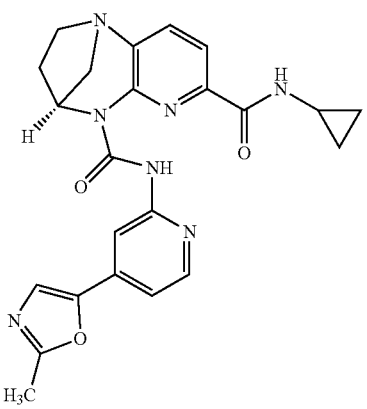

(9S)-5-N-cyclopropyl-8-N-[4-(2-methyl-1,3-oxazol-5-
yl)pyridin-2-yl]-1,6,8-triazatricyclo[7.2.1.0²,⁷]dodeca-
2(7),3,5-triene-5,8-dicarboxamide

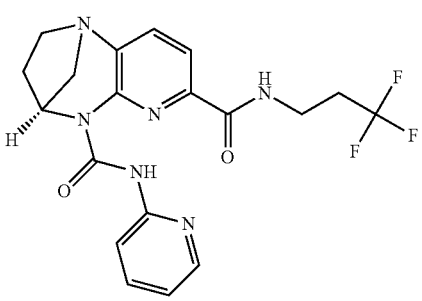

(9S)-8-N-(pyridin-2-yl)-5-N-(3,3,3-trifluoropropyl)-1,6,8-
triazatricyclo[7.2.1.0²,⁷]dodeca-
2(7),3,5-triene-5,8-dicarboxamide

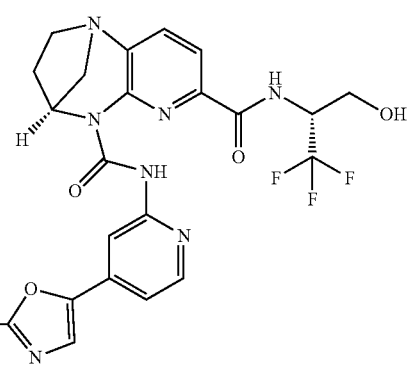

(9S)-8-N-[4-(2-methyl-1,3-oxazol-5-yl)pyridin-2-yl]-
5-N-[(2R)-1,1,1-trifluoro-3-hydroxypropan-2-yl]-
1,6,8-triazatricyclo[7.2.1.0²,⁷]dodeca-
2(7),3,5-triene-5,8-dicarboxamide 843
-continued

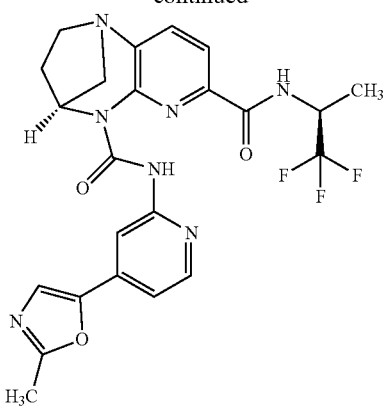

(9S)-8-N-[4-(2-methyl-1,3-oxazol-5-yl)pyridin-2-yl]-
5-N-[(2S)-1,1,1-trifluoropropan-2-yl]-1,6,8-triazatricyclo
[7.2.1.0²,⁷]dodeca-2(7),3,5-triene-5,8-dicarboxamide

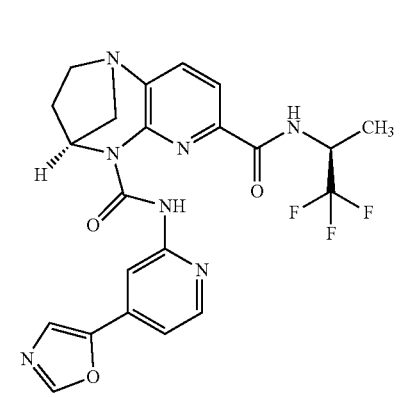

(9S)-8-N-[4-(1,3-oxazol-5-yl)pyridin-2-yl]-5-N-[(2S)-
1,1,1-trifluoropropan-2-yl]-1,6,8-triazatricyclo
[7.2.1.0²,⁷]dodeca-2(7),3,5-triene-5,8-dicarboxamide

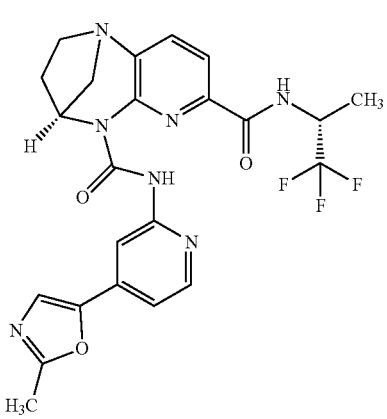

(9S)-8-N-[4-(2-methyl-1,3-oxazol-5-yl)pyridin-2-yl]-5-N-
[(2R)-1,1,1-trifluoropropan-2-yl]-1,6,8-triazatricyclo[7.2.1.0²,⁷]
dodeca-2(7),3,5-triene-5,8-dicarboxamide 844
-continued

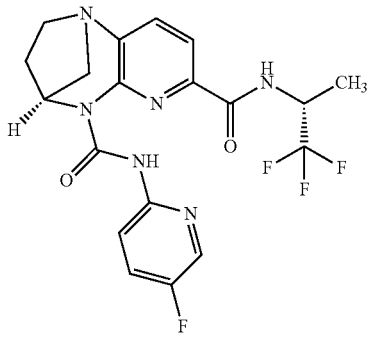

(9S)-8-N-(5-fluoropyridin-2-yl)-5-N-[(2R)-1,1,1-
trifluoropropan-2-yl]-1,6,8-triazatricyclo
[7.2.1.0²,⁷]dodeca-2(7),3,5-triene-5,8-dicarboxamide

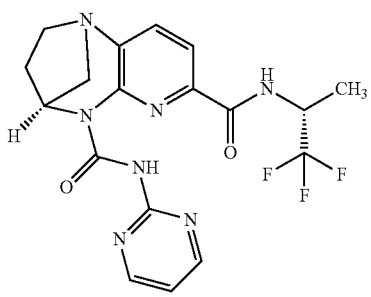

(9S)-8-N-(pyrimidin-2-yl)-5-N-[(2R)-1,1,1-
trifluoropropan-2-yl]-1,6,8-triazatricyclo
[7.2.1.0²,⁷]dodeca-2(7),3,5-triene-5,8-dicarboxamide

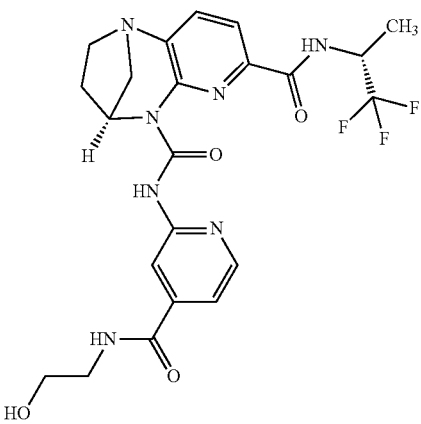

(9S)-8-N-{4-[(2-hydroxyethyl)carbamoyl]pyridin-2-
yl}-5-N-[(2R)-1,1,1-trifluoropropan-2-yl]-1,6,8-
triazatricyclo[7.2.1.0²,⁷]dodeca-
2(7),3,5-triene-5,8-dicarboxamide

845

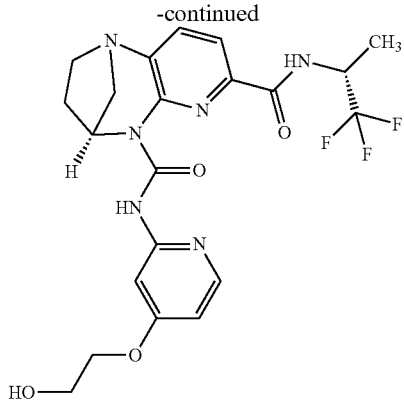

(9S)-8-N-[4-(2-hydroxyethyl)pyridin-2-yl]-5-N-[(2R)-1,1,1-trifluoropropan-2-yl]-1,6,8-triazatricyclo[7.2.1.0²,⁷]dodeca-2(7),3,5-triene-5,8-dicarboxamide

846

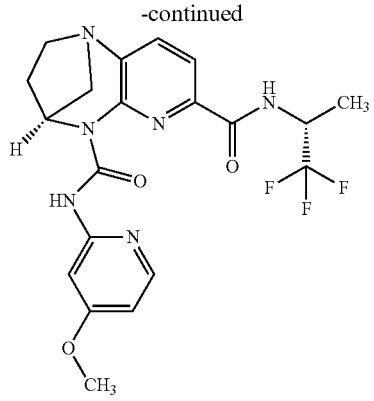

(9S)-8-N-(4-methoxypyridin-2-yl)-5-N-[(2R)-1,1,1-trifluoropropan-2-yl]-1,6,8-triazatricyclo[7.2.1.0²,⁷]dodeca-2(7),3,5-triene-5,8-dicarboxamide (9S)-8-N-{2H,3H,4H-pyrano[2,3-c]pyridin-6-yl}-5-N-(2,2,2-trifluoroethyl)-1,6,8-triazatricyclo[7.2.1.0²,⁷]dodeca-2,4,6-triene-5,8-dicarboxamide

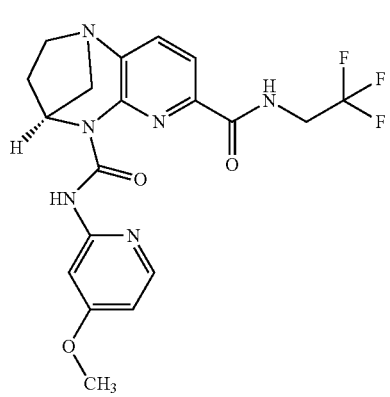

(9S)-8-N-(4-methoxypyridin-2-yl)-5-N-(2,2,2-trifluoroethyl)-1,6,8-triazatricyclo[7.2.1.0²,⁷]dodeca-2(7),3,5-triene-5,8-dicarboxamide (9S)-8-N-[4-(1,3-oxazol-5-yl)pyridin-2-yl]-5-N-[(2R)-1,1,1-trifluoropropan-2-yl]-1,6,8-triazatricyclo[7.2.1.0²,⁷]dodeca-2,4,6-triene-5,8-dicarboxamide

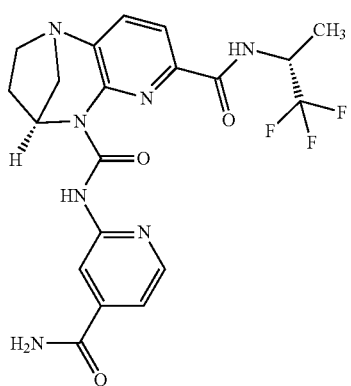

(9S)-8-N-(4-carbamoylpyridin-2-yl)-5-N-[(2R)-1,1,1-trifluoropropan-2-yl]-1,6,8-triazatricyclo[7.2.1.0²,⁷]dodeca-2(7),3,5-triene-5,8-dicarboxamide -continued

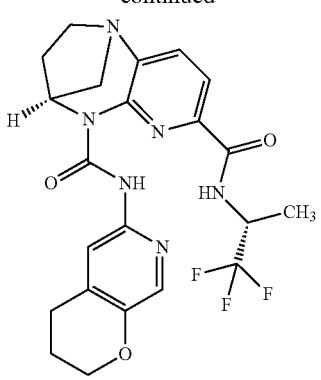

(9S)-8-N-{2H,3H,4H-pyrano[2,3-c]pyridin-6-yl}-5-N-
[(2R)-1,1,1-trifluoropropan-2-yl]-1,6,8-triazatricyclo
[7.2.1.0²,⁷]dodeca-2,4,6-triene-5,8-dicarboxamide

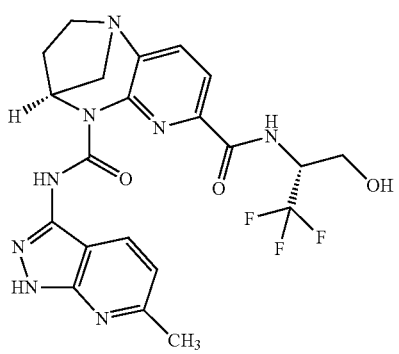

(9S)-8-N-{6-methyl-1H-pyrazolo[3,4-b]pyridin-3-yl}-5-N-
[(2R)-1,1,1-trifluoro-3-hydroxypropan-2-yl]-
1,6,8-triazatricyclo[7.2.1.0²,⁷]dodeca-
2,4,6-triene-5,8-dicarboxamide

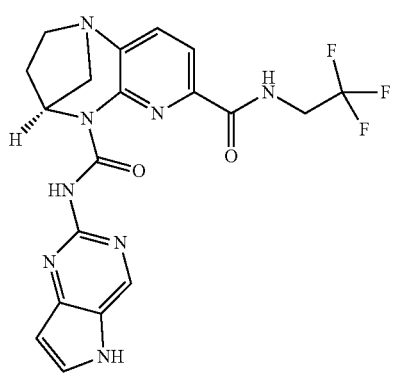

(9S)-8-N-{5H-pyrrolo[3,2-d]pyrimidin-2-yl}-5-N-
(2,2,2-trifluoroethyl)-1,6,8-triazatricyclo[7.2.1.0²,⁷]
dodeca-2,4,6-triene-5,8-dicarboxamide -continued

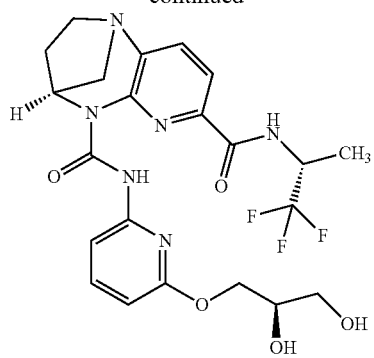

(9S)-8-N-{6-[(2R)-2,3-dihydroxypropoxy]pyridin-2-yl}-5-N-
[(2R)-1,1,1-trifluoropropan-2-yl]-1,6,8-triazatricyclo
[7.2.1.0²,⁷]dodeca-2(7),3,5-triene-5,8-dicarboxamide

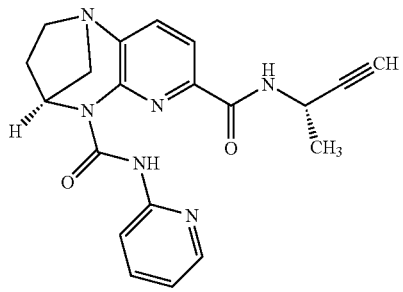

(9S)-5-N-[(2S)-but-3-yn-2-yl]-8-N-(pyridin-2-yl)-
1,6,8-triazatricyclo[7.2.1.0²,⁷]
dodeca-2(7),3,5-triene-5,8-dicarboxamide

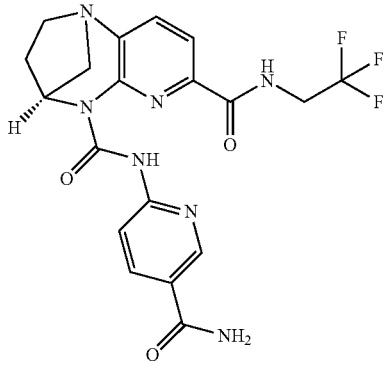

(9S)-8-N-(5-carbamoylpyridin-2-yl)-5-N-(2,2,2-
trifluoroethyl)-1,6,8-triazatricyclo[7.2.1.0²,⁷]
dodeca-2(7),3,5-triene-5,8-dicarboxamide

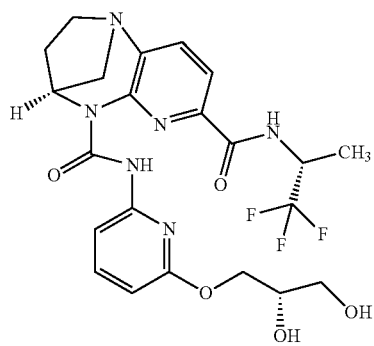

(9S)-8-N-{6-[(2S)-2,3-dihydroxypropoxy]pyridin-2-yl}-5-N-
[(2R)-1,1,1-trifluoropropan-2-yl]-1,6,8-triazatricyclo
[7.2.1.0²,⁷]dodeca-2(7),3,5-triene-5,8-dicarboxamide 849
-continued

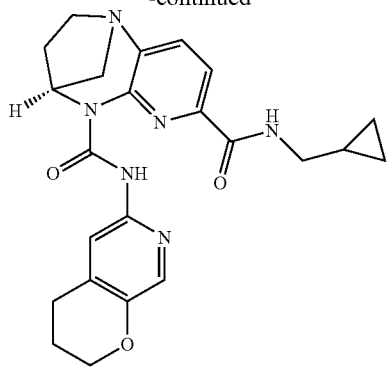

(9S)-5-N-(cyclopropylmethyl)-8-N-{2H,3H,4H-
pyrano[2,3-c]pyridin-6-yl}-1,6,8-triazatricyclo
[7.2.1.0²,⁷]dodeca-2,4,6-triene-5,8-dicarboxamide

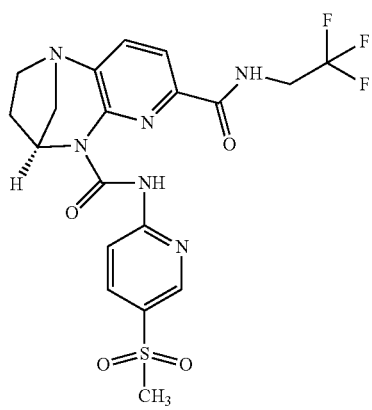

(9S)-8-N-(5-methanesulfonylpyridin-2-yl)-5-N-(2,2,2-
trifluoroethyl)-1,6,8-triazatricyclo[7.2.1.0²,⁷]
dodeca-2(7),3,5-triene-5,8-dicarboxamide

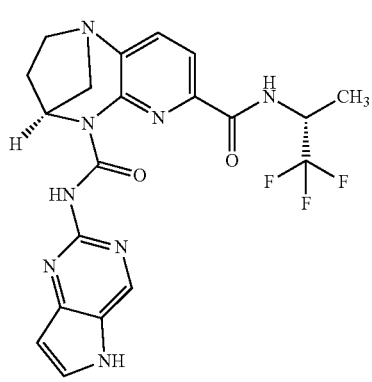

(9S)-8-N-{5H-pyrrolo[3,2-d]pyrimidin-2-yl}-5-N-[(2R)-1,1,1-
trifluoropropan-2-yl]-1,6,8-triazatricyclo
[7.2.1.0²,⁷]dodeca-2,4,6-triene-5,8-dicarboxamide 850
-continued

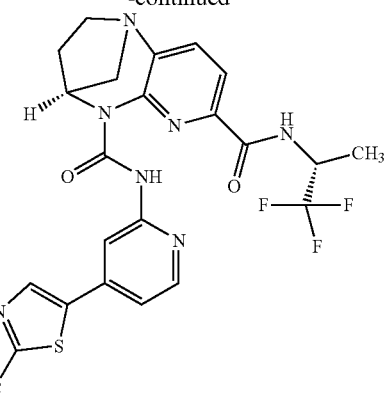

(9S)-8-N-[4-(2-methyl-1,3-thiazol-5-yl)pyridin-2-yl]-5-N-
[(2R)-1,1,1-trifluoropropan-2-yl]-1,6,8-triazatricyclo
[7.2.1.0²,⁷]dodeca-2,4,6-triene-5,8-dicarboxamide

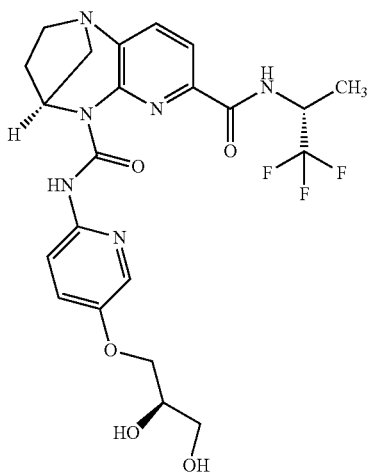

(9S)-8-N-{5-[(2R)-2,3-dihydroxypropoxy]pyridin-2-yl}-
5-N-[(2R)-1,1,1-trifluoropropan-2-yl]-1,6,8-triazatricyclo
[7.2.1.0²,⁷]dodeca-2(7),3,5-triene-5,8-dicarboxamide

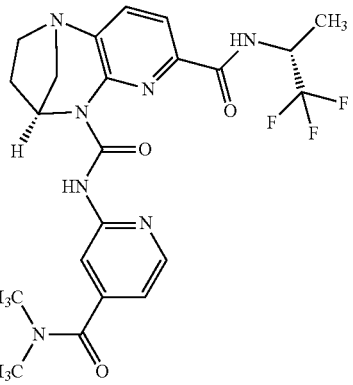

(9S)-8-N-[4-(dimethylcarbamoyl)pyridin-2-yl]-5-N-
[(2R)-1,1,1-trifluoropropan-2-yl]-1,6,8-triazatricyclo
[7.2.1.0²,⁷]dodeca-2(7),3,5-triene-5,8-dicarboxamide

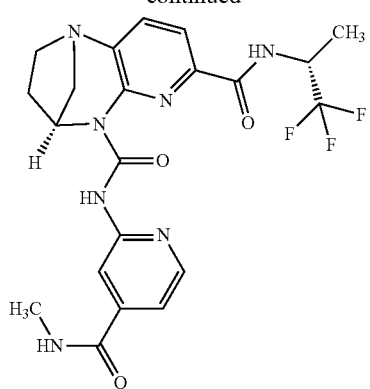

(9S)-8-N-[4-(methylcarbamoyl)pyridin-2-yl]-5-N-
[(2R)-1,1,1-trifluoropropan-2-yl]-1,6,8-triazatricyclo
[7.2.1.0²,⁷]dodeca-2(7),3,5-triene-5,8-dicarboxamide

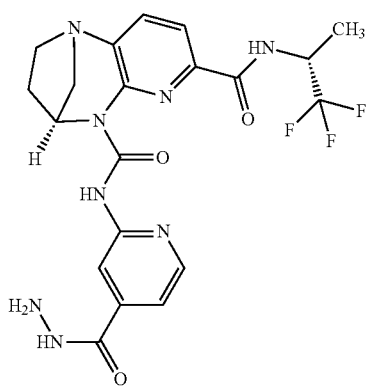

(9S)-8-N-[4-(hydrazinecarbonyl)pyridin-2-yl]-5-N-
[(2R)-1,1,1-trifluoropropan-2-yl]-1,6,8-triazatricyclo
[7.2.1.0²,⁷]dodeca-2(7),3,5-triene-5,8-dicarboxamide

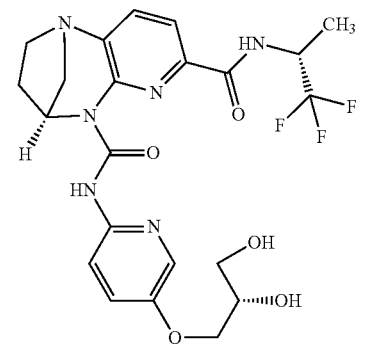

(9S)-8-N-{5-[(2S)-2,3-dihydroxypropoxy]pyridin-2-yl}-5-N-
[(2R)-1,1,1-trifluoropropan-2-yl]-1,6,8-triazatricyclo
[7.2.1.0²,⁷]dodeca-2(7),3,5-triene-5,8-dicarboxamide

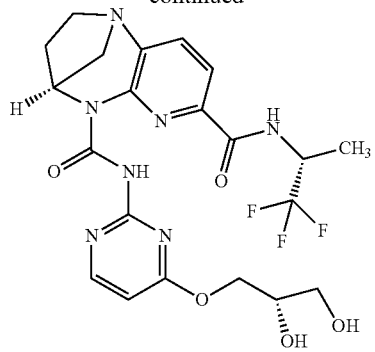

(9S)-8-N-{4-[(2S)-2,3-dihydroxypropoxy]pyrimidin-2-yl}-5-N-
[(2R)-1,1,1-trifluoropropan-2-yl]-1,6,8-triazatricyclo
[7.2.1.0²,⁷]dodeca-2(7),3,5-triene-5,8-dicarboxamide

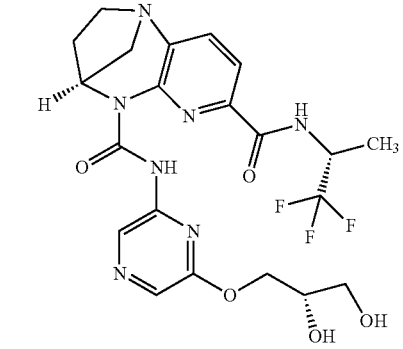

(9S)-8-N-{6-[(2R)-2,3-dihydroxypropoxy]pyrazin-2-yl}-5-N-
[(2R)-1,1,1-trifluoropropan-2-yl]-1,6,8-triazatricyclo
[7.2.1.0²,⁷]dodeca-2(7),3,5-triene-5,8-dicarboxamide

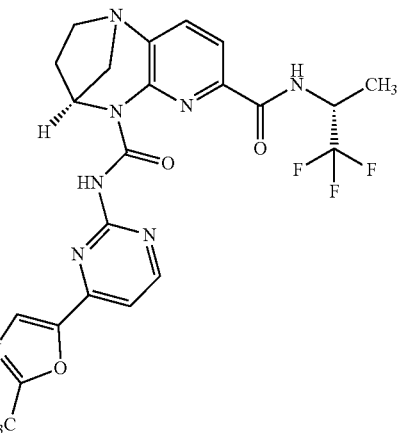

(9S)-8-N-[4-(2-methyl-1,3-oxazol-5-yl)pyrimidin-2-yl]-5-N-
[(2R)-1,1,1-trifluoropropan-2-yl]-1,6,8-triazatricyclo
[7.2.1.0²,⁷]dodeca-2(7),3,5-triene-5,8-dicarboxamide

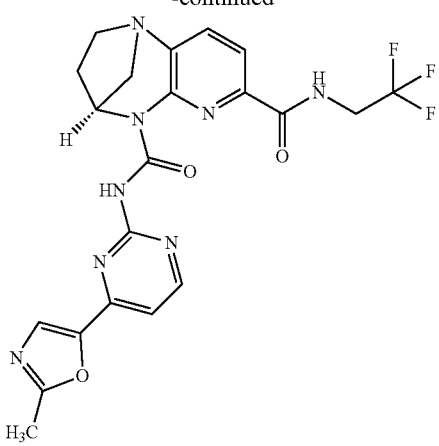

(9S)-8-N-[4-(2-methyl-1,3-oxazol-5-yl)pyrimidin-2-yl]-5-N-
(2,2,2)-trifluoroethyl)-1,6,8-triazatricyclo
[7.2.1.0²,⁷]dodeca-2(7),3,5-triene-5,8-dicarboxamide

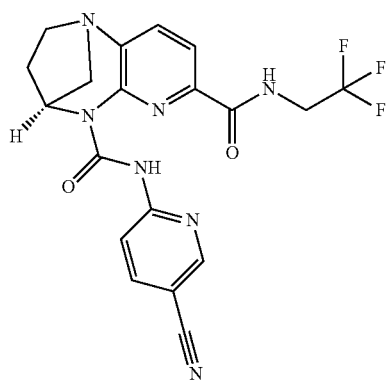

(9S)-8-N-(5-cyanopyridin-2-yl)-5-N-
(2,2,2)-trifluoroethyl)-1,6,8-triazatricyclo
[7.2.1.0²,⁷]dodeca-2(7),3,5-triene-5,8-dicarboxamide

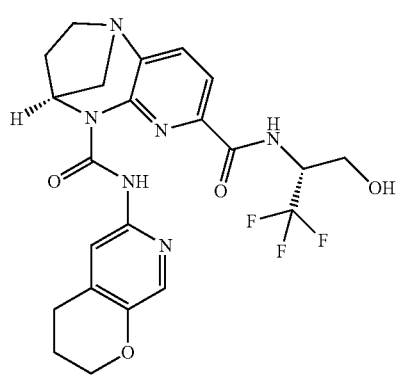

(9S)-8-N-{2H,3H,4H-pyrano[2,3-c]pyridin-6-yl}-5-N-
[(2R)-1,1,1-trifluoro-3-hydroxypropan-2-yl]-1,6,8-triazatricyclo
[7.2.1.0²,⁷]dodeca-2,4,6-triene-5,8-dicarboxamide

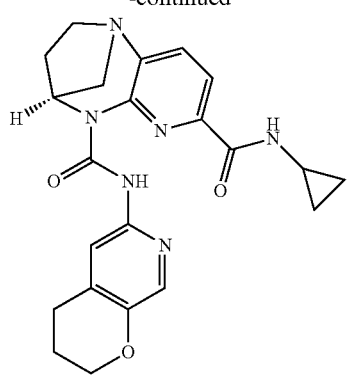

(9S)-5-N-cyclopropyl-8-N-{2H,3H,4H-pyrano
[2,3-c]pyridin-6-yl}-1,6,8-triazatricyclo
[7.2.1.0²,⁷]dodeca-2,4,6-triene-5,8-dicarboxamide

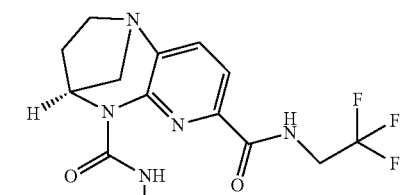

(9S)-8-N-[4-(2-hydroxyethoxy)pyridin-2-yl]-
5-N-(2,2,2-trifluoroethyl)-1,6,8-triazatricyclo
[7.2.1.0²,⁷]dodeca-2,4,6-triene-5,8-dicarboxamide

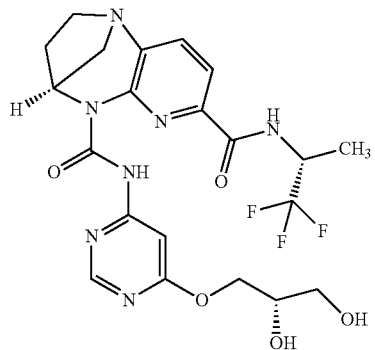

(9S)-8-N-{6-[(2S)-2,3-dihydroxypropoxy]pyrimidin-4-yl}-
5-N-[(2R)-1,1,1-trifluoropropan-2-yl]-1,6,8-triazatricyclo
[7.2.1.0²,⁷]dodeca-2(7),3,5-triene-5,8-dicarboxamide

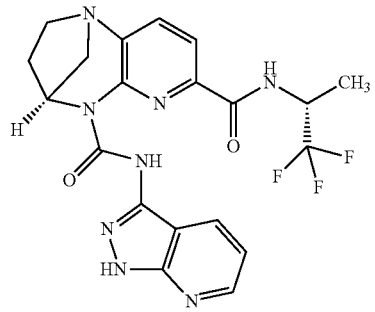

(9S)-8-N-{1H-pyrazolo[3,4-b]pyridin-3-yl}-5-N-
[(2R)-1,1,1-trifluoropropan-2-yl]-1,6,8-triazatricyclo
[7.2.1.0²,⁷]dodeca-2(7),3,5-triene-5,8-dicarboxamide

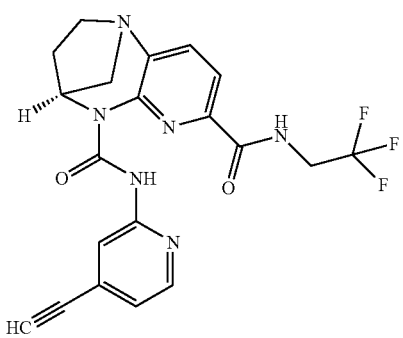

(9S)-8-N-(4-ethynylpyridin-2-yl)-5-N-
(2,2,2-trifluoroethyl)-1,6,8-triazatricyclo
[7.2.1.0²,⁷]dodeca-2,4,6-triene-5,8-dicarboxamide

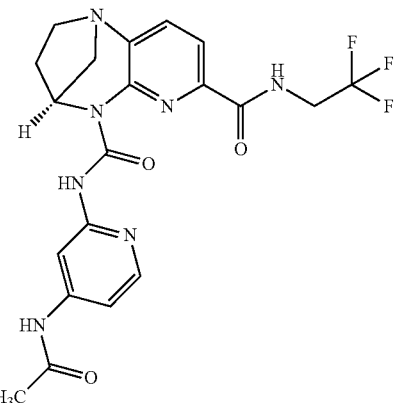

(9S)-8-N-(4-acetamidopyridin-2-yl)-5-N-
(2,2,2-trifluoroethyl)-1,6,8-triazatricyclo
[7.2.1.0²,⁷]dodeca-2,4,6-triene-5,8-dicarboxamide

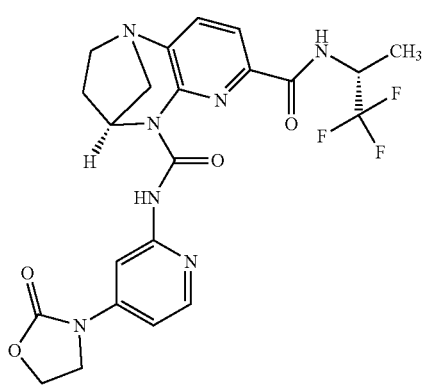

(9S)-8-N-[4-(2-oxo-1,3-oxazolidin-3-yl)pyridin-2-yl]-5-N-
[(2R)-1,1,1-trifluoropropan-2-yl]-1,6,8-triazatricyclo
[7.2.1.0²,⁷]dodeca-2(7),3,5-triene-5,8-dicarboxamide

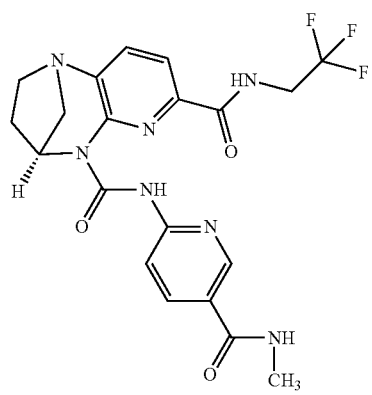

(9S)-8-N-[5-(methylcarbamoyl)pyridin-2-yl]-5-N-
[(2,2,2-trifluoroethyl)]-1,6,8-triazatricyclo
[7.2.1.0²,⁷]dodeca-2(7),3,5-triene-5,8-dicarboxamide

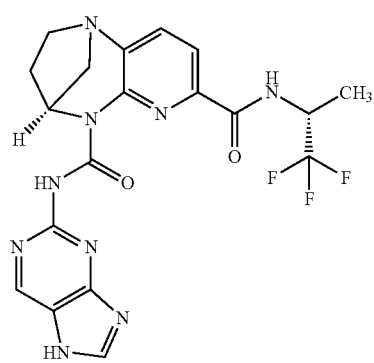

(9S)-8-N-(7H-purin-2-yl)-5-N-[(2R)-1,1,1-
trifluoropropan-2-yl]-1,6,8-triazatricyclo
[7.2.1.0²,⁷]dodeca-2(7),3,5-triene-5,8-dicarboxamide

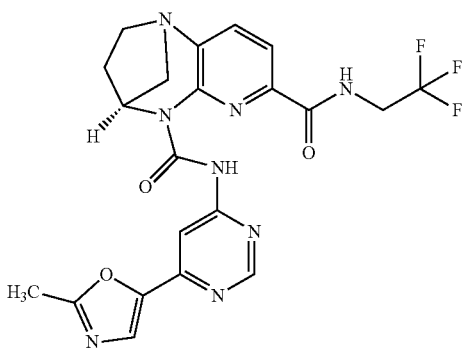

(9S)-8-N-[6-(2-methyl-1,3,-oxazol-5-yl)pyrimidin-4-yl]-5-N-
(2,2,2-trifluoroethyl)-1,6,8-triazatricyclo
[7.2.1.0²,⁷]dodeca-2(7),3,5-triene-5,8-dicarboxamide -continued

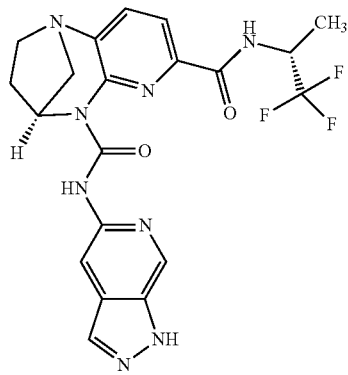

(9S)-8-N-{1H-pyrazolo[3,4-c]pyridin-5-yl}-5-N-
[(2R)-1,1,1-trifluoropropan-2-yl]-1,6,8-triazatricyclo
[7.2.1.0$^{2,7}$]dodeca-2,4,6-triene-5,8-dicarboxamide

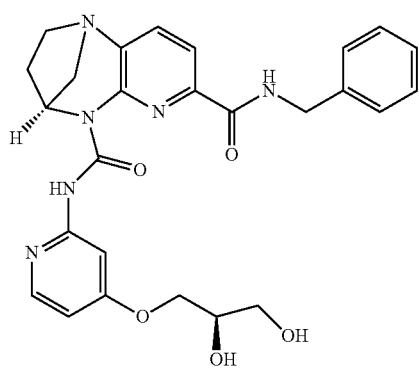

(9S)-5-N-benzyl-8-N-{4-[(2R)-2,3,-dihydroxypropoxy]
pyridin-2-yl}-1,6,8-triazatricyclo[7.2.1.0$^{2,7}$]dodeca-
2(7),3,5-triene-5,8-dicarboxamide

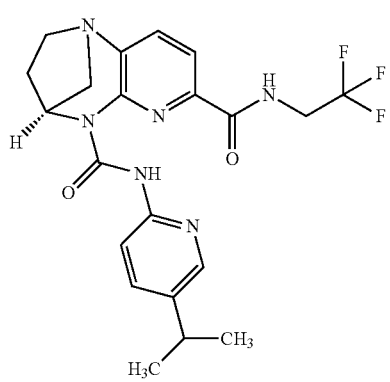

(9S)-8-N-[5-(propan-2-yl)pyridin-2-yl]-5-N-
(2,2,2-trifluoroethyl)-1,6,8-triazatricyclo
[7.2.1.0$^{2,7}$]dodeca-2(7),3,5-triene-5,8-dicarboxamide -continued

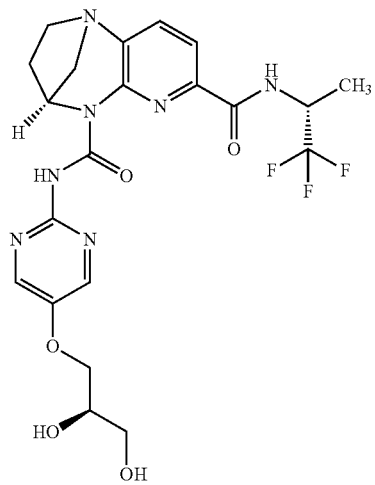

(9S)-8-N-{5-[(2R)-2,3-dihydroxypropoxy]pyrimidin-2-yl}-5-N-
[(2R)-1,1,1-trifluoropropan-2-yl]-1,6,8-triazatricyclo
[7.2.1.0$^{2,7}$]dodeca-2(7),3,5-triene-5,8-dicarboxamide

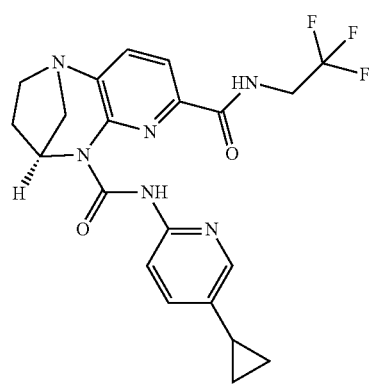

(9S)-8-N-(5-cyclopropylpyridin-2-yl)-5-N-
(2,2,2-trifluoroethyl)-1,6,8-triazatricyclo
[7.2.1.0$^{2,7}$]dodeca-2(7),3,5-triene-5,8-dicarboxamide

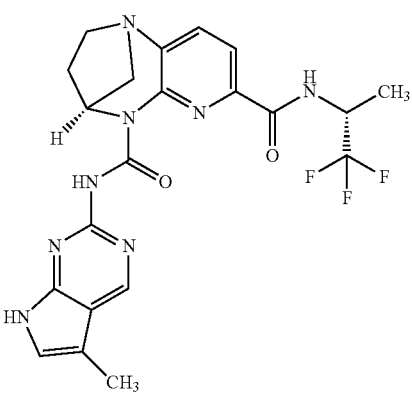

(9S)-8-N-{5-methyl-7H-pyrrolo[2,3-d]pyrimidin-2-yl}-5-N-
[(2R)-1,1,1-trifluoropropan-2-yl]-1,6,8-triazatricyclo
[7.2.1.0$^{2,7}$]dodeca-2,4,6-triene-5,8-dicarboxamide

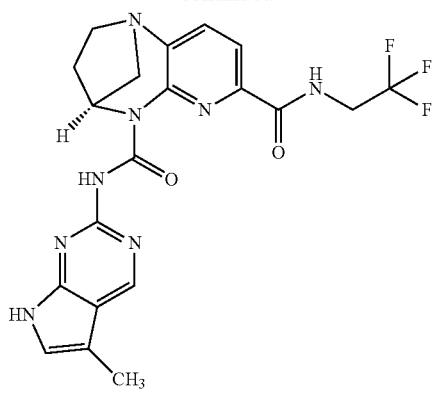

(9S)-8-N-{5-methyl-7H-pyrrolo[2,3-d]pyrimidin-2-yl}-5-N-(2,2,2-trifluoroethyl)-1,6,8-triazatricyclo[7.2.1.0²,⁷]dodeca-2,4,6-triene-5,8-dicarboxamide

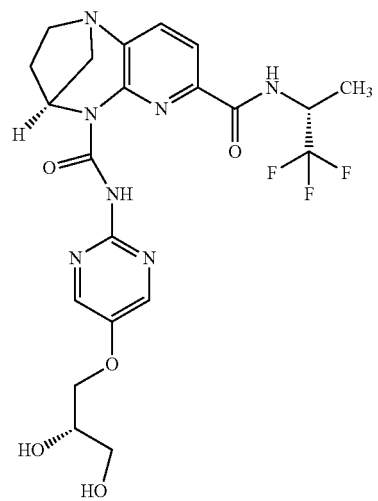

(9S)-8-N-{5-[(2S)-2,3-dihydroxypropoxy]pyrimidin-2-yl}-5-N-[(2R)-1,1,1-trifluoropropan-2-yl]-1,6,8-triazatricyclo[7.2.1.0²,⁷]dodeca-2(7),3,5-triene-5,8-dicarboxamide

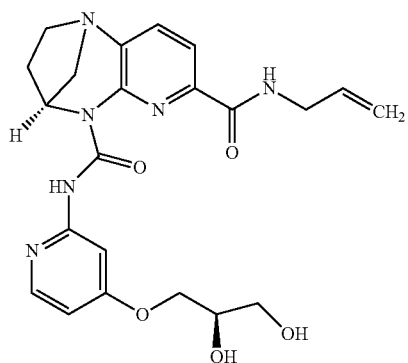

(9S)-8-N-{4-[(2R)-2,3-dihydroxypropoxy]pyridin-2-yl}-5-N-(prop-2-en-1-yl)-1,6,8-triazatricyclo[7.2.1.0²,⁷]dodeca-2(7),3,5-triene-5,8-dicarboxamide

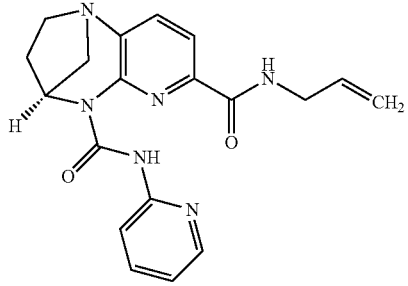

(9S)-5-N-(prop-2-en-1-yl)-8-N-(pyridin-2-yl)-1,6,8-triazatricyclo[7.2.1.0²,⁷]dodeca-2(7),3,5-triene-5,8-dicarboxamide

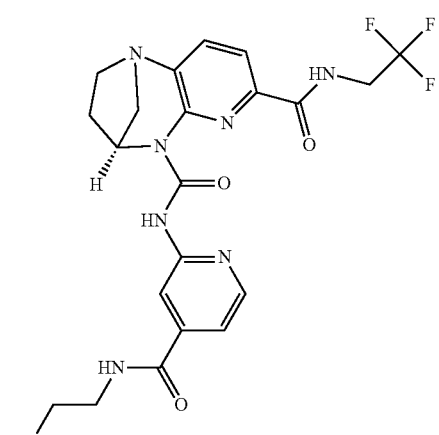

(9S)-8-N-{4-[(2-hydroxyethyl)carbamoyl]pyridin-2-yl}-5-N-(2,2,2-trifluoroethyl)-1,6,8-triazatricyclo[7.2.1.0²,⁷]dodeca-2(7),3,5-triene-5,8-dicarboxamide

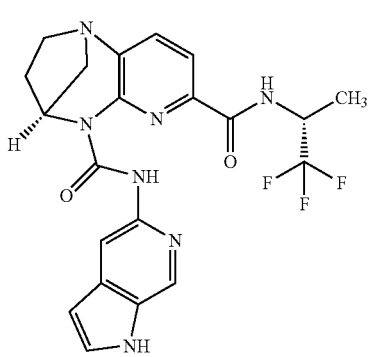

(9S)-8-N-{1H-pyrrolo[2,3-c]pyridin-5-yl}-5-N-[(2R)-1,1,1-trifluoropropan-2-yl]-1,6,8-triazatricyclo[7.2.1.0²,⁷]dodeca-2(7),3,5-triene-5,8-dicarboxamide

861

-continued

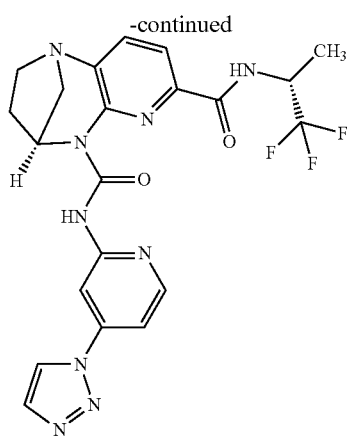

(9S)-8-N-[4-(1H-1,2,3-triazol-1-yl)pyridin-2-yl]-5-N-
[(2R)-1,1,1-trifluoropropan-2-yl]-1,6,8-triazatricyclo
[7.2.1.0²,⁷]dodeca-2(7),3,5-triene-5,8-dicarboxamide

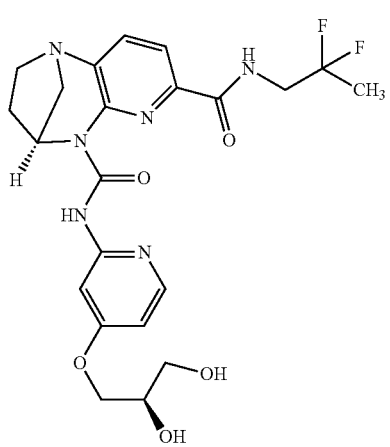

(9S)-5-N-(2,2-difluoropropyl)-8-N-{4-[(2R)-2,3-
dihydroxypropoxy]pyridin-2-yl}-1,6,8-triazatricyclo
[7.2.1.0²,⁷]dodeca-2(7),3,5-triene-5,8-dicarboxamide

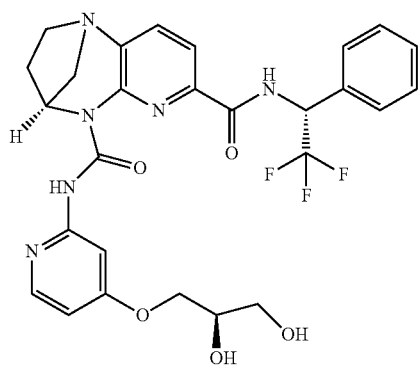

(9S)-8-N-{4-[(2R)-2,3-dihydroxypropoxy]
pyridin-2-yl}-5-N-[(1R)-2,2,2-trifluoro-1-phenylethyl]-
1,6,8-triazatricyclo[7.2.1.0²,⁷]dodeca-2(7),3,5-triene-5,8-dicarboxamide

862

-continued

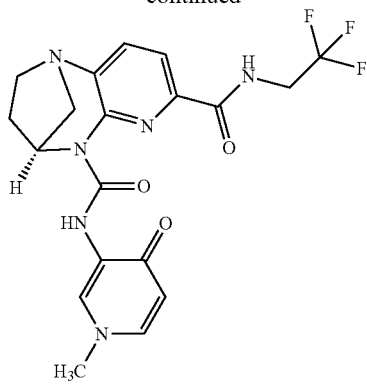

(9S)-8-N-(1-methyl-4-oxo-1,4-dihydropyridin-3-yl)-
5-N-(2,2,2-trifluoroethyl)-1,6,8-triazatricyclo
[7.2.1.0²,⁷]dodeca-2,4,6-triene-5,8-dicarboxamide

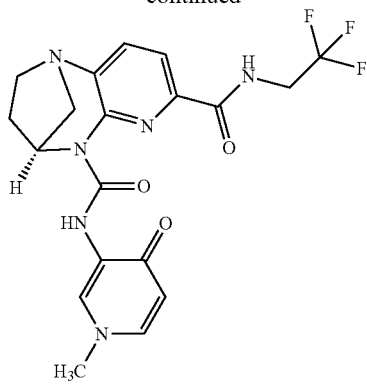

(9S)-8-N-[4-(2-aminoethoxy)pyridin-2-yl]-
5-N-[(2R)-1,1,1-trifluoropropan-2-yl]-1,6,8-
triazatricyclo[7.2.1.0²,⁷]dodeca-2(7),3,5-triene-5,8-dicarboxamide

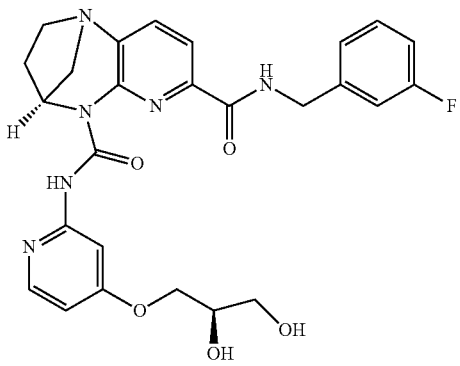

(9S)-8-N-{4-[(2R)-2,3-dihydroxypropoxy]pyridin-2-yl}-
5-N-[(3-fluorophenyl)methyl]-1,6,8-triazatricyclo[7.2.1.0²,⁷]
dodeca-2(7),3,5-triene-5,8-dicarboxamide

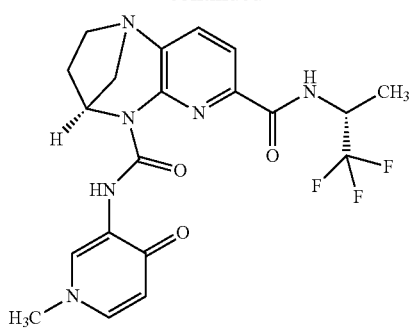

(9S)-8-N-(1-methyl-4-oxo-1,4-dihydropyridin-3-yl)-
5-N-[(2R)-1,1,1-trifluoropropan-2-yl]-
1,6,8-triazatricyclo[7.2.1.0²,⁷]
dodeca-2(7),3,5-triene-5,8-dicarboxamide

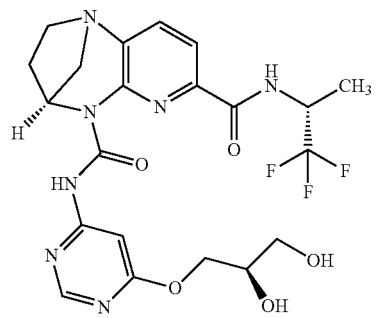

(9S)-8-N-{6-[(2R)-2,3-dihydroxypropoxy]pyrimidin-4-
yl}-5-N-[(2R)-1,1,1-trifluoropropan-2-yl]-1,6,8-triazatricyclo
[7.2.1.0²,⁷]dodeca-2(7),3,5-triene-5,8-dicarboxamide

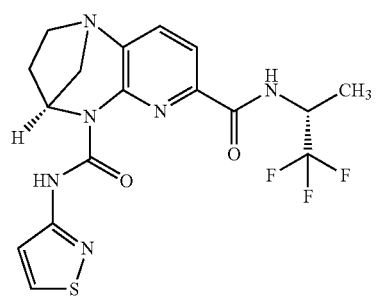

(9S)-8-N-(1,2-thiazol-3-yl)-5-N-[(2R)-1,1,1-
trifluoropropan-2-yl]-1,6,8-triazatricyclo
[7.2.1.0²,⁷]dodeca-2(7),3,5-triene-5,8-dicarboxamide

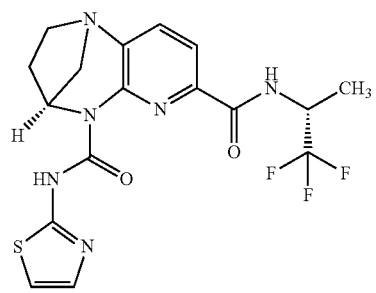

(9S)-8-N-(1,3-thiazol-2-yl)-5-N-[(2R)-1,1,1-
trifluoropropan-2-yl]-1,6,8-triazatricyclo
[7.2.1.0²,⁷]dodeca-2(7),3,5-triene-5,8-dicarboxamide

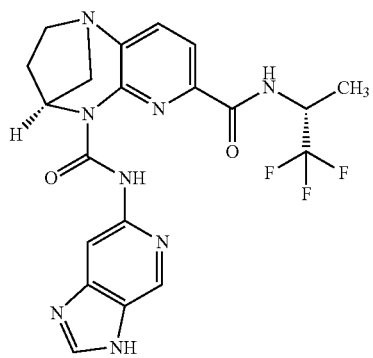

(9S)-8-N-{3H-imidazo[4,5-c]pyridin-6-yl}-5-N-
[(2R)-1,1,1-trifluoropropan-2-yl]-1,6,8-triazatricyclo
[7.2.1.0²,⁷]dodeca-2,4,6-triene-5,8-dicarboxamide

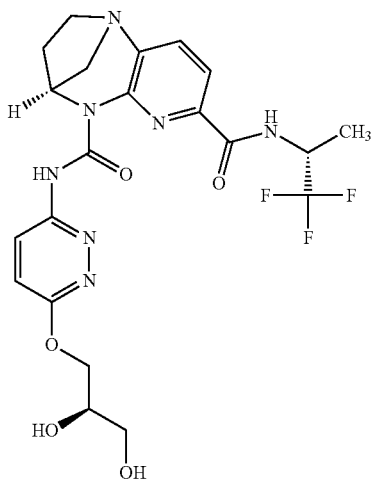

(9S)-8-N-{6-[(2R)-2,3-dihydroxypropoxy]pyridazin-3-yl}-
5-N-[(2R)-1,1,1-trifluoropropan-2-yl]-1,6,8-triazatricyclo[7.2.1.0²,⁷]
dodeca-2(7),3,5-triene-5,8-dicarboxamide

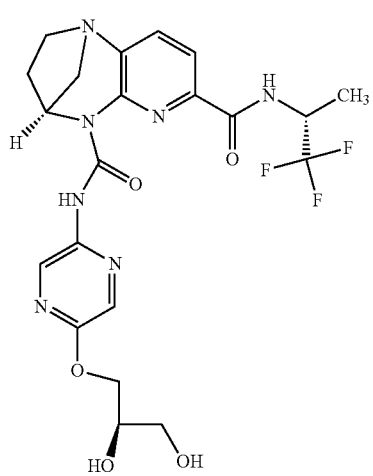

(9S)-8-N-{5-[(2R)-2,3-dihydroxypropoxy]pyrazin-2-yl}-5-N-
[(2R)-1,1,1-trifluoropropan-2-yl]-1,6,8-triazatricyclo
[7.2.1.0²,⁷]dodeca-2(7),3,5-triene-5,8-dicarboxamide

865

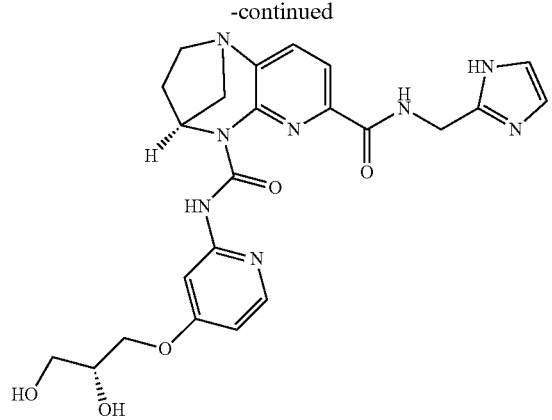

(9S)-8-N-{4-[(2R)-2,3-dihydroxypropoxy]pyridin-2-yl}-5-N-(1H-imidazol-2-ylmethyl)-1,6,8-triazatricyclo[7.2.1.0²,⁷]dodeca-2,4,6-triene-5,8-dicarboxamide

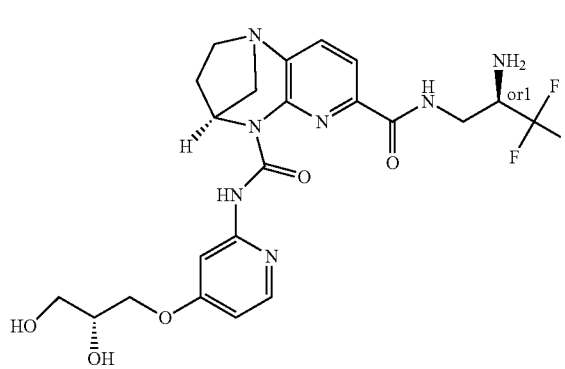

ISOMER 1

(9S)-5-N-[(2R)-2-amino-3,3,3-trifluoropropyl]-8-N-{4-[(2R)-2,3-dihydroxypropoxy]pyridin-2-yl}-1,6,8-triazatricyclo[7.2.1.0²,⁷]dodeca-2(7),3,5-triene-5,8-dicarboxamide

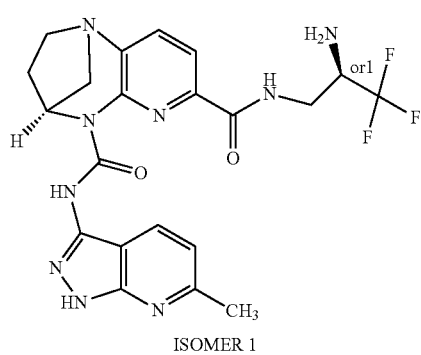

ISOMER 1

(9S)-5-N-[(2R)-2-amino-3,3,3-trifluoropropyl]-8-N-{6-methyl-1H-pyrazolo[3,4-b]pyridin-3-yl}-1,6,8-triazatricyclo[7.2.1.0²,⁷]dodeca-2(7),3,5-triene-5,8-dicarboxamide

866

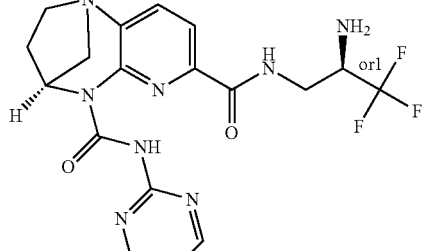

ISOMER 1

(9S)-5-N-[(2R)-2-amino-3,3,3-trifluoropropyl]-8-N-(pyrimidin-2-yl)-1,6,8-triazatricyclo[7.2.1.0²,⁷]dodeca-2,4,6-triene-5,8-dicarboxamide

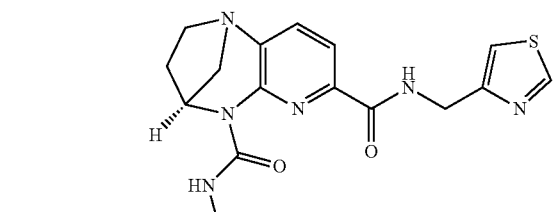

(9S)-8-N-{4-[(2R)-2,3-dihydroxypropoxy]pyridin-2-yl}-5-N-(1,3-thiazol-4-ylmethyl)-1,6,8-triazatricyclo[7.2.1.0²,⁷]dodeca-2(7),3,5-triene-5,8-dicarboxamide

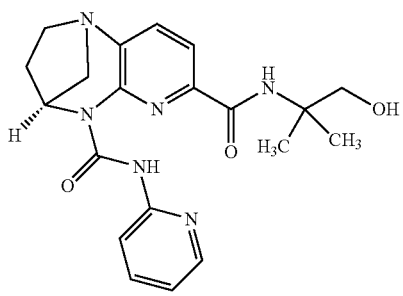

(9S)-5-N-(1-hydroxy-2-methylpropan-2-yl)-8-N-(pyridin-2-yl)-1,6,8-triazatricyclo[7.2.1.0²,⁷]dodeca-2,(7),3,5-triene-5,8-dicarboxamide

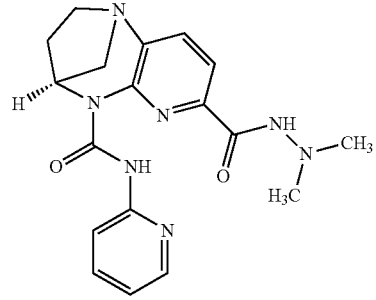

(9S)-5-(N',N'-dimethylhydrazinecarbonyl)-N-(pyridin-2-yl)-1,6,8-triazatricyclo[7.2.1.0²,⁷]dodeca-2,(7),3,5-triene-8-carboxamide -continued

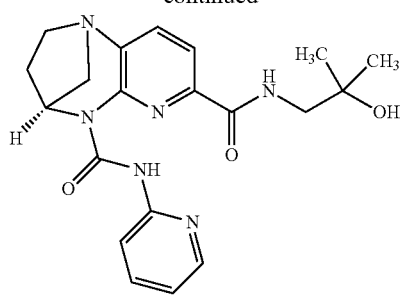

(9S)-5-N-(2-hydroxy-2-methylpropyl)-8-N-
(pyridin-2-yl)-1,6,8-triazatricyclo[7.2.1.0$^{2,7}$]dodeca-
2,(7),3,5-triene-5,8-dicarboxamide

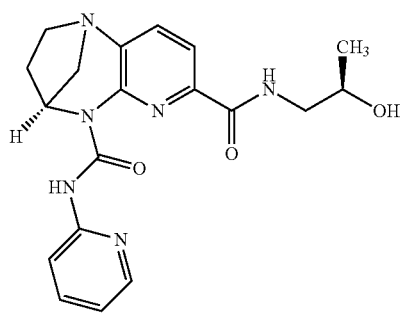

(9S)-5-N-[(2R)-2-hydroxypropyl]-8-N-(pyridin-2-yl)-
1,6,8-triazatricyclo[7.2.1.0$^{2,7}$]dodeca-2(7),3,5-triene-
5,8-dicarboxamide

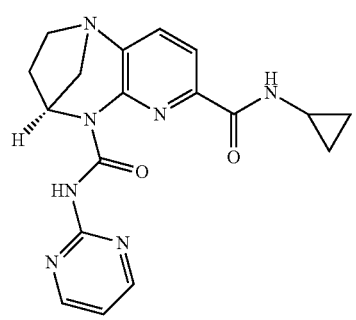

(9S)-5-N-cyclopropyl-8-N-(pyrimidin-2-yl)-
1,6,8-triazatricyclo[7.2.1.0$^{2,7}$]dodeca-2(7),3,5-triene-
5,8-dicarboxamide

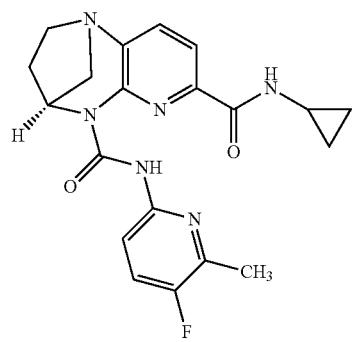

(9S)-5-N-cyclopropyl-8-N-(5-fluoro-6-methylpyridin-2-yl)-
1,6,8-triazatricyclo[7.2.1.0$^{2,7}$]dodeca-
2,(7),3,5-triene-5,8-dicarboxamide -continued

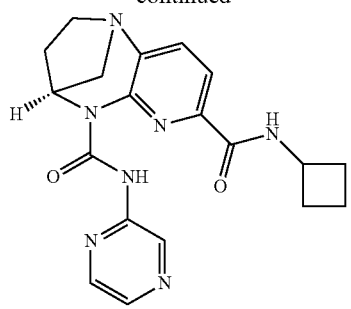

(9S)-5-N-cyclobutyl-8-N-(pyrazin-2-yl)-1,6,8-
triazatricyclo[7.2.1.0$^{2,7}$]dodeca-
2,4,6-triene-8-carboxamide

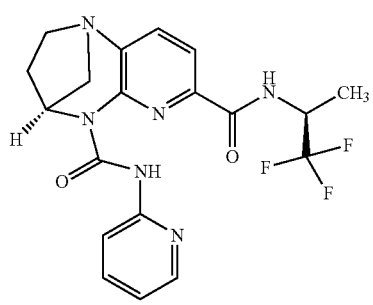

(9S)-8-N-(pyridin-2-yl)-5-N-[(2S)-1,1,1-trifluoropropan-2-yl]-
1,6,8-triazatricyclo[7.2.1.0$^{2,7}$]dodeca-
2,(7),3,5-triene-5,8-dicarboxamide

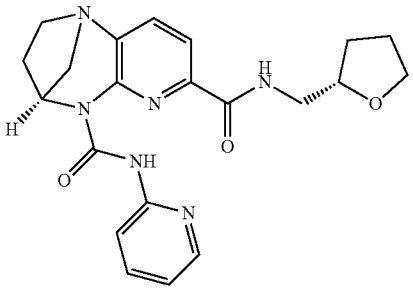

(9S)-5-N-[(2S)-oxolan-2-ylmethyl]-8-N-(pyridin-2-yl)-
1,6,8-triazatricyclo[7.2.1.0$^{2,7}$]dodeca-
2,(7),3,5-triene-5,8-dicarboxamide

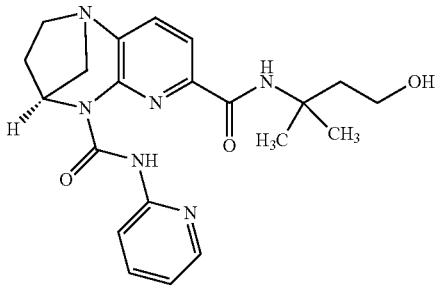

(9S)-5-N-(4-hydroxy-2-methylbutan-2-yl)-8-N-
(pyridin-2-yl)-1,6,8-triazatricyclo[7.2.1.0$^{2,7}$]dodeca-
2,(7),3,5-triene-5,8-dicarboxamide

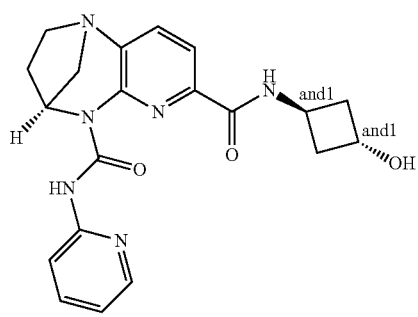

(9S)-8-N-(pyridin-2-yl)-5-N-[(1r,3r)-3-hydroxycyclobutyl]-
1,6,8-triazatricyclo[7.2.1.0²,⁷]dodeca-2(7),3,5-triene-
5,8-dicarboxamide

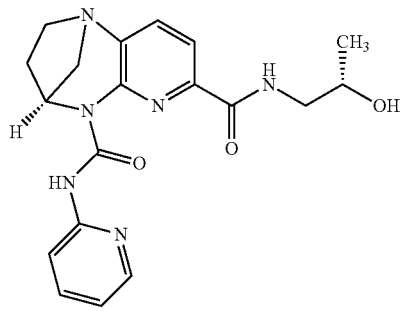

(9S)-5-N-[(2S)-2-hydroxypropyl]-8-N-(pyridin-2-yl)-
1,6,8-triazatricyclo[7.2.1.0²,⁷]dodeca-2(7),3,5-triene-
5,8-dicarboxamide

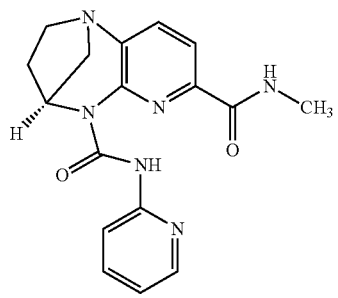

(9S)-5-N-methyl-8-N-(pyridin-2-yl)-
1,6,8-triazatricyclo[7.2.1.0²,⁷]dodeca-
2,(7),3,5-triene-5,8-dicarboxamide

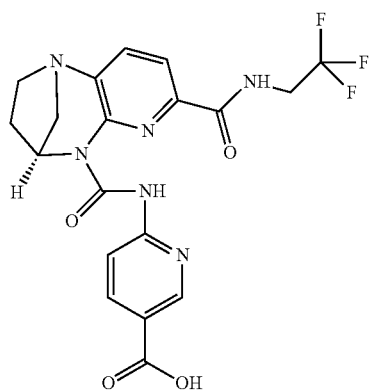

6-{[(9S)-5-[(2,2,2-trifluoroethyl)carbamoyl]-
1,6,8-triazatricyclo[7.2.1.0²,⁷]dodeca-
2,(7),3,5-triene-8-carbonyl]amino}pyridine-3-carboxylic acid

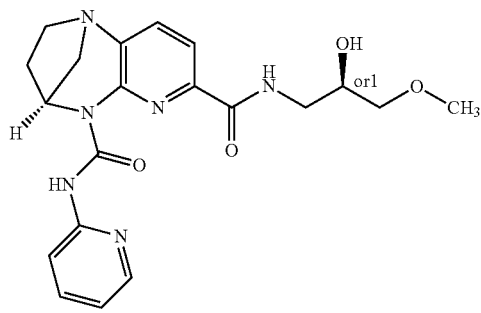

ISOMER 1

(9S)-5-N-[(2R)-2-hydroxy-3-methoxypropyl]-8-N-
(pyridin-2-yl)-1,6,8-triazatricyclo[7.2.1.0²,⁷]dodeca-
2(7),3,5-triene-5,8-dicarboxamide

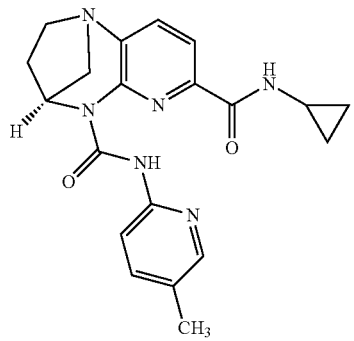

(9S)-5-N-cyclopropyl-8-N-(5-methylpyridin-2-yl)-1,6,8-
triazatricyclo[7.2.1.0²,⁷]dodeca-
2(7),3,5-triene-5,8-dicarboxamide

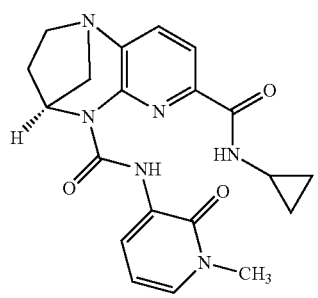

(9S)-5-N-cyclopropyl-8-N-(1-methyl-2-oxo-1,2-
dihydropyridin-3-yl)-1,6,8-triazatricyclo[7.2.1.0²,⁷]
dodeca-2(7),3,5-triene-5,8-dicarboxamide

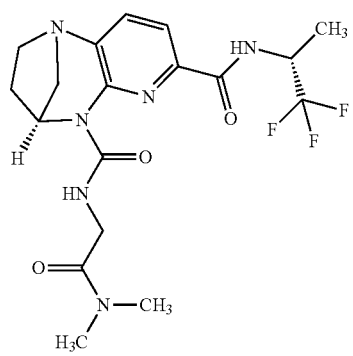

(9S)-8-N-[(dimethylcarbamoyl)methyl]-5-N-[(2R)-
1,1,1-trifluoropropan-2-yl]-1,6,8-triazatricyclo[7.2.1.0²,⁷]
dodeca-2,(7),3,5-triene-5,8-dicarboxamide

871

-continued

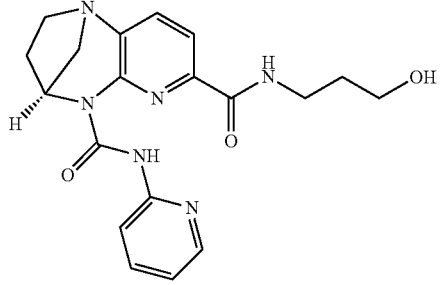

(9S)-5-N-(3-hydroxypropyl)-8-N-(pyridin-2-yl)-1,6,8-
triazatricyclo[7.2.1.0$^{2,7}$]dodeca-
2(7),3,5-triene-5,8-dicarboxamide

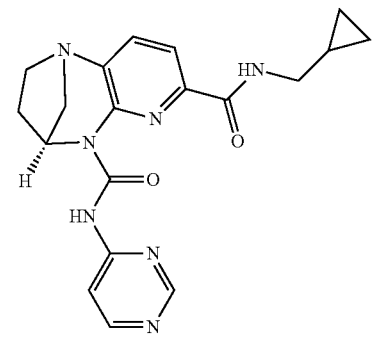

(9S)-5-N-(cyclopropylmethyl)-8-N-(pyrimidin-4-yl)-
1,6,8-triazatricyclo[7.2.1.0$^{2,7}$]dodeca-
2,(7),3,5-triene-5,8-dicarboxamide

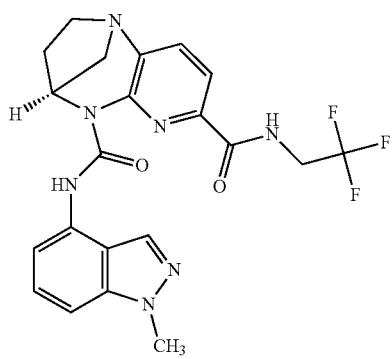

(9S)-8-N-(1-methyl-1H-indazol-4-yl)-5-N-
(2,2,2-trifluoroethyl)-1,6,8-triazatricyclo
[7.2.1.0$^{2,7}$]dodeca-2(7),3,5-triene-5,8-dicarboxamide

872

-continued

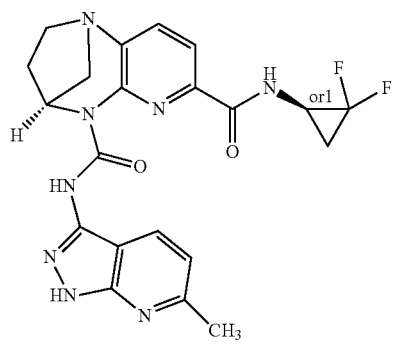

ISOMER 2

(9S)-5-N-[(1R)-2,2-difluorocyclopropyl]-8-N-
{6-methyl-1H-pyrazolo[3,4-b]pyridin-3-yl}-
1,6,8-triazatricyclo[7.2.1.0$^{2,7}$]dodeca
-2(7),3,5-triene-5,8-dicarboxamide

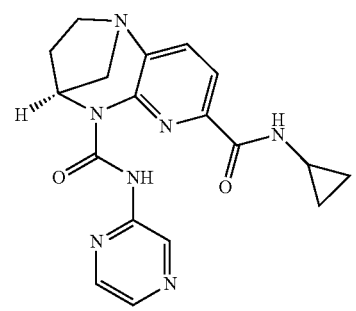

(9S)-5-N-cyclopropyl-8-N-(pyrazin-2-yl)-1,6,8-
triazatricyclo[7.2.1.0$^{2,7}$]dodeca-
2,4,6-triene-5,8-dicarboxamide

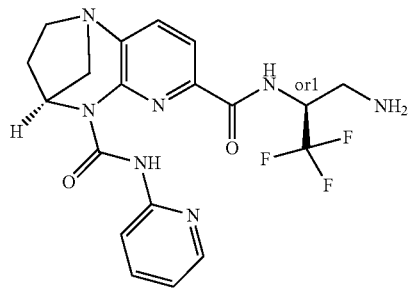

ISOMER 2

(9S)-5-N-[(2S)-3-amino-1,1,1-trifluoropropan-2-yl]-
8-N-(pyridin-2-yl)-1,6,8-triazatricyclo[7.2.1.0$^{2,7}$]
dodeca-2(7),3,5-triene-5,8-dicarboxamide

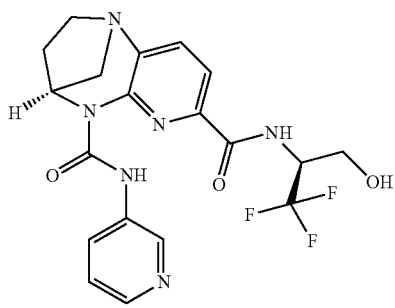

(9S)-8-N-(pyridin-3-yl)-5-N-[(2S)-1,1,1-trifluoro-3-
hydroxypropan-2-yl]-1,6,8-triazatricyclo[7.2.1.0$^{2,7}$]dodeca-
2,4,6-triene-5,8-dicarboxamide

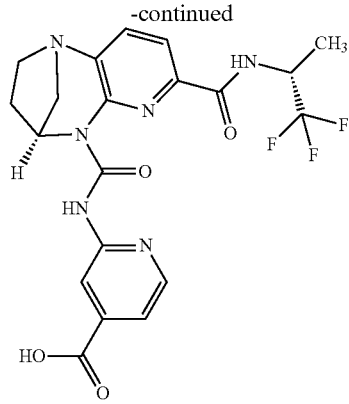

2-{[(9S)-5-{[2R)-1,1,1-trifluoropropan-2-yl]carbamoyl}-1,6,8-triazatricyclo[7.2.1.0²,⁷]dodeca-2,(7),3,5-triene-8-carbonyl]amino}pyridine-4-carboxylic acid

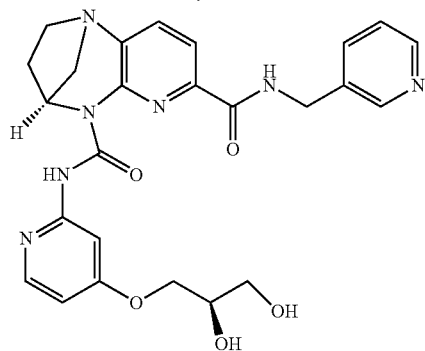

(9S)-8-N-{4-[(2R)-2,3-dihydroxypropoxy]pyridin-2-yl}-5-N-(pyridin-3-ylmethyl)-1,6,8-triazatricyclo[7.2.1.0²,⁷]dodeca-2,(7),3,5-triene-5,8-dicarboxamide

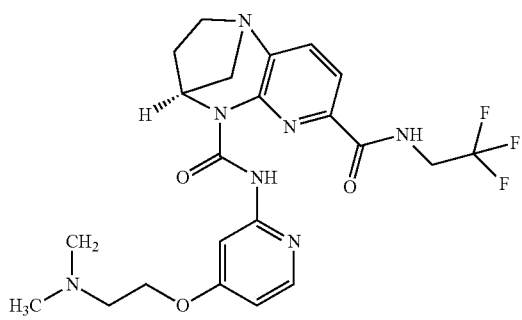

(9S)-8-N-{4-[2-(dimethylamino)ethoxy]pyridin-2-yl}-5-N-(2,2,2-trifluoroethyl)-1,6,8-triazatricyclo[7.2.1.0²,⁷]dodeca-2(7),3,5-triene-5,8-dicarboxamide

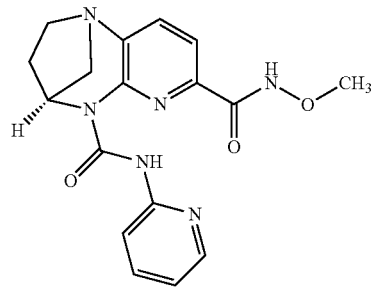

(9S)-5-N-methoxy-8-N-(pyridin-2-yl)-1,6,8-triazatricyclo[7.2.1.0²,⁷]dodeca-2(7),3,5-triene-5,8-dicarboxamide

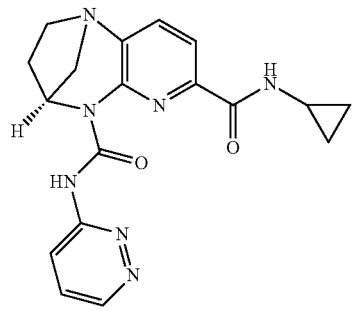

(9S)-5-N-cyclopropyl-8-N-(pyridazin-3-yl)-1,6,8-triazatricyclo[7.2.1.0²,⁷]dodeca-2(7),3,5-triene-5,8-dicarboxamide

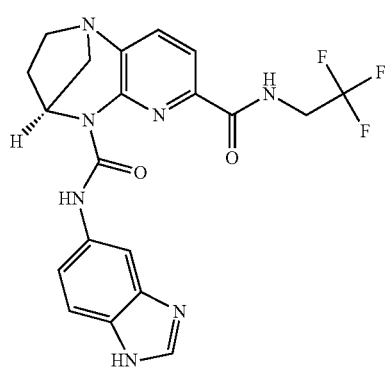

(9S)-8-N-(1H-1,3-benzodiazol-5-yl)-5-N-(2,2,2-trifluoroethyl)-1,6,8-triazatricyclo[7.2.1.0²,⁷]dodeca-2(7),3,5-triene-5,8-dicarboxamide

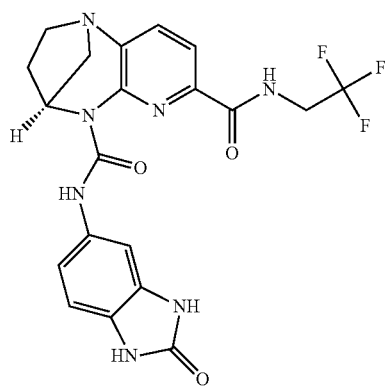

(9S)-8-N-(2-oxo-2,3-dihydro-1H-1,3-benzodiazol-5-yl)-5-N-(2,2,2-trifluoroethyl)-1,6,8-triazatricyclo[7.2.1.0²,⁷]dodeca-2(7),3,5-triene-5,8-dicarboxamide 875
-continued

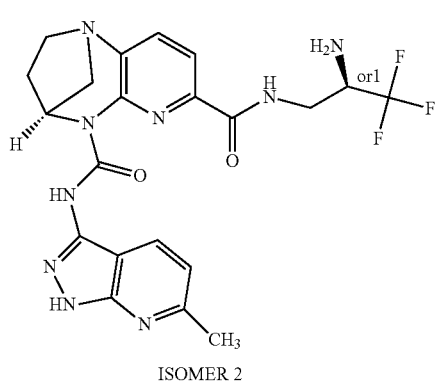

ISOMER 2

(9S)-5-N-[(2R)-2-amino-3,3,3-trifluoropropyl]-8-N-
{6-methyl-1H-pyrazolo[3,4-b]pyridin-3-yl}-
1,6,8-triazatricyclo[7.2.1.0²,⁷]dodeca
-2(7),3,5-triene-5,8-dicarboxamide

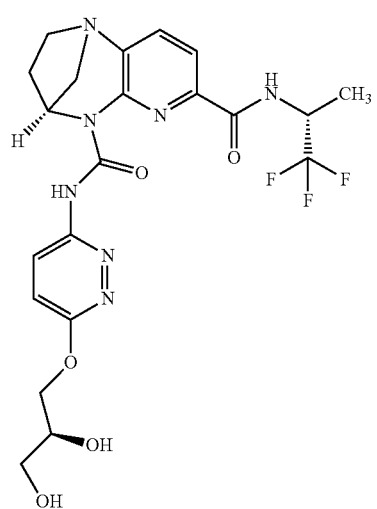

(9S)-8-N-{6-[(2S)-2,3-dihydroxypropoxy]pyridazin-3-yl}-
5-N-[(2R)-1,1,1-trifluoropropan-2-yl]-1,6,8-
triazatricyclo[7.2.1.0²,⁷]
dodeca-2(7),3,5-triene-5,8-dicarboxamide

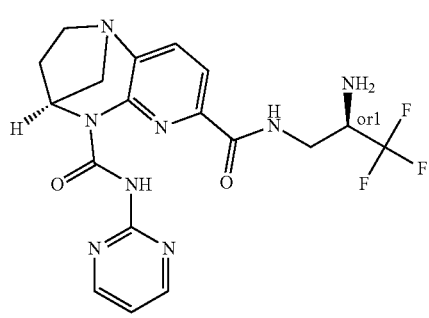

ISOMER 2

(9S)-5-N-[(2R)-2-amino-3,3,3-trifluoropropyl]-8-N-
(pyrimidin-2-yl)-1,6,8-triazatricyclo[7.2.1.0²,⁷]dodeca-
2,4,6-triene-5,8-dicarboxamide 876
-continued

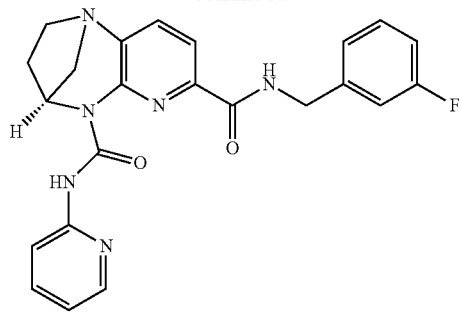

(9S)-5-N-[(3-fluorophenyl)methyl]-8-N-(pyridin-2-yl)-
1,6,8-triazatricyclo[7.2.1.0²,⁷]
dodeca-2(7),3,5-triene-5,8-dicarboxamide

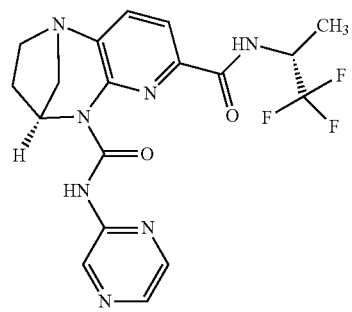

(9S)-8-N-(pyrazin-2-yl)-5-N-[(2R)-1,1,1-trifluoropropan-2-yl]-
1,6,8-triazatricyclo[7.2.1.0²,⁷]
dodeca-2(7),3,5-triene-5,8-dicarboxamide

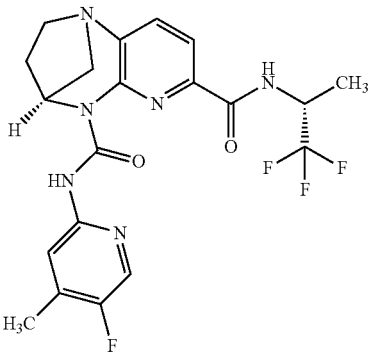

(9S)-8-N-(5-fluoro-4-methylpyridin-2-yl)-5-N-
[(2R)-1,1,1-trifluoropropan-2-yl]-
1,6,8-triazatricyclo[7.2.1.0²,⁷]
dodeca-2(7),3,5-triene-5,8-dicarboxamide

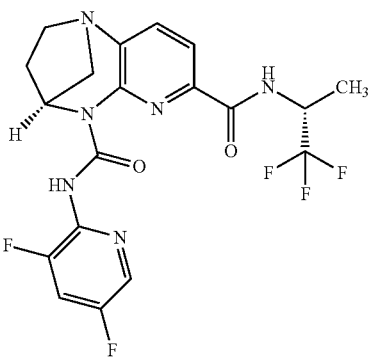

(9S)-8-N-(3,5-difluoropyridin-2-yl)-5-N-[(2R)-1,1,1-
trifluoropropan-2-yl]-1,6,8-triazatricyclo[7.2.1.0²,⁷]
dodeca-2(7),3,5-triene-5,8-dicarboxamide 877
-continued

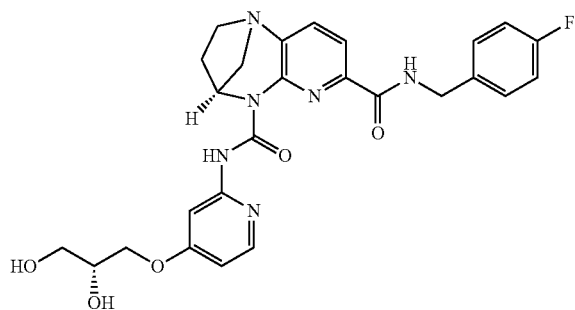

(9S)-8-N-{4-[(2R)-2,3-dihydroxypropoxy]pyridin-2-yl}-
5-N-[(4-fluorophenyl)methyl]-1,6,8-triazatricyclo[7.2.1.0²,⁷]
dodeca-2(7),3,5-triene-5,8-dicarboxamide

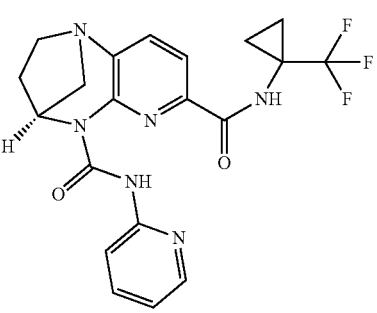

(9S)-8-N-(pyridin-2-yl)-5-N-[1-(trifluoromethyl)cyclopropyl]-
1,6,8-triazatricyclo[7.2.1.0²,⁷]dodeca-
2(7),3,5-triene-5,8-dicarboxamide

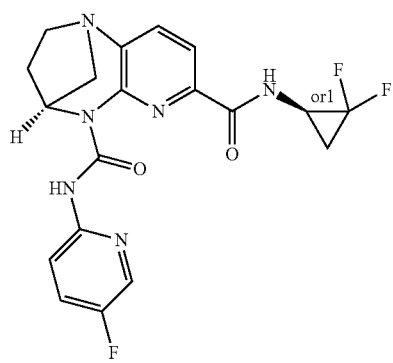

ISOMER 1
(9S)-5-N-[(1R)-2,2-difluorocyclopropyl]-8-N-
(5-fluoropyridin-2-yl)-1,6,8-triazatricyclo[7.2.1.0²,⁷]dodeca-
2(7),3,5-triene-5,8-dicarboxamide 878
-continued

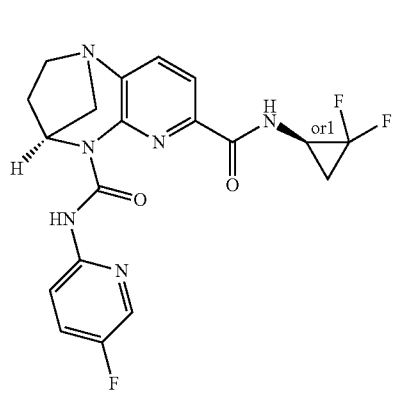

ISOMER 2
(9S)-5-N-[(1R)-2,2-difluorocyclopropyl]-8-N-
(5-fluoropyridin-2-yl)-1,6,8-triazatricyclo[7.2.1.0²,⁷]dodeca-
2(7),3,5-triene-5,8-dicarboxamide

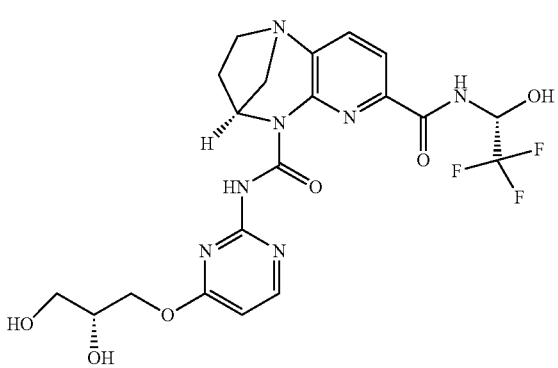

(9S)-8-N-{4-[(2R)-2,3-dihydroxypropoxy]pyrimidin-2-yl}-
5-N-[(2R)-1,1,1-trifluoropropan-2-yl]-1,6,8-triazatricyclo
[7.2.1.0²,⁷]dodeca-2(7),3,5-triene-5,8-dicarboxamide

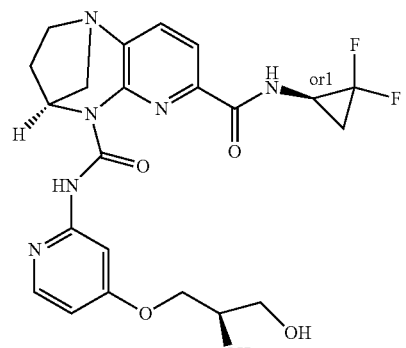

ISOMER 2
(9S)-5-N-[(1R)-2,2-difluorocyclopropyl]-8-N-{4-[(2R)-
2,3-dihydroxypropoxy]pyridin-2-yl}-1,6,8-triazatricyclo[7.2.1.0²,⁷]
dodeca-2(7),3,5-triene-5,8-dicarboxamide

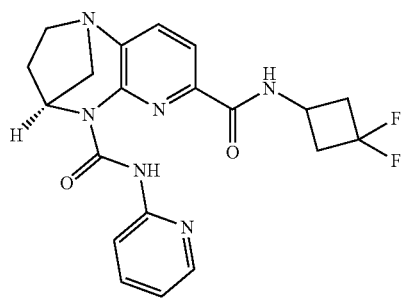

(9S)-5-N-(3,3-difluorocyclobutyl)-8-N-(pyridin-2-yl)-
1,6,8-triazatricyclo[7.2.1.0$^{2,7}$]dodeca-
2(7),3,5-triene-5,8-dicarboxamide

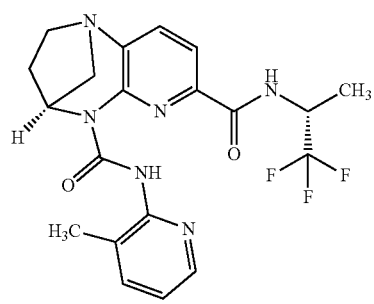

(9S)-8-N-(3-methylpyridin-2-yl)-5-N-
[(2R)-1,1,1-trifluoropropan-2-yl]-1,6,8-
triazatricyclo[7.2.1.0$^{2,7}$]dodeca-
2(7),3,5-triene-5,8-dicarboxamide

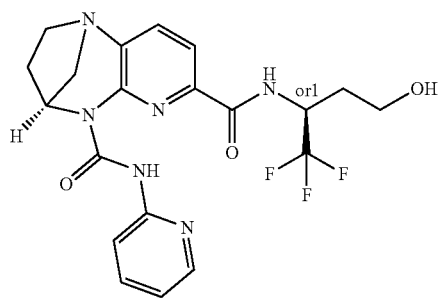

ISOMER 2

(9S)-8-N-(pyridin-2-yl)-5-N-[(2S)-1,1,1-trifluoro-4-
hydroxybutan-2-yl]-1,6,8-triazatricyclo[7.2.1.0$^{2,7}$]dodeca-
2(7),3,5-triene-5,8-dicarboxamide

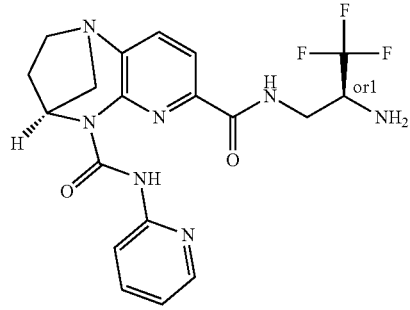

ISOMER 1

(9S)-5-N-[(2S)-2-amino-3,3,3-trifluoropropyl]-8-N-
(pyridin-2-yl)-1,6,8-triazatricyclo[7.2.1.0$^{2,7}$]dodeca-
2(7),3,5-triene-5,8-dicarboxamide

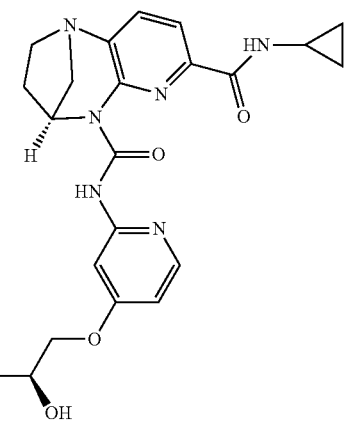

(9S)-5-N-cyclopropyl-8-N-{4-[(2S)-2,3-
dihydroxypropoxy]pyridin-2-yl}-
1,6,8-triazatricyclo[7.2.1.0$^{2,7}$]dodeca-
2(7),3,5-triene-5,8-dicarboxamide

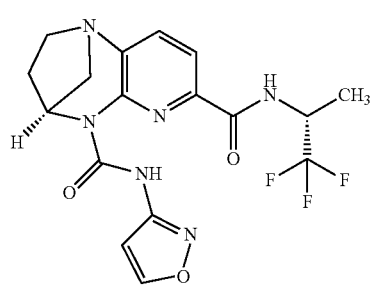

(9S)-8-N-(1,2-oxazol-3-yl)-5-N-[(2R)-1,1,1-trifluoropropan-2-yl]-
1,6,8-triazatricyclo[7.2.1.0$^{2,7}$]dodeca-
2(7),3,5-triene-5,8-dicarboxamide

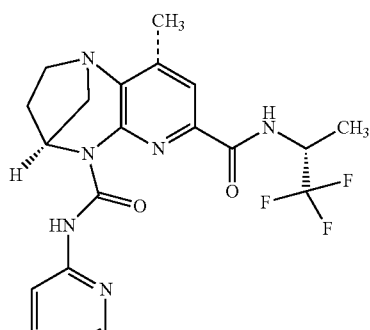

(9S)-3-methyl-8-N-[4-(2-methyl-1,3-oxazol-5-yl)
pyridin-2-yl]-5-N-[(2R)-1,1,1-trifluoropropan-2-yl]-
1,6,8-triazatricyclo[7.2.1.0$^{2,7}$]dodeca-
2(7),3,5-triene-5,8-dicarboxamide

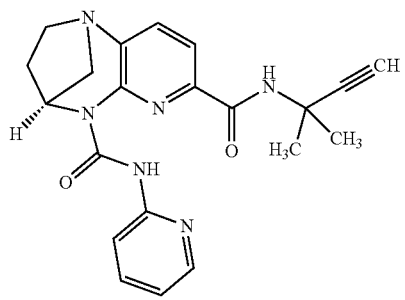

(9S)-5-N-(2-methylbut-3-yn-2-yl)-8-N-(pyridin-2-yl)-
1,6,8-triazatricyclo[7.2.1.0$^{2,7}$]dodeca-
2(7),3,5-triene-5,8-dicarboxamide

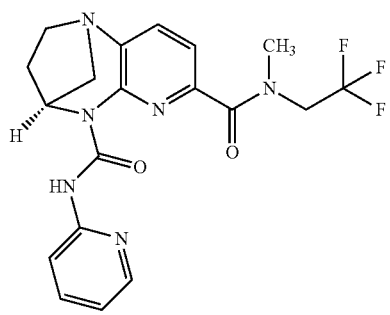

(9S)-5-N-methyl-8-N-(pyridin-2-yl)-5-N-(2,2,2-
trifluoroethyl)-1,6,8-triazatricyclo[7.2.1.0$^{2,7}$]dodeca-
2(7),3,5-triene-5,8-dicarboxamide

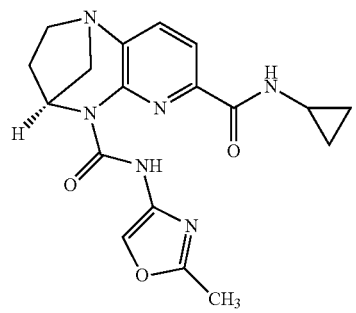

(9S)-5-N-cyclopropyl-8-N-(2-methyl-1,3-oxazol-4-yl)-
1,6,8-triazatricyclo[7.2.1.0$^{2,7}$]dodeca-
2(7),3,5-triene-5,8-dicarboxamide

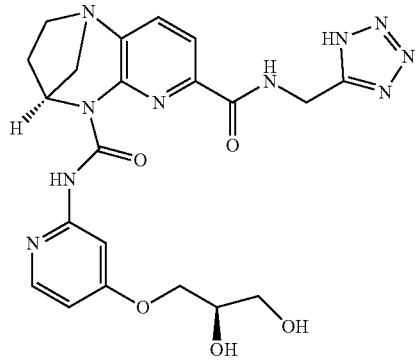

(9S)-8-N-{4-[(2R)-2,3-dihydroxypropoxy]pyridin-2-yl}-5-N-
(1H-1,2,3,4-tetrazol-5-ylmethyl)-1,6,8-triazatricyclo[7.2.1.0$^{2,7}$]
dodeca-2(7),3,5-triene-5,8-dicarboxamide

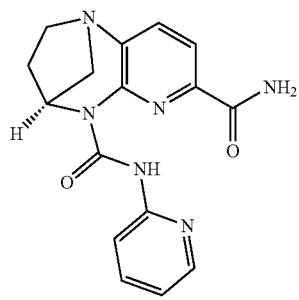

(9S)-8-N-(pyridin-2-yl)-1,6,8-
triazatricyclo[7.2.1.0$^{2,7}$]dodeca-
2(7),3,5-triene-5,8-dicarboxamide

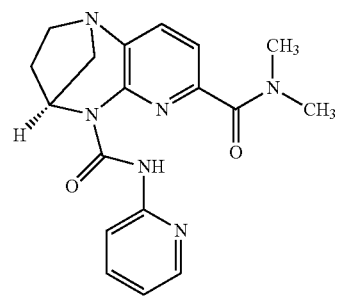

(9S)-5-N,5-N-dimethyl-8-N-(pyridin-2-yl)-
1,6,8-triazatricyclo[7.2.1.0$^{2,7}$]dodeca-
2(7),3,5-triene-5,8-dicarboxamide

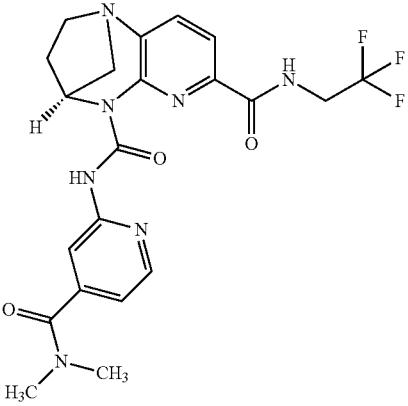

(9S)-8-N-[4-(dimethylcarbamoyl)pyridin-2-yl]-5-N-(2,2,2-
trifluoroethyl)-1,6,8-triazatricyclo[7.2.1.0$^{2,7}$]dodeca-
2(7),3,5-triene-5,8-dicarboxamide

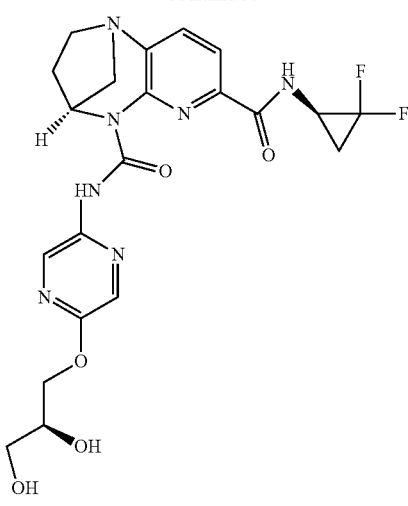

ISOMER 2
(9S)-5-N-[(1R)-2,2-difluorocyclopropyl]-8-N-
{5-[(2R)-2,3-dihydroxypropoxy]pyrazin-2-yl}-
1,6,8-triazatricyclo[7.2.1.0²,⁷]dodeca
-2(7),3,5-triene-5,8-dicarboxamide

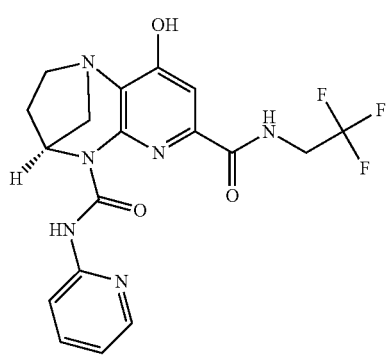

(9S)-3-hydroxy-8-N-(pyridin-2-yl)-5-N-(2,2,2-
trifluoroethyl)-1,6,8-triazatricyclo[7.2.1.0²,⁷]dodeca-
2(7),3,5-triene-5,8-dicarboxamide

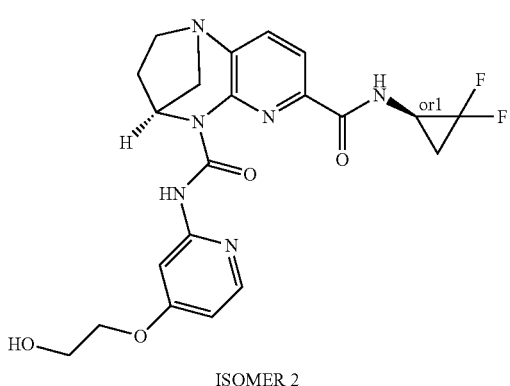

ISOMER 2
(9S)-5-N-[(1R)-2,2-difluorocyclopropyl]-8-N-
[4-(2-hydroxyethoxy)pyridin-2-yl]-
1,6,8-triazatricyclo[7.2.1.0²,⁷]dodeca-
2(7),3,5-triene-5,8-dicarboxamide

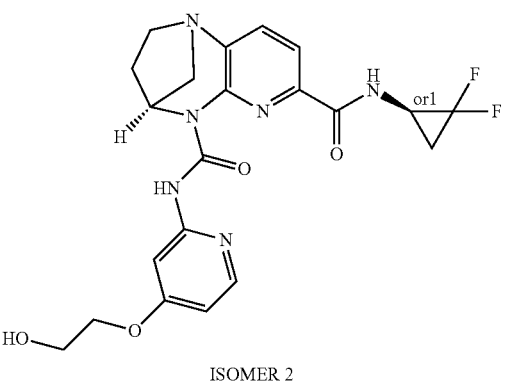

ISOMER 2
(9S)-5-N-[(1R)-2,2-difluorocyclopropyl]-8-N-
[4-(2-hydroxyethoxy)pyridin-2-yl]-
1,6,8-triazatricyclo[7.2.1.0²,⁷]dodeca-
2(7),3,5-triene-5,8-dicarboxamide

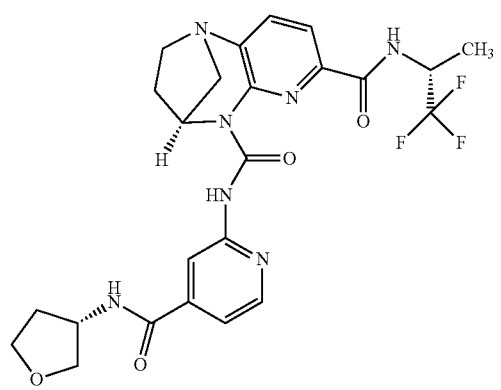

(9S)-8-N-(4-{[(3S)-oxolan-3-yl]carbamoyl}pyridin-2-yl)-
5-N-[(2R)-1,1,1-trifluoropropan-2-yl]-1,6,8-triazatricyclo[7.2.1.0²,⁷]
dodeca-2(7),3,5-triene-5,8-dicarboxamide

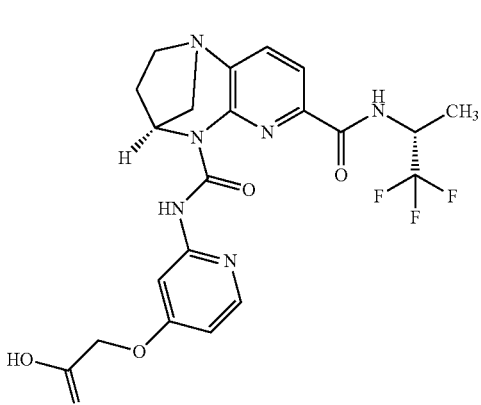

2-[(2-{[(9S)-5-{[(2R)-1,1,1-trifluoropropan-2-yl]
carbamoyl}-1,6,8-triazatricyclo[7.2.1.0²,⁷]dodeca-
2(7),3,5-triene-8-carbonyl]amino}pyridin-4-yl)oxy]acetic acid

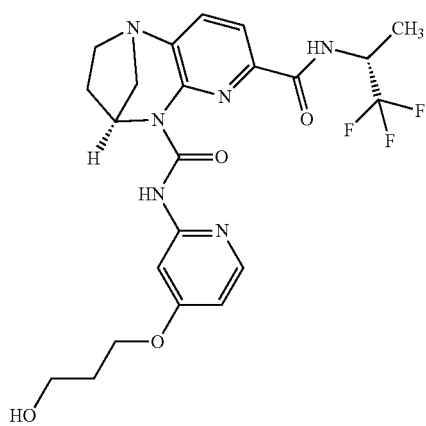

(9S)-8-N-[4-(3-hydroxypropoxy)pyridin-2-yl]-
5-N-[(2R)-1,1,1-trifluoropropan-2-yl]-
1,6,8-triazatricyclo[7.2.1.0²,⁷]
dodeca-2(7),3,5-triene-5,8-dicarboxamide

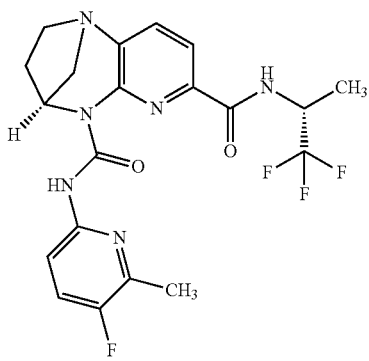

(9S)-8-N-(5-fluoro-6-methylpyridin-2-yl)-5-N-
[(2R)1,1,1-trifluoropropan-2-yl]-1,6,8-
triazatricyclo[7.2.1.0²,⁷]dodeca-
2(7),3,5-triene-5,8-dicarboxamide 2-{[(9S)-5-[(2,2,2-trifluoroethyl)carbamoyl]-1,6,8-
triazatricyclo[7.2.1.0²,⁷]dodeca-2(7),3,5-
triene-8-carbonyl]amino}pyridine-4-carboxylic acid

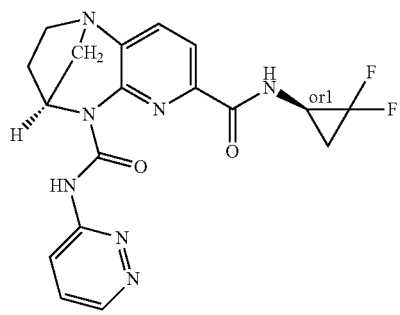

ISOMER 2

(9S)-5-N-[(1R)-2,2-difluorocyclopropyl]-8-N-
(pyridazin-3-yl)-1,6,8-triazatricyclo[7.2.1.0²,⁷]dodeca-
2,4,6-triene-5,8-dicarboxamide

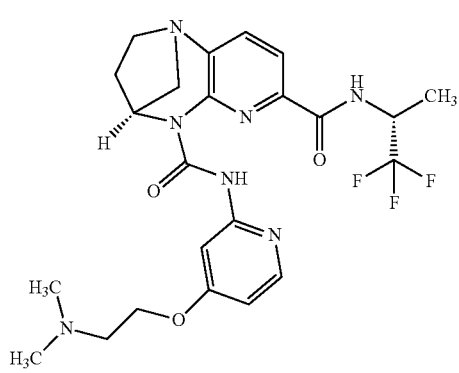

(9S)-8-N-{4-[2-(dimethylamino)ethoxy]pyridin-2-yl}-
5-N[(2R)-1,1,1-trifluoropropan-2-yl]-1,6,8-
triazatricyclo[7.2.1.0²,⁷]dodeca-
2(7),3,5-triene-5,8-dicarboxamide

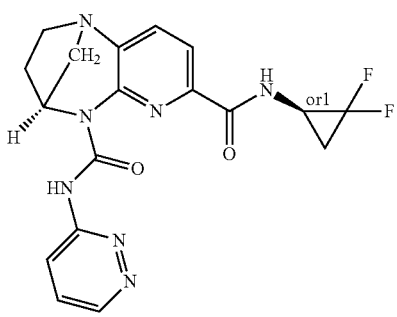

ISOMER 1

(9S)-5-N-[(1R)-2,2-difluorocyclopropyl]-8-N-
(pyridazin-3-yl)-1,6,8-triazatricyclo[7.2.1.0²,⁷]dodeca-
2,4,6-triene-5,8-dicarboxamide

887

-continued

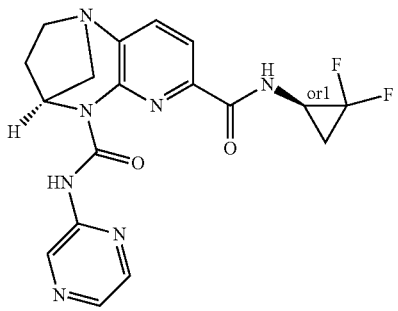

ISOMER 2

(9S)-5-N-[(1R)-2,2-difluorocyclopropyl]-8-N-
(pyrazin-2-yl)-1,6,8-triazatricyclo[7.2.1.0²,⁷]dodeca-
2(7),3,5-triene-5,8-dicarboxamide

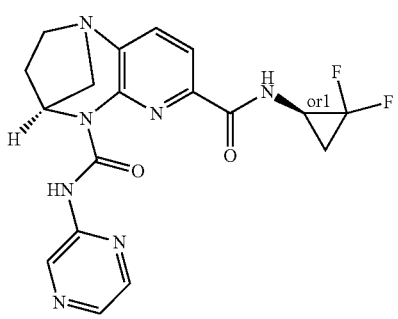

ISOMER 1

(9S)-5-N-[(1R)-2,2-difluorocyclopropyl]-8-N-
(pyrazin-2-yl)-1,6,8-triazatricyclo[7.2.1.0²,⁷]dodeca-
2(7),3,5-triene-5,8-dicarboxamide

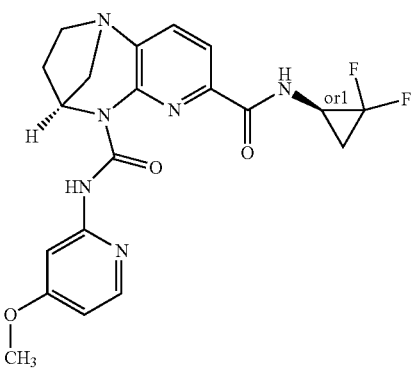

ISOMER 1

(9S)-5-N-[(1R)-2,2-difluorocyclopropyl]-8-N-
(4-methoxypyridin-2-yl)-1,6,8-triazatricyclo[7.2.1.0²,⁷]dodeca-
2(7),3,5-triene-5,8-dicarboxamide

888

-continued

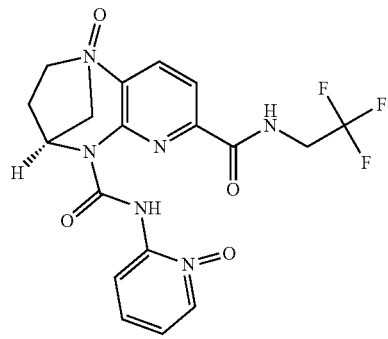

(9S)-1-oxo-8-N-(1-oxo-1λ⁵-pyridin-2-yl)-
5-N-(2,2,2-trifluoroethyl)-1λ⁵,6,8-
triazatricyclo[7.2.1.0²,⁷]dodeca-
2(7),3,5-triene-5,8-dicarboxamide

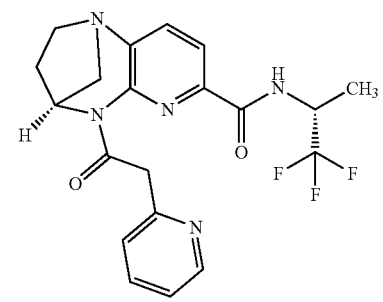

(9S)-8-[2-(pyridin-2-yl)acetyl]-N-[(2R)-1,1,1-
trifluoropropan-2-yl]-1,6,8-triazatricyclo[7.2.1.0²,⁷]
dodeca-2(7),3,5-triene-5-dicarboxamide

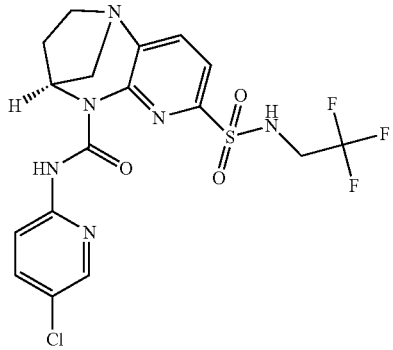

(9S)-N-(5-chloropyridin-2-yl)-5-[(2,2,2-trifluoroethyl)
sulfamoyl]-1,6,8-triazatricyclo[7.2.1.0²,⁷]dodeca-
2,4,6-triene-8-carboxamide

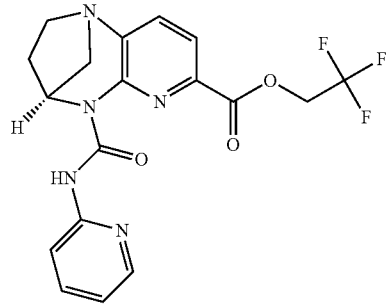

2,2,2-trifluoroethyl (9S)-8-[(pyridin-2-yl)carbamoyl]-1,6,8-
triazatricyclo[7.2.1.0²,⁷]dodeca-
2(7),3,5-triene-5-carboxylate

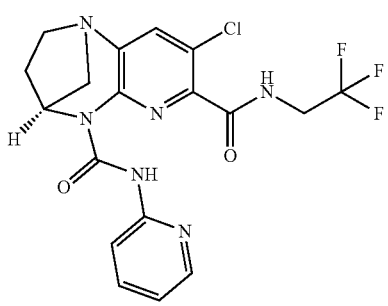

(9S)-4-chloro-8-N-(pyridin-2-yl)-5-N-(2,2,2-trifluoroethyl)-1,6,8-triazatricyclo[7.2.1.0²,⁷]dodeca-2(7),3,5-triene-5,8-dicarboxamide

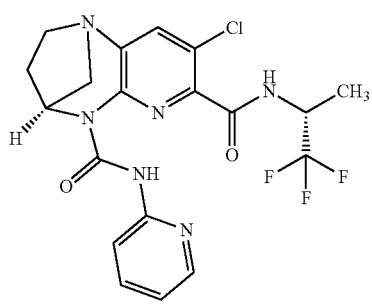

(9S)-4-chloro-8-N-(pyridin-2-yl)-5-N-[(2R)-1,1,1-trifluoropropan-2-yl]-1,6,8-triazatricyclo[7.2.1.0²,⁷]dodeca-2(7),3,5-triene-5,8-dicarboxamide

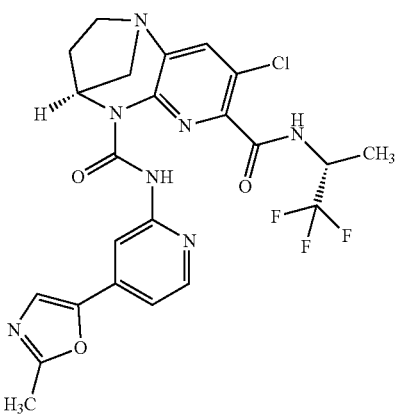

(9S)-4-chloro-8-N-[4-(2-methyl-1,3-oxazol-5-yl)pyridin-2-yl]-5-N-[(2R)-1,1,1-trifluoropropan-2-yl]-1,6,8-triazatricyclo[7.2.1.0²,⁷]dodeca-2,4,6-triene-5,8-dicarboxamide

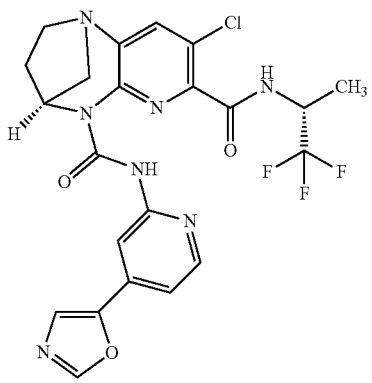

(9S)-4-chloro-8-N-[4-(1,3-oxazol-5-yl)pyridin-2-yl]-5-N-[(2R)-1,1,1-trifluoropropan-2-yl]-1,6,8-triazatricyclo[7.2.1.0²,⁷]dodeca-2,4,6-triene-5,8-dicarboxamide

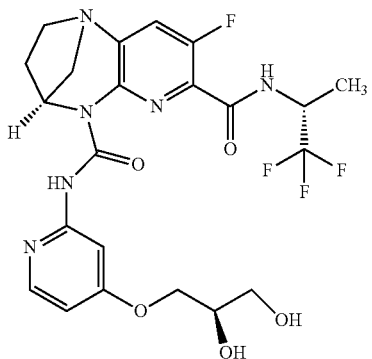

(9S)-8-N-{4-[(2R)-2,3-dihydroxypropoxy]pyridin-2-yl}-4-fluoro-5-N-[(2R)-1,1,1-trifluoropropan-2-yl]-1,6,8-triazatricyclo[7.2.1.0²,⁷]dodeca-2(7),3,5-triene-5,8-dicarboxamide

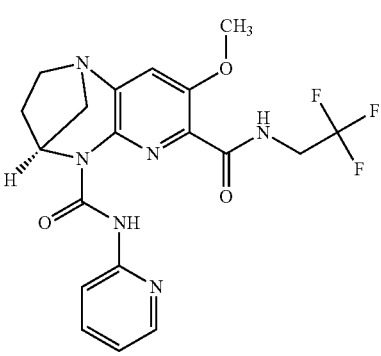

(9S)-4-methoxy-8-N-(pyridin-2-yl)-5-N-(2,2,2-trifluoroethyl)-1,6,8-triazatricyclo[7.2.1.0²,⁷]dodeca-2(7),3,5-triene-5,8-dicarboxamide

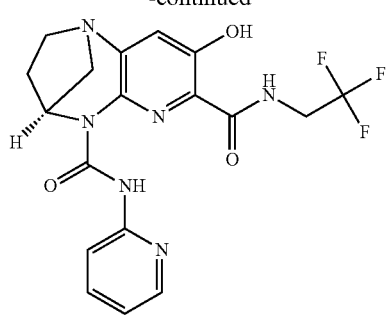

(9S)-4-hydroxy-8-N-(pyridin-2-yl)-5-N-(2,2,2-trifluoroethyl)-1,6,8-triazatricyclo[7.2.1.0²,⁷]dodeca-2(7),3,5-triene-5,8-dicarboxamide

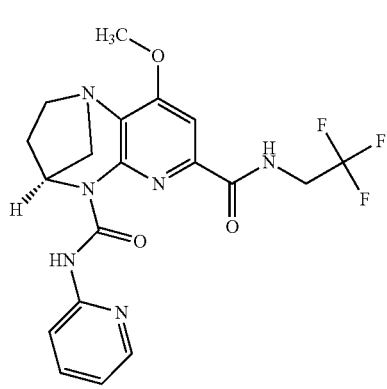

(9S)-3-methoxy-8-N-(pyridin-2-yl)-5-N-(2,2,2-trifluoroethyl)-1,6,8-triazatricyclo[7.2.1.0²,⁷]dodeca-2(7),3,5-triene-5,8-dicarboxamide

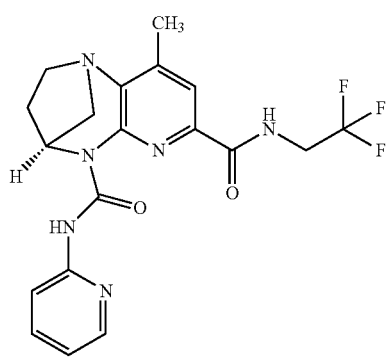

(9S)-3-methyl-8-N-(pyridin-2-yl)-5-N-(2,2,2-trifluoroethyl)-1,6,8-triazatricyclo[7.2.1.0²,⁷]dodeca-2(7),3,5-triene-5,8-dicarboxamide

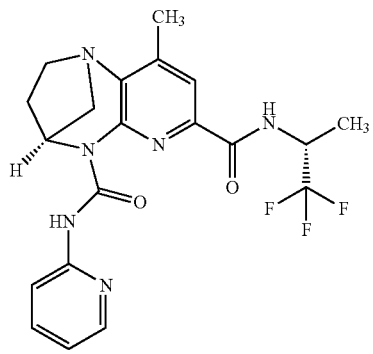

(9S)-3-methyl-8-N-(pyridin-2-yl)-5-N-[(2R)-1,1,1-trifluoropropan-2-yl]-1,6,8-triazatricyclo[7.2.1.0²,⁷]dodeca-2(7),3,5-triene-5,8-dicarboxamide

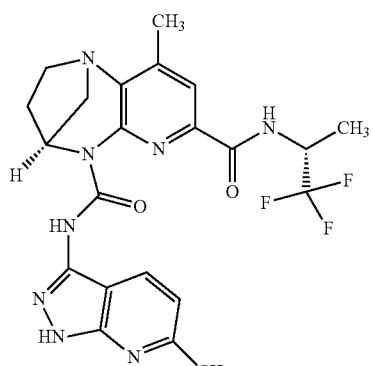

(9S)-3-methyl-8-N-{6-methyl-1H-pyrazolo[3,4-b]pyridin-3-yl}-5-N-[(2R)-1,1,1-trifluoropropan-2-yl]-1,6,8-triazatricyclo[7.2.1.0²,⁷]dodeca-2(7),3,5-triene-5,8-dicarboxamide

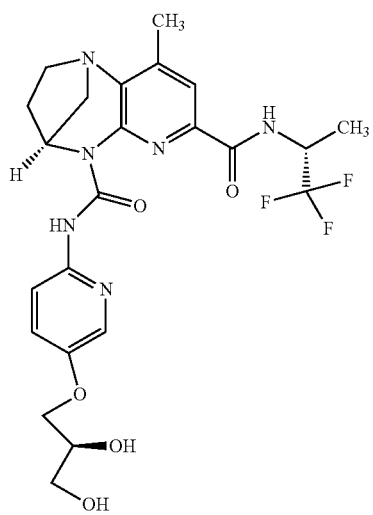

(9S)-8-N-{5-[(2S)-2,3-dihydroxypropoxy]pyridin-2-yl}-3-methyl-5-N-[(2R)-1,1,1-trifluoropropan-2-yl]-1,6,8-triazatricyclo[7.2.1.0²,⁷]dodeca-2(7),3,5-triene-5,8-dicarboxamide

893

-continued

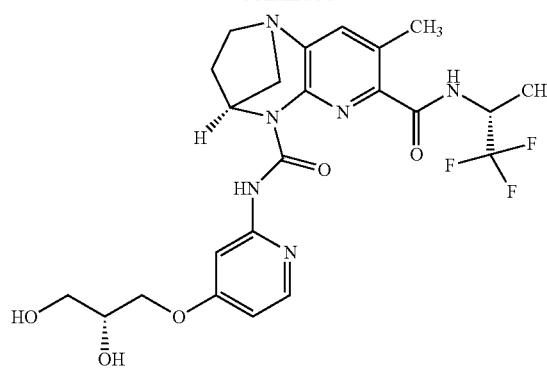

(9S)-8-N-{4-[(2R)-2,3-dihydroxypropoxy]pyridin-2-yl}-4-
methyl-5-N-[(2R)-1,1,1-trifluoropropan-2-yl]-1,6,8-
triazatricyclo[7.2.1.0²,⁷]dodeca-2(7),3,5-
triene-5,8-dicarboxamide

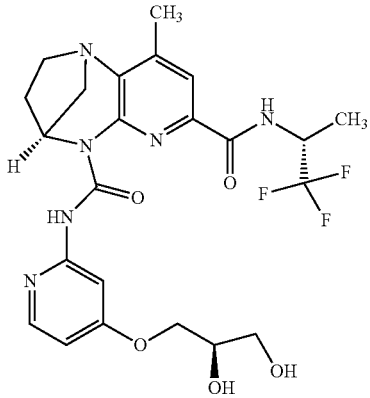

(9S)-8-N-{4-[(2R)-2,3-dihydroxypropoxy]pyridin-2-yl}-3-
methyl-5-N-[(2R)-1,1,1-trifluoropropan-2-yl]-1,6,8-
triazatricyclo[7.2.1.0²,⁷]dodeca-2(7),3,5-
triene-5,8-dicarboxamide

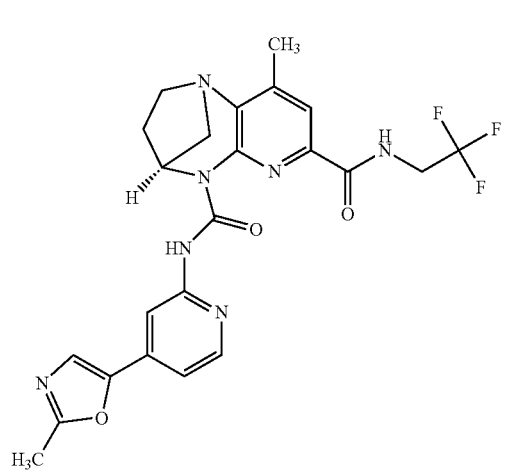

(9S)-3-methyl-8-N-[4-(2-methyl-1,3-oxazol-5-yl)pyridin-2-yl]-
5-N-(2,2,2-trifluoroethyl)-1,6,8-triazatricyclo[7.2.1.0²,⁷]
dodeca-2(7),3,5-triene-5,8-dicarboxamide

894

-continued

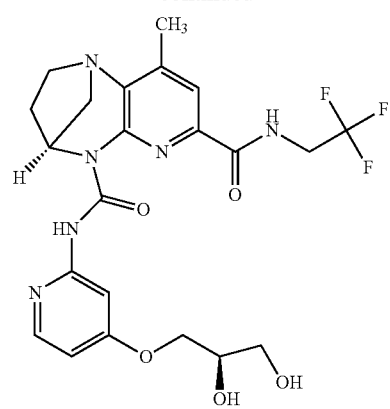

(9S)-8-N-{4-[(2R)-2,3-dihydroxypropoxy]pyridin-2-yl}-3-
methyl-5-N-(2,2,2-trifluoroethyl)-1,6,8-
triazatricyclo[7.2.1.0²,⁷]dodeca-2(7),3,5-
triene-5,8-dicarboxamide

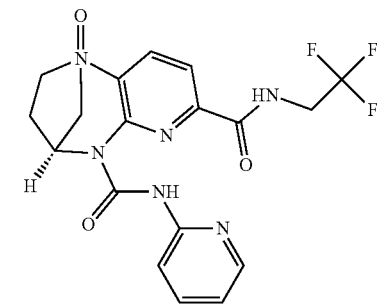

(9S)-1-oxo-8-N-(pyridin-2-yl)-5-N-(2,2,2-
trifluoroethyl)-1λ⁵,6,8-triazatricyclo[7.2.1.0²,⁷]
dodeca-2(7),3,5-triene-5,8-dicarboxamide

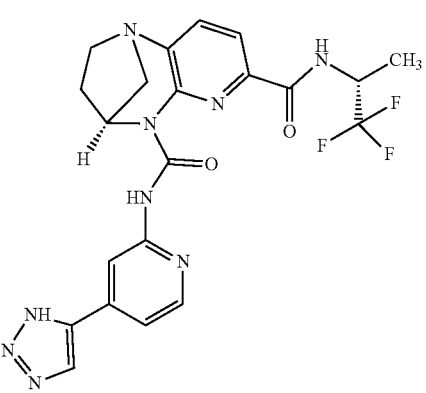

(9S)-8-N-[4-(1H-1,2,3-triazol-5-yl)pyridin-2-yl]-
5-N-[(2R)-1,1,1-trifluoropropan-2-yl]-1,6,8-triazatricyclo[7.2.1.0²,⁷]
dodeca-2(7),3,5-triene-5,8-dicarboxamide

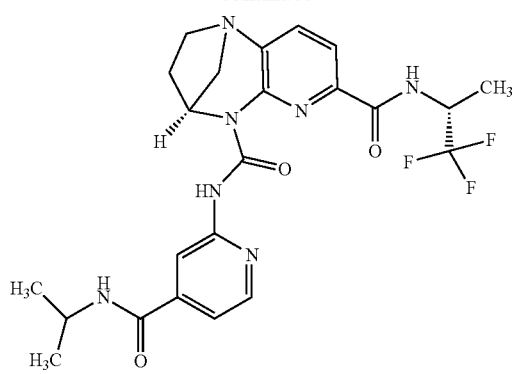

(9S)-8-N-{4-[(propan-2-yl)carbamoyl]pyridin-2-yl}-5-N-[(2R)-1,1,1-trifluoropropan-2-yl]-1,6,8-triazatricyclo[7.2.1.0²,⁷]dodeca-2(7),3,5-triene-5,8-dicarboxamide

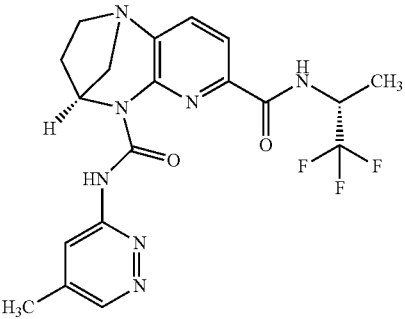

(9S)-8-N-(5-methylpyridazin-3-yl)-5-N-[(2R)-1,1,1-trifluoropropan-2-yl]-1,6,8-triazatricyclo[7.2.1.0²,⁷]dodeca-2(7),3,5-triene-5,8-dicarboxamide

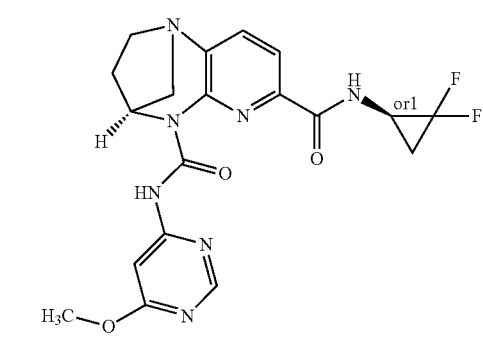

ISOMER 1
(9S)-5-N-[(1R)-2,2-difluorocyclopropyl]-8-N-(6-methoxypyrimidin-4-yl)-1,6,8-triazatricyclo[7.2.1.0²,⁷]dodeca-2(7),3,5-triene-5,8-dicarboxamide

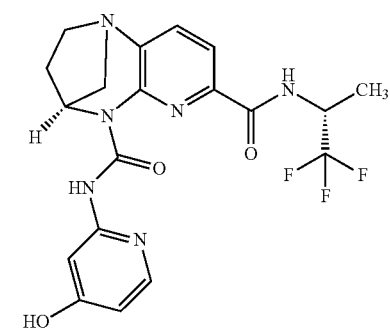

(9S)-8-N-(4-hydroxypyridin-2-yl)-5-N-[(2R)-1,1,1-trifluoropropan-2-yl]-1,6,8-triazatricyclo[7.2.1.0²,⁷]dodeca-2(7),3,5-triene-5,8-dicarboxamide

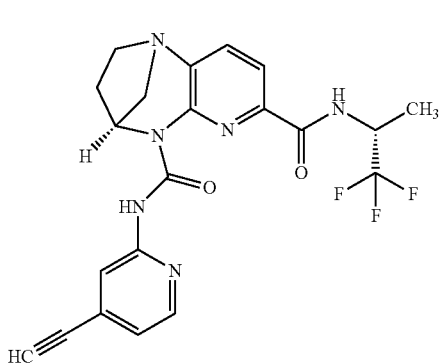

(9S)-8-N-(4-ethynylpyridin-2-yl)-5-N-[(2R)-1,1,1-trifluoropropan-2-yl]-1,6,8-triazatricyclo[7.2.1.0²,⁷]dodeca-2(7),3,5-triene-5,8-dicarboxamide

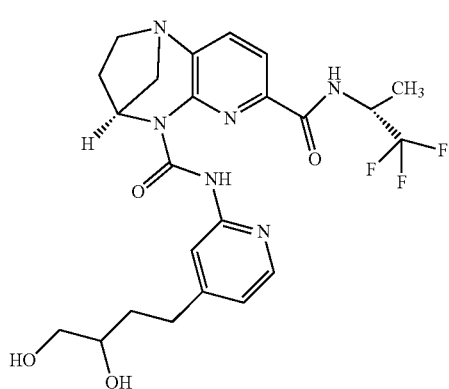

ISOMER 1
(9S)-8-N-{4-[(3R)-3,4-dihydroxybutyl]pyridin-2-yl}-5-N-[(2R)-1,1,1-trifluoropropan-2-yl]-1,6,8-triazatricyclo[7.2.1.0²,⁷]dodeca-2(7),3,5-triene-5,8-dicarboxamide

| 897 | 898 |
|---|---|
| -continued | -continued |
| 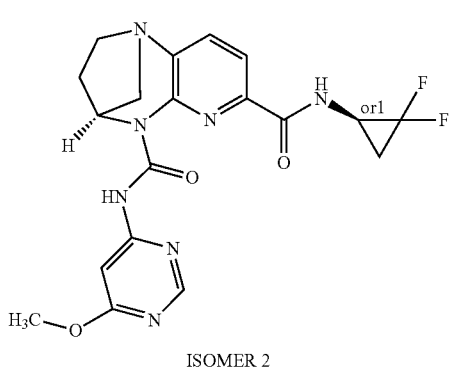 | 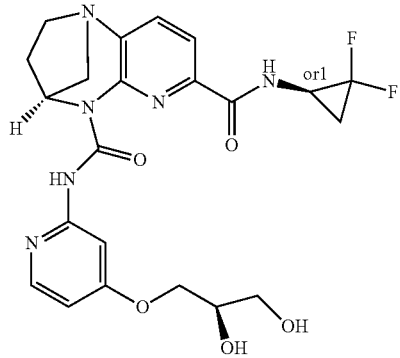 |
| ISOMER 2 | ISOMER 1 |
| (9S)-5-N-[(1R)-2,2-difluorocyclopropyl]-8-N-(6-methoxypyrimidin-4-yl)-1,6,8-triazatricyclo[7.2.1.0²,⁷]dodeca-2(7),3,5-triene-5,8-dicarboxamide | (9S)-5-N-[(1R)-2,2-difluorocyclopropyl]-8-N-{4-[(2R)-2,3-dihydroxypropoxy]pyridin-2-yl}-1,6,8-triazatricyclo[7.2.1.0²,⁷]dodeca-2(7),3,5-triene-5,8-dicarboxamide |
| 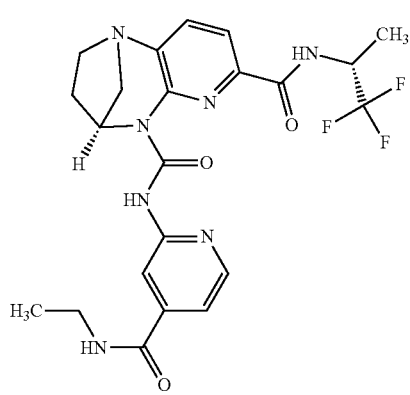 | 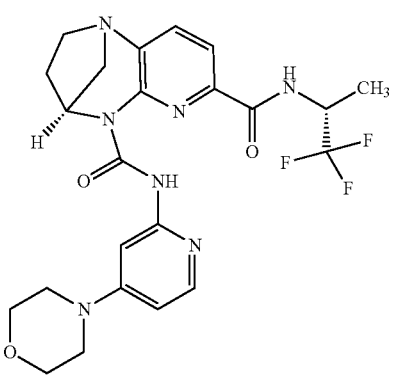 |
| (9S)-8-N-[4-(ethylcarbamoyl)pyridin-2-yl]-5-N-[(2R)-1,1,1-trifluoropropan-2-yl]-1,6,8-triazatricyclo[7.2.1.0²,⁷]dodeca-2(7),3,5-triene-5,8-dicarboxamide | (9S)-8-N-[4-(morpholin-4-yl)pyridin-2-yl]-5-N-[(2R)-1,1,1-trifluoropropan-2-yl]-1,6,8-triazatricyclo[7.2.1.0²,⁷]dodeca-2(7),3,5-triene-5,8-dicarboxamide |
| 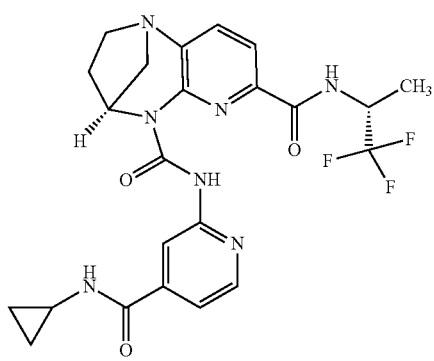 | 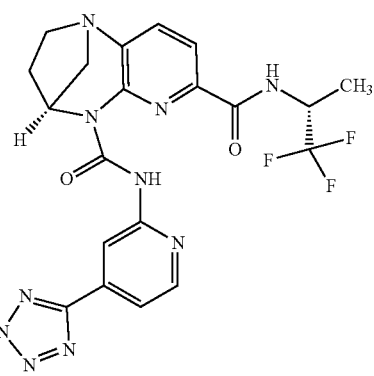 |
| (9S)-8-N-[4-(cyclopropylcarbamoyl)pyridin-2-yl]-5-N-[(2R)-1,1,1-trifluoropropan-2-yl]-1,6,8-triazatricyclo[7.2.1.0²,⁷]dodeca-2(7),3,5-triene-5,8-dicarboxamide | (9S)-8-N-[4-(2H-1,2,3,4-tetrazol-5-yl)pyridin-2-yl]-5-N-[(2R)-1,1,1-trifluoropropan-2-yl]-1,6,8-triazatricyclo[7.2.1.0²,⁷]dodeca-2(7),3,5-triene-5,8-dicarboxamide |

899
-continued

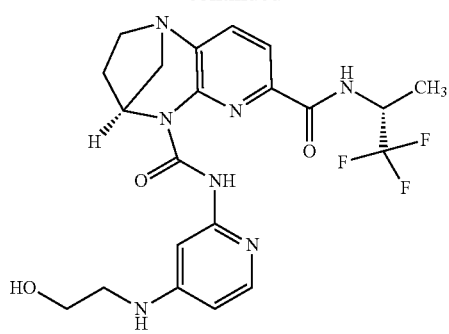

(9S)-8-N-{4-[(2-hydroxyethyl)amino]pyridin-2-yl}-5-N-
[(2R)-1,1,1-trifluoropropan-2-yl]-1,6,8-triazatricyclo[7.2.1.0²,⁷]
dodeca-2(7),3,5-triene-5,8-dicarboxamide

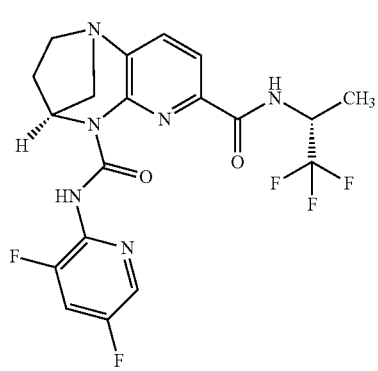

(9S)-8-N-(3,5-difluoropyridin-2-yl)-5-N-
[(2R)-1,1,1-trifluoropropan-2-yl]-1,6,8-
triazatricyclo[7.2.1.0²,⁷]
dodeca-2(7),3,5-triene-5,8-dicarboxamide

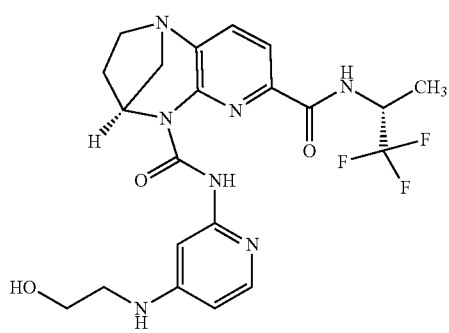

(9S)-8-N-{4-[(2-hydroxyethyl)amino]pyridin-2-yl}-5-N-
[(2R)-1,1,1-trifluoropropan-2-yl]-1,6,8-triazatricyclo[7.2.1.0²,⁷]
dodeca-2(7),3,5-triene-5,8-dicarboxamide 900
-continued

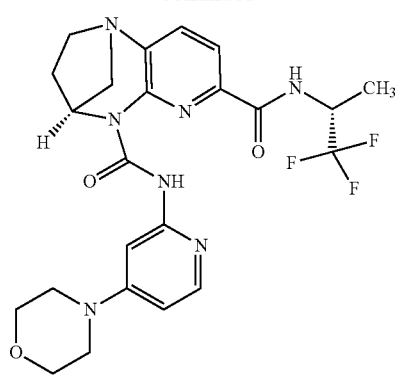

(9S)-8-N-[4-(morpholin-4-yl)pyridin-2-yl]-5-N-
[(2R)-1,1,1-trifluoropropan-2-yl]-1,6,8-triazatricyclo[7.2.1.0²,⁷]
dodeca-2(7),3,5-triene-5,8-dicarboxamide

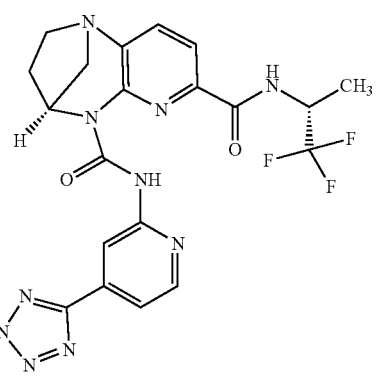

(9S)-8-N-[4-(2H-1,2,3,4-tetrazol-5-yl)pyridin-2-yl]-5-N-
[(2R)-1,1,1-trifluoropropan-2-yl]-1,6,8-triazatricyclo[7.2.1.0²,⁷]
dodeca-2(7),3,5-triene-5,8-dicarboxamide

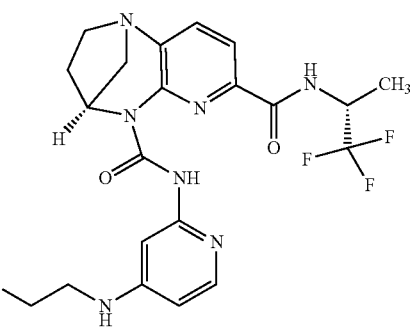

(9S)-8-N-{4-[(2-hydroxyethyl)amino]pyridin-2-yl}-5-N-
[(2R)-1,1,1-trifluoropropan-2-yl]-1,6,8-triazatricyclo[7.2.1.0²,⁷]
dodeca-2(7),3,5-triene-5,8-dicarboxamide

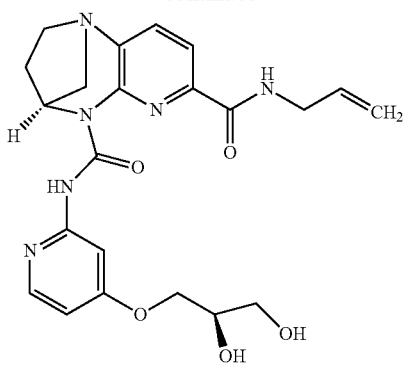

(9S)-8-N-{4-[(2R)-2,3-dihydroxypropoxy]pyridin-2-yl}-
5-N-(prop-2-en-1-yl)-1,6,8-triazatricyclo[7.2.1.0²,⁷]
dodeca-2(7),3,5-triene-5,8-dicarboxamide

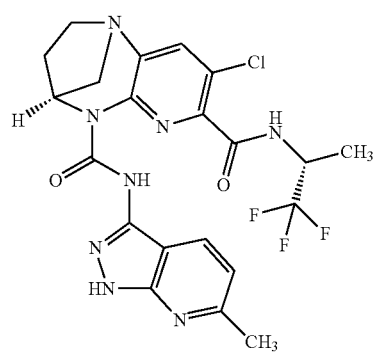

(9S)-4-chloro-8-N-{6-methyl-1H-pyrazolo[3,4-b]pyridin-3-yl}-
5-N-[(2R)-1,1,1-trifluoropropan-2-yl]-1,6,8-triazatricyclo[7.2.1.0²,⁷]
dodeca-2(7),3,5-triene-5,8-dicarboxamide

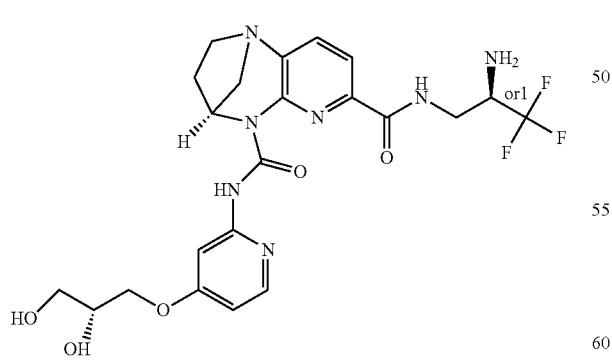

ISOMER 2

(9S)-5-N-[(2R)-2-amino-3,3,3-trifluoropropyl]-8-N-
{4-[(2R)-2,3-dihydroxypropoxy]pyridin-2-yl}-
1,6,8-triazatricyclo[7.2.1.0²,⁷]
dodeca-2(7),3,5-triene-5,8-dicarboxamide

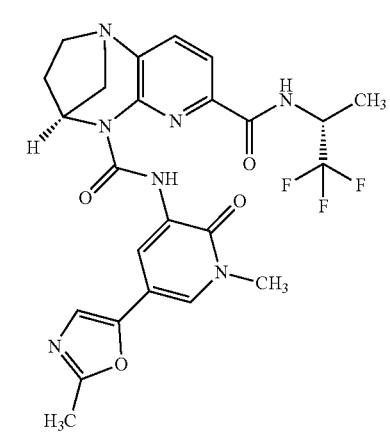

(9S)-8-N-[6-(2-methyl-1,3-oxazol-5-yl)pyrimidin-4-yl]-
5-N-[(2R)-1,1,1-trifluoropropan-2-yl]-1,6,8-
triazatricyclo[7.2.1.0²,⁷]
dodeca-2(7),3,5-triene-5,8-dicarboxamide (9S)-8-N-[1-methyl-5-(2-methyl-1,3-oxazol-5-yl)-2-oxo-1,2-
dihydropyridin-3-yl]-5-N-[(2R)-1,1,1-trifluoropropan-2-yl]-1,6,8-
triazatricyclo[7.2.1.0²,⁷]
dodeca-2(7),3,5-triene-5,8-dicarboxamide

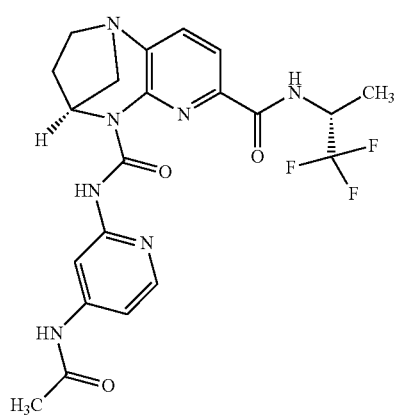

(9S)-8-N-(4-acetamidopyridin-2-yl)-5-N-
[(2R)-1,1,1-trifluoropropan-2-yl]-1,6,8-
triazatricyclo[7.2.1.0²,⁷]
dodeca-2,4,6-triene-5,8-dicarboxamide -continued

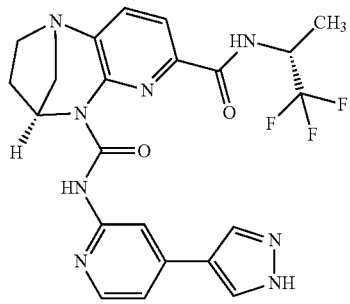

(9S)-8-N-[4-(1H-pyrazol-4-yl)pyridin-2-yl]-
5-N-[(2R)-1,1,1-trifluoropropan-2-yl]-1,6,8-
triazatricyclo[7.2.1.0$^{2,7}$]
dodeca-2(7),3,5-triene-5,8-dicarboxamide

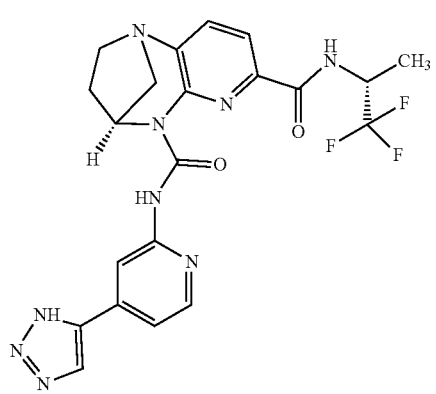

(9S)-8-N-[4-(1H-1,2,4-triazol-5-yl)pyridin-2-yl]-
5-N-[(2R)-1,1,1-trifluoropropan-2-yl]-1,6,8-triazatricyclo[7.2.1.0$^{2,7}$]
dodeca-2(7),3,5-triene-5,8-dicarboxamide

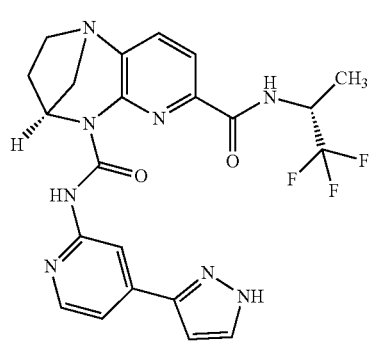

(9S)-8-N-[4-(1H-pyrazol-3-yl)pyridin-2-yl]-
5-N-[(2R)-1,1,1-trifluoropropan-2-yl]-1,6,8-
triazatricyclo[7.2.1.0$^{2,7}$]
dodeca-2(7),3,5-triene-5,8-dicarboxamide -continued

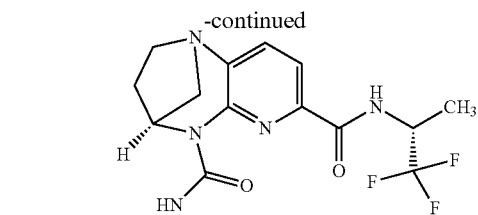

(9S)-8-N-(4-methanesulfonamidopyridin-2-yl)-5-N-
[(2R)-1,1,1-trifluoropropan-2-yl]-1,6,8-
triazatricyclo[7.2.1.0$^{2,7}$]
dodeca-2,4,6-triene-5,8-dicarboxamide

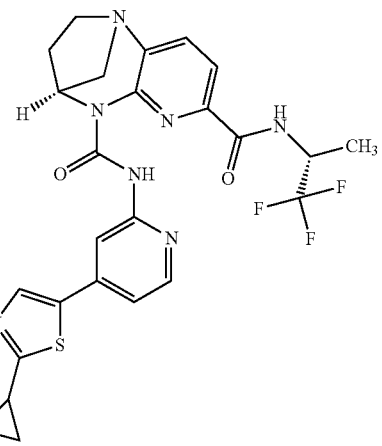

(9S)-8-N-[4-(2-cyclopropyl-1,3-thiazol-5-yl)pyridin-2-yl]-
5-N-[(2R)-1,1,1-trifluoropropan-2-yl]-1,6,8-triazatricyclo[7.2.1.0$^{2,7}$]
dodeca-2,4,6-triene-5,8-dicarboxamide.

2. A compound or pharmaceutically acceptable salt according to claim 1 wherein the compound is (4S)—N5-(5-((R)-2,3-dihydroxypropoxy)pyrazin-2-yl)-N7-(2,2,2-trifluoroethyl)-3,4-dihydro-1,4-methanopyrido[2,3-b][1,4]diazepine-5,7(2H)-dicarboxamide

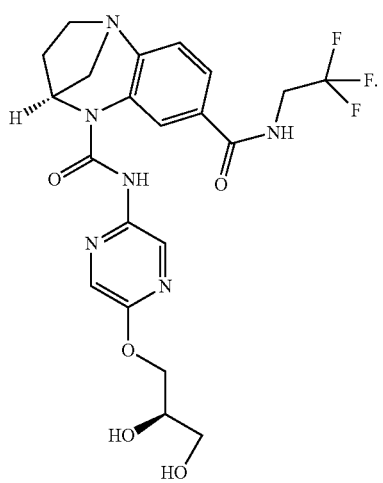 [SMILES: O=C(NCC(F)(F)F)c1ccc2c(c1)N(C(=O)Nc1cnc(OC[C@H](O)CO)cn1)[C@H]1CCN2C1]

3. A pharmaceutical composition comprising a compound of claim 1 and a pharmaceutically acceptable carrier.

4. The pharmaceutical composition of claim 3 further comprising an additional active agent.

5. A method for treating insulin resistance, a metabolic syndrome, metabolic dysfunctions, or complications thereof, or for increasing insulin sensitivity, comprising administering compound or pharmaceutically acceptable salt according to claim 1 to a subject in need thereof.

6. A method for treating diseases or disorders resulting from diminished SIRT1 expression or activity, which comprises administering compound or pharmaceutically acceptable salt according to claim 1 to a subject in need thereof.

7. The method according to claim 6 wherein the diseases or disorders resulting from diminished SIRT1 expression or activity are elected from aging or stress, metabolic dysfunctions, neurodegenerative diseases, cardiovascular disease, or inflammatory disease.

8. The method according to claim 6, wherein diseases or disorders are selected from psoriasis, atopic dermatitis, acne, rosacea, warts, inflammatory bowel disease, Crohn's Disease, ulcerative colitis, osteoporosis, sepsis, arthritis, COPD, systemic lupus erythematosus, phthalmic inflammation, alopetia, treatment of wounds, ocular disorders, dry eye, keratitis and uveitis.

9. The method according to claim 8, wherein the disease is inflammatory bowel disease, Crohn's Disease, or ulcerative colitis.

10. A method for treating insulin resistance, a metabolic syndrome, metabolic dysfunctions, or complications thereof, or for increasing insulin sensitivity, comprising administering a pharmaceutical composition according to claim 3 to a subject in need thereof.

11. A method for treating diseases or disorders resulting from diminished SIRT1 expression or activity, comprising administering a pharmaceutical composition according to claim 3 to a subject in need thereof.

12. The method according to claim 11 wherein the diseases or disorders resulting from diminished SIRT1 expression or activity are elected from aging or stress, metabolic dysfunctions, neurodegenerative diseases, cardiovascular disease, or inflammatory disease.

13. The method according to claim 11, wherein diseases or disorders are selected from psoriasis, atopic dermatitis, acne, rosacea, warts, inflammatory bowel disease, Crohn's Disease, ulcerative colitis, osteoporosis, sepsis, arthritis, COPD, systemic lupus erythematosus, phthalmic inflammation, alopetia, treatment of wounds, ocular disorders, dry eye, keratitis and uveitis.

14. The method according to claim 13, wherein the disease is inflammatory bowel disease, Crohn's Disease, or ulcerative colitis.

* * * * *

UNITED STATES PATENT AND TRADEMARK OFFICE
CERTIFICATE OF CORRECTION

PATENT NO. : 10,072,011 B2
APPLICATION NO. : 15/527581
DATED : September 11, 2018
INVENTOR(S) : James Lamond Ellis et al.

Page 1 of 1

It is certified that error appears in the above-identified patent and that said Letters Patent is hereby corrected as shown below:

In the Claims

Column 904, In Claim 2, please delete the existing structure and replace with the following structure:

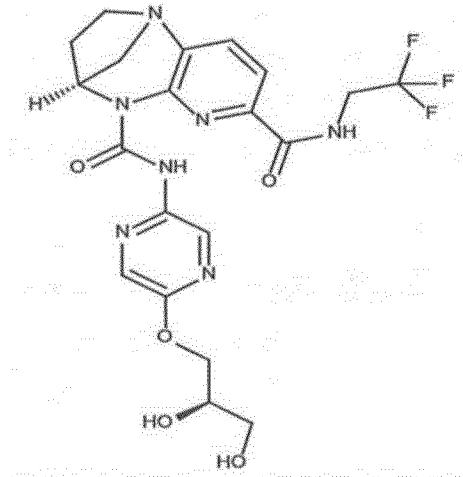

Signed and Sealed this
Eleventh Day of December, 2018

Andrei Iancu
*Director of the United States Patent and Trademark Office*